US012595257B2

(12) United States Patent
Kim et al.

(10) Patent No.: US 12,595,257 B2
(45) Date of Patent: Apr. 7, 2026

(54) HETEROCYCLIC COMPOUND, ORGANIC LIGHT EMITTING DEVICE INCLUDING THE SAME AND COMPOSITION FOR ORGANIC LAYER OF ORGANIC LIGHT EMITTING DEVICE

(71) Applicants: LG DISPLAY CO., LTD., Seoul (KR); LT Materials Co., Ltd., Yongin-si (KR)

(72) Inventors: Sang-Beom Kim, Paju-si (KR); Young-Jun Yu, Paju-si (KR); Seon-Keun Yoo, Paju-si (KR); Seung-Kwang Roh, Paju-si (KR); Woo-Chul Choi, Paju-si (KR); Ji-Ho Baek, Paju-si (KR); Kyung-Hoon Lee, Paju-si (KR); Ki-Min Lim, Paju-si (KR); Dong-Jun Kim, Yongin-si (KR); Young-Seok No, Yongin-si (KR); Hyun-Joo Lee, Yongin-si (KR); Eui-Jeong Choi, Yongin-si (KR)

(73) Assignees: LG DISPLAY CO., LTD., Seoul (KR); LT MATERIALS CO., LTD., Yongin-si (KR)

( * ) Notice: Subject to any disclaimer, the term of this patent is extended or adjusted under 35 U.S.C. 154(b) by 974 days.

(21) Appl. No.: 17/720,608

(22) Filed: Apr. 14, 2022

(65) Prior Publication Data

US 2023/0107166 A1 Apr. 6, 2023

(30) Foreign Application Priority Data

Apr. 16, 2021 (KR) ........................ 10-2021-0049748
Dec. 31, 2021 (KR) ........................ 10-2021-0194155

(51) Int. Cl.
*C07D 405/14* (2006.01)
*H10K 85/30* (2023.01)
*H10K 85/60* (2023.01)
*H10K 50/11* (2023.01)
*H10K 50/18* (2023.01)
*H10K 101/00* (2023.01)
*H10K 101/10* (2023.01)

(52) U.S. Cl.
CPC ......... *C07D 405/14* (2013.01); *H10K 85/342* (2023.02); *H10K 85/624* (2023.02); *H10K 85/626* (2023.02); *H10K 85/633* (2023.02); *H10K 85/654* (2023.02); *H10K 85/6572* (2023.02); *H10K 85/6574* (2023.02); *H10K 85/6576* (2023.02); *H10K 50/11* (2023.02); *H10K 50/18* (2023.02); *H10K 50/181* (2023.02); *H10K 2101/10* (2023.02); *H10K 2101/90* (2023.02)

(58) Field of Classification Search
None
See application file for complete search history.

(56) References Cited

U.S. PATENT DOCUMENTS

| | | | | |
|---|---|---|---|---|
| 2018/0138425 A1 | 5/2018 | Ma et al. | | |
| 2020/0119285 A1* | 4/2020 | No | ........................ | C07D 409/14 |
| 2022/0029108 A1* | 1/2022 | Kim | .................... | H10K 85/6572 |
| 2022/0306613 A1* | 9/2022 | Parham | ................. | C07D 417/14 |
| 2024/0206323 A1* | 6/2024 | Lui | ....................... | H10K 85/622 |

FOREIGN PATENT DOCUMENTS

| | | | | |
|---|---|---|---|---|
| CN | 108084081 A | 5/2018 | | |
| CN | 109535138 A | 3/2019 | | |
| CN | 110818670 A | 2/2020 | | |
| EP | 3604297 A1 | 2/2020 | | |
| KR | 10-2018-0041581 A | 4/2018 | | |
| KR | 10-2021-0018128 A | 2/2021 | | |
| KR | 2021-0031205 A | 3/2021 | | |
| KR | 10-2021-0112838 A | 9/2021 | | |
| TW | 201920102 A | 6/2019 | | |
| WO | 2021/029616 A1 | 2/2021 | | |
| WO | 2021/029634 A1 | 2/2021 | | |
| WO | WO-2021037401 A1 * | 3/2021 | ........... | C07D 209/82 |
| WO | 2021/125552 A1 | 6/2021 | | |
| WO | 2021/125648 A1 | 6/2021 | | |
| WO | 2021/137565 A1 | 7/2021 | | |
| WO | 2022/025714 A1 | 2/2022 | | |
| WO | 2022/031013 A1 | 2/2022 | | |
| WO | 2022/031016 A1 | 2/2022 | | |
| WO | 2022/031028 A1 | 2/2022 | | |

OTHER PUBLICATIONS

Office Action issued in corresponding Taiwan Patent Application No. 111114528 dated Jan. 18, 2023.

(Continued)

*Primary Examiner* — Robert S Loewe
(74) *Attorney, Agent, or Firm* — Morgan, Lewis & Bockius LLP

(57) ABSTRACT

The present disclosure relates to a heterocyclic compound being represented by Formula, an organic light emitting device including the heterocyclic compound and an organic light emitting display device including the organic light emitting device. The organic heterocyclic is included in an organic material layer of the organic light emitting device.

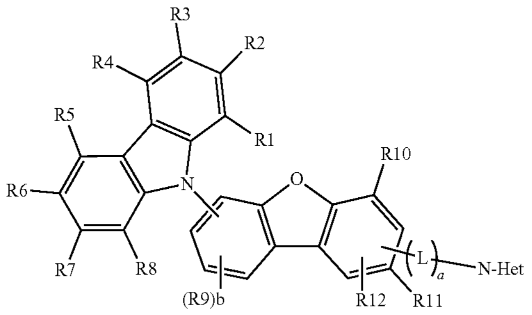

17 Claims, 5 Drawing Sheets

(56) References Cited

OTHER PUBLICATIONS

Office Action issued Dec. 1, 2023 for corresponding Chinese Patent Application No. 202210400119.2 (See English Translation).
Extended European Search Report issued in corresponding European Patent Application No. 22167818.8 dated Aug. 31, 2022.

* cited by examiner

HETEROCYCLIC COMPOUND, ORGANIC LIGHT EMITTING DEVICE INCLUDING THE SAME AND COMPOSITION FOR ORGANIC LAYER OF ORGANIC LIGHT EMITTING DEVICE

CROSS-REFERENCE TO RELATED APPLICATIONS

The present application claims the benefit of Korean Patent Application No. 10-2021-0049748 filed in the Republic of Korea on Apr. 16, 2021 and Korean Patent Application No. 10-2021-0194155 filed in the Republic of Korea on Dec. 31, 2021, all of which are hereby incorporated by reference in their entirety.

BACKGROUND

Field of Technology

The present disclosure relates to a heterocyclic compound, and more particularly, to a heterocyclic compound, an organic light emitting device including the heterocyclic compound and a composition for an organic layer of the organic light emitting device.

Discussion of the Related Art

An organic light emitting display device, which may be referred to as an electroluminescent display device, is a type of a self-emission type display device, and has advantages of a wide viewing angle, excellent contrast, and fast response speed.

An organic light emitting device has a structure in which an organic thin film is disposed between two electrodes. When a voltage is applied to the organic light emitting device, electrons and holes respectively injected from the two electrodes combine in the organic thin film to form a pair, and then disappear and emit light. The organic thin film may have a single-layered structure or a multi-layered structure.

The material of the organic thin film may have a light emitting function. For example, a single compound may be used for the organic thin film. Alternatively, a compound serving as a host and a compound serving as a dopant may be used for the organic thin film in a host-guest system. In addition, as a material of the organic thin film, a compound capable of performing the roles of hole injection, hole transport, electron blocking, hole blocking, electron transport, electron injection, and the like may be used.

In order to improve the performance, lifespan, or efficiency of the organic light emitting device, the development of a material for the organic thin film is continuously required.

Research of a compound having a chemical structure that can satisfy conditions required for materials usable in an organic light emitting device, such as an appropriate energy level, electrochemical stability, and thermal stability, and can play various roles required in an organic light emitting device according to substituents is needed.

SUMMARY

The embodiments of the present disclosure are directed to a heterocyclic compound, an organic light emitting device and a composition for an organic layer of the organic light emitting device that substantially obviate one or more of the problems associated with the limitations and disadvantages of the related conventional art.

Additional features and advantages of the present disclosure are set forth in the description which follows, and will be apparent from the description, or evident by practice of the present disclosure. The objectives and other advantages of the present disclosure are realized and attained by the features described herein as well as in the appended drawings.

To achieve these and other advantages in accordance with the purpose of the embodiments of the present disclosure, as described herein, an aspect of the present disclosure is a heterocyclic compound of Formula 1:

[Formula 1]

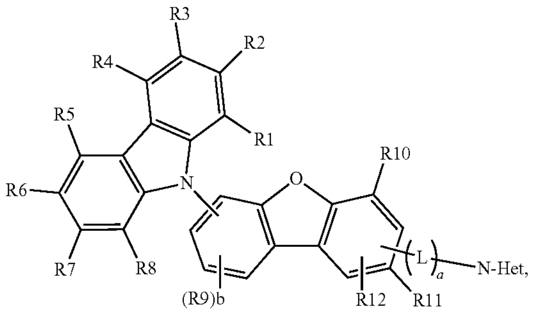

wherein N-Het is substituted or unsubstituted and a monocyclic or polycyclic C2 to C60 heterocyclic group having at least one nitrogen atom, wherein L is a direct bond, a substituted or unsubstituted C6 to C60 arylene group or a substituted or unsubstituted C2 to C60 heteroarylene group, and a is an integer of 1 to 3, wherein when a is 2 or more, two or more L are same or different, wherein R1 to R12 are same or different, wherein each of R1 to R12 is independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —P(═O)RR'; —SiRR'R"; and —NRR', or adjacent two or more of R1 to R12 are bonded to each other to form a substituted or unsubstituted C6 to C60 aromatic hydrocarbon ring or a substituted or unsubstituted C2 to C60 heterocyclic ring, wherein b is an integer of 1 to 3, wherein when b is 2 or more, two or more R9 are the same as or different, wherein R, R' and R" are the same or different, wherein each of R, R' and R" is independently selected from the group consisting of a substituted or unsubstituted C1 to C60 alkyl group; a substituted or unsubstituted C6 to C60 aryl group; or a substituted or unsubstituted C2 to C60 a heteroaryl group, and wherein a deuteration ratio of the heterocyclic compound is 20% to 100%.

Another aspect of the present disclosure is an organic light emitting device comprising a first electrode; a second electrode facing the first electrode; at least one organic material layer between the first and second electrodes, wherein one or more of the at least one organic material layer includes a first compound being the above heterocyclic compound.

It is to be understood that both the foregoing general description and the following detailed description are exemplary and explanatory and are intended to further explain the present disclosure as claimed.

BRIEF DESCRIPTION OF THE DRAWINGS

The accompanying drawings, which are included to provide a further understanding of the present disclosure and are incorporated in and constitute a part of this specification, illustrate embodiments of the present disclosure and together with the description serve to explain the principles of the present disclosure.

DETAILED DESCRIPTION

Figure 1:
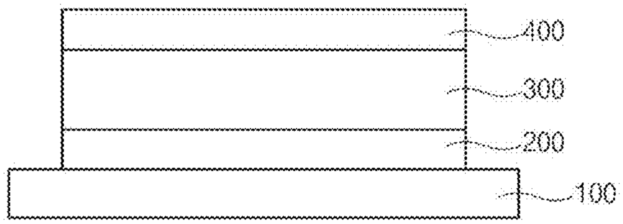
FIG. 1 is a schematic cross-sectional view of an organic light emitting device according to an embodiment of the present disclosure.

Reference will now be made in detail to some of the examples and preferred embodiments, which are illustrated in the accompanying drawings.

In an exemplary embodiment of the present disclosure, deuterium is one of the isotopes of hydrogen and is an element having a deuteron consisting of one proton and one neutron as an atomic nucleus, and can be expressed as hydrogen-2. The element symbol of deuterium can be D or 2H.

In an exemplary embodiment of the present disclosure, isotopes refer to atoms having the same atomic number (Z), but different mass numbers (A). Isotopes can also be interpreted as elements that have the same number of protons but different numbers of neutrons.

In an exemplary embodiment of the present disclosure, the meaning of the content of specific substituents T % is defined as T2/T1*100. T1 is the total number of substituents, and T2 is the number of specific substituent.

For example, when one possible substituent (T2) of five possible substituents (T1) in the phenyl group represented by

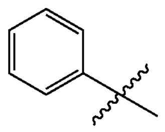 [SMILES: *c1ccccc1]

is substituted with deuterium, the content of deuterium in in the phenyl group represented by

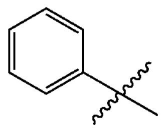 [SMILES: *c1ccccc1]

can be expressed as 20%.

In the present specification, the deuteration ratio (e.g., a deuterium rate) means a ratio of hydrogen in the compound substituted with deuterium. That is, if the compound contains “a” hydrogens and “b” deuterium, the deuteration ratio can be calculated as b*100/(a+b). In the present specification, the deuteration ratio may be referred to as the content of deuterium.

In the present specification, the phenyl group having a deuteration ratio of 20% may be represented by followings:

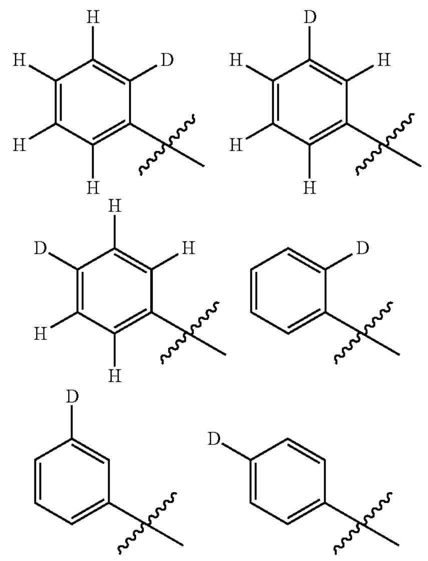

In the present specification, the phenyl group having a deuteration ratio of 0% may be a phenyl group having no deuterium, i.e., five hydrons.

In the present specification, the halogen may include fluorine, chlorine, bromine and iodine.

In the present specification, the alkyl group includes a straight or branched chain having 1 to 60 carbon atoms, and may be substituted. The number of carbon atoms in the alkyl group may be 1 to 60, specifically 1 to 40, more specifically, 1 to 20. For example, the alkyl group may include methyl group, ethyl group, propyl group, n-propyl group, isopropyl group, butyl group, n-butyl group, isobutyl group, tert-butyl group, sec-butyl group, 1-methyl-butyl group, 1-ethyl-butyl group, pentyl group, n-pentyl group, isopentyl group, neopentyl group, tert-pentyl group, hexyl group, n-hexyl group, 1-methylpentyl group, 2-methylpentyl group, 4-methyl-2-pentyl group, 3,3-dimethylbutyl group, 2-ethylbutyl group, heptyl group, n-heptyl group, 1-methylhexyl group, cyclopentylmethyl group, cyclohexylmethyl group, octyl group, n-octyl group, tert-octyl group, 1-methylheptyl group, 2-ethylhexyl group, 2-propylpentyl group, n-nonyl group, 2,2-dimethylheptyl group, 1-ethyl-propyl group, 1,1-dimethyl-propyl group, isohexyl group, 2-methylpentyl group, 4-methylhexyl group, 5-methylhexyl group, and the like, but it is not limited thereto.

In the present specification, the alkenyl group includes a straight or branched chain having 2 to 60 carbon atoms, and may be substituted. The carbon number of the alkenyl group may be 2 to 60, specifically 2 to 40, more specifically, 2 to 20. For example, the alkenyl group may include a vinyl group, 1-propenyl group, isopropenyl group, 1-butenyl group, 2-butenyl group, 3-butenyl group, 1-pentenyl group, 2-pentenyl group, 3-pentenyl group, 3-methyl-1-Butenyl group, 1,3-butadienyl group, allyl group, 1-phenylvinyl-1-yl group, 2-phenylvinyl-1-yl group, 2,2-diphenylvinyl-1-yl group, 2-phenyl-2-(naphthyl-1-yl)vinyl-1-yl group, 2,2-bis (diphenyl-1-yl)vinyl-1-yl group, stilbenyl group, styrenyl group, and the like, but it is not limited thereto.

In the present specification, the alkynyl group includes a straight or branched chain having 2 to 60 carbon atoms, and may be substituted. The carbon number of the alkynyl group may be 2 to 60, specifically 2 to 40, more specifically, 2 to 20.

In the present specification, the alkoxy group may be a straight chain, branched chain or cyclic chain. Although carbon number of an alkoxy group is not specifically limited, it is preferable that the carbon number of an alkoxy group is 1 to 20. For example, the alkoxy group may include methoxy, ethoxy, n-propoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but it is not limited thereto.

In the present specification, the cycloalkyl group includes a monocyclic or polycyclic ring having 3 to 60 carbon atoms, and may be substituted. Here, polycyclic means a group in which a cycloalkyl group is directly connected to or condensed with another ring group, which may be a cycloalkyl group, a heterocycloalkyl group, an aryl group, a heteroaryl group, or the like. The cycloalkyl group may have 3 to 60 carbon atoms, specifically 3 to 40 carbon atoms, and more specifically 5 to 20 carbon atoms. For example, the cycloalkyl group may include cyclopropyl group, cyclobutyl group, cyclopentyl group, 3-methylcyclopentyl group, 2,3-dimethylcyclopentyl group, cyclohexyl group, 3-methylcyclohexyl group, 4-methylcyclohexyl group, 2,3-dimethylcyclohexyl group, 3,4,5-trimethylcyclohexyl group, 4-tert-butylcyclohexyl group, cycloheptyl group, cyclooctyl group, and the like, but it is not limited thereto.

In the present specification, the heterocycloalkyl group includes O, S, Se, N or Si as a hetero atom and may be a monocyclic or polycyclic ring having 2 to 60 carbon atoms. The heterocycloalkyl group may be substituted. Here, polycyclic refers to a group in which a heterocycloalkyl group is directly connected to or condensed with another ring group, which may be a heterocycloalkyl group, a cycloalkyl group, an aryl group, a heteroaryl group, or the like. The heterocycloalkyl group may have 2 to 60 carbon atoms, specifically 2 to 40 carbon atoms, and more specifically 3 to 20 carbon atoms.

In the present specification, the aryl group includes a monocyclic or polycyclic ring having 6 to 60 carbon atoms, and may be substituted. Here, polycyclic means a group in which an aryl group is directly connected to or condensed with another ring group, which may be an aryl group, a cycloalkyl group, a heterocycloalkyl group, a heteroaryl group, or the like. The number of carbon atoms of the aryl group may be 6 to 60, specifically 6 to 40, more specifically 6 to 25. For example, the aryl group may include a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, an indenyl group, an acenaphthylenyl group, a 2,3-dihydro-1H-indenyl group, a condensed cyclic group thereof, and the like, but it is not limited thereto.

In the present specification, the fluorenyl group may be substituted, and adjacent substituents may combine with (connected to or linked with) each other to form a ring. Namely, the substituted fluorenyl group may include a spiro-fluorenyl group.

The substituted fluorenyl group may be represented by followings, but it is not limited thereto.

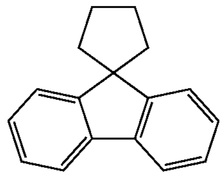
,
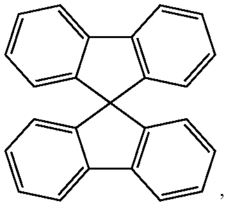
,
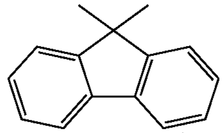
,
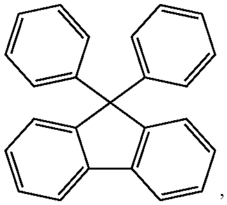
,
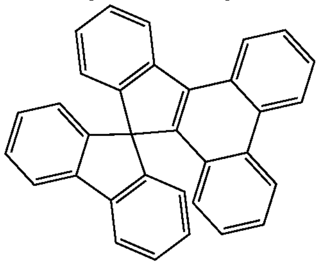
,
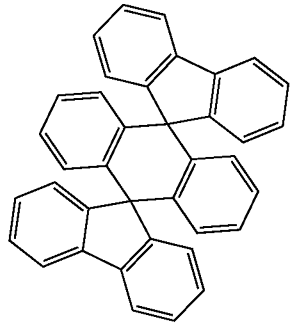

In the present specification, the heteroaryl group includes O, S, Se, N or Si as a hetero atom and may be a monocyclic or polycyclic ring having 2 to 60 carbon atoms. The heteroaryl group may be substituted. Here, polycyclic refers to a group in which a heteroaryl group is directly connected to or condensed with another ring group, which may be a heteroaryl group, a cycloalkyl group, a heterocyclic group, an aryl group, or the like. The heteroaryl group may have 2 to 60 carbon atoms, specifically 2 to 40 carbon atoms, and more specifically 3 to 25 carbon atoms. For example, the heteroaryl group may include pyridyl group, pyrrolyl group, pyrimidyl group, pyridazinyl group, furanyl group, thiophene group, imidazolyl group, pyrazolyl group, oxazolyl group, isoxazolyl group, thiazolyl group, isothiazolyl group, triazolyl group, furazanyl group, oxadiazolyl group, thiadiazolyl group, dithiazolyl group, tetrazolyl group, pyranyl group, thiopyranyl group, diazinyl group, oxazinyl group, thiazinyl group, dioxynyl group, triazinyl group, tetrazinyl group, quinolyl group, isoquinolyl group, quinazolinyl group, isoquinazolinyl group, quinazolylyl group, naphthyridyl group, acridinyl group, phenanthridinyl group, imidazopyridinyl group, diazanaphthalenyl group, triazaindene group, indolyl group, indolizinyl group, benzothiazolyl group, benzoxazolyl group, benzimidazolyl group, benzothiophene group, benzofuran group, dibenzothiophene group, dibenzofuran group, carbazolyl group, benzocarbazolyl group, dibenzocarbazolyl group, phenazinyl group, dibenzosilol group, dihydrophenazinyl group, phenoxazinyl group, phenantridyl group, imidazopyridinyl group, thienyl group, indolo[2,3-a]carbazolyl group, indolo[2,3-b]carbazolyl group, indolinyl group, 10,11-dihydro-dibenzo[b,f]azepine group, 9,10-dihydroacridinyl group, phenantrazinyl group, phenothiazinyl group, phthalazinyl group, naphthylidinyl group, phenanthrolinyl group, benzo[c][1,2,5]thiadiazolyl group, 5,10-dihydrodibenzo[b, e][1,4]azasilinyl, pyrazolo[1,5-c]quinazolinyl group, pyrido[1,2-b]indazolyl group, pyrido[1,2-a]imidazo[1,2-e]indolinyl group, 5,11-dihydroindeno[1,2-b]carbazolyl group, and the like, but it is not limited thereto.

In the present specification, the amine group is selected from the group consisting of a monoalkylamine group, monoarylamine group, monoheteroarylamine group, —$NH_2$, dialkylamine group, diarylamine group, diheteroarylamine group, an alkylarylamine group, an alkyl heteroarylamine group, and an aryl-heteroarylamine group. The number of carbon atoms of the amine group is not particularly limited, but it is preferably 1 to 30. For example, the amine group may include a methylamine group, a dimethylamine group, an ethylamine group, a diethylamine group, a phenylamine group, a naphthylamine group, a biphenylamine group, a dibiphenylamine group, an anthracenylamine group, 9-methyl-anthracenylamine group, diphenylamine group, phenylnaphthylamine group, ditolylamine group, phenyltolylamine group, triphenylamine group, biphenylnaphthylamine group, phenylbiphenylamine group, biphenylfluorenylamine group, a phenyltriphenylenylamine group, a biphenyltriphenylenylamine group, and the like, but it is not limited thereto.

In the present specification, the arylene group means that the aryl group has two bonding positions, i.e., a divalent group. Except that each of these is a divalent group, the description of the aryl group described above may be applied. In addition, the heteroarylene group means that the heteroaryl group has two bonding positions, i.e., a divalent group. Except that each of these is a divalent group, the description of the heteroaryl group described above may be applied.

In the present specification, the phosphine oxide group is represented by —P(═O)$R_{101}R_{102}$. $R_{101}$ and $R_{102}$ are the same as or different from each other, and each of $R_{101}$ and $R_{102}$ is independently selected from the group consisting of hydrogen, deuterium, halogen, an alkyl group, an alkenyl group, an alkoxy group, a cycloalkyl group, an aryl group and a heterocyclic group. The phosphine oxide group may include a diphenylphosphine oxide group, a dinaphthyl phosphine oxide, and the like, but it is not limited thereto.

In the present specification, the silyl group is a substituent including Si atom, which is directly connected as a radical, and is represented by —Si$R_{104}R_{105}R_{106}$. $R_{104}$ to $R_{106}$ are the same as or different from each other, and each of $R_{104}$ to $R_{106}$ is independently selected from the group consisting of hydrogen, deuterium, halogen, an alkyl group, an alkenyl group, an alkoxy group, a cycloalkyl group, an aryl group and a heterocyclic group. The silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but it is not limited thereto.

As used herein, the "adjacent" groups may mean a pair of one substituent substituted on one atom and another substituent substituted on another atom, which is directly connected to the one atom, a pair of one substituent and another substituent sterically closest to the one substituent, and a pair of one substituent and another substituent, which is substituted on the atom in which the substituent is substituted. For example, two substituents substituted at an ortho position in a benzene ring and two substituents substituted at the same carbon in an aliphatic ring may be interpreted as "adjacent" groups.

The aliphatic or aromatic hydrocarbon ring or heterocycle, which is formed by the adjacent groups may have the structures exemplified by the above-described cycloalkyl group, cycloheteroalkyl group, aryl group and heteroaryl group except that the aliphatic or aromatic hydrocarbon ring or heterocycle that adjacent groups may form is not a monovalent group.

In the present specification, the term "substitution" means that a hydrogen atom bonded to a carbon atom of the compound is changed to another substituent, and the position to be substituted is not limited as long as the position at which the hydrogen atom is substituted, that is, the position where the substituent is substitutable. When two or more substituents are substituted, two or more substituents may be the same as or different from each other.

In the present specification, "substituted" means that at least one hydrogens in a compound is substituted with at least one selected from the group consisting of deuterium; C1 to C60 straight-chain or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(═O)RR'; C1 to C20 alkylamine; C6 to C60 monocyclic or polycyclic arylamine; and C2 to C60 monocyclic or polycyclic heteroarylamine or substituted with a substituent formed from at least two of the group. In this case, each of R, R' and R" may be same or different, and each of R, R' and R" may be independently selected from the group consisting of a substituted or unsubstituted C1 to C60 alkyl group; a substituted or unsubstituted C6 to C60 aryl group; and a substituted or unsubstituted C2 to C60 heteroaryl group.

The heterocyclic compound of the present disclosure is represented by Formula 1.

[Formula 1]

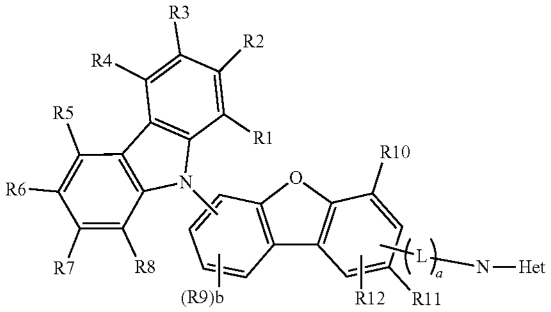

In Formula 1, "N-Het" is substituted or unsubstituted and a monocyclic or polycyclic C2 to C60 heterocyclic group having (or containing) at least one nitrogen atom (N).

L is a direct bond (single bond), a substituted or unsubstituted C6 to C60 arylene group or a substituted or unsubstituted C2 to C60 heteroarylene group, and a is an integer of 1 to 3. When a is 2 or more, two or more L are same or different.

R1 to R12 are same or different. Each of R1 to R12 is independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —P(═O)RR'; —SiRR'R"; and —NRR', or adjacent two or more of R1 to R12 are bonded to each other to form a substituted or unsubstituted C6 to C60 aromatic hydrocarbon ring or a substituted or unsubstituted C2 to C60 heterocyclic ring. b is an integer of 1 to 3. When b is 2 or more, two or more R9 are the same as or different.

R, R' and R" are the same or different, and each of R, R' and R" is independently selected from the group consisting of a substituted or unsubstituted C1 to C60 alkyl group; a substituted or unsubstituted C6 to C60 aryl group; or a substituted or unsubstituted C2 to C60 a heteroaryl group.

For example, the heterocyclic compound of Formula 1 may have a deuteration ratio of 20% to 100%.

In an exemplary embodiment of the present disclosure, the heterocyclic compound of Formula 1 may be represented by one of Formulas 3 to 6.

[Formula 3]

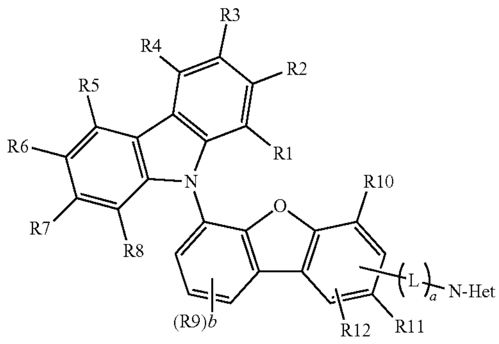

[Formula 4]

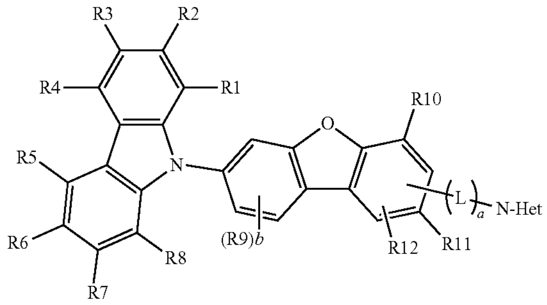

[Formula 5]

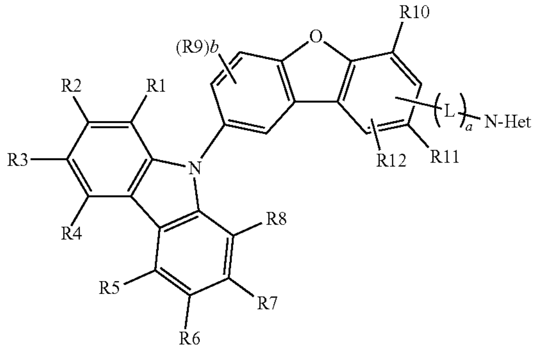

[Formula 6]

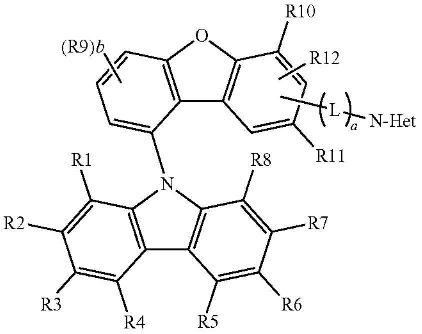

In Formulas 3 to 6, the definitions of N-Het, R1 to R12, L, a, and b are same as those in Formula 1.

In an exemplary embodiment of the present disclosure, the heterocyclic compound of Formula 1 may be represented by one of Formulas 7 and 8.

[Formula 7]

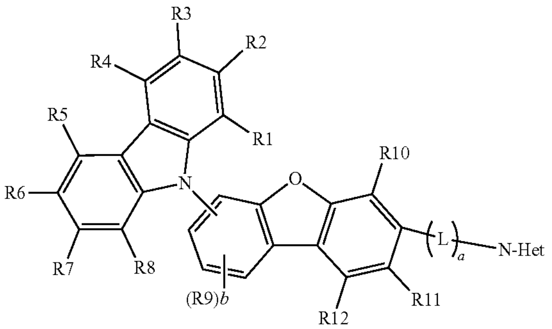

[Formula 8]

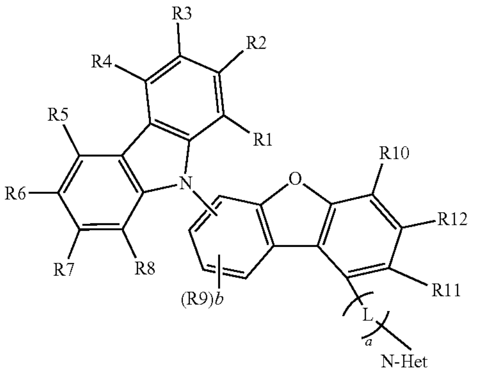

In Formulas 7 and 8, the definitions of N-Het, R1 to R12, L, a, and b are the same as those in Formula 1.

In an exemplary embodiment of the present disclosure, R9 to R12 may be same or different. Each of R9 to R12 may be independently selected from the group consisting of hydrogen; deuterium; a substituted or unsubstituted C1 to C60 alkyl group; a substituted or unsubstituted C6 to C60 aryl group and a substituted or unsubstituted C2 to C60 heteroaryl group, or adjacent two or more of R9 to R12 are bonded to each other to form a substituted or unsubstituted C6 to C60 aromatic hydrocarbon ring or a substituted or unsubstituted C2 to C60 heterocyclic ring.

In an exemplary embodiment of the present disclosure, R9 to R12 may be same or different. Each of R9 to R12 may be independently selected from the group consisting of hydrogen; deuterium; a substituted or unsubstituted C1 to C40 alkyl group; a substituted or unsubstituted C6 to C40 aryl group and a substituted or unsubstituted C2 to C40 heteroaryl group, or adjacent two or more of R9 to R12 are bonded to each other to form a substituted or unsubstituted C6 to C40 aromatic hydrocarbon ring or a substituted or unsubstituted C2 to C40 heterocyclic ring.

In an exemplary embodiment of the present disclosure, R9 to R12 may be same or different, and each of R9 to R12 may be independently selected from the group consisting of hydrogen and deuterium.

In an exemplary embodiment of the present disclosure, L is a direct bond, a substituted or unsubstituted C6 to C60 arylene group or a substituted or unsubstituted C2 to C60 heteroarylene group.

In an exemplary embodiment of the present disclosure, L is a direct bond, a substituted or unsubstituted C6 to C40 arylene group or a substituted or unsubstituted C2 to C40 heteroarylene group.

In an exemplary embodiment of the present disclosure, L is a direct bond, a substituted or unsubstituted C6 to C30 arylene group or a substituted or unsubstituted C2 to C30 heteroarylene group.

In an exemplary embodiment of the present disclosure, L is a direct bond, a substituted or unsubstituted C6 to C20 arylene group or a substituted or unsubstituted C2 to C20 heteroarylene group.

In an exemplary embodiment of the present disclosure, L is a direct bond, a C6 to C20 arylene group or a C2 to C20 heteroarylene group.

In an exemplary embodiment of the present disclosure, L is a direct bond or a monocyclic or polycyclic C6 to C20 arylene group.

In an exemplary embodiment of the present disclosure, L is a direct bond, phenylene, biphenylene, or naphthalenylene.

In an exemplary embodiment of the present disclosure, "N-Het" is substituted or unsubstituted and a monocyclic or polycyclic C2 to C60 heterocyclic group having (or containing) at least one nitrogen atom (N).

In an exemplary embodiment of the present disclosure, "N-Het" is substituted or unsubstituted and a monocyclic or polycyclic C2 to C40 heterocyclic group having (or containing) at least one nitrogen atom (N).

In an exemplary embodiment of the present disclosure, "N-Het" is substituted or unsubstituted and a monocyclic or polycyclic C2 to C20 heterocyclic group having (or containing) at least one nitrogen atom (N).

In an exemplary embodiment of the present disclosure, "N-Het" is substituted with at least one substituent selected from the group consisting of deuterium, a C1 to C20 alkyl group, a C6 to C20 aryl group and a C2 to C20 heteroaryl group and is a monocyclic or polycyclic C2 to C20 heterocyclic group having (or containing) at least one nitrogen atom (N).

In an exemplary embodiment of the present disclosure, the N-Het may be a substituted or unsubstituted pyridine group; a substituted or unsubstituted pyrimidine group; a substituted or unsubstituted triazine group; a substituted or unsubstituted quinoline group; a substituted or unsubstituted isoquinoline group; a substituted or unsubstituted benzimidazole group; or a substituted or unsubstituted phenanthroline group.

In an exemplary embodiment of the present disclosure, the N-Het may be represented by one of the structures in Formula 1a

[Formula 1a]

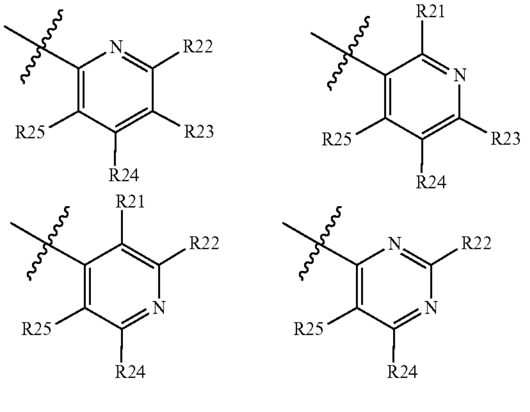

-continued

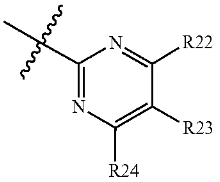

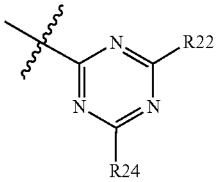

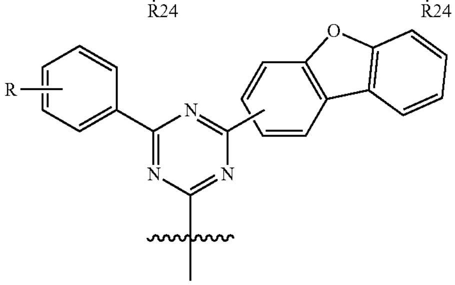

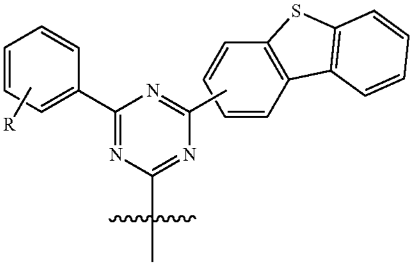

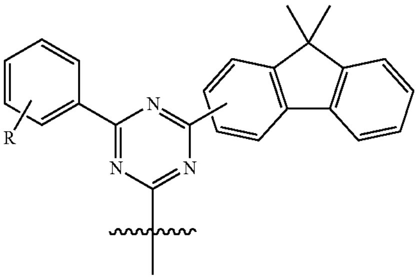

In Formula 1a, R21 to R25 are same or different. Each of R21 to R25 is independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; and a substituted or unsubstituted C2 to C60 heteroaryl group, or adjacent two or more of R21 to R25 are bonded to each other to form a substituted or unsubstituted C6 to C60 aromatic hydrocarbon ring or a substituted or unsubstituted C2 to C60 heterocyclic ring. R is selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; and a substituted or unsubstituted C2 to C60 heteroaryl group.

In an exemplary embodiment of the present disclosure, R21 to R25 are same or different. Each of R21 to R25 is independently selected from the group consisting of hydrogen; deuterium; a substituted or unsubstituted C1 to C60 alkyl group; a substituted or unsubstituted C6 to C60 aryl group; and a substituted or unsubstituted C2 to C60 heteroaryl group, or adjacent two or more of R21 to R25 are bonded to each other to form a substituted or unsubstituted C6 to C60 aromatic hydrocarbon ring or a substituted or unsubstituted C2 to C60 heterocyclic ring.

In an exemplary embodiment of the present disclosure, R21 to R25 are same or different, and each of R21 to R25 is independently selected from the group consisting of hydrogen; deuterium; a substituted or unsubstituted C1 to C60 alkyl group; a substituted or unsubstituted C6 to C60 aryl group; and a substituted or unsubstituted C2 to C60 heteroaryl group.

In an exemplary embodiment of the present disclosure, R21 to R25 are same or different, and each of R21 to R25 is independently selected from the group consisting of hydrogen; deuterium; a substituted or unsubstituted C1 to C40 alkyl group; a substituted or unsubstituted C6 to C40 aryl group; and a substituted or unsubstituted C2 to C40 heteroaryl group.

In an exemplary embodiment of the present disclosure, R21 to R25 are same or different, and each of R21 to R25 is independently selected from the group consisting of hydrogen; deuterium; a C1 to C40 alkyl group unsubstituted or substituted with deuterium; a C6 to C40 aryl group unsubstituted or substituted with deuterium or C1 to C20 alkyl; and a C2 to C40 heteroaryl group unsubstituted or substituted with deuterium.

In an exemplary embodiment of the present disclosure, R21 to R25 are the same or different, and each of R21 to R25 is independently selected from the group consisting of hydrogen; deuterium; phenyl unsubstituted or substituted with deuterium; biphenyl unsubstituted or substituted with deuterium; dimethyl-fluorenyl unsubstituted or substituted with deuterium; dibenzofuran unsubstituted or substituted with deuterium and dibenzothiophene unsubstituted or substituted with deuterium.

In an exemplary embodiment of the present disclosure, R1 to R8 in Formula 1 are same or different. Each of R1 to R8 may be independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —P(═O)RR'; —SiRR'R"; and —NRR', or adjacent two or more of R1 to R8 are bonded to each other to form a substituted or unsubstituted C6 to C60 aromatic hydrocarbon ring or a substituted or unsubstituted C2 to C60 heterocyclic ring.

In an exemplary embodiment of the present disclosure, R1 to R8 may be same or different. Each of R1 to R8 may be independently selected from the group consisting of hydrogen; deuterium; a substituted or unsubstituted C1 to C60 alkyl group; a substituted or unsubstituted C6 to C60 aryl group and a substituted or unsubstituted C2 to C60 heteroaryl group, or adjacent two or more of R1 to R8 may be bonded to each other to form a substituted or unsubstituted C6 to C60 aromatic hydrocarbon ring or a substituted or unsubstituted C2 to C60 heterocyclic ring.

In an exemplary embodiment of the present disclosure, R1 to R8 may be same or different. Each of R1 to R8 may be independently selected from the group consisting of hydrogen; deuterium; a substituted or unsubstituted C6 to C60 aryl group; and a substituted or unsubstituted C2 to C60 heteroaryl group, or adjacent two or more of R1 to R8 may be bonded to each other to form a substituted or unsubstituted C6 to C60 aromatic hydrocarbon ring or a substituted or unsubstituted C2 to C60 heterocyclic ring.

In an exemplary embodiment of the present disclosure, R1 to R8 may be same or different. Each of R1 to R8 may be independently selected from the group consisting of hydrogen; deuterium; a substituted or unsubstituted C6 to C40 aryl group; and a substituted or unsubstituted C2 to C40 heteroaryl group, or adjacent two or more of R1 to R8 may be bonded to each other to form a substituted or unsubstituted C6 to C40 aromatic hydrocarbon ring or a substituted or unsubstituted C2 to C40 heterocyclic ring.

In an exemplary embodiment of the present disclosure, R1 to R8 may be same or different. Each of R1 to R8 may be independently selected from the group consisting of hydrogen; deuterium; a C6 to C40 aryl group unsubstituted or substituted with deuterium; and a C2 to C40 heteroaryl group unsubstituted or substituted with deuterium, or adjacent two or more of R1 to R8 may be bonded to each other to form a C6 to C40 aromatic hydrocarbon ring unsubstituted or substituted with deuterium or C6 to C40 aryl or a C2 to C40 heterocyclic ring unsubstituted or substituted with deuterium or C6 to C40 aryl.

In an exemplary embodiment of the present disclosure, R1 to R8 may be same or different. Each of R1 to R8 may be independently selected from the group consisting of hydrogen; deuterium; a substituted or unsubstituted phenyl group; and a substituted or unsubstituted dibenzothiophene group, or adjacent two or more of R1 to R8 may be bonded to each other to form a substituted or unsubstituted indole ring; a substituted or unsubstituted indene ring; a substituted or unsubstituted benzofuran ring; or a substituted or unsubstituted benzothiophene ring.

In an exemplary embodiment of the present disclosure,

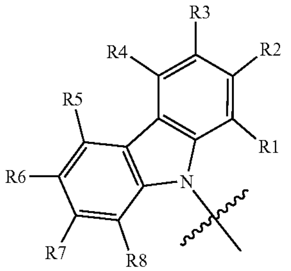

may be represented by Formula 9 or 10, and

is a position bonded to a dibenzofuran structure.

[Formula 9]

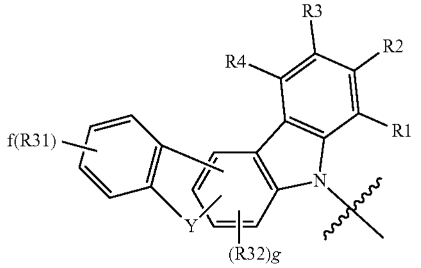

[Formula 10]

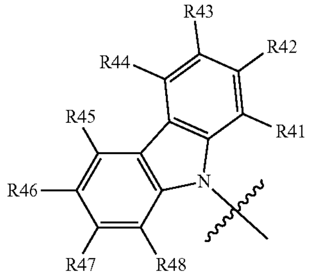

In Formulas 9 and 10, the definitions of R1 to R4 are same as those in Formula 1, and Y is O, S, NRb or CRbRb'.

Each of R41 to R48 is independently selected from the group consisting of hydrogen, deuterium, a substituted or unsubstituted C6 to C60 aryl group and a substituted or unsubstituted C2 to C60 heteroaryl group.

Rb, Rb', R31 and R32 are same or different. Each of Rb, Rb', R31 and R32 is independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; and a substituted or unsubstituted C2 to C60 heteroaryl group, or adjacent two or more of Rb, Rb', R31 and R32 are bonded to each other to form a substituted or unsubstituted C6 to C60 aromatic hydrocarbon ring or a substituted or unsubstituted C2 to C60 heterocyclic ring. f is an integer of 0 to 4. When f is 2 or more, R31 is the same as or different. g is an integer of 0 to 2. When f is 2, R32 is the same as or different.

In an exemplary embodiment of the present disclosure, the structure of Formula 9 may be represented by one of structures in Formula 9a.

[Formula 9a]

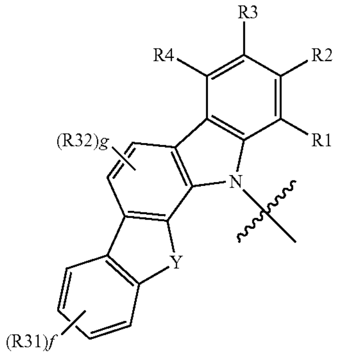

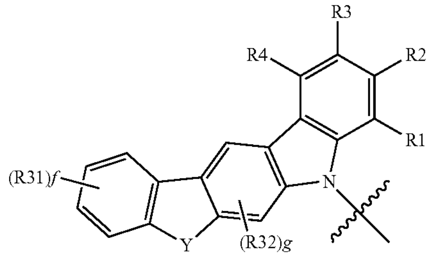

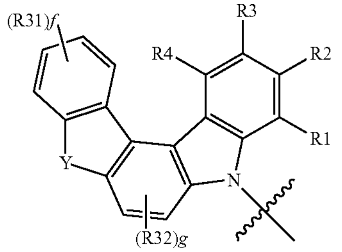

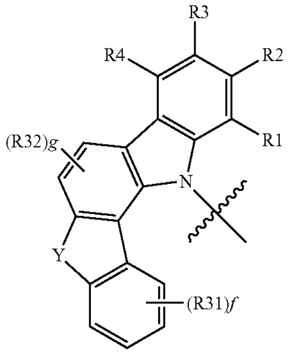

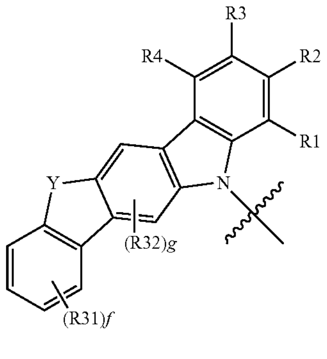

-continued

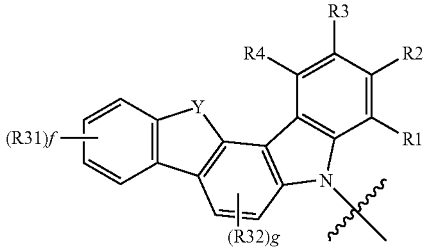

In Formula 9a, the definitions of substituents are same as those in Formula 9.

In an exemplary embodiment of the present disclosure, R31 and R32 may be same as each other, and each of R31 and R32 may be independently selected from hydrogen and deuterium.

In an exemplary embodiment of the present disclosure, Rb and Rb' may be same as each other, and each of Rb and Rb' may be selected from the group consisting of hydrogen, deuterium, a substituted or unsubstituted C1 to C60 alkyl group and a substituted or unsubstituted C6 to C60 aryl group.

In an exemplary embodiment of the present disclosure, Rb and Rb' may be same as each other, and each of Rb and Rb' may be selected from the group consisting of hydrogen, deuterium, a substituted or unsubstituted C1 to C40 alkyl group and a substituted or unsubstituted C6 to C40 aryl group.

In an exemplary embodiment of the present disclosure, Rb and Rb' may be same as each other, and each of Rb and Rb' may be selected from the group consisting of hydrogen, deuterium, a C1 to C40 alkyl group unsubstituted or substituted with deuterium and a C6 to C40 aryl group unsubstituted or substituted with deuterium.

In an exemplary embodiment of the present disclosure, Rb and Rb' may be same as each other, and each of Rb and Rb' may be selected from the group consisting of hydrogen, deuterium, a C1 to C20 alkyl group unsubstituted or substituted with deuterium and a C6 to C20 aryl group unsubstituted or substituted with deuterium.

In an exemplary embodiment of the present disclosure, Rb and Rb' may be same as each other, and each of Rb and Rb' may be selected from the group consisting of hydrogen, deuterium, phenyl unsubstituted or substituted with deuterium and methyl unsubstituted or substituted with deuterium.

In an exemplary embodiment of the present disclosure, each of R41 to R48 may be selected from the group consisting of hydrogen, deuterium, a substituted or unsubstituted C6 to C60 aryl group and a substituted or unsubstituted C2 to C60 heteroaryl group.

In an exemplary embodiment of the present disclosure, each of R41 to R48 may be selected from the group consisting of hydrogen, deuterium, a substituted or unsubstituted C6 to C40 aryl group and a substituted or unsubstituted C2 to C40 heteroaryl group.

In an exemplary embodiment of the present disclosure, each of R41 to R48 may be selected from the group consisting of hydrogen, deuterium, a substituted or unsubstituted C6 to C20 aryl group and a substituted or unsubstituted C2 to C20 heteroaryl group.

In an exemplary embodiment of the present disclosure, each of R41 to R48 may be selected from the group consisting of hydrogen, deuterium, a C6 to C20 aryl group unsubstituted or substituted with deuterium and a C2 to C20 heteroaryl group unsubstituted or substituted with deuterium.

In an exemplary embodiment of the present disclosure, each of R41 to R48 may be selected from the group consisting of hydrogen, deuterium, dibenzofuran unsubstituted or substituted with deuterium and dibenzothiophene unsubstituted or substituted with deuterium.

In an exemplary embodiment of the present disclosure, the deuteration ratio of the heterocyclic compound of Formula 1 may be 20% to 100%.

In an exemplary embodiment of the present disclosure, the deuteration ratio of the heterocyclic compound of Formula 1 may be 40% to 100%, and preferably 50% to 100%.

In an exemplary embodiment of the present disclosure, the deuteration ratio of the heterocyclic compound of Formula 1 satisfies the above range, and the photochemical characteristics of the compound containing no deuterium and the compound containing deuterium are almost similar. However, in a thin film, materials containing deuterium tend to be packed with narrower intermolecular distances.

Accordingly, when EOD (Electron Only Device) and HOD (Hole Only Device) were manufactured and the current density according to voltage was checked, it can be seen that the compound of Formula 1 containing deuterium according to the present application had a much more balanced charge transport property than the compound not containing deuterium.

In addition, when looking at the surface of the thin film with an atomic force microscope (AFM), it can be seen that the thin film made of a compound containing deuterium is deposited on a more uniform surface without aggregation.

In addition, the single bond dissociation energy of carbon and deuterium is higher than the single bond dissociation energy of carbon and hydrogen. Accordingly, in the heterocyclic compound of Formula 1 according to the present disclosure having the deuteration ratio within the above range, the stability of the entire molecule is increased, thereby improving the device lifespan.

In an exemplary embodiment of the present disclosure, the structure of Formula 1 may be divided into partial structures of Formulas 1-1 to 1-3.

[Formula 1-1]

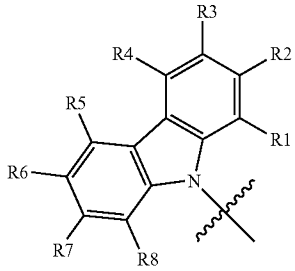

[Formula 1-2]

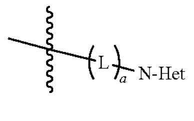

-continued

[Formula 1-3]

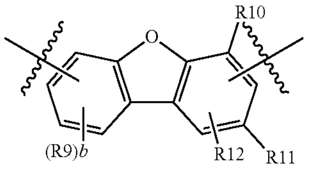

In Formulas 1-1 to 1-3, the definitions of N-Het, R1 to R12, L, a, and b are same as those in Formula 1, and the mark

is a bonding position between the partial structures of Formulas 1-1 to 1-3.

In an exemplary embodiment of the present disclosure, the partial structure of Formula 1-1 in Formula 1 may have the deuteration ratio of 0%.

In an exemplary embodiment of the present disclosure, the partial structure of Formula 1-1 in Formula 1 may have the deuteration ratio of 100%.

In an exemplary embodiment of the present disclosure, the partial structure of Formula 1-1 in Formula 1 may have the deuteration ratio of 0% to 100%.

In an exemplary embodiment of the present disclosure, the partial structure of Formula 1-2 in Formula 1 may have the deuteration ratio of 0%.

In an exemplary embodiment of the present disclosure, the partial structure of Formula 1-2 in Formula 1 may have the deuteration ratio of 100%.

In an exemplary embodiment of the present disclosure, the partial structure of Formula 1-3 in Formula 1 may have the deuteration ratio of 0%.

In an exemplary embodiment of the present disclosure, the partial structure of Formula 1-3 in Formula 1 may have the deuteration ratio of 100%.

In an exemplary embodiment of the present disclosure, the partial structures of Formulas 1-1 to 1-3 in Formula 1 may have the deuteration ratio of 100%.

In an exemplary embodiment of the present disclosure, the structure of Formula 1 may be divided into partial structures of Formulas 1-1 to 1-3, where the definitions of substituents are same as those in Formula 1, and the mark

is a bonding position between the partial structures of Formulas 1-1 to 1-3, one of the partial structure of Formula 1-1, the partial structure of Formula 1-2 and the partial structure of Formula 1-3 in Formula 1 may have the deuteration ratio of 100%.

For example, the structure of Formula 1 may be represented by Formula 1b, and each of a1, a2 and a3 may be independently 0 or a positive integer.

[Formula 1b]

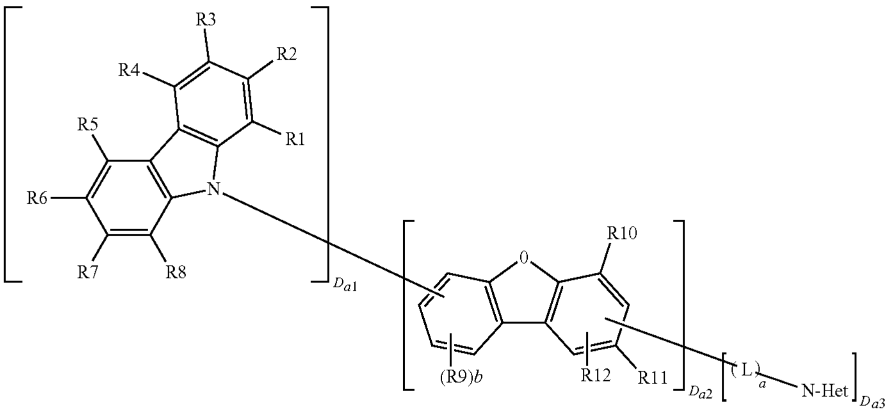

In Formula 1b, a1 may be a positive integer. Preferably, a1 may be a positive integer, and a2 and a3 may be 0. In this instance, the lifespan and the operation performance of the device can be improved with minimizing the increase of the production cost of the heterocyclic compound by deuterium.

In Formula 1b, "D" denotes deuterium atom, and each of "a1", "a2" and "a3" denotes a number of deuterium atom. For example, "Da2" denotes a number of deuterium atom included in the dibenzofuran moiety.

In an exemplary embodiment of the present disclosure, the heterocyclic compound of Formula 1 may be one of the compounds in Formula 1c, but it is not limited thereto.

[Formula 1c]

1

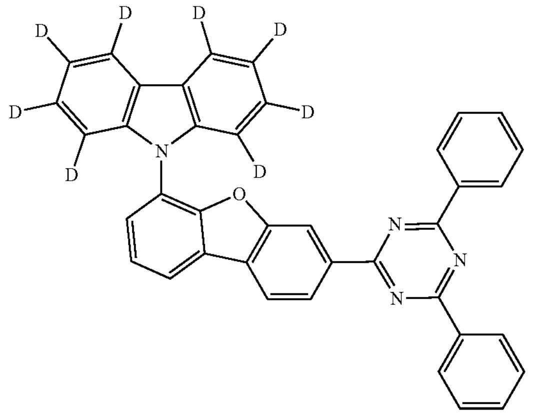

2

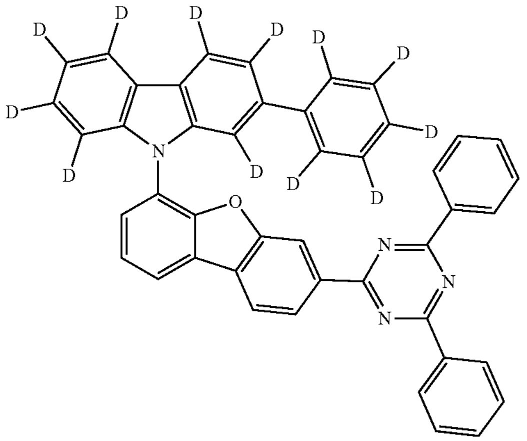

-continued
3
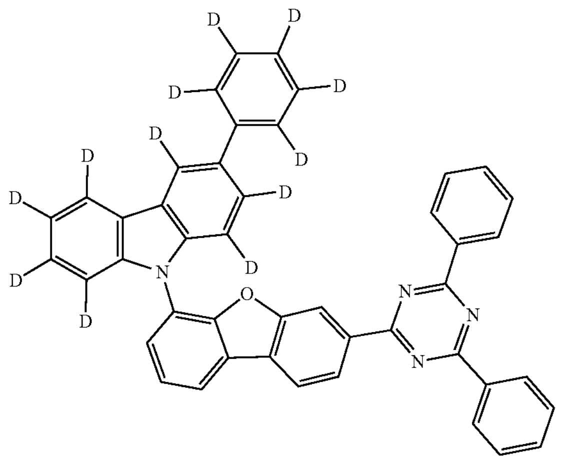
4
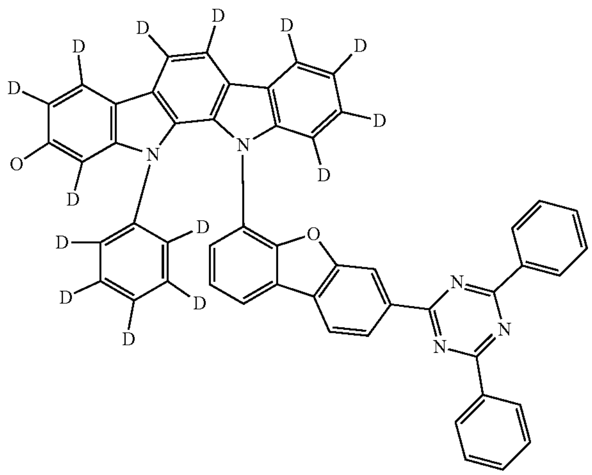
5
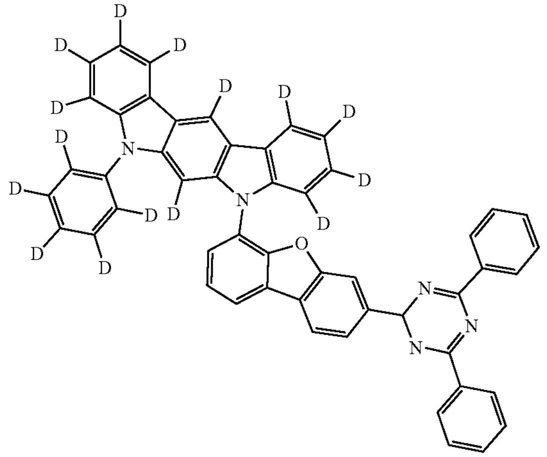
6
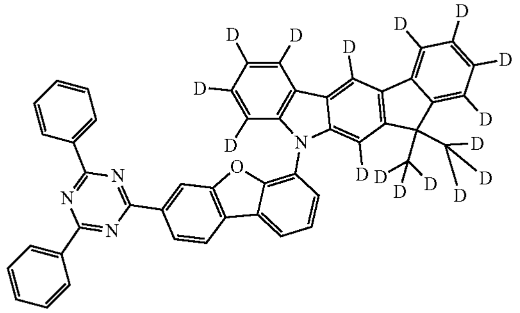
7
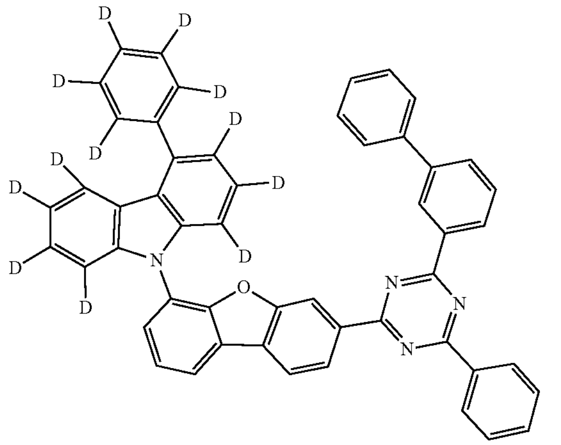
8
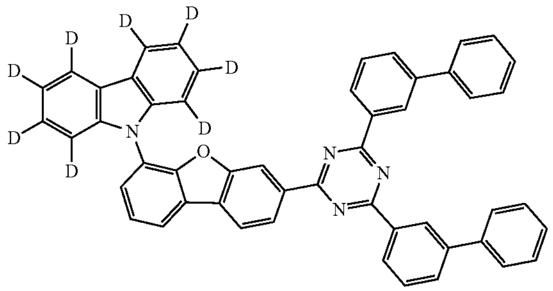

-continued
9
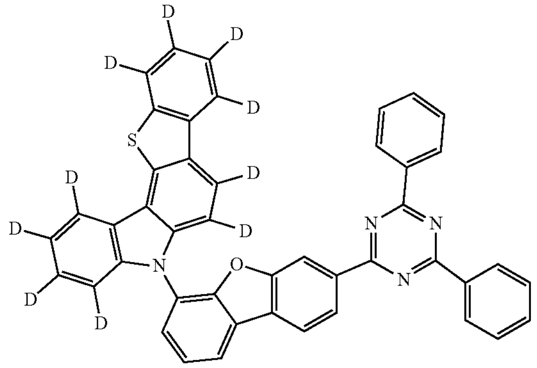
10
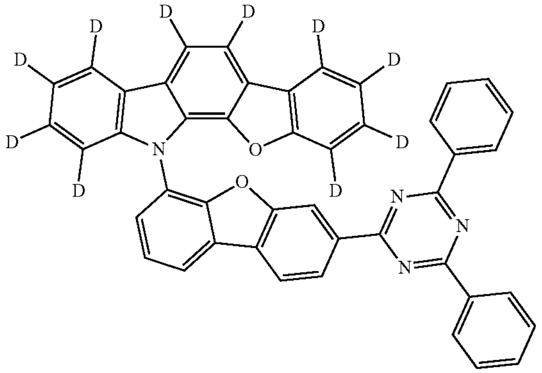
11
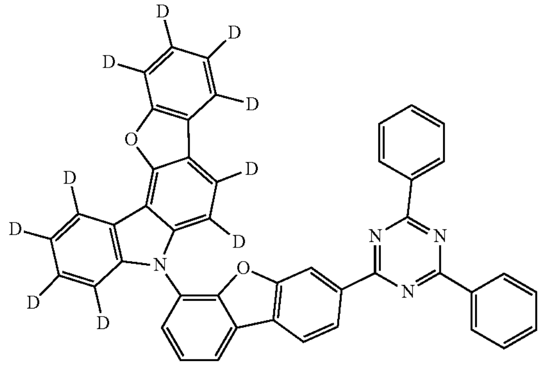
12
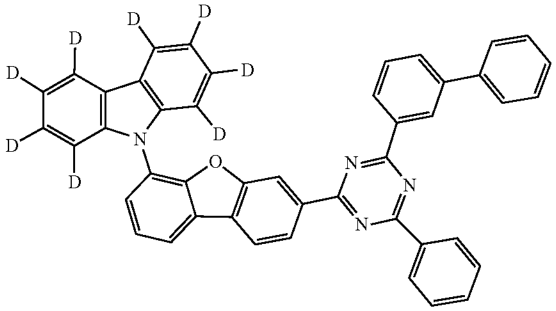
13
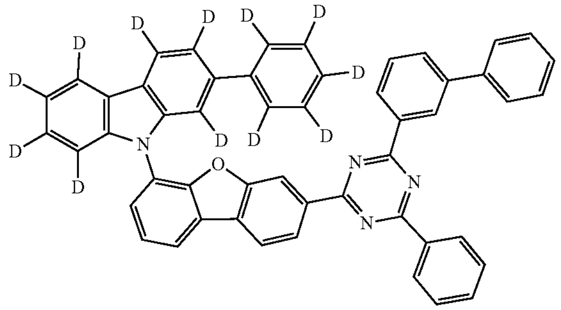
14
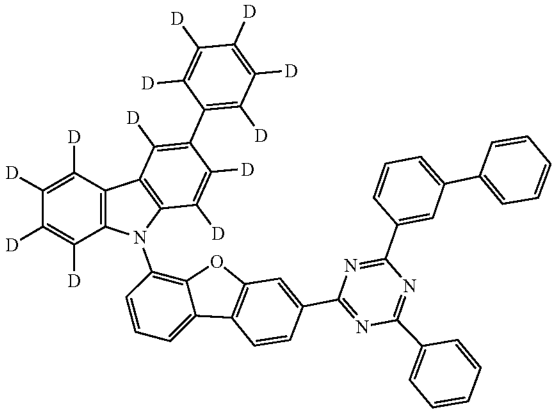
15
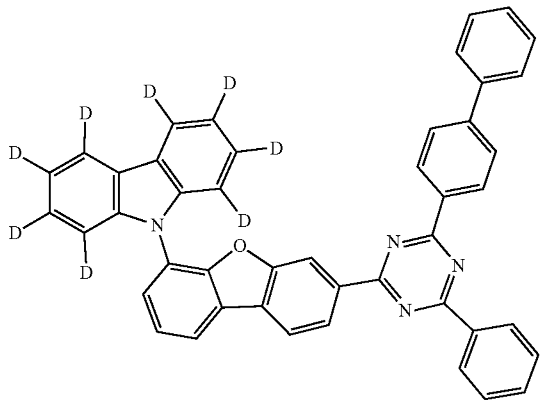
16
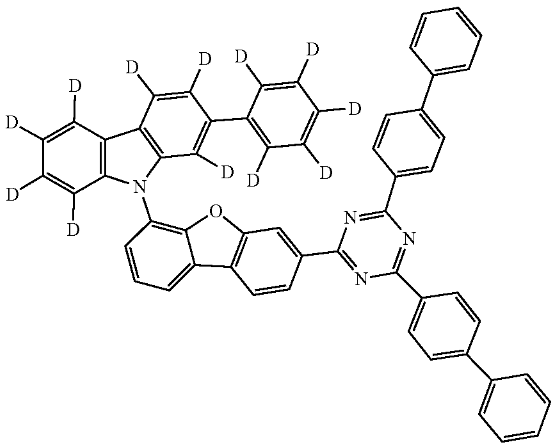

-continued
17
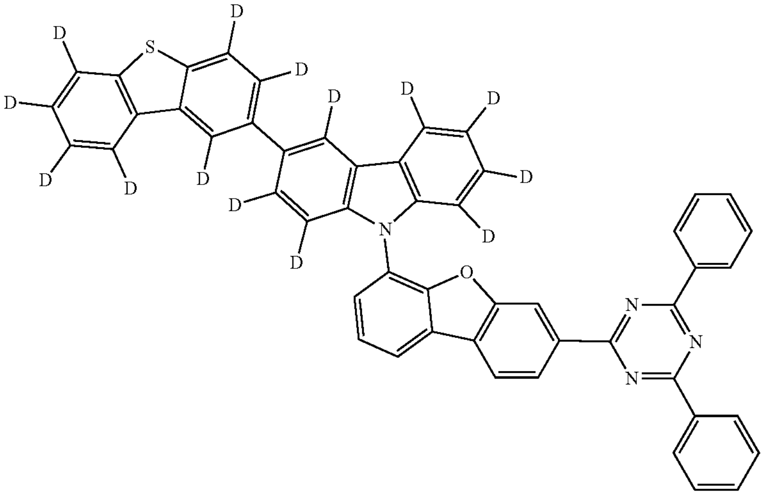
18
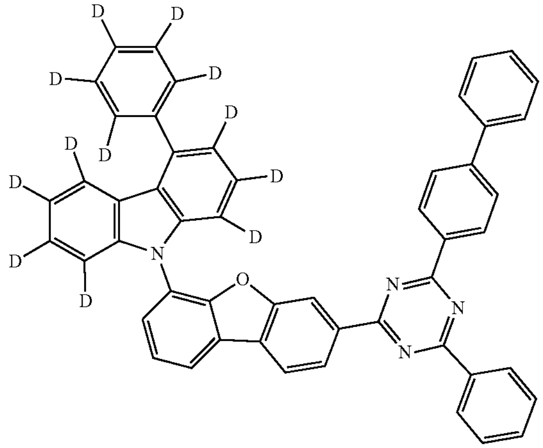
19
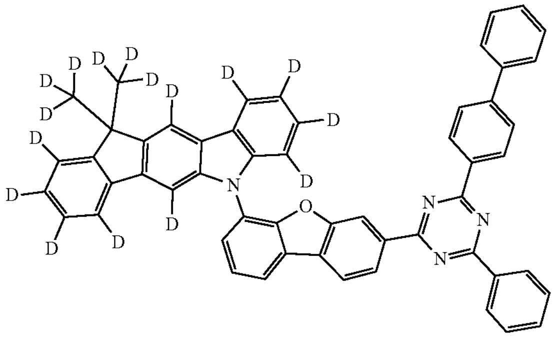
20
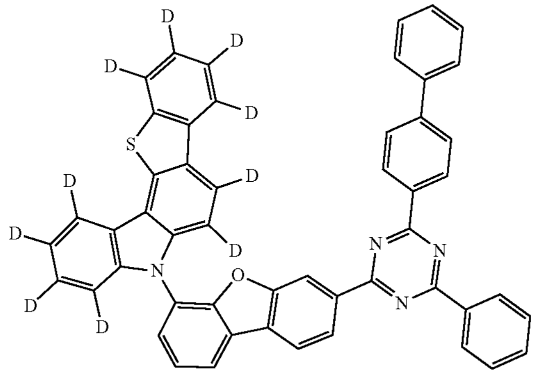
21
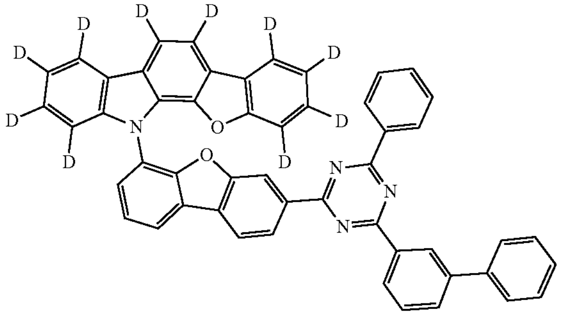

-continued
22
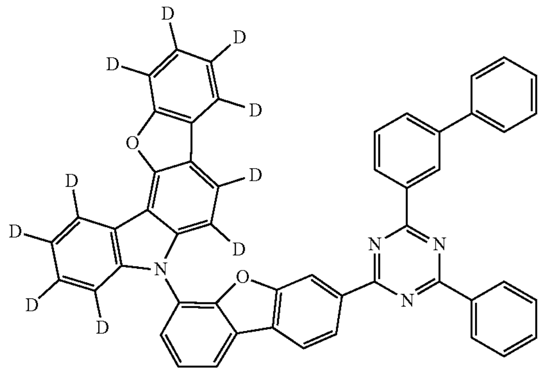
23
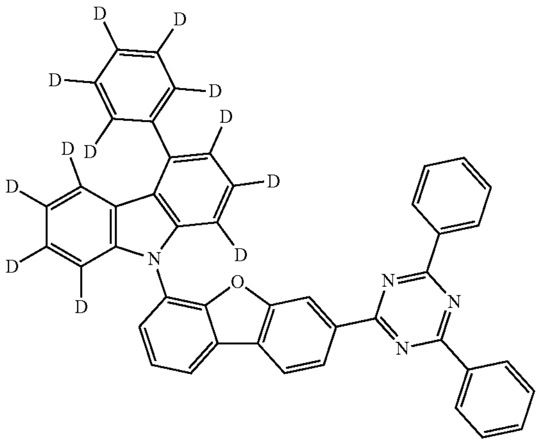
24
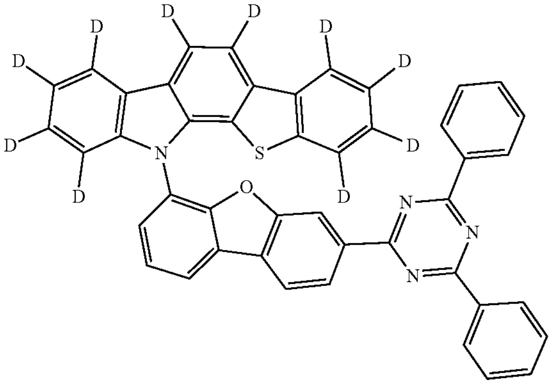
25
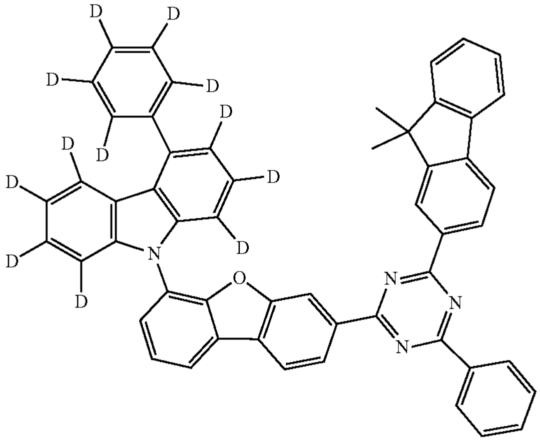
26
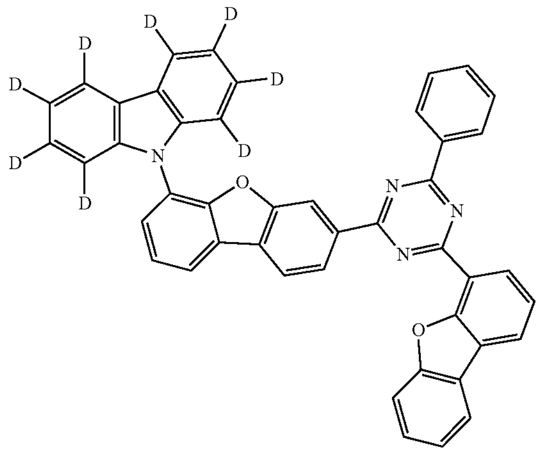
27
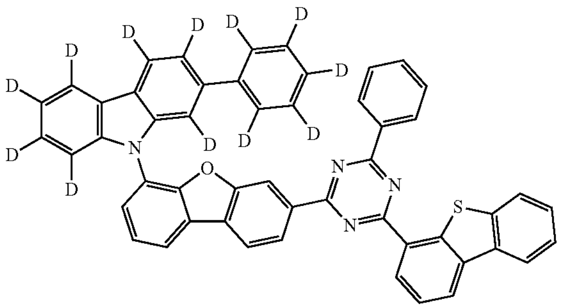

-continued
28
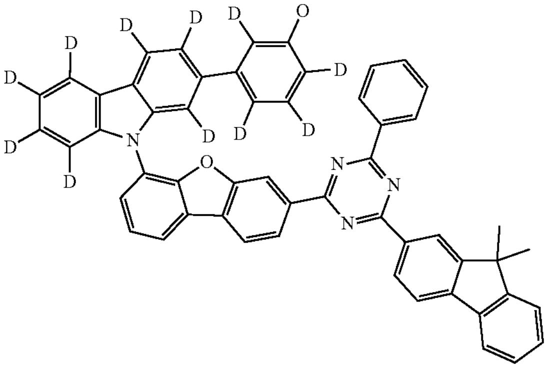
29
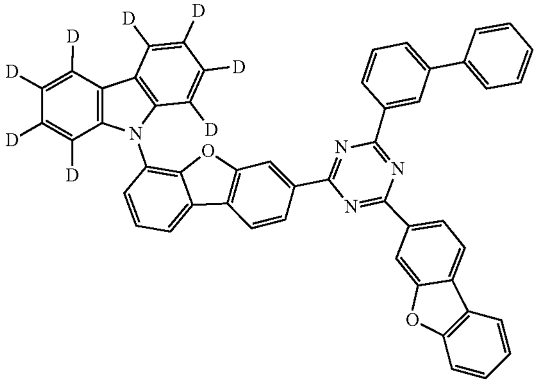
30
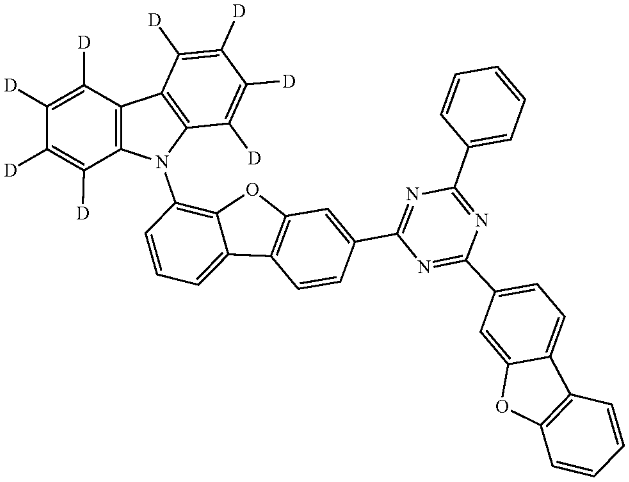
31
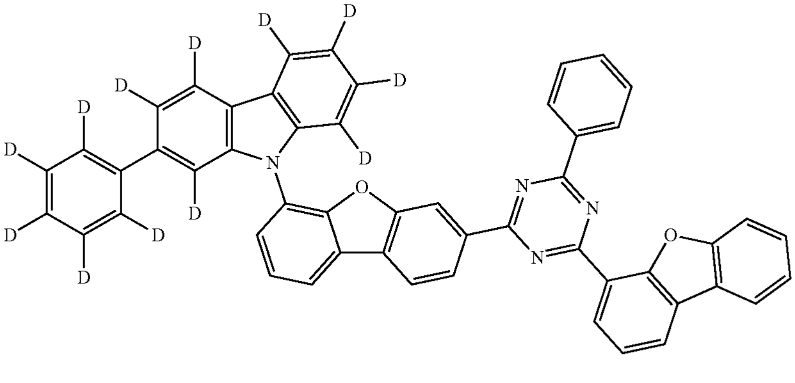

-continued
32
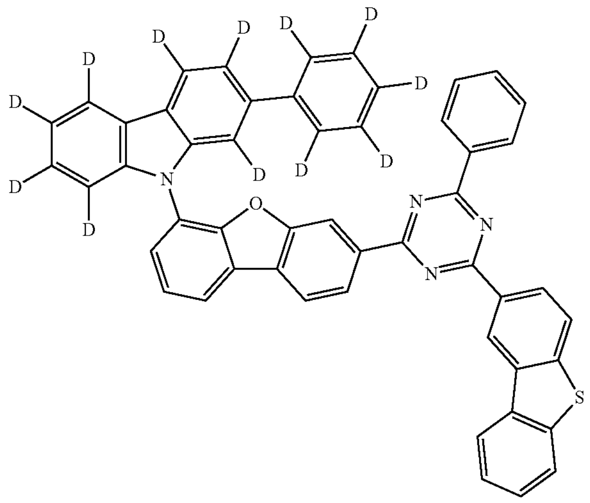
33
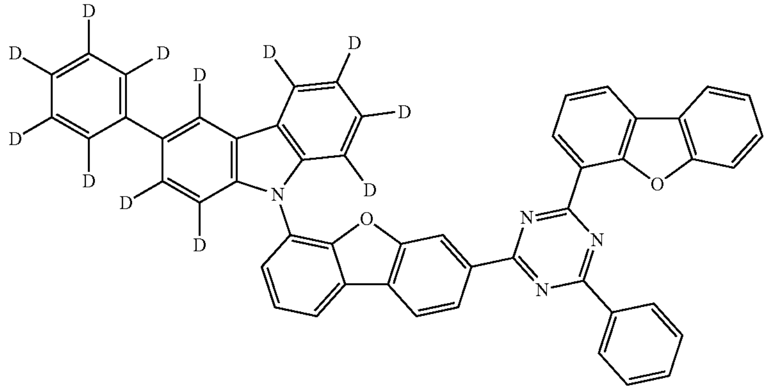
34
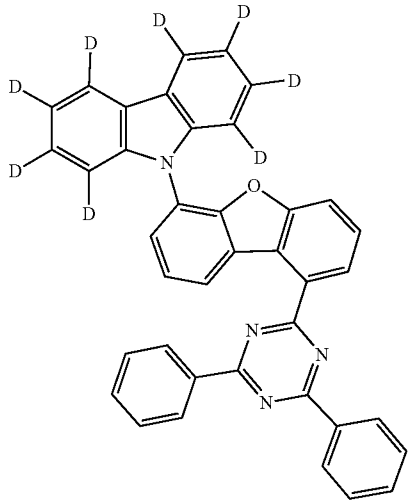
35
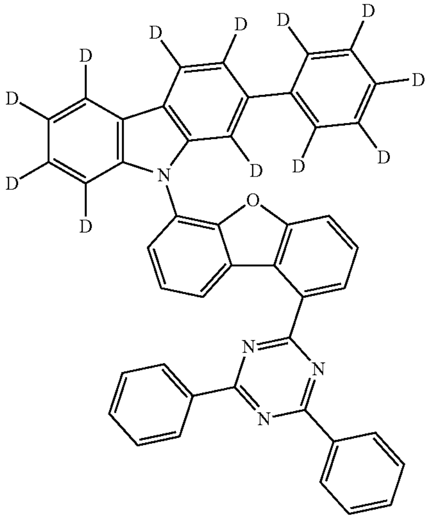

-continued
36
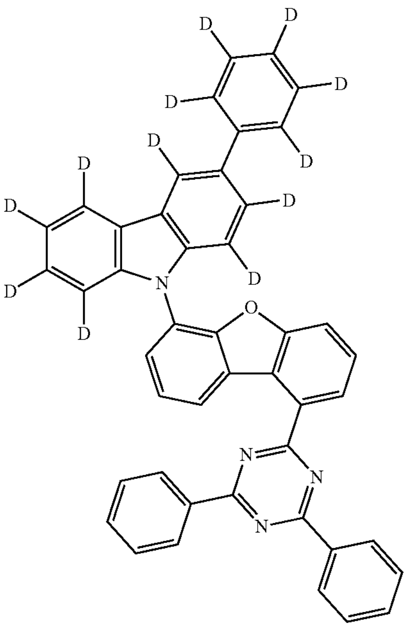
37
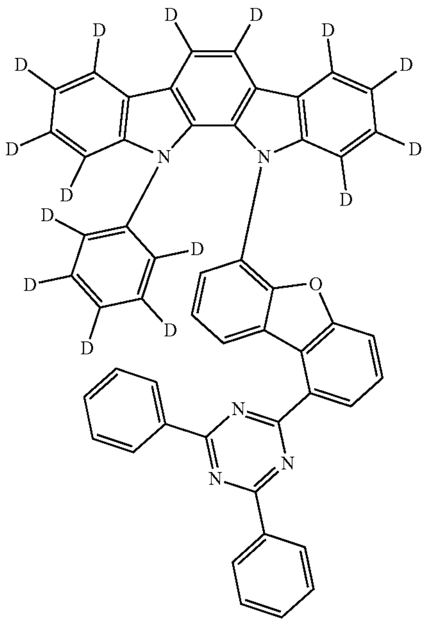
38
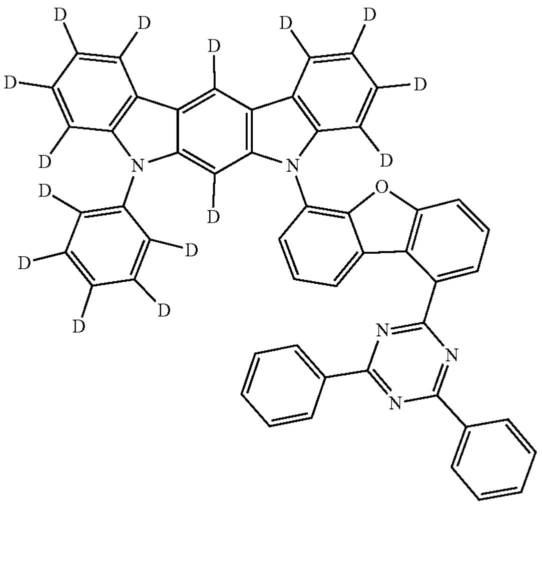
39
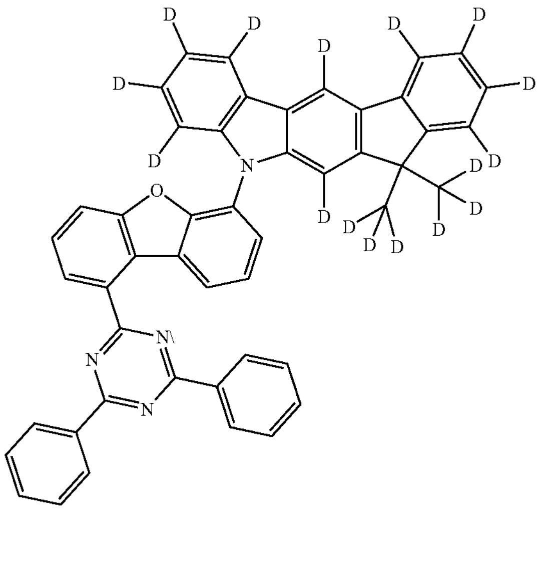

-continued
40
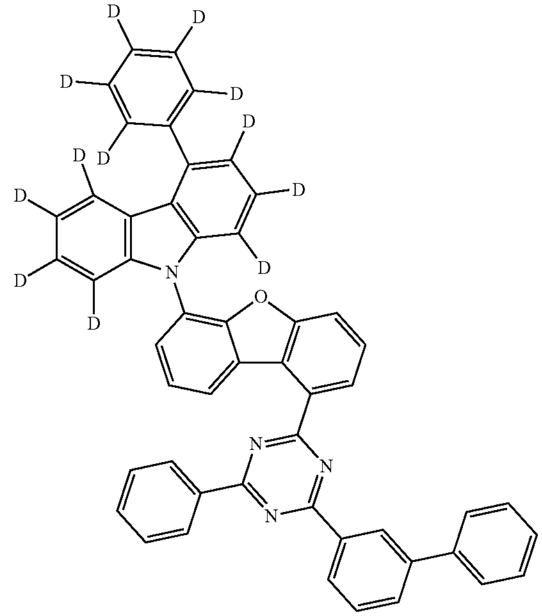
41
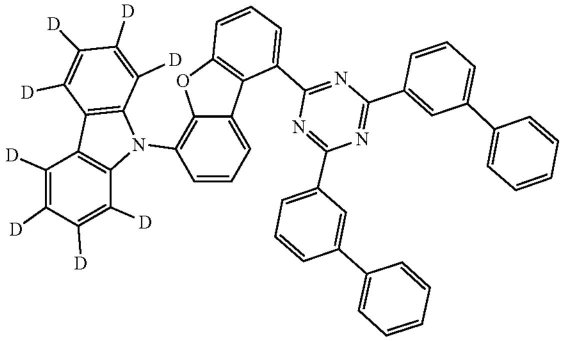
42
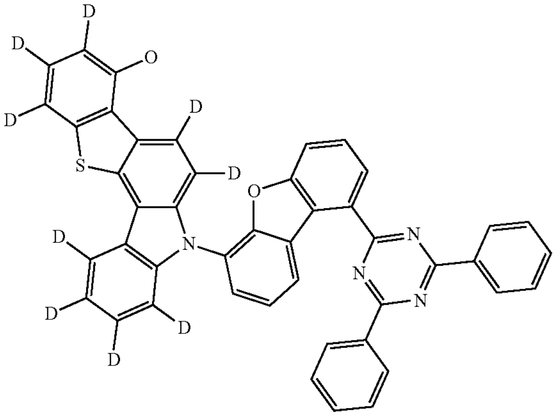
43
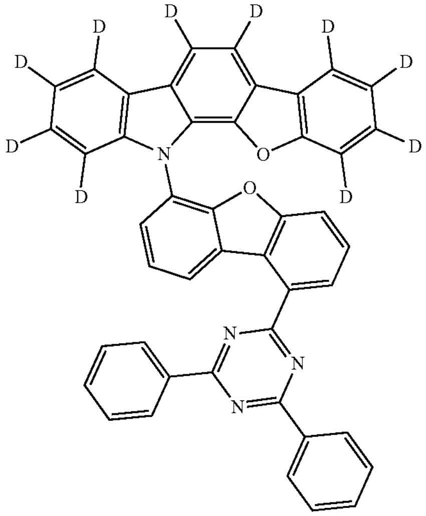
44
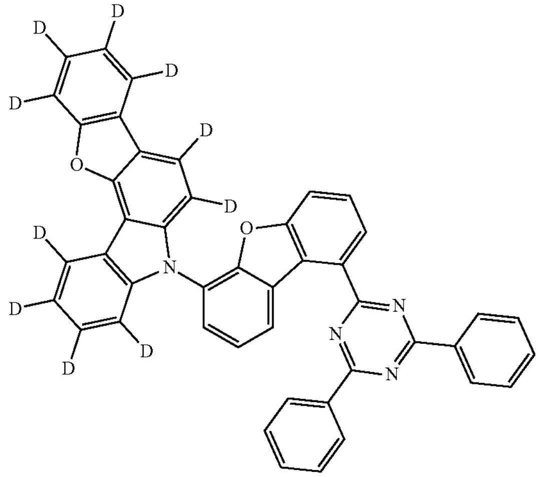
45
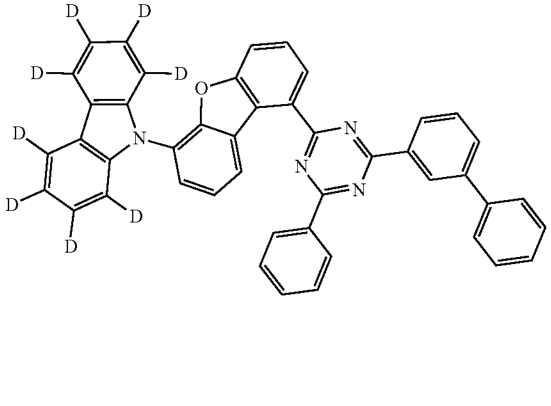

-continued
46
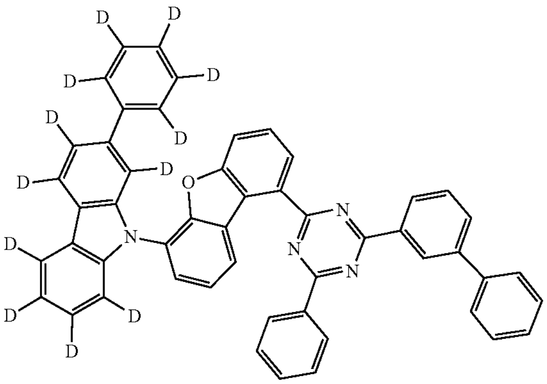
47
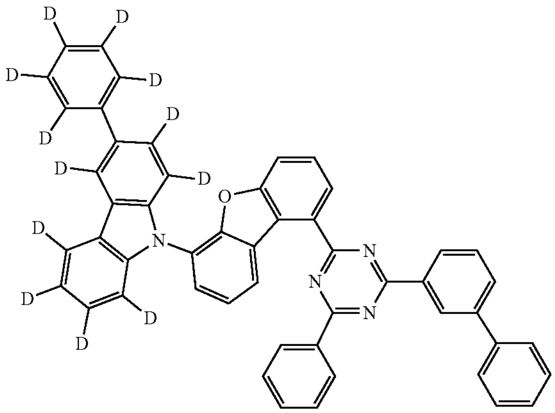
48
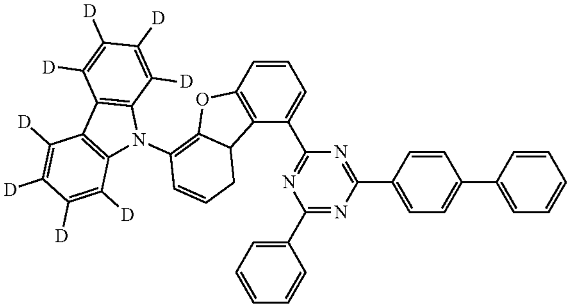
49
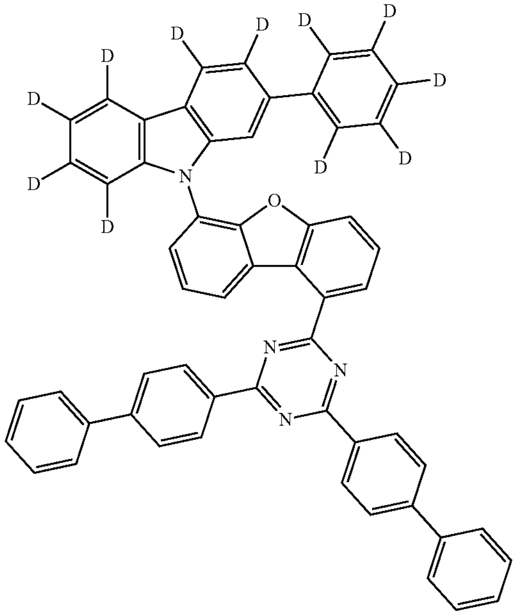
50
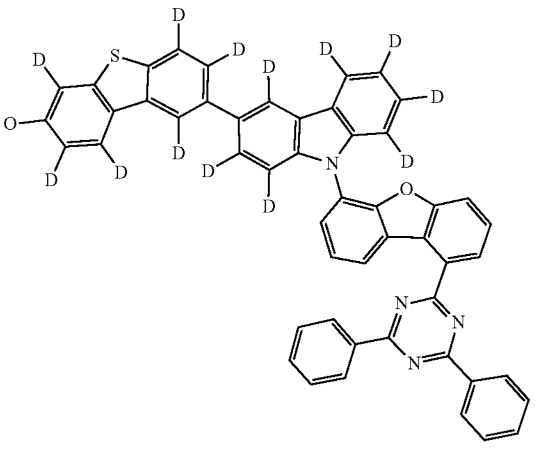
51
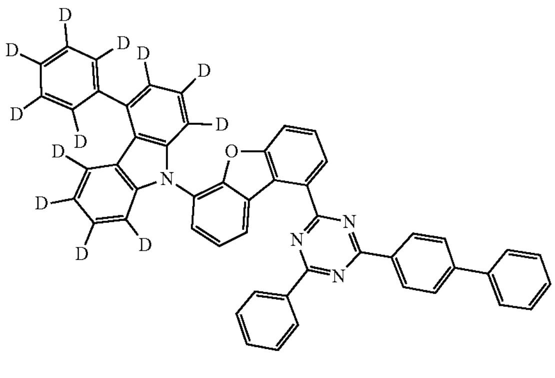

-continued
52
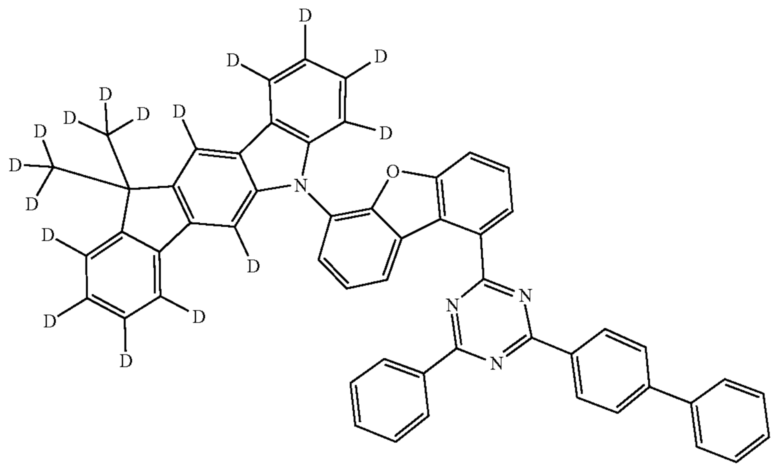
53
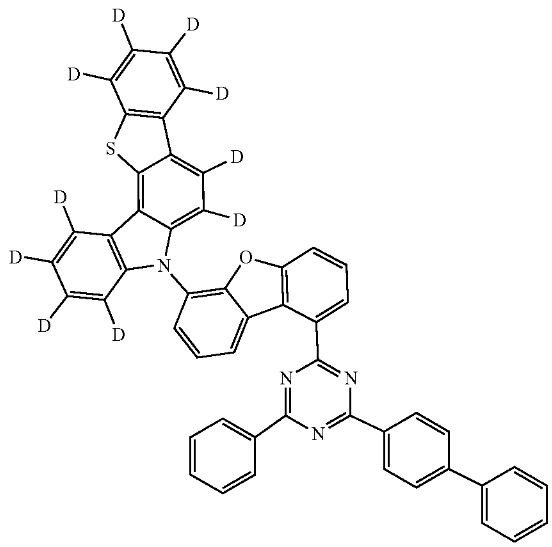
54
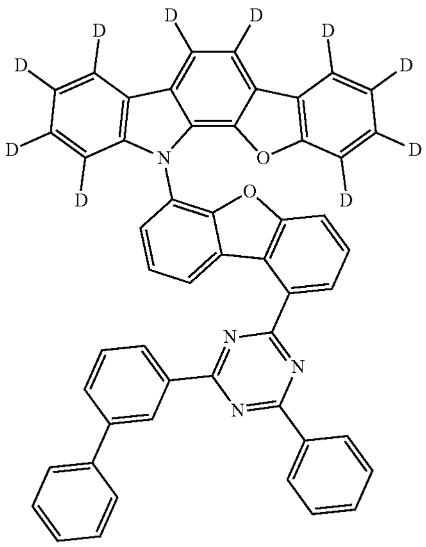
55
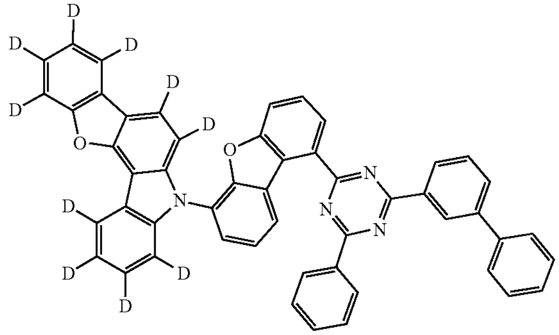
56
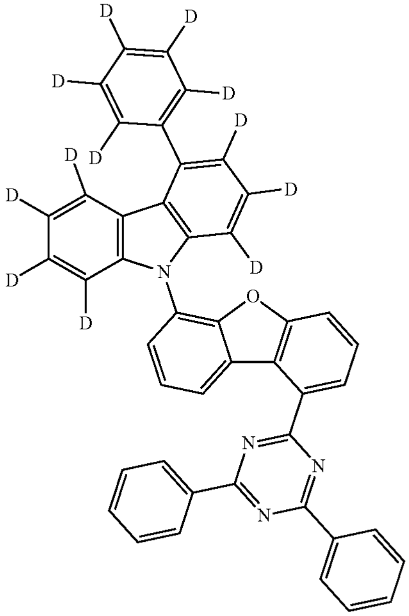

-continued
57
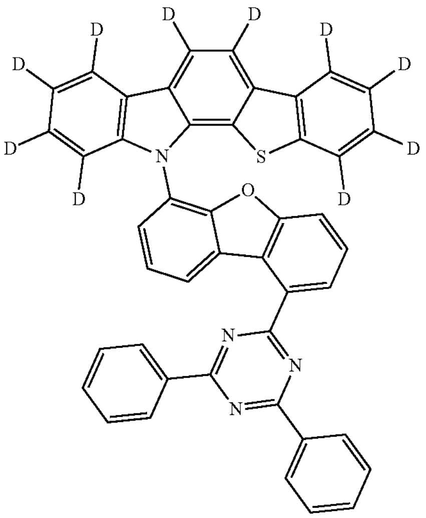
58
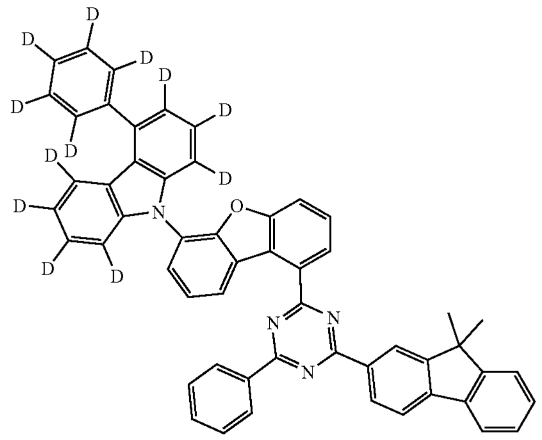
59
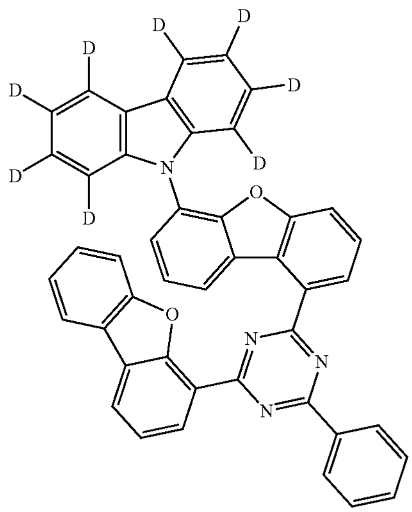
60
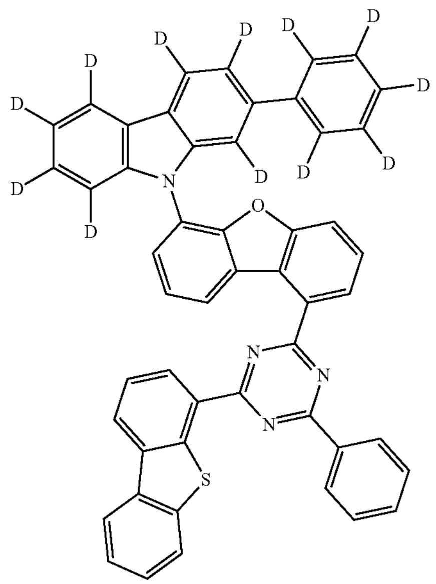
61
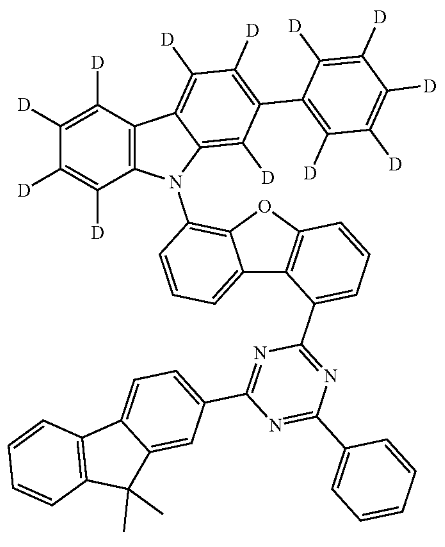
62
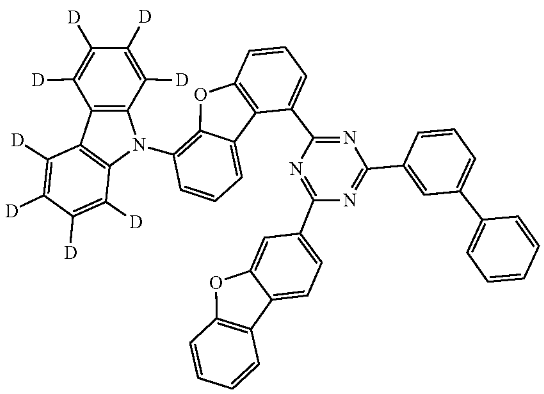

-continued
63
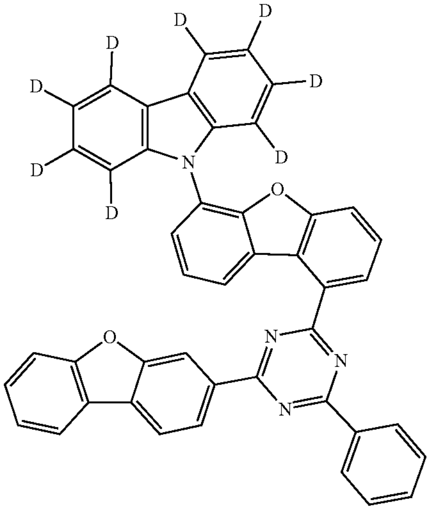
64
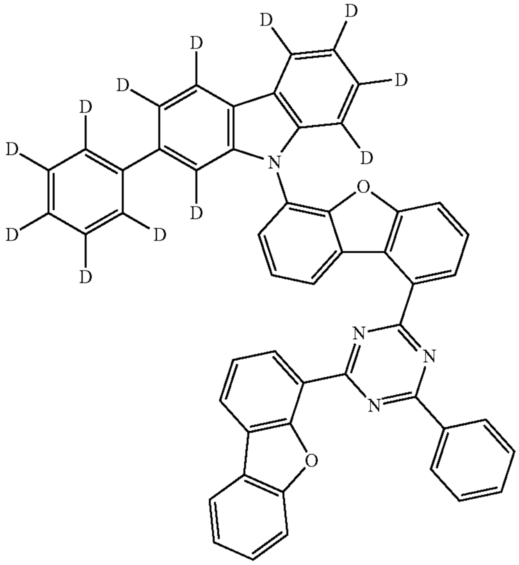
65
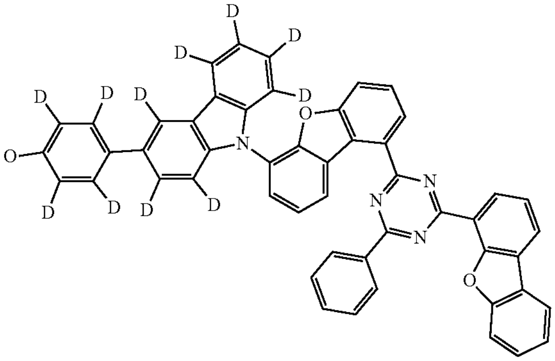
66
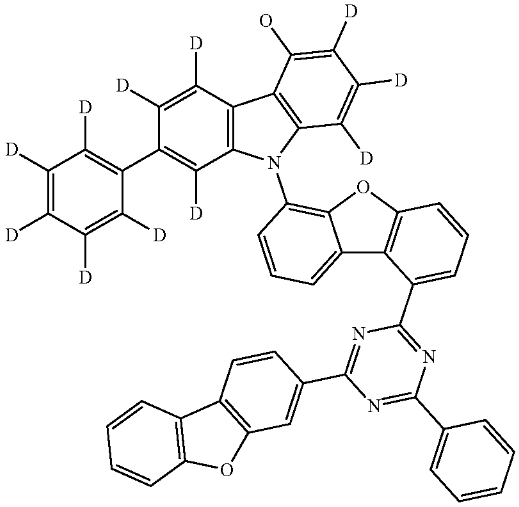
67
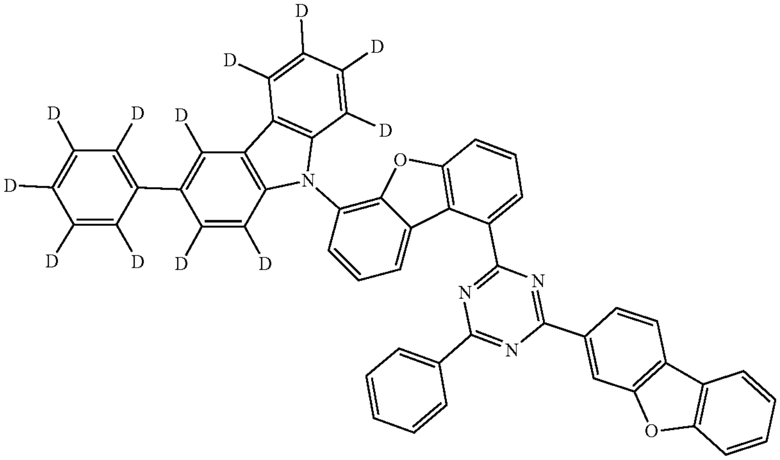

-continued
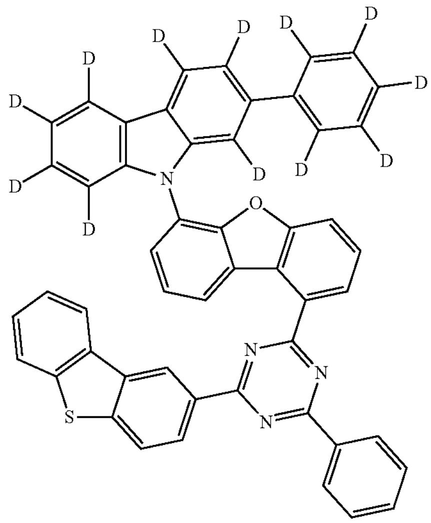
68
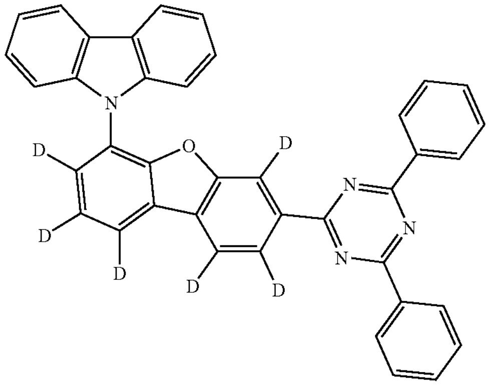
69
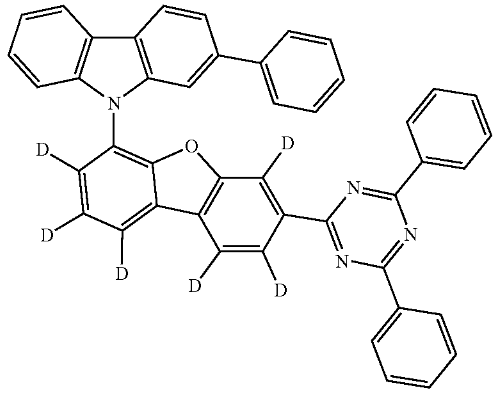
70
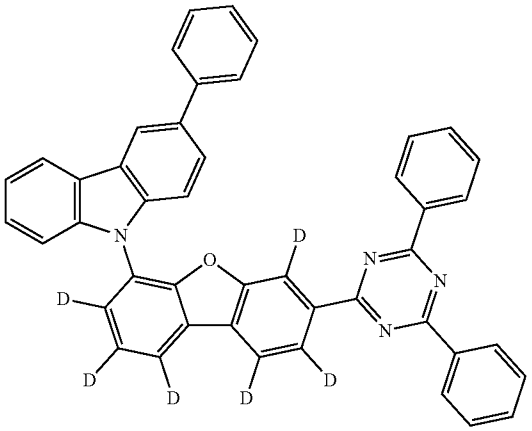
71
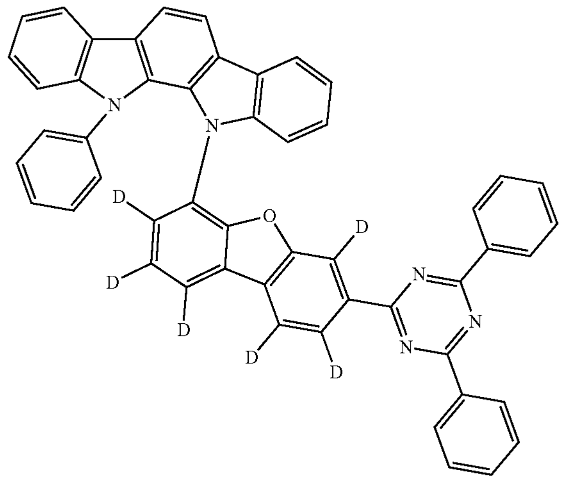
72
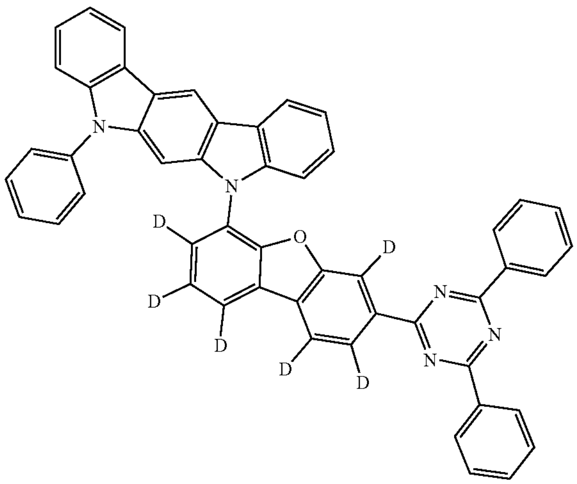
73

-continued
74
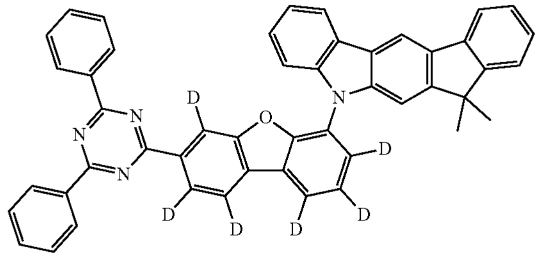
75
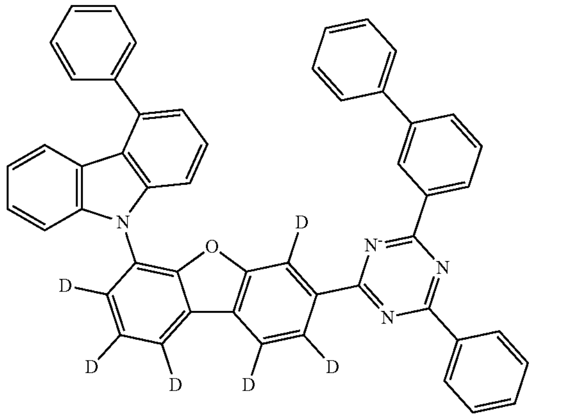
76
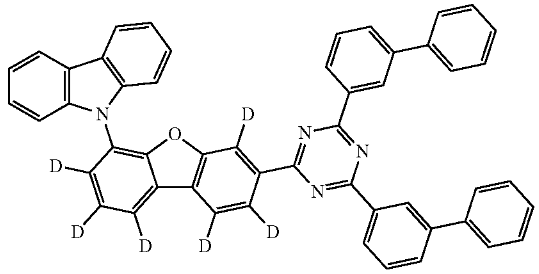
77
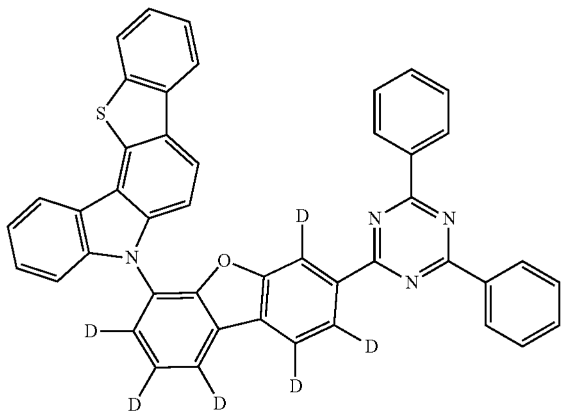
78
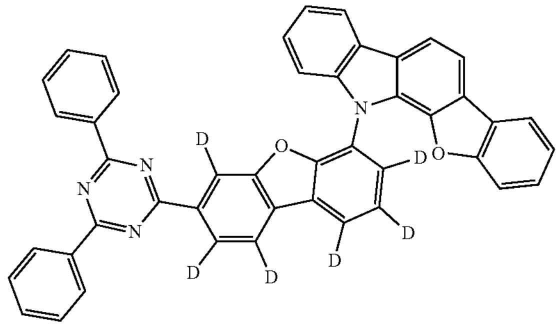
79
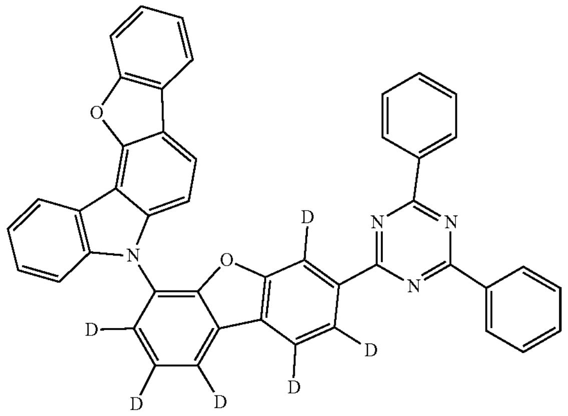
80
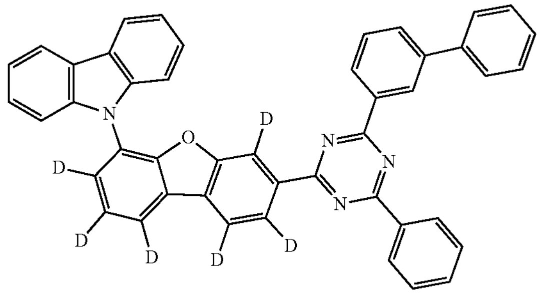
81
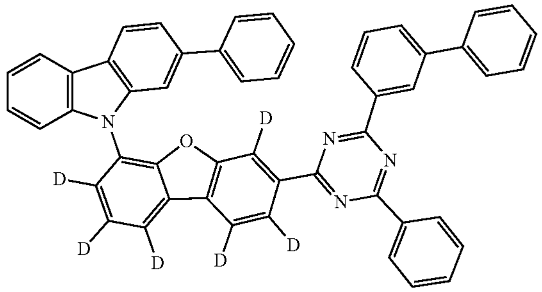

-continued
82
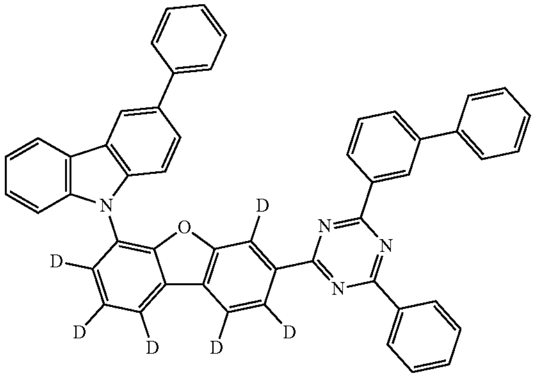
83
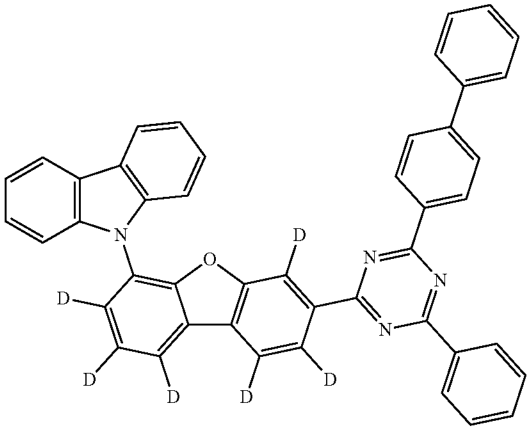
84
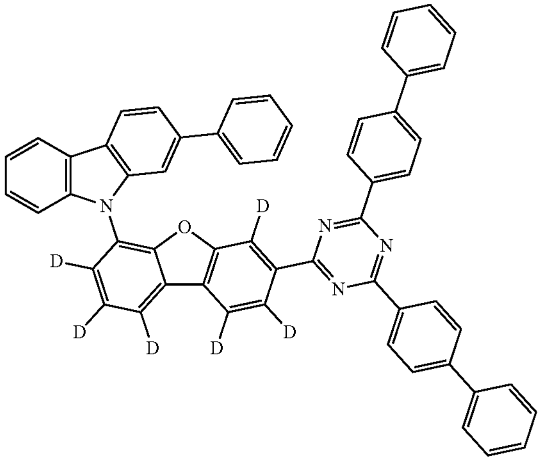
85
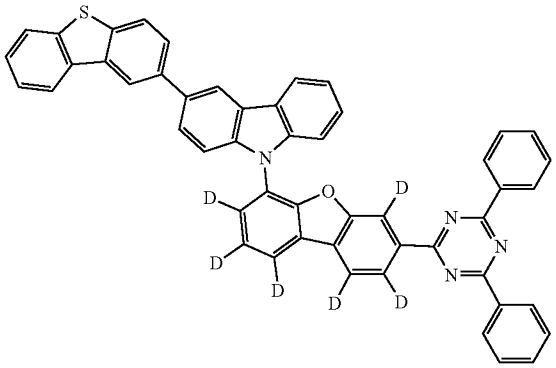
86
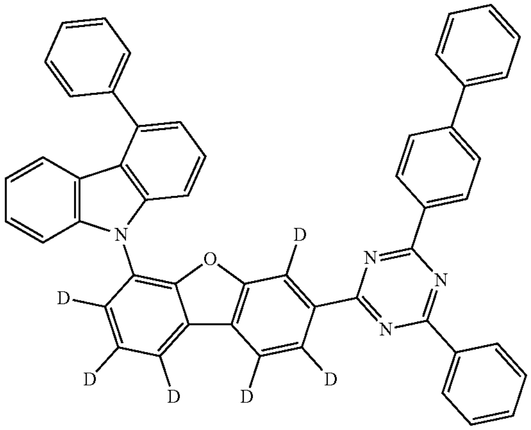
87
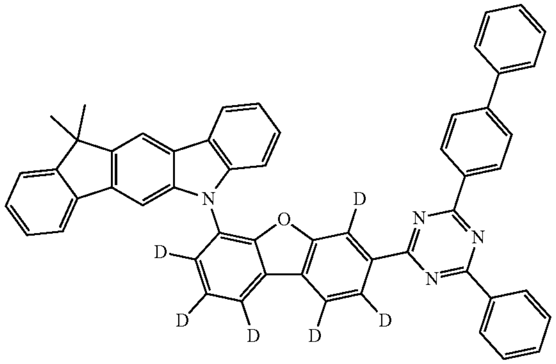

-continued
88
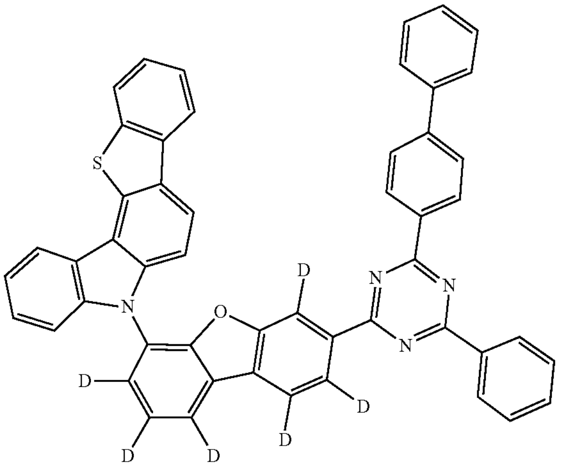
89
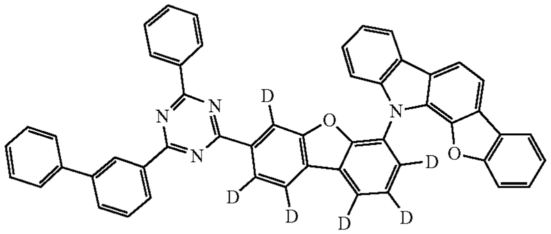
90
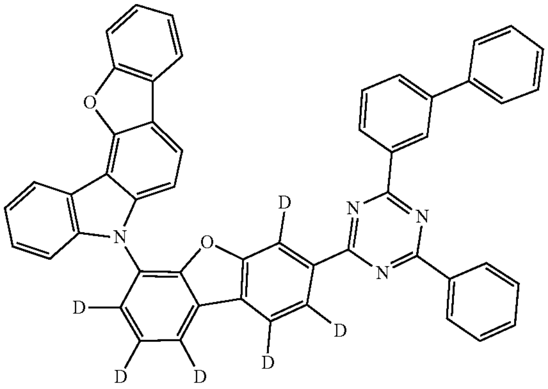
91
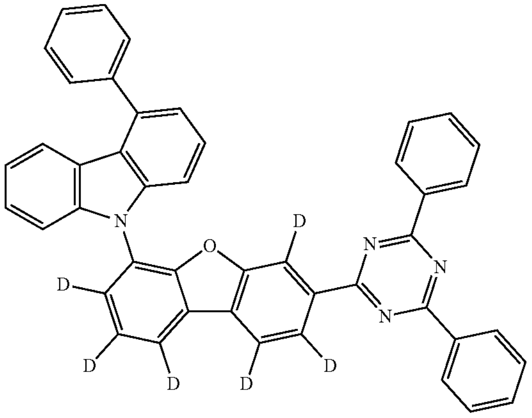
92
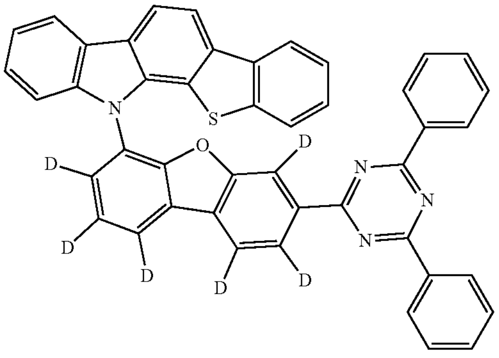
93
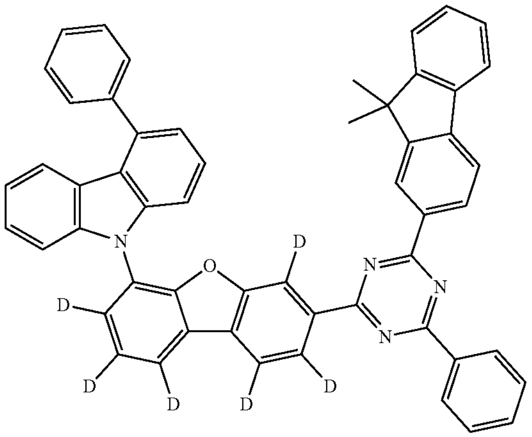

-continued
94
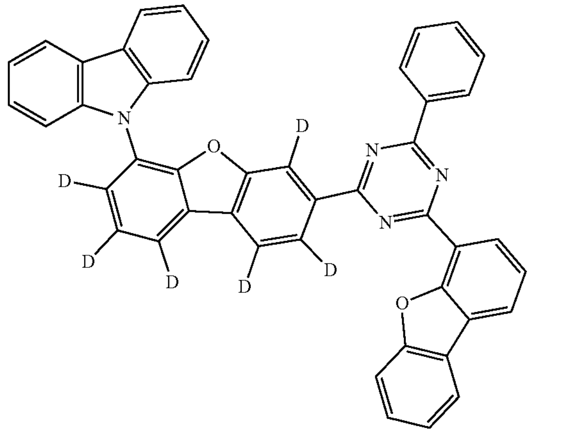
95
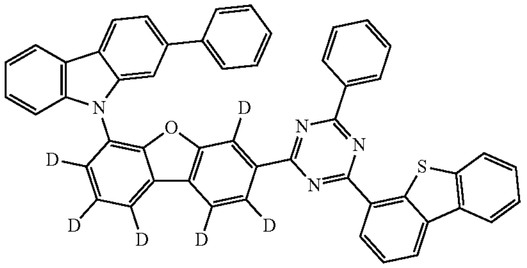
96
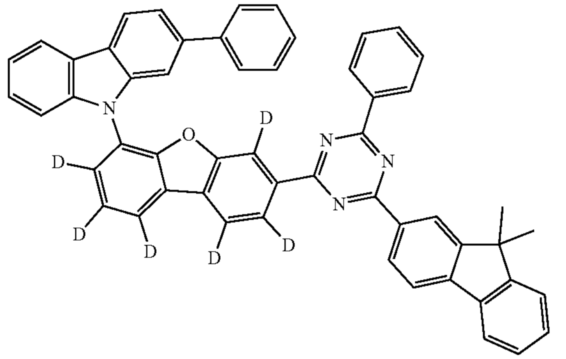
97
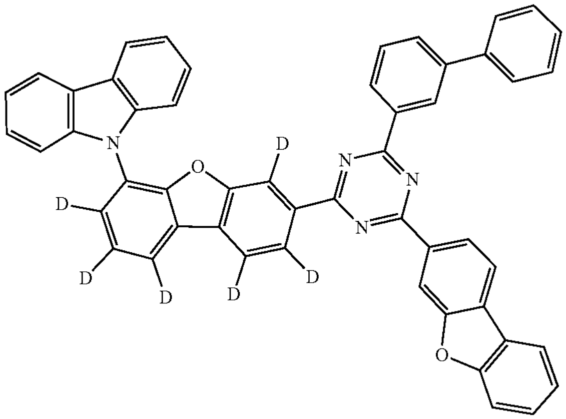
98
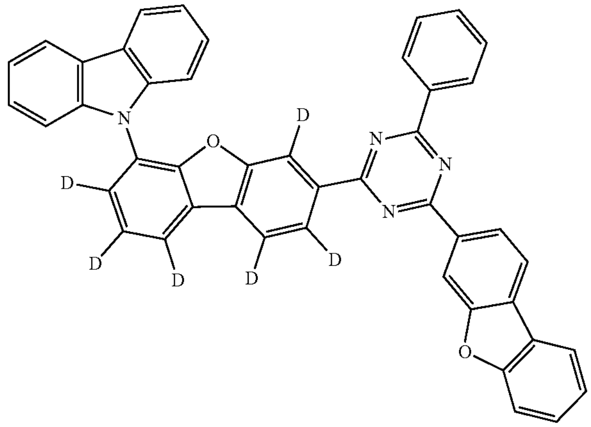
99
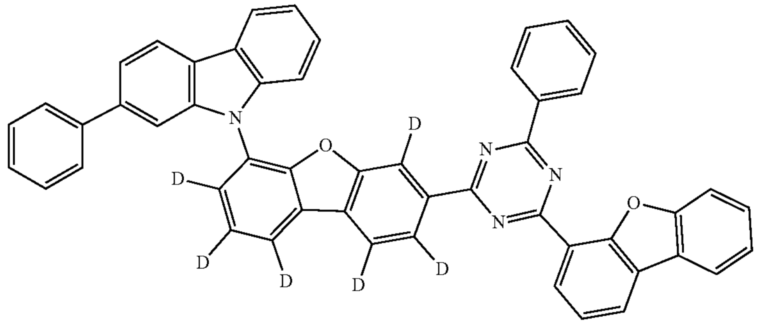

-continued
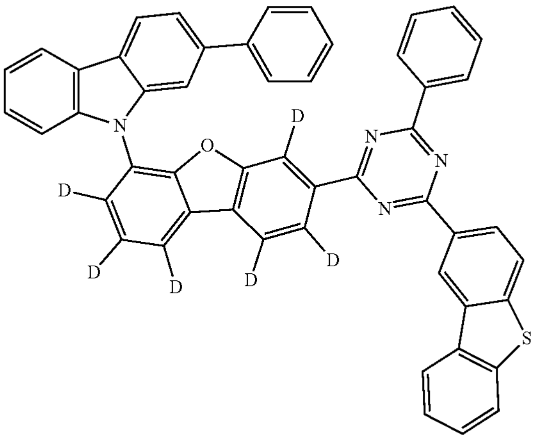
100
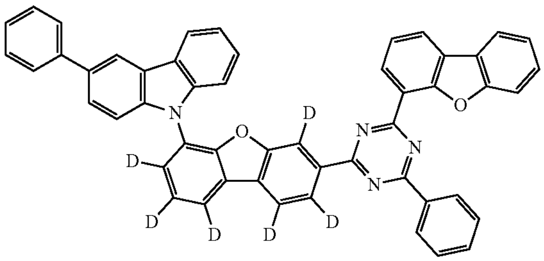
101
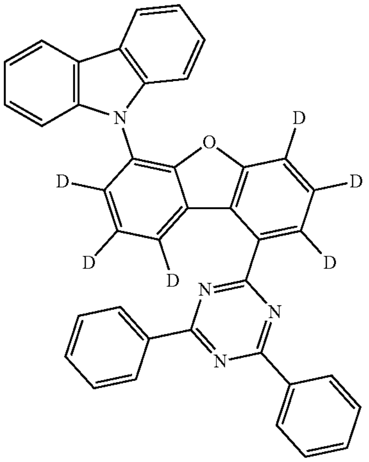
102
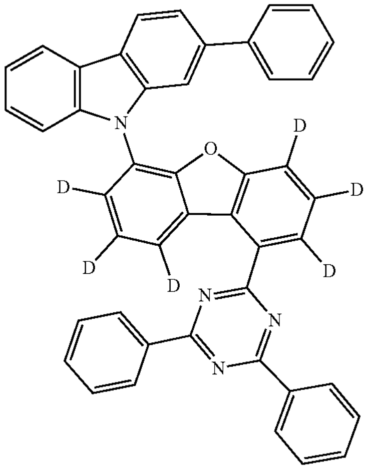
103
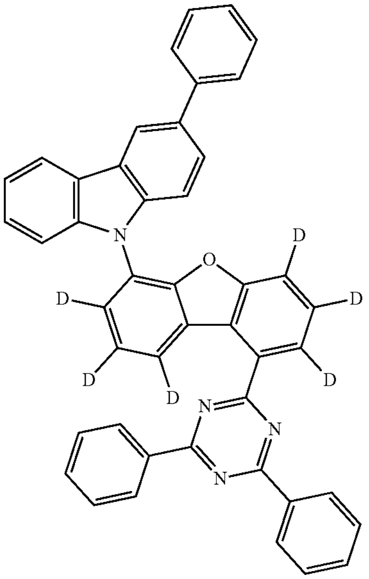
104
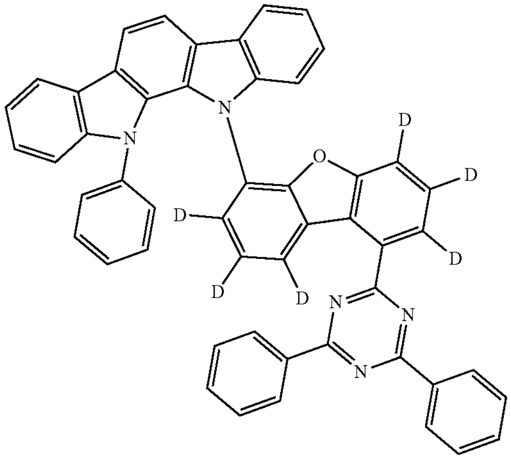
105

-continued
106
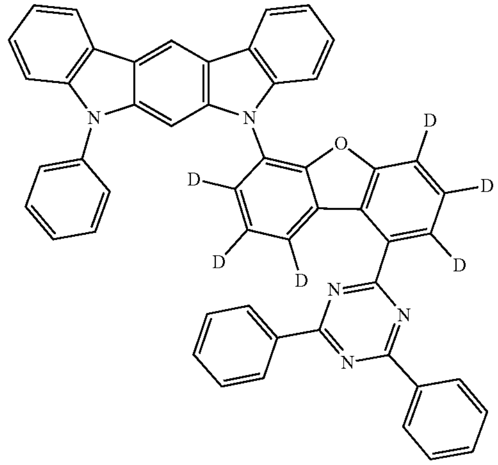
107
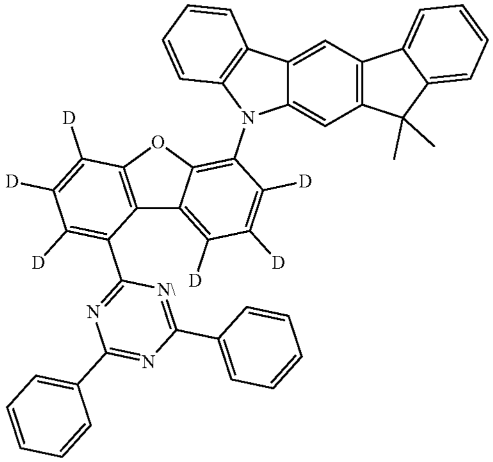
108
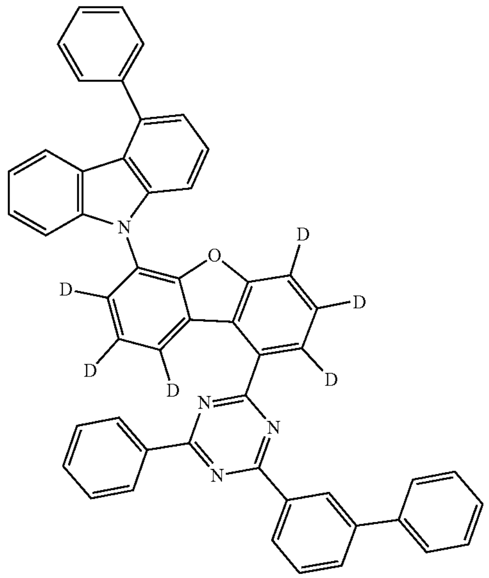
109
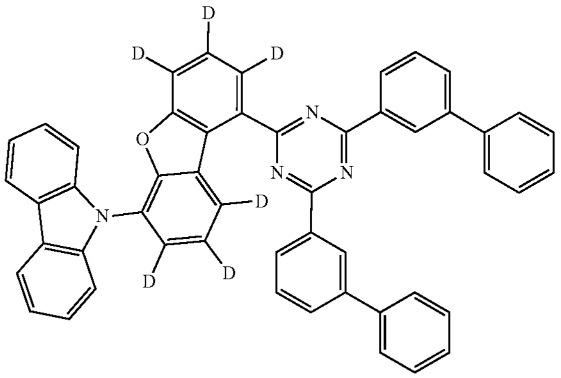
110
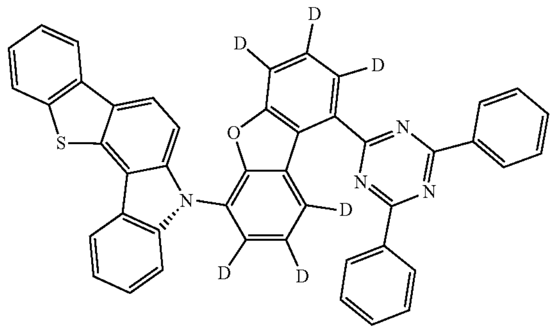
111
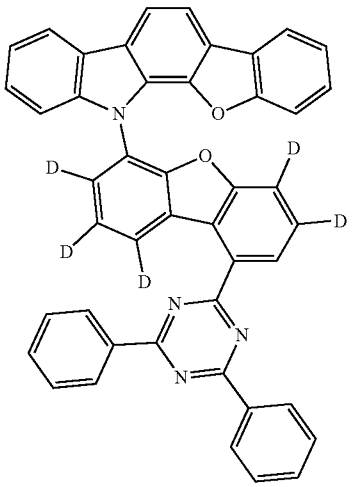

-continued
112
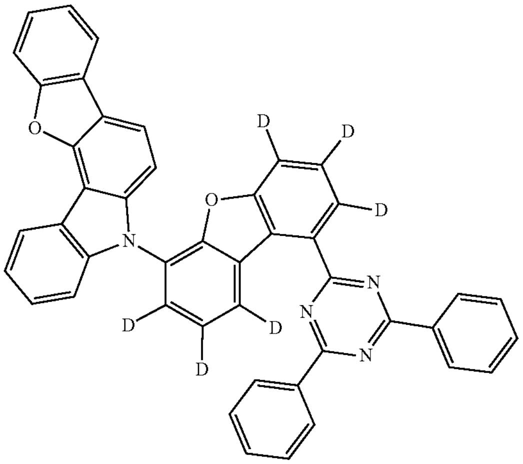
113
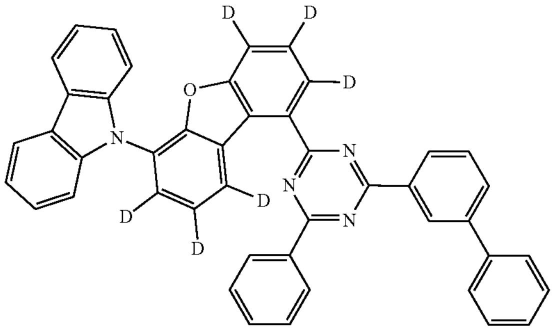
114
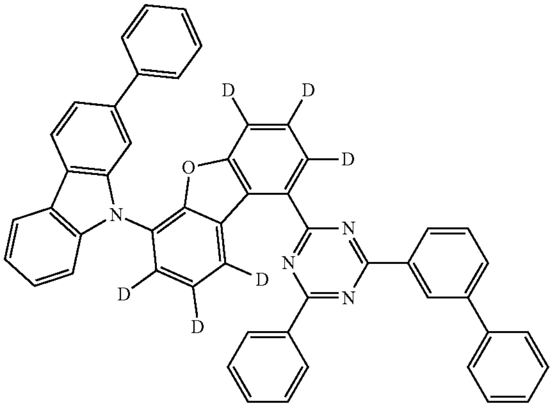
115
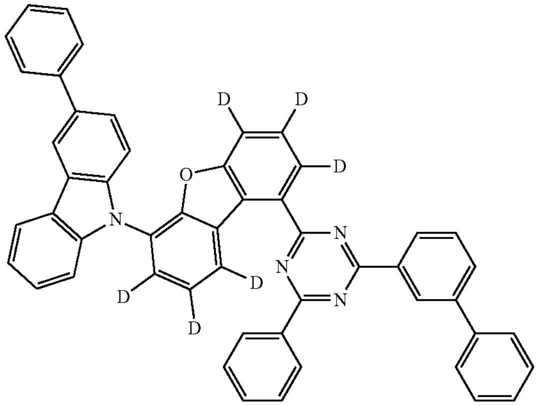
116
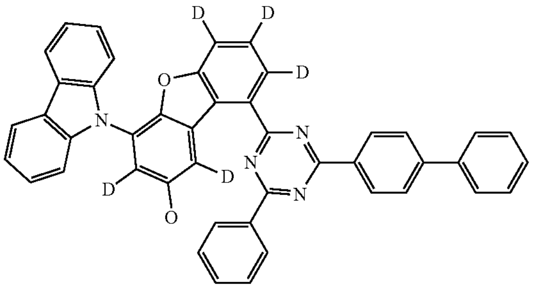
117
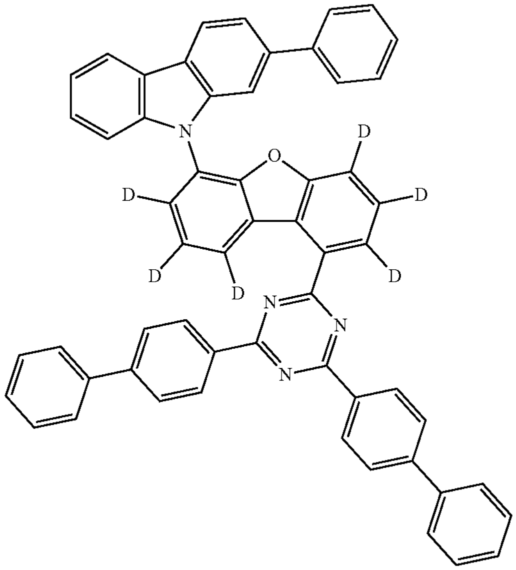

-continued
118
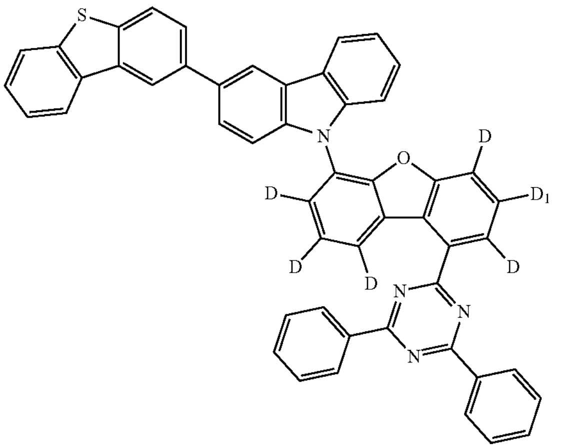
119
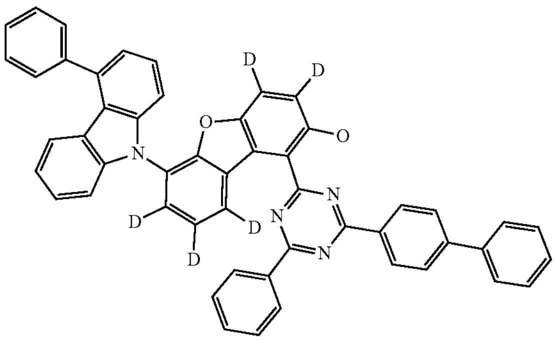
120
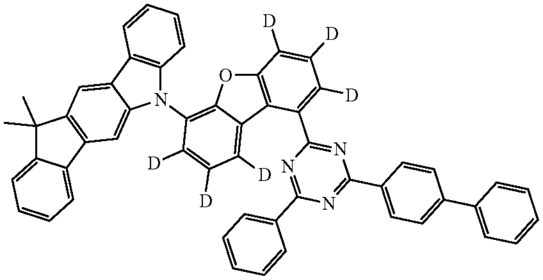
121
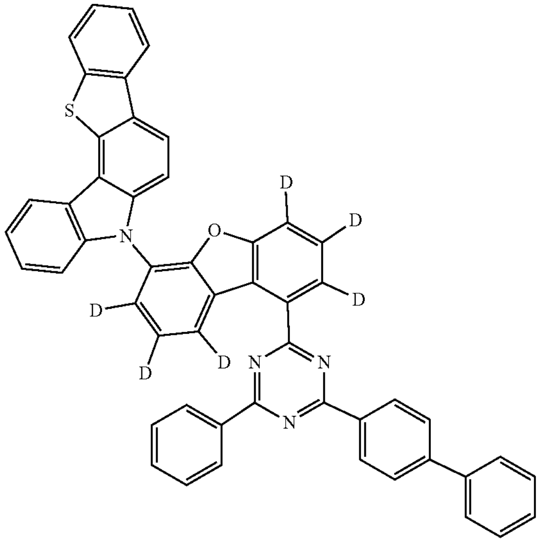
122
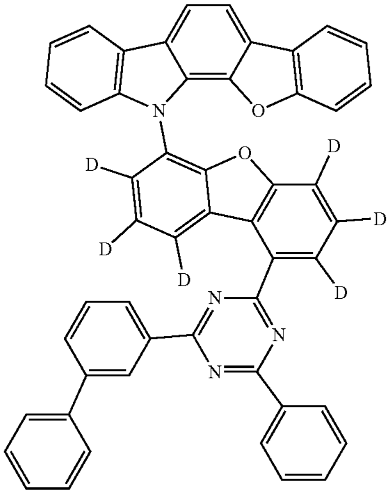
123
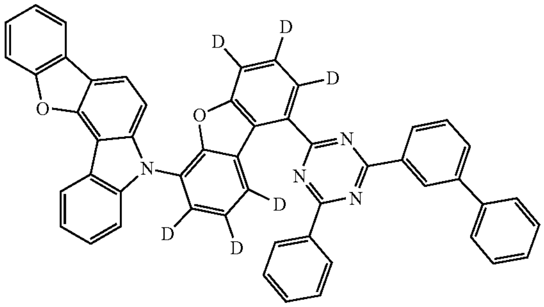

-continued
124
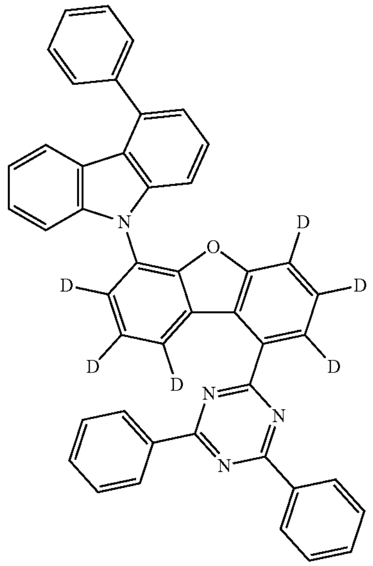
125
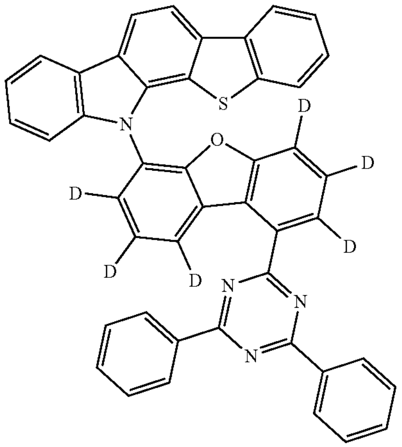
126
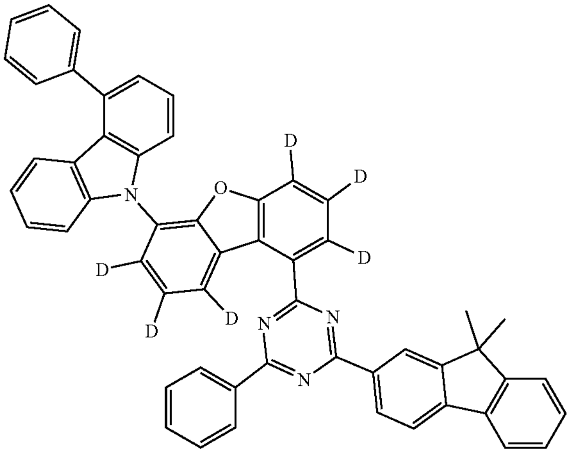
127
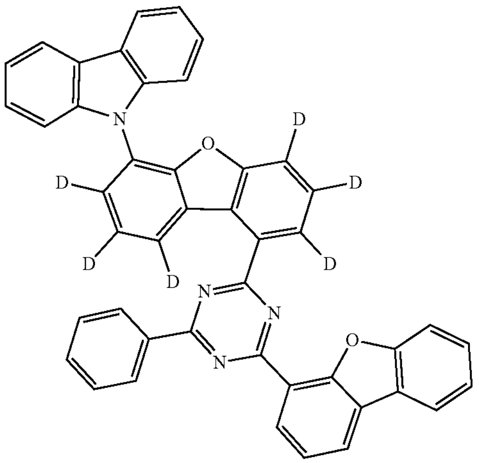
128
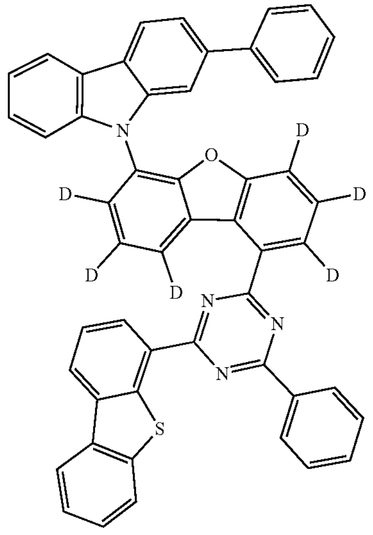
129
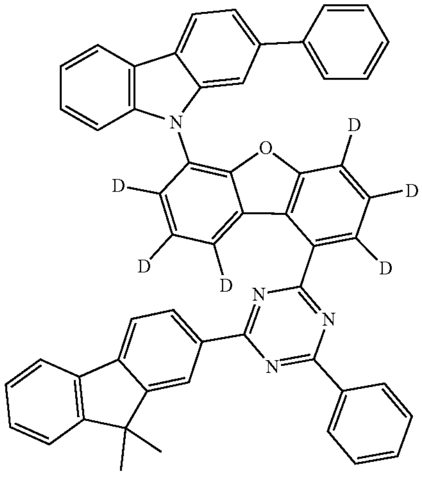

-continued
130
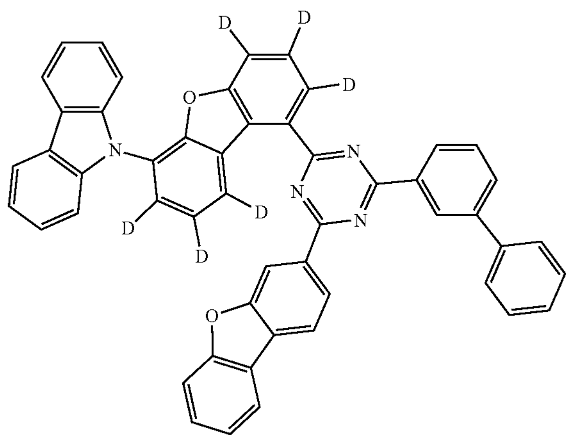
131
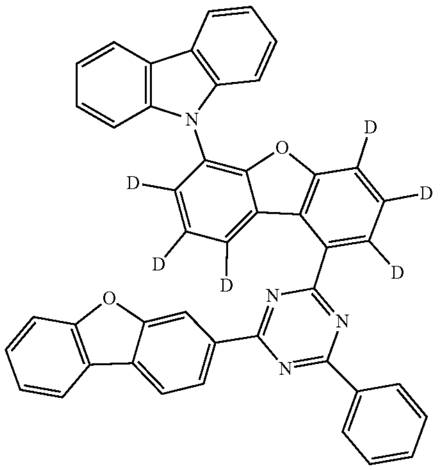
132
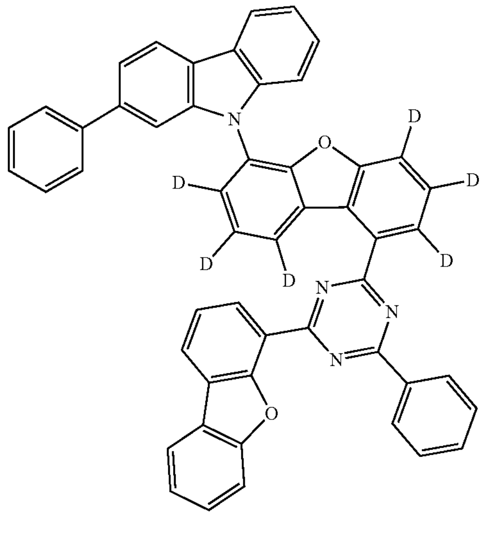
133
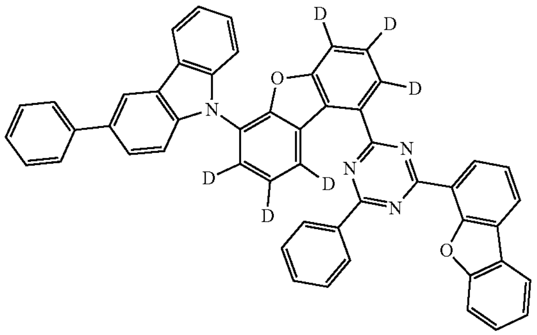
134
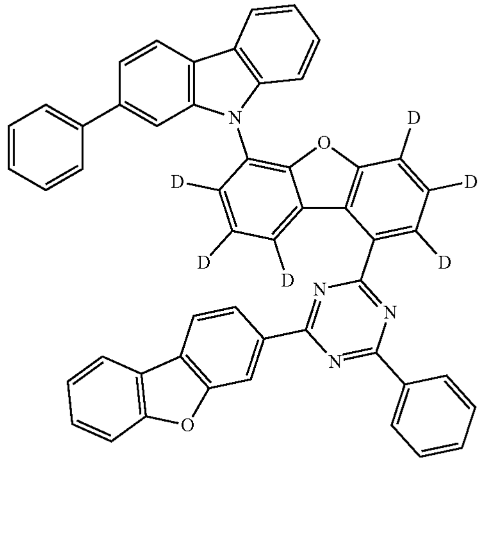
135
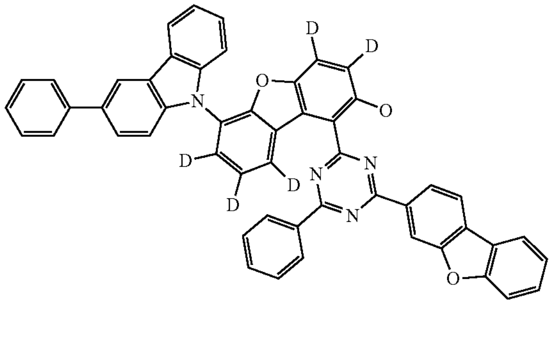

-continued
136
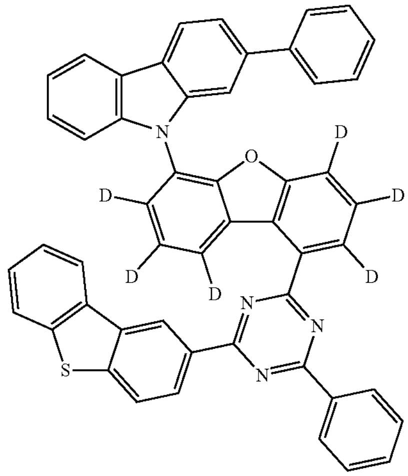
137
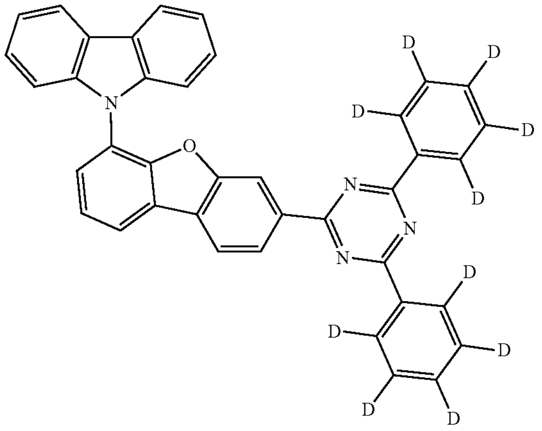
138
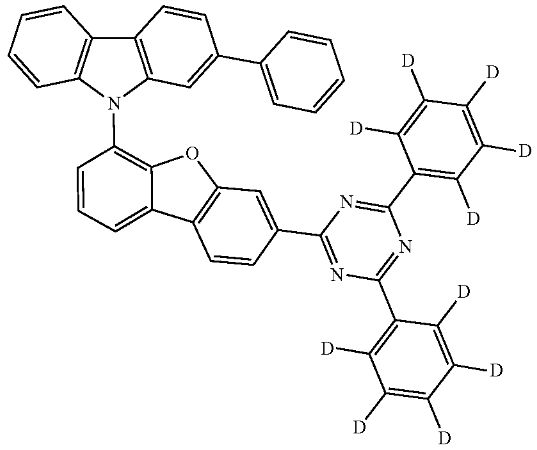
139
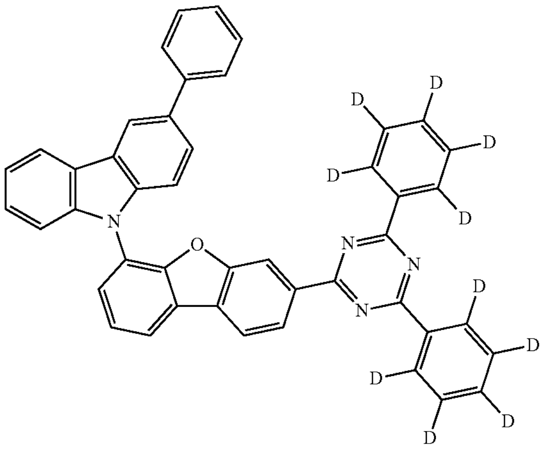
140
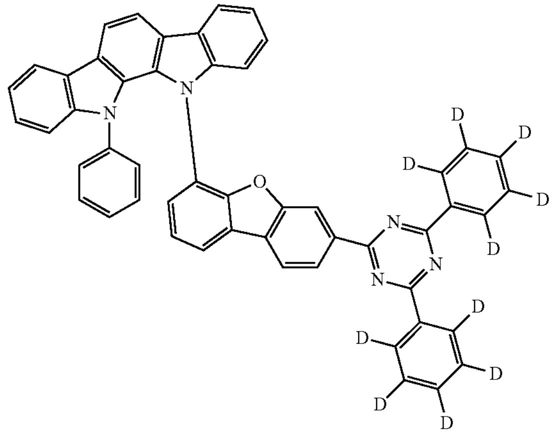
141
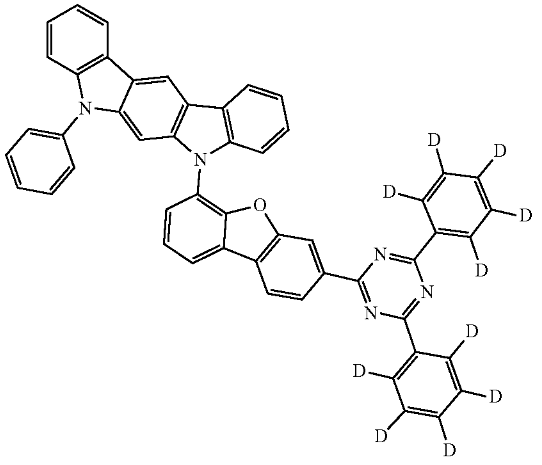

-continued
142
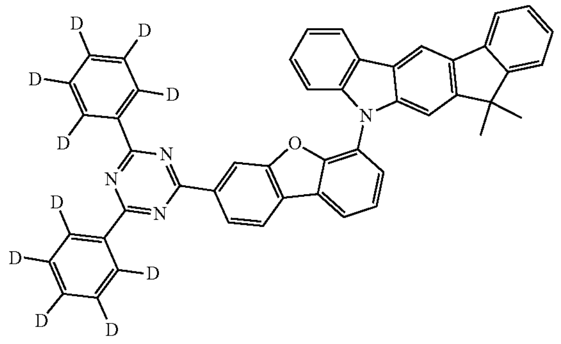
143
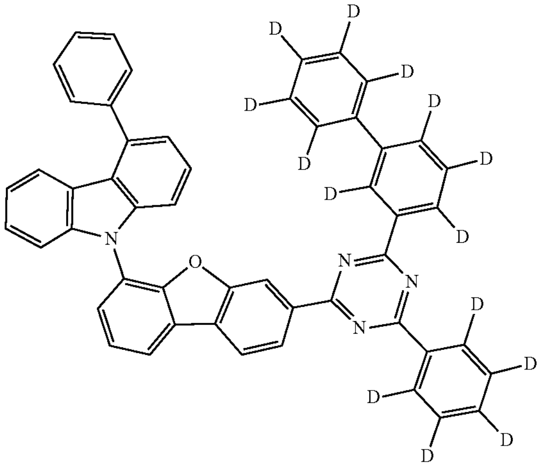
144
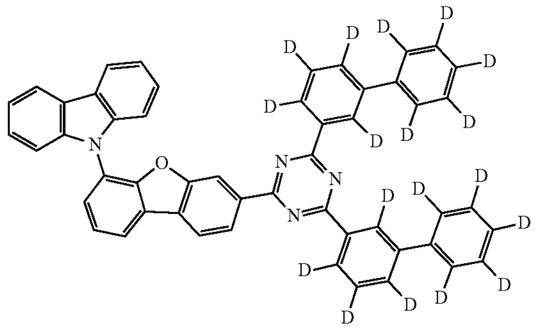
145
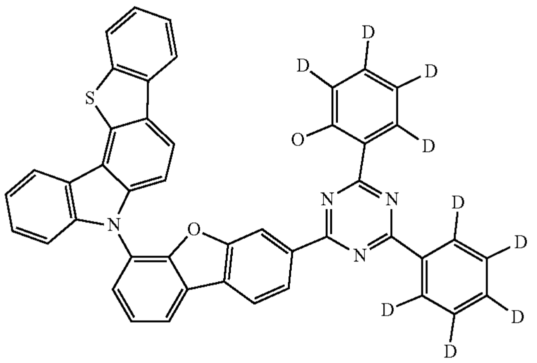
146
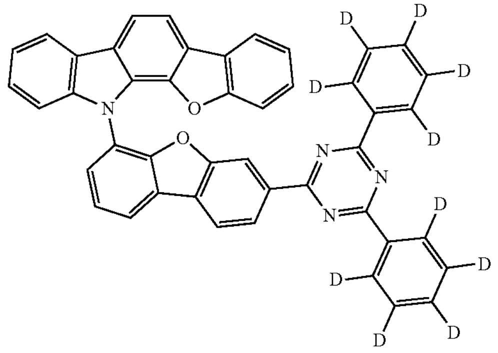
147
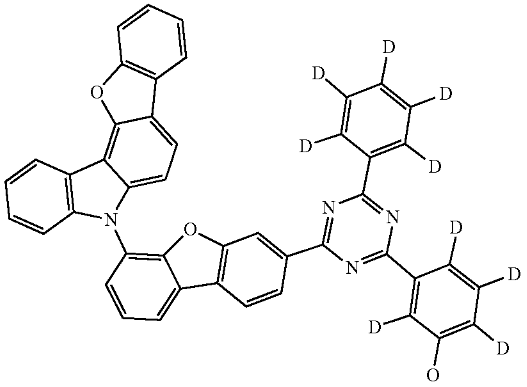
148
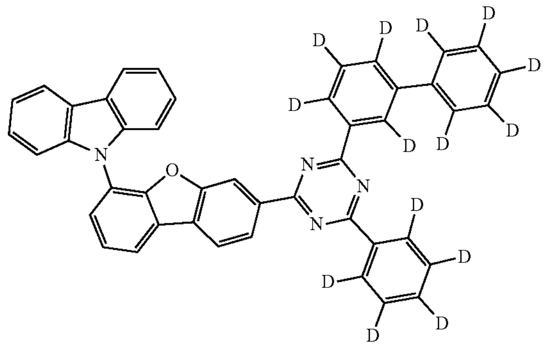
149
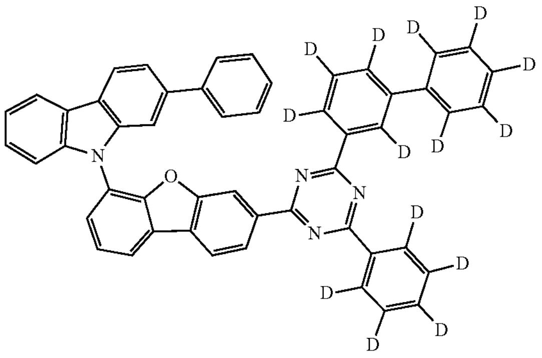

-continued
150
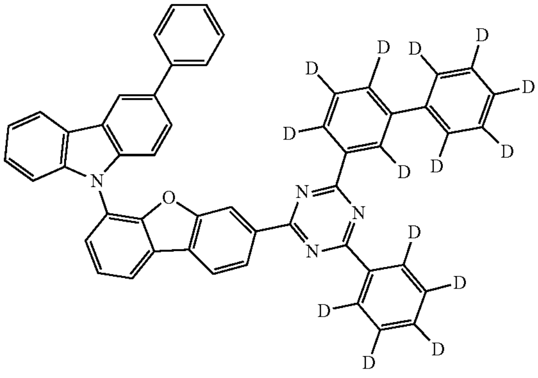
151
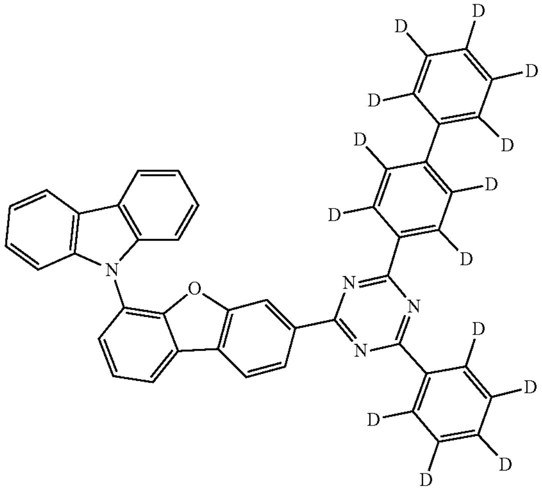
152
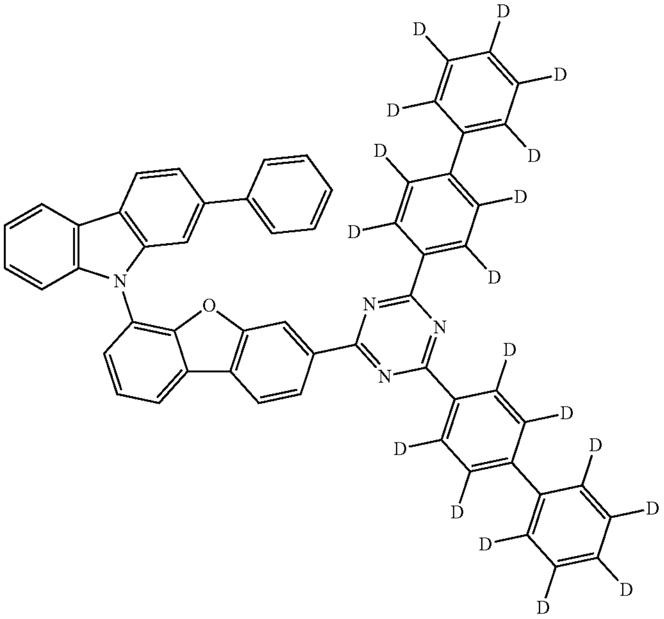
153
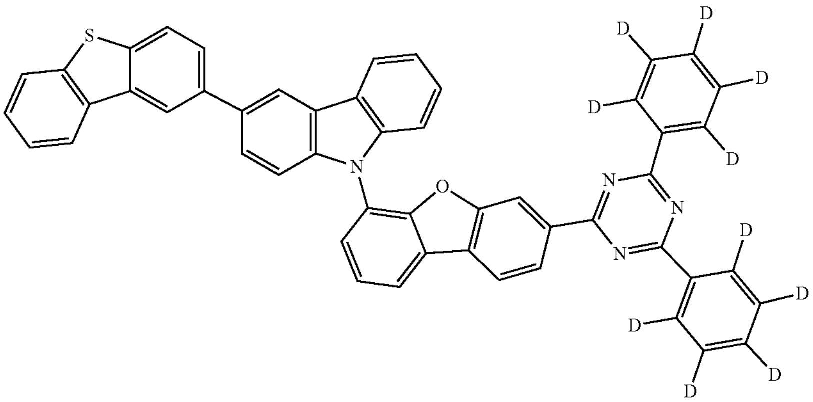

-continued
154
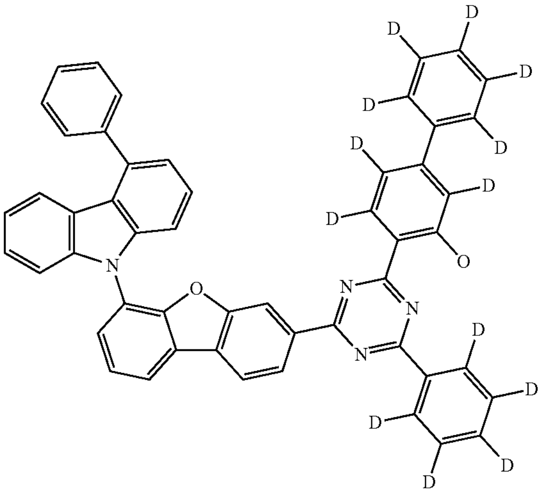
155
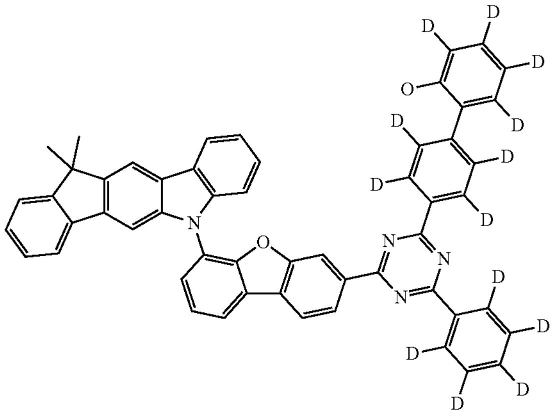
156
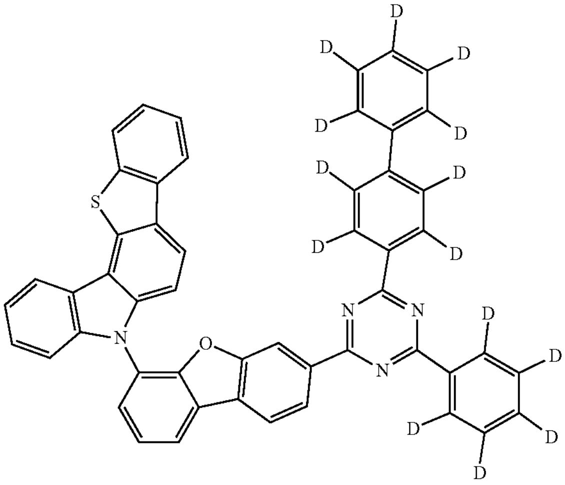
157
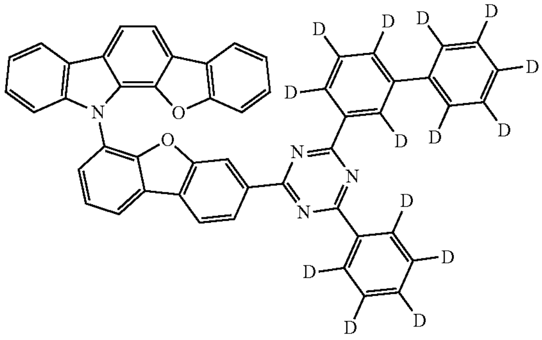
158
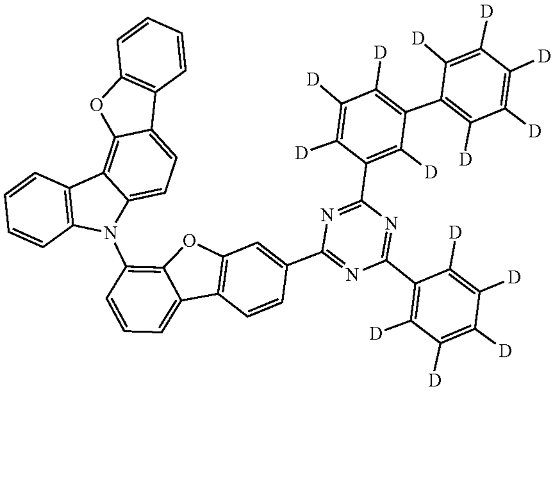
159
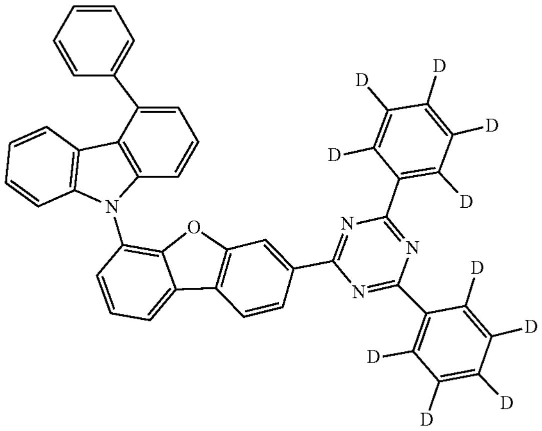

-continued
160
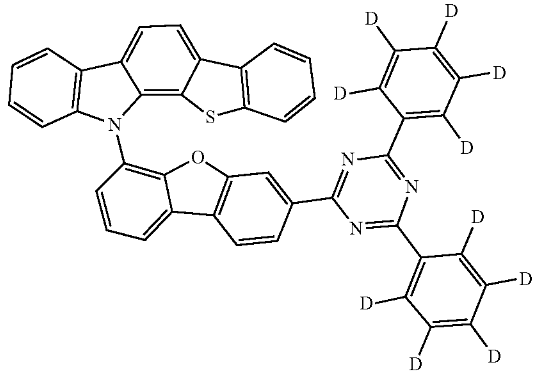
161
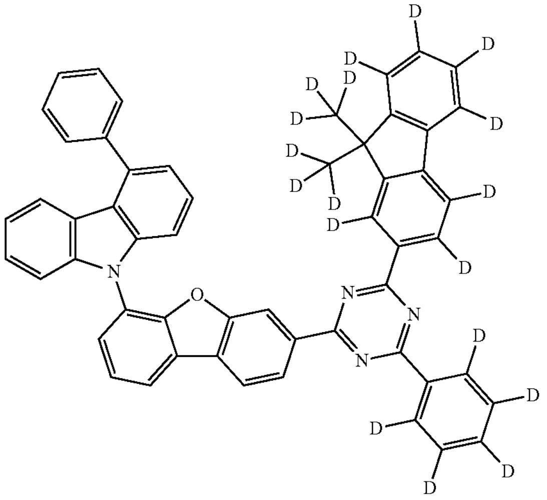
162
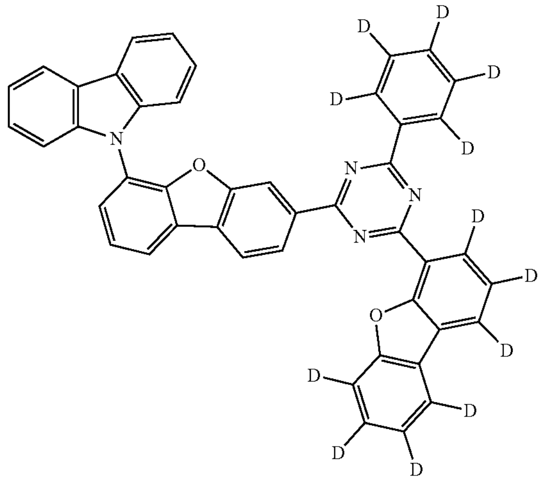
163
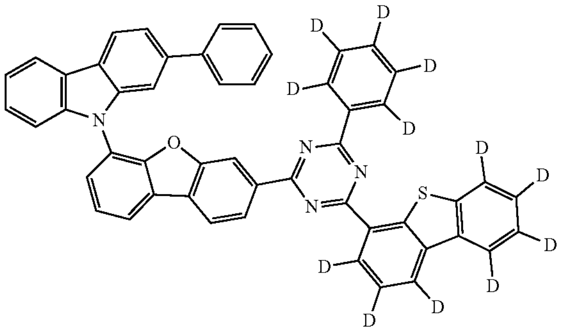
164
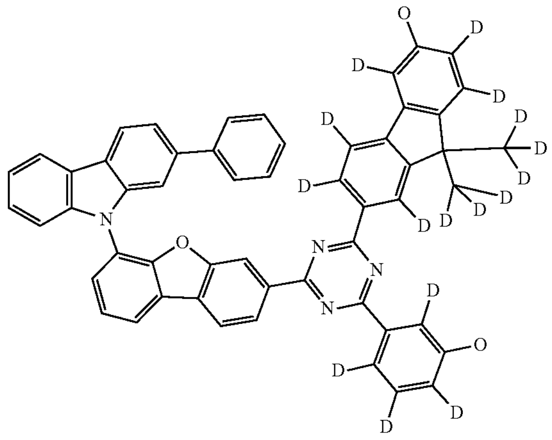
165
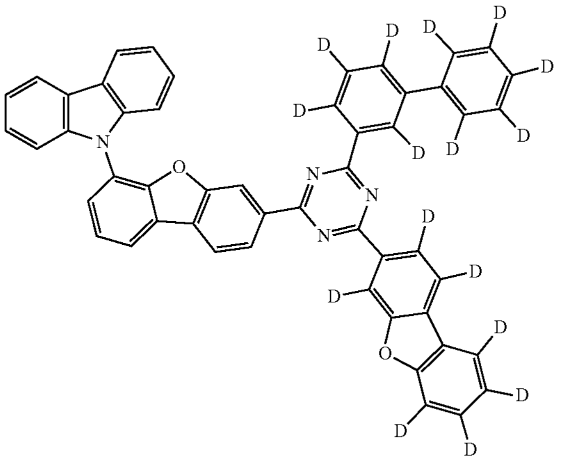

-continued
166
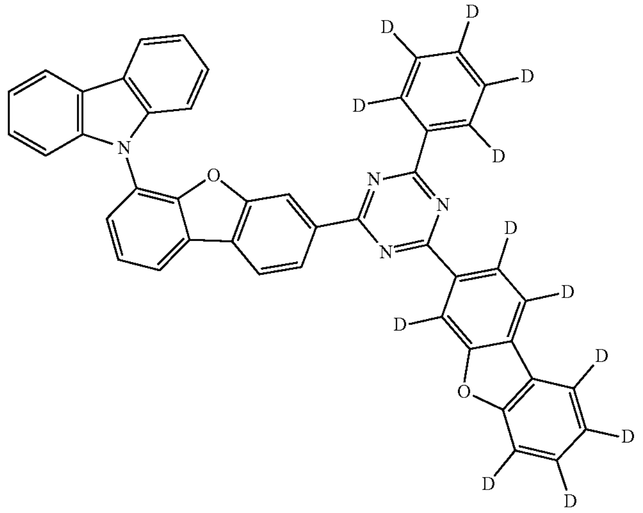
167
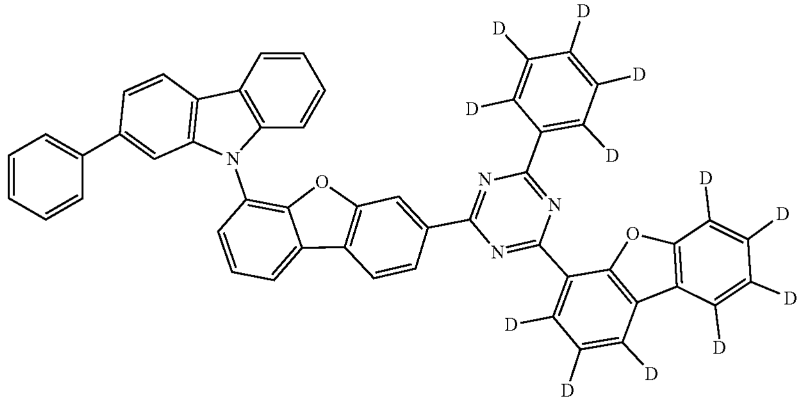
168
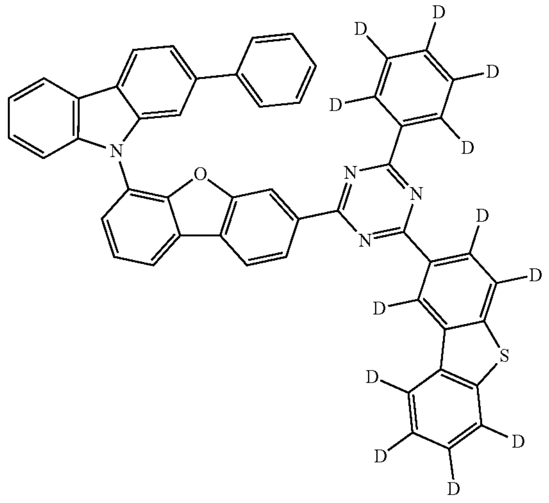
169
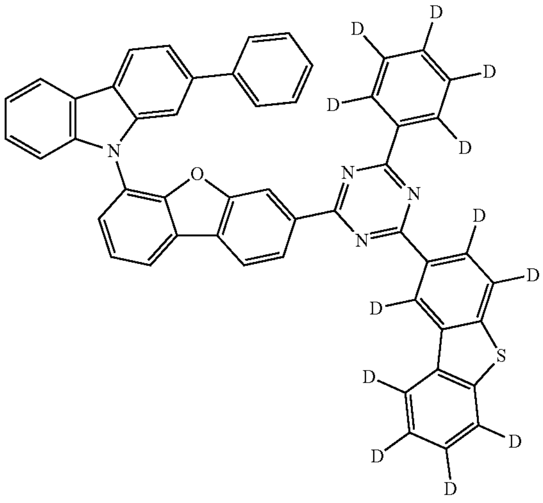

-continued
170
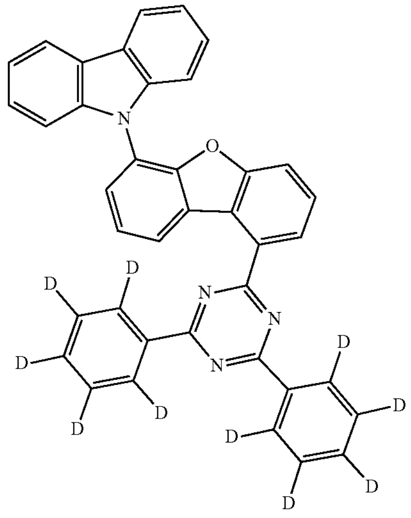
171
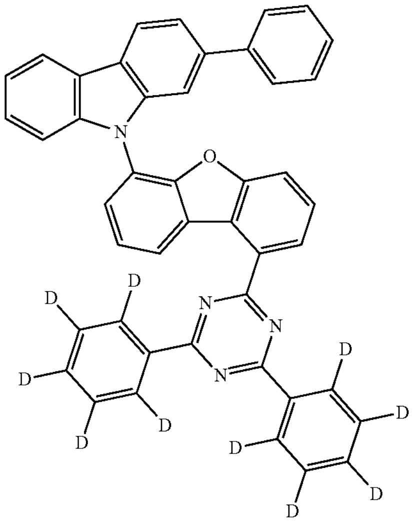
172
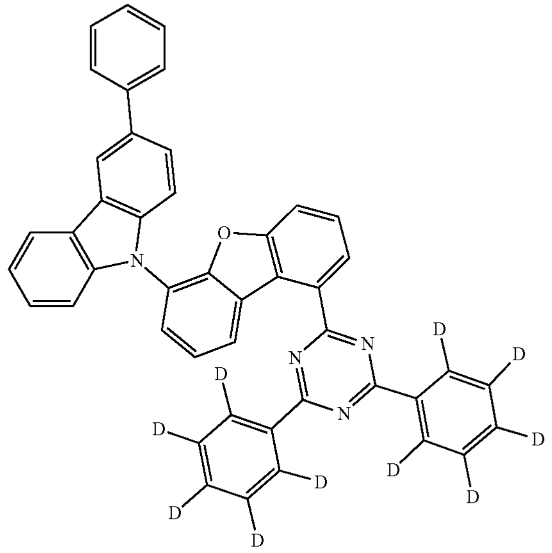
173
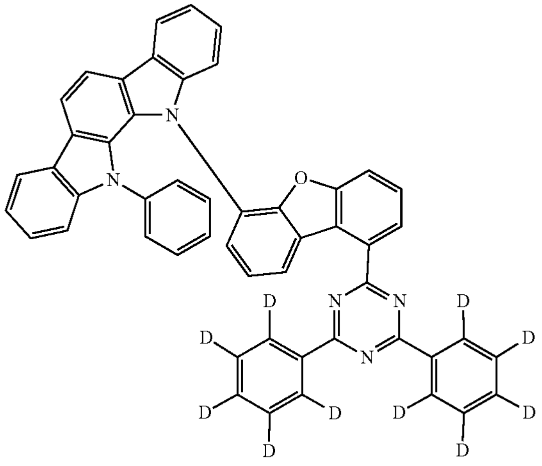
174
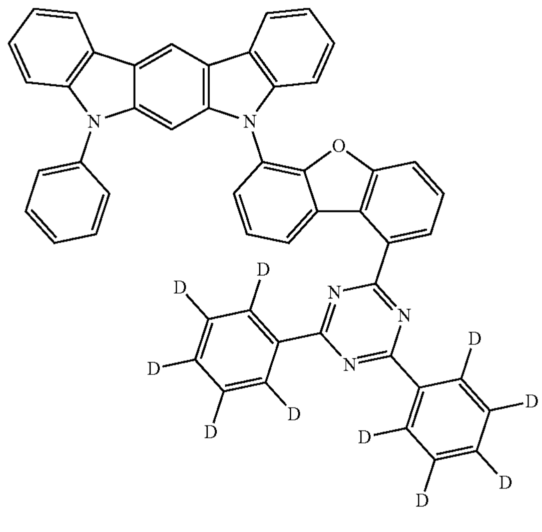
175
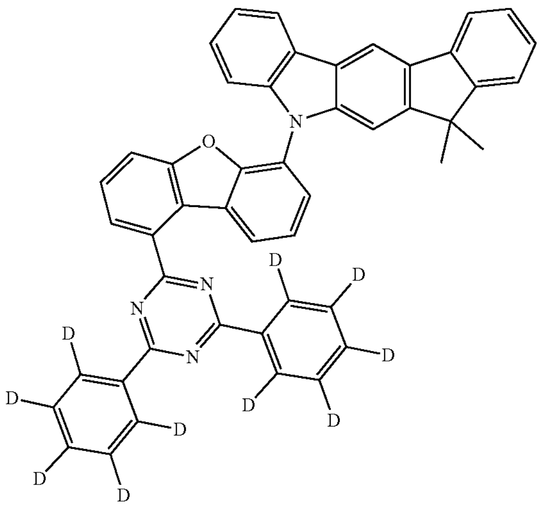

-continued
176
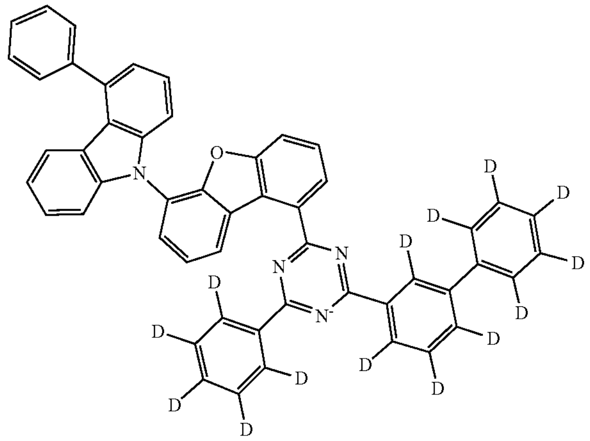
177
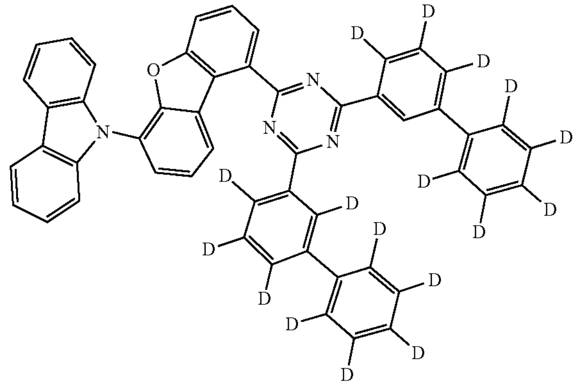
178
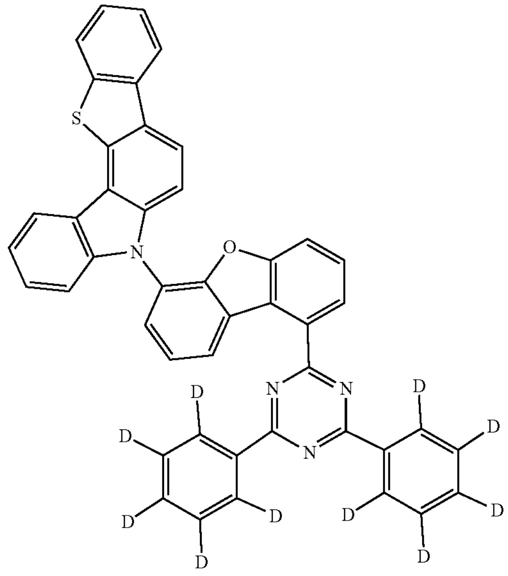
179
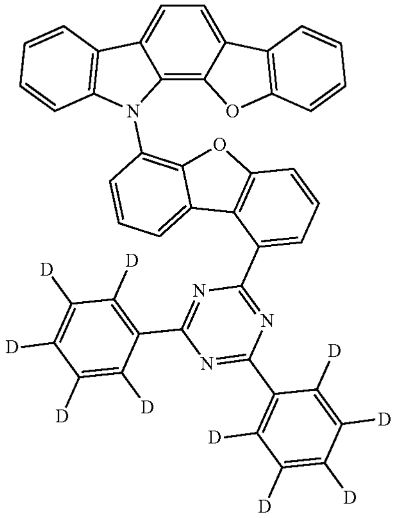
180
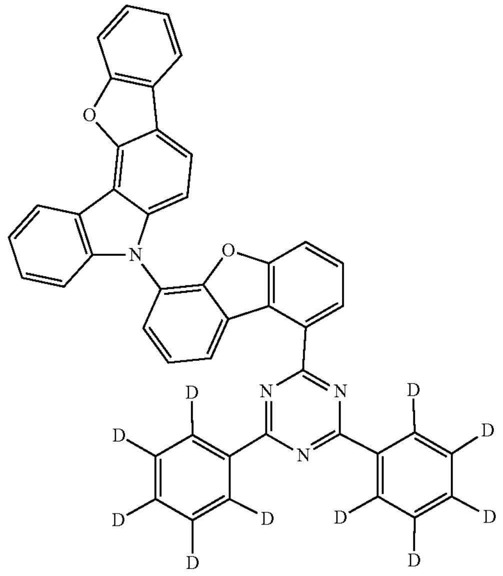
181
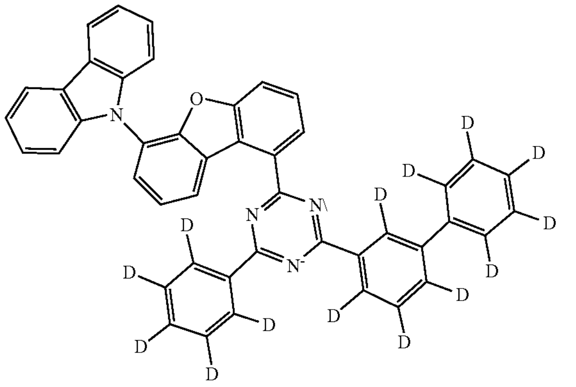

-continued
182
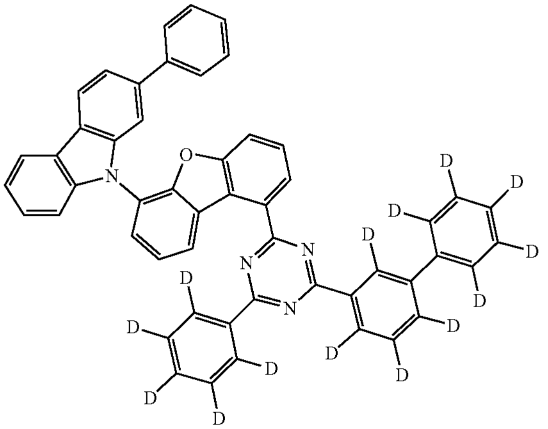
183
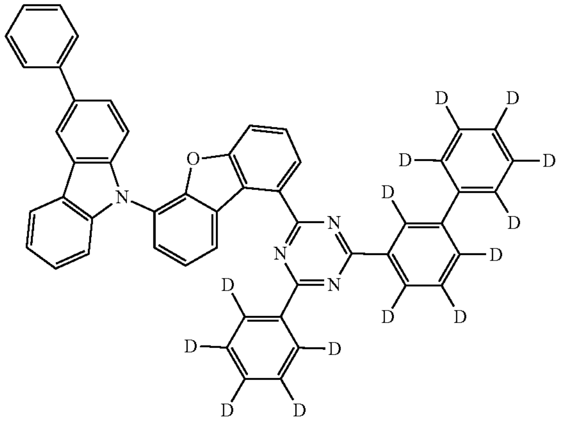
184
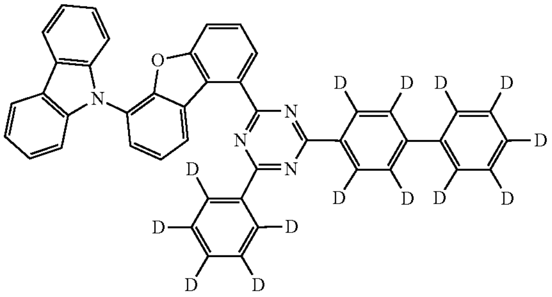
185
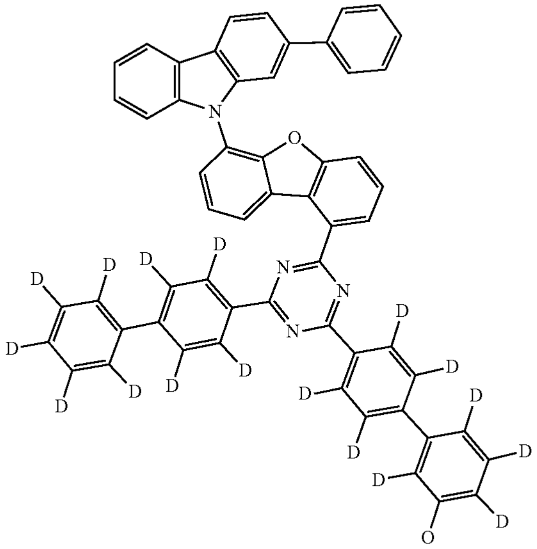
186
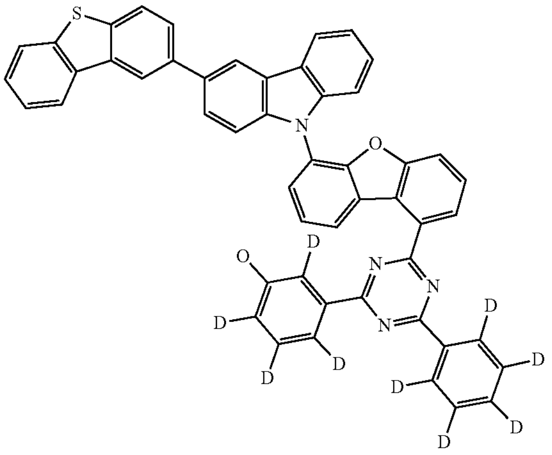
187
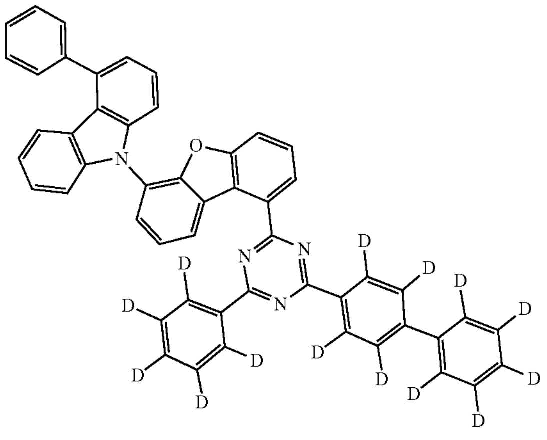

-continued
188
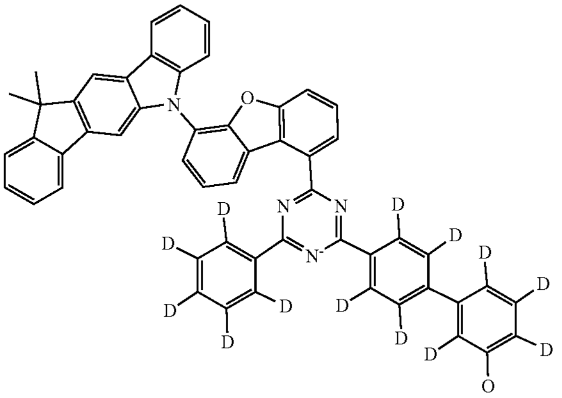
189
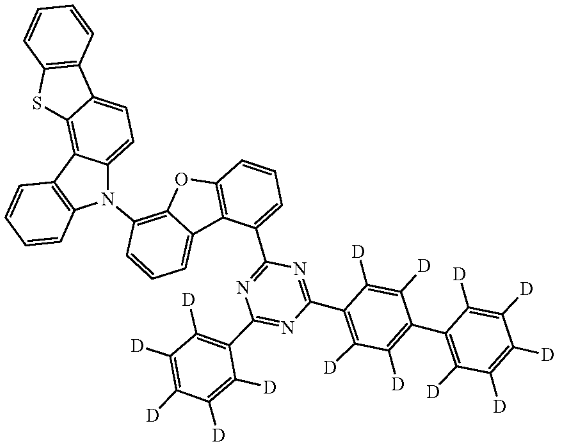
190
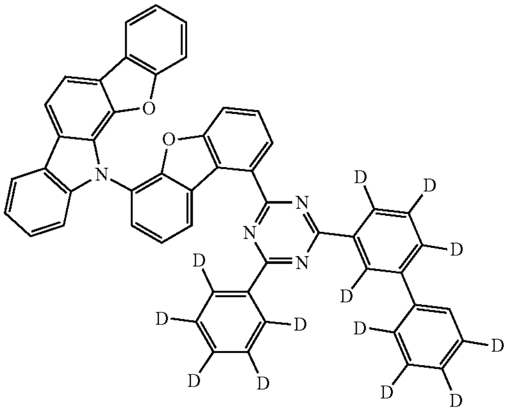
191
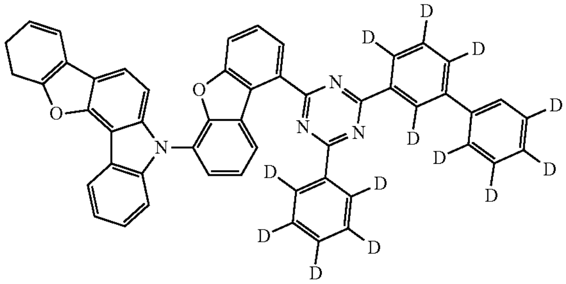
192
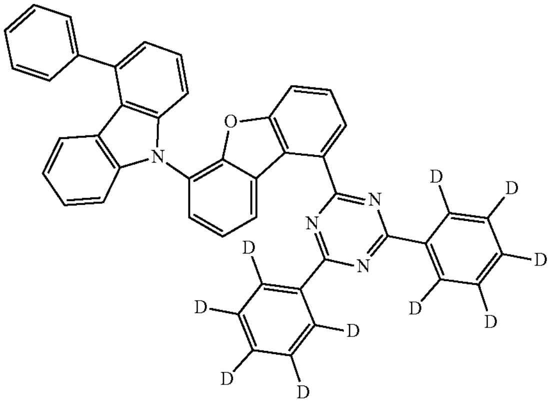
193
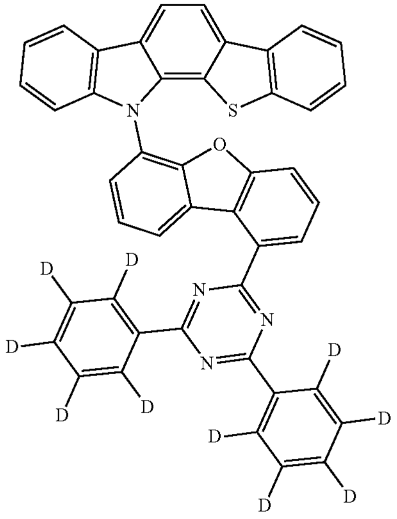

-continued
194
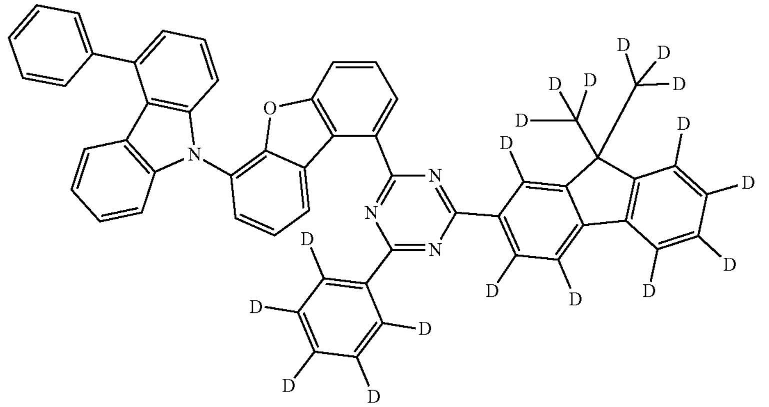
195
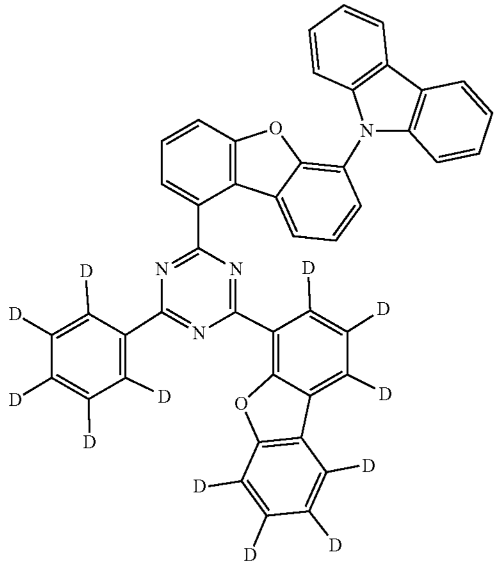
196
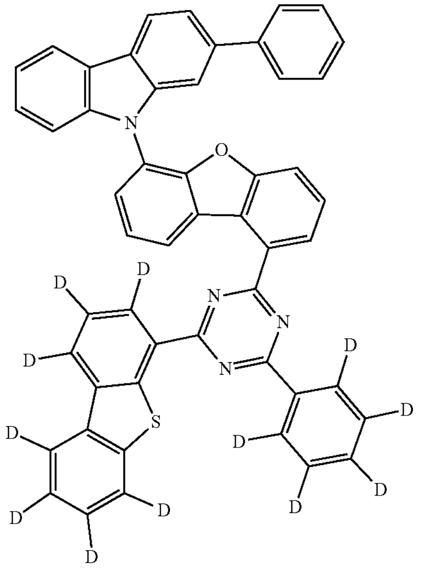
197
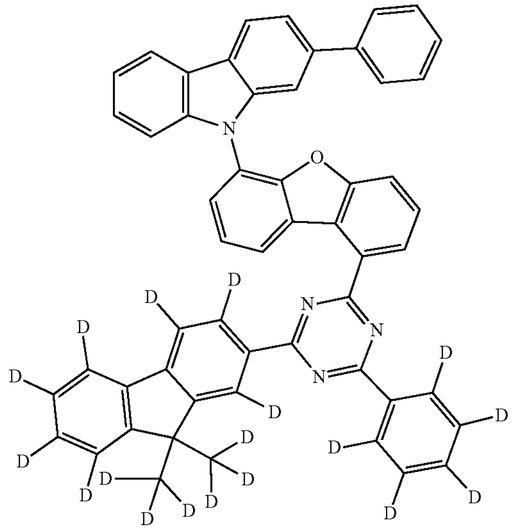
198
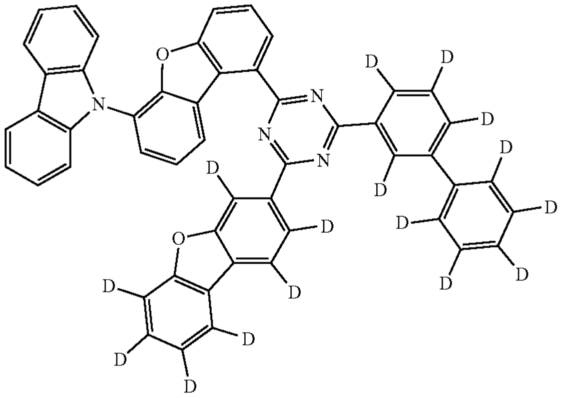

-continued
199
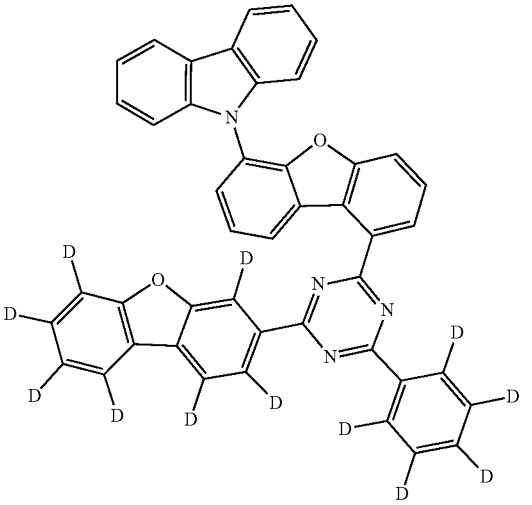
200
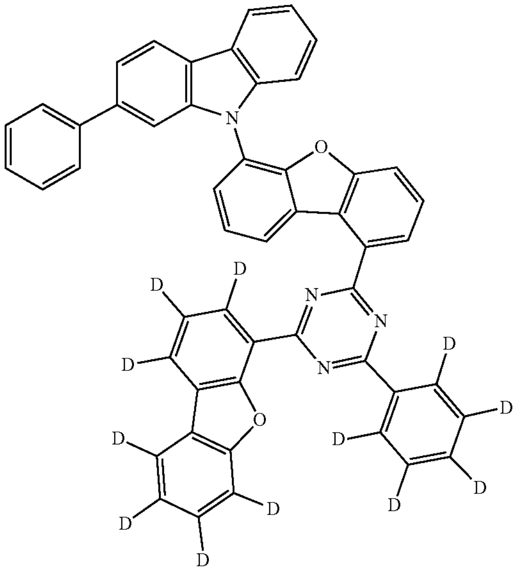
201
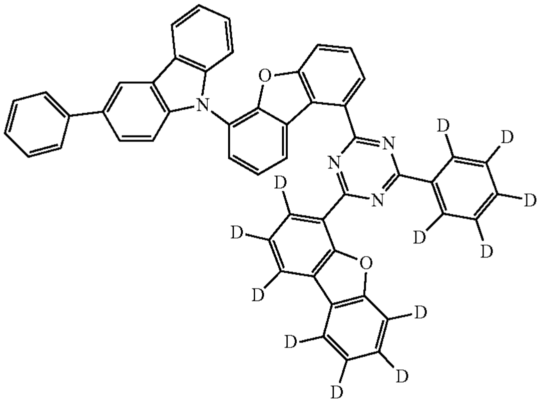
202
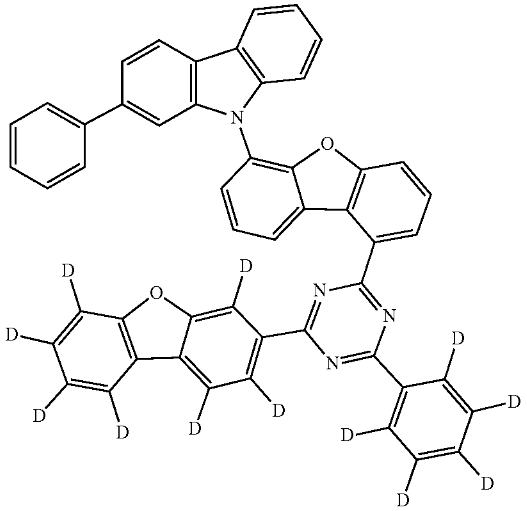
203
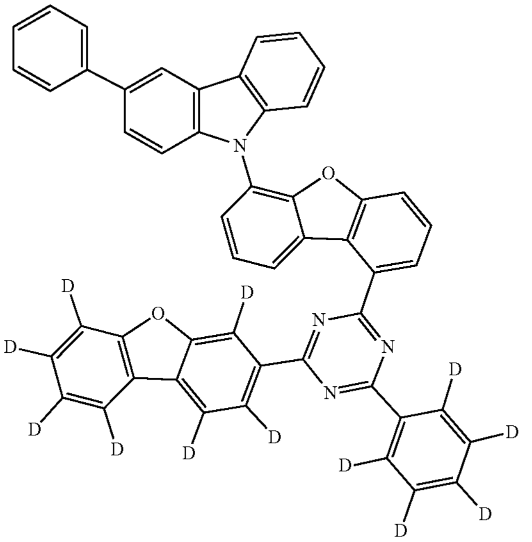
204
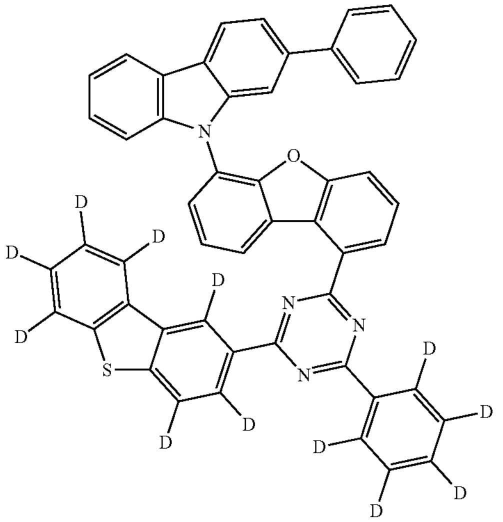

-continued
205
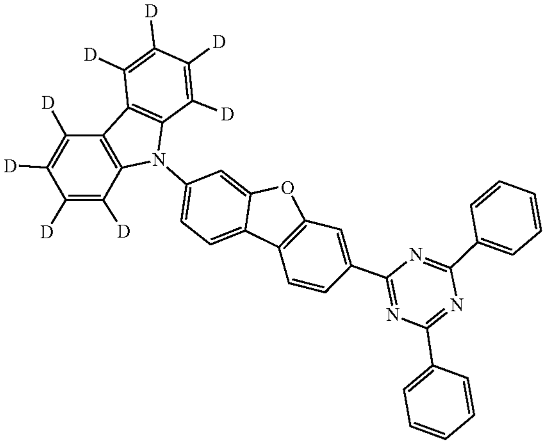
206
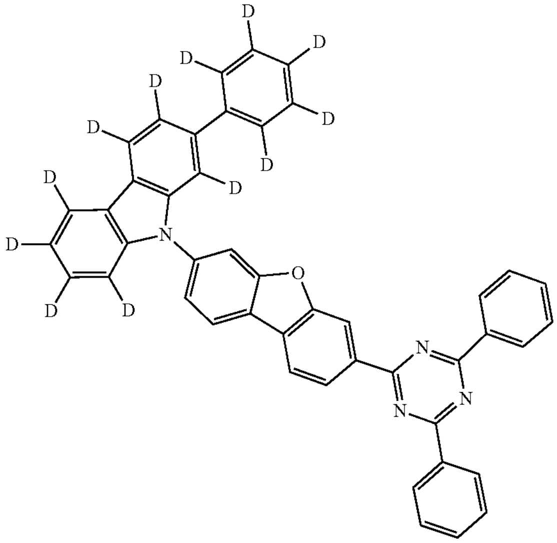
207
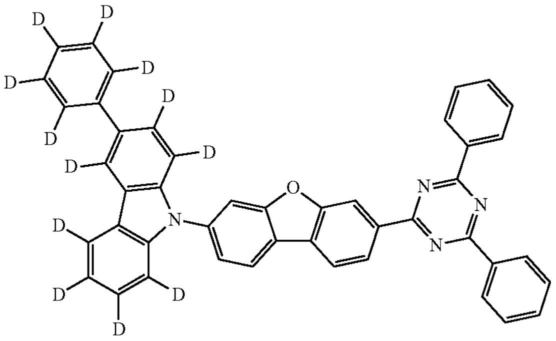
208
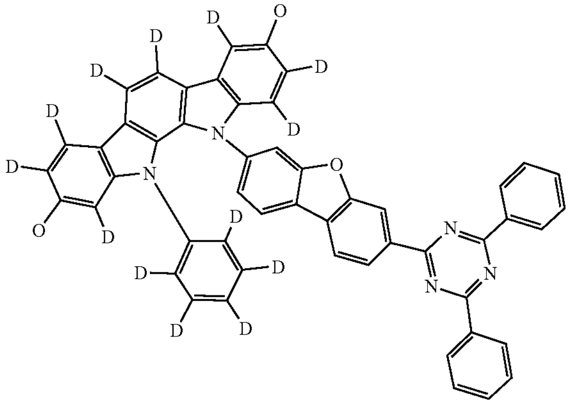
209
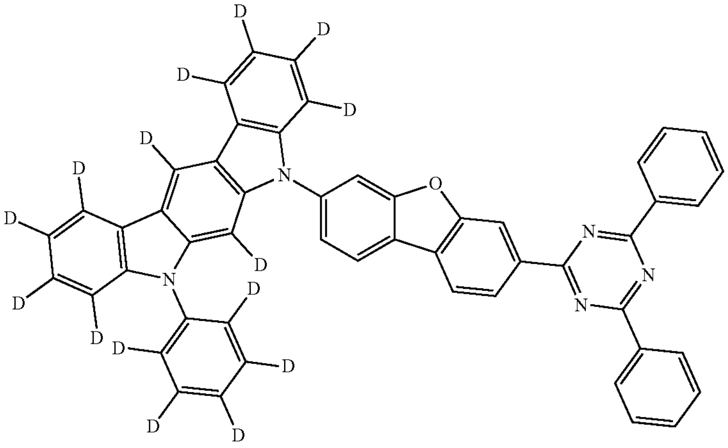

-continued
210
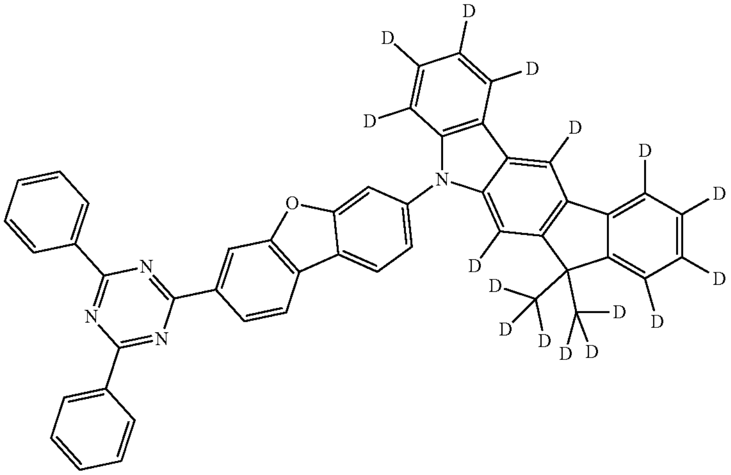
211
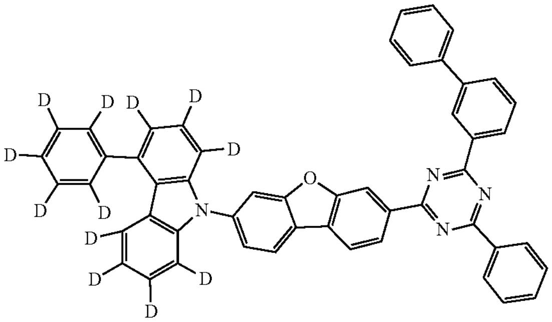
212
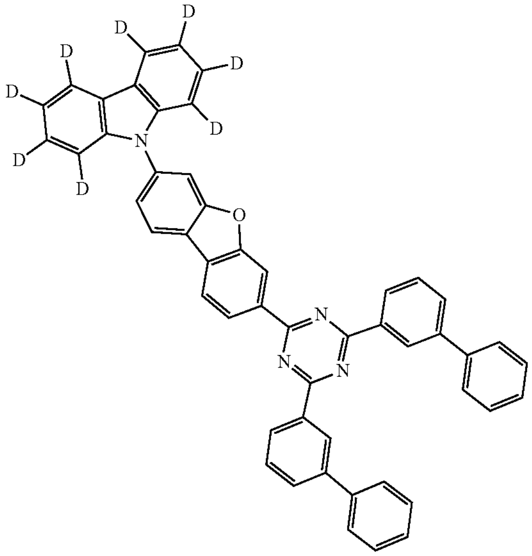
213
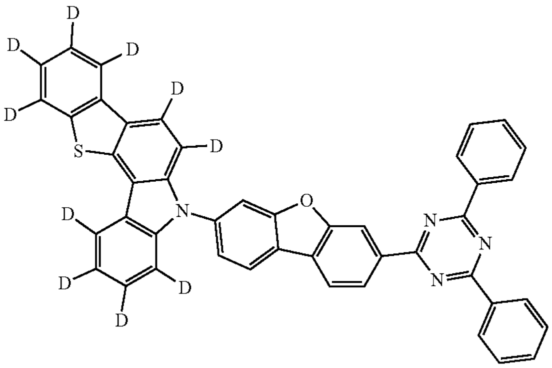
214
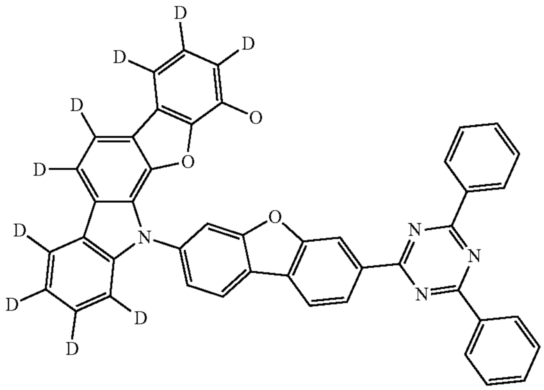

-continued
215
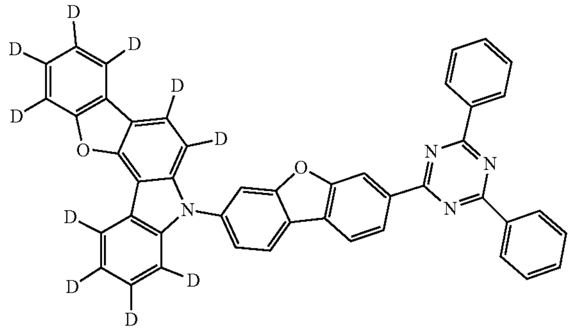
216
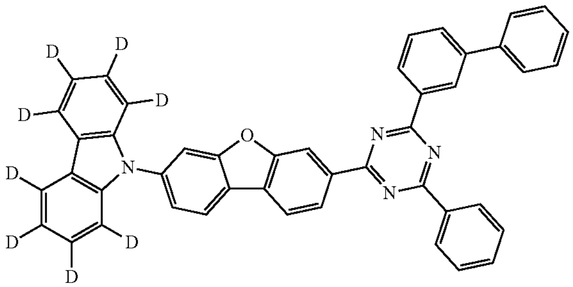
217
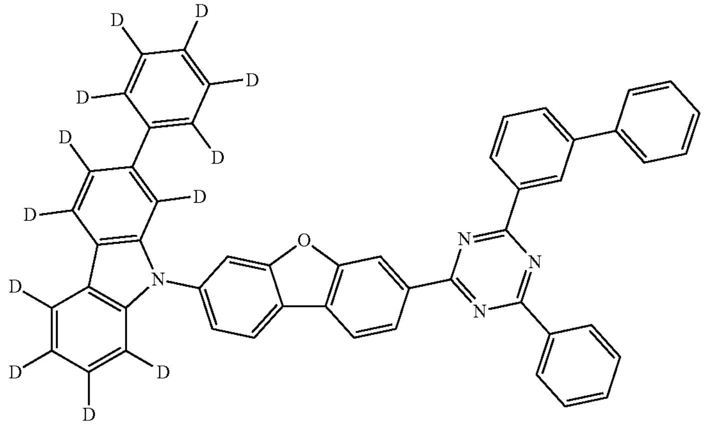
218
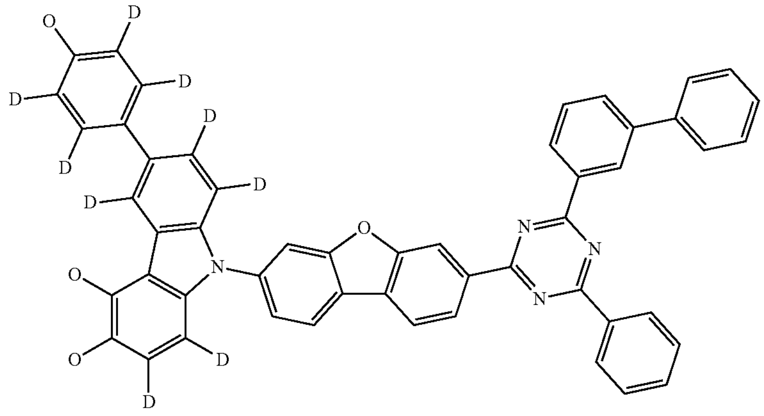
219
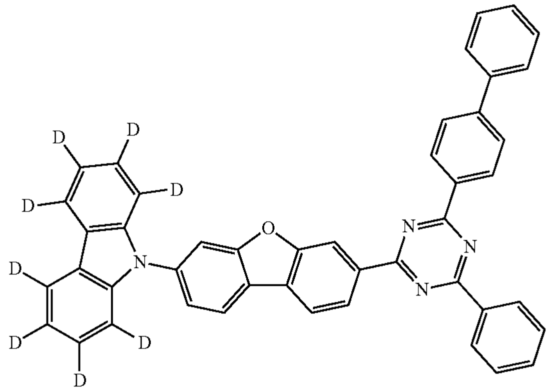
220
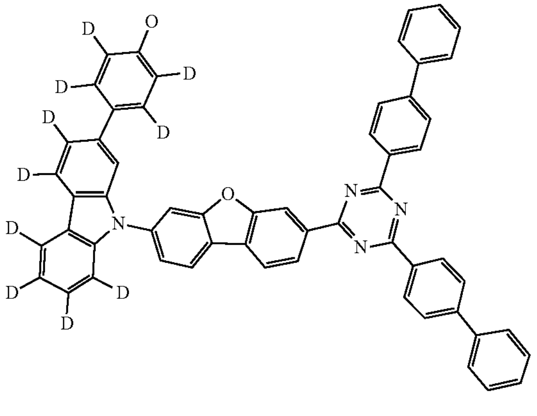

-continued
221
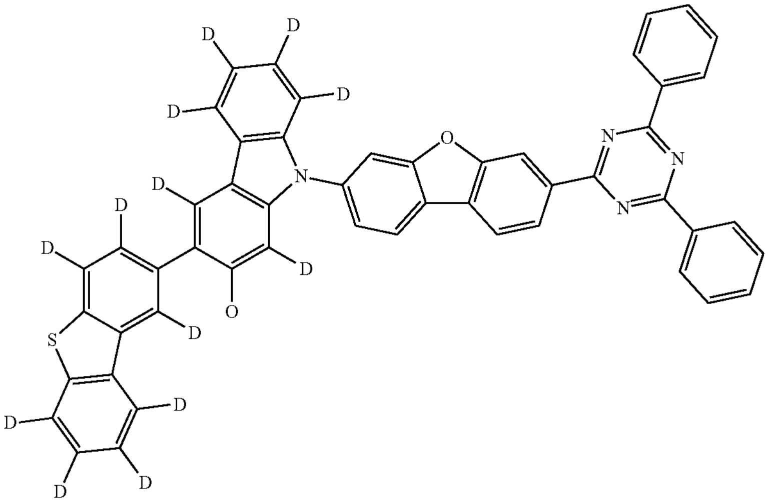
222
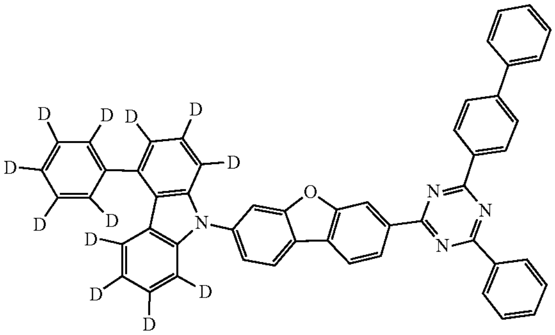
223
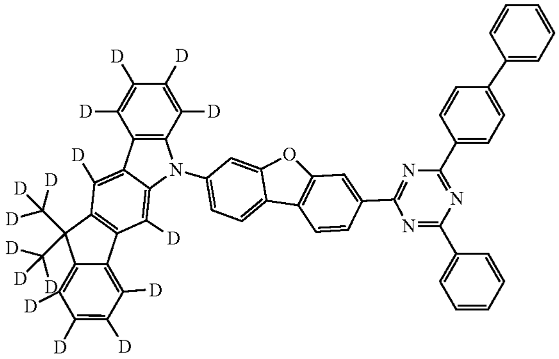
224
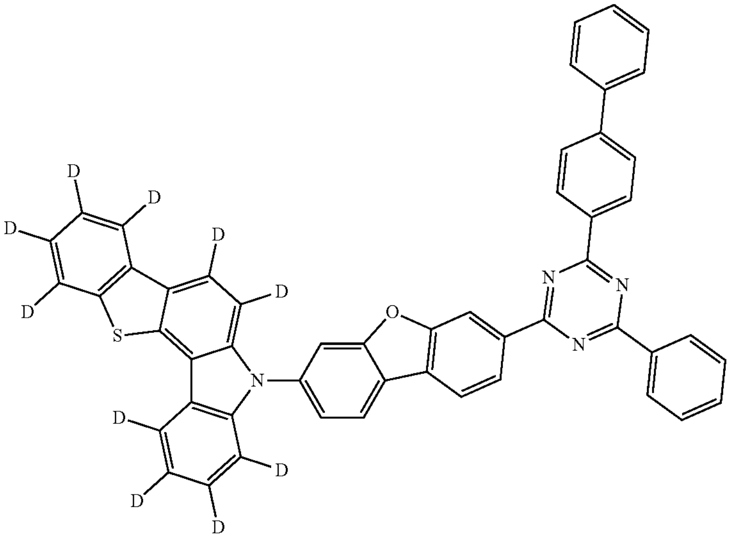

-continued
225
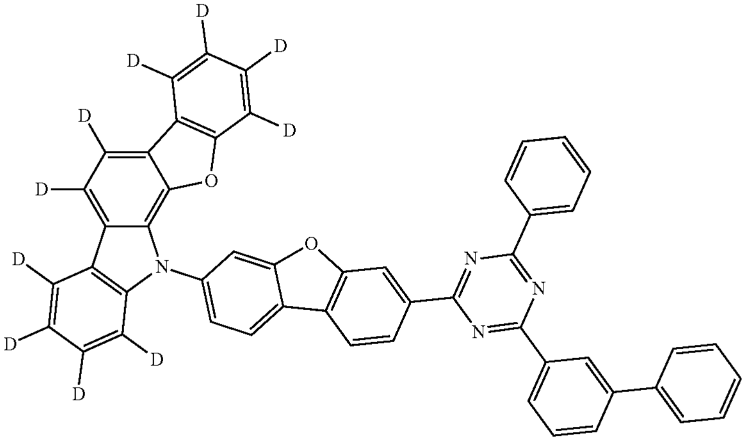
226
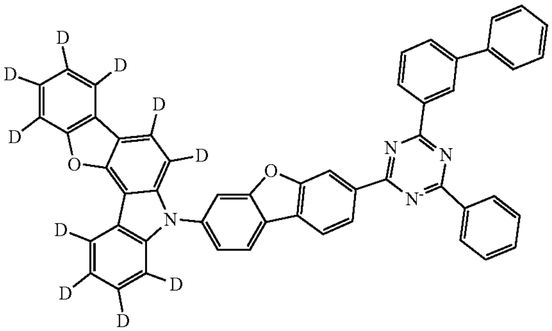
227
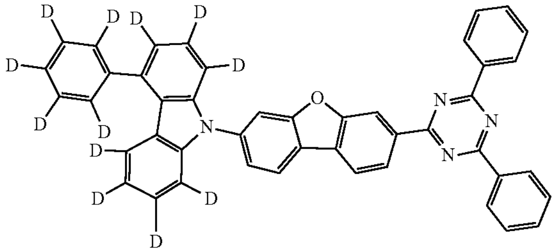
228
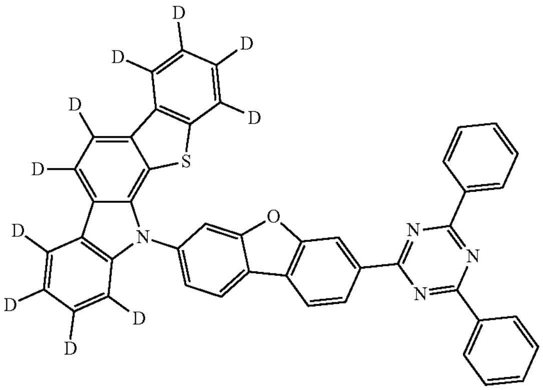
229
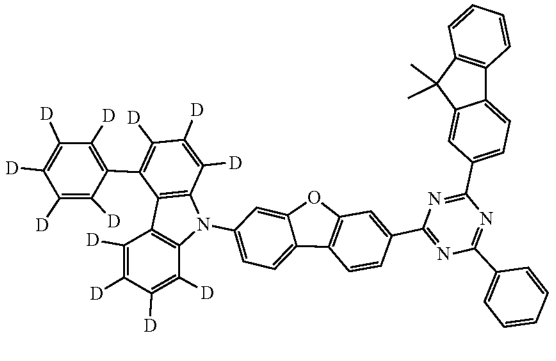
230
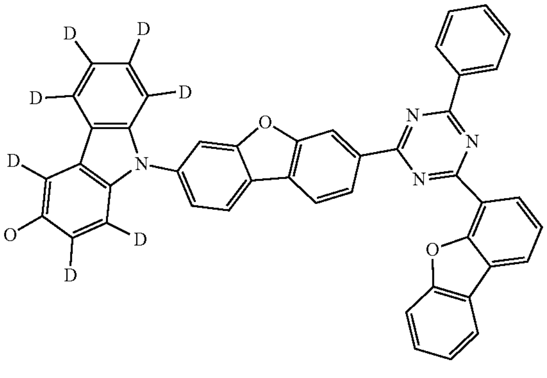
231
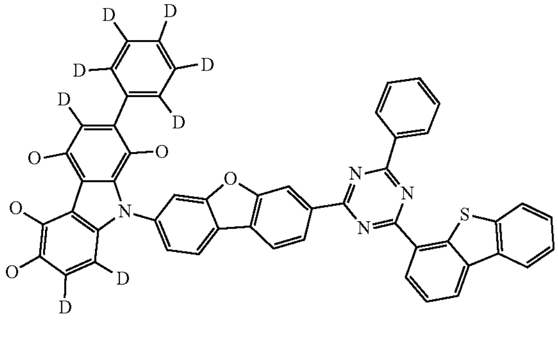

-continued
232
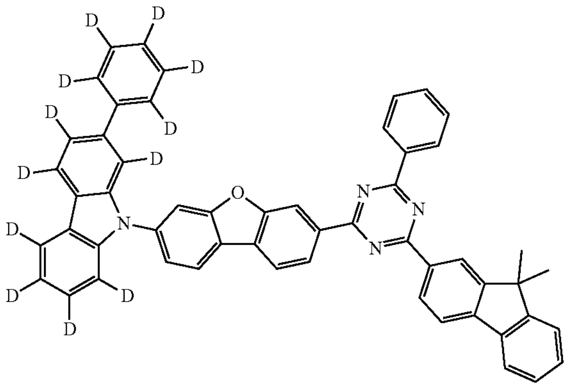
233
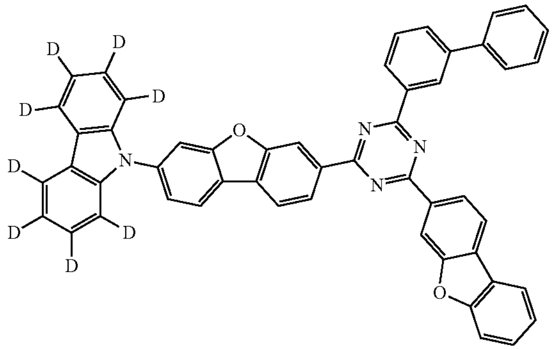
234
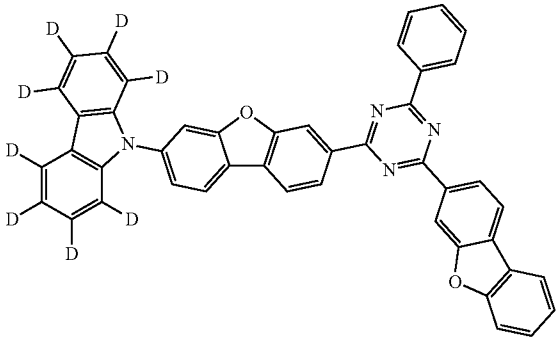
235
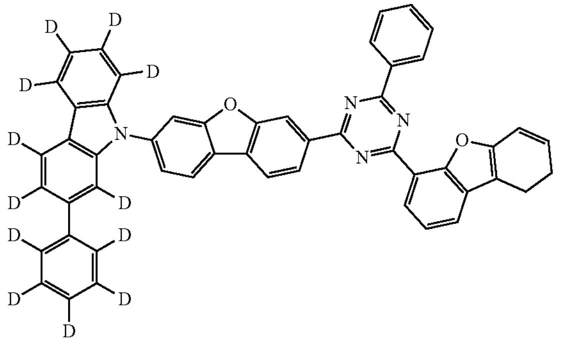
236
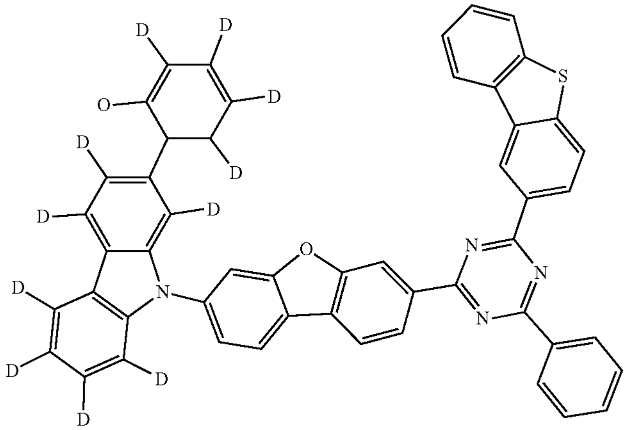
237
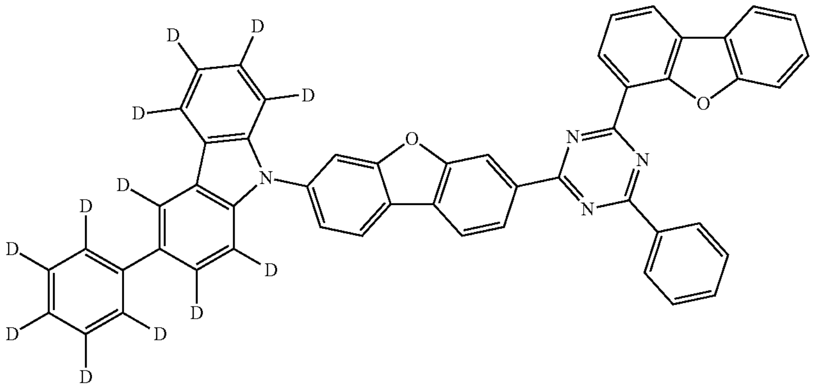

-continued
238
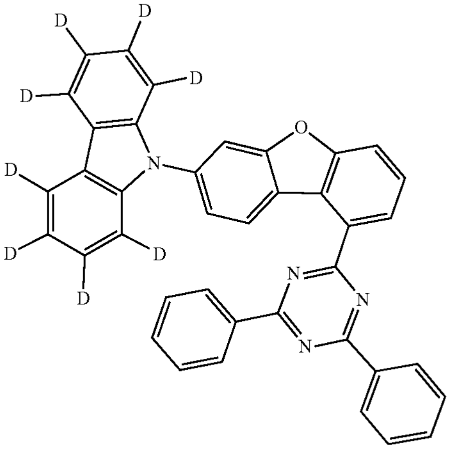
239
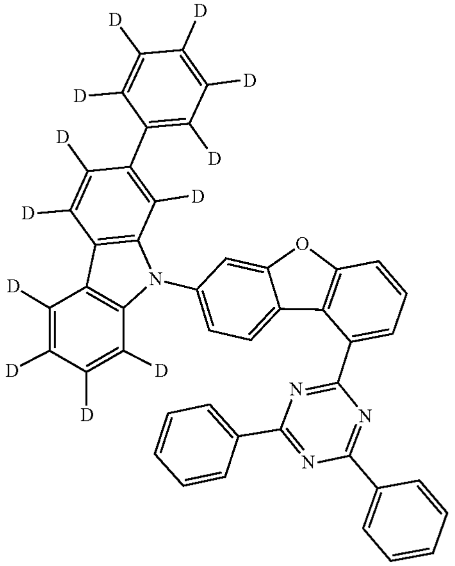
240
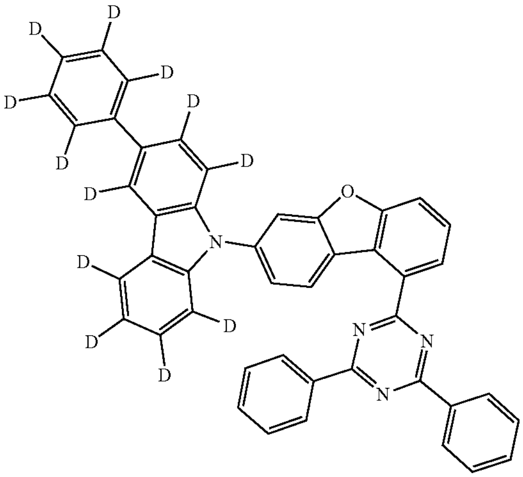
241
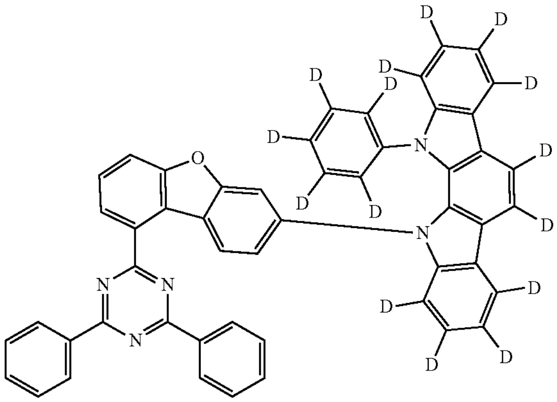
242
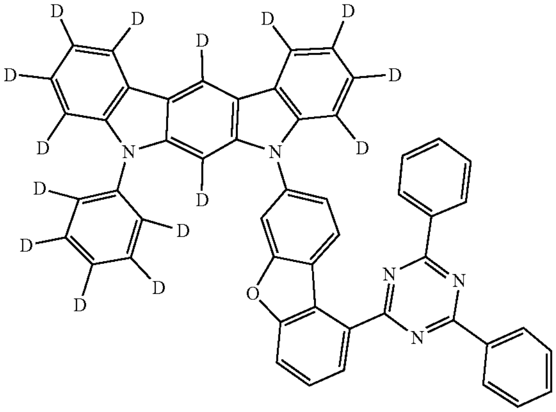
243
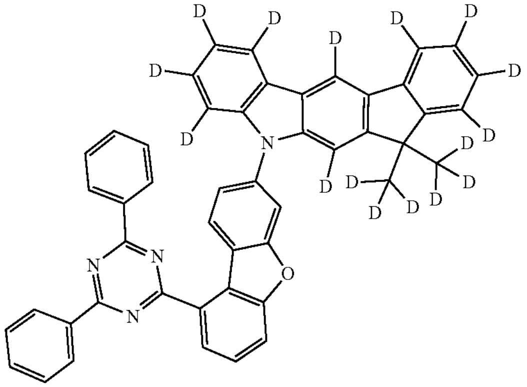

-continued
244
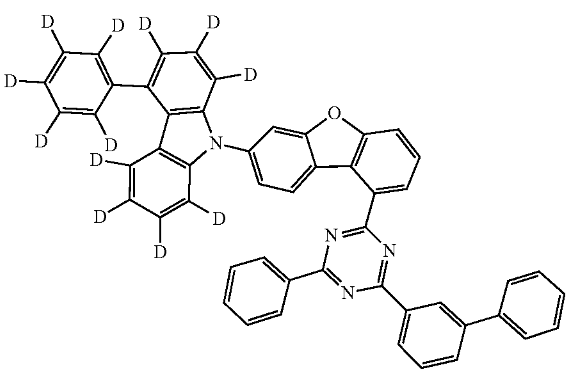
245
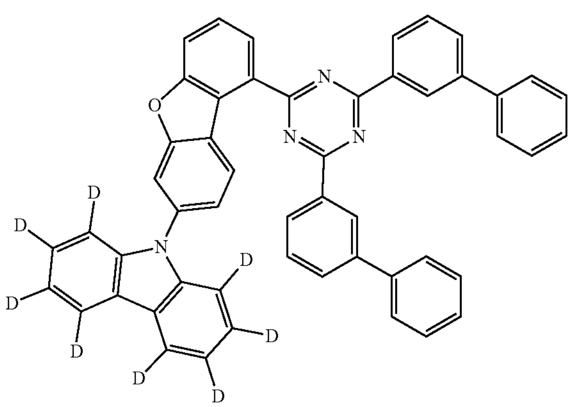
246
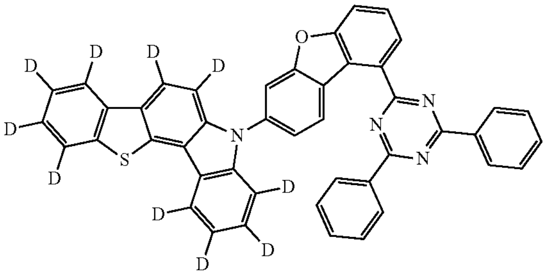
247
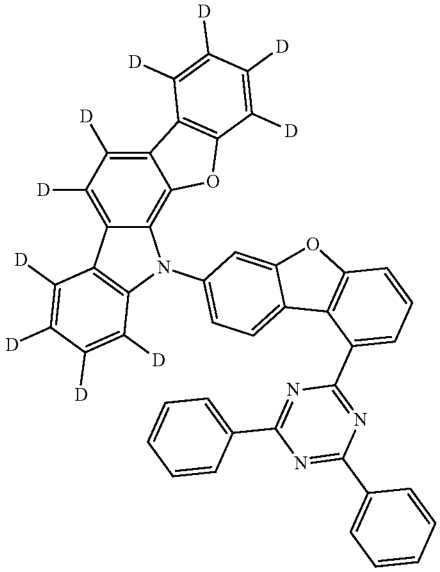
248
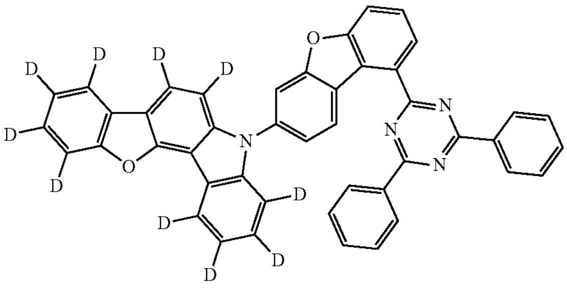
249
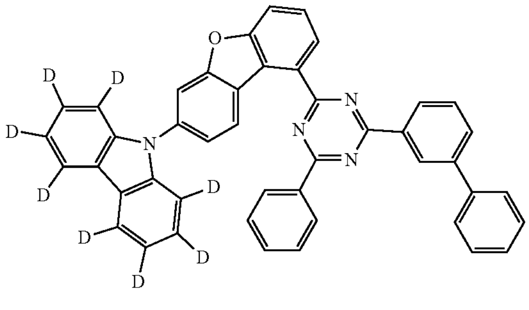

-continued
250
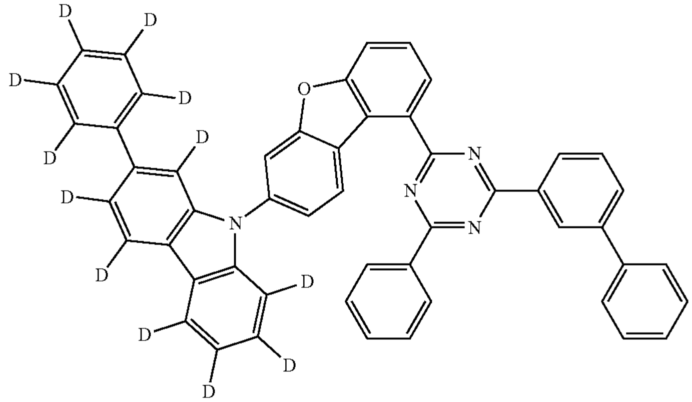
251
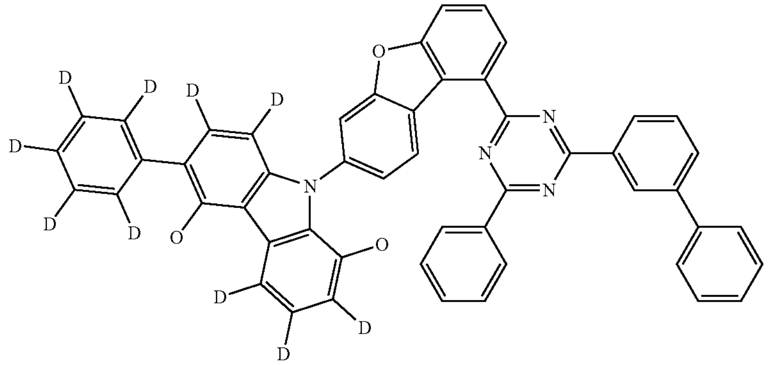
252
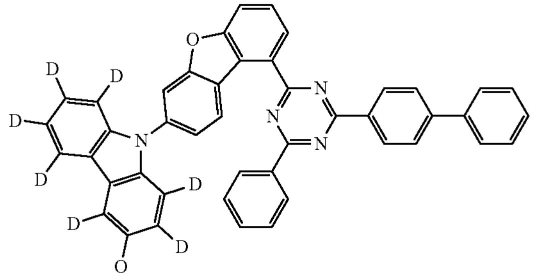
253
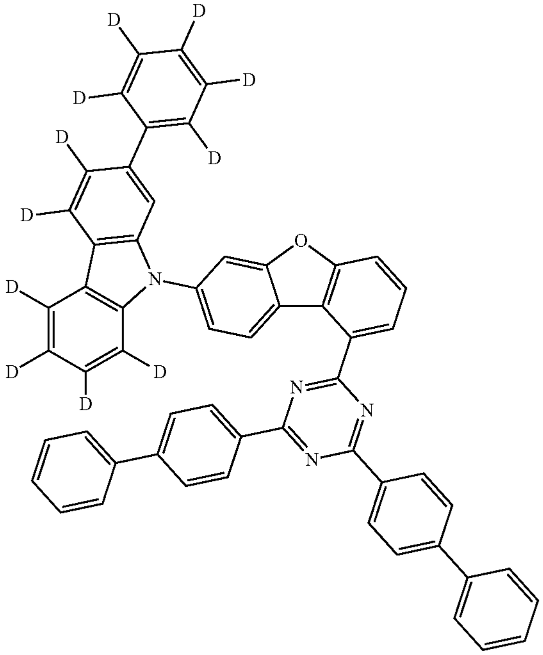

-continued
254
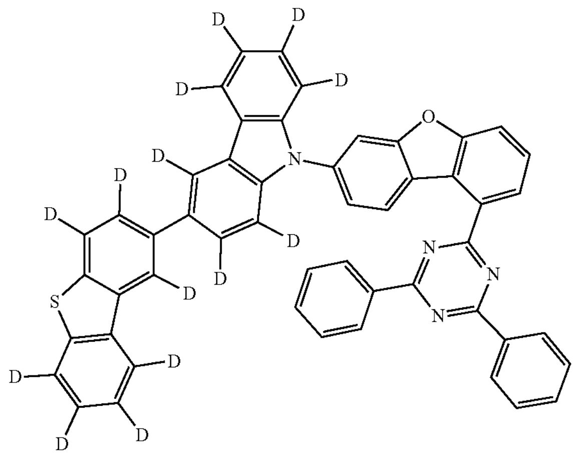
255
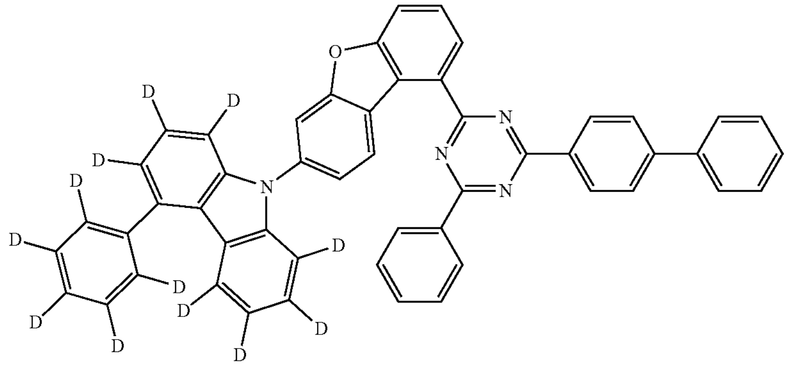
256
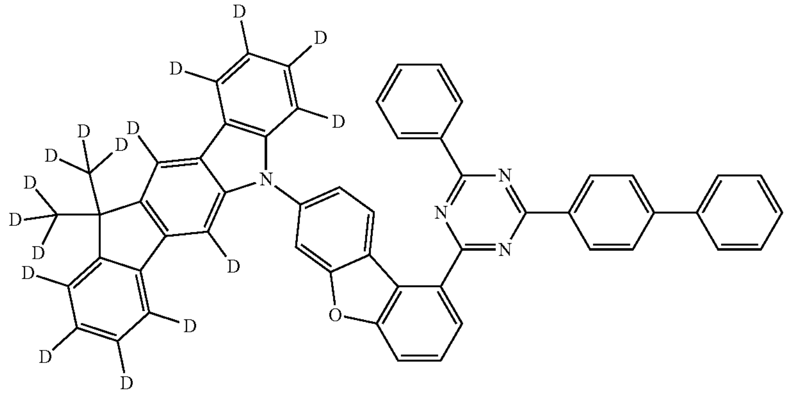

-continued
257
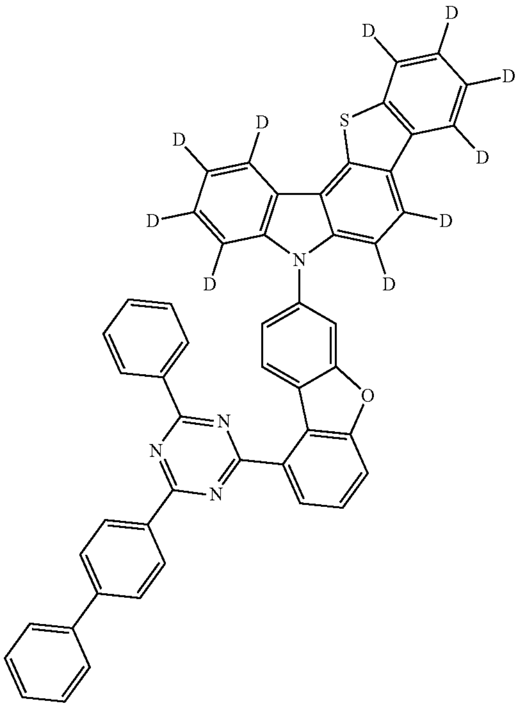
258
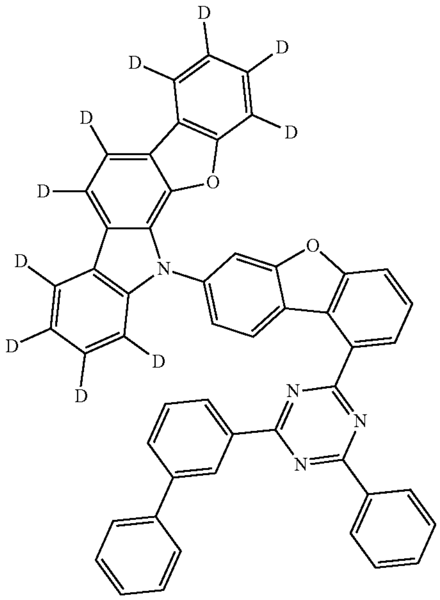
259
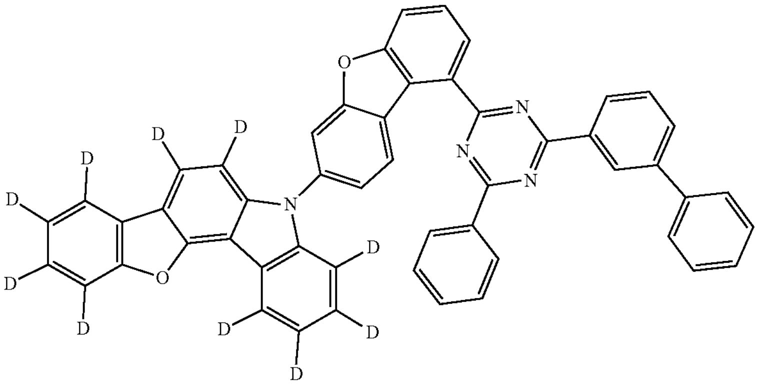
260
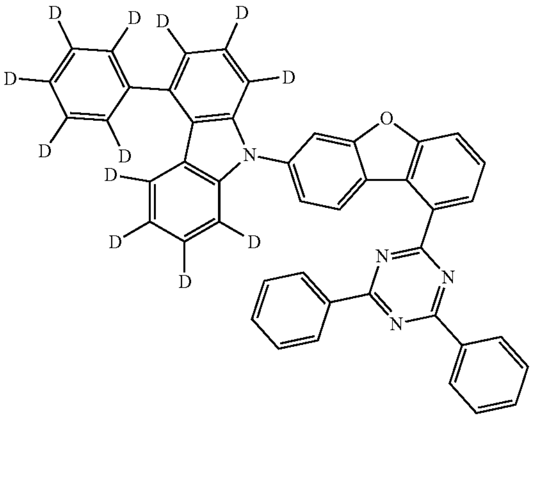
261
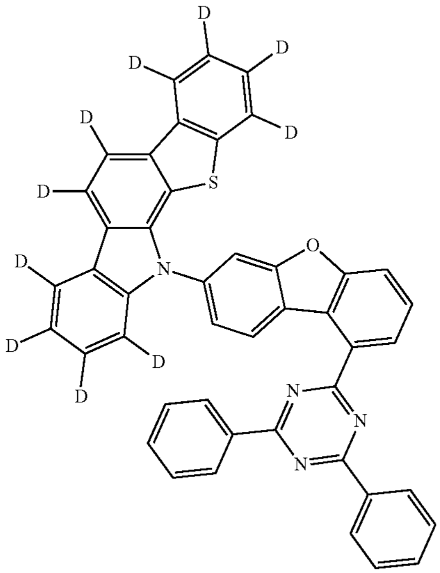

-continued
262
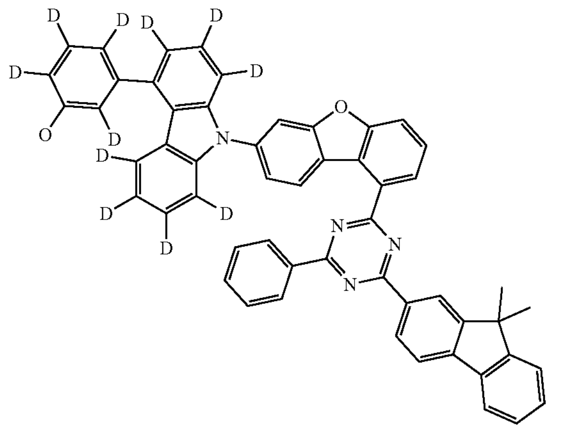
263
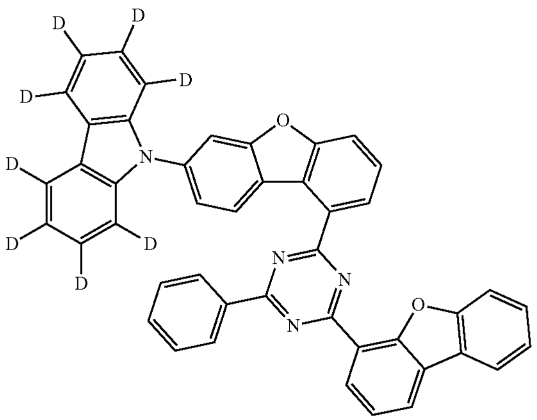
264
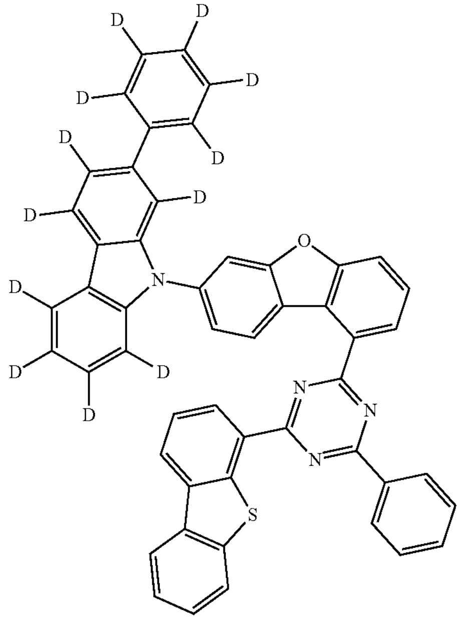
265
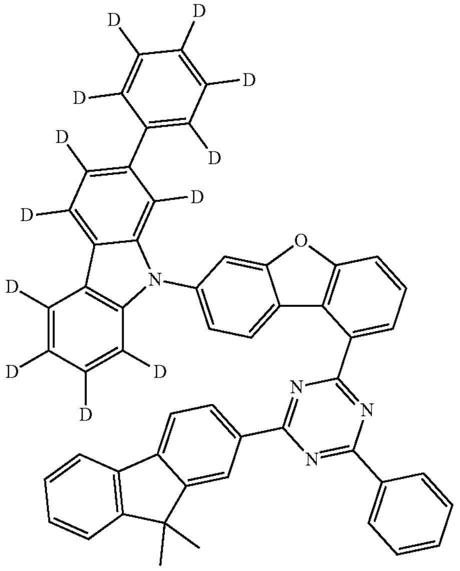
266
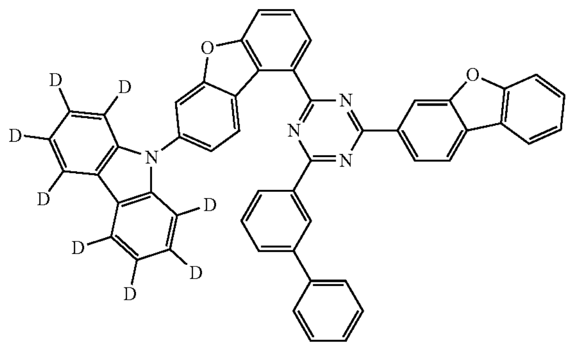
267
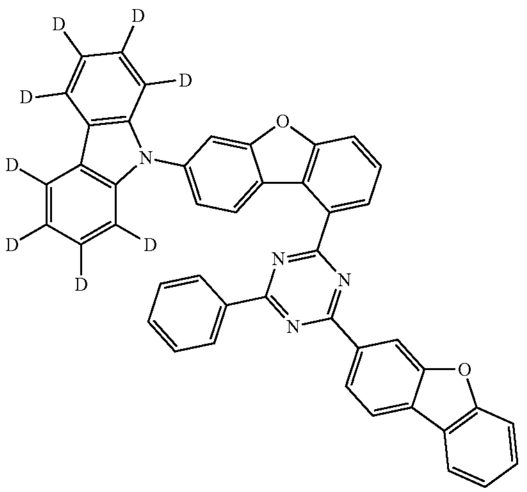

-continued
268
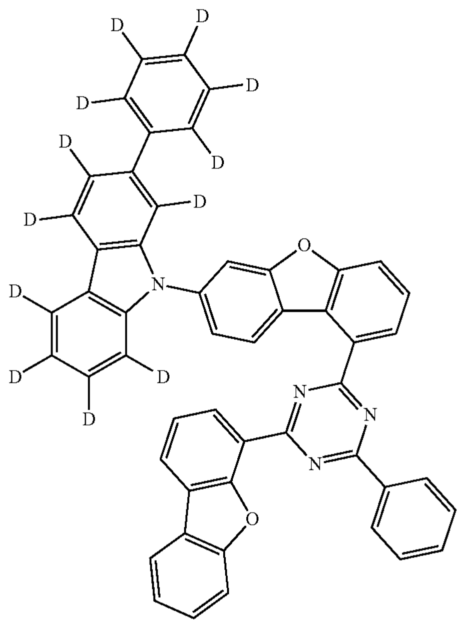
269
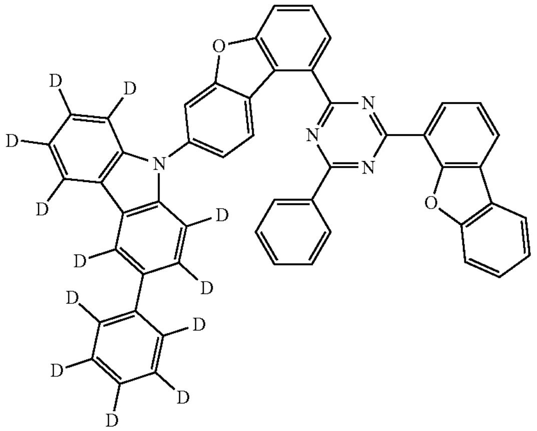
270
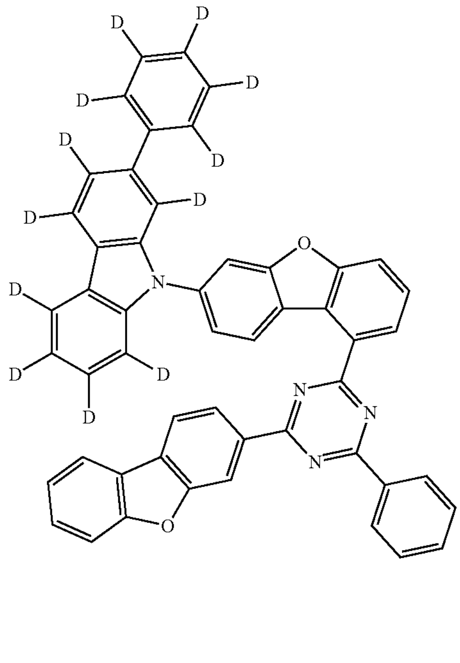
271
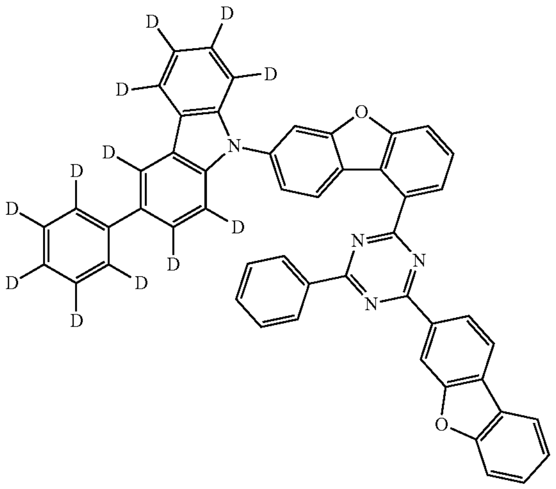

-continued
272
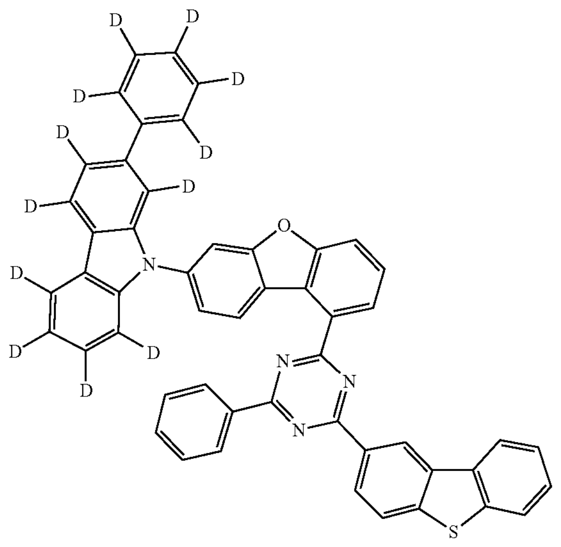
273
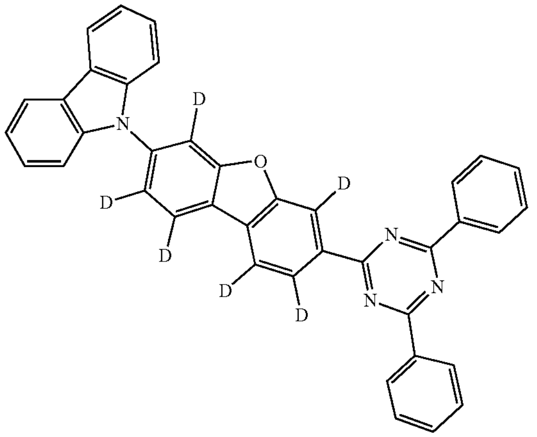
274
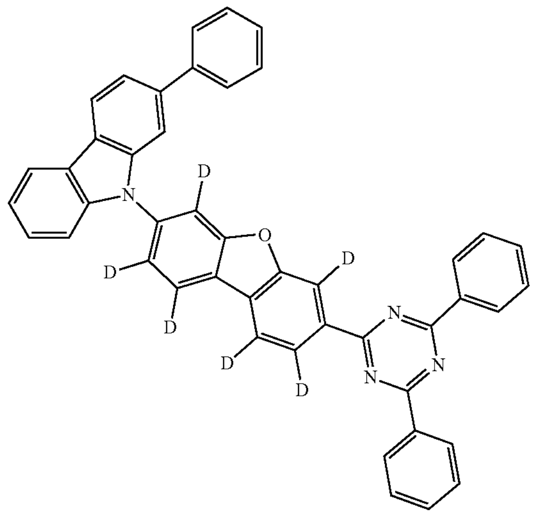
275
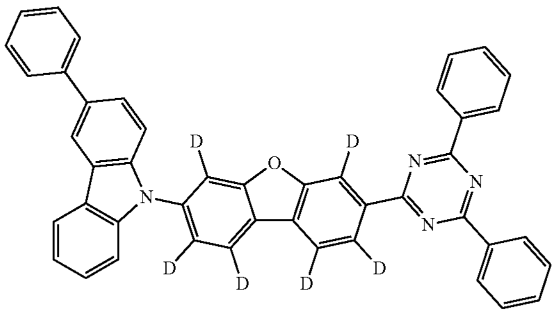
276
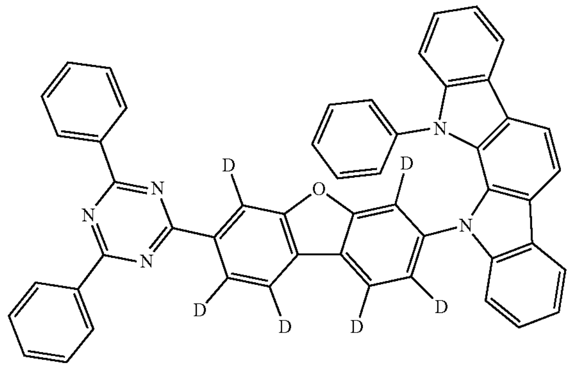
277
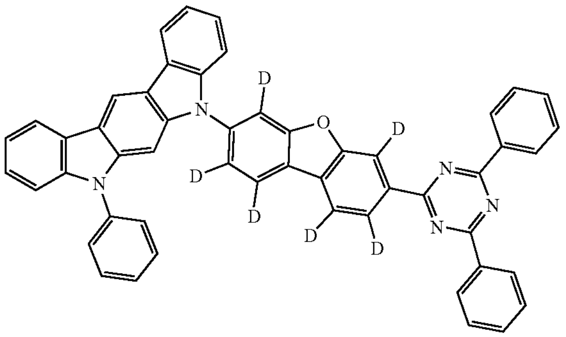

-continued
278
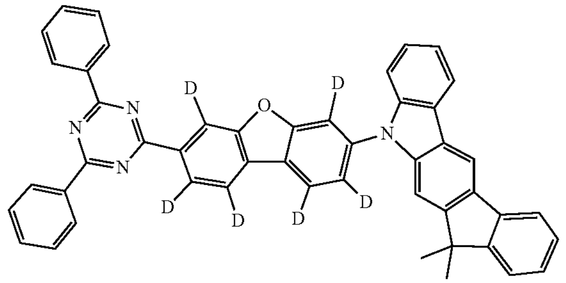
279
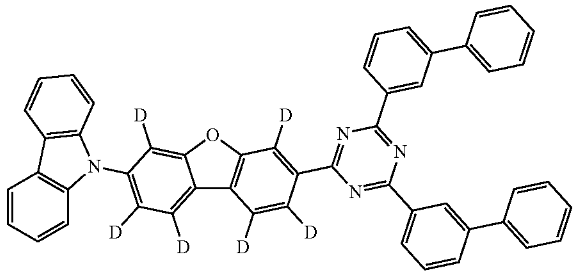
280
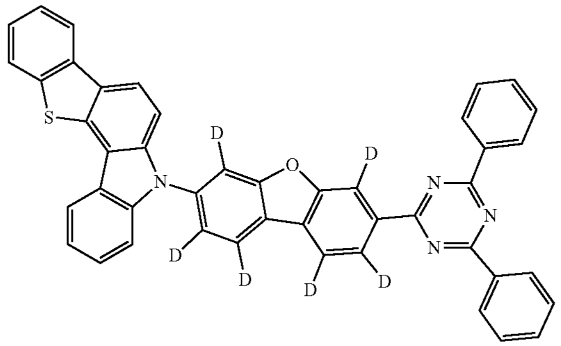
281
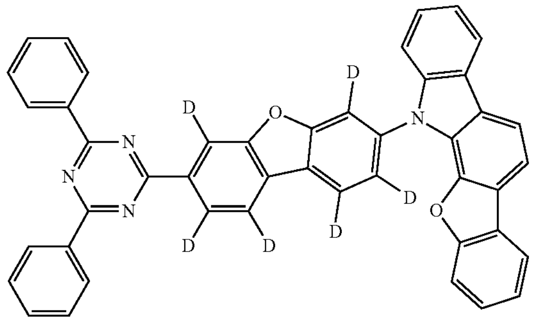
282
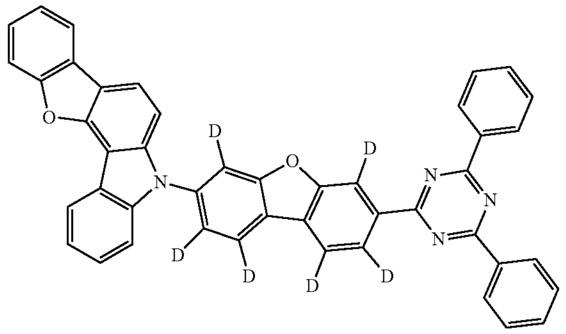
283
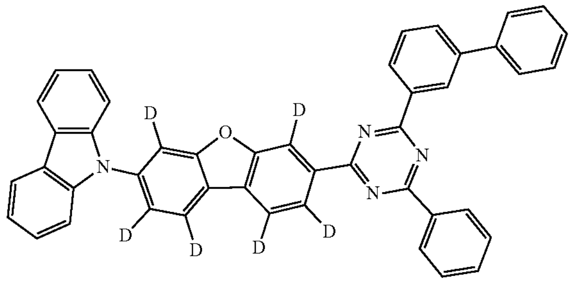
284
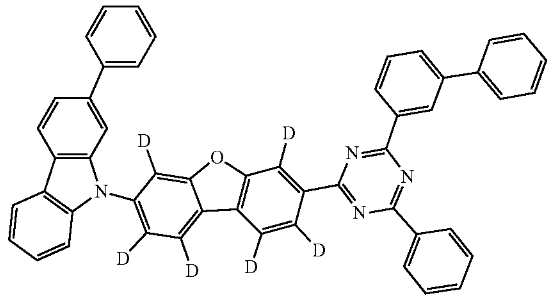
285
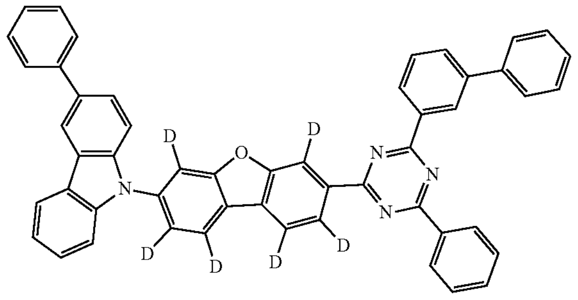

-continued
286
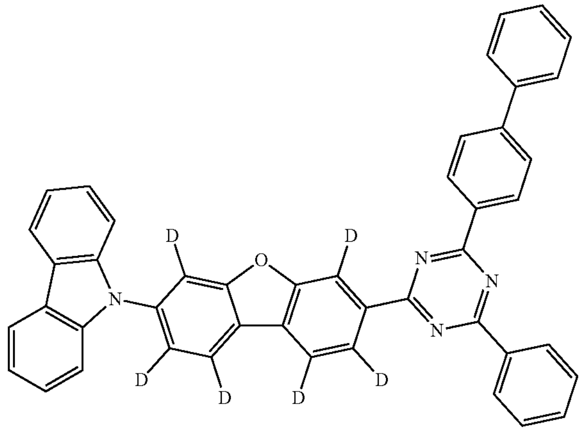
287
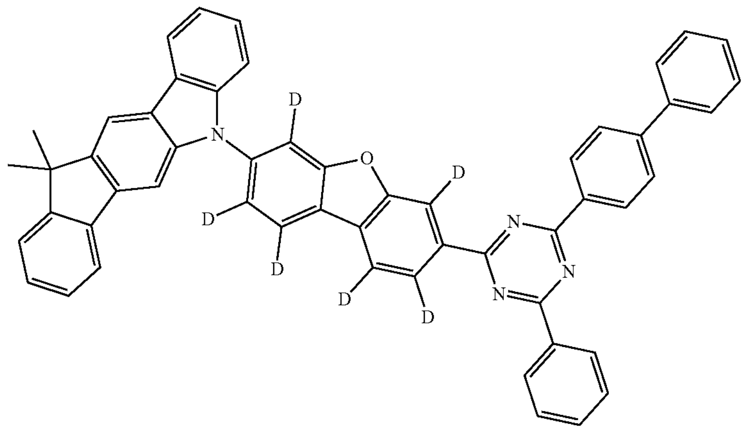
288
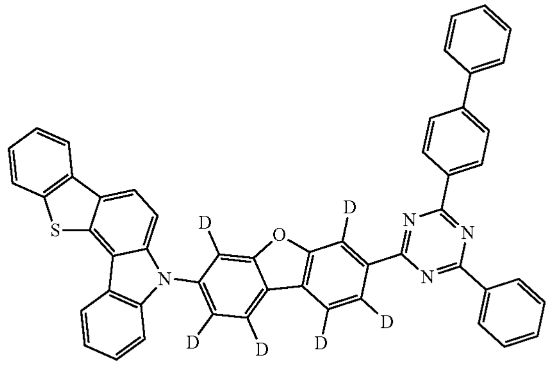
289
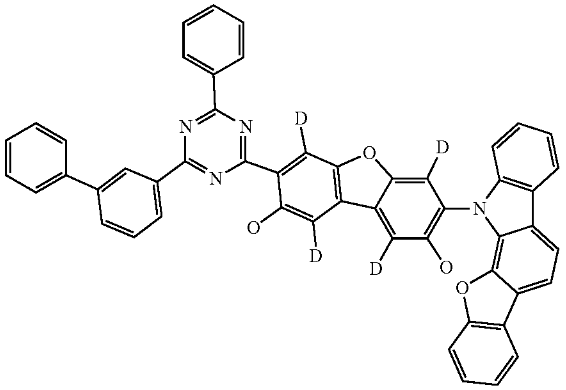
290
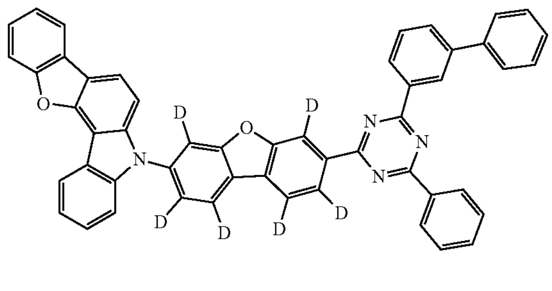
291
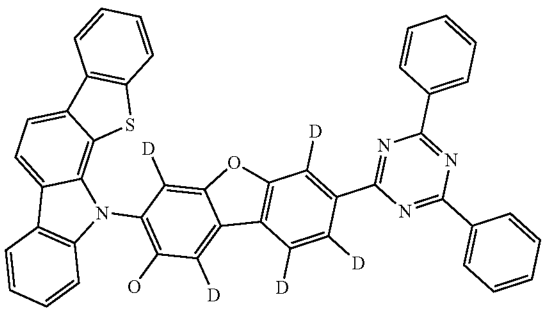

-continued
292
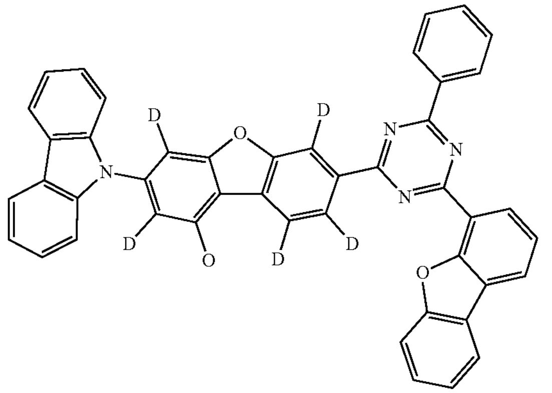
293
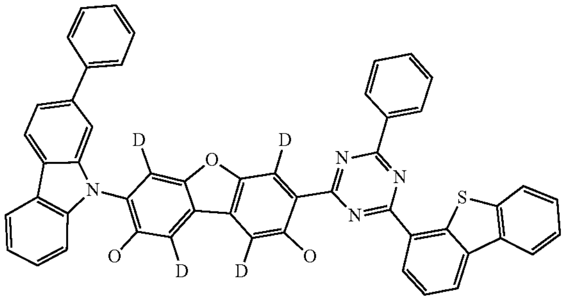
294
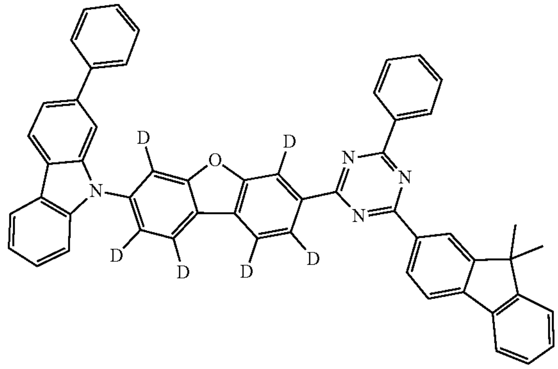
295
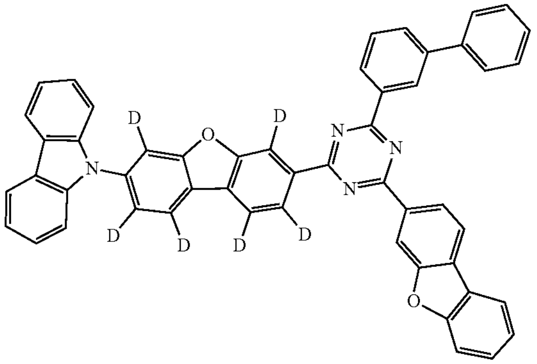
296
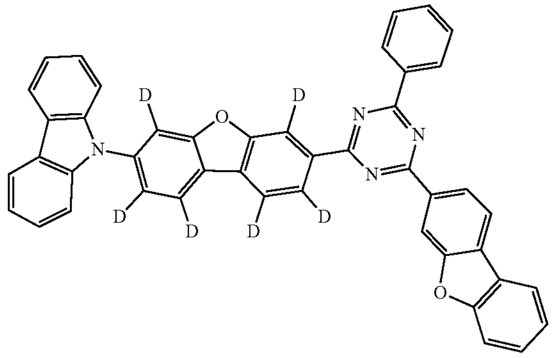
297
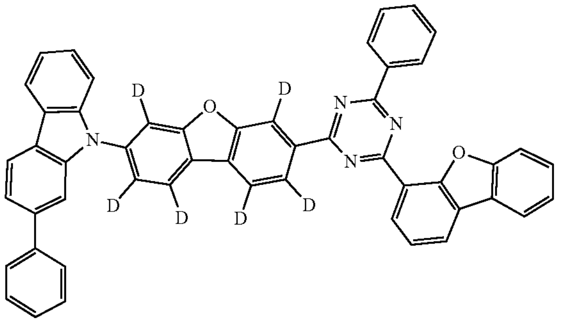

298
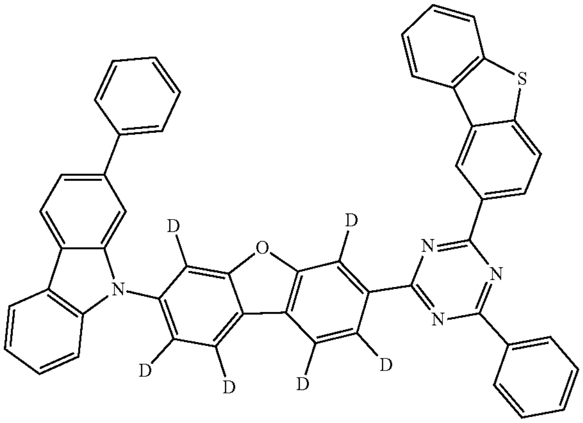
299
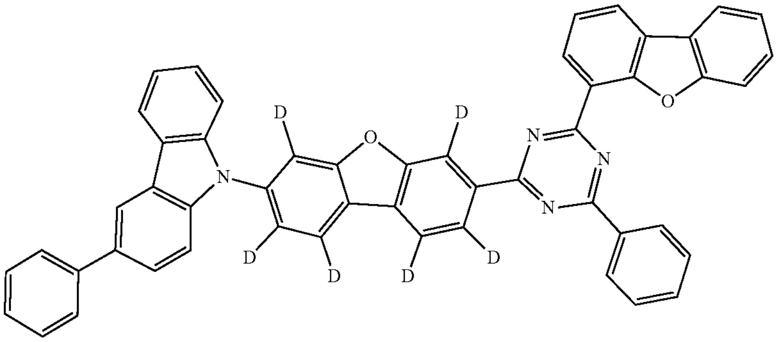
300
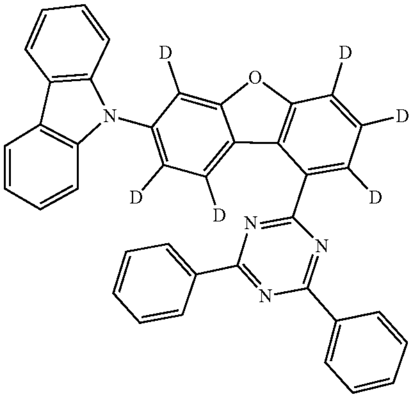
301
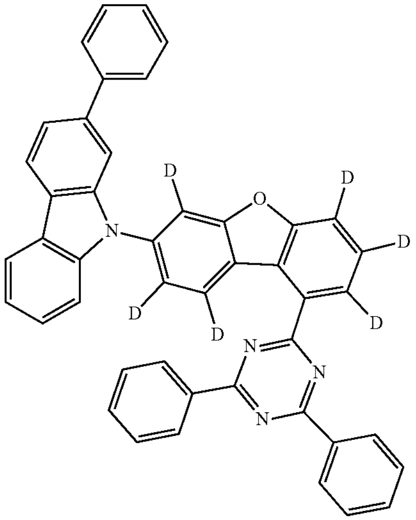

-continued
302
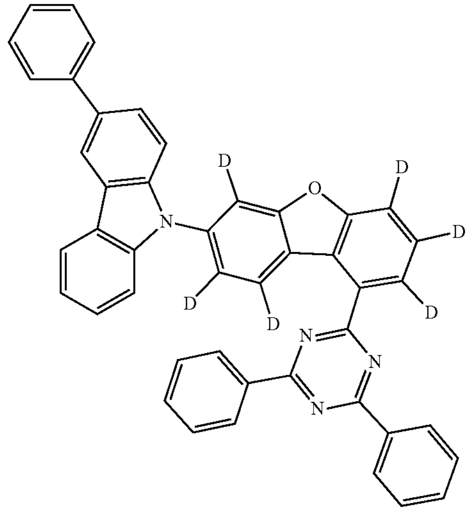
303
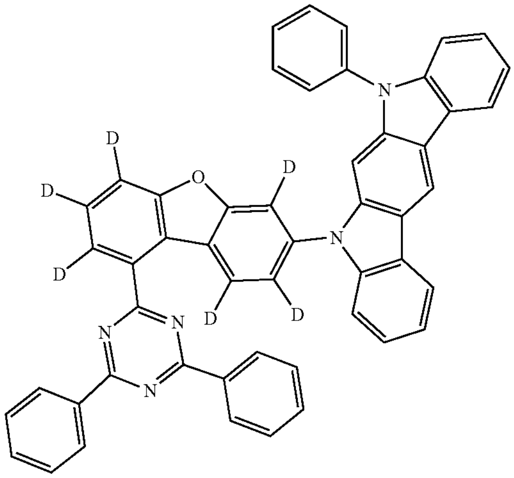
304
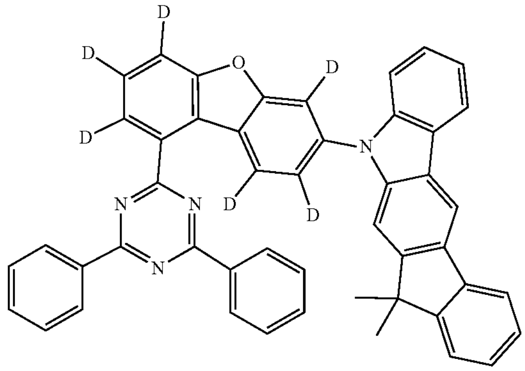
305
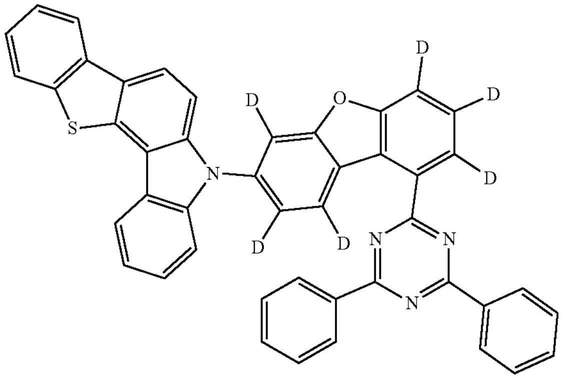
306
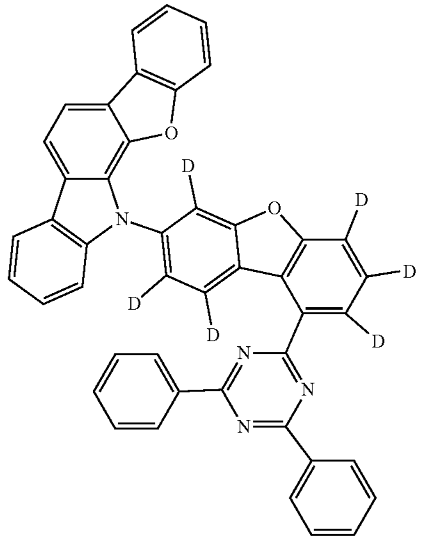
307
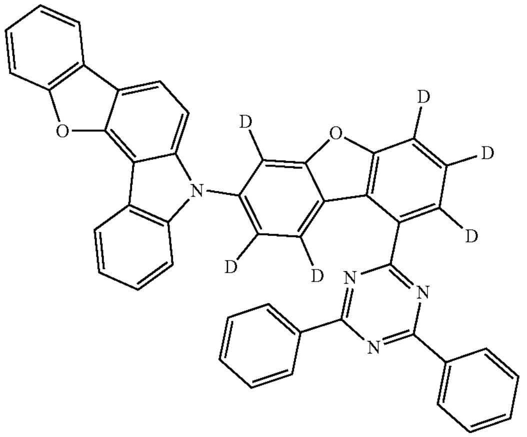

-continued
308
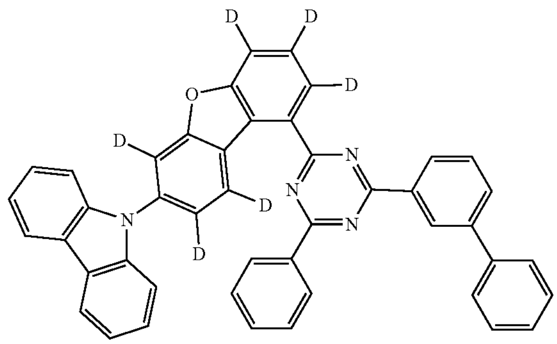
309
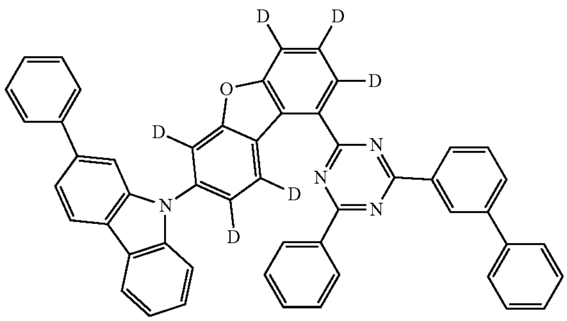
310
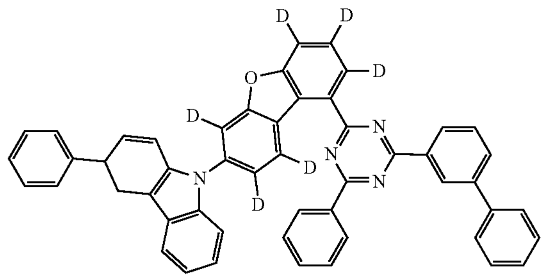
311
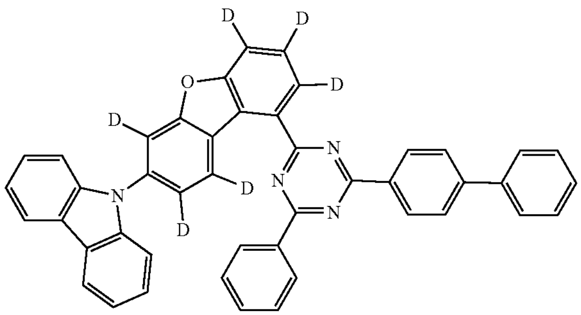
312
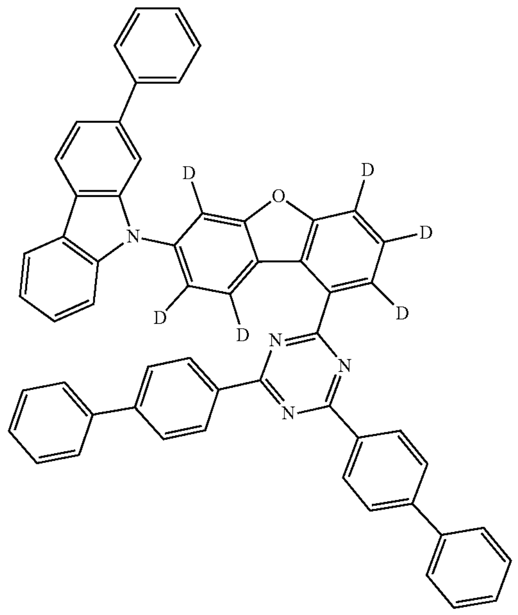
313
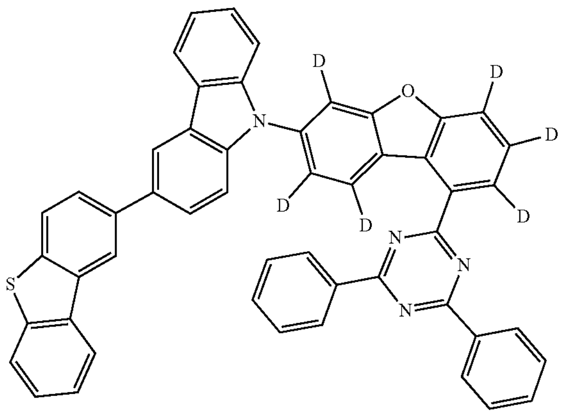

-continued
314
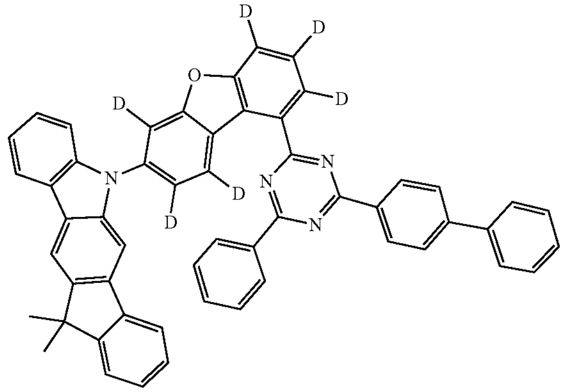
315
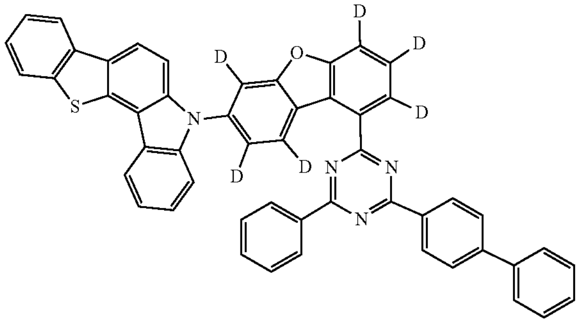
317
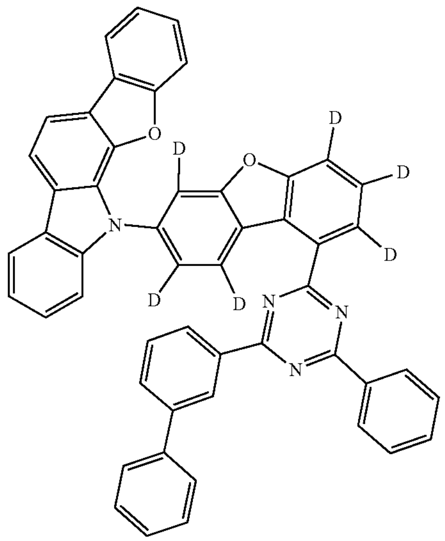
316
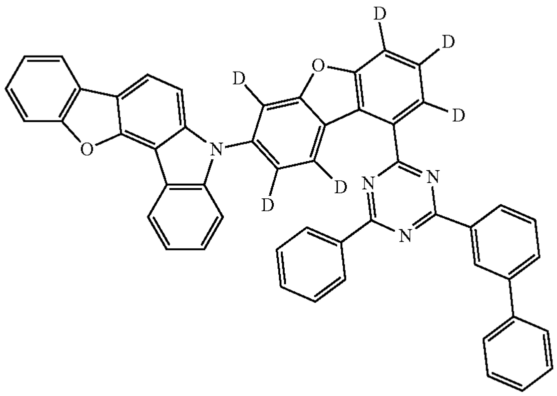
318
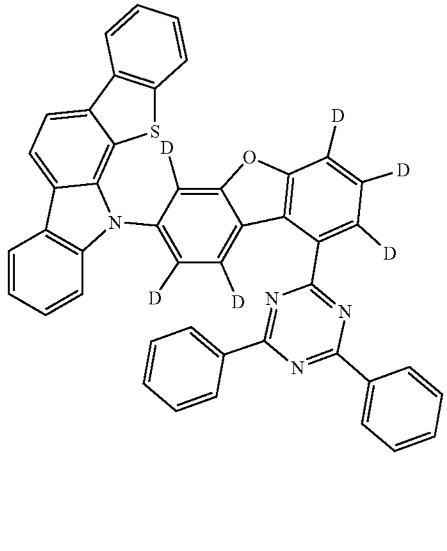
319
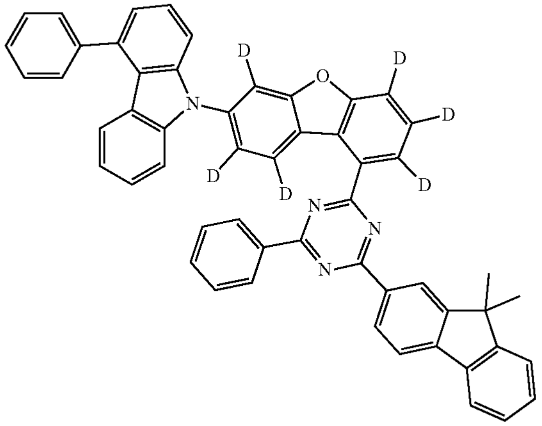

-continued
320
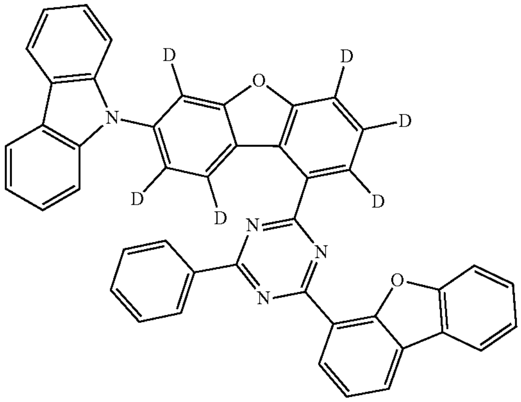
321
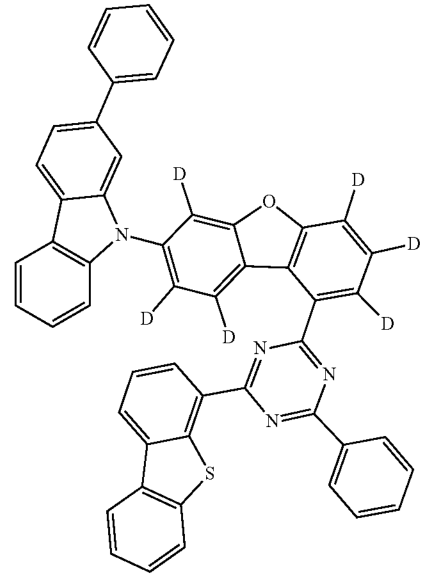
323
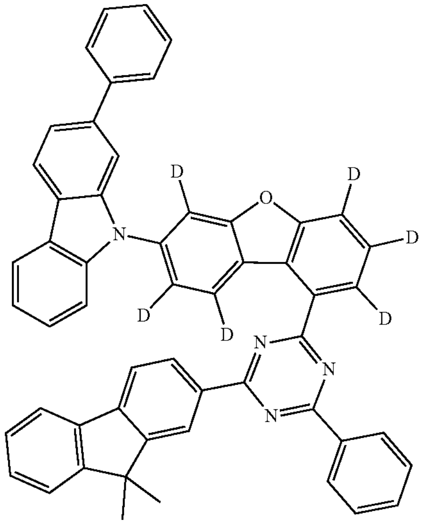
322
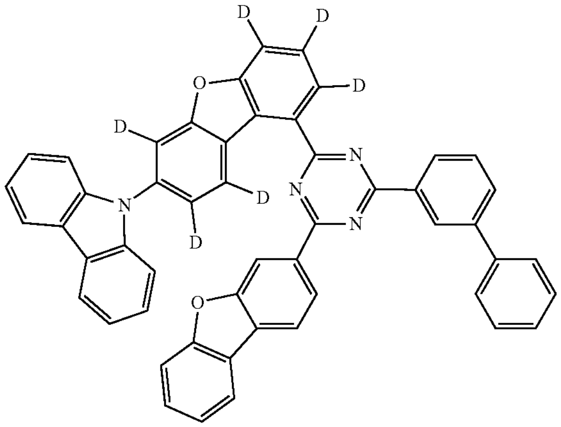
324
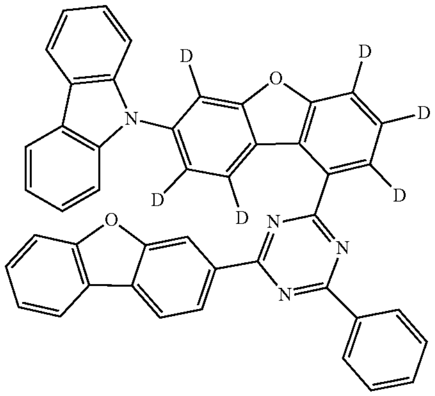
325
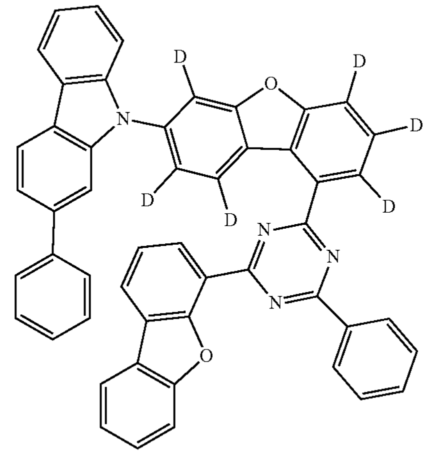

-continued
326
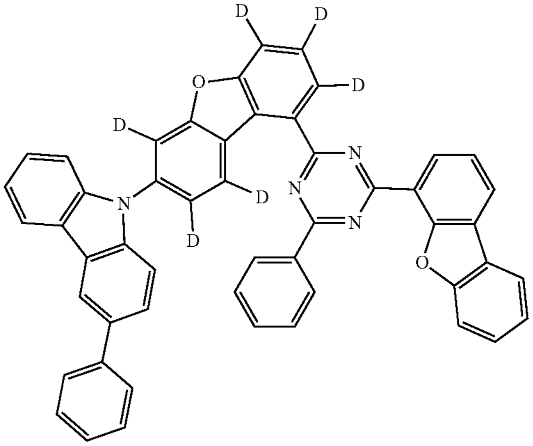
327
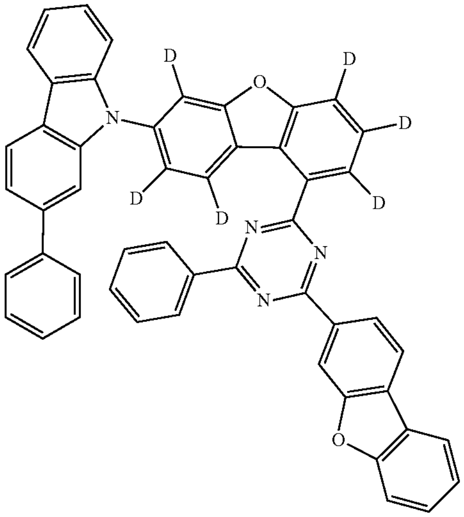
328
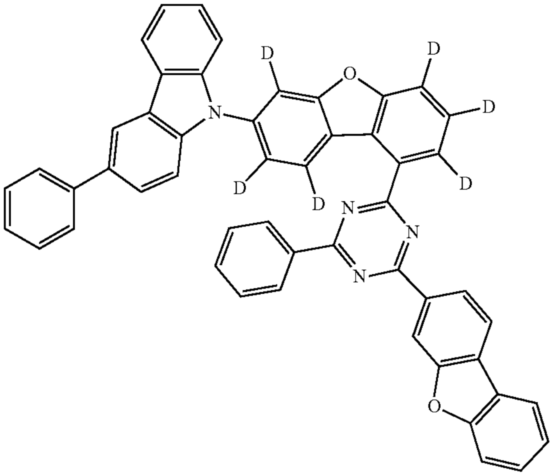
329
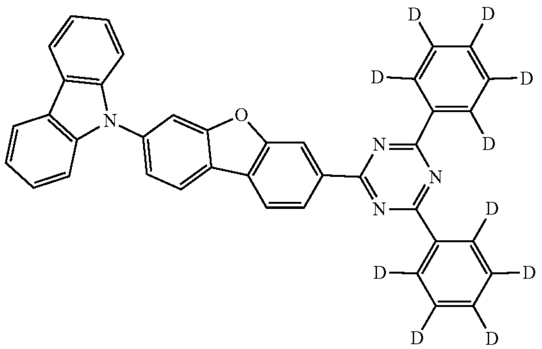
330
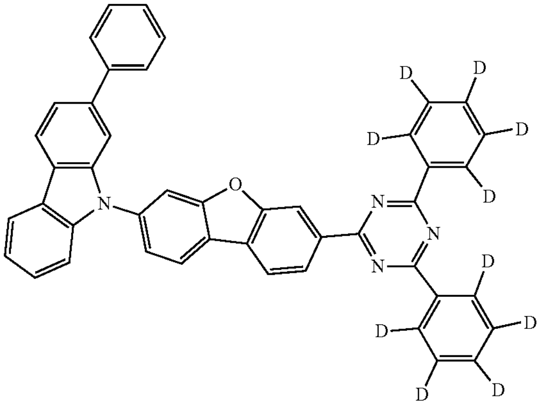
331
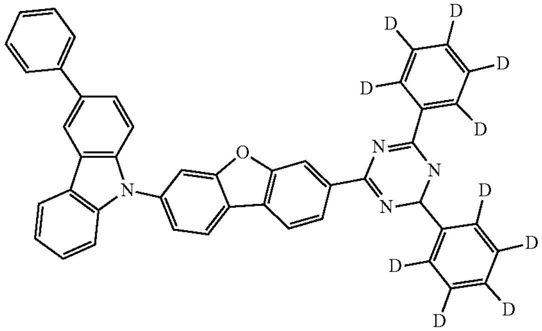

-continued
332
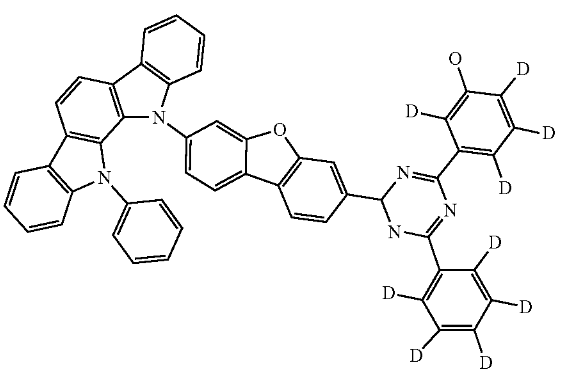
333
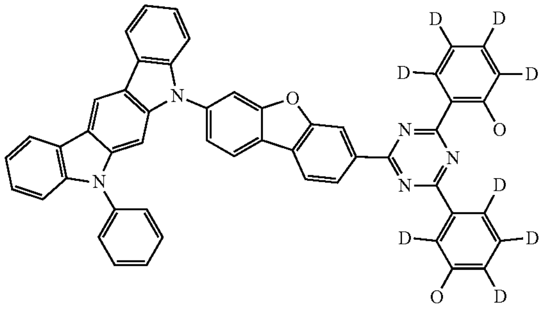
334
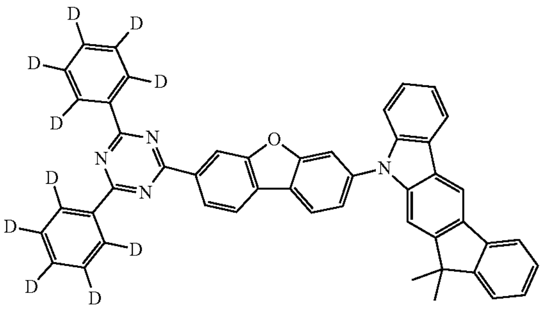
335
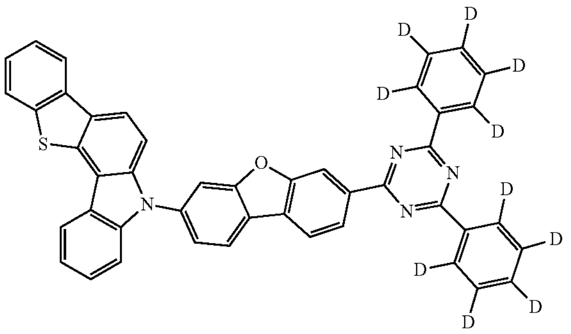
337
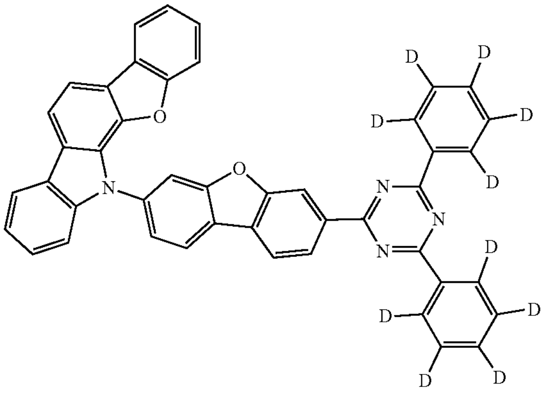
336
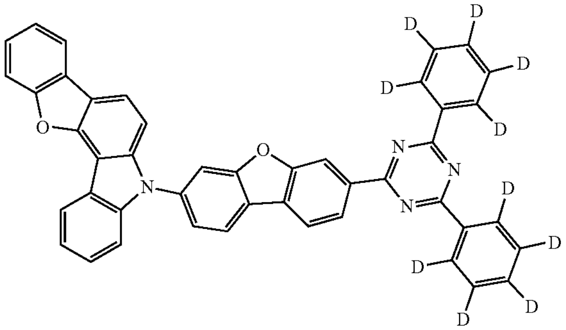
338
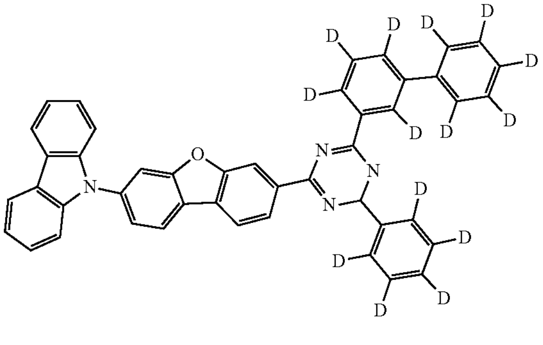
339
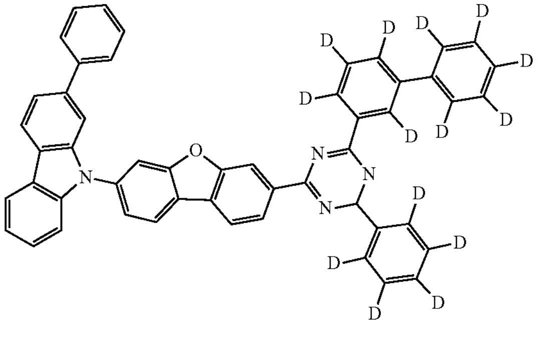

-continued
340
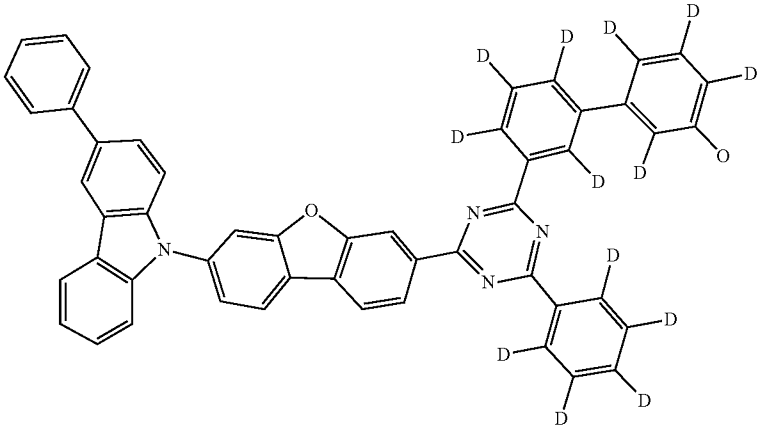
341
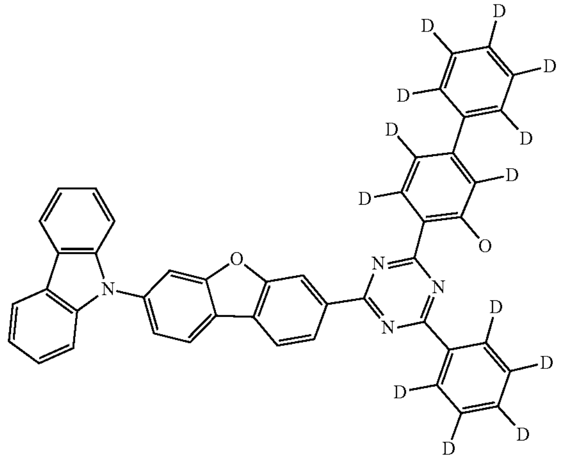
342
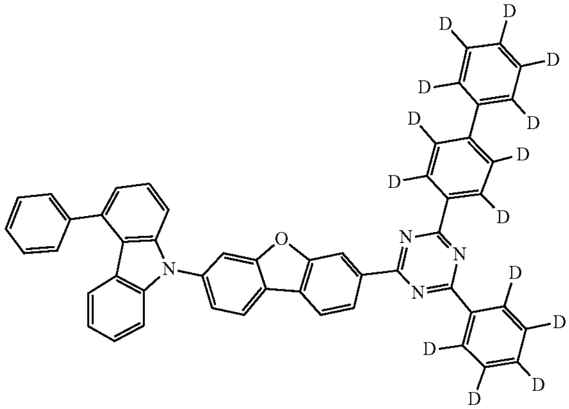
343
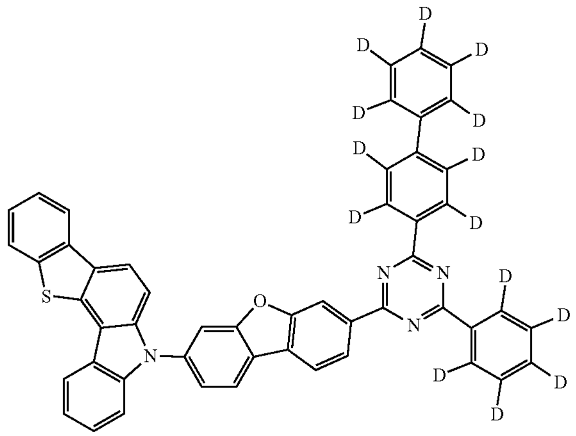
344
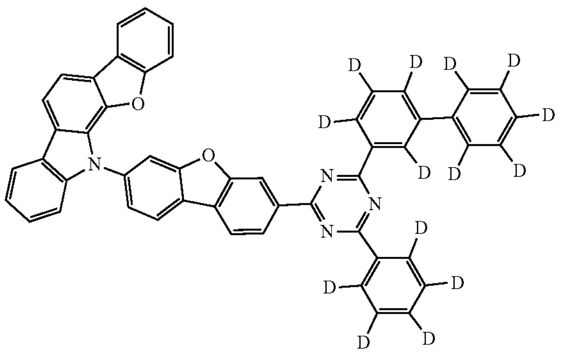

-continued
345
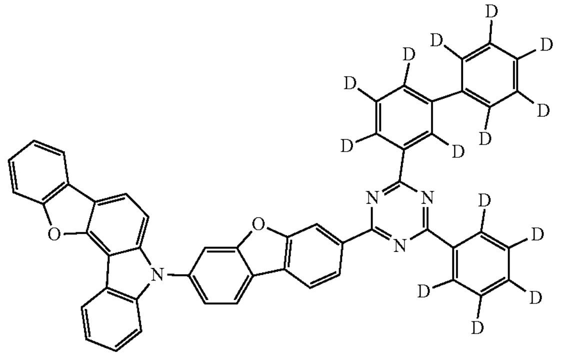
346
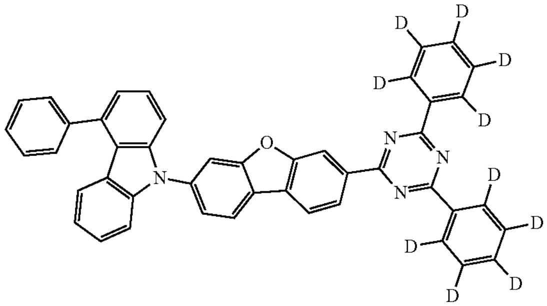
347
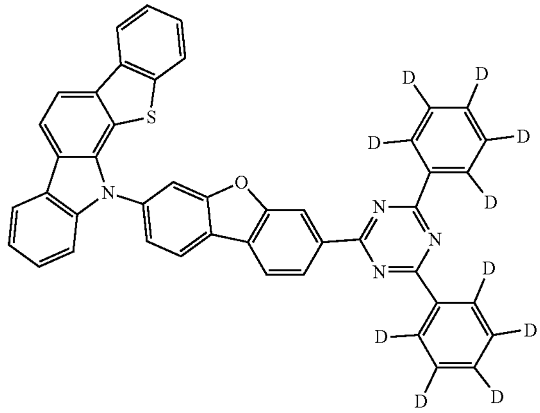
348
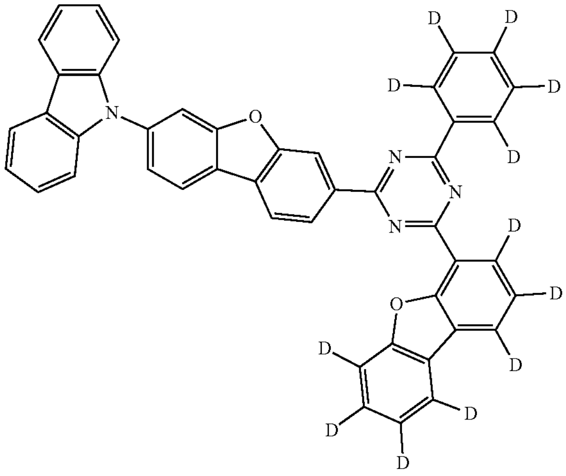
349
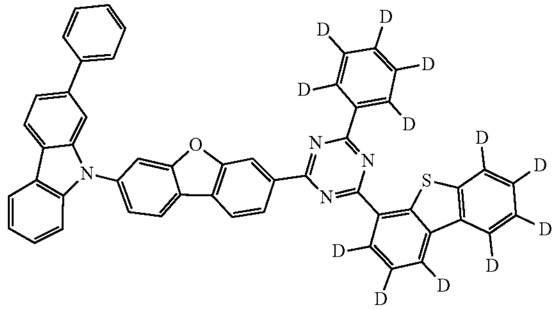
350
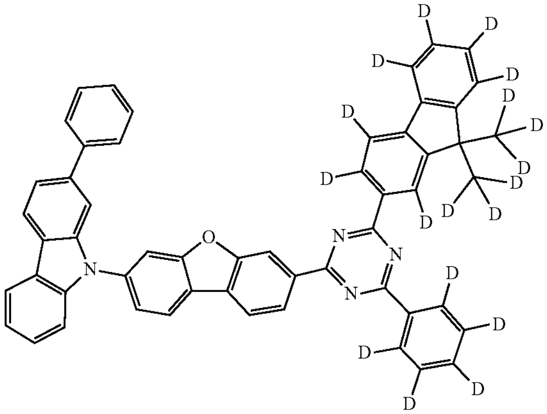

-continued
351
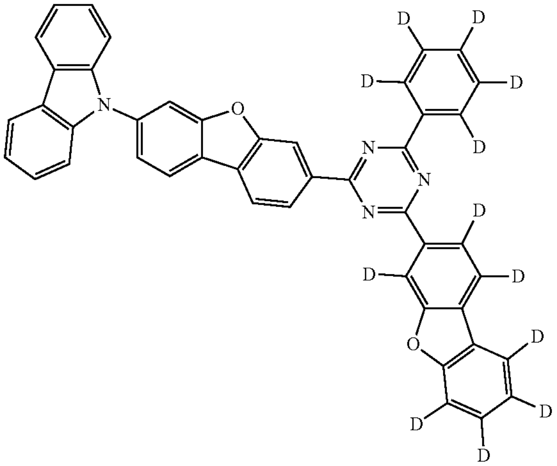
352
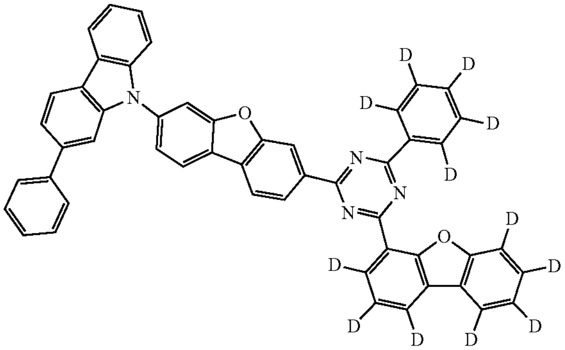
353
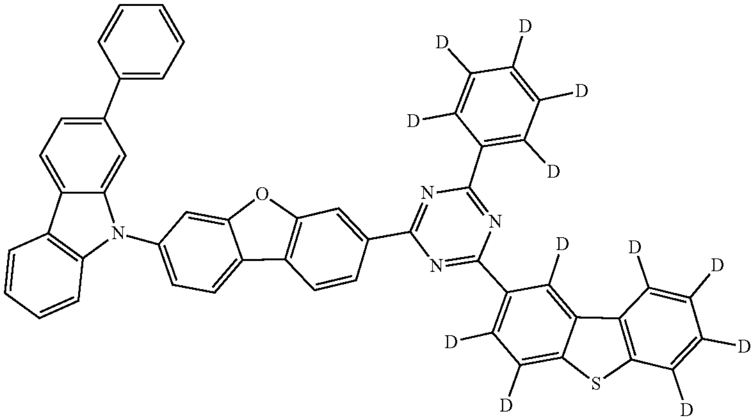
354
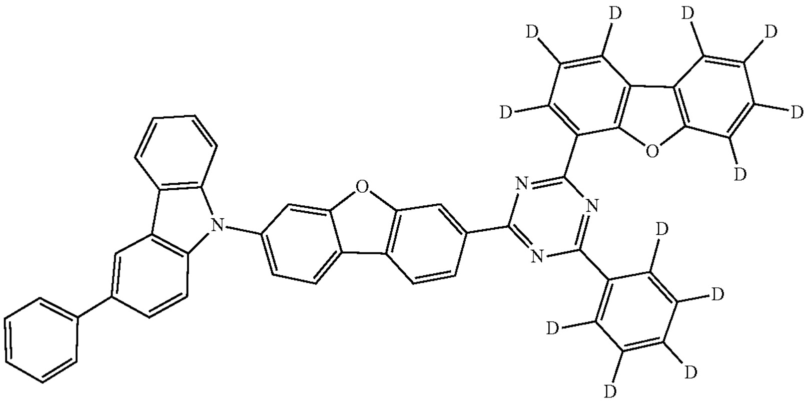

-continued
355
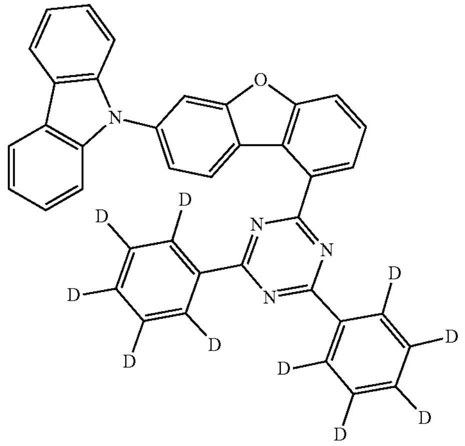
356
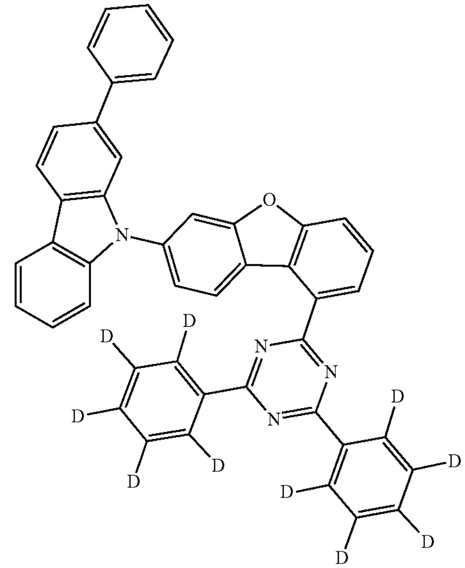
357
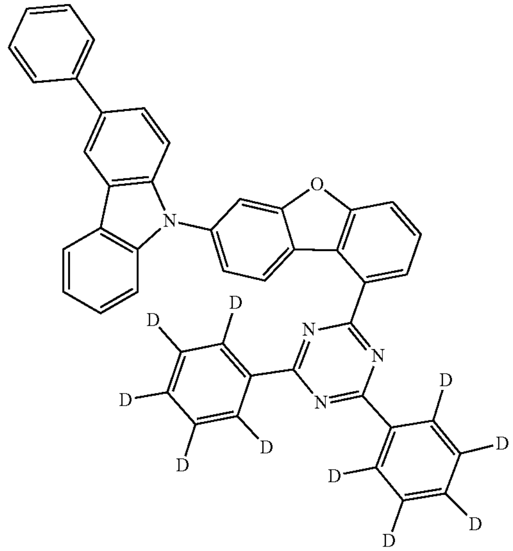
358
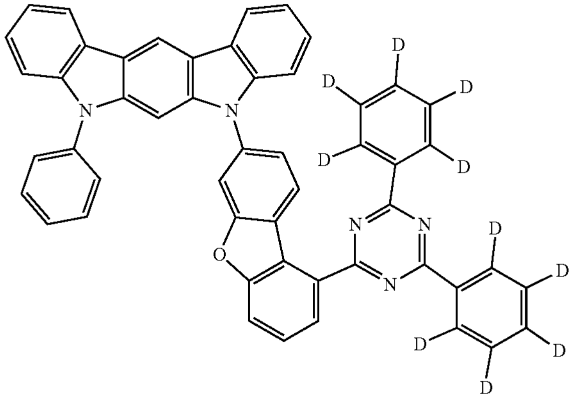
359
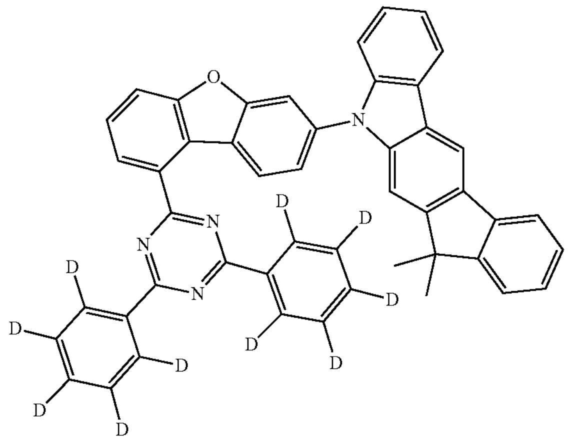
360
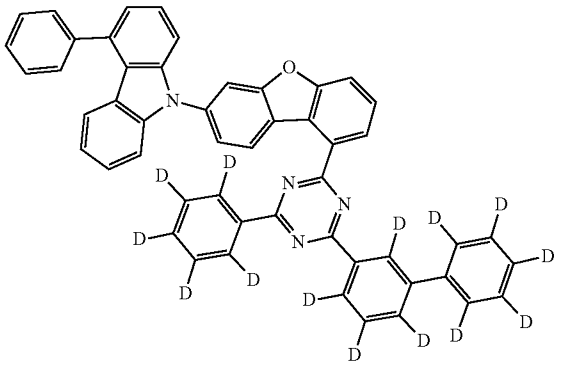

-continued
361
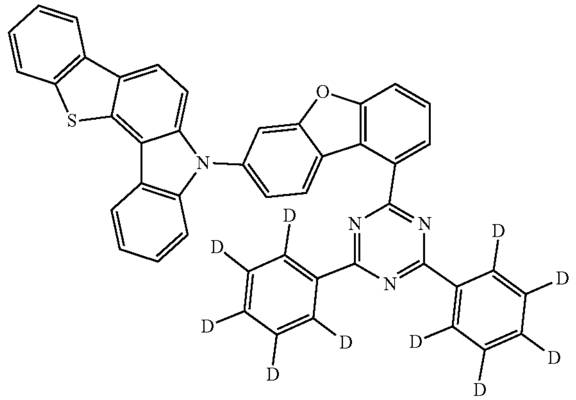
362
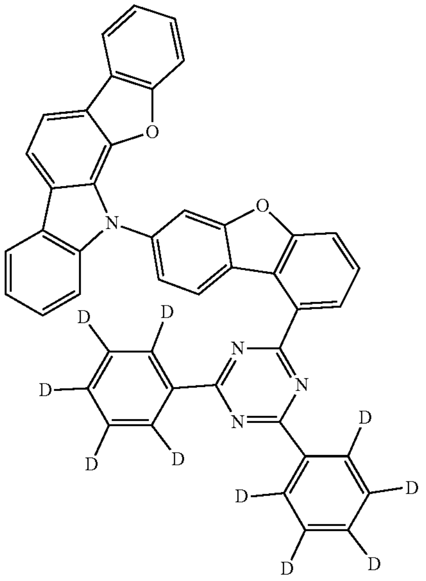
363
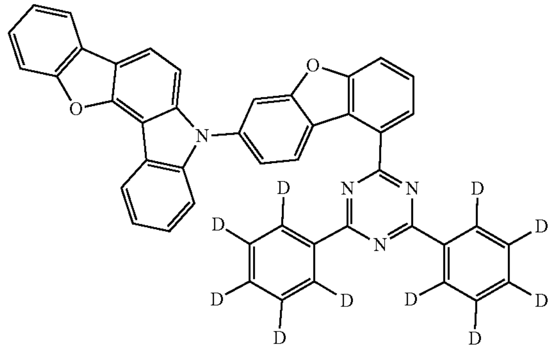
364
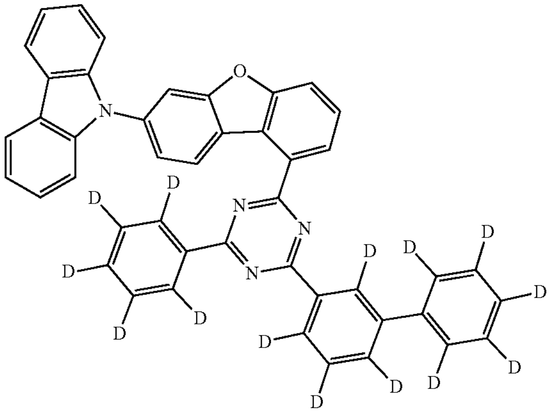
365
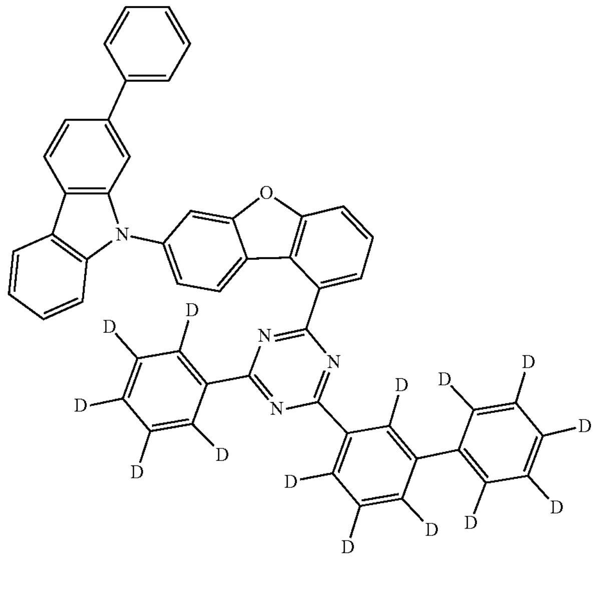

-continued
366
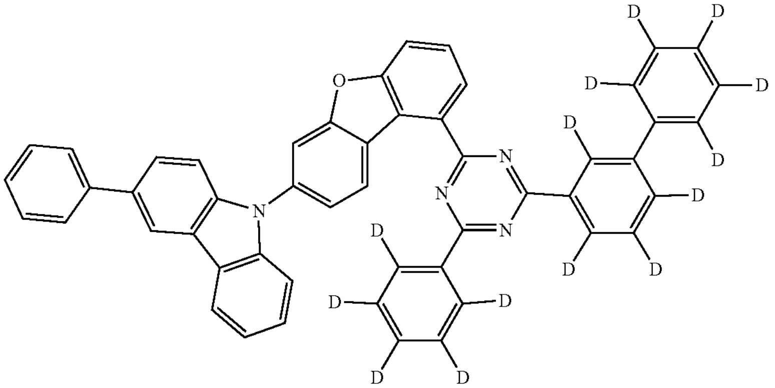
367
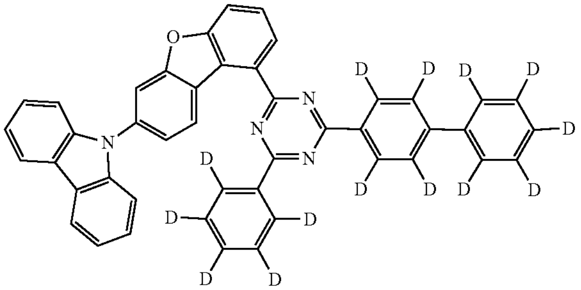
368
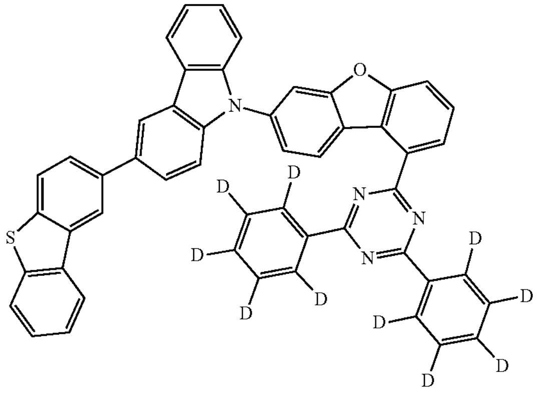
369
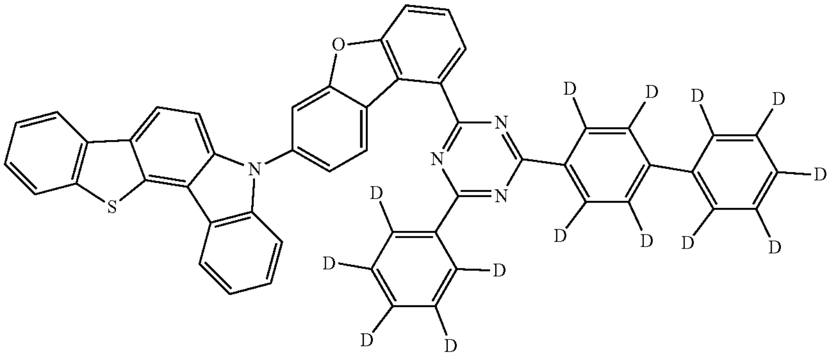
370
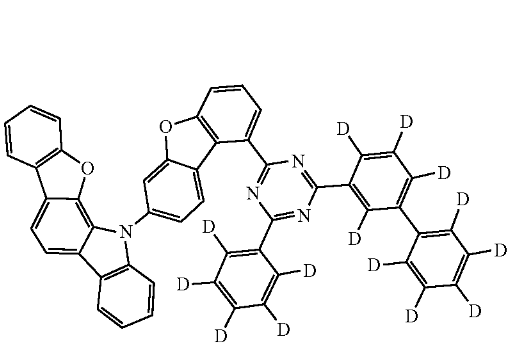
371
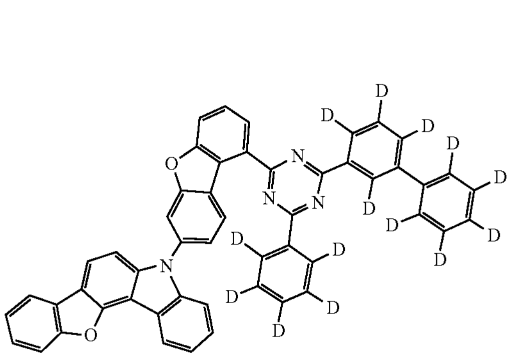

-continued
372
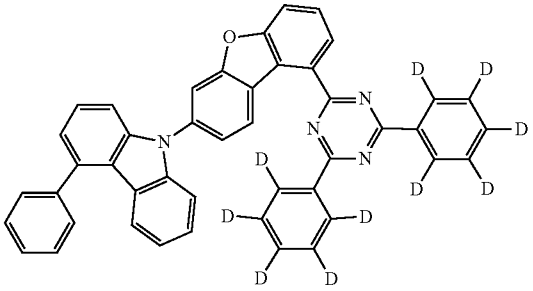
373
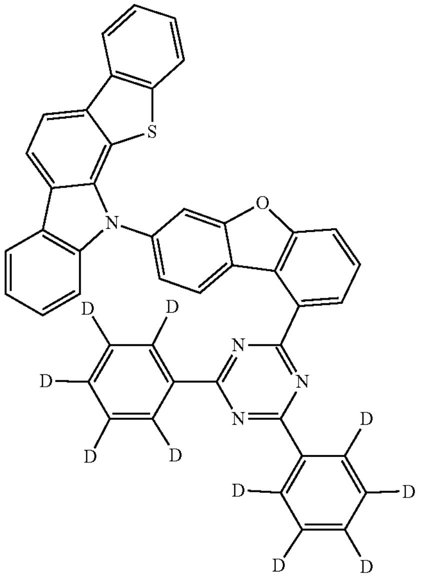
374
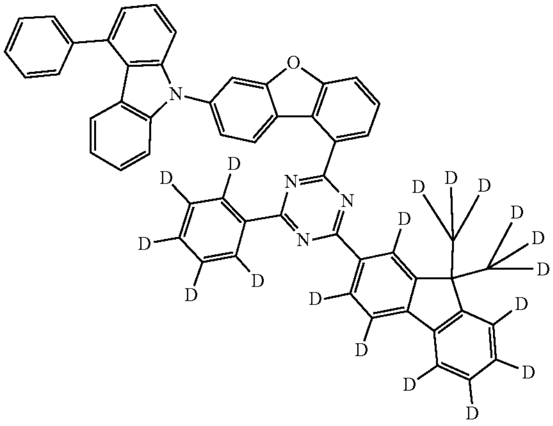
375
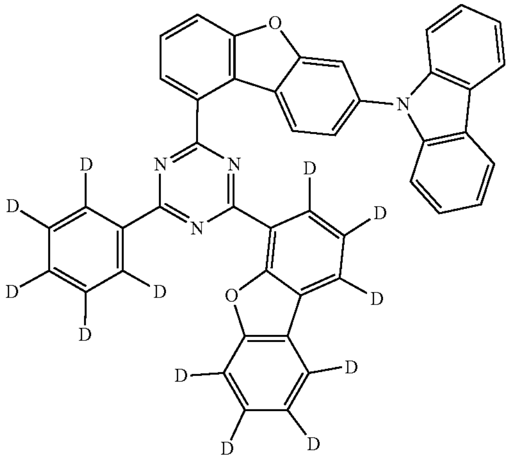

-continued
376
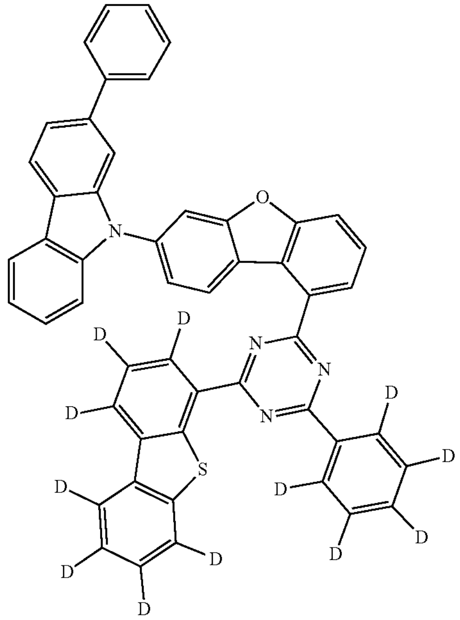
377
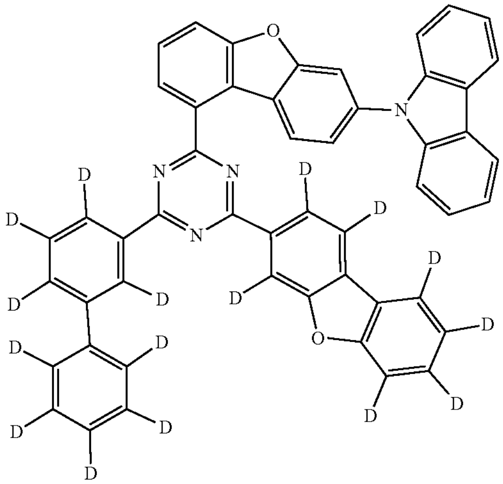
378
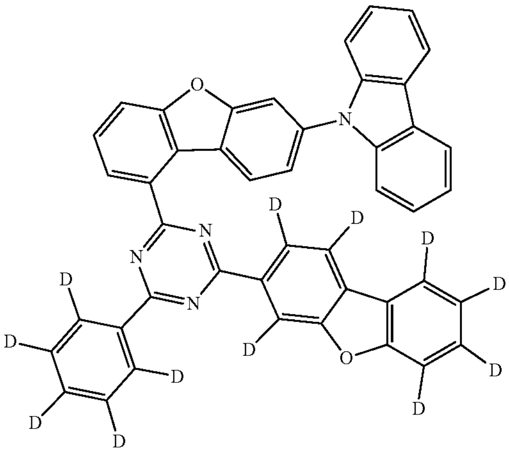
379
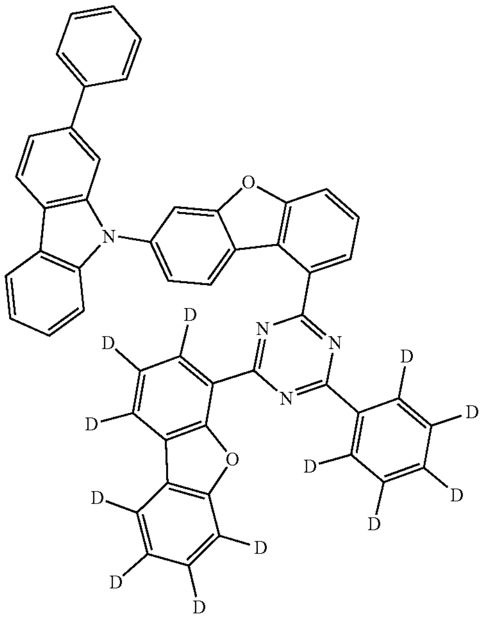

-continued
380
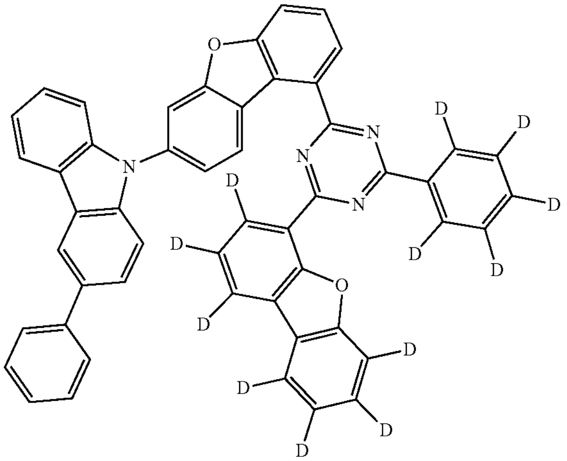
381
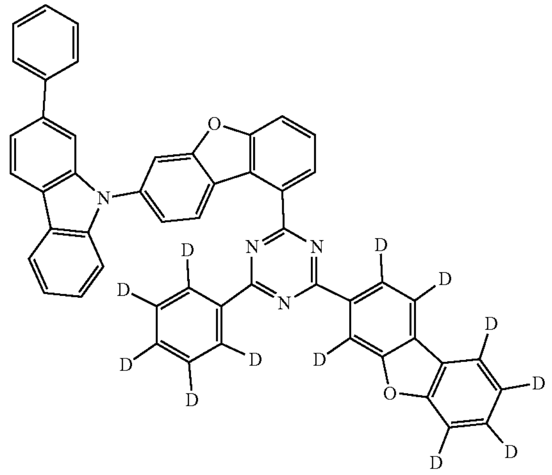
382
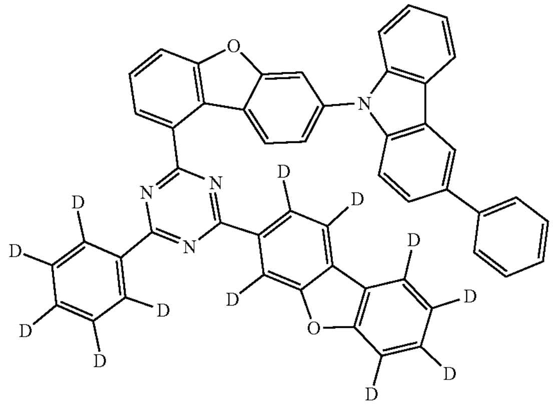
383
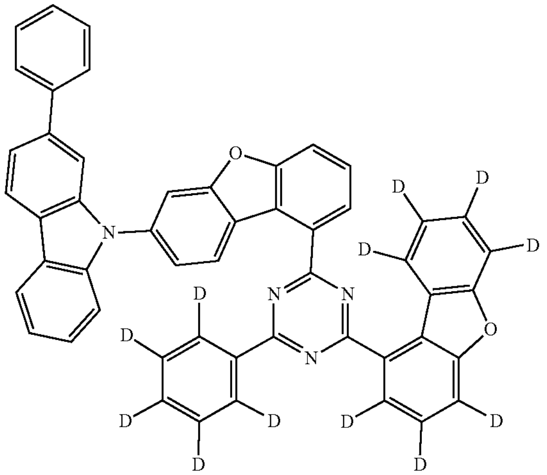
384
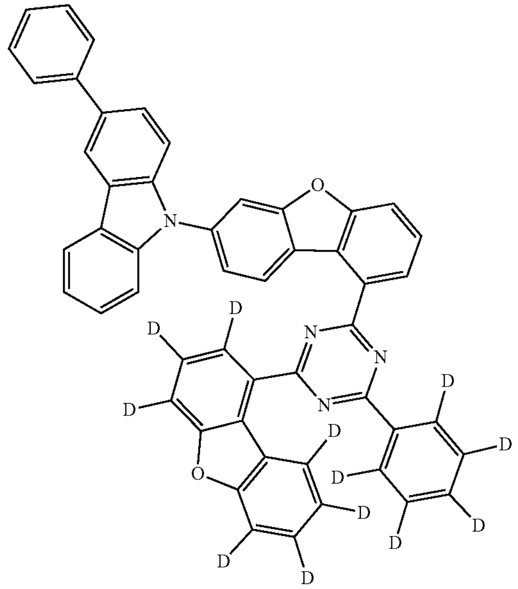
385
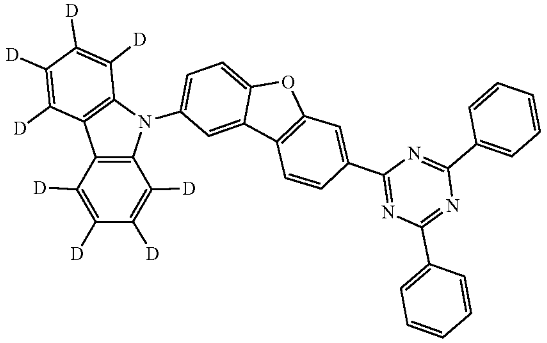

-continued
386
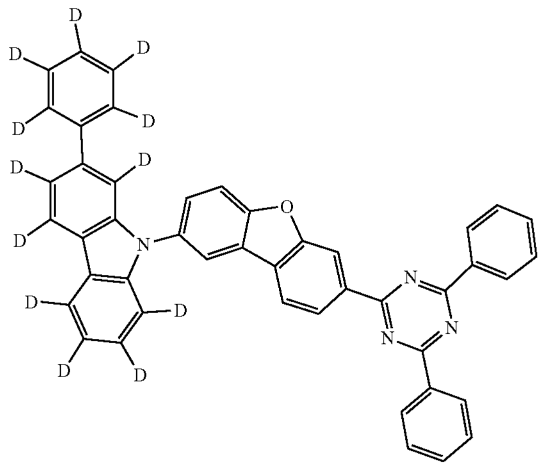
387
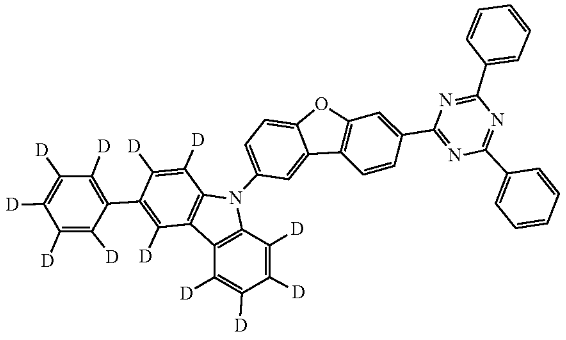
388
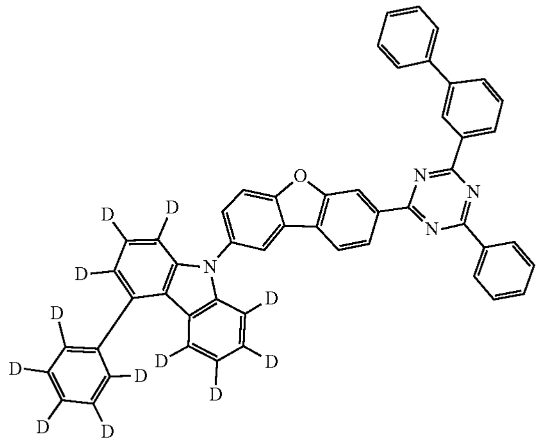
389
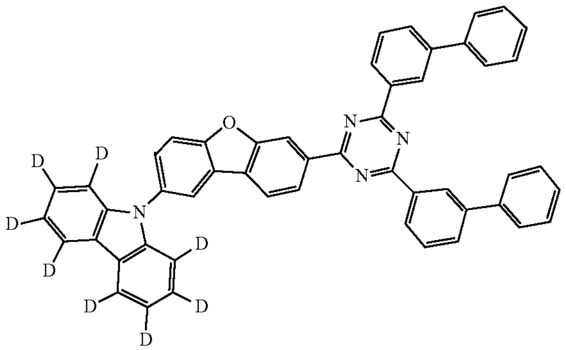
390
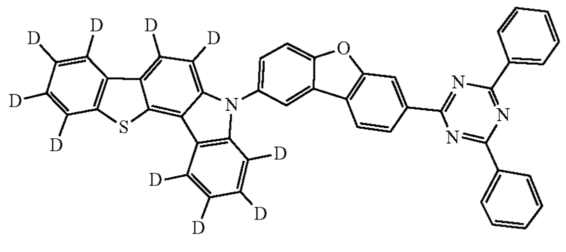
391
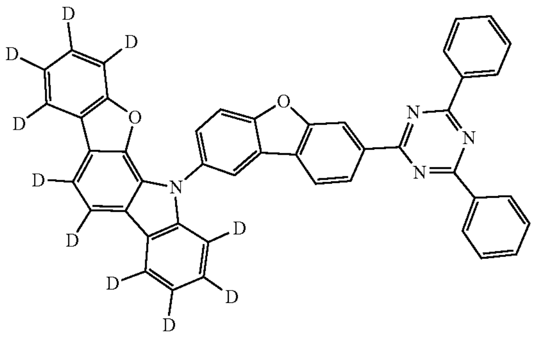

-continued
392
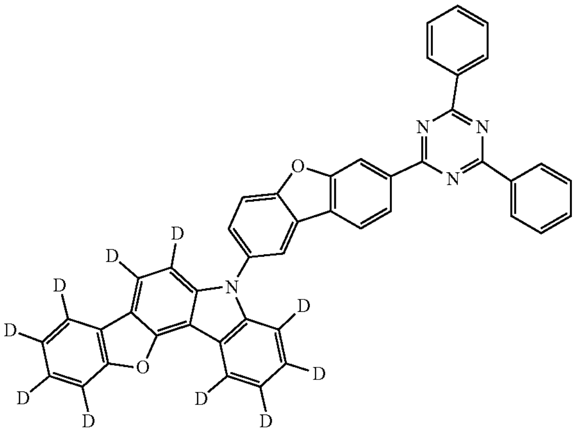
393
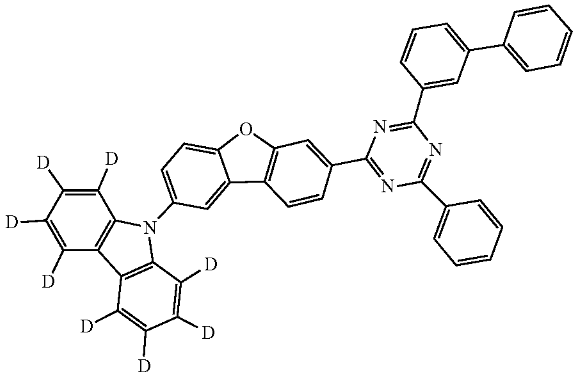
394
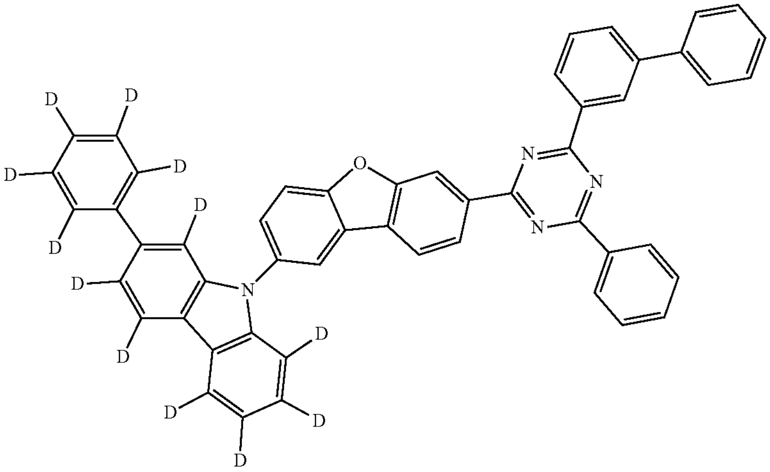
395
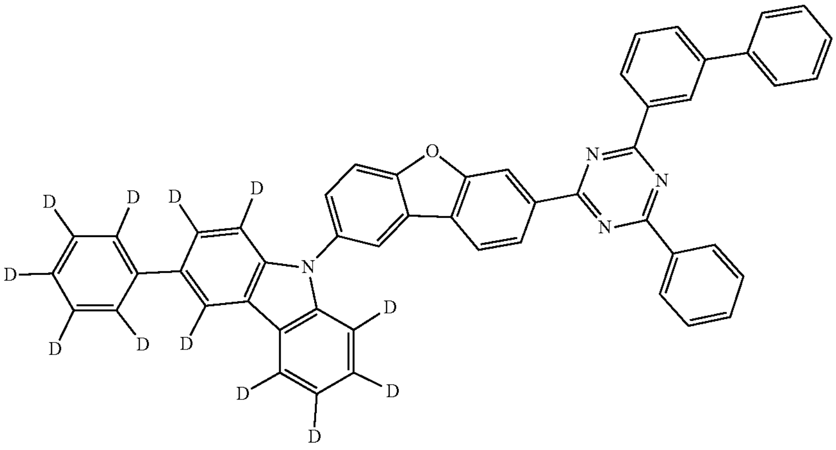

-continued
396
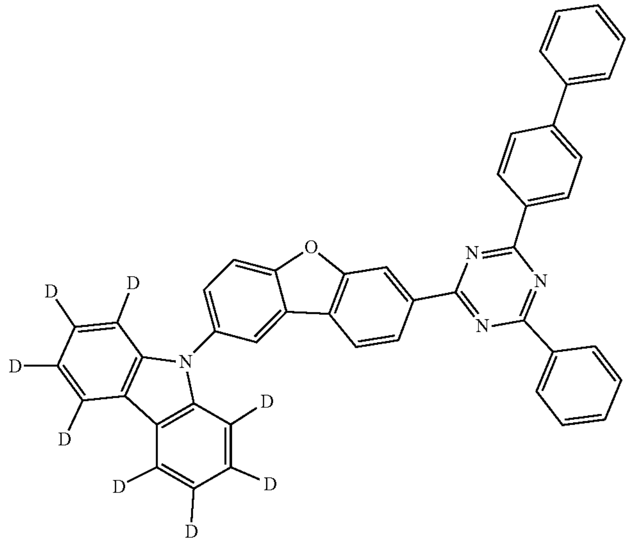
397
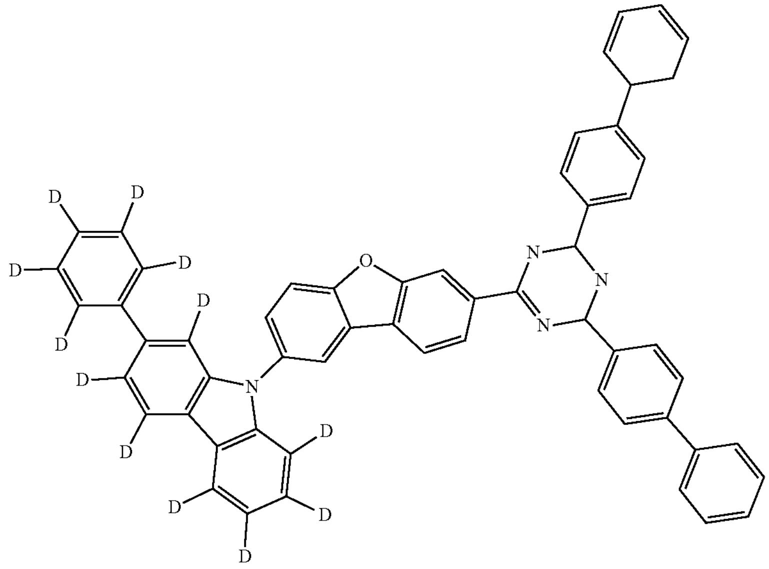
398
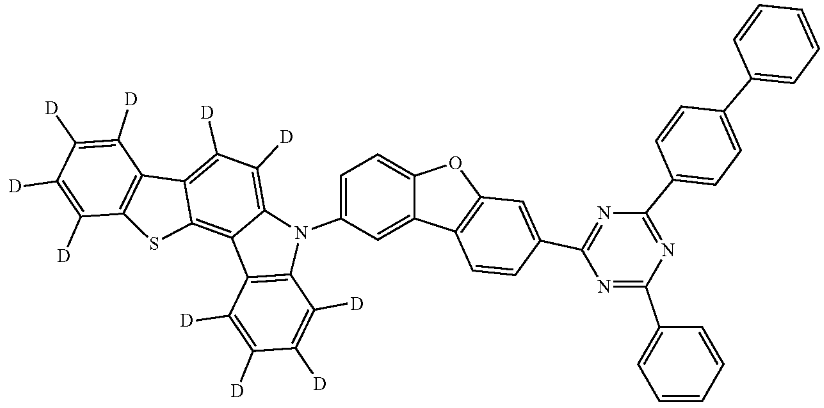

-continued
399
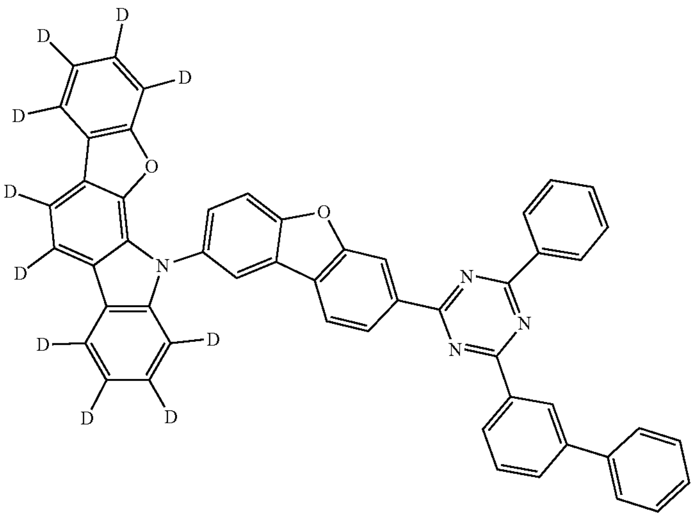
400
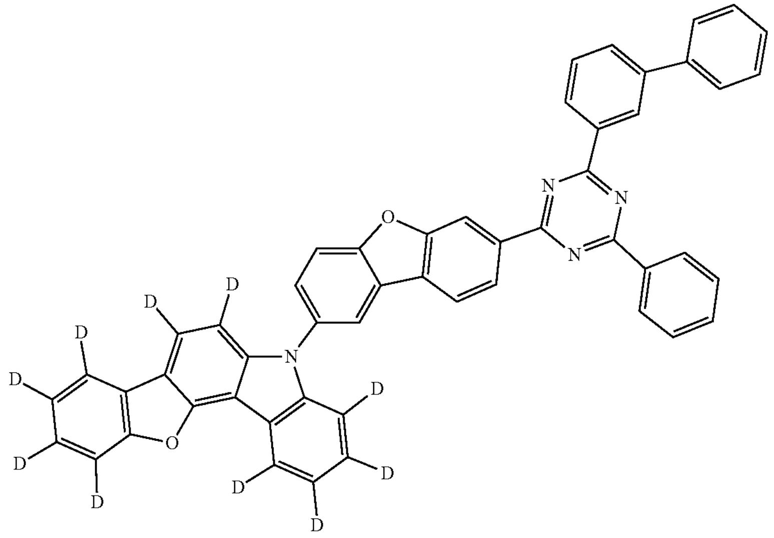
401
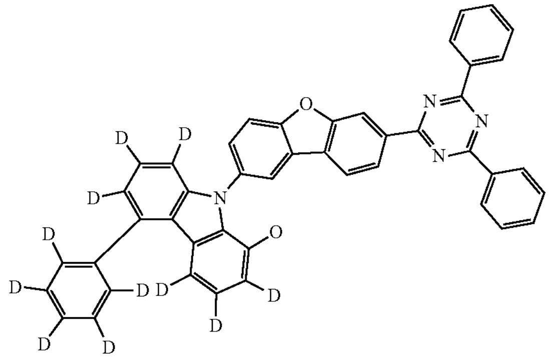
402
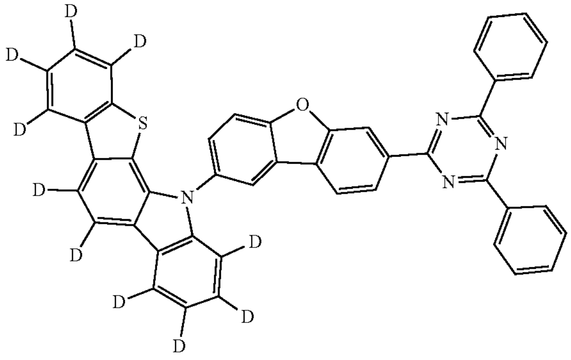

-continued
403
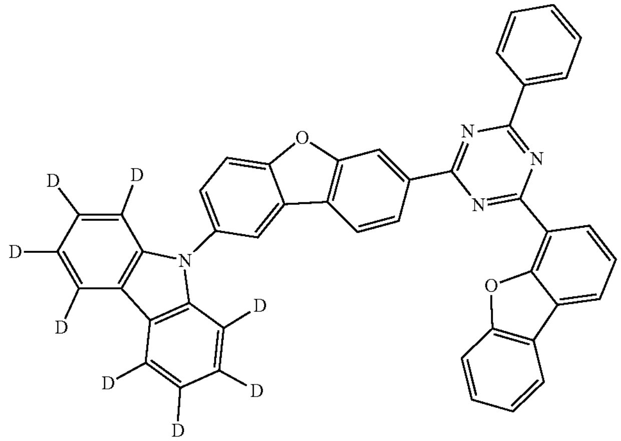
404
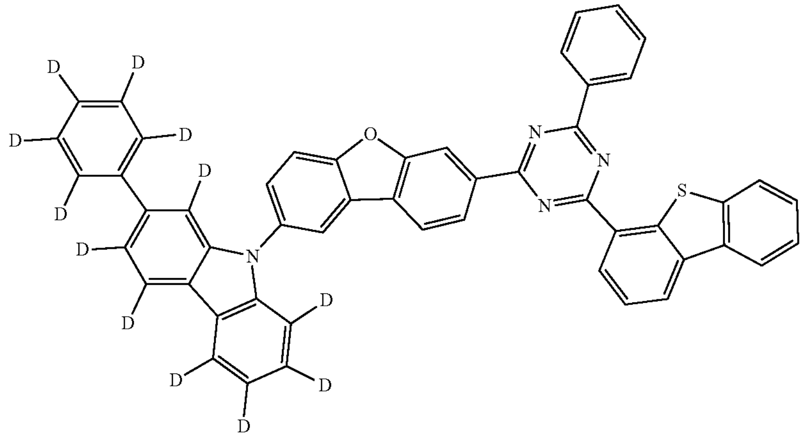
405
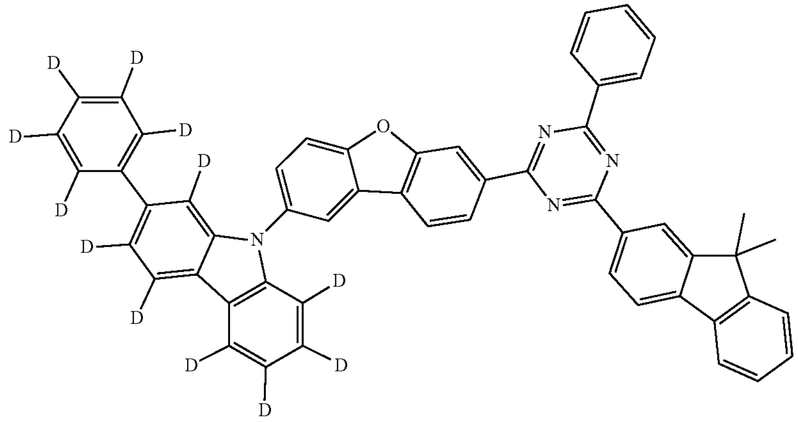

-continued
406
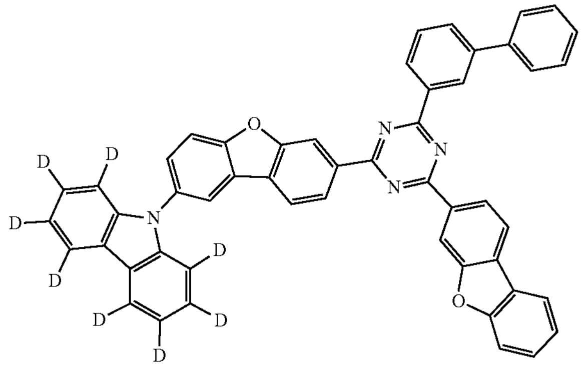
407
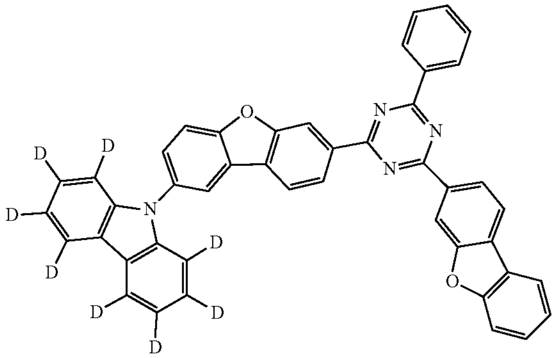
408
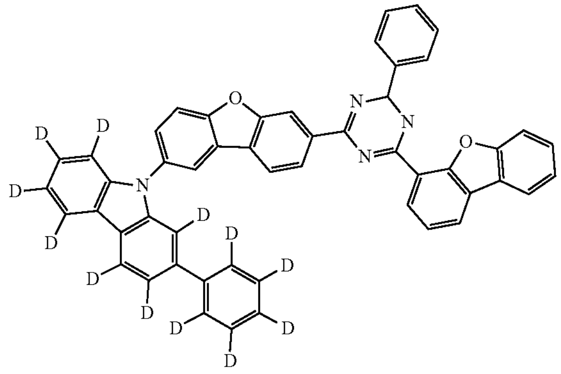
409
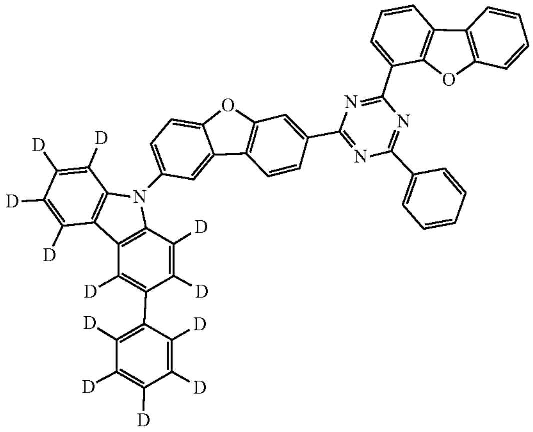
410
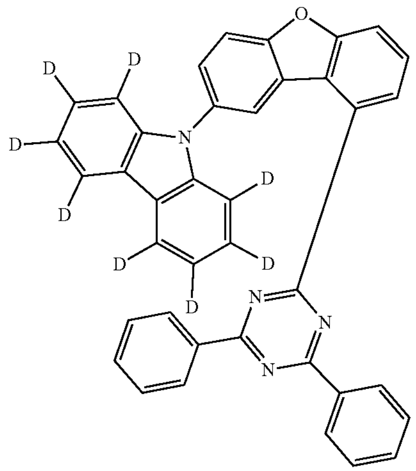
411
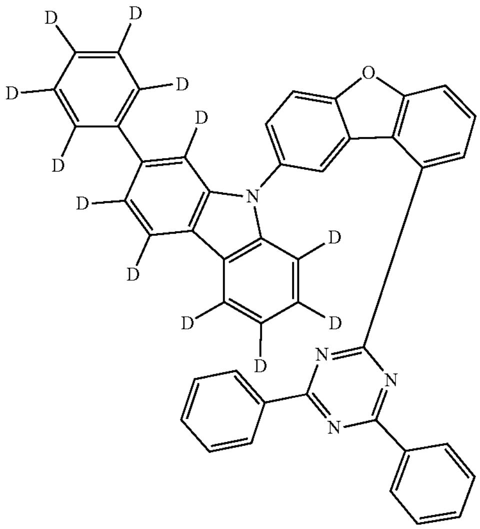

-continued
412
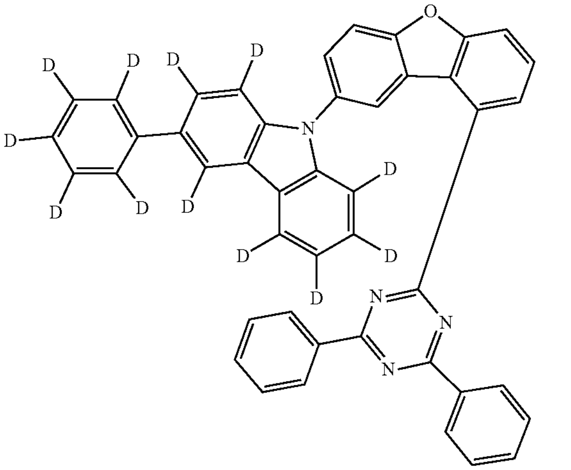
413
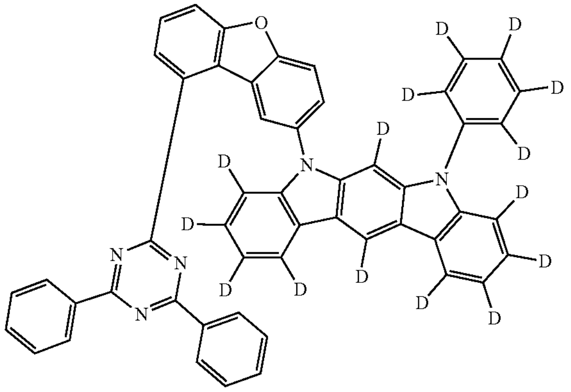
414
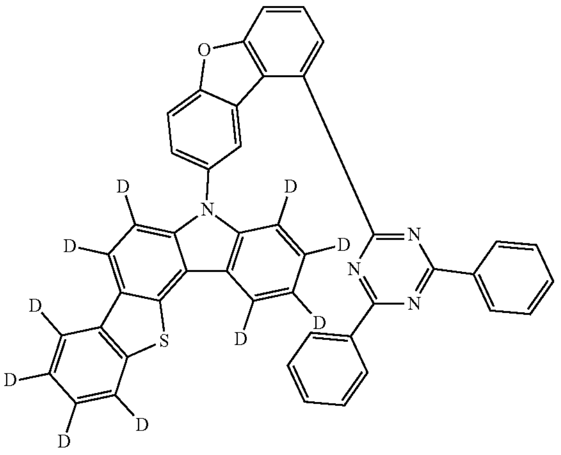
415
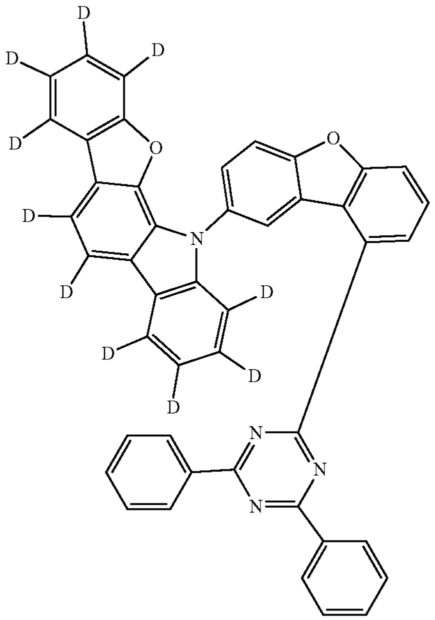
416
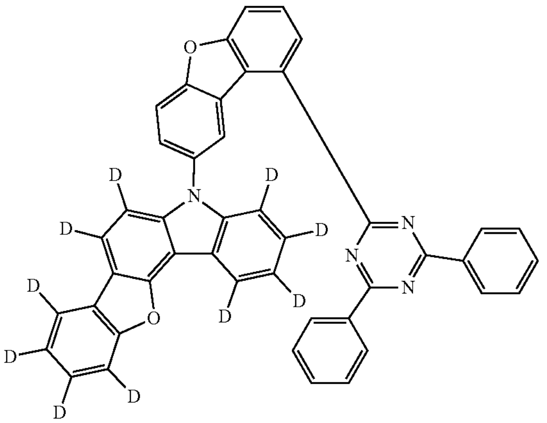
417
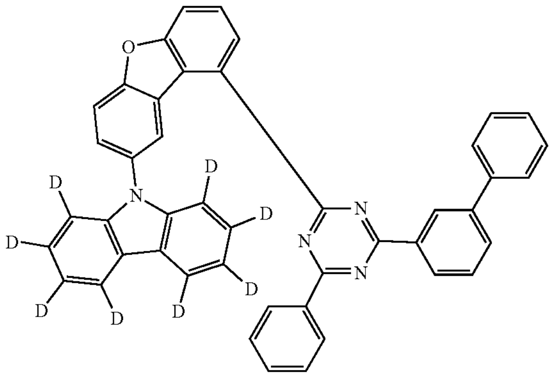

-continued
418
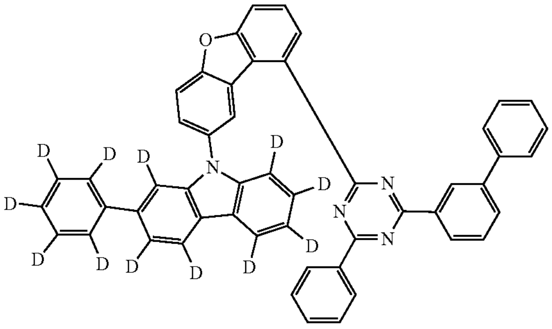
419
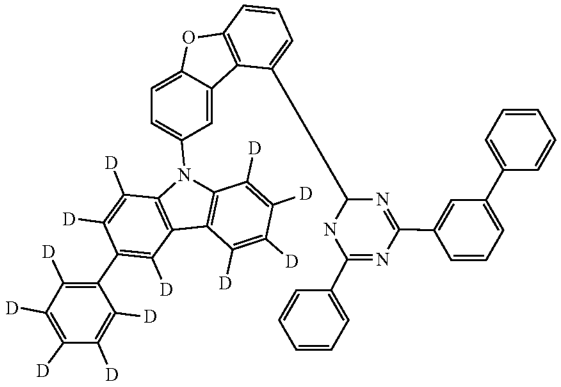
420
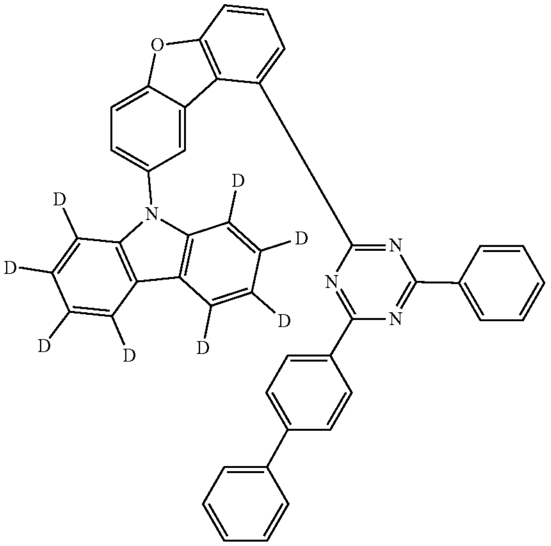
421
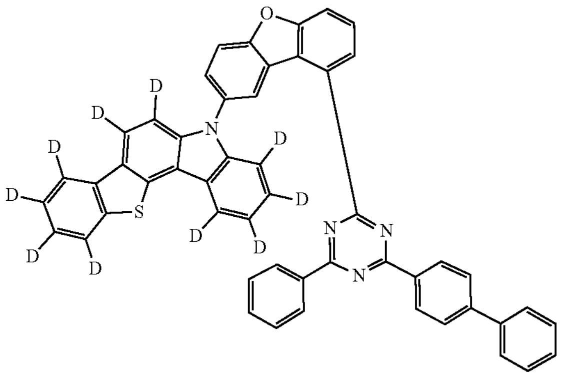
422
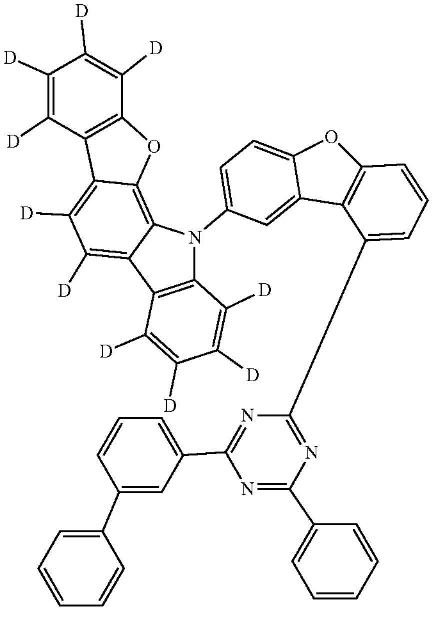
423
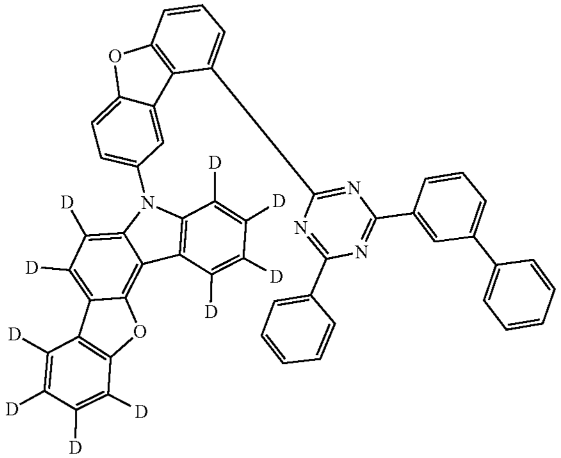

-continued
424
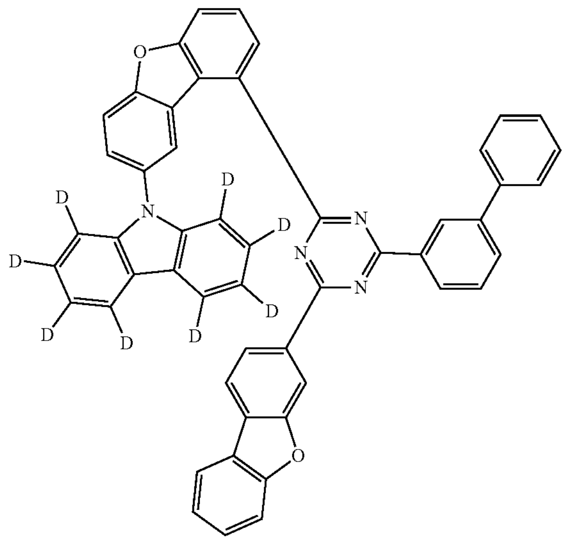
425
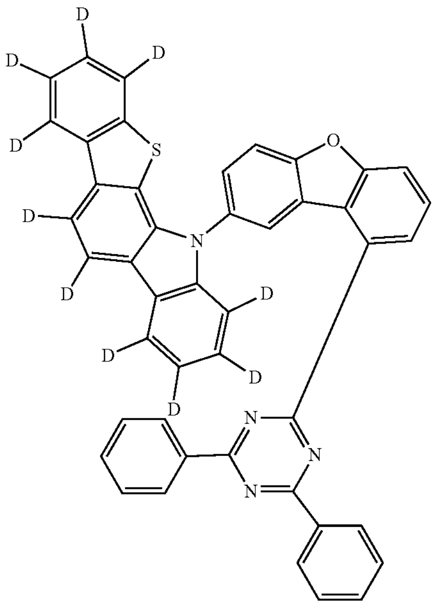
426
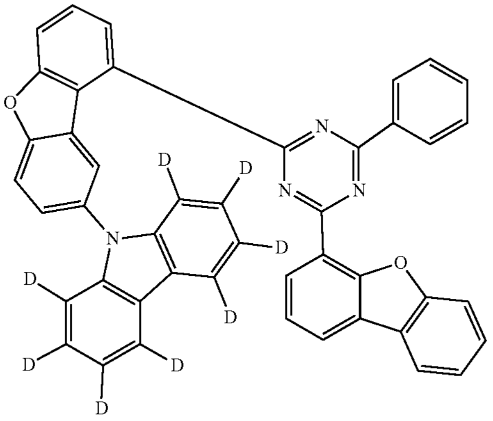
427
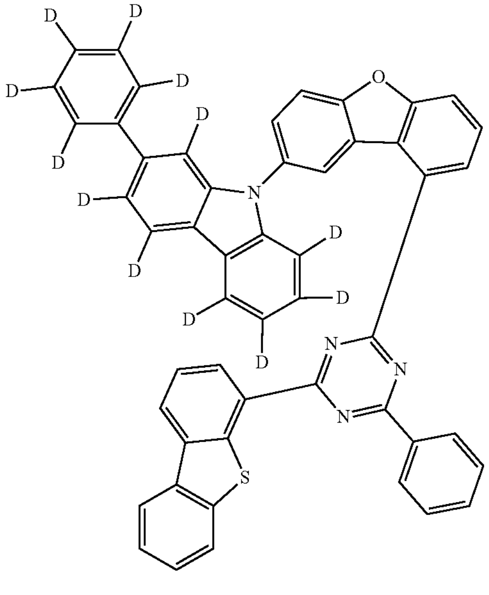

-continued
428
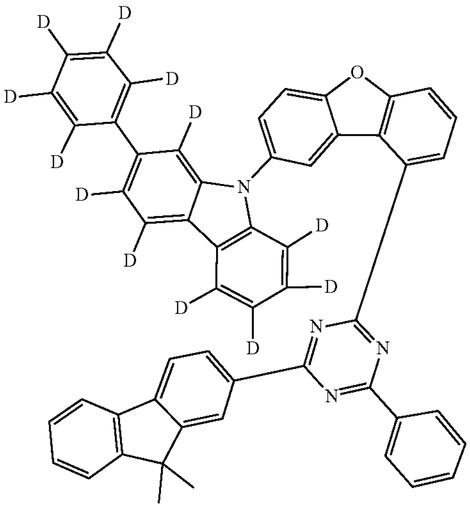
429
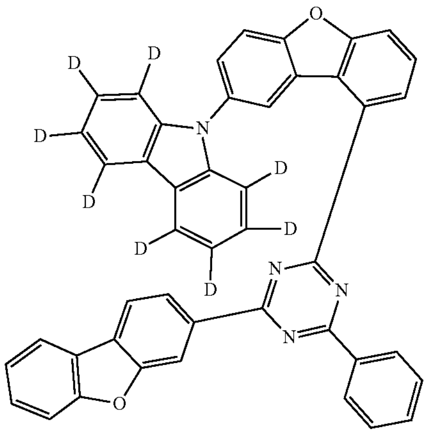
430
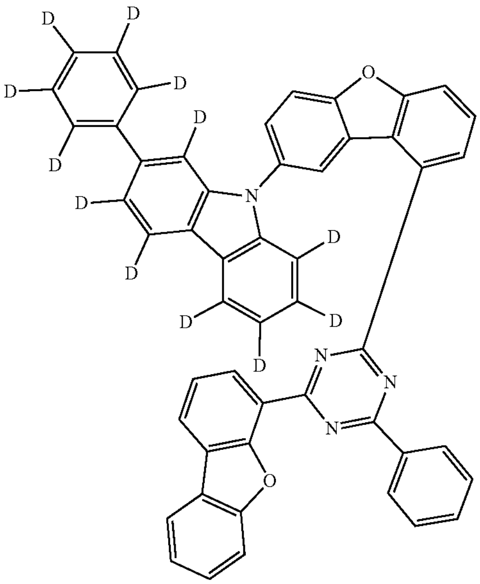
431
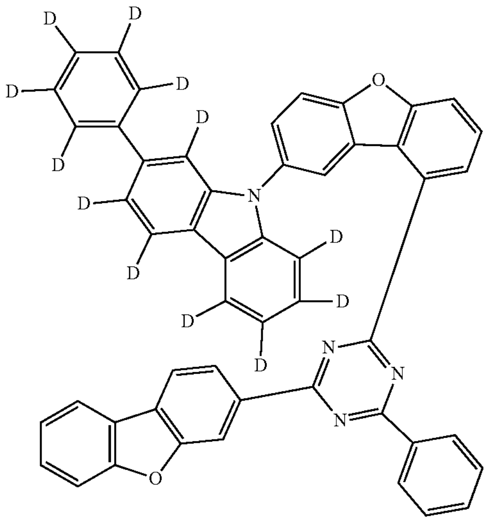
432
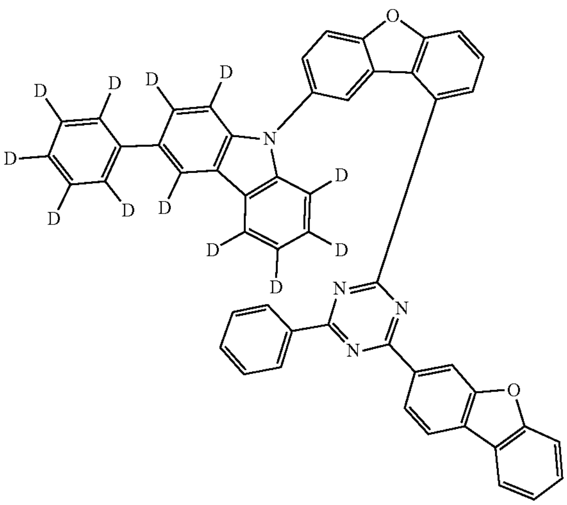
433
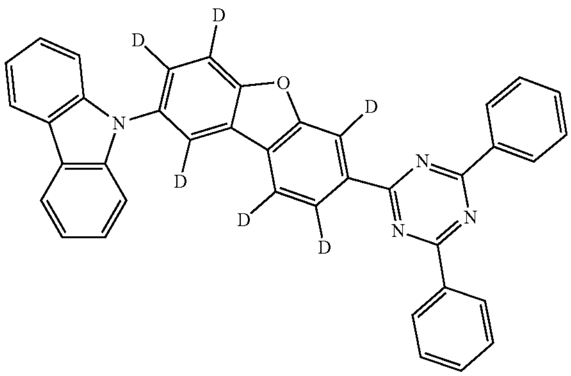

-continued
434
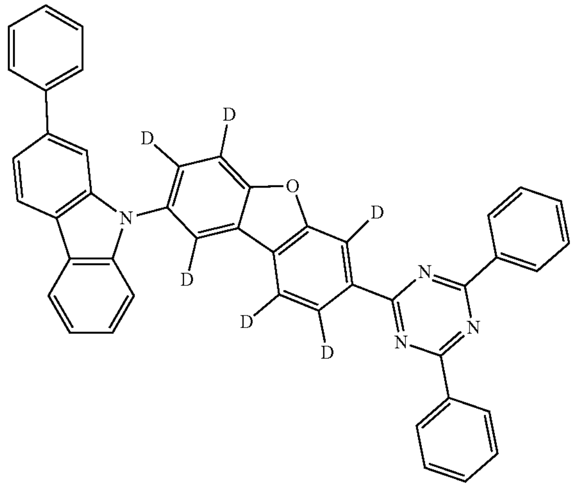
435
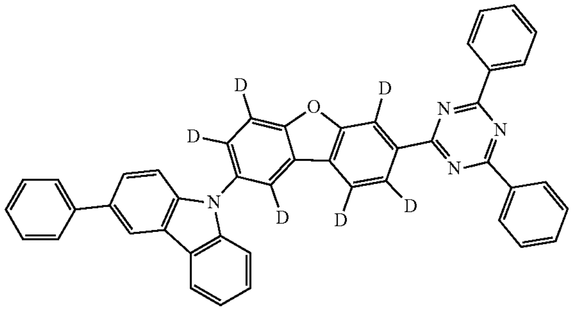
436
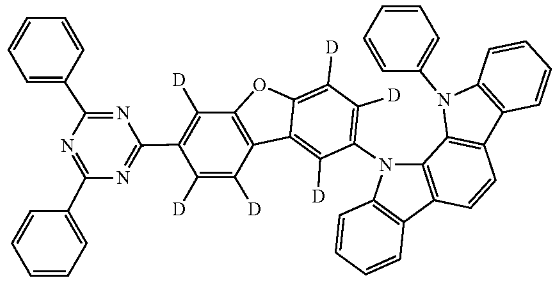
437
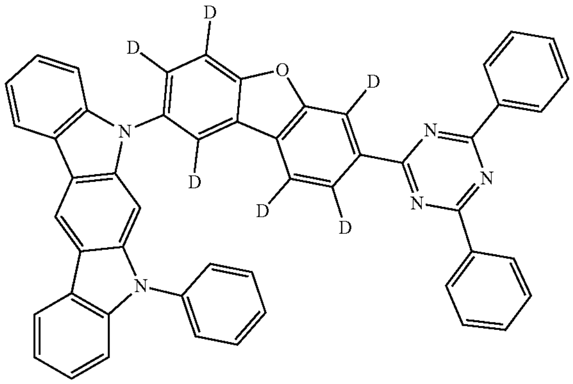
438
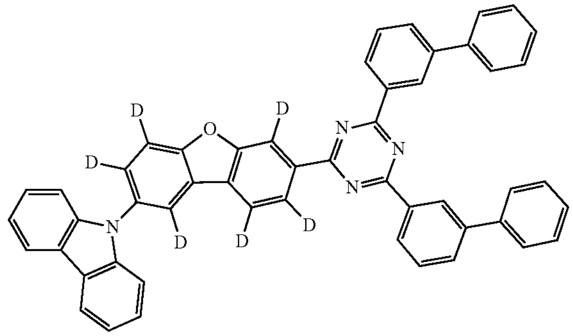
439
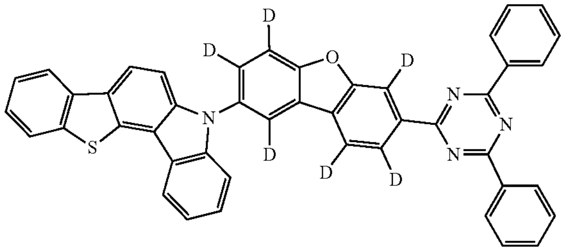

-continued
440
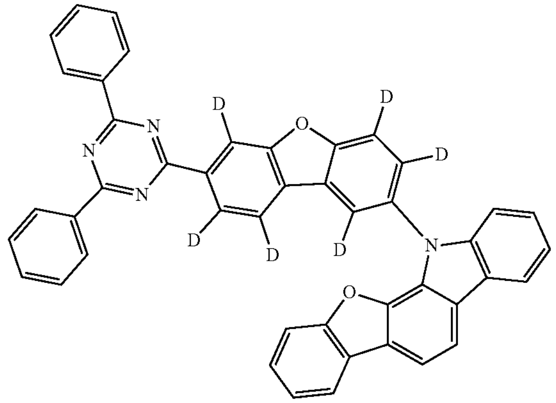
441
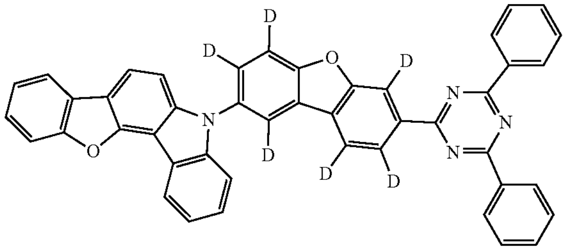
442
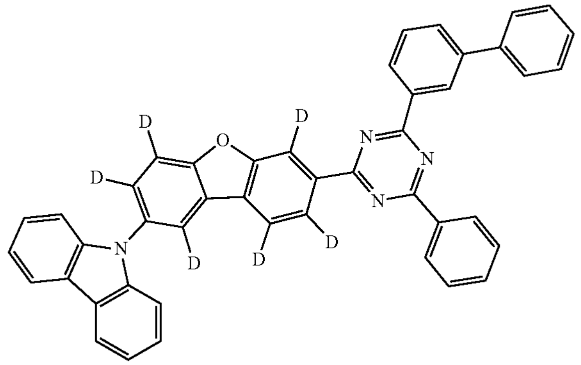
443
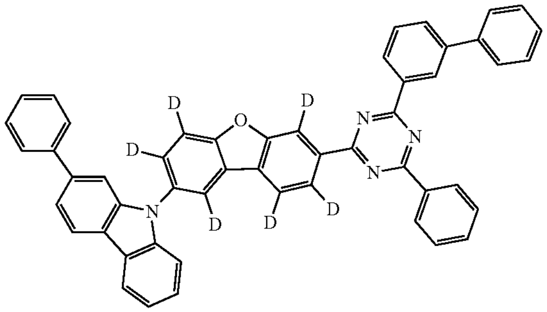
444
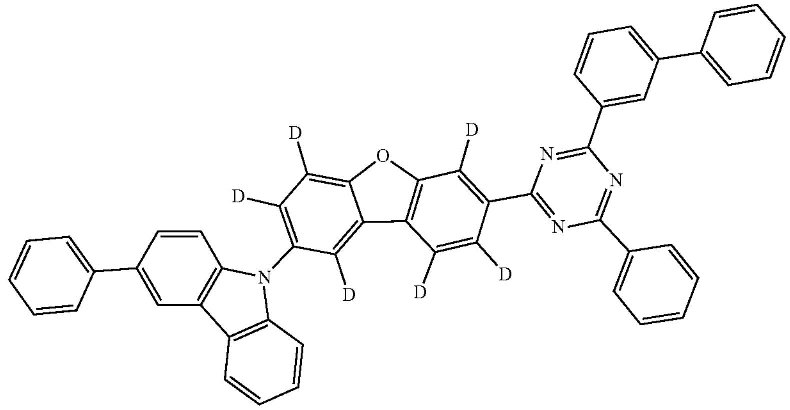

-continued
445
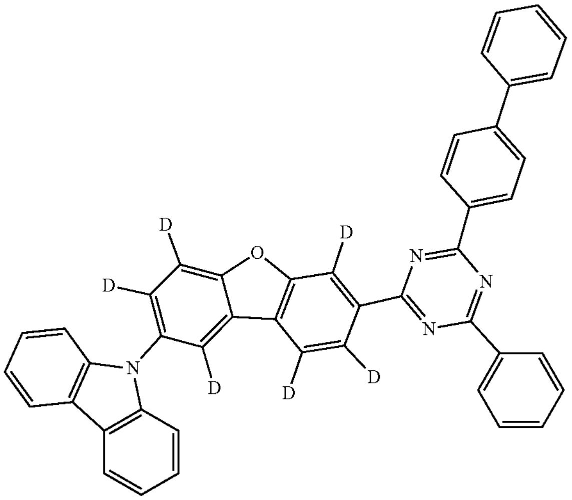
446
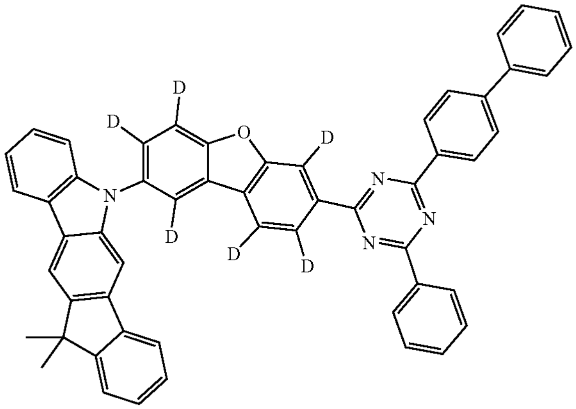
447
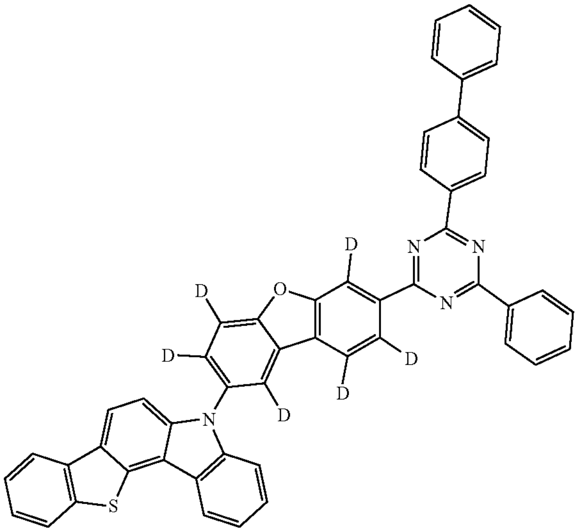
448
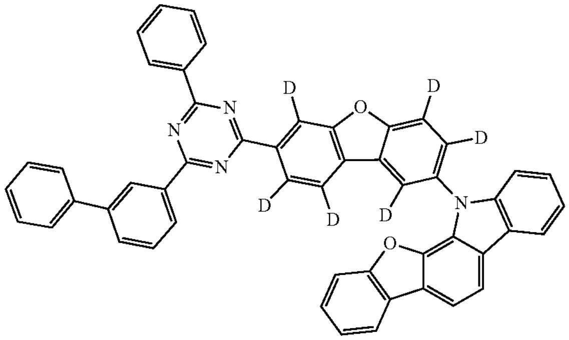
449
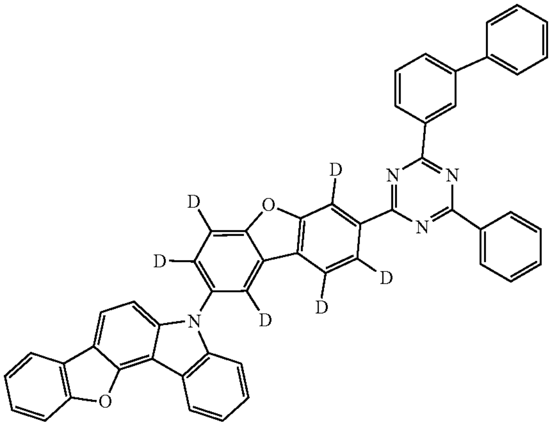
450
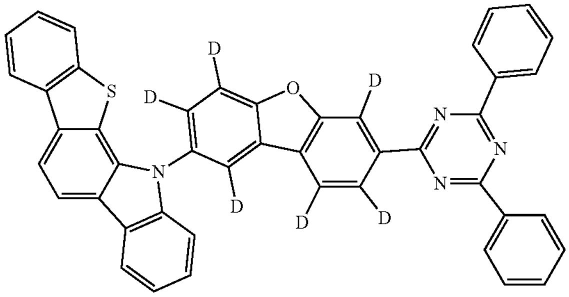

-continued
451
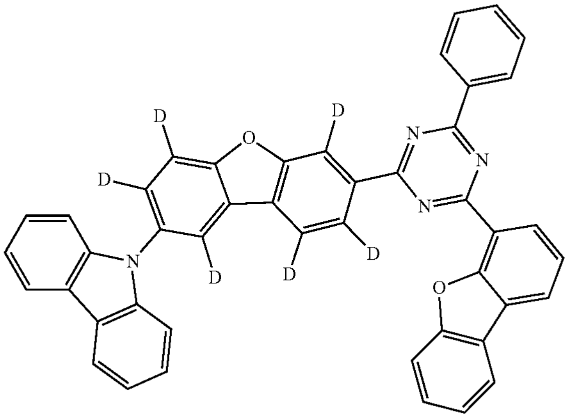
452
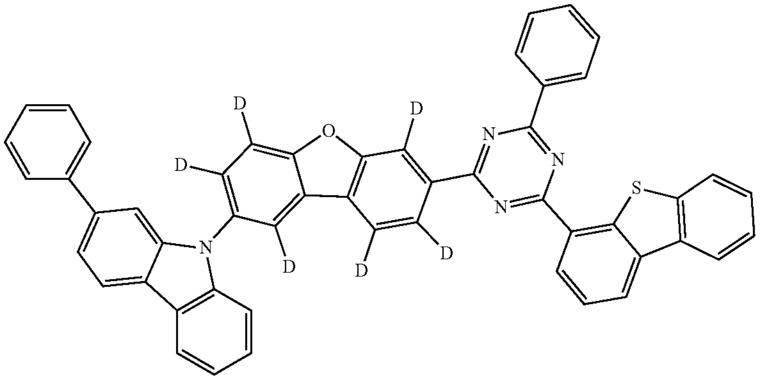
453
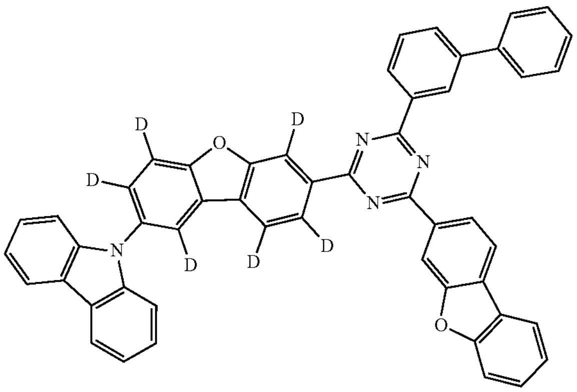
454
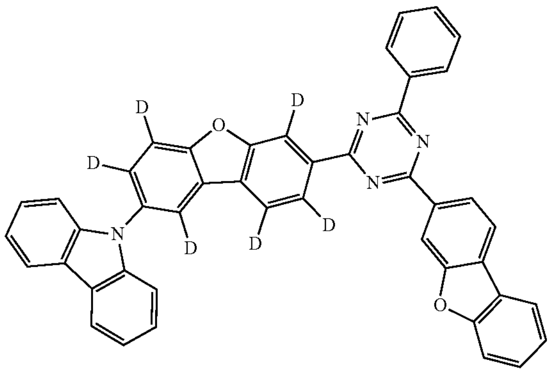

-continued
455
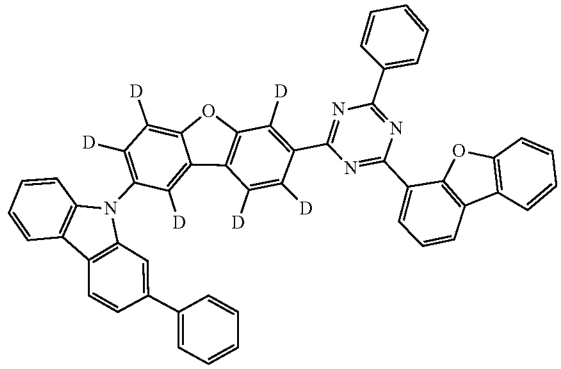
456
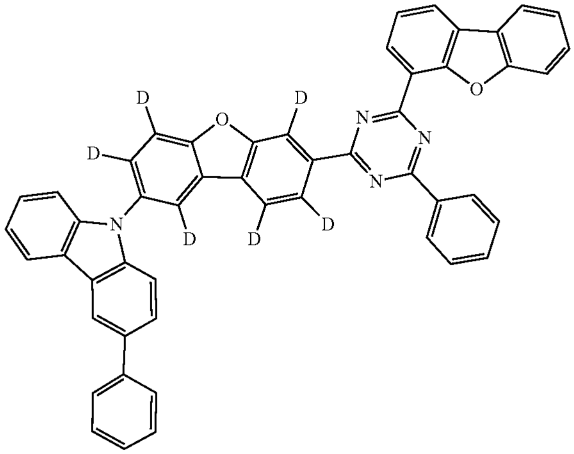
457
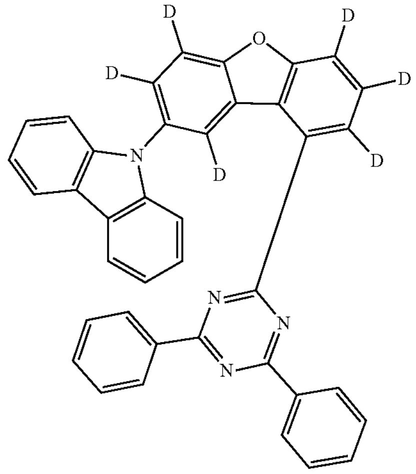
458
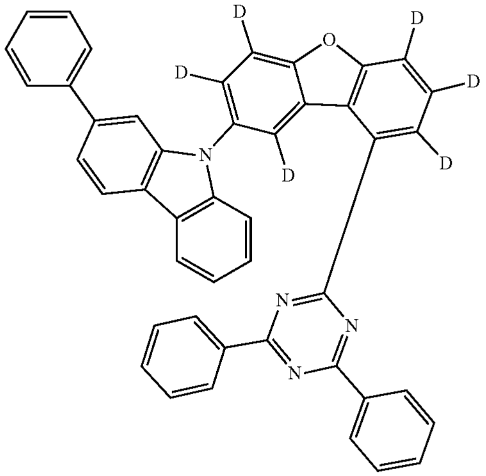
459
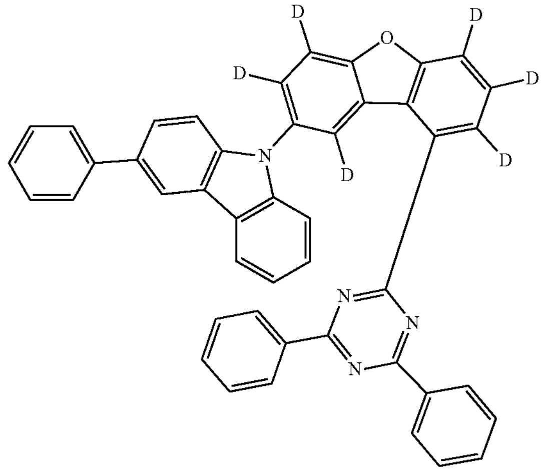
460
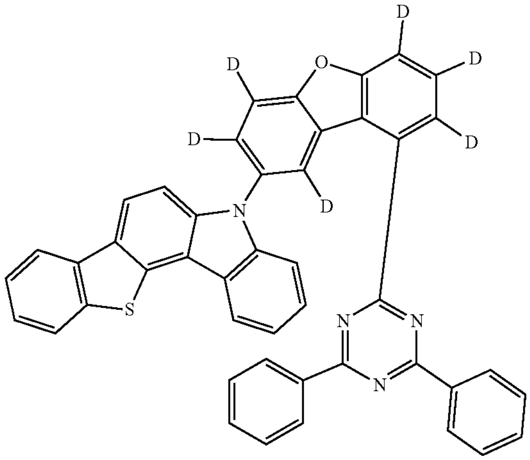

-continued
461
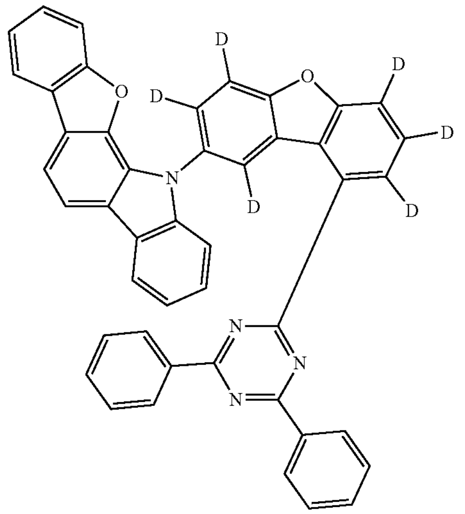
462
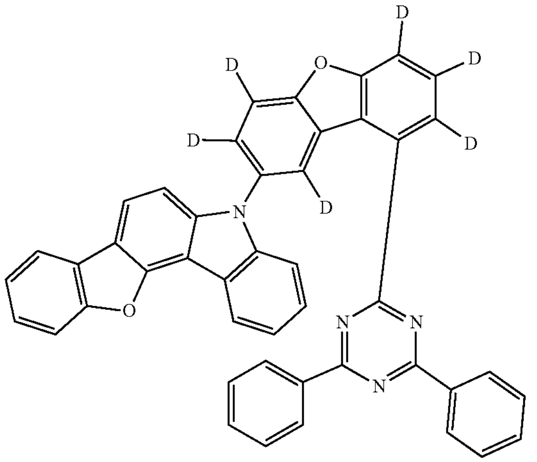
463
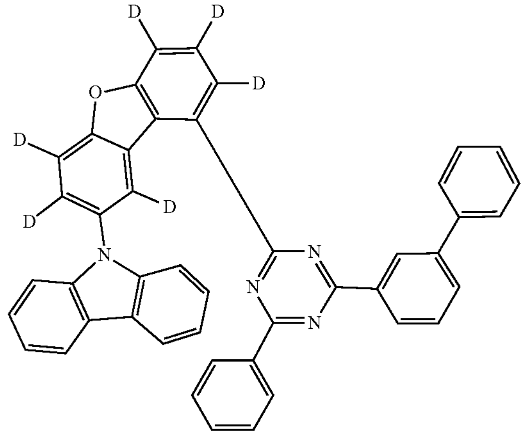
464
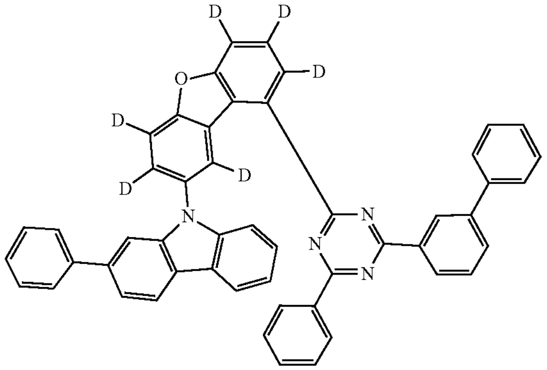
465
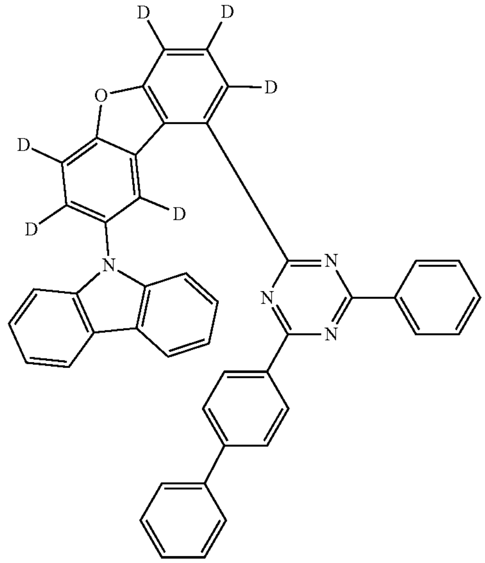
466
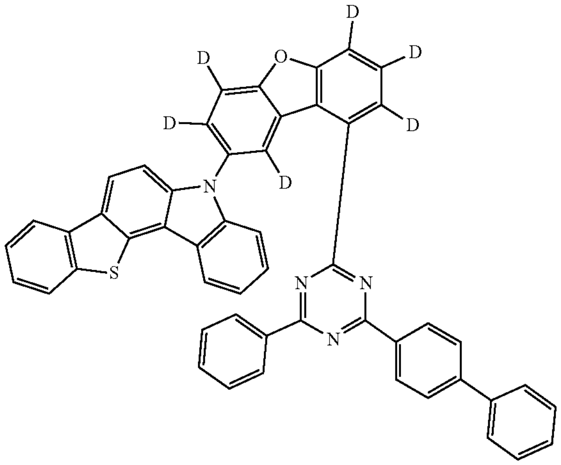

-continued
467
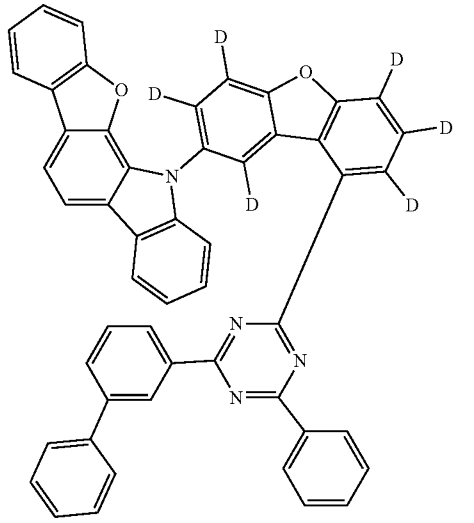
468
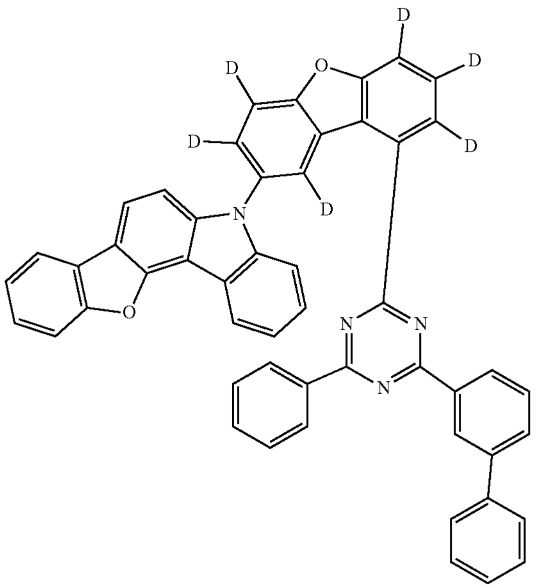
469
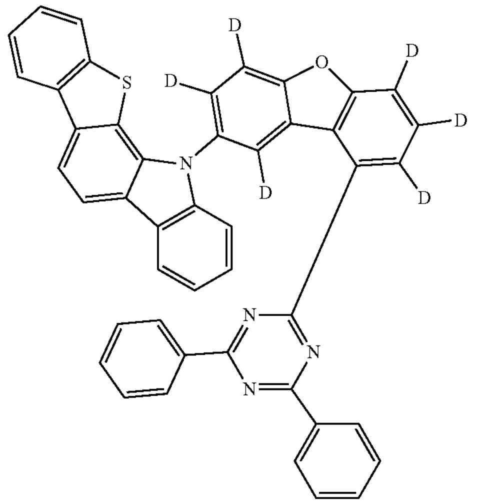
470
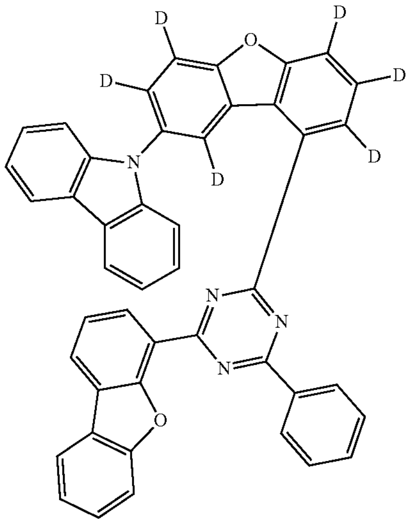

-continued
471
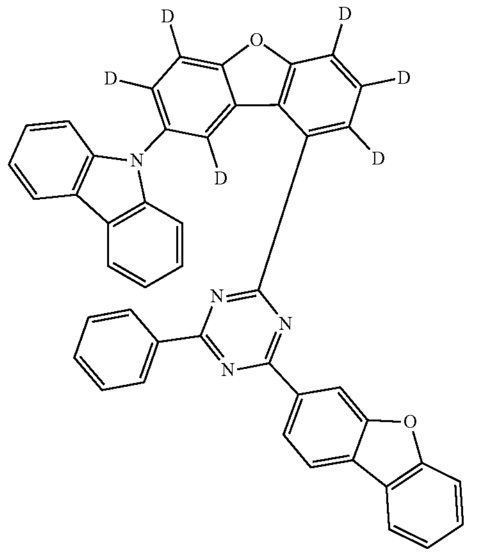
472
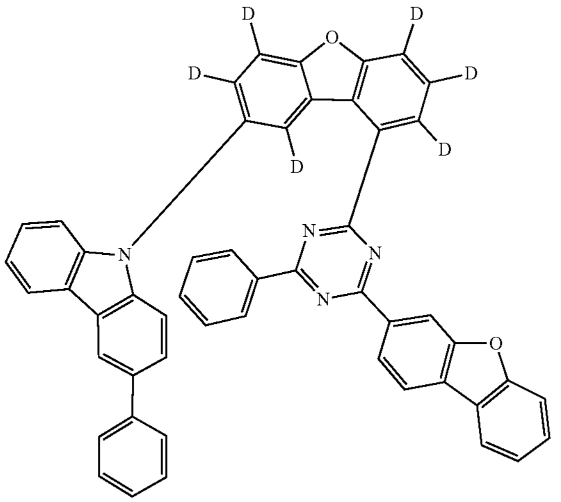
473
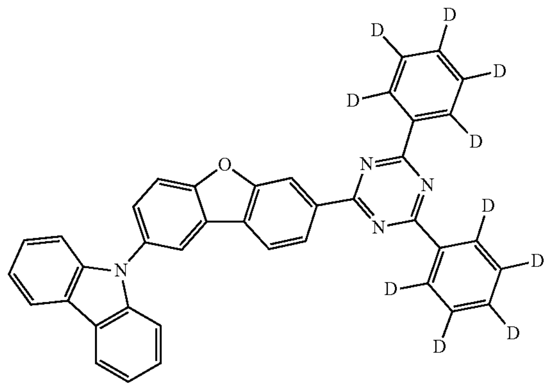
474
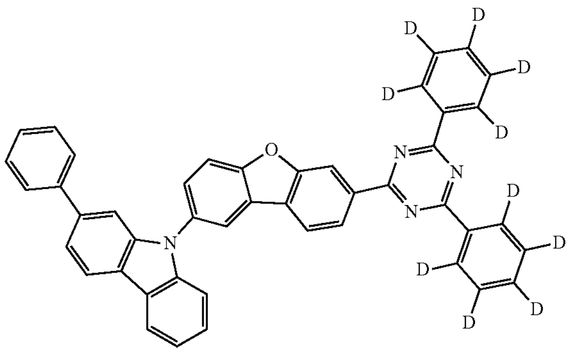
475
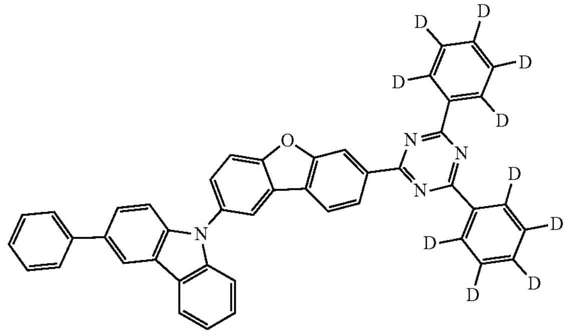
476
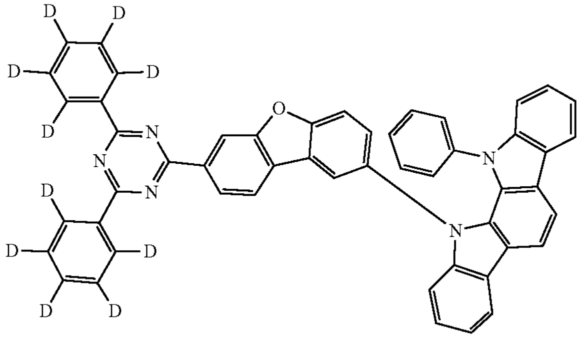

-continued
477
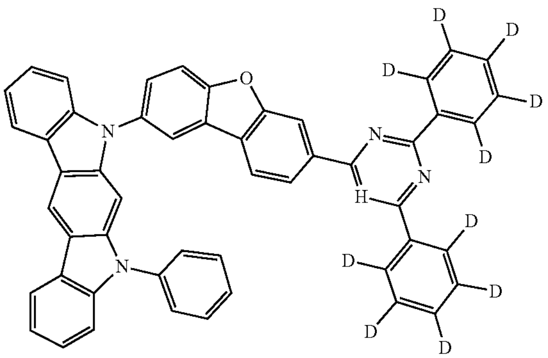
478
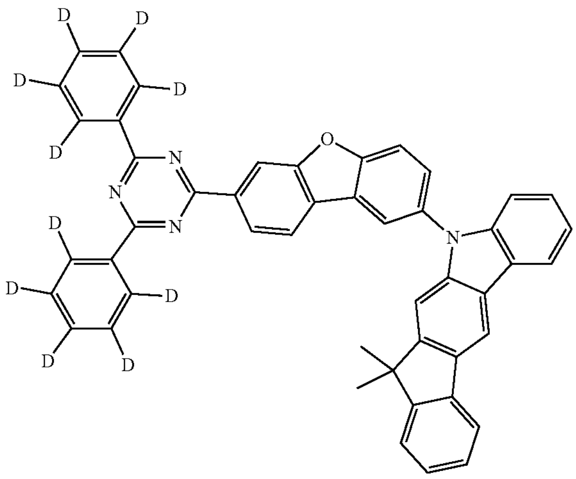
479
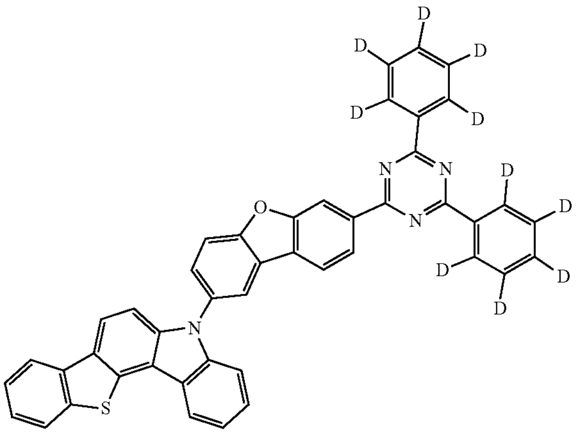
480
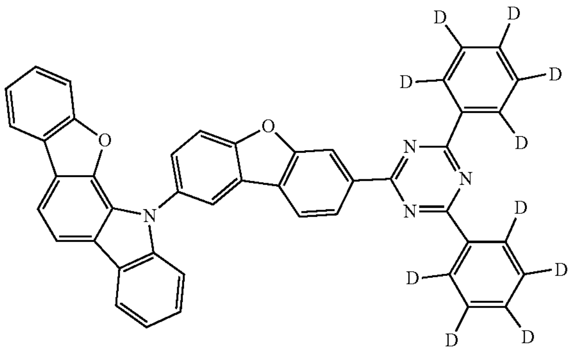
481
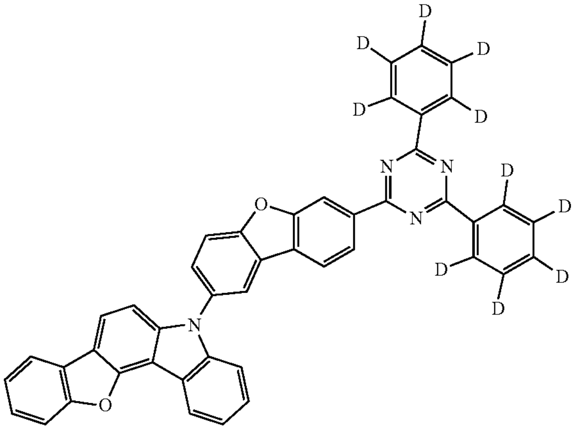
482
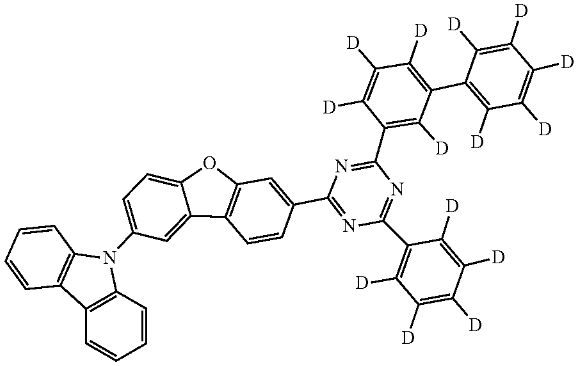

-continued
483
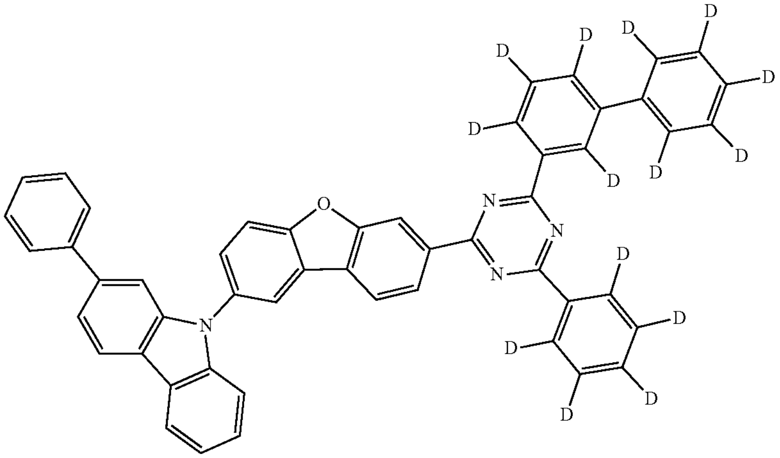
484
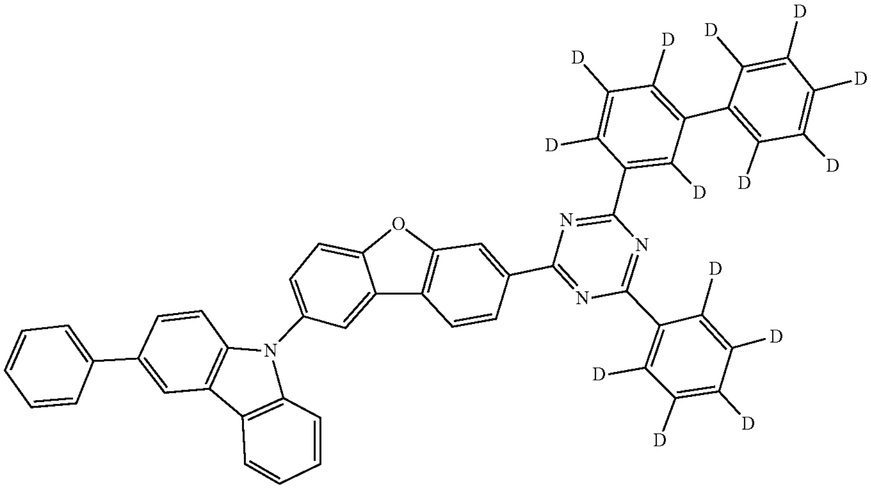
485
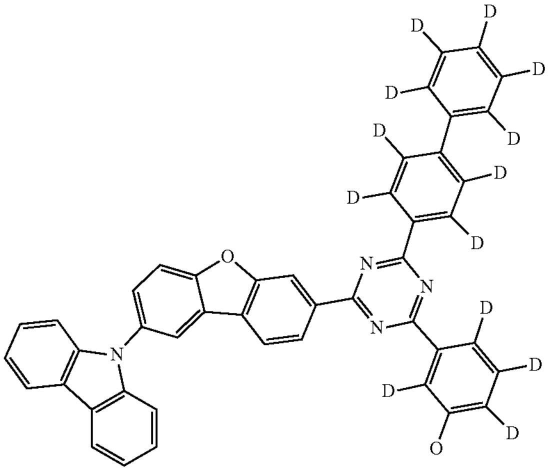
486
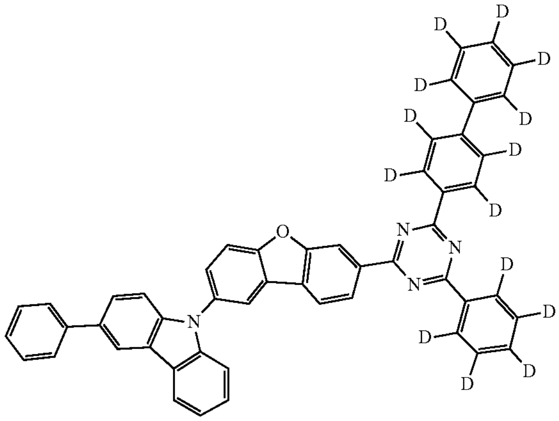

-continued
487
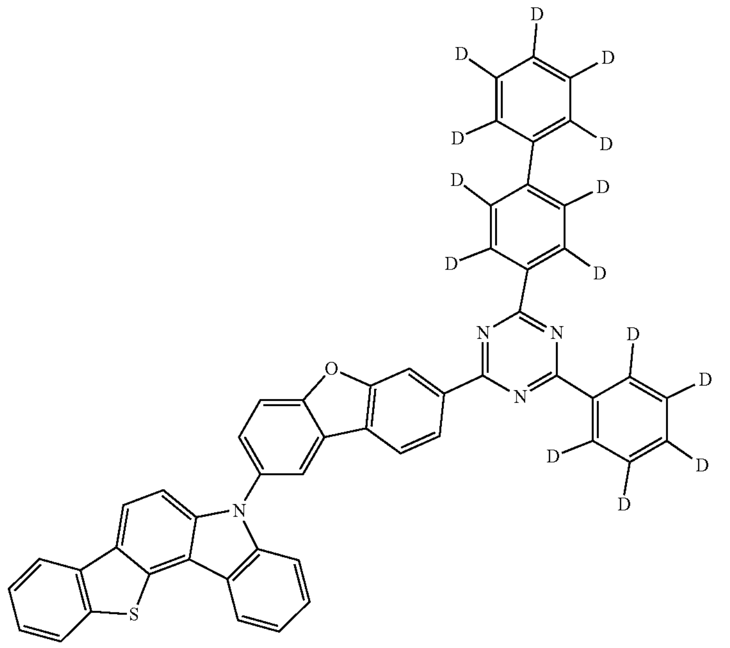
488
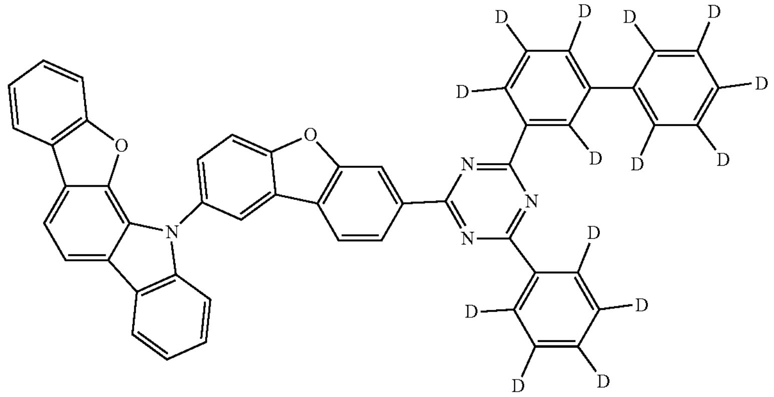
489
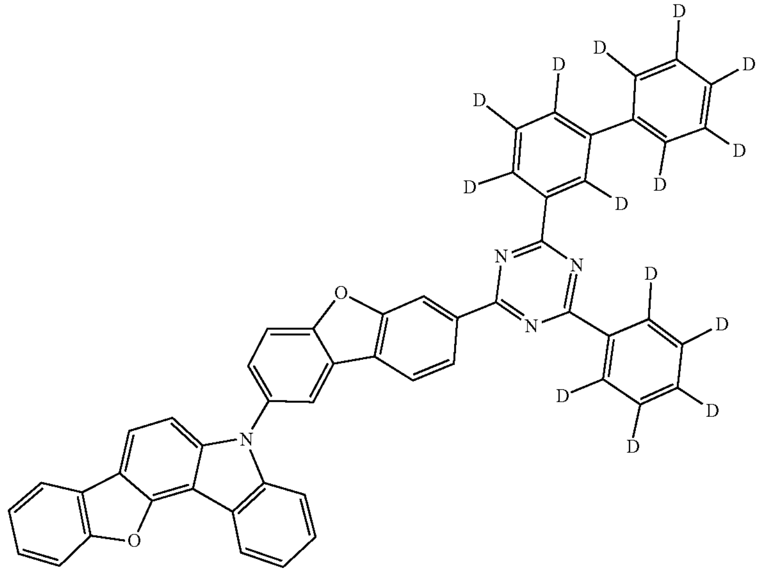

-continued
490
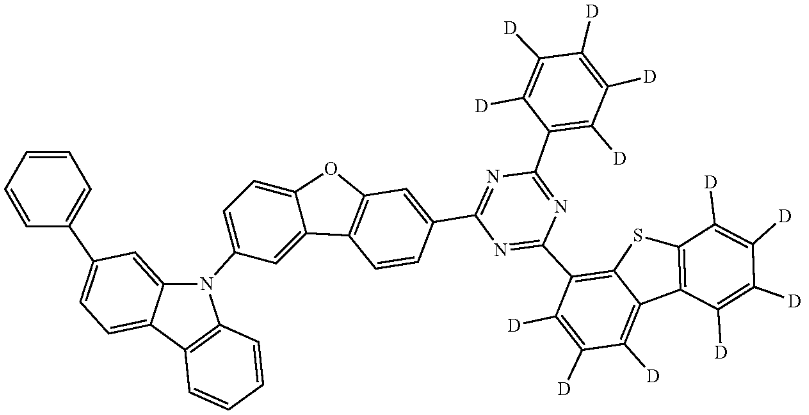
491
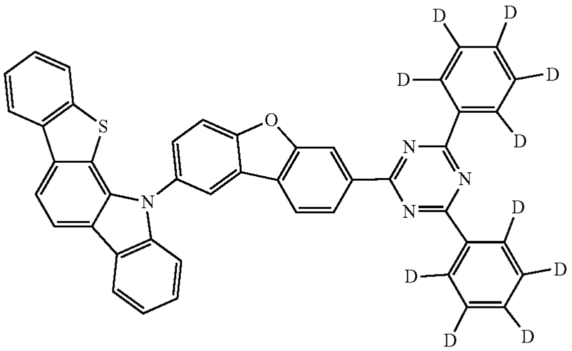
492
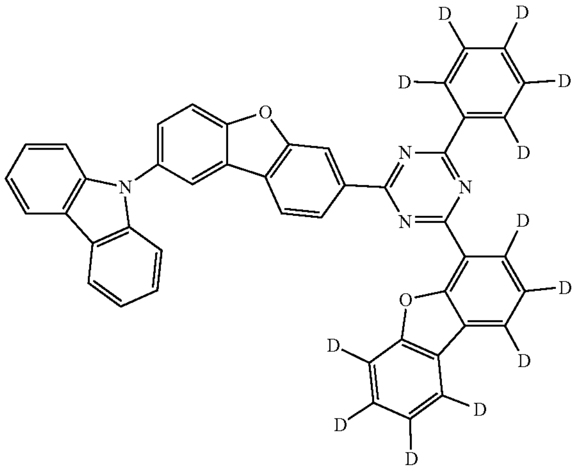
493
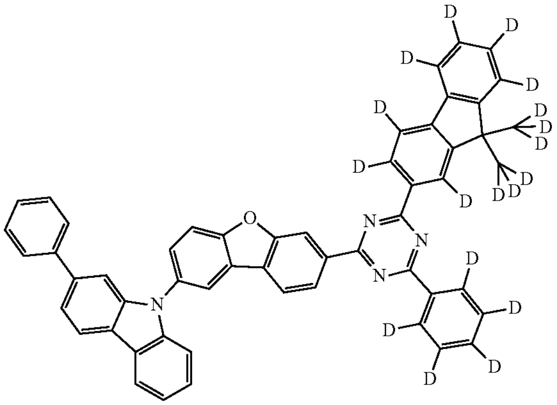
494
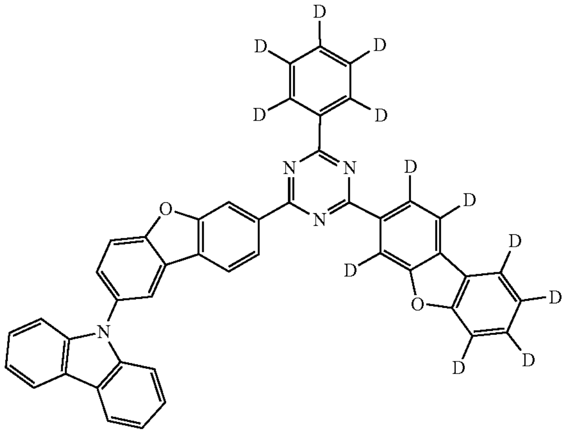

-continued
495
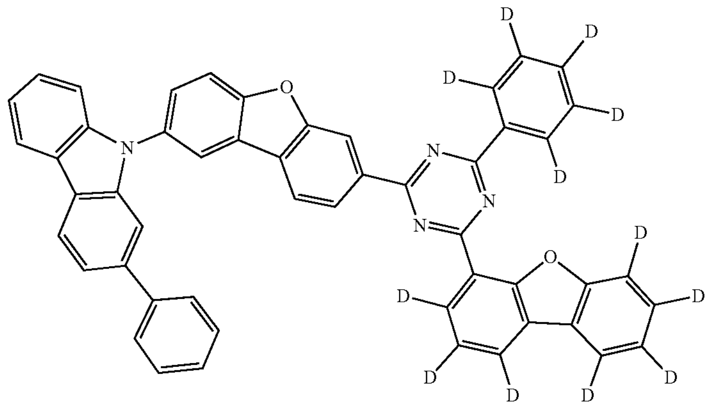
496
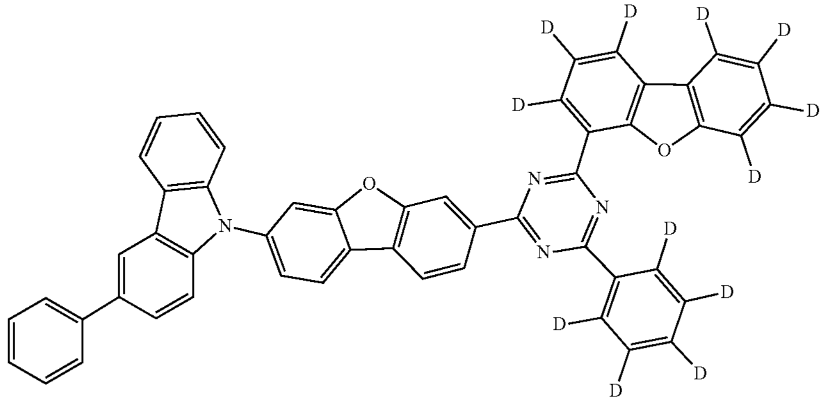
497
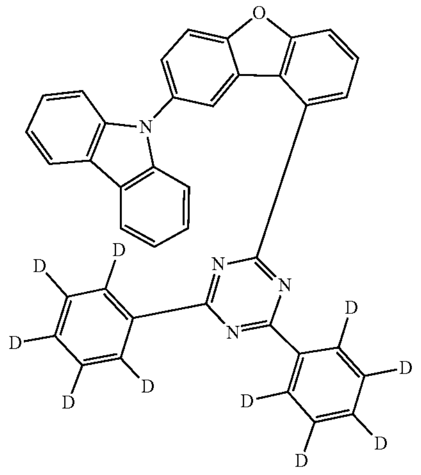
498
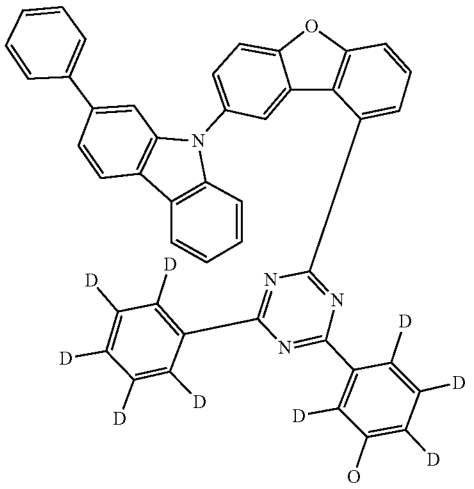

-continued
499
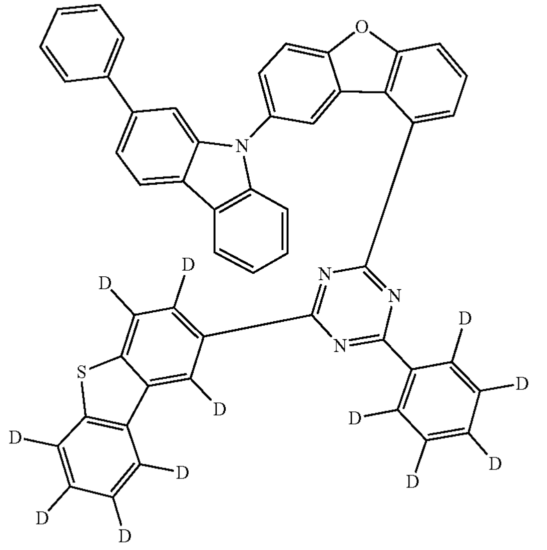
500
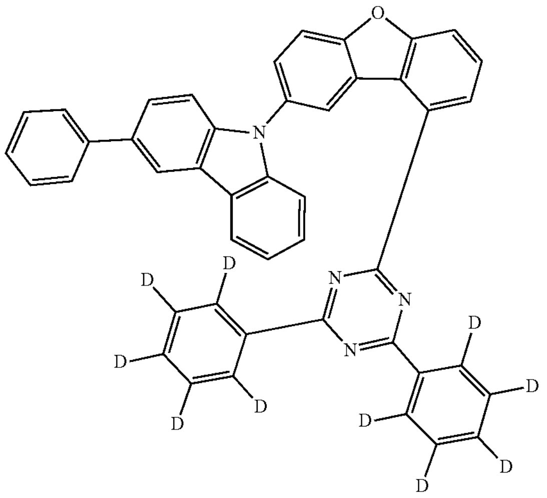
501
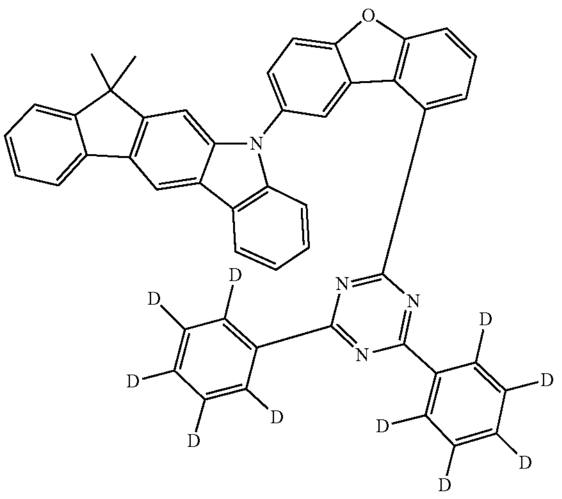
502
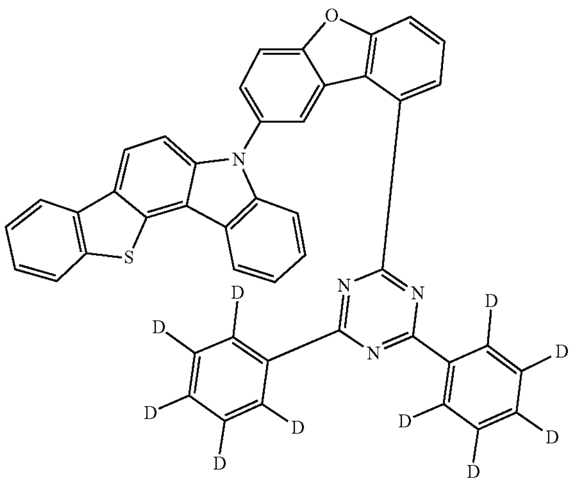
503
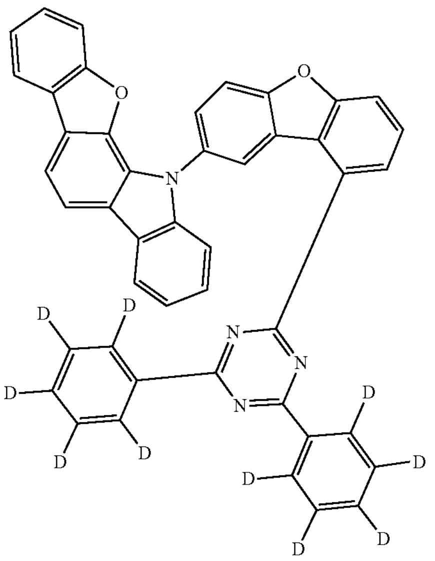
504
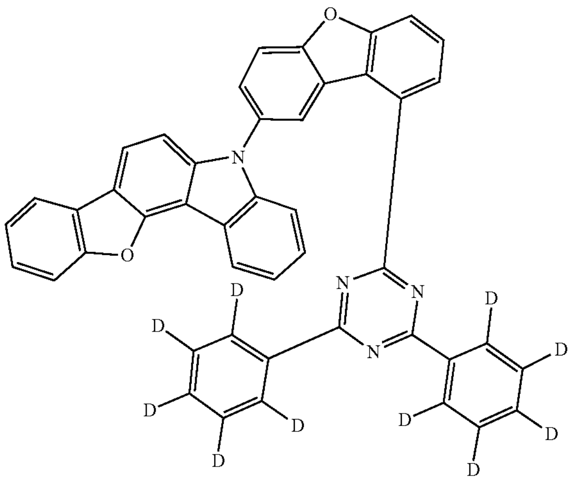

-continued
505
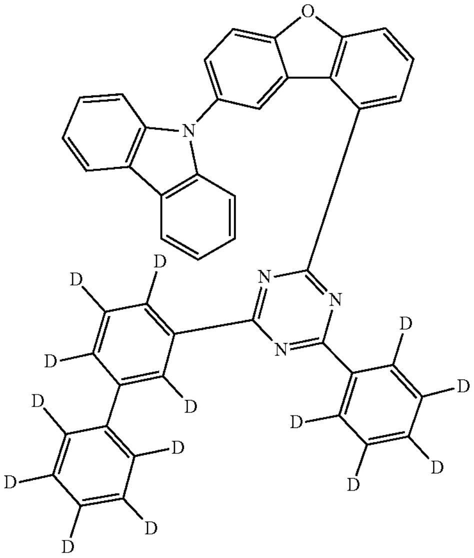
506
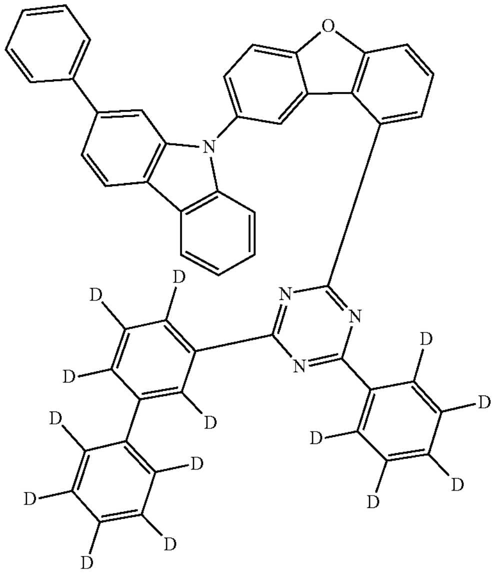
507
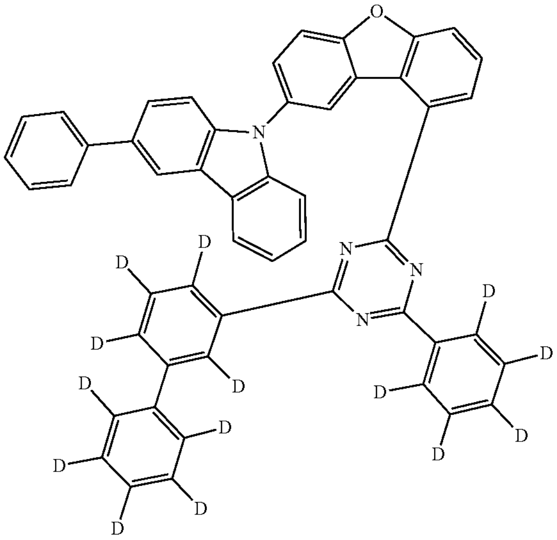
508
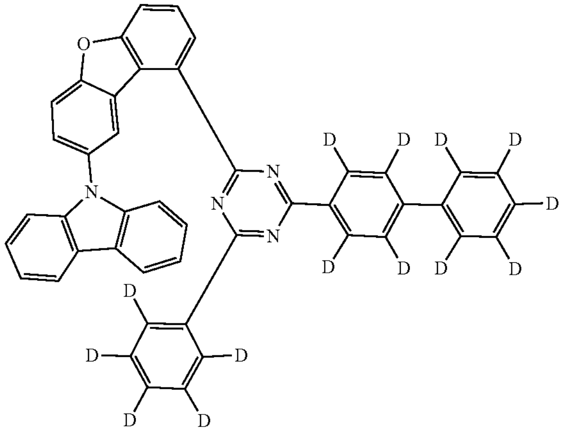

-continued
509
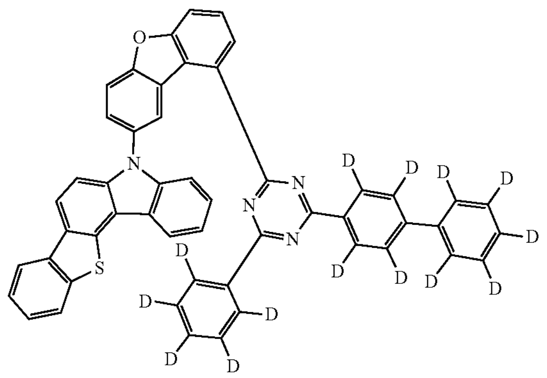
510
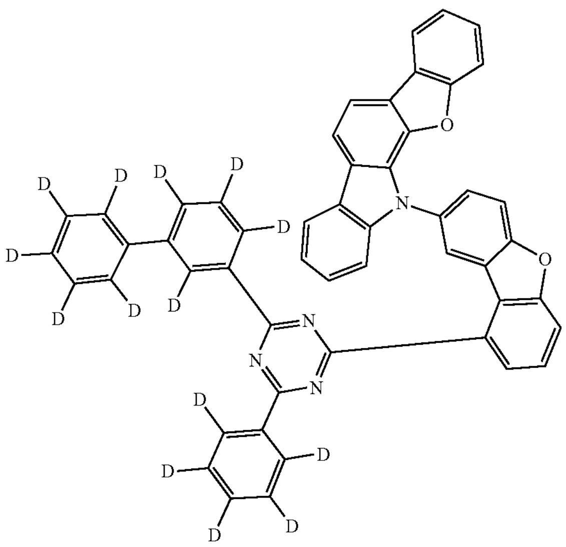
511
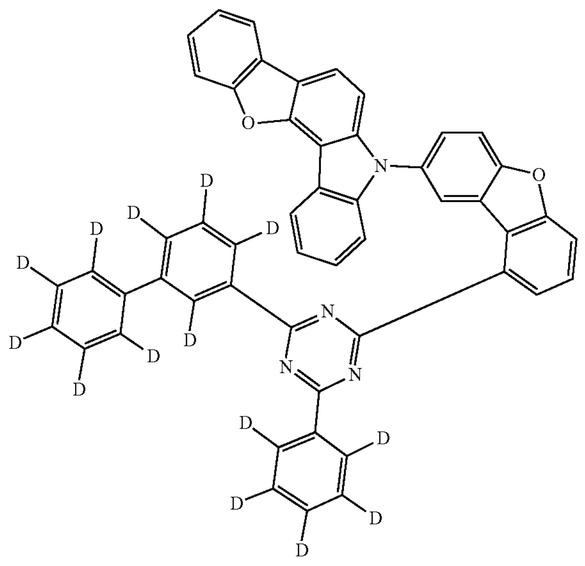
512
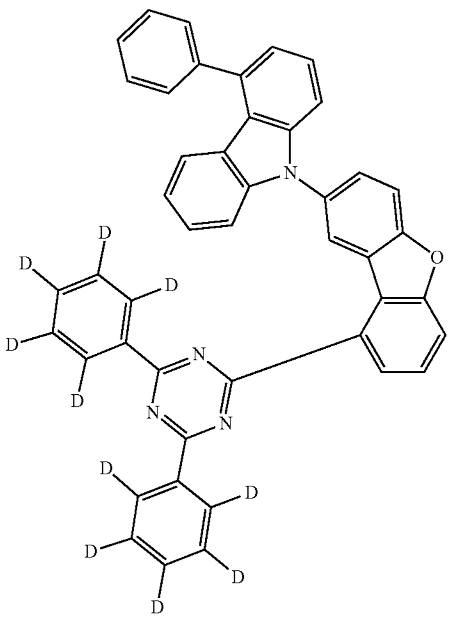

-continued
513
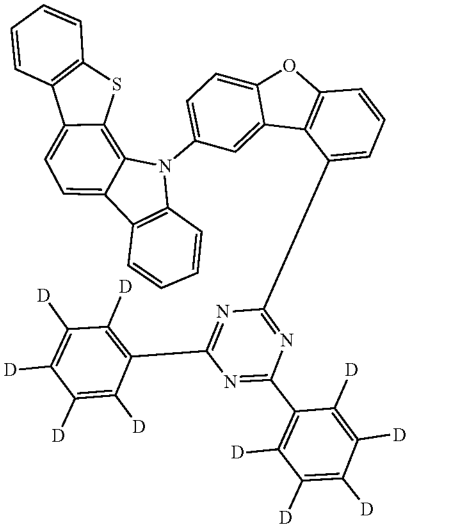
514
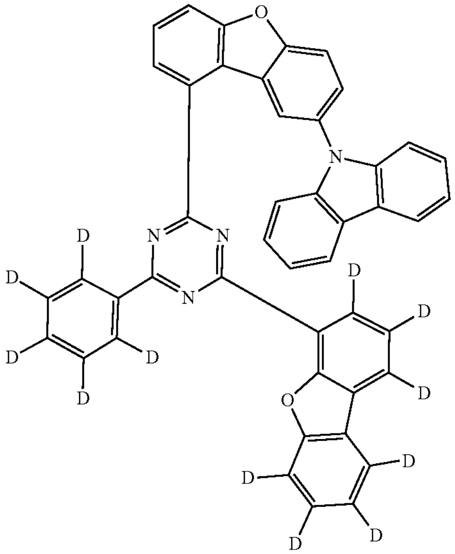
515
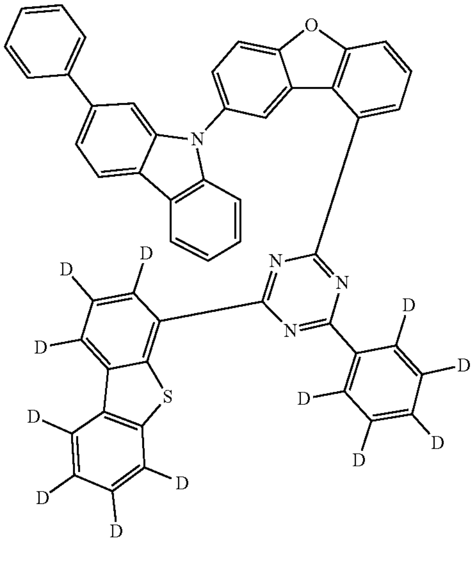
516
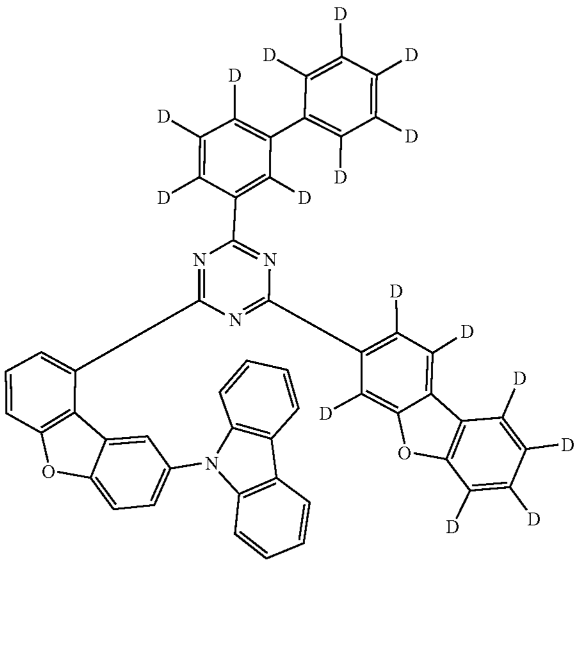

-continued
517
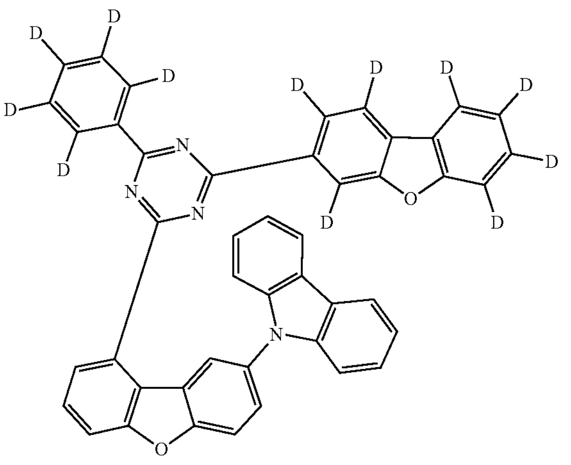
518
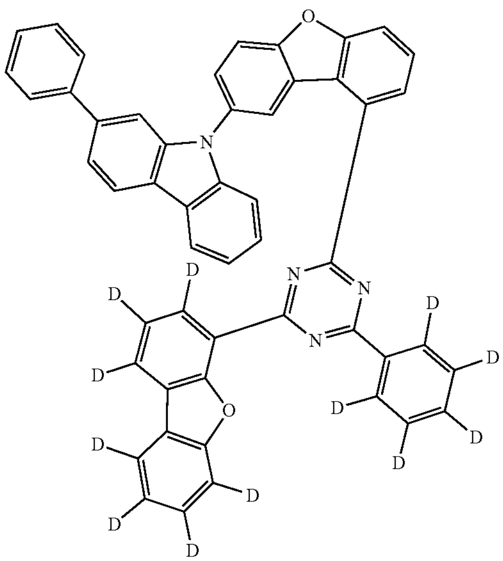
519
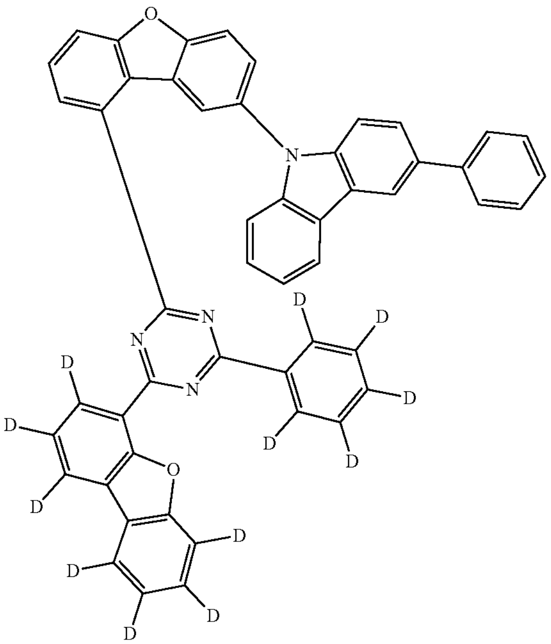
520
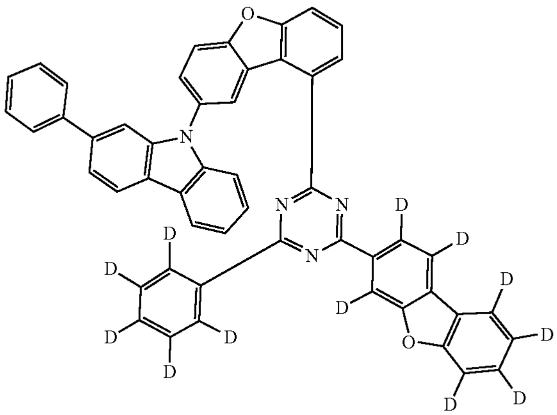

-continued
521
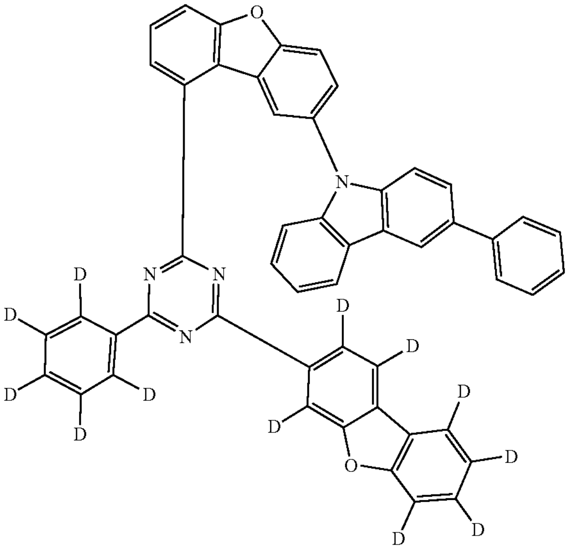
522
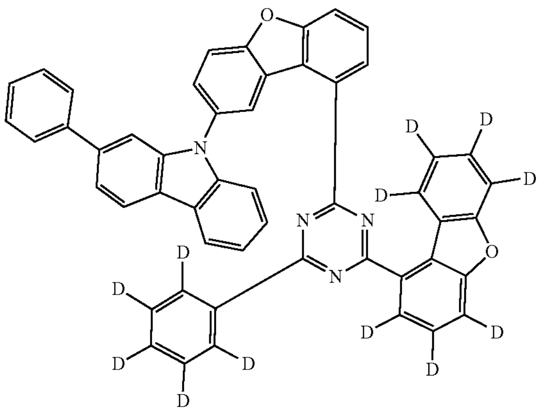
523
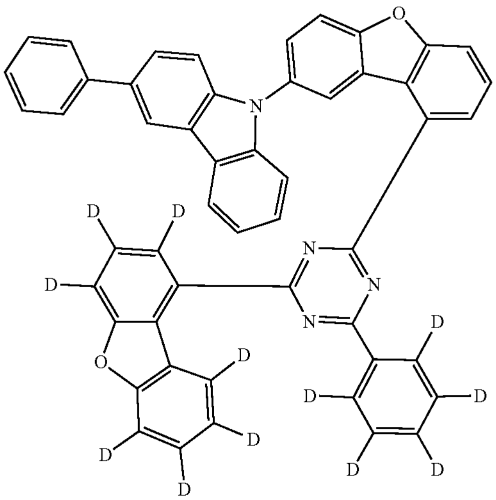
524
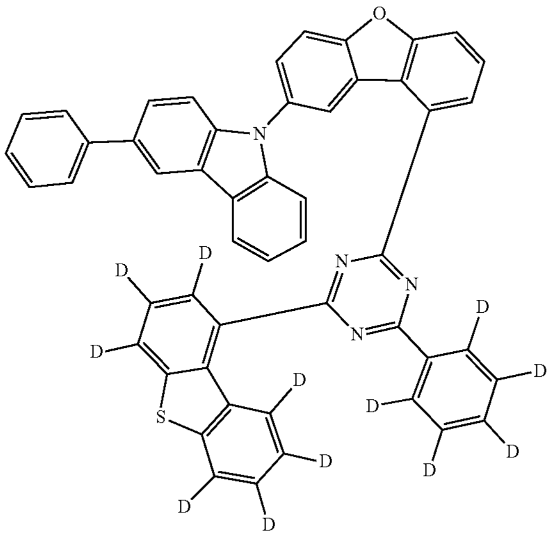
525
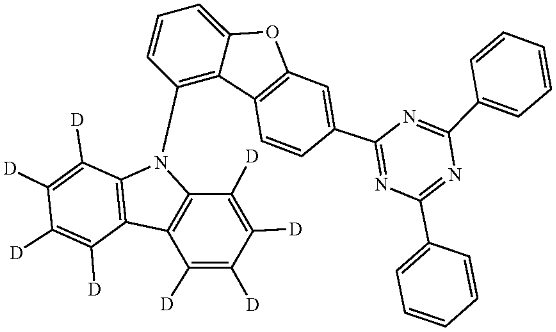
526
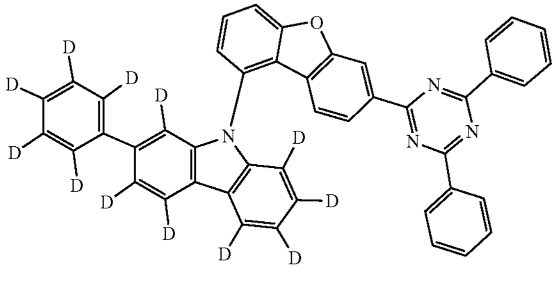

-continued
527
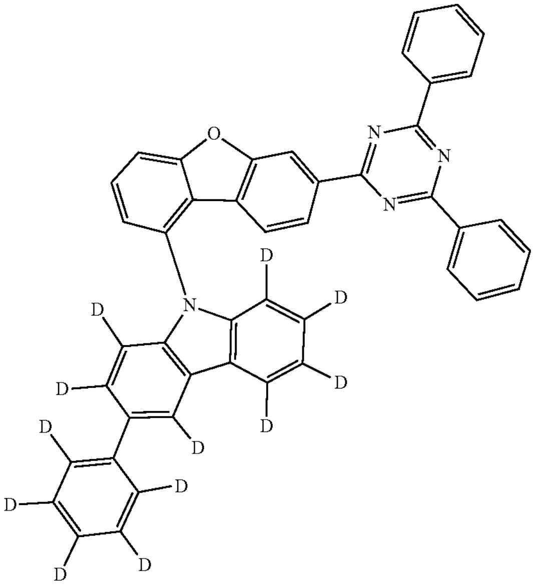
528
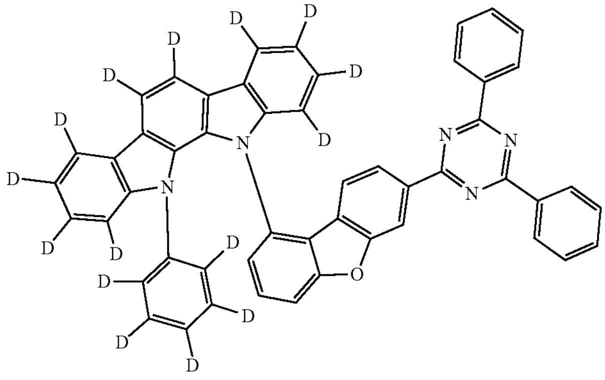
529
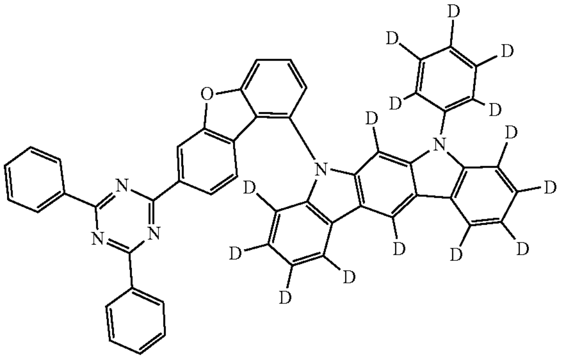
530
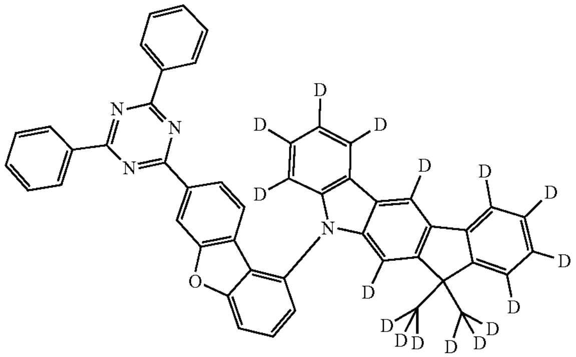
531
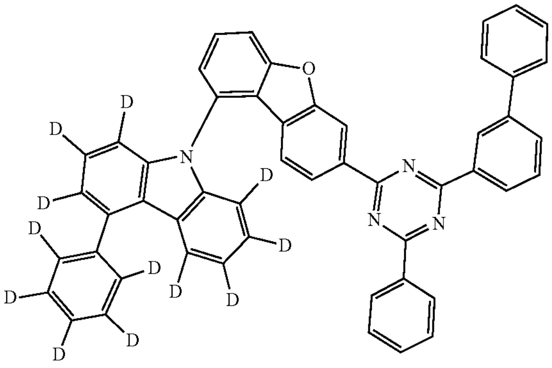
532
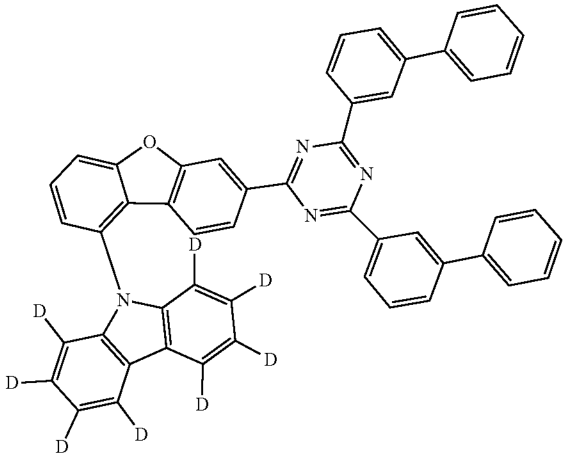

-continued
533
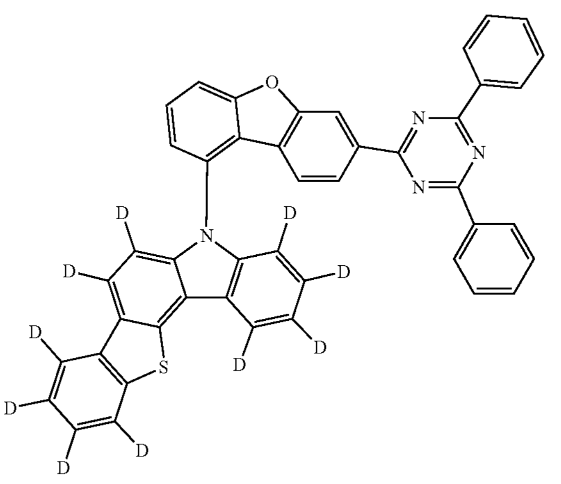
534
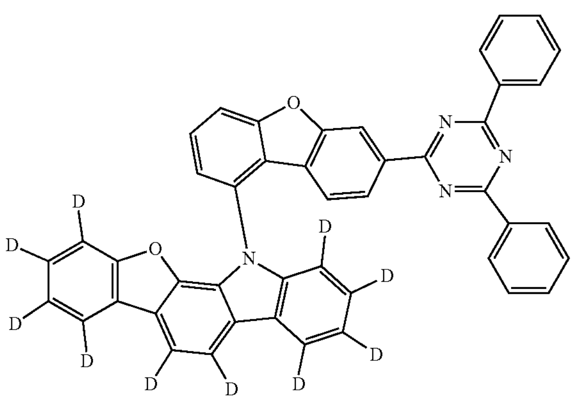
535
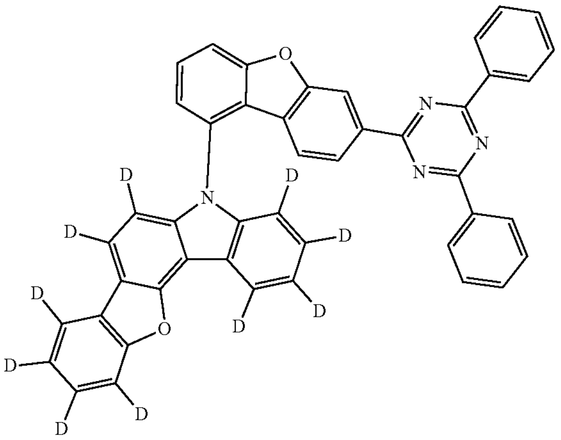
536
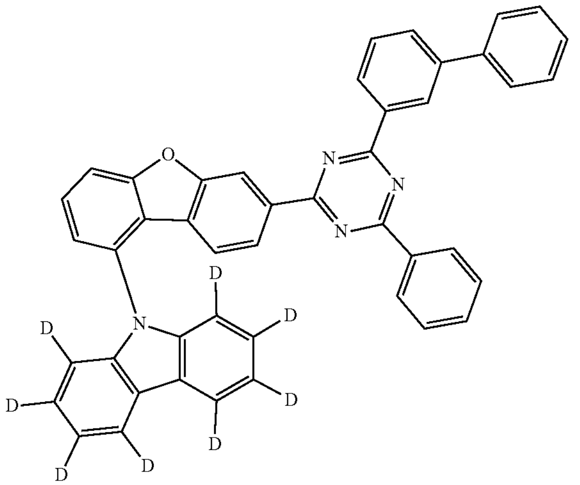
537
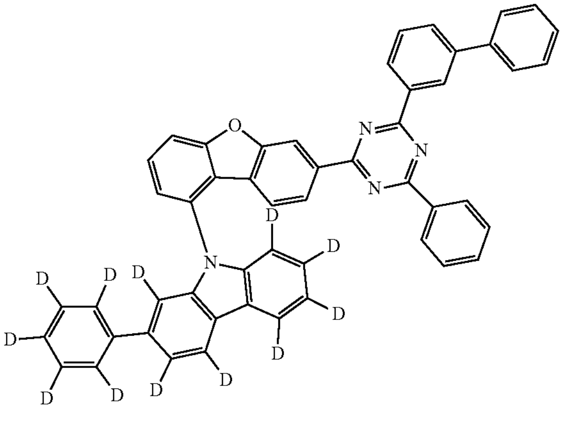
538
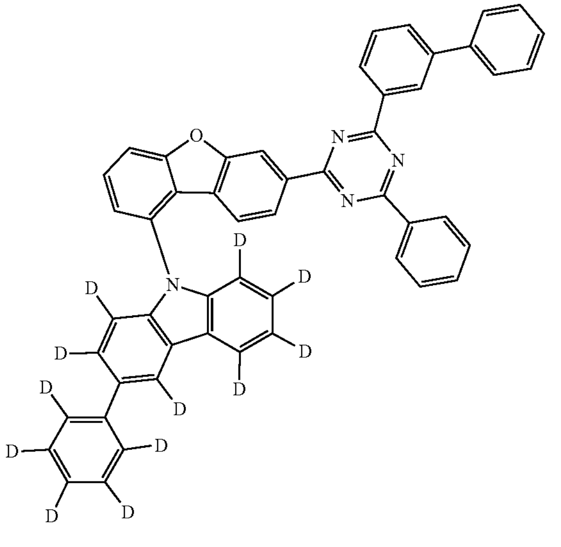

-continued
539
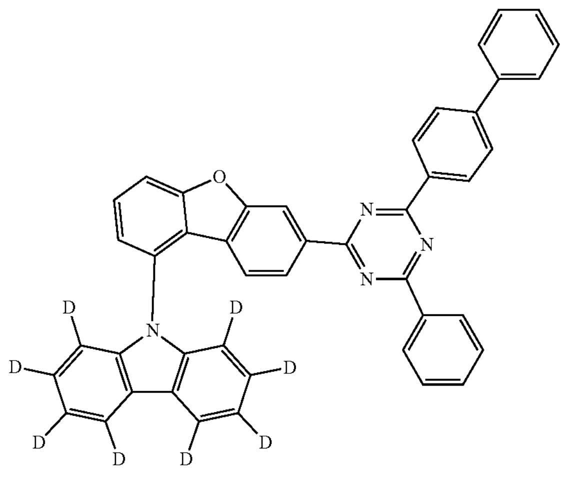
540
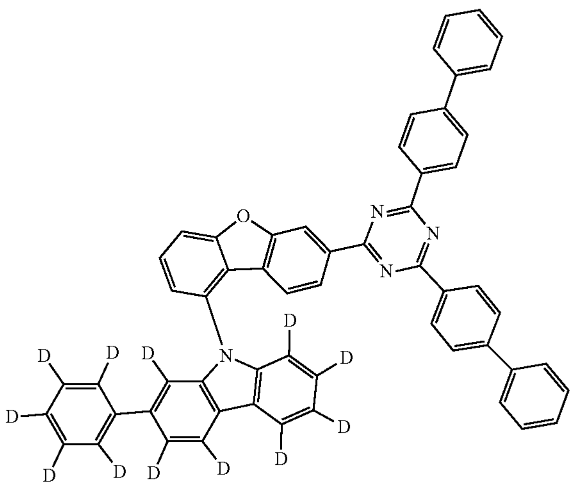
541
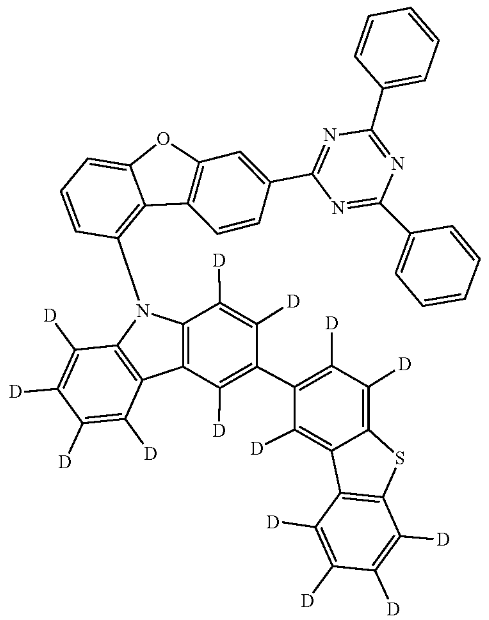
542
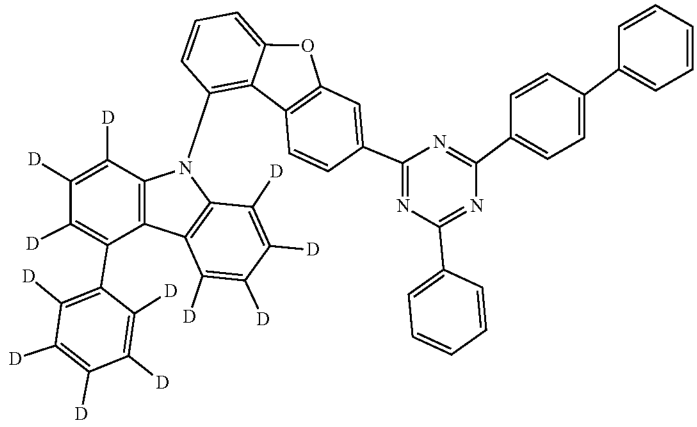

-continued
543
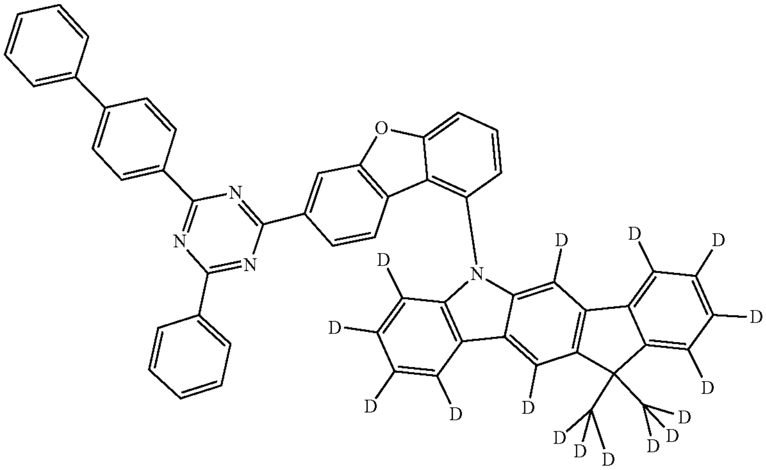
544
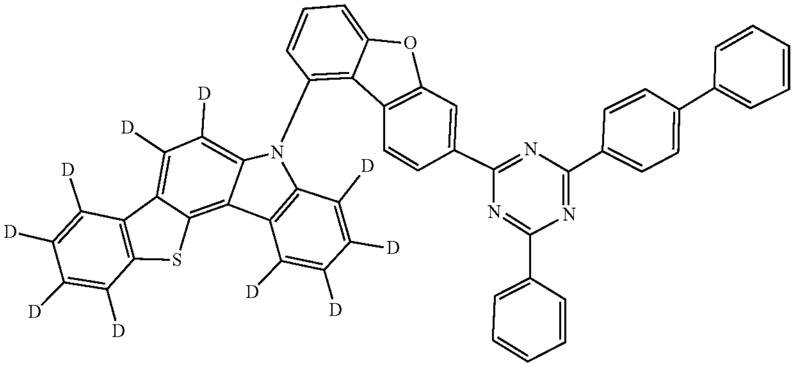
545
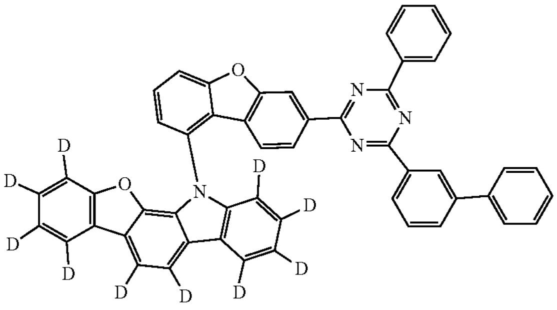
546
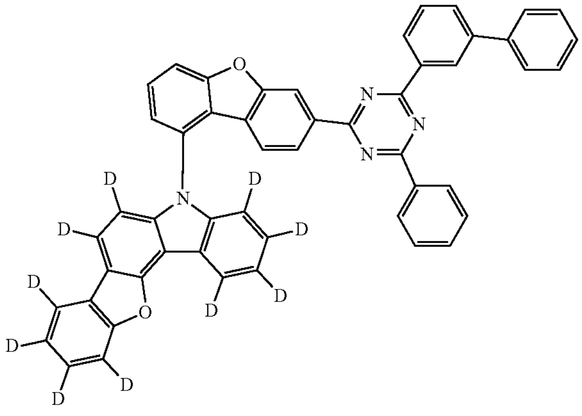

-continued
547
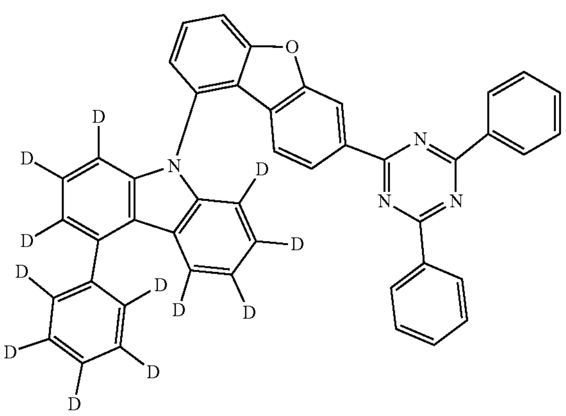
548
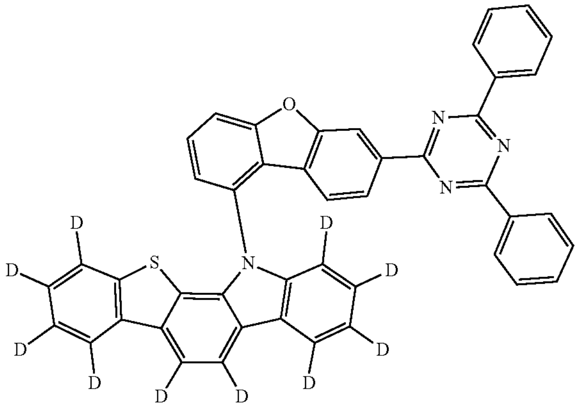
549
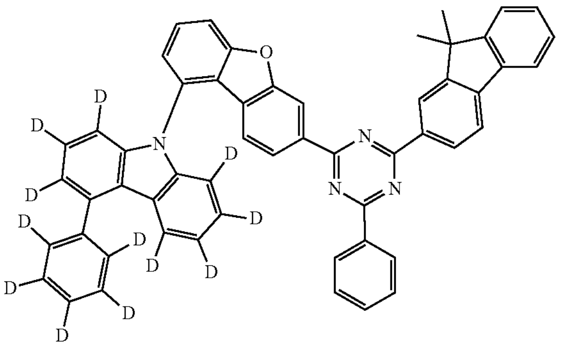
550
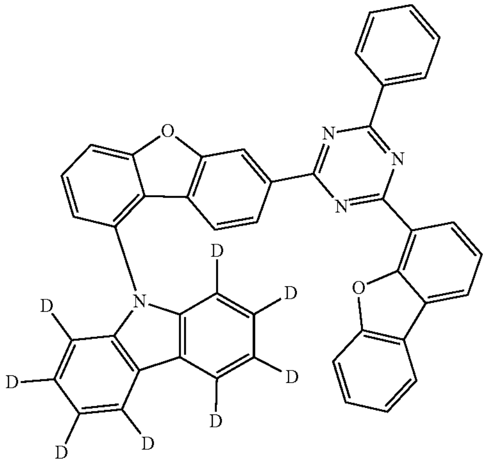
551
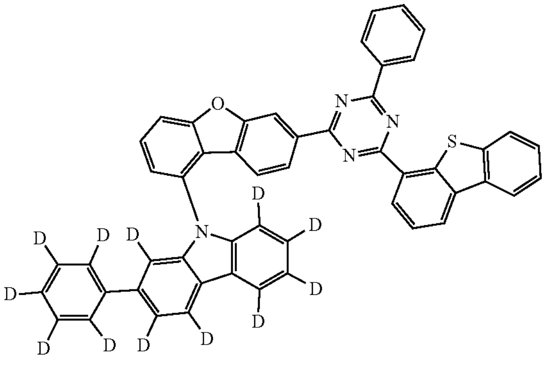
552
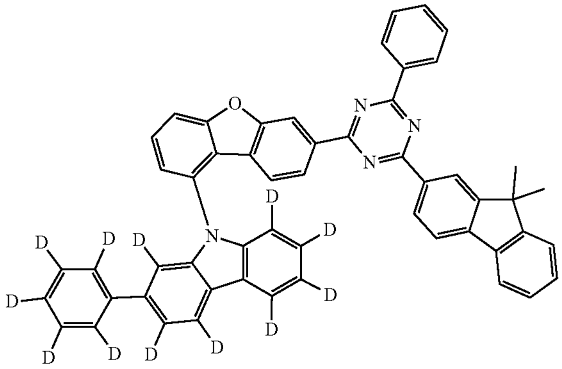

-continued
553
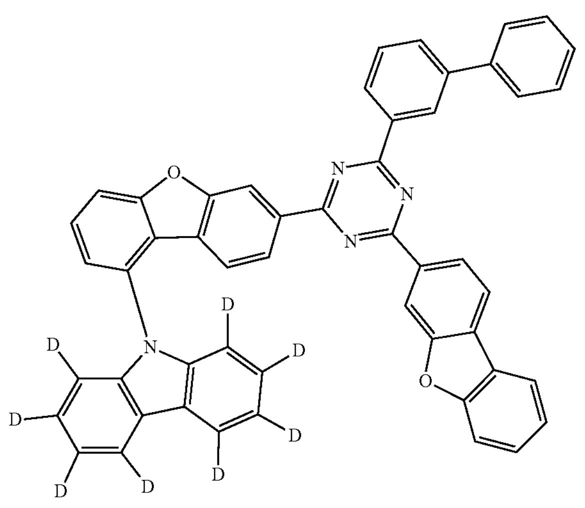
554
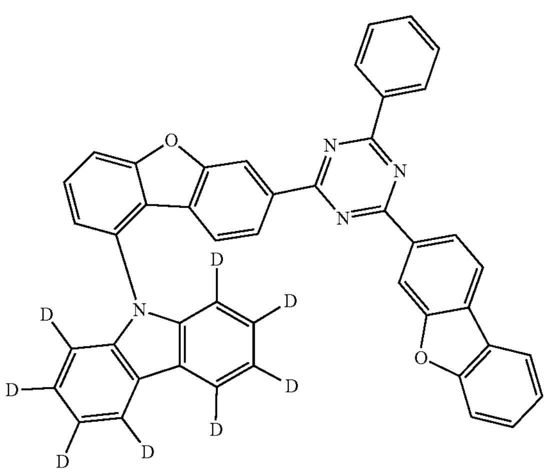
555
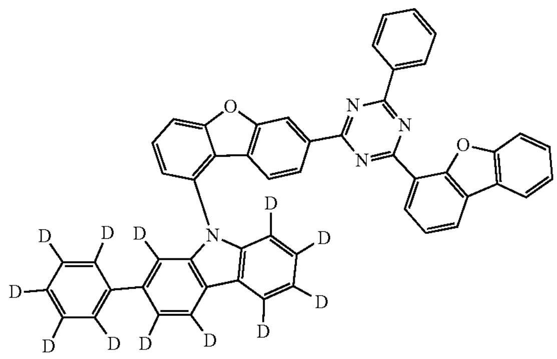
556
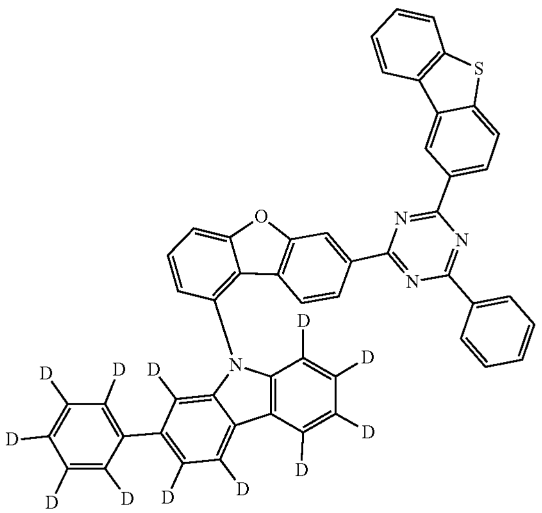
558
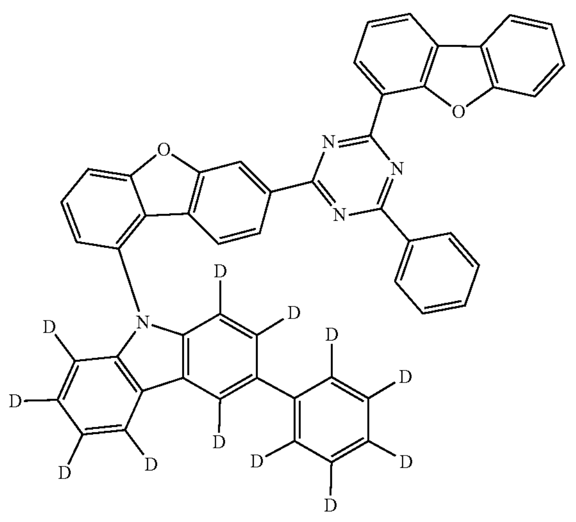
557
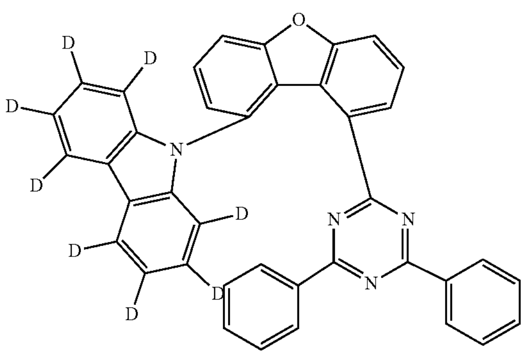

-continued
559
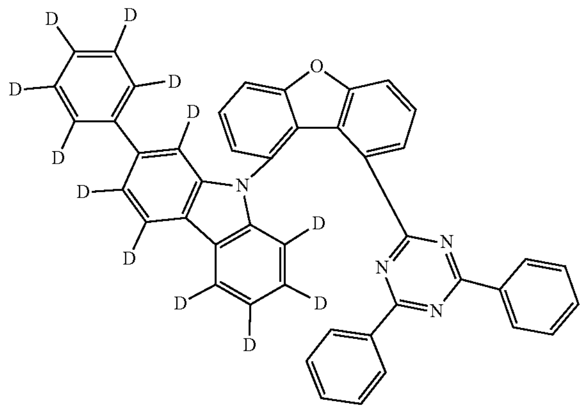
560
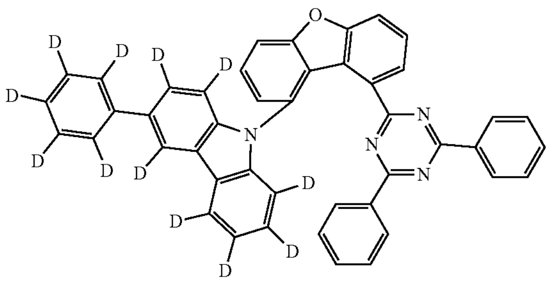
561
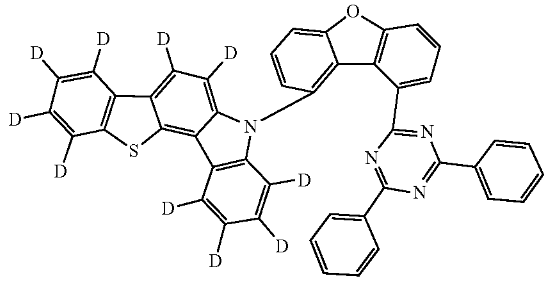
562
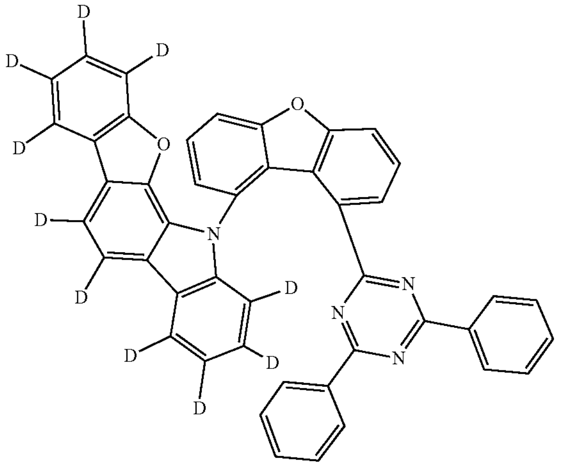
563
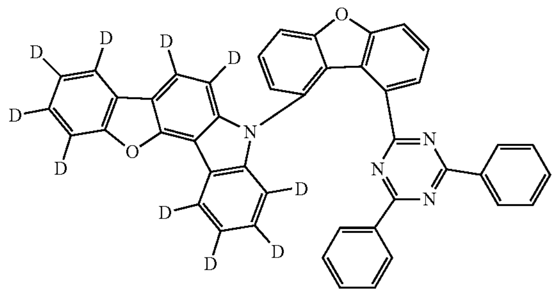
564
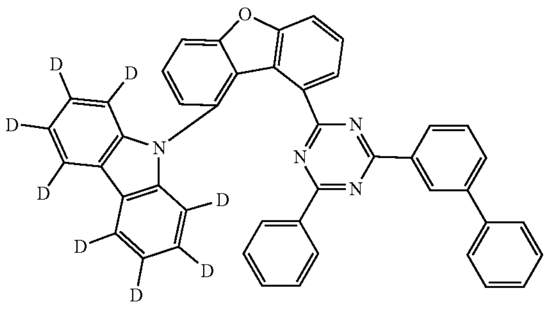
565
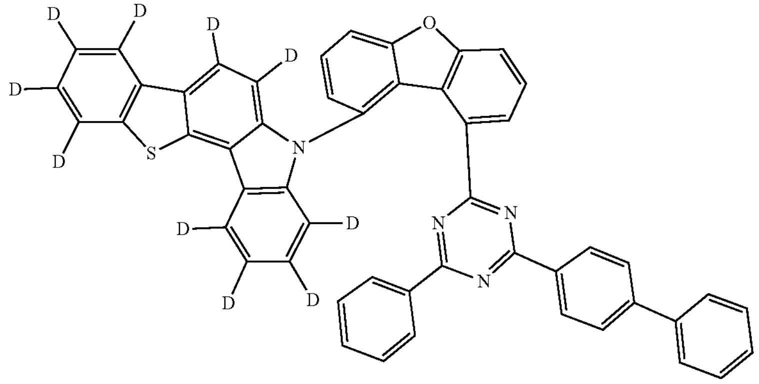

-continued
566
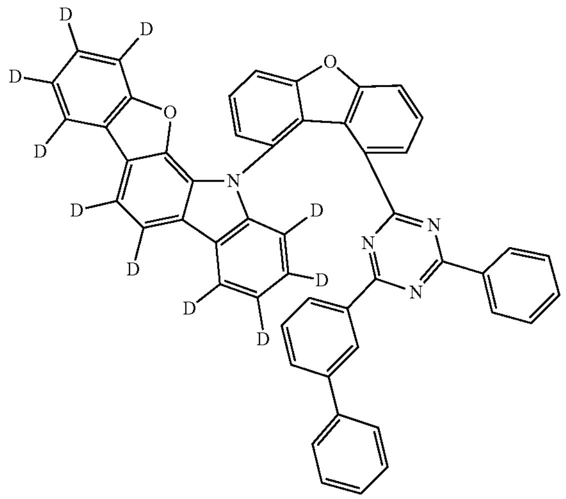
567
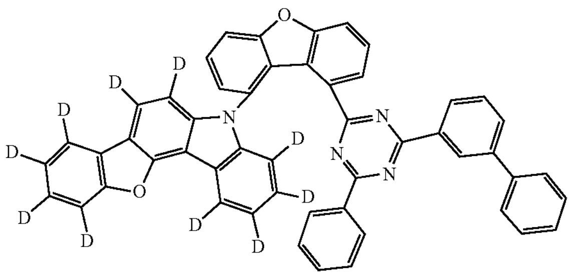
568
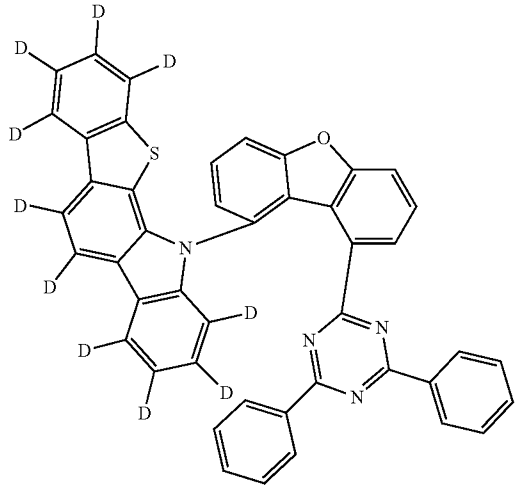
569
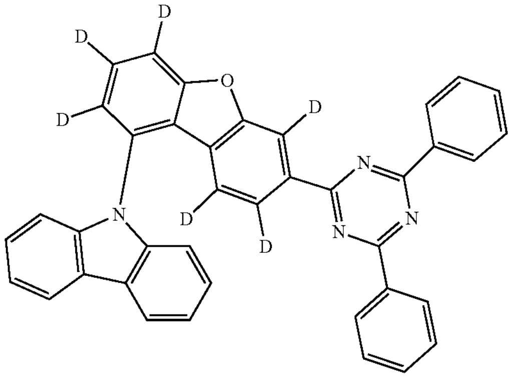
570
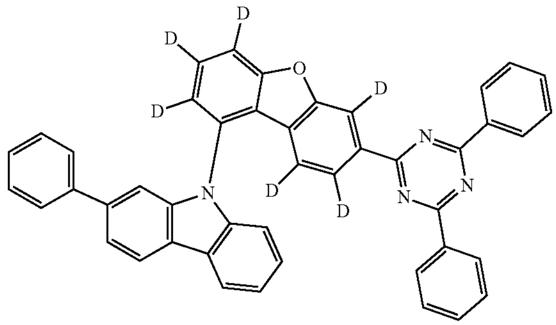
571
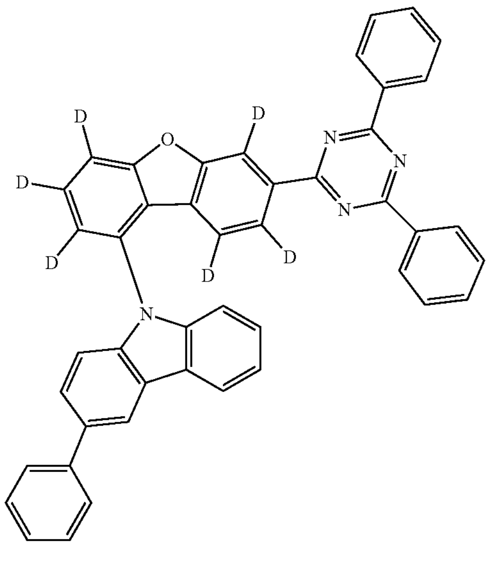

-continued
572
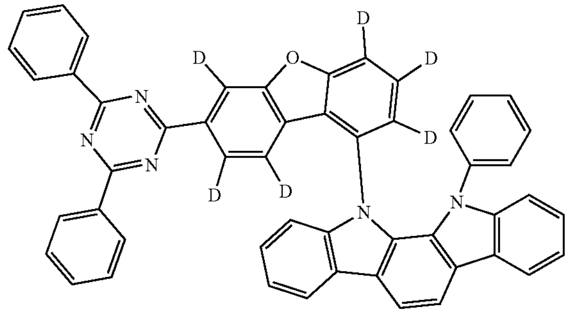
573
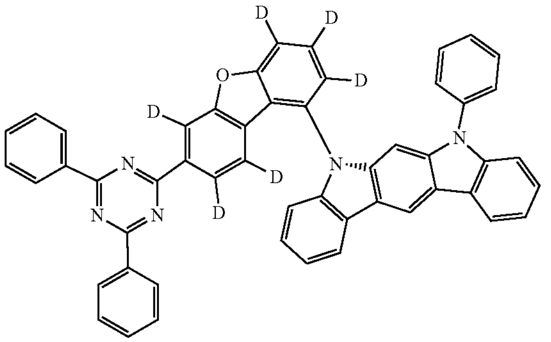
574
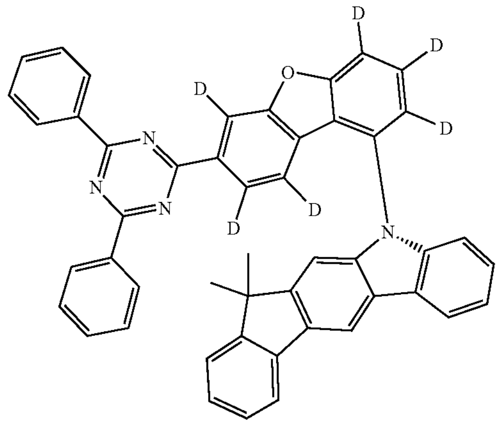
575
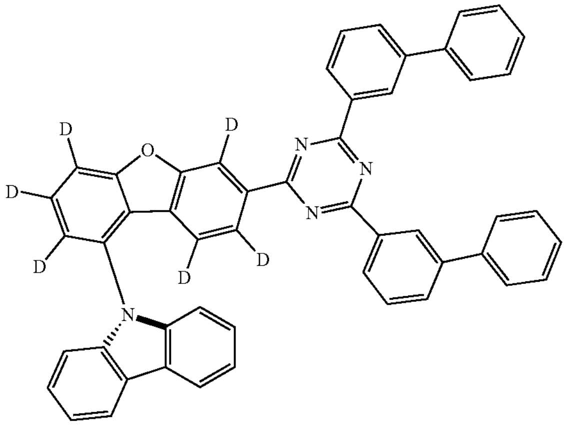
576
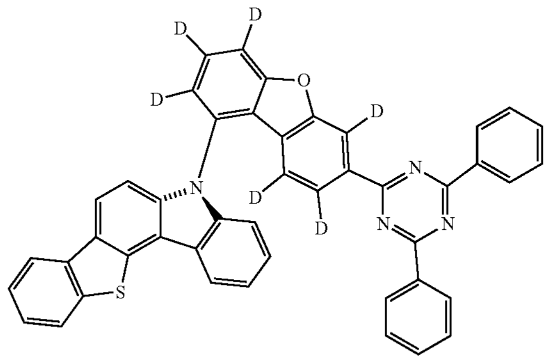
577
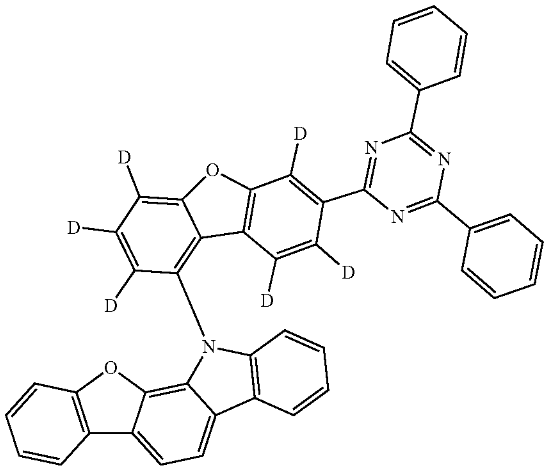

-continued
578
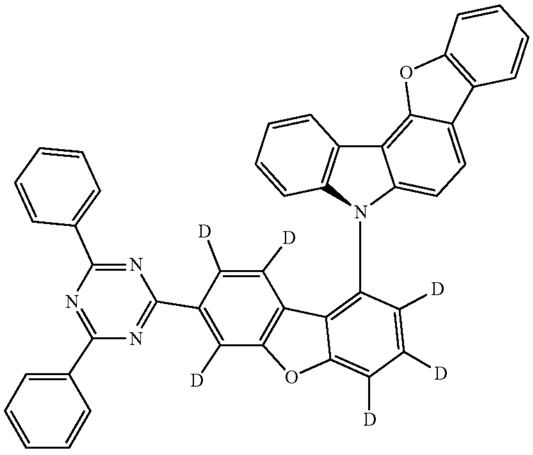
579
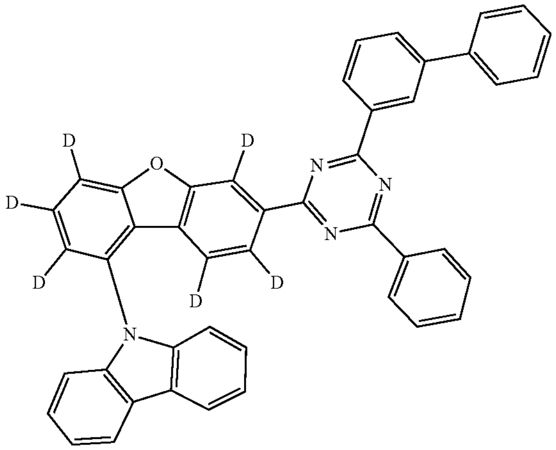
580
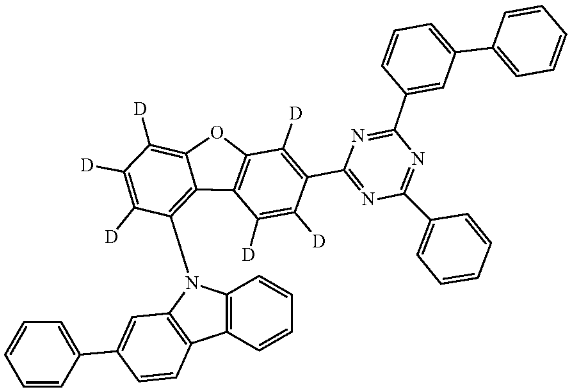
581
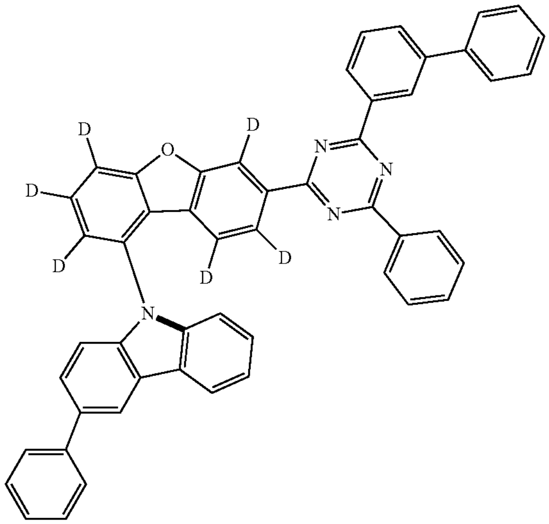
582
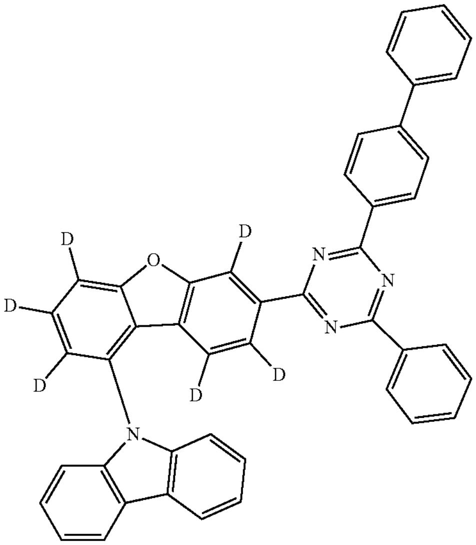
583
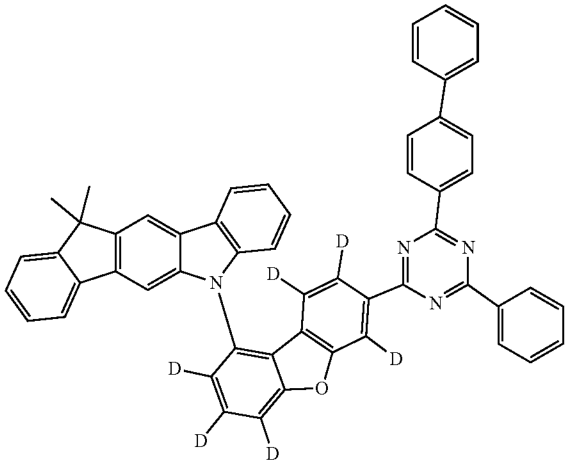

-continued
584
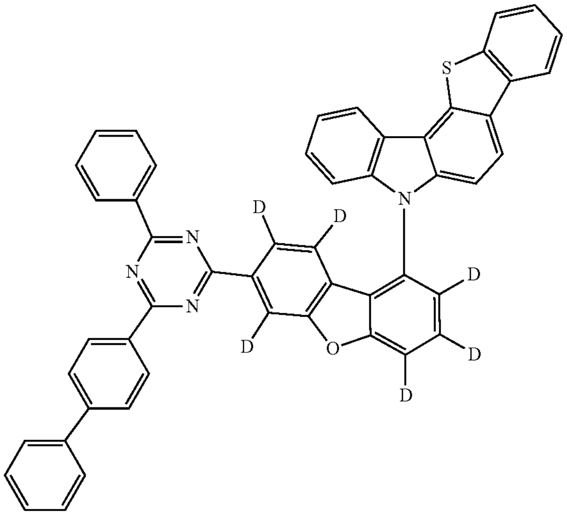
585
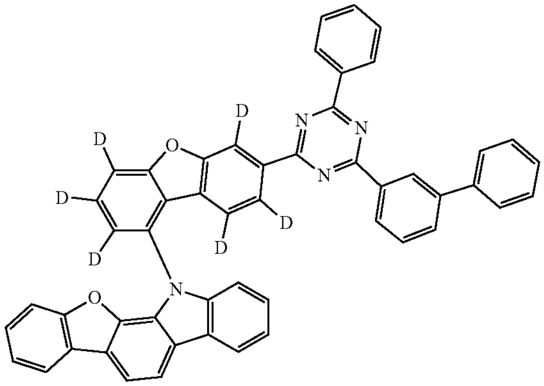
586
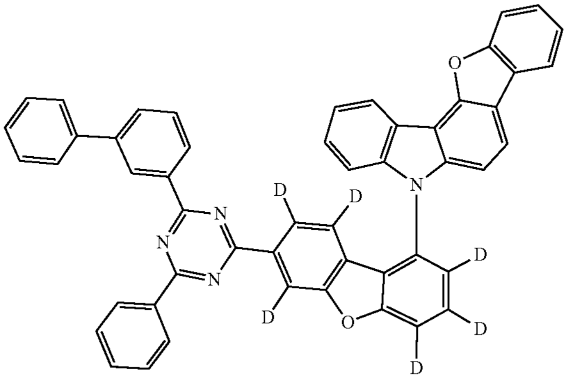
587
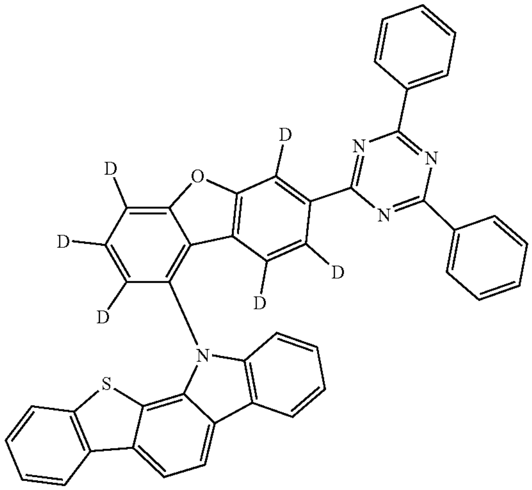

588
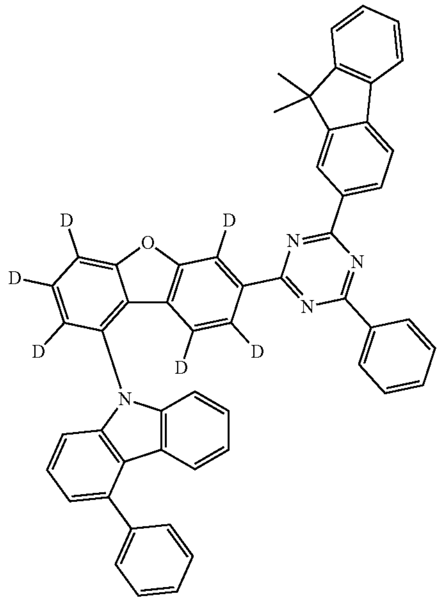
589
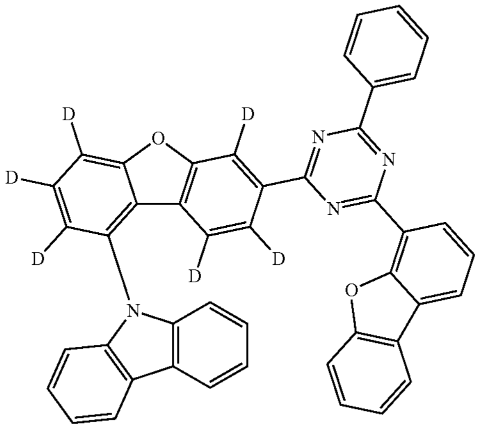
590
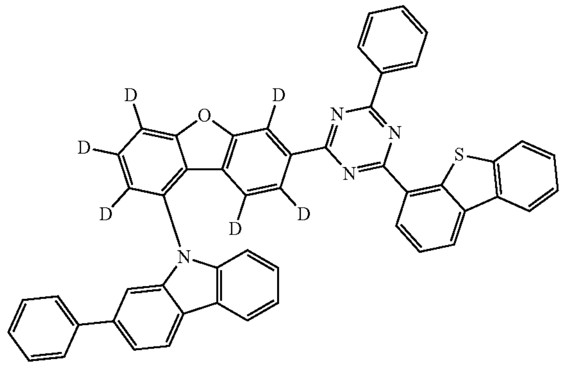
591
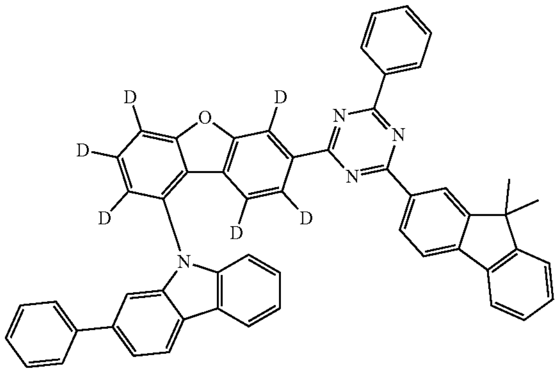
592
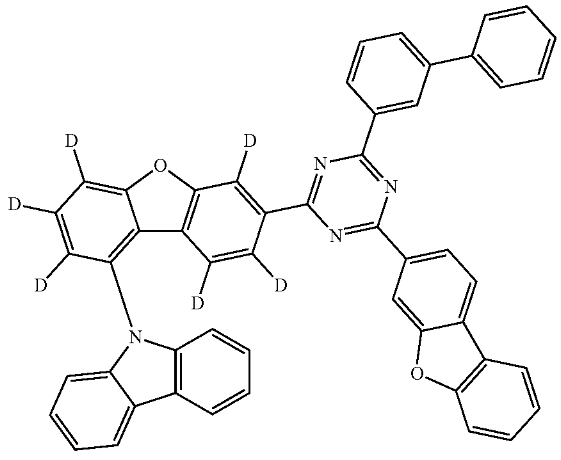
593
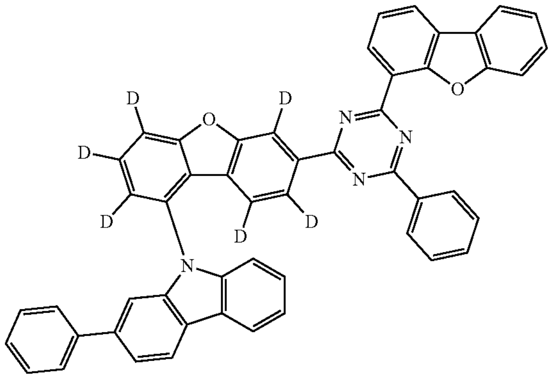

-continued
594
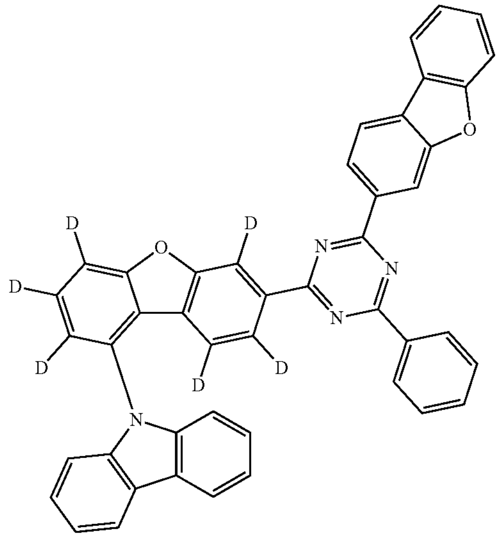
595
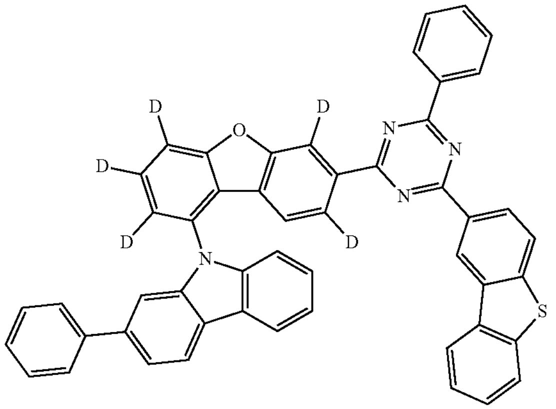
596
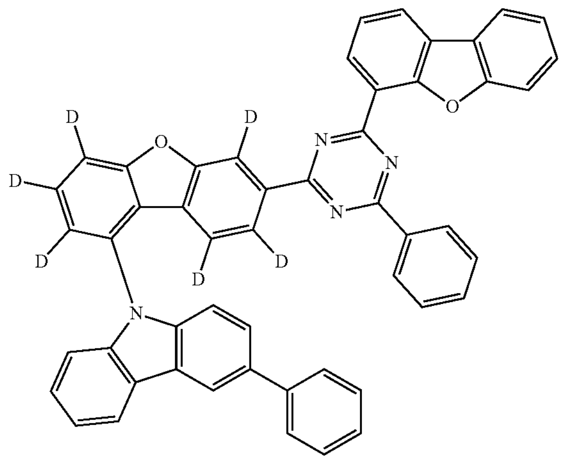
597
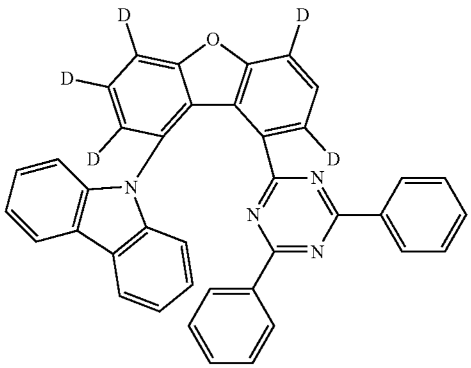
598
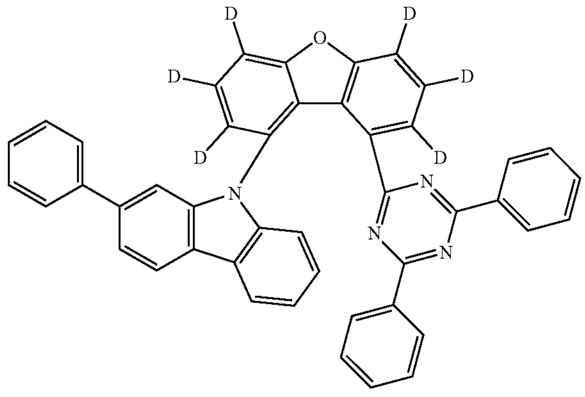
599
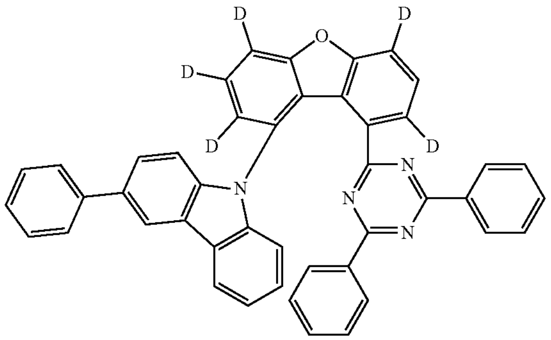

-continued
600
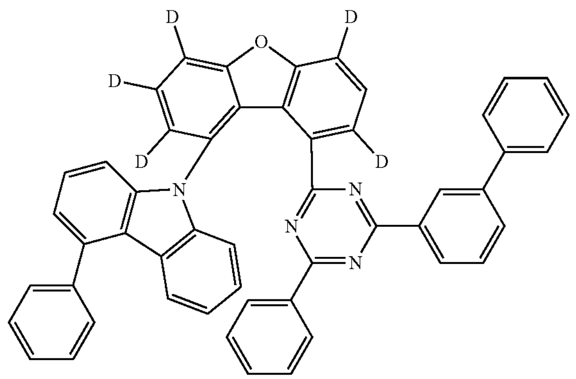
601
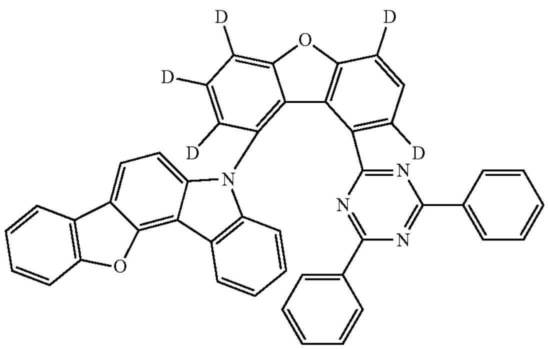
602
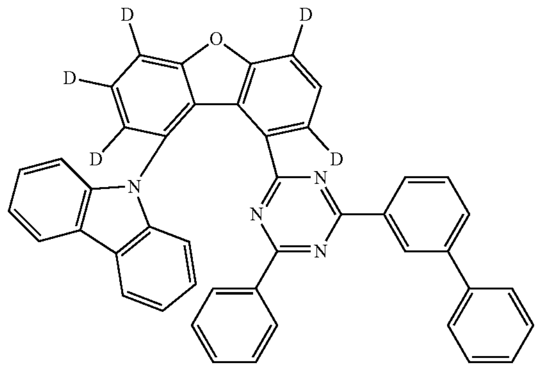
603
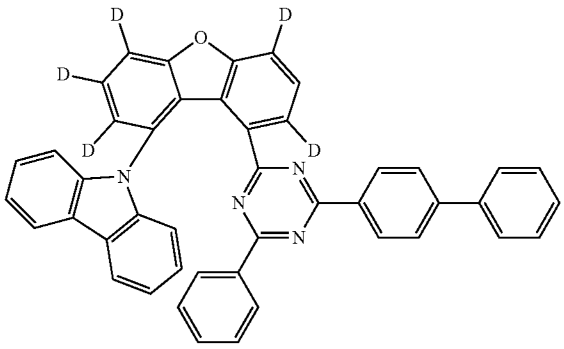
604
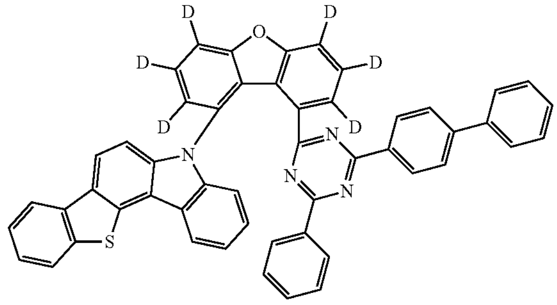
605
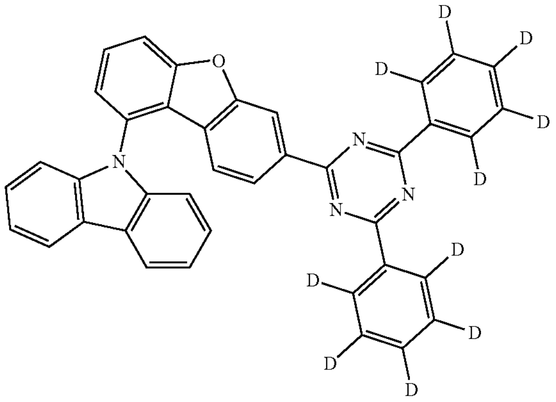

-continued
606
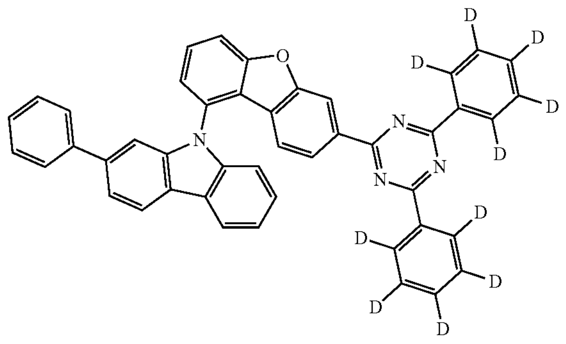
607
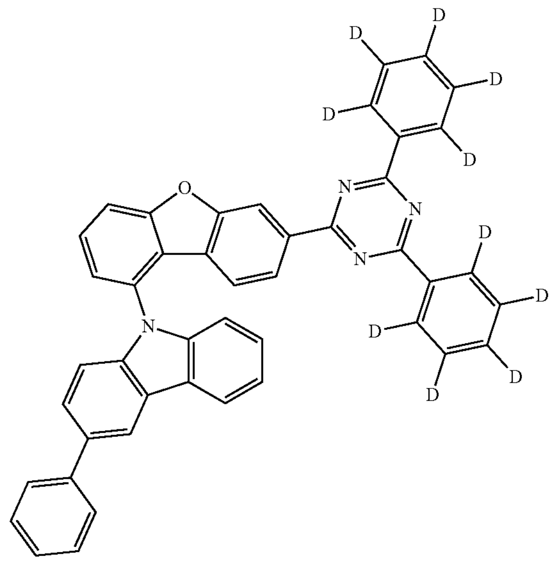
608
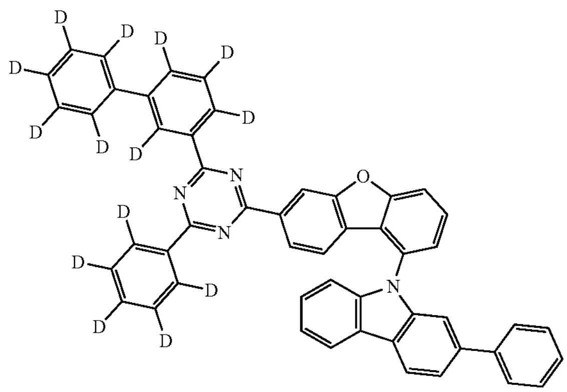
609
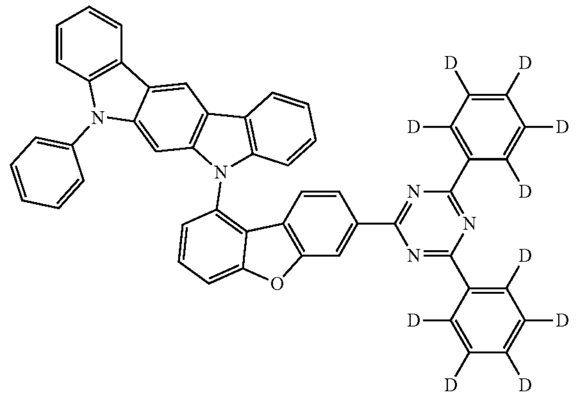
610
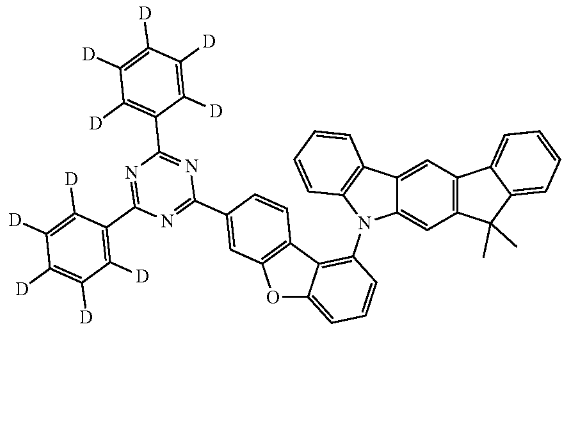
611
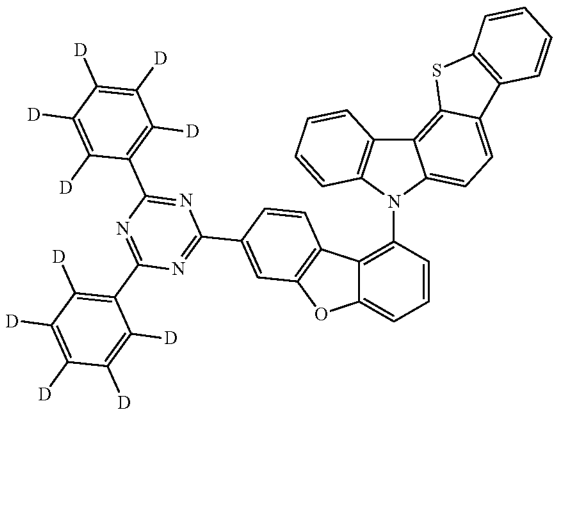

-continued
612
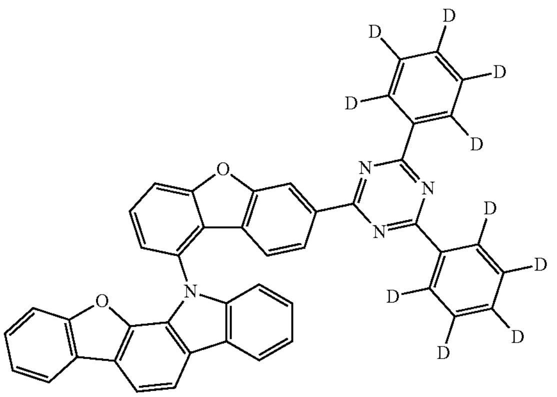
613
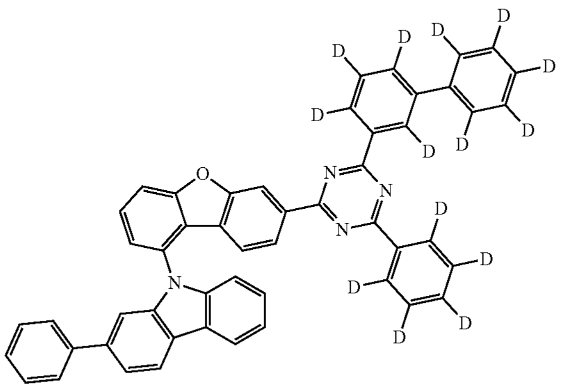
614
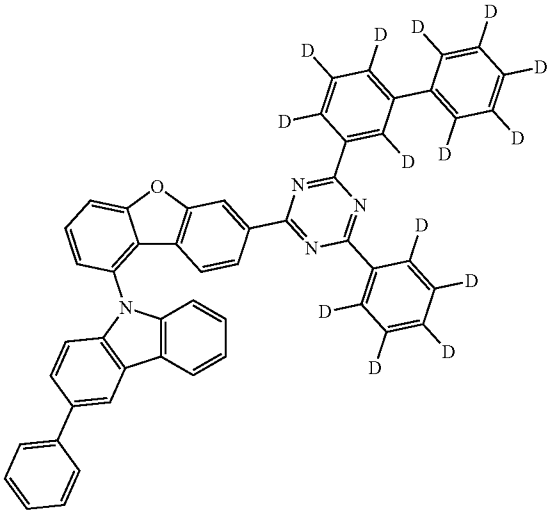
615
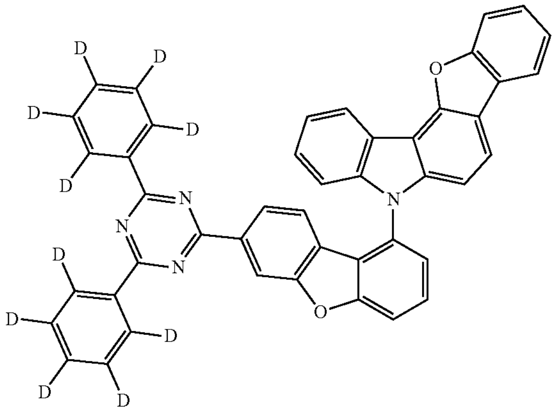
616
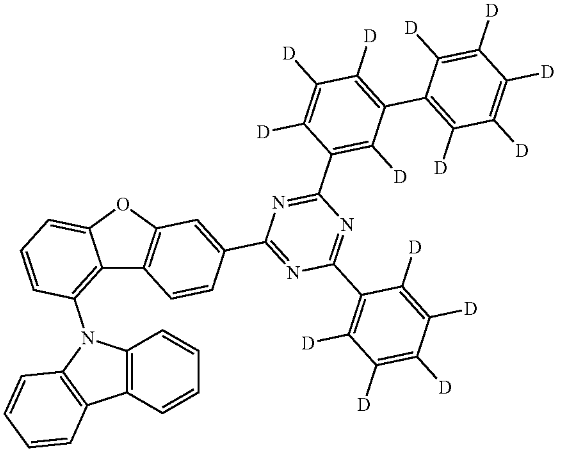
617
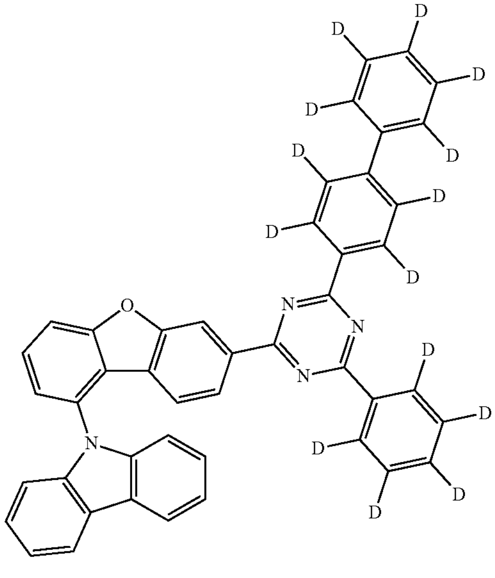

-continued
618
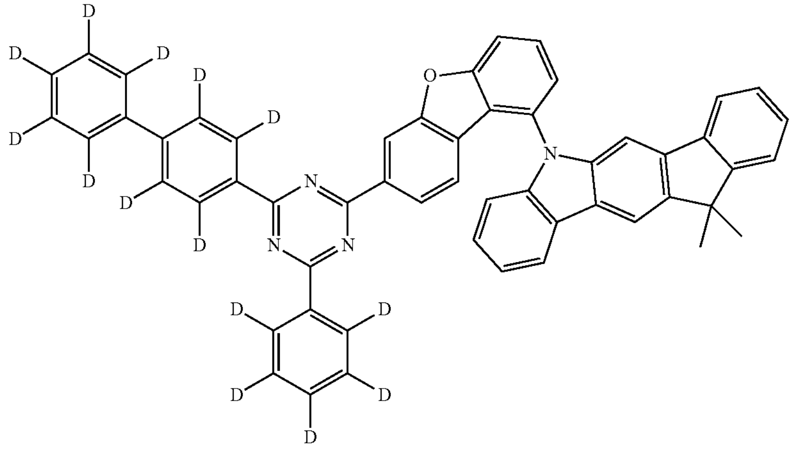
619
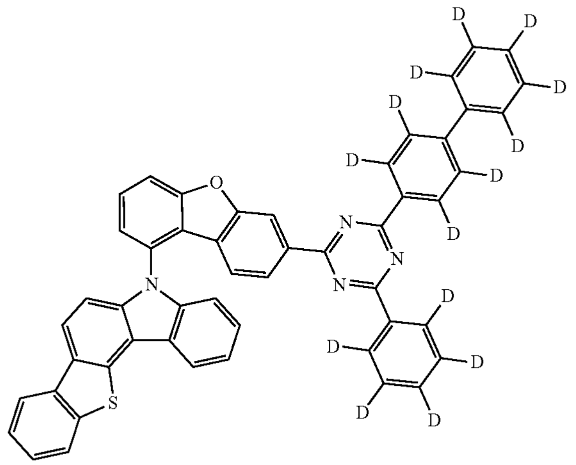
620
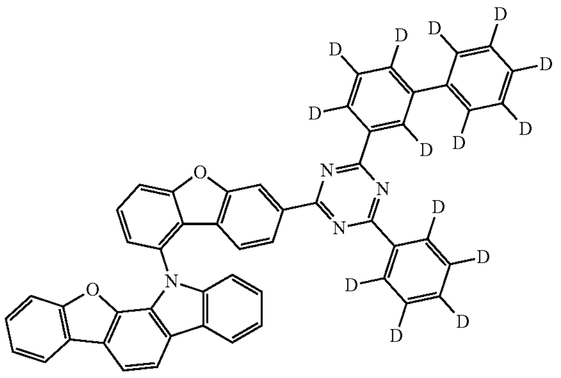
621
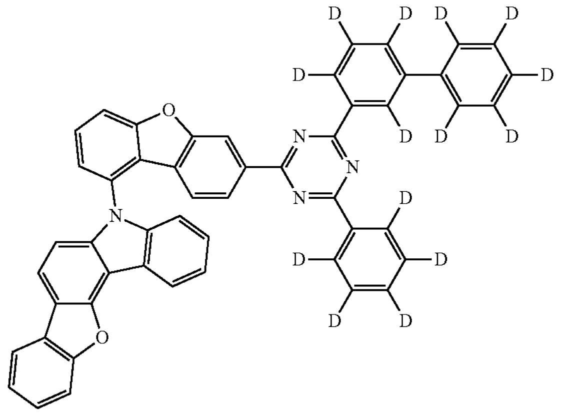
622
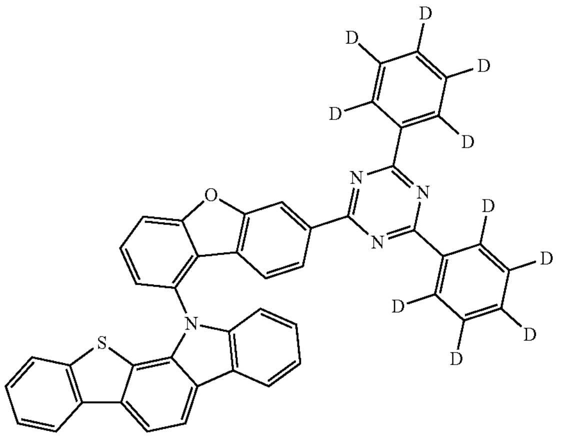

-continued
623
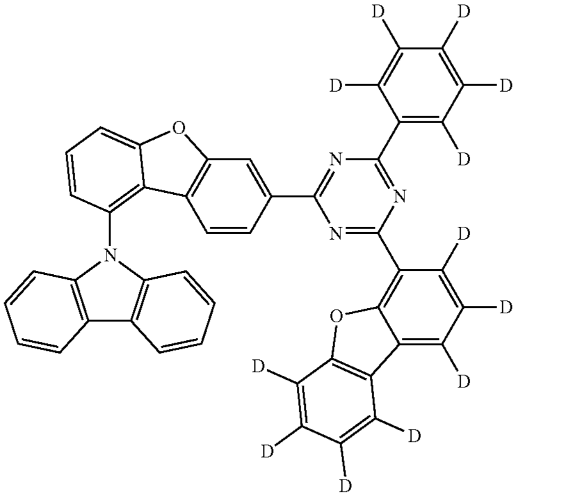
624
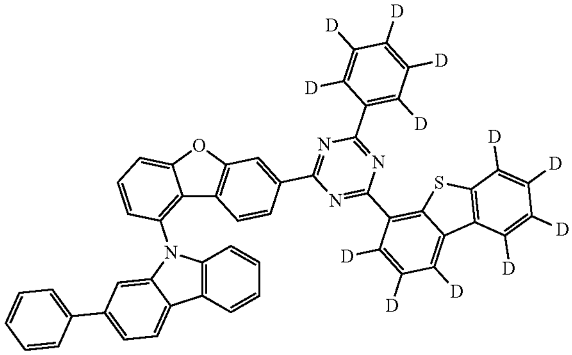
625
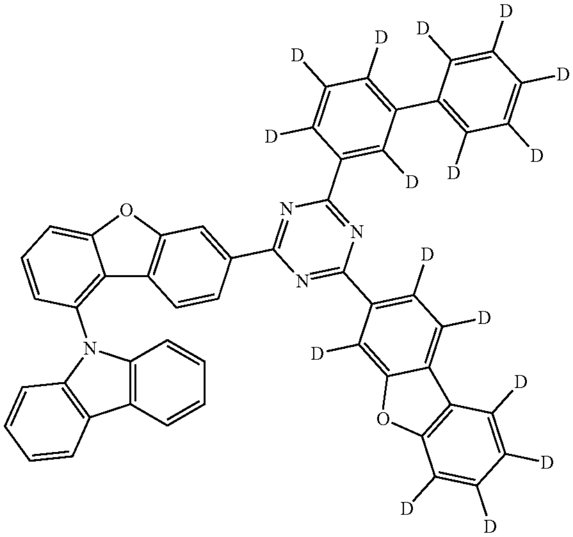
626
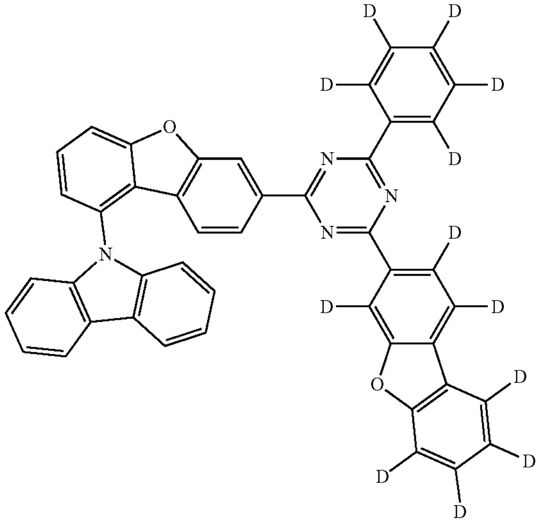
627
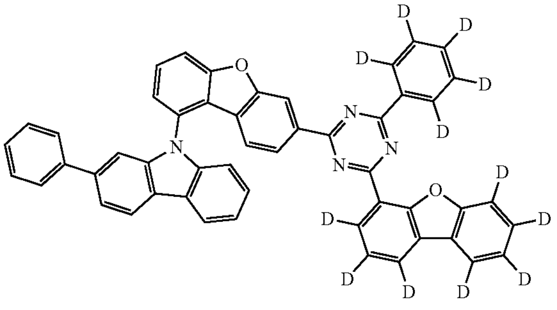
628
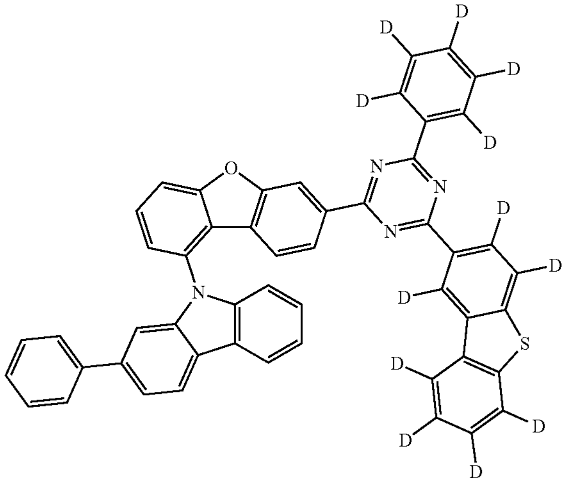

-continued
629
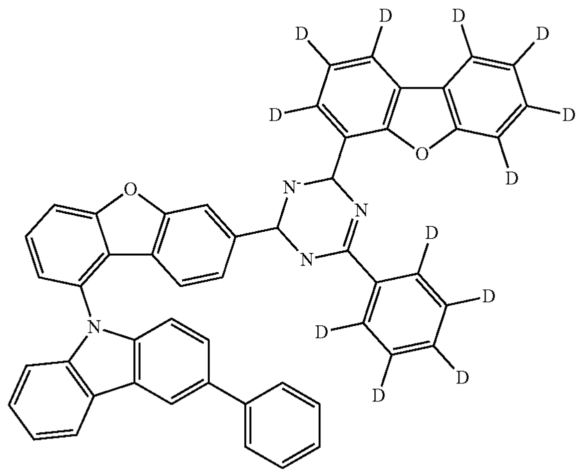
630
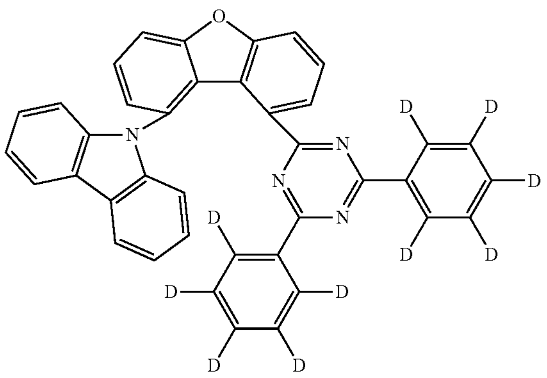
631
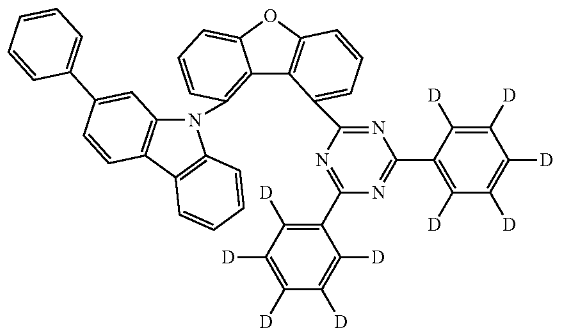
632
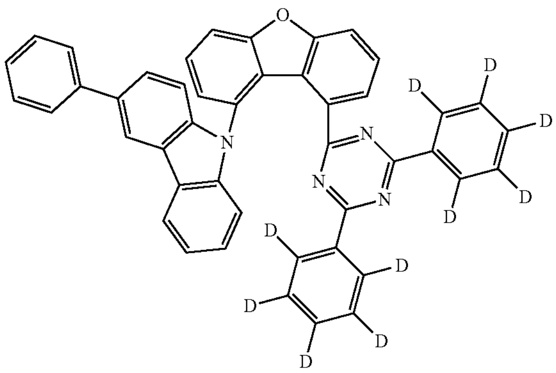
633
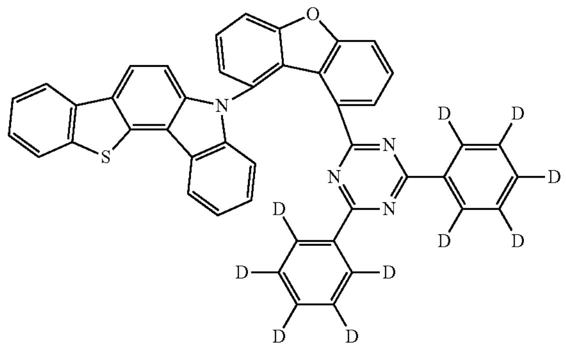
634
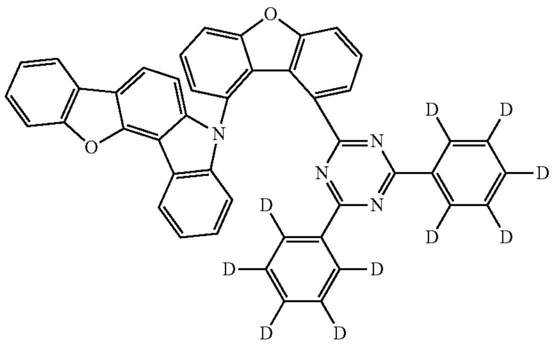

-continued
635
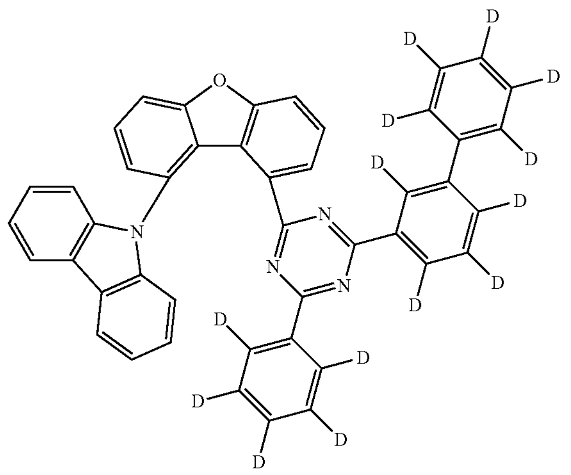
636
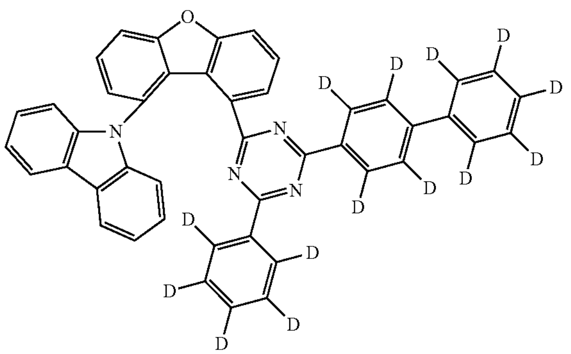
637
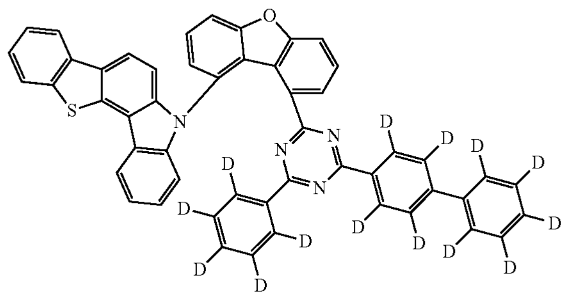
638
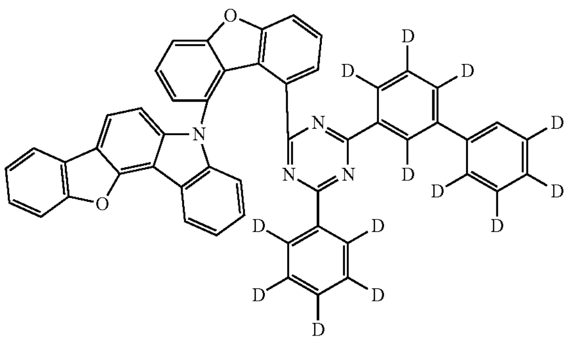
639
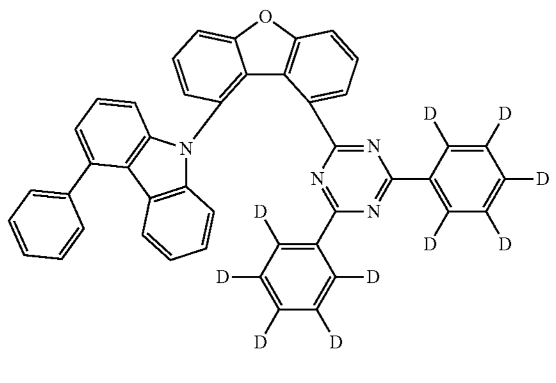
640
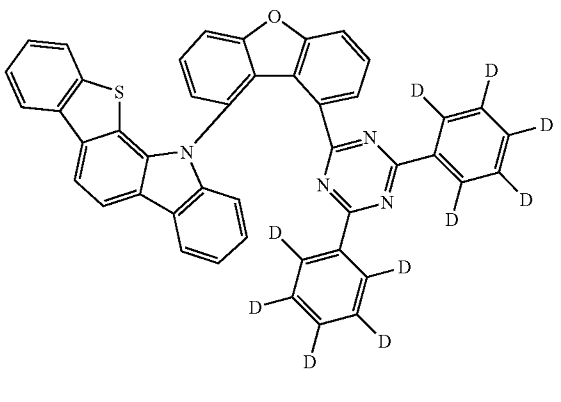

-continued
641
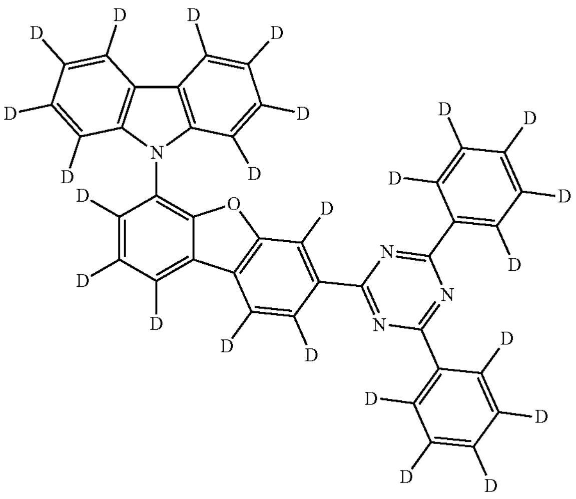
642
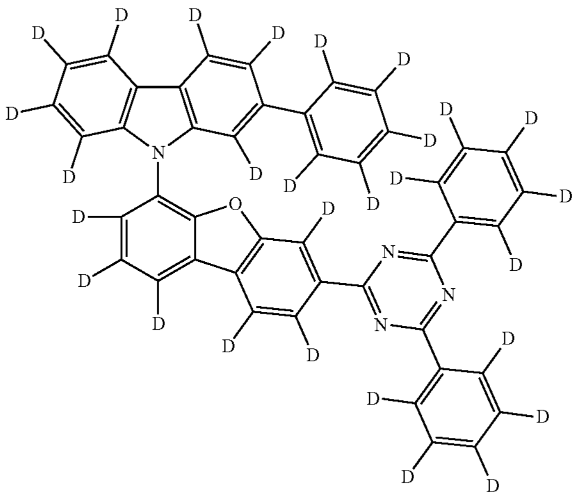
643
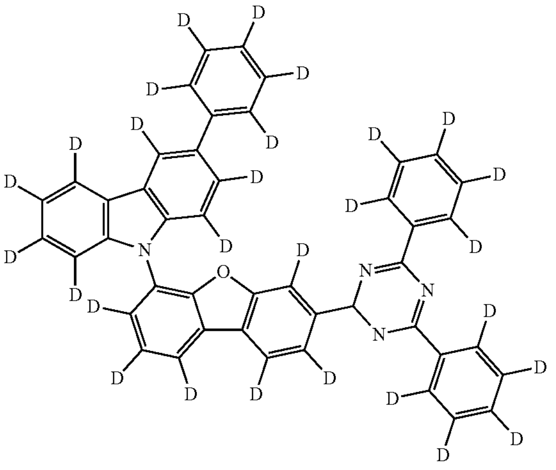
644
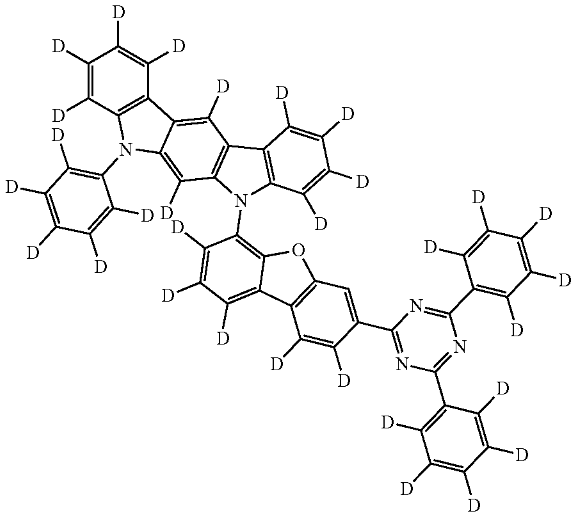
645
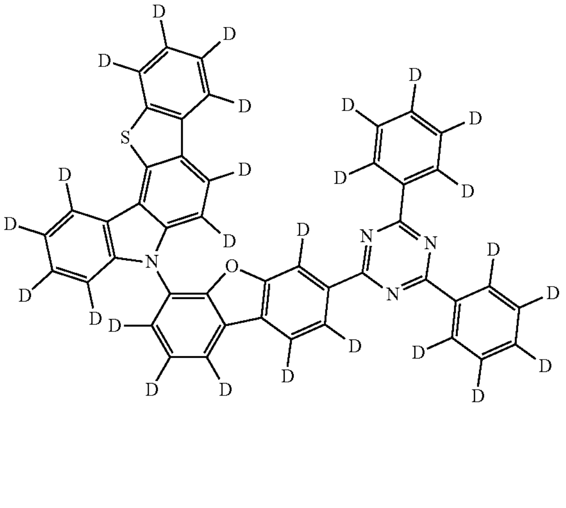
646
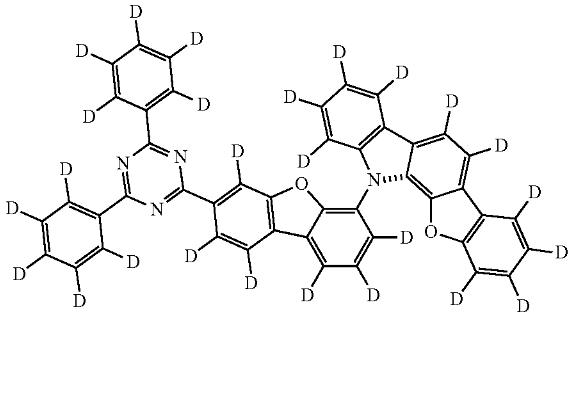

-continued
647
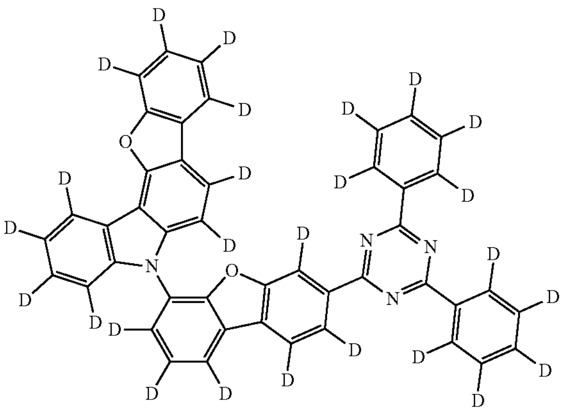
648
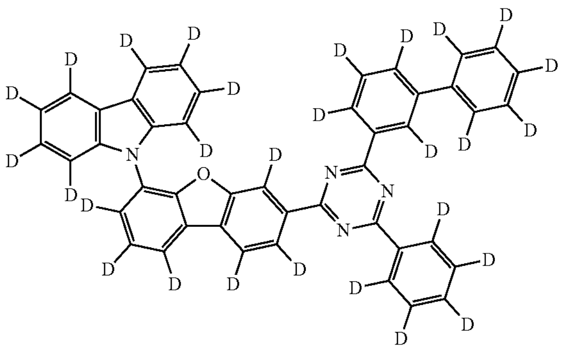
649
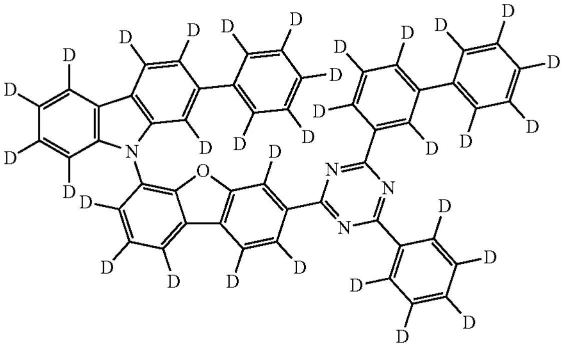
650
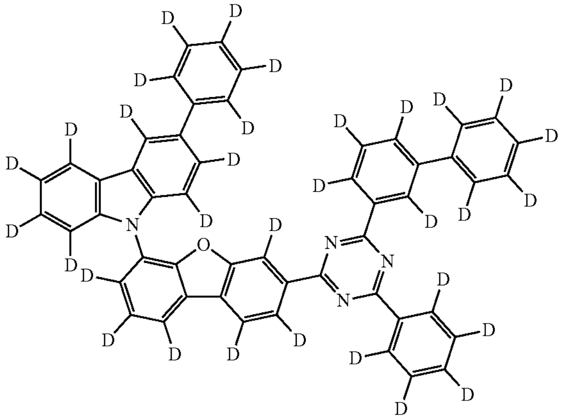
651
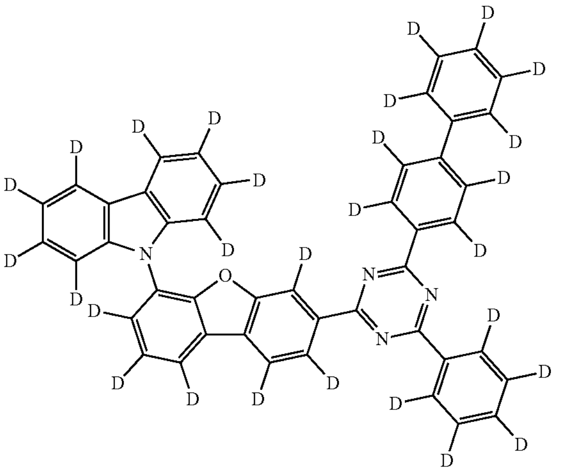
652
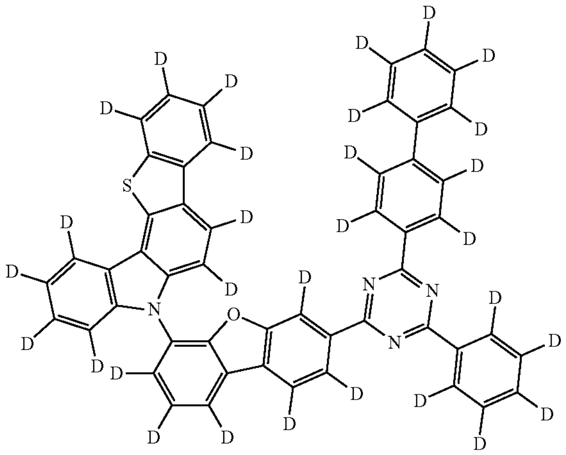

-continued
653
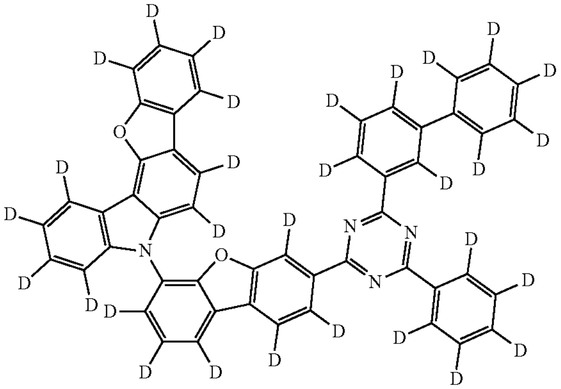
654
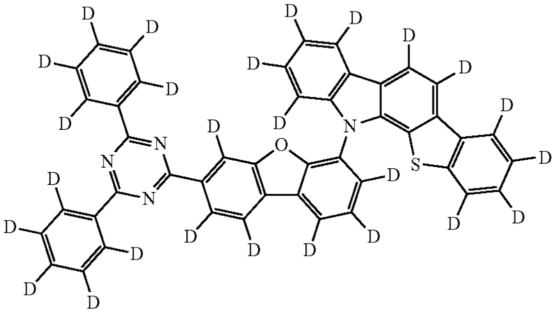
655
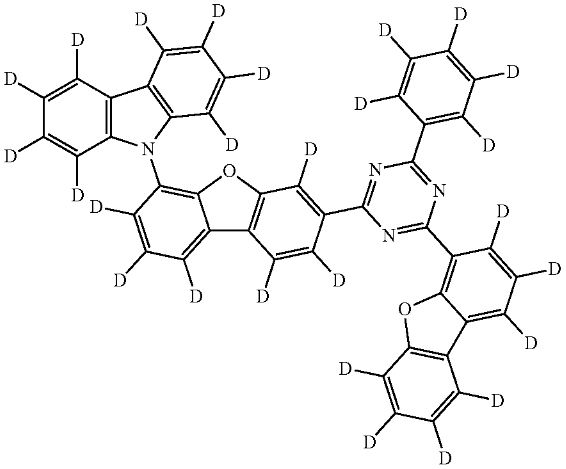
656
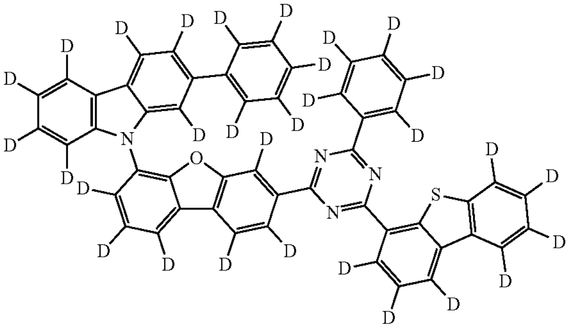
657
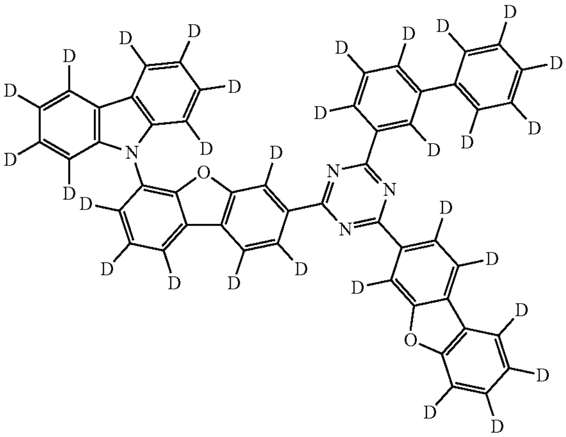
658
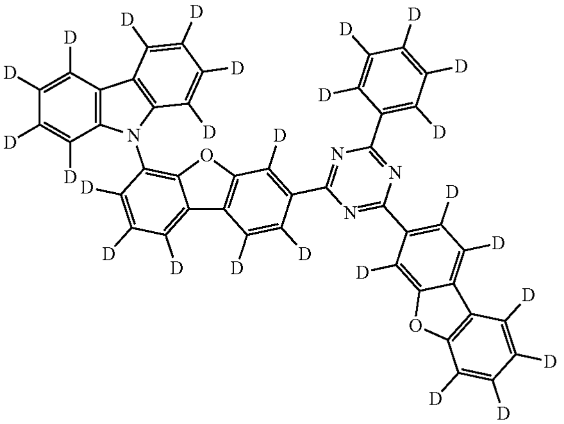

-continued
659
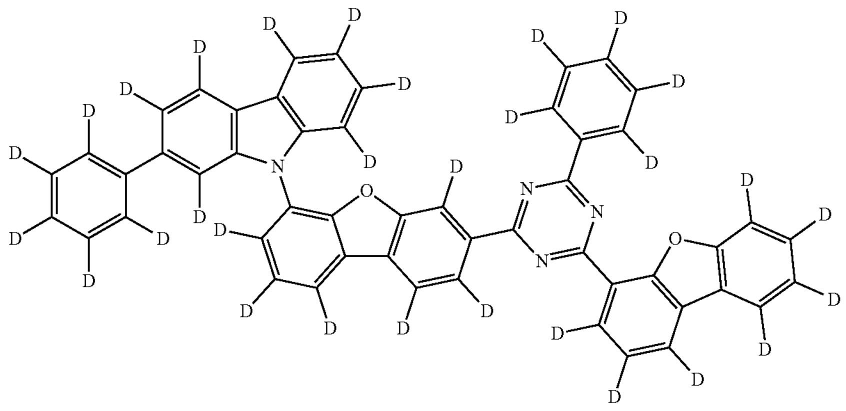
660
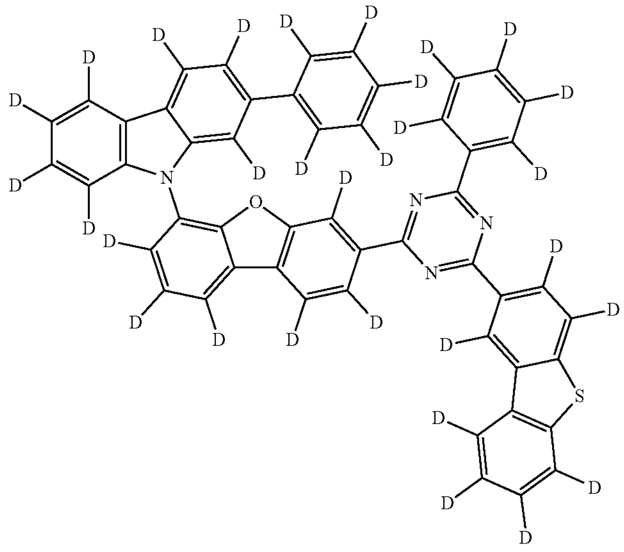
661
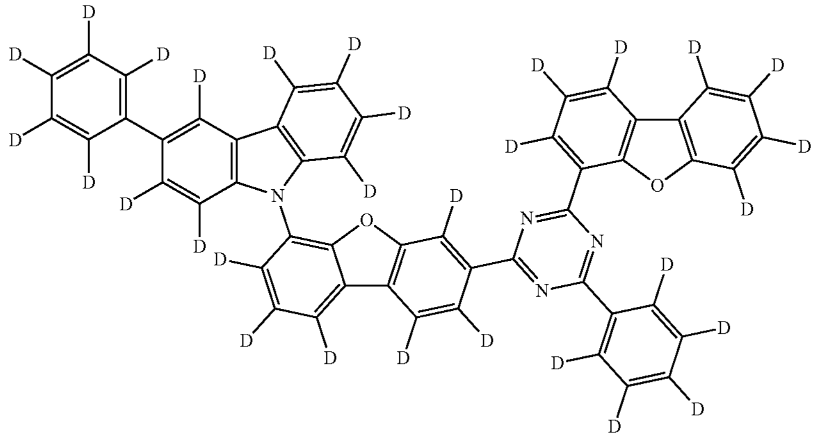

-continued
662
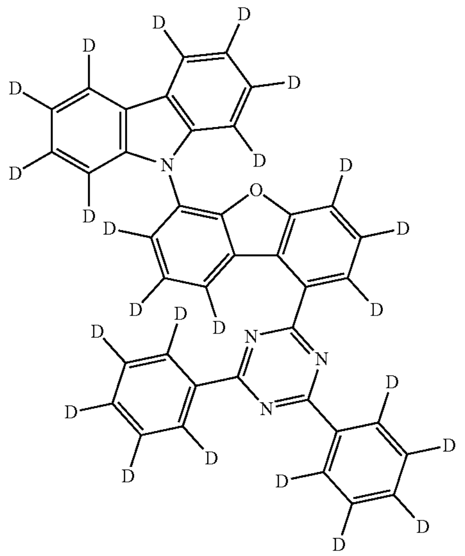
663
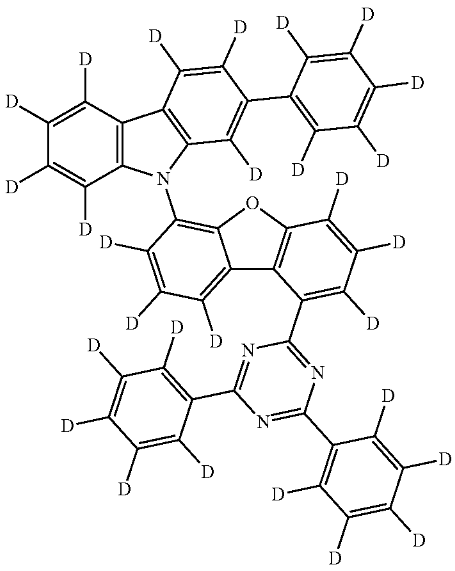
664
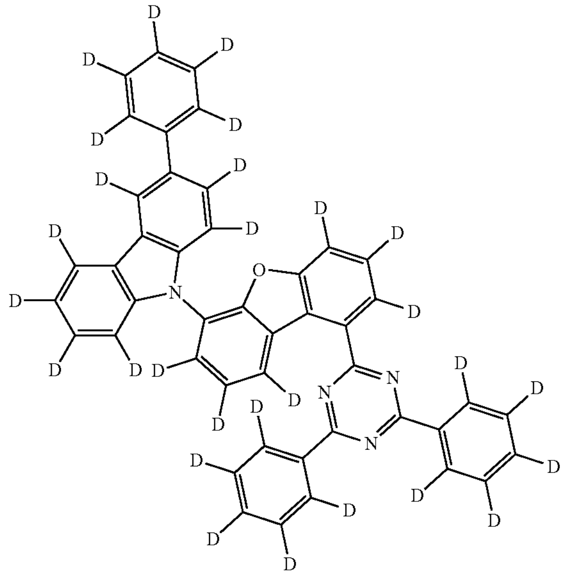
665
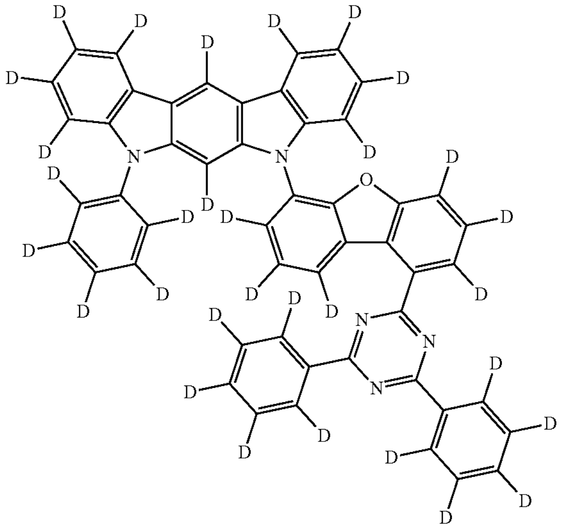

-continued
666
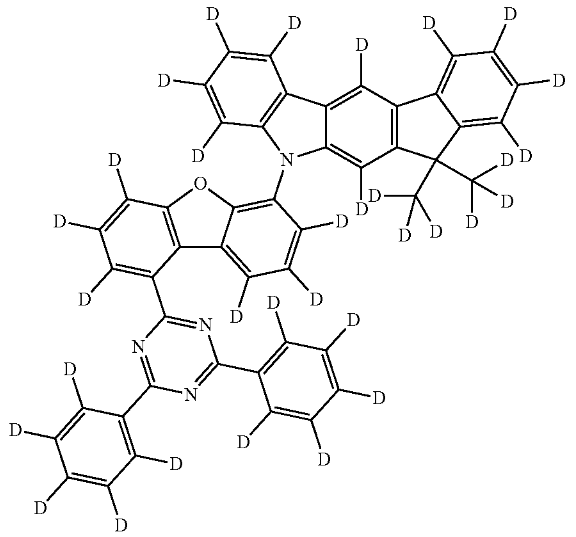
667
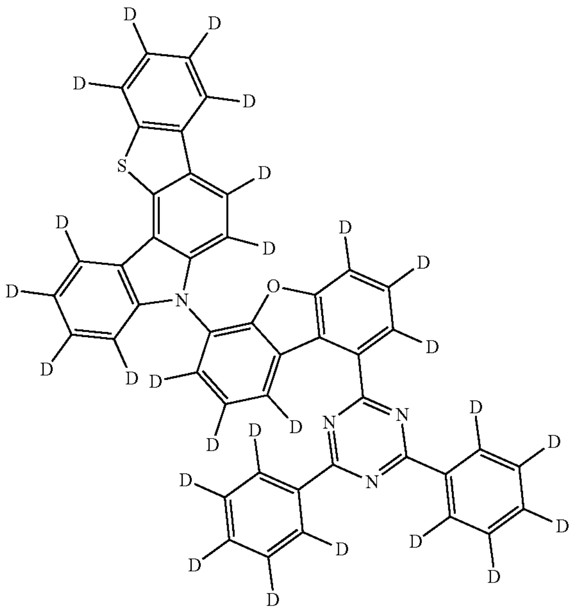
668
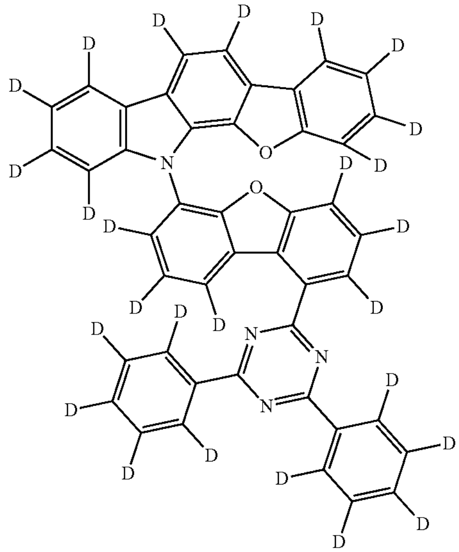
669
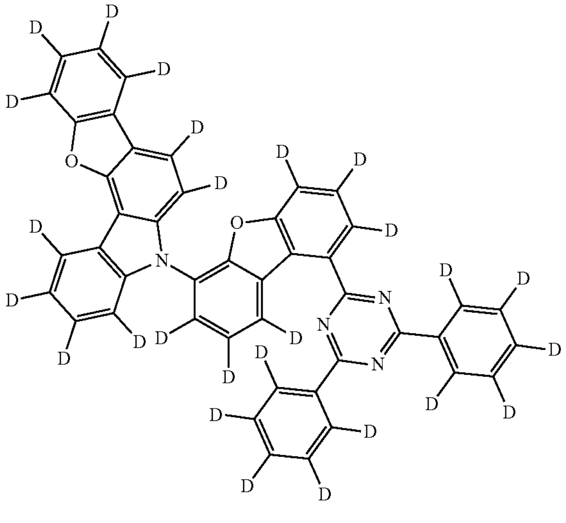
670
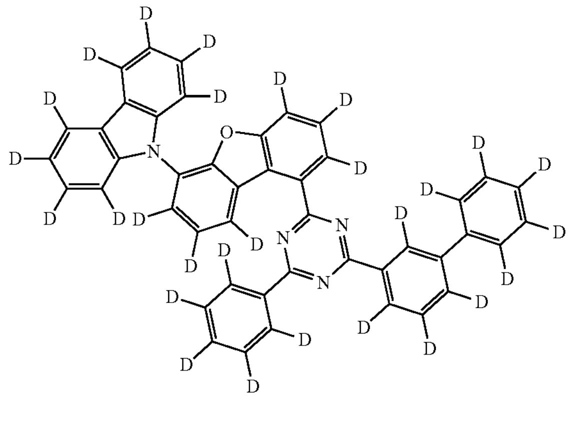
671
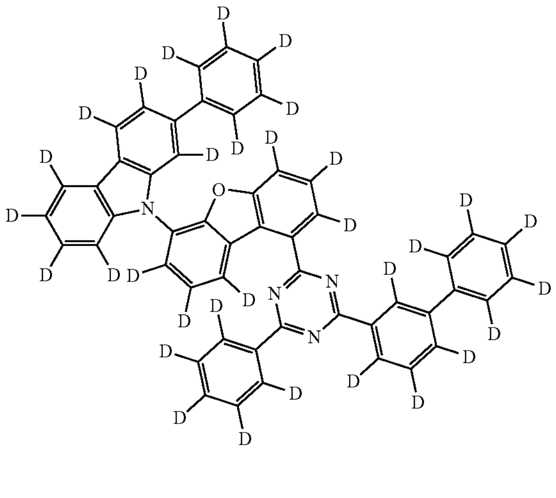

-continued
672
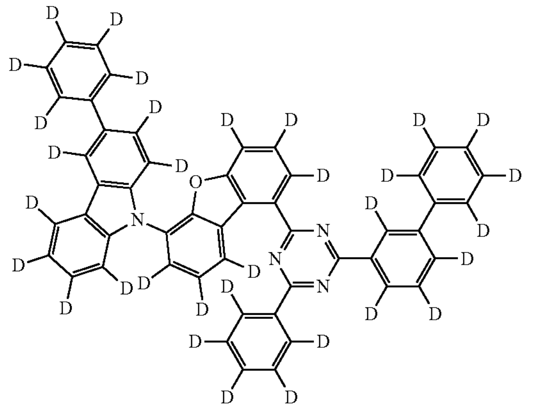
673
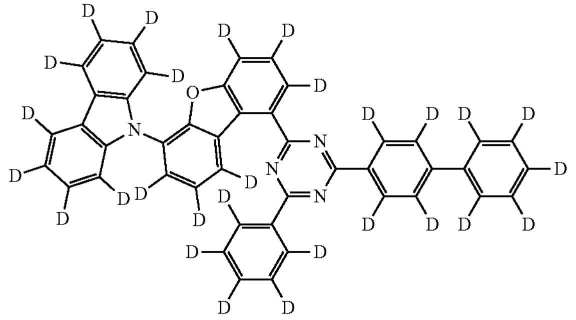
674
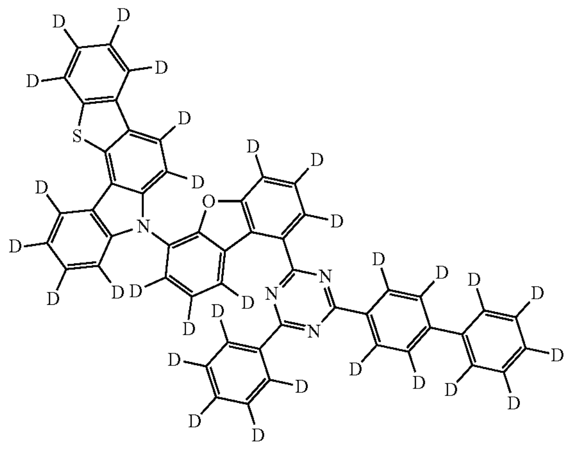
675
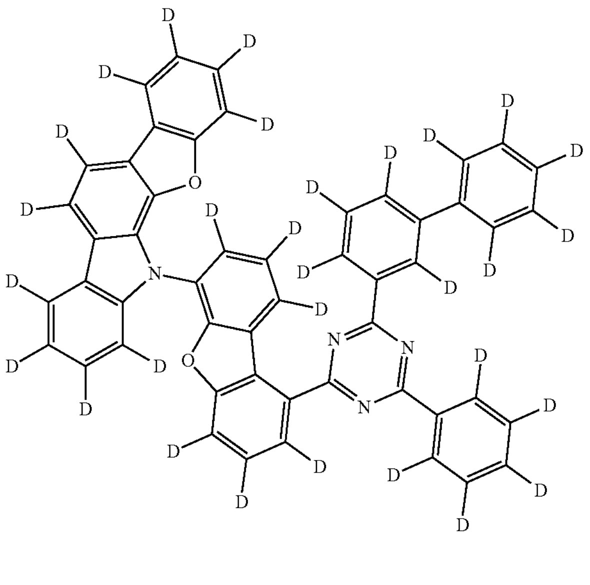

-continued
676
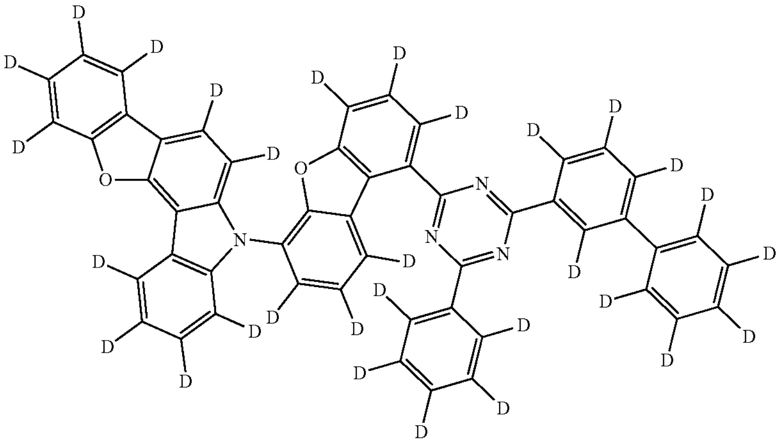
677
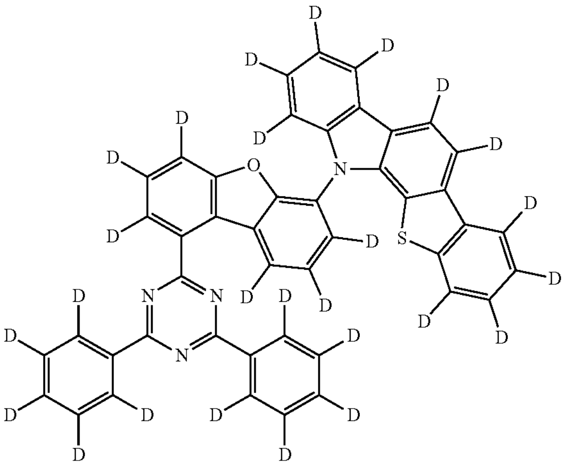
678
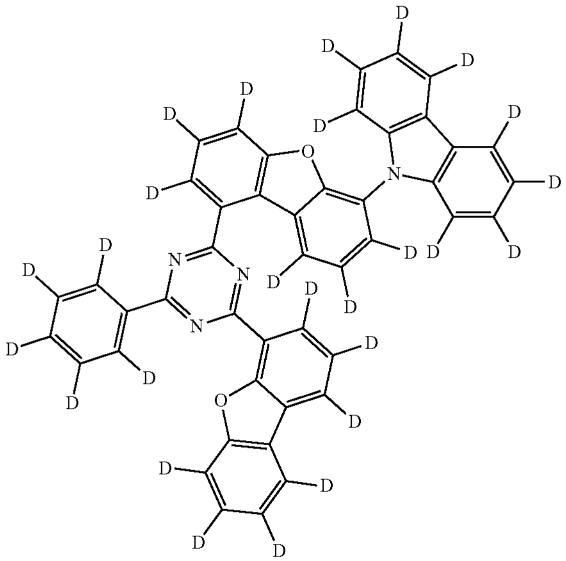
679
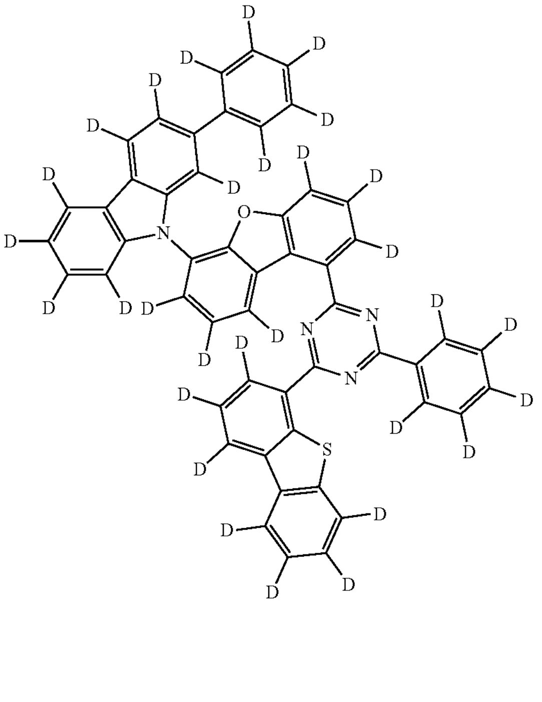
680
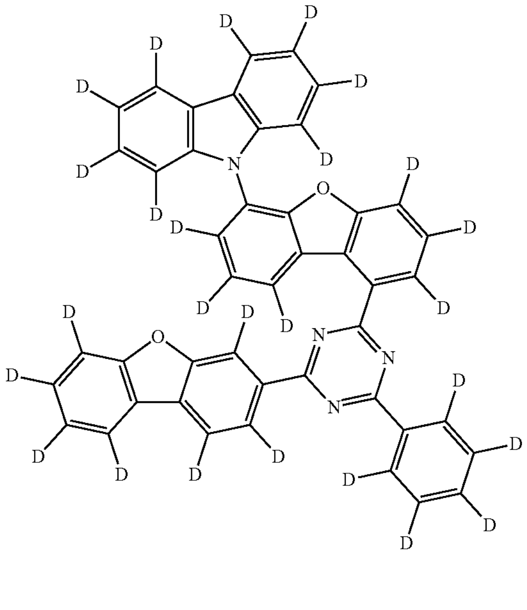

-continued
681
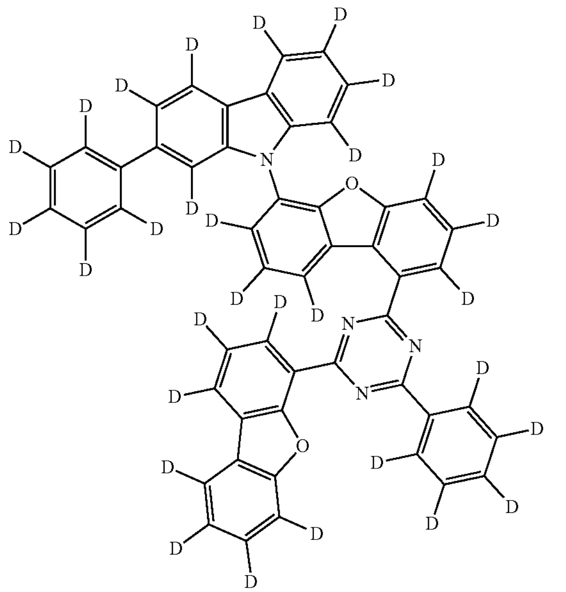
682
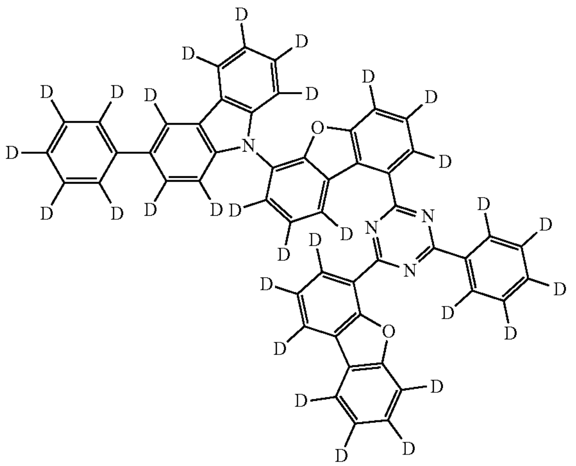
683
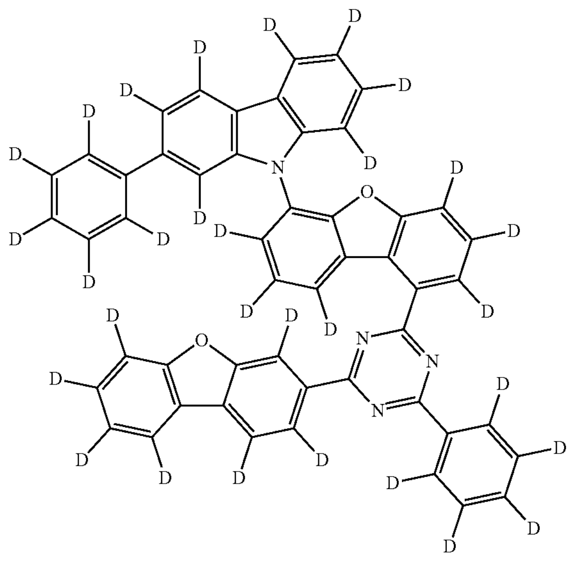
684
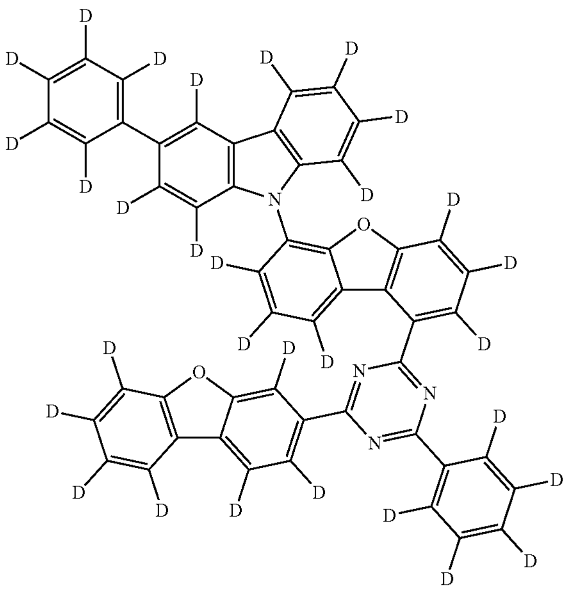
685
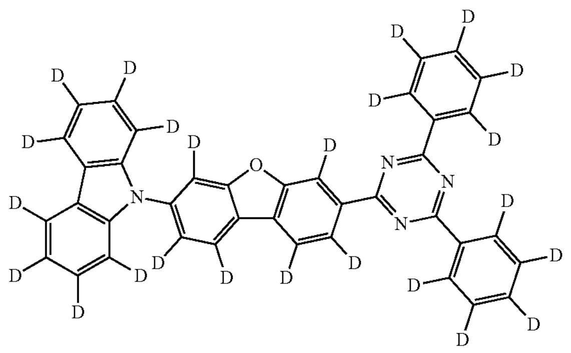
686
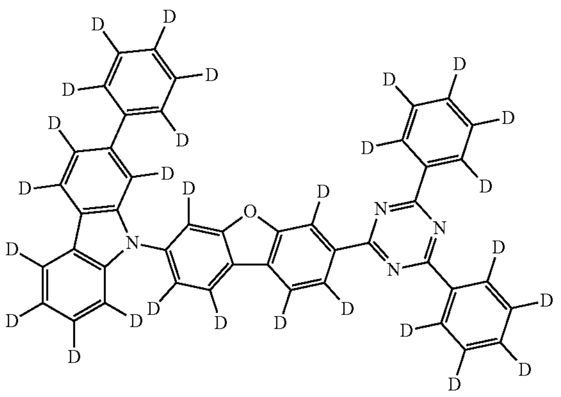

-continued
687
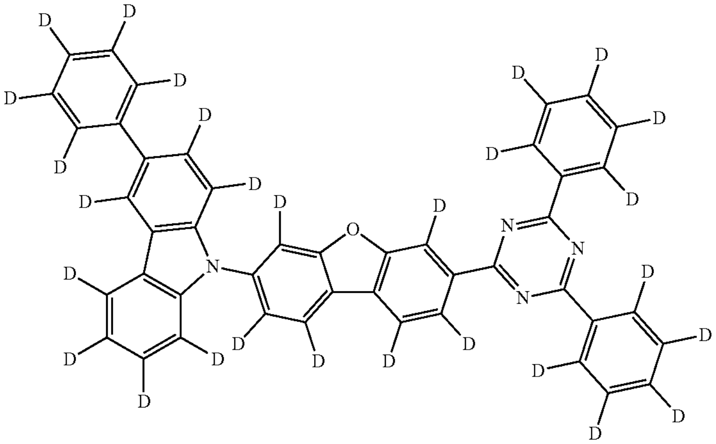
688
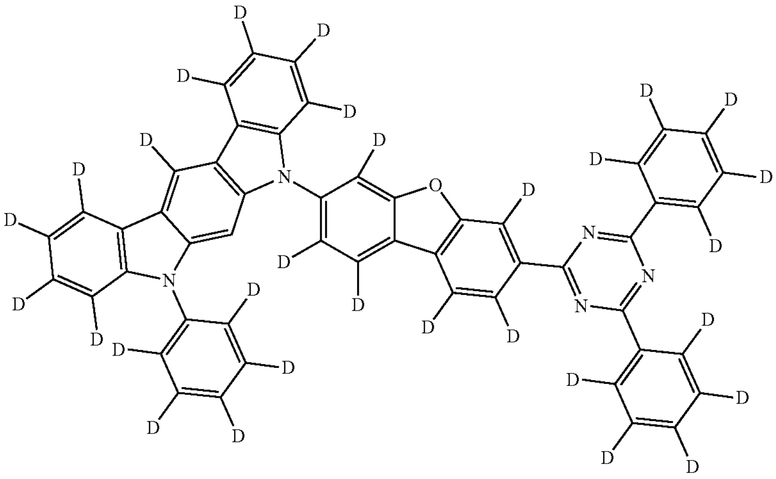
689
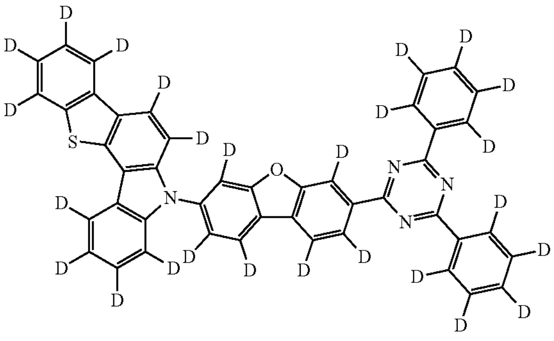
690
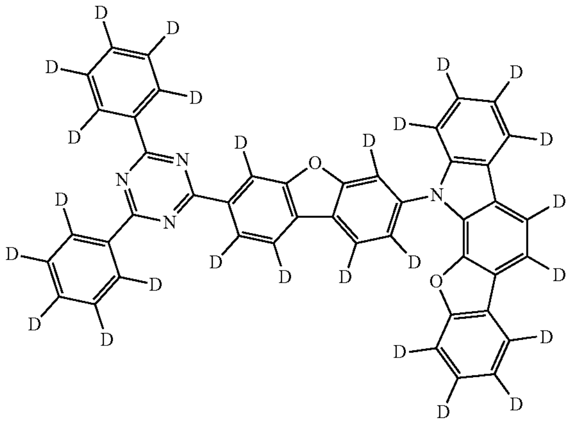

-continued
691
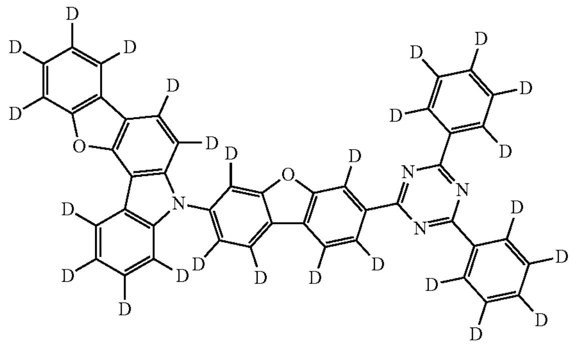
692
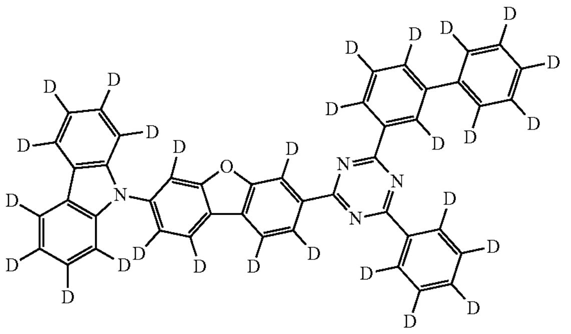
693
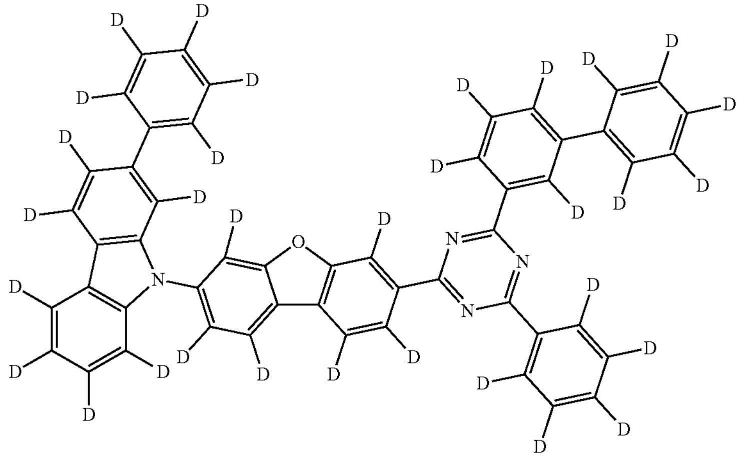
694
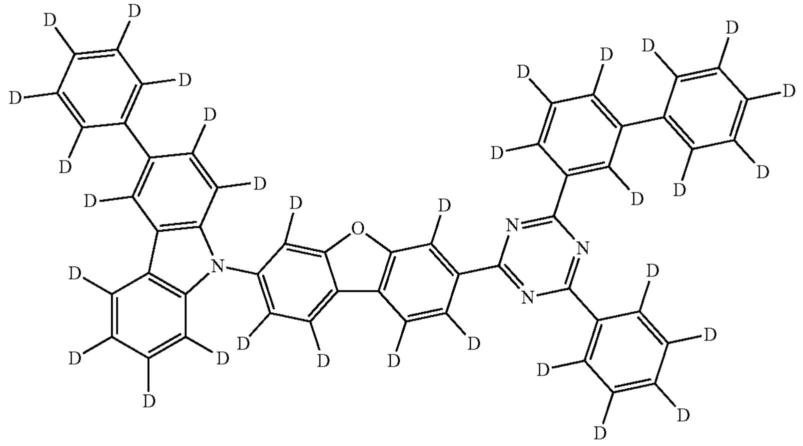

-continued
695
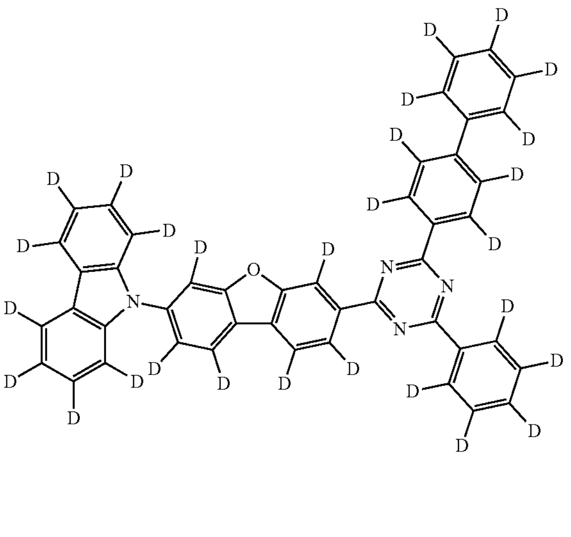
696
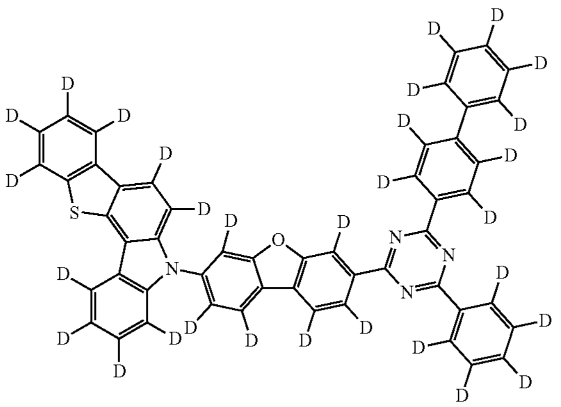
697
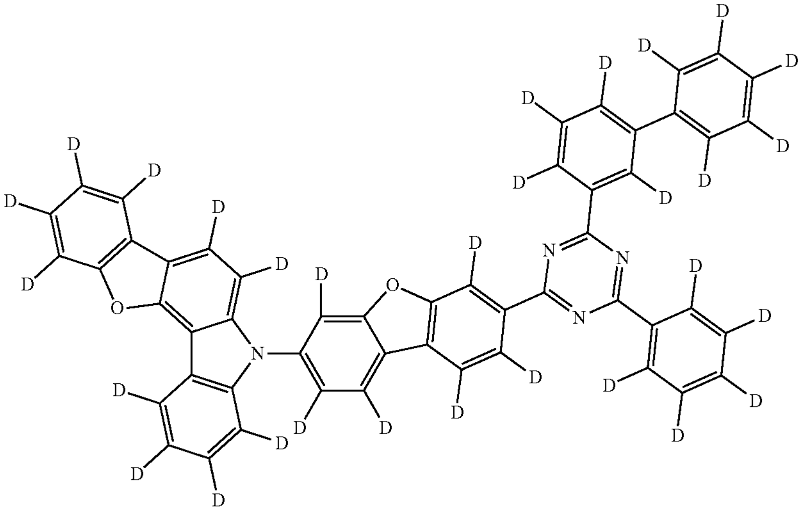
698
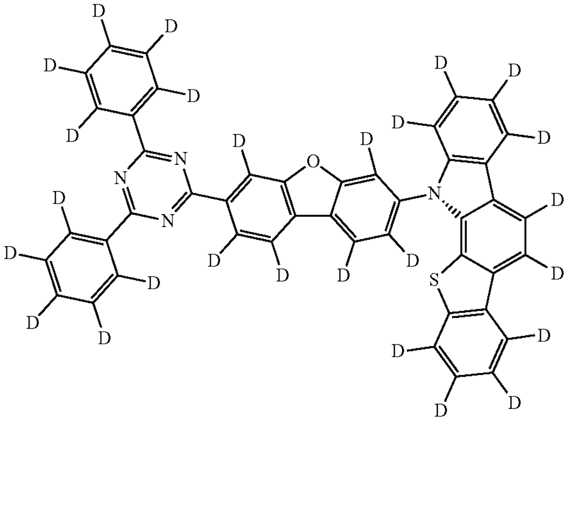
699
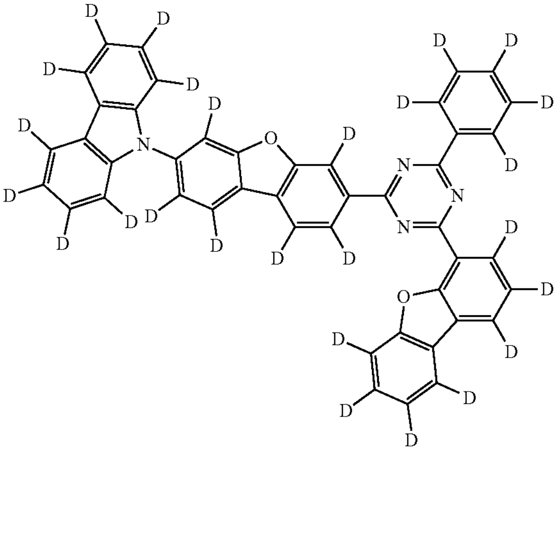

-continued
700
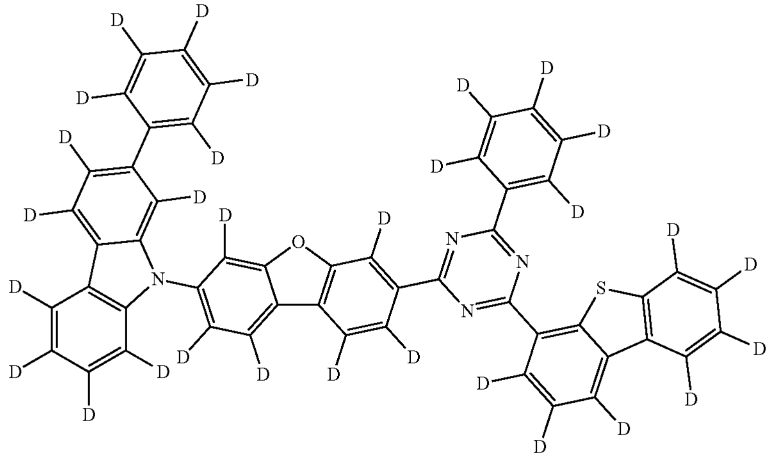
701
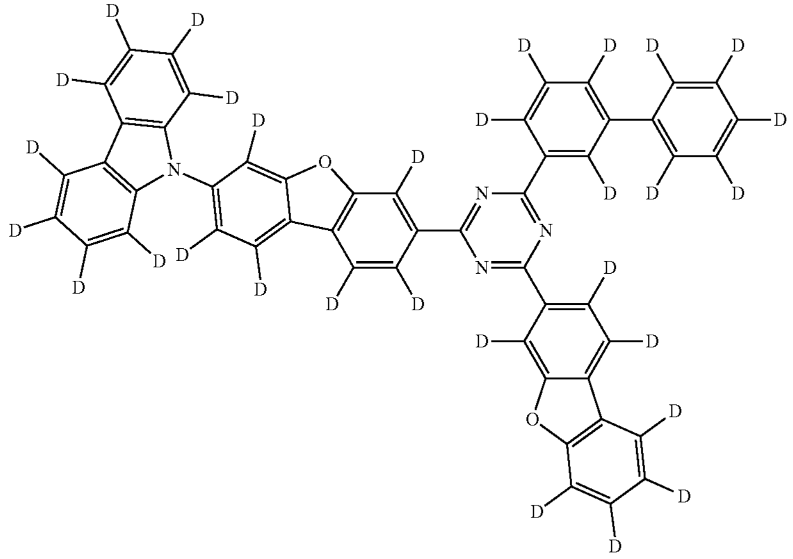
702
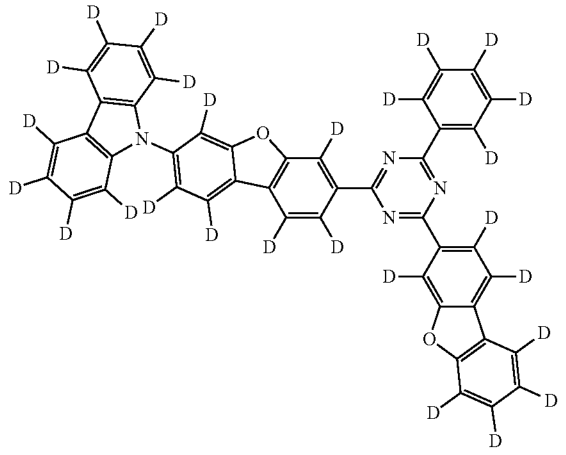
703
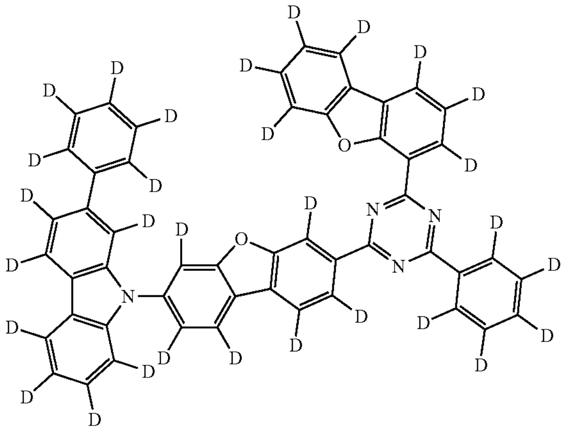

-continued
704
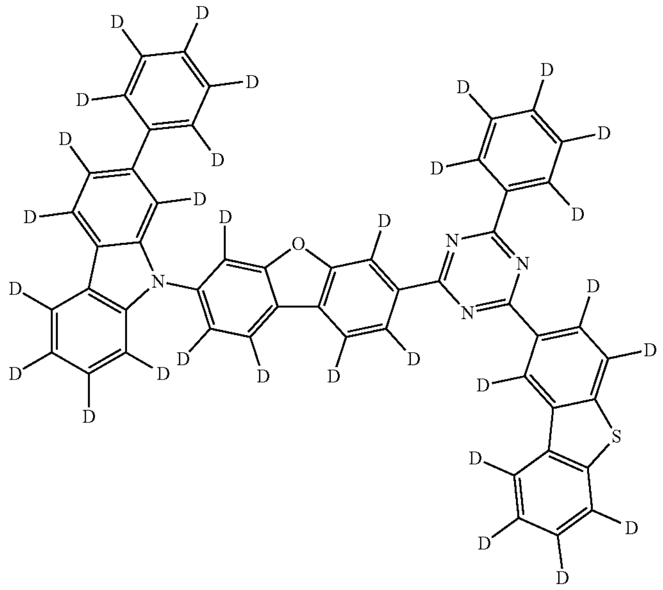
705
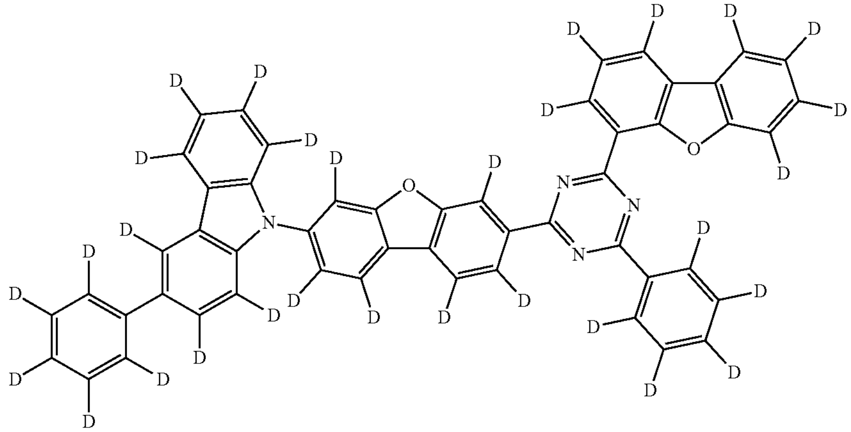
706
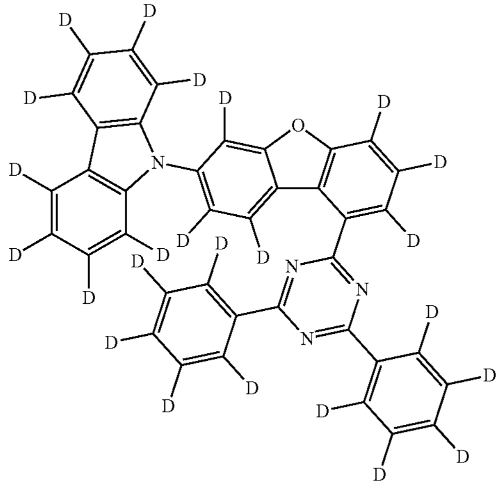
707
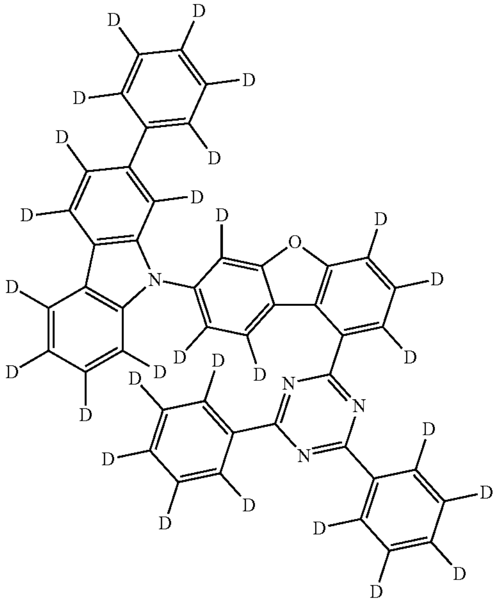

-continued
708
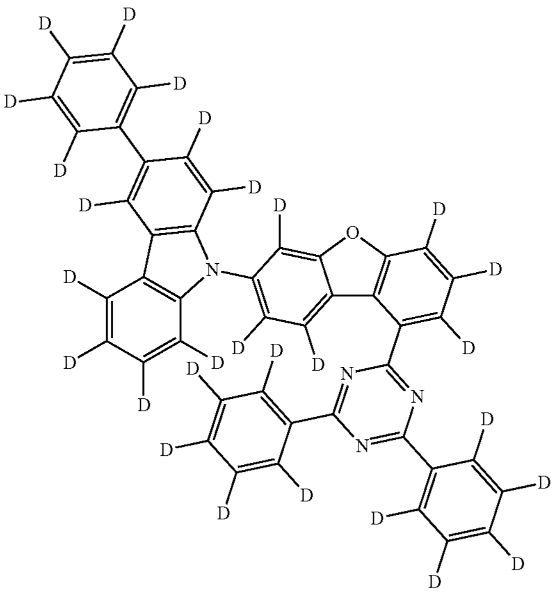
709
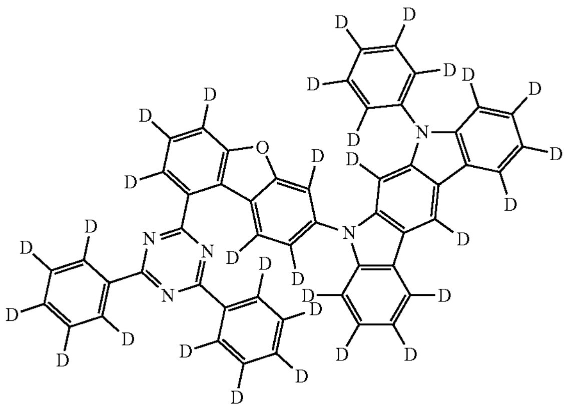
710
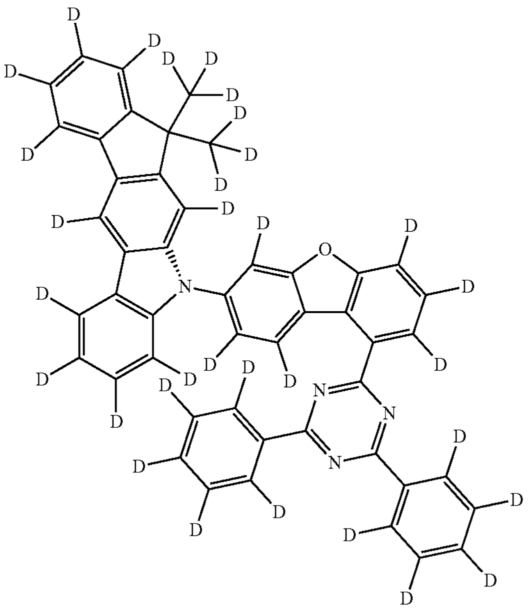
711
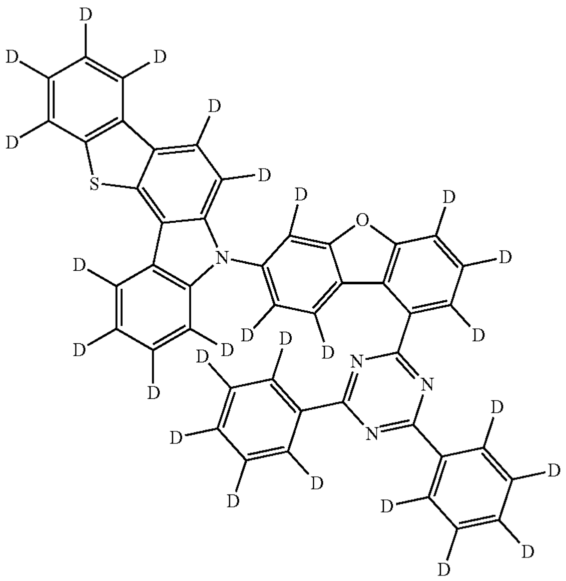

-continued
712
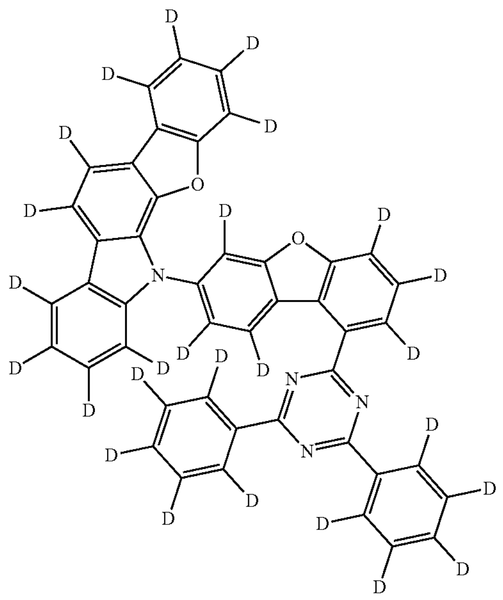
713
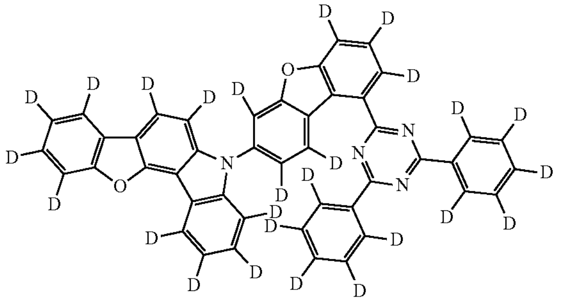
714
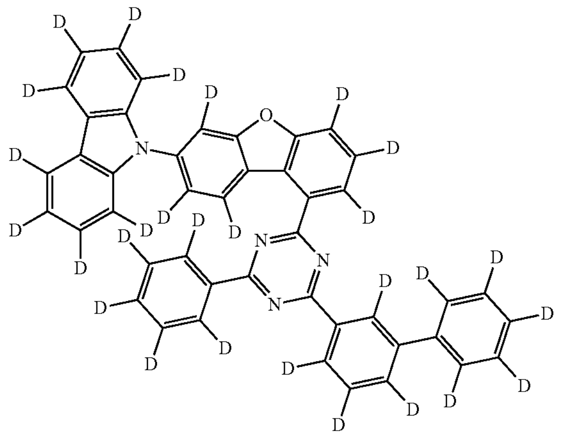
715
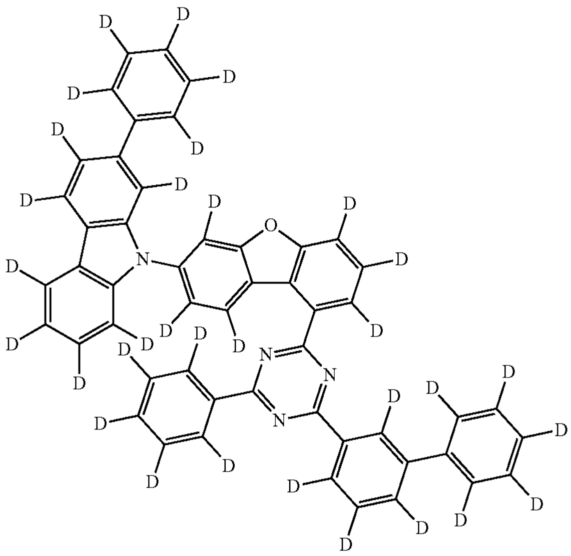
716
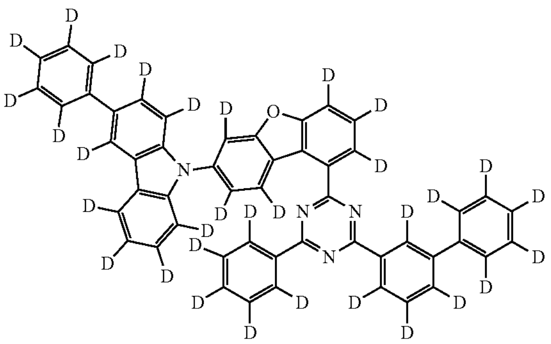
717
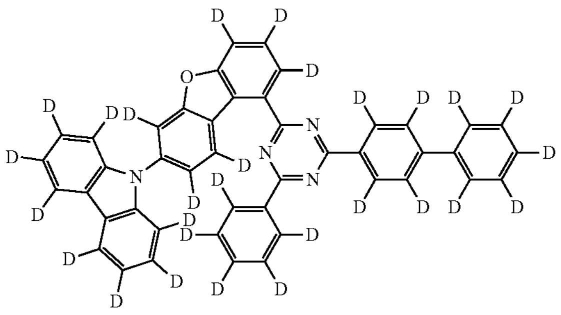

-continued
718
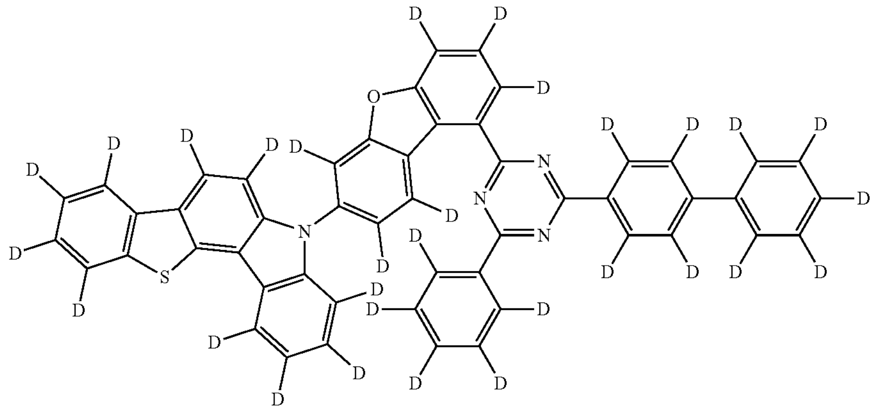
719
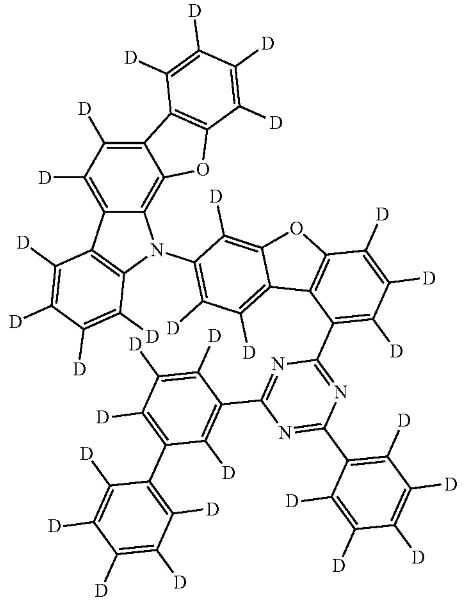
720
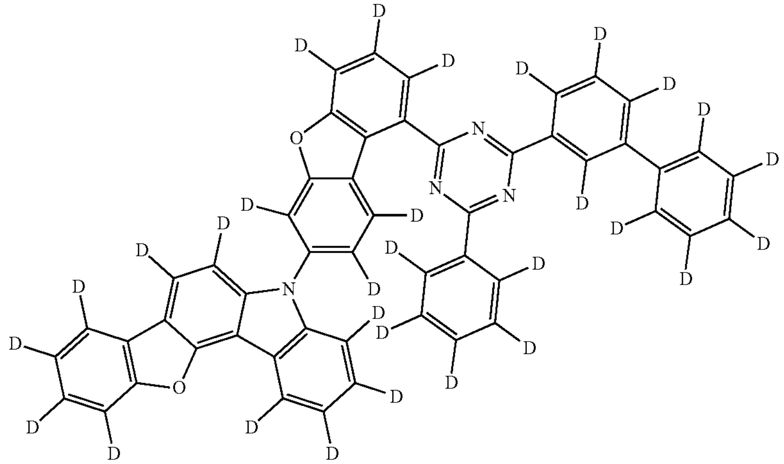

-continued
721
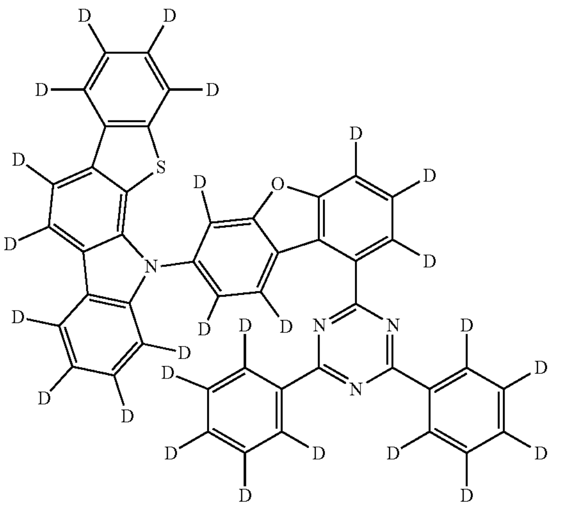
722
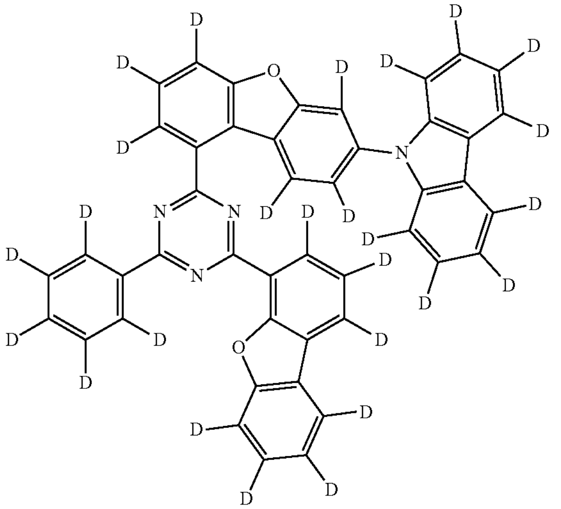
723
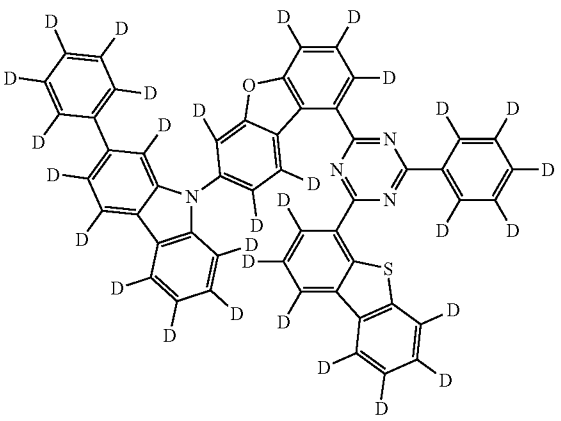
724
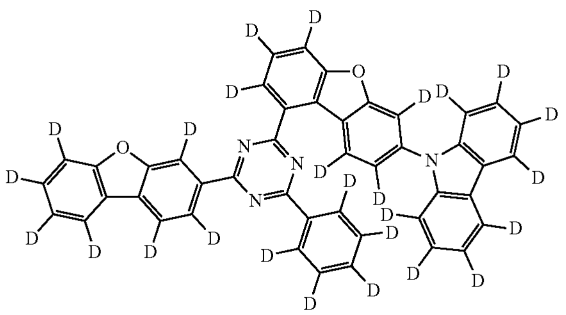
725
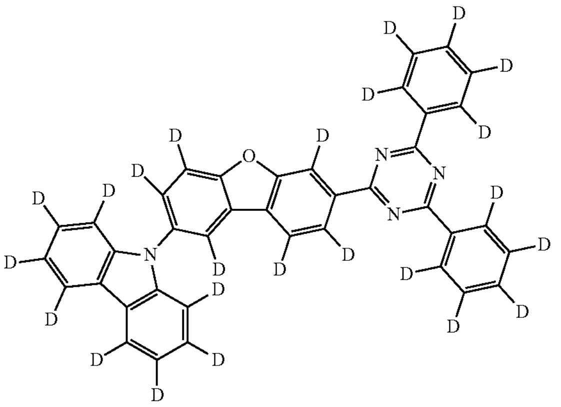
726
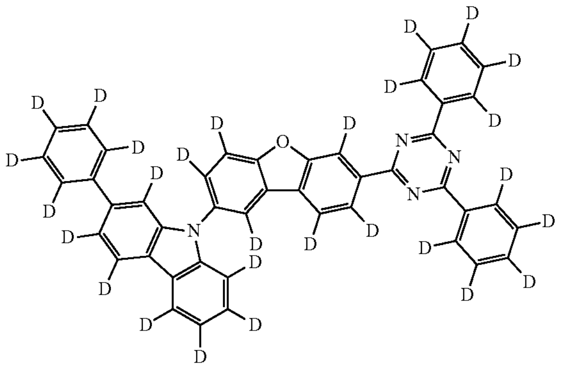

-continued
727
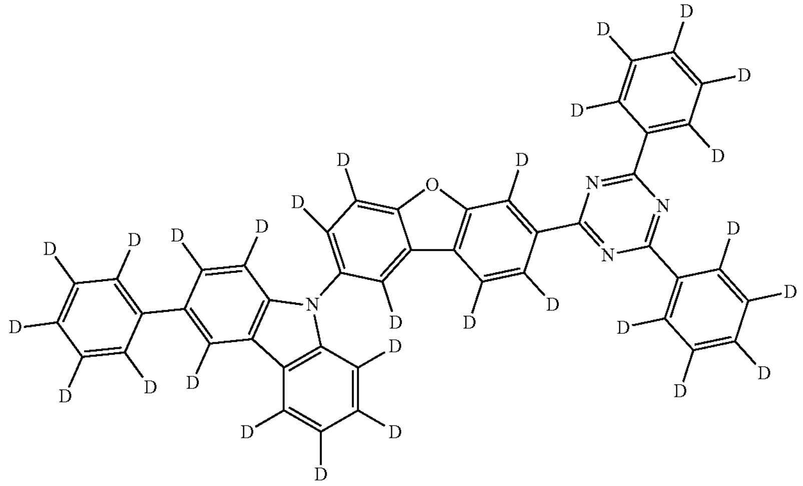
728
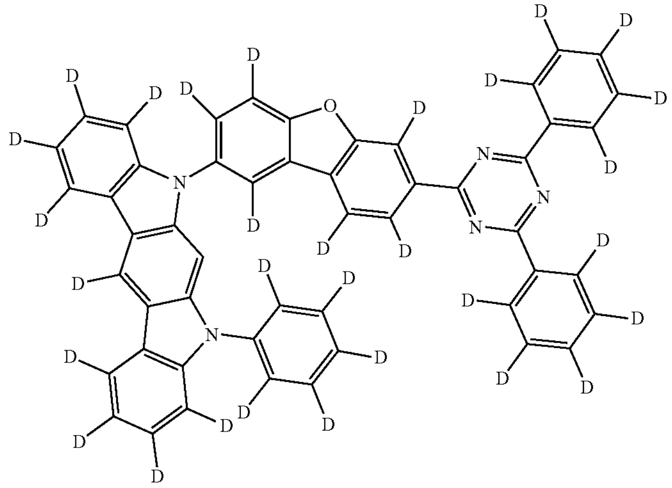
729
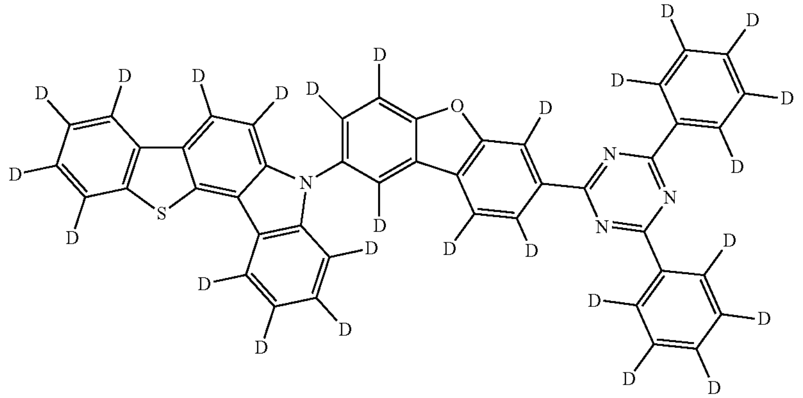

-continued
730
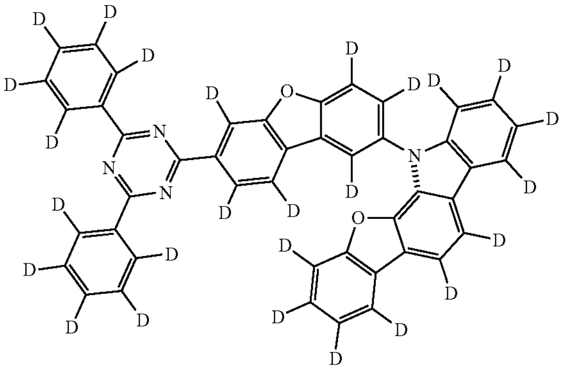
731
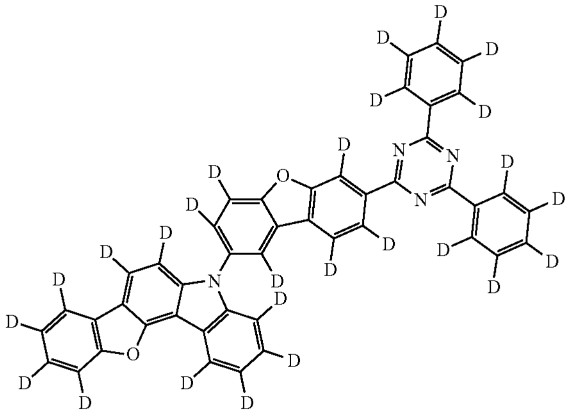
732
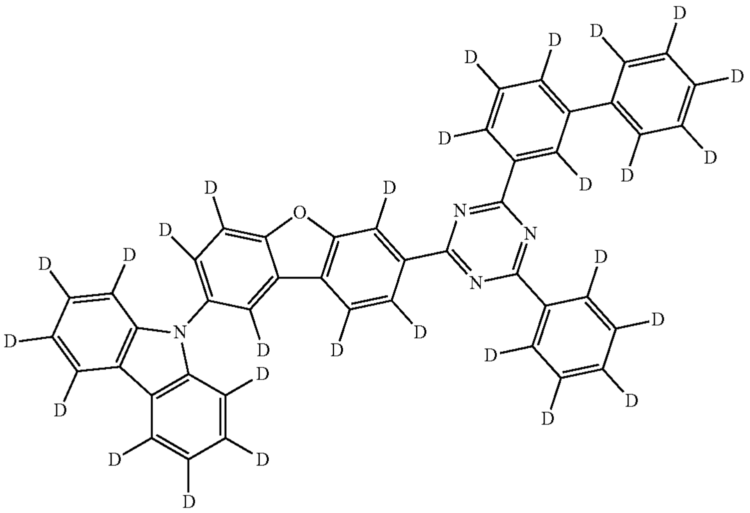
733
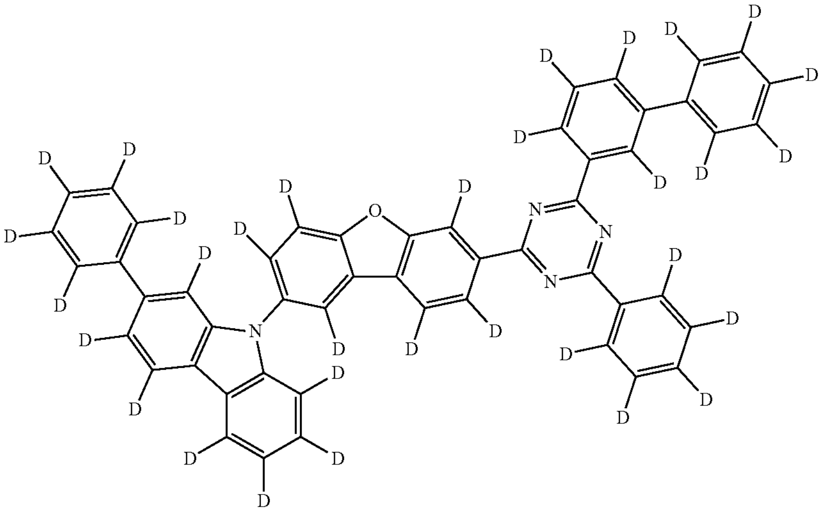

-continued
734
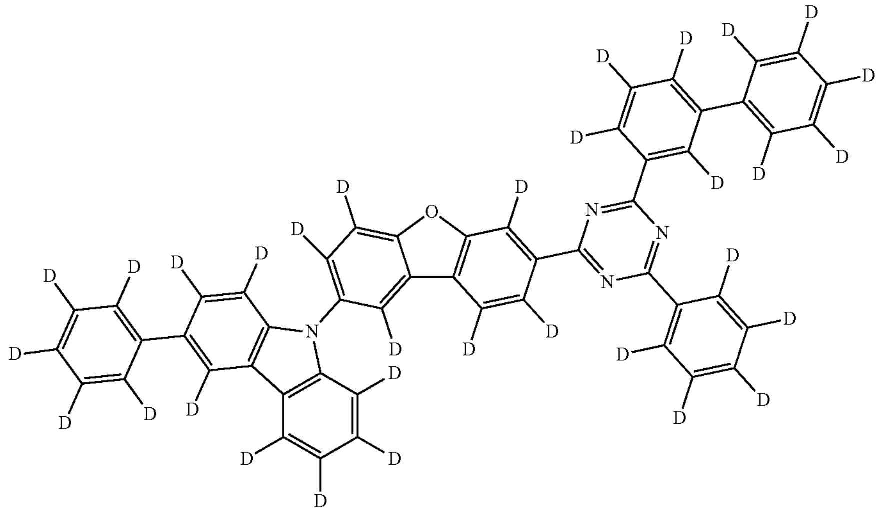
735
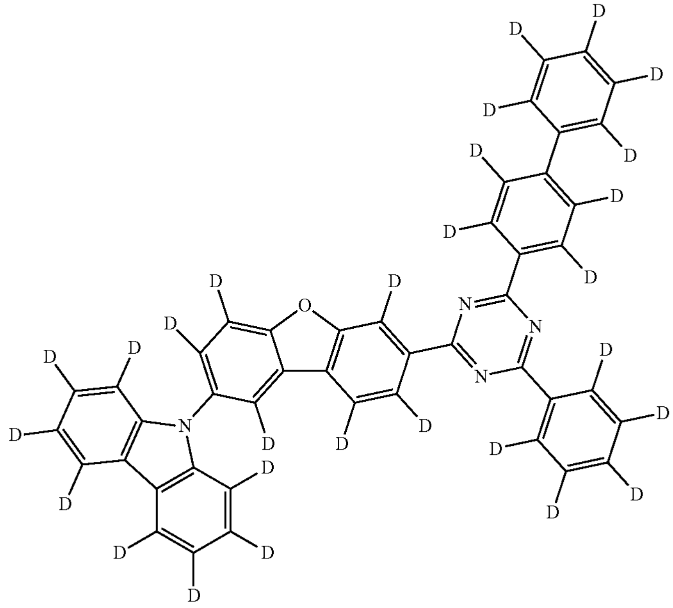
736
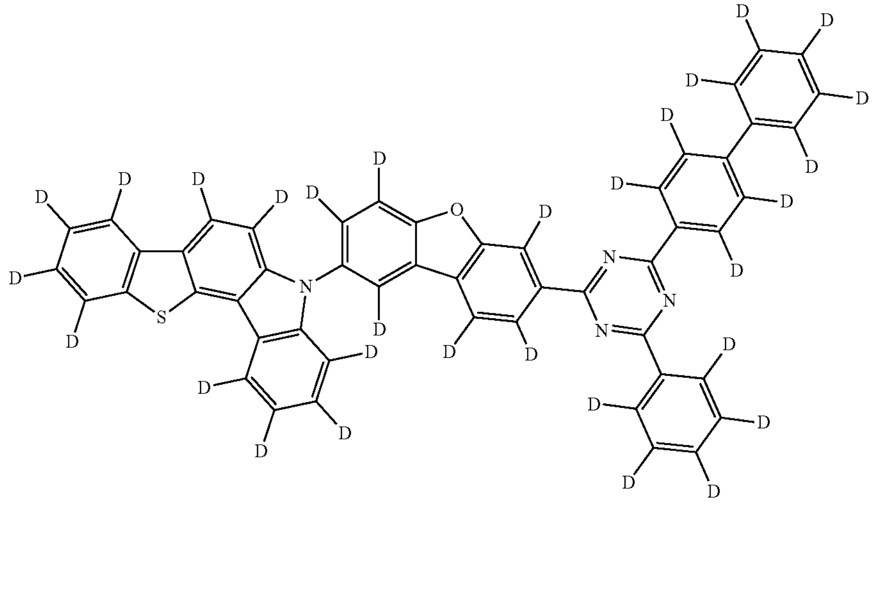

-continued
737
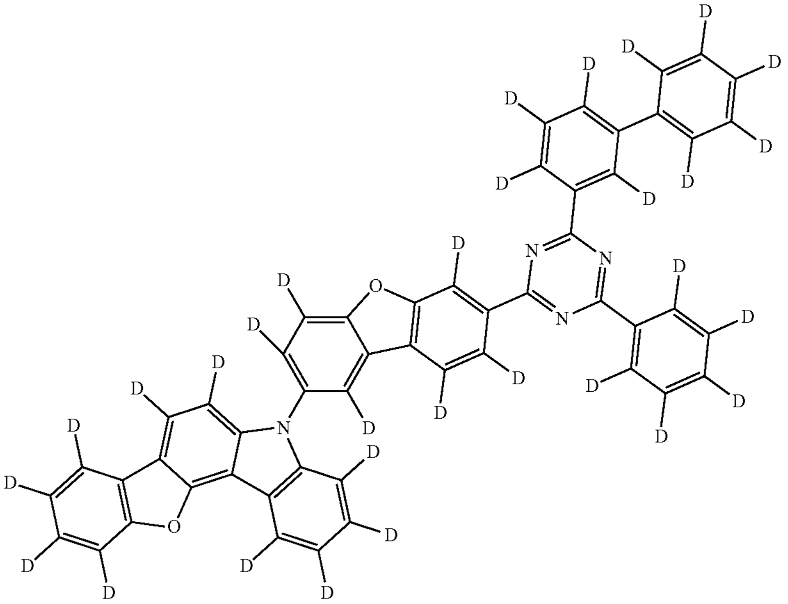
738
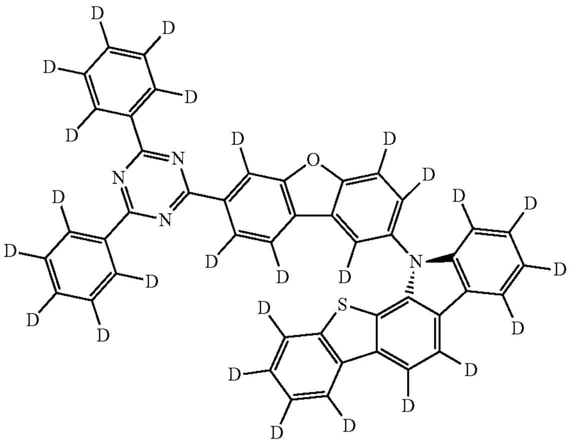
739
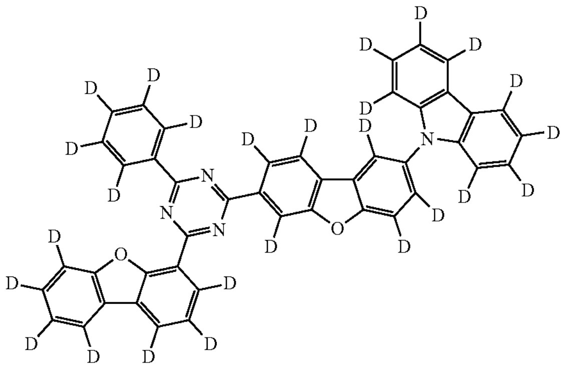
740
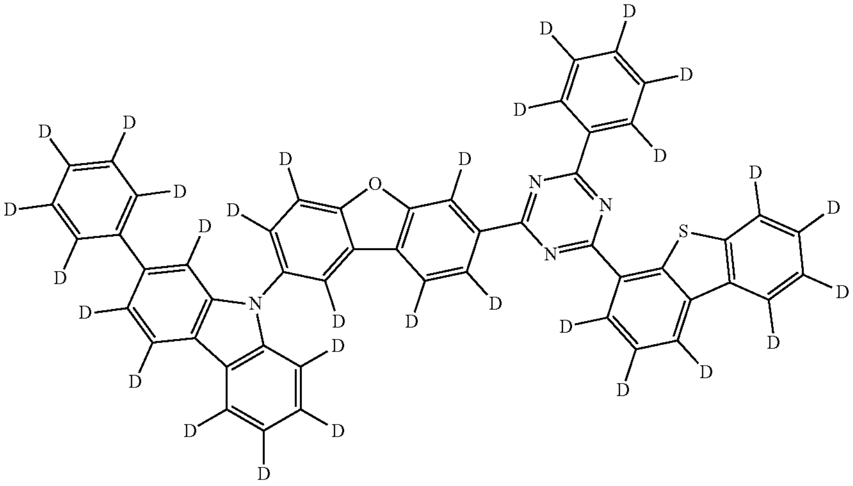

-continued
741
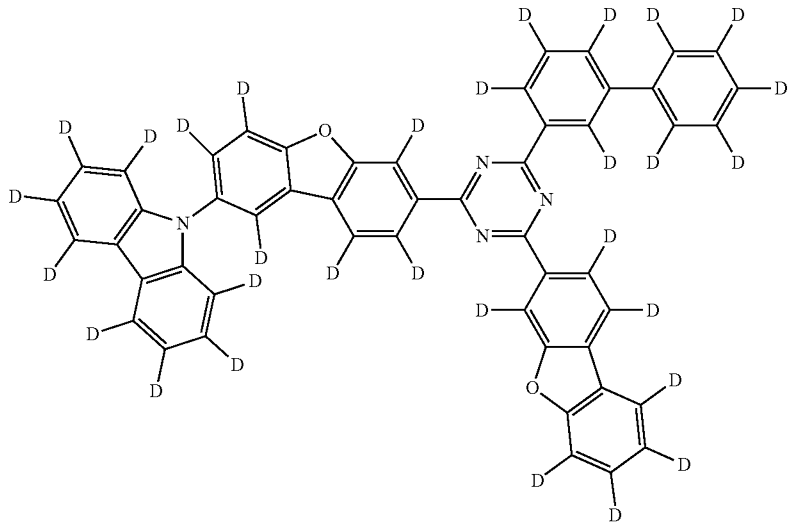
742
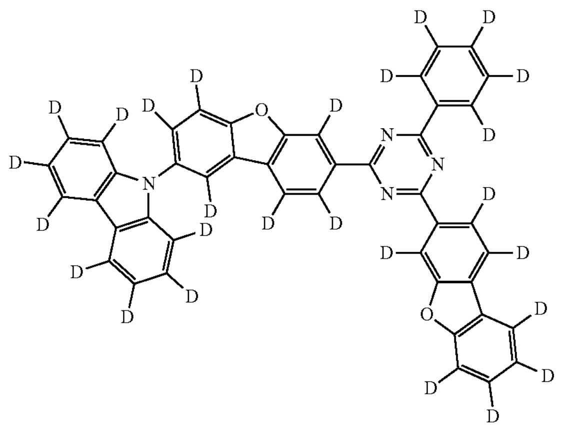
743
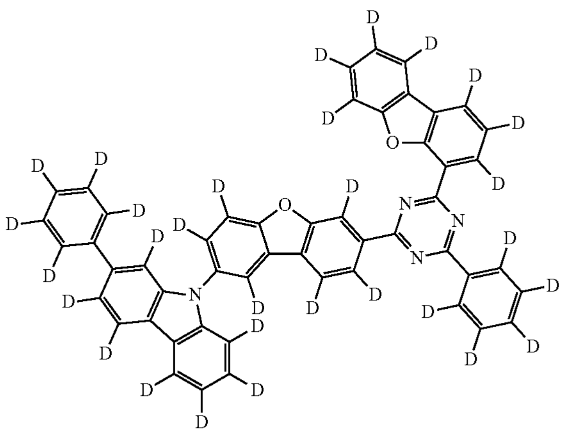
744
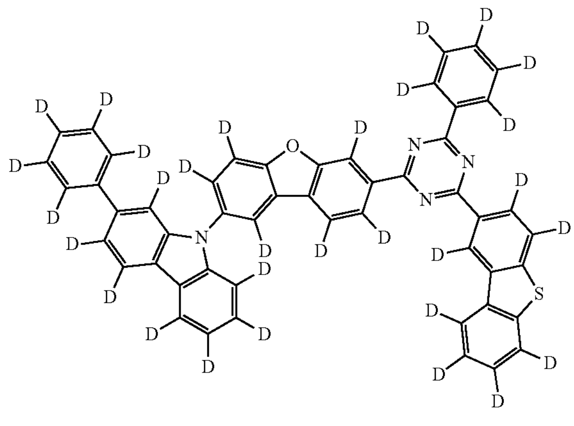
745
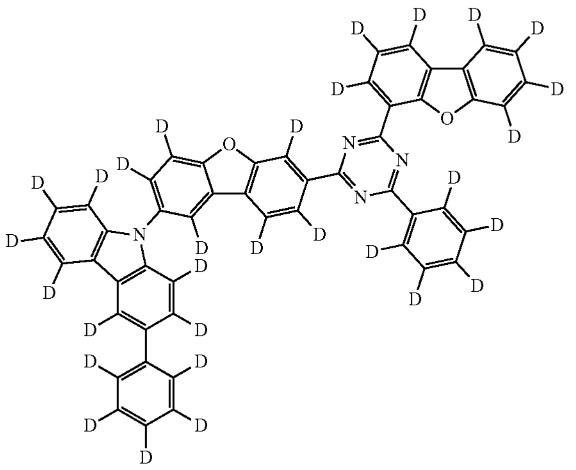

-continued
746
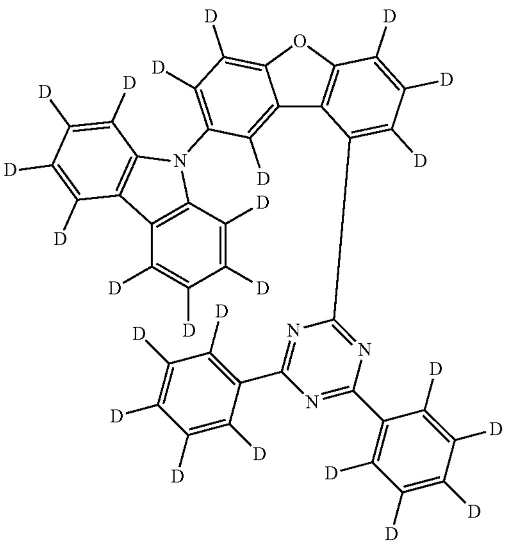
747
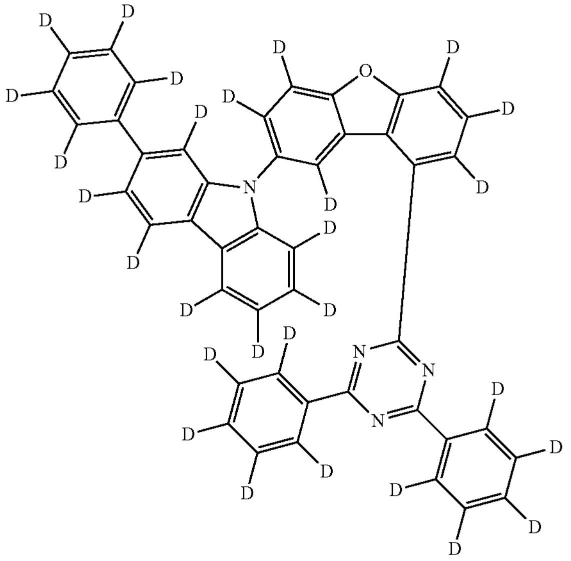
748
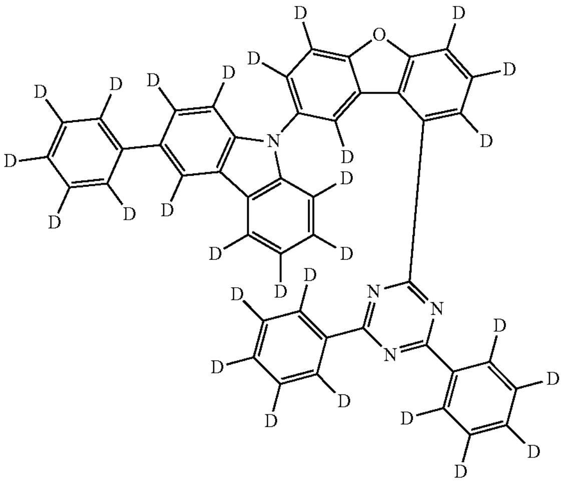
749
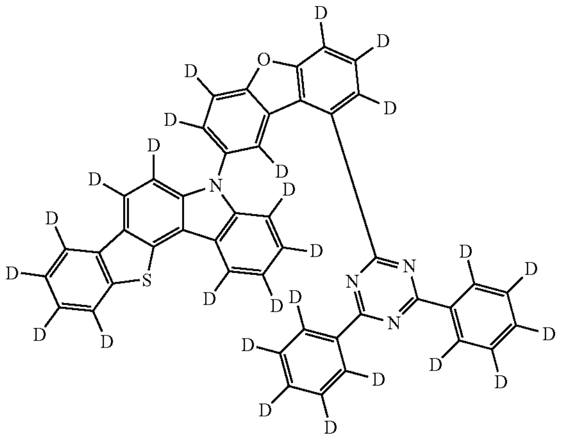
750
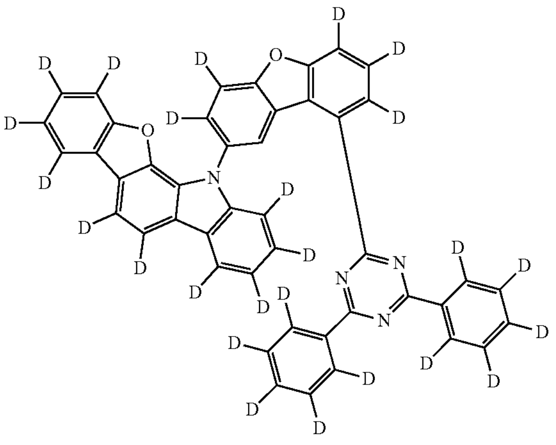
751
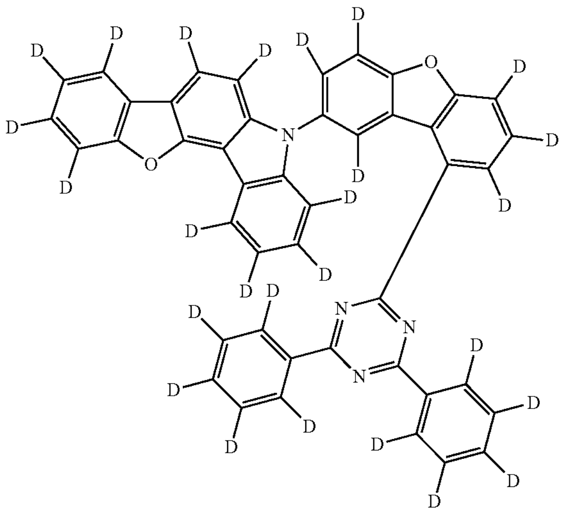

-continued
752
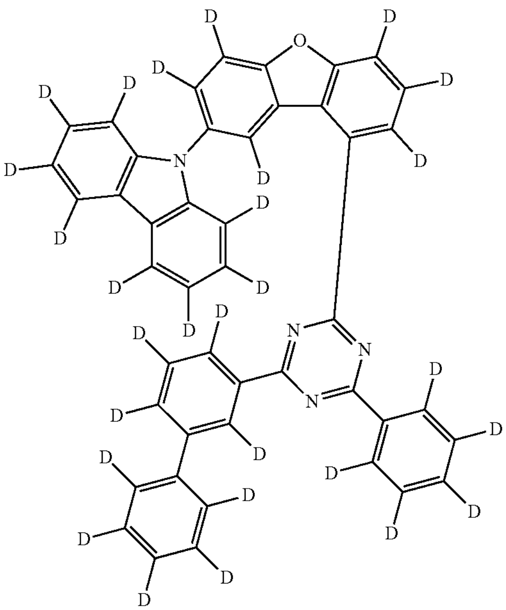
753
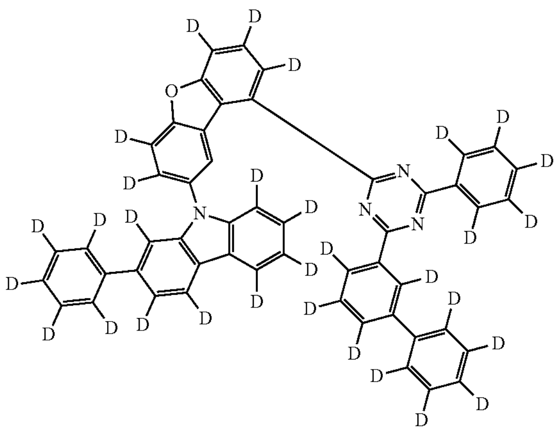
754
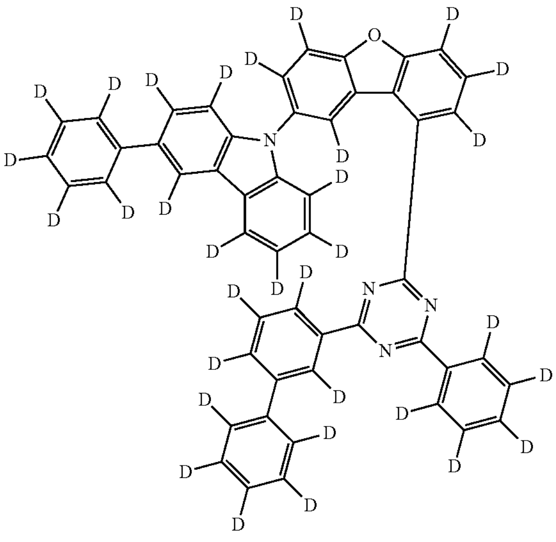
755
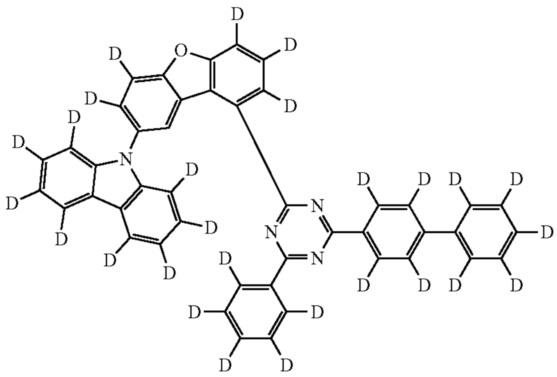

-continued
756
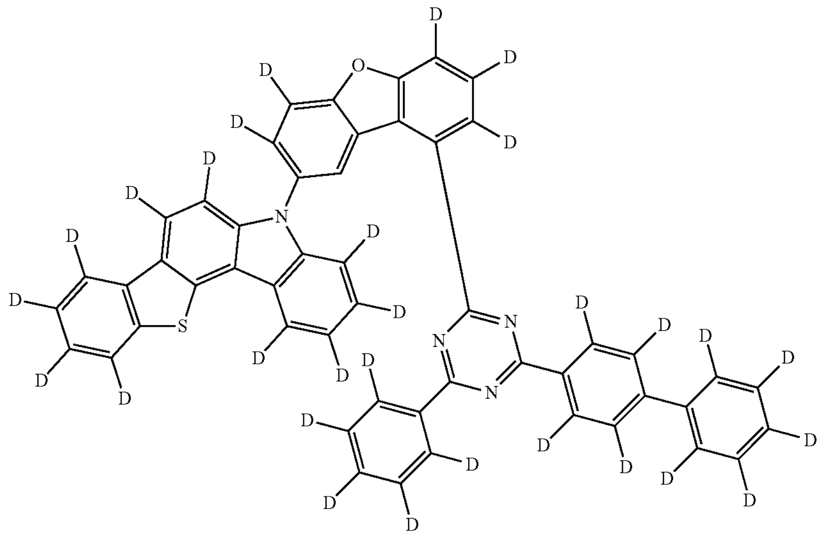
757
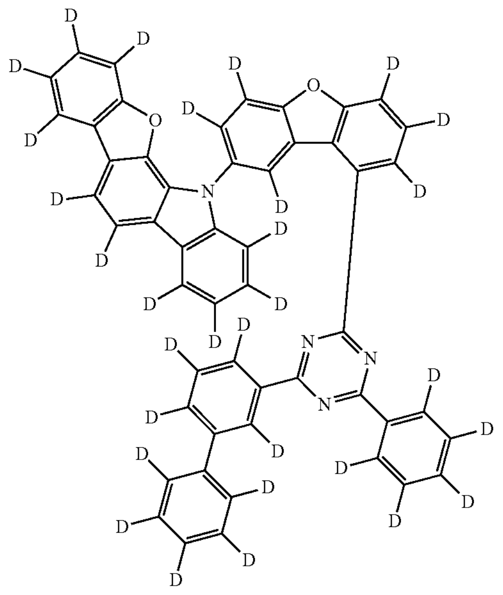
758
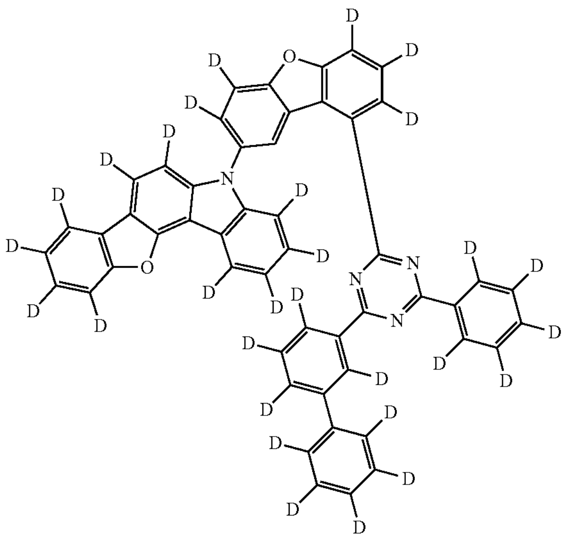

-continued
759
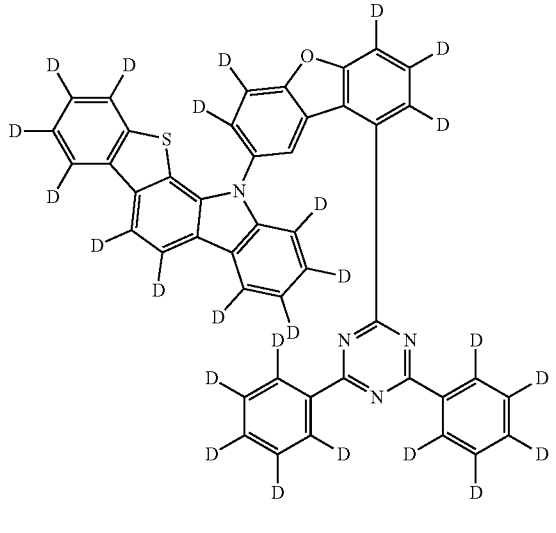
760
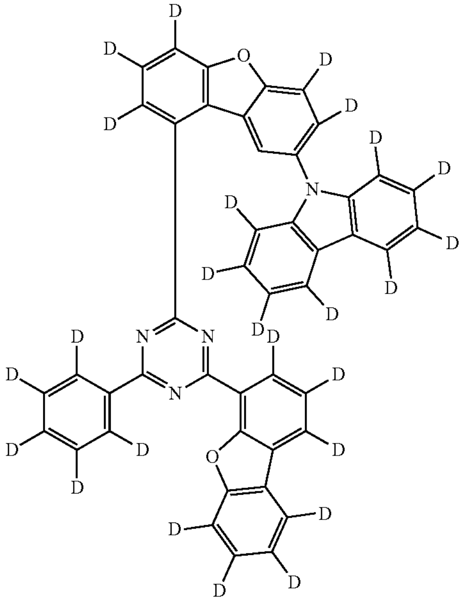
761
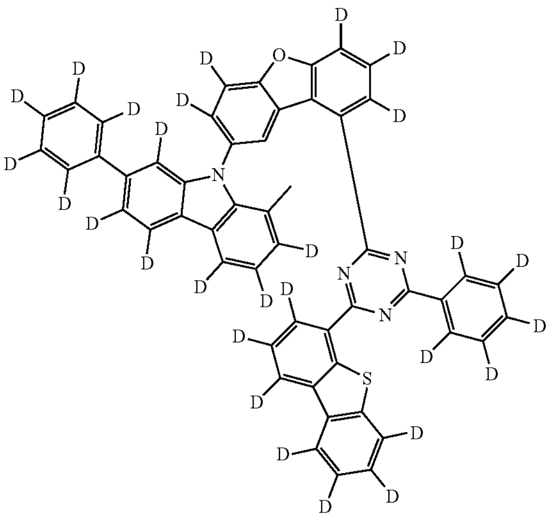
762
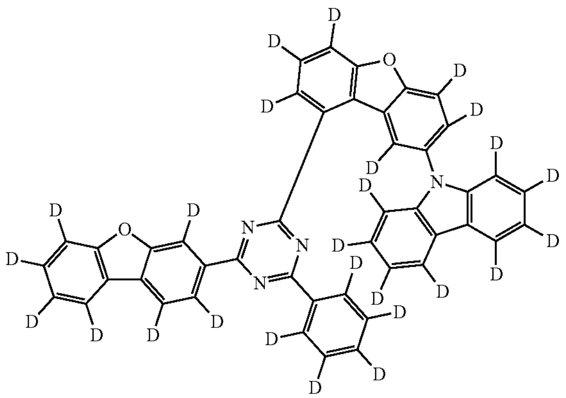

-continued
763
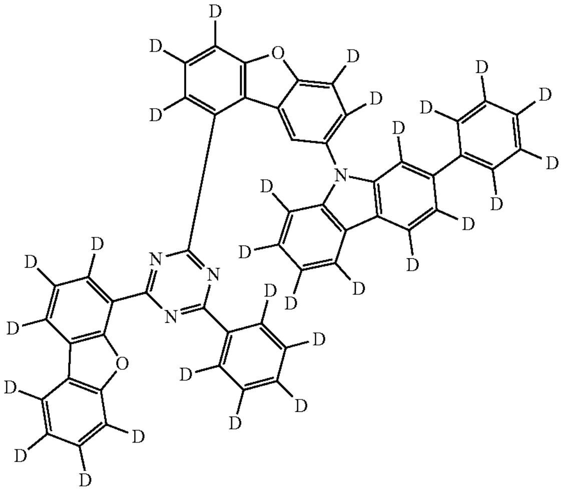
764
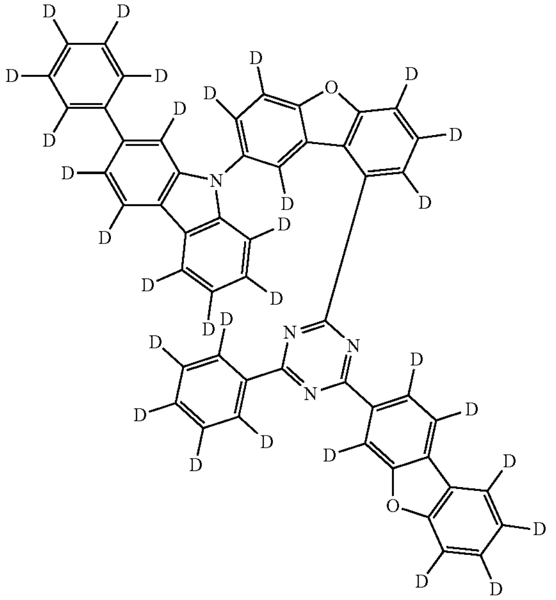
765
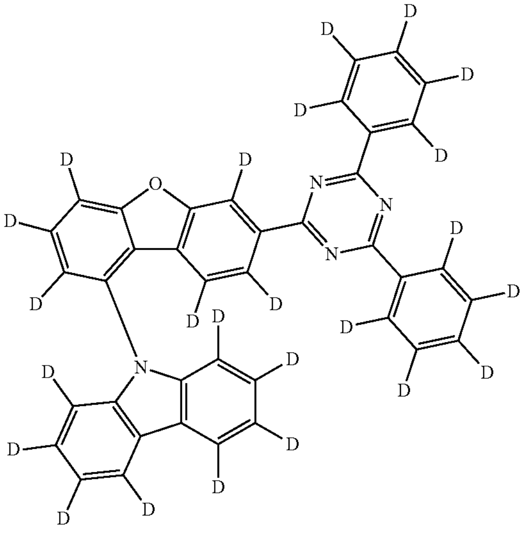
766
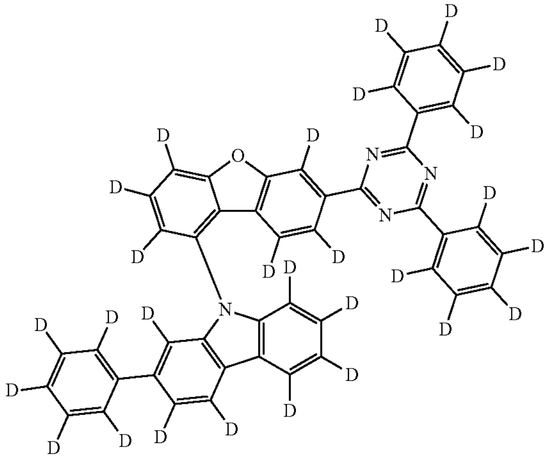
767
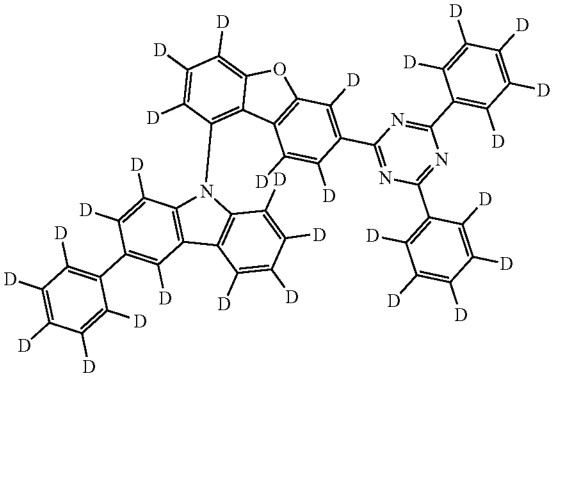
768
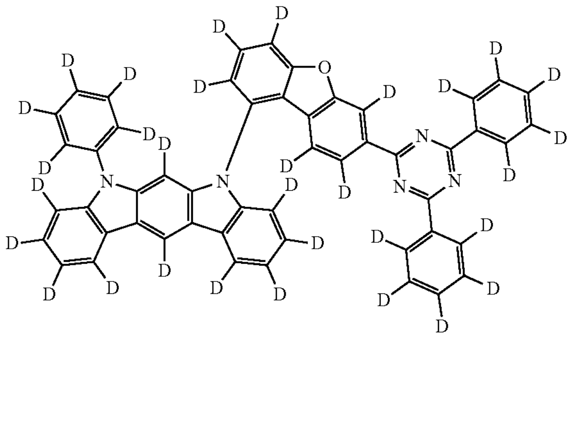

-continued
769
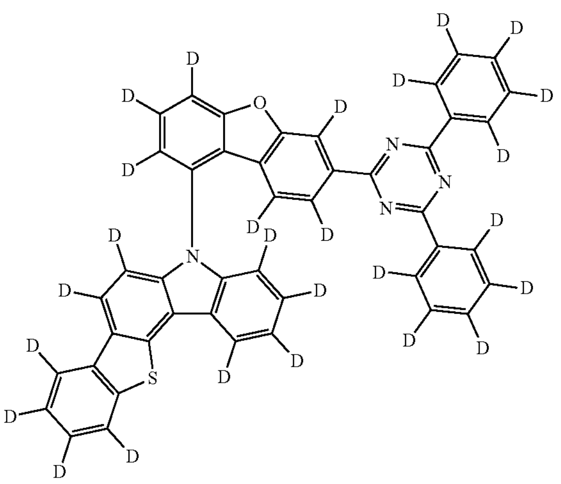
770
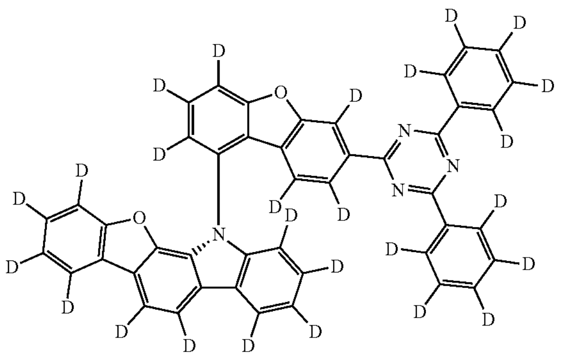
771
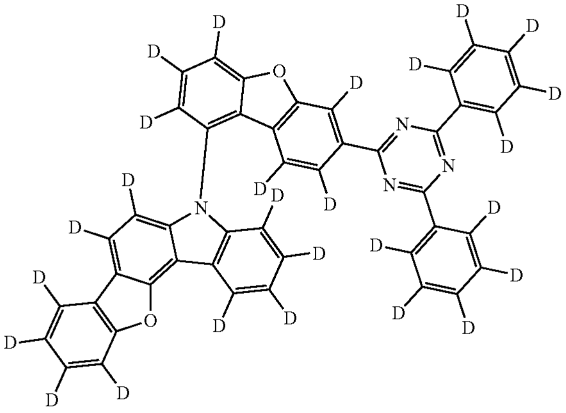
772
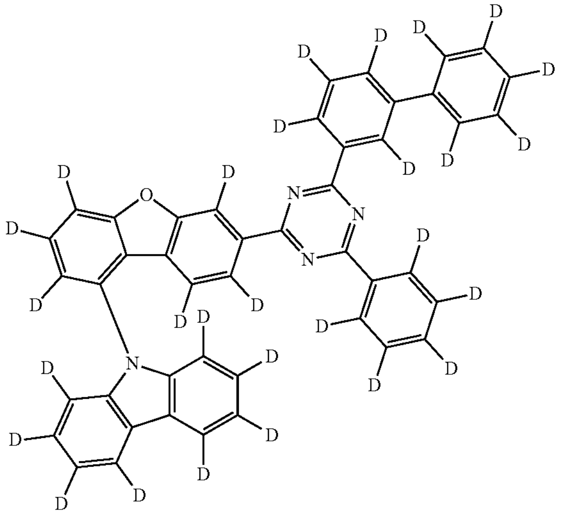
773
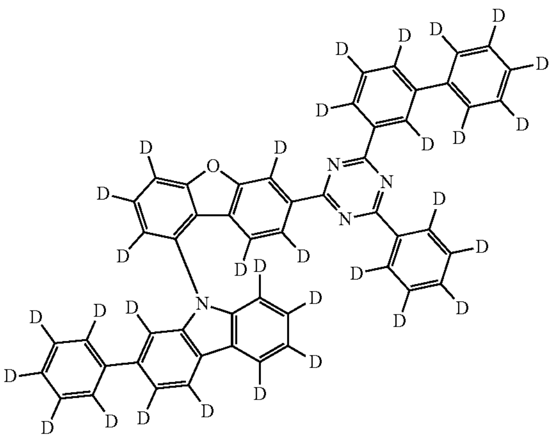
774
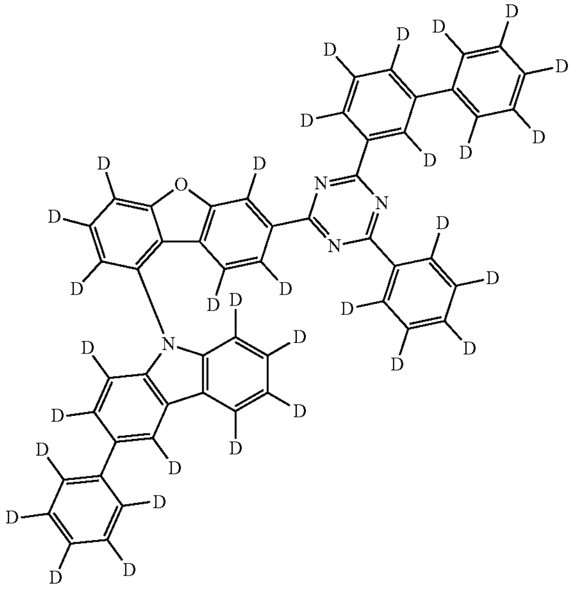

-continued
775
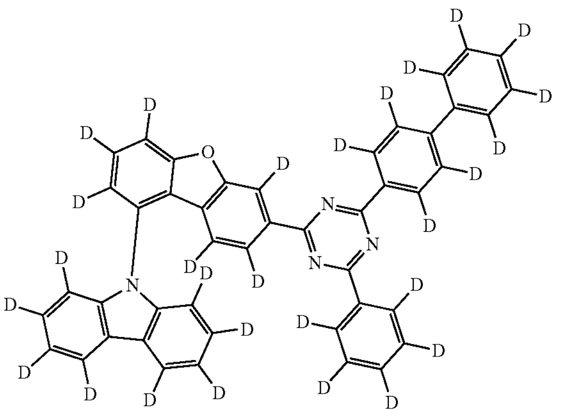
776
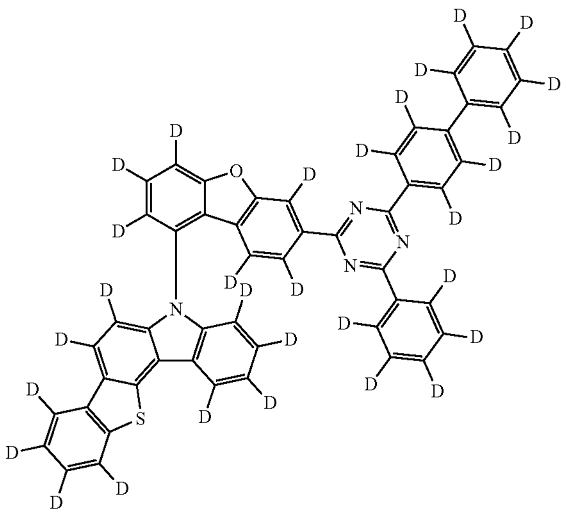
777
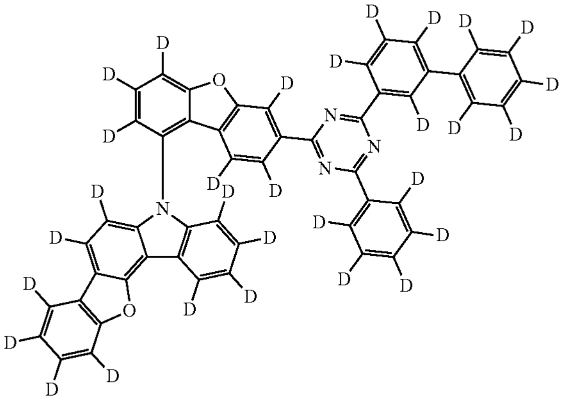
778
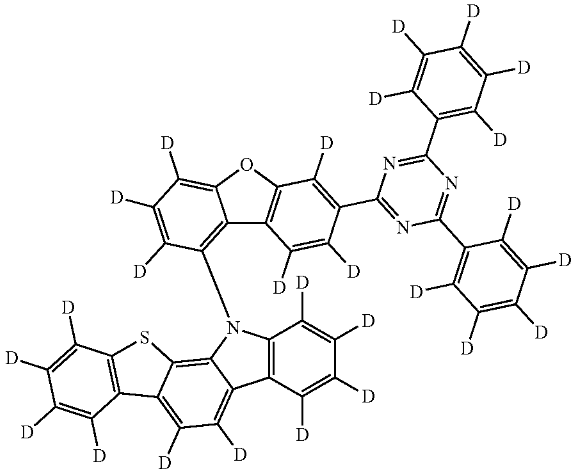
779
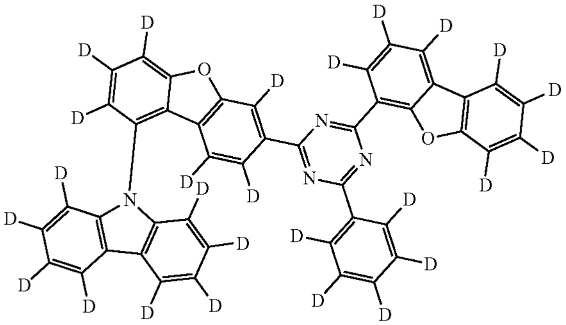
780
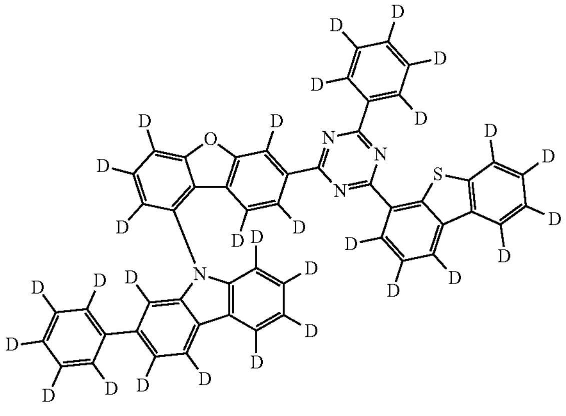

-continued
781
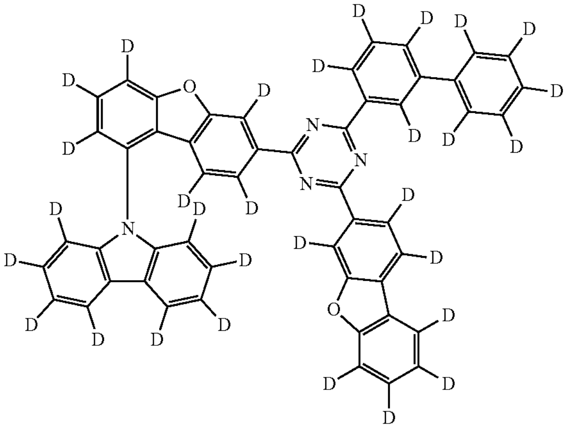
782
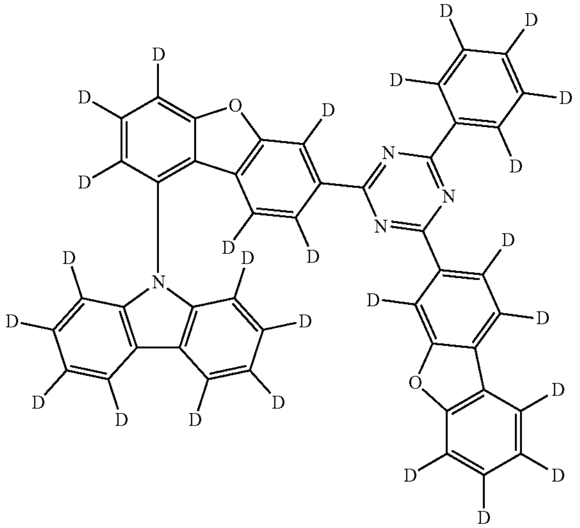
783
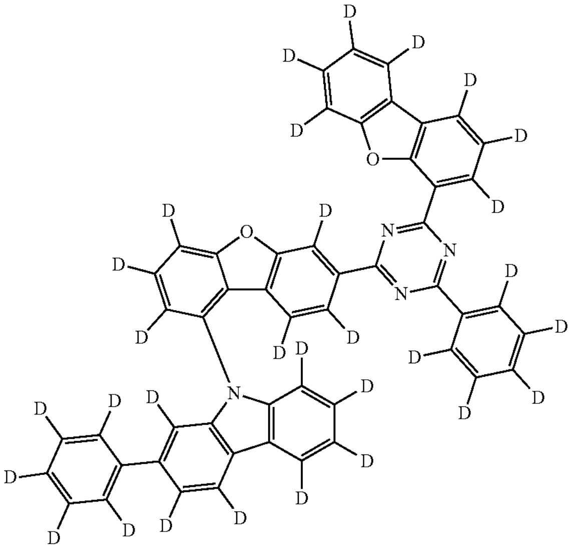
784
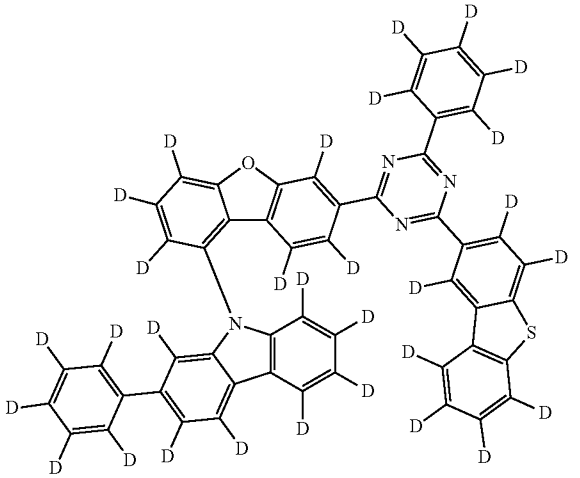
785
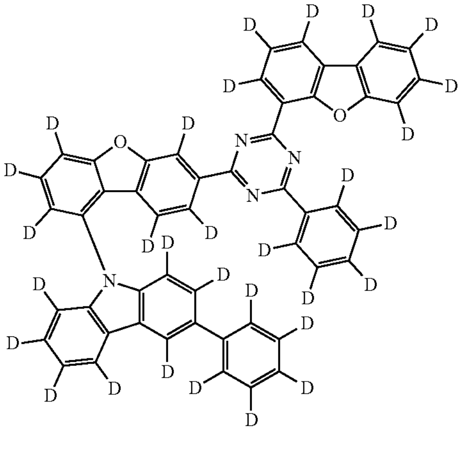
786
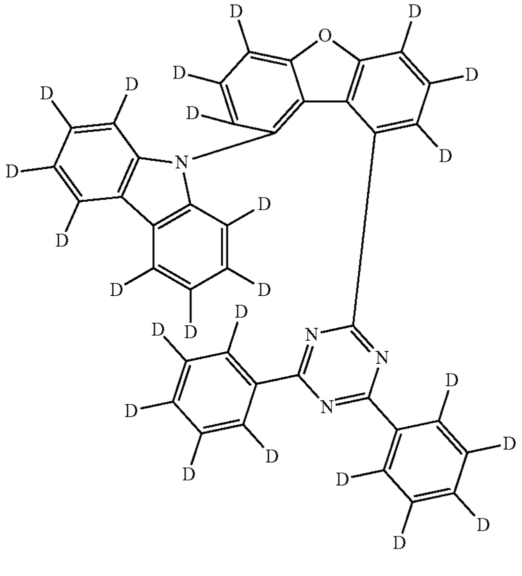

-continued
787
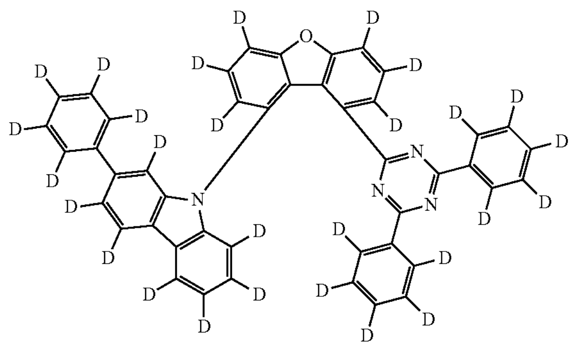
788
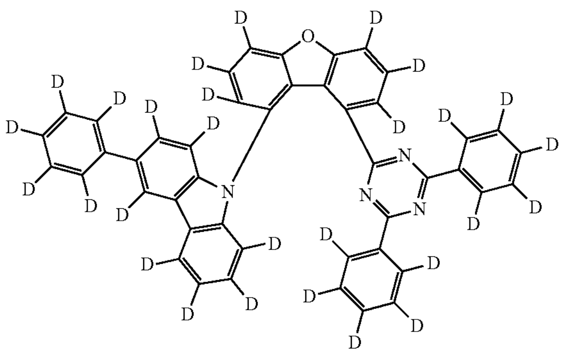
789
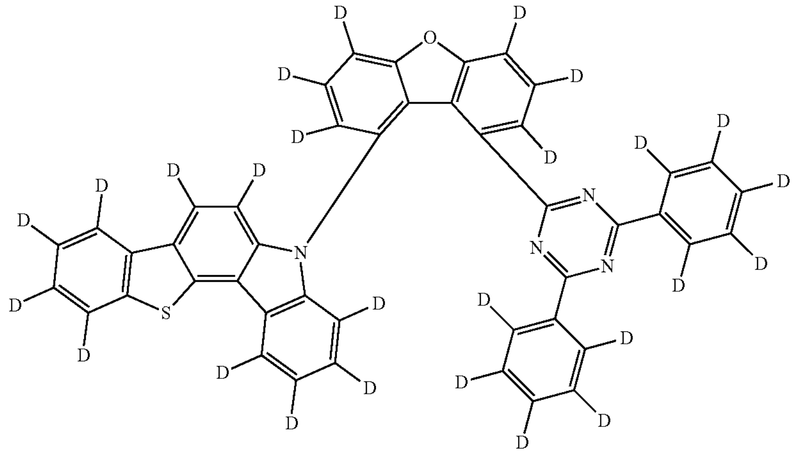
790
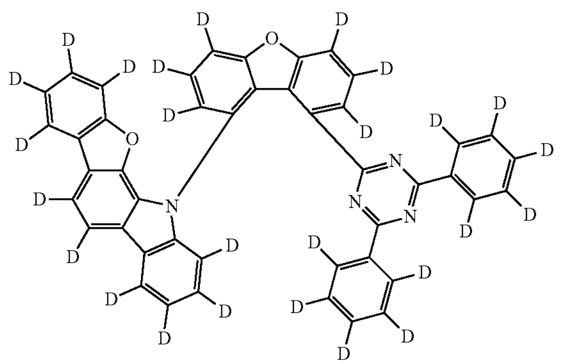
791
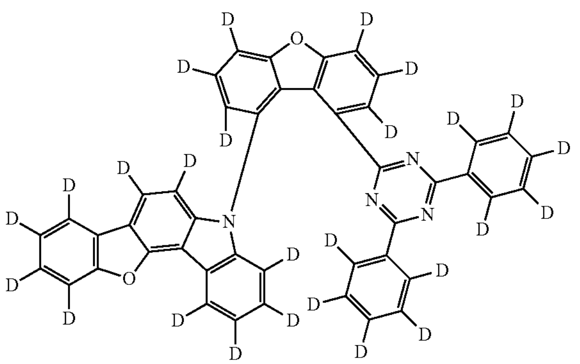

-continued
792
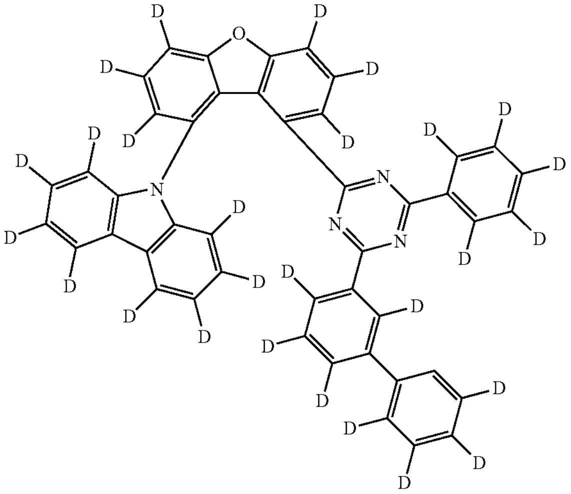
793
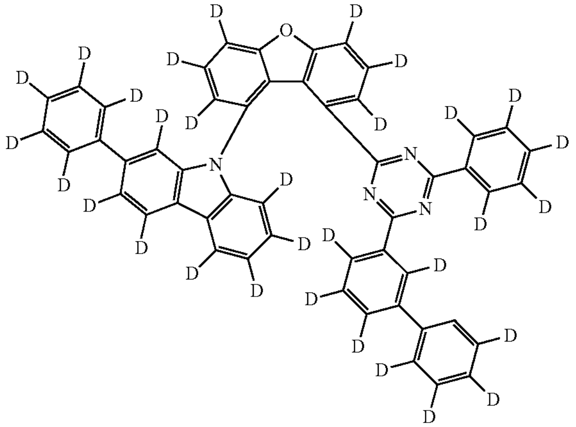
794
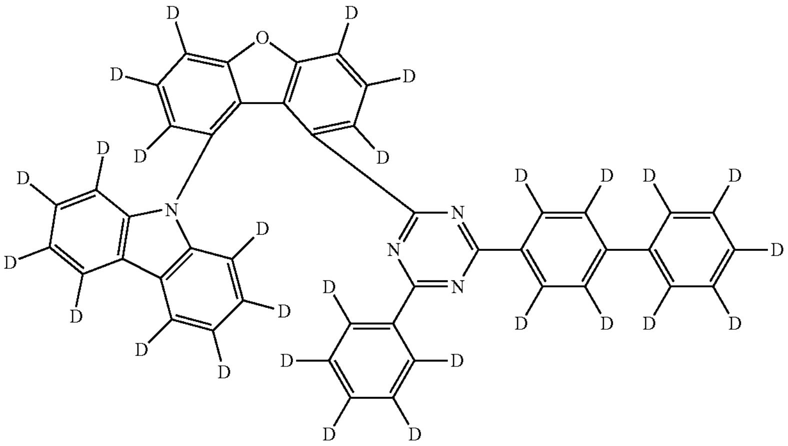
795
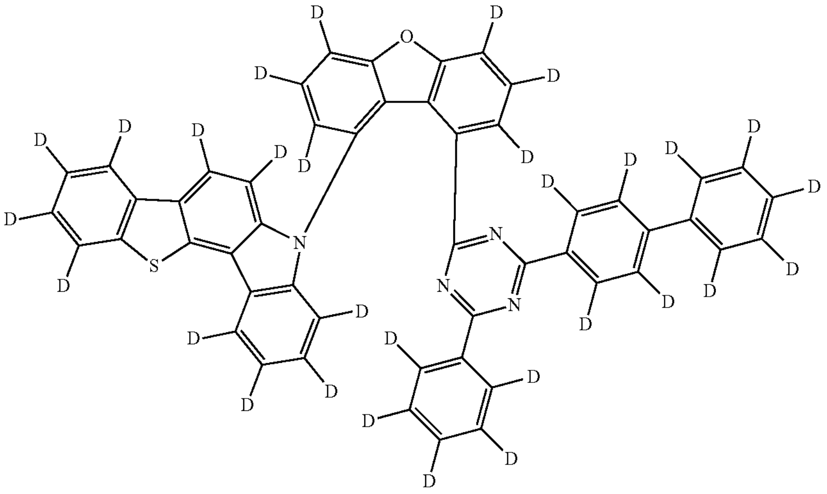

-continued
796
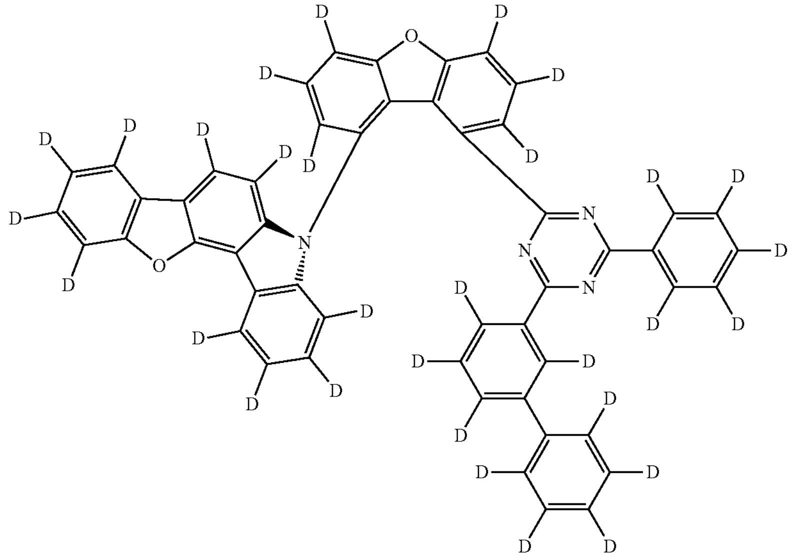
797
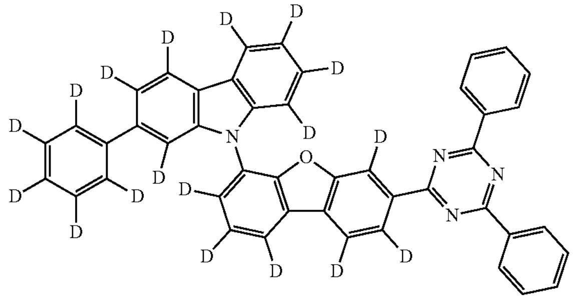
798
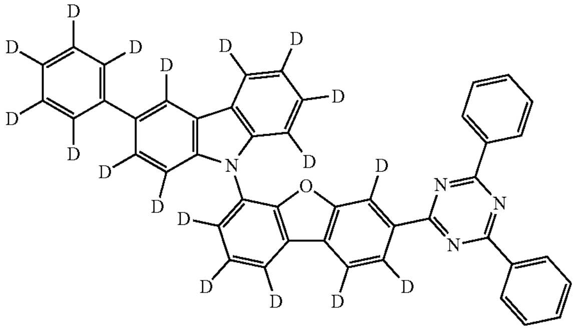
799
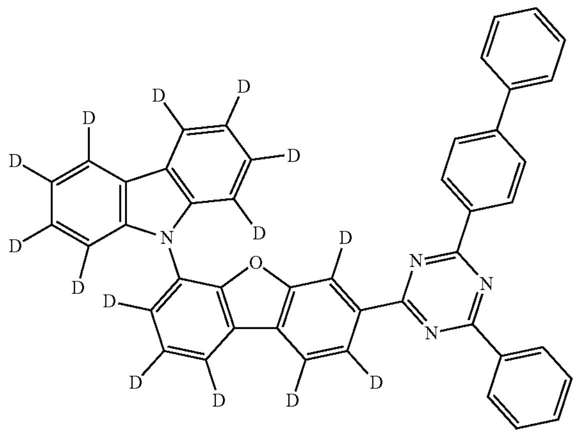
800
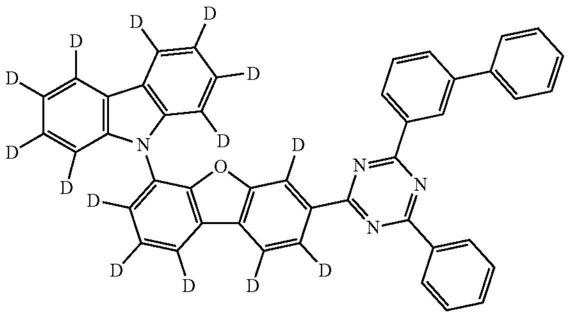

-continued
801
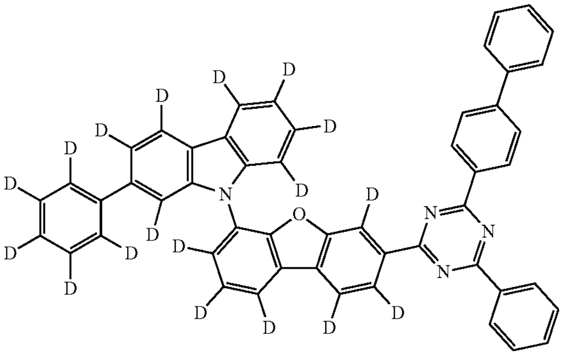
802
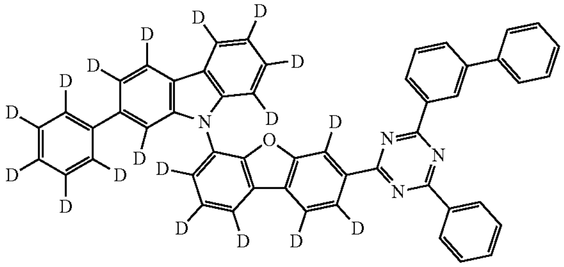
803
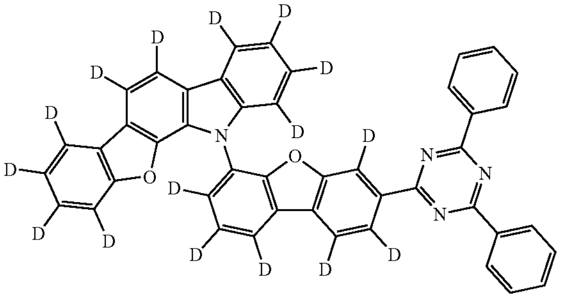
804
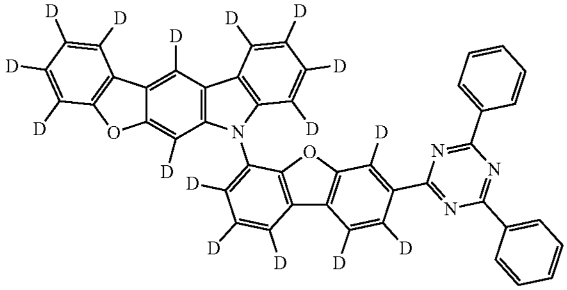
805
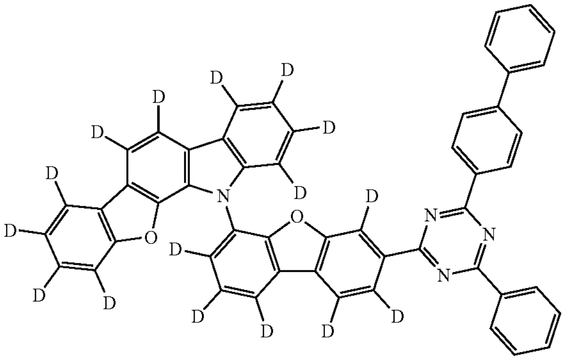
806
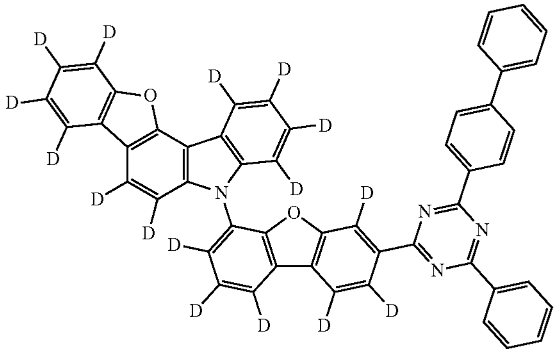
807
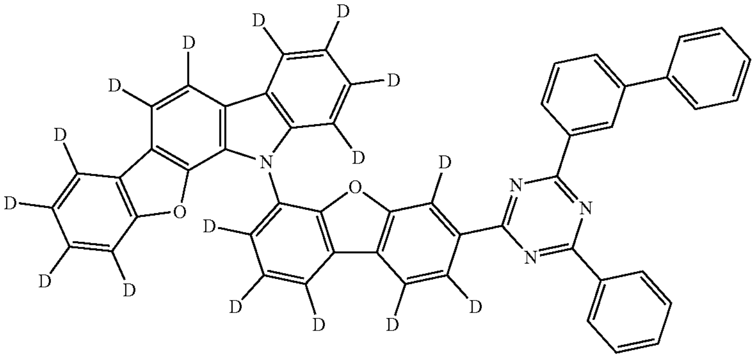

-continued
808
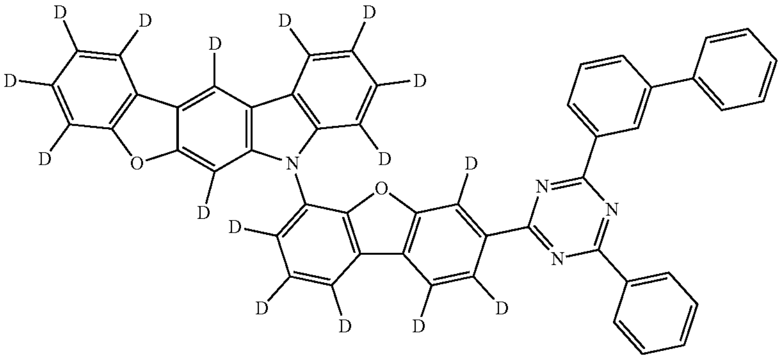
809
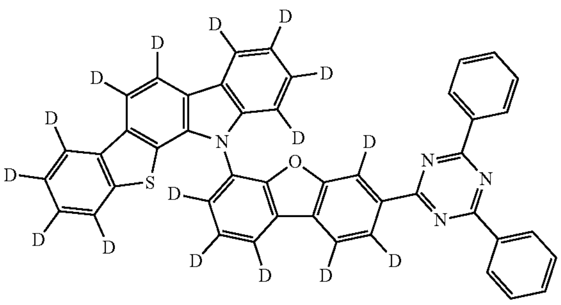
810
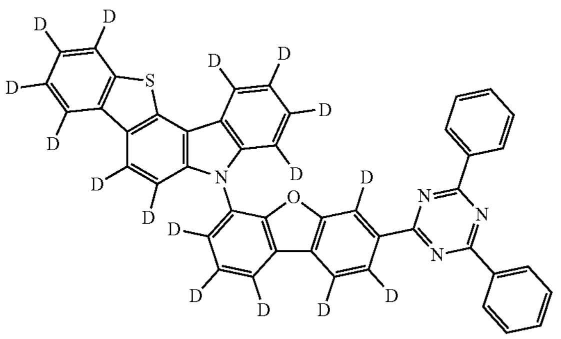
811
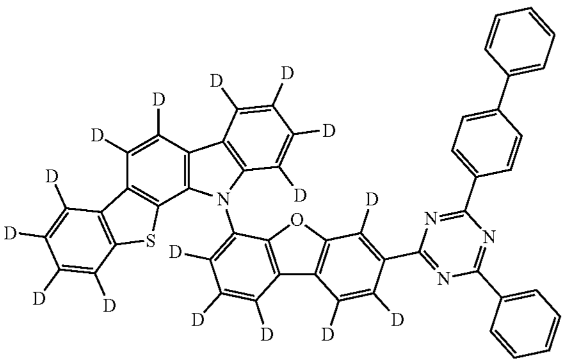
812
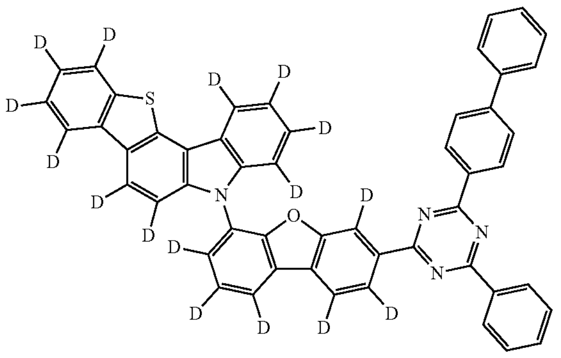
813
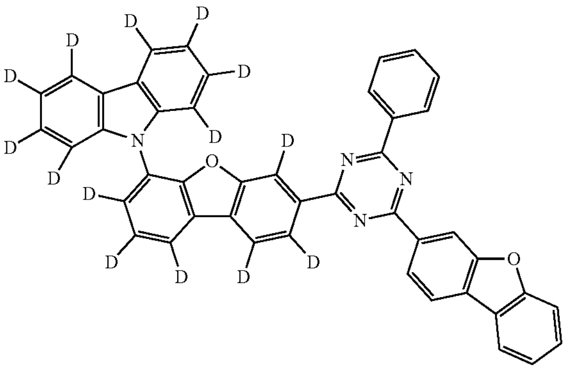
814
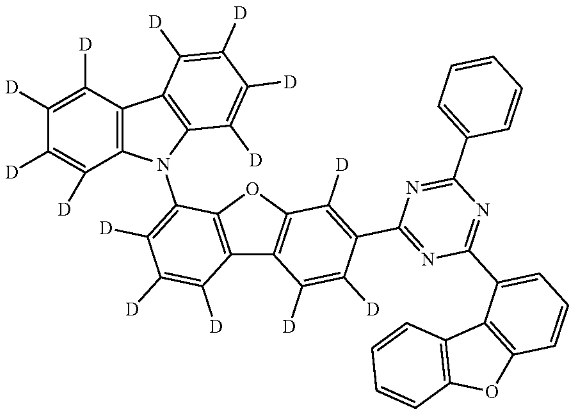

-continued
815
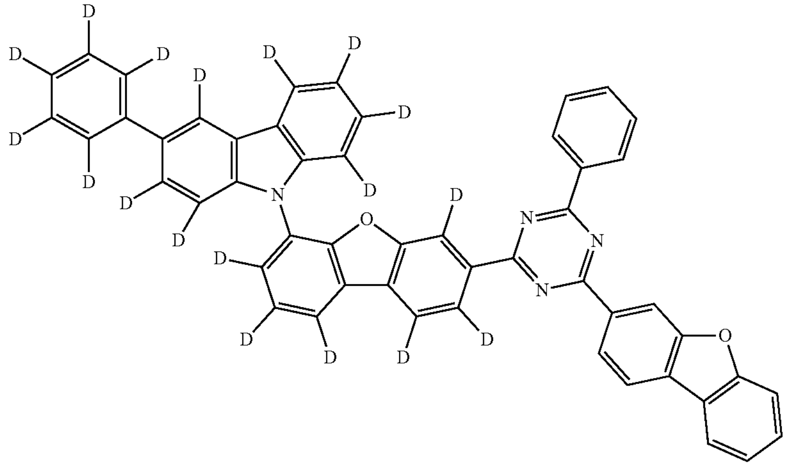
816
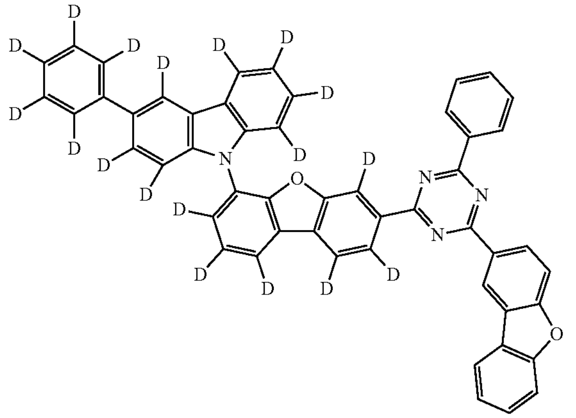
817
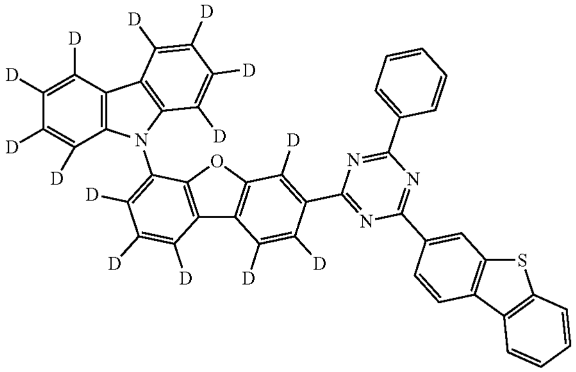
818
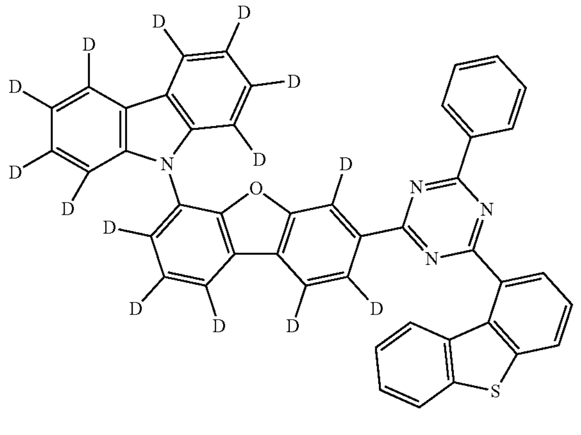

-continued
819
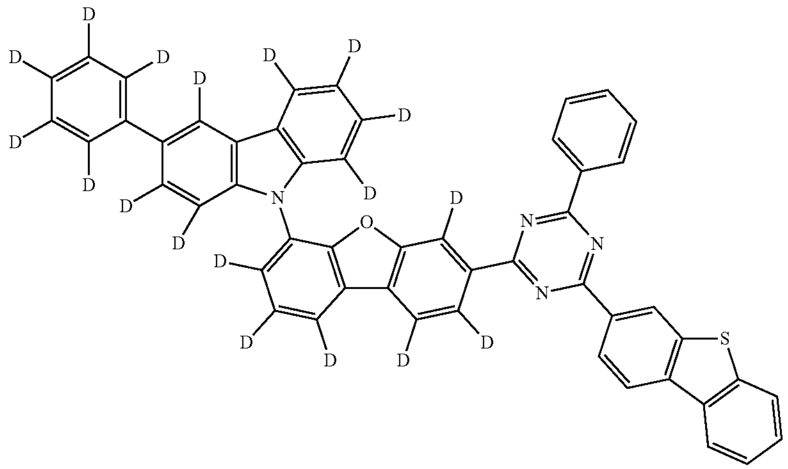
820
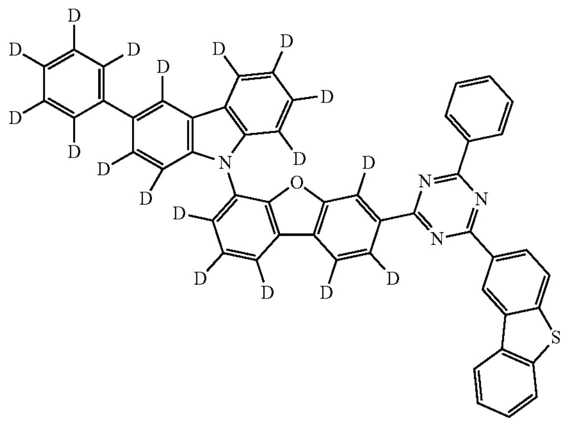
821
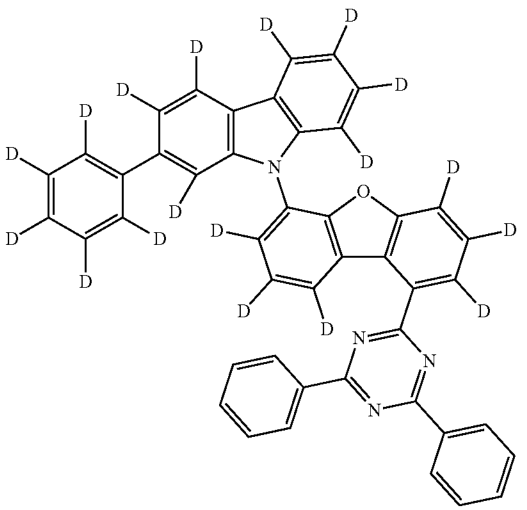
822
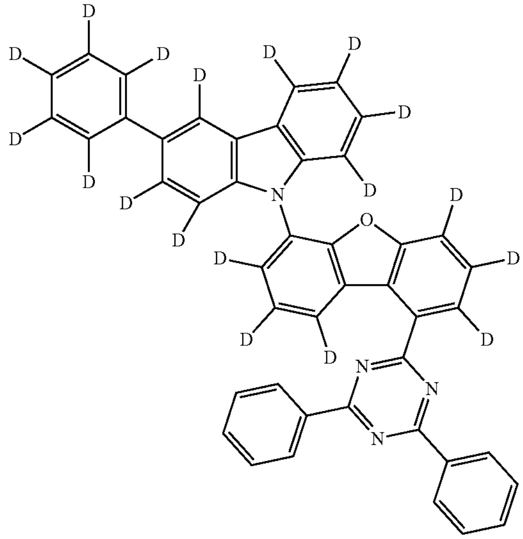
823
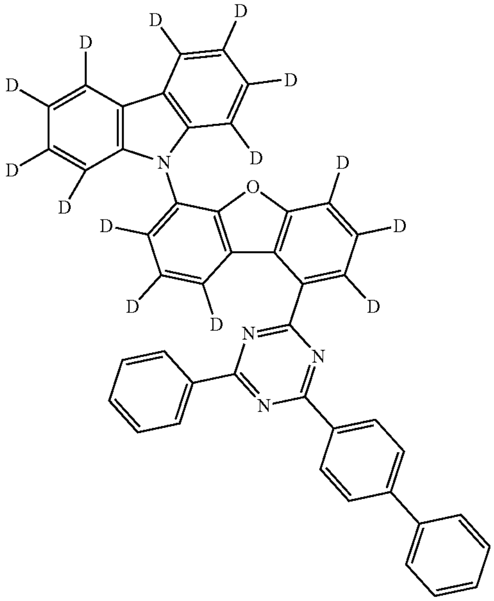

-continued
824
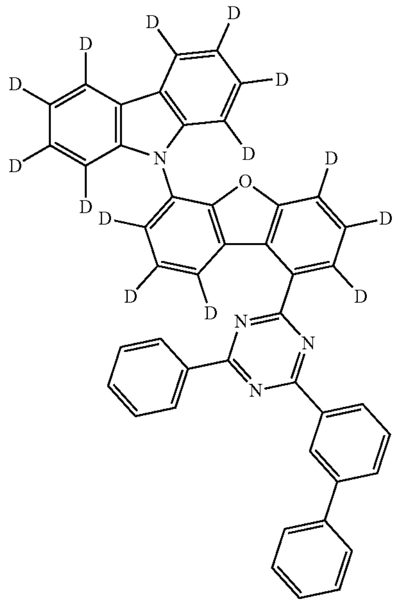
825
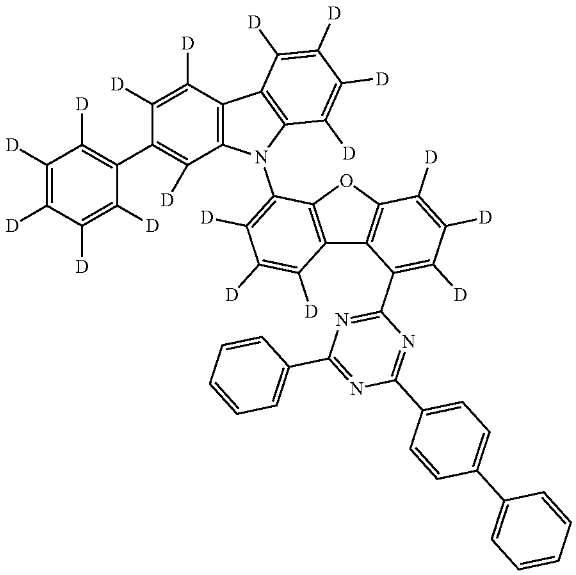
826
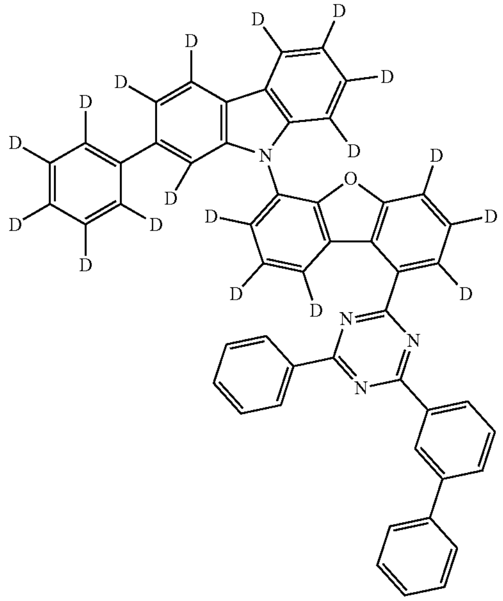
827
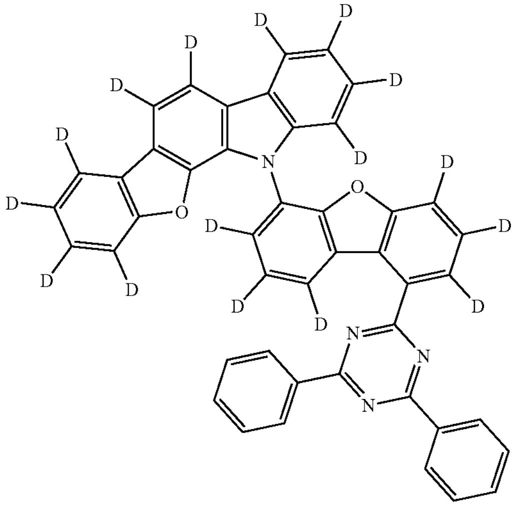

-continued
828
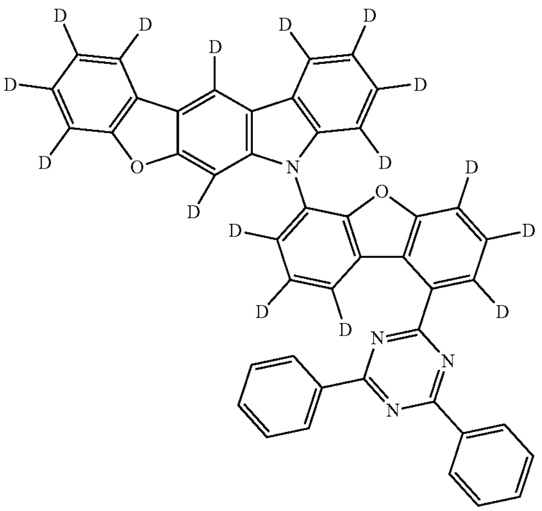
829
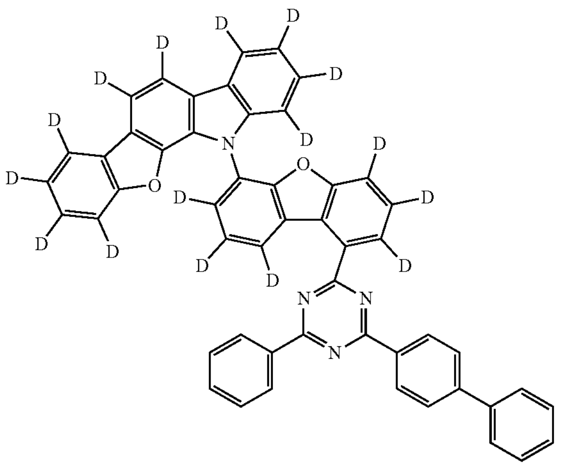
830
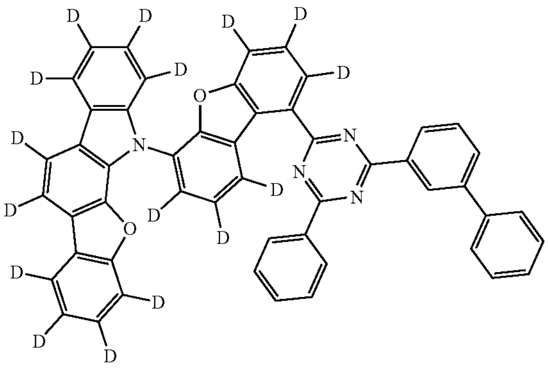
831
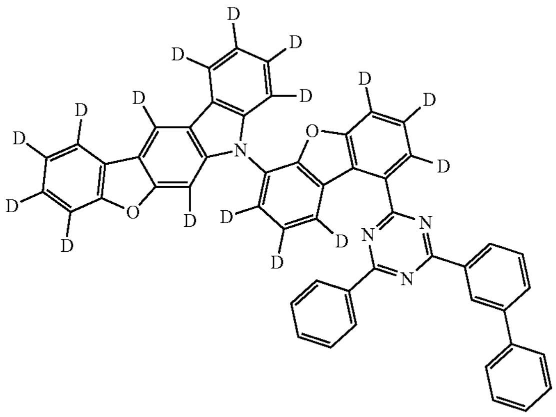
832
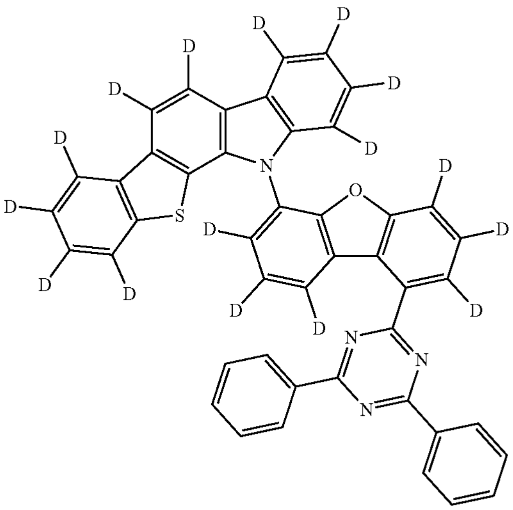
833
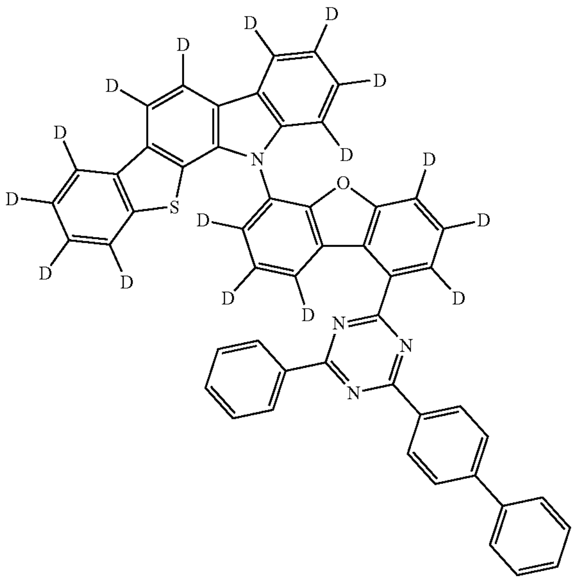

-continued
834
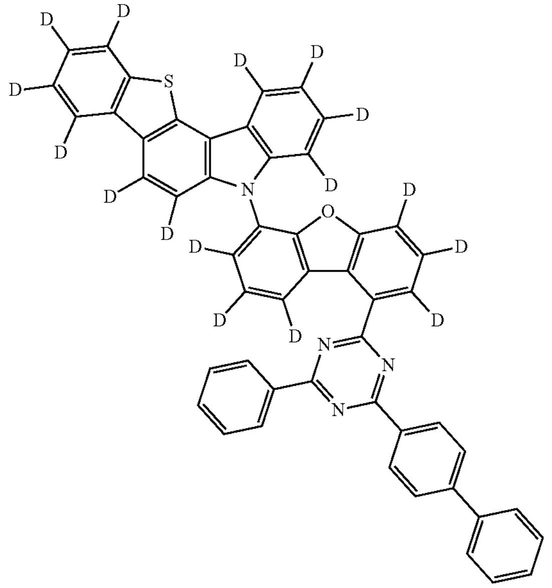
835
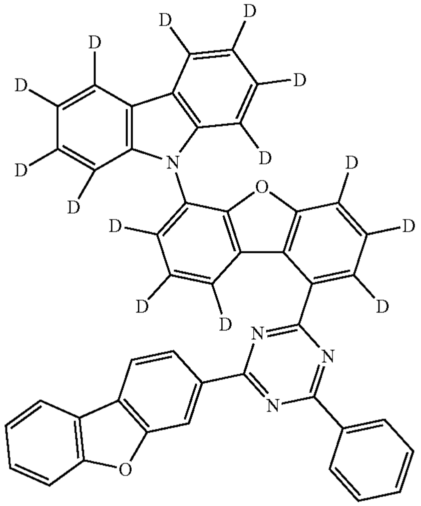
836
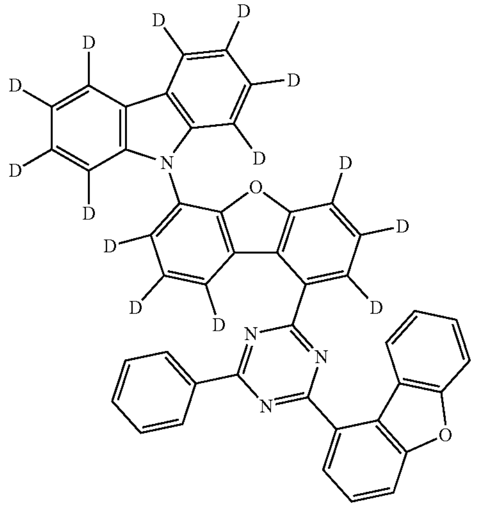
837
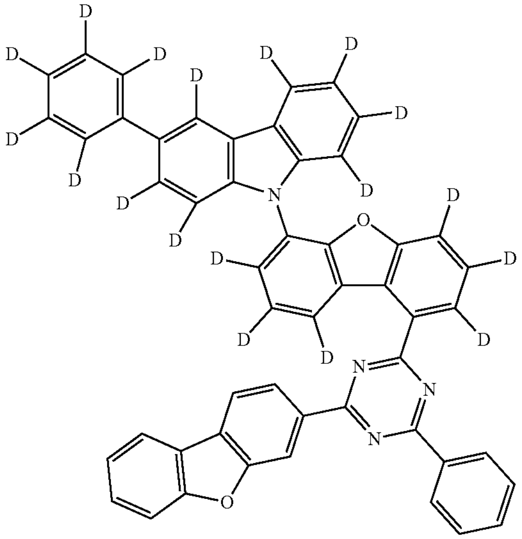
838
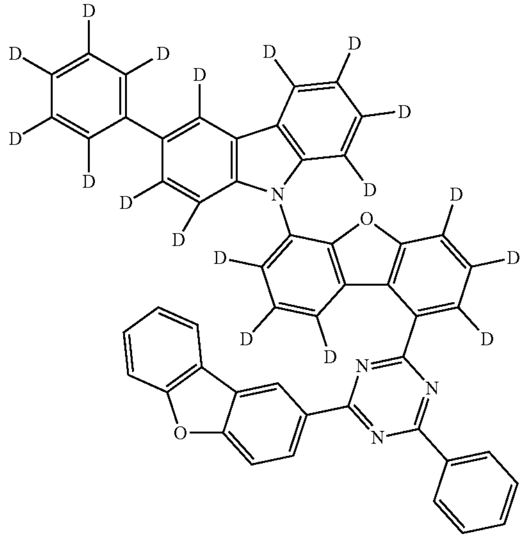
839
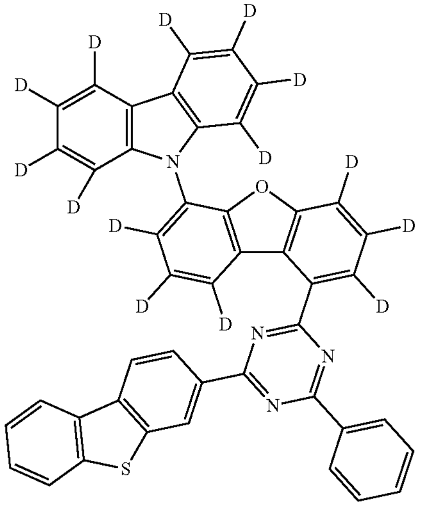

-continued
840
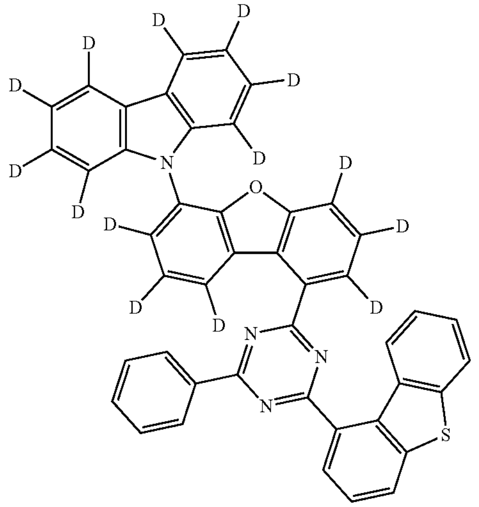
841
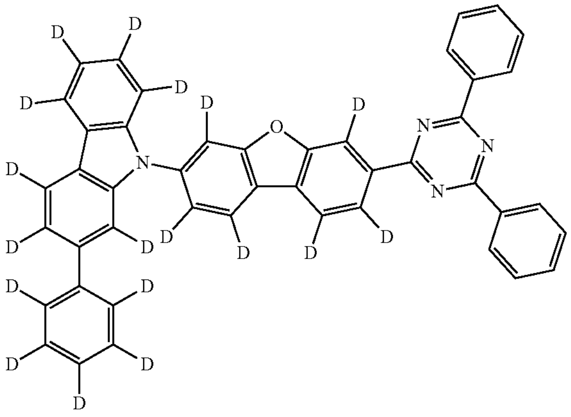
842
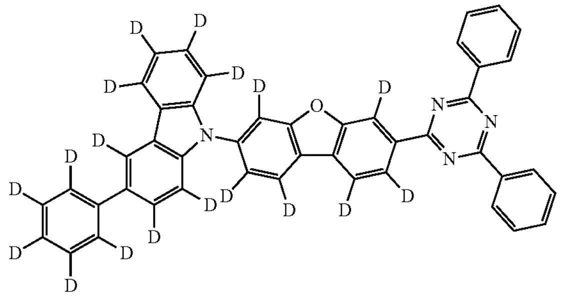
843
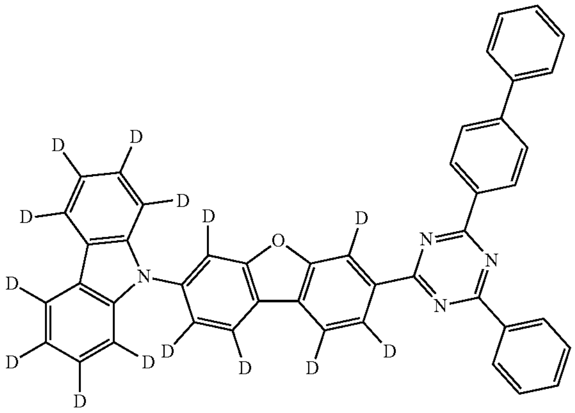
844
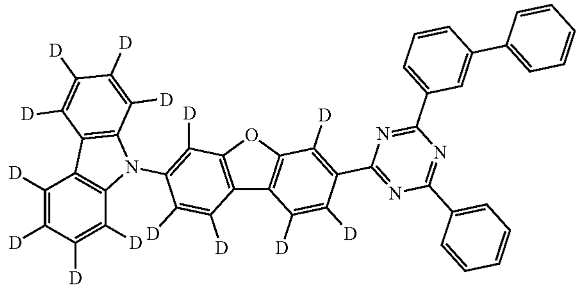
845
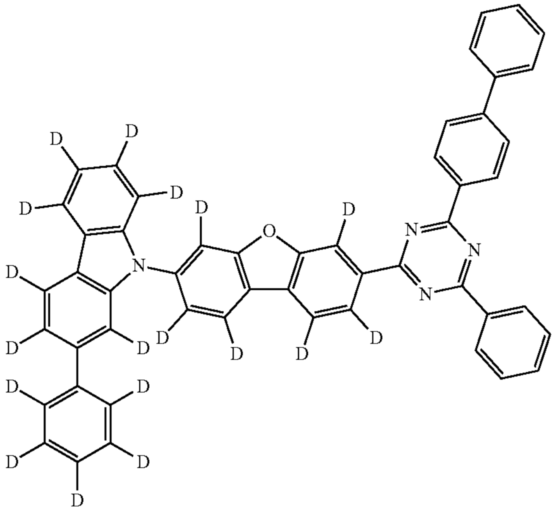

-continued
846
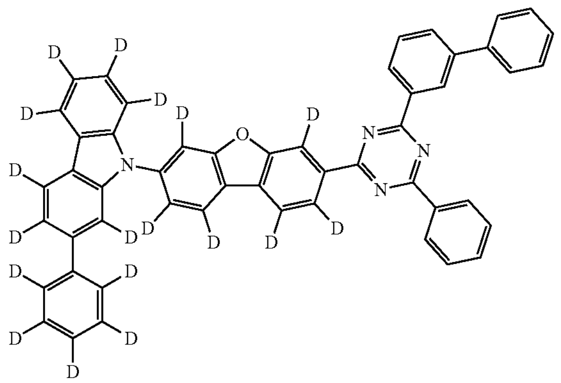
847
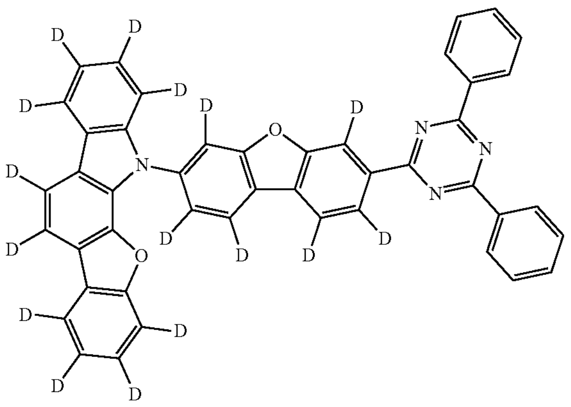
848
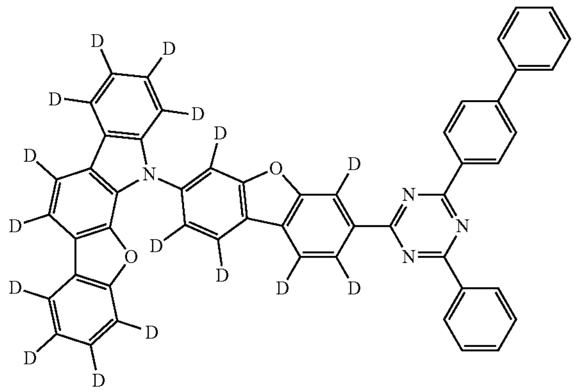
849
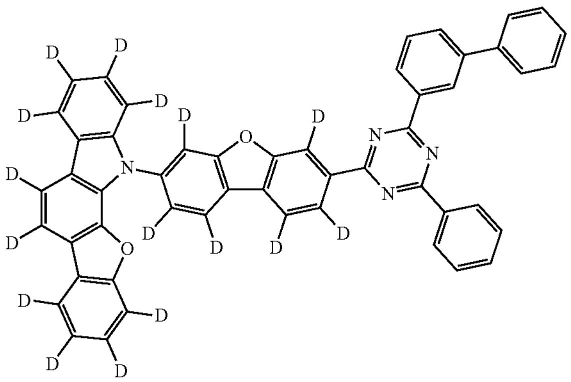
850
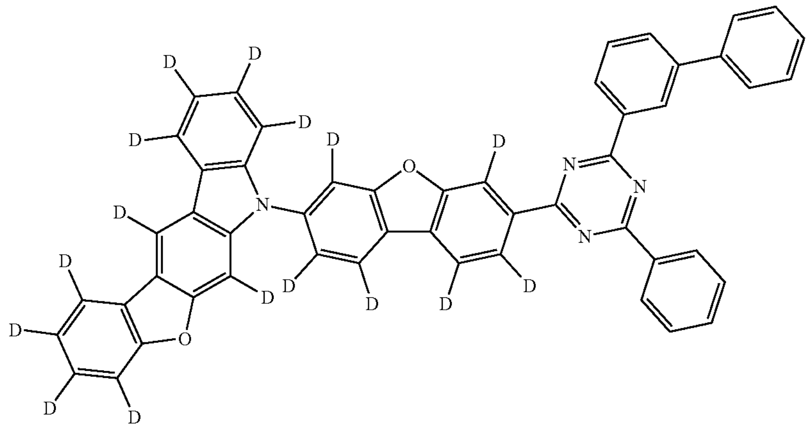

-continued
851
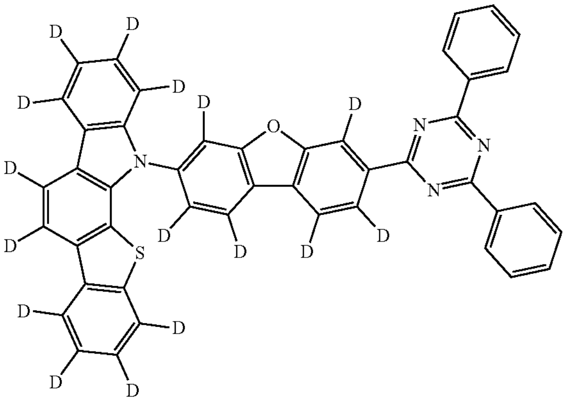
852
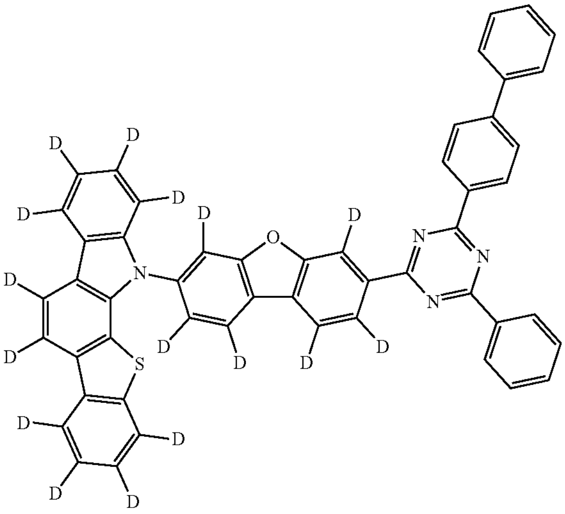
853
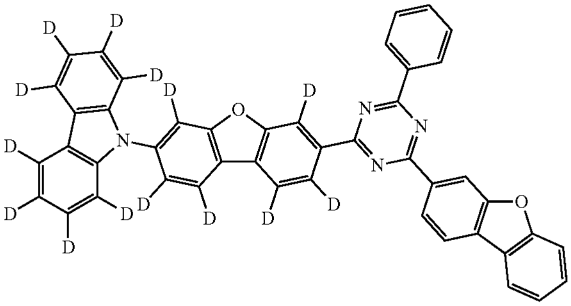
854
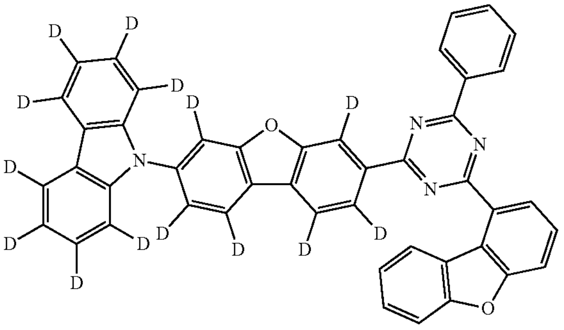
855
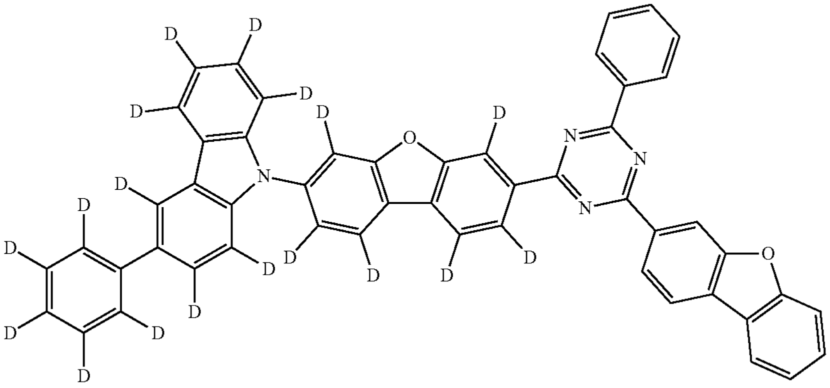

-continued
856
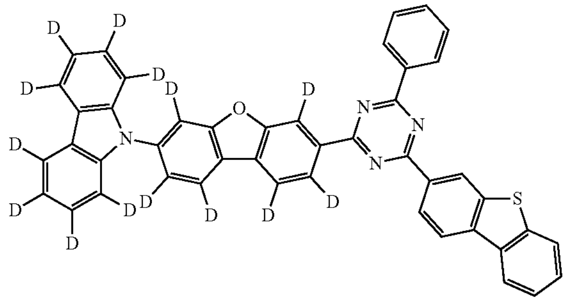
857
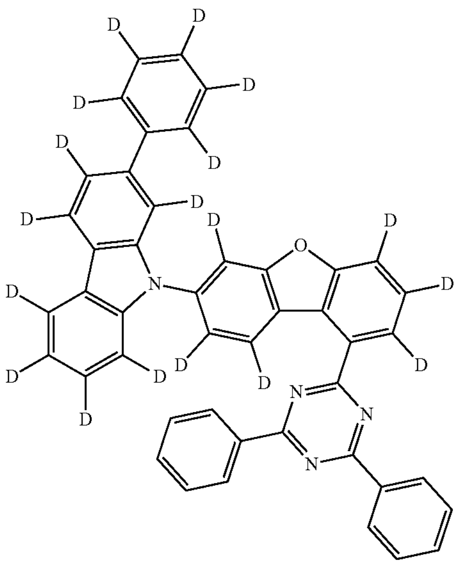
858
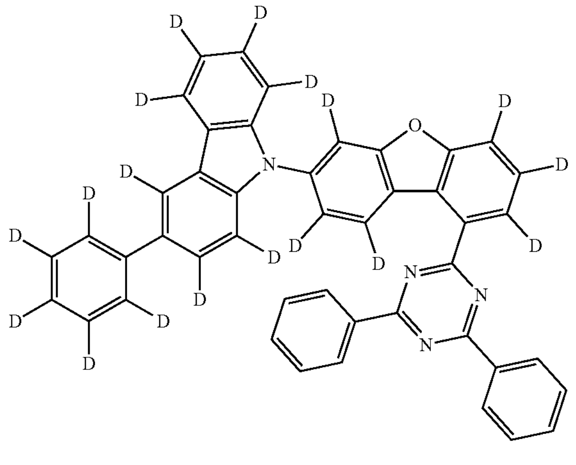
859
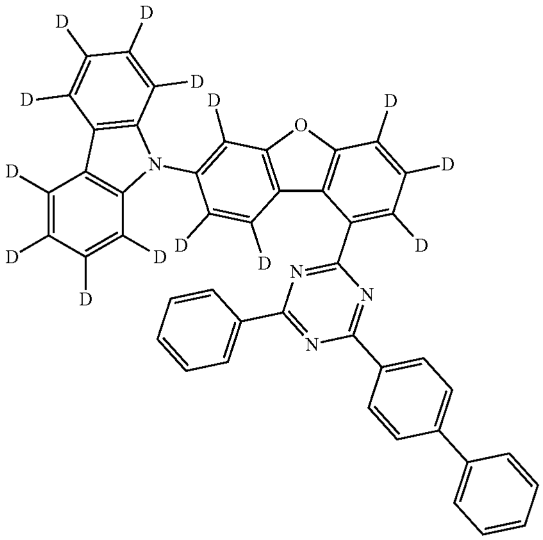

-continued
860
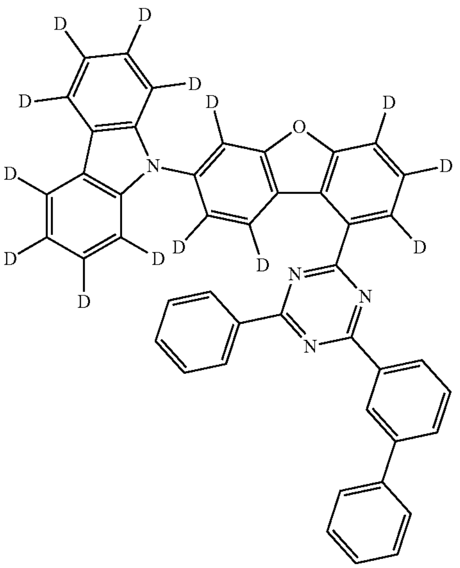
861
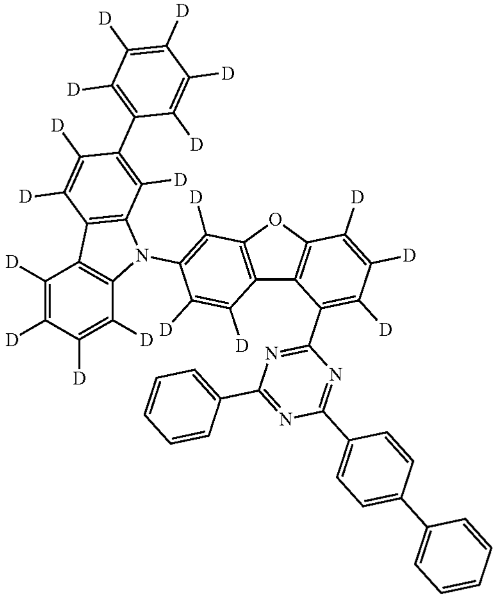
862
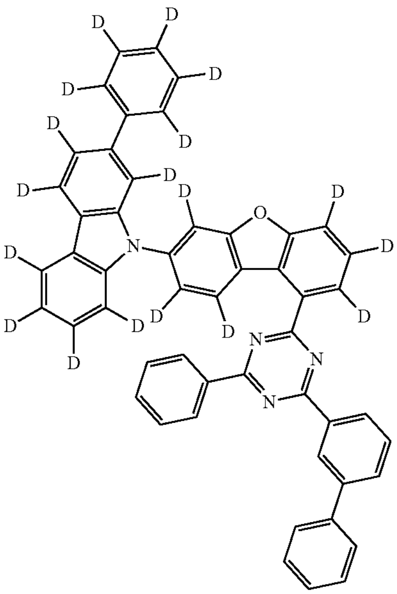
863
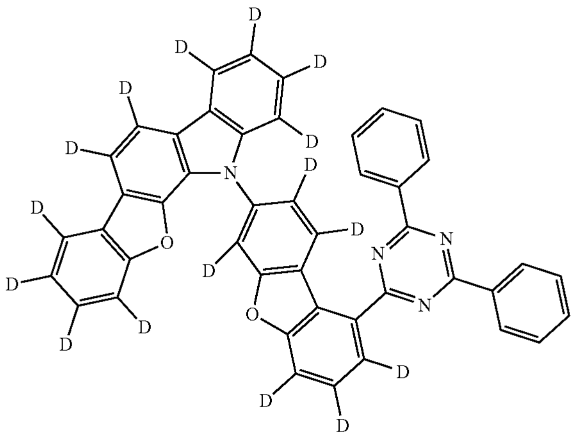

-continued
864
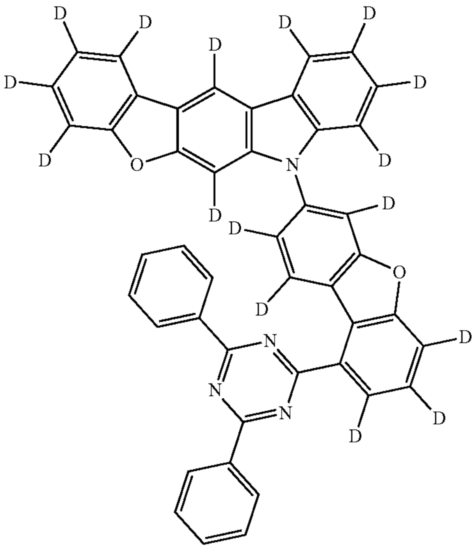
865
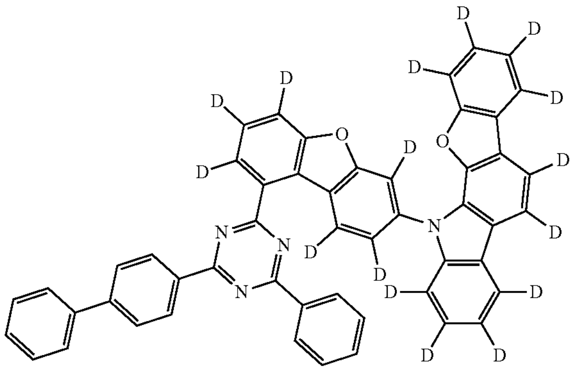
866
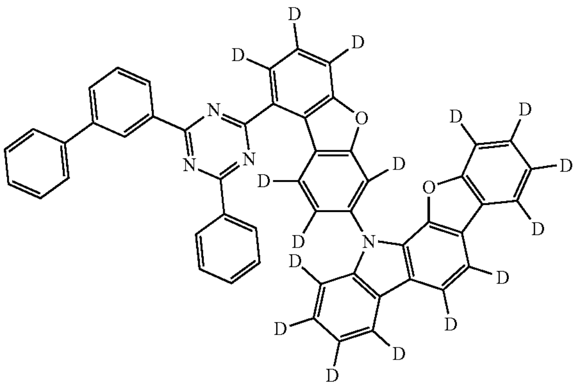
867
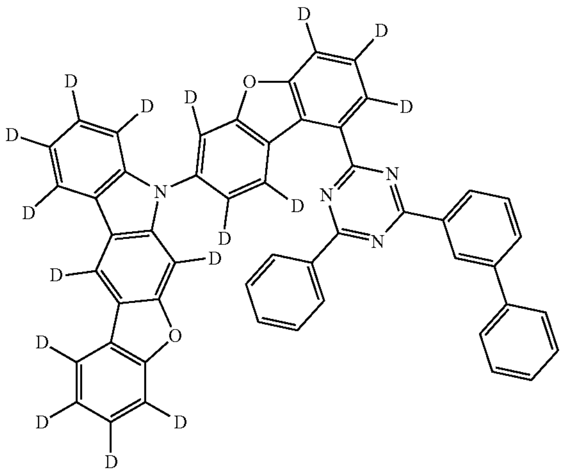
868
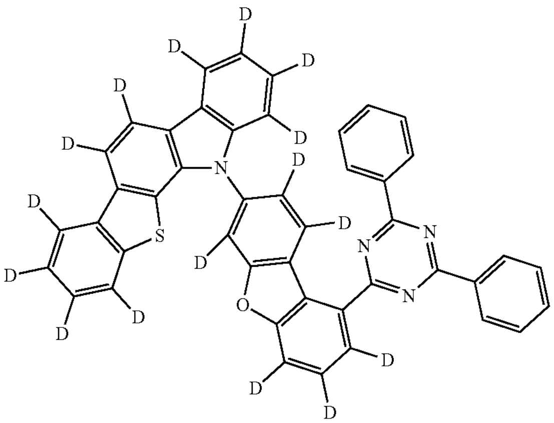
869
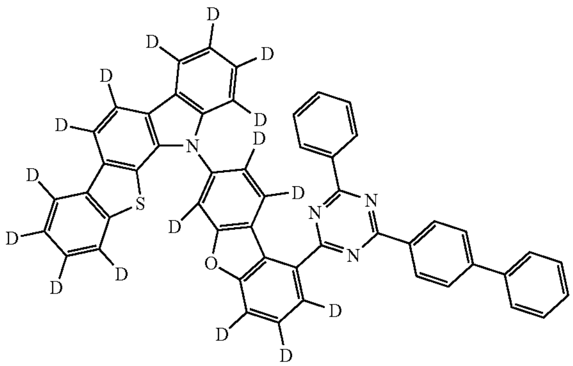

870
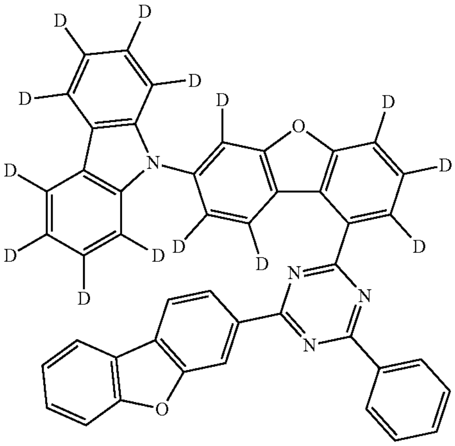
871
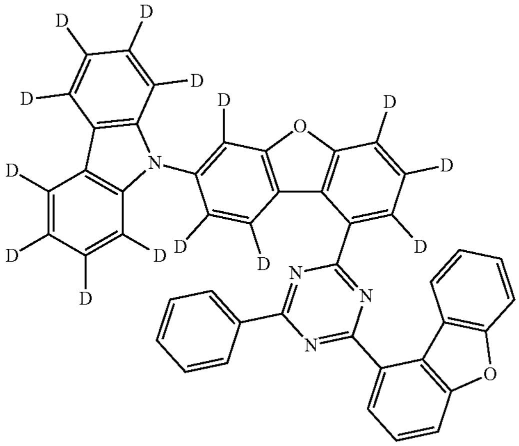
872
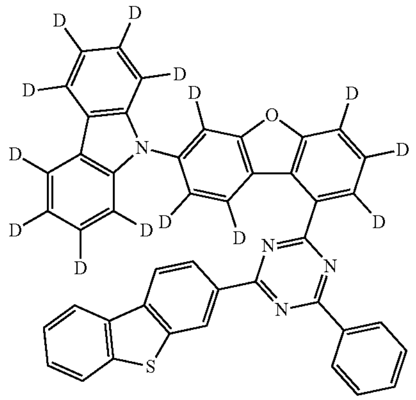
873
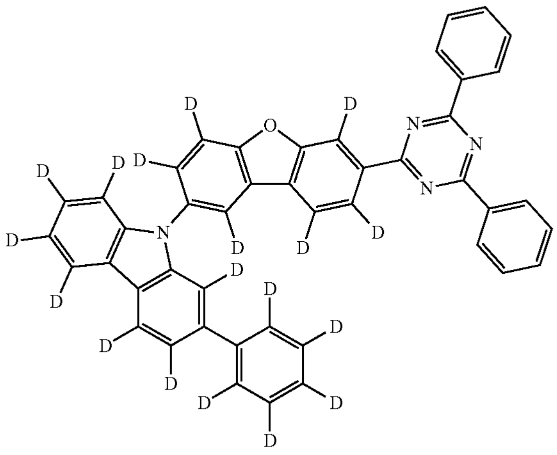
874
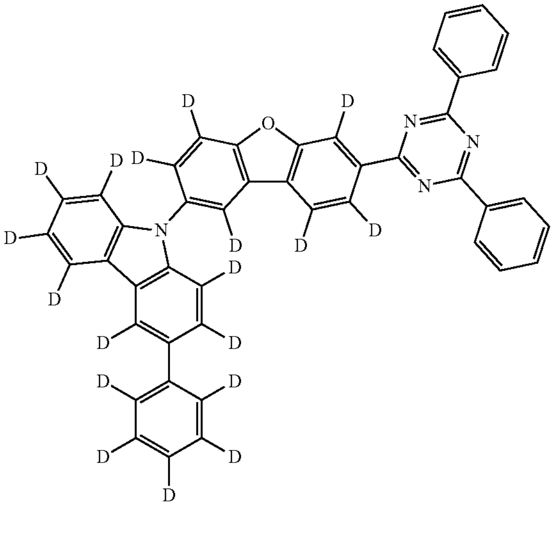
875
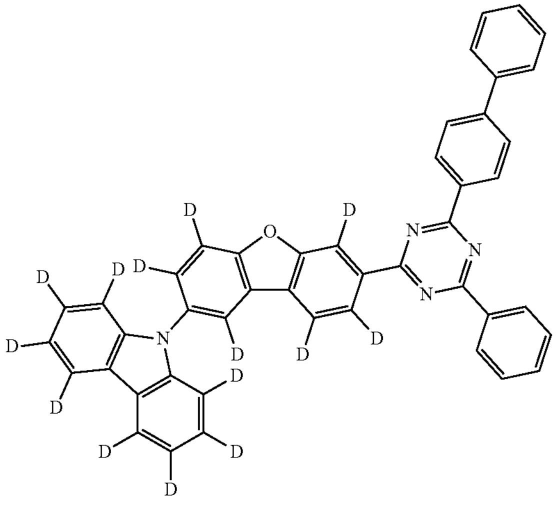

-continued
876
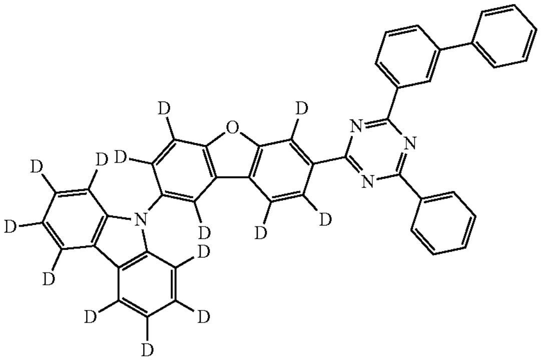
877
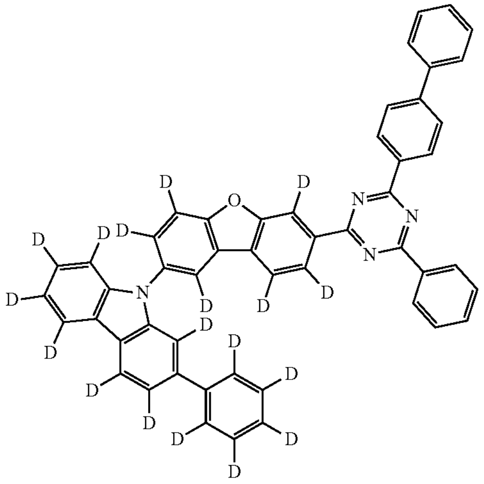
878
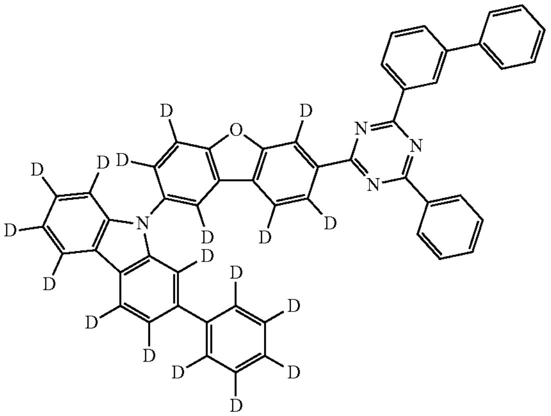
879
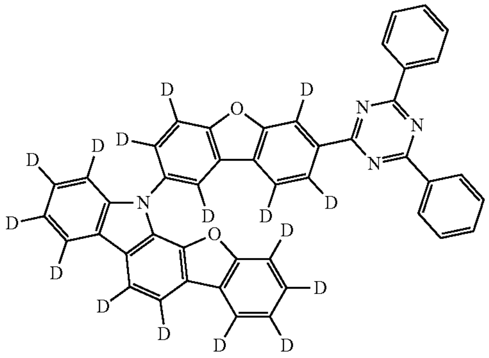
880
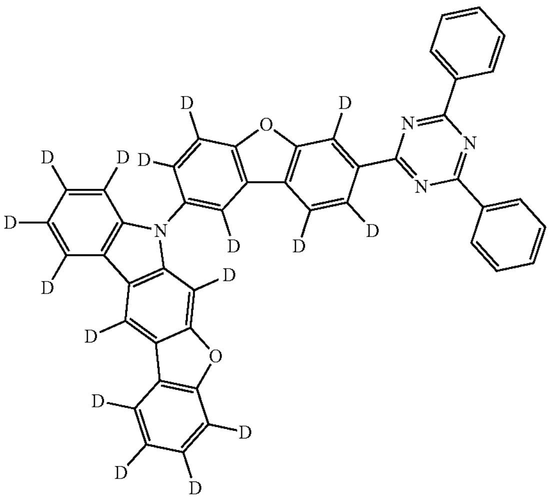
881
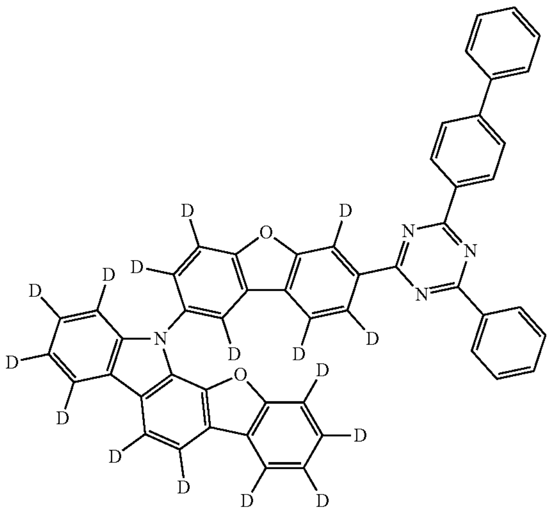

-continued
882
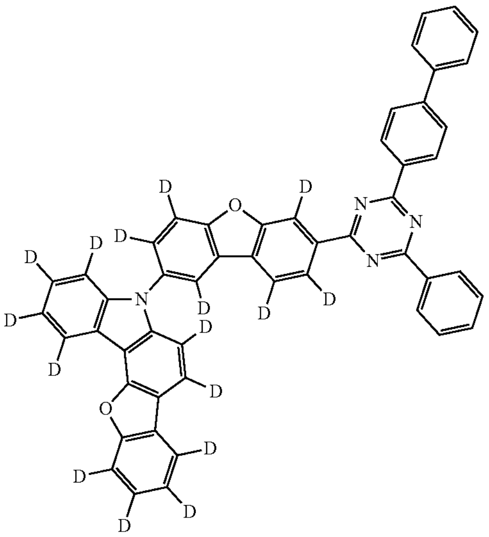
883
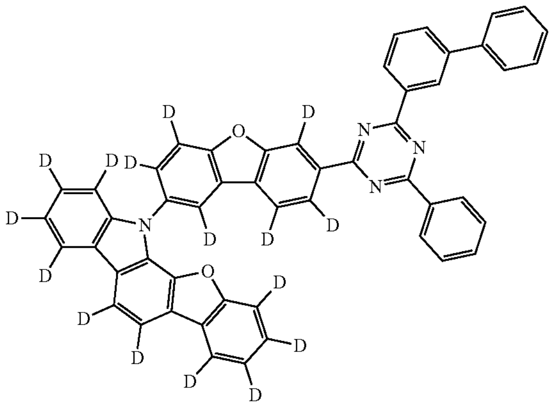
884
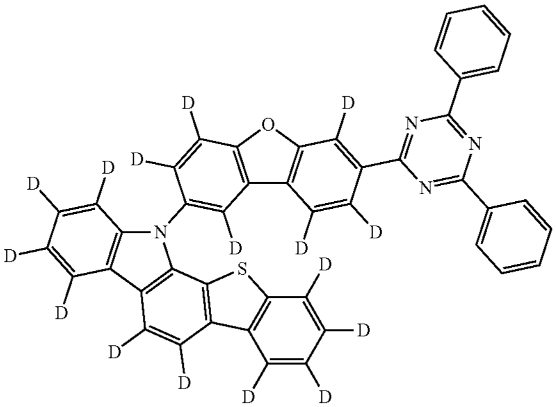
885
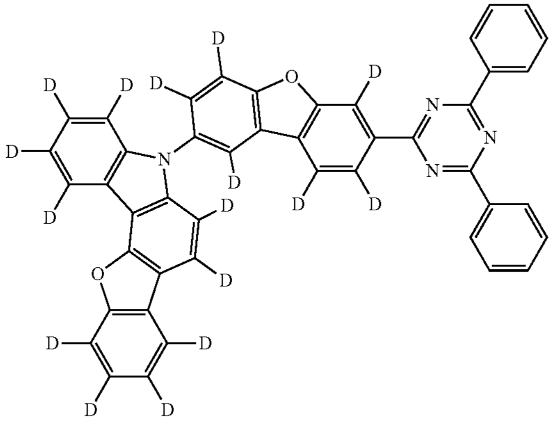
886
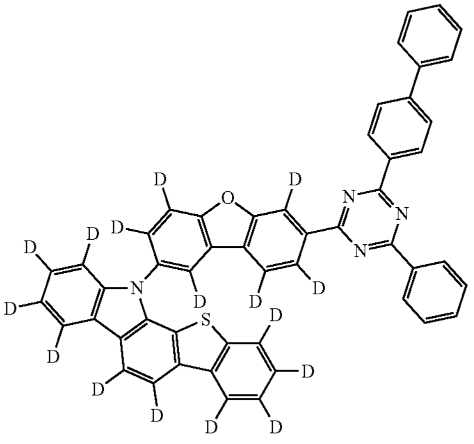
887
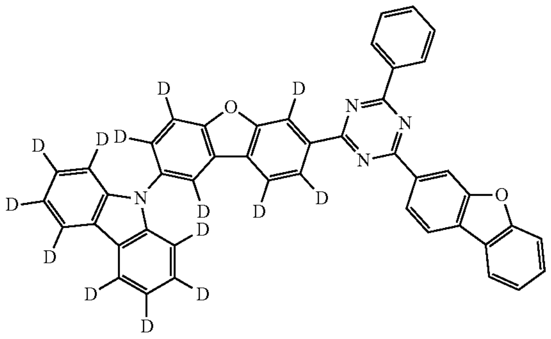

-continued
888
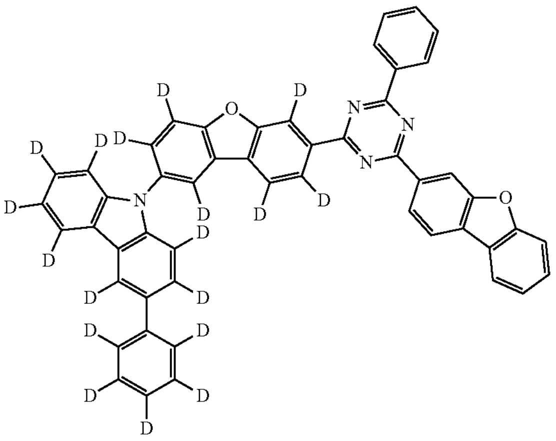
889
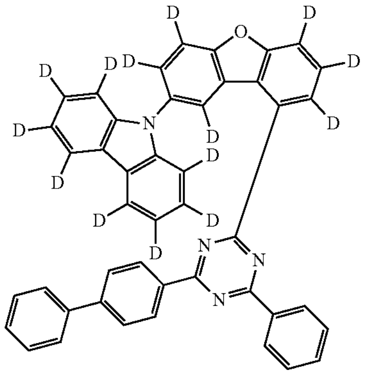
890
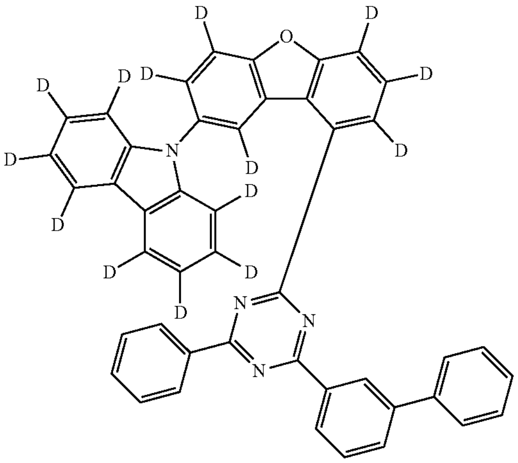
891
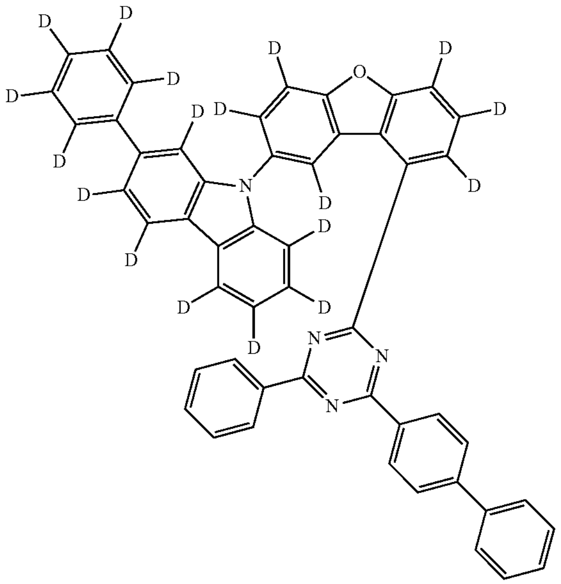
892
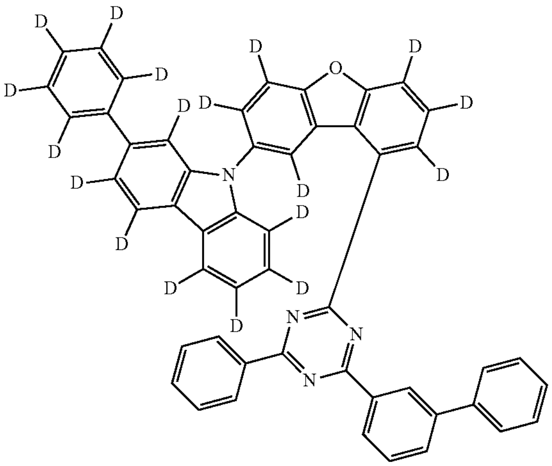
893
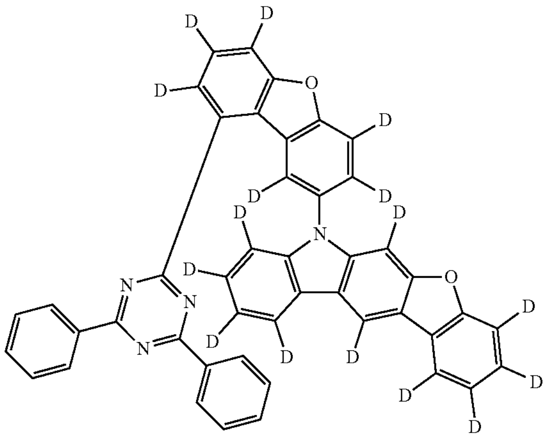

-continued
894
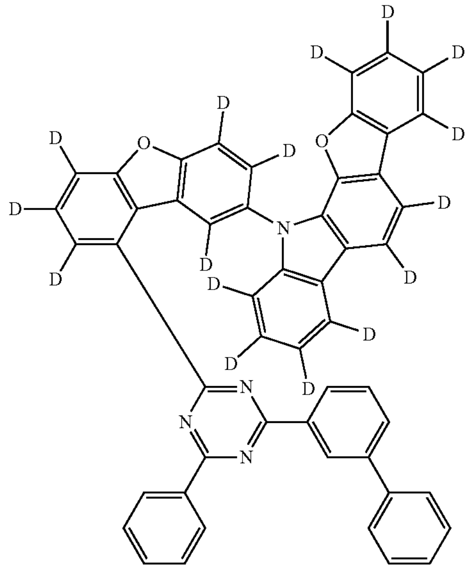
895
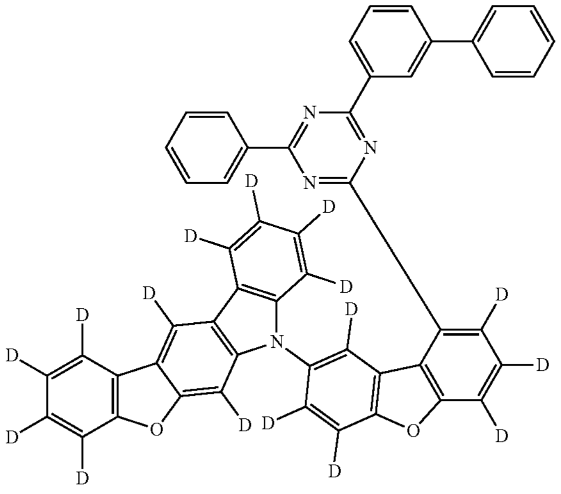
896
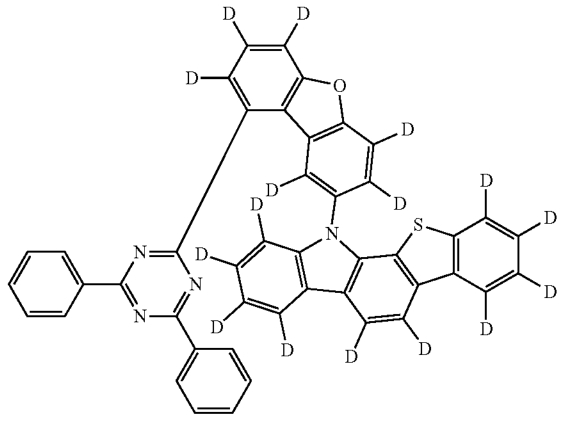
897
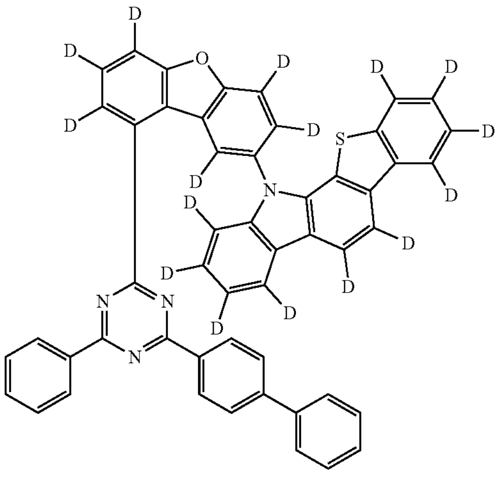
898
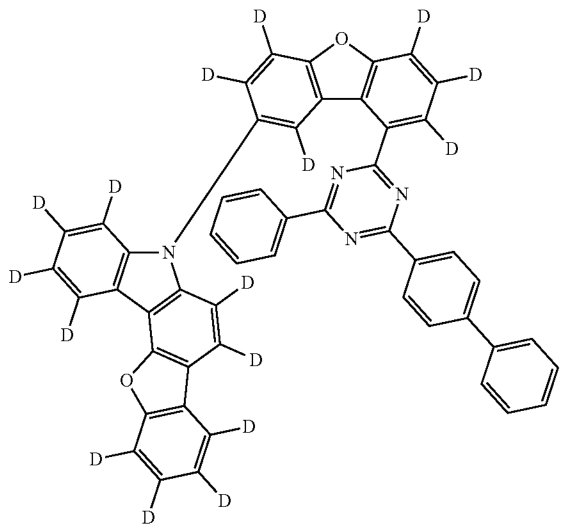
899
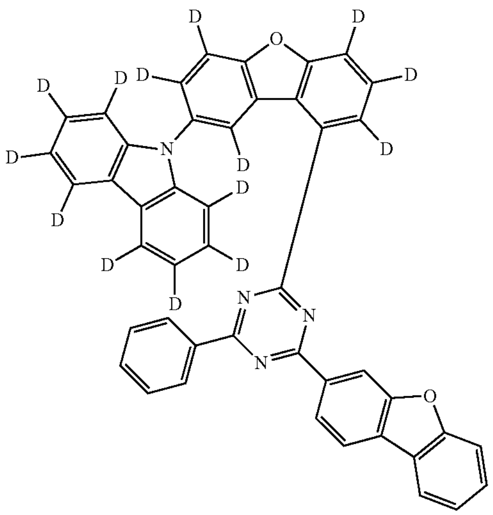

-continued
900
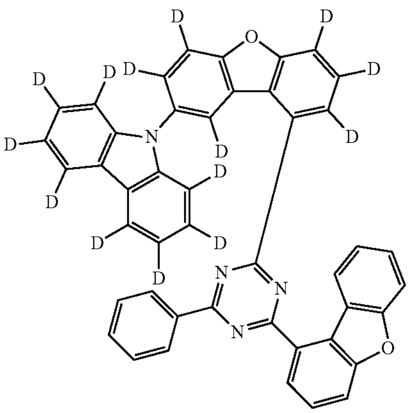
901
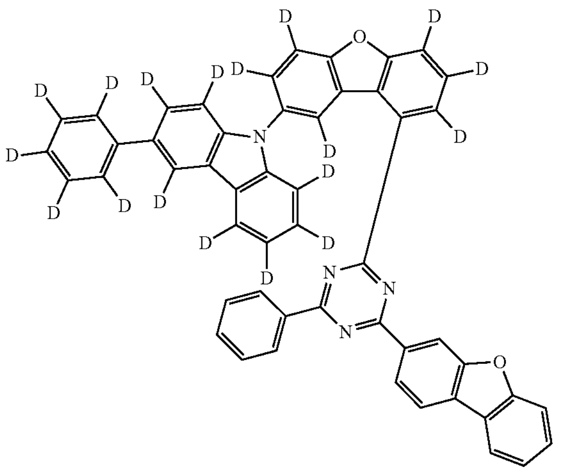
902
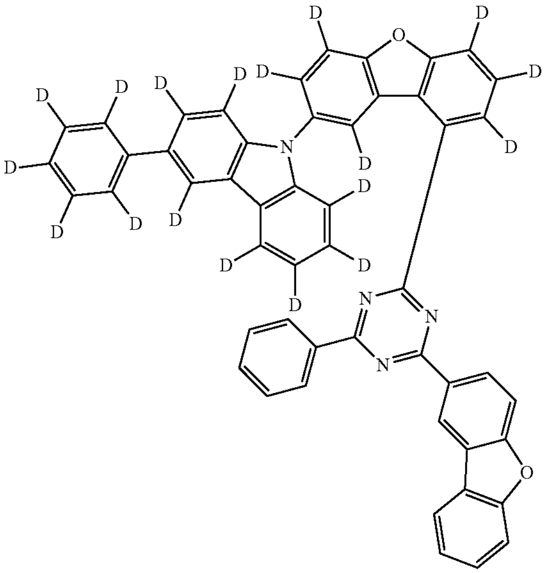
903
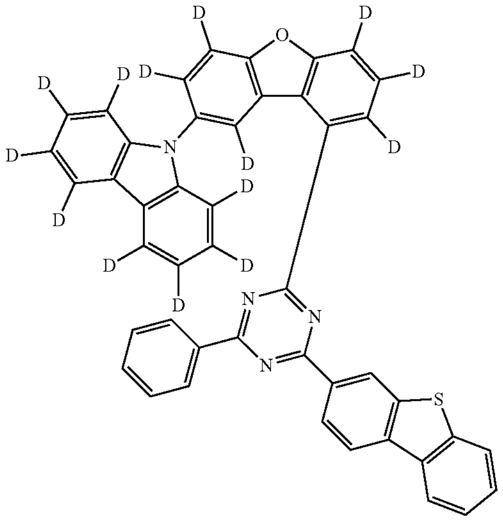
904
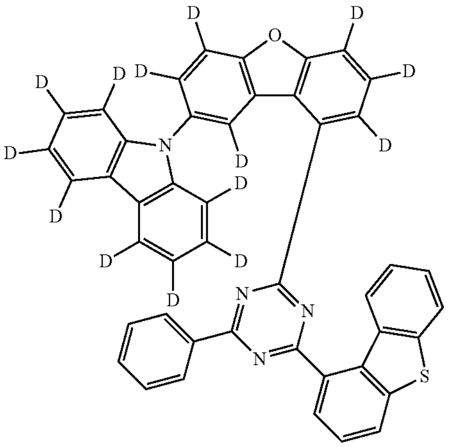
905
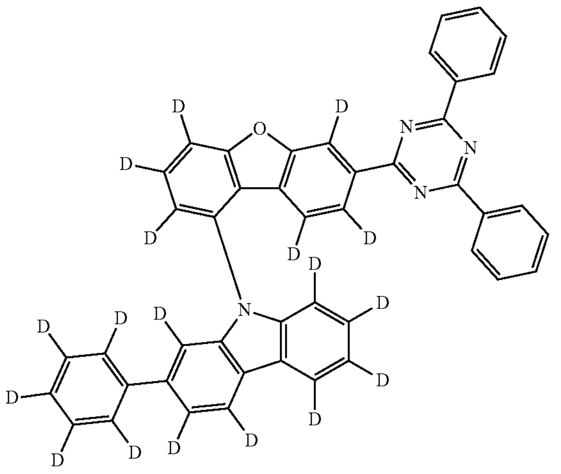

-continued
906
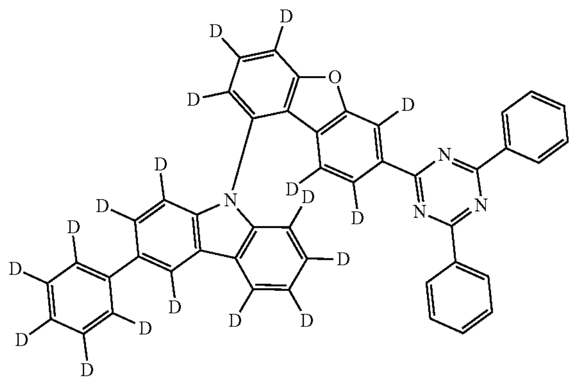
907
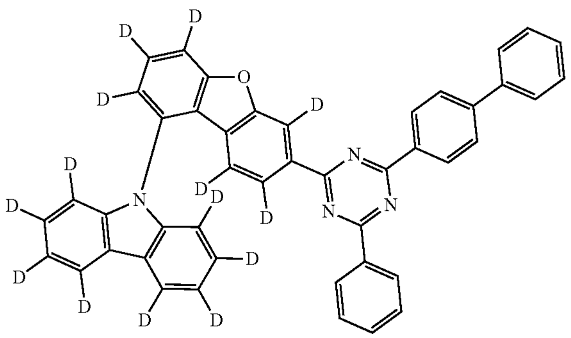
908
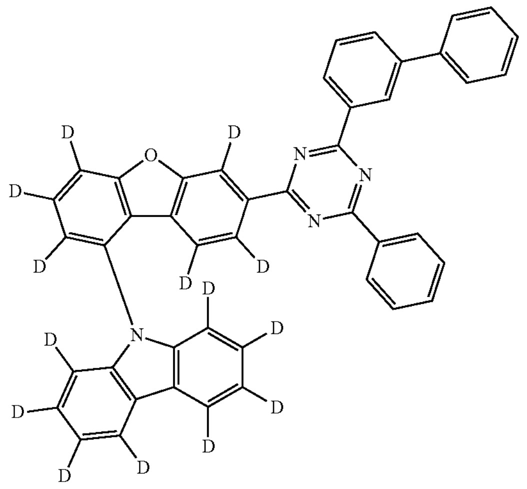
909
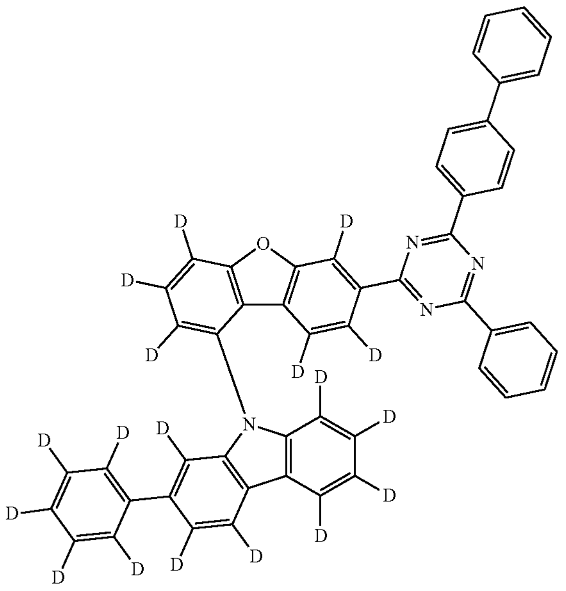
910
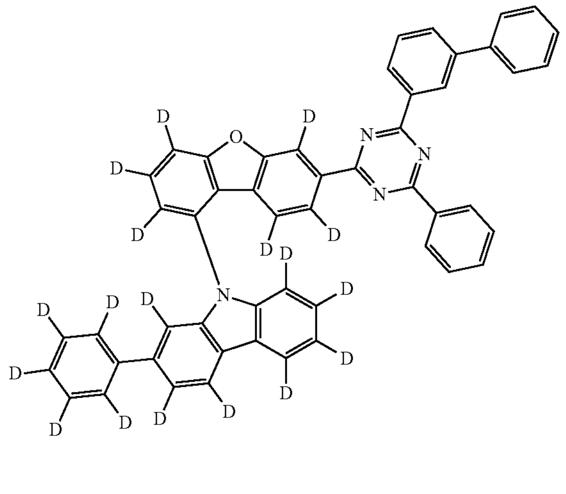
911
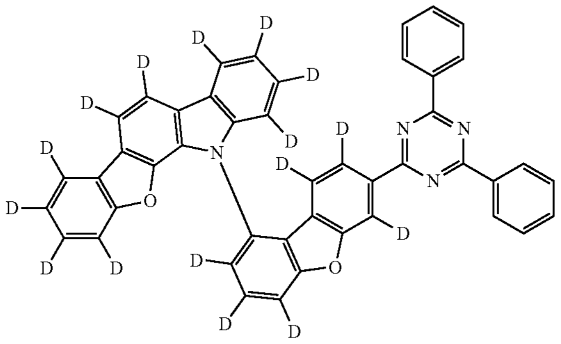

-continued
912
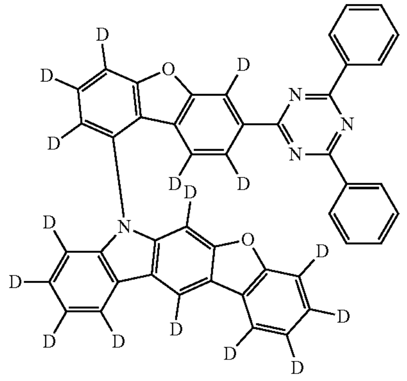
913
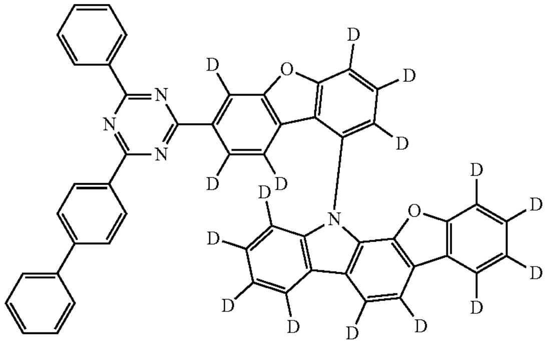
914
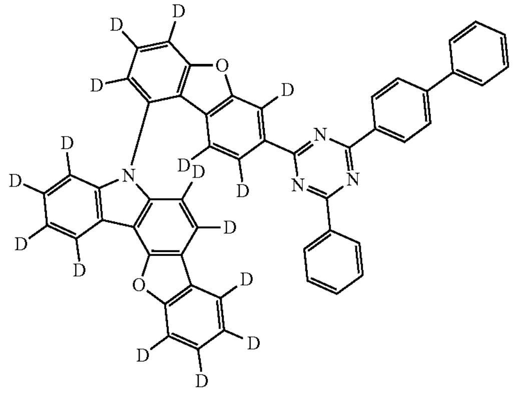
915
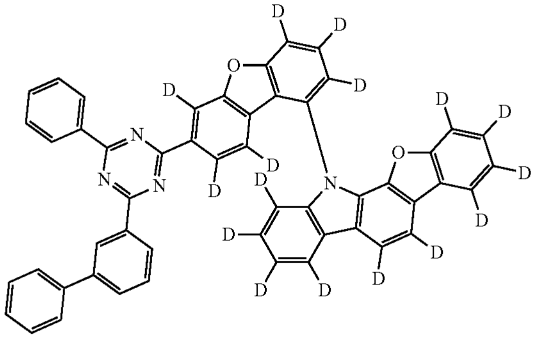
916
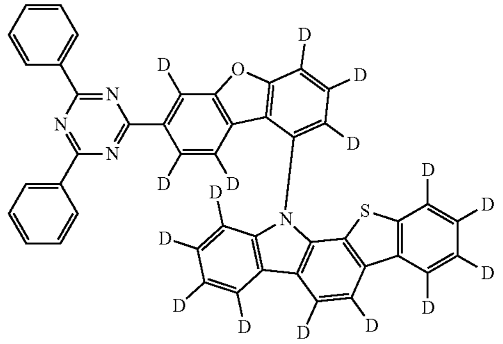
917
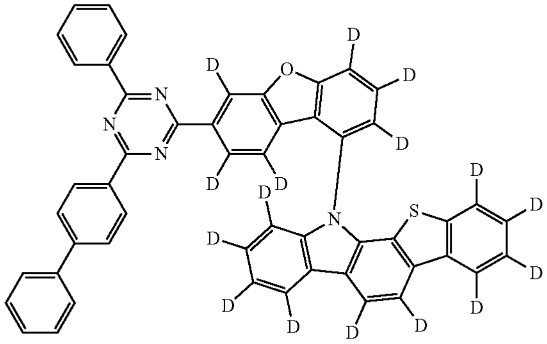
918
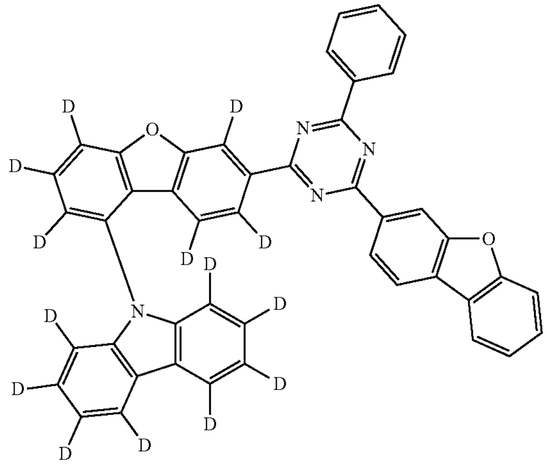
919
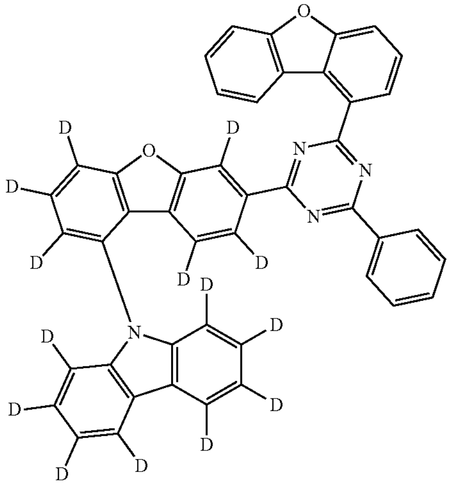

-continued
920
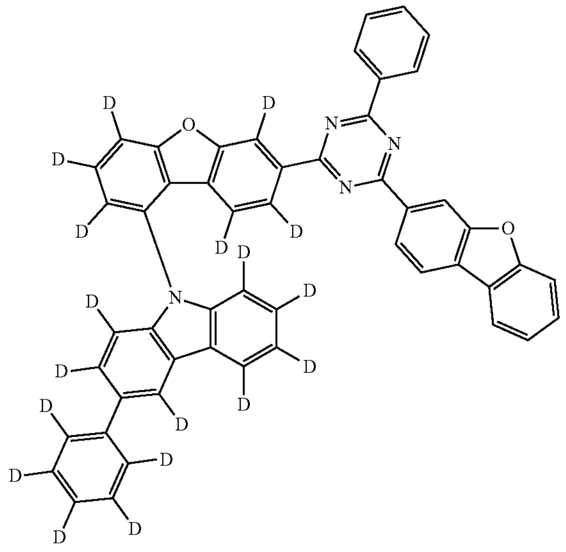
921
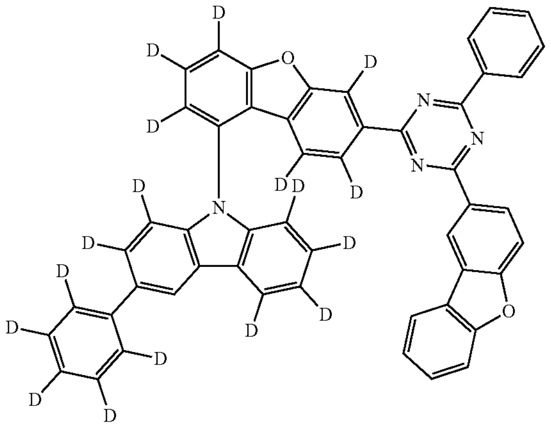
922
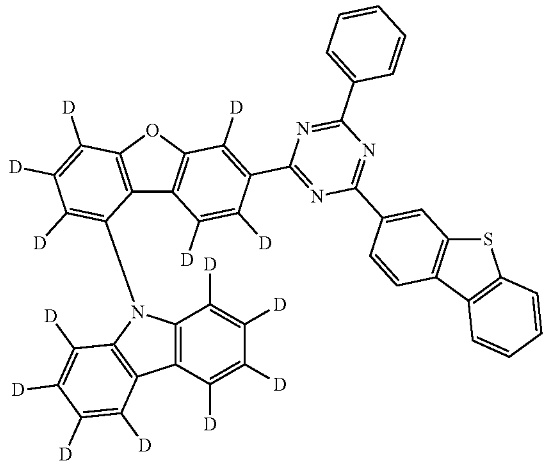
923
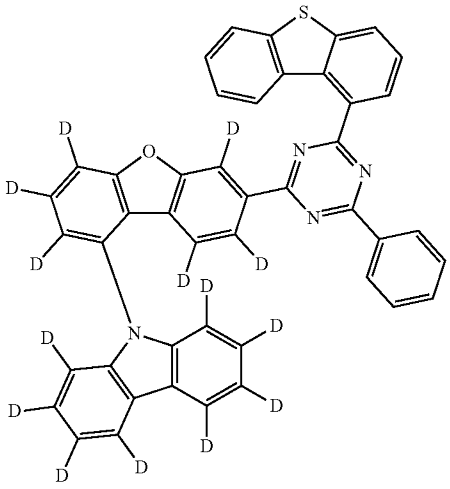
924
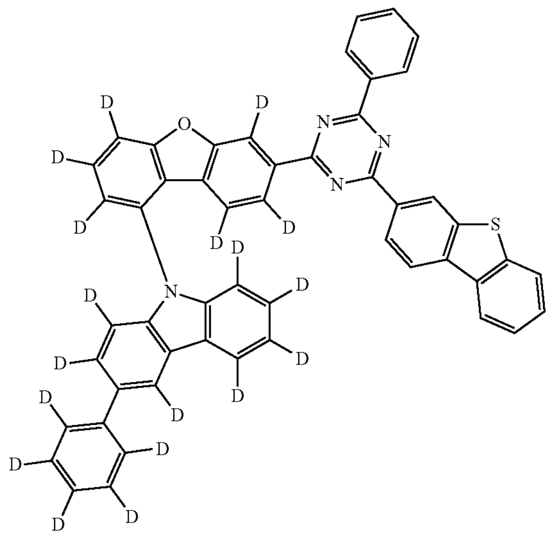
925
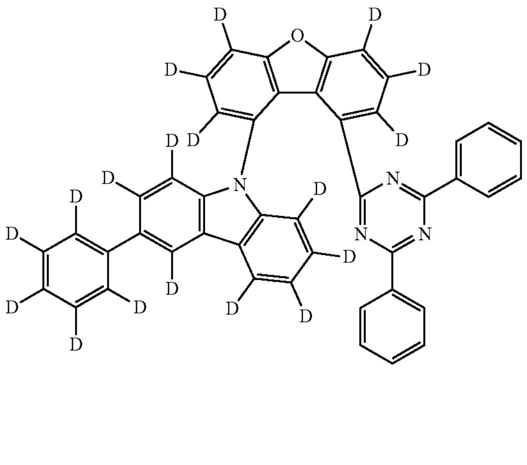

-continued
926
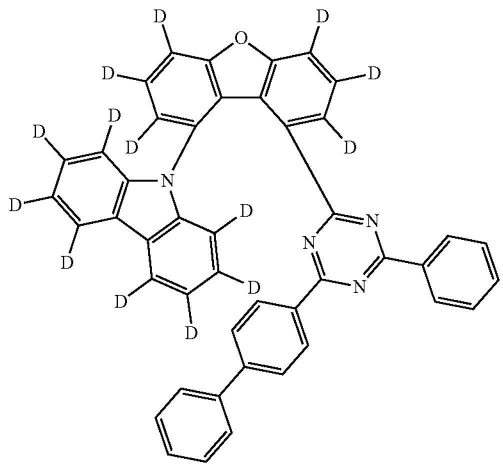
927
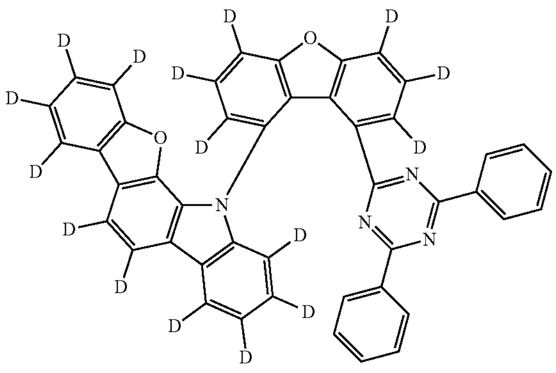
928
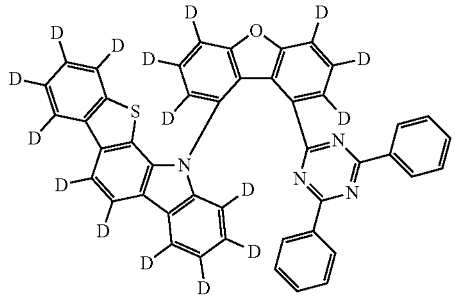
929
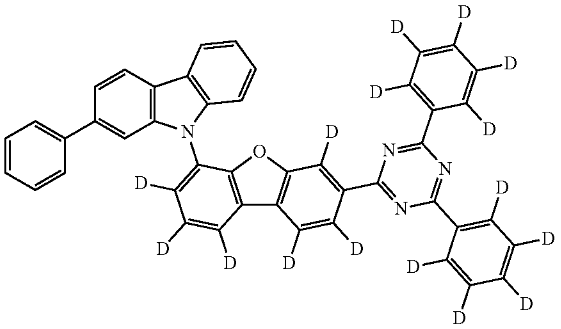
930
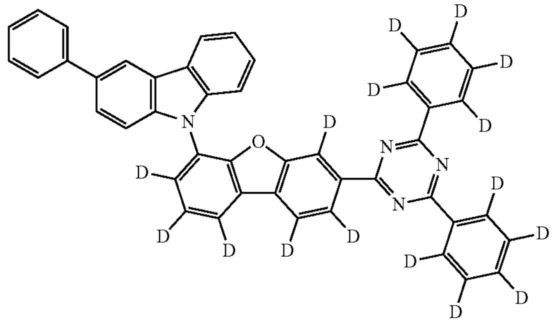
931
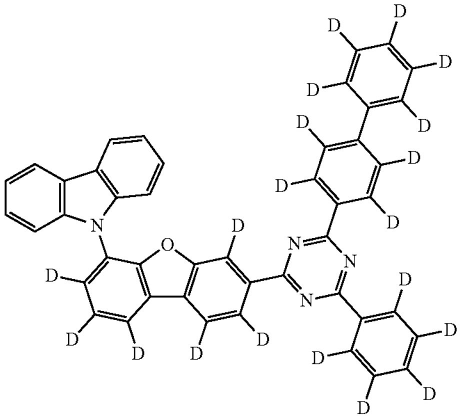

-continued
932
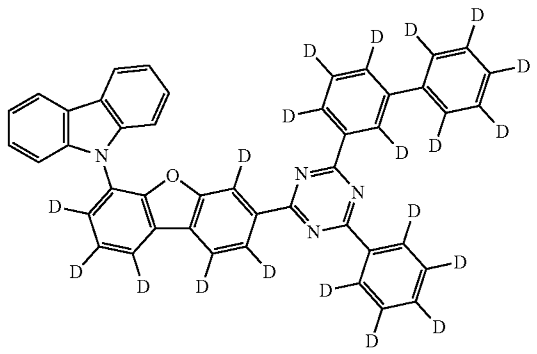
933
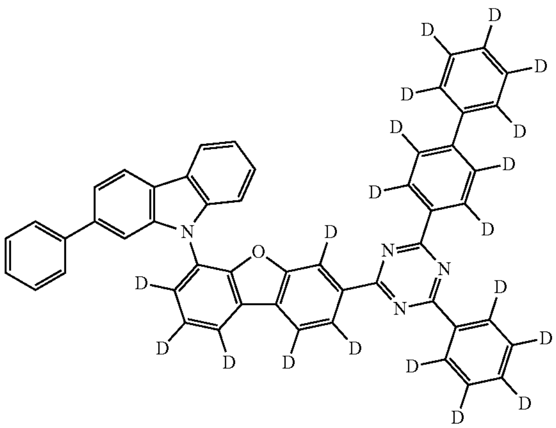
934
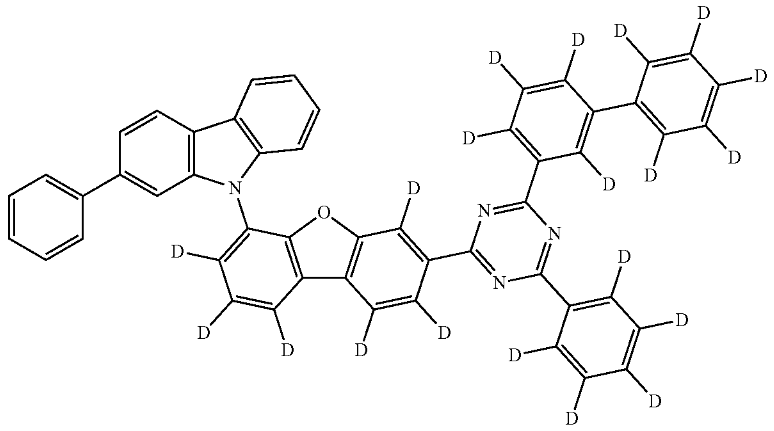
935
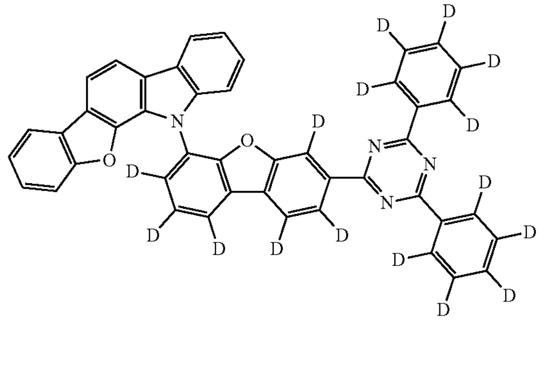
936
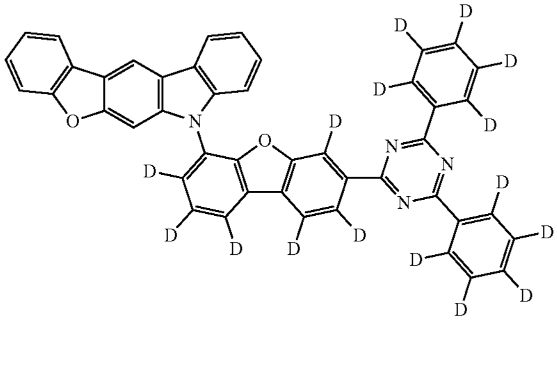

-continued
937
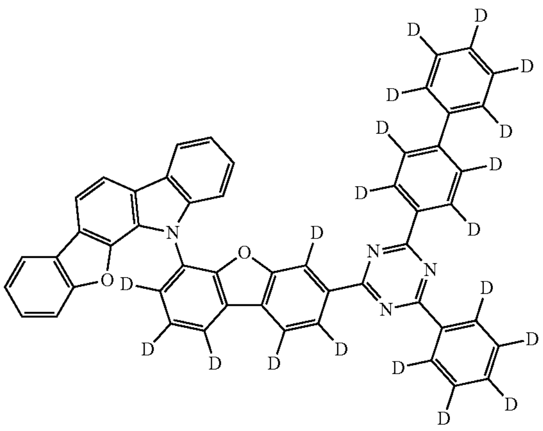
938
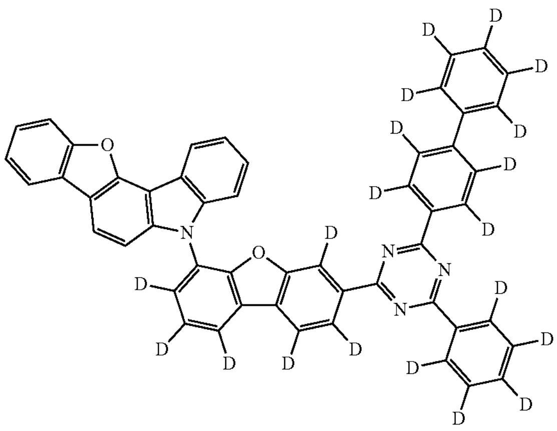
939
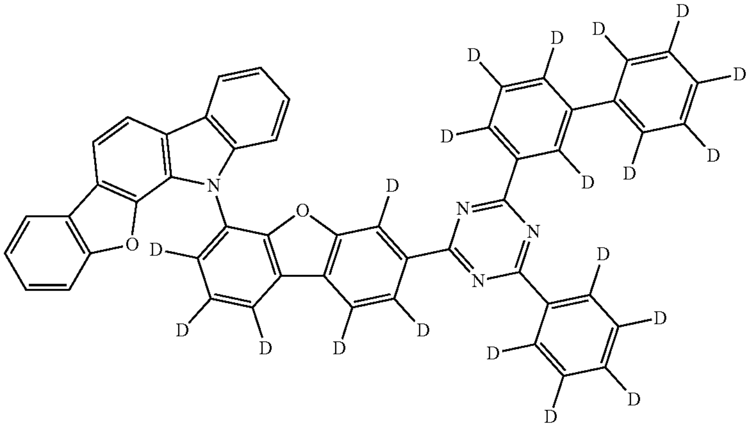
940
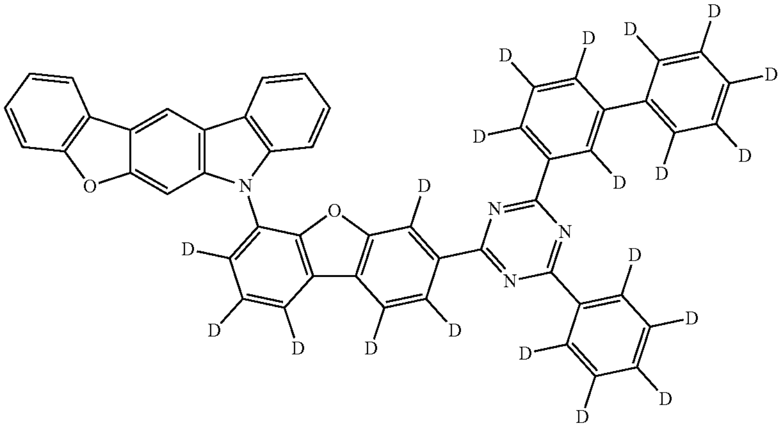
941
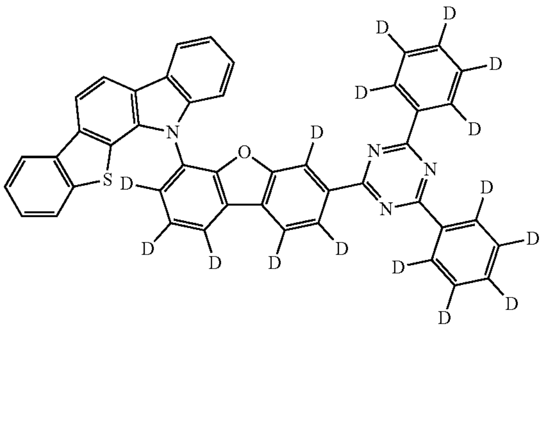
942
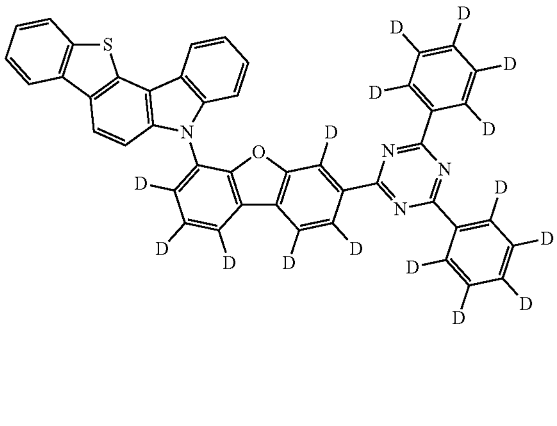

-continued
943
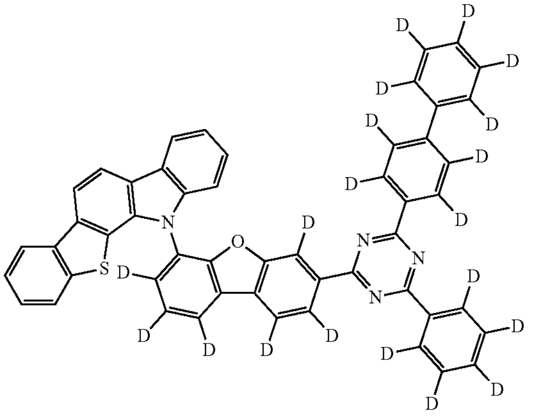
944
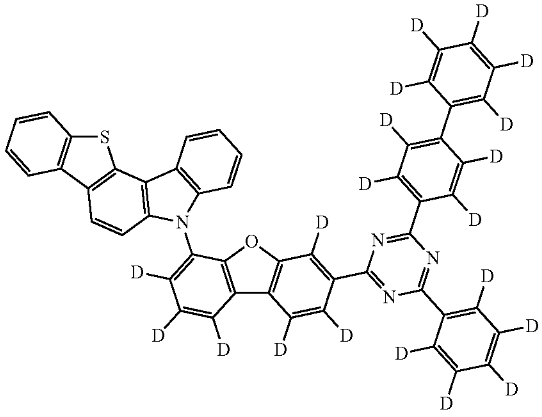
945
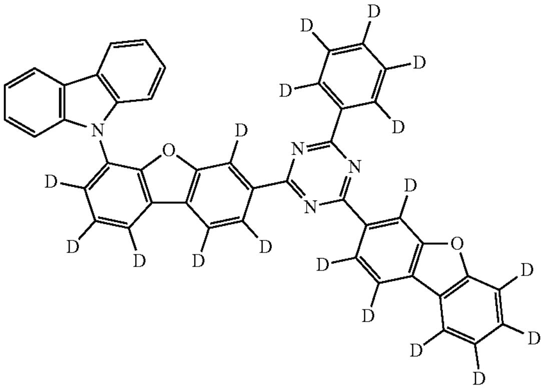
946
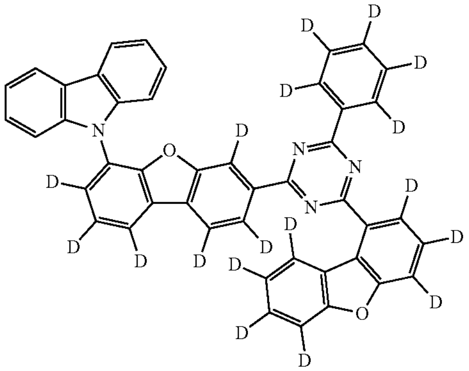
947
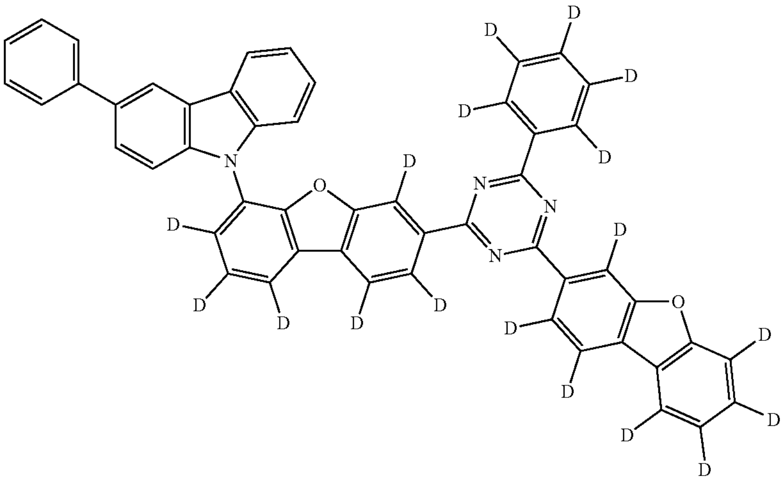

-continued
948
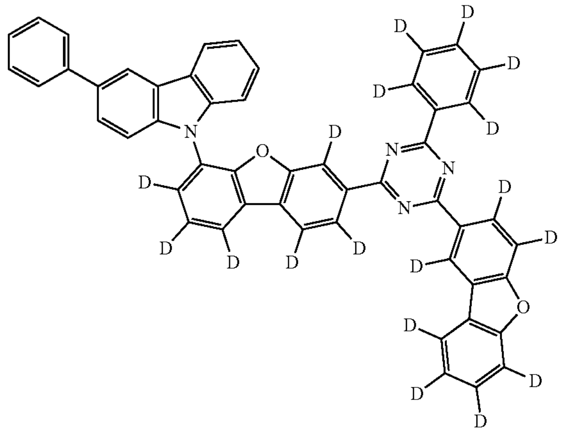
949
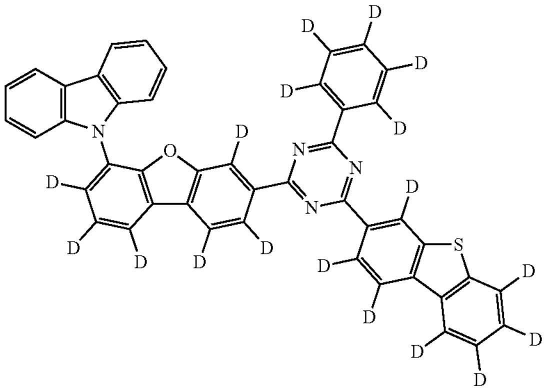
950
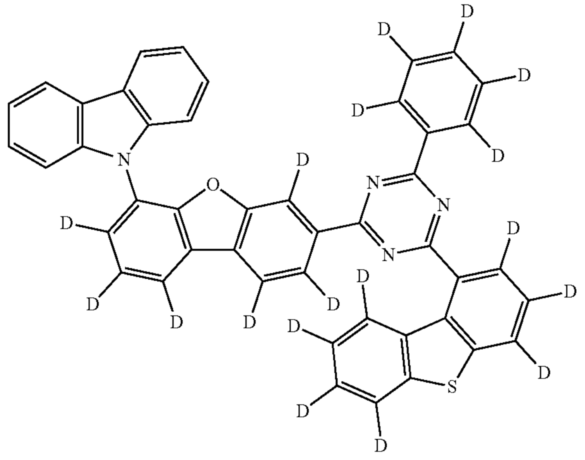
951
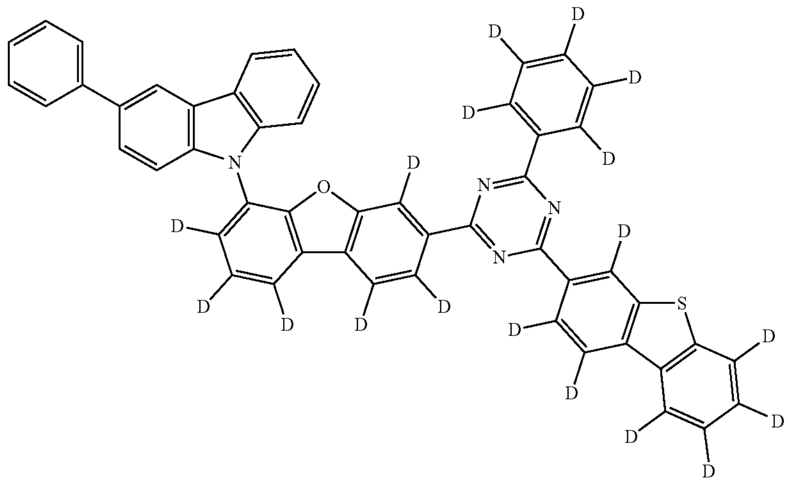

-continued
952
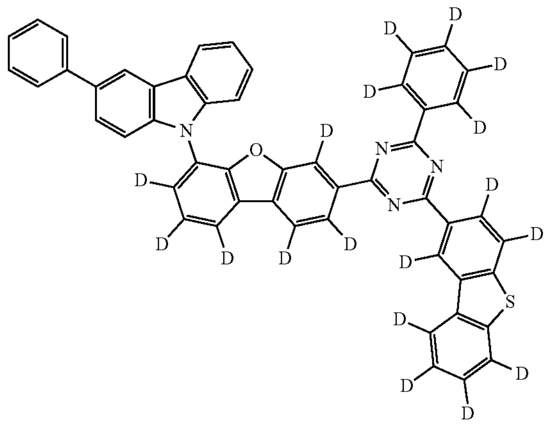
953
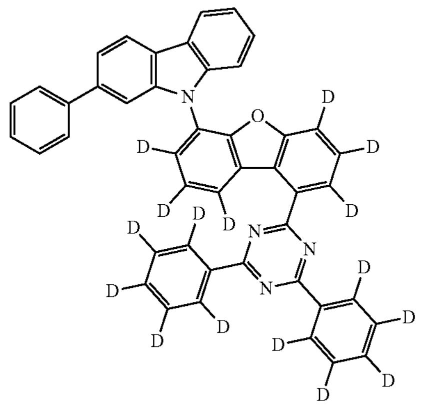
954
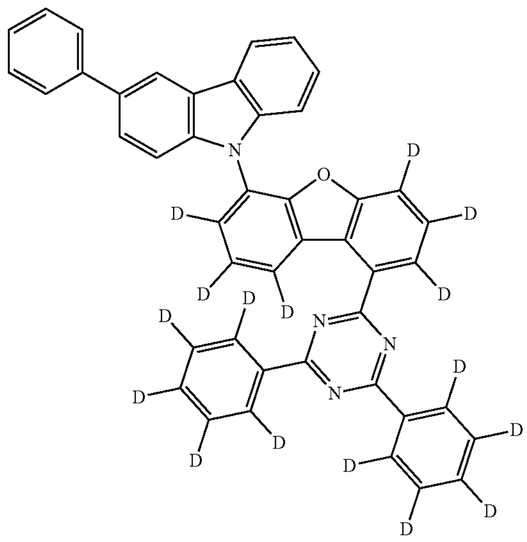
955
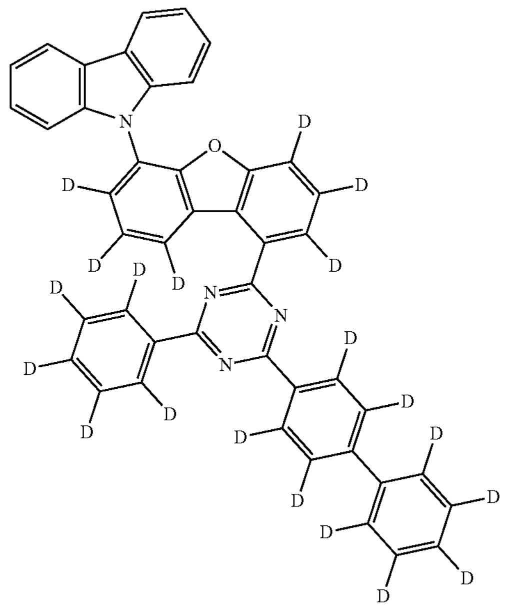
956
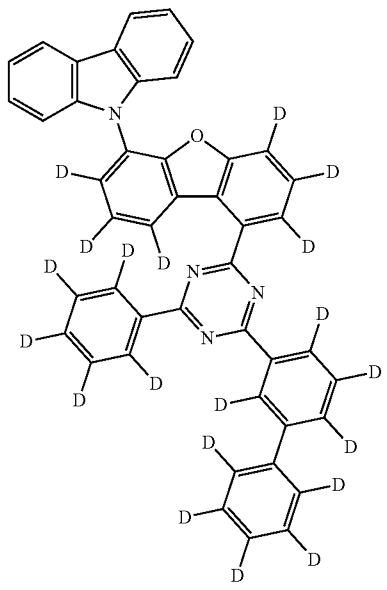
957
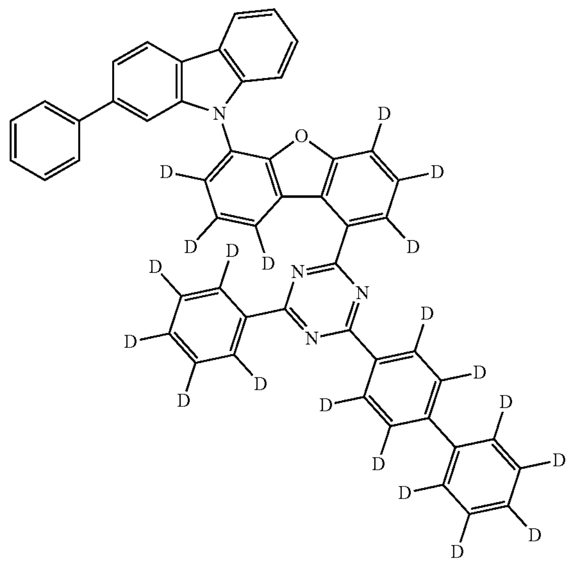

-continued
958
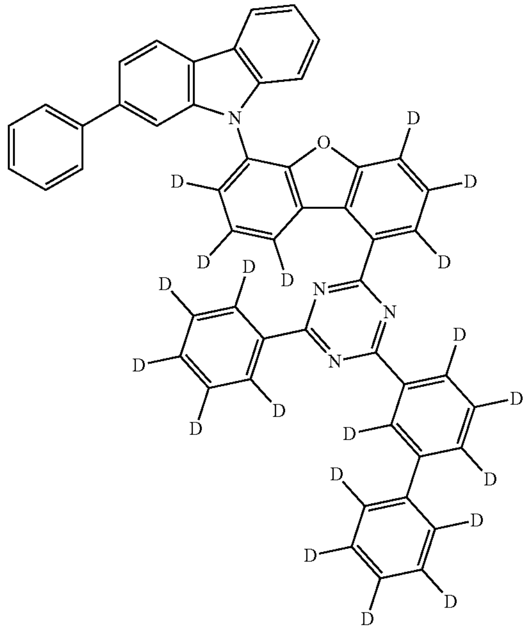
959
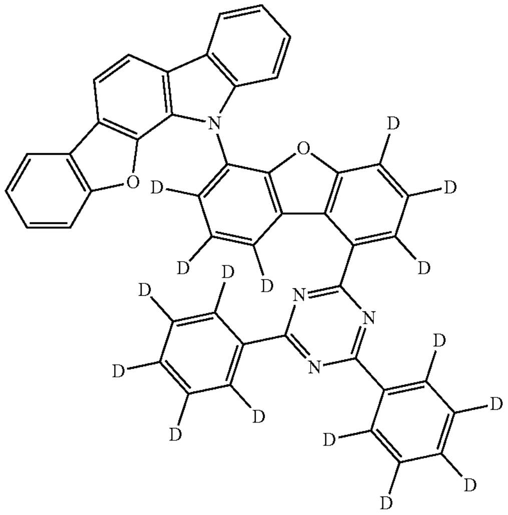
960
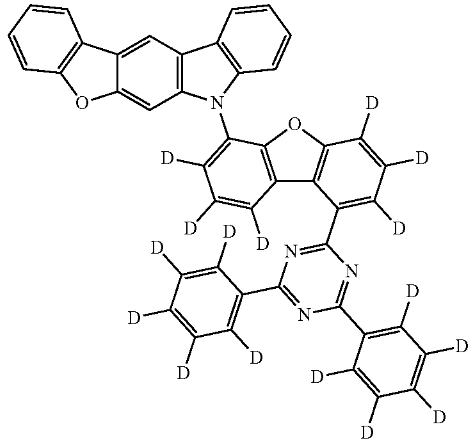
961
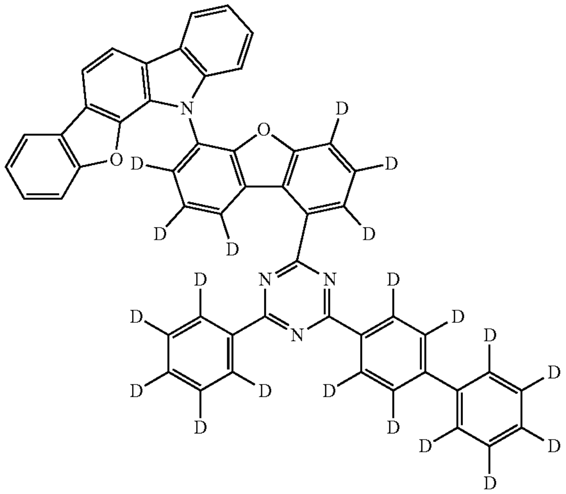
962
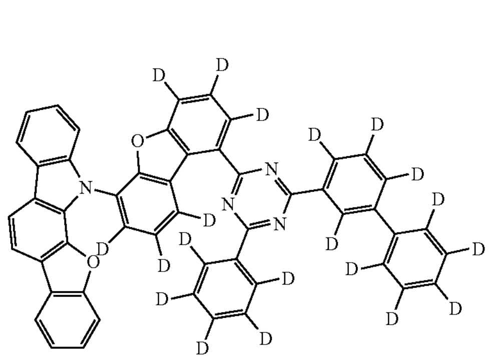
963
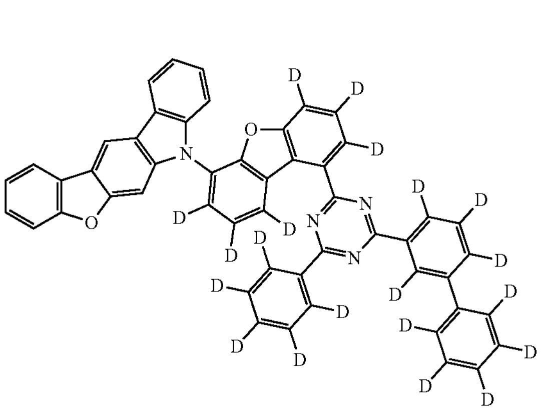

-continued
964
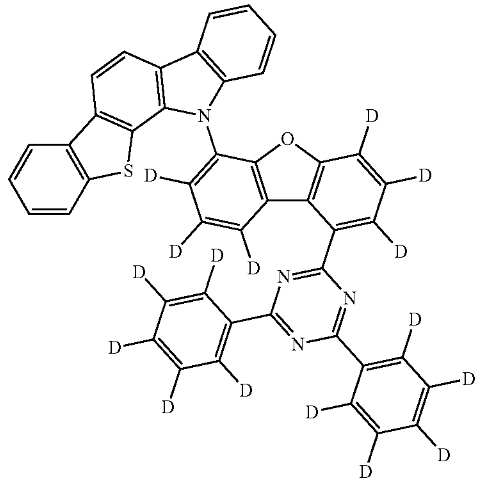
965
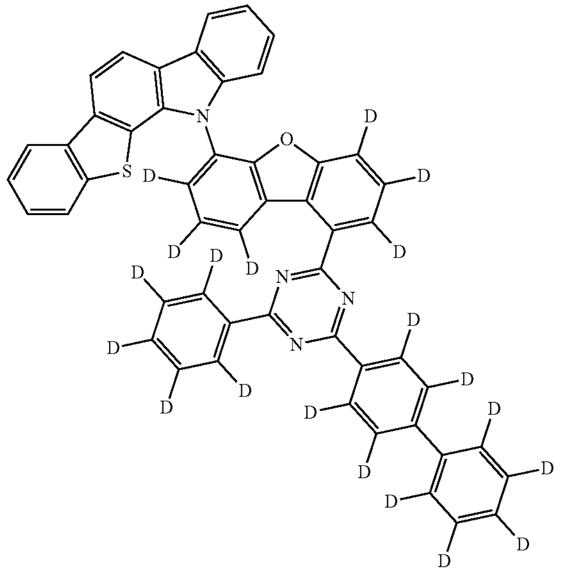
966
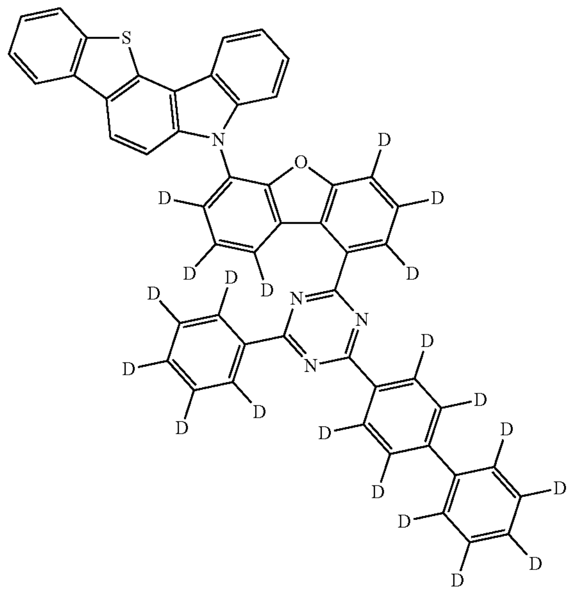
967
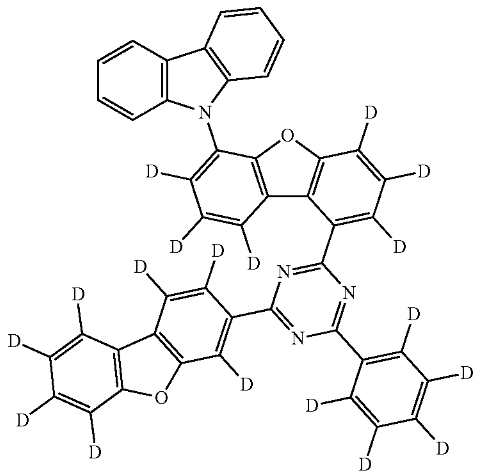

-continued
968
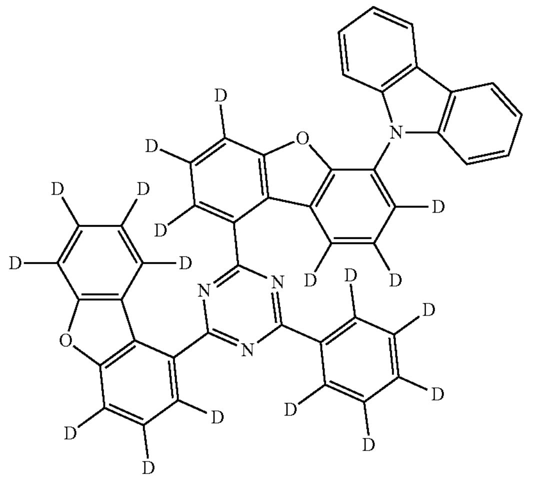
969
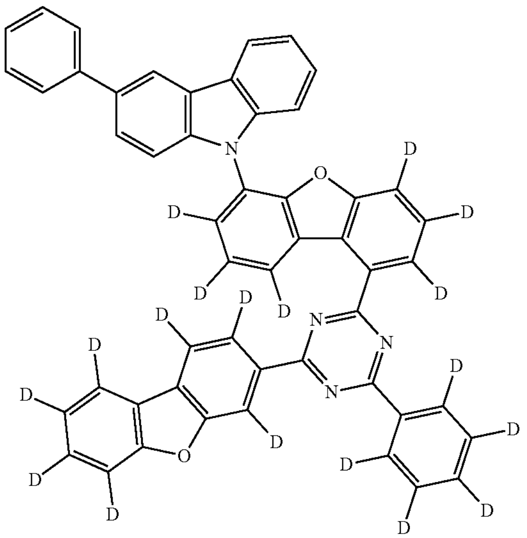
970
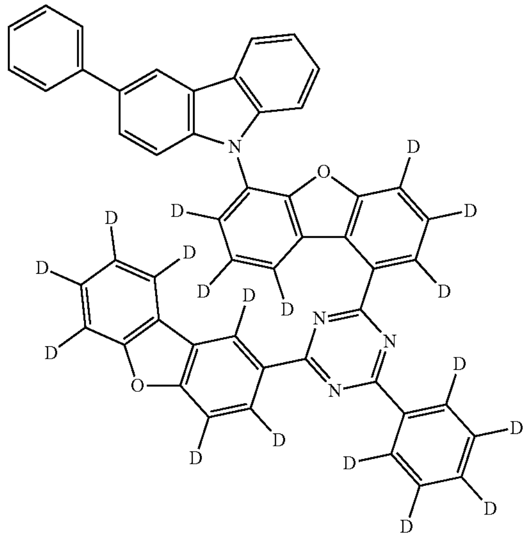
971
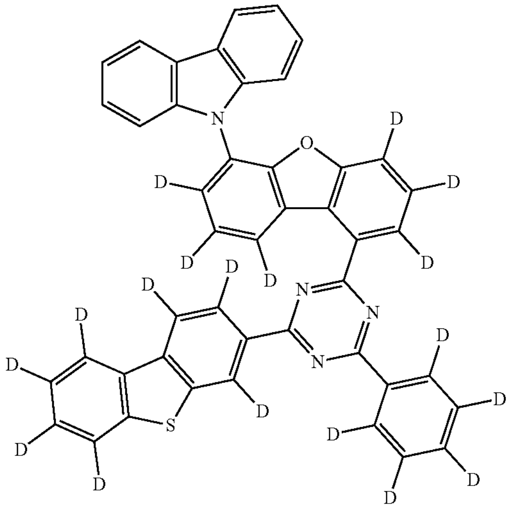
972
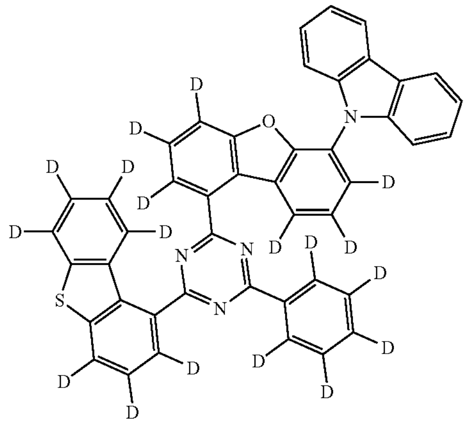
973
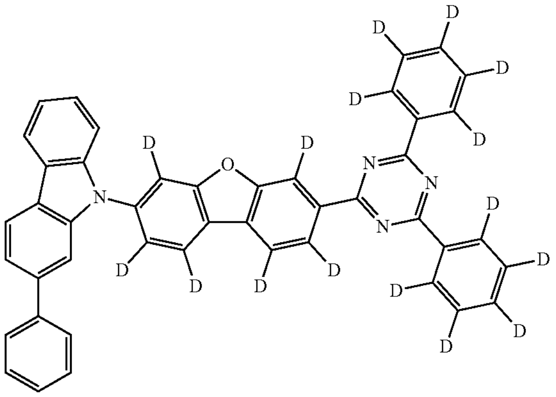

-continued
974
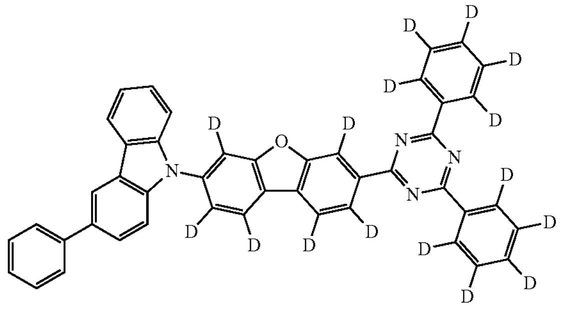
975
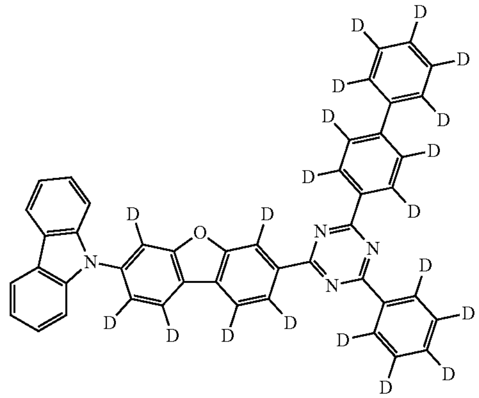
976
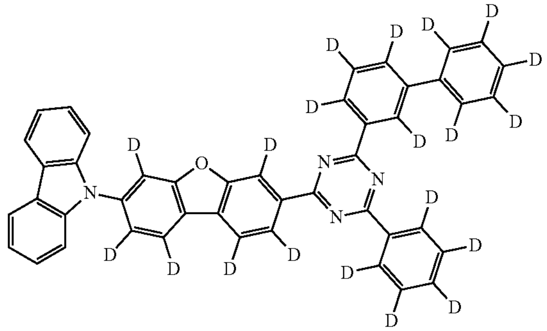
977
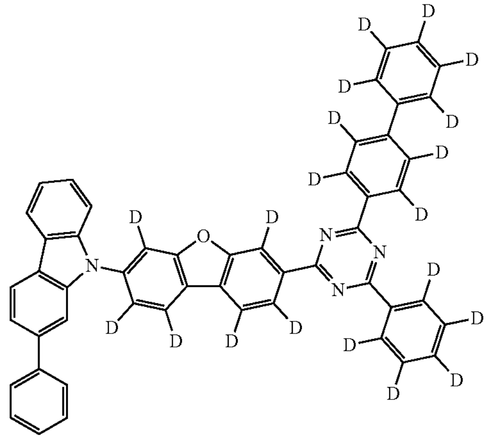
978
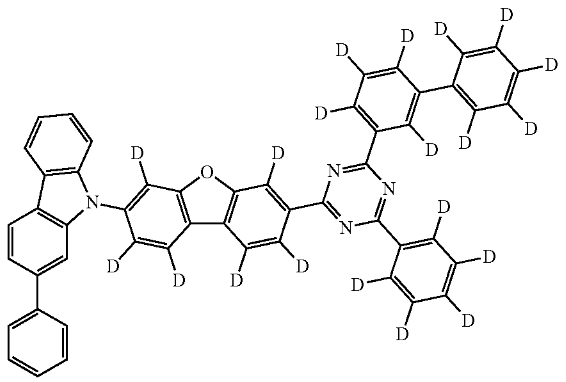
979
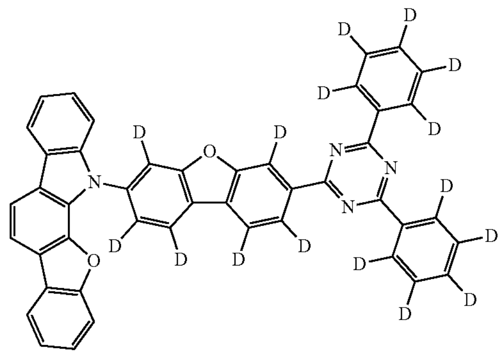

-continued
980
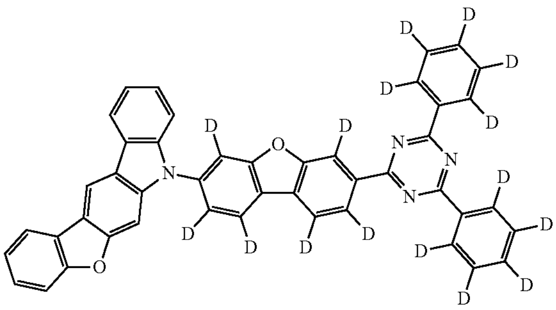
981
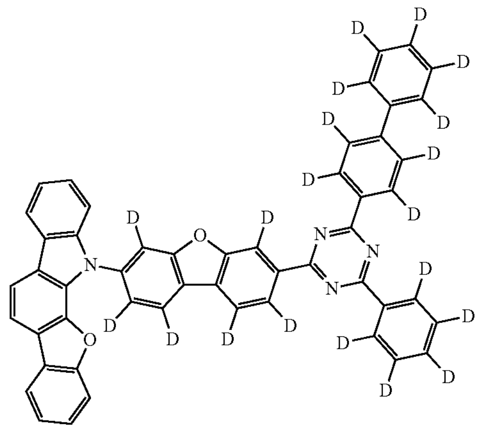
982
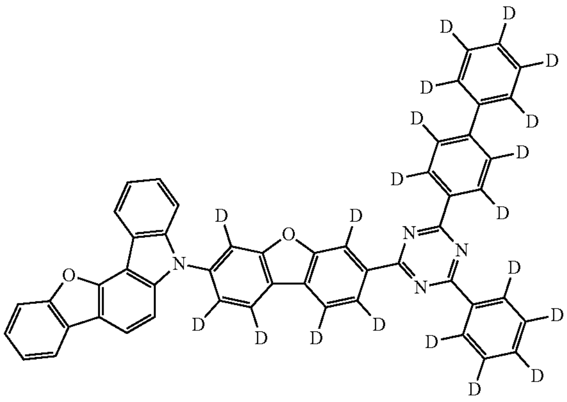
983
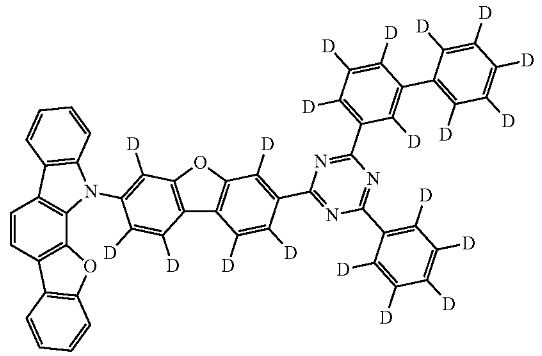
984
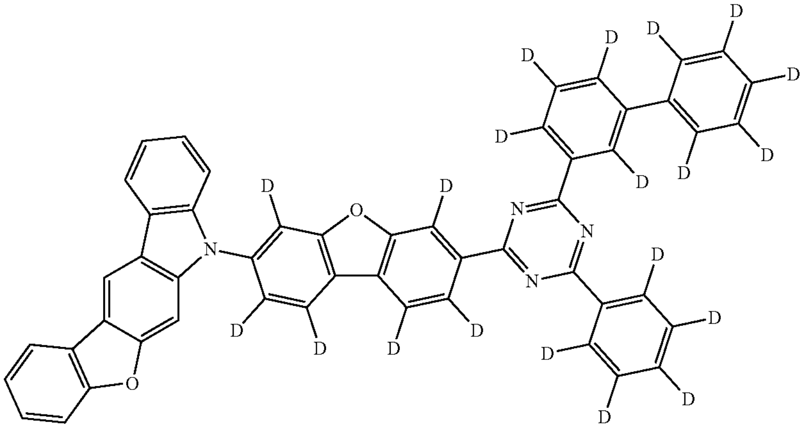

-continued
985
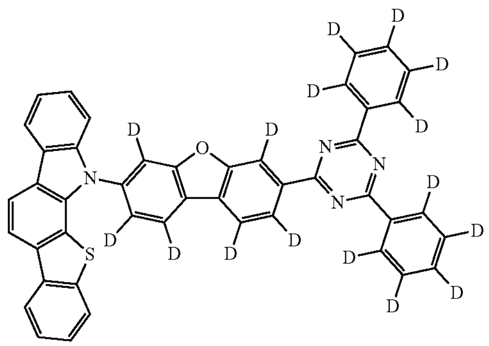
986
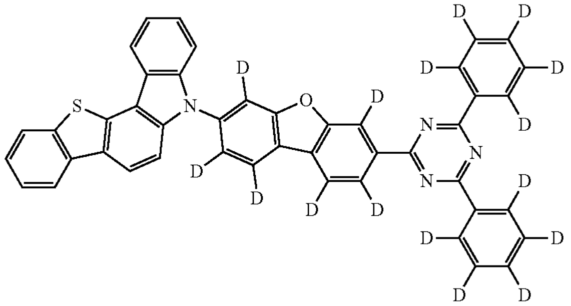
987
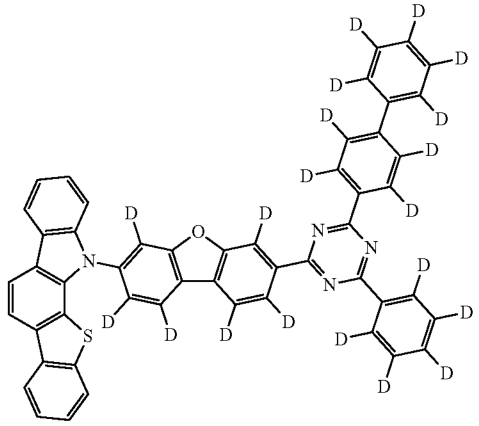
988
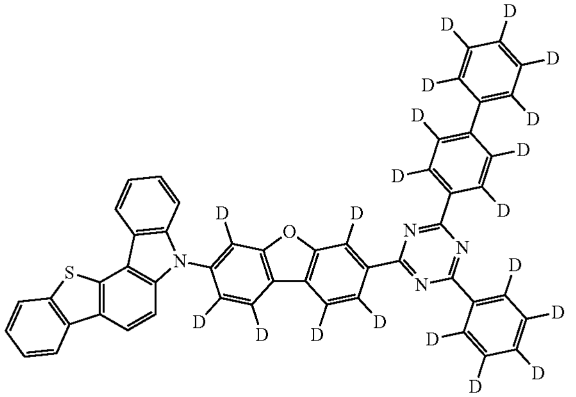
989
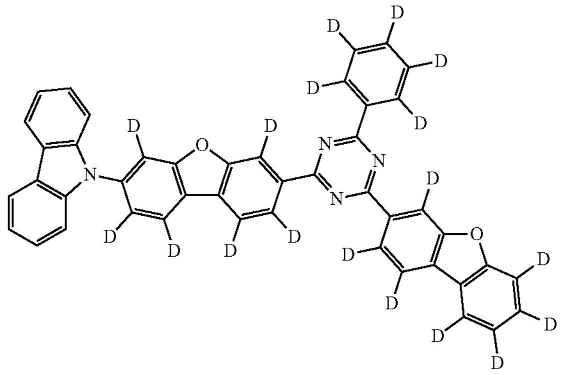
990
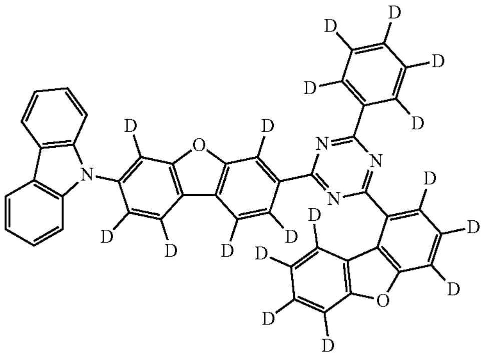

-continued
991
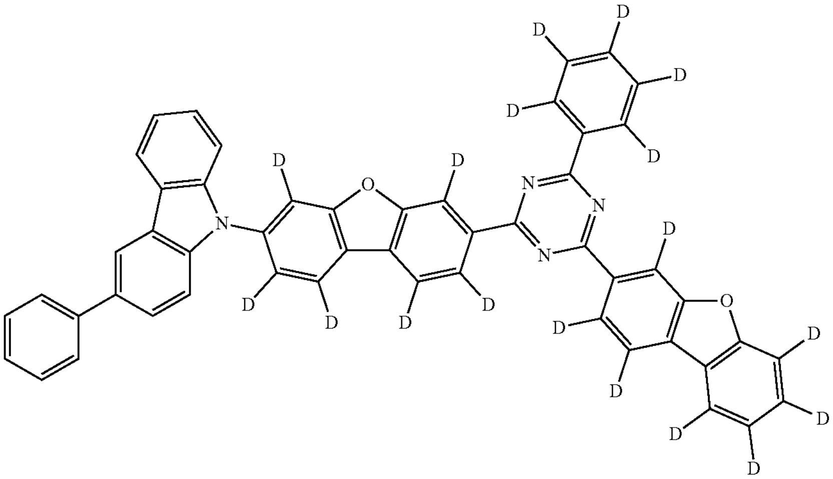
992
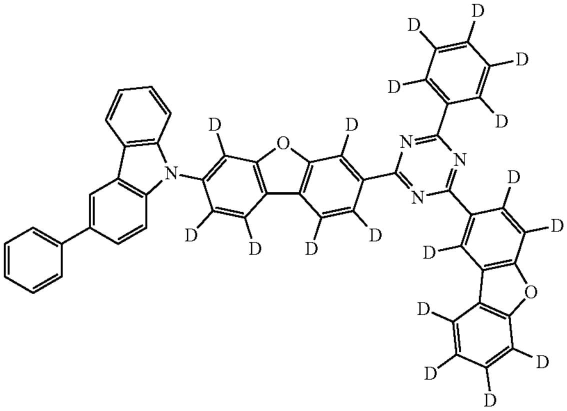
993
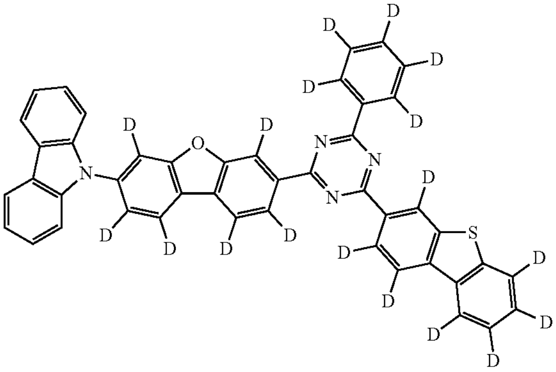
994
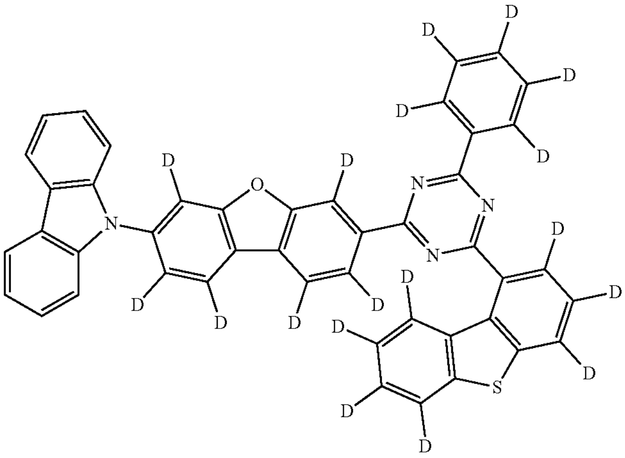

-continued
995
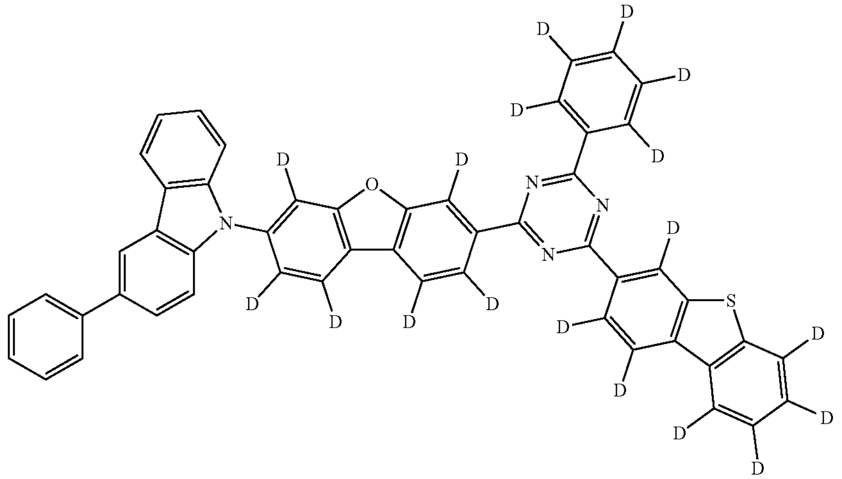
996
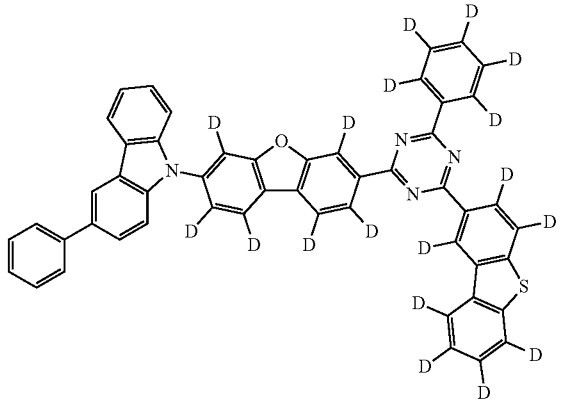
997
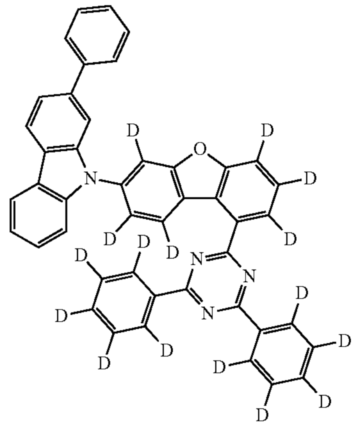
998
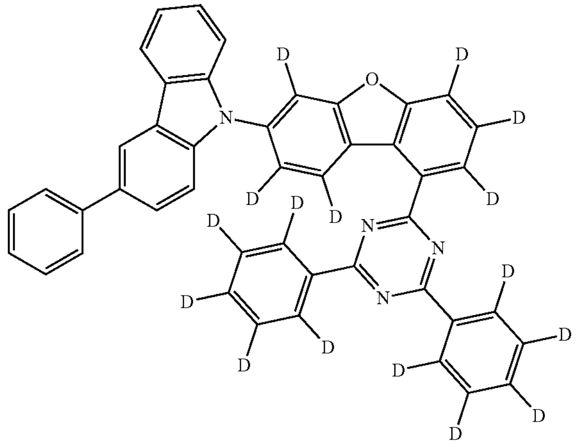
999
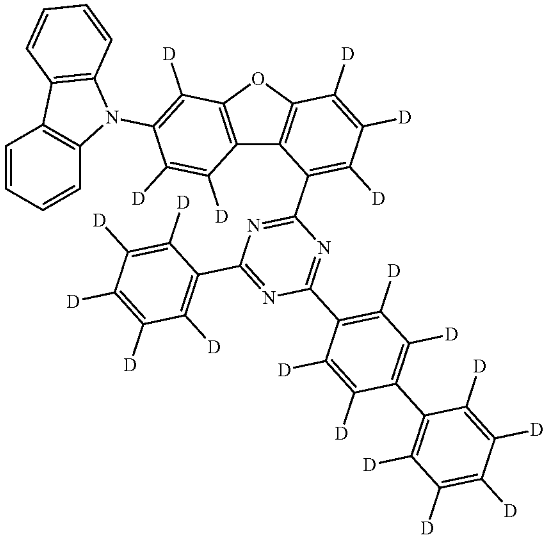

-continued
1000
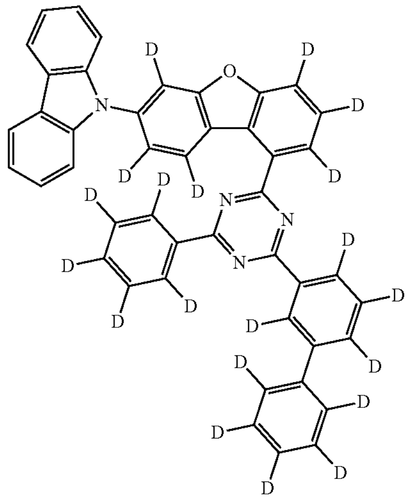
1001
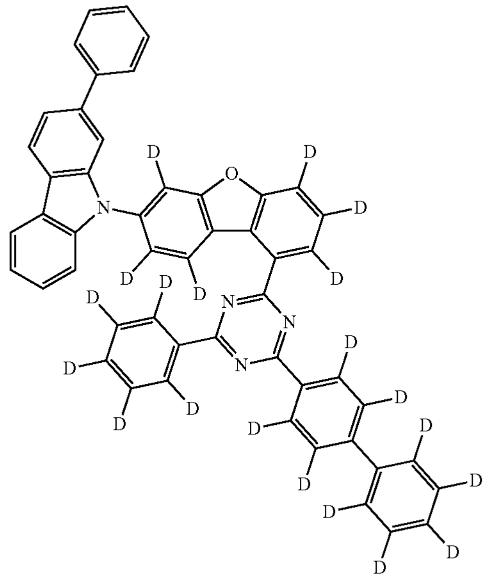
1002
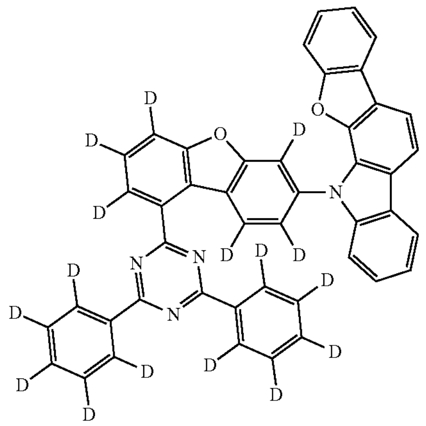
1003
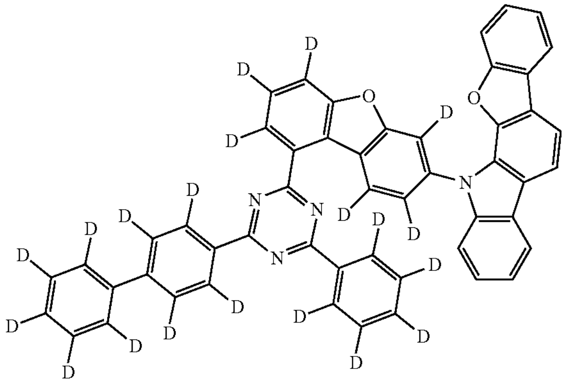
1004
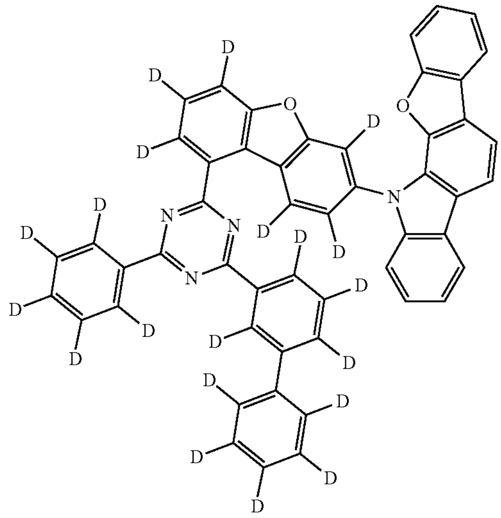
1005
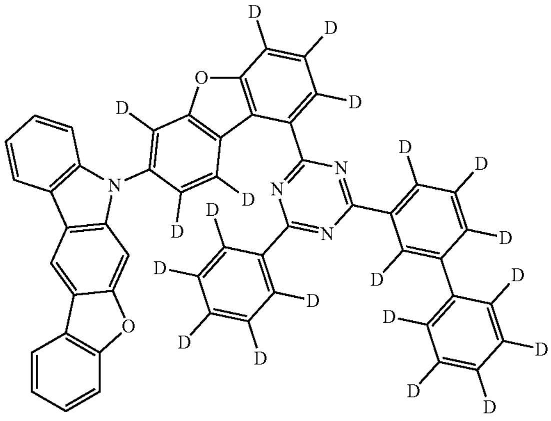

-continued
1006
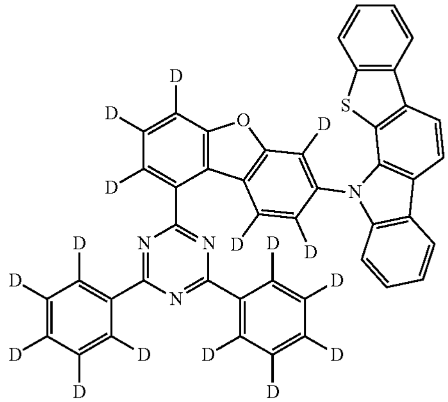
1007
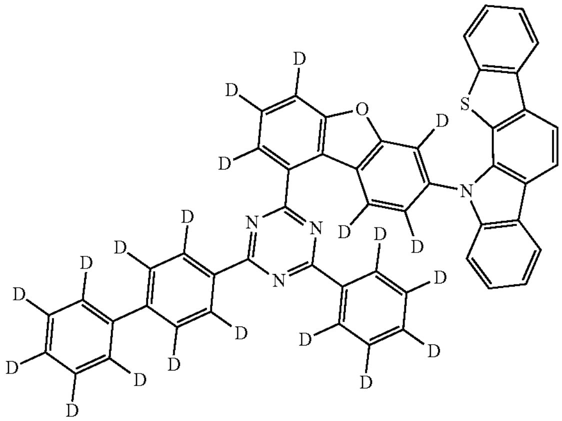
1008
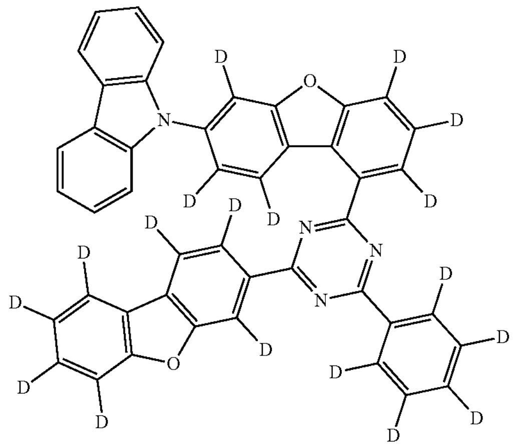
1009
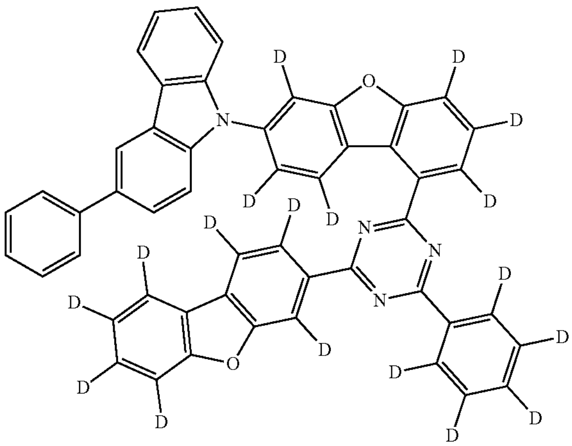
1010
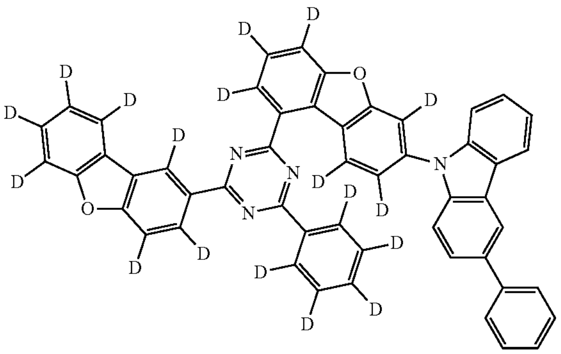
1011
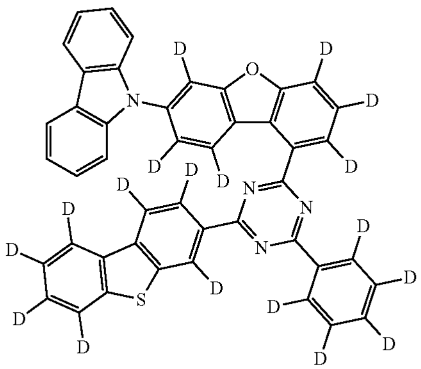

-continued
1012
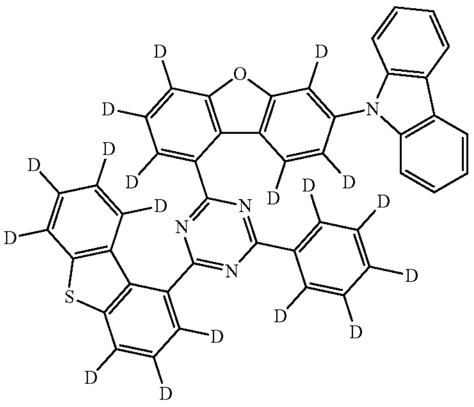
1013
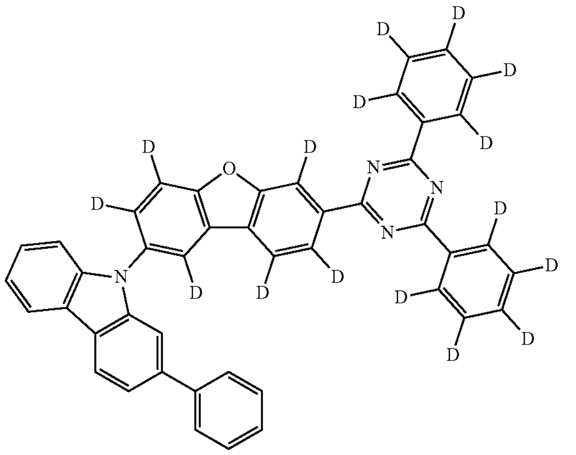
1014
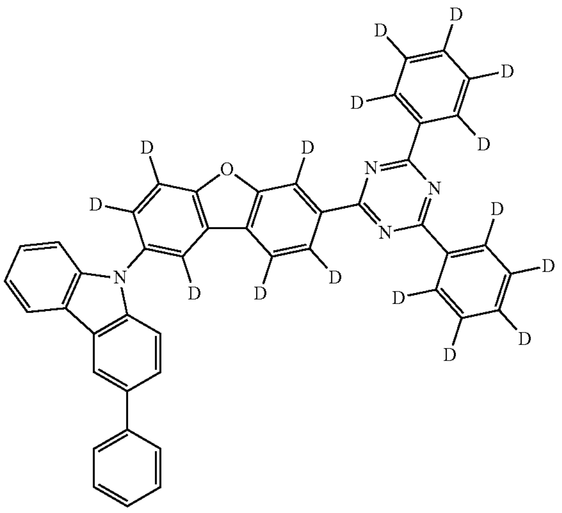
1015
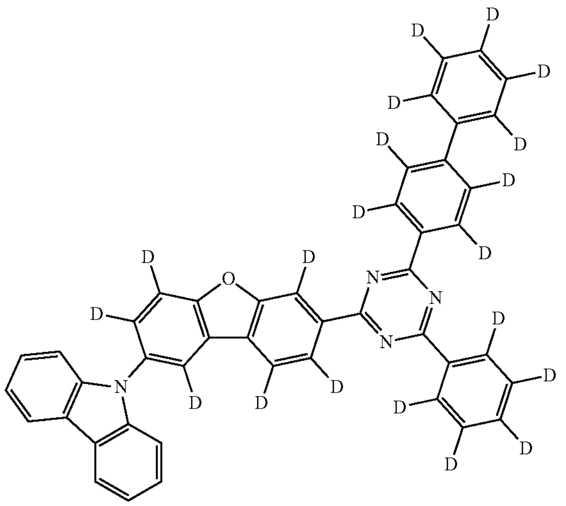
1016
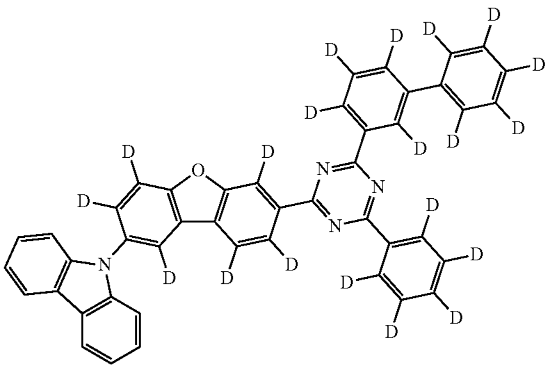
1017
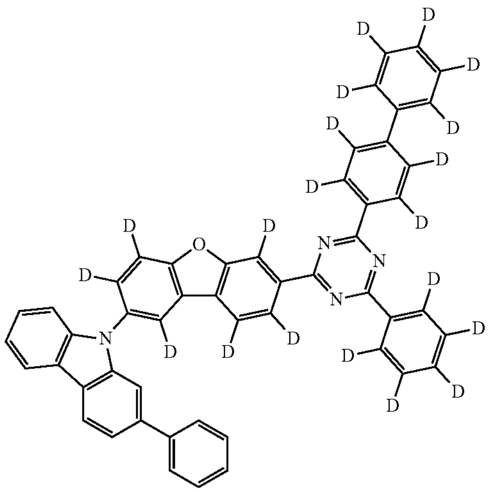

-continued
1018
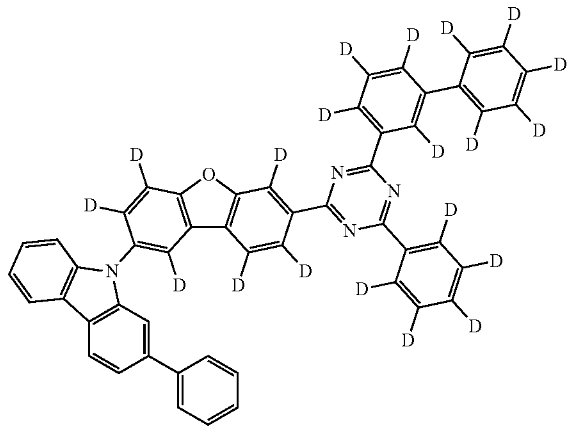
1019
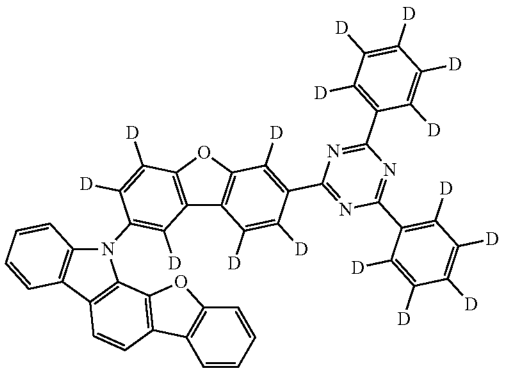
1020
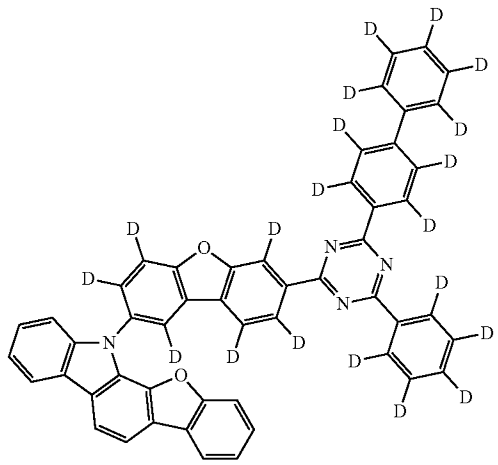
1021
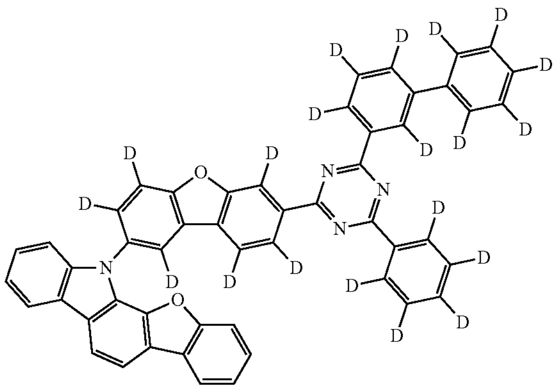
1022
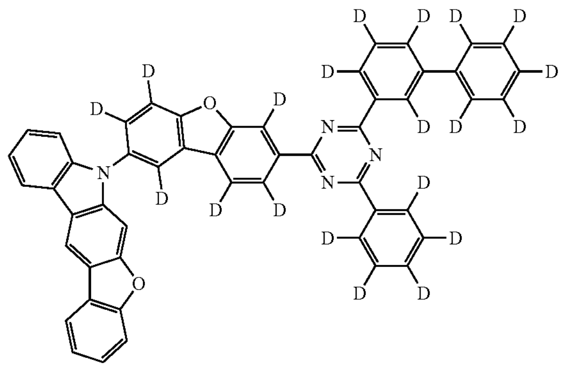
1023
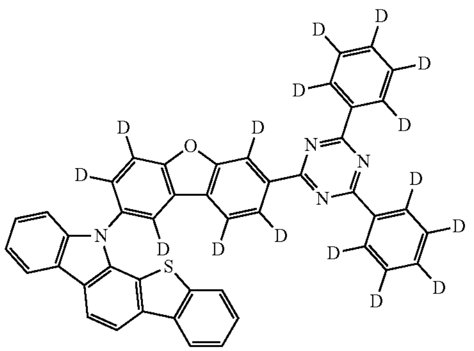

-continued
1024
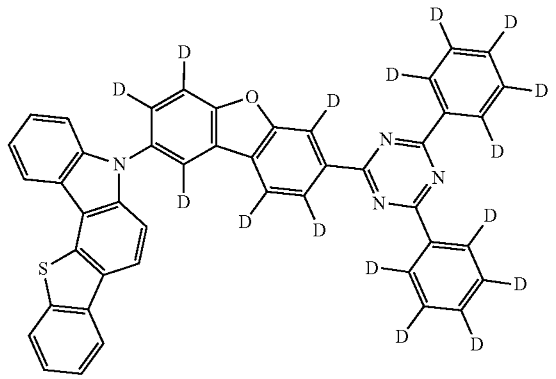
1025
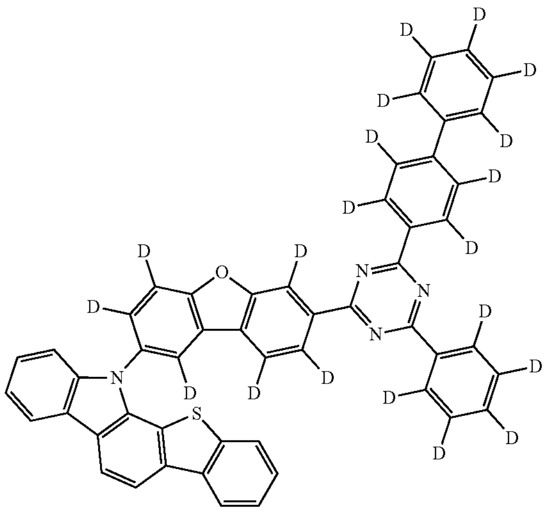
1026
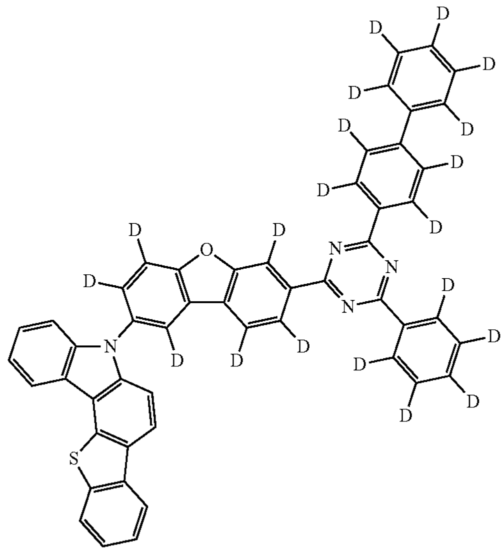
1027
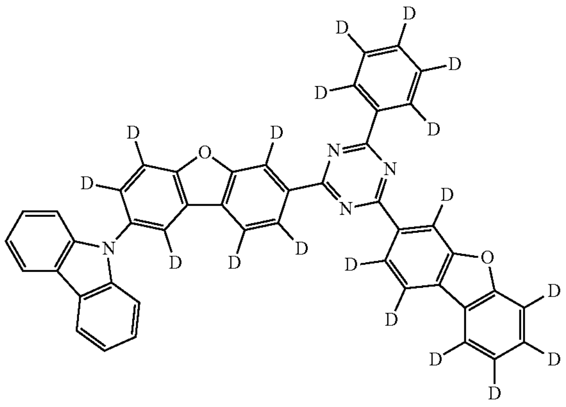
1028
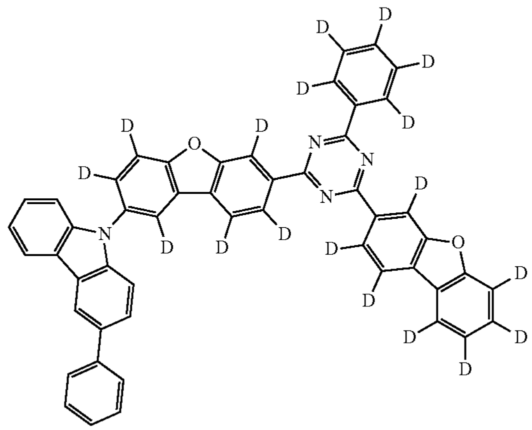
1029
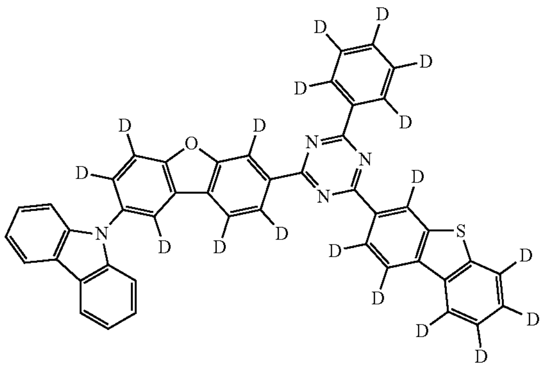

-continued
1030
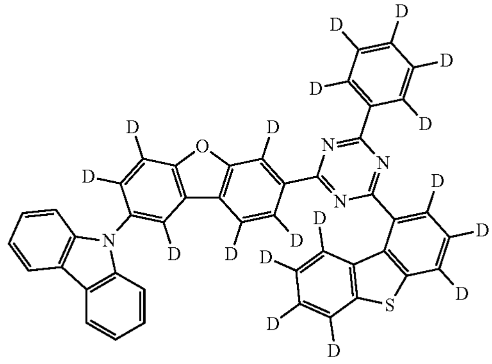
1031
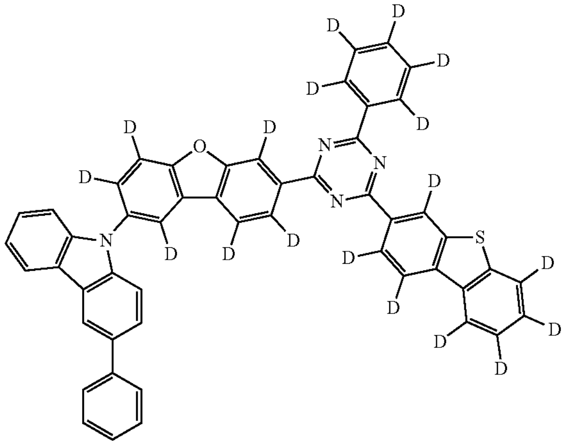
1032
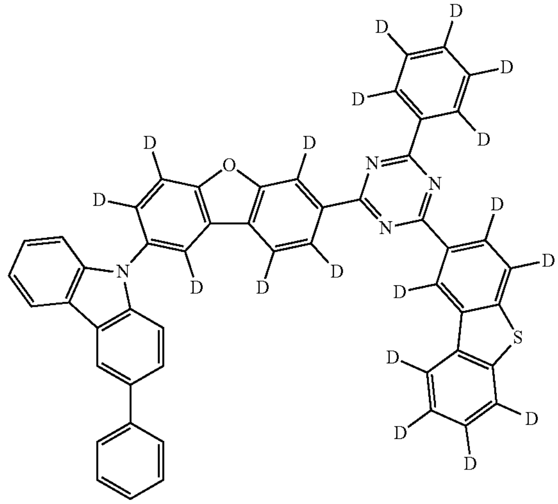
1033
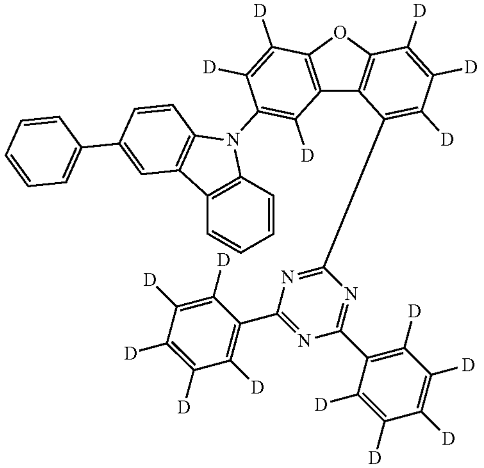
1034
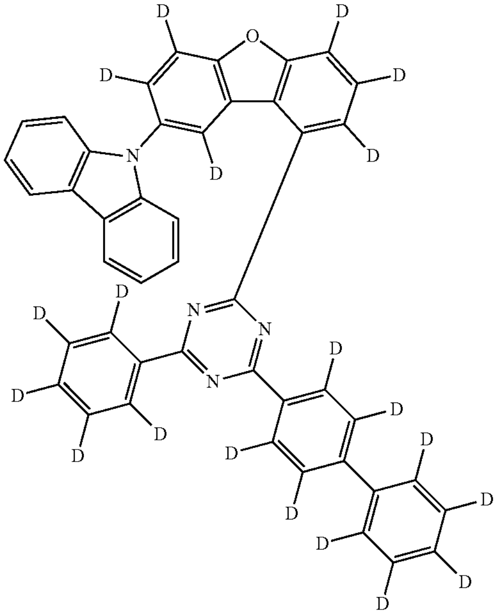
1035
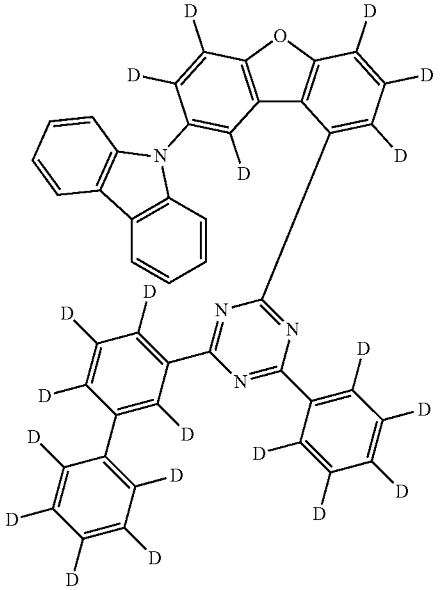

-continued
1036
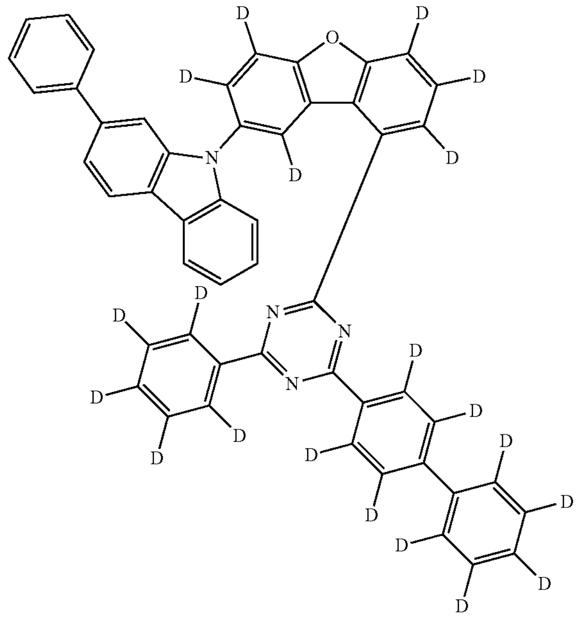
1037
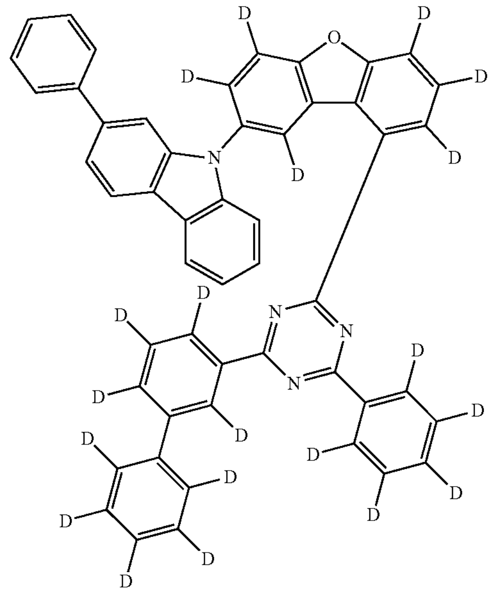
1038
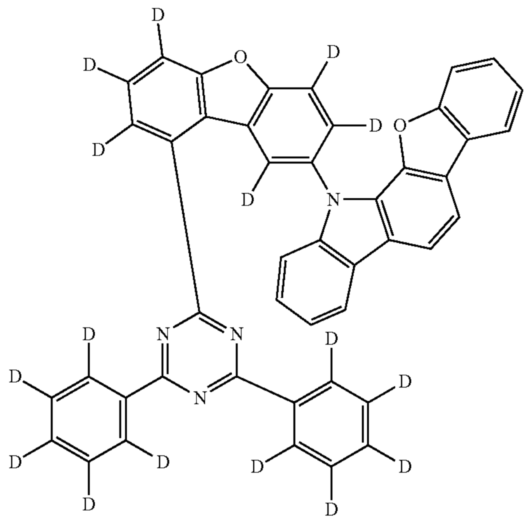
1039
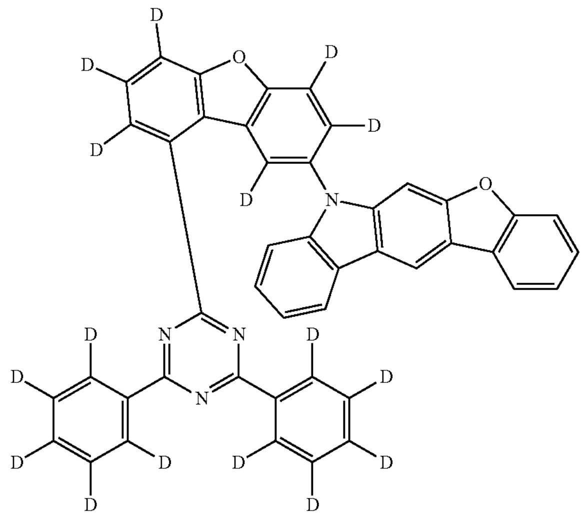

-continued
1040
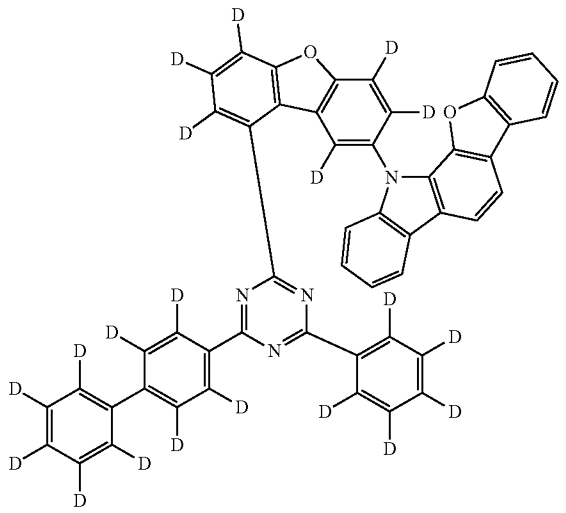
1041
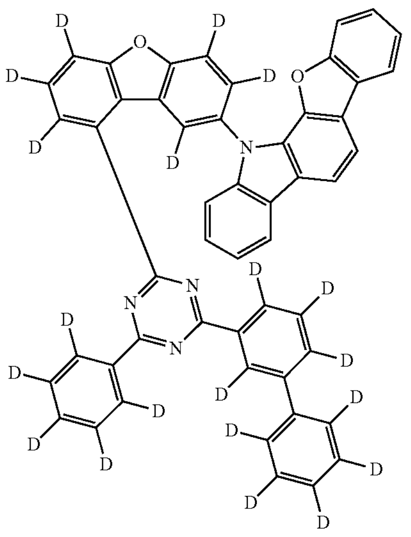
1042
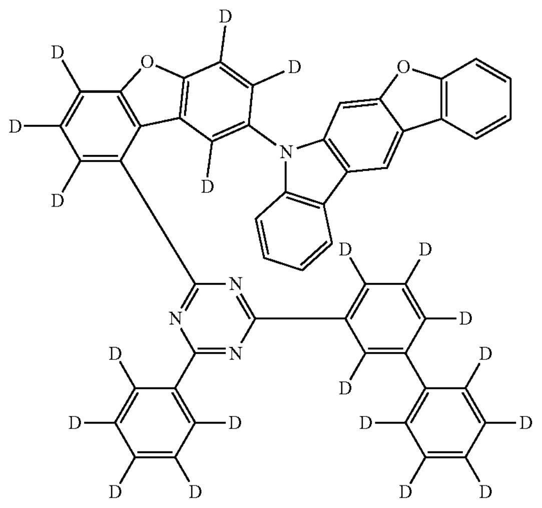
1043
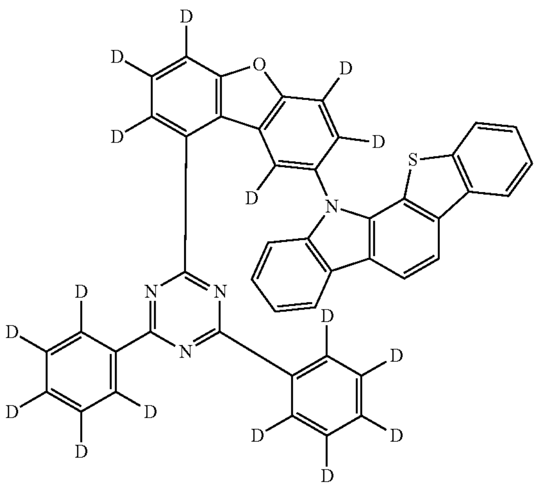
1044
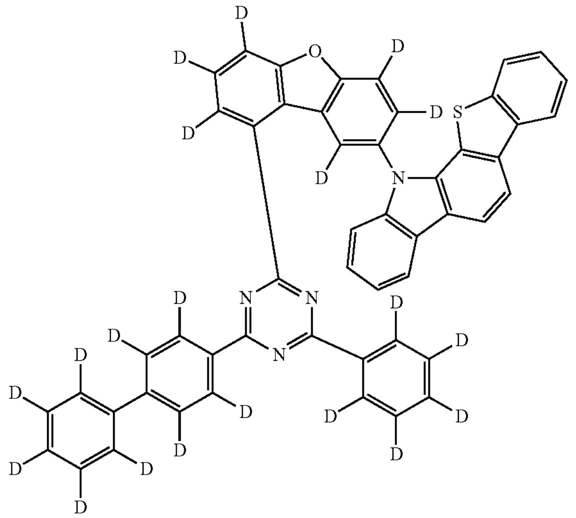
1045
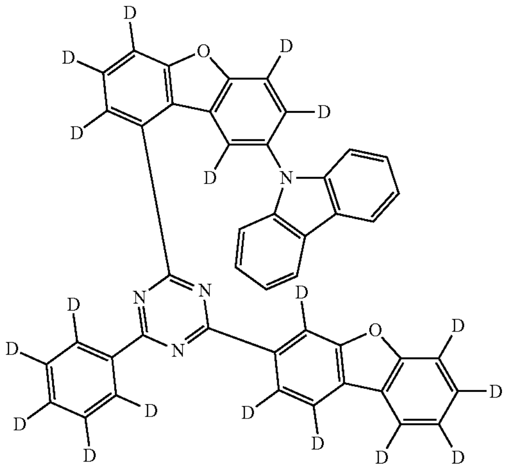

-continued
1046
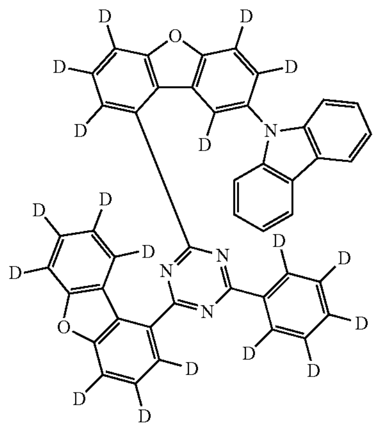
1047
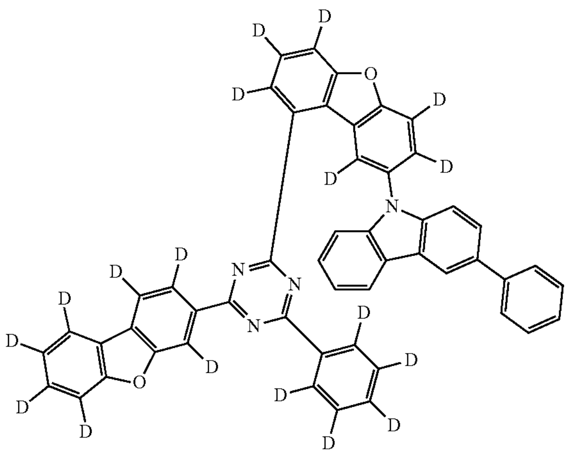
1048
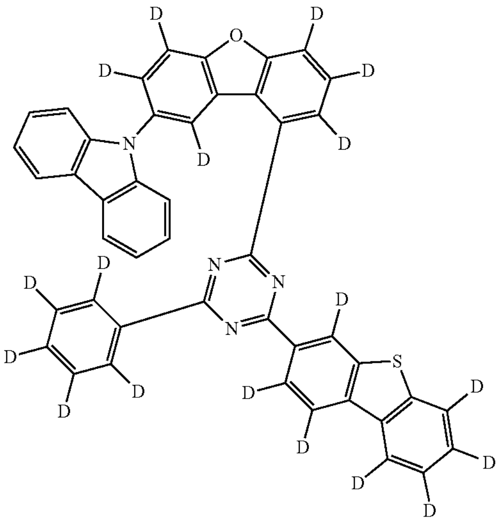
1049
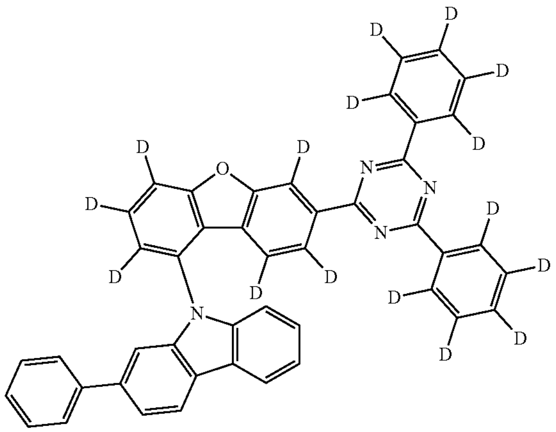
1050
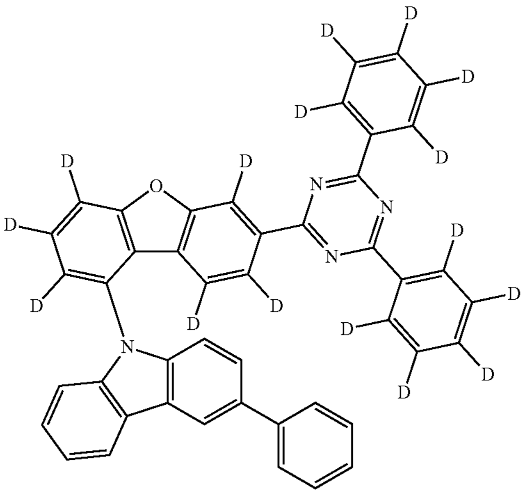
1051
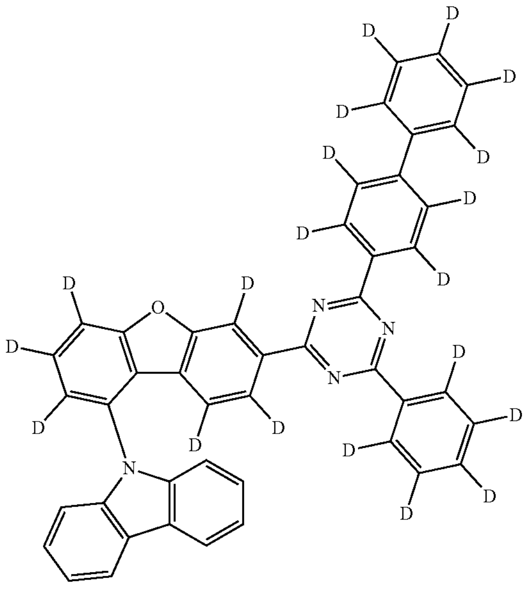

-continued
1052
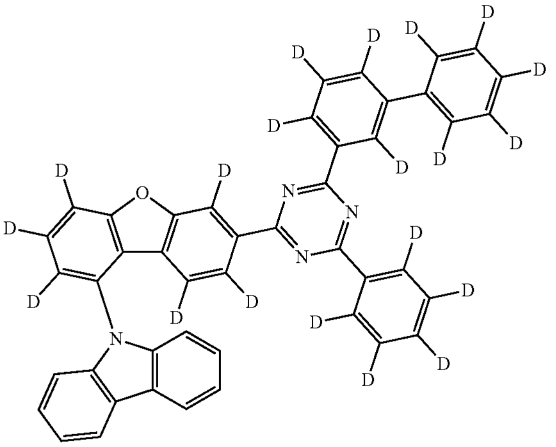
1053
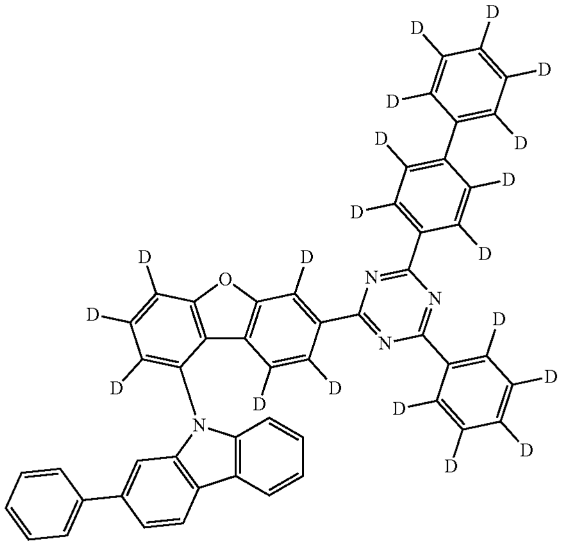
1054
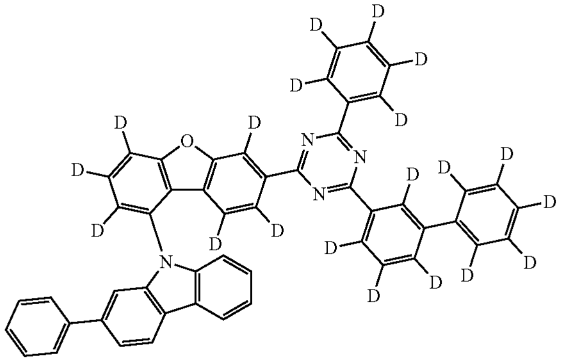
1055
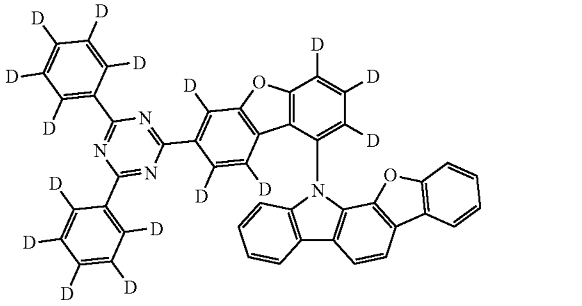
1056
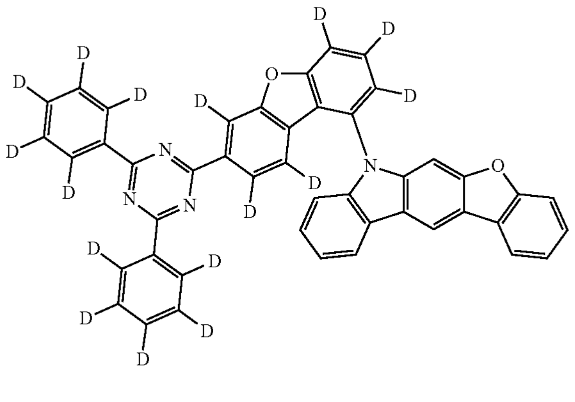
1057
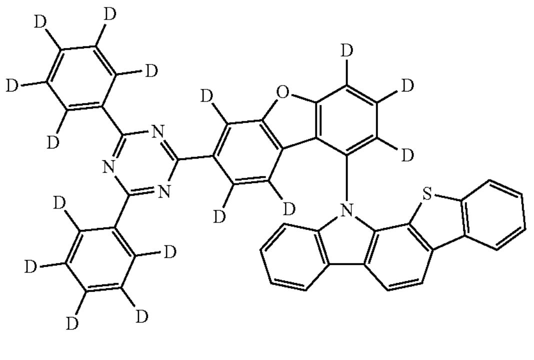

-continued
1058
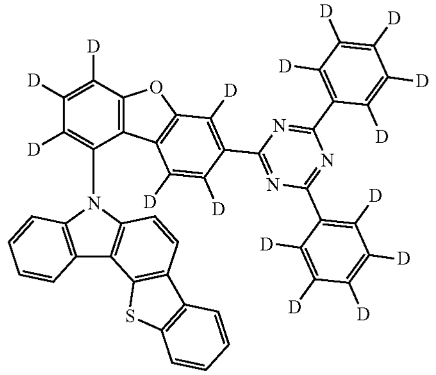
1059
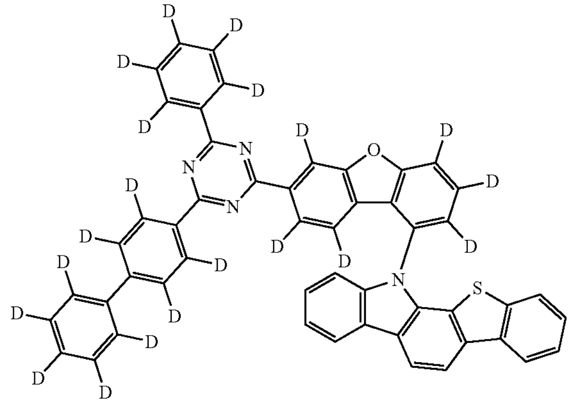
1060
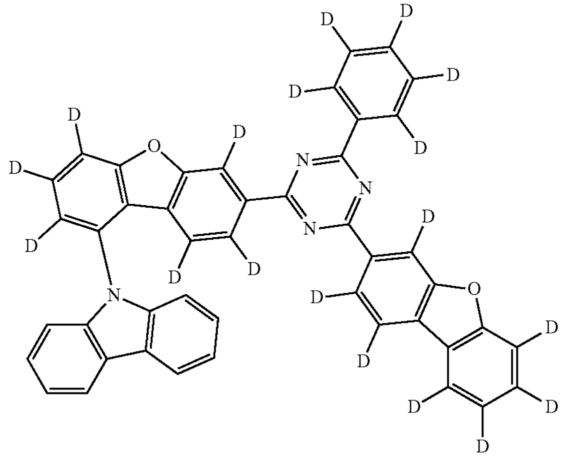
1061
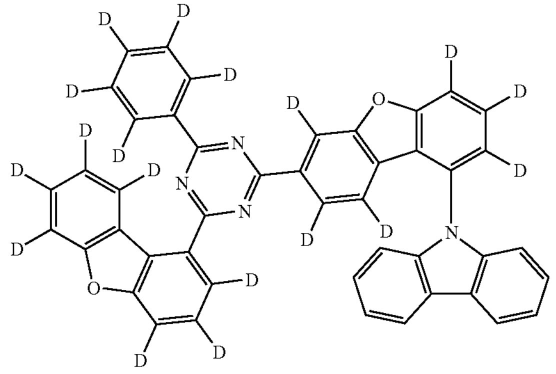
1062
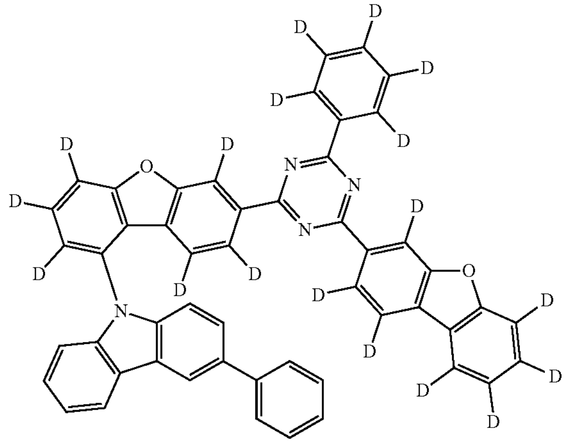
1063
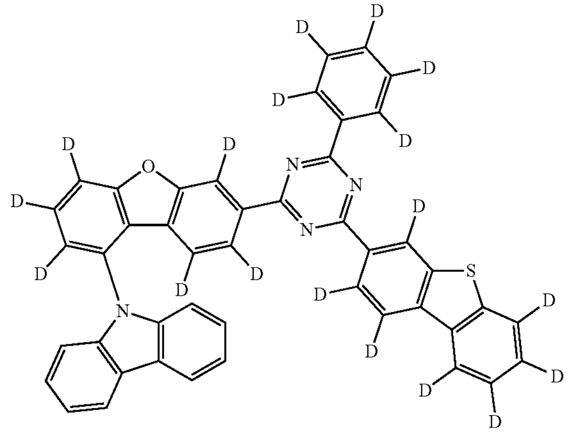

-continued
1064
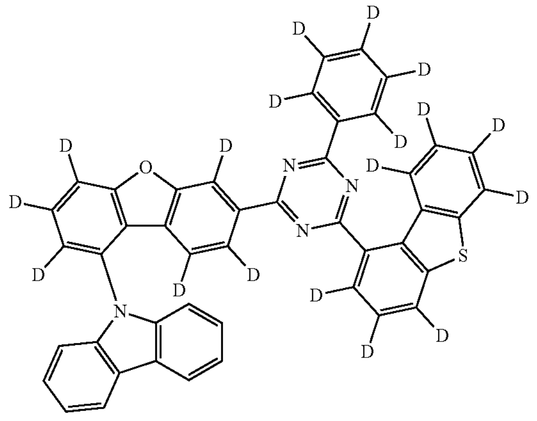
1065
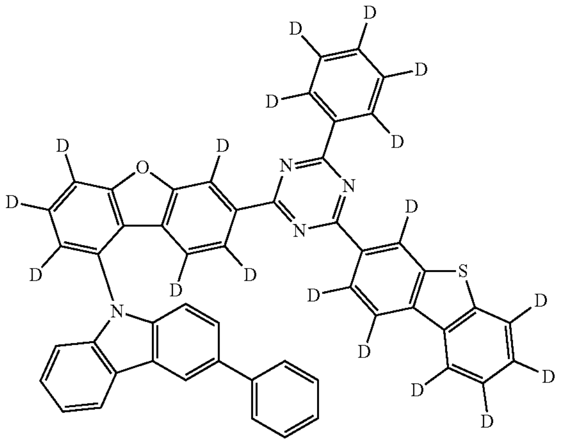
1066
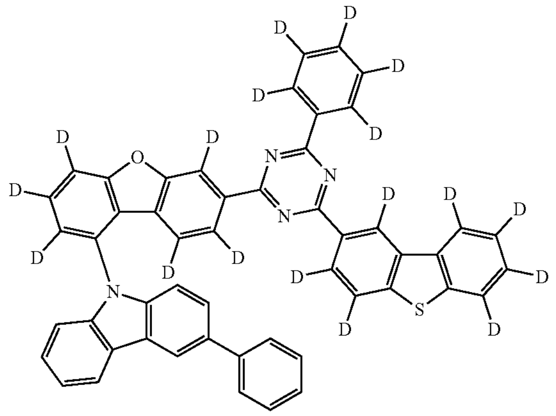
1067
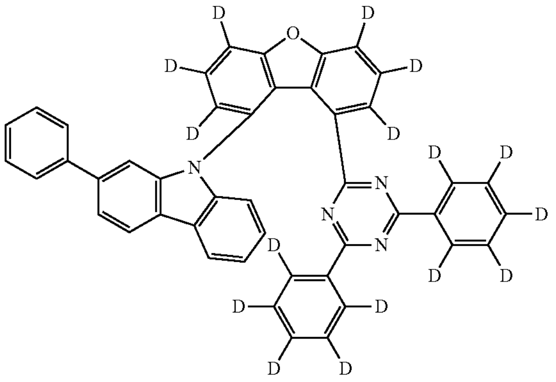
1068
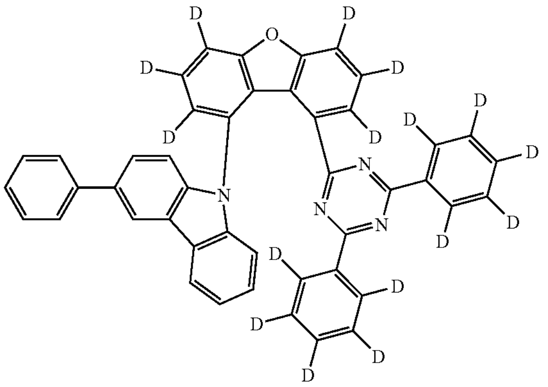
1649
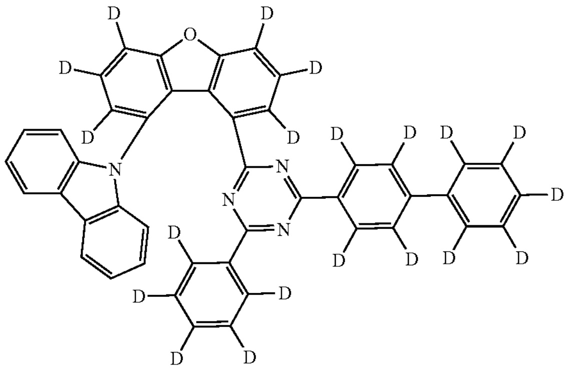

-continued
1070
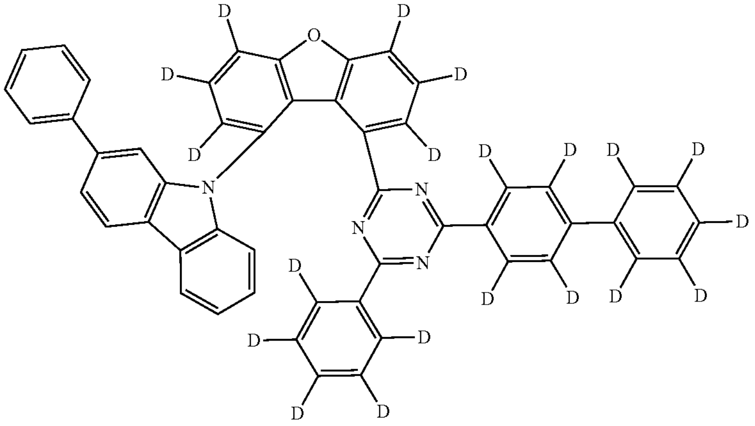
1071
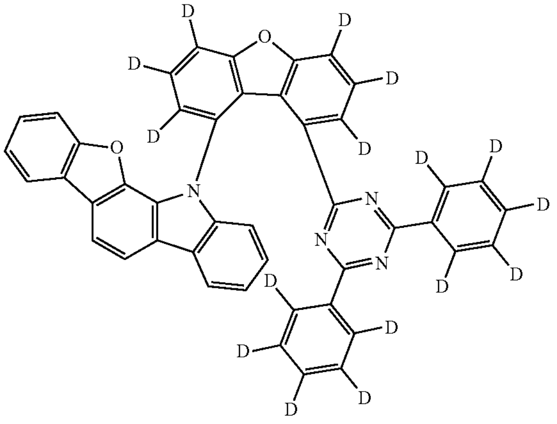
1072
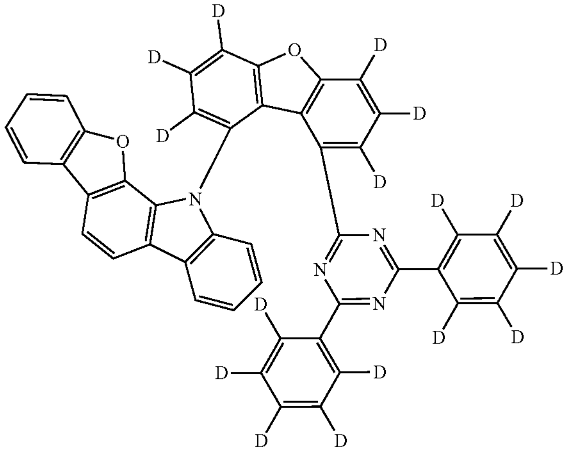
1073
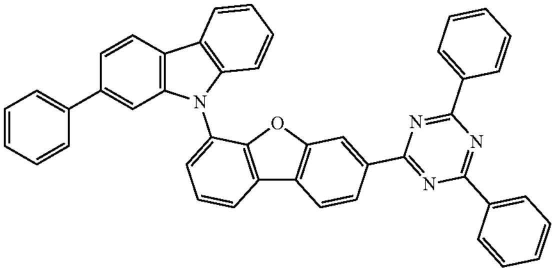
1074
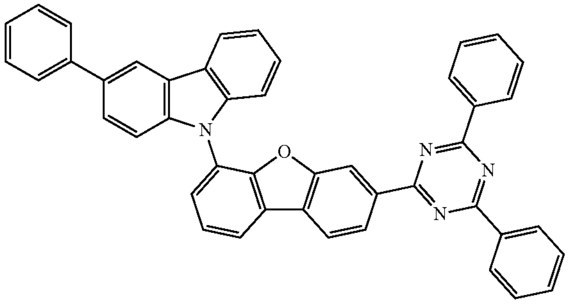

-continued
1075
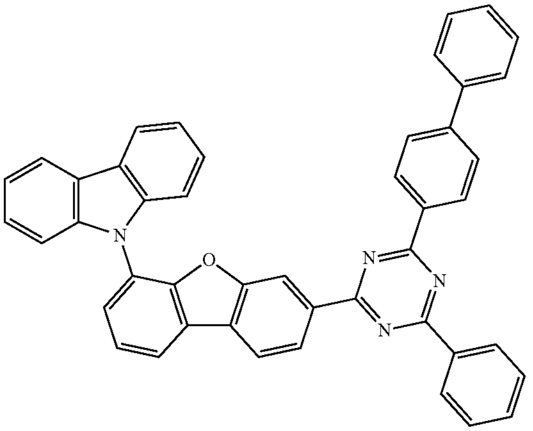
1076
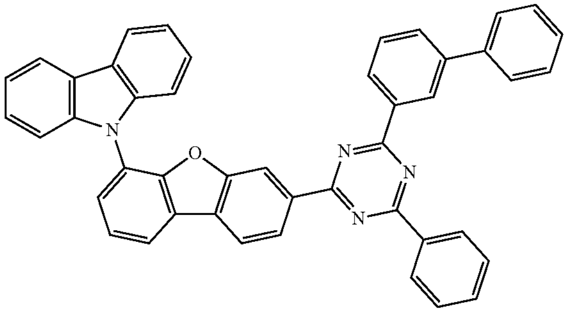
1077
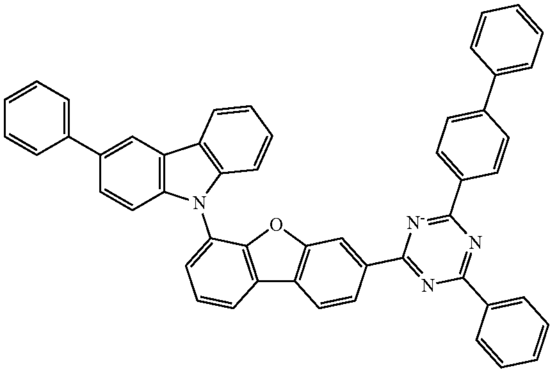
1078
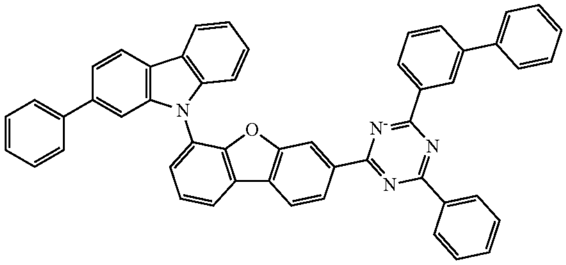
1079
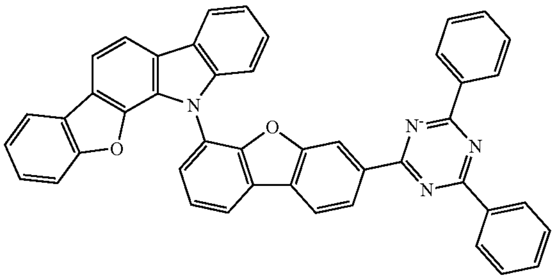
1080
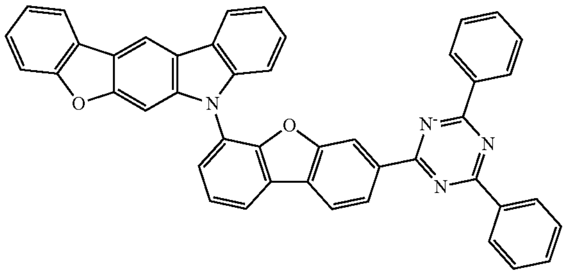
1081
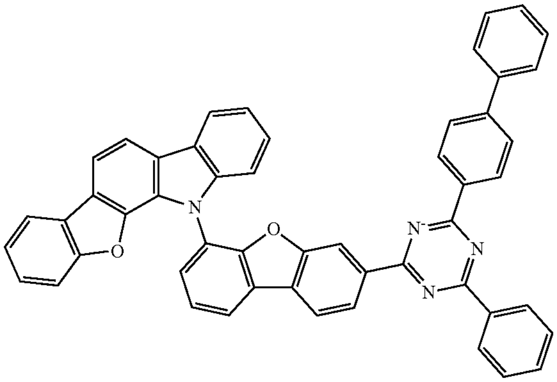
1082
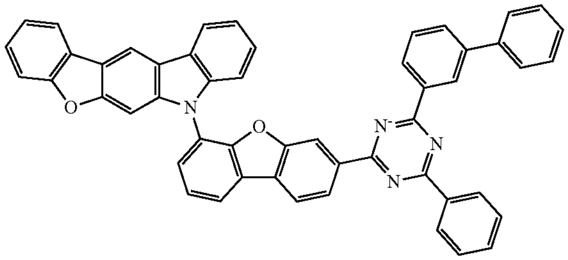

-continued
1083
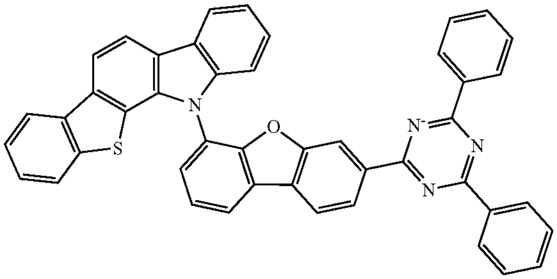
1084
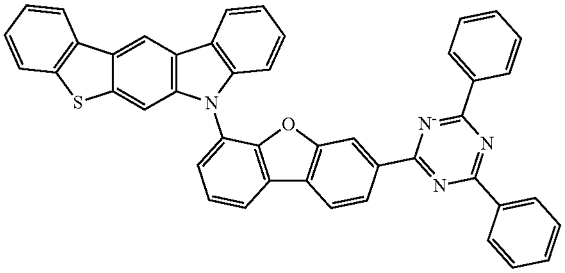
1085
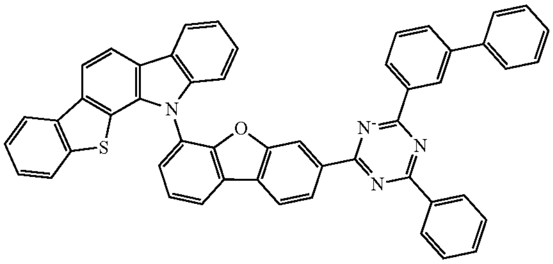
1086
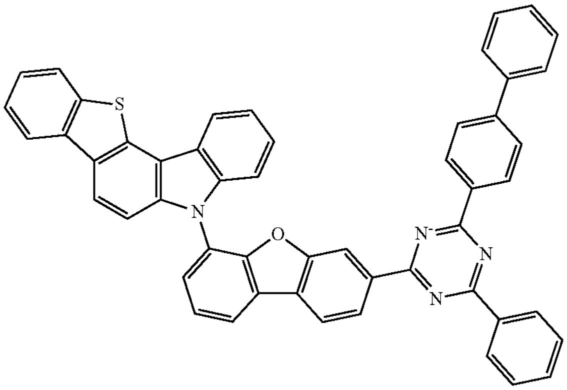
1087
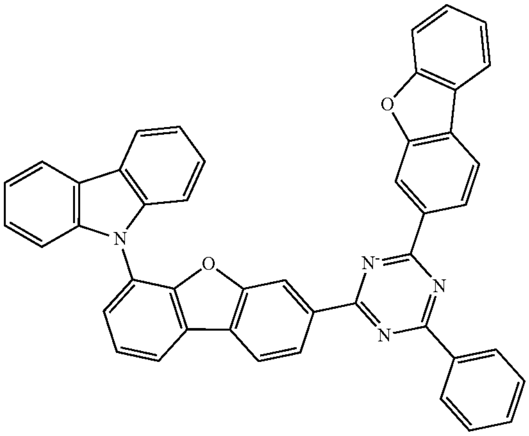
1088
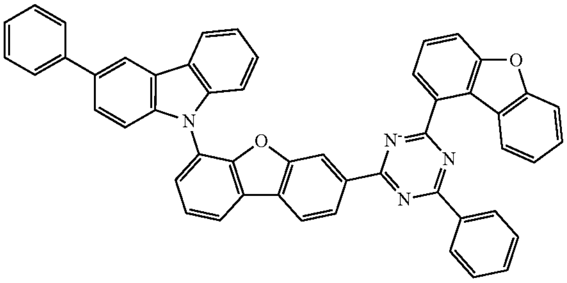
1089
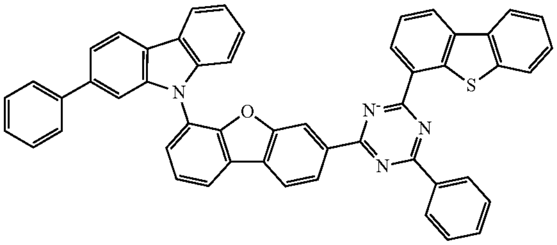
1090
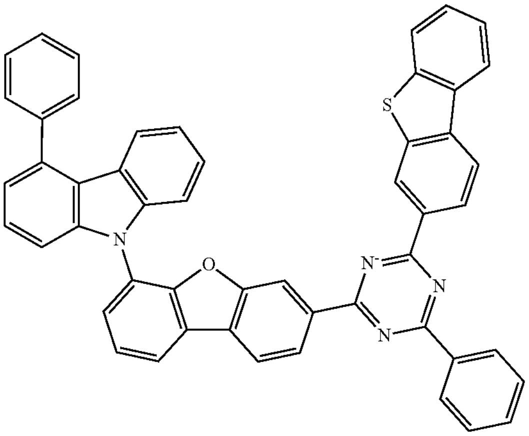

-continued
1091
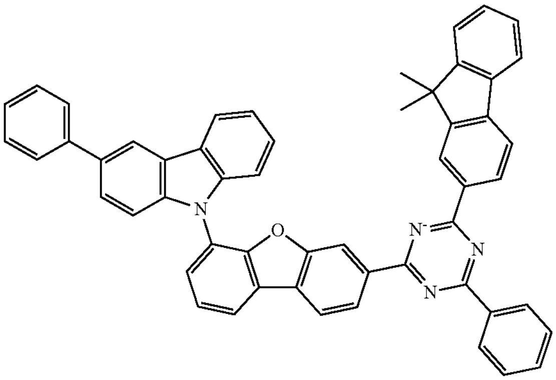
1092
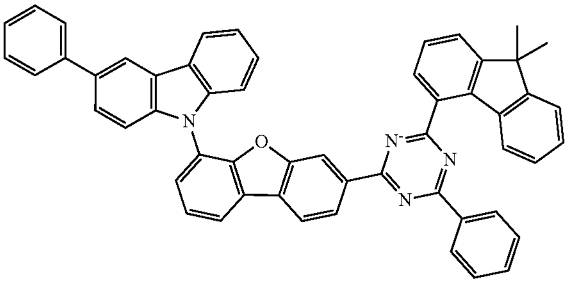
1093
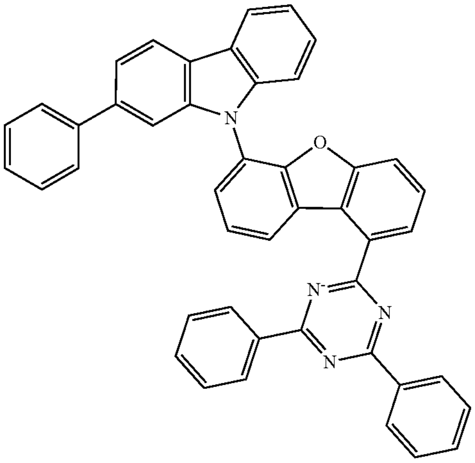
1094
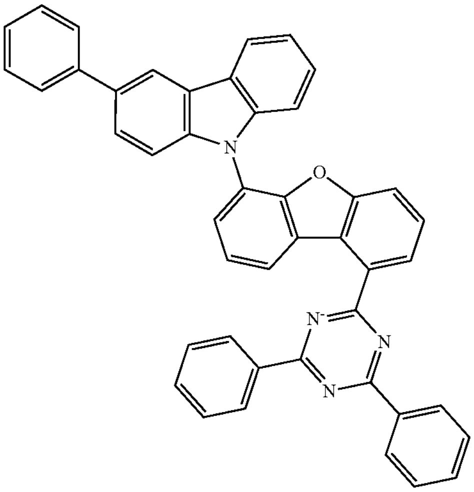
1095
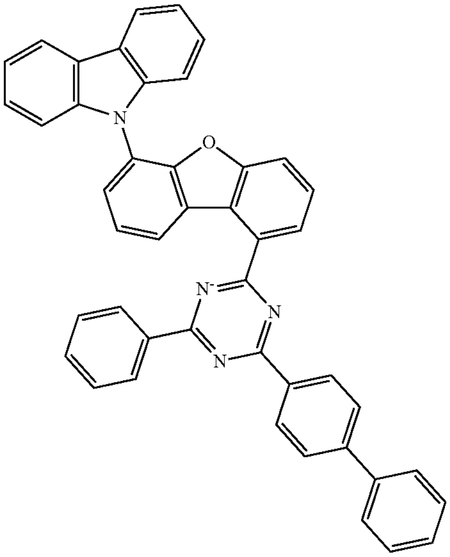
1096
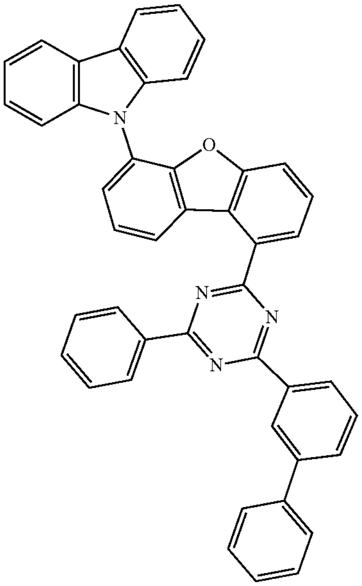

-continued
1097
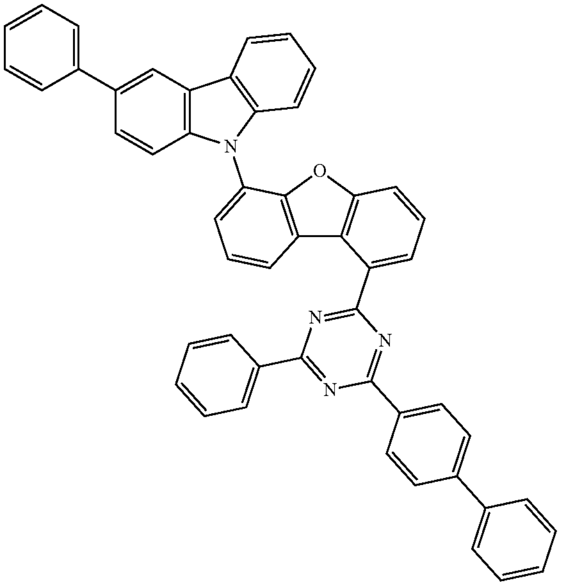
1098
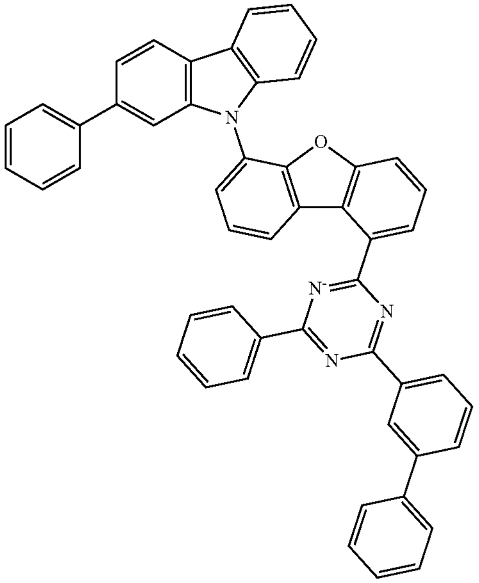
1099
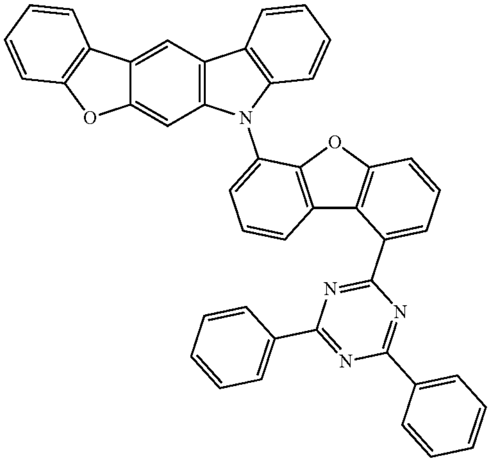
1100
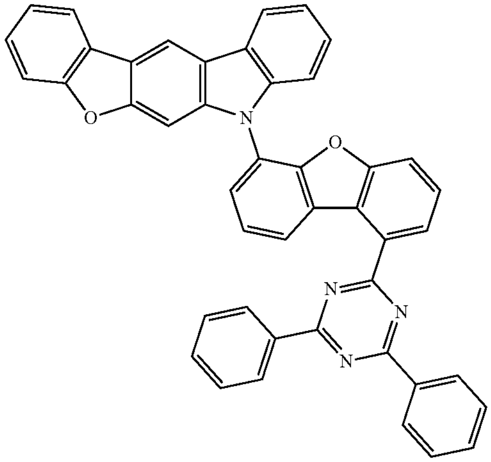

-continued
1101
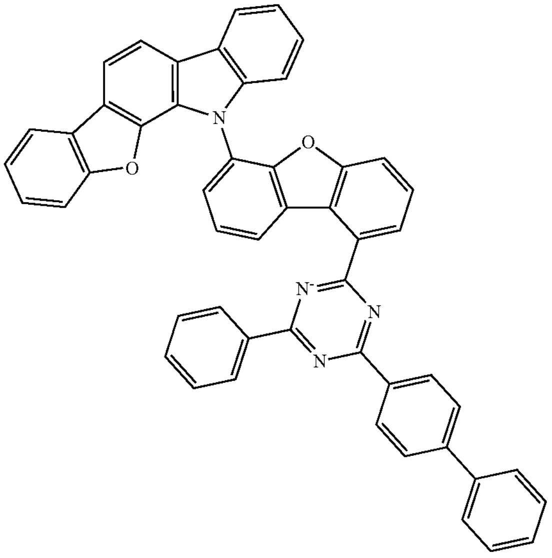
1102
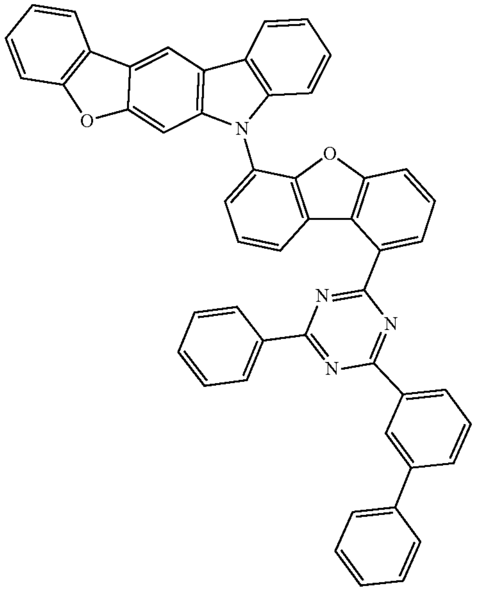
1103
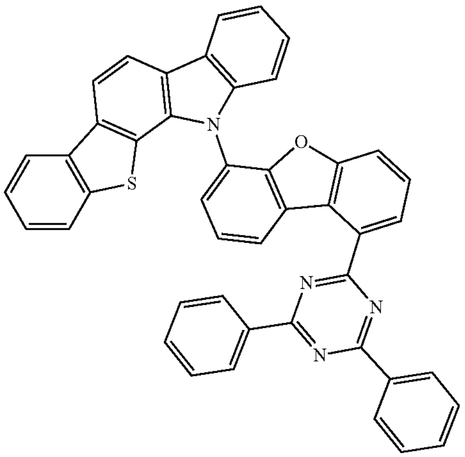
1104
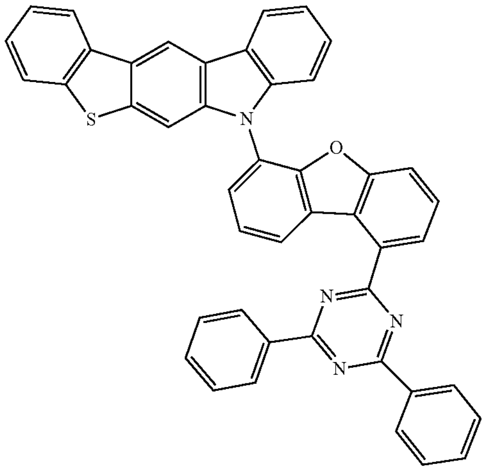

-continued
1105
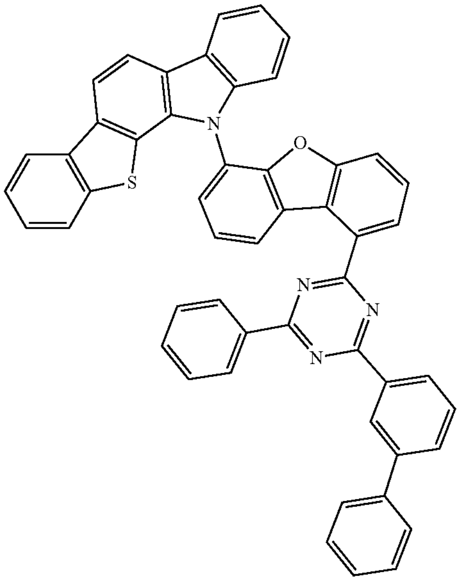
1106
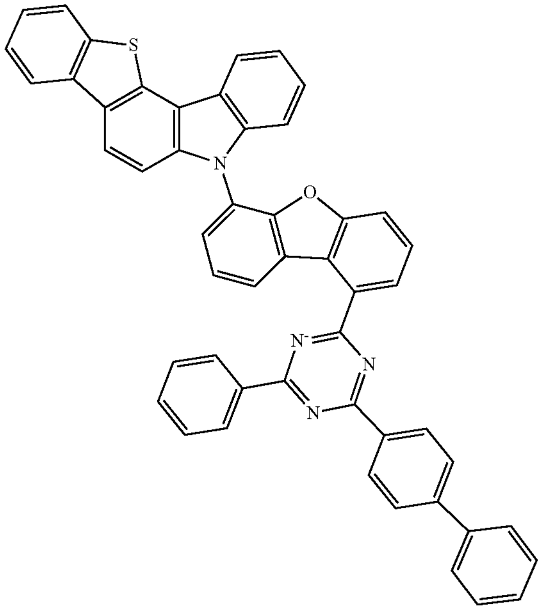
1107
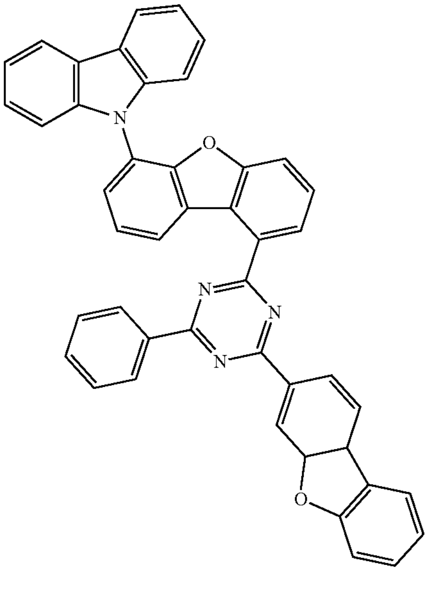
1108
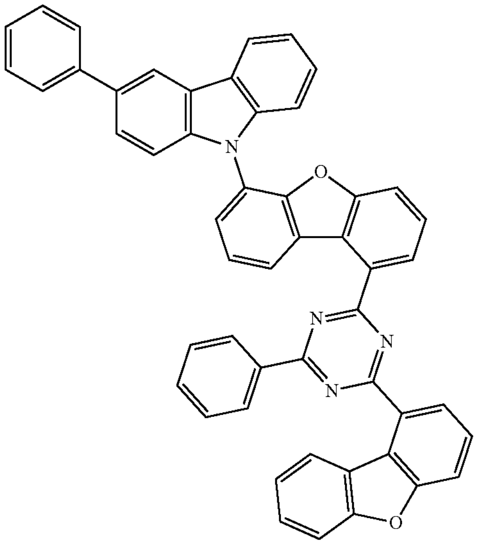

-continued
1109
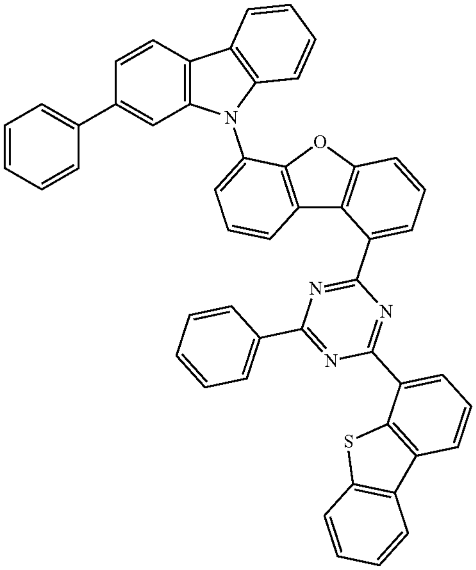
1110
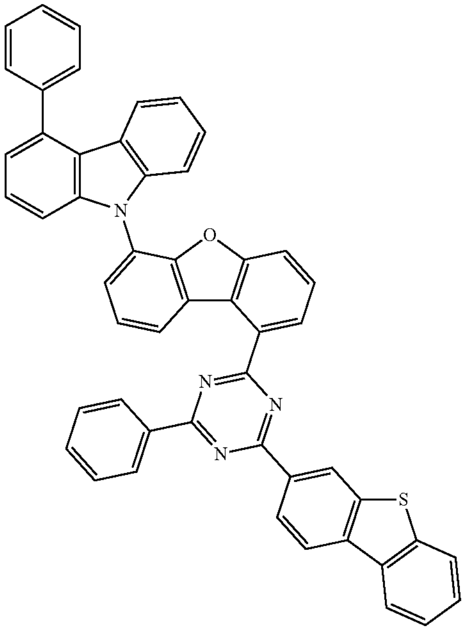
1111
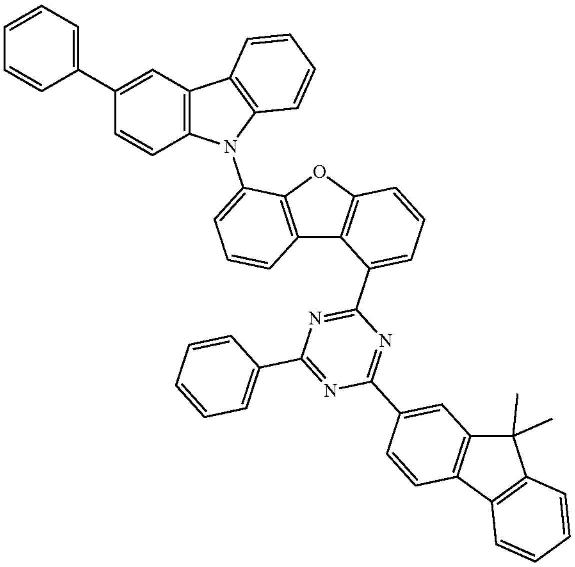
1112
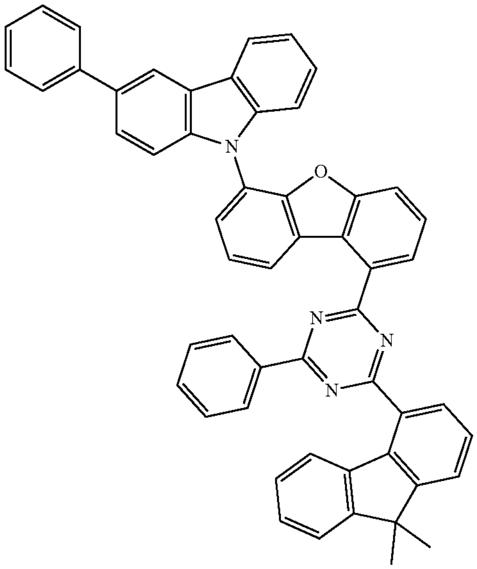
1113
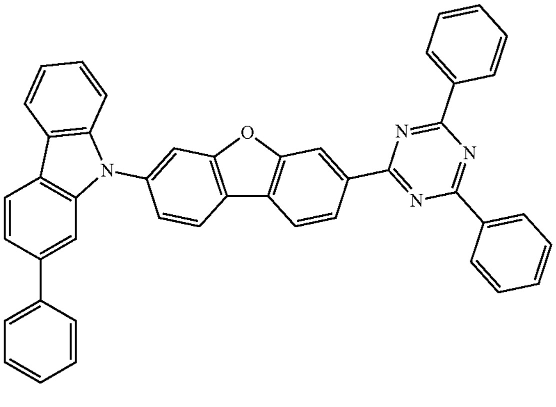
1114
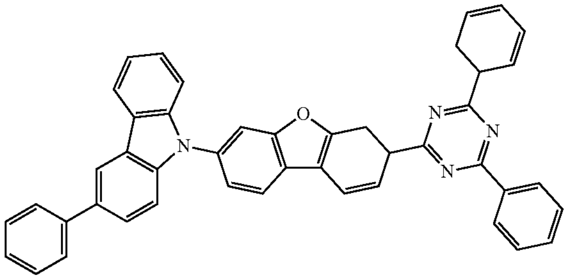

-continued
1115
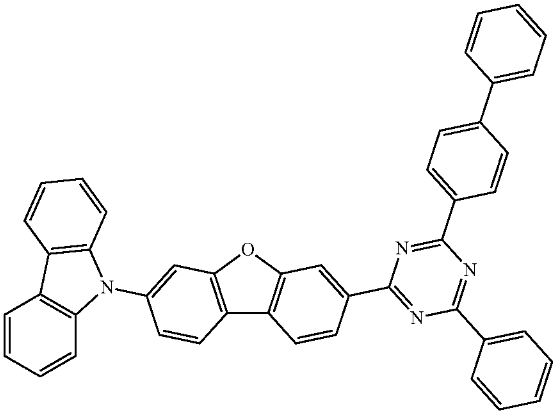
1116
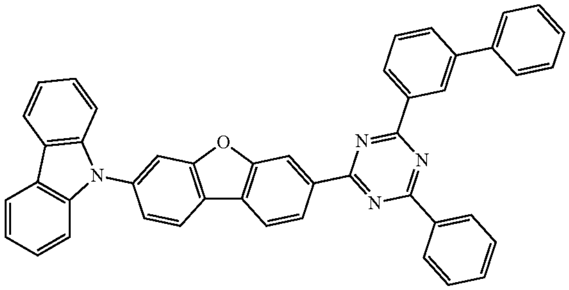
1117
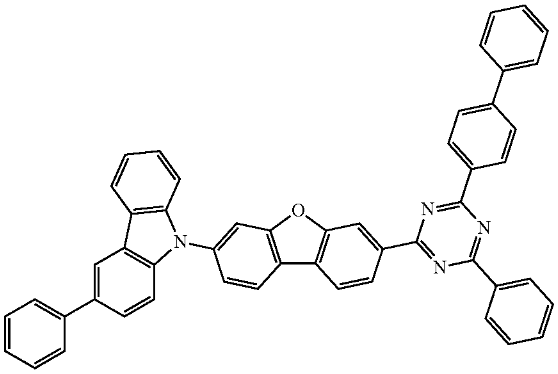
1118
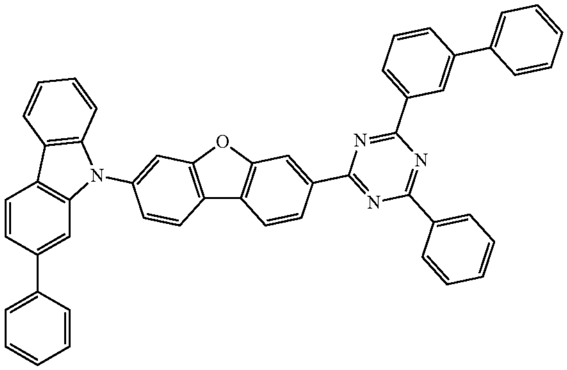
1119
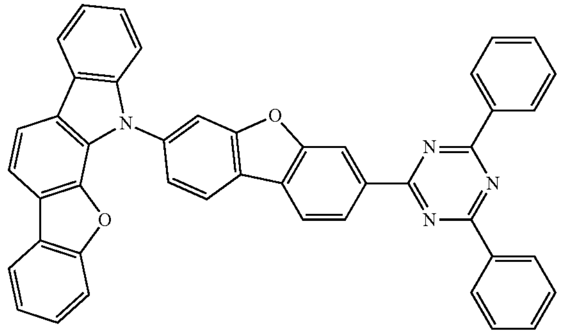
1120
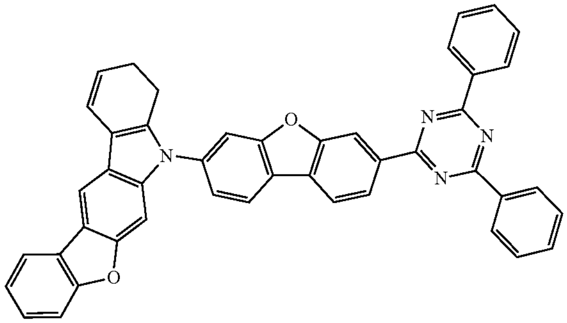
1121
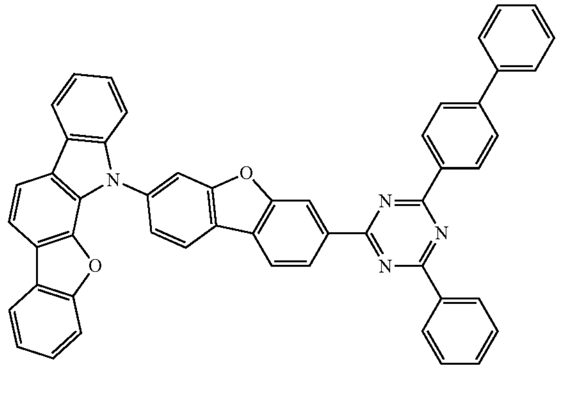

-continued
1122
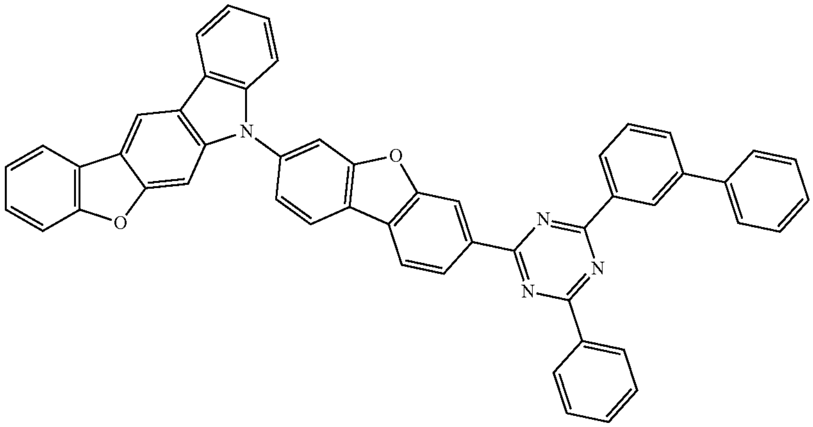
1123
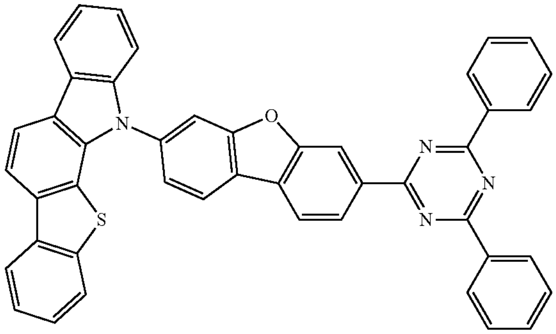
1124
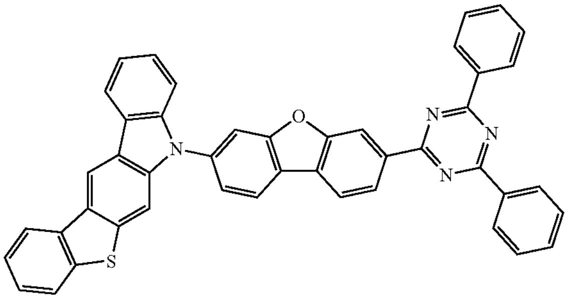
1125
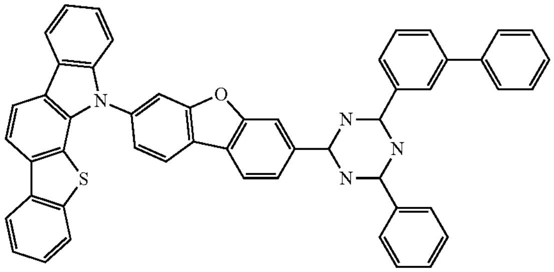
1126
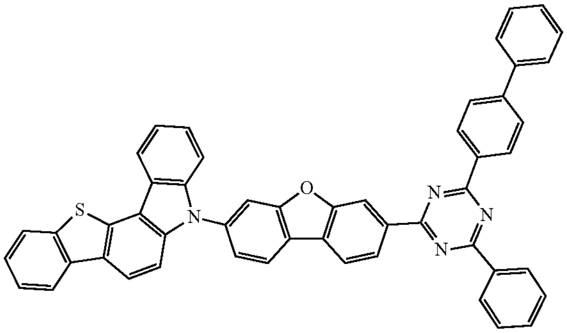
1127
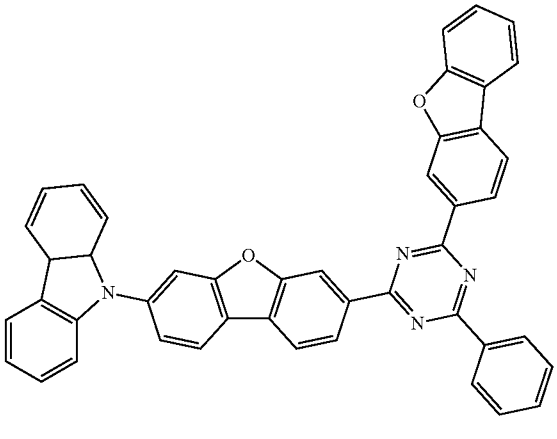
1128
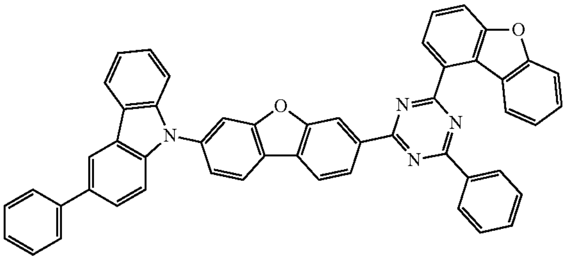

-continued
1129
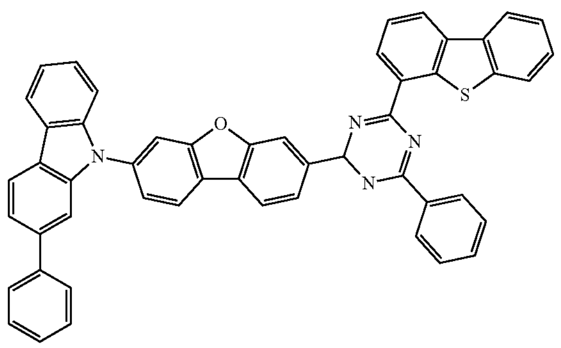
1130
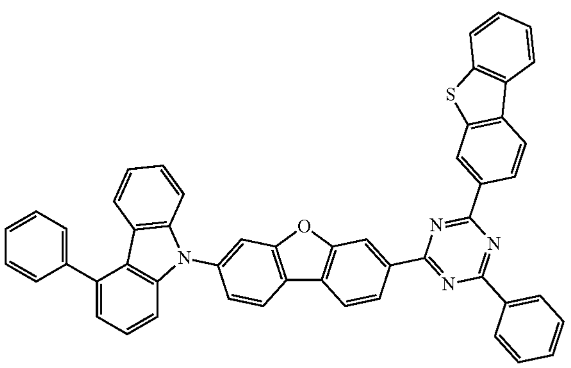
1131
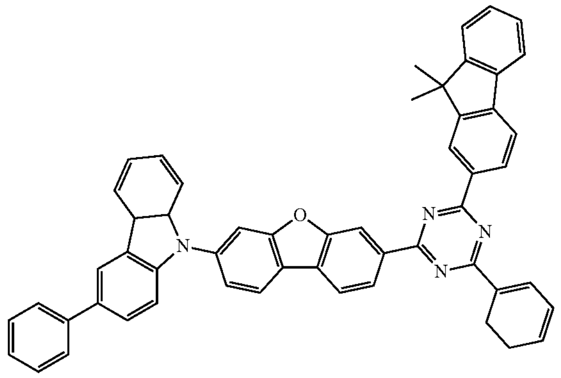
1132
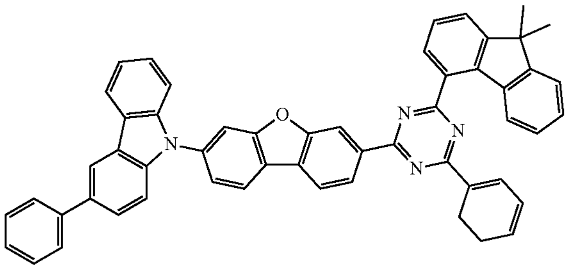
1133
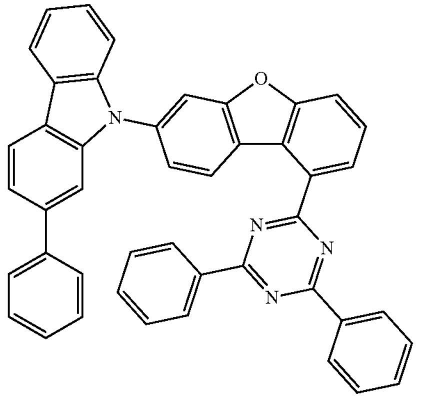
1134
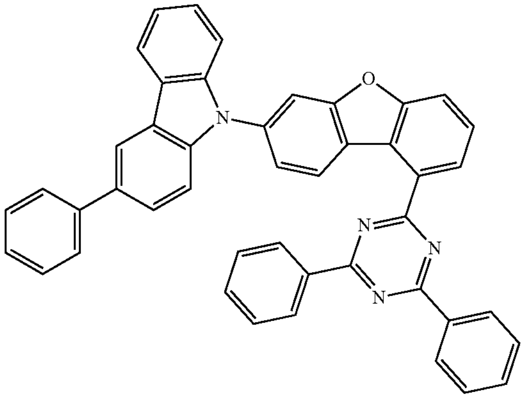

-continued
1135
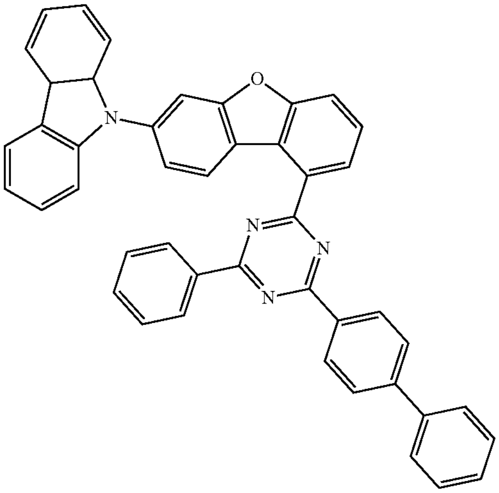
1136
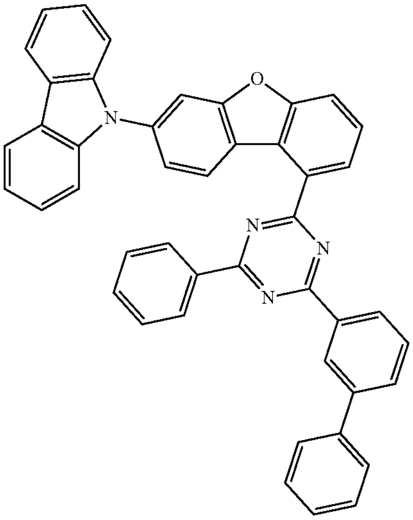
1137
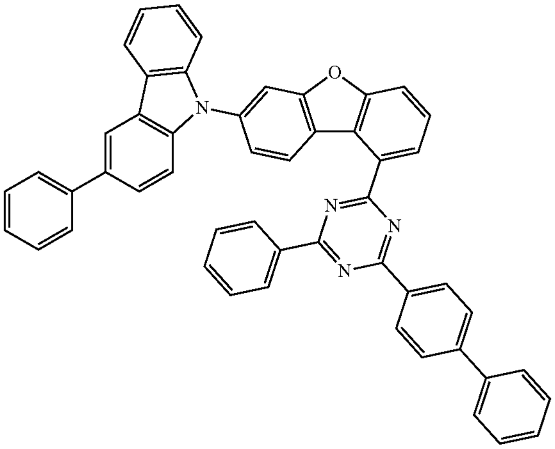
1138
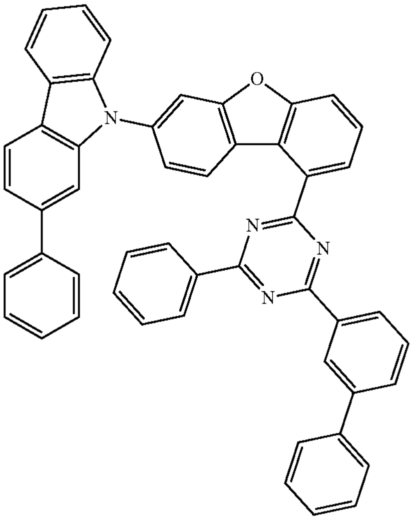
1139
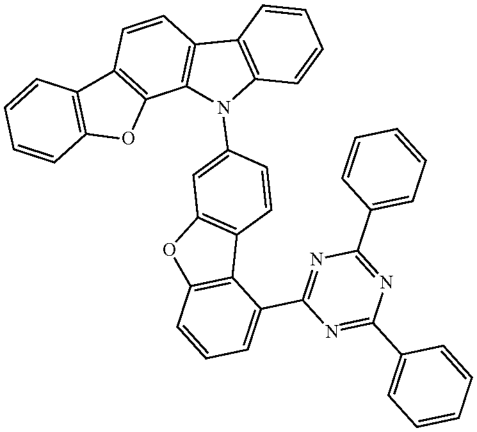
1140
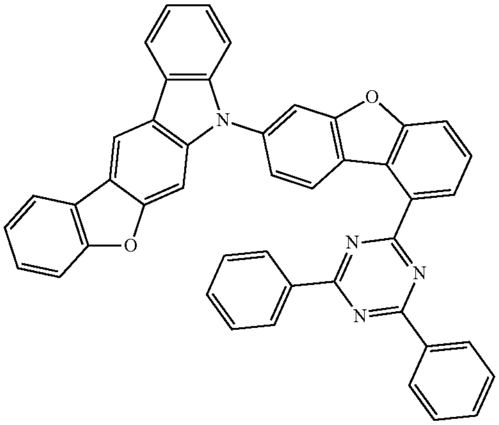

-continued
1141
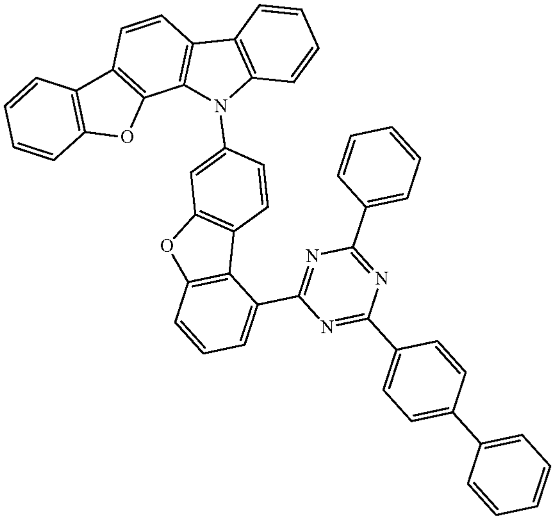
1142
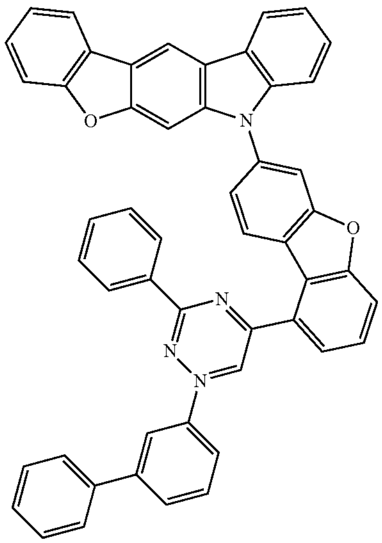
1143
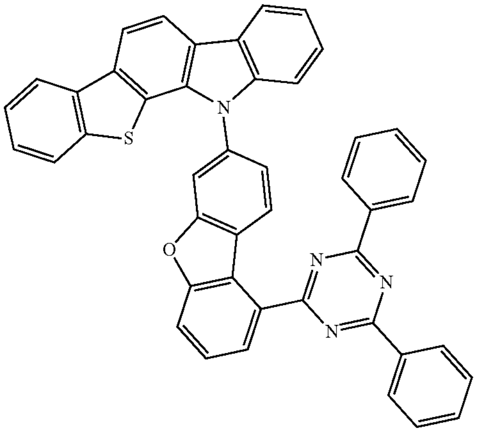
1144
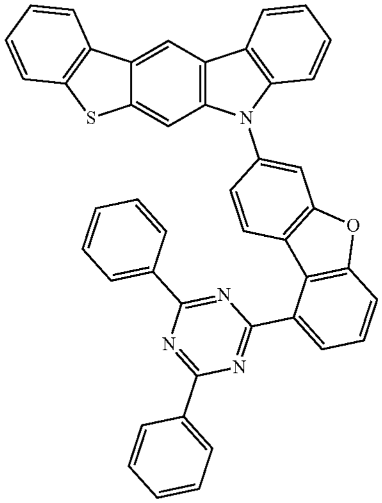
1145
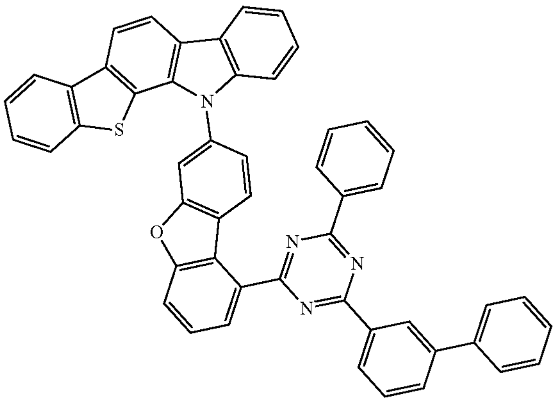
1146
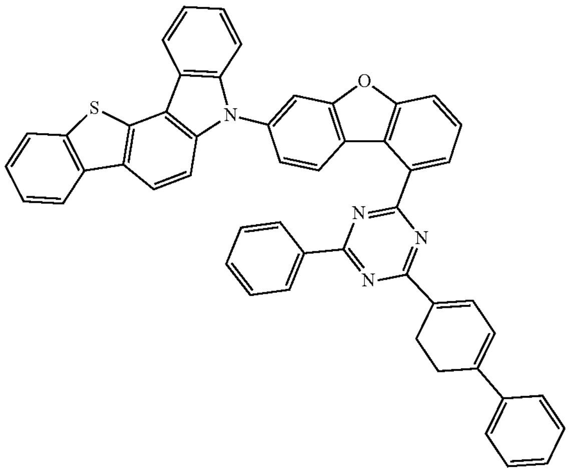

-continued
1147
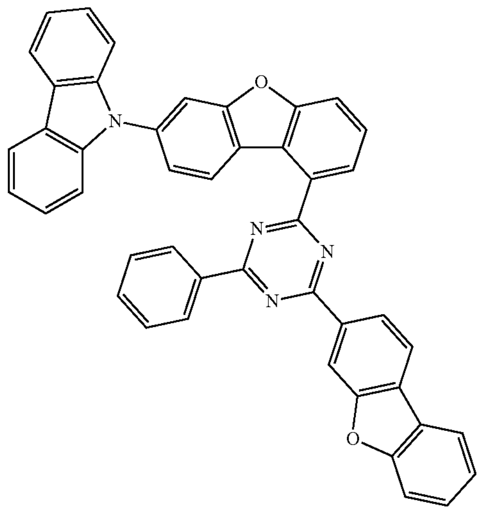
1148
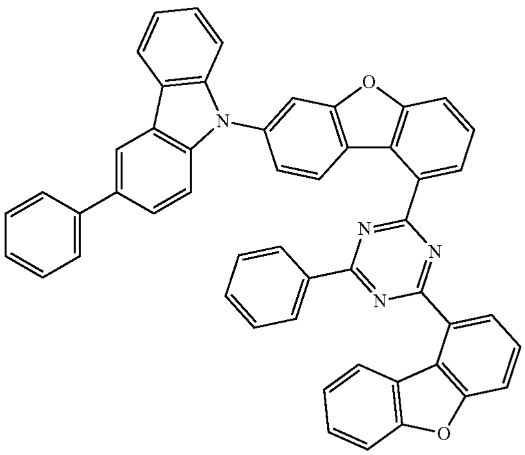
1149
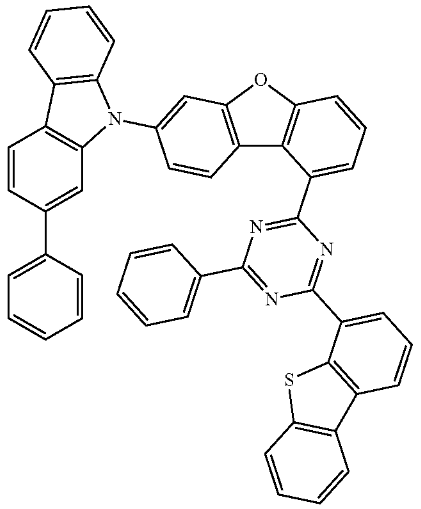
1150
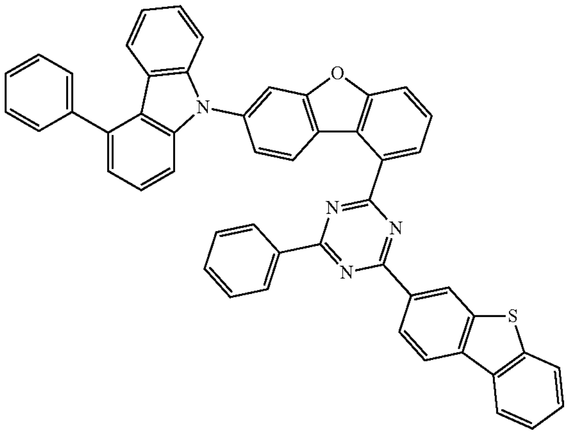
1151
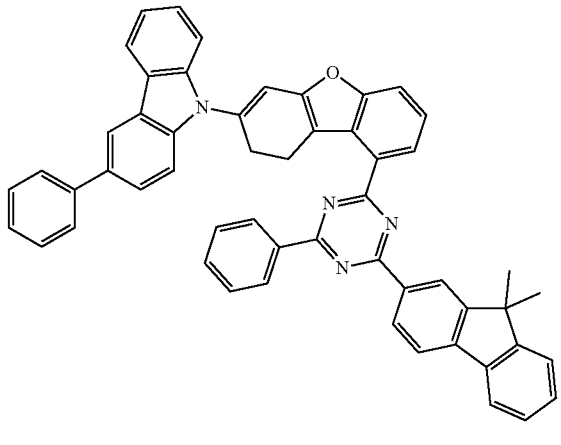
1152
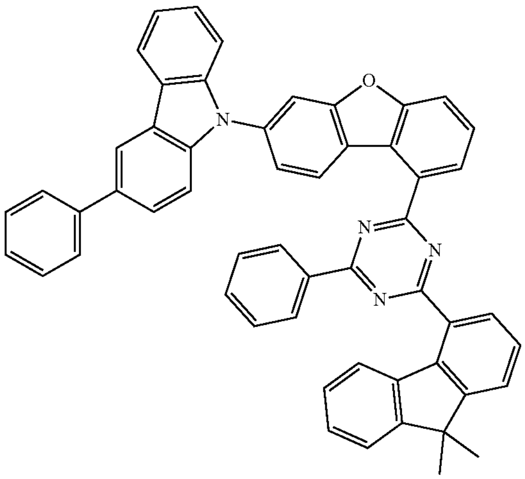

-continued
1153
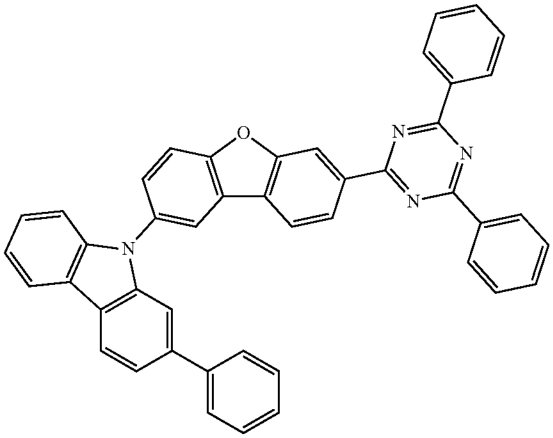
1154
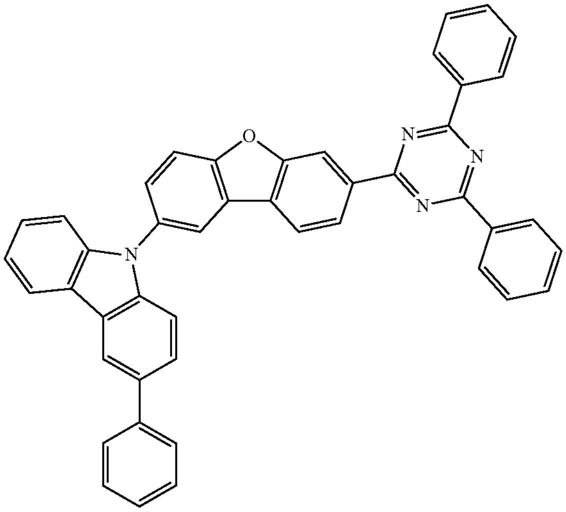
1155
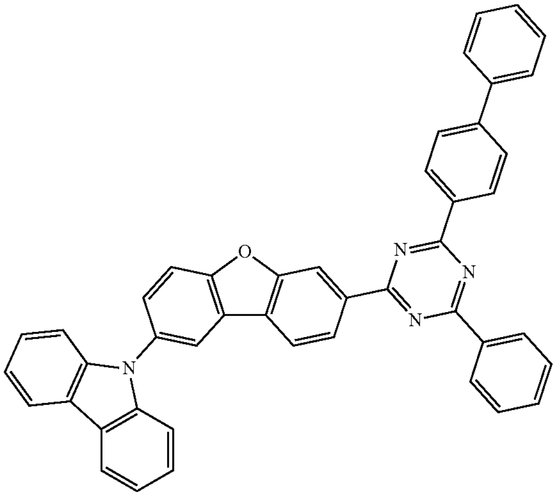
1156
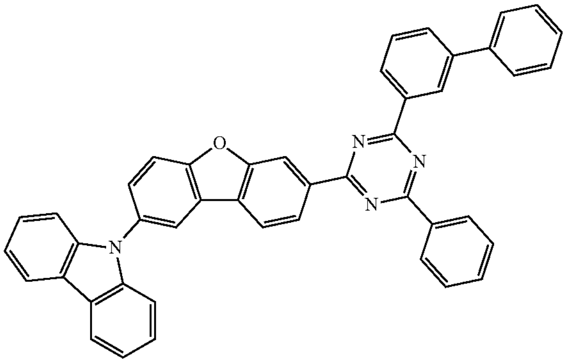

-continued
1157
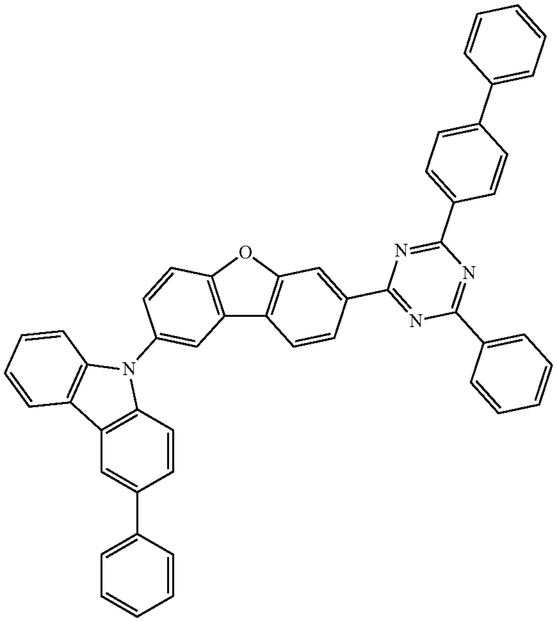
1158
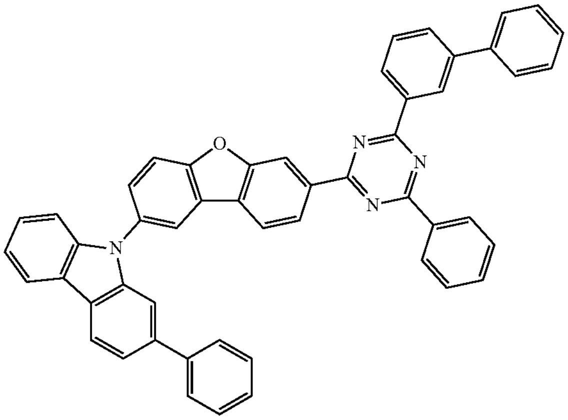
1159
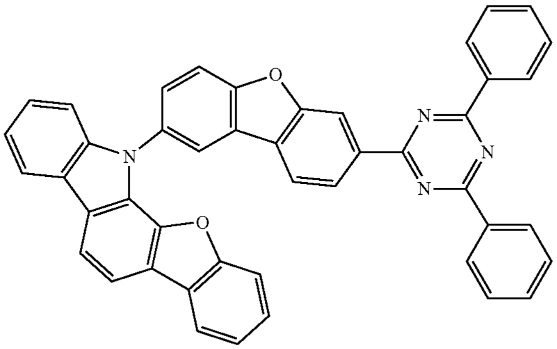
1160
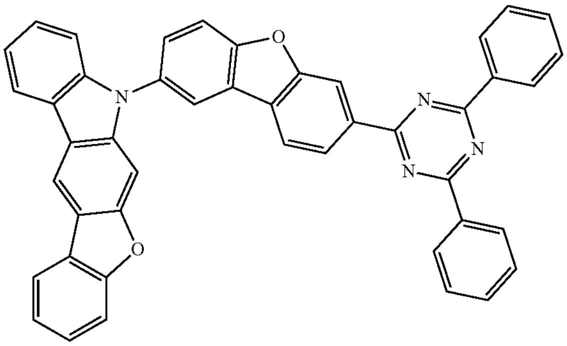
1161
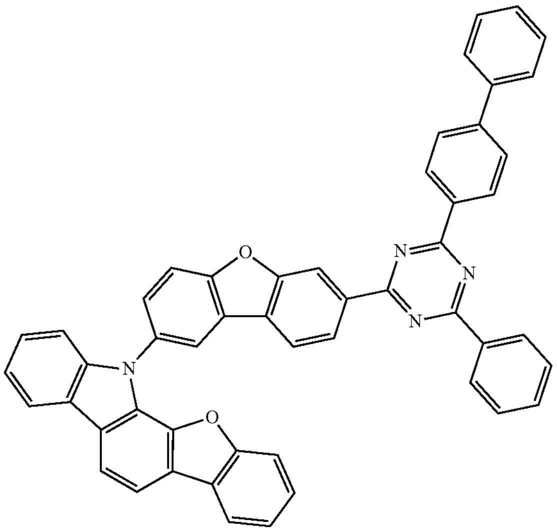
1162
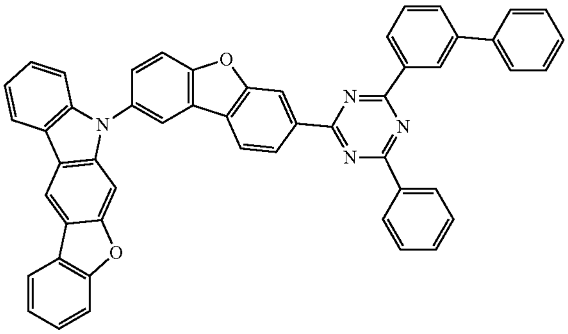

-continued
1163
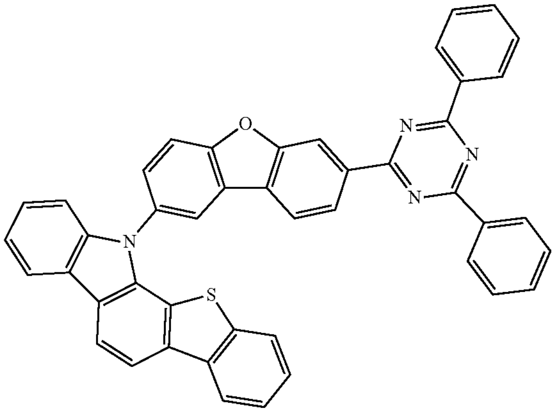
1164
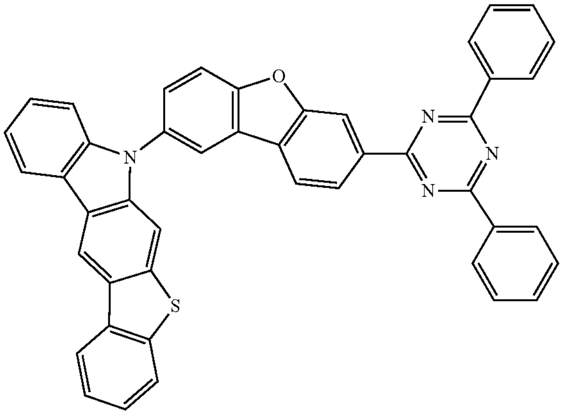
1165
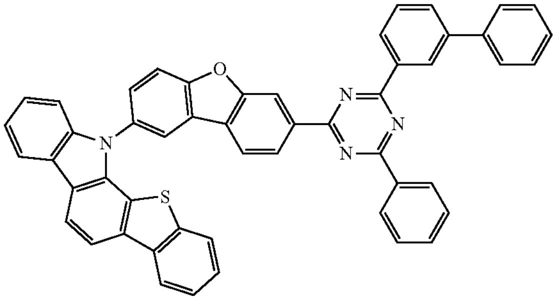
1166
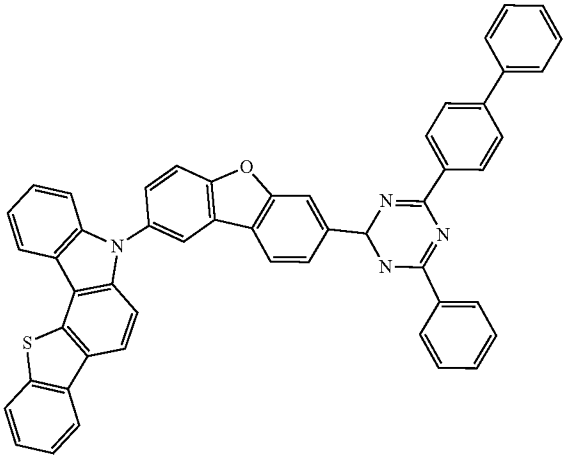
1167
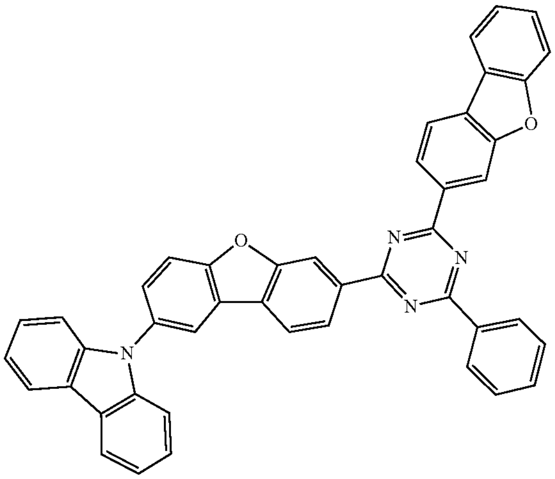
1168
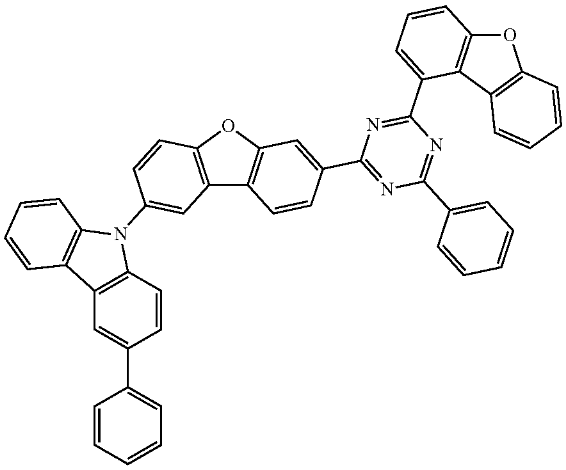

-continued
1169
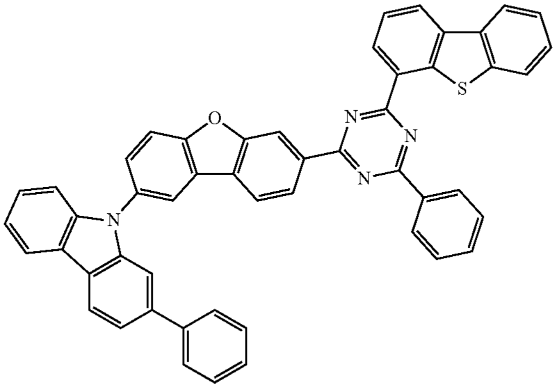
1170
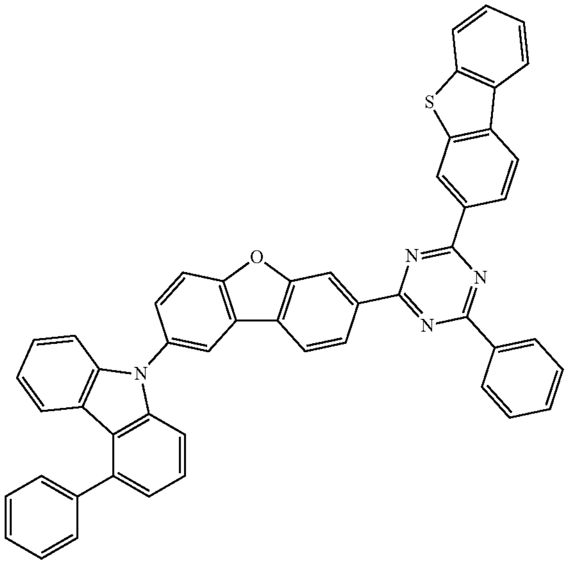
1171
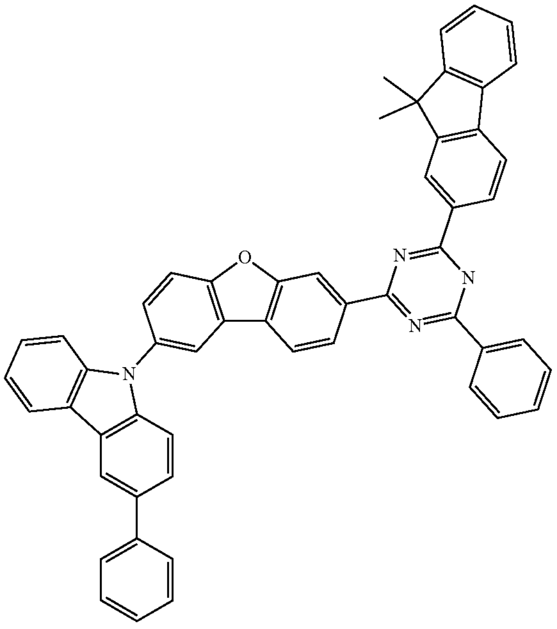
1172
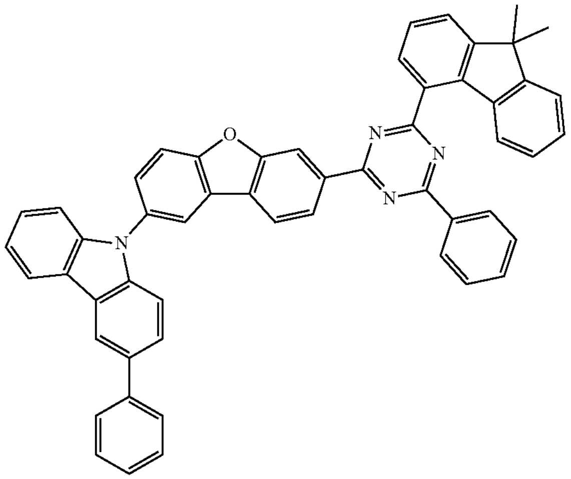

-continued
1173
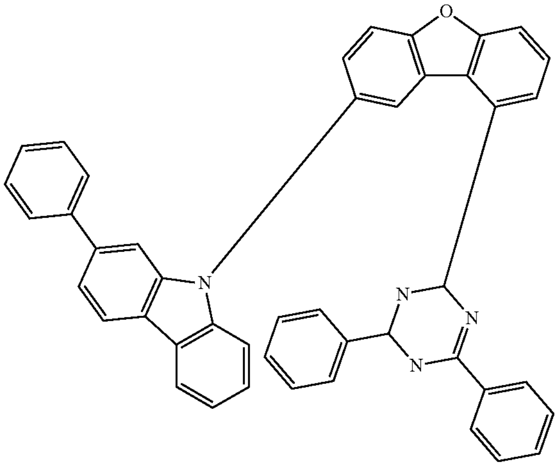
1174
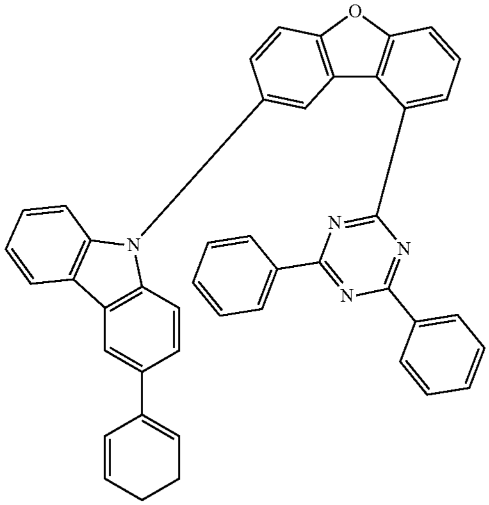
1175
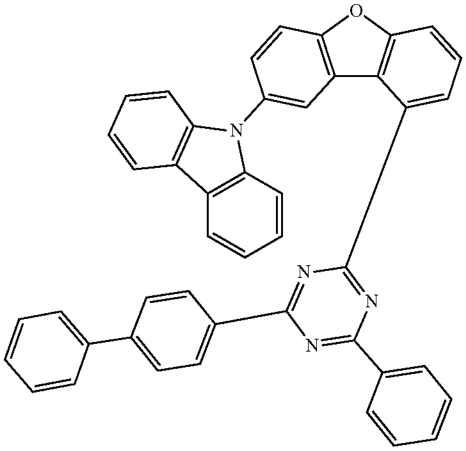
1176
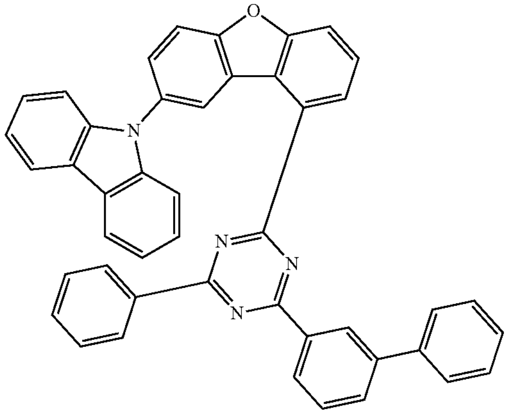
1177
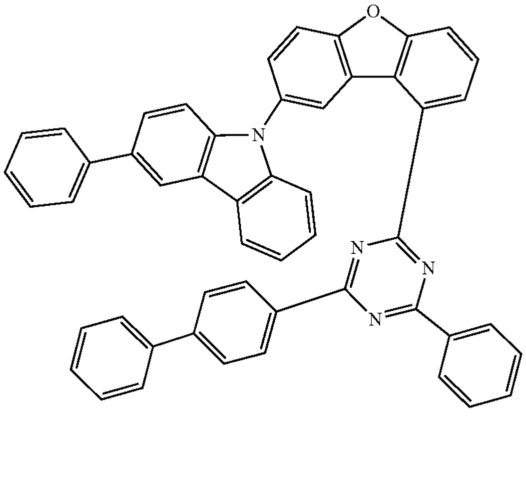
1178
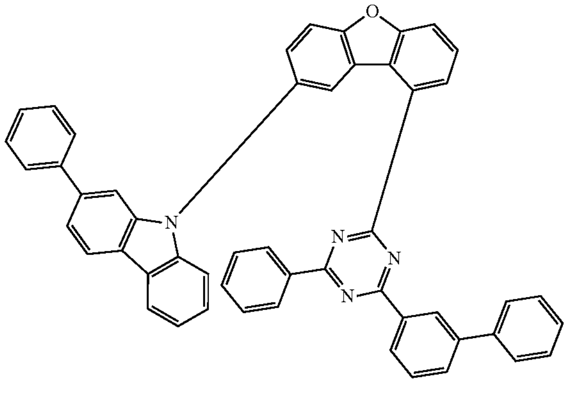

-continued
1179
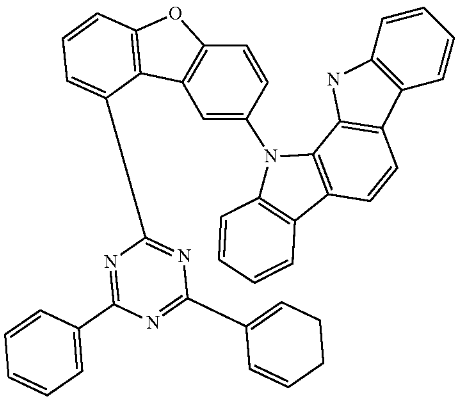
1180
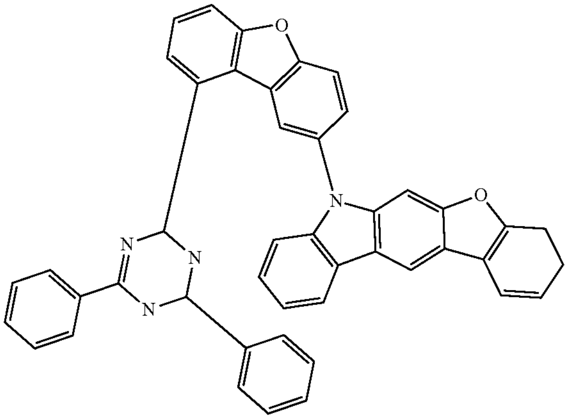
1181
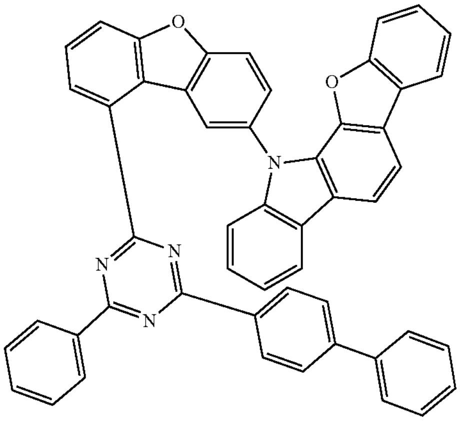
1182
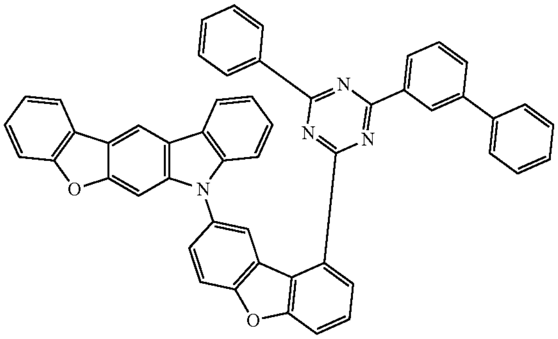
1183
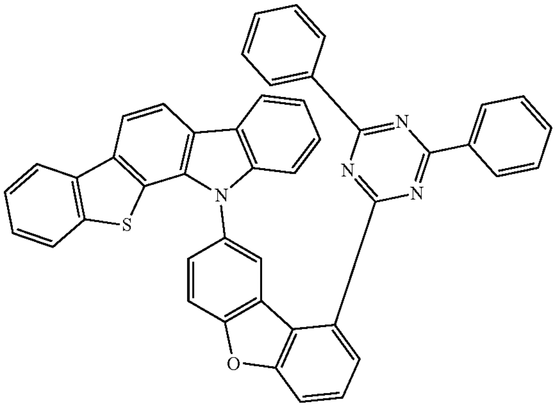
1184
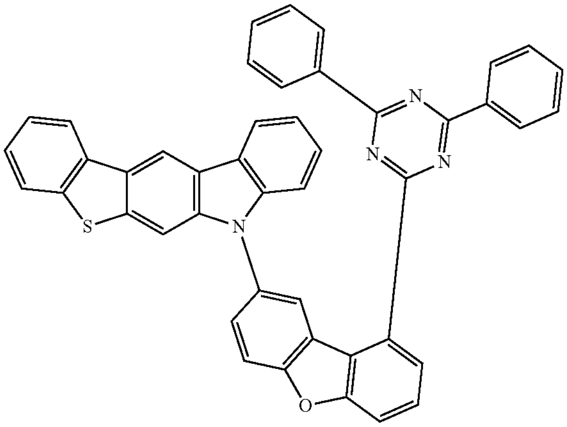

-continued
1185
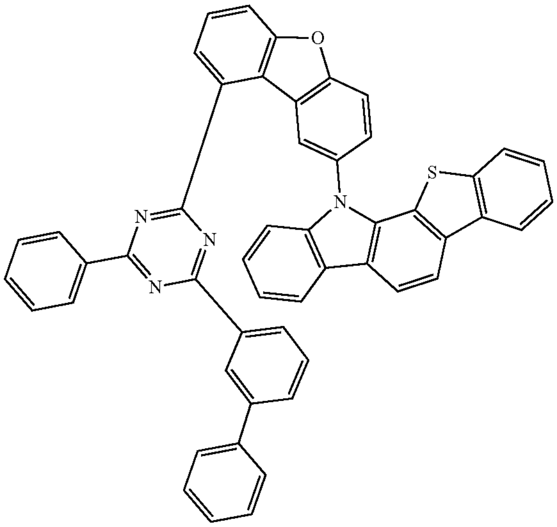
1186
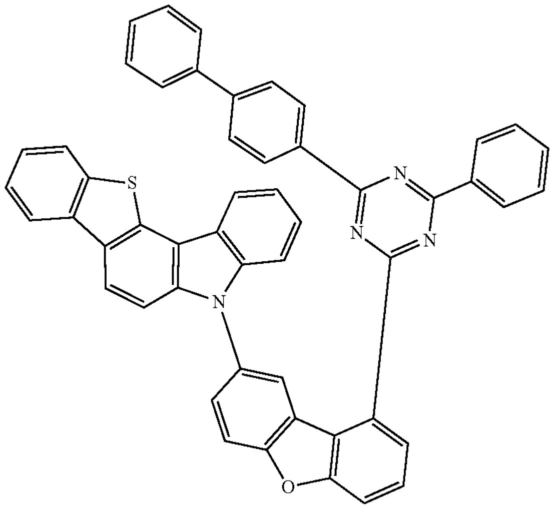
1187
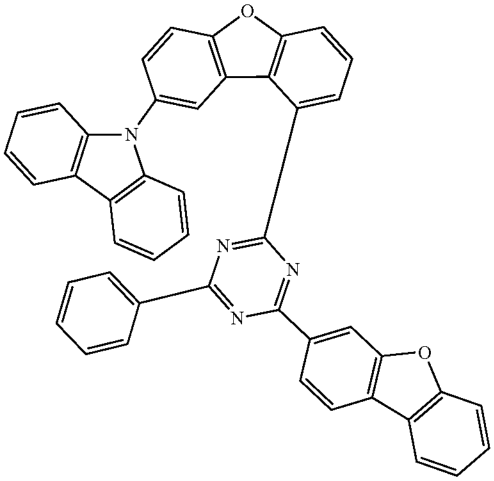
1188
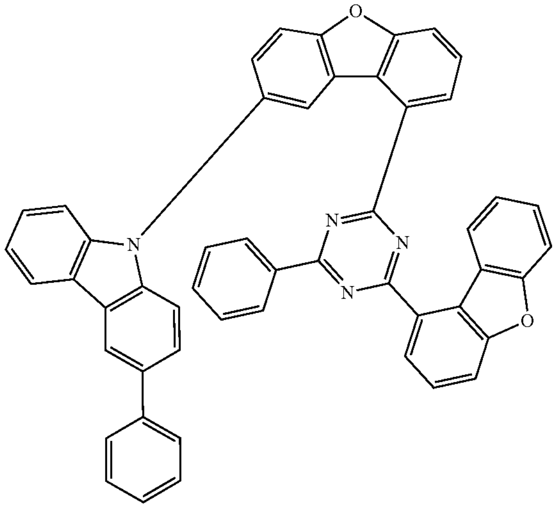
1189
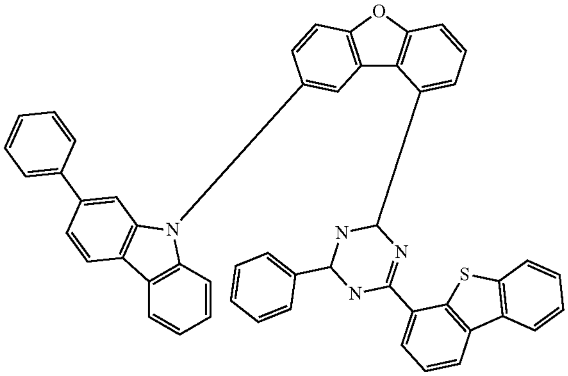
1190
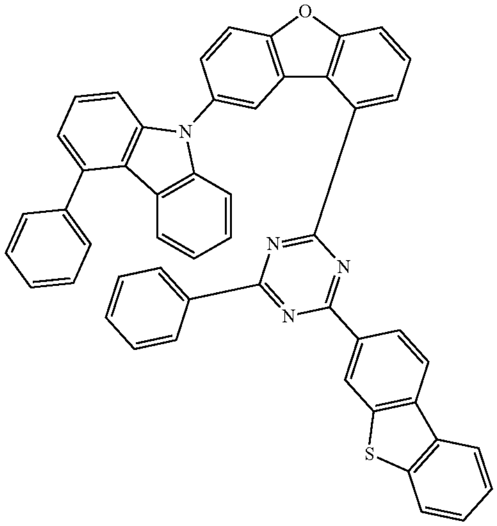

-continued
1191
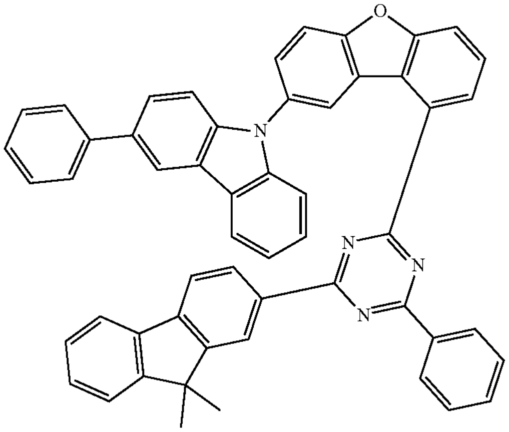
1192
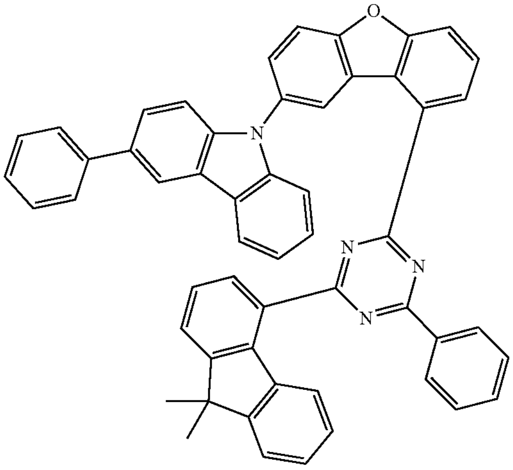
1193
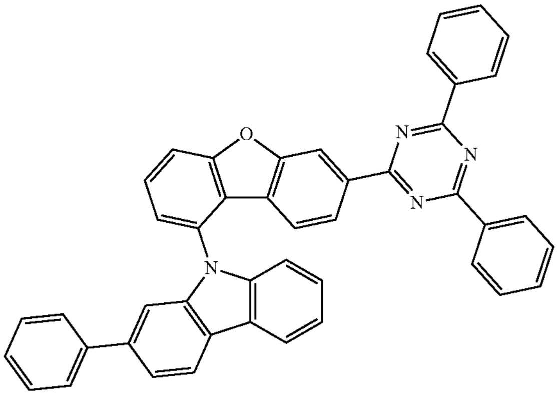
1194
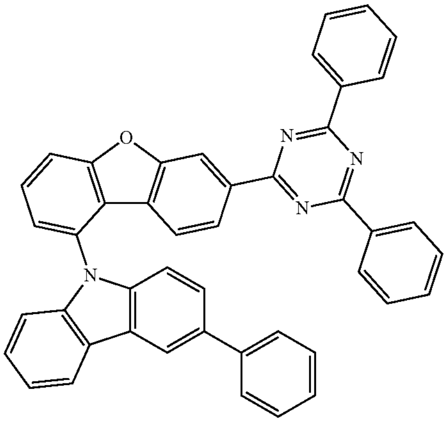
1195
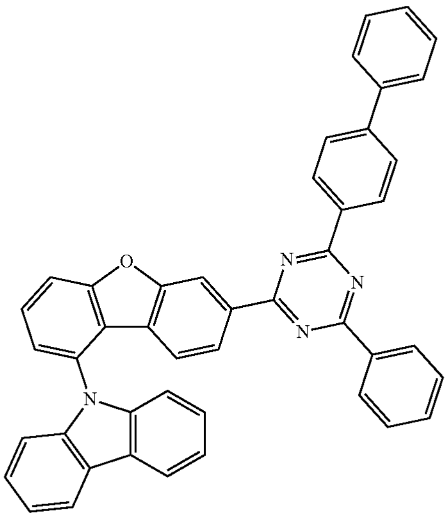
1196
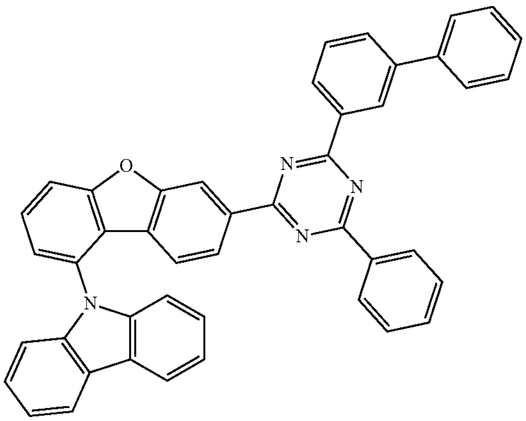

-continued
1197
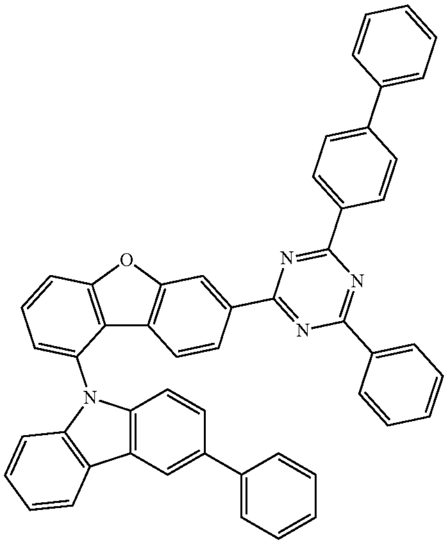
1198
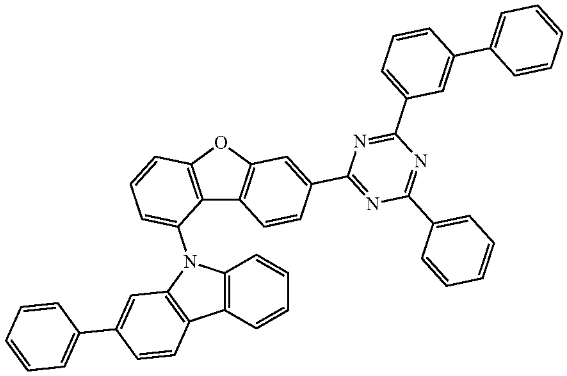
1199
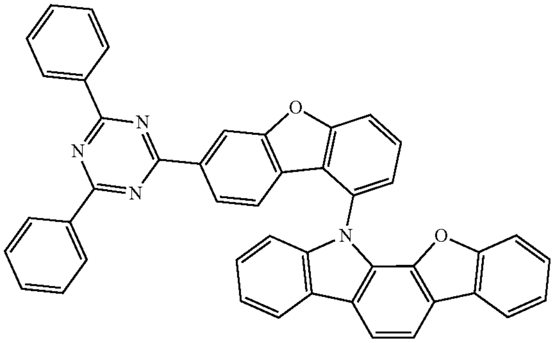
1200
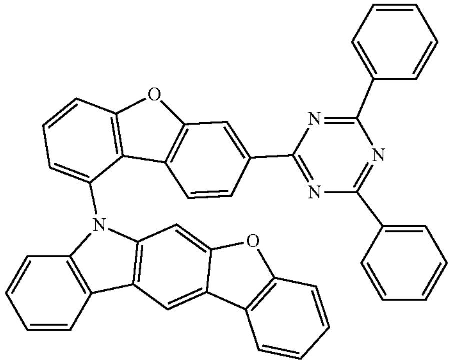
1201
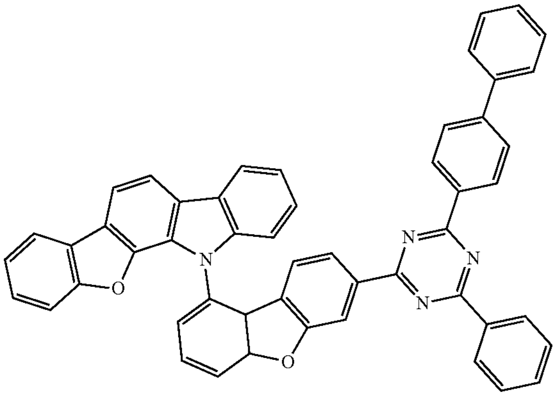
1202
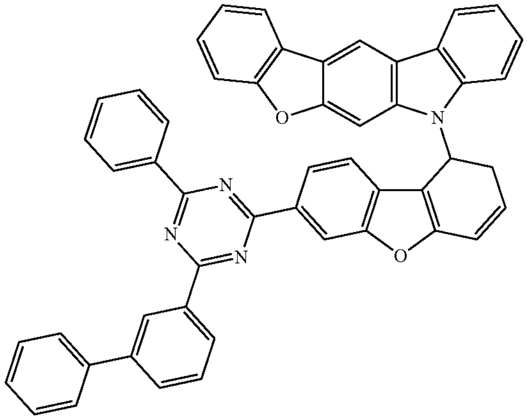

-continued
1203
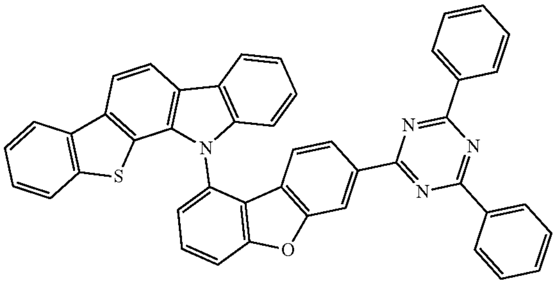
1204
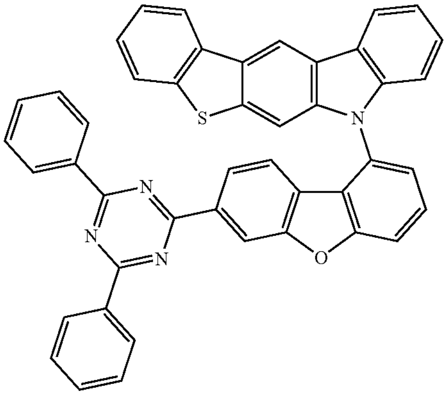
1205
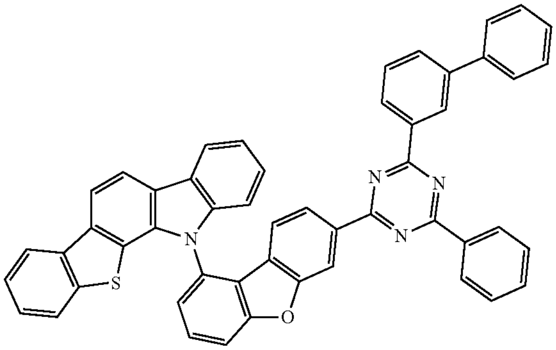
1206
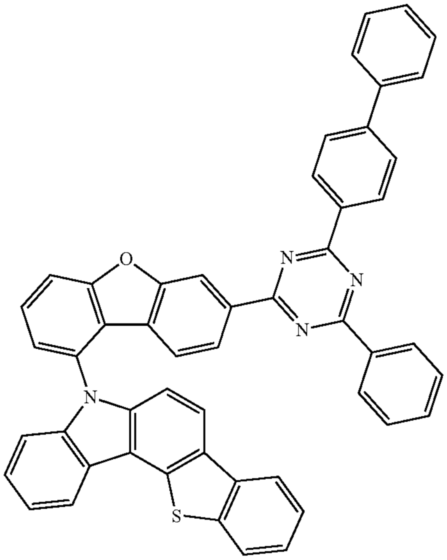
1207
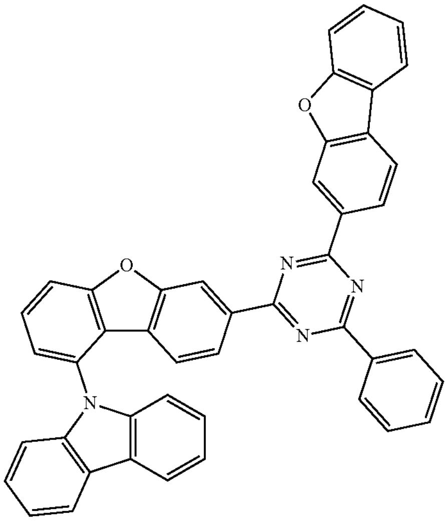
1208
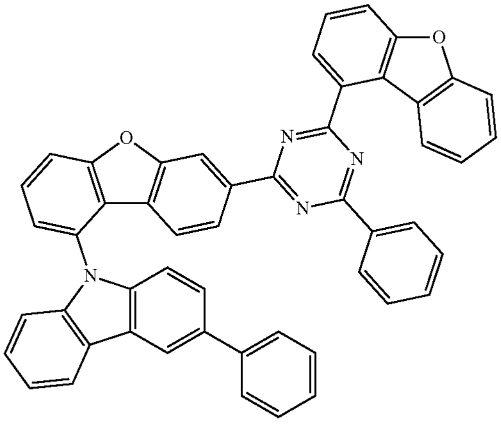

-continued
1209
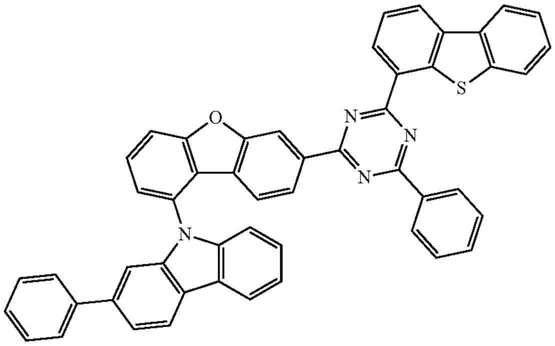
1210
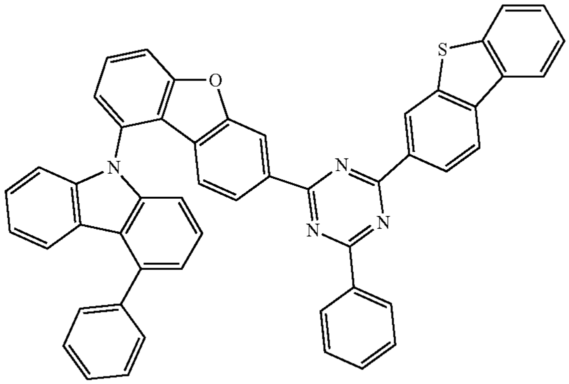
1211
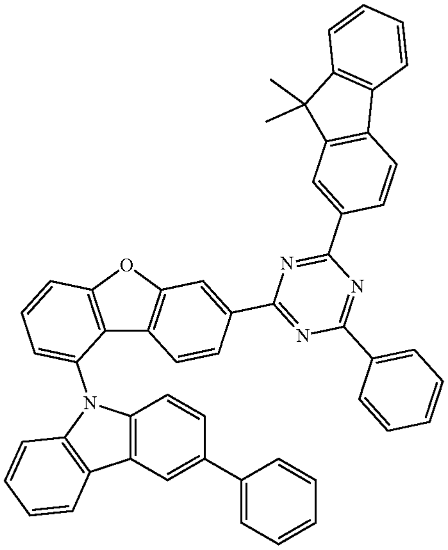
1212
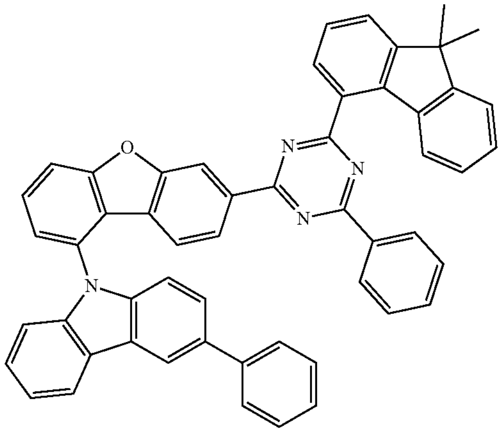
1213
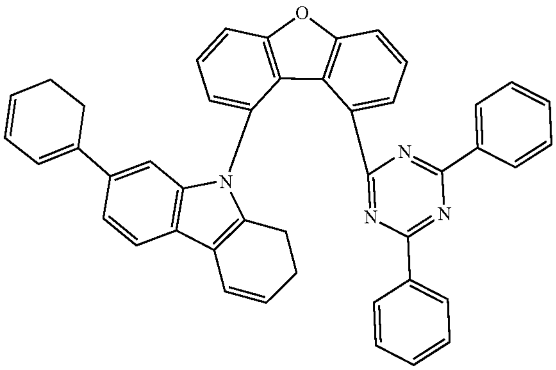
1214
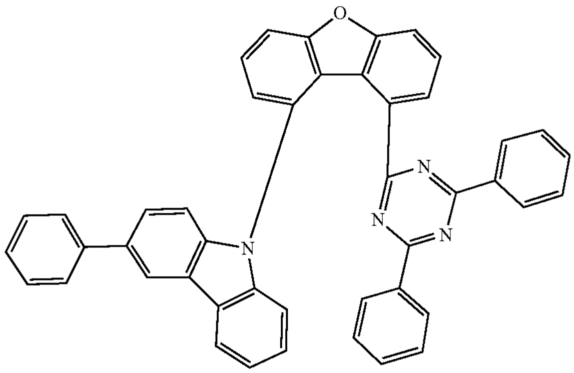

-continued

1215

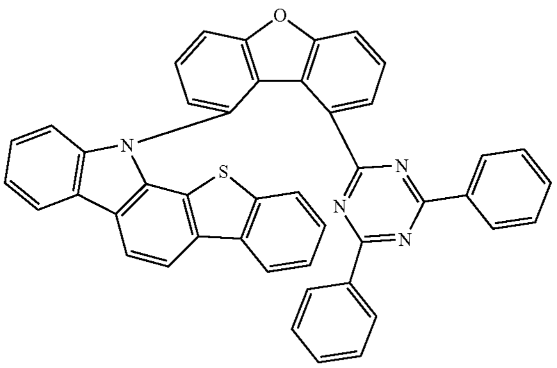

1216

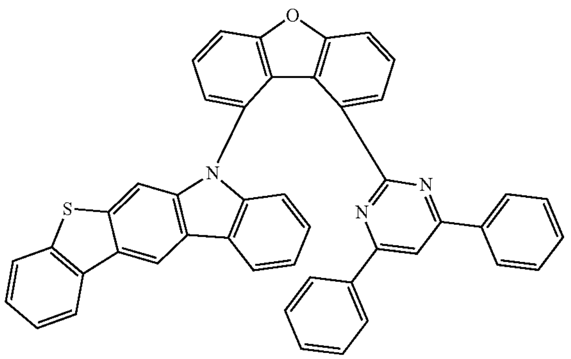

In addition, by introducing various substituents into the structure of Formula 1, compounds having intrinsic properties of the introduced substituents can be synthesized. For example, by introducing a substituent mainly used for a hole injection layer material, a hole transport material, a light emitting layer material, an electron transport layer material, and a charge generation layer material used in manufacturing an organic light emitting device into the core structure, compounds satisfying the conditions required for each organic material layer can be synthesized.

In addition, by introducing various substituents into the structure of Formula 1, it is possible to finely control the energy band gap, improve the properties at the interface between organic materials, and diversify the use of the material.

In an exemplary embodiment of the present disclosure, the organic light emitting device includes a first electrode, a second electrode facing the first electrode, at least one organic material layer between the first and second electrodes, and the at least one of the at least one organic material layer includes at least one of the heterocyclic compounds in Formula 1.

In an exemplary embodiment of the present disclosure, the organic light emitting device includes a first electrode, a second electrode facing the first electrode, at least one organic material layer between the first and second electrodes, and the at least one of the at least one organic material layer includes one of the heterocyclic compounds in Formula 1.

In an exemplary embodiment of the present disclosure, the organic light emitting device includes a first electrode, a second electrode facing the first electrode, at least one organic material layer between the first and second electrodes, and the at least one of the at least one organic material layer includes two of the heterocyclic compounds in Formula 1.

When at least two of the heterocyclic compounds of the present disclosure are included in the organic light emitting device, the heterocyclic compounds may be same or different.

In an exemplary embodiment of the present disclosure, the first electrode may be anode, and the second electrode may be cathode.

In an exemplary embodiment of the present disclosure, the first electrode may be cathode, and the second electrode may be anode.

In an exemplary embodiment of the present disclosure, the organic light emitting device may be a blue organic light emitting device, and the heterocyclic compound of Formula 1 may be used as a material of the blue organic light emitting device. For example, the heterocyclic compound of Formula 1 may be included as a host material of a blue light emitting layer in the blue organic light emitting device.

In an exemplary embodiment of the present disclosure, the organic light emitting device may be a green organic light emitting device, and the heterocyclic compound of Formula 1 may be used as a material of the green organic light emitting device. For example, the heterocyclic compound of Formula 1 may be included as a host material of a green light emitting layer in the green organic light emitting device.

In an exemplary embodiment of the present disclosure, the organic light emitting device may be a red organic light emitting device, and the heterocyclic compound of Formula 1 may be used as a material of the red organic light emitting device. For example, the heterocyclic compound of Formula 1 may be included as a host material of a red light emitting layer in the red organic light emitting device.

The organic light emitting device of the present disclosure may be manufactured by a conventional method and material for manufacturing an organic light emitting device, except for forming one or more organic material layers using the above-described heterocyclic compound.

The heterocyclic compound may be formed as an organic material layer by a solution coating method as well as a vacuum deposition method when manufacturing an organic light emitting device. Here, the solution coating method may be spin coating, dip coating, inkjet printing, screen printing, spraying, roll coating, and the like, but it is not limited thereto.

The organic material layer of the organic light emitting device of the present disclosure may have a single-layered structure. Alternatively, the organic material layer may have a multi-layered structure including two or more layers. For example, the organic material layer may include a hole injection layer (HIL), a hole transporting layer (HTL), an emitting layer (e.g., an emitting material layer (EML)), an electron transporting layer (ETL) and an electron injection layer. However, the structure of the organic light emitting device is not limited thereto, and a number of the layers may be less than the above structure.

In the organic light emitting device, the organic material layer includes an EML, and the EML may include the heterocyclic compound of Formula 1.

In the organic light emitting device, the organic material layer includes an EML including a host material, and the host material may include the heterocyclic compound of Formula 1.

In an exemplary embodiment of the present disclosure, the EML may include the heterocyclic compound of Formula 1 as a host with an iridium compound as a dopant.

In the organic light emitting device, the organic material layer may include an electron auxiliary layer including at least one of the EIL or the ETL, and the electron auxiliary layer may include the heterocyclic compound of Formula 1. Namely, the EIL or the ETL may include the heterocyclic compound of Formula 1.

In the organic light emitting device, the organic material layer may include an electron blocking layer (EBL) or a hole blocking layer (HBL), and the hole blocking layer (HBL) may include the heterocyclic compound of Formula 1.

The organic light emitting device of the present disclosure may further include at least one being selected from the group consisting of the HIL, the HTL, the ETL, the EIL, the EBL and the HBL.

Figure 2:
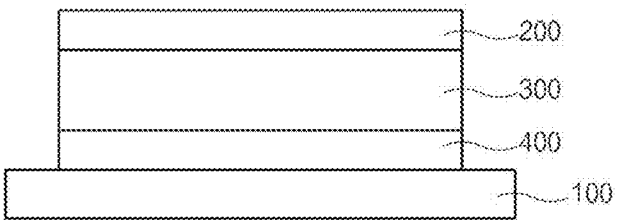
FIG. 2 is a schematic cross-sectional view of an organic light emitting device according to an embodiment of the present disclosure.
Figure 3:
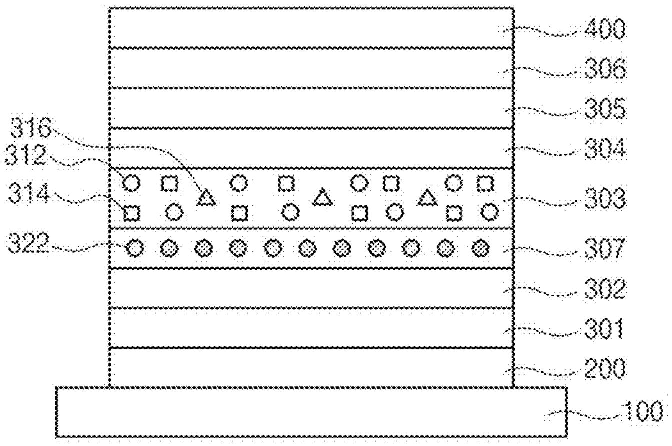
FIG. 3 is a schematic cross-sectional view of an organic light emitting device according to an embodiment of the present disclosure.

The stack order of the electrodes and the organic material layer of the organic light emitting device of the present disclosure are shown in FIGS. 1 to 3.

However, it is not intended that the scope of the present disclosure be limited by these drawings, and the structure of an organic light emitting device known in the art may also be applied to the present disclosure.

As shown in FIG. 1, the anode 200, the organic material layer (e.g., an organic emitting layer) 300 and the cathode 400 are sequentially stacked on the substrate 100 to form the organic light emitting device (e.g., organic light emitting diode). Alternatively, as shown in FIG. 2, the cathode 400, the organic material layer 300 and the anode 200 may be sequentially stacked on the substrate 100 to form the organic light emitting device.

FIG. 3 shows an organic material layer having a multi-layered structure. As shown in FIG. 3, the organic material layer includes the HIL 301, the HTL 302, the EBL 307, the EML 303, the HBL 304, the ETL 305 and the EIL 306. However, the structure of the organic material layer is not limited thereto. At least one layer of the organic material layer except the EML may be omitted, or at least one functional layer may be further included.

A layer of the organic material layer including the compound of Formula 1 may further include another material.

Referring to FIG. 3, the EML 303 may include the compound of Formula 1 as a first compound 312.

In the organic light emitting device according to an exemplary embodiment of the present disclosure, the organic material layer may further include a compound of Formula 2. For example, the EML 303 may include the compound of Formula 2 as a second compound 314 with the first compound 312 being the compound of Formula 1.

[Formula 2]

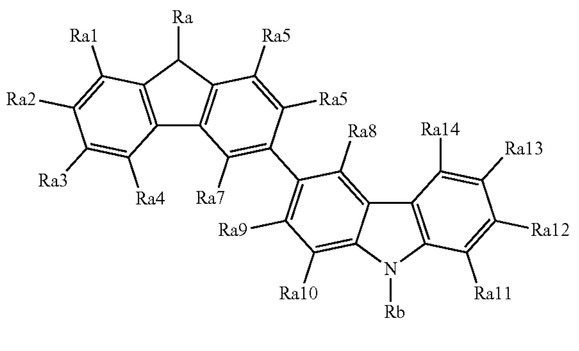

In Formula 2, Ra and Rb are same or different, and each of Ra and Rb is independently a substituted or unsubstituted C6 to C60 aryl group or a substituted or unsubstituted C2 to C60 heteroaryl group.

Ra1 to Ra14 are same or different, each of Ra1 to Ra14 is independently selected from the group consisting of hydrogen; deuterium; halogen; a cyano group; a substituted or unsubstituted C1 to C60 alkyl group; a substituted or unsubstituted C6 to C60 aryl group and a substituted or unsubstituted C2 to C60 heteroaryl group, or adjacent two or more of Ra1 to Ra14 are bonded to each other to form a substituted or unsubstituted C6 to C60 aromatic hydrocarbon ring or a substituted or unsubstituted C2 to C60 heterocyclic ring.

In particular, when the heterocyclic compound of Formula 2 is further included, an exciplex phenomenon occurs. The exciplex phenomenon refers to the formation of a binary complex in an excited state by electron exchange between a molecule having a strong donor property and a molecule having a strong acceptor property.

Figure 4:
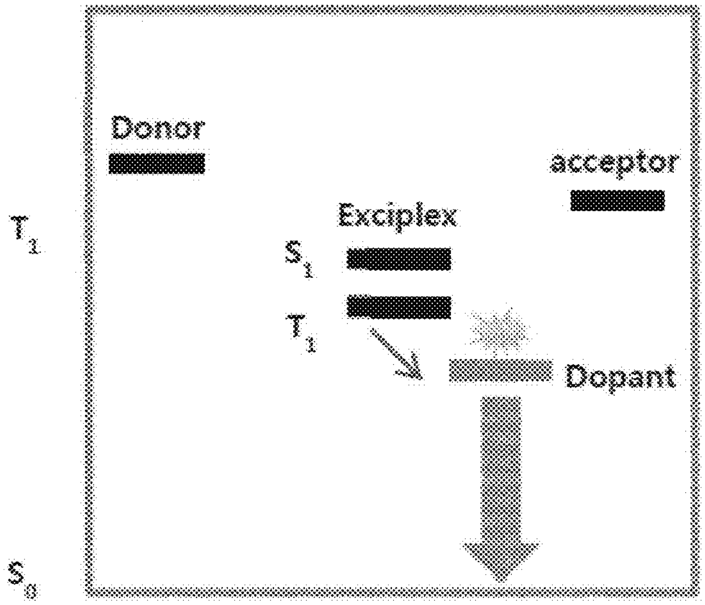
FIG. 4 is a schematic view illustrating an exciplex phenomenon.

FIG. 4 is a schematic view illustrating an exciplex phenomenon. When an exciplex phenomenon occurs as shown in FIG. 4, a new Si energy level and a new T1 energy level are formed, and a change in PL that is redshifted from each molecule can be confirmed.

In this way, when an exciplex phenomenon between two molecules occurs, Reverse Intersystem Crossing (RISC) occurs, thereby increasing the internal quantum efficiency to 100%.

In particular, although the compound of Formula 1 being a bipolar compound does not have a strong acceptor ability. However, a red-shifted PL change is shown by injecting donor (p-Host), i.e., the compound of Formula 2, which has good hole transport ability. Namely, the compound of Formula 1 is included in the organic material layer with the compound of Formula 2 so that the exciplex phenomenon occurs and the emitting property is improved. In addition, as the heterocyclic compound (donor (p-host)) of Formula 2 of the present disclosure having good hole transport ability is included, the lifespan can be significantly improved by proper movement of the light emitting zone in the light emitting layer.

In an exemplary embodiment of the present disclosure, Ra and Rb in Formula 2 may be same or different, and each of Ra and Rb may be a substituted or unsubstituted C6 to C60 aryl group; or a substituted or unsubstituted C2 to C60 a heteroaryl group.

In an exemplary embodiment of the present disclosure, Ra and Rb in Formula 2 may be same or different, and each of Ra and Rb may be a substituted or unsubstituted C6 to C40 aryl group; or a substituted or unsubstituted C2 to C40 a heteroaryl group.

In an exemplary embodiment of the present disclosure, Ra and Rb in Formula 2 may be same or different, and each of Ra and Rb may be a C6 to C30 aryl group unsubstituted or substituted with deuterium, a C1 to C30 alkyl or C6 to C30; or a C2 to C30 heteroaryl group unsubstituted or substituted with deuterium.

In an exemplary embodiment of the present disclosure, Ra and Rb in Formula 2 may be same or different, and each of Ra and Rb may be selected from the group consisting of substituted or unsubstituted phenyl, substituted or unsubstituted biphenyl, substituted or unsubstituted terphenyl, substituted or unsubstituted triphenylenyl, substituted or unsubstituted dimethylfluorenyl, substituted or unsubstituted dibenzofuranyl and substituted or unsubstituted dibenzothiophenyl.

In an exemplary embodiment of the present disclosure, Ra1 and Ra14 in Formula 2 may be same or different, and each of Ra1 and Ra14 may be independently selected from the group consisting of hydrogen; deuterium; halogen; a cyano group; a substituted or unsubstituted C1 to C60 alkyl group; a substituted or unsubstituted C6 to C60 aryl group; and a substituted or unsubstituted C2 to C60 heteroaryl group, or adjacent two or more of Ra1 and Ra14 are bonded to each other to form a substituted or unsubstituted C6 to C60 aromatic hydrocarbon ring or a substituted or unsubstituted C2 to C60 heterocyclic ring.

In an exemplary embodiment of the present disclosure, Ra1 and Ra14 may be same or different, and each of Ra1 and Ra14 may be independently selected from the group consisting of hydrogen; deuterium; a substituted or unsubstituted C1 to C60 alkyl group; a substituted or unsubstituted C6 to C60 aryl group; and a substituted or unsubstituted C2 to C60 heteroaryl group, or adjacent two or more of Ra1 and Ra14 are bonded to each other to form a substituted or unsubstituted C6 to C60 aromatic hydrocarbon ring or a substituted or unsubstituted C2 to C60 heterocyclic ring.

In an exemplary embodiment of the present disclosure, Ra1 and Ra14 may be same or different, and each of Ra1 and Ra14 may be independently selected from the group consisting of hydrogen; deuterium; a substituted or unsubstituted C1 to C40 alkyl group; a substituted or unsubstituted C6 to C40 aryl group; and a substituted or unsubstituted C2 to C40 heteroaryl group, or adjacent two or more of Ra1 and Ra14 are bonded to each other to form a substituted or unsubstituted C6 to C40 aromatic hydrocarbon ring or a substituted or unsubstituted C2 to C40 heterocyclic ring.

In an exemplary embodiment of the present disclosure, Ra1 and Ra14 may be same or different, and each of Ra1 and Ra14 may be independently selected from the group consisting of hydrogen; deuterium; a substituted or unsubstituted C1 to C20 alkyl group; a substituted or unsubstituted C6 to C20 aryl group; and a substituted or unsubstituted C2 to C20 heteroaryl group.

In an exemplary embodiment of the present disclosure, Ra1 and Ra14 may be same or different, and each of Ra1 and Ra14 may be hydrogen or deuterium.

In an exemplary embodiment of the present disclosure, the deuteration ratio of the heterocyclic compound of Formula 2 may be 20% to 100%.

In an exemplary embodiment of the present disclosure, the deuteration ratio of the heterocyclic compound of Formula 2 may be 25% to 100%, preferably 30% to 100%.

In an exemplary embodiment of the present disclosure, the structure of Formula 2 may be divided into the partial structures in Formulas 2-1 to 2-3.

[Formula 2-1]

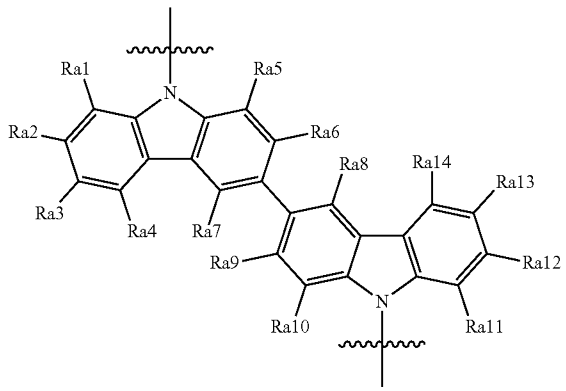

-continued

[Formula 2-2]

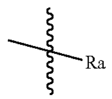

[Formula 2-3]

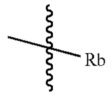

In Formulas 2-1 to 2-3, the definitions of substituents are same as those in Formula 2, and the mark

is a bonding position between the partial structures of Formulas 2-1 to 2-3.

In an exemplary embodiment of the present disclosure, the partial structure of Formula 2-1 in Formula 2 may have the deuteration ratio of 0%.

In an exemplary embodiment of the present disclosure, the partial structure of Formula 2-1 in Formula 2 may have the deuteration ratio of 100%.

In an exemplary embodiment of the present disclosure, the partial structure of Formula 2-1 in Formula 2 may have the deuteration ratio of 0% to 100%.

In an exemplary embodiment of the present disclosure, the partial structure of Formula 2-2 in Formula 2 may have the deuteration ratio of 0%.

In an exemplary embodiment of the present disclosure, the partial structure of Formula 2-2 in Formula 2 may have the deuteration ratio of 100%.

In an exemplary embodiment of the present disclosure, the partial structure of Formula 2-3 in Formula 2 may have the deuteration ratio of 0%.

In an exemplary embodiment of the present disclosure, the partial structure of Formula 2-3 in Formula 2 may have the deuteration ratio of 100%.

In an exemplary embodiment of the present disclosure, the partial structures of Formulas 2-1 to 2-3 in Formula 2 may have the deuteration ratio of 100%.

When the compound of Formula 1 and the compound of Formula 2 are simultaneously included in the organic material layer of the organic light emitting device, better efficiency and lifespan effects are exhibited. The exciplex phenomenon can be expected when both compounds are included at the same time.

In the exciplex phenomenon, energy having an intensity of a HOMO level of a donor (p-host) and a LUMO level of an acceptor (n-host) is emitted through electron exchange between two molecules. When the exciplex phenomenon occurs between two molecules, Reverse Intersystem Crossing (RISC) occurs so that the internal quantum efficiency of fluorescence can be increased to 100%. When a donor (p-host) with good hole transport ability and an acceptor (n-host) with good electron transport ability are used as the host of the emitting layer, the driving voltage can be lowered and the lifespan can be improved because holes are injected into the p-host and electrons are injected into the n-host.

In an exemplary embodiment of the present disclosure, the heterocyclic compound of Formula 2 may be one of the compounds in Formula 2a.
2-1
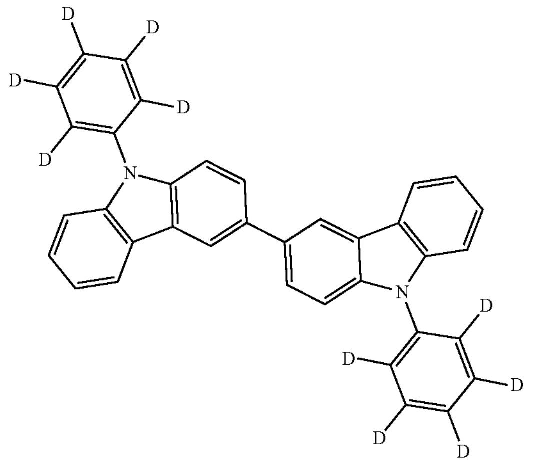
2-2
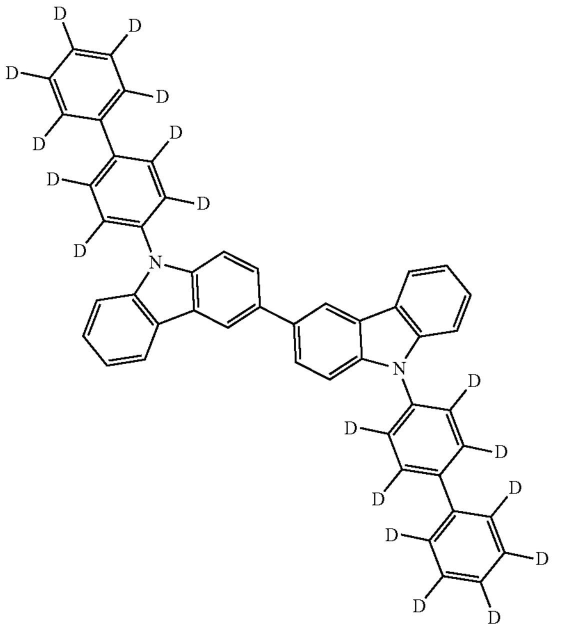
2-3
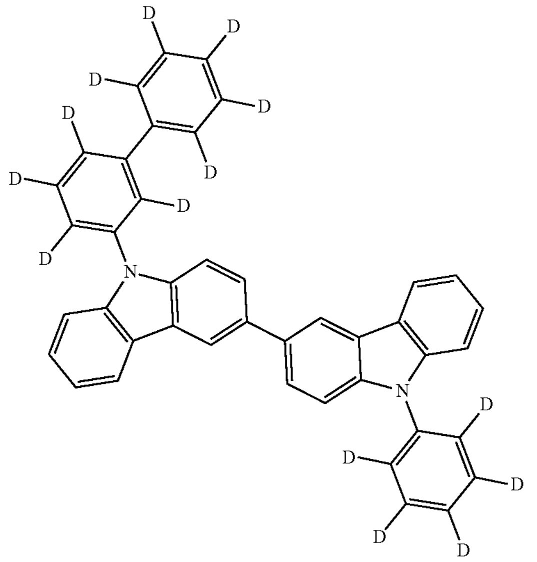
2-4
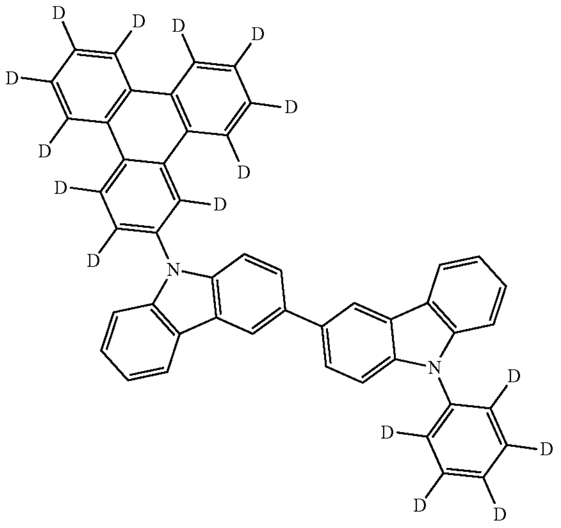

-continued
2-5
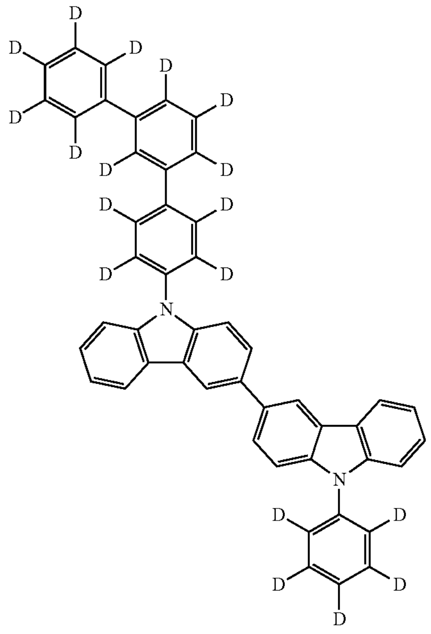
2-6
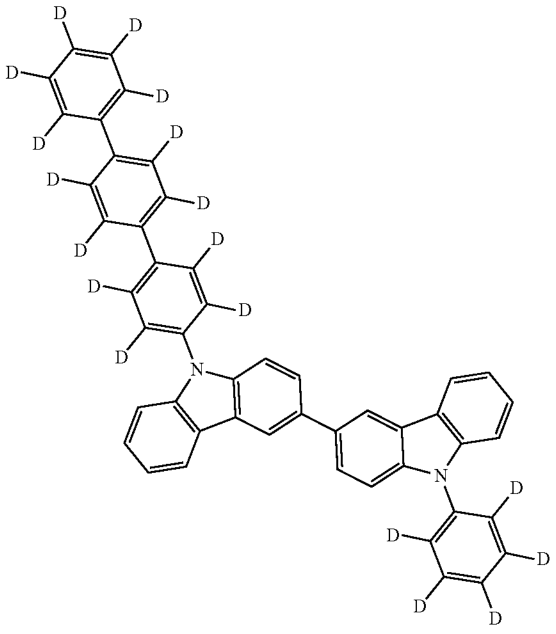
2-7
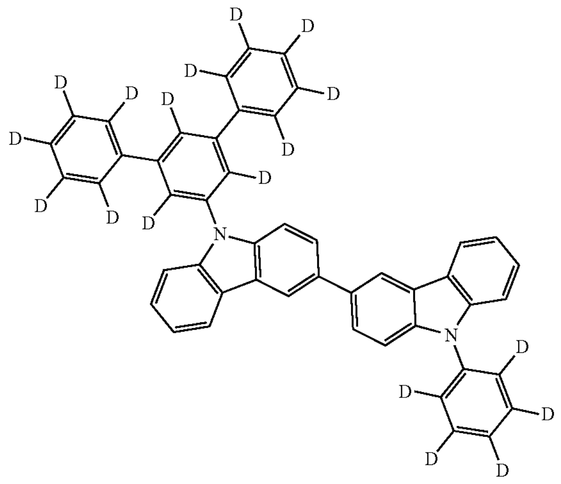
2-8
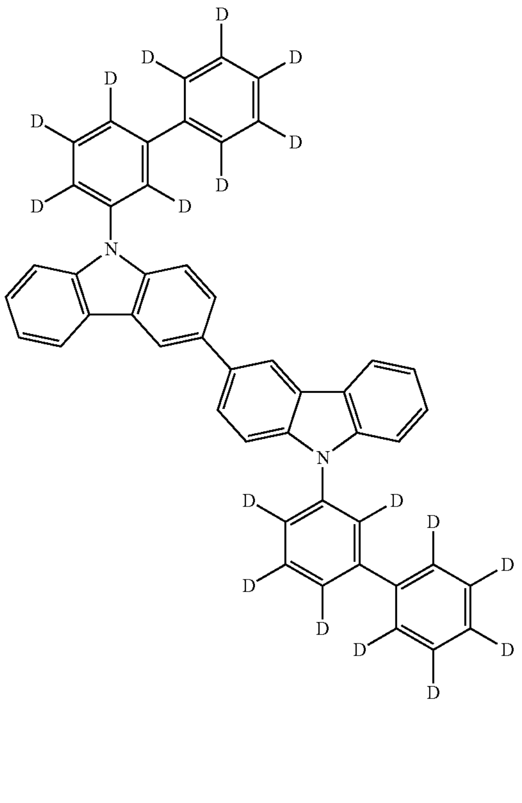

-continued
2-9
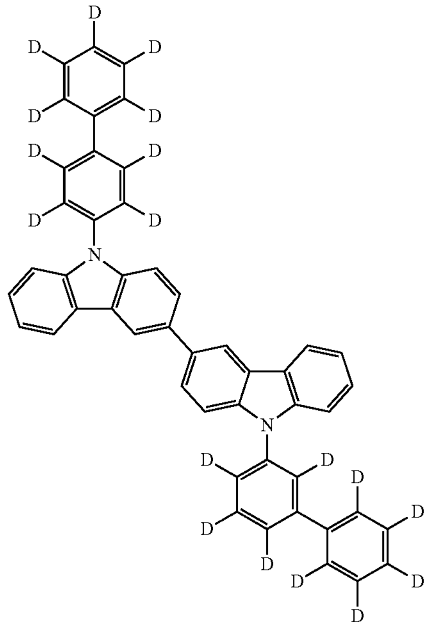
2-10
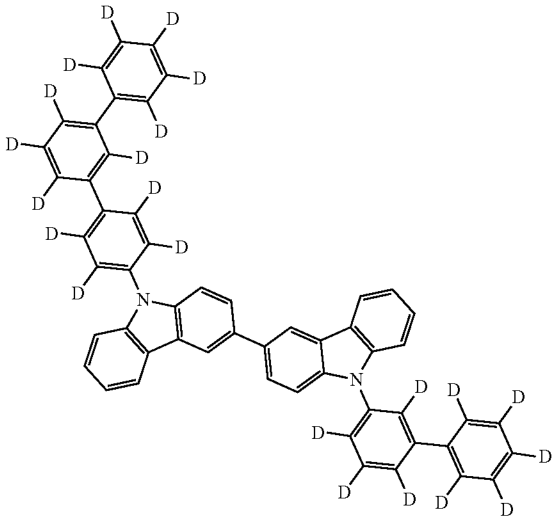
2-11
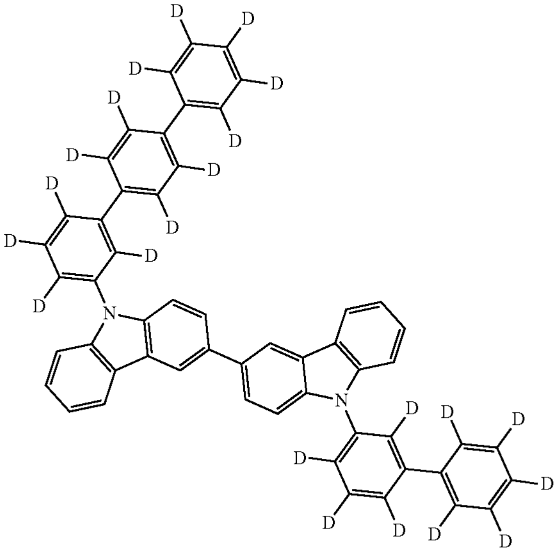
2-12
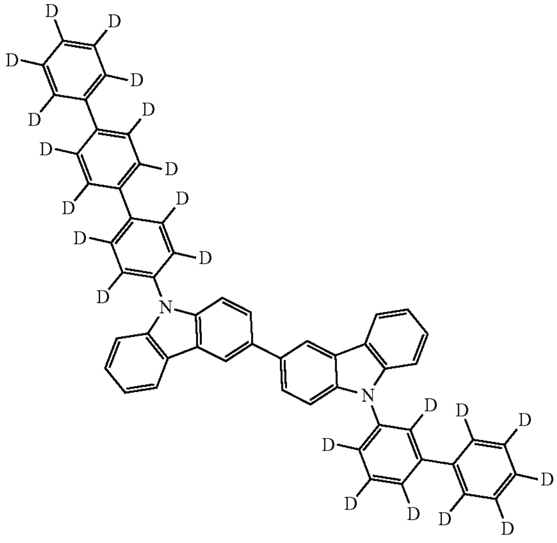

-continued
2-13
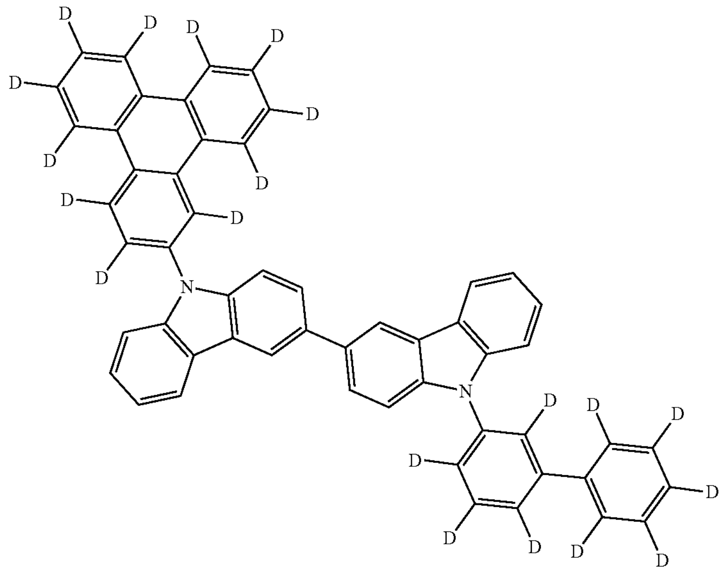
2-14
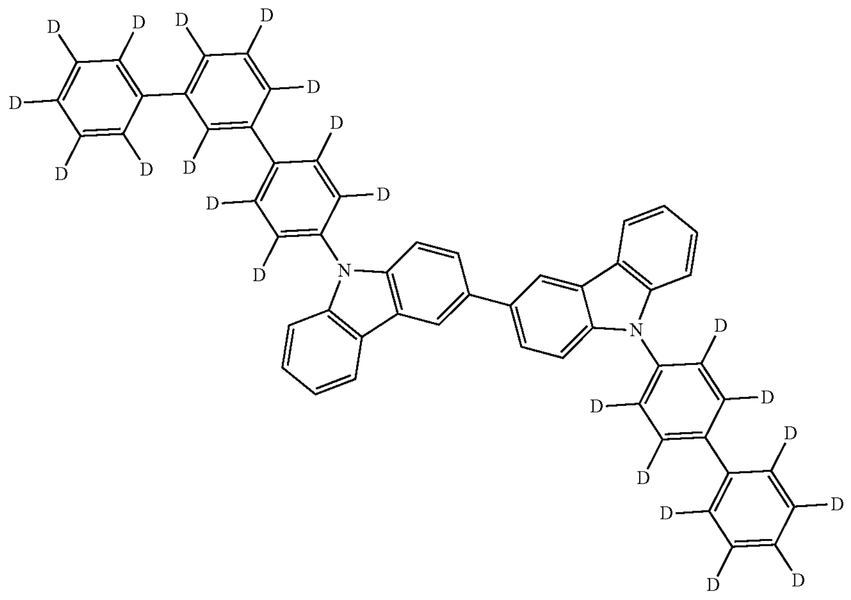

-continued
2-15
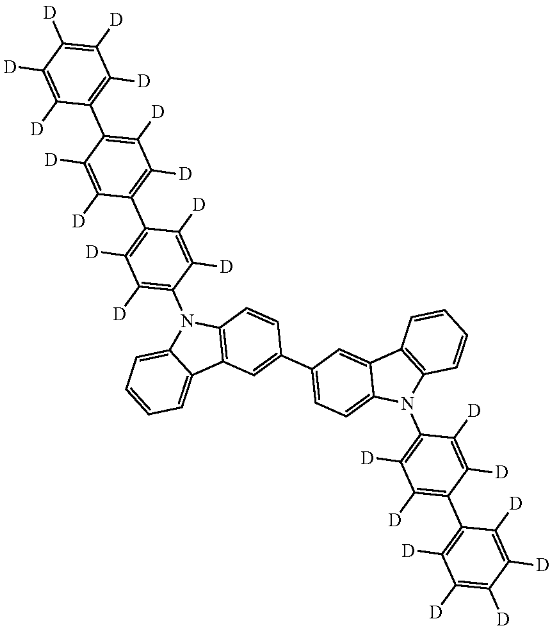
2-16
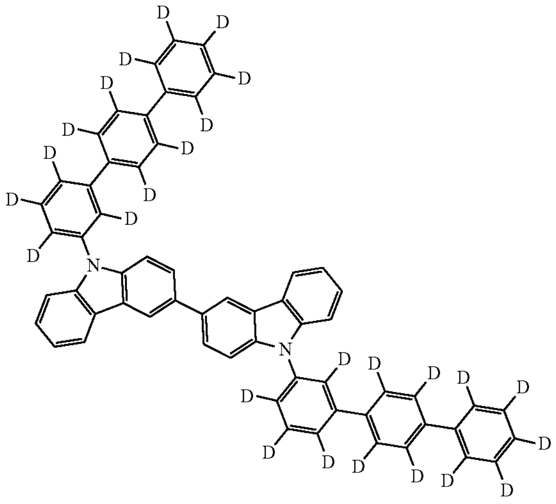
2-17
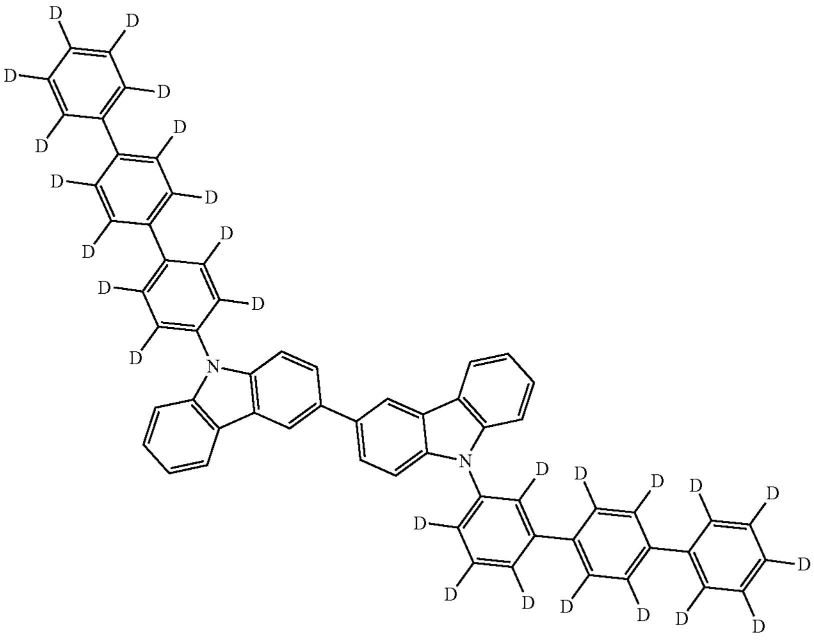

-continued
2-18
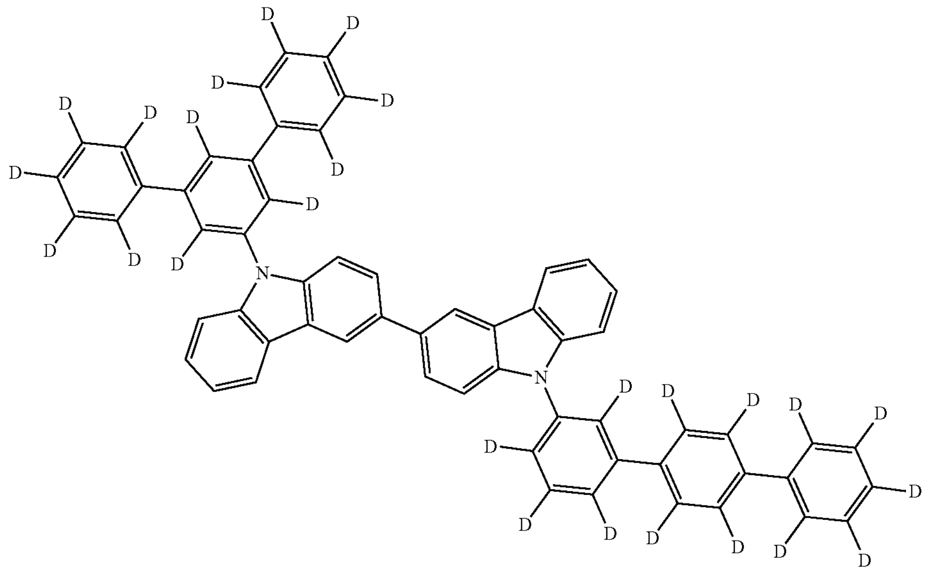
2-19
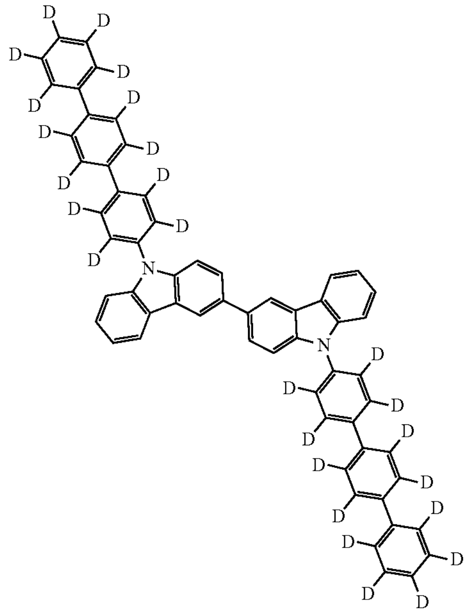
2-20
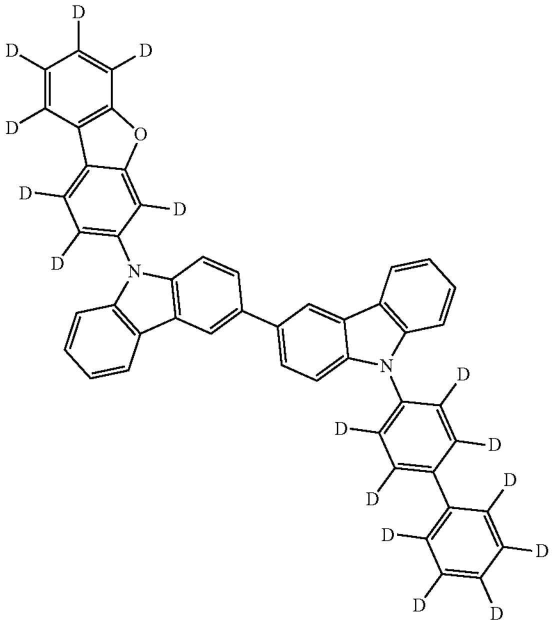

-continued
2-21
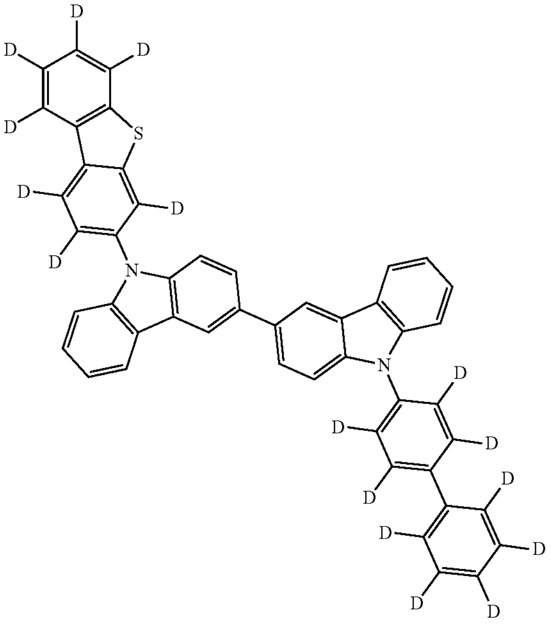
2-22
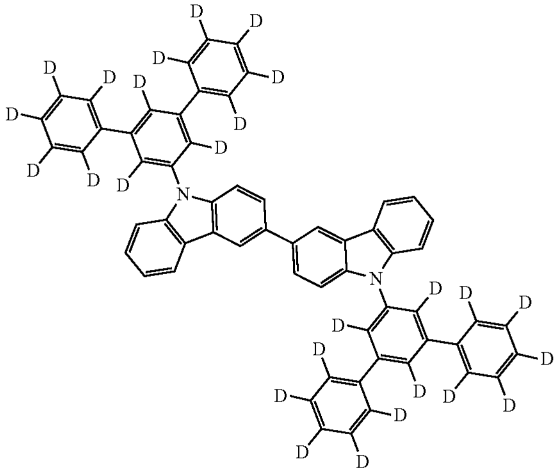
2-23
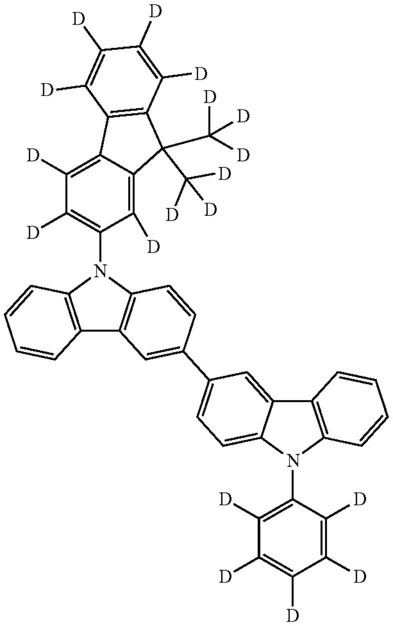
2-24
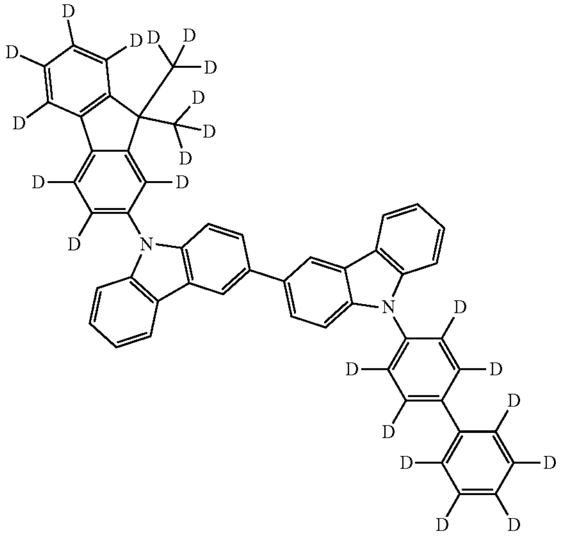

-continued
2-25
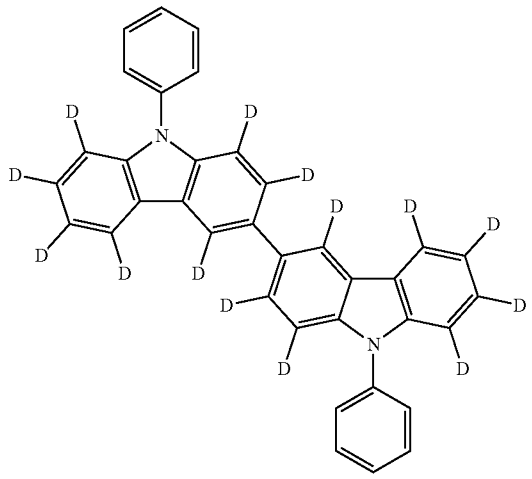
2-26
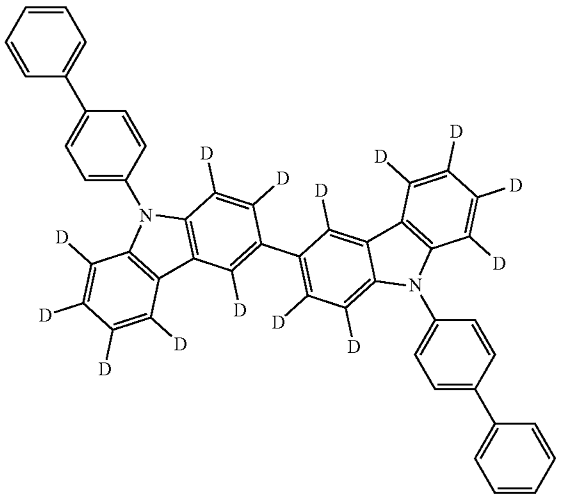
2-27
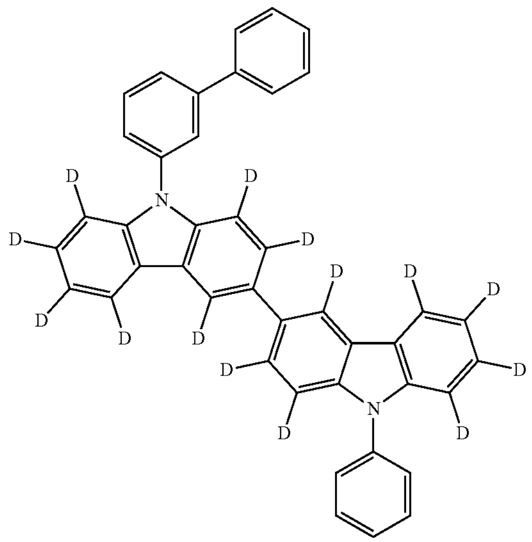
2-28
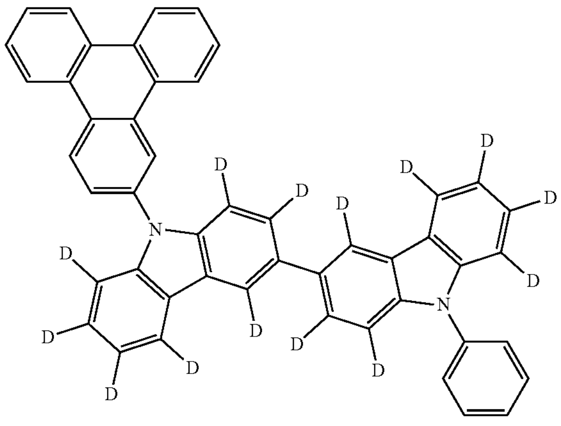

-continued
2-29
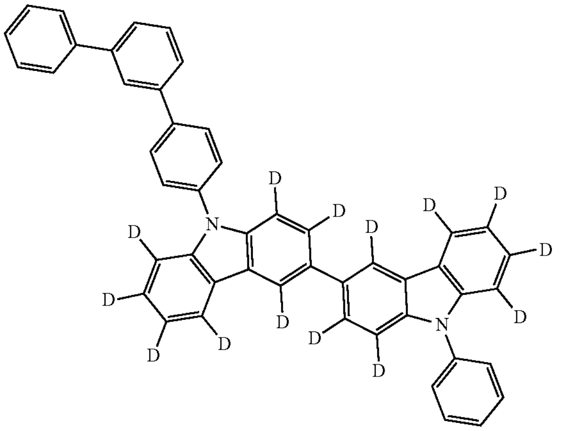
2-30
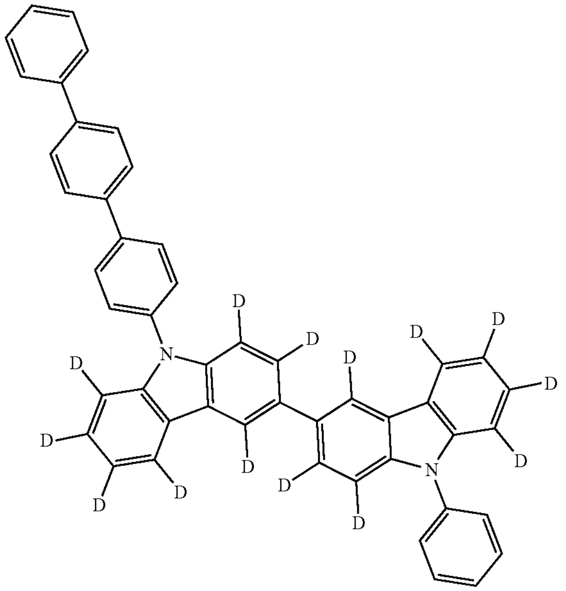
2-31
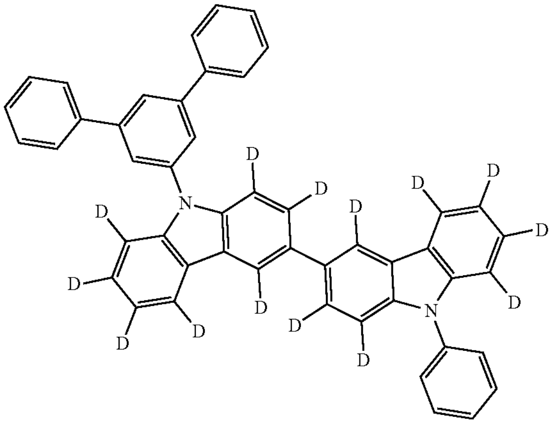
2-32
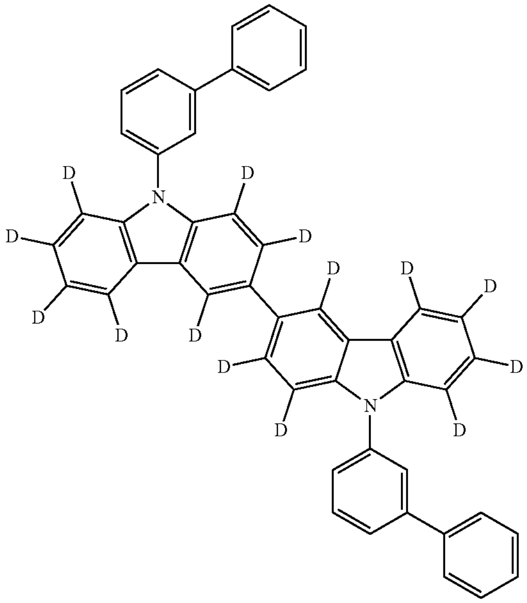

-continued
2-33
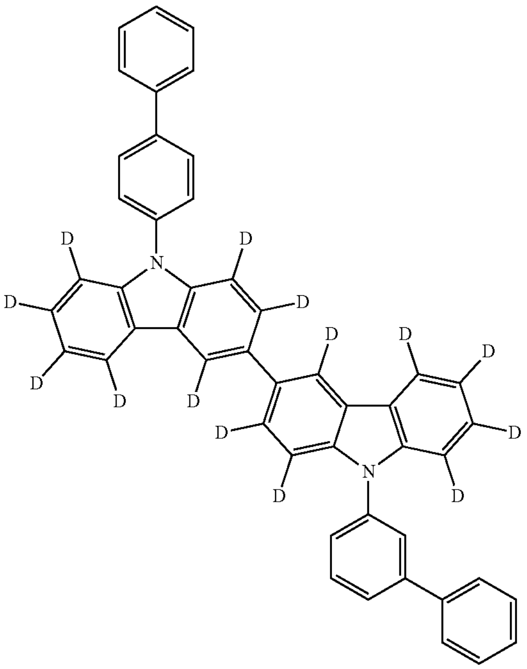
2-34
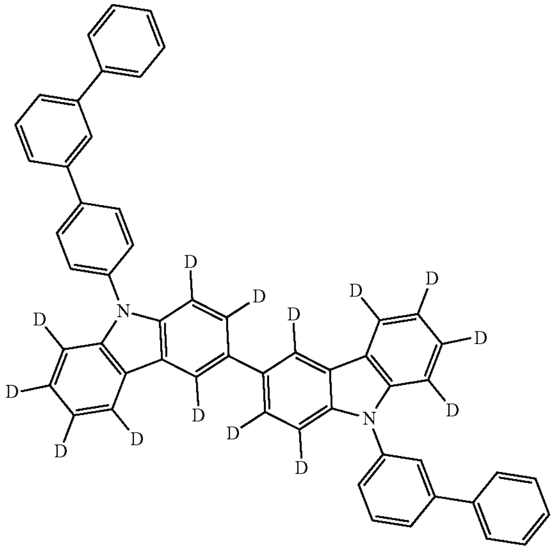
2-35
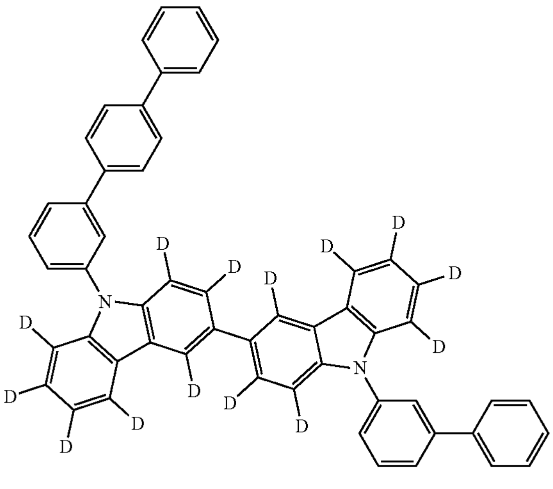
2-36
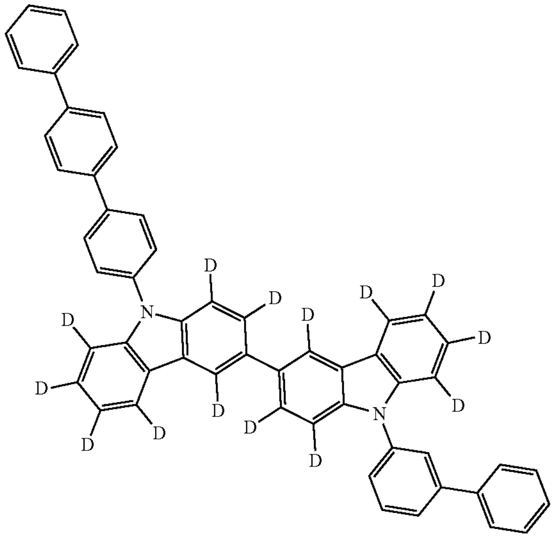

-continued
2-37
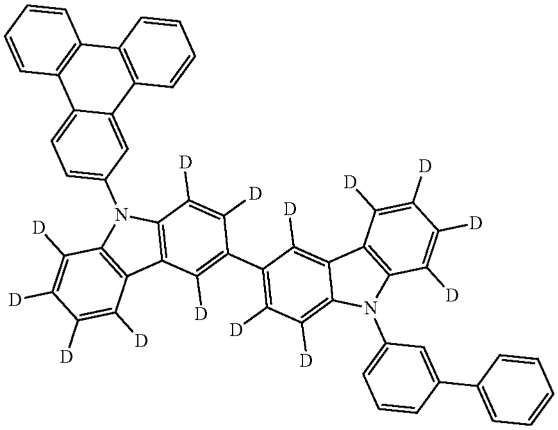
2-38
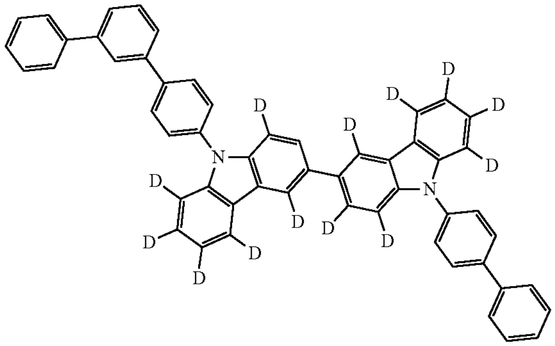
2-39
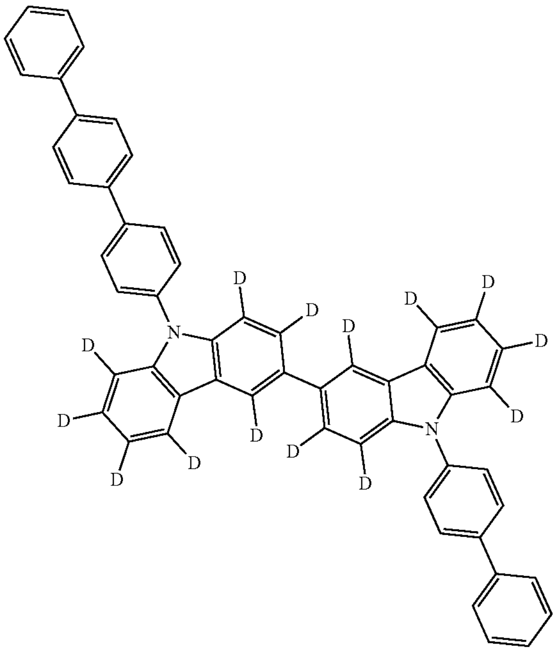
2-40
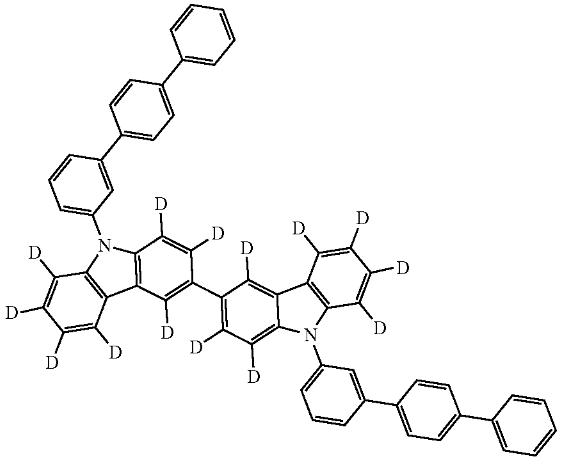

-continued
2-41
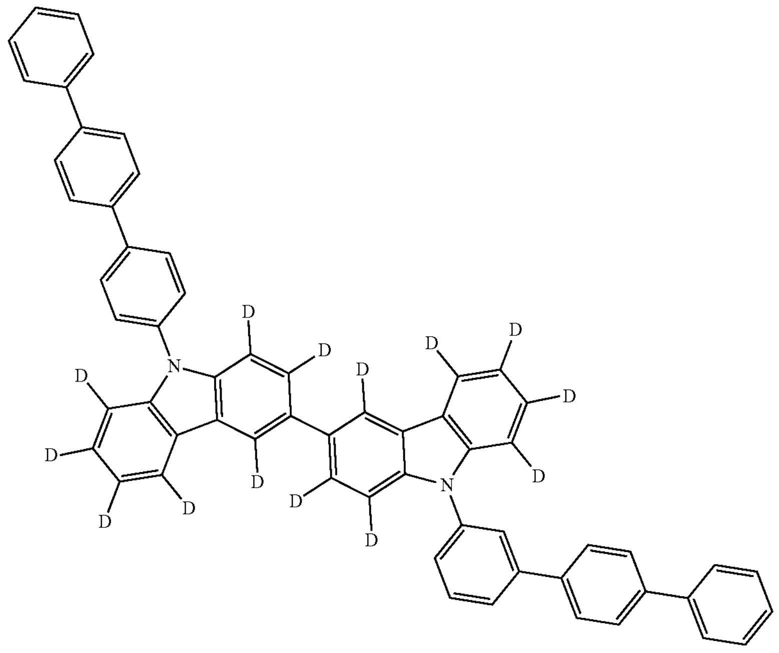
2-42
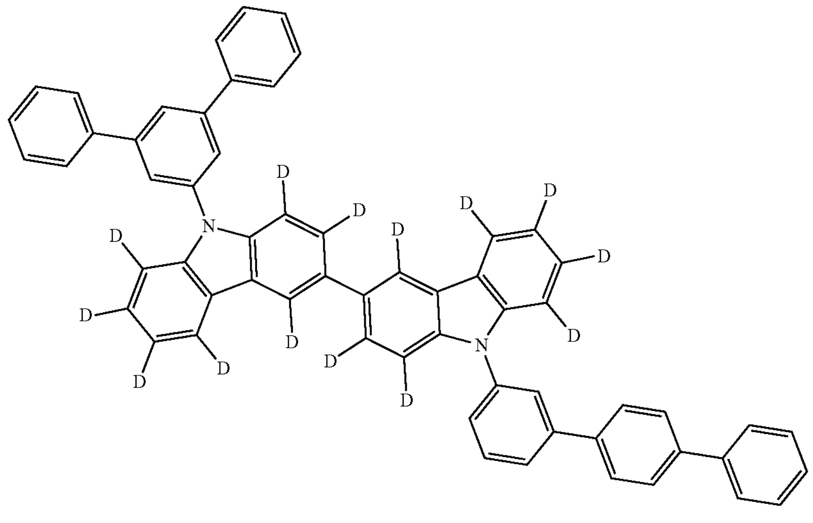

-continued
2-43
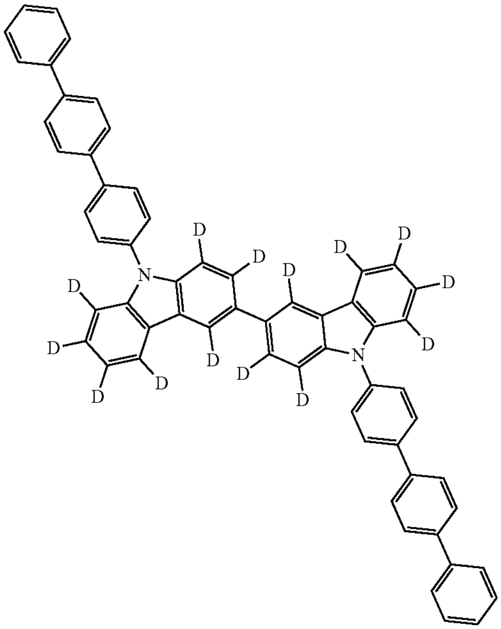
2-44
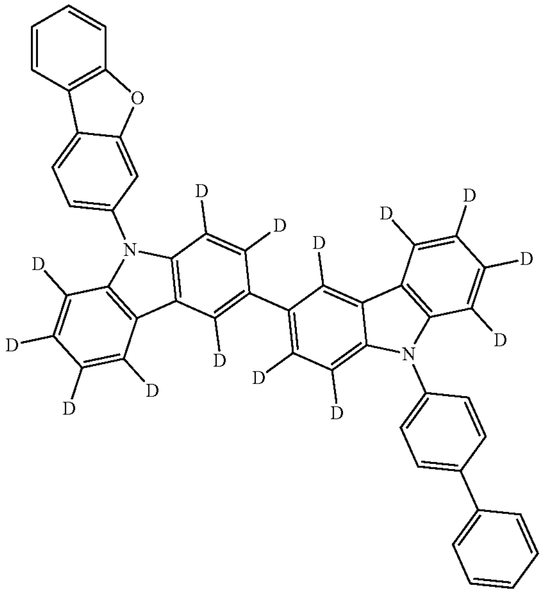
2-45
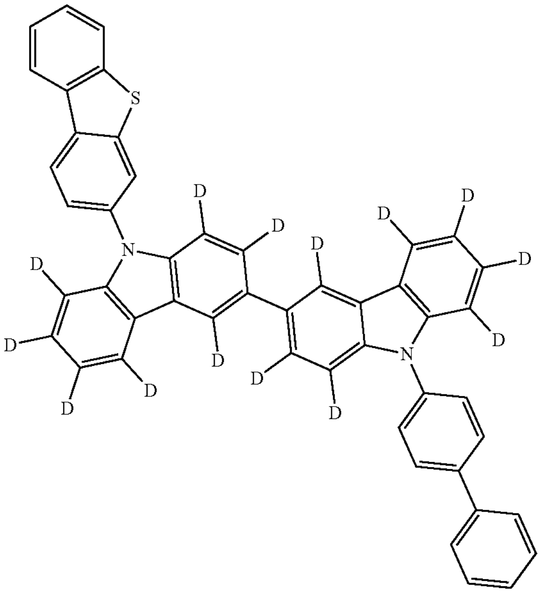
2-46
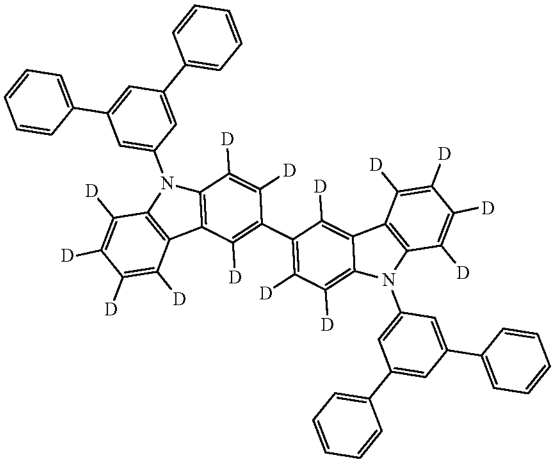

-continued
2-47
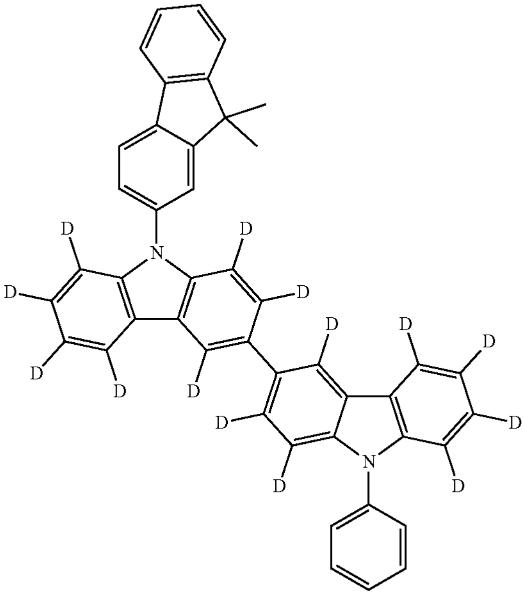
2-48
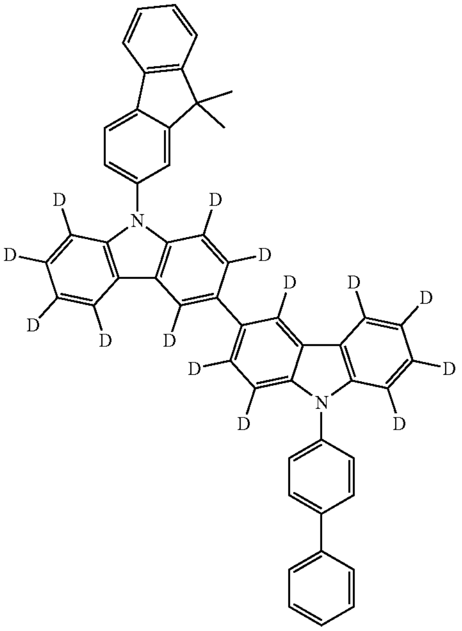
2-49
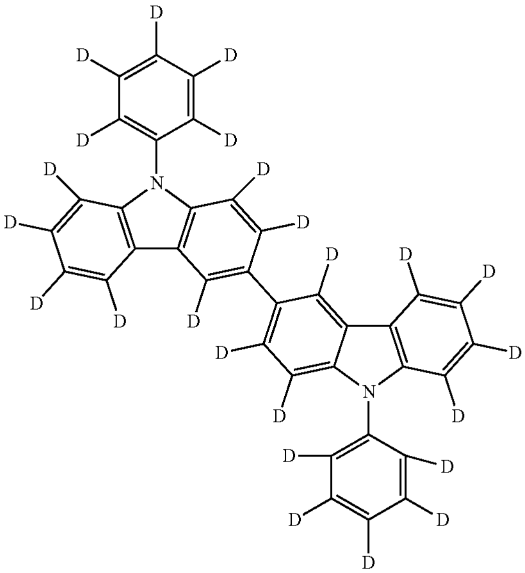
2-50
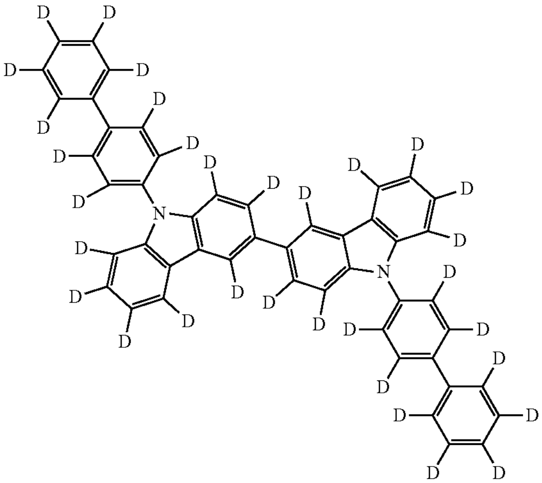

-continued
2-51
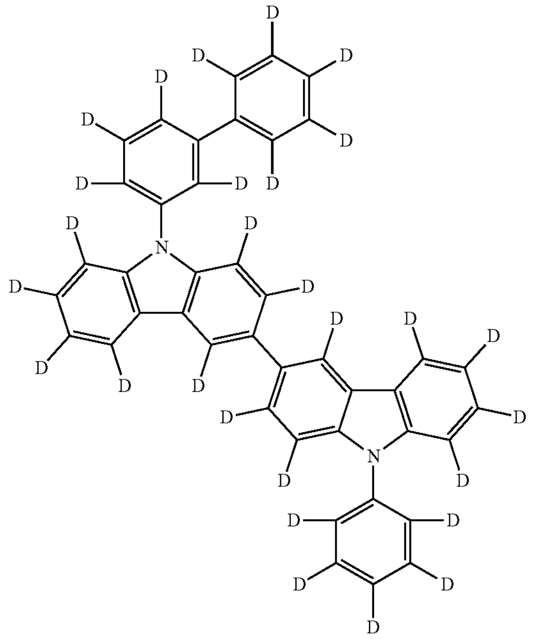
2-52
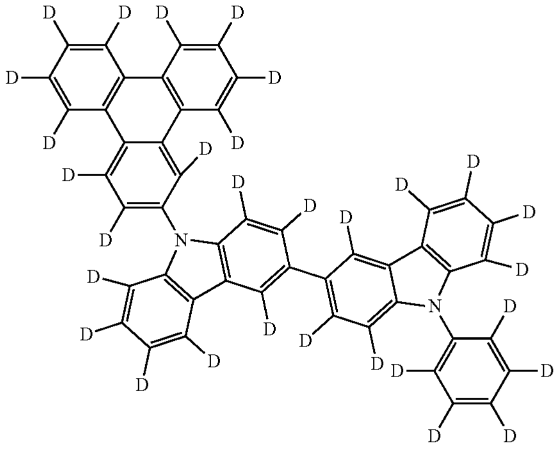
2-53
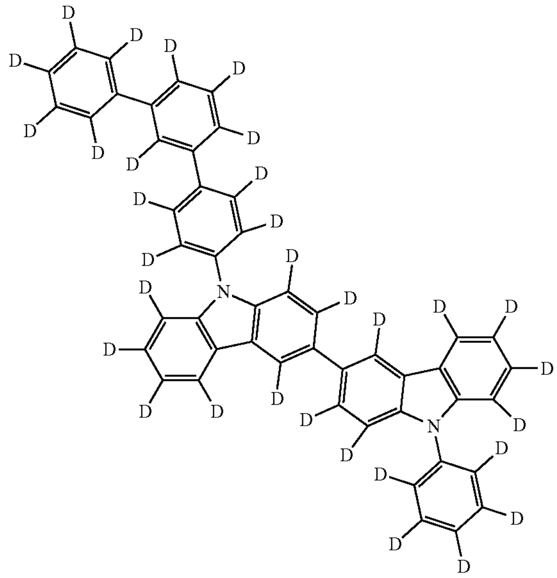
2-54
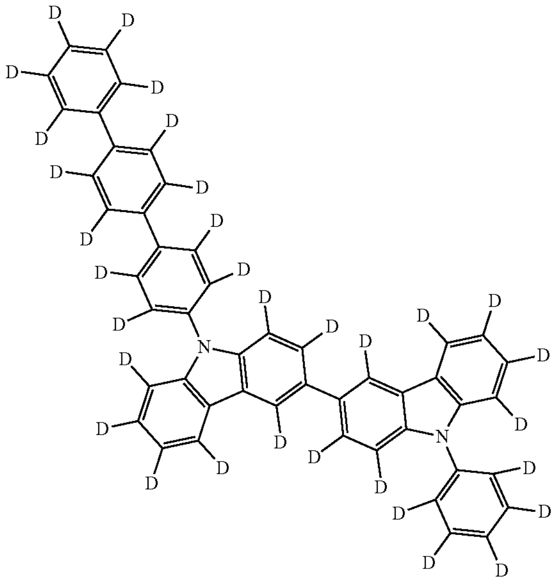

-continued
2-55
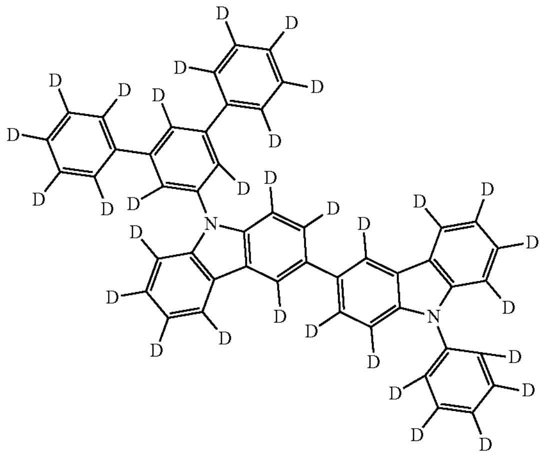
2-56
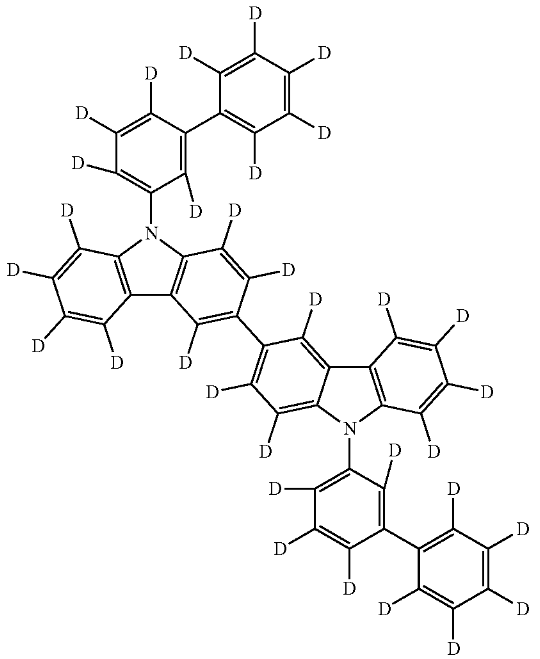
2-57
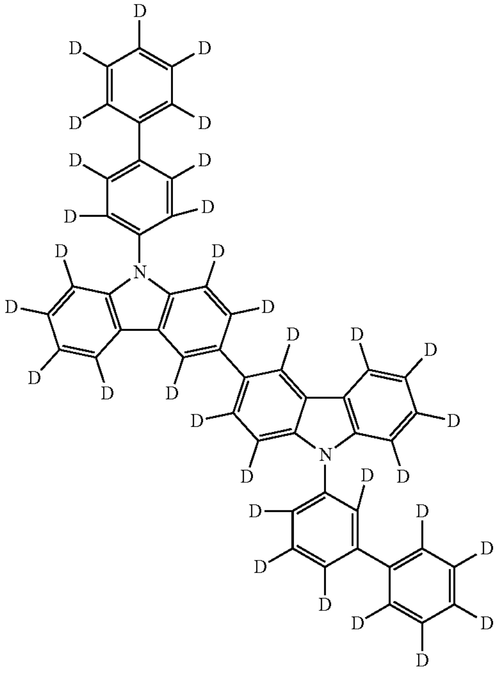
2-58
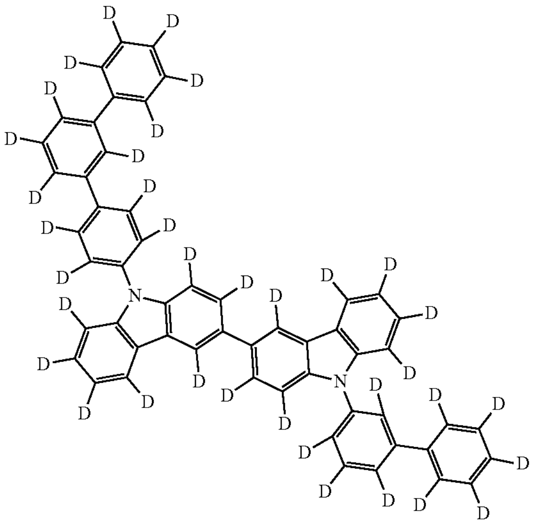

-continued
2-59
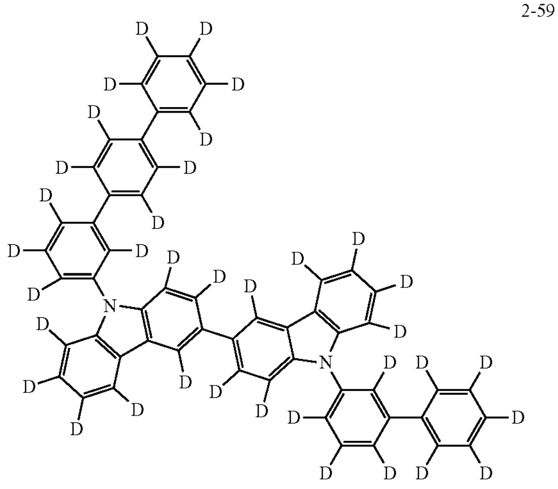
2-60
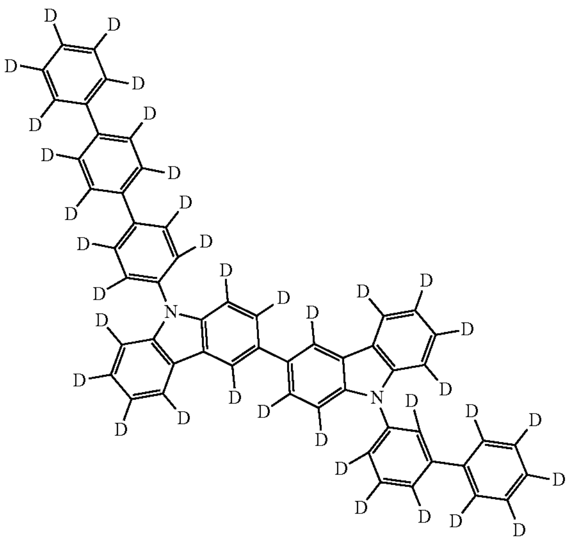
2-61
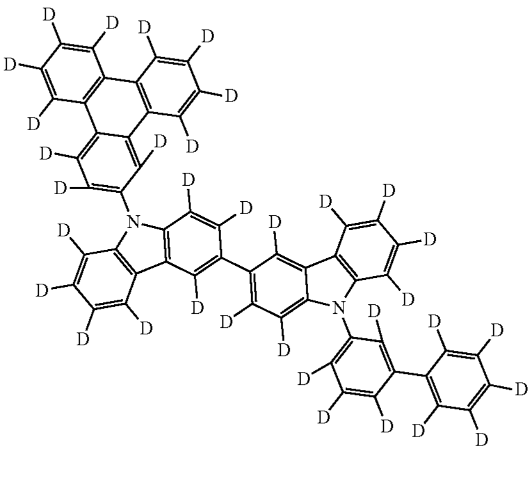
-continued
2-62
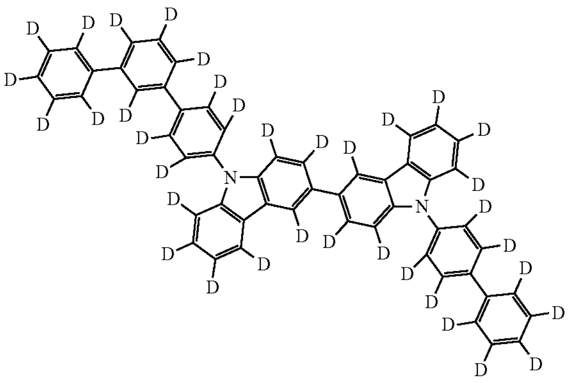
2-63
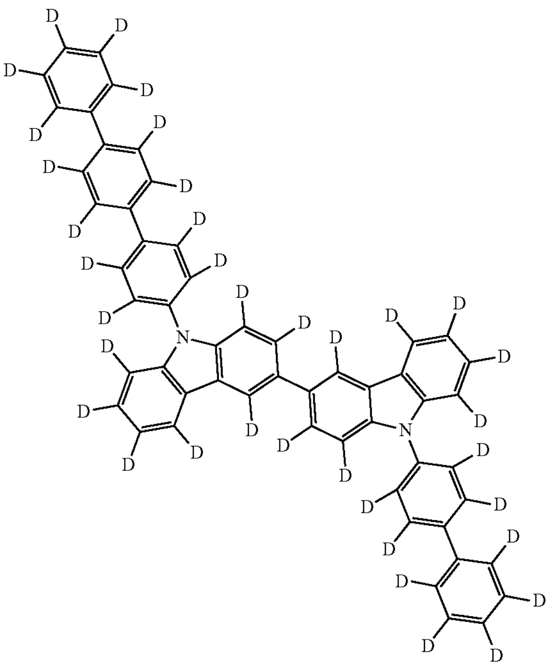
2-64
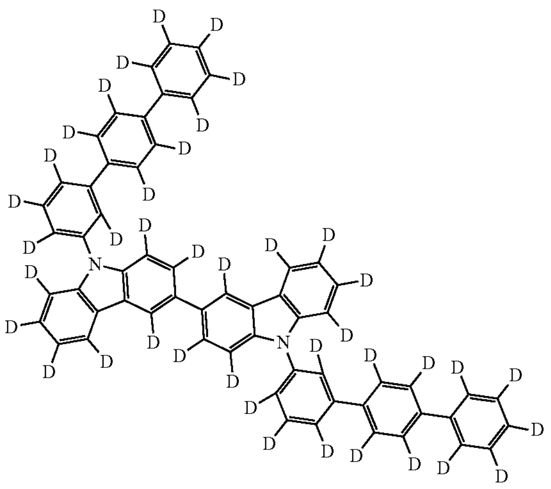

-continued
2-65
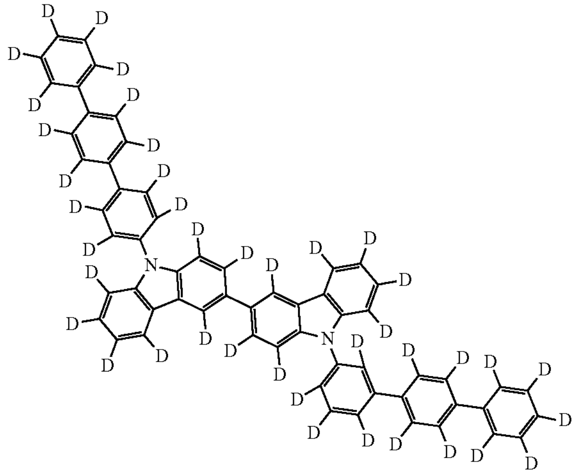
2-66
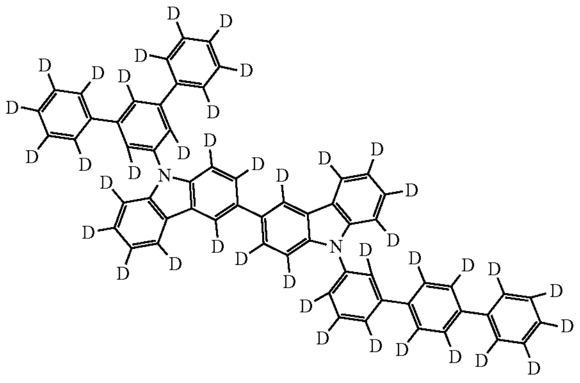
2-67
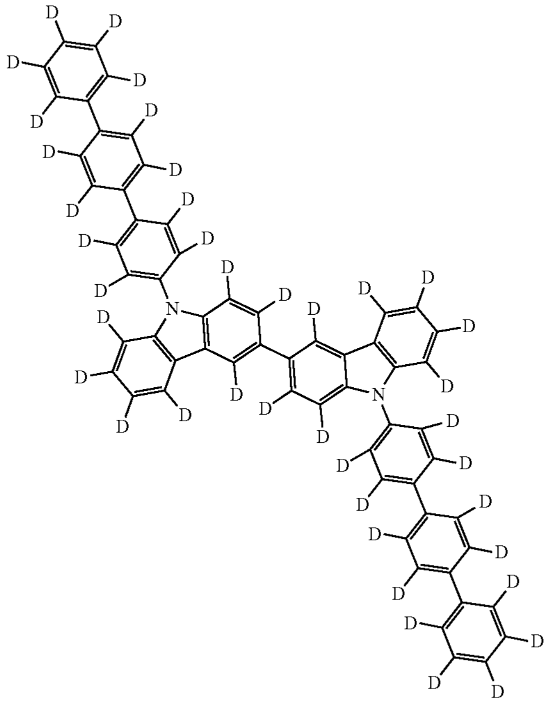
-continued
2-68
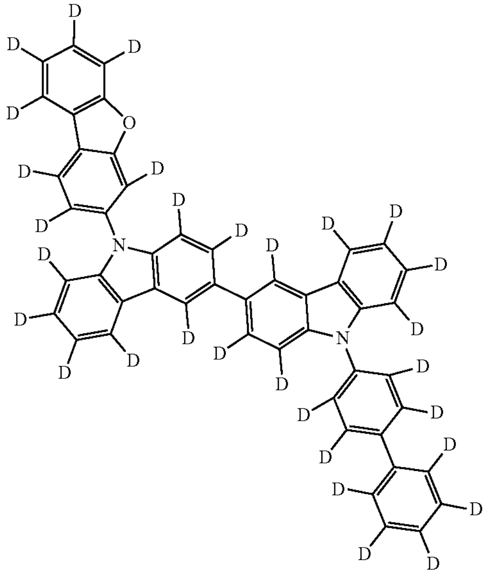
2-69
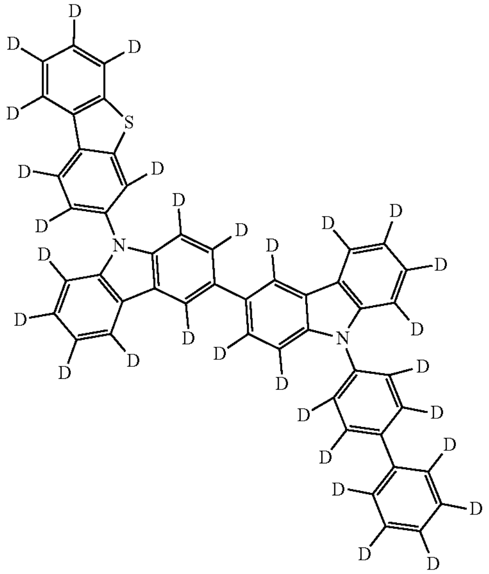
2-70
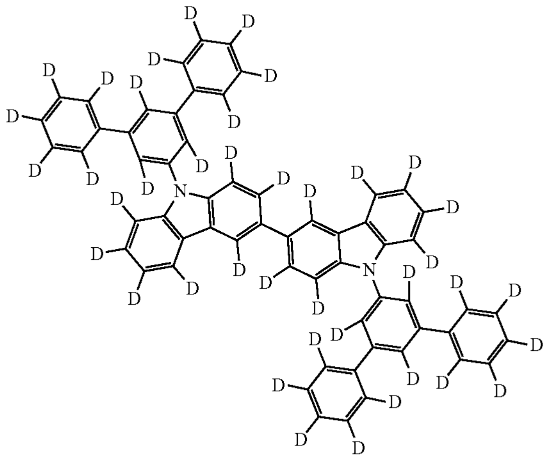

-continued
2-71
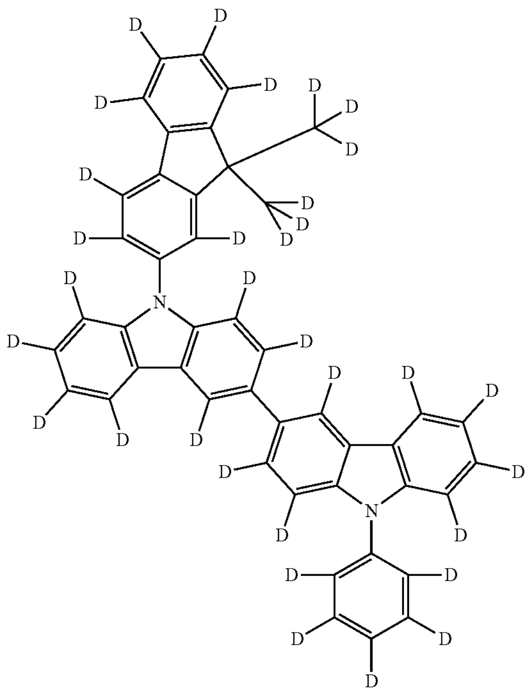
2-72
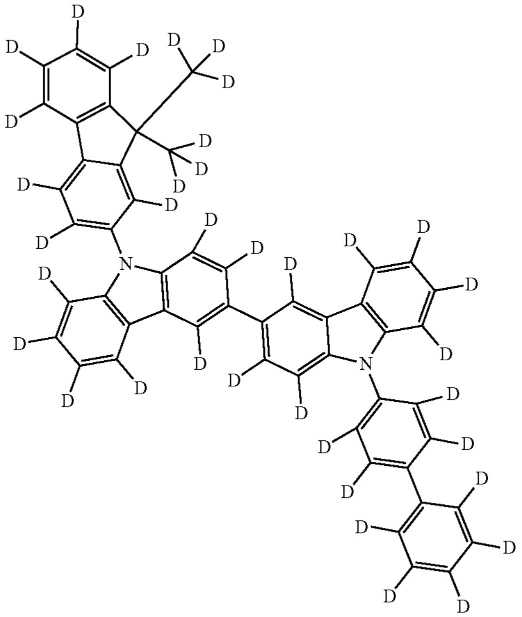
-continued
2-73
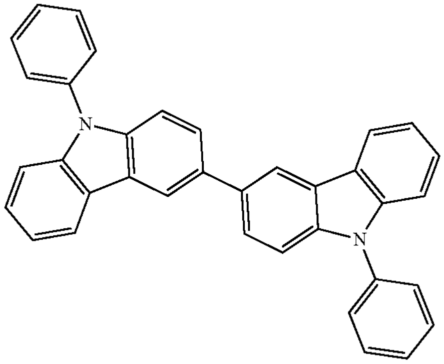
2-74
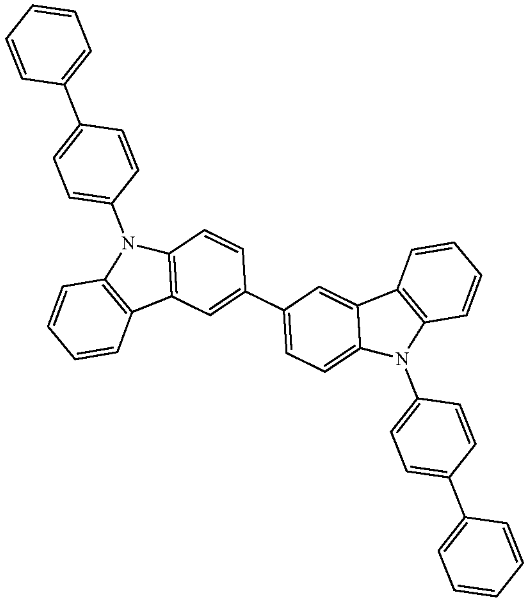
2-75
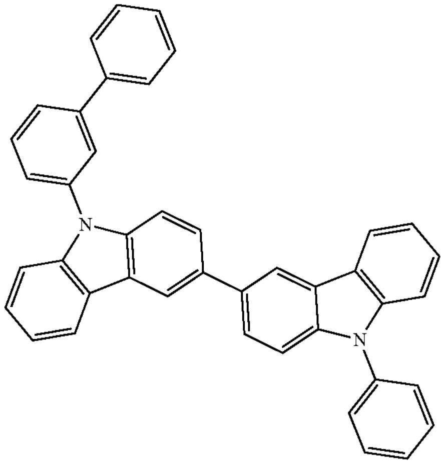

-continued
2-76
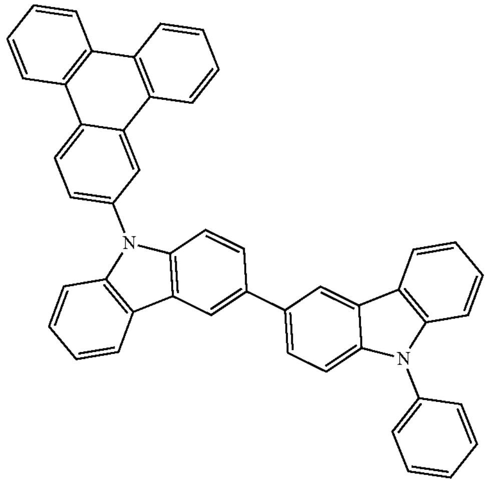
2-77
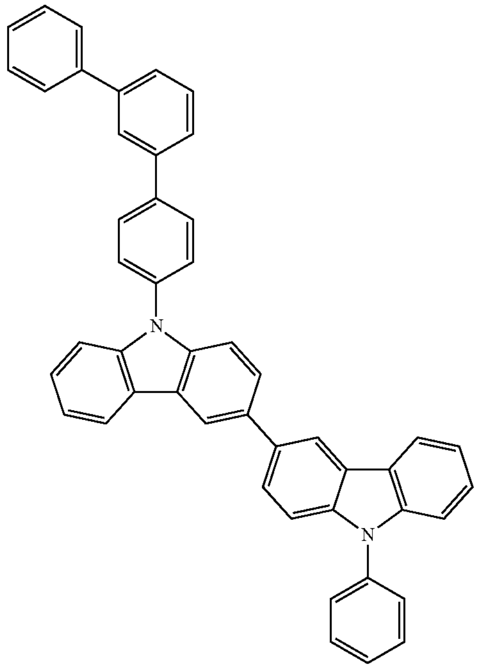
-continued
2-78
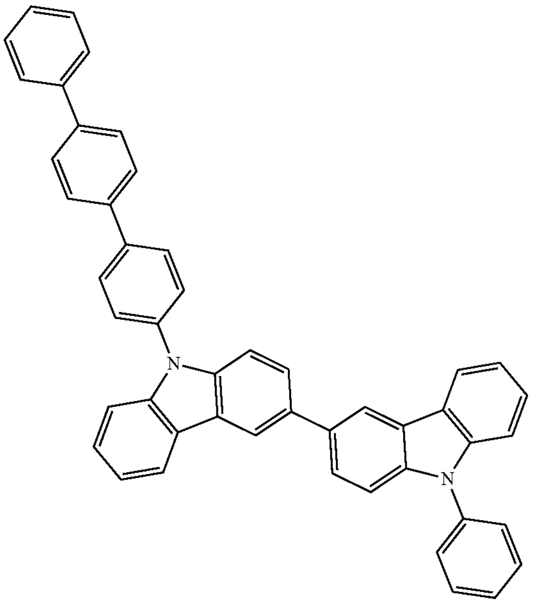
2-79
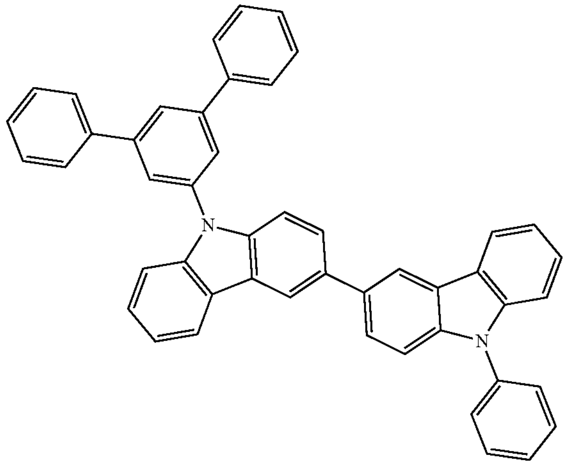

-continued
2-80
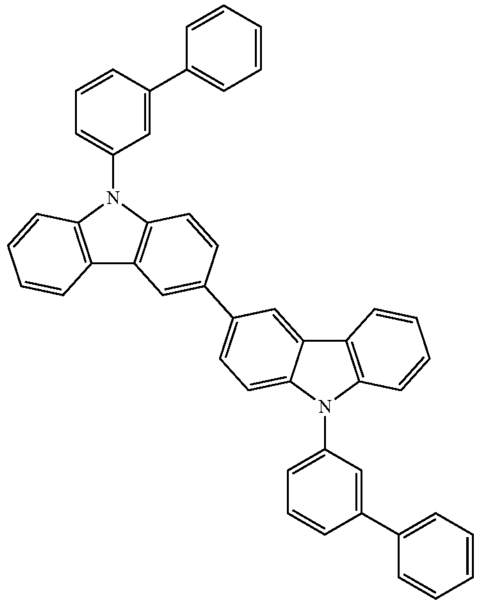
2-81
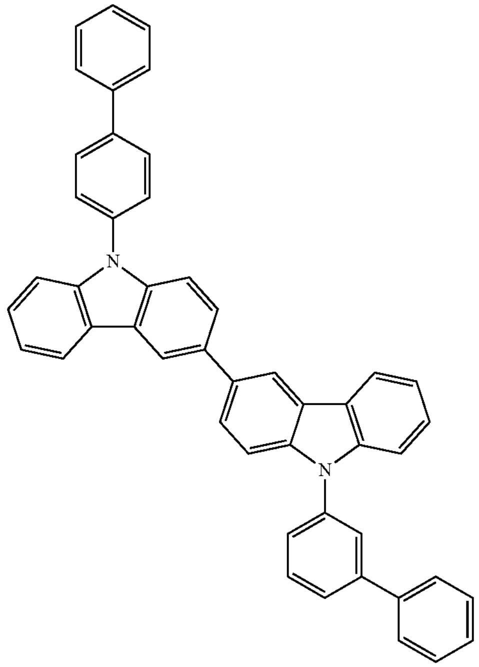
-continued
2-82
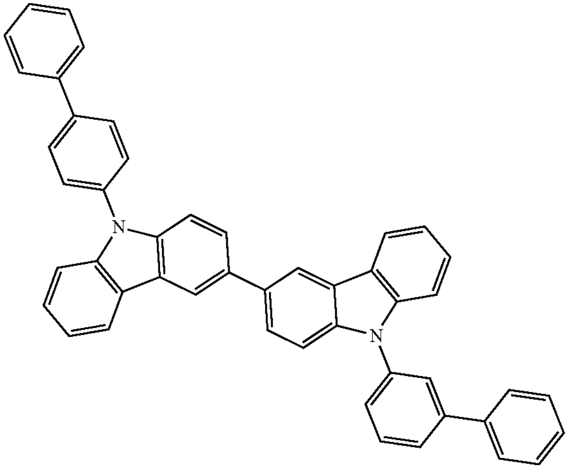
2-83
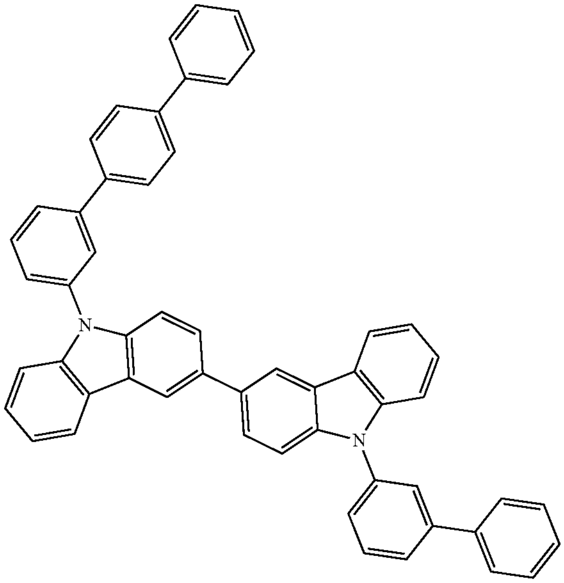
2-84
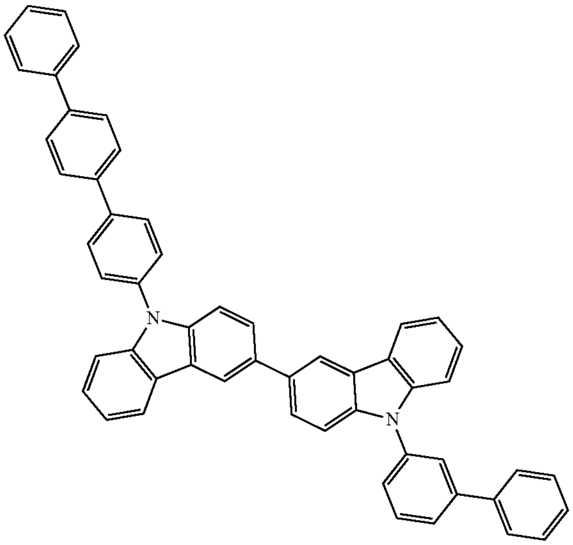

-continued
2-85
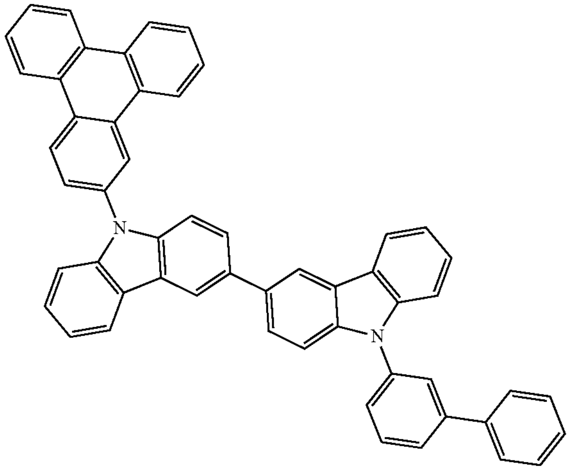
2-86
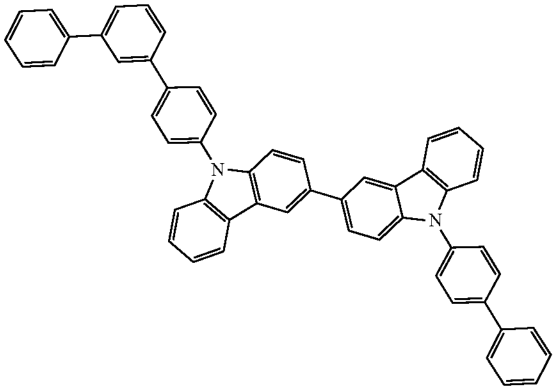
2-87
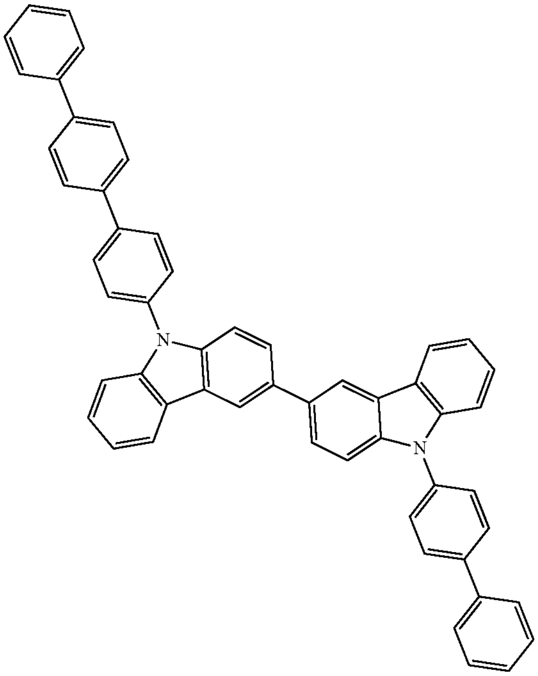
-continued
2-88
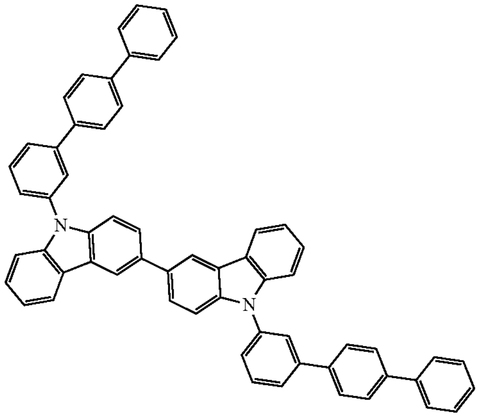
2-89
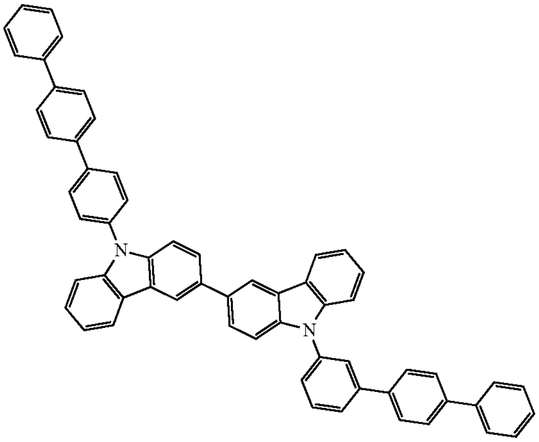
2-90
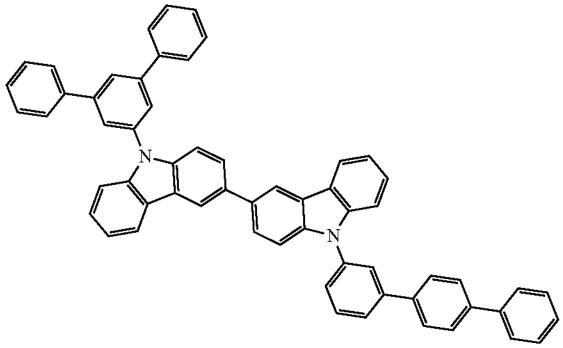

-continued
2-91
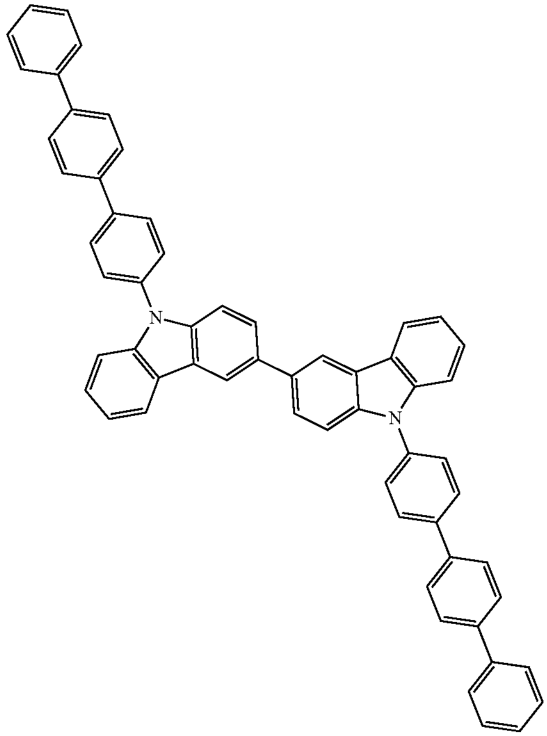
2-92
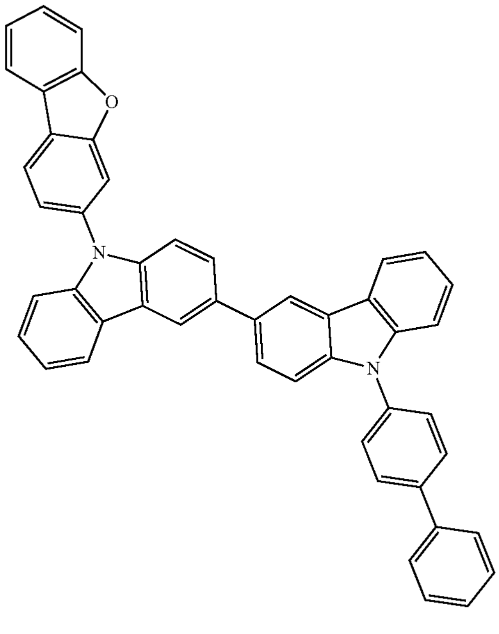
-continued
2-93
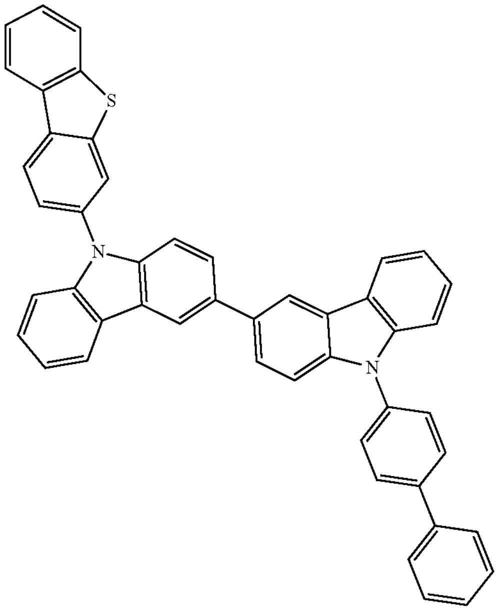
2-94
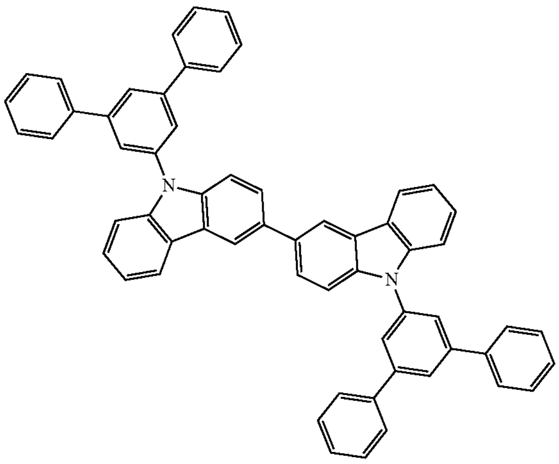

-continued 2-95

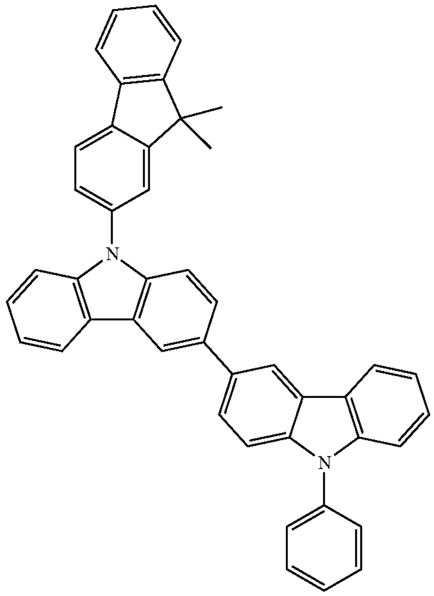

2-96

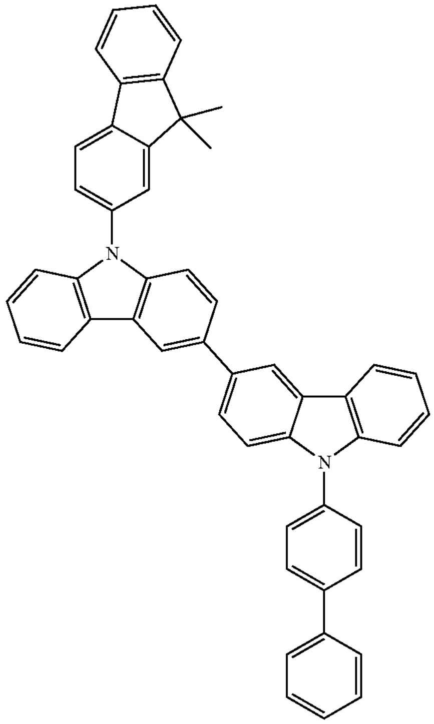

In the organic light emitting device of the present disclosure, the organic material layer may include the heterocyclic compound containing deuterium (e.g., "deuterated heterocyclic compound") of Formula 1, the deuterated heterocyclic compound of Formula 1 and the heterocyclic compound having the deuteration ratio of 0% (e.g., "non-deuterated heterocyclic compound") of Formula 2, or the deuterated heterocyclic compound of Formula 1 and the deuterated heterocyclic compound of Formula 2.

In the organic light emitting device of the present disclosure including both the N-type compound, i.e., the compound of Formula 1, and the P-type compound, i.e., the compound of Formula 2, as more deuterium is substituted on the compound of Formula 1, i.e., the N-type compound, the device performance may be further improved. Namely, the compound of Formula 1 may have a first deuteration ratio, and the compound of Formula 2 may have a second deuteration ratio being smaller than the first deuteration ratio.

In the organic light emitting device of the present disclosure, the compound of Formula 2 may be included in the EML of the organic material layer.

In the organic light emitting device of the present disclosure, the compound of Formula 2 may be included in the EML of the organic material layer as a host material.

In the organic light emitting device of the present disclosure, the host material in the EML of the organic material layer may include both the heterocyclic compound of Formula 1 and the heterocyclic compound of Formula 2.

In an exemplary embodiment of the present disclosure, a composition for the organic material layer of the organic light emitting device including the heterocyclic compound of Formula 1 and the heterocyclic compound of Formula 2 is provided.

In the composition, a weight ratio of the heterocyclic compound of Formula 1 to the heterocyclic compound of Formula 2 may be 1:10 to 10:1, beneficially 1:8 to 8:1, more beneficially 1:5 to 5:1, further beneficially 1:2 to 2:1, but it is not limited thereto. For example, the weight ratio of the compound of Formula 2 may be greater than that of the compound of Formula 1. In this instance, the hole injection and transporting property in the device is improved so that the driving voltage of the device can be reduced.

The composition can be used for forming the organic material of the organic light emitting device. Preferably, the composition can be used for forming the host of the EML.

The composition is a form in which two or more compounds are simply mixed. Materials in a powder state may be mixed before forming the organic material layer of the organic light emitting device, or compounds in a liquid state may be mixed at an appropriate temperature or higher. The composition is in a solid state below the melting point of each material, and can be maintained in a liquid state by adjusting the temperature.

The composition may further include materials known in the art, such as solvents and additives.

The organic light emitting device according to an exemplary embodiment of the present disclosure may be manufactured according to the manufacturing method and material of a conventional organic light emitting device, except for forming one or more organic material layers using the heterocyclic compound represented by Formula 1 and the heterocyclic compound represented by Formula 2.

In an exemplary embodiment of the present disclosure, a method of manufacturing an organic light emitting device includes preparing a substrate; forming a first electrode on the substrate; forming one or more organic material layer on the first electrode; forming a second electrode on the organic material layer. The step of forming one or more organic material layer includes using the composition for the organic material layer of the present disclosure.

In an exemplary embodiment of the present disclosure, the step of forming the organic material layer includes pre-mixing the heterocyclic compound of Formula 1 and the heterocyclic compound of Formula 2 and forming the organic material layer with the mixture by thermal vacuum deposition.

In this instance, the pre-mixing step may mean that the heterocyclic compound of Formula 1 and the heterocyclic compound of Formula 2 are mixed and stored in the bottle before depositing the mixture.

The pre-mixture may be referred to as the composition for the organic material layer in the present disclosure.

The anode may include a material having a relatively high work function, e.g., a transparent conductive oxide, metal or conductive polymer. For example, the anode may be formed of metals, such as vanadium, chromium, copper, zinc, gold, or their alloys; metal oxides, such as zinc oxide, indium oxide, indium tin oxide (ITO), or indium zinc oxide (IZO); a combination of metal and oxide, such as ZnO:Al or $SnO_2$:Sb; conductive polymers, such as poly(3-methylthiophene), poly[3,4-(ethylene-1,2-dioxy)thiophene](PEDOT), polypyrrole, or polyaniline, but it is not limited thereto.

The cathode may include a material having a relatively low work function, e.g., metal, metal oxide or conductive polymer. For example, the cathode may be formed of metal, such as magnesium, calcium, sodium, potassium, titanium, indium, yttrium, lithium, gadolinium, aluminum, silver, tin, lead, or their alloys; or a multi-layered structure such as LiF/Al or $LiO_2$/Al, but it is not limited thereto.

As the hole injection material, a known hole injection material may be used, for example, a phthalocyanine compound, such as copper phthalocyanine, disclosed in U.S. Pat. No. 4,356,429, starburst-type amine derivatives, such as tris(4-carbazolyl-9-ylphenyl)amine (TCTA), 4,4',4"-tri[phenyl(m-tolyl)amino]triphenylamine (m-MTDATA), or 1,3,5-tris[4-(3-methylphenylphenylamino)phenyl]benzene (m-MTDAPB), disclosed in Advanced Material, 6, p. 677 (1994), or conductive polymer, such as polyaniline/dodecylbenzenesulfonic acid, poly(3,4-ethylenedioxythiophene)/poly(4-styrenesulfonate), polyaniline/camphor sulfonic acid or polyaniline/poly(4-styrenesulfonate), and the like.

For example, a pyrazoline derivative, an arylamine derivative, a stilbene derivative, or a triphenyldiamine derivative may be used as a hole transporting material. The hole transporting material may be a low molecular weight or high molecular polymer material.

For example, an oxadiazole derivatives, anthraquinodimethane and its derivative, benzoquinone and its derivative, naphthoquinone and its derivative, anthraquinone and its derivative, tetracyanoanthraquinodimethane and its derivative, and a fluorenone derivative, diphenyldicyanoethylene and its derivative, a diphenoquinone derivative, metal complexes, such as 8-hydroxyquinoline and its derivative may be used as an electron transporting material. The electron transporting material may be a low molecular weight or high molecular polymer material.

As the electron injection material, LiF is typically used, but it is not limited thereto.

A red, green, or blue light emitting material may be used as the light emitting material, and if necessary, two or more light emitting materials may be mixed and used. In this case, two or more light emitting materials may be deposited from individual sources, or may be premixed and deposited from a single source. In addition, the light emitting material may be a fluorescent material or a phosphorescent material. As the light emitting material, a material that emits light by combining holes and electrons respectively injected from the anode and the cathode may be used alone, but materials in which the host material and the dopant material together participate in light emission may be used.

When host materials of a light emitting material is mixed and used, the host materials of the same type may be mixed and used, or the host materials of a different type may be mixed and used. For example, two or more types of an n-type host material or a p-type host material may be selected and used as the host material of the light emitting layer.

The organic light emitting device according to the exemplary embodiment of the present disclosure may be a top emission type, a bottom emission type, or a double side emission type depending on a material used.

The heterocyclic compound according to an exemplary embodiment of the present disclosure may act with similar principle to that applied to an organic light emitting device in an organic electronic device including an organic solar cell, an organic photoreceptor, and an organic transistor.

Hereinafter, the present specification will be described in more detail through examples, but these are only for illustrating the present disclosure and not for limiting the scope of the present disclosure.

Synthesis

[Synthesis 1] The compound 3 (E)

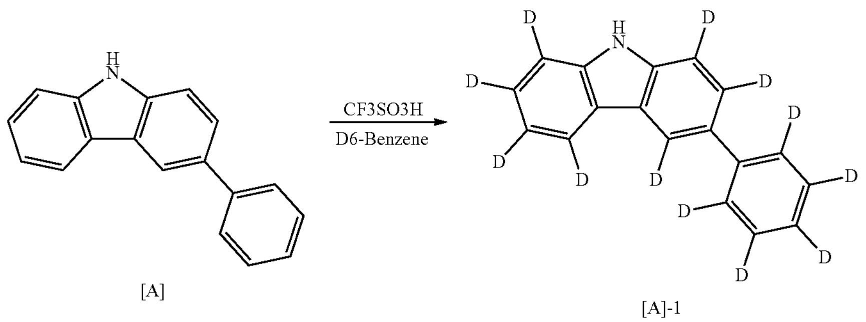

[A]

[A]-1

-continued
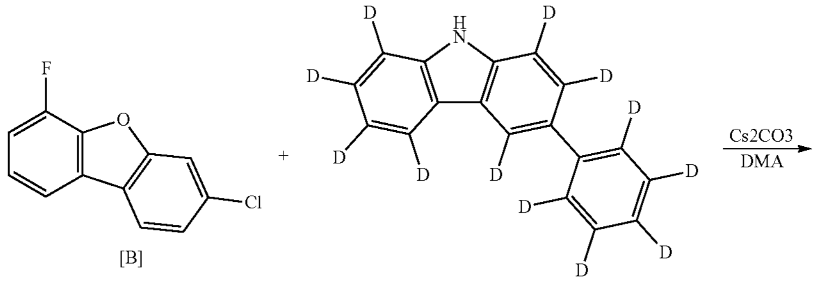
[B] [A]-1
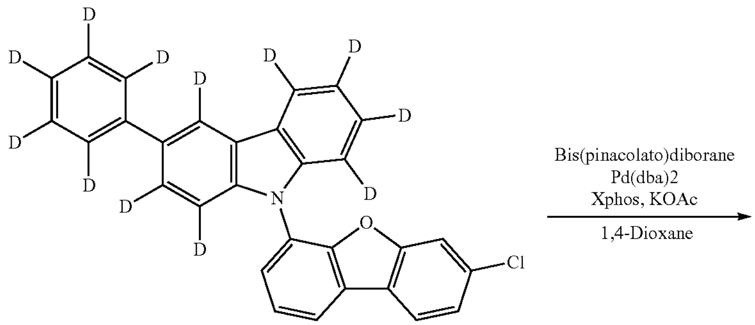
3-1
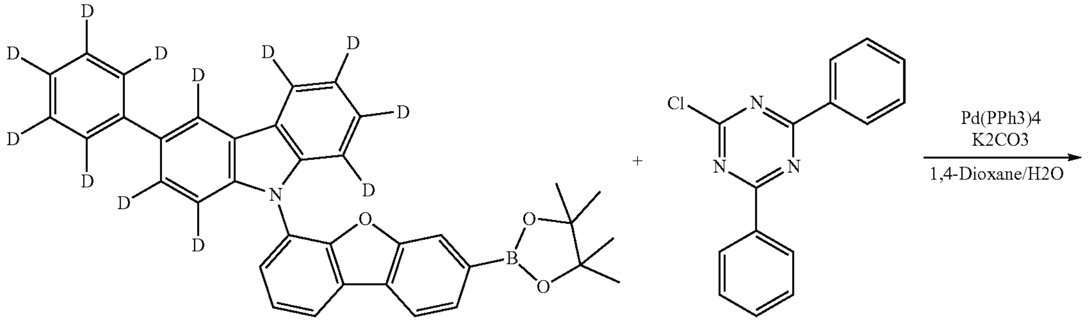
3-2 [C]
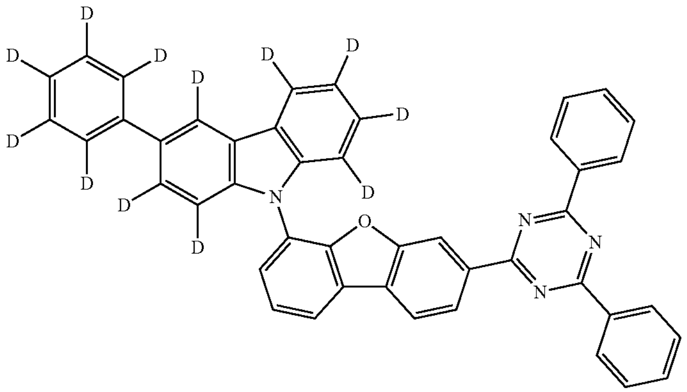
3[E]

(1) The Compound [A]-1

In the one-neck round bottom flask, a mixture of 3-phenyl-9H-carbazole (10 g, 0.041 mol), triflic acid (34 g, 0.23 mol) and D6-benzene (200 mL) was refluxed at 70° C. After quenching and extraction with dichloromethane and $H_2O$, the resultant was concentrated and filtered through silica gel. After concentration, the resultant was treated with methanol to obtain the compound [A]-1. (7.02 g, 67%)

(2) The Compound 3-1

In the one-neck round bottom flask, a mixture of 3-chloro-6-fluorodibenzo[b, d]furan (10 g, 0.045 mol), 3-(phenyl-d5)-9H-carbazole-1,2,4,5,6,7,8-d7(3-(phenyl-d5)-9H-carbazole-1,2,4,5,6,7,8-d7) (12.64 g, 0.050 mol), $Cs_2CO_3$ (29.32 g, 0.09 mol) and dimethylacetamide (100 mL) were refluxed at 170° C. After cooling, the resultant was filtered to remove the solvent and purified by column to obtain the compound 3-1. (17.03 g, 83%)

(3) The Compound 3-2

In the one-neck round bottom flask, a mixture of 9-(7-chlorobenzo[b,d]furan-4-yl)-3-(phenyl-d5)-9H-carbazole-1,2,4,5,6,7,8-d7 (17.03 g, 0.037 mol), bis(pinacolato)diborn ((18.79 g, 0.074 mol), $Pd(dba)_2$ (3.39 g, 0.0037 mol), Xphos (3.53 g, 0.0074 mol), potassium acetate (10.89 g, 0.11 mol) and 1,4-dioxane (170 mL) was refluxed at 120° C. After cooling, the resultant was concentrated and filtered through silica gel to obtain the compound 3-2 (19.85 g, 98%)

(4) The Compound 3[E]

In the one-neck round bottom flask, a mixture of 3-(phenyl-d5)-9-(7-(4,4,5,5-tetramethyl-1,3,2-dioxaborolan-2-yl)dibenzo[b,d]furan-4-yl)-9H-carbazole-1,2,4,5,6,7,8-d7 (19.85 g, 0.036 mol), 2-chloro-4,6-diphenyl-1,3,5-triazine (10.71 g, 0.040 mol), $Pd(PPh_3)_4$ (2.08 g, 0.0018 mol), $K_2CO_3$ (9.95 g, 0.072 mol), 1,4-dioxane (170 mL) and water (80 mL) was refluxed at 120° C. After cooling, the resultant was concentrated and filtered through silica gel to obtain the compound 3 [E]. (17.16 g, 73%)

The following compound E was synthesized in the same manner as in the synthesis 1 except that intermediates A, B, and C of Table 1 were used.

TABLE 1
| Compound | A | B | C |
| --- | --- | --- | --- |
| 9 | 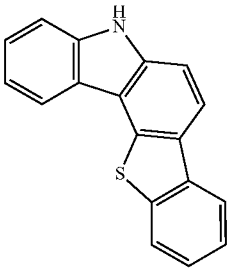 | 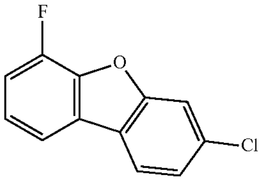 | 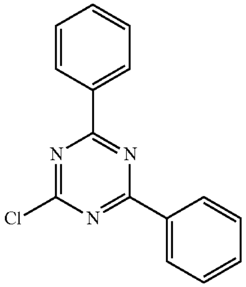 |
| 11 | 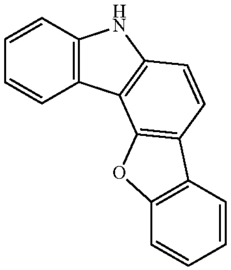 | 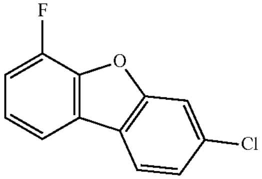 | 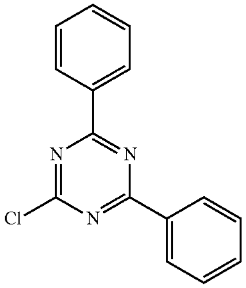 |
| 12 | 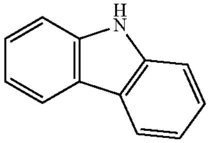 | 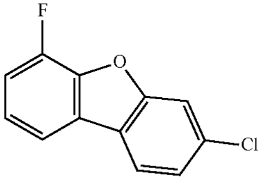 | 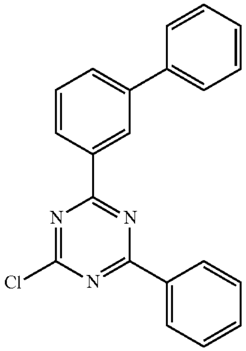 |

TABLE 1-continued
| | | | |
|---|---|---|---|
| 15 | 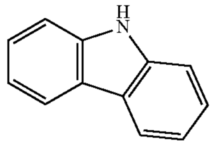 | 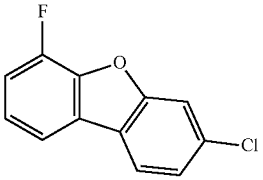 | 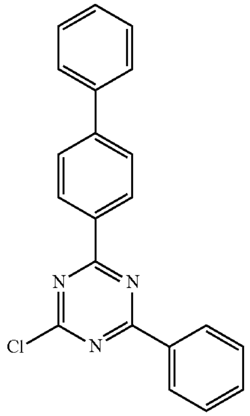 |
| 26 | 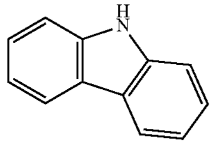 | 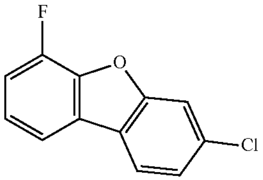 | 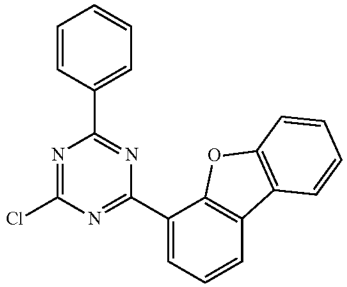 |
| 31 | 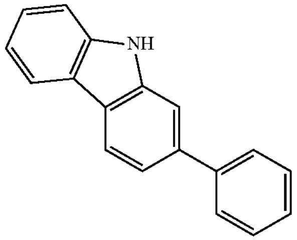 | 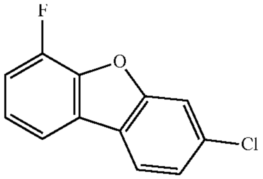 | 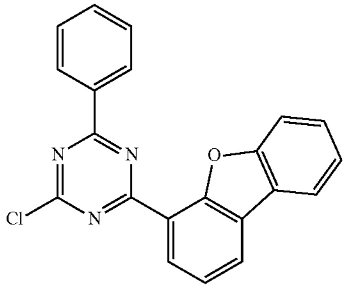 |

TABLE 1-continued
| | | | |
|---|---|---|---|
| 33 | 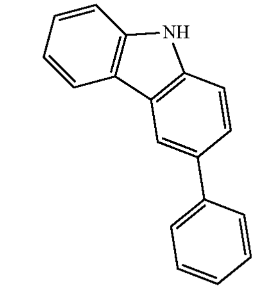 | 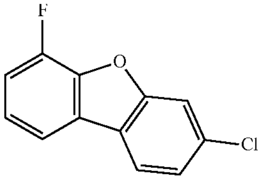 | 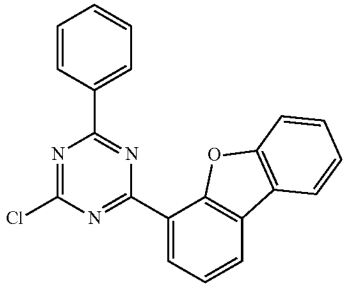 |
| 34 | 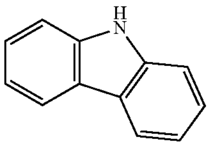 | 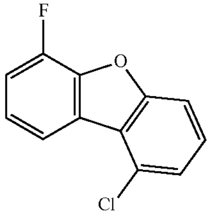 | 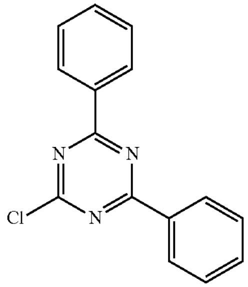 |
| 35 | 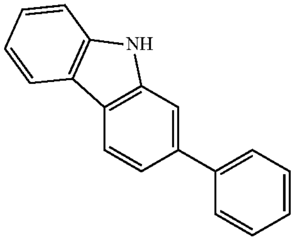 | 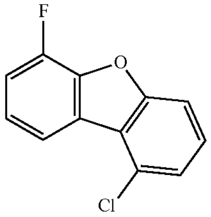 | 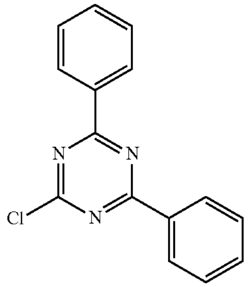 |

TABLE 1-continued
| | | | |
|---|---|---|---|
| 42 | 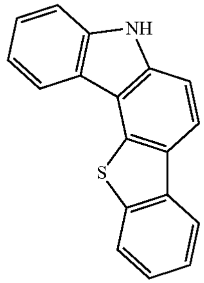 | 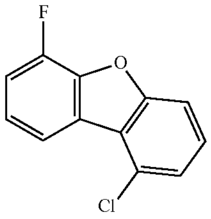 | 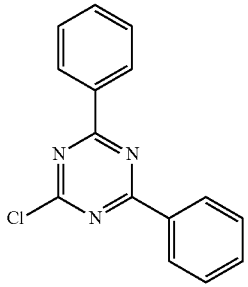 |
| 43 | 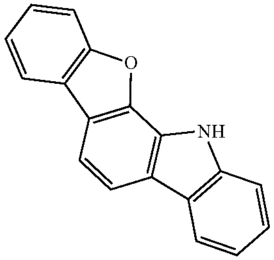 | 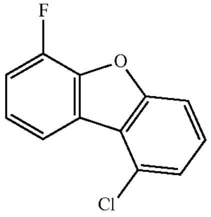 | 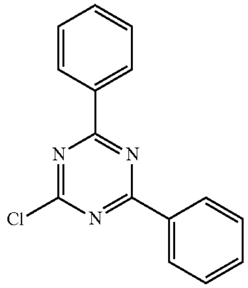 |
| 54 | 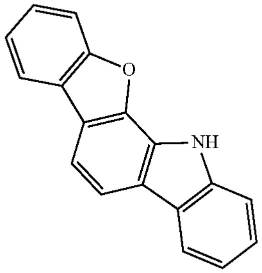 | 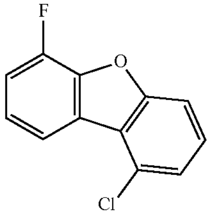 | 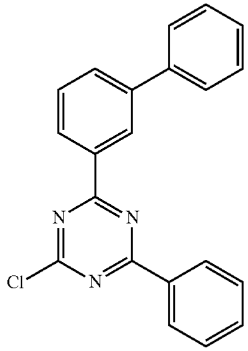 |

TABLE 1-continued
| | | | |
|---|---|---|---|
| 60 | 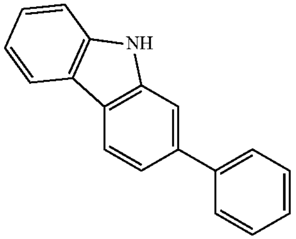 | 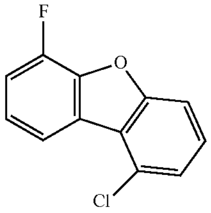 | 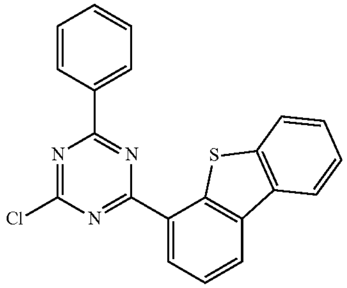 |
| 205 | 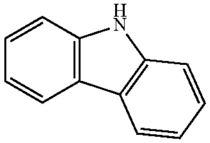 | 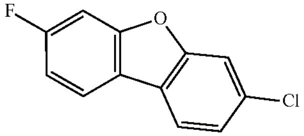 | 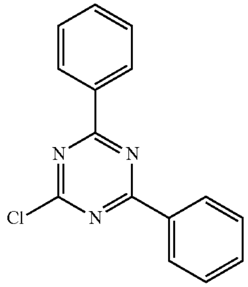 |
| 206 | 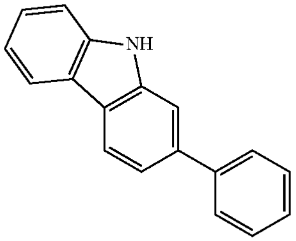 | 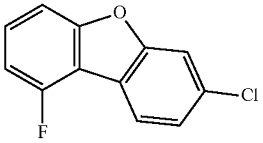 | 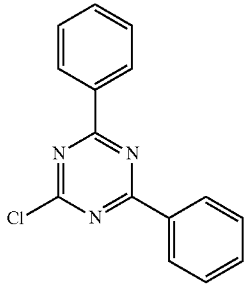 |

TABLE 1-continued
| | | | |
|---|---|---|---|
| 207 | 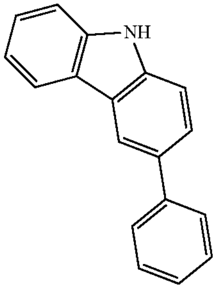 [SMILES: c1ccc(-c2ccc3[nH]c4ccccc4c3c2)cc1] | 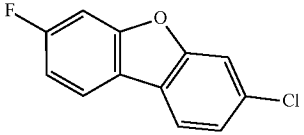 [SMILES: Fc1ccc2c(c1)oc1cc(Cl)ccc12] | 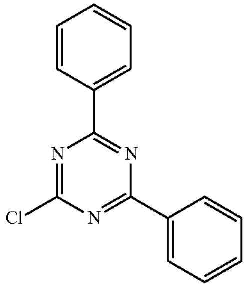 [SMILES: Clc1nc(-c2ccccc2)nc(-c2ccccc2)n1] |
| 213 | 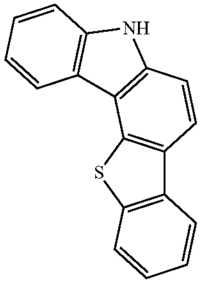 [SMILES: c1ccc2c(c1)[nH]c1ccc3c4ccccc4sc3c12] | 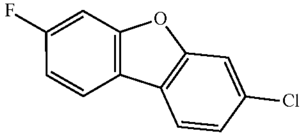 | 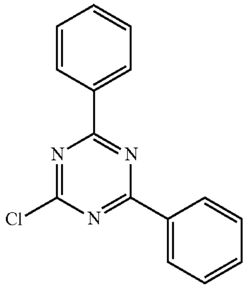 [SMILES: Clc1nc(-c2ccccc2)nc(-c2ccccc2)n1] |
| 214 | 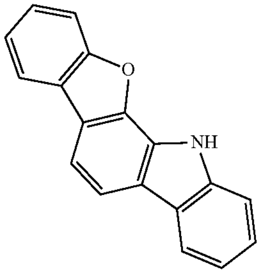 [SMILES: c1ccc2c(c1)[nH]c1c2ccc2c3ccccc3oc21] | 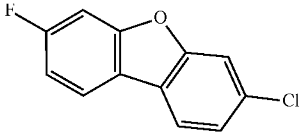 [SMILES: Fc1ccc2c(c1)oc1cc(Cl)ccc12] | 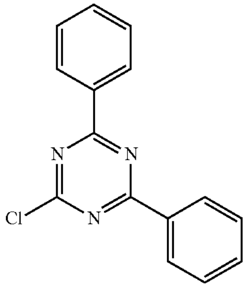 [SMILES: Clc1nc(-c2ccccc2)nc(-c2ccccc2)n1] |

TABLE 1-continued
| | | | |
|---|---|---|---|
| 216 | 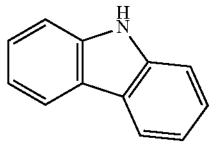 [SMILES: c1ccc2c(c1)[nH]c1ccccc12] | 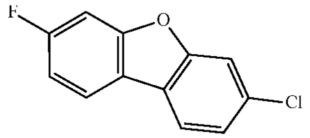 [SMILES: Fc1ccc2c(c1)oc1cc(Cl)ccc12] | 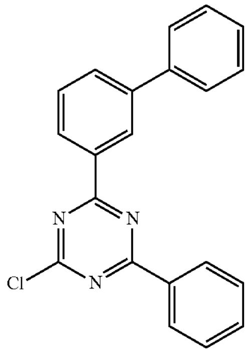 [SMILES: Clc1nc(-c2ccccc2)nc(-c2cccc(-c3ccccc3)c2)n1] |
| 217 | 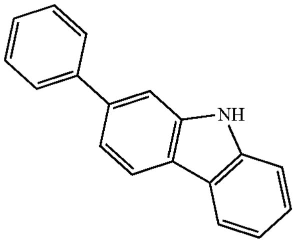 [SMILES: c1ccc(-c2ccc3c(c2)[nH]c2ccccc23)cc1] | 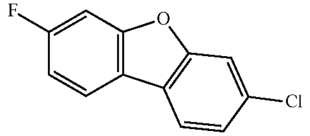 | 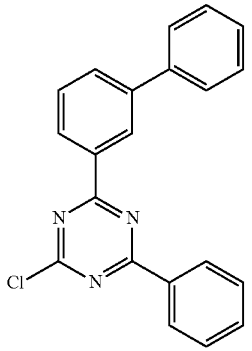 [SMILES: Clc1nc(-c2ccccc2)nc(-c2cccc(-c3ccccc3)c2)n1] |
| 218 | 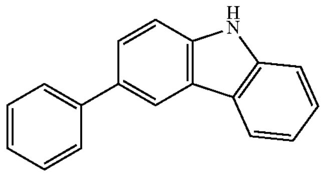 [SMILES: c1ccc(-c2ccc3[nH]c4ccccc4c3c2)cc1] | 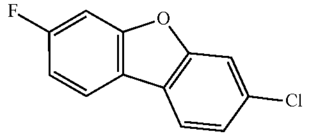 [SMILES: Fc1ccc2c(c1)oc1cc(Cl)ccc12] | 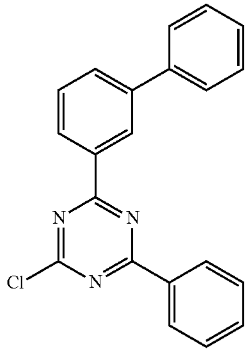 [SMILES: Clc1nc(-c2ccccc2)nc(-c2cccc(-c3ccccc3)c2)n1] |

TABLE 1-continued
| | | | |
|---|---|---|---|
| 219 | 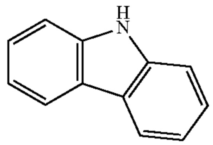 [SMILES: c1ccc2c(c1)[nH]c1ccccc12] | 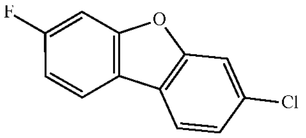 [SMILES: Fc1ccc2c(c1)oc1cc(Cl)ccc12] | 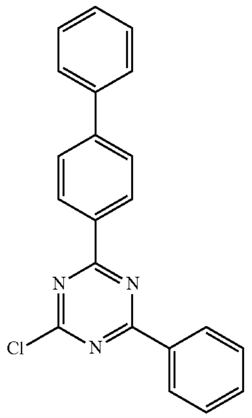 [SMILES: Clc1nc(-c2ccccc2)nc(-c2ccc(-c3ccccc3)cc2)n1] |
| 225 | 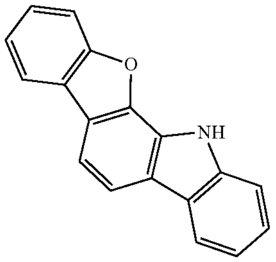 | 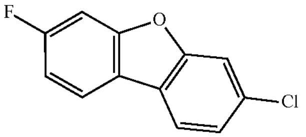 [SMILES: Fc1ccc2c(c1)oc1cc(Cl)ccc12] | 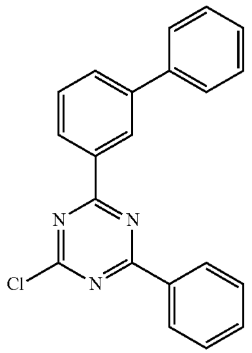 [SMILES: Clc1nc(-c2ccccc2)nc(-c2cccc(-c3ccccc3)c2)n1] |
| 228 | 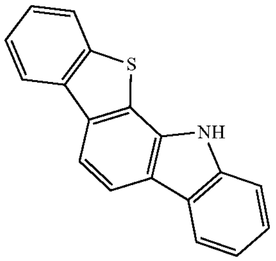 [SMILES: c1ccc2c(c1)[nH]c1c2ccc2c3ccccc3sc21] | 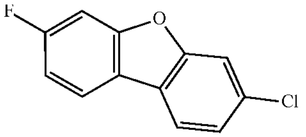 [SMILES: Fc1ccc2c(c1)oc1cc(Cl)ccc12] | 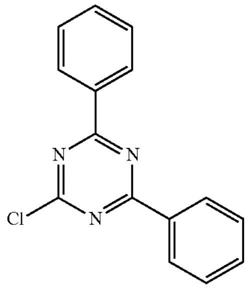 [SMILES: Clc1nc(-c2ccccc2)nc(-c2ccccc2)n1] |

TABLE 1-continued
| | | | |
|---|---|---|---|
| 230 | 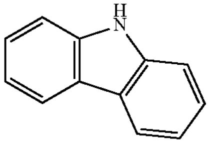 [SMILES: c1ccc2c(c1)[nH]c1ccccc12] | 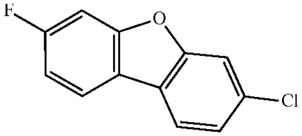 [SMILES: Fc1ccc2c(c1)oc1cc(Cl)ccc12] | 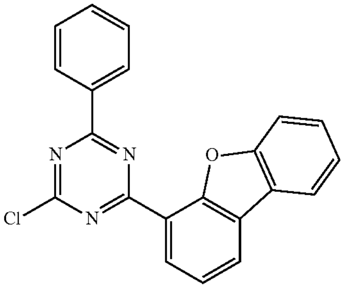 |
| 234 | 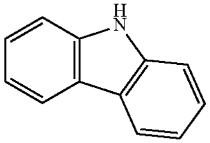 [SMILES: c1ccc2c(c1)[nH]c1ccccc12] | 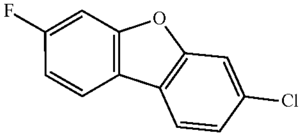 [SMILES: Fc1ccc2c(c1)oc1cc(Cl)ccc12] | 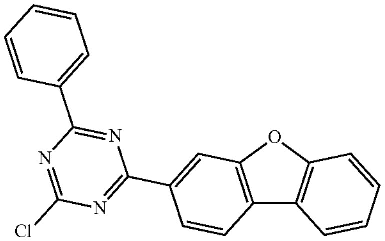 [SMILES: Clc1nc(-c2ccccc2)nc(-c2ccc3c(c2)oc2ccccc23)n1] |
| 235 | 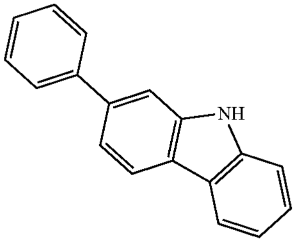 [SMILES: c1ccc(-c2ccc3c(c2)[nH]c2ccccc23)cc1] | 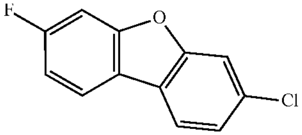 [SMILES: Fc1ccc2c(c1)oc1cc(Cl)ccc12] | 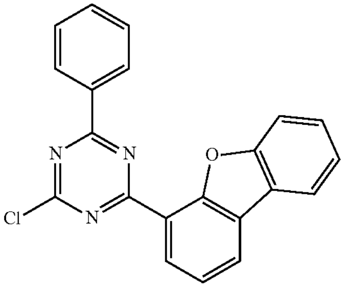 |
| 236 | 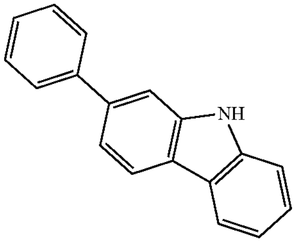 [SMILES: c1ccc(-c2ccc3c(c2)[nH]c2ccccc23)cc1] | 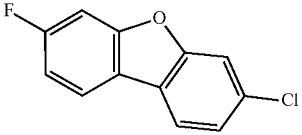 [SMILES: Fc1ccc2c(c1)oc1cc(Cl)ccc12] | 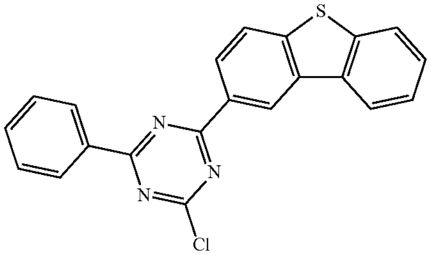 [SMILES: Clc1nc(-c2ccccc2)nc(-c2ccc3sc4ccccc4c3c2)n1] |

TABLE 1-continued
| | | | |
|---|---|---|---|
| 237 | 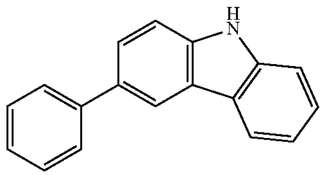 [SMILES: c1ccc(-c2ccc3[nH]c4ccccc4c3c2)cc1] | 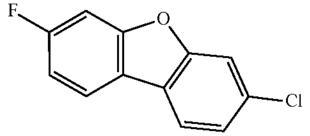 | 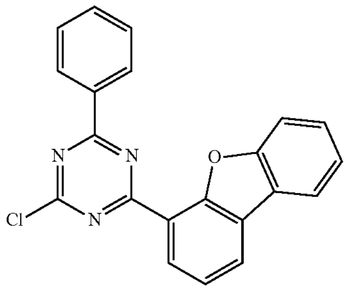 [SMILES: Clc1nc(-c2ccccc2)nc(-c2cccc3c2oc2ccccc23)n1] |
| 238 | 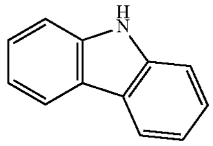 [SMILES: c1ccc2c(c1)[nH]c1ccccc12] | 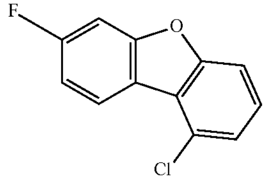 | 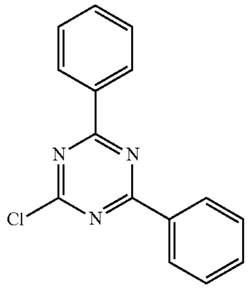 [SMILES: Clc1nc(-c2ccccc2)nc(-c2ccccc2)n1] |
| 240 | 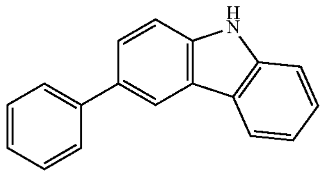 [SMILES: c1ccc(-c2ccc3[nH]c4ccccc4c3c2)cc1] | 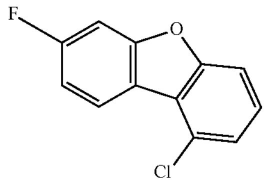 | 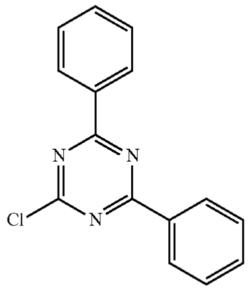 [SMILES: Clc1nc(-c2ccccc2)nc(-c2ccccc2)n1] |

TABLE 1-continued
| | | | |
|---|---|---|---|
| 246 | 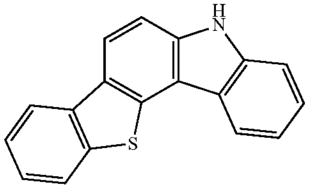 [SMILES: c1ccc2c(c1)[nH]c1ccc3c4ccccc4sc3c12] | 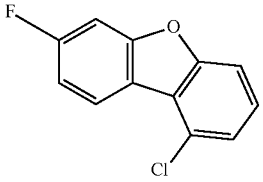 [SMILES: Fc1ccc2c(c1)oc1cccc(Cl)c12] | 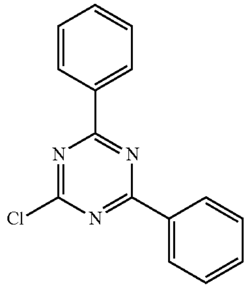 [SMILES: Clc1nc(-c2ccccc2)nc(-c2ccccc2)n1] |
| 248 | 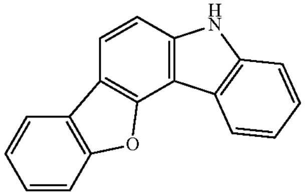 [SMILES: c1ccc2c(c1)[nH]c1ccc3c4ccccc4oc3c12] | 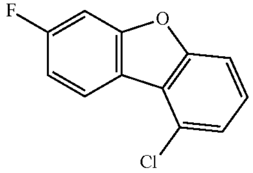 | 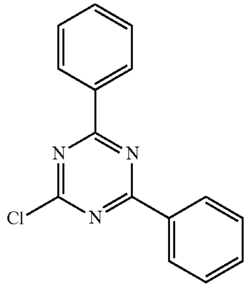 [SMILES: Clc1nc(-c2ccccc2)nc(-c2ccccc2)n1] |
| 249 | 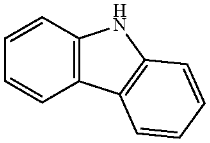 [SMILES: c1ccc2c(c1)[nH]c1ccccc12] | 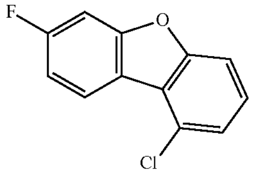 [SMILES: Fc1ccc2c(c1)oc1cccc(Cl)c12] | 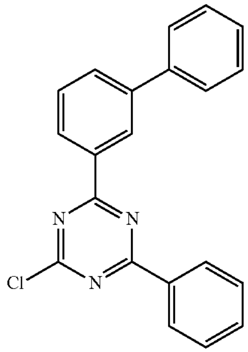 [SMILES: Clc1nc(-c2ccccc2)nc(-c2cccc(-c3ccccc3)c2)n1] |

TABLE 1-continued
| | | | |
|---|---|---|---|
| 251 | 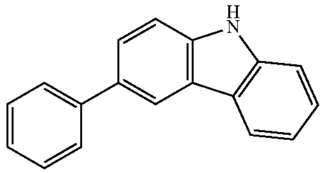 [SMILES: c1ccc(-c2ccc3[nH]c4ccccc4c3c2)cc1] | 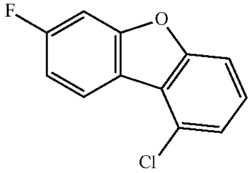 | 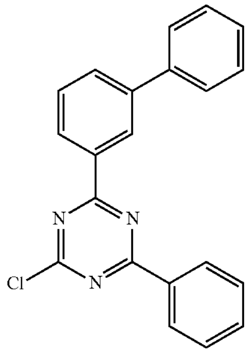 [SMILES: Clc1nc(-c2ccccc2)nc(-c2cccc(-c3ccccc3)c2)n1] |
| 252 | 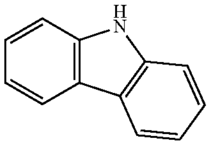 [SMILES: c1ccc2c(c1)[nH]c1ccccc12] | 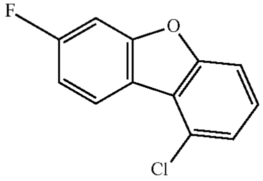 [SMILES: Fc1ccc2c(c1)oc1cccc(Cl)c12] | 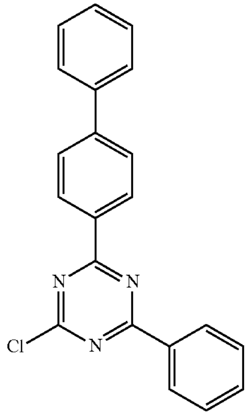 [SMILES: Clc1nc(-c2ccccc2)nc(-c2ccc(-c3ccccc3)cc2)n1] |

TABLE 1-continued
| | | | |
|---|---|---|---|
| 257 | 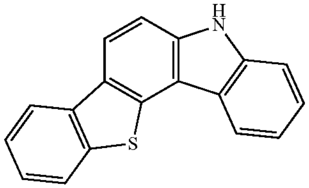 [SMILES: c1ccc2c(c1)[nH]c1ccc3c4ccccc4sc3c12] | 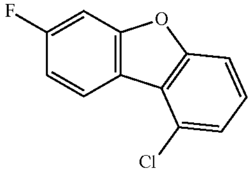 [SMILES: Fc1ccc2c(c1)oc1cccc(Cl)c12] | 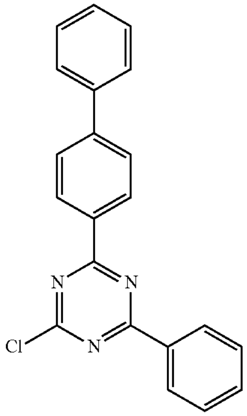 [SMILES: Clc1nc(-c2ccccc2)nc(-c2ccc(-c3ccccc3)cc2)n1] |
| 261 | 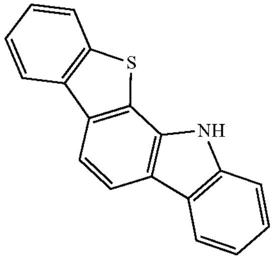 | 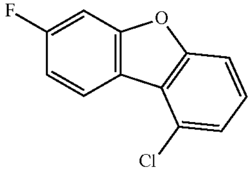 | 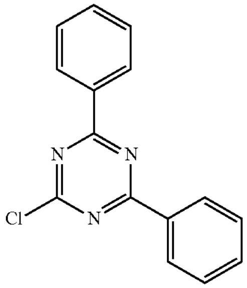 [SMILES: Clc1nc(-c2ccccc2)nc(-c2ccccc2)n1] |
| 263 | 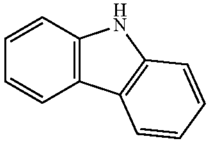 [SMILES: c1ccc2c(c1)[nH]c1ccccc12] | 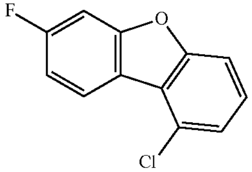 | 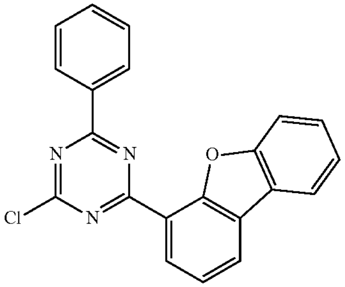 |

TABLE 1-continued
| | | | |
|---|---|---|---|
| 270 | 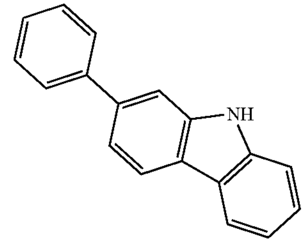 [SMILES: c1ccc(-c2ccc3c(c2)[nH]c2ccccc23)cc1] | 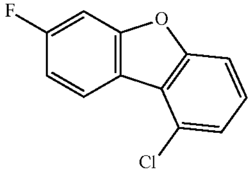 | 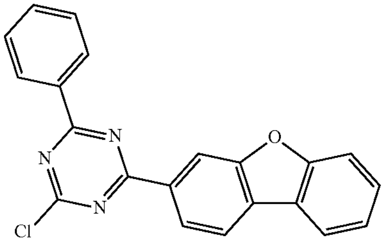 [SMILES: Clc1nc(-c2ccccc2)nc(-c2ccc3c(c2)oc2ccccc23)n1] |
| 386 | 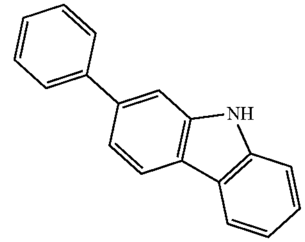 [SMILES: c1ccc(-c2ccc3c(c2)[nH]c2ccccc23)cc1] | 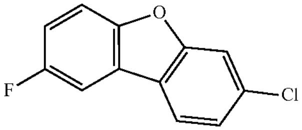 [SMILES: Fc1ccc2oc3cc(Cl)ccc3c2c1] | 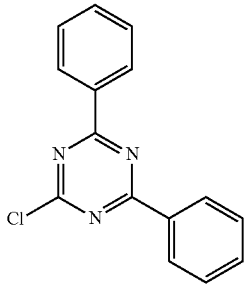 [SMILES: Clc1nc(-c2ccccc2)nc(-c2ccccc2)n1] |
| 387 | 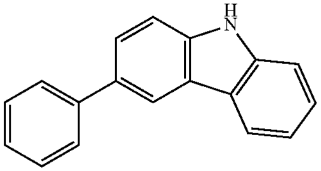 [SMILES: c1ccc(-c2ccc3[nH]c4ccccc4c3c2)cc1] | 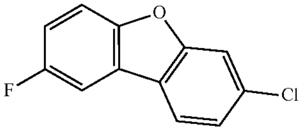 [SMILES: Fc1ccc2oc3cc(Cl)ccc3c2c1] | 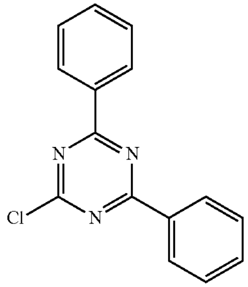 [SMILES: Clc1nc(-c2ccccc2)nc(-c2ccccc2)n1] |

TABLE 1-continued
| | | | |
|---|---|---|---|
| 390 | 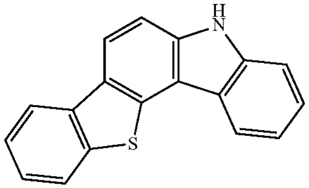 [SMILES: c1ccc2c(c1)[nH]c1ccc3c4ccccc4sc3c12] | 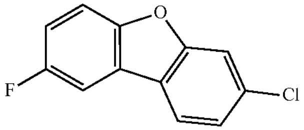 [SMILES: Fc1ccc2oc3cc(Cl)ccc3c2c1] | 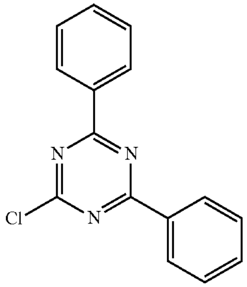 [SMILES: Clc1nc(-c2ccccc2)nc(-c2ccccc2)n1] |
| 392 | 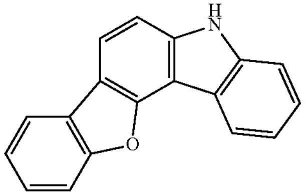 [SMILES: c1ccc2c(c1)[nH]c1ccc3c4ccccc4oc3c12] | 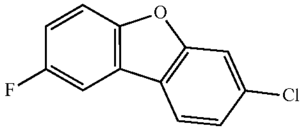 [SMILES: Fc1ccc2oc3cc(Cl)ccc3c2c1] | 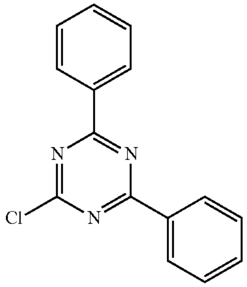 [SMILES: Clc1nc(-c2ccccc2)nc(-c2ccccc2)n1] |
| 393 | 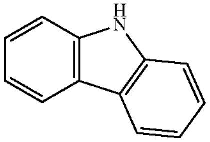 [SMILES: c1ccc2c(c1)[nH]c1ccccc12] | 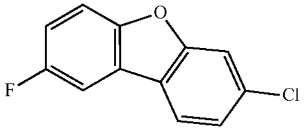 [SMILES: Fc1ccc2oc3cc(Cl)ccc3c2c1] | 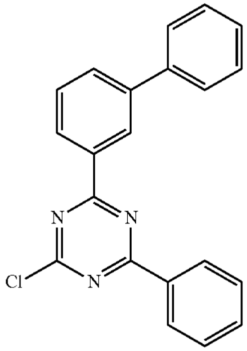 [SMILES: Clc1nc(-c2ccccc2)nc(-c2cccc(-c3ccccc3)c2)n1] |

TABLE 1-continued
| | | | |
|---|---|---|---|
| 395 | 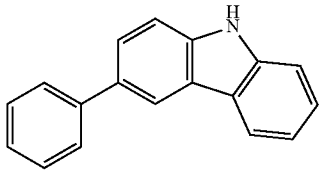 [SMILES: c1ccc(-c2ccc3[nH]c4ccccc4c3c2)cc1] | 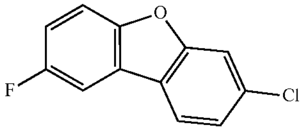 [SMILES: Fc1ccc2oc3cc(Cl)ccc3c2c1] | 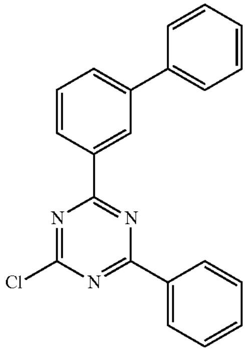 [SMILES: Clc1nc(-c2ccccc2)nc(-c2cccc(-c3ccccc3)c2)n1] |
| 396 | 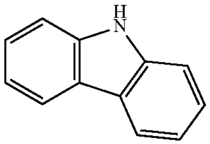 [SMILES: c1ccc2c(c1)[nH]c1ccccc12] | 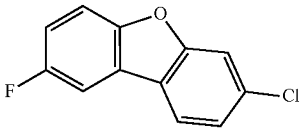 [SMILES: Fc1ccc2oc3cc(Cl)ccc3c2c1] | 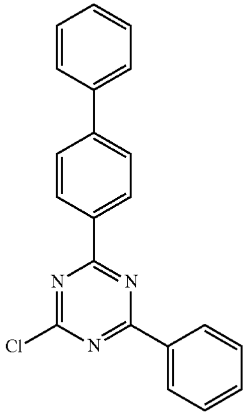 [SMILES: Clc1nc(-c2ccccc2)nc(-c2ccc(-c3ccccc3)cc2)n1] |

TABLE 1-continued
| | | | |
|---|---|---|---|
| 398 | 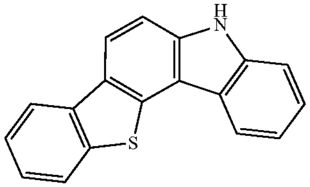 [SMILES: c1ccc2c(c1)[nH]c1ccc3c4ccccc4sc3c12] | 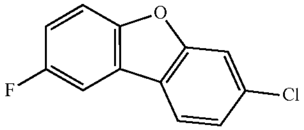 [SMILES: Fc1ccc2oc3cc(Cl)ccc3c2c1] | 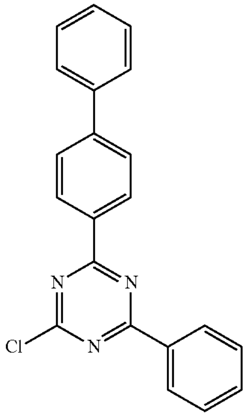 [SMILES: Clc1nc(-c2ccccc2)nc(-c2ccc(-c3ccccc3)cc2)n1] |
| 399 | 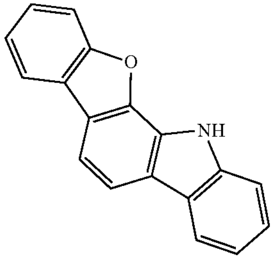 [SMILES: c1ccc2c(c1)[nH]c1c2ccc2c3ccccc3oc21] | 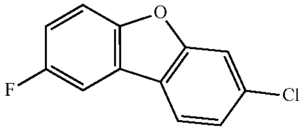 [SMILES: Fc1ccc2oc3cc(Cl)ccc3c2c1] | 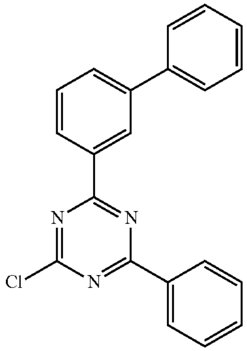 [SMILES: Clc1nc(-c2ccccc2)nc(-c2cccc(-c3ccccc3)c2)n1] |

TABLE 1-continued
| | | | |
|---|---|---|---|
| 400 | 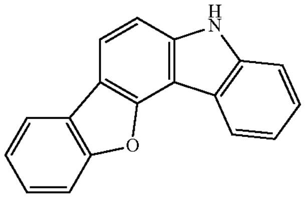 [SMILES: c1ccc2c(c1)[nH]c1ccc3c4ccccc4oc3c12] | 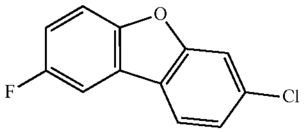 [SMILES: Fc1ccc2oc3cc(Cl)ccc3c2c1] | 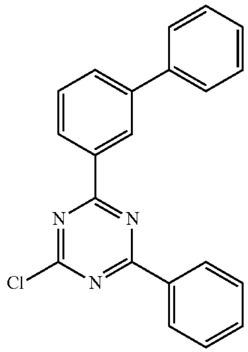 [SMILES: Clc1nc(-c2ccccc2)nc(-c2cccc(-c3ccccc3)c2)n1] |
| 402 | 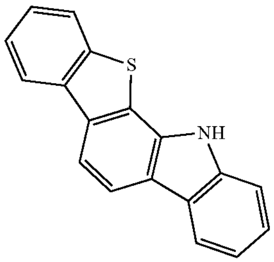 [SMILES: c1ccc2c(c1)[nH]c1c2ccc2c3ccccc3sc21] | 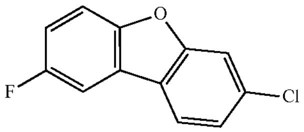 [SMILES: Fc1ccc2oc3cc(Cl)ccc3c2c1] | 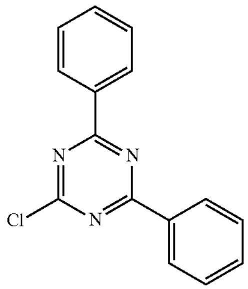 [SMILES: Clc1nc(-c2ccccc2)nc(-c2ccccc2)n1] |
| 404 | 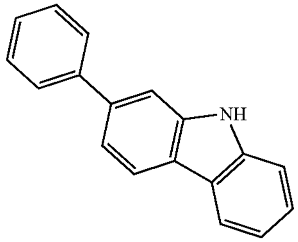 [SMILES: c1ccc(-c2ccc3c(c2)[nH]c2ccccc23)cc1] | 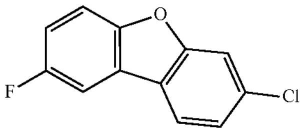 [SMILES: Fc1ccc2oc3cc(Cl)ccc3c2c1] | 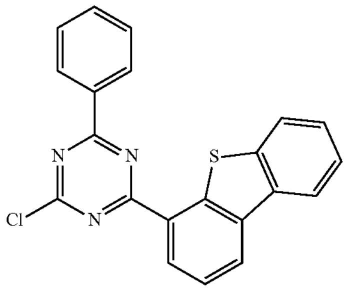 |

TABLE 1-continued
| | | | |
|---|---|---|---|
| 406 | 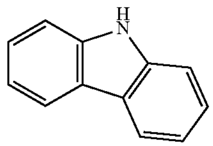 [SMILES: c1ccc2c(c1)[nH]c1ccccc12] | 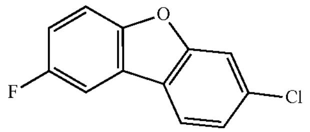 [SMILES: Fc1ccc2oc3cc(Cl)ccc3c2c1] | 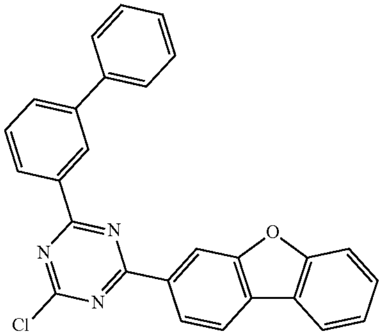 [SMILES: Clc1nc(-c2cccc(-c3ccccc3)c2)nc(-c2ccc3c(c2)oc2ccccc23)n1] |
| 410 | 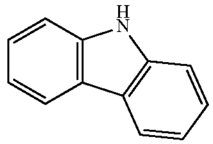 [SMILES: c1ccc2c(c1)[nH]c1ccccc12] | 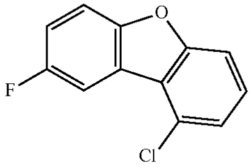 [SMILES: Fc1ccc2oc3cccc(Cl)c3c2c1] | 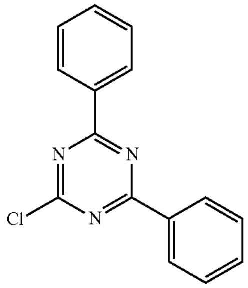 [SMILES: Clc1nc(-c2ccccc2)nc(-c2ccccc2)n1] |
| 411 | 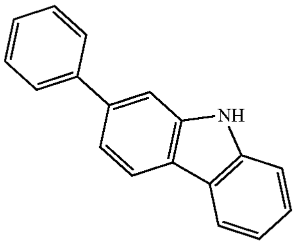 [SMILES: c1ccc(-c2ccc3c(c2)[nH]c2ccccc23)cc1] | 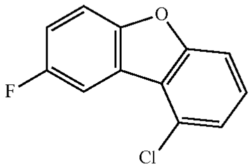 [SMILES: Fc1ccc2oc3cccc(Cl)c3c2c1] | 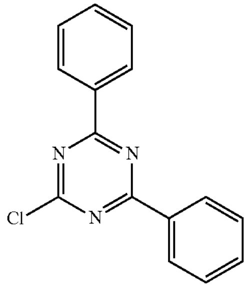 [SMILES: Clc1nc(-c2ccccc2)nc(-c2ccccc2)n1] |

TABLE 1-continued
| | | | |
|---|---|---|---|
| 525 | 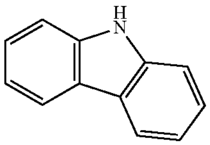 [SMILES: c1ccc2c(c1)[nH]c1ccccc12] | 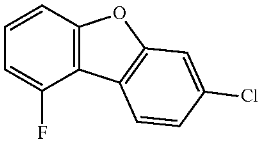 [SMILES: Fc1cccc2oc3cc(Cl)ccc3c12] | 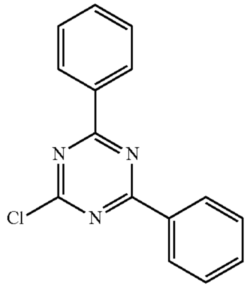 [SMILES: Clc1nc(-c2ccccc2)nc(-c2ccccc2)n1] |
| 526 | 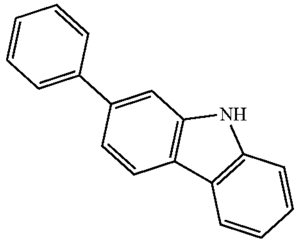 [SMILES: c1ccc(-c2ccc3c(c2)[nH]c2ccccc23)cc1] | 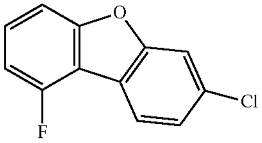 [SMILES: Fc1cccc2oc3cc(Cl)ccc3c12] | 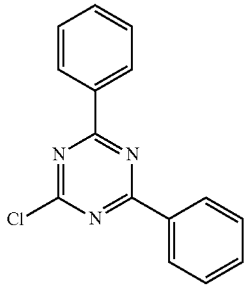 [SMILES: Clc1nc(-c2ccccc2)nc(-c2ccccc2)n1] |
| 527 | 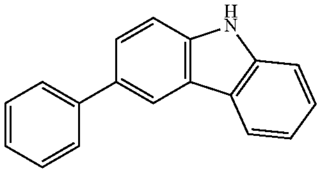 [SMILES: c1ccc(-c2ccc3[nH]c4ccccc4c3c2)cc1] | 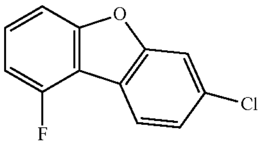 [SMILES: Fc1cccc2oc3cc(Cl)ccc3c12] | 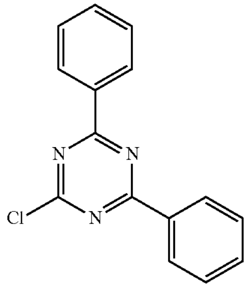 [SMILES: Clc1nc(-c2ccccc2)nc(-c2ccccc2)n1] |

TABLE 1-continued
| | | | |
|---|---|---|---|
| 531 | 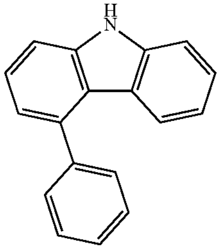 [SMILES: c1ccc(-c2cccc3[nH]c4ccccc4c23)cc1] | 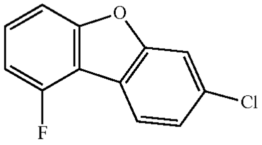 [SMILES: Fc1cccc2oc3cc(Cl)ccc3c12] | 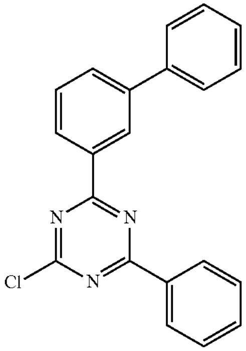 [SMILES: Clc1nc(-c2ccccc2)nc(-c2cccc(-c3ccccc3)c2)n1] |
| 533 | 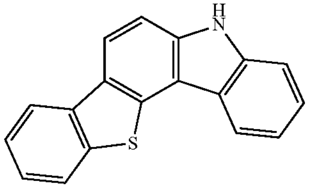 [SMILES: c1ccc2c(c1)[nH]c1ccc3c4ccccc4sc3c12] | 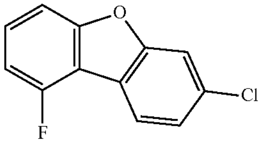 [SMILES: Fc1cccc2oc3cc(Cl)ccc3c12] | 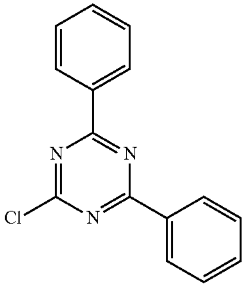 [SMILES: Clc1nc(-c2ccccc2)nc(-c2ccccc2)n1] |
| 535 | 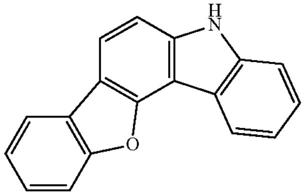 [SMILES: c1ccc2c(c1)[nH]c1ccc3c4ccccc4oc3c12] | 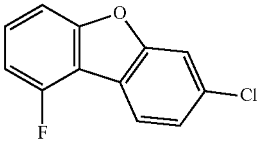 [SMILES: Fc1cccc2oc3cc(Cl)ccc3c12] | 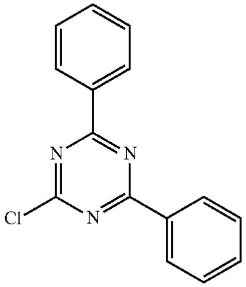 [SMILES: Clc1nc(-c2ccccc2)nc(-c2ccccc2)n1] |

TABLE 1-continued
| | | | |
|---|---|---|---|
| 536 | 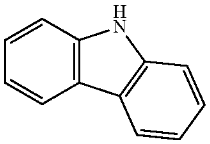 [SMILES: c1ccc2c(c1)[nH]c1ccccc12] | 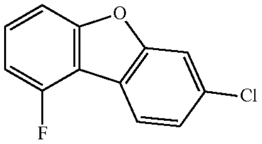 [SMILES: Fc1cccc2oc3cc(Cl)ccc3c12] | 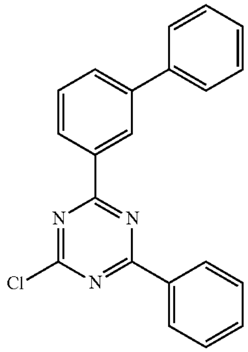 [SMILES: Clc1nc(-c2ccccc2)nc(-c2cccc(-c3ccccc3)c2)n1] |
| 538 | 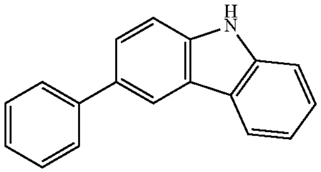 [SMILES: c1ccc(-c2ccc3[nH]c4ccccc4c3c2)cc1] | 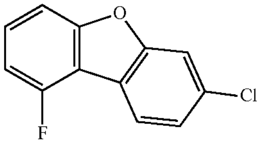 [SMILES: Fc1cccc2oc3cc(Cl)ccc3c12] | 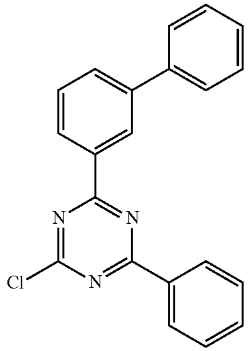 [SMILES: Clc1nc(-c2ccccc2)nc(-c2cccc(-c3ccccc3)c2)n1] |

TABLE 1-continued
| | | | |
|---|---|---|---|
| 539 | 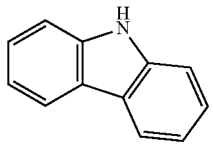 | 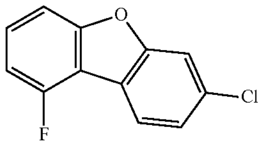 [SMILES: Fc1cccc2oc3cc(Cl)ccc3c12] | 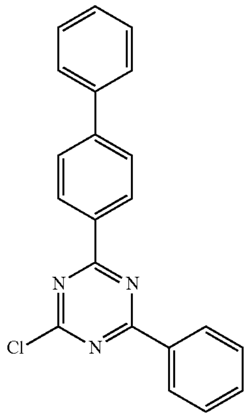 [SMILES: Clc1nc(-c2ccccc2)nc(-c2ccc(-c3ccccc3)cc2)n1] |
| 544 | 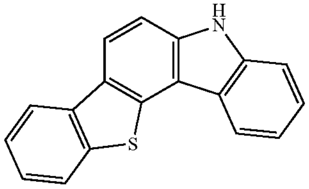 [SMILES: c1ccc2c(c1)[nH]c1ccc3c4ccccc4sc3c12] | 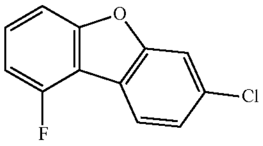 [SMILES: Fc1cccc2oc3cc(Cl)ccc3c12] | 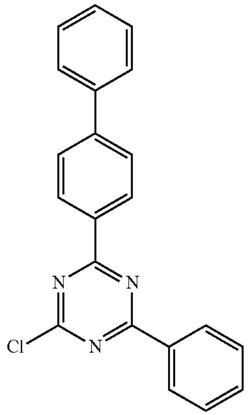 [SMILES: Clc1nc(-c2ccccc2)nc(-c2ccc(-c3ccccc3)cc2)n1] |

TABLE 1-continued
| | | | |
|---|---|---|---|
| 545 | 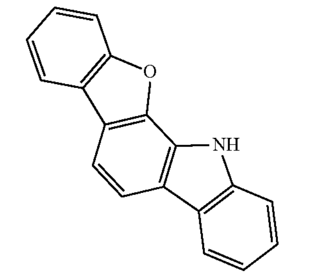 [SMILES: c1ccc2c(c1)[nH]c1c2ccc2c3ccccc3oc21] | 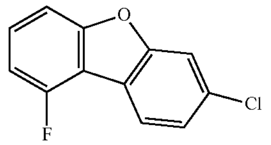 [SMILES: Fc1cccc2oc3cc(Cl)ccc3c12] | 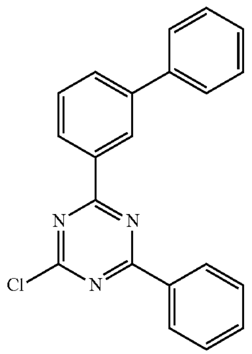 [SMILES: Clc1nc(-c2ccccc2)nc(-c2cccc(-c3ccccc3)c2)n1] |
| 546 | 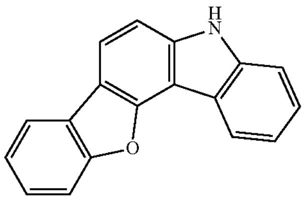 [SMILES: c1ccc2c(c1)[nH]c1ccc3c4ccccc4oc3c12] | 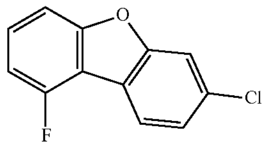 [SMILES: Fc1cccc2oc3cc(Cl)ccc3c12] | 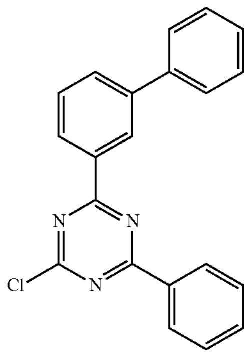 [SMILES: Clc1nc(-c2ccccc2)nc(-c2cccc(-c3ccccc3)c2)n1] |
| 550 | 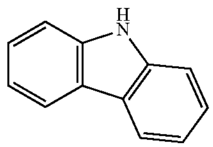 [SMILES: c1ccc2c(c1)[nH]c1ccccc12] | 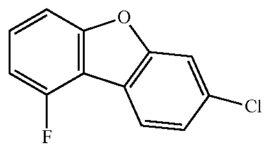 [SMILES: Fc1cccc2oc3cc(Cl)ccc3c12] | 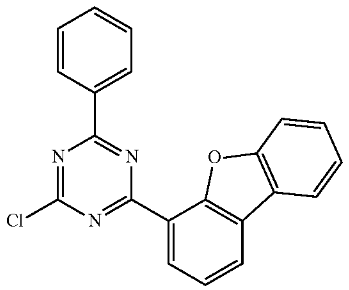 [SMILES: Clc1nc(-c2ccccc2)nc(-c2cccc3c2oc2ccccc23)n1] |

TABLE 1-continued
| Compound | E | yield |
| --- | --- | --- |
| 9 | 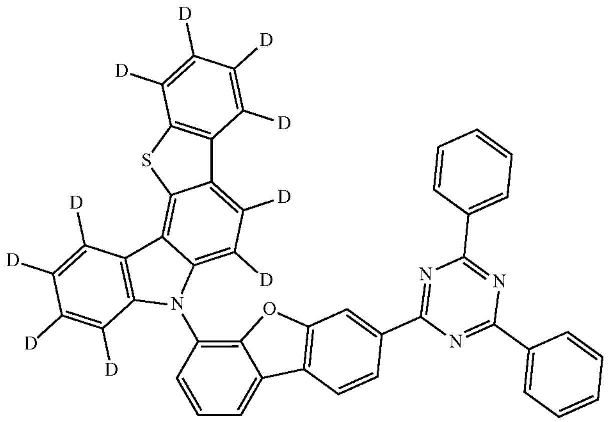 | 87% |
| 11 | 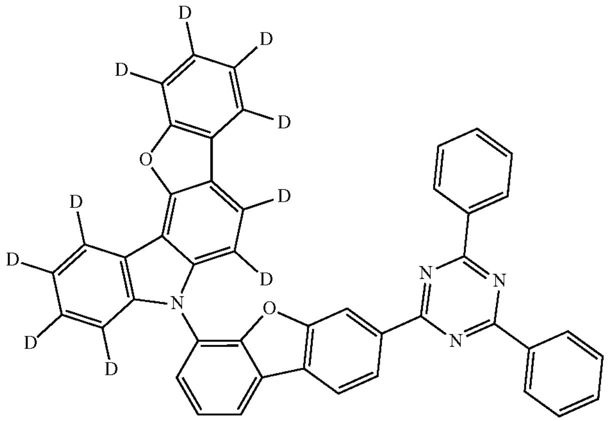 | 67% |

TABLE 1-continued
| | | |
|---|---|---|
| 12 | 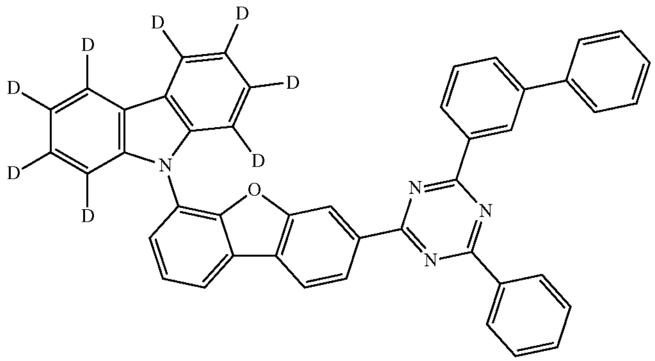 | 55% |
| 15 | 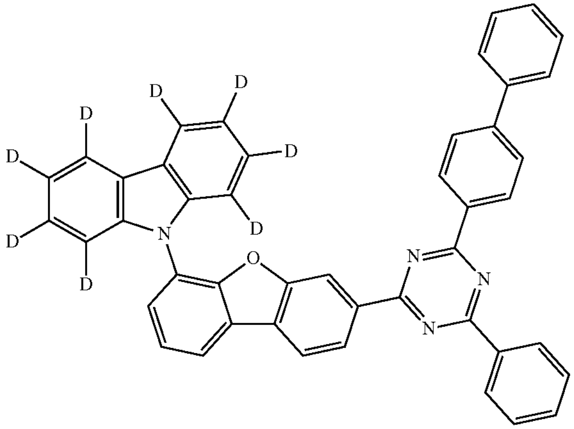 | 69% |

TABLE 1-continued
| | | |
|---|---|---|
| 26 | 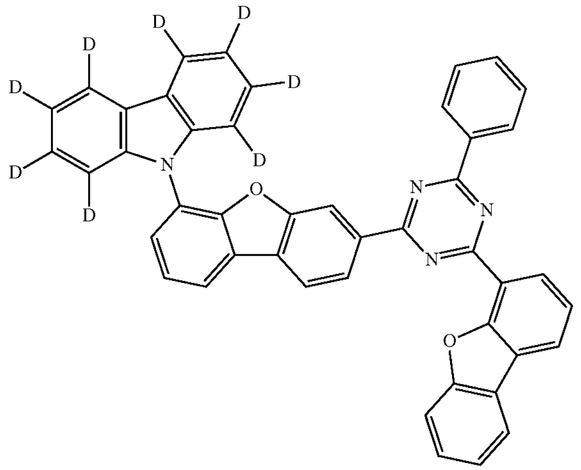 | 76% |
| 31 | 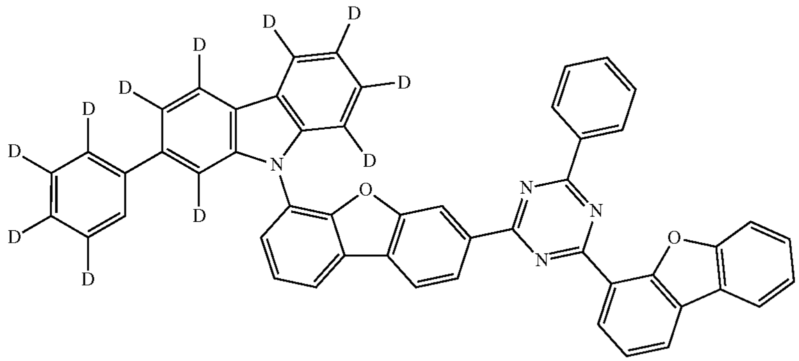 | 79% |

TABLE 1-continued
| | | |
|---|---|---|
| 33 | 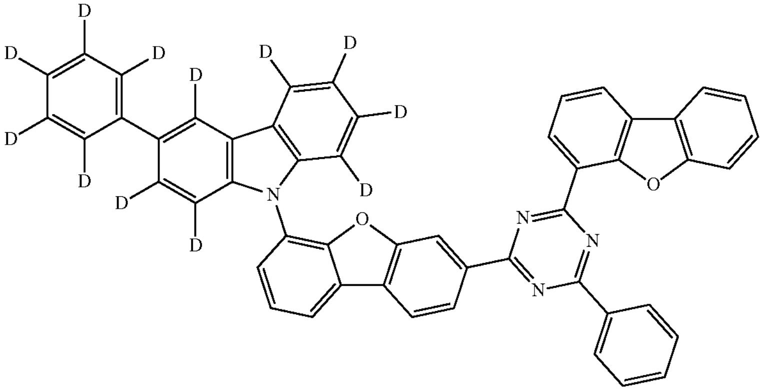 | 81% |
| 34 | 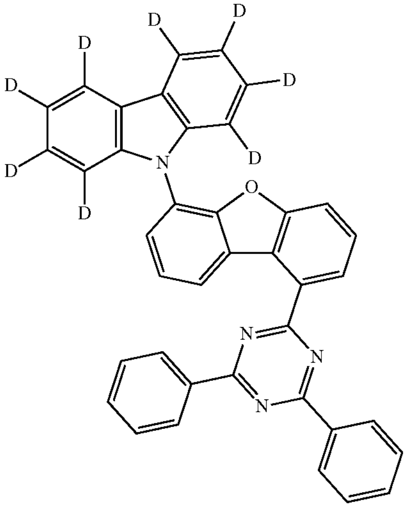 | 83% |

TABLE 1-continued
| | | |
|---|---|---|
| 35 | 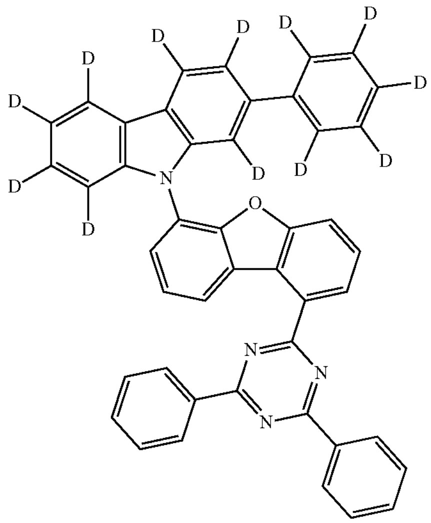 | 85% |
| 42 | 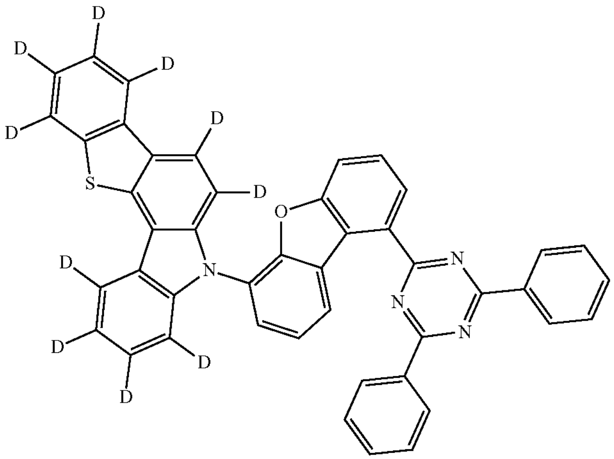 | 91% |

TABLE 1-continued
| | | |
|---|---|---|
| 43 | 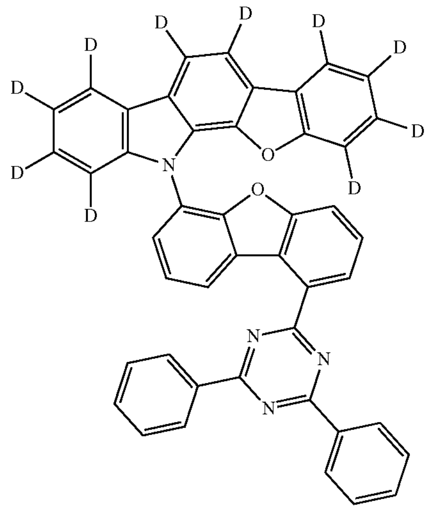 [SMILES: [2H]c1c([2H])c([2H])c2c(oc3c2c([2H])c([2H])c2c4c([2H])c([2H])c([2H])c([2H])c4n(-c4cccc5c4oc4cccc(-c6nc(-c7ccccc7)nc(-c7ccccc7)n6)c45)c32)c1[2H]] | 88% |
| 54 | 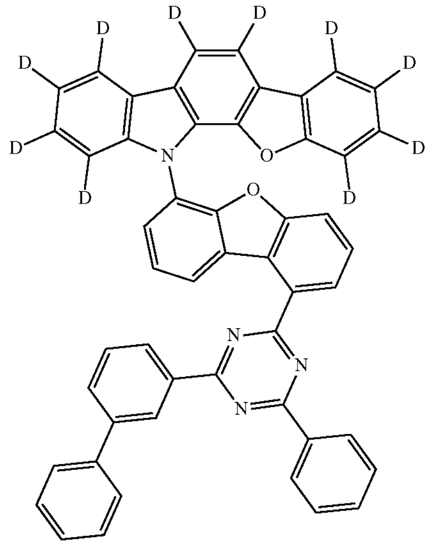 [SMILES: [2H]c1c([2H])c([2H])c2c(oc3c2c([2H])c([2H])c2c4c([2H])c([2H])c([2H])c([2H])c4n(-c4cccc5c4oc4cccc(-c6nc(-c7ccccc7)nc(-c7cccc(-c8ccccc8)c7)n6)c45)c32)c1[2H]] | 87% |

TABLE 1-continued
| | | |
|---|---|---|
| 60 | 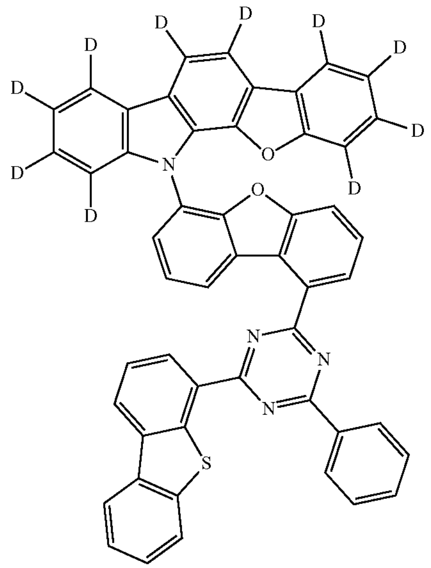 [SMILES: [2H]c1c([2H])c([2H])c2c(oc3c2c([2H])c([2H])c2c4c([2H])c([2H])c([2H])c([2H])c4n(-c4cccc5c4oc4cccc(-c6nc(-c7ccccc7)nc(-c7cccc8c7sc7ccccc78)n6)c45)c32)c1[2H]] | 93% |
| 205 | 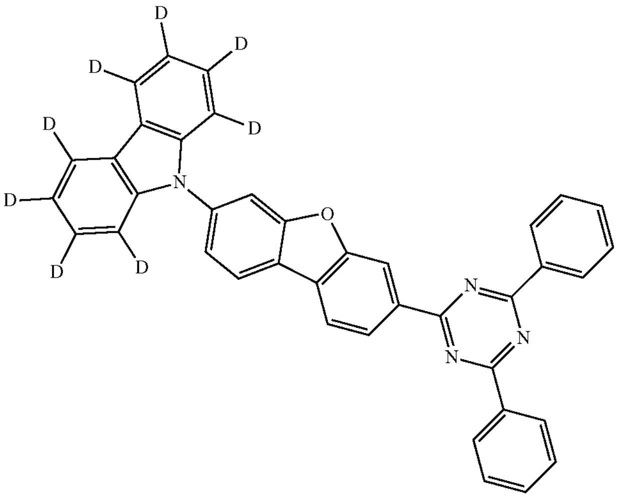 [SMILES: [2H]c1c([2H])c([2H])c2c(c1[2H])c1c([2H])c([2H])c([2H])c([2H])c1n2-c1ccc2c(c1)oc1cc(-c3nc(-c4ccccc4)nc(-c4ccccc4)n3)ccc12] | 53% |

TABLE 1-continued
| | | |
|---|---|---|
| 206 | 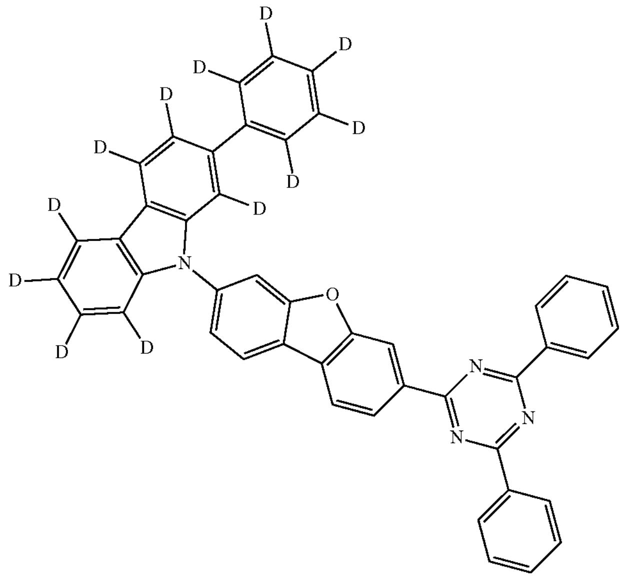 [SMILES: [2H]c1c([2H])c([2H])c(-c2c([2H])c([2H])c3c4c([2H])c([2H])c([2H])c([2H])c4n(-c4ccc5c(c4)oc4cc(-c6nc(-c7ccccc7)nc(-c7ccccc7)n6)ccc45)c3c2[2H])c([2H])c1[2H]] | 68% |
| 207 | 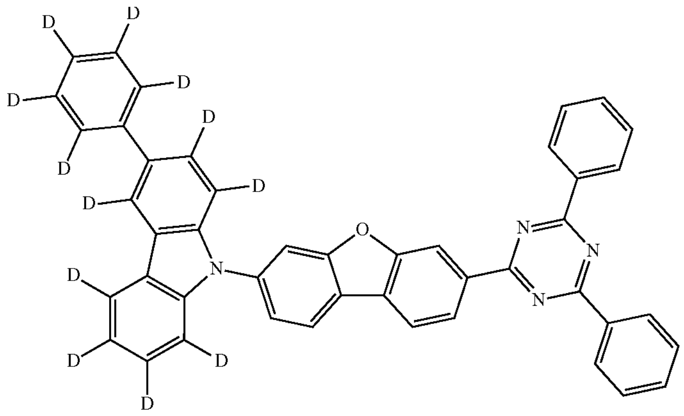 [SMILES: [2H]c1c([2H])c([2H])c(-c2c([2H])c([2H])c3c(c2[2H])c2c([2H])c([2H])c([2H])c([2H])c2n3-c2ccc3c(c2)oc2cc(-c4nc(-c5ccccc5)nc(-c5ccccc5)n4)ccc23)c([2H])c1[2H]] | 67% |

TABLE 1-continued
| | | |
|---|---|---|
| 213 | 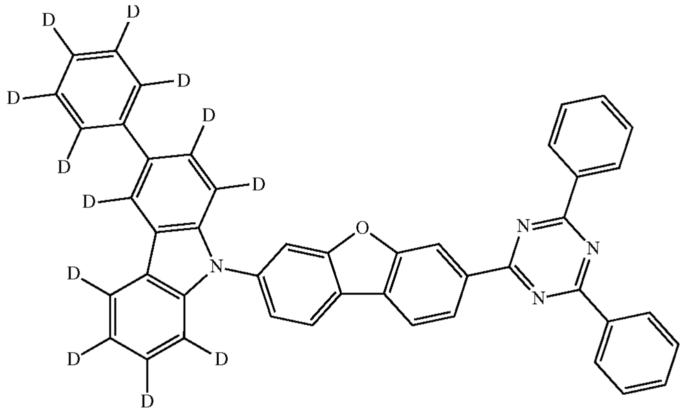 [SMILES: [2H]c1c([2H])c([2H])c(-c2c([2H])c([2H])c3c(c2[2H])c2c([2H])c([2H])c([2H])c([2H])c2n3-c2ccc3c(c2)oc2cc(-c4nc(-c5ccccc5)nc(-c5ccccc5)n4)ccc23)c([2H])c1[2H]] | 66% |
| 214 | 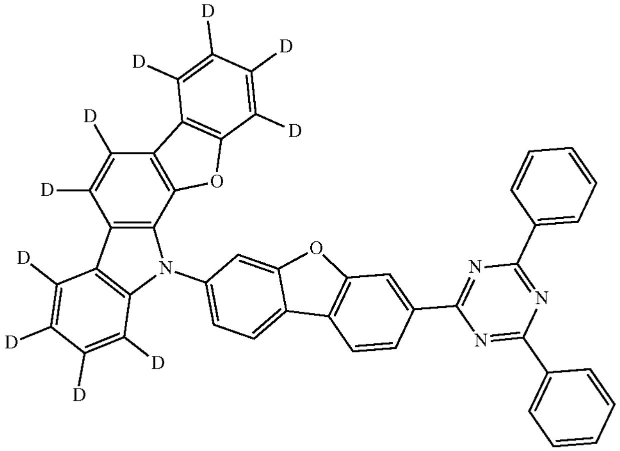 [SMILES: [2H]c1c([2H])c([2H])c2c(oc3c2c([2H])c([2H])c2c4c([2H])c([2H])c([2H])c([2H])c4n(-c4ccc5c(c4)oc4cc(-c6nc(-c7ccccc7)nc(-c7ccccc7)n6)ccc45)c32)c1[2H]] | 73% |

TABLE 1-continued
| | | |
|---|---|---|
| 216 | 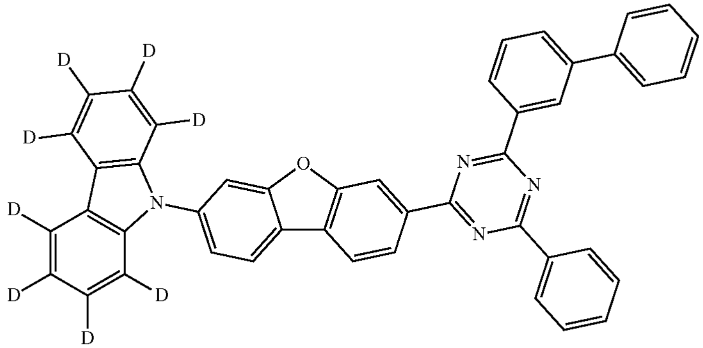 [SMILES: [2H]c1c([2H])c([2H])c2c(c1[2H])c1c([2H])c([2H])c([2H])c([2H])c1n2-c1ccc2c(c1)oc1cc(-c3nc(-c4ccccc4)nc(-c4cccc(-c5ccccc5)c4)n3)ccc12] | 75% |
| 217 | 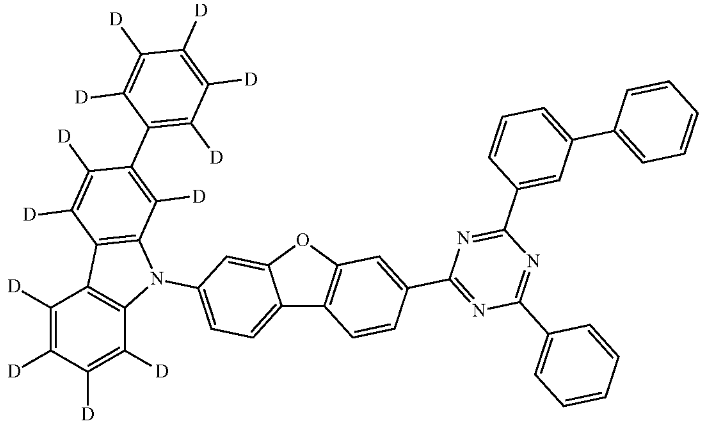 [SMILES: [2H]c1c([2H])c([2H])c(-c2c([2H])c([2H])c3c4c([2H])c([2H])c([2H])c([2H])c4n(-c4ccc5c(c4)oc4cc(-c6nc(-c7ccccc7)nc(-c7cccc(-c8ccccc8)c7)n6)ccc45)c3c2[2H])c([2H])c1[2H]] | 90% |

TABLE 1-continued
| | | |
|---|---|---|
| 218 | 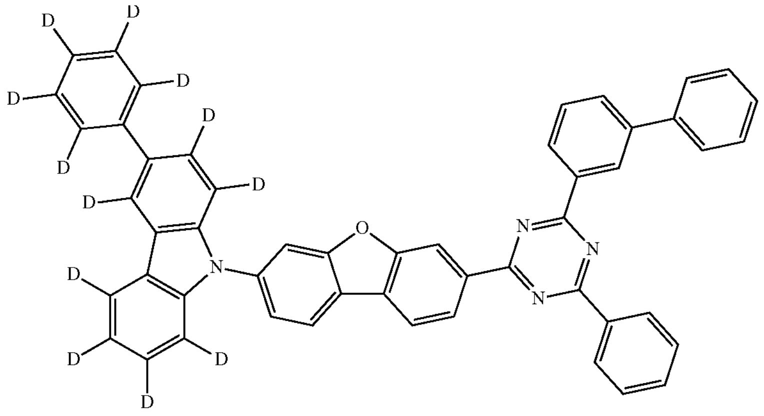 [SMILES: [2H]c1c([2H])c([2H])c(-c2c([2H])c([2H])c3c(c2[2H])c2c([2H])c([2H])c([2H])c([2H])c2n3-c2ccc3c(c2)oc2cc(-c4nc(-c5ccccc5)nc(-c5cccc(-c6ccccc6)c5)n4)ccc23)c([2H])c1[2H]] | 91% |
| 219 | 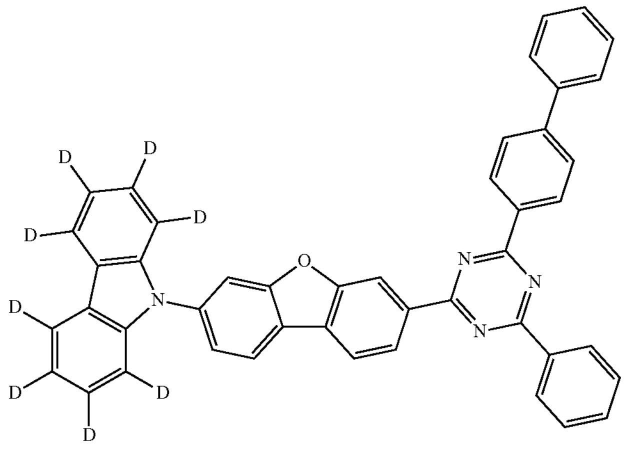 [SMILES: [2H]c1c([2H])c([2H])c2c(c1[2H])c1c([2H])c([2H])c([2H])c([2H])c1n2-c1ccc2c(c1)oc1cc(-c3nc(-c4ccccc4)nc(-c4ccc(-c5ccccc5)cc4)n3)ccc12] | 88% |

TABLE 1-continued
| | | |
|---|---|---|
| 225 | 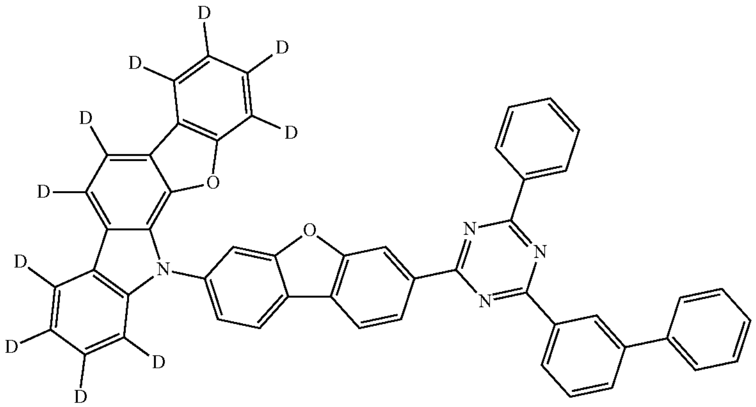 [SMILES: [2H]c1c([2H])c([2H])c2c(oc3c2c([2H])c([2H])c2c4c([2H])c([2H])c([2H])c([2H])c4n(-c4ccc5c(c4)oc4cc(-c6nc(-c7ccccc7)nc(-c7cccc(-c8ccccc8)c7)n6)ccc45)c32)c1[2H]] | 83% |
| 228 | 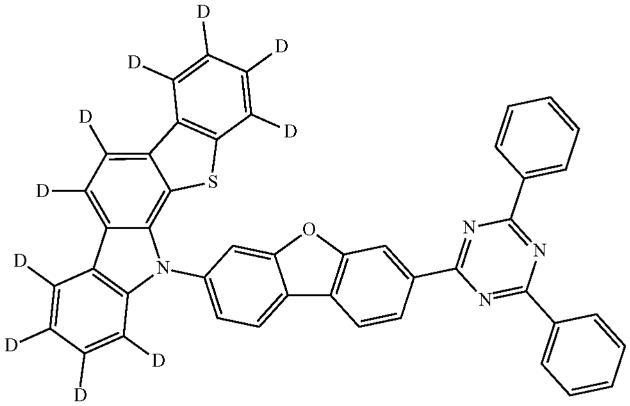 [SMILES: [2H]c1c([2H])c([2H])c2c(sc3c2c([2H])c([2H])c2c4c([2H])c([2H])c([2H])c([2H])c4n(-c4ccc5c(c4)oc4cc(-c6nc(-c7ccccc7)nc(-c7ccccc7)n6)ccc45)c32)c1[2H]] | 76% |

TABLE 1-continued
| | | |
|---|---|---|
| 230 | 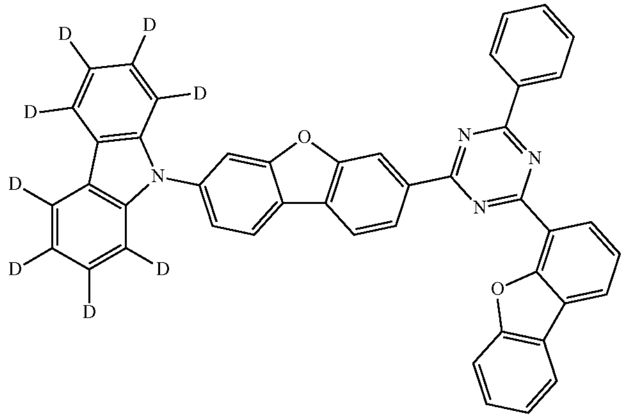 [SMILES: [2H]c1c([2H])c([2H])c2c(c1[2H])c1c([2H])c([2H])c([2H])c([2H])c1n2-c1ccc2c(c1)oc1cc(-c3nc(-c4ccccc4)nc(-c4cccc5c4oc4ccccc45)n3)ccc12] | 72% |
| 234 | 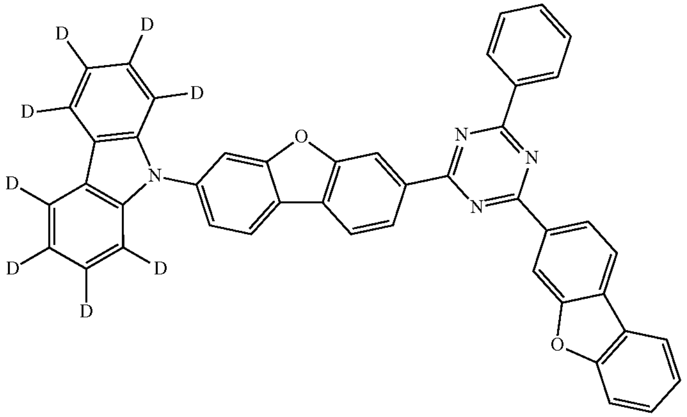 [SMILES: [2H]c1c([2H])c([2H])c2c(c1[2H])c1c([2H])c([2H])c([2H])c([2H])c1n2-c1ccc2c(c1)oc1cc(-c3nc(-c4ccccc4)nc(-c4ccc5c(c4)oc4ccccc45)n3)ccc12] | 83% |

TABLE 1-continued
| | | |
|---|---|---|
| 235 | 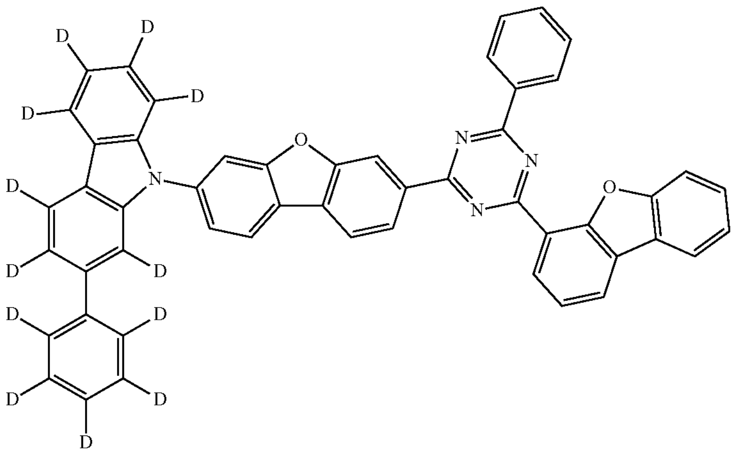 [SMILES: [2H]c1c([2H])c([2H])c(-c2c([2H])c([2H])c3c4c([2H])c([2H])c([2H])c([2H])c4n(-c4ccc5c(c4)oc4cc(-c6nc(-c7ccccc7)nc(-c7cccc8c7oc7ccccc78)n6)ccc45)c3c2[2H])c([2H])c1[2H]] | 85% |
| 236 | 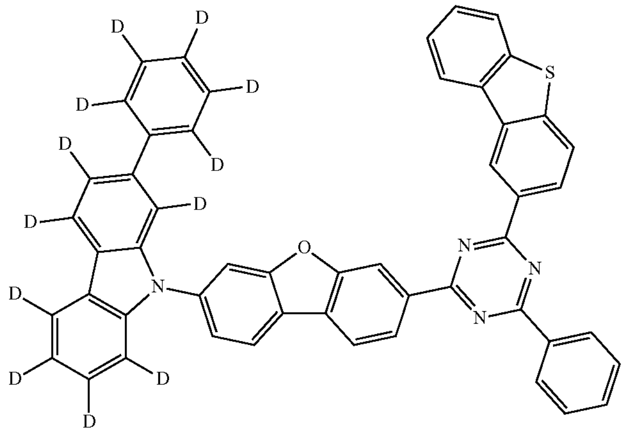 [SMILES: [2H]c1c([2H])c([2H])c(-c2c([2H])c([2H])c3c4c([2H])c([2H])c([2H])c([2H])c4n(-c4ccc5c(c4)oc4cc(-c6nc(-c7ccccc7)nc(-c7ccc8sc9ccccc9c8c7)n6)ccc45)c3c2[2H])c([2H])c1[2H]] | 93% |

TABLE 1-continued
| | | |
|---|---|---|
| 237 | 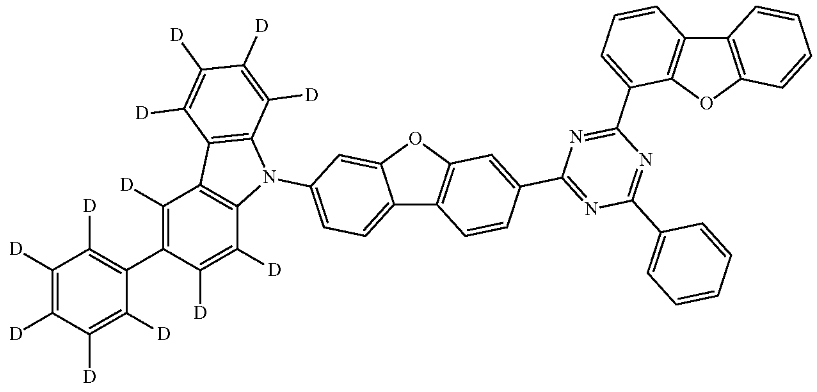 [SMILES: [2H]c1c([2H])c([2H])c(-c2c([2H])c([2H])c3c(c2[2H])c2c([2H])c([2H])c([2H])c([2H])c2n3-c2ccc3c(c2)oc2cc(-c4nc(-c5ccccc5)nc(-c5cccc6c5oc5ccccc56)n4)ccc23)c([2H])c1[2H]] | 90% |
| 238 | 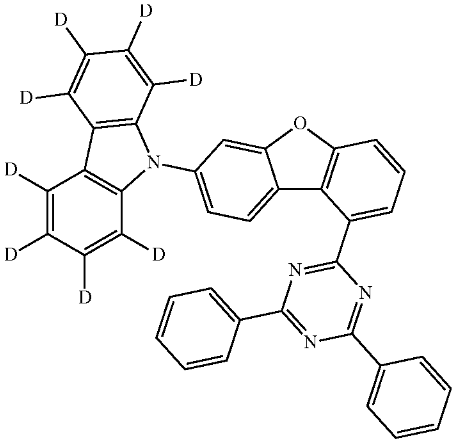 [SMILES: [2H]c1c([2H])c([2H])c2c(c1[2H])c1c([2H])c([2H])c([2H])c([2H])c1n2-c1ccc2c(c1)oc1cccc(-c3nc(-c4ccccc4)nc(-c4ccccc4)n3)c12] | 87% |

TABLE 1-continued
| | | |
|---|---|---|
| 240 | 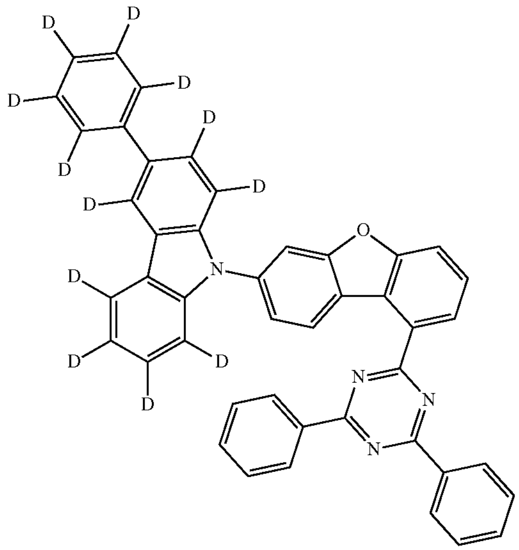 [SMILES: [2H]c1c([2H])c([2H])c(-c2c([2H])c([2H])c3c(c2[2H])c2c([2H])c([2H])c([2H])c([2H])c2n3-c2ccc3c(c2)oc2cccc(-c4nc(-c5ccccc5)nc(-c5ccccc5)n4)c23)c([2H])c1[2H]] | 88% |
| 246 | 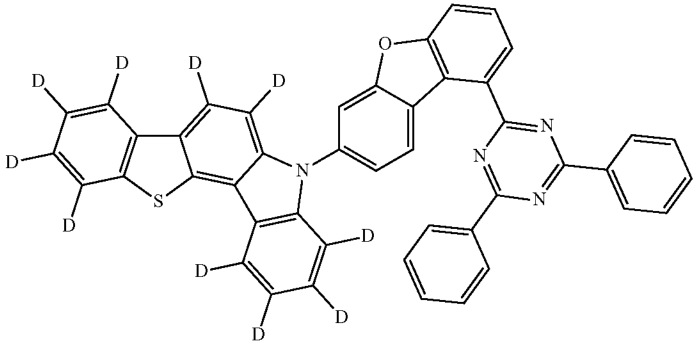 [SMILES: [2H]c1c([2H])c([2H])c2c(sc3c2c([2H])c([2H])c2c3c3c([2H])c([2H])c([2H])c([2H])c3n2-c2ccc3c(c2)oc2cccc(-c4nc(-c5ccccc5)nc(-c5ccccc5)n4)c23)c1[2H]] | 82% |

TABLE 1-continued
| | | |
|---|---|---|
| 248 | 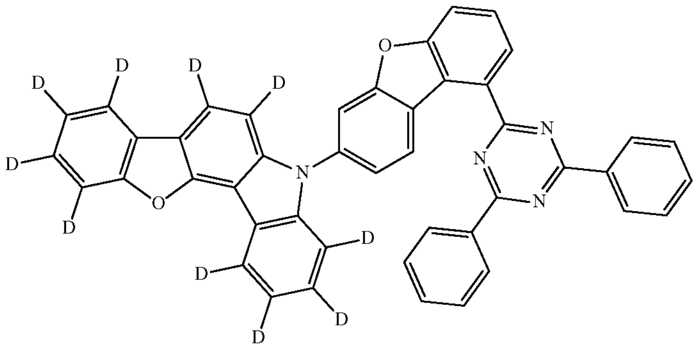 [SMILES: [2H]c1c([2H])c([2H])c2c(oc3c2c([2H])c([2H])c2c3c3c([2H])c([2H])c([2H])c([2H])c3n2-c2ccc3c(c2)oc2cccc(-c4nc(-c5ccccc5)nc(-c5ccccc5)n4)c23)c1[2H]] | 73% |
| 249 | 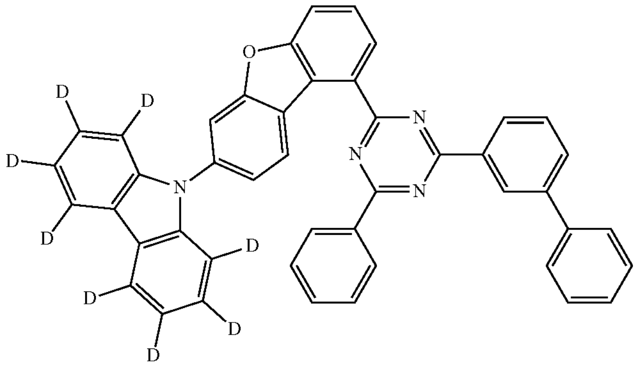 [SMILES: [2H]c1c([2H])c([2H])c2c(c1[2H])c1c([2H])c([2H])c([2H])c([2H])c1n2-c1ccc2c(c1)oc1cccc(-c3nc(-c4ccccc4)nc(-c4cccc(-c5ccccc5)c4)n3)c12] | 75% |
| 251 | 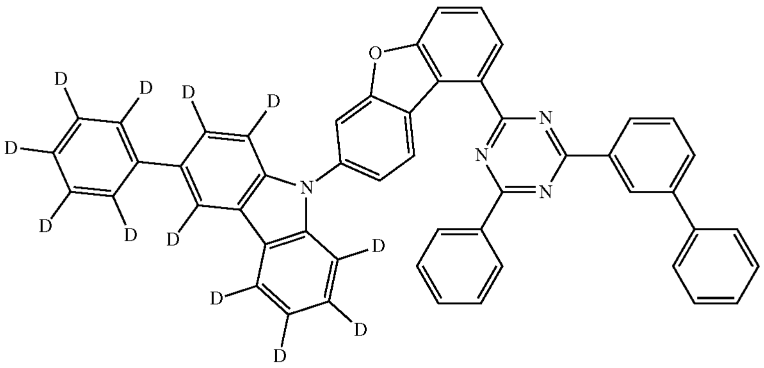 [SMILES: [2H]c1c([2H])c([2H])c(-c2c([2H])c([2H])c3c(c2[2H])c2c([2H])c([2H])c([2H])c([2H])c2n3-c2ccc3c(c2)oc2cccc(-c4nc(-c5ccccc5)nc(-c5cccc(-c6ccccc6)c5)n4)c23)c([2H])c1[2H]] | 77% |

TABLE 1-continued
| | | |
|---|---|---|
| 252 | 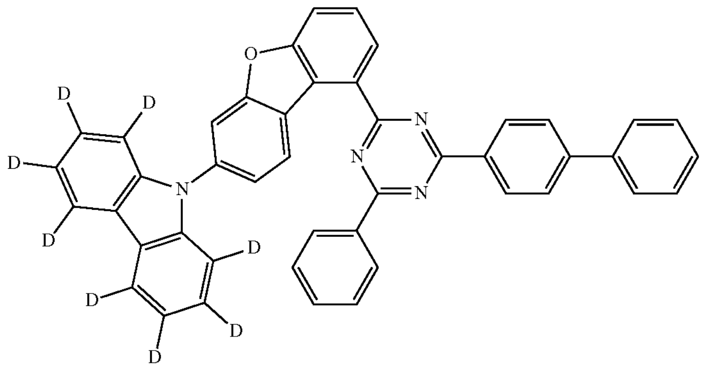 [SMILES: [2H]c1c([2H])c([2H])c2c(c1[2H])c1c([2H])c([2H])c([2H])c([2H])c1n2-c1ccc2c(c1)oc1cccc(-c3nc(-c4ccccc4)nc(-c4ccc(-c5ccccc5)cc4)n3)c12] | 85% |
| 257 | 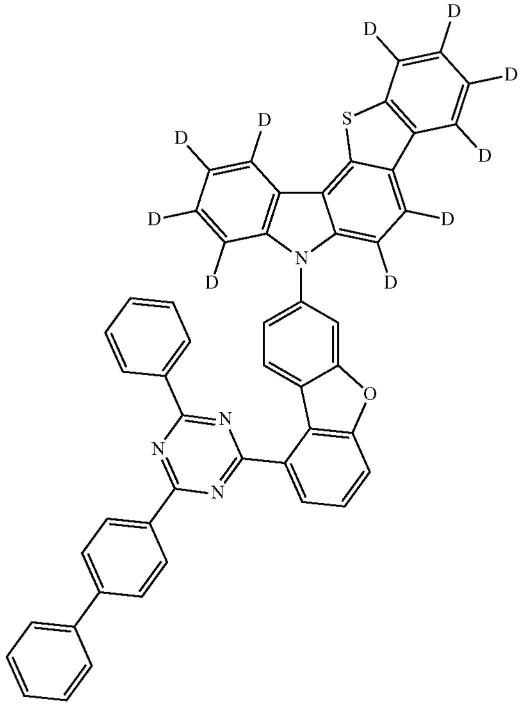 [SMILES: [2H]c1c([2H])c([2H])c2c(sc3c2c([2H])c([2H])c2c3c3c([2H])c([2H])c([2H])c([2H])c3n2-c2ccc3c(c2)oc2cccc(-c4nc(-c5ccccc5)nc(-c5ccc(-c6ccccc6)cc5)n4)c23)c1[2H]] | 79% |

TABLE 1-continued
| | | |
|---|---|---|
| 261 | 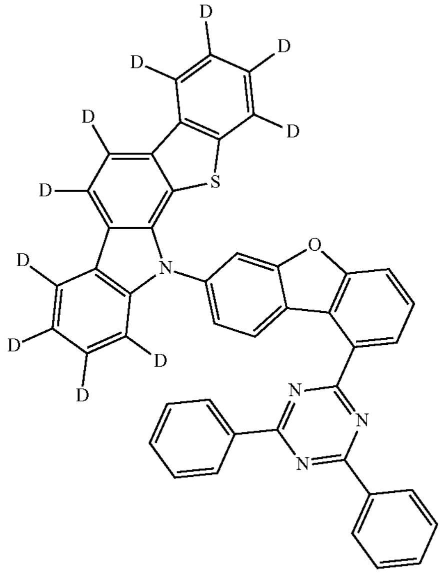 [SMILES: [2H]c1c([2H])c([2H])c2c(sc3c2c([2H])c([2H])c2c4c([2H])c([2H])c([2H])c([2H])c4n(-c4ccc5c(c4)oc4cccc(-c6nc(-c7ccccc7)nc(-c7ccccc7)n6)c45)c32)c1[2H]] | 76% |
| 263 | 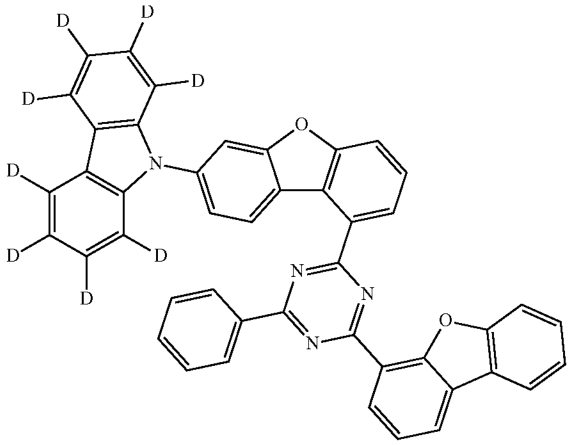 [SMILES: [2H]c1c([2H])c([2H])c2c(c1[2H])c1c([2H])c([2H])c([2H])c([2H])c1n2-c1ccc2c(c1)oc1cccc(-c3nc(-c4ccccc4)nc(-c4cccc5c4oc4ccccc45)n3)c12] | 62% |

TABLE 1-continued
| | | |
|---|---|---|
| 270 | 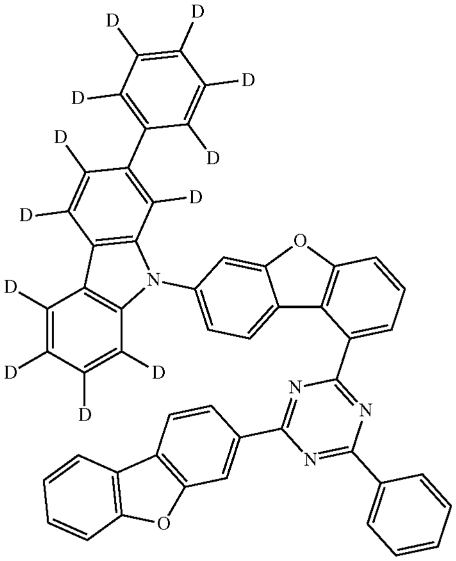 [SMILES: [2H]c1c([2H])c([2H])c(-c2c([2H])c([2H])c3c4c([2H])c([2H])c([2H])c([2H])c4n(-c4ccc5c(c4)oc4cccc(-c6nc(-c7ccccc7)nc(-c7ccc8c(c7)oc7ccccc78)n6)c45)c3c2[2H])c([2H])c1[2H]] | 66% |
| 386 | 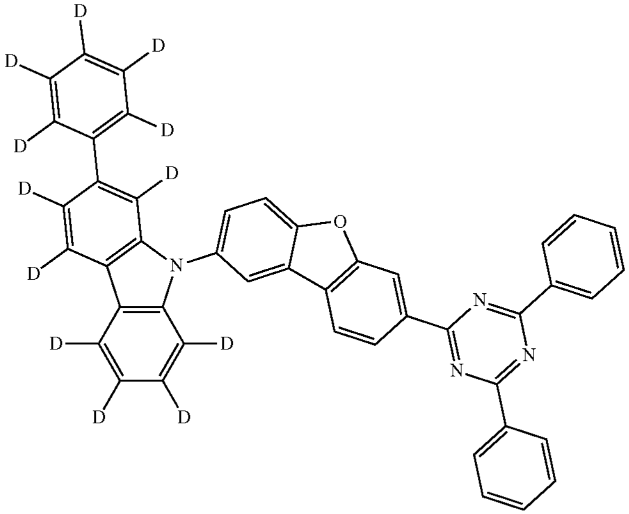 [SMILES: [2H]c1c([2H])c([2H])c(-c2c([2H])c([2H])c3c4c([2H])c([2H])c([2H])c([2H])c4n(-c4ccc5oc6cc(-c7nc(-c8ccccc8)nc(-c8ccccc8)n7)ccc6c5c4)c3c2[2H])c([2H])c1[2H]] | 65% |

TABLE 1-continued
| | | |
|---|---|---|
| 387 | 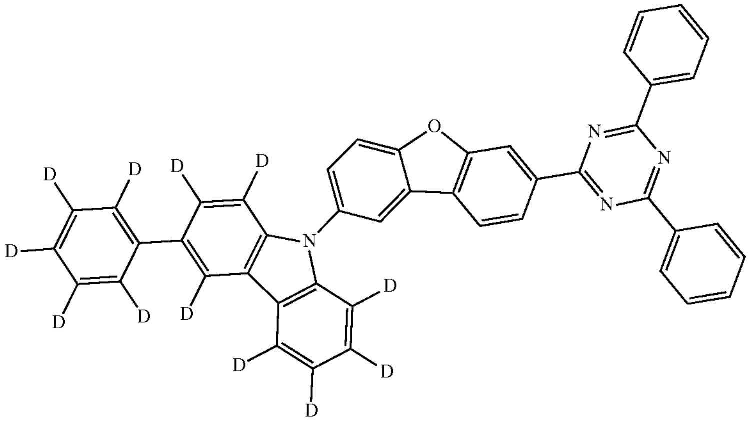 [SMILES: [2H]c1c([2H])c([2H])c(-c2c([2H])c([2H])c3c(c2[2H])c2c([2H])c([2H])c([2H])c([2H])c2n3-c2ccc3oc4cc(-c5nc(-c6ccccc6)nc(-c6ccccc6)n5)ccc4c3c2)c([2H])c1[2H]] | 63% |
| 390 | 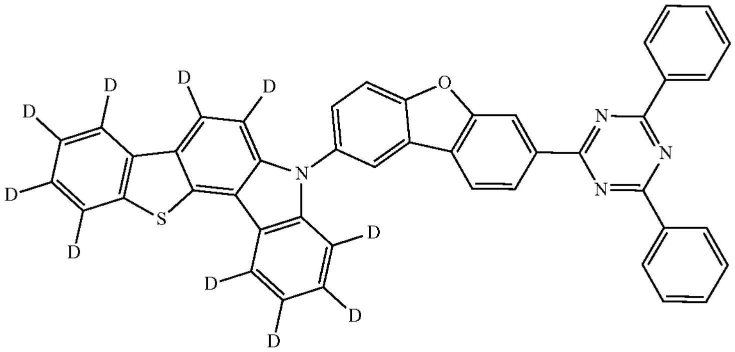 [SMILES: [2H]c1c([2H])c([2H])c2c(sc3c2c([2H])c([2H])c2c3c3c([2H])c([2H])c([2H])c([2H])c3n2-c2ccc3oc4cc(-c5nc(-c6ccccc6)nc(-c6ccccc6)n5)ccc4c3c2)c1[2H]] | 58% |

TABLE 1-continued
| | | |
|---|---|---|
| 392 | 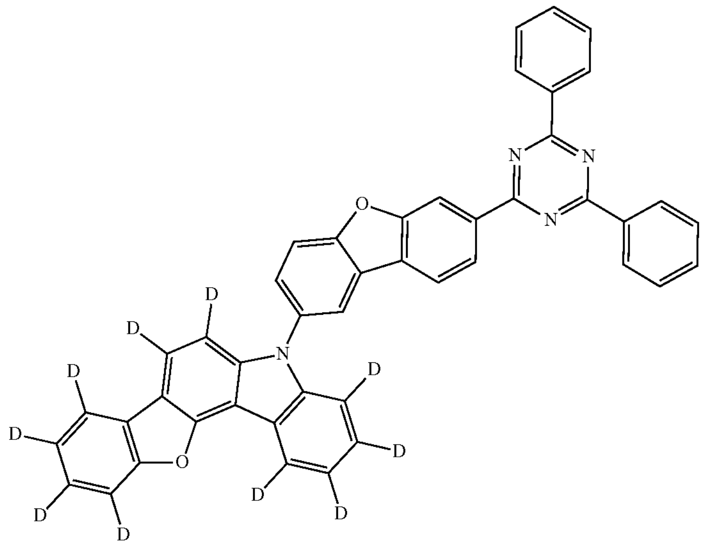 [SMILES: [2H]c1c([2H])c([2H])c2c(oc3c2c([2H])c([2H])c2c3c3c([2H])c([2H])c([2H])c([2H])c3n2-c2ccc3oc4cc(-c5nc(-c6ccccc6)nc(-c6ccccc6)n5)ccc4c3c2)c1[2H]] | 57% |
| 393 | 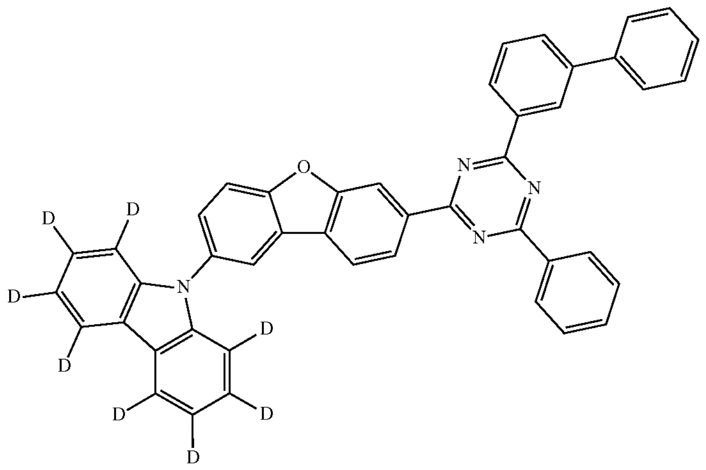 [SMILES: [2H]c1c([2H])c([2H])c2c(c1[2H])c1c([2H])c([2H])c([2H])c([2H])c1n2-c1ccc2oc3cc(-c4nc(-c5ccccc5)nc(-c5cccc(-c6ccccc6)c5)n4)ccc3c2c1] | 68% |

TABLE 1-continued
| | | |
|---|---|---|
| 395 | 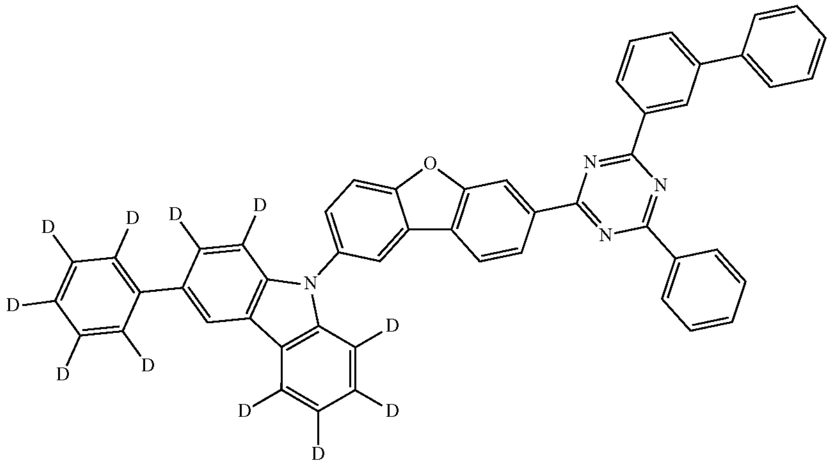 [SMILES: [2H]c1c([2H])c([2H])c(-c2cc3c4c([2H])c([2H])c([2H])c([2H])c4n(-c4ccc5oc6cc(-c7nc(-c8ccccc8)nc(-c8cccc(-c9ccccc9)c8)n7)ccc6c5c4)c3c([2H])c2[2H])c([2H])c1[2H]] | 63% |
| 396 | 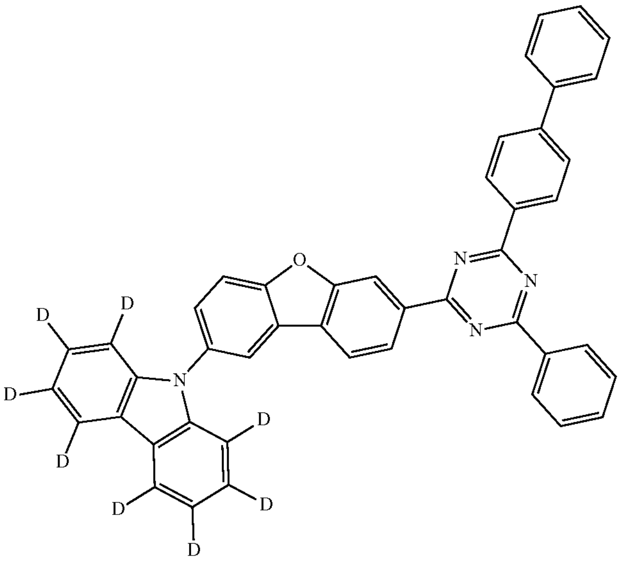 [SMILES: [2H]c1c([2H])c([2H])c2c(c1[2H])c1c([2H])c([2H])c([2H])c([2H])c1n2-c1ccc2oc3cc(-c4nc(-c5ccccc5)nc(-c5ccc(-c6ccccc6)cc5)n4)ccc3c2c1] | 78% |

TABLE 1-continued
| | | |
|---|---|---|
| 398 | 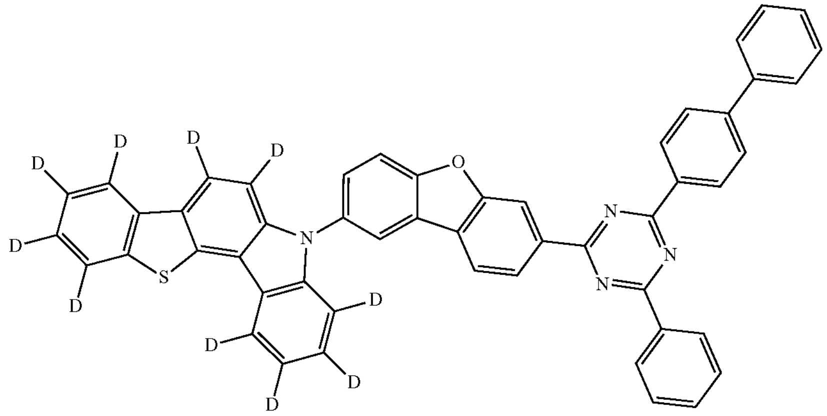 [SMILES: [2H]c1c([2H])c([2H])c2c(sc3c2c([2H])c([2H])c2c3c3c([2H])c([2H])c([2H])c([2H])c3n2-c2ccc3oc4cc(-c5nc(-c6ccccc6)nc(-c6ccc(-c7ccccc7)cc6)n5)ccc4c3c2)c1[2H]] | 72% |
| 399 | 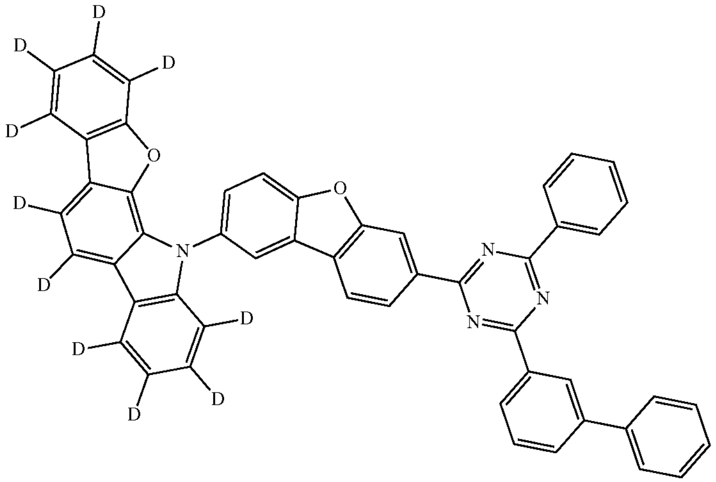 [SMILES: [2H]c1c([2H])c([2H])c2c(oc3c2c([2H])c([2H])c2c4c([2H])c([2H])c([2H])c([2H])c4n(-c4ccc5oc6cc(-c7nc(-c8ccccc8)nc(-c8cccc(-c9ccccc9)c8)n7)ccc6c5c4)c32)c1[2H]] | 52% |

TABLE 1-continued
| | | |
|---|---|---|
| 400 | 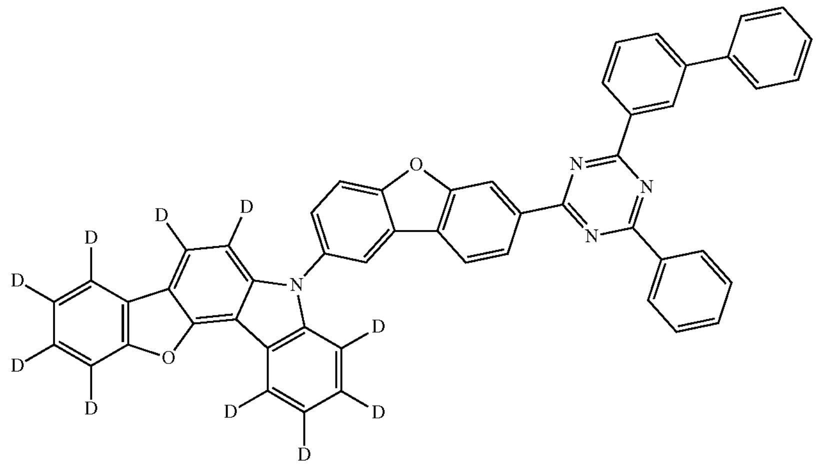 [SMILES: [2H]c1c([2H])c([2H])c2c(oc3c2c([2H])c([2H])c2c3c3c([2H])c([2H])c([2H])c([2H])c3n2-c2ccc3oc4cc(-c5nc(-c6ccccc6)nc(-c6cccc(-c7ccccc7)c6)n5)ccc4c3c2)c1[2H]] | 59% |
| 402 | 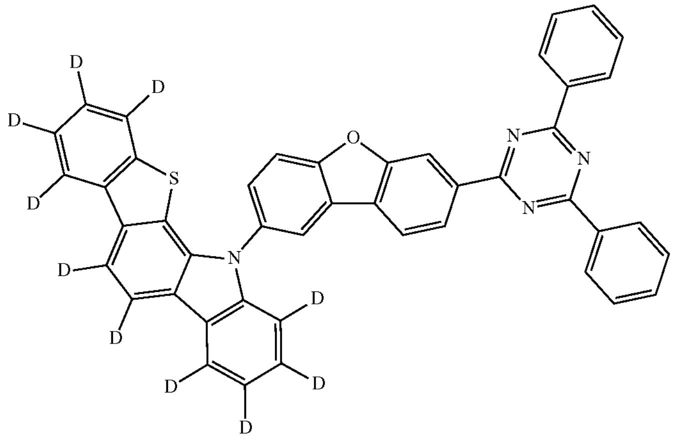 [SMILES: [2H]c1c([2H])c([2H])c2c(sc3c2c([2H])c([2H])c2c4c([2H])c([2H])c([2H])c([2H])c4n(-c4ccc5oc6cc(-c7nc(-c8ccccc8)nc(-c8ccccc8)n7)ccc6c5c4)c32)c1[2H]] | 60% |

TABLE 1-continued
| | | |
|---|---|---|
| 404 | 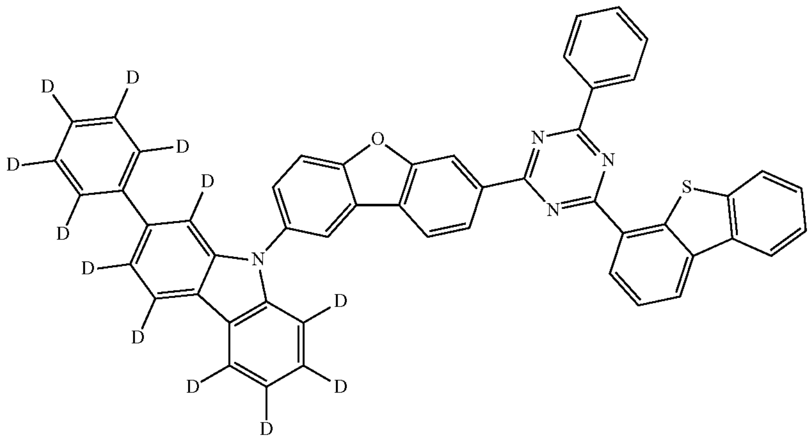 [SMILES: [2H]c1c([2H])c([2H])c(-c2c([2H])c([2H])c3c4c([2H])c([2H])c([2H])c([2H])c4n(-c4ccc5oc6cc(-c7nc(-c8ccccc8)nc(-c8cccc9c8sc8ccccc89)n7)ccc6c5c4)c3c2[2H])c([2H])c1[2H]] | 87% |
| 406 | 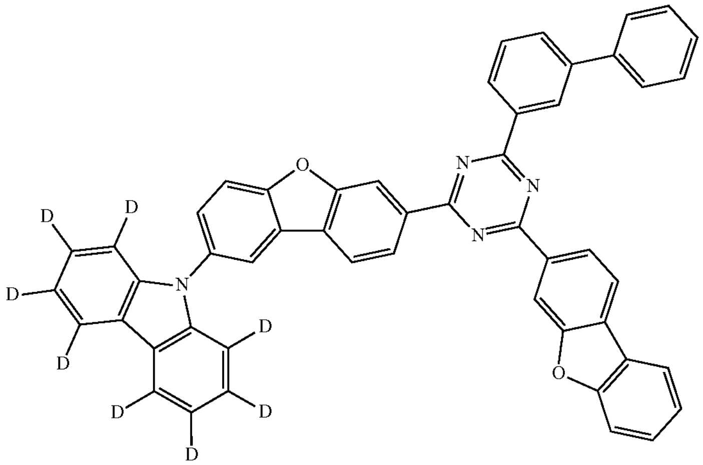 [SMILES: [2H]c1c([2H])c([2H])c2c(c1[2H])c1c([2H])c([2H])c([2H])c([2H])c1n2-c1ccc2oc3cc(-c4nc(-c5cccc(-c6ccccc6)c5)nc(-c5ccc6c(c5)oc5ccccc56)n4)ccc3c2c1] | 80% |

TABLE 1-continued
| | | |
|---|---|---|
| 410 | 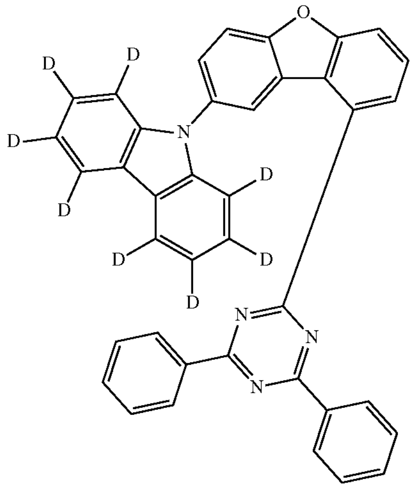 [SMILES: [2H]c1c([2H])c([2H])c2c(c1[2H])c1c([2H])c([2H])c([2H])c([2H])c1n2-c1ccc2oc3cccc(-c4nc(-c5ccccc5)nc(-c5ccccc5)n4)c3c2c1] | 82% |
| 411 | 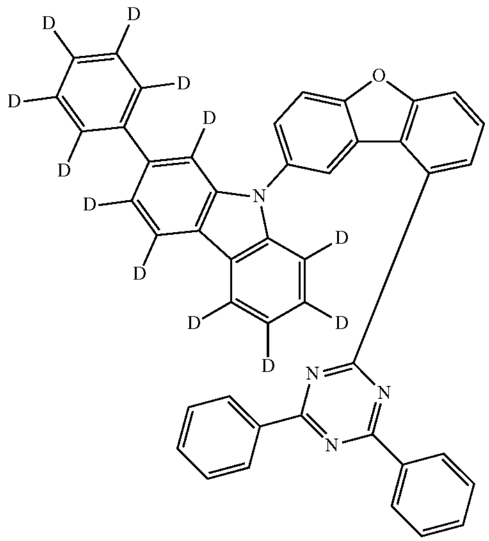 [SMILES: [2H]c1c([2H])c([2H])c(-c2c([2H])c([2H])c3c4c([2H])c([2H])c([2H])c([2H])c4n(-c4ccc5oc6cccc(-c7nc(-c8ccccc8)nc(-c8ccccc8)n7)c6c5c4)c3c2[2H])c([2H])c1[2H]] | 86% |

TABLE 1-continued
| | | |
|---|---|---|
| 525 | 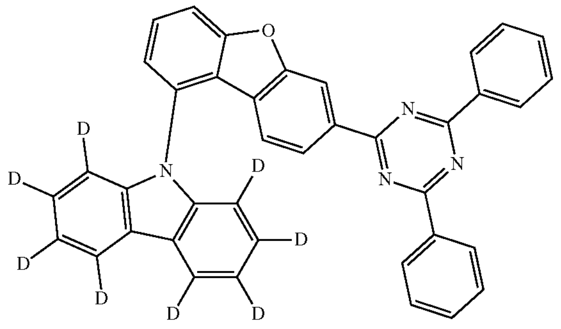 [SMILES: [2H]c1c([2H])c([2H])c2c(c1[2H])c1c([2H])c([2H])c([2H])c([2H])c1n2-c1cccc2oc3cc(-c4nc(-c5ccccc5)nc(-c5ccccc5)n4)ccc3c12] | 79% |
| 526 | 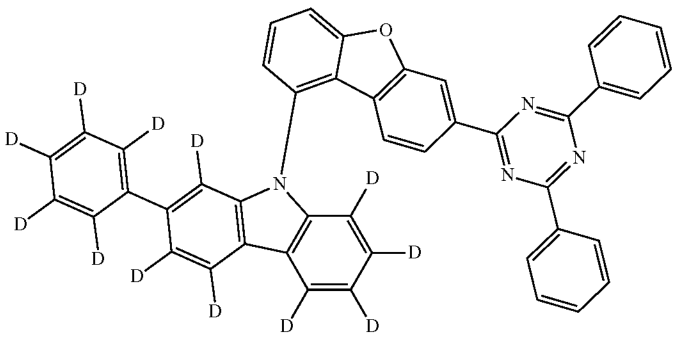 [SMILES: [2H]c1c([2H])c([2H])c(-c2c([2H])c([2H])c3c4c([2H])c([2H])c([2H])c([2H])c4n(-c4cccc5oc6cc(-c7nc(-c8ccccc8)nc(-c8ccccc8)n7)ccc6c45)c3c2[2H])c([2H])c1[2H]] | 88% |

TABLE 1-continued
| | | |
|---|---|---|
| 527 | 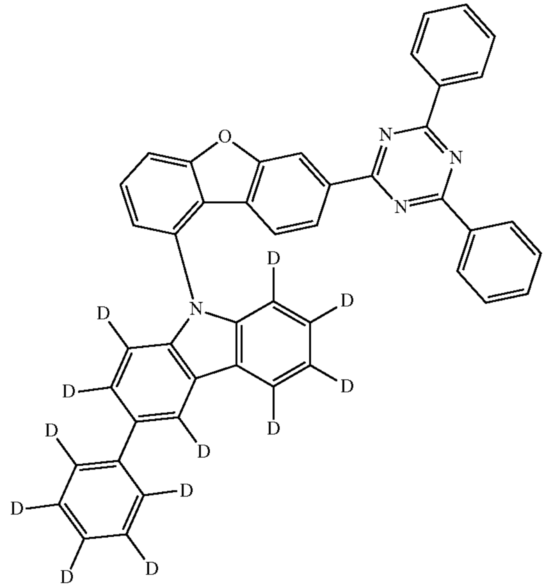 [SMILES: [2H]c1c([2H])c([2H])c(-c2c([2H])c([2H])c3c(c2[2H])c2c([2H])c([2H])c([2H])c([2H])c2n3-c2cccc3oc4cc(-c5nc(-c6ccccc6)nc(-c6ccccc6)n5)ccc4c23)c([2H])c1[2H]] | 76% |
| 531 | 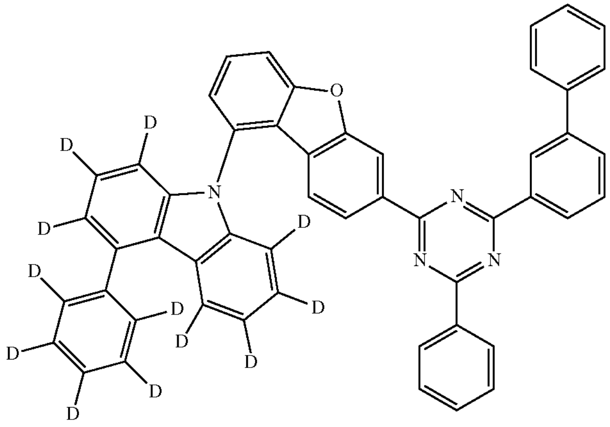 [SMILES: [2H]c1c([2H])c([2H])c(-c2c([2H])c([2H])c([2H])c3c2c2c([2H])c([2H])c([2H])c([2H])c2n3-c2cccc3oc4cc(-c5nc(-c6ccccc6)nc(-c6cccc(-c7ccccc7)c6)n5)ccc4c23)c([2H])c1[2H]] | 92% |

TABLE 1-continued
| | | |
|---|---|---|
| 533 | 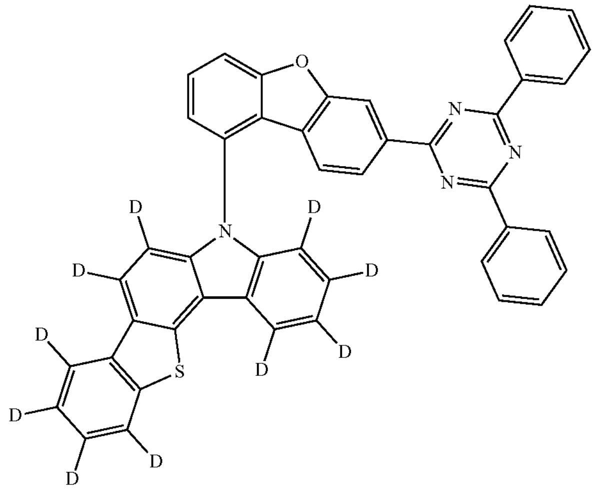 | 93% |
| 535 | 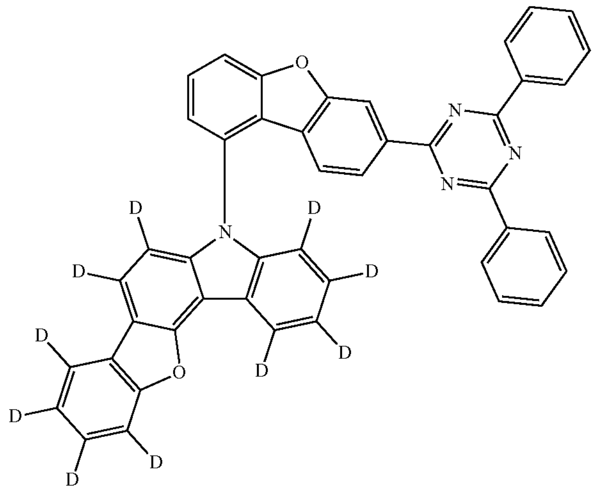 [SMILES: [2H]c1c([2H])c([2H])c2c(oc3c2c([2H])c([2H])c2c3c3c([2H])c([2H])c([2H])c([2H])c3n2-c2cccc3oc4cc(-c5nc(-c6ccccc6)nc(-c6ccccc6)n5)ccc4c23)c1[2H]] | 88% |

TABLE 1-continued
| | | |
|---|---|---|
| 536 | 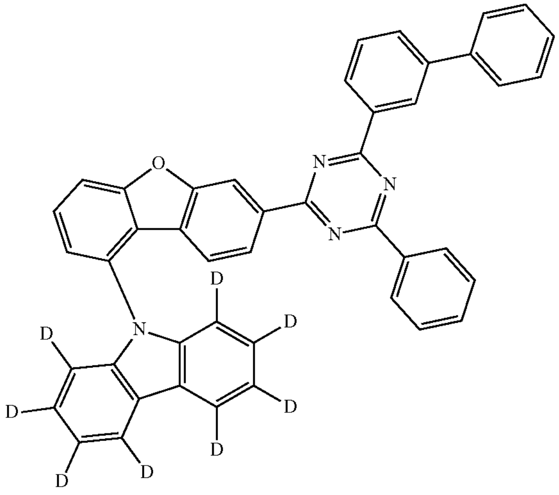 [SMILES: [2H]c1c([2H])c([2H])c2c(c1[2H])c1c([2H])c([2H])c([2H])c([2H])c1n2-c1cccc2oc3cc(-c4nc(-c5ccccc5)nc(-c5cccc(-c6ccccc6)c5)n4)ccc3c12] | 75% |
| 538 | 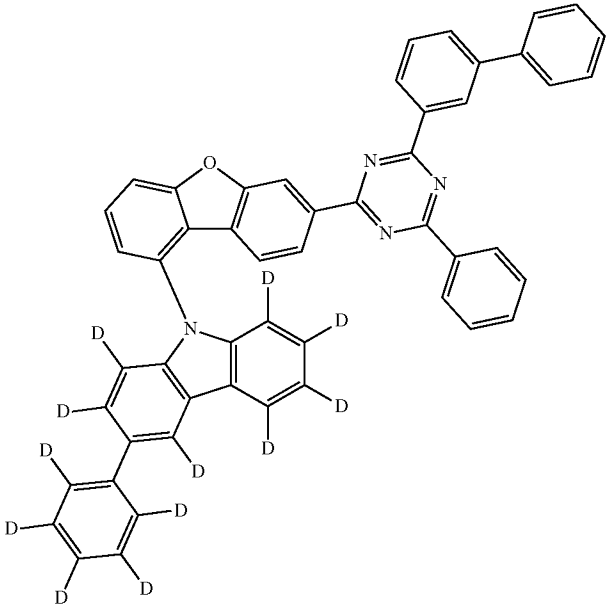 [SMILES: [2H]c1c([2H])c([2H])c(-c2c([2H])c([2H])c3c(c2[2H])c2c([2H])c([2H])c([2H])c([2H])c2n3-c2cccc3oc4cc(-c5nc(-c6ccccc6)nc(-c6cccc(-c7ccccc7)c6)n5)ccc4c23)c([2H])c1[2H]] | 71% |

TABLE 1-continued
| | | |
|---|---|---|
| 539 | 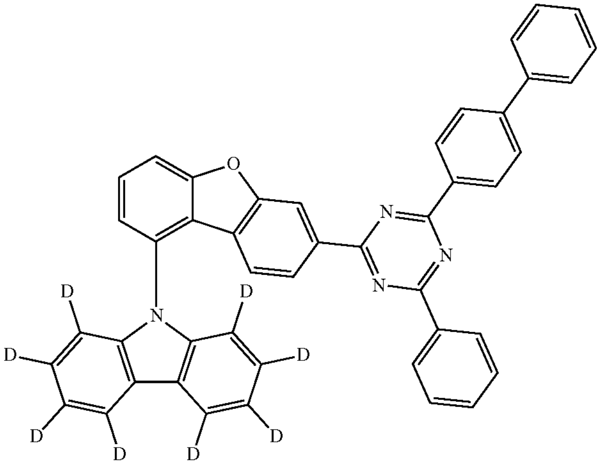 [SMILES: [2H]c1c([2H])c([2H])c2c(c1[2H])c1c([2H])c([2H])c([2H])c([2H])c1n2-c1cccc2oc3cc(-c4nc(-c5ccccc5)nc(-c5ccc(-c6ccccc6)cc5)n4)ccc3c12] | 73% |
| 544 | 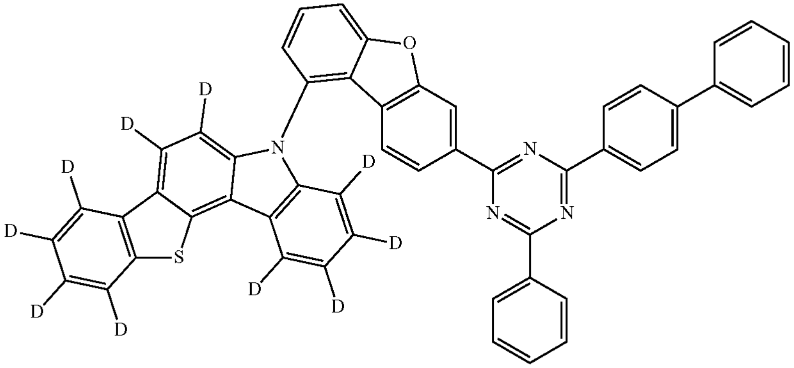 [SMILES: [2H]c1c([2H])c([2H])c2c(sc3c2c([2H])c([2H])c2c3c3c([2H])c([2H])c([2H])c([2H])c3n2-c2cccc3oc4cc(-c5nc(-c6ccccc6)nc(-c6ccc(-c7ccccc7)cc6)n5)ccc4c23)c1[2H]] | 72% |

TABLE 1-continued
| | | |
|---|---|---|
| 545 | 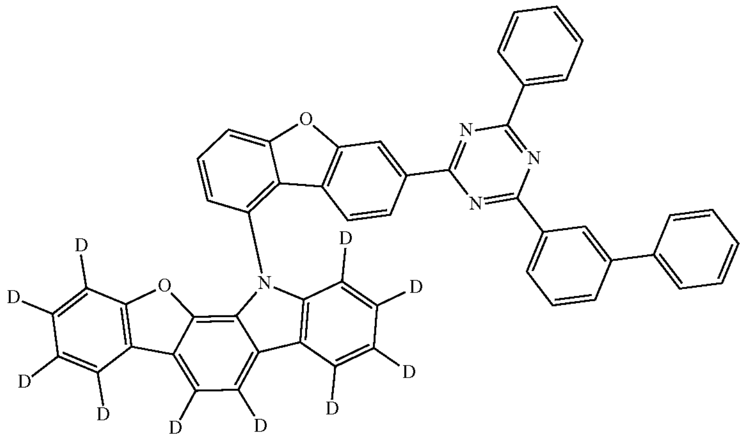 [SMILES: [2H]c1c([2H])c([2H])c2c(oc3c2c([2H])c([2H])c2c4c([2H])c([2H])c([2H])c([2H])c4n(-c4cccc5oc6cc(-c7nc(-c8ccccc8)nc(-c8cccc(-c9ccccc9)c8)n7)ccc6c45)c32)c1[2H]] | 71% |
| 546 | 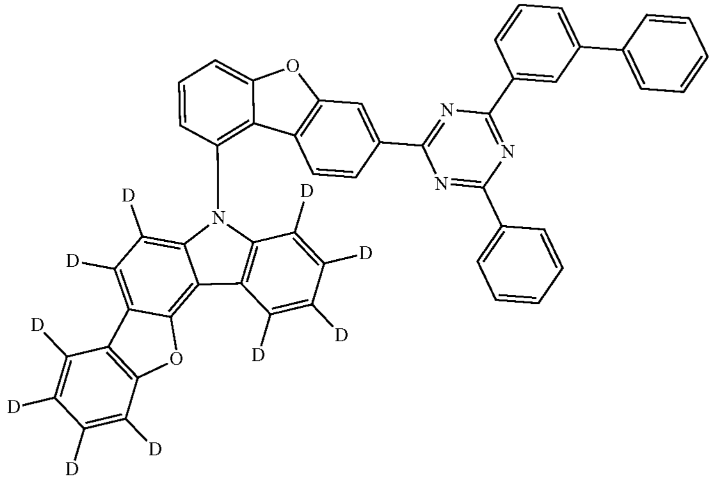 [SMILES: [2H]c1c([2H])c([2H])c2c(oc3c2c([2H])c([2H])c2c3c3c([2H])c([2H])c([2H])c([2H])c3n2-c2cccc3oc4cc(-c5nc(-c6ccccc6)nc(-c6cccc(-c7ccccc7)c6)n5)ccc4c23)c1[2H]] | 76% |

TABLE 1-continued
| | | |
|---|---|---|
| 550 | 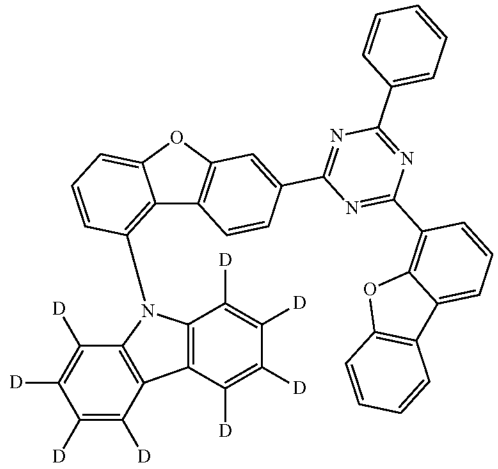 [SMILES: [2H]c1c([2H])c([2H])c2c(c1[2H])c1c([2H])c([2H])c([2H])c([2H])c1n2-c1cccc2oc3cc(-c4nc(-c5ccccc5)nc(-c5cccc6c5oc5ccccc56)n4)ccc3c12] | 82% |

[Synthesis 2] The compound 71 (F)

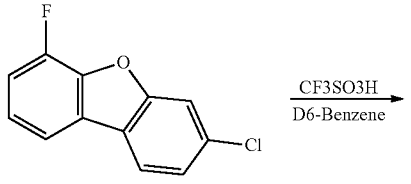

[A]

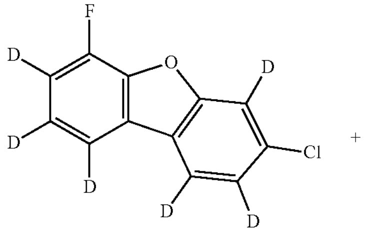

[A]-1

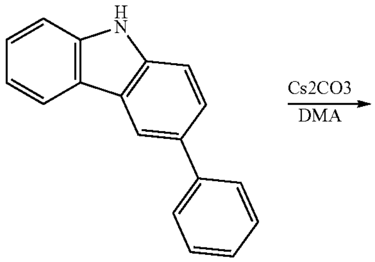

[B]

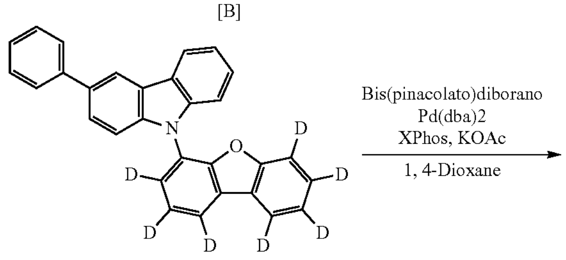

71-1

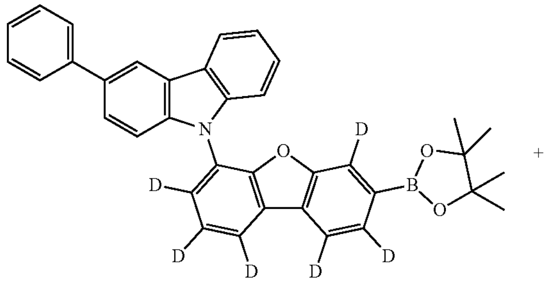

71-2

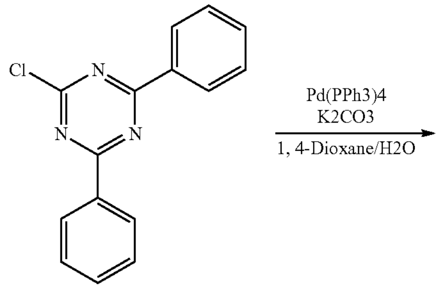

[C]

-continued

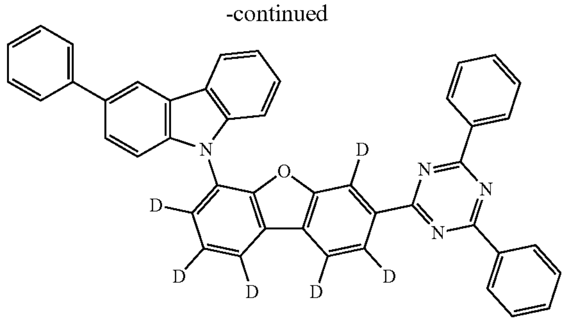

71[F]

(1) The Compound [A]-1

In the one-neck round bottom flask, a mixture of 3-chloro-6-fluorodibenzo [b, d]furan (10 g, 0.045 mol), triflic acid (34 g, 0.23 mol) and D6-benzene (200 mL) was refluxed at 70° C. After quenching and extraction with dichloromethane and $H_2O$, the resultant was concentrated and filtered through silica gel. After concentration, the resultant was treated with methanol to obtain the compound [A]-1. (9.89 g, 97%)

(2) The Compound 71-1

In the one-neck round bottom flask, a mixture of 3-chloro-6-fluorodibenzo[b,d]furan-1,2,4,7,8,9-d6 (9.89 g, 0.044 mol), 3-phenyl-9H-carbazole (11.78 g, 0.048 mol), $Cs_2CO_3$ (28.67 g, 0.088 mol) and dimethylacetamide (100 mL) was refluxed at 170° C. After cooling, the resultant was filtered to remove the solvent and purified by column to obtain the compound 71-1. (16.83 g, 85%)

(3) The Compound 71-2

In the one-neck round bottom flask, a mixture of 9-(7-chlorodibenzo[b,d]furan-4-yl-1,2,3,6,8,9-d6)-3-phenyl-9H-carbazole (16.83 g, 0.037 mol), bis(pinacolato)diboron (Bis(pinacolato)diborn) (18.79 g, 0.074 mol), $Pd(dba)_2$ (3.39 g, 0.0037 mol), Xphos (3.53 g, 0.0074 mol), potassium acetate (10.89 g, 0.11 mol) and 1,4-dioxane (160 mL) was refluxed at 120° C. After cooling, the resultant was concentrated and filtered through silica gel to obtain the compound 71-2. (19.43 g, 97%)

(4) The Compound 71[E]

In the one-neck round bottom flask, a mixture of 3-phenyl-9-(7-(4,4,5,5-tetramethyl-1,3,2-dioxaborolan-2-yl)dibenzo[b,d]furan-4-yl-1,2,3,6,8,9-d6)-9H-carbazole (19.43 g, 0.036 mol), 2-chloro-4,6-diphenyl-1,3,5-triazine (10.71 g, 0.040 mol), $Pd(PPh_3)_4$ (2.08 g, 0.0018 mol), $K_2CO_3$ (9.95 g, 0.072 mol), 1,4-dioxane (190 mL) and water (80 mL) was refluxed at 120° C. After cooling, the resultant was concentrated and filtered through silica gel to obtain the compound 71 [F]. (16.30 g, 70%)

The following compound F was synthesized in the same manner as in the synthesis 2 except that intermediates A, B, and C of Table 2 were used.

TABLE 2
| Compound | A | B | C |
|---|---|---|---|
| 71 | 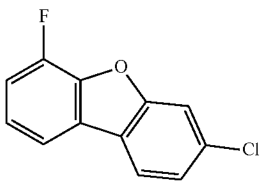 | 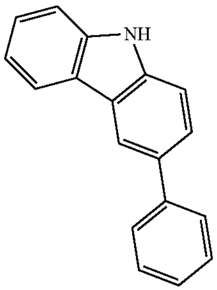 | 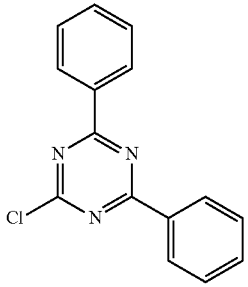 |
| 73 | 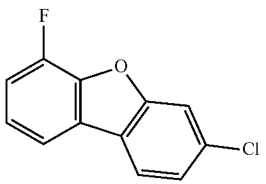 | 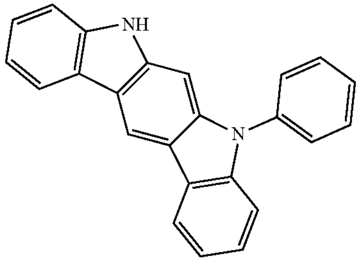 | 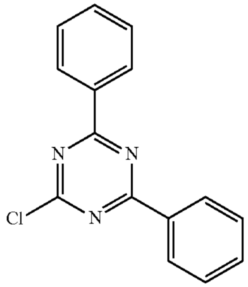 |
| 82 | 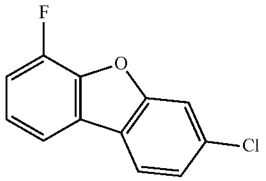 | 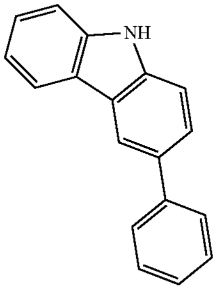 | 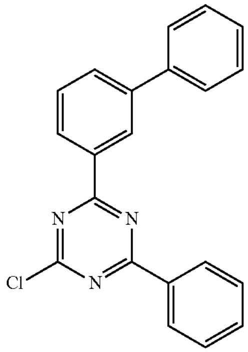 |

TABLE 2-continued
| | | | |
|---|---|---|---|
| 98 | 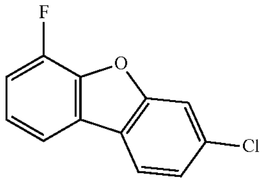 | 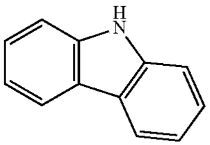 | 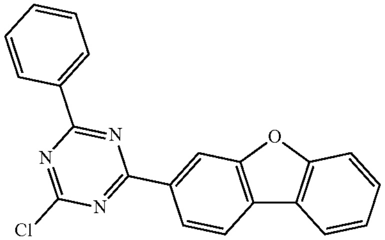 |
| 103 | 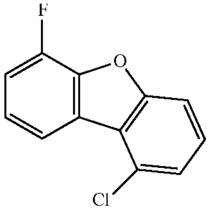 | 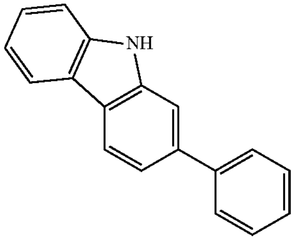 | 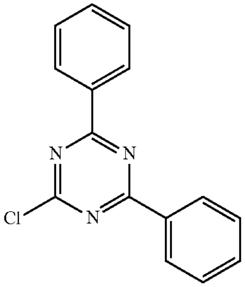 |
| 110 | 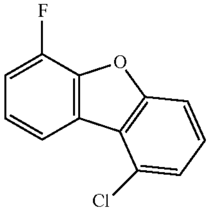 | 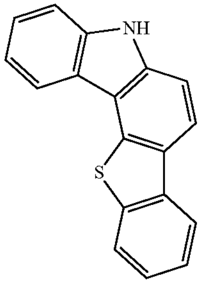 | 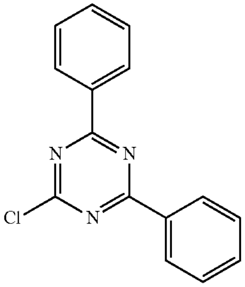 |

TABLE 2-continued
| | | | |
|---|---|---|---|
| 116 | 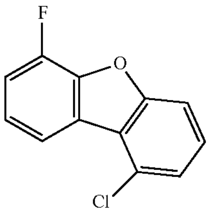 | 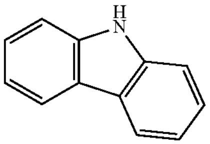 | 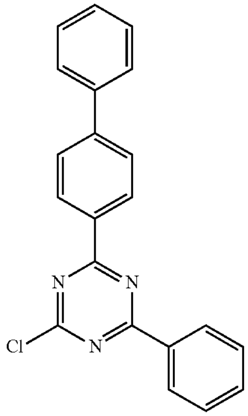 |
| 273 | 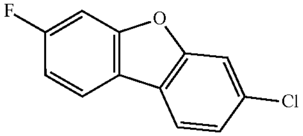 | 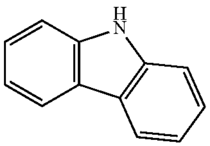 | 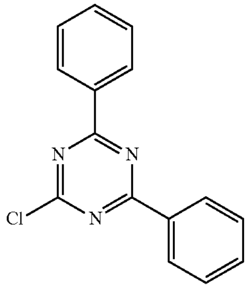 |
| 274 | 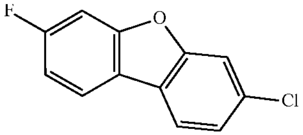 | 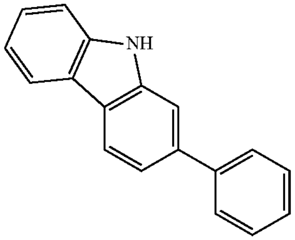 | 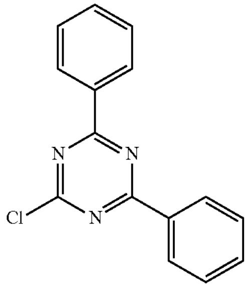 |

TABLE 2-continued
| | | | |
|---|---|---|---|
| 278 | 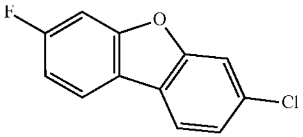 | 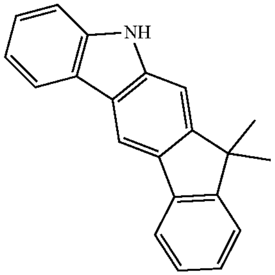 | 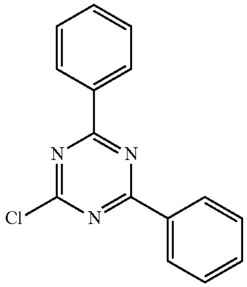 |
| 280 | 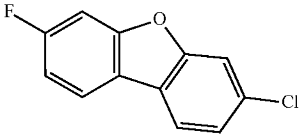 | 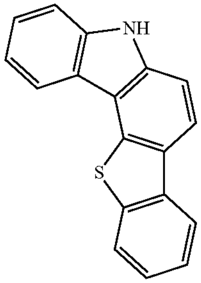 | 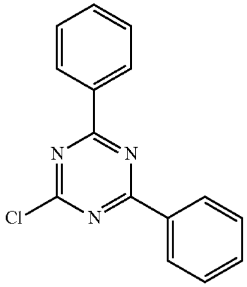 |
| 286 | 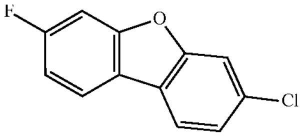 | 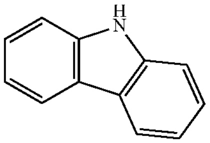 | 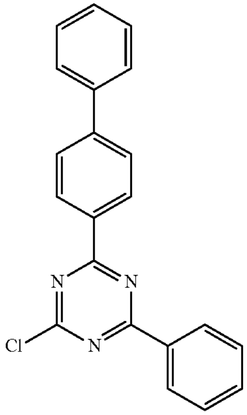 |

TABLE 2-continued
| | | | |
|---|---|---|---|
| 300 | 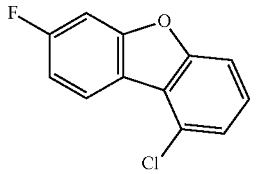 | 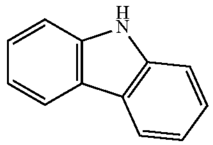 | 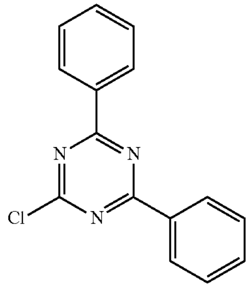 |
| 303 | 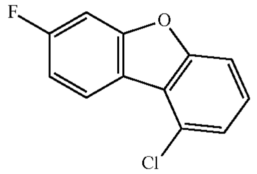 | 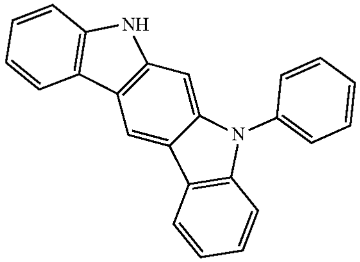 | 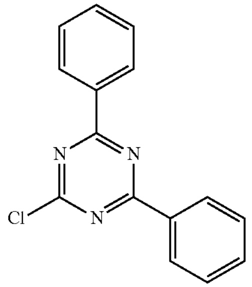 |
| 307 | 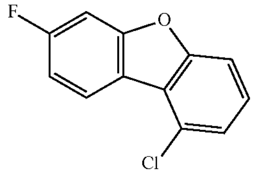 | 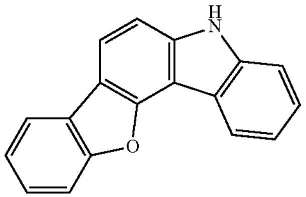 | 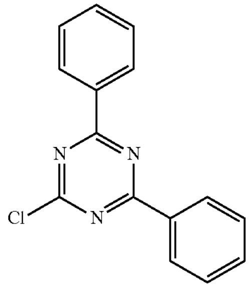 |

TABLE 2-continued
| | | | |
|---|---|---|---|
| 308 | 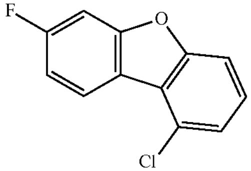 [SMILES: Fc1ccc2c(c1)oc1cccc(Cl)c12] | 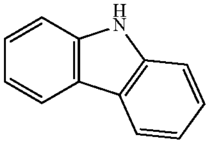 [SMILES: c1ccc2c(c1)[nH]c1ccccc12] | 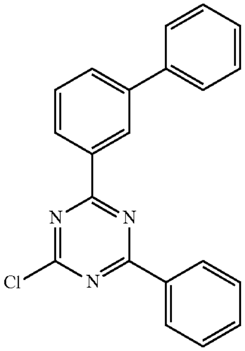 [SMILES: Clc1nc(-c2ccccc2)nc(-c2cccc(-c3ccccc3)c2)n1] |
| 315 | 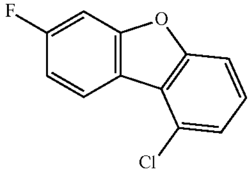 [SMILES: Fc1ccc2c(c1)oc1cccc(Cl)c12] | 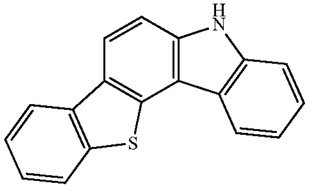 [SMILES: c1ccc2c(c1)[nH]c1ccc3c4ccccc4sc3c12] | 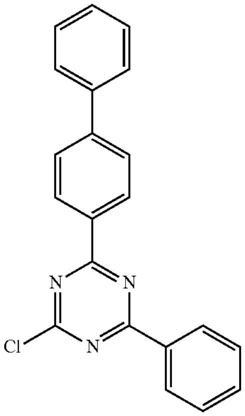 [SMILES: Clc1nc(-c2ccccc2)nc(-c2ccc(-c3ccccc3)cc2)n1] |
| 318 | 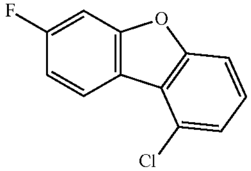 [SMILES: Fc1ccc2c(c1)oc1cccc(Cl)c12] | 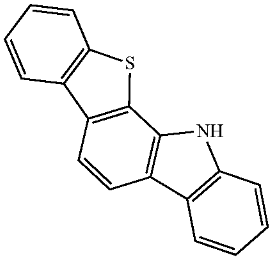 | 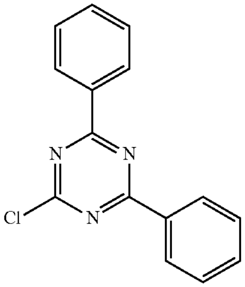 [SMILES: Clc1nc(-c2ccccc2)nc(-c2ccccc2)n1] |

TABLE 2-continued
| | | | |
|---|---|---|---|
| 320 | 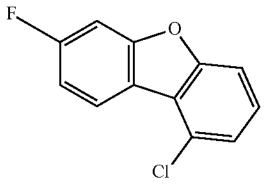 | 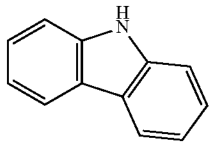 [SMILES: c1ccc2c(c1)[nH]c1ccccc12] | 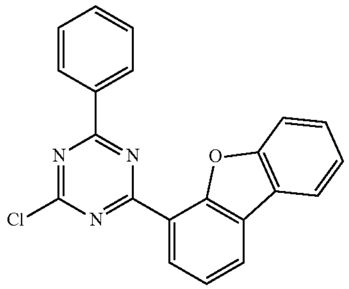 |
| 324 | 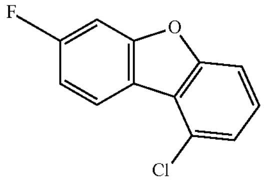 | 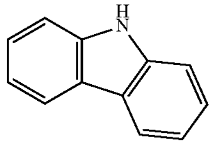 [SMILES: c1ccc2c(c1)[nH]c1ccccc12] | 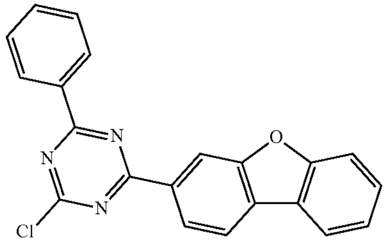 [SMILES: Clc1nc(-c2ccccc2)nc(-c2ccc3c(c2)oc2ccccc23)n1] |
| 328 | 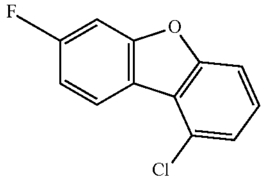 | 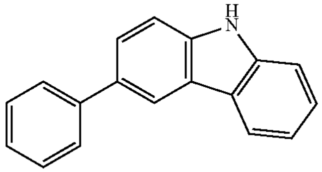 [SMILES: c1ccc(-c2ccc3[nH]c4ccccc4c3c2)cc1] | 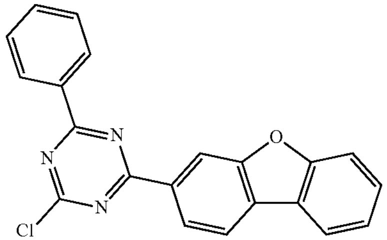 [SMILES: Clc1nc(-c2ccccc2)nc(-c2ccc3c(c2)oc2ccccc23)n1] |
| 435 | 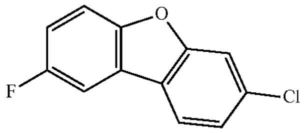 [SMILES: Fc1ccc2oc3cc(Cl)ccc3c2c1] | 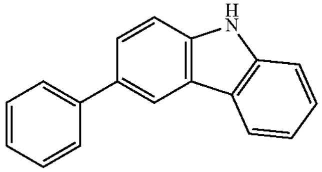 [SMILES: c1ccc(-c2ccc3[nH]c4ccccc4c3c2)cc1] | 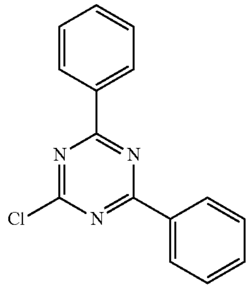 [SMILES: Clc1nc(-c2ccccc2)nc(-c2ccccc2)n1] |

TABLE 2-continued
| | | | |
|---|---|---|---|
| 440 | 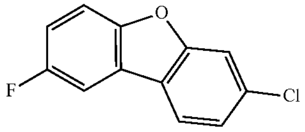 [SMILES: Fc1ccc2oc3cc(Cl)ccc3c2c1] | 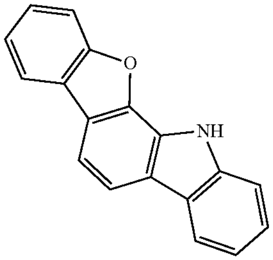 | 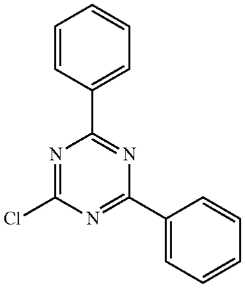 [SMILES: Clc1nc(-c2ccccc2)nc(-c2ccccc2)n1] |
| 442 | 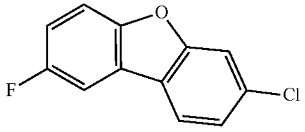 [SMILES: Fc1ccc2oc3cc(Cl)ccc3c2c1] | 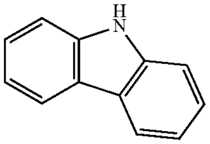 | 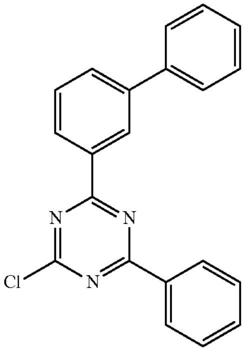 [SMILES: Clc1nc(-c2ccccc2)nc(-c2cccc(-c3ccccc3)c2)n1] |
| 444 | 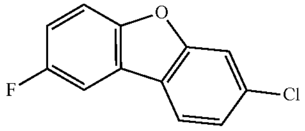 [SMILES: Fc1ccc2oc3cc(Cl)ccc3c2c1] | 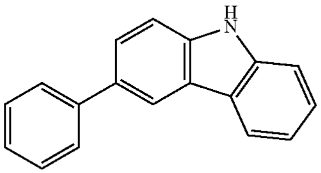 [SMILES: c1ccc(-c2ccc3[nH]c4ccccc4c3c2)cc1] | 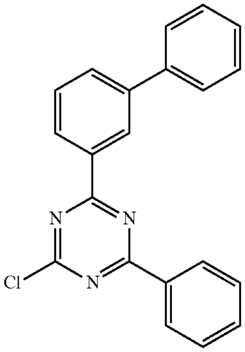 [SMILES: Clc1nc(-c2ccccc2)nc(-c2cccc(-c3ccccc3)c2)n1] |

TABLE 2-continued
| | | | |
|---|---|---|---|
| 445 | 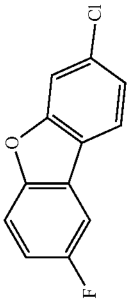 | 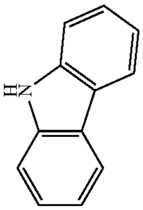 | 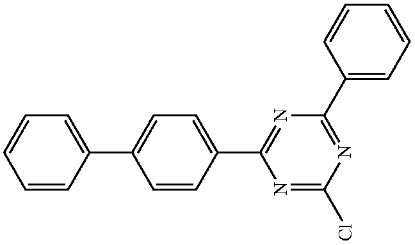 |
| 455 | 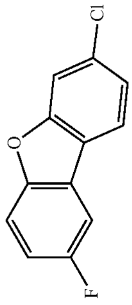 | 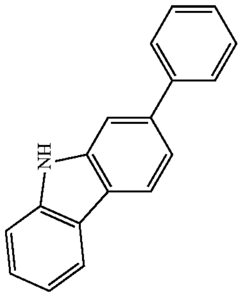 | 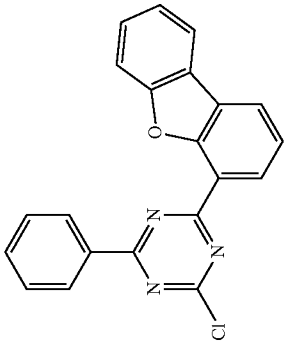 |
| 457 | 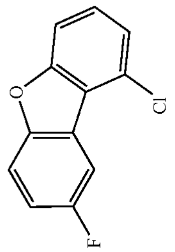 | 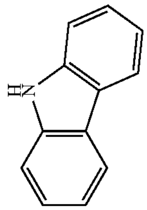 | 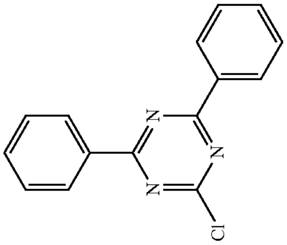 |

TABLE 2-continued
| | | | |
|---|---|---|---|
| 569 | 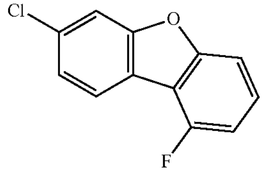 [SMILES: Fc1cccc2oc3cc(Cl)ccc3c12] | 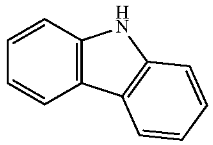 [SMILES: c1ccc2c(c1)[nH]c1ccccc12] | 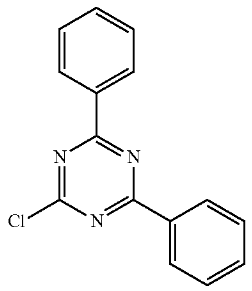 [SMILES: Clc1nc(-c2ccccc2)nc(-c2ccccc2)n1] |
| 571 | 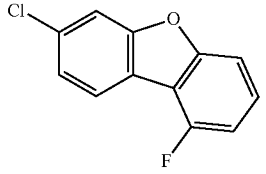 [SMILES: Fc1cccc2oc3cc(Cl)ccc3c12] | 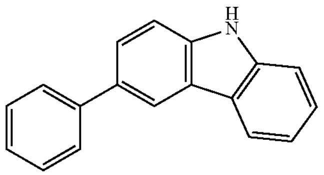 [SMILES: c1ccc(-c2ccc3[nH]c4ccccc4c3c2)cc1] | 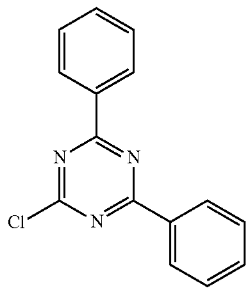 [SMILES: Clc1nc(-c2ccccc2)nc(-c2ccccc2)n1] |
| 573 | 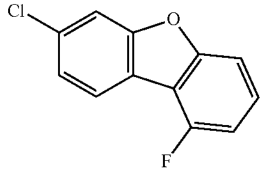 [SMILES: Fc1cccc2oc3cc(Cl)ccc3c12] | 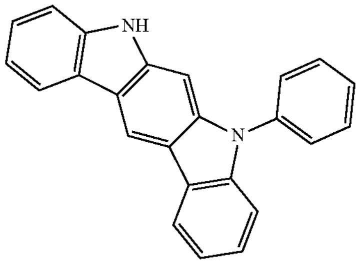 [SMILES: c1ccc(-n2c3ccccc3c3cc4c(cc32)[nH]c2ccccc24)cc1] | 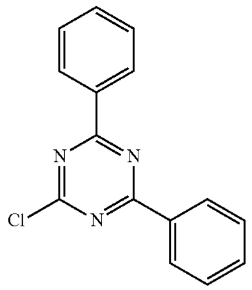 [SMILES: Clc1nc(-c2ccccc2)nc(-c2ccccc2)n1] |

TABLE 2-continued
| | | | |
|---|---|---|---|
| 579 | 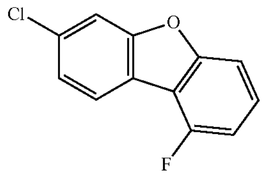 [SMILES: Fc1cccc2oc3cc(Cl)ccc3c12] | 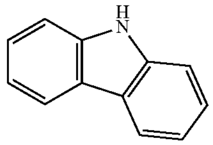 [SMILES: c1ccc2c(c1)[nH]c1ccccc12] | 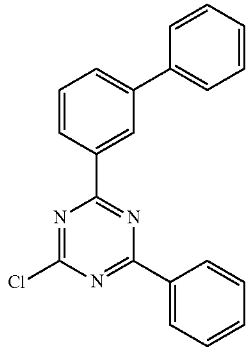 [SMILES: Clc1nc(-c2ccccc2)nc(-c2cccc(-c3ccccc3)c2)n1] |
| 580 | 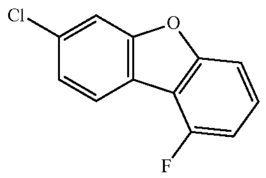 [SMILES: Fc1cccc2oc3cc(Cl)ccc3c12] | 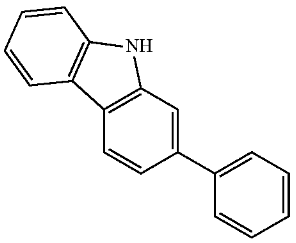 [SMILES: c1ccc(-c2ccc3c(c2)[nH]c2ccccc23)cc1] | 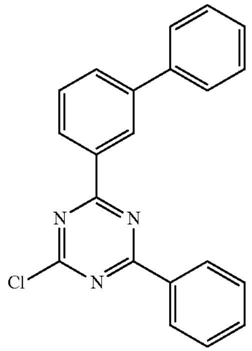 [SMILES: Clc1nc(-c2ccccc2)nc(-c2cccc(-c3ccccc3)c2)n1] |

TABLE 2-continued
| | | | |
|---|---|---|---|
| 582 | 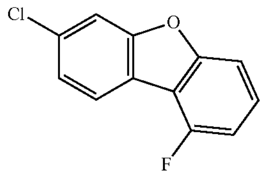 [SMILES: Fc1cccc2oc3cc(Cl)ccc3c12] | 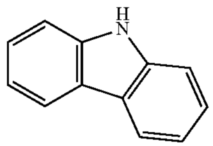 | 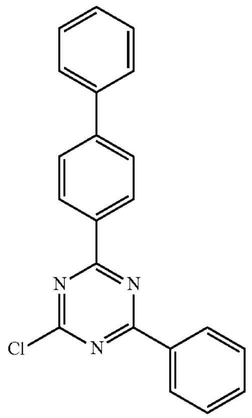 [SMILES: Clc1nc(-c2ccccc2)nc(-c2ccc(-c3ccccc3)cc2)n1] |
| 592 | 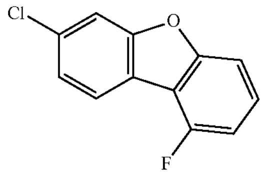 [SMILES: Fc1cccc2oc3cc(Cl)ccc3c12] | 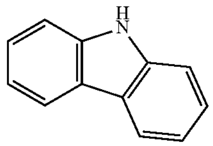 [SMILES: c1ccc2c(c1)[nH]c1ccccc12] | 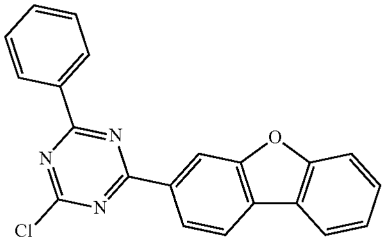 [SMILES: Clc1nc(-c2ccccc2)nc(-c2ccc3c(c2)oc2ccccc23)n1] |

TABLE 2-continued
| Compound | F | yield |
| --- | --- | --- |
| 71 | 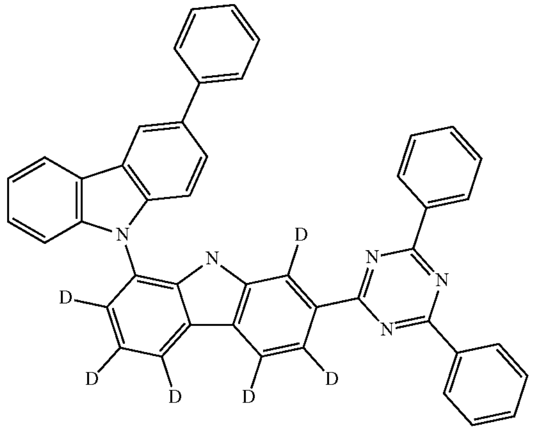 | 70% |
| 73 | 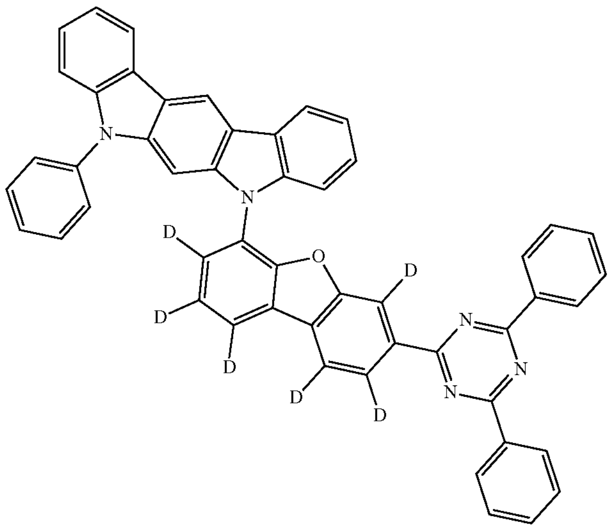 | 75% |

TABLE 2-continued
| | | |
|---|---|---|
| 82 | 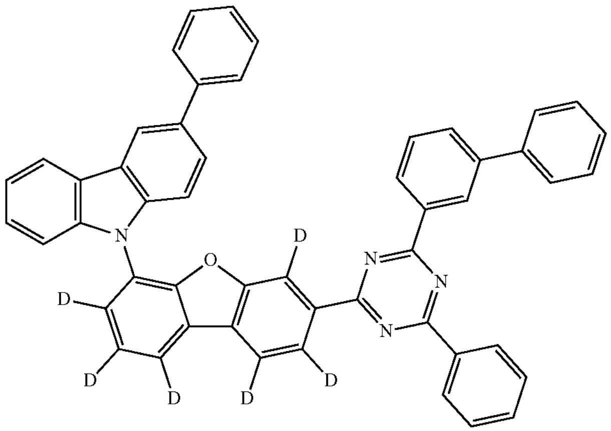 | 83% |
| 98 | 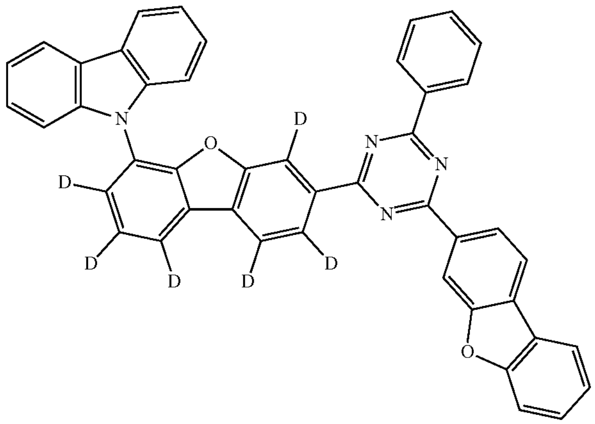 | 89% |

TABLE 2-continued
| | | |
|---|---|---|
| 103 | 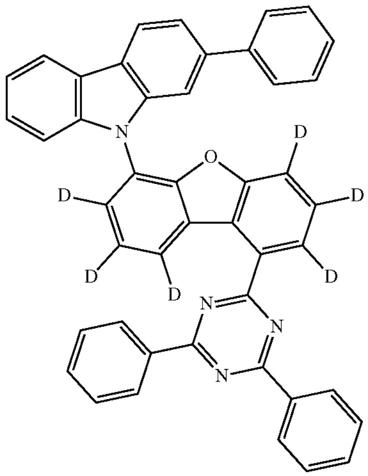 | 83% |
| 110 | 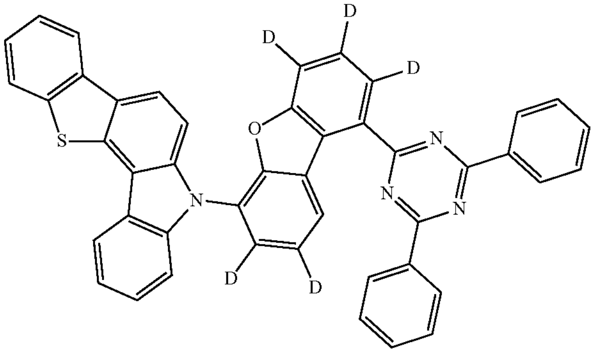 | 59% |

TABLE 2-continued
| | | |
|---|---|---|
| 116 | 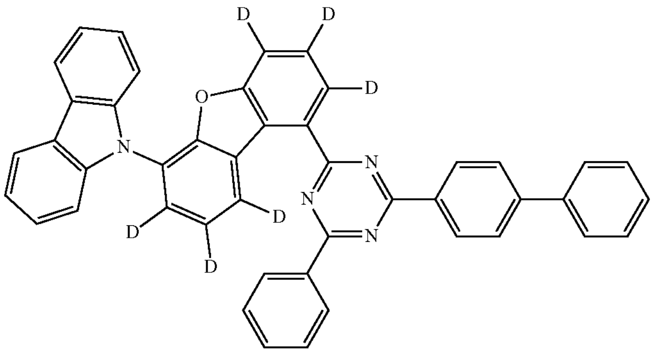 | 66% |
| 273 | 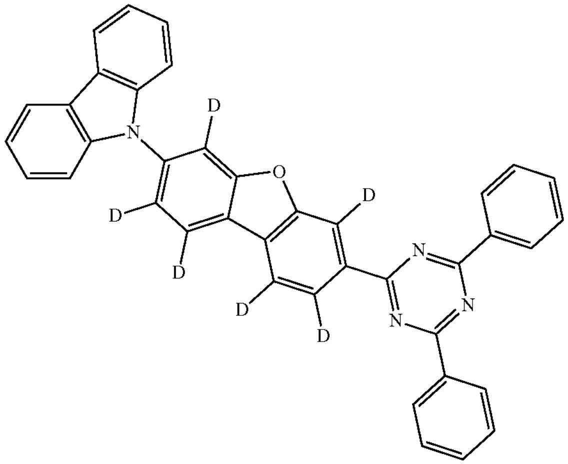 | 68% |

TABLE 2-continued
| | | |
|---|---|---|
| 274 | 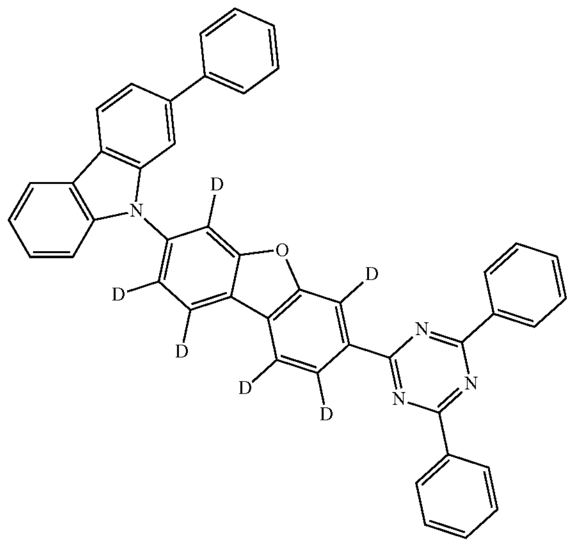 | 71% |
| 278 | 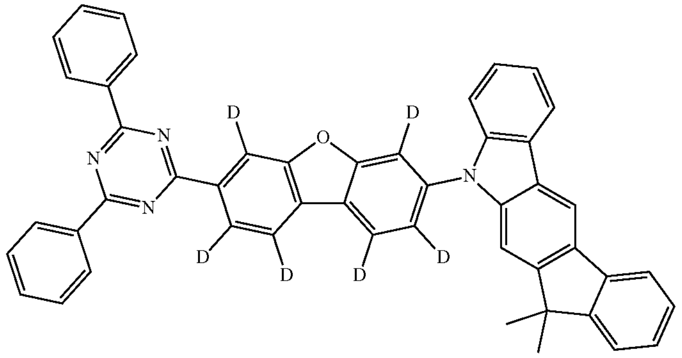 | 77% |

TABLE 2-continued
| | | |
|---|---|---|
| 280 | 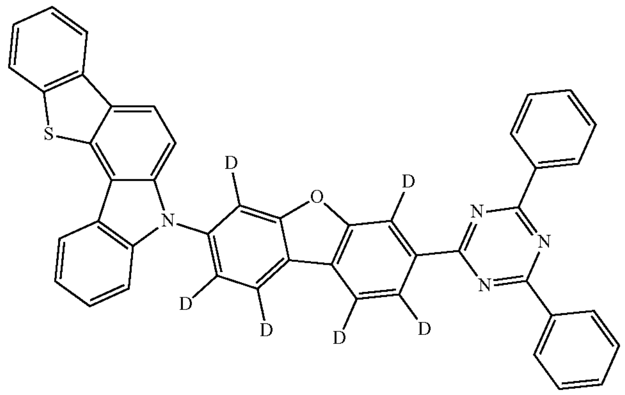 [SMILES: [2H]c1c(-c2nc(-c3ccccc3)nc(-c3ccccc3)n2)c([2H])c2oc3c([2H])c(-n4c5ccccc5c5c6sc7ccccc7c6ccc54)c([2H])c([2H])c3c2c1[2H]] | 69% |
| 286 | 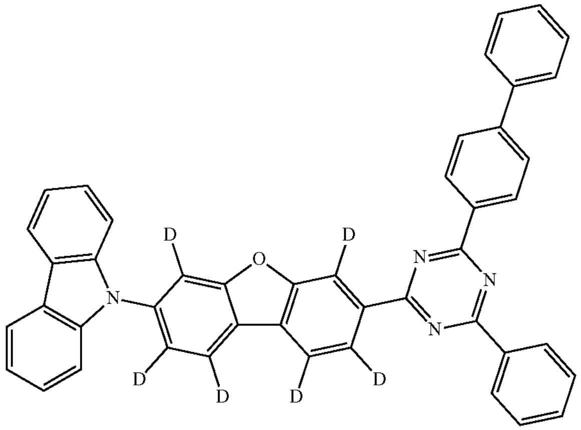 [SMILES: [2H]c1c(-c2nc(-c3ccccc3)nc(-c3ccc(-c4ccccc4)cc3)n2)c([2H])c2oc3c([2H])c(-n4c5ccccc5c5ccccc54)c([2H])c([2H])c3c2c1[2H]] | 54% |

TABLE 2-continued
| | | |
|---|---|---|
| 300 | 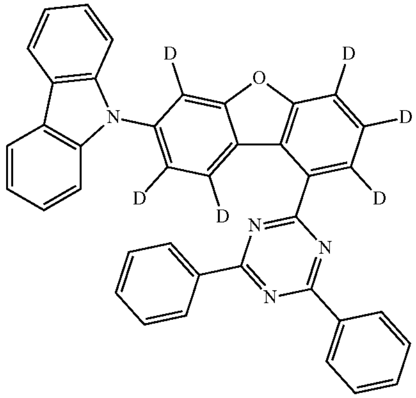 [SMILES: [2H]c1c([2H])c(-c2nc(-c3ccccc3)nc(-c3ccccc3)n2)c2c(oc3c([2H])c(-n4c5ccccc5c5ccccc54)c([2H])c([2H])c32)c1[2H]] | 97% |
| 303 | 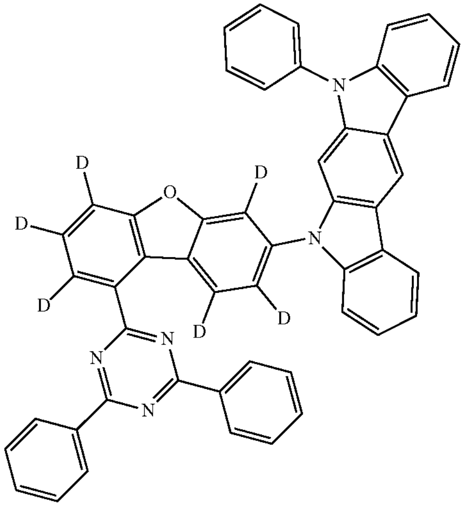 [SMILES: [2H]c1c([2H])c(-c2nc(-c3ccccc3)nc(-c3ccccc3)n2)c2c(oc3c([2H])c(-n4c5ccccc5c5cc6c7ccccc7n(-c7ccccc7)c6cc54)c([2H])c([2H])c32)c1[2H]] | 62% |

TABLE 2-continued
| | | |
|---|---|---|
| 307 | 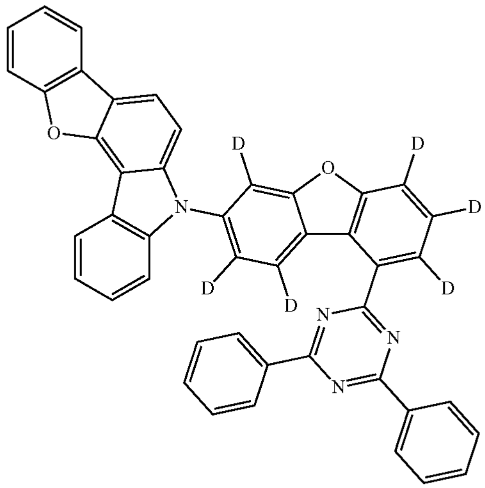 [SMILES: [2H]c1c([2H])c(-c2nc(-c3ccccc3)nc(-c3ccccc3)n2)c2c(oc3c([2H])c(-n4c5ccccc5c5c6oc7ccccc7c6ccc54)c([2H])c([2H])c32)c1[2H]] | 87% |
| 308 | 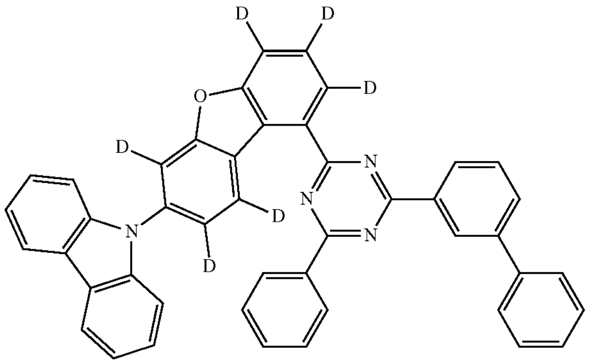 [SMILES: [2H]c1c([2H])c(-c2nc(-c3ccccc3)nc(-c3cccc(-c4ccccc4)c3)n2)c2c(oc3c([2H])c(-n4c5ccccc5c5ccccc54)c([2H])c([2H])c32)c1[2H]] | 72% |

TABLE 2-continued
| | | |
|---|---|---|
| 315 | 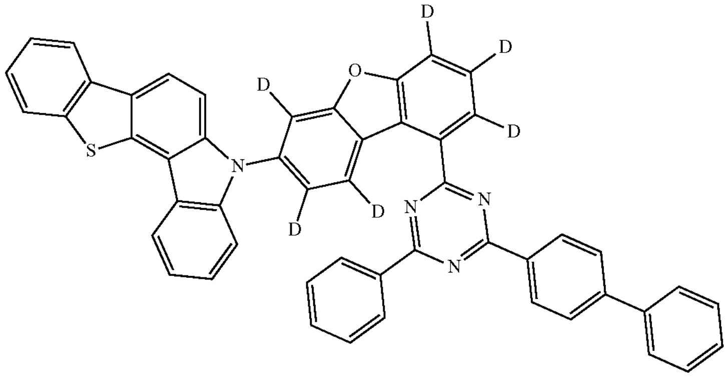 [SMILES: [2H]c1c([2H])c(-c2nc(-c3ccccc3)nc(-c3ccc(-c4ccccc4)cc3)n2)c2c(oc3c([2H])c(-n4c5ccccc5c5c6sc7ccccc7c6ccc54)c([2H])c([2H])c32)c1[2H]] | 73% |
| 318 | 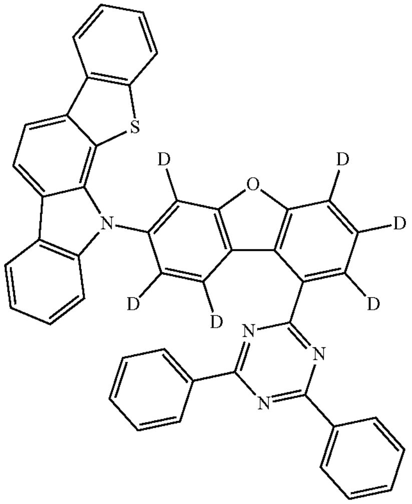 [SMILES: [2H]c1c([2H])c(-c2nc(-c3ccccc3)nc(-c3ccccc3)n2)c2c(oc3c([2H])c(-n4c5ccccc5c5ccc6c7ccccc7sc6c54)c([2H])c([2H])c32)c1[2H]] | 78% |

TABLE 2-continued
| | | |
|---|---|---|
| 320 | 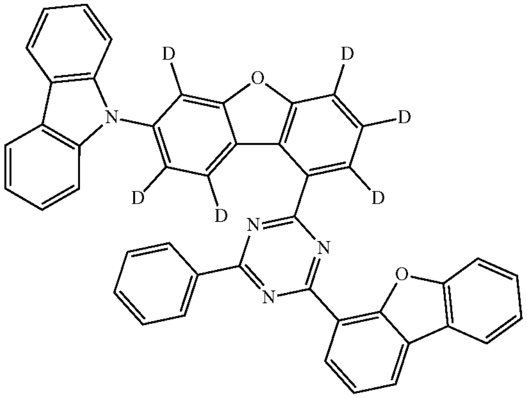 [SMILES: [2H]c1c([2H])c(-c2nc(-c3ccccc3)nc(-c3cccc4c3oc3ccccc34)n2)c2c(oc3c([2H])c(-n4c5ccccc5c5ccccc54)c([2H])c([2H])c32)c1[2H]] | 69% |
| 324 | 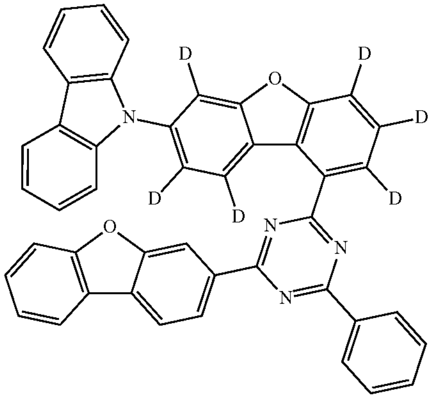 [SMILES: [2H]c1c([2H])c(-c2nc(-c3ccccc3)nc(-c3ccc4c(c3)oc3ccccc34)n2)c2c(oc3c([2H])c(-n4c5ccccc5c5ccccc54)c([2H])c([2H])c32)c1[2H]] | 48% |

TABLE 2-continued
| | | |
|---|---|---|
| 328 | 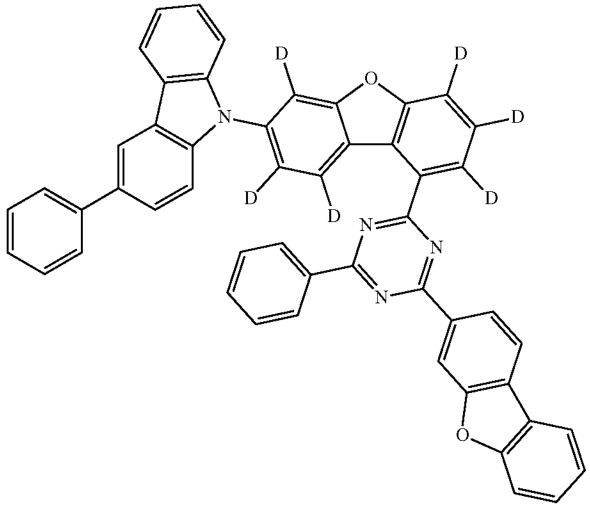 [SMILES: [2H]c1c([2H])c(-c2nc(-c3ccccc3)nc(-c3ccc4c(c3)oc3ccccc34)n2)c2c(oc3c([2H])c(-n4c5ccccc5c5cc(-c6ccccc6)ccc54)c([2H])c([2H])c32)c1[2H]] | 63% |
| 435 | 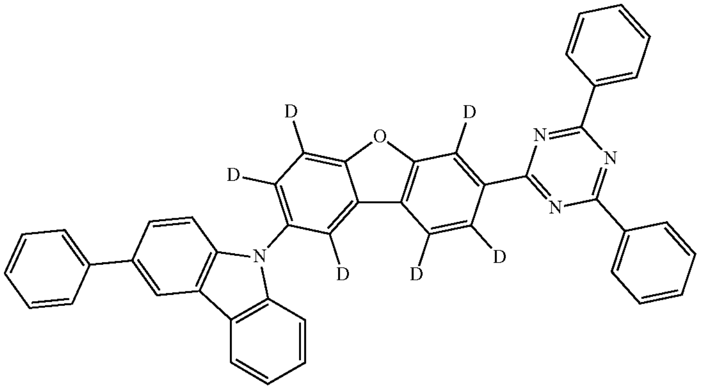 [SMILES: [2H]c1c(-n2c3ccccc3c3cc(-c4ccccc4)ccc32)c([2H])c2c(oc3c([2H])c(-c4nc(-c5ccccc5)nc(-c5ccccc5)n4)c([2H])c([2H])c32)c1[2H]] | 76% |

TABLE 2-continued
| | | |
|---|---|---|
| 440 | 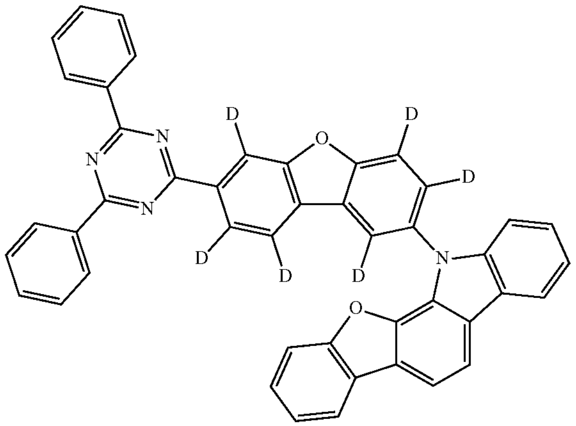 [SMILES: [2H]c1c(-n2c3ccccc3c3ccc4c5ccccc5oc4c32)c([2H])c2c(oc3c([2H])c(-c4nc(-c5ccccc5)nc(-c5ccccc5)n4)c([2H])c([2H])c32)c1[2H]] | 72% |
| 442 | 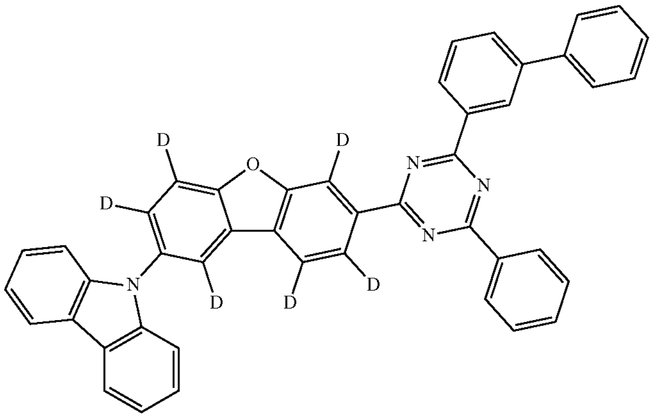 [SMILES: [2H]c1c(-n2c3ccccc3c3ccccc32)c([2H])c2c(oc3c([2H])c(-c4nc(-c5ccccc5)nc(-c5cccc(-c6ccccc6)c5)n4)c([2H])c([2H])c32)c1[2H]] | 59% |

TABLE 2-continued
| | | |
|---|---|---|
| 444 | 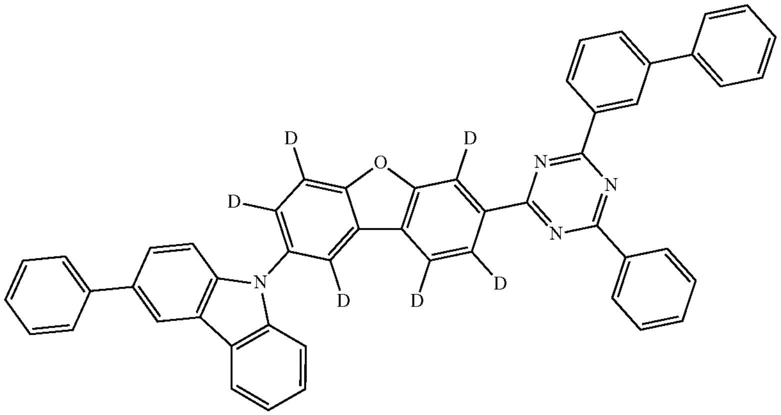 [SMILES: [2H]c1c(-n2c3ccccc3c3cc(-c4ccccc4)ccc32)c([2H])c2c(oc3c([2H])c(-c4nc(-c5ccccc5)nc(-c5cccc(-c6ccccc6)c5)n4)c([2H])c([2H])c32)c1[2H]] | 68% |
| 445 | 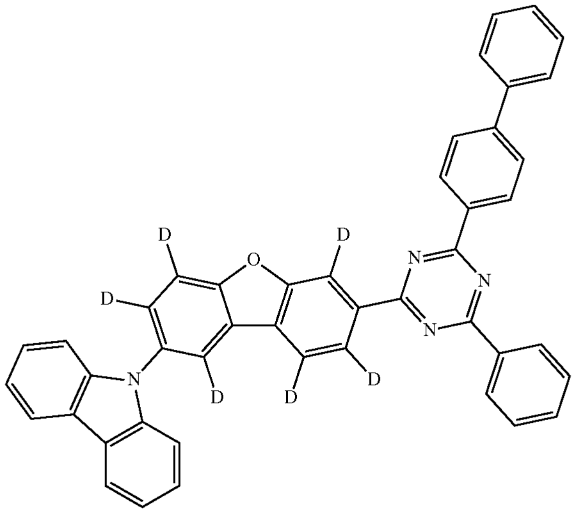 [SMILES: [2H]c1c(-n2c3ccccc3c3ccccc32)c([2H])c2c(oc3c([2H])c(-c4nc(-c5ccccc5)nc(-c5ccc(-c6ccccc6)cc5)n4)c([2H])c([2H])c32)c1[2H]] | 69% |

TABLE 2-continued
| | | |
|---|---|---|
| 455 | 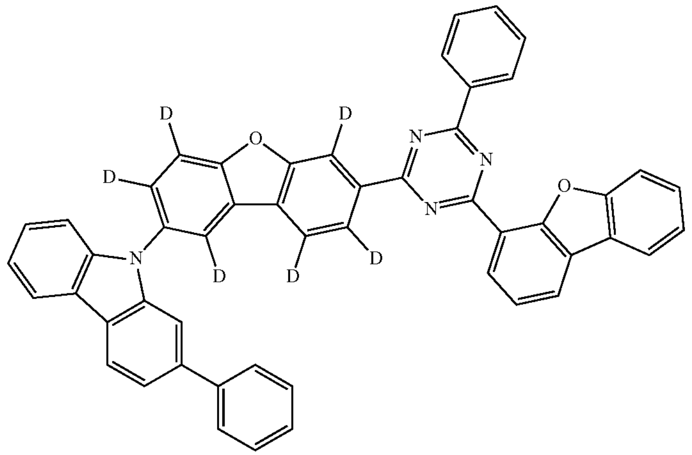 [SMILES: [2H]c1c(-n2c3ccccc3c3ccc(-c4ccccc4)cc32)c([2H])c2c(oc3c([2H])c(-c4nc(-c5ccccc5)nc(-c5cccc6c5oc5ccccc56)n4)c([2H])c([2H])c32)c1[2H]] | 73% |
| 457 | 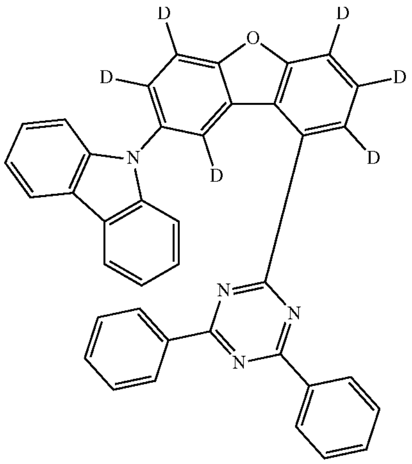 [SMILES: [2H]c1c(-n2c3ccccc3c3ccccc32)c([2H])c2c(oc3c([2H])c([2H])c([2H])c(-c4nc(-c5ccccc5)nc(-c5ccccc5)n4)c32)c1[2H]] | 91% |

TABLE 2-continued
| | | |
|---|---|---|
| 569 | 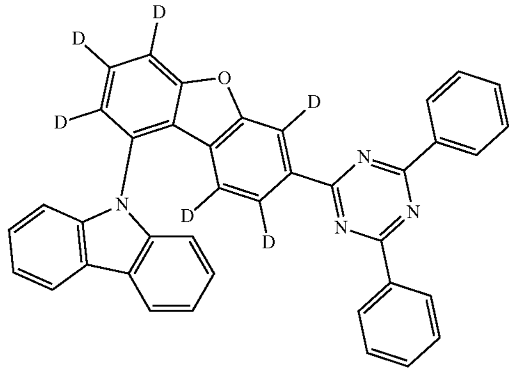 [SMILES: [2H]c1c([2H])c(-n2c3ccccc3c3ccccc32)c2c(oc3c([2H])c(-c4nc(-c5ccccc5)nc(-c5ccccc5)n4)c([2H])c([2H])c32)c1[2H]] | 94% |
| 571 | 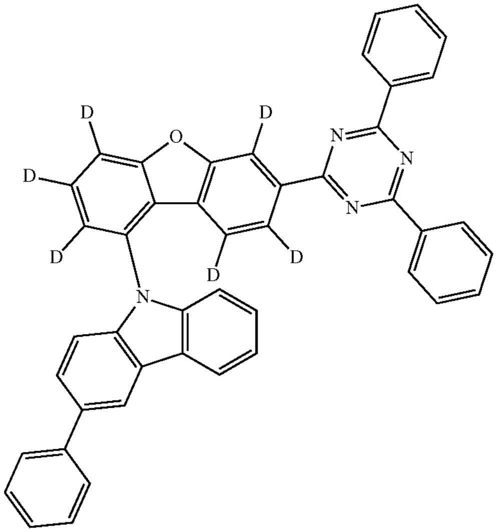 [SMILES: [2H]c1c([2H])c(-n2c3ccccc3c3cc(-c4ccccc4)ccc32)c2c(oc3c([2H])c(-c4nc(-c5ccccc5)nc(-c5ccccc5)n4)c([2H])c([2H])c32)c1[2H]] | 80% |

TABLE 2-continued
| | | |
|---|---|---|
| 573 | 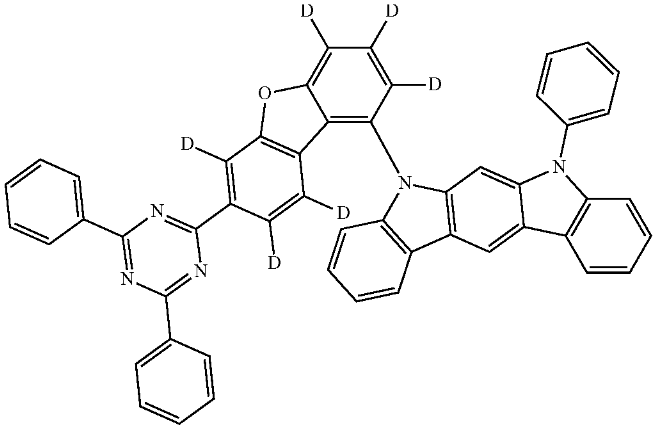 [SMILES: [2H]c1c([2H])c(-n2c3ccccc3c3cc4c5ccccc5n(-c5ccccc5)c4cc32)c2c(oc3c([2H])c(-c4nc(-c5ccccc5)nc(-c5ccccc5)n4)c([2H])c([2H])c32)c1[2H]] | 82% |
| 579 | 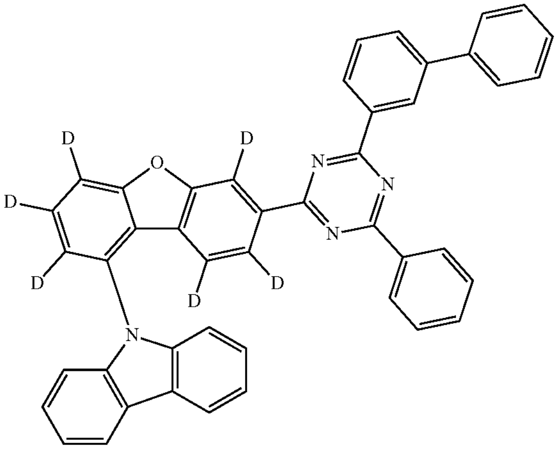 [SMILES: [2H]c1c([2H])c(-n2c3ccccc3c3ccccc32)c2c(oc3c([2H])c(-c4nc(-c5ccccc5)nc(-c5cccc(-c6ccccc6)c5)n4)c([2H])c([2H])c32)c1[2H]] | 68% |

TABLE 2-continued
| | | |
|---|---|---|
| 580 | 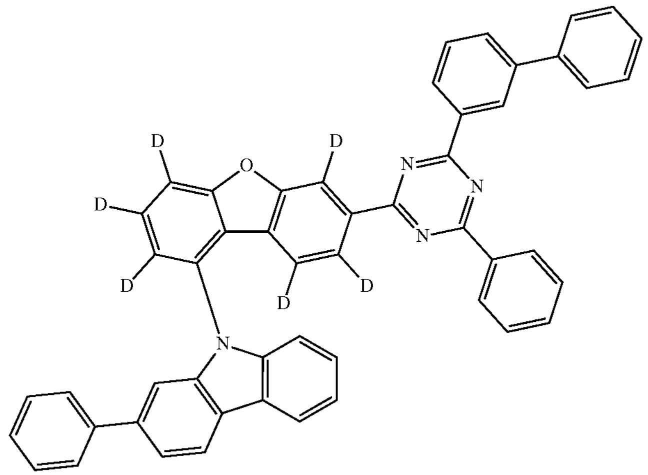 [SMILES: [2H]c1c([2H])c(-n2c3ccccc3c3ccc(-c4ccccc4)cc32)c2c(oc3c([2H])c(-c4nc(-c5ccccc5)nc(-c5cccc(-c6ccccc6)c5)n4)c([2H])c([2H])c32)c1[2H]] | 56% |
| 582 | 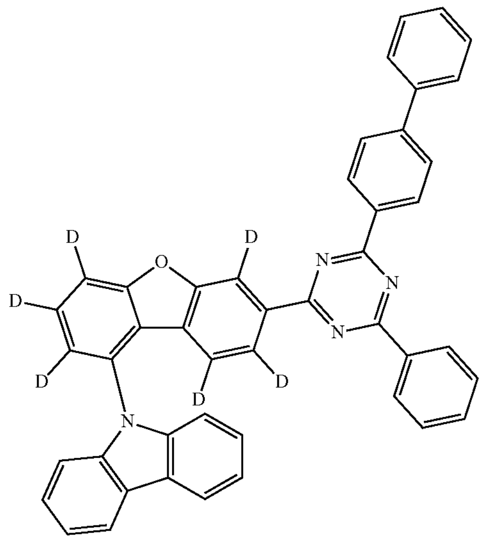 [SMILES: [2H]c1c([2H])c(-n2c3ccccc3c3ccccc32)c2c(oc3c([2H])c(-c4nc(-c5ccccc5)nc(-c5ccc(-c6ccccc6)cc5)n4)c([2H])c([2H])c32)c1[2H]] | 79% |

TABLE 2-continued
| | | |
|---|---|---|
| 592 | 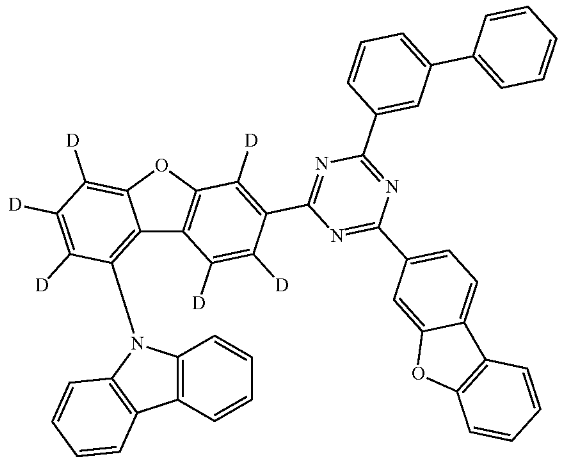 [SMILES: [2H]c1c([2H])c(-n2c3ccccc3c3ccccc32)c2c(oc3c([2H])c(-c4nc(-c5cccc(-c6ccccc6)c5)nc(-c5ccc6c(c5)oc5ccccc56)n4)c([2H])c([2H])c32)c1[2H]] | 88% |

[Synthesis 3] The compound 137 (G)

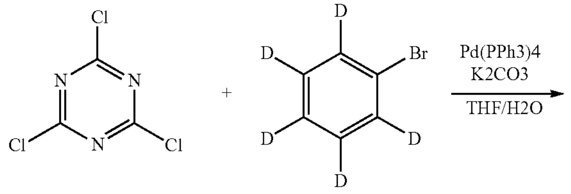

[A]

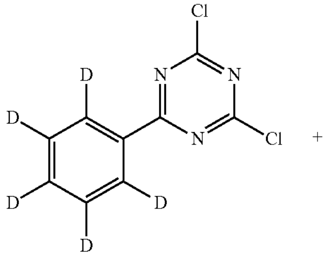

[A]-1

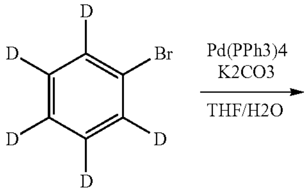

[A′]

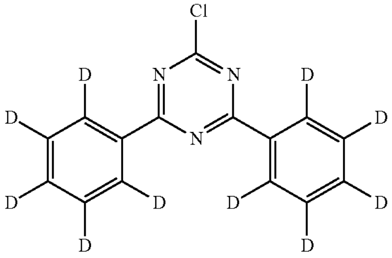

[A]-2

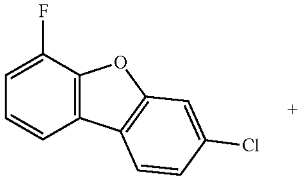

[B]

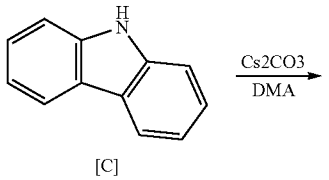

[C]

-continued

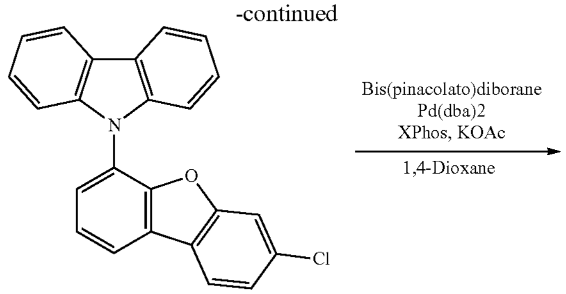

137-1

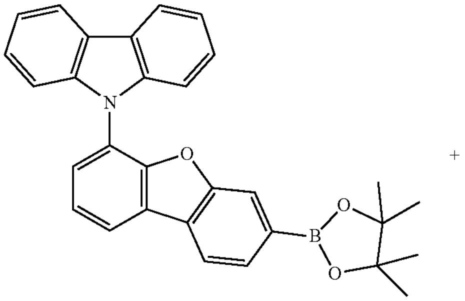

137-2

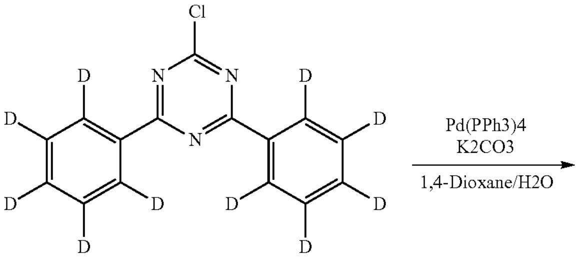

[A]-2

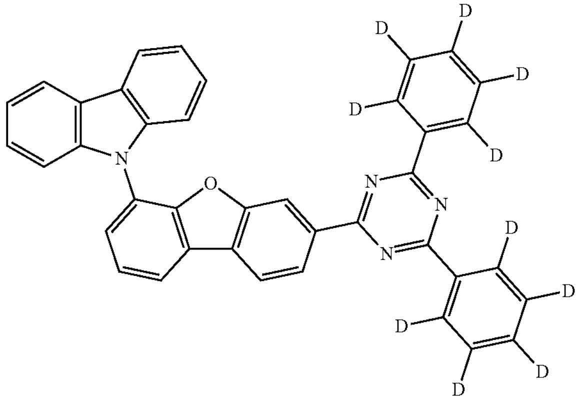

137[G]

(1) The Compound [A]-1

In the one-neck round bottom flask, a mixture of 2,4,6-trichloro-1,3,5-triazine (10 g, 0.054 mol), 1-bromobenzene-2,3,4,5,6-d5 (9.63 g, 0.059 mol) $Pd(PPh_3)_4$ (3.12 g, 0.0027 mol), $K_2CO_3$ (14.93 g, 0.11 mol), tetrahydrofuran (100 mL) and water (30 mL) was refluxed at 120° C. After cooling, the resultant was concentrated and filtered through silica gel to obtain the compound [A]-1. (6.99 g, 56%)

(2) The Compound [A]-2

In the one-neck round bottom flask, a mixture of 2,4-dichloro-6-(phenyl-d5)-1,3,5-triazine (6.99 g, 0.030 mol), 1-bromobenzene-2,3,4,5,6-d5 (5.35 g, 0.033 mol), $Pd(PPh_3)_4$ (1.73 g, 0.0015 mol), $K_2CO_3$ (8.29 g, 0.06 mol), tetrahydrofuran (70 mL) and water (20 mL) was refluxed at 120° C. After cooling, the resultant was concentrated and filtered through silica gel to obtain the compound [A]-2. (5.58 g, 67%)

(3) The Compound 137-1

In the one-neck round bottom flask, a mixture of 3-chloro-6-fluorodibenzo[b,d]furan (10 g, 0.045 mol), 9H-carbazole (8.28 g, 0.050 mol), $Cs_2CO_3$ (29.32 g, 0.09 mol) and dimethylacetamide (100 mL) were refluxed at 170° C. After cooling, the resultant was filtered to remove the solvent and was purified by column to the obtain compound 137-1. (15.39 g, 93%)

(4) The Compound 137-2

In the one-neck round bottom flask, a mixture of 9-(7-chlorodibenzo[b,d]furan-4-yl)-9H-carbazole (15.39 g, 0.042 mol), bis(pinacolato)diborn (21.33 g, 0.084 mol), Pd(dba)2 (3.85 g, 0.0042 mol), Xphos (4.00 g, 0.0084 mol), potassium acetate (12.37 g, 0.13 mol) and 1,4-dioxane (150 mL) was refluxed at 120° C. After cooling, the resultant was concentrated and filtered through silica gel to obtain the compound 137-2. (18.33 g, 95%)

(5) The Compound 137[G]

In the one-neck round bottom flask, a mixture of 9-(7-(4,4,5,5-tetramethyl-1,3,2-dioxaborolan-2-yl)dibenzo[b,d]furan-4-yl)-9H-carbazole (18.33 g, 0.040 mol), 2-chloro-4,6-bis(phenyl-5d)-1,3,5-triazine (12.22 g, 0.044 mol), $Pd(PPh_3)_4$ (2.31 g, 0.002 mol), $K_2CO_3$ (11.06 g, 0.008 mol), 1,4-dioxane (180 mL) and water (50 mL) was refluxed at 120° C. After cooling, the resultant was concentrated and filtered through silica gel to obtain the compound 137[G]. (16.78 g, 73%)

When the compound A and A' are same, the A-2 can be directly synthesized by adding 2 equivalents of compound A in the first reaction. Namely, when A and A' are same, the second reaction step may be omitted.

The following compound G was synthesized in the same manner as in the synthesis 3 except that intermediates A, A', B, and C of Table 3 were used.

TABLE 3
| Compound | A | A' | B |
| --- | --- | --- | --- |
| 137 | 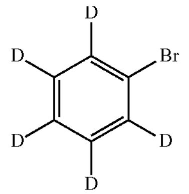 | 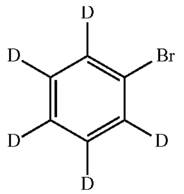 | 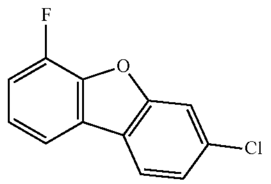 |
| 147 | 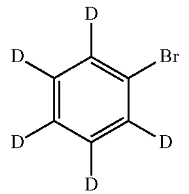 | 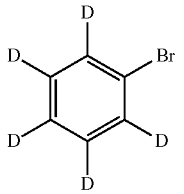 | 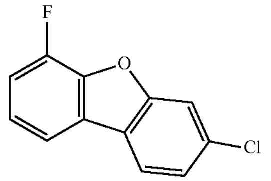 |
| 156 | 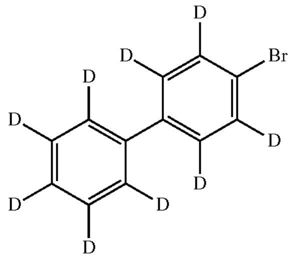 | 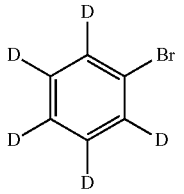 | 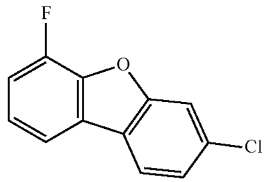 |
| 170 | 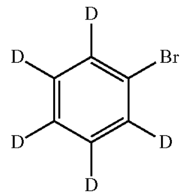 | 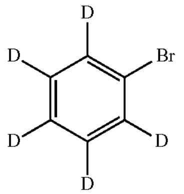 | 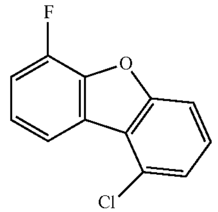 |

TABLE 3-continued
| | | | |
|---|---|---|---|
| 178 | 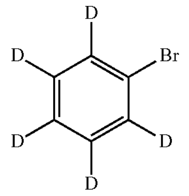 | 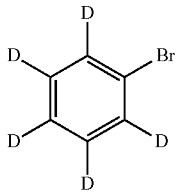 | 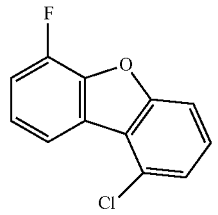 |
| 183 | 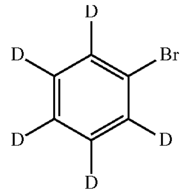 | 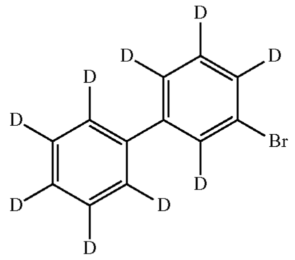 | 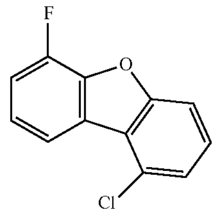 |
| 195 | 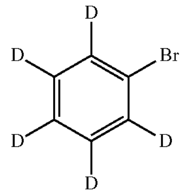 | 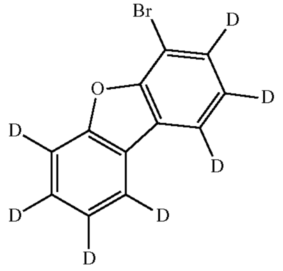 | 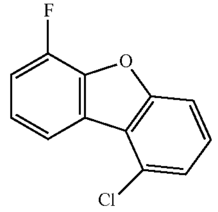 |
| 199 | 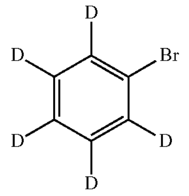 | 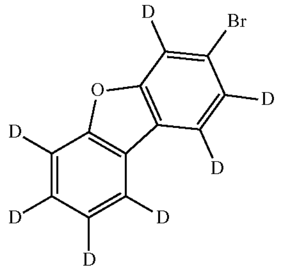 | 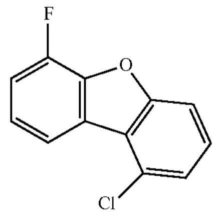 |

TABLE 3-continued
| | | | |
|---|---|---|---|
| 329 | 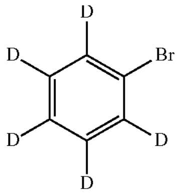 | 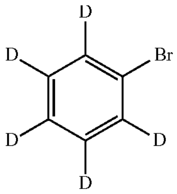 | 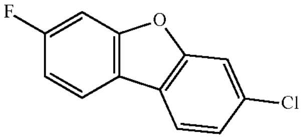 |
| 330 | 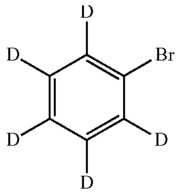 | 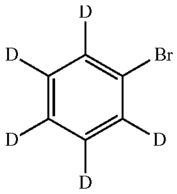 | 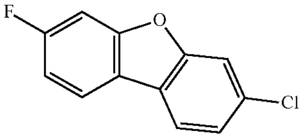 |
| 331 | 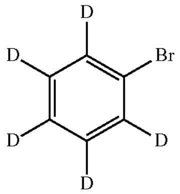 | 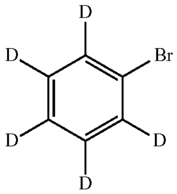 | 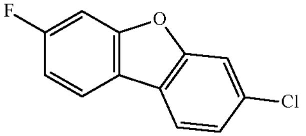 |
| 334 | 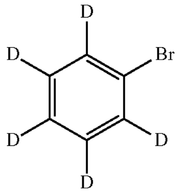 | 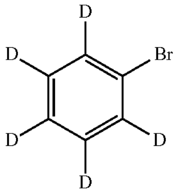 | 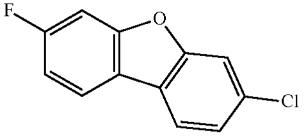 |
| 336 | 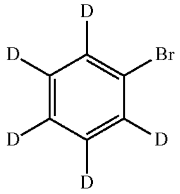 | 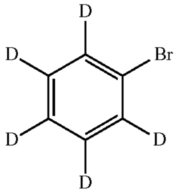 | 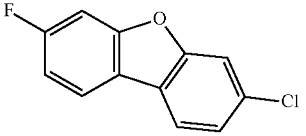 |

TABLE 3-continued
| | | | |
|---|---|---|---|
| 338 | 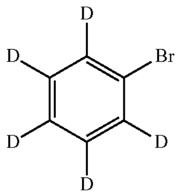 | 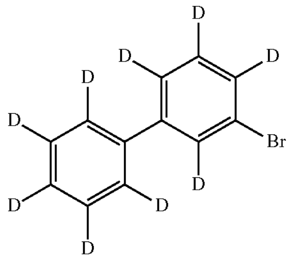 | 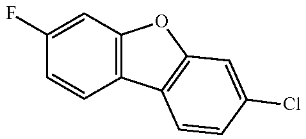 |
| 339 | 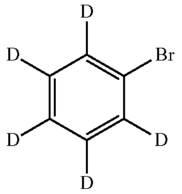 | 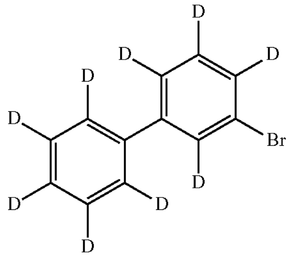 | 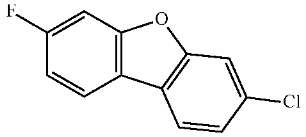 |
| 340 | 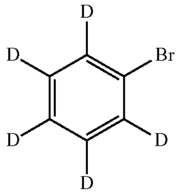 | 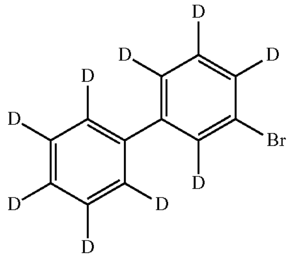 | 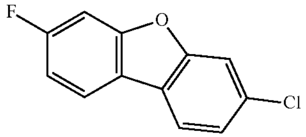 |
| 341 | 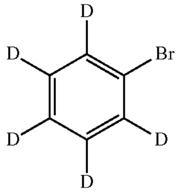 | 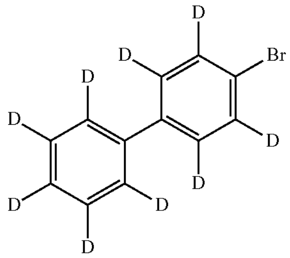 | 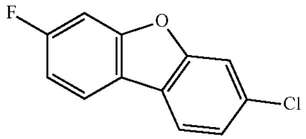 |

TABLE 3-continued
| | | | |
|---|---|---|---|
| 344 | 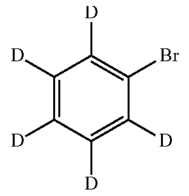 | 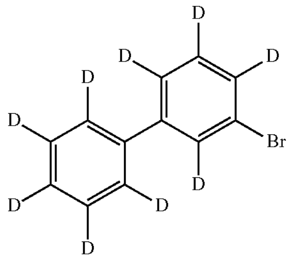 | 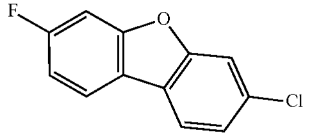 |
| 347 | 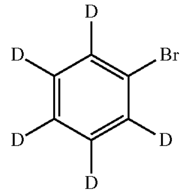 | 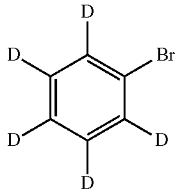 | 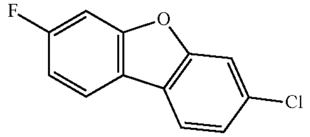 |
| 351 | 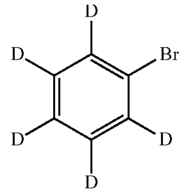 | 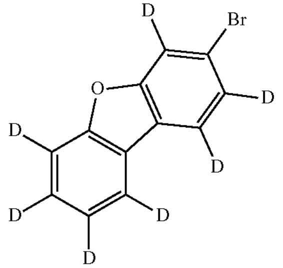 | 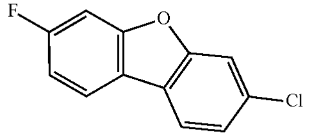 |
| 355 | 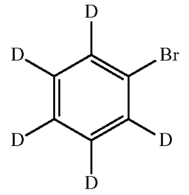 | 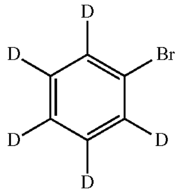 | 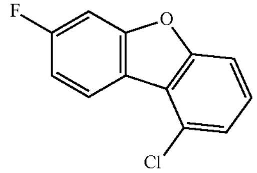 |

TABLE 3-continued
| | | | |
|---|---|---|---|
| 356 | 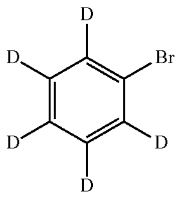 | 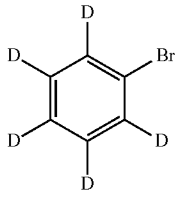 | 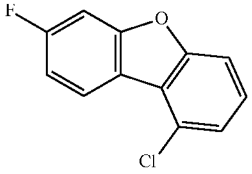 [SMILES: Fc1ccc2c(c1)oc1cccc(Cl)c12] |
| 357 | 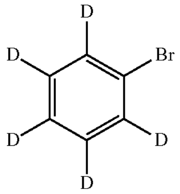 | 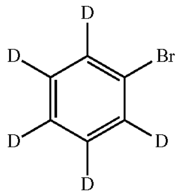 | 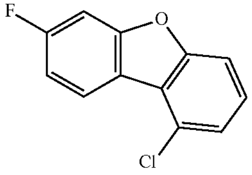 [SMILES: Fc1ccc2c(c1)oc1cccc(Cl)c12] |
| 359 | 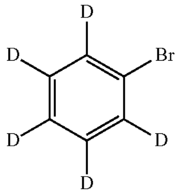 | 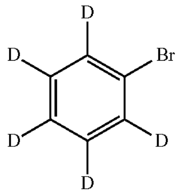 | 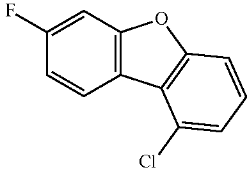 [SMILES: Fc1ccc2c(c1)oc1cccc(Cl)c12] |
| 362 | 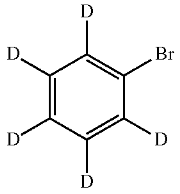 | 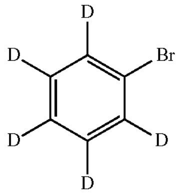 | 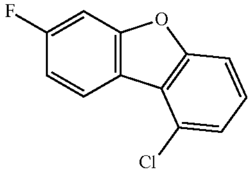 [SMILES: Fc1ccc2c(c1)oc1cccc(Cl)c12] |
| 366 | 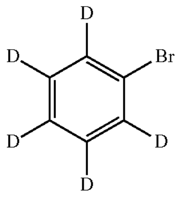 | 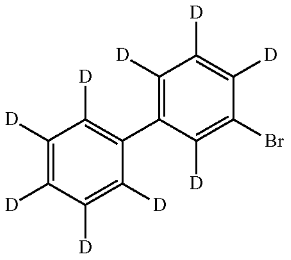 | 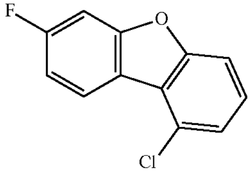 |

TABLE 3-continued
| | | | |
|---|---|---|---|
| 371 | 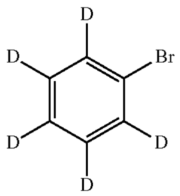 | 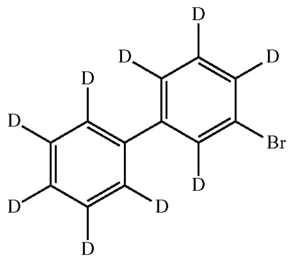 | 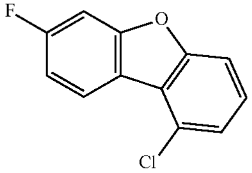 |
| 373 | 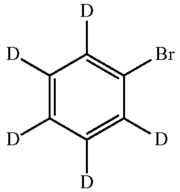 | 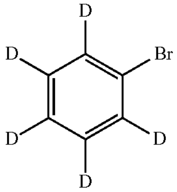 | 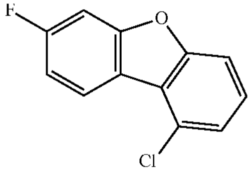 [SMILES: Fc1ccc2c(c1)oc1cccc(Cl)c12] |
| 380 | 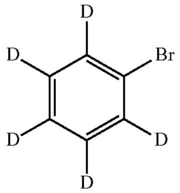 | 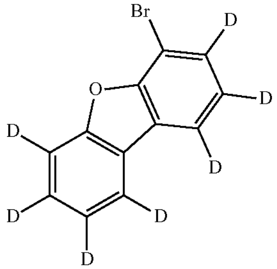 | 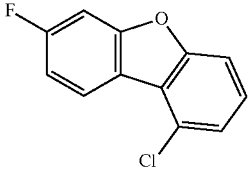 [SMILES: Fc1ccc2c(c1)oc1cccc(Cl)c12] |
| 473 | 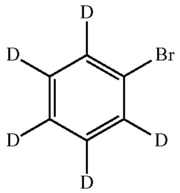 | 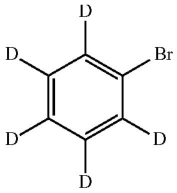 | 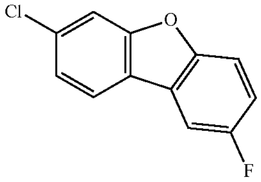 [SMILES: Fc1ccc2oc3cc(Cl)ccc3c2c1] |

TABLE 3-continued
| | | | |
|---|---|---|---|
| 474 | 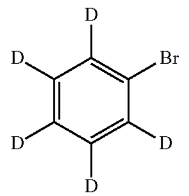 | 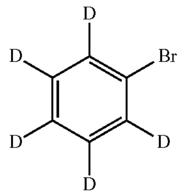 | 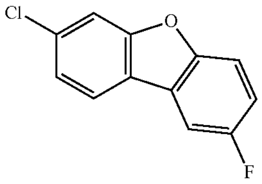 [SMILES: Fc1ccc2oc3cc(Cl)ccc3c2c1] |
| 475 | 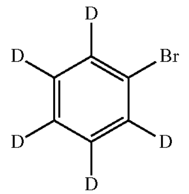 | 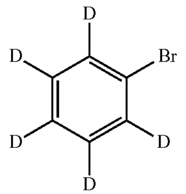 | 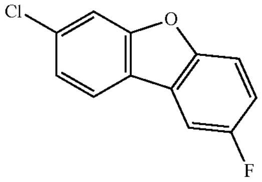 [SMILES: Fc1ccc2oc3cc(Cl)ccc3c2c1] |
| 479 | 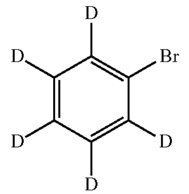 | 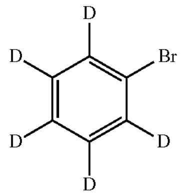 | 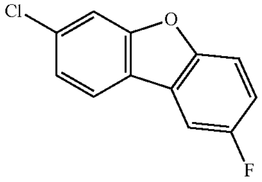 [SMILES: Fc1ccc2oc3cc(Cl)ccc3c2c1] |
| 480 | 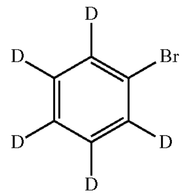 | 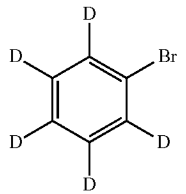 | 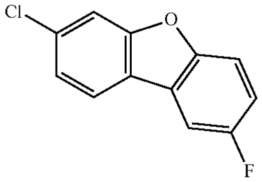 [SMILES: Fc1ccc2oc3cc(Cl)ccc3c2c1] |
| 482 | 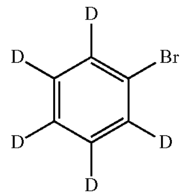 | 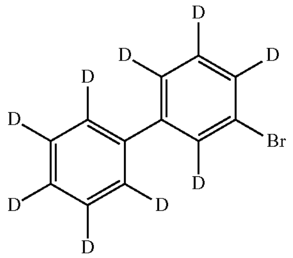 | 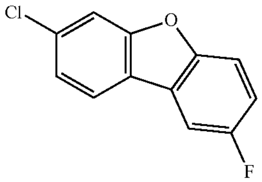 [SMILES: Fc1ccc2oc3cc(Cl)ccc3c2c1] |

TABLE 3-continued
| | | | |
|---|---|---|---|
| 483 | 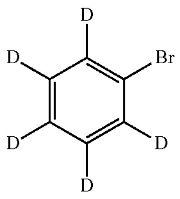 | 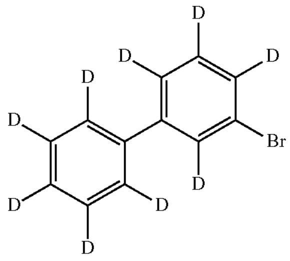 | 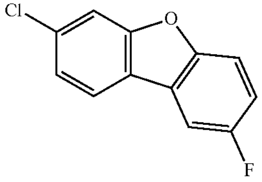 [SMILES: Fc1ccc2oc3cc(Cl)ccc3c2c1] |
| 484 | 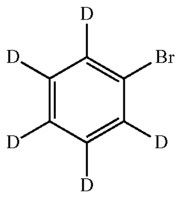 | 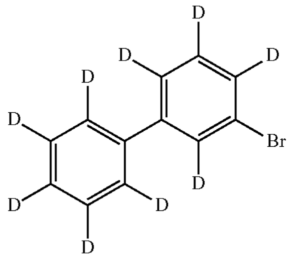 | 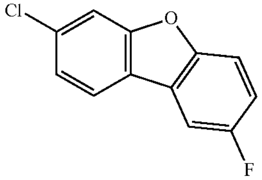 [SMILES: Fc1ccc2oc3cc(Cl)ccc3c2c1] |
| 485 | 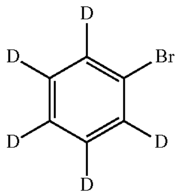 | 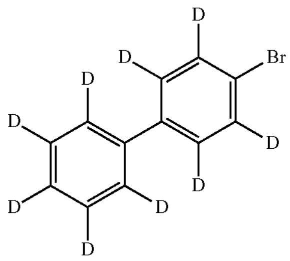 | 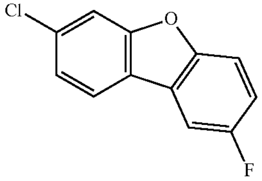 [SMILES: Fc1ccc2oc3cc(Cl)ccc3c2c1] |
| 488 | 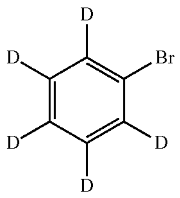 | 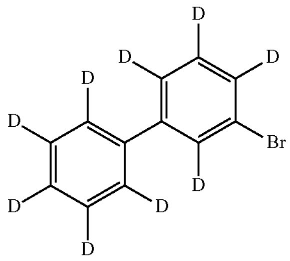 | 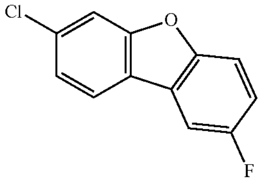 [SMILES: Fc1ccc2oc3cc(Cl)ccc3c2c1] |

TABLE 3-continued
| | | | |
|---|---|---|---|
| 495 | 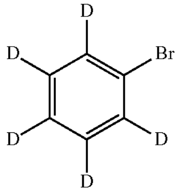 | 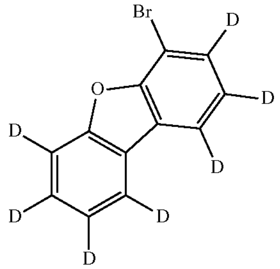 | 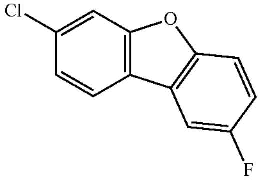 [SMILES: Fc1ccc2oc3cc(Cl)ccc3c2c1] |
| 497 | 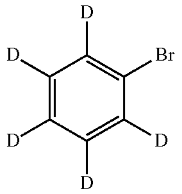 | 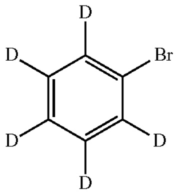 | 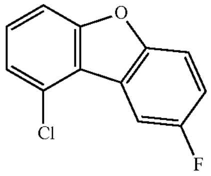 [SMILES: Fc1ccc2oc3cccc(Cl)c3c2c1] |
| 500 | 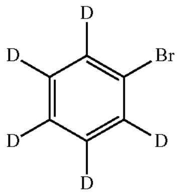 | 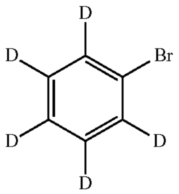 | 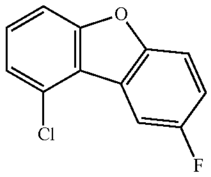 [SMILES: Fc1ccc2oc3cccc(Cl)c3c2c1] |
| 605 | 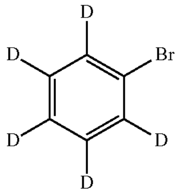 | 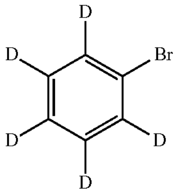 | 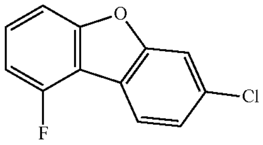 [SMILES: Fc1cccc2oc3cc(Cl)ccc3c12] |
| 606 | 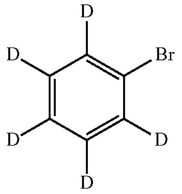 | 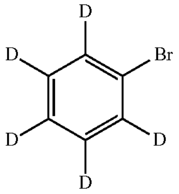 | 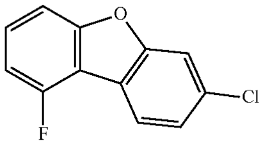 [SMILES: Fc1cccc2oc3cc(Cl)ccc3c12] |

TABLE 3-continued
| | | | |
|---|---|---|---|
| 607 | 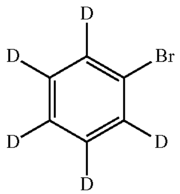 | 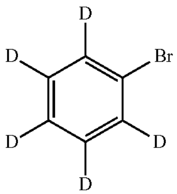 | 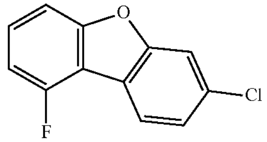 [SMILES: Fc1cccc2oc3cc(Cl)ccc3c12] |
| 608 | 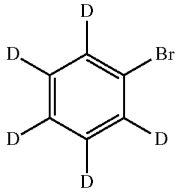 | 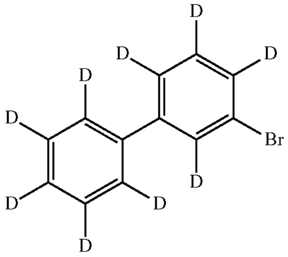 | 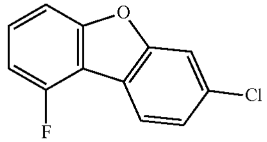 [SMILES: Fc1cccc2oc3cc(Cl)ccc3c12] |
| 611 | 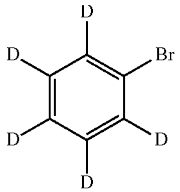 | 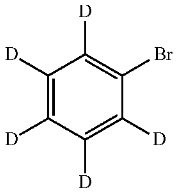 | 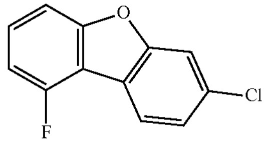 [SMILES: Fc1cccc2oc3cc(Cl)ccc3c12] |
| 612 | 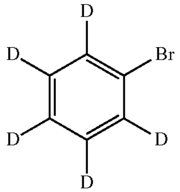 | 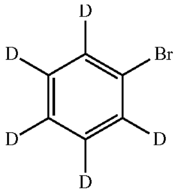 | 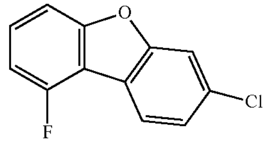 [SMILES: Fc1cccc2oc3cc(Cl)ccc3c12] |

TABLE 3-continued
| | | | |
|---|---|---|---|
| 614 | 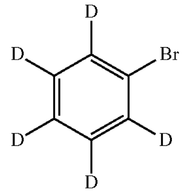 | 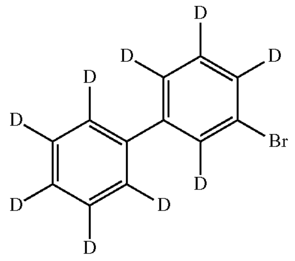 | 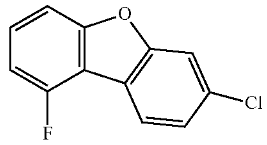 [SMILES: Fc1cccc2oc3cc(Cl)ccc3c12] |
| 616 | 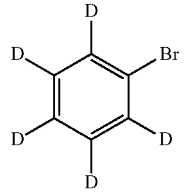 | 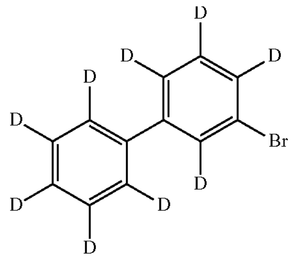 | 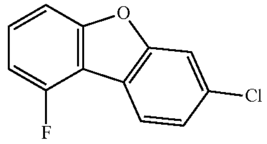 [SMILES: Fc1cccc2oc3cc(Cl)ccc3c12] |
| 620 | 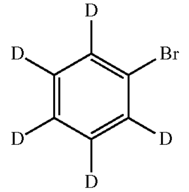 | 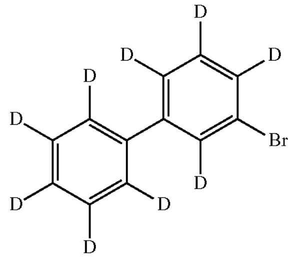 | 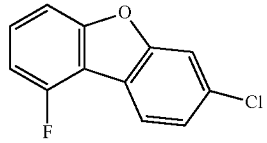 [SMILES: Fc1cccc2oc3cc(Cl)ccc3c12] |
| 625 | 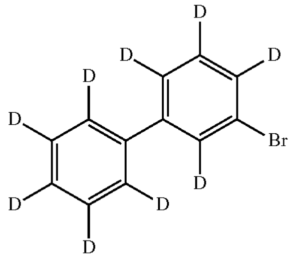 [SMILES: [2H]c1c([2H])c([2H])c(-c2c([2H])c([2H])c([2H])c(Br)c2[2H])c([2H])c1[2H]] | 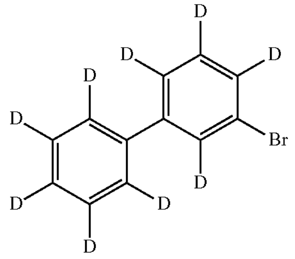 | 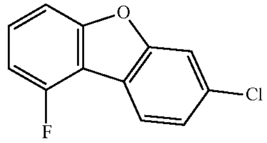 [SMILES: Fc1cccc2oc3cc(Cl)ccc3c12] |

TABLE 3-continued
| | | | |
|---|---|---|---|
| 627 | 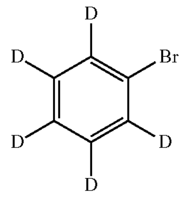 | 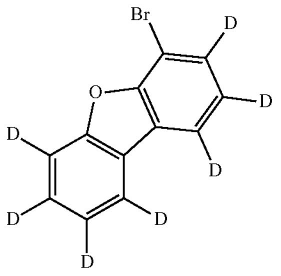 [SMILES: [2H]c1c([2H])c([2H])c2c(oc3c(Br)c([2H])c([2H])c([2H])c32)c1[2H]] | 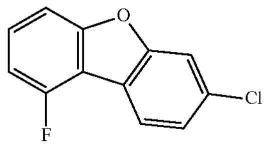 [SMILES: Fc1cccc2oc3cc(Cl)ccc3c12] |
| 629 | 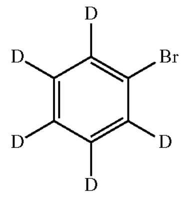 | 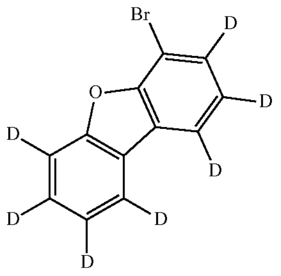 [SMILES: [2H]c1c([2H])c([2H])c2c(oc3c(Br)c([2H])c([2H])c([2H])c32)c1[2H]] | 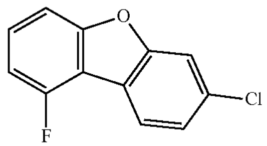 [SMILES: Fc1cccc2oc3cc(Cl)ccc3c12] |
| 630 | 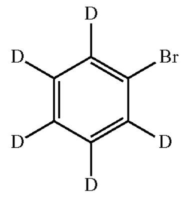 | 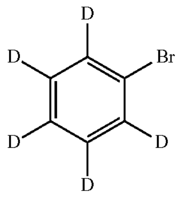 | 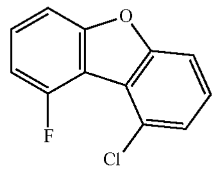 [SMILES: Fc1cccc2oc3cccc(Cl)c3c12] |

TABLE 3-continued
| Compound | C | G | yield |
| --- | --- | --- | --- |
| 137 | 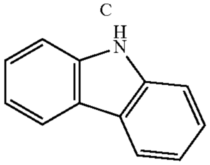 | 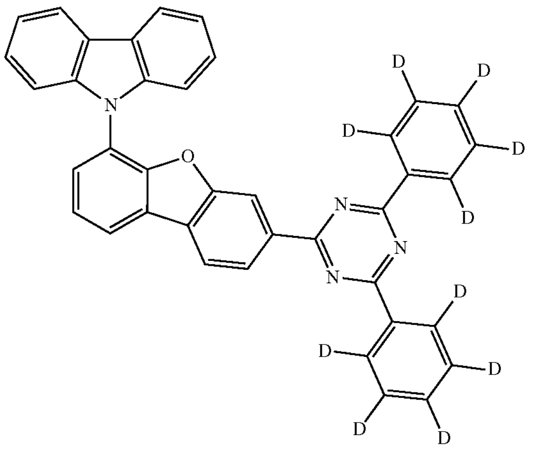 | 73% |
| 147 | 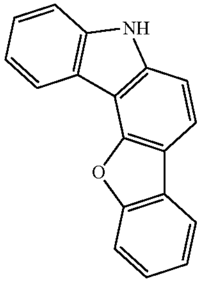 | 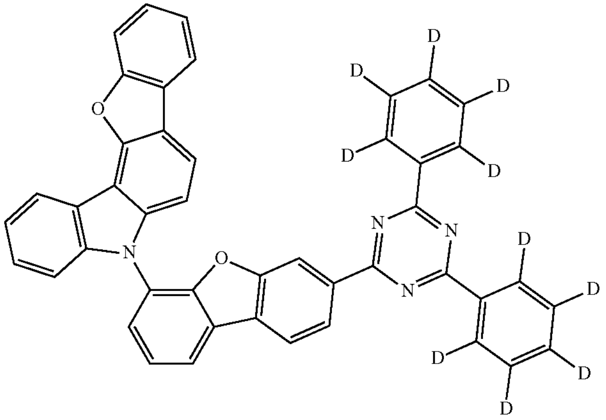 | 75% |

TABLE 3-continued
| | | | |
|---|---|---|---|
| 156 | 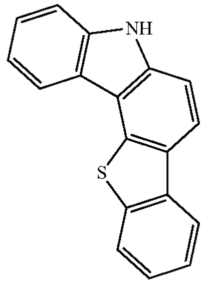 | 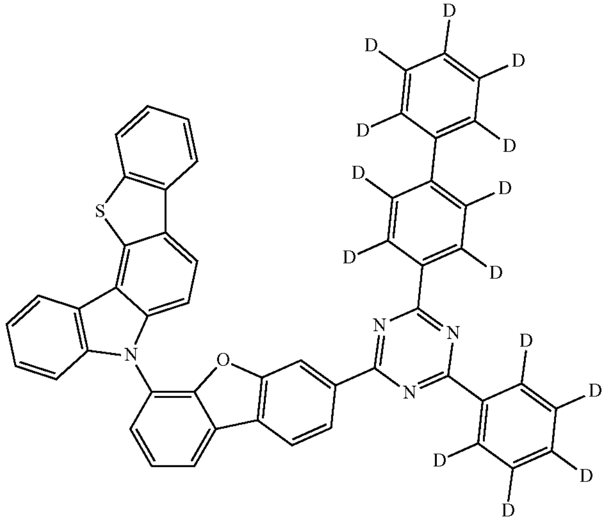 | 87% |
| 170 | 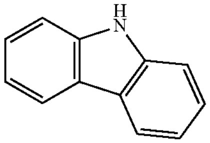 | 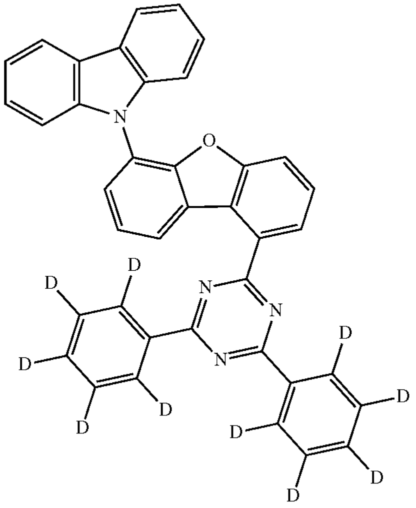 | 82% |

TABLE 3-continued
| | | | |
|---|---|---|---|
| 178 | 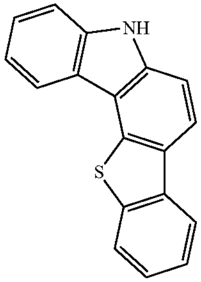 | 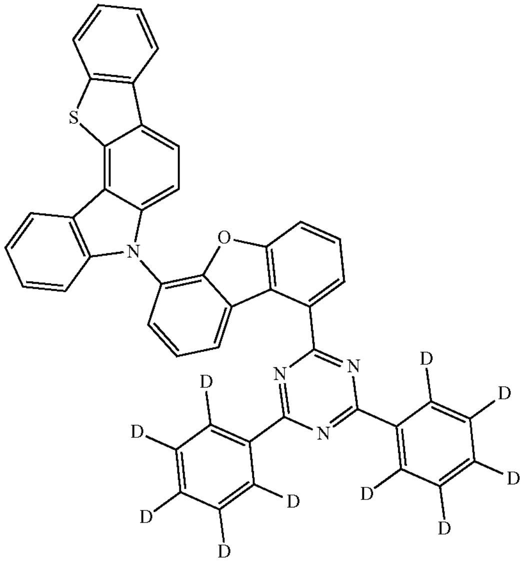 | 80% |
| 183 | 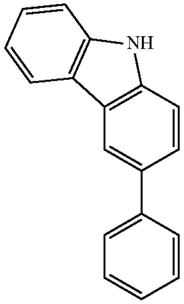 | 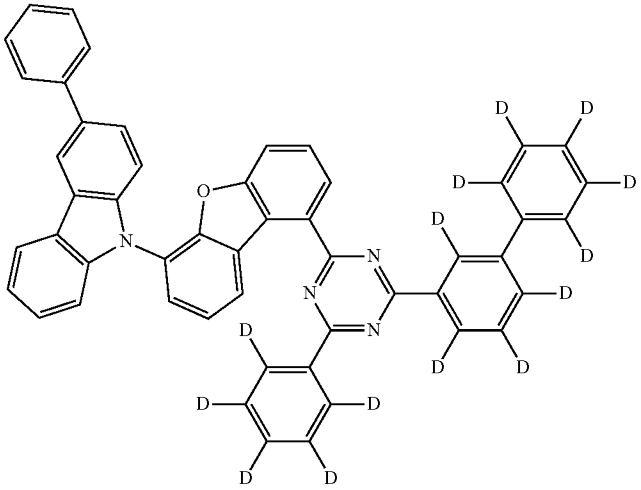 | 76% |

TABLE 3-continued
| | | | |
|---|---|---|---|
| 195 | 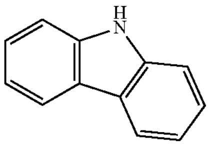 | 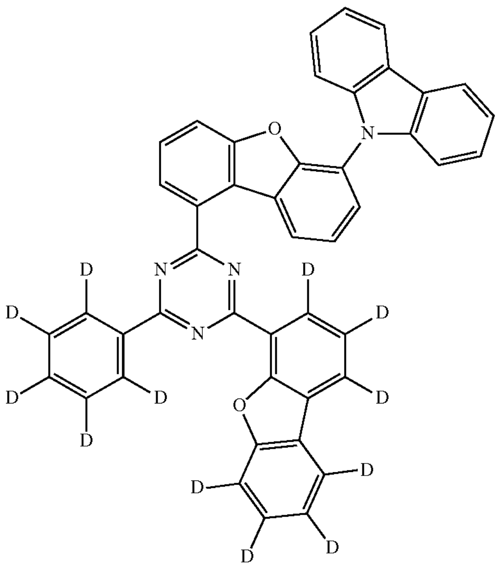 | 67% |
| 199 | 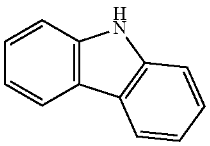 | 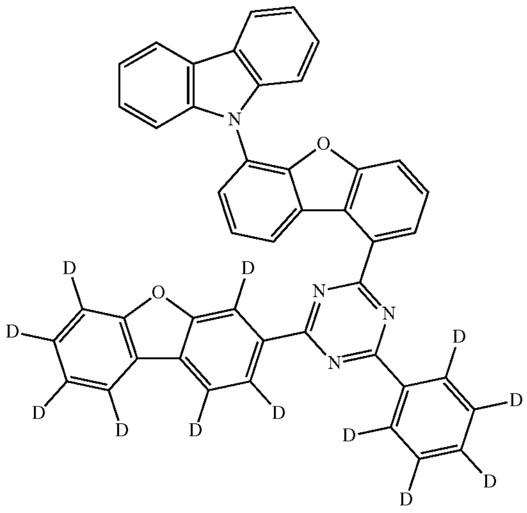 | 79% |

TABLE 3-continued
| | | | |
|---|---|---|---|
| 329 | 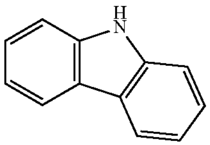 | 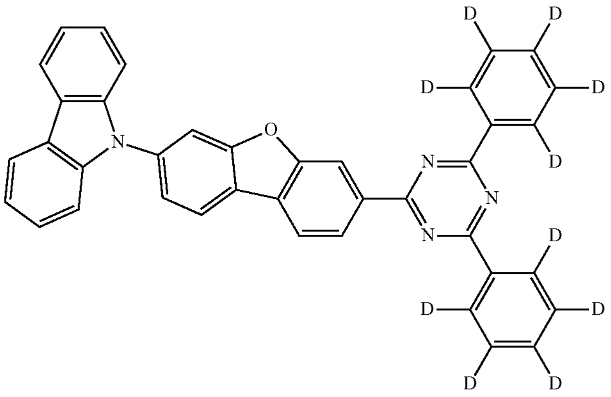 | 83% |
| 330 | 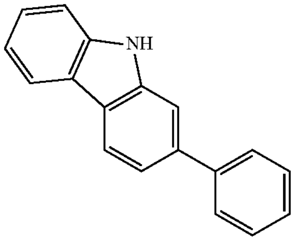 | 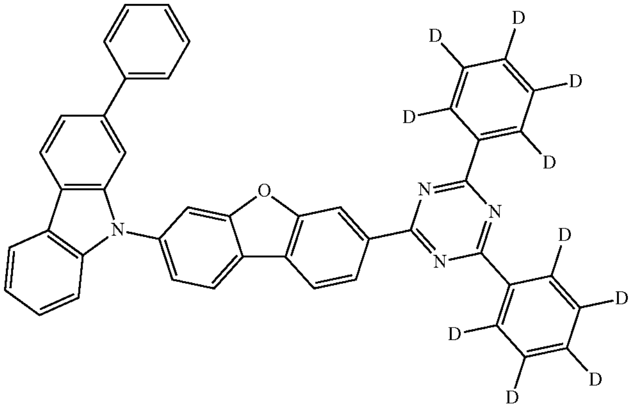 | 88% |

TABLE 3-continued
| | | | |
|---|---|---|---|
| 331 | 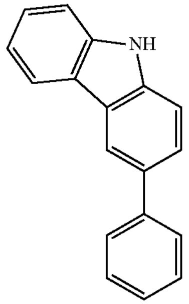 [SMILES: c1ccc(-c2ccc3[nH]c4ccccc4c3c2)cc1] | 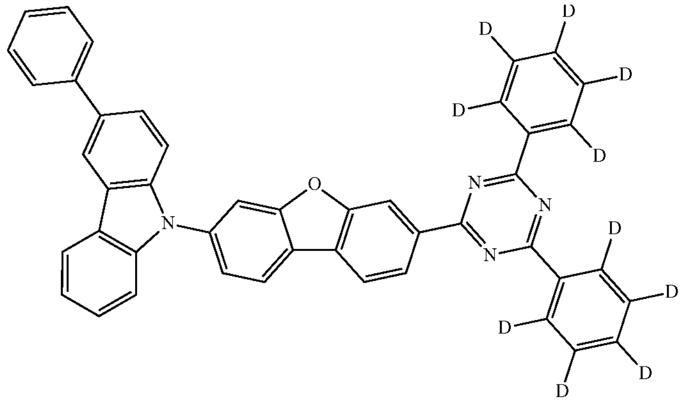 [SMILES: [2H]c1c([2H])c([2H])c(-c2nc(-c3ccc4c(c3)oc3cc(-n5c6ccccc6c6cc(-c7ccccc7)ccc65)ccc34)nc(-c3c([2H])c([2H])c([2H])c([2H])c3[2H])n2)c([2H])c1[2H]] | 76% |
| 334 | 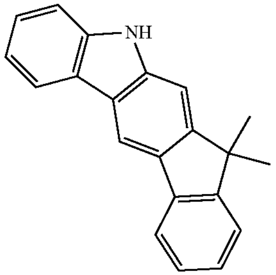 [SMILES: CC1(C)c2ccccc2-c2cc3c(cc21)[nH]c1ccccc13] | 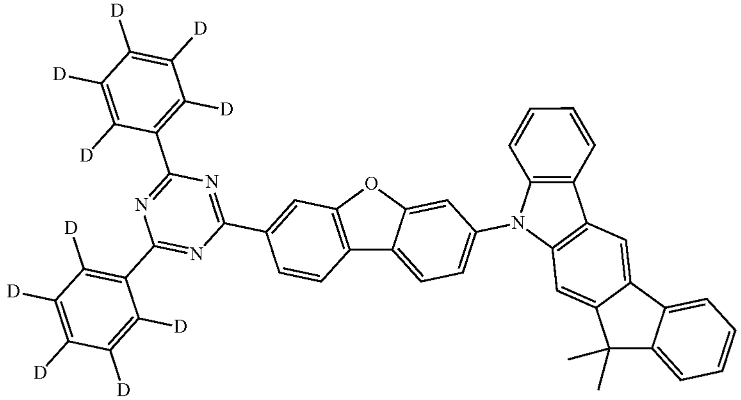 [SMILES: [2H]c1c([2H])c([2H])c(-c2nc(-c3ccc4c(c3)oc3cc(-n5c6ccccc6c6cc7c(cc65)C(C)(C)c5ccccc5-7)ccc34)nc(-c3c([2H])c([2H])c([2H])c([2H])c3[2H])n2)c([2H])c1[2H]] | 71% |

TABLE 3-continued
| | | | |
|---|---|---|---|
| 336 | 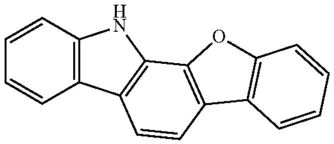 [SMILES: c1ccc2c(c1)[nH]c1c2ccc2c3ccccc3oc21] | 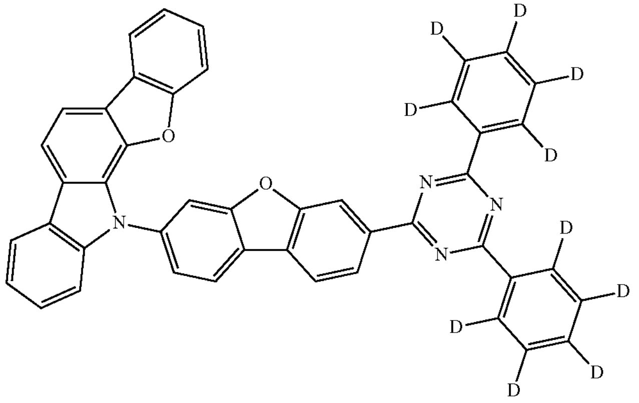 [SMILES: [2H]c1c([2H])c([2H])c(-c2nc(-c3ccc4c(c3)oc3cc(-n5c6ccccc6c6ccc7c8ccccc8oc7c65)ccc34)nc(-c3c([2H])c([2H])c([2H])c([2H])c3[2H])n2)c([2H])c1[2H]] | 77% |
| 338 | 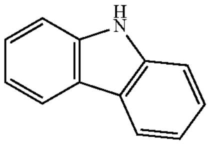 [SMILES: c1ccc2c(c1)[nH]c1ccccc12] | 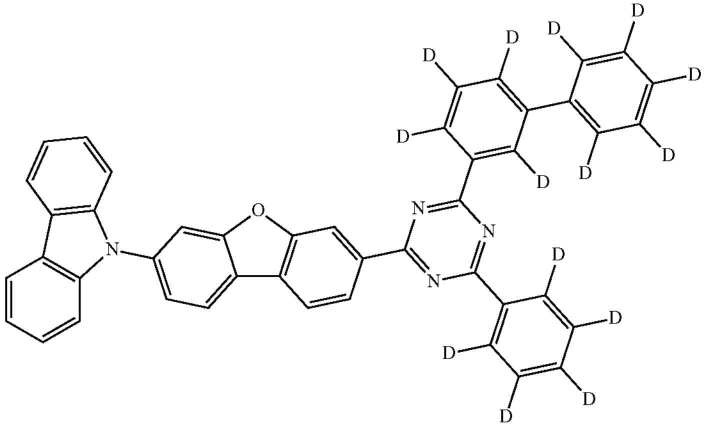 [SMILES: [2H]c1c([2H])c([2H])c(-c2nc(-c3ccc4c(c3)oc3cc(-n5c6ccccc6c6ccccc65)ccc34)nc(-c3c([2H])c([2H])c([2H])c(-c4c([2H])c([2H])c([2H])c([2H])c4[2H])c3[2H])n2)c([2H])c1[2H]] | 76% |

TABLE 3-continued
| | | | |
|---|---|---|---|
| 339 | 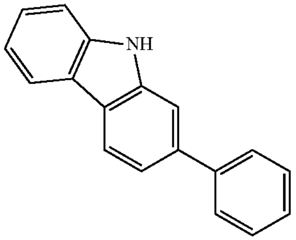 [SMILES: c1ccc(-c2ccc3c(c2)[nH]c2ccccc23)cc1] | 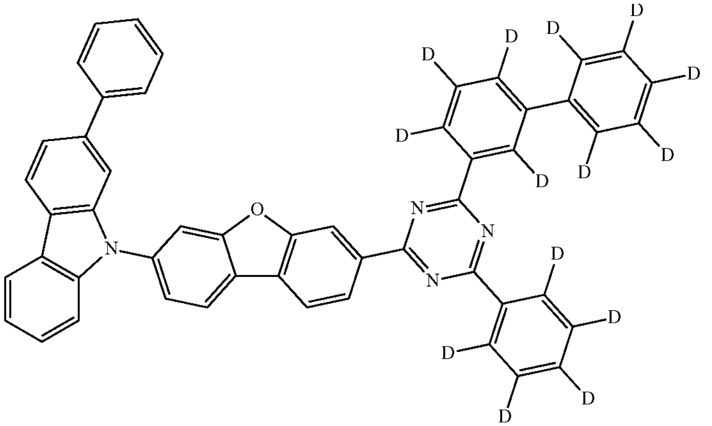 [SMILES: [2H]c1c([2H])c([2H])c(-c2nc(-c3ccc4c(c3)oc3cc(-n5c6ccccc6c6ccc(-c7ccccc7)cc65)ccc34)nc(-c3c([2H])c([2H])c([2H])c(-c4c([2H])c([2H])c([2H])c([2H])c4[2H])c3[2H])n2)c([2H])c1[2H]] | 85% |
| 340 | 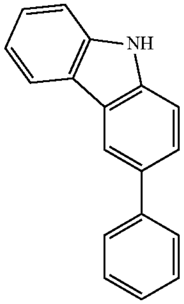 [SMILES: c1ccc(-c2ccc3[nH]c4ccccc4c3c2)cc1] | 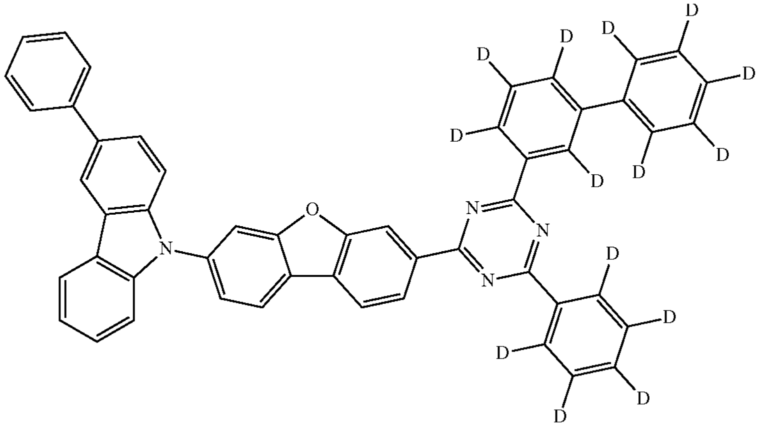 [SMILES: [2H]c1c([2H])c([2H])c(-c2nc(-c3ccc4c(c3)oc3cc(-n5c6ccccc6c6cc(-c7ccccc7)ccc65)ccc34)nc(-c3c([2H])c([2H])c([2H])c(-c4c([2H])c([2H])c([2H])c([2H])c4[2H])c3[2H])n2)c([2H])c1[2H]] | 90% |

TABLE 3-continued
| | | | |
|---|---|---|---|
| 341 | 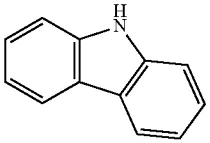 [SMILES: c1ccc2c(c1)[nH]c1ccccc12] | 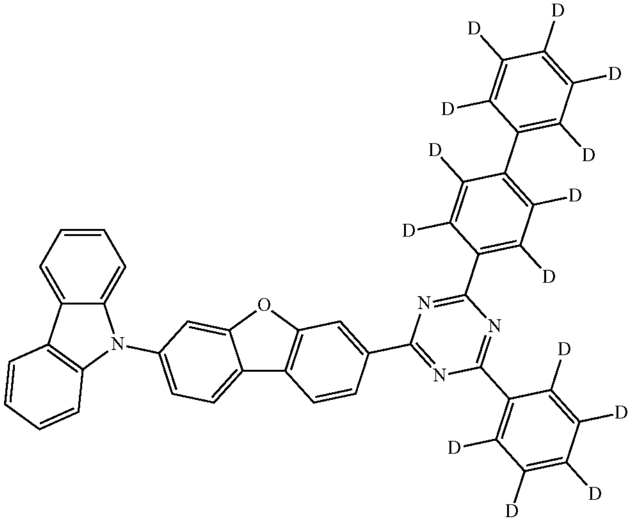 [SMILES: [2H]c1c([2H])c([2H])c(-c2nc(-c3ccc4c(c3)oc3cc(-n5c6ccccc6c6ccccc65)ccc34)nc(-c3c([2H])c([2H])c(-c4c([2H])c([2H])c([2H])c([2H])c4[2H])c([2H])c3[2H])n2)c([2H])c1[2H]] | 68% |
| 344 | 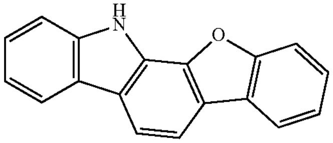 | 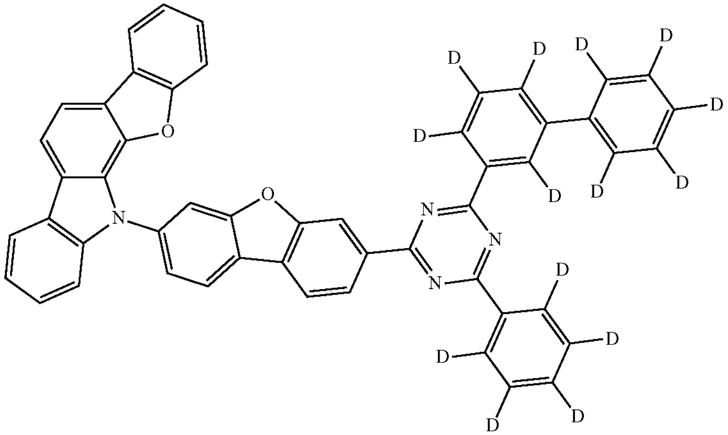 [SMILES: [2H]c1c([2H])c([2H])c(-c2nc(-c3ccc4c(c3)oc3cc(-n5c6ccccc6c6ccc7c8ccccc8oc7c65)ccc34)nc(-c3c([2H])c([2H])c([2H])c(-c4c([2H])c([2H])c([2H])c([2H])c4[2H])c3[2H])n2)c([2H])c1[2H]] | 67% |

TABLE 3-continued
| | | | |
|---|---|---|---|
| 347 | 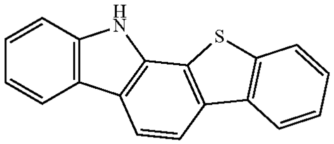 | 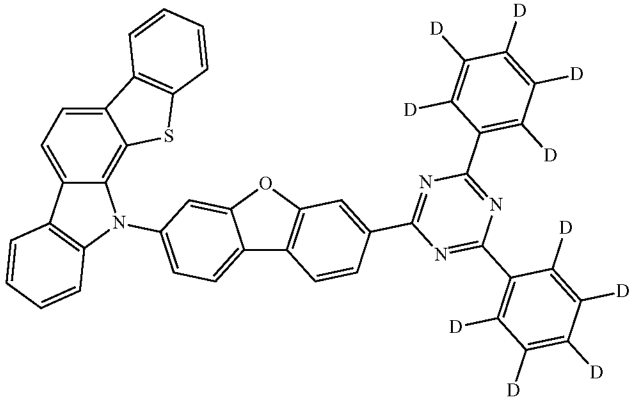 [SMILES: [2H]c1c([2H])c([2H])c(-c2nc(-c3ccc4c(c3)oc3cc(-n5c6ccccc6c6ccc7c8ccccc8sc7c65)ccc34)nc(-c3c([2H])c([2H])c([2H])c([2H])c3[2H])n2)c([2H])c1[2H]] | 65%: |
| 351 | 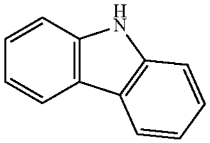 [SMILES: c1ccc2c(c1)[nH]c1ccccc12] | 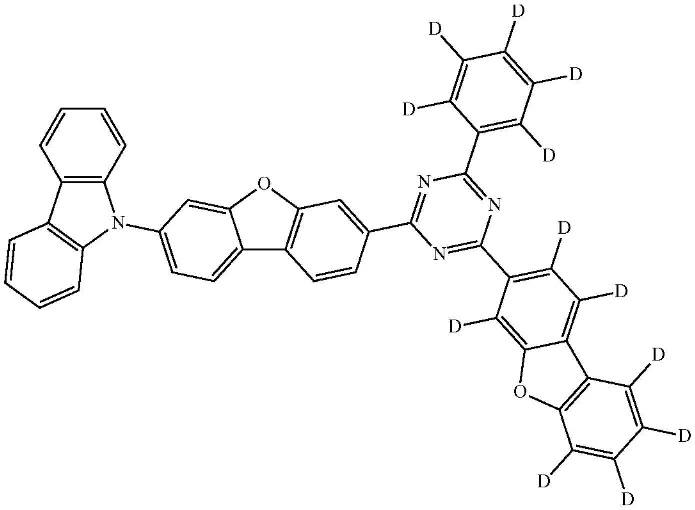 [SMILES: [2H]c1c([2H])c([2H])c(-c2nc(-c3ccc4c(c3)oc3cc(-n5c6ccccc6c6ccccc65)ccc34)nc(-c3c([2H])c([2H])c4c(oc5c([2H])c([2H])c([2H])c([2H])c54)c3[2H])n2)c([2H])c1[2H]] | 68% |

TABLE 3-continued
| | | | |
|---|---|---|---|
| 355 | 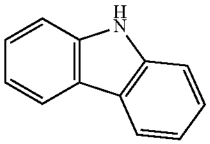 [SMILES: c1ccc2c(c1)[nH]c1ccccc12] | 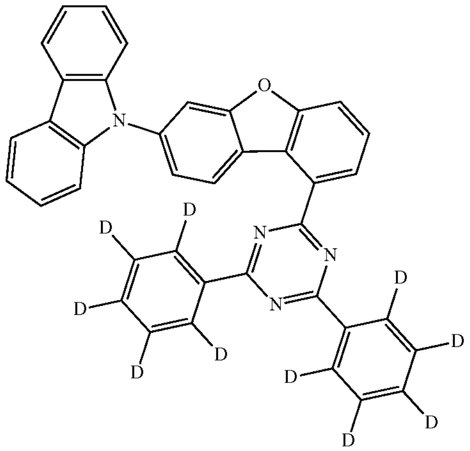 [SMILES: [2H]c1c([2H])c([2H])c(-c2nc(-c3c([2H])c([2H])c([2H])c([2H])c3[2H])nc(-c3cccc4oc5cc(-n6c7ccccc7c7ccccc76)ccc5c34)n2)c([2H])c1[2H]] | 76% |
| 356 | 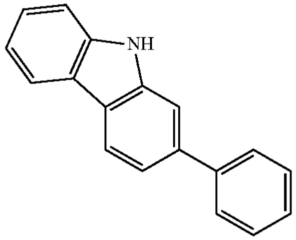 [SMILES: c1ccc(-c2ccc3c(c2)[nH]c2ccccc23)cc1] | 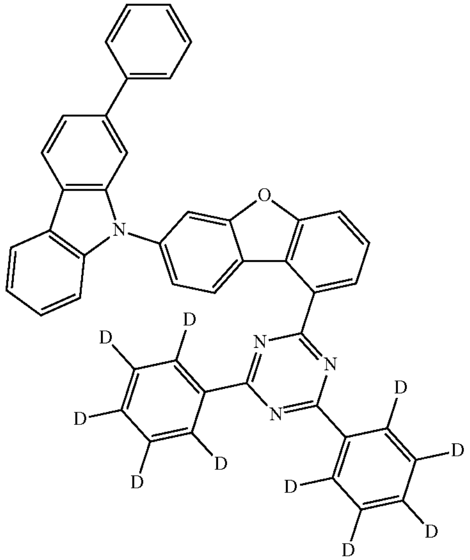 [SMILES: [2H]c1c([2H])c([2H])c(-c2nc(-c3c([2H])c([2H])c([2H])c([2H])c3[2H])nc(-c3cccc4oc5cc(-n6c7ccccc7c7ccc(-c8ccccc8)cc76)ccc5c34)n2)c([2H])c1[2H]] | 79% |

TABLE 3-continued
| | | | |
|---|---|---|---|
| 357 | 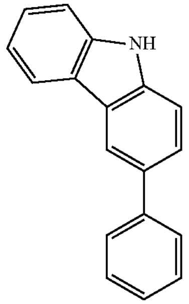 [SMILES: c1ccc(-c2ccc3[nH]c4ccccc4c3c2)cc1] | 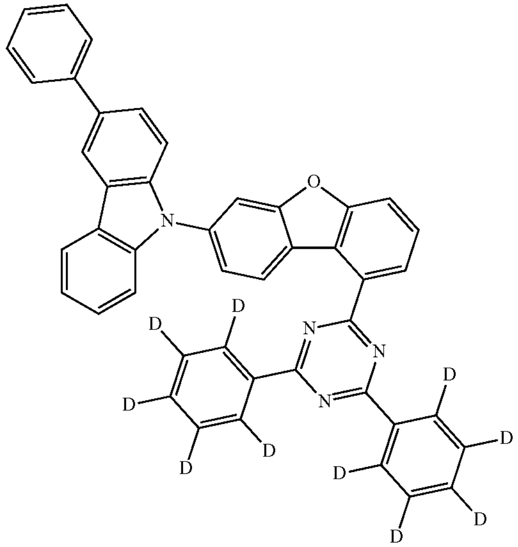 [SMILES: [2H]c1c([2H])c([2H])c(-c2nc(-c3c([2H])c([2H])c([2H])c([2H])c3[2H])nc(-c3cccc4oc5cc(-n6c7ccccc7c7cc(-c8ccccc8)ccc76)ccc5c34)n2)c([2H])c1[2H]] | 93% |
| 359 | 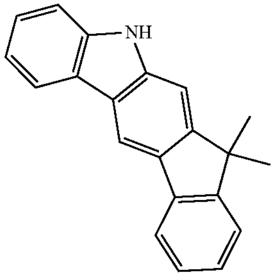 [SMILES: CC1(C)c2ccccc2-c2cc3c(cc21)[nH]c1ccccc13] | 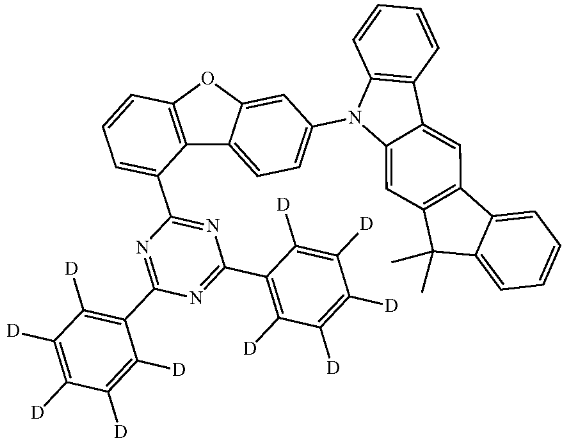 [SMILES: [2H]c1c([2H])c([2H])c(-c2nc(-c3c([2H])c([2H])c([2H])c([2H])c3[2H])nc(-c3cccc4oc5cc(-n6c7ccccc7c7cc8c(cc76)C(C)(C)c6ccccc6-8)ccc5c34)n2)c([2H])c1[2H]] | 95% |

TABLE 3-continued
| | | | |
|---|---|---|---|
| 362 | 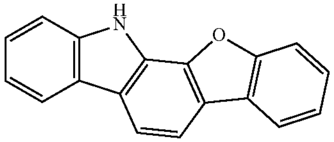 [SMILES: c1ccc2c(c1)[nH]c1c2ccc2c3ccccc3oc21] | 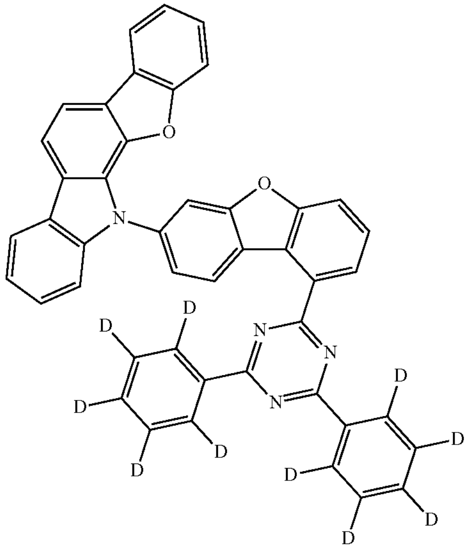 [SMILES: [2H]c1c([2H])c([2H])c(-c2nc(-c3c([2H])c([2H])c([2H])c([2H])c3[2H])nc(-c3cccc4oc5cc(-n6c7ccccc7c7ccc8c9ccccc9oc8c76)ccc5c34)n2)c([2H])c1[2H]] | 66% |
| 366 | 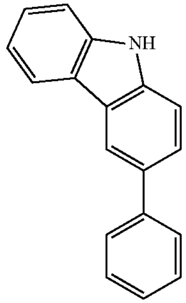 [SMILES: c1ccc(-c2ccc3[nH]c4ccccc4c3c2)cc1] | 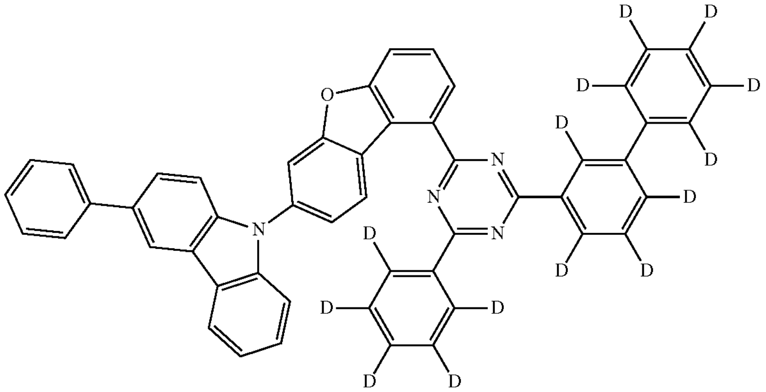 [SMILES: [2H]c1c([2H])c([2H])c(-c2nc(-c3c([2H])c([2H])c([2H])c(-c4c([2H])c([2H])c([2H])c([2H])c4[2H])c3[2H])nc(-c3cccc4oc5cc(-n6c7ccccc7c7cc(-c8ccccc8)ccc76)ccc5c34)n2)c([2H])c1[2H]] | 84% |

TABLE 3-continued
| | | | |
|---|---|---|---|
| 371 | 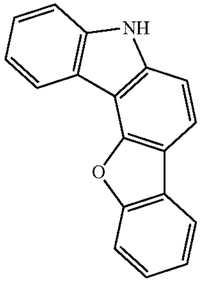 [SMILES: c1ccc2c(c1)[nH]c1ccc3c4ccccc4oc3c12] | 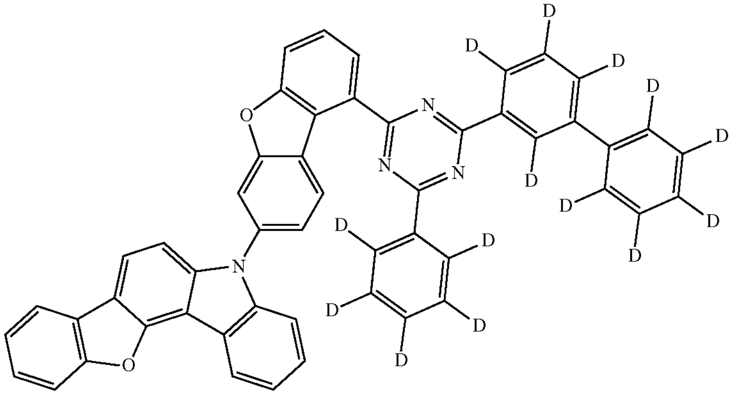 [SMILES: [2H]c1c([2H])c([2H])c(-c2nc(-c3c([2H])c([2H])c([2H])c(-c4c([2H])c([2H])c([2H])c([2H])c4[2H])c3[2H])nc(-c3cccc4oc5cc(-n6c7ccccc7c7c8oc9ccccc9c8ccc76)ccc5c34)n2)c([2H])c1[2H]] | 82% |
| 373 | 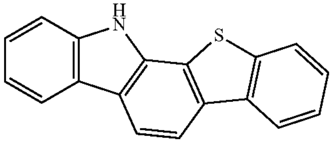 [SMILES: c1ccc2c(c1)[nH]c1c2ccc2c3ccccc3sc21] | 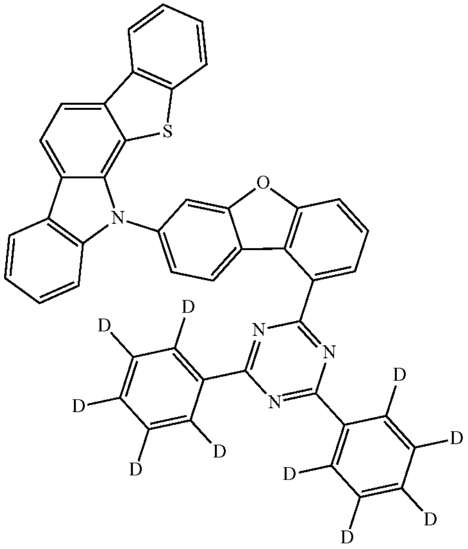 | 71% |

TABLE 3-continued
| | | | |
|---|---|---|---|
| 380 | 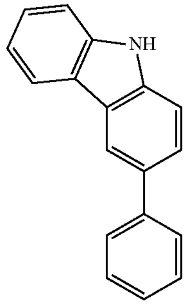 [SMILES: c1ccc(-c2ccc3[nH]c4ccccc4c3c2)cc1] | 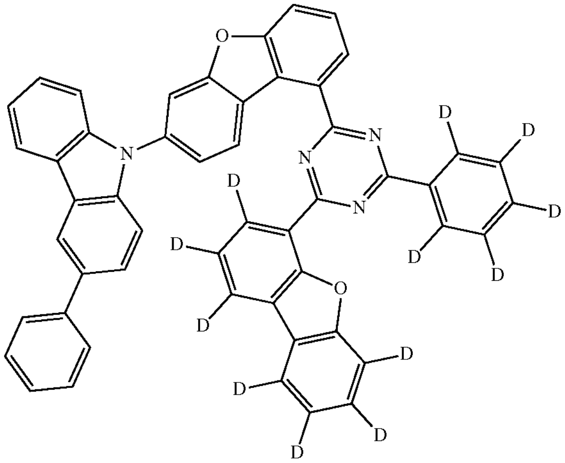 [SMILES: [2H]c1c([2H])c([2H])c(-c2nc(-c3c([2H])c([2H])c([2H])c4c3oc3c([2H])c([2H])c([2H])c([2H])c34)nc(-c3cccc4oc5cc(-n6c7ccccc7c7cc(-c8ccccc8)ccc76)ccc5c34)n2)c([2H])c1[2H]] | 75% |
| 473 | 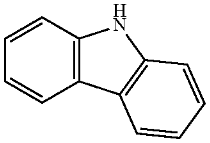 [SMILES: c1ccc2c(c1)[nH]c1ccccc12] | 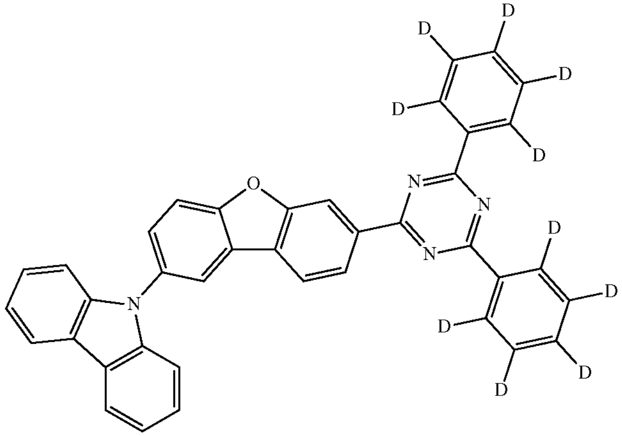 [SMILES: [2H]c1c([2H])c([2H])c(-c2nc(-c3ccc4c(c3)oc3ccc(-n5c6ccccc6c6ccccc65)cc34)nc(-c3c([2H])c([2H])c([2H])c([2H])c3[2H])n2)c([2H])c1[2H]] | 76% |

TABLE 3-continued
| | | | |
|---|---|---|---|
| 474 | 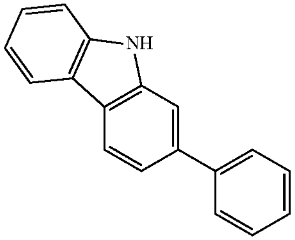 [SMILES: c1ccc(-c2ccc3c(c2)[nH]c2ccccc23)cc1] | 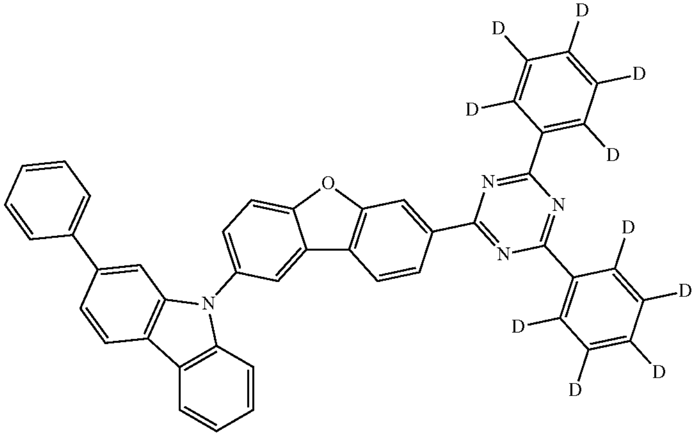 [SMILES: [2H]c1c([2H])c([2H])c(-c2nc(-c3ccc4c(c3)oc3ccc(-n5c6ccccc6c6ccc(-c7ccccc7)cc65)cc34)nc(-c3c([2H])c([2H])c([2H])c([2H])c3[2H])n2)c([2H])c1[2H]] | 87% |
| 475 | 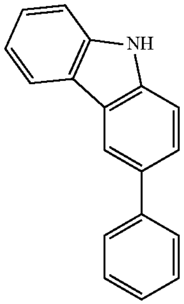 [SMILES: c1ccc(-c2ccc3[nH]c4ccccc4c3c2)cc1] | 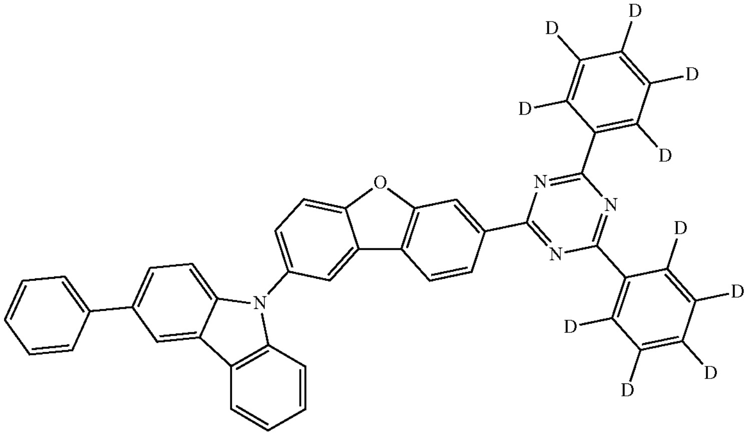 [SMILES: [2H]c1c([2H])c([2H])c(-c2nc(-c3ccc4c(c3)oc3ccc(-n5c6ccccc6c6cc(-c7ccccc7)ccc65)cc34)nc(-c3c([2H])c([2H])c([2H])c([2H])c3[2H])n2)c([2H])c1[2H]] | 84% |

TABLE 3-continued
| | | | |
|---|---|---|---|
| 479 | 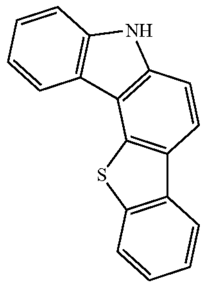 [SMILES: c1ccc2c(c1)[nH]c1ccc3c4ccccc4sc3c12] | 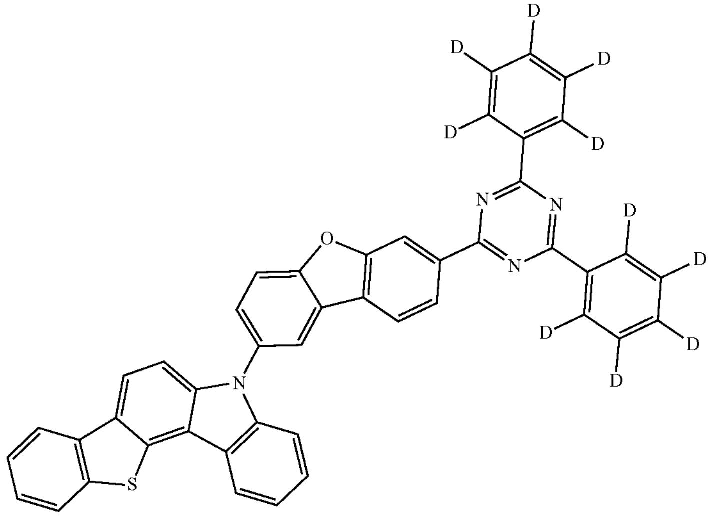 [SMILES: [2H]c1c([2H])c([2H])c(-c2nc(-c3ccc4c(c3)oc3ccc(-n5c6ccccc6c6c7sc8ccccc8c7ccc65)cc34)nc(-c3c([2H])c([2H])c([2H])c([2H])c3[2H])n2)c([2H])c1[2H]] | 86% |
| 480 | 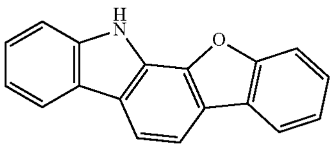 | 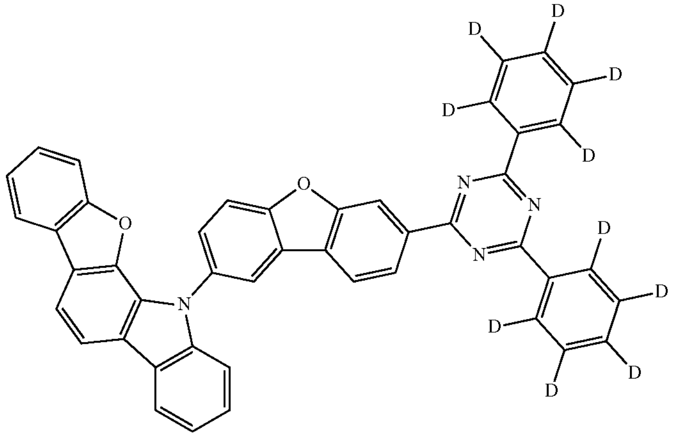 [SMILES: [2H]c1c([2H])c([2H])c(-c2nc(-c3ccc4c(c3)oc3ccc(-n5c6ccccc6c6ccc7c8ccccc8oc7c65)cc34)nc(-c3c([2H])c([2H])c([2H])c([2H])c3[2H])n2)c([2H])c1[2H]] | 71% |

TABLE 3-continued
| | | | |
|---|---|---|---|
| 482 | 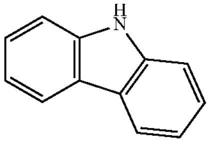 [SMILES: c1ccc2c(c1)[nH]c1ccccc12] | 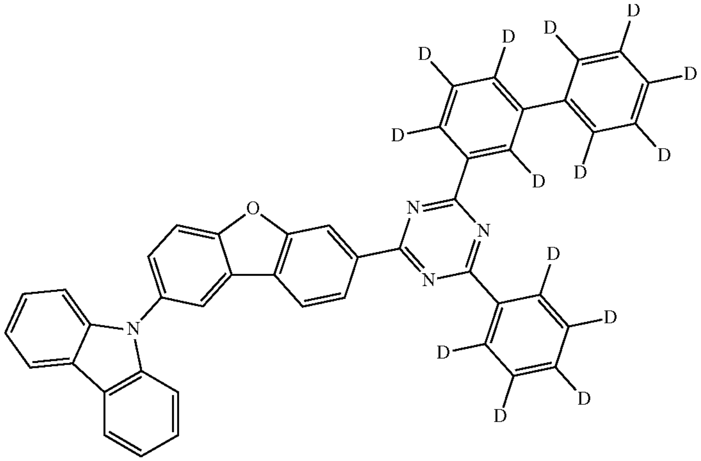 [SMILES: [2H]c1c([2H])c([2H])c(-c2nc(-c3ccc4c(c3)oc3ccc(-n5c6ccccc6c6ccccc65)cc34)nc(-c3c([2H])c([2H])c([2H])c(-c4c([2H])c([2H])c([2H])c([2H])c4[2H])c3[2H])n2)c([2H])c1[2H]] | 76% |
| 483 | 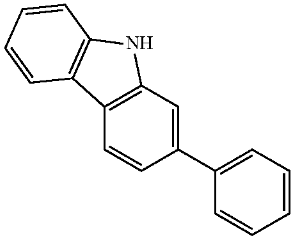 [SMILES: c1ccc(-c2ccc3c(c2)[nH]c2ccccc23)cc1] | 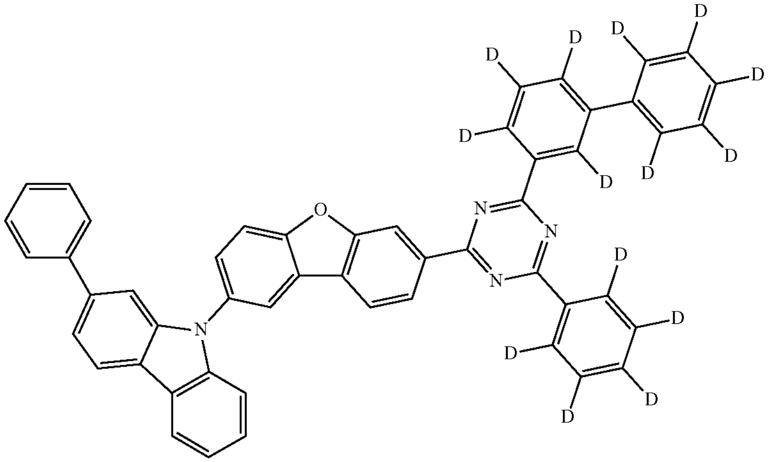 [SMILES: [2H]c1c([2H])c([2H])c(-c2nc(-c3ccc4c(c3)oc3ccc(-n5c6ccccc6c6ccc(-c7ccccc7)cc65)cc34)nc(-c3c([2H])c([2H])c([2H])c(-c4c([2H])c([2H])c([2H])c([2H])c4[2H])c3[2H])n2)c([2H])c1[2H]] | 65% |

TABLE 3-continued
| | | | |
|---|---|---|---|
| 484 | 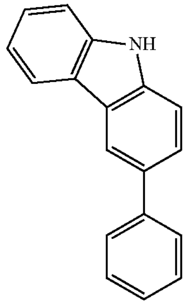 [SMILES: c1ccc(-c2ccc3[nH]c4ccccc4c3c2)cc1] | 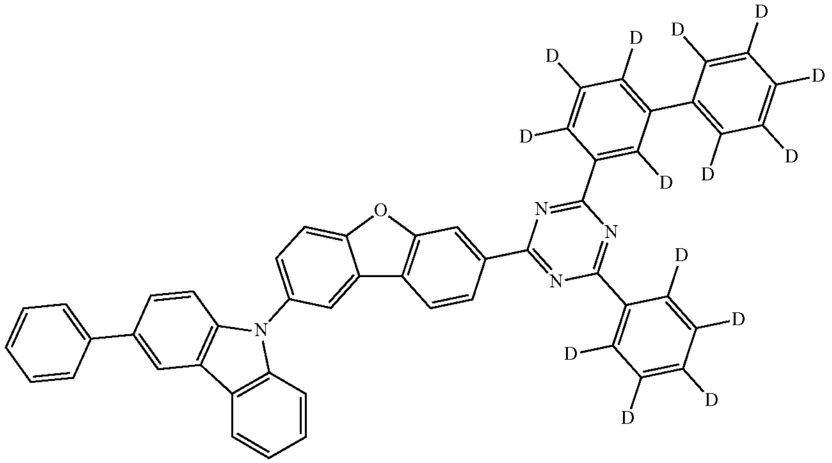 [SMILES: [2H]c1c([2H])c([2H])c(-c2nc(-c3ccc4c(c3)oc3ccc(-n5c6ccccc6c6cc(-c7ccccc7)ccc65)cc34)nc(-c3c([2H])c([2H])c([2H])c(-c4c([2H])c([2H])c([2H])c([2H])c4[2H])c3[2H])n2)c([2H])c1[2H]] | 56% |
| 485 | 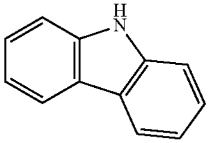 [SMILES: c1ccc2c(c1)[nH]c1ccccc12] | 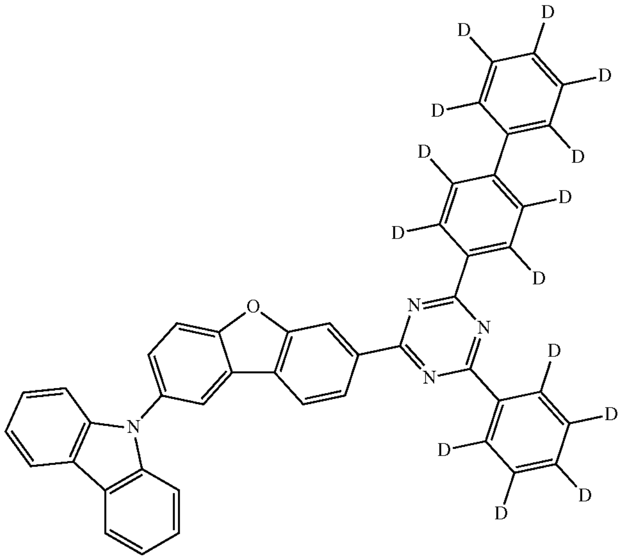 [SMILES: [2H]c1c([2H])c([2H])c(-c2nc(-c3ccc4c(c3)oc3ccc(-n5c6ccccc6c6ccccc65)cc34)nc(-c3c([2H])c([2H])c(-c4c([2H])c([2H])c([2H])c([2H])c4[2H])c([2H])c3[2H])n2)c([2H])c1[2H]] | 69% |

TABLE 3-continued
| | | | |
|---|---|---|---|
| 488 | 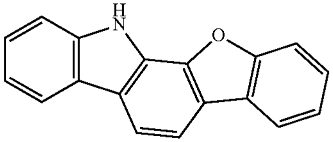 [SMILES: c1ccc2c(c1)[nH]c1c2ccc2c3ccccc3oc21] | 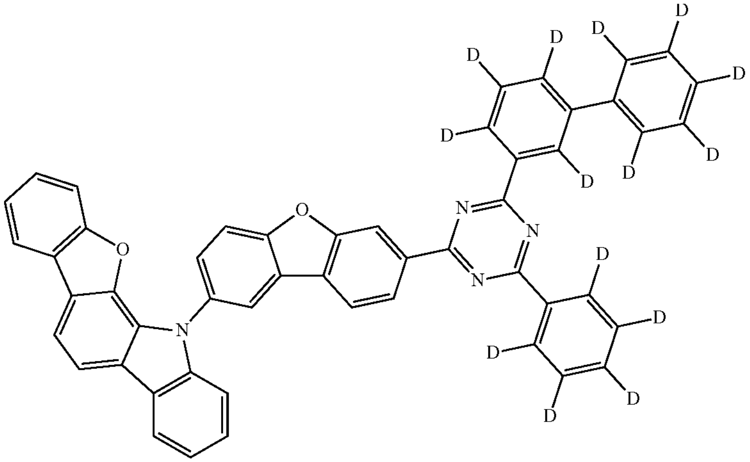 [SMILES: [2H]c1c([2H])c([2H])c(-c2nc(-c3ccc4c(c3)oc3ccc(-n5c6ccccc6c6ccc7c8ccccc8oc7c65)cc34)nc(-c3c([2H])c([2H])c([2H])c(-c4c([2H])c([2H])c([2H])c([2H])c4[2H])c3[2H])n2)c([2H])c1[2H]] | 77% |
| 495 | 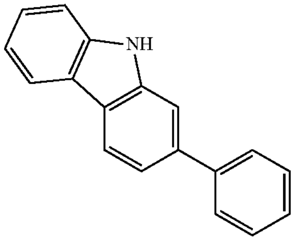 [SMILES: c1ccc(-c2ccc3c(c2)[nH]c2ccccc23)cc1] | 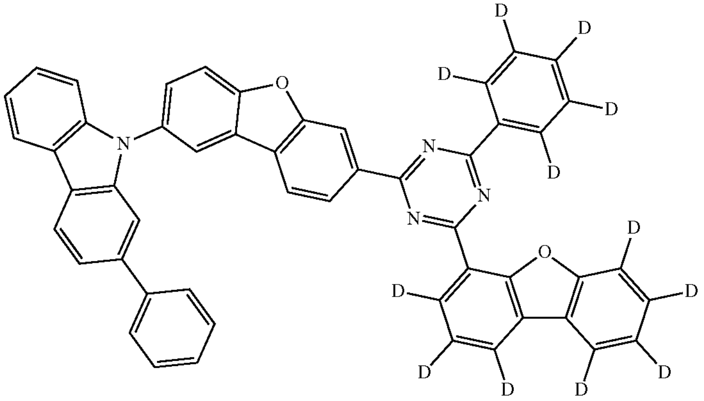 [SMILES: [2H]c1c([2H])c([2H])c(-c2nc(-c3ccc4c(c3)oc3ccc(-n5c6ccccc6c6ccc(-c7ccccc7)cc65)cc34)nc(-c3c([2H])c([2H])c([2H])c4c3oc3c([2H])c([2H])c([2H])c([2H])c34)n2)c([2H])c1[2H]] | 75% |

TABLE 3-continued
| | | | |
|---|---|---|---|
| 497 | 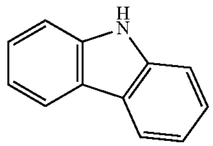 [SMILES: c1ccc2c(c1)[nH]c1ccccc12] | 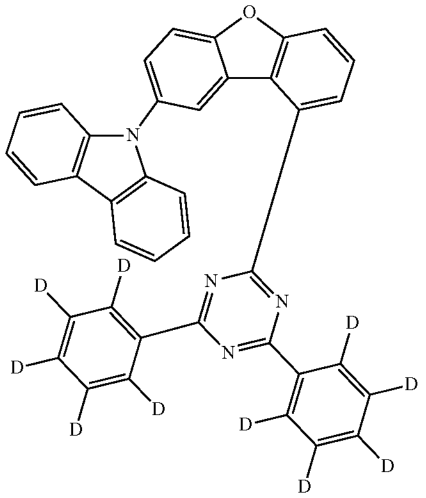 [SMILES: [2H]c1c([2H])c([2H])c(-c2nc(-c3c([2H])c([2H])c([2H])c([2H])c3[2H])nc(-c3cccc4oc5ccc(-n6c7ccccc7c7ccccc76)cc5c34)n2)c([2H])c1[2H]] | 57% |
| 500 | 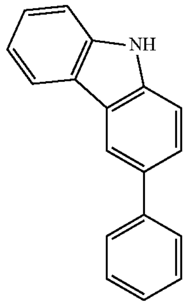 [SMILES: c1ccc(-c2ccc3[nH]c4ccccc4c3c2)cc1] | 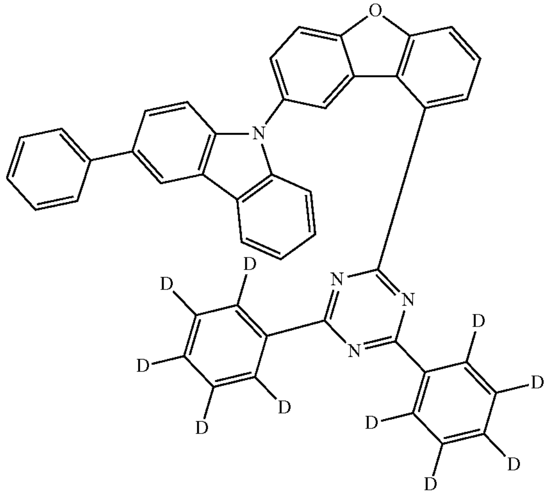 [SMILES: [2H]c1c([2H])c([2H])c(-c2nc(-c3c([2H])c([2H])c([2H])c([2H])c3[2H])nc(-c3cccc4oc5ccc(-n6c7ccccc7c7cc(-c8ccccc8)ccc76)cc5c34)n2)c([2H])c1[2H]] | 66% |

TABLE 3-continued
| | | | |
|---|---|---|---|
| 605 | 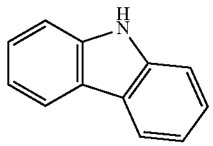 [SMILES: c1ccc2c(c1)[nH]c1ccccc12] | 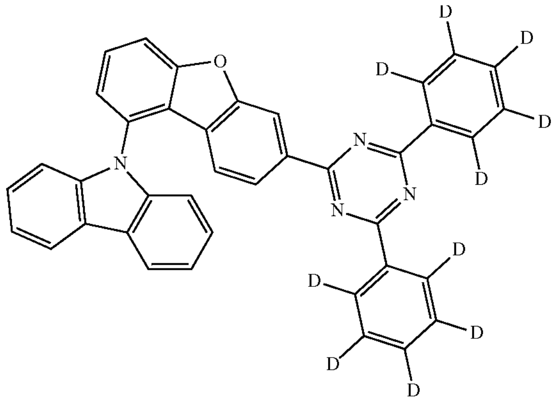 [SMILES: [2H]c1c([2H])c([2H])c(-c2nc(-c3ccc4c(c3)oc3cccc(-n5c6ccccc6c6ccccc65)c34)nc(-c3c([2H])c([2H])c([2H])c([2H])c3[2H])n2)c([2H])c1[2H]] | 73% |
| 606 | 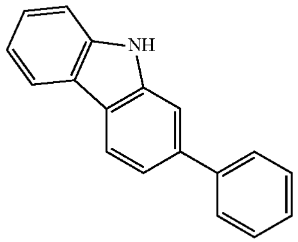 [SMILES: c1ccc(-c2ccc3c(c2)[nH]c2ccccc23)cc1] | 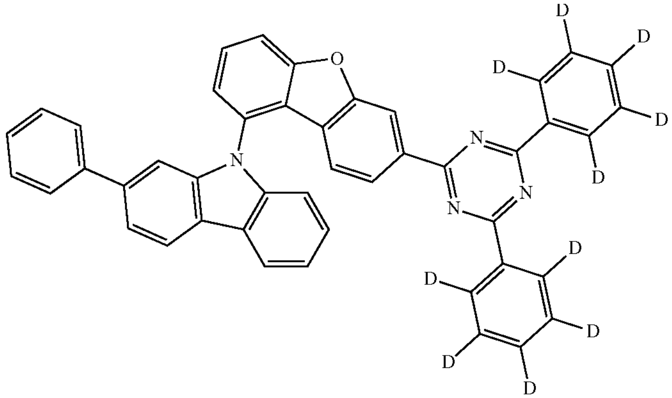 [SMILES: [2H]c1c([2H])c([2H])c(-c2nc(-c3ccc4c(c3)oc3cccc(-n5c6ccccc6c6ccc(-c7ccccc7)cc65)c34)nc(-c3c([2H])c([2H])c([2H])c([2H])c3[2H])n2)c([2H])c1[2H]] | 82% |

TABLE 3-continued
| | | | |
|---|---|---|---|
| 607 | 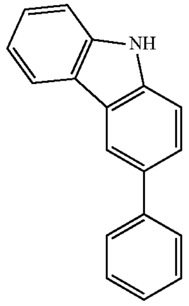 [SMILES: c1ccc(-c2ccc3[nH]c4ccccc4c3c2)cc1] | 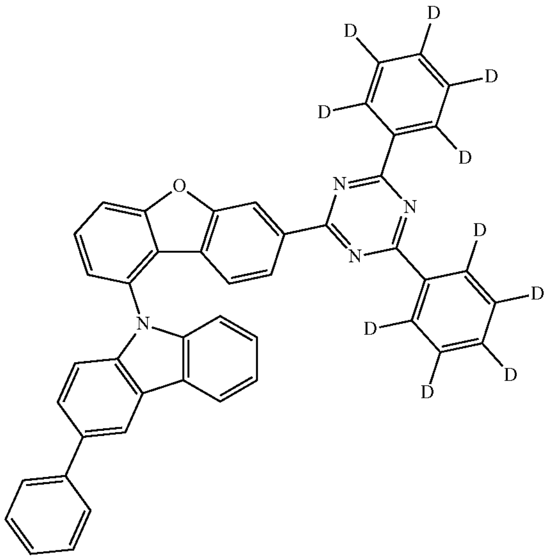 [SMILES: [2H]c1c([2H])c([2H])c(-c2nc(-c3ccc4c(c3)oc3cccc(-n5c6ccccc6c6cc(-c7ccccc7)ccc65)c34)nc(-c3c([2H])c([2H])c([2H])c([2H])c3[2H])n2)c([2H])c1[2H]] | 92% |
| 608 | 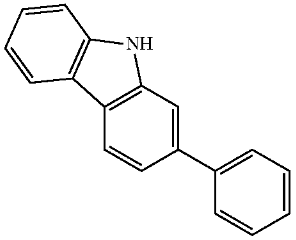 [SMILES: c1ccc(-c2ccc3c(c2)[nH]c2ccccc23)cc1] | 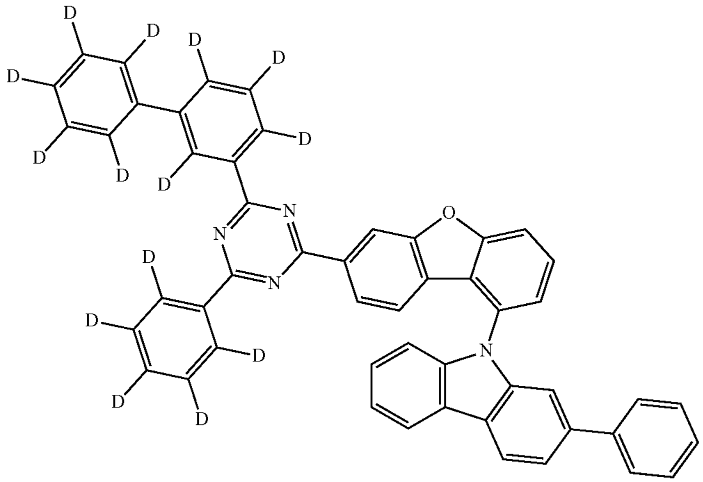 [SMILES: [2H]c1c([2H])c([2H])c(-c2nc(-c3ccc4c(c3)oc3cccc(-n5c6ccccc6c6ccc(-c7ccccc7)cc65)c34)nc(-c3c([2H])c([2H])c([2H])c(-c4c([2H])c([2H])c([2H])c([2H])c4[2H])c3[2H])n2)c([2H])c1[2H]] | 74% |

TABLE 3-continued
| | | | |
|---|---|---|---|
| 611 | 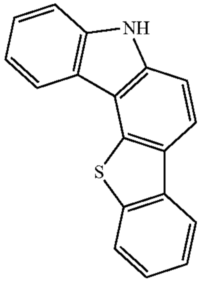 [SMILES: c1ccc2c(c1)[nH]c1ccc3c4ccccc4sc3c12] | 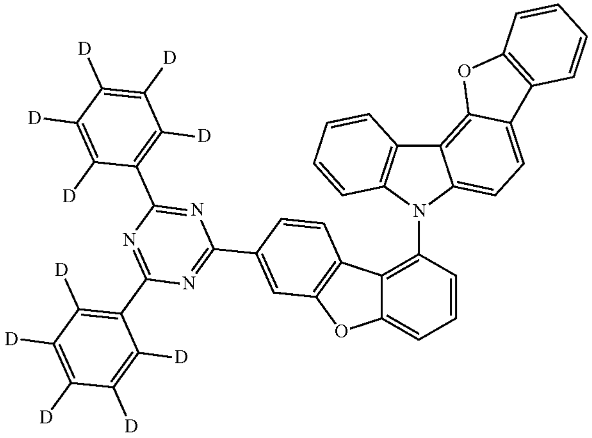 [SMILES: [2H]c1c([2H])c([2H])c(-c2nc(-c3ccc4c(c3)oc3cccc(-n5c6ccccc6c6c7oc8ccccc8c7ccc65)c34)nc(-c3c([2H])c([2H])c([2H])c([2H])c3[2H])n2)c([2H])c1[2H]] | 63% |
| 612 | 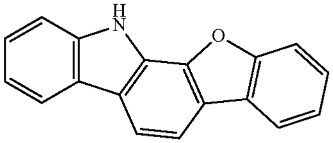 [SMILES: c1ccc2c(c1)[nH]c1c2ccc2c3ccccc3oc21] | 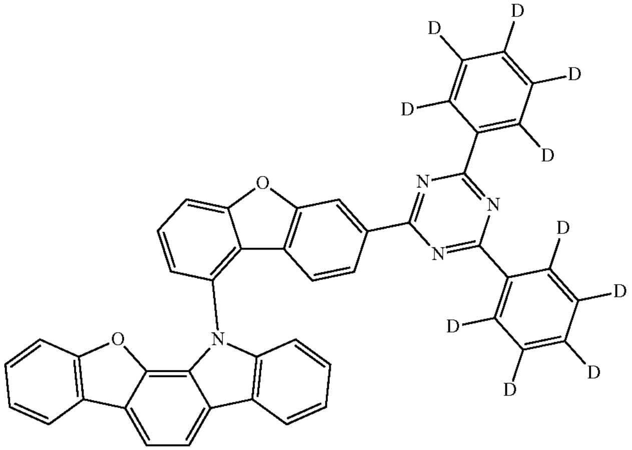 [SMILES: [2H]c1c([2H])c([2H])c(-c2nc(-c3ccc4c(c3)oc3cccc(-n5c6ccccc6c6ccc7c8ccccc8oc7c65)c34)nc(-c3c([2H])c([2H])c([2H])c([2H])c3[2H])n2)c([2H])c1[2H]] | 65% |

TABLE 3-continued
| | | | |
|---|---|---|---|
| 614 | 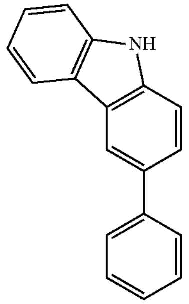 [SMILES: c1ccc(-c2ccc3[nH]c4ccccc4c3c2)cc1] | 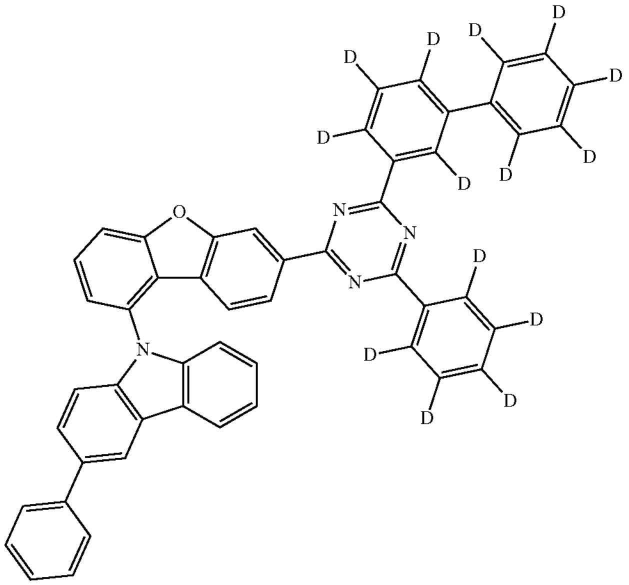 [SMILES: [2H]c1c([2H])c([2H])c(-c2nc(-c3ccc4c(c3)oc3cccc(-n5c6ccccc6c6cc(-c7ccccc7)ccc65)c34)nc(-c3c([2H])c([2H])c([2H])c(-c4c([2H])c([2H])c([2H])c([2H])c4[2H])c3[2H])n2)c([2H])c1[2H]] | 69% |
| 616 | 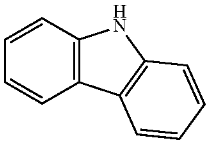 [SMILES: c1ccc2c(c1)[nH]c1ccccc12] | 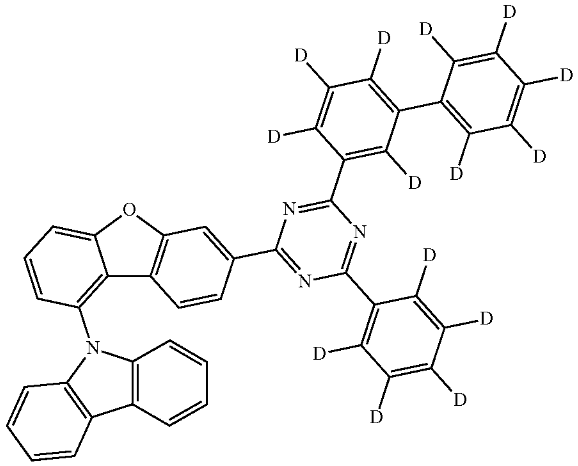 [SMILES: [2H]c1c([2H])c([2H])c(-c2nc(-c3ccc4c(c3)oc3cccc(-n5c6ccccc6c6ccccc65)c34)nc(-c3c([2H])c([2H])c([2H])c(-c4c([2H])c([2H])c([2H])c([2H])c4[2H])c3[2H])n2)c([2H])c1[2H]] | 56% |

TABLE 3-continued
| | | | |
|---|---|---|---|
| 620 | 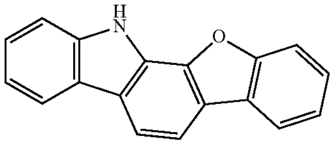 | 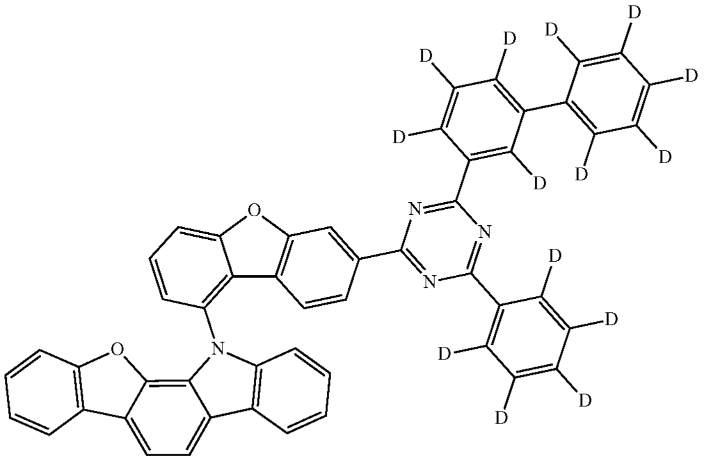 [SMILES: [2H]c1c([2H])c([2H])c(-c2nc(-c3ccc4c(c3)oc3cccc(-n5c6ccccc6c6ccc7c8ccccc8oc7c65)c34)nc(-c3c([2H])c([2H])c([2H])c(-c4c([2H])c([2H])c([2H])c([2H])c4[2H])c3[2H])n2)c([2H])c1[2H]] | 74% |
| 625 | 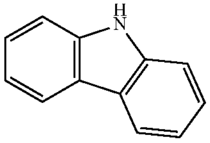 [SMILES: c1ccc2c(c1)[nH]c1ccccc12] | 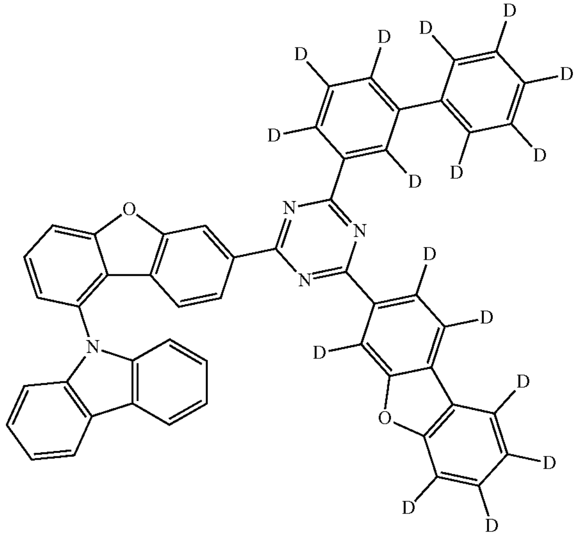 [SMILES: [2H]c1c([2H])c([2H])c(-c2c([2H])c([2H])c([2H])c(-c3nc(-c4ccc5c(c4)oc4cccc(-n6c7ccccc7c7ccccc76)c45)nc(-c4c([2H])c([2H])c5c(oc6c([2H])c([2H])c([2H])c([2H])c65)c4[2H])n3)c2[2H])c([2H])c1[2H]] | 66% |

TABLE 3-continued
| | | | |
|---|---|---|---|
| 627 | 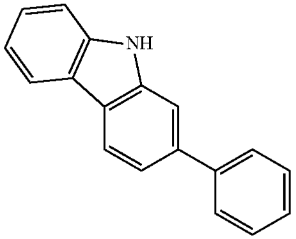 [SMILES: c1ccc(-c2ccc3c(c2)[nH]c2ccccc23)cc1] | 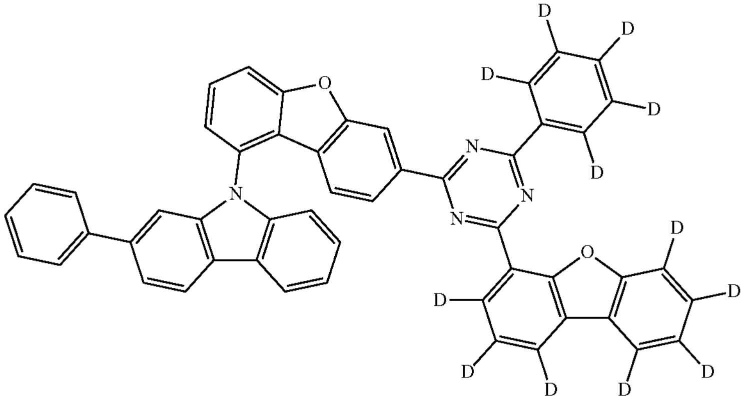 [SMILES: [2H]c1c([2H])c([2H])c(-c2nc(-c3ccc4c(c3)oc3cccc(-n5c6ccccc6c6ccc(-c7ccccc7)cc65)c34)nc(-c3c([2H])c([2H])c([2H])c4c3oc3c([2H])c([2H])c([2H])c([2H])c34)n2)c([2H])c1[2H]] | 58% |
| 629 | 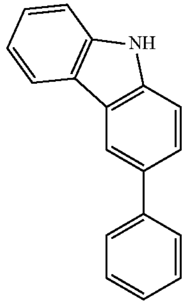 [SMILES: c1ccc(-c2ccc3[nH]c4ccccc4c3c2)cc1] | 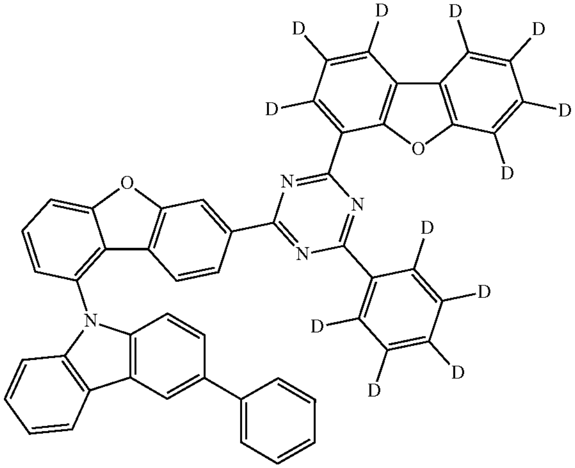 [SMILES: [2H]c1c([2H])c([2H])c(-c2nc(-c3ccc4c(c3)oc3cccc(-n5c6ccccc6c6cc(-c7ccccc7)ccc65)c34)nc(-c3c([2H])c([2H])c([2H])c4c3oc3c([2H])c([2H])c([2H])c([2H])c34)n2)c([2H])c1[2H]] | 89% |

TABLE 3-continued
| | | | |
|---|---|---|---|
| 630 | 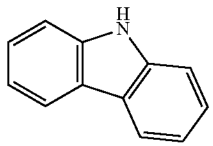 [SMILES: c1ccc2c(c1)[nH]c1ccccc12] | 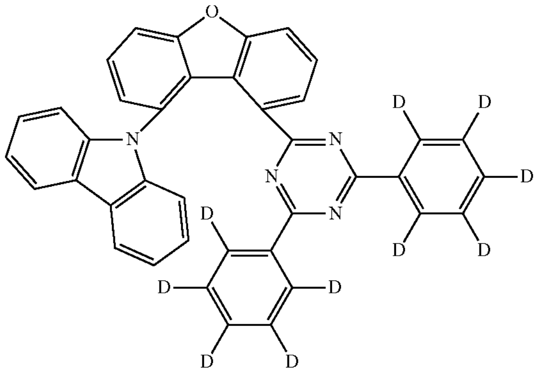 [SMILES: [2H]c1c([2H])c([2H])c(-c2nc(-c3c([2H])c([2H])c([2H])c([2H])c3[2H])nc(-c3cccc4oc5cccc(-n6c7ccccc7c7ccccc76)c5c34)n2)c([2H])c1[2H]] | 91% |

[Synthesis 4] The compound 641 (H)
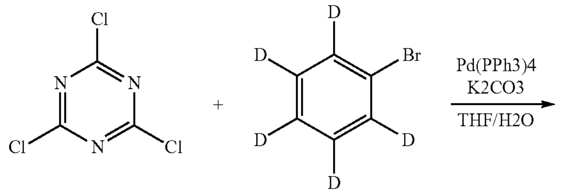
[A]
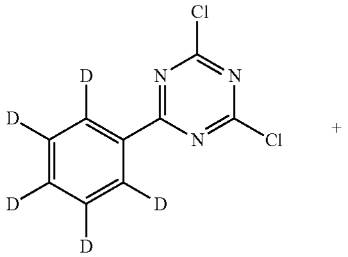
[A]-1
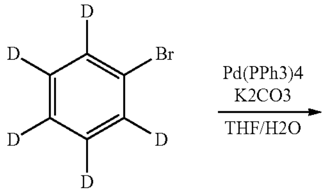
[A′]
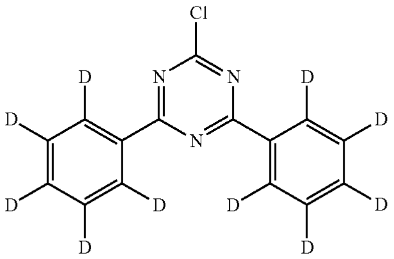
[A]-2
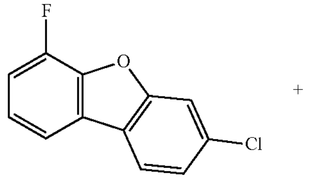
[B]
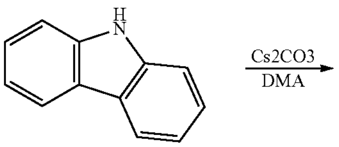
[C]
-continued
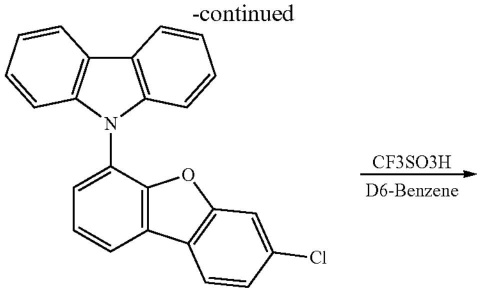
641-1
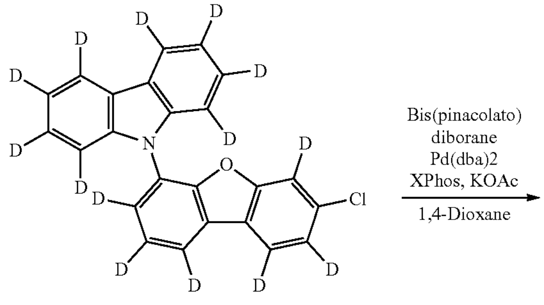
641-2
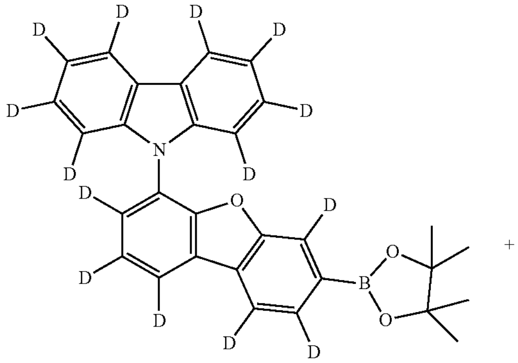
641-3
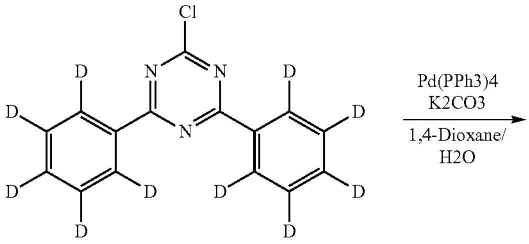
[A]-2
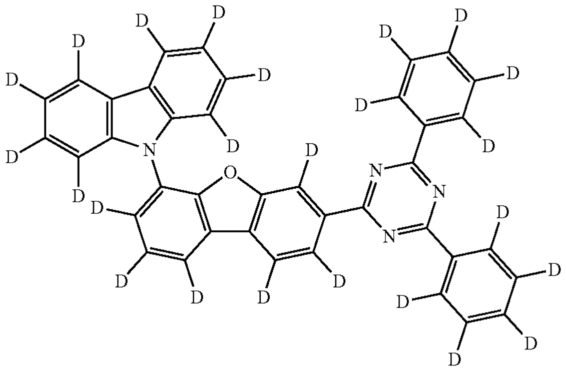
641[H]

(1) The Compound [A]-1

In the one-neck round bottom flask, a mixture of 2,4,6-trichloro-1,3,5-triazine (log, 0.054 mol), 1-bromobenzene-2,3,4,5,6-d5 (9.63 g, 0.059 mol), $Pd(PPh_3)_4$ (3.12 g, 0.0027 mol), $K_2CO_3$ (14.93 g, 0.11 mol), tetrahydrofuran (100 mL) and water (30 mL) was refluxed at 120° C. After cooling, the resultant was concentrated and filtered through silica gel to obtain the compound [A]-1. (6.99 g, 56%)

(2) The Compound [A]-2

In the one-neck round bottom flask, a mixture of 2,4-dichloro-6-(phenyl-d5)-1,3,5-triazine (6.99 g, 0.030 mol), 1-bromobenzene-2,3,4,5,6-d5 (5.35 g, 0.033 mol) $Pd(PPh_3)_4$ (1.73 g, 0.0015 mol), $K_2CO_3$ (8.29 g, 0.06 mol), tetrahydrofuran (70 mL) and water (20 mL) was refluxed at 120° C. After cooling, the resultant was concentrated and filtered through silica gel to obtain the compound [A]-2. (5.58 g, 67%)

(3) The Compound 641-1

In the one-neck round bottom flask, a mixture of 3-chloro-6-fluorodibenzo[b,d]furan (10 g, 0.045 mol), 9H-carbazole (8.28 g, 0.050 mol), $Cs_2CO_3$ (29.32 g, 0.09 mol) and dimethylacetamide (100 mL) were refluxed at 170° C. After cooling, the resultant was filtered to remove the solvent and was purified by column to obtain the compound 641-1. (15.39 g, 93%)

(4) The Compound 641-2

In the one-neck round bottom flask, a mixture of 9-(7-chlorodibenzo[b,d]furan-4-yl)-9H-carbazole (15.39 g, 0.042 mol), triflic acid (51 g, 0.34 mol) and D6-benzene (150 mL) was refluxed at 70° C. After quenching and extraction with dichloromethane and $H_2O$, the resultant was concentrated and filtered through silica gel. After concentration, the resultant was treated with methanol to obtain the compound 641-2. (10.11 g, 63%)

(5) The Compound 641-3

In the one-neck round bottom flask, a mixture of 9-(7-chlorodibenzo[b,d]furan-4-yl-1,2,3,6,8,9-d6)-9H-carbazole-1,2,3,4,5,6,7,8-d8 (10.11 g, 0.026 mol), bis(pinacolato)diborn (13.20 g, 0.052 mol), $Pd(dba)_2$ (2.38 g), 0.0026 mol), Xphos (2.48 g, 0.0052 mol), potassium acetate (7.66 g, 0.078 mol) and 1,4-dioxane (100 mL) were refluxed at 120° C. After cooling, the resultant was concentrated and filtered through silica gel to obtain the compound 641-3. (11.30 g, 92%)

(6) The Compound 641 [H]

In the one-neck round bottom flask, a mixture of (2-(6-(9H-carbazol-9-yl-d8)dibenzo[b,d]furan-3-yl-1,2,4,7,8,9-d6)-4,5,5-trimethyl-1,3,2-dioxaborolan-4-yl)methylium (11.30 g, 0.024 mol), 2-chloro-4,6-bis(phenyl-d5)-1,3,5-triazine (7.33 g, 0.026 mol), Pd(PPh3)4 (1.39 g, 0.0012 mol), K2CO3 (6.63 g, 0.048 mol), 1,4-dioxane (110 mL) and water (50 mL) was refluxed at 120° C. After cooling, the resultant was concentrated and filtered through silica gel to obtain the compound 641[H]. (11.73 g, 83%)

When compounds A and A' are same, the compound A-2 can be directly synthesized by adding 2 equivalents of compound A in the first reaction. Namely, when the compounds A and A' are same, the second reaction step may be omitted.

The following compound H was synthesized in the same manner as in the synthesis 4 except that intermediates A, A', B, and C of Table 4 were used.

TABLE 4

| Compound | A | A' | B |
|---|---|---|---|
| 641 | 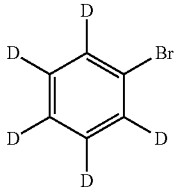 | 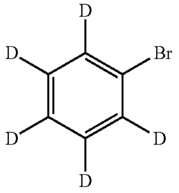 | 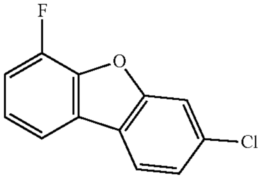 |
| 643 | 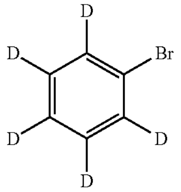 | 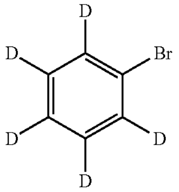 | 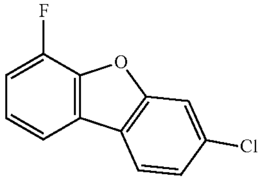 |
| 645 | 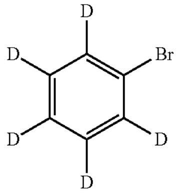 | 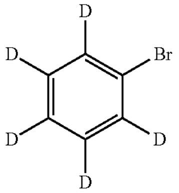 | 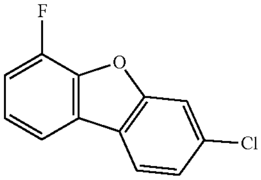 |

TABLE 4-continued
| | | | |
|---|---|---|---|
| 648 | 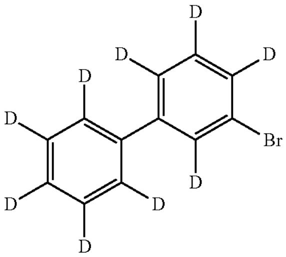 | 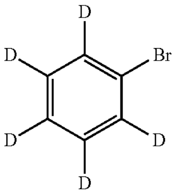 | 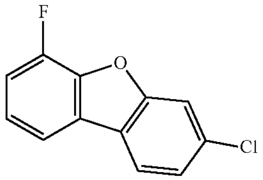 |
| 652 | 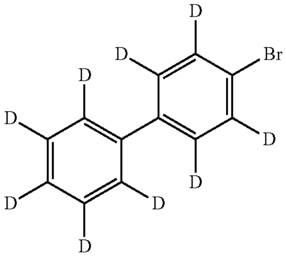 | 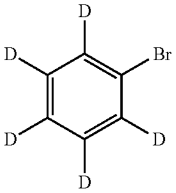 | 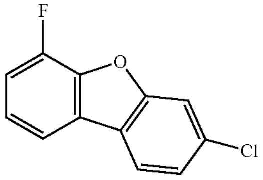 |
| 662 | 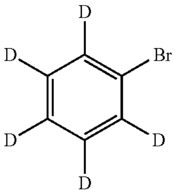 | 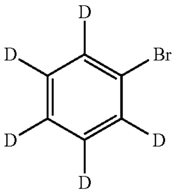 | 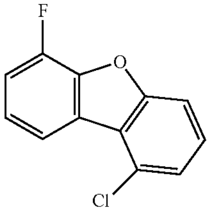 |
| 664 | 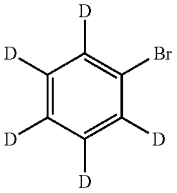 | 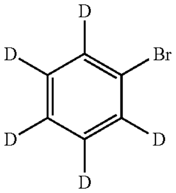 | 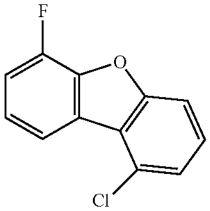 |
| 667 | 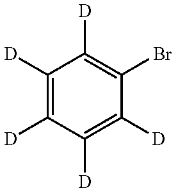 | 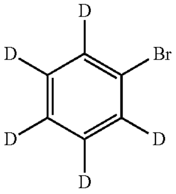 | 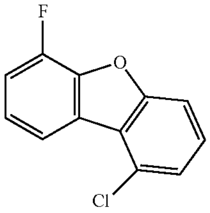 |
| 669 | 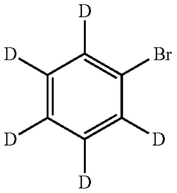 | 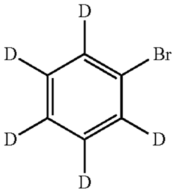 | 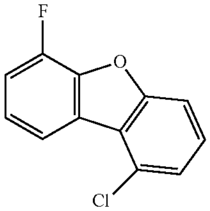 |

TABLE 4-continued
| | | | |
|---|---|---|---|
| 672 | 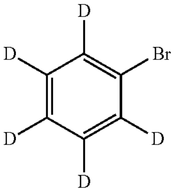 | 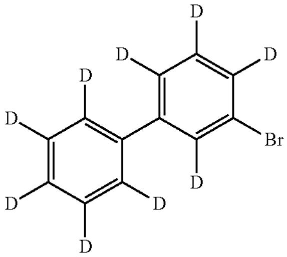 | 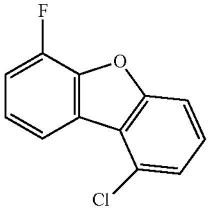 |
| 676 | 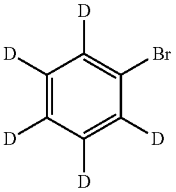 | 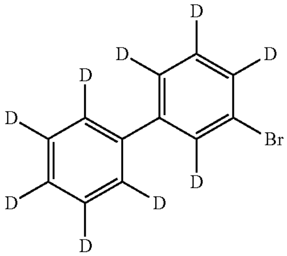 | 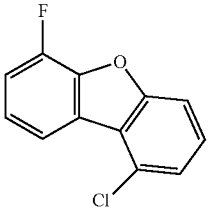 |
| 677 | 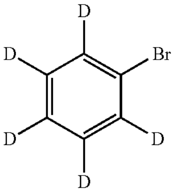 | 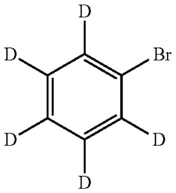 | 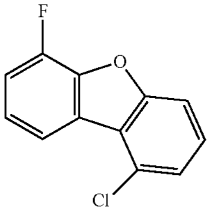 |
| 680 | 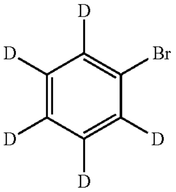 | 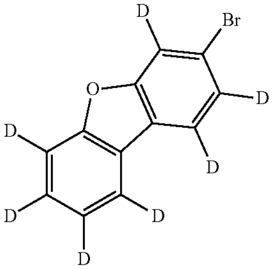 | 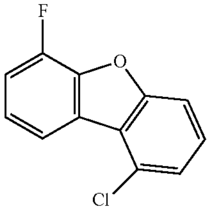 |
| 684 | 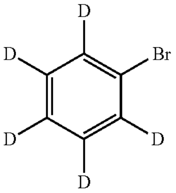 | 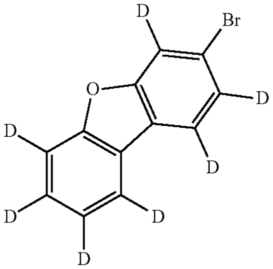 | 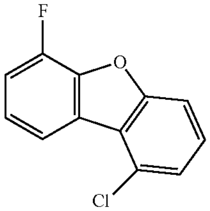 |
| 685 | 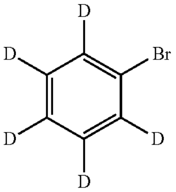 | 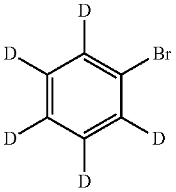 | 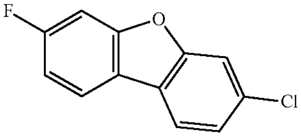 |

TABLE 4-continued
| | | | |
|---|---|---|---|
| 686 | 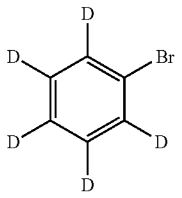 | 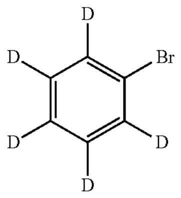 | 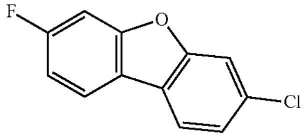 |
| 689 | 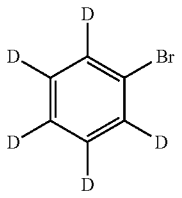 | 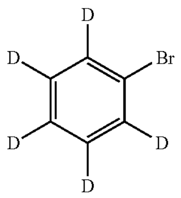 | 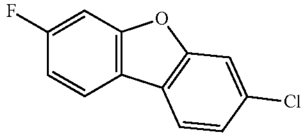 |
| 690 | 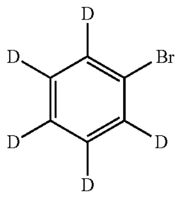 | 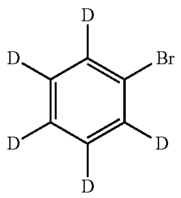 | 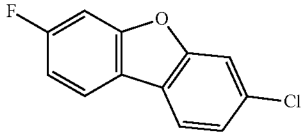 |
| 692 | 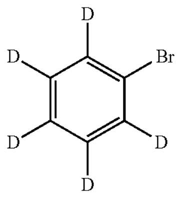 | 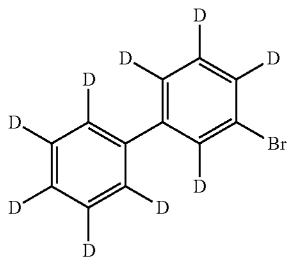 | 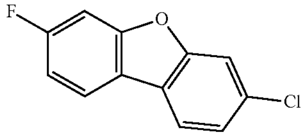 |
| 693 | 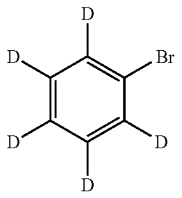 | 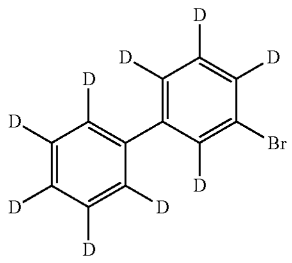 | 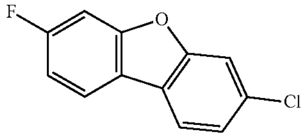 |
| 695 | 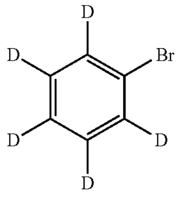 | 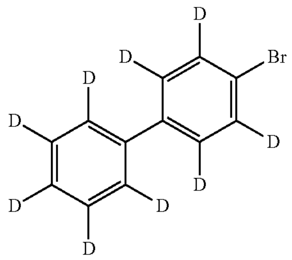 | 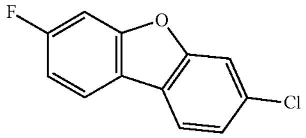 |

TABLE 4-continued
| | | | |
|---|---|---|---|
| 696 | 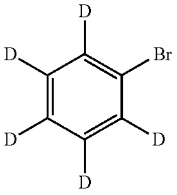 | 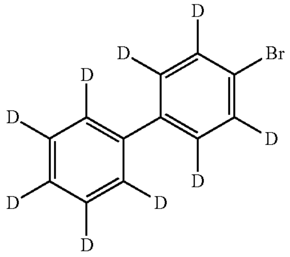 | 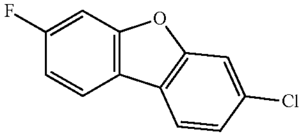 |
| 698 | 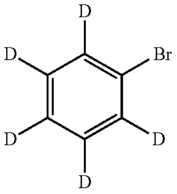 | 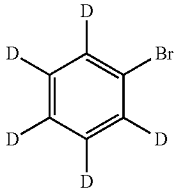 | 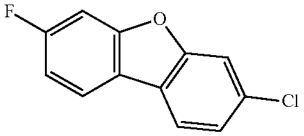 |
| 708 | 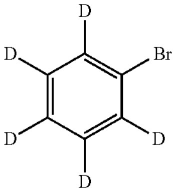 | 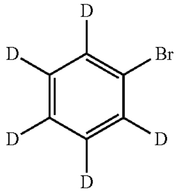 | 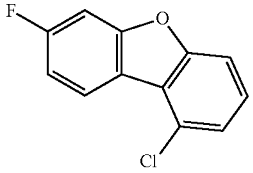 |
| 711 | 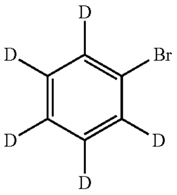 | 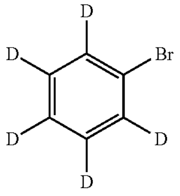 | 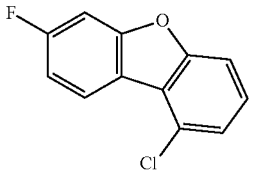 |
| 714 | 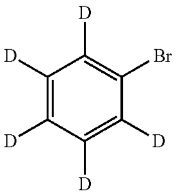 | 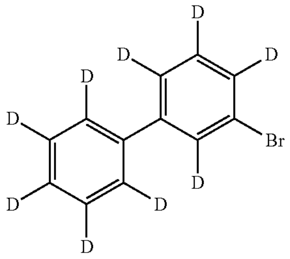 | 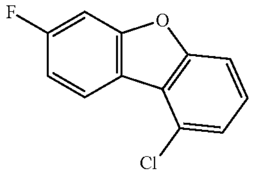 |
| 720 | 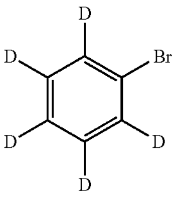 | 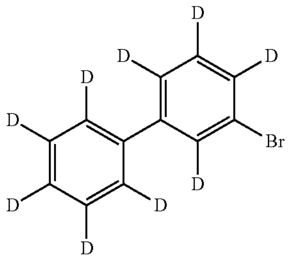 | 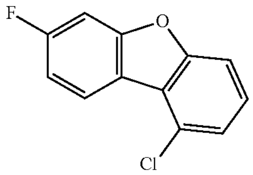 |
| 721 | 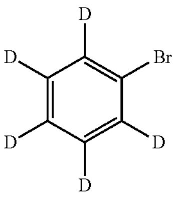 | 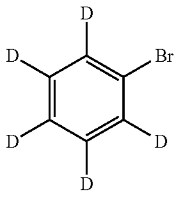 | 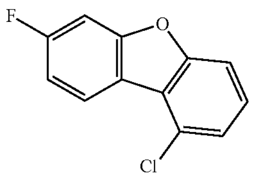 |

TABLE 4-continued
| | | | |
|---|---|---|---|
| 724 | 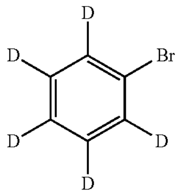 [SMILES: [2H]c1c([2H])c([2H])c(Br)c([2H])c1[2H]] | 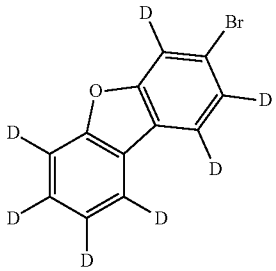 [SMILES: [2H]c1c([2H])c([2H])c2c(oc3c([2H])c(Br)c([2H])c([2H])c32)c1[2H]] | 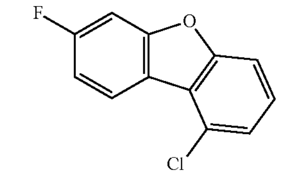 [SMILES: Fc1ccc2c(c1)oc1cccc(Cl)c12] |
| 725 | 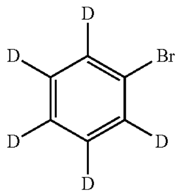 [SMILES: [2H]c1c([2H])c([2H])c(Br)c([2H])c1[2H]] | 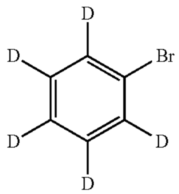 | 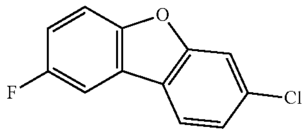 |
| 726 | 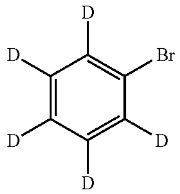 [SMILES: [2H]c1c([2H])c([2H])c(Br)c([2H])c1[2H]] | 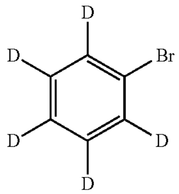 | 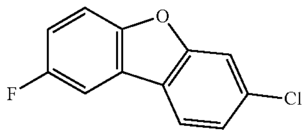 [SMILES: Fc1ccc2oc3cc(Cl)ccc3c2c1] |
| 727 | 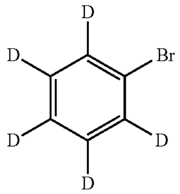 [SMILES: [2H]c1c([2H])c([2H])c(Br)c([2H])c1[2H]] | 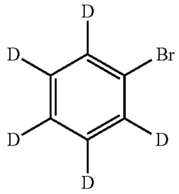 | 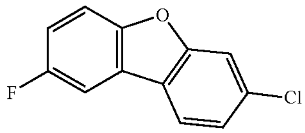 [SMILES: Fc1ccc2oc3cc(Cl)ccc3c2c1] |
| 729 | 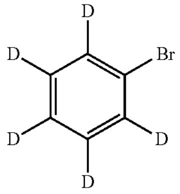 [SMILES: [2H]c1c([2H])c([2H])c(Br)c([2H])c1[2H]] | 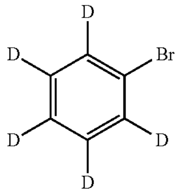 | 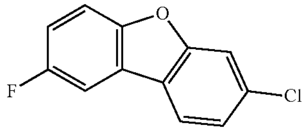 [SMILES: Fc1ccc2oc3cc(Cl)ccc3c2c1] |
| 730 | 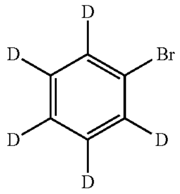 [SMILES: [2H]c1c([2H])c([2H])c(Br)c([2H])c1[2H]] | 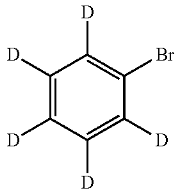 [SMILES: [2H]c1c([2H])c([2H])c(Br)c([2H])c1[2H]] | 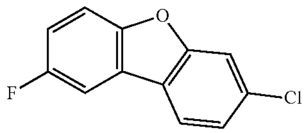 [SMILES: Fc1ccc2oc3cc(Cl)ccc3c2c1] |
| 732 | 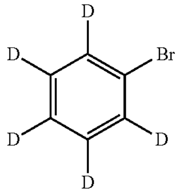 [SMILES: [2H]c1c([2H])c([2H])c(Br)c([2H])c1[2H]] | 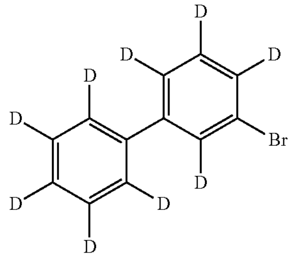 [SMILES: [2H]c1c([2H])c([2H])c(-c2c([2H])c([2H])c([2H])c(Br)c2[2H])c([2H])c1[2H]] | 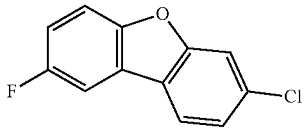 [SMILES: Fc1ccc2oc3cc(Cl)ccc3c2c1] |

TABLE 4-continued
| | | | |
|---|---|---|---|
| 734 | 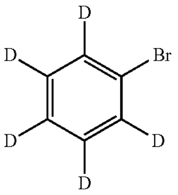 [SMILES: [2H]c1c([2H])c([2H])c(Br)c([2H])c1[2H]] | 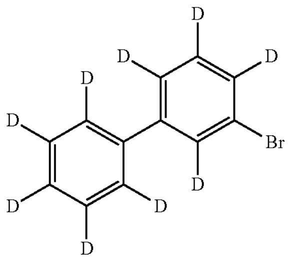 [SMILES: [2H]c1c([2H])c([2H])c(-c2c([2H])c([2H])c([2H])c(Br)c2[2H])c([2H])c1[2H]] | 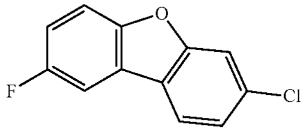 [SMILES: Fc1ccc2oc3cc(Cl)ccc3c2c1] |
| 735 | 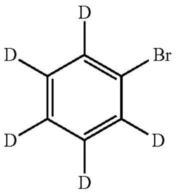 [SMILES: [2H]c1c([2H])c([2H])c(Br)c([2H])c1[2H]] | 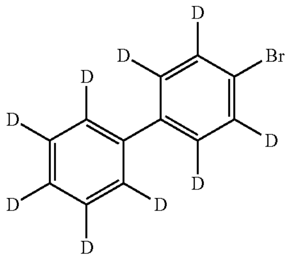 [SMILES: [2H]c1c([2H])c([2H])c(-c2c([2H])c([2H])c(Br)c([2H])c2[2H])c([2H])c1[2H]] | 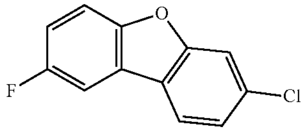 [SMILES: Fc1ccc2oc3cc(Cl)ccc3c2c1] |
| 738 | 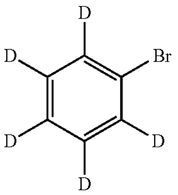 [SMILES: [2H]c1c([2H])c([2H])c(Br)c([2H])c1[2H]] | 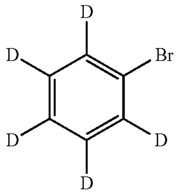 | 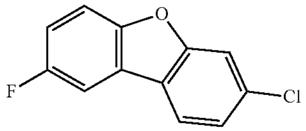 [SMILES: Fc1ccc2oc3cc(Cl)ccc3c2c1] |
| 741 | 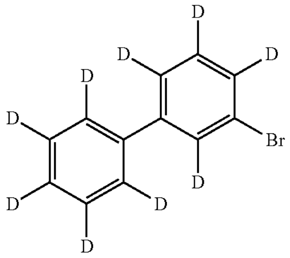 [SMILES: [2H]c1c([2H])c([2H])c(-c2c([2H])c([2H])c([2H])c(Br)c2[2H])c([2H])c1[2H]] | 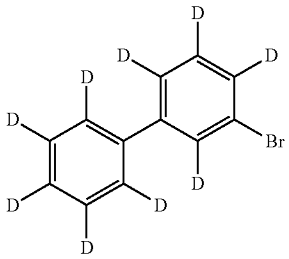 [SMILES: [2H]c1c([2H])c([2H])c(-c2c([2H])c([2H])c([2H])c(Br)c2[2H])c([2H])c1[2H]] | 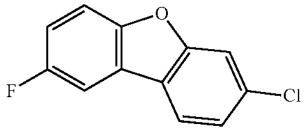 [SMILES: Fc1ccc2oc3cc(Cl)ccc3c2c1] |
| 743 | 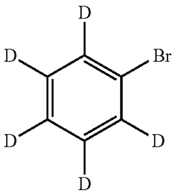 [SMILES: [2H]c1c([2H])c([2H])c(Br)c([2H])c1[2H]] | 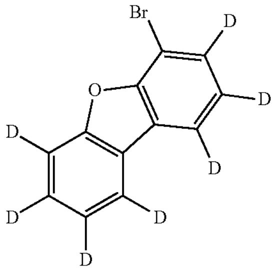 [SMILES: [2H]c1c([2H])c([2H])c2c(oc3c(Br)c([2H])c([2H])c([2H])c32)c1[2H]] | 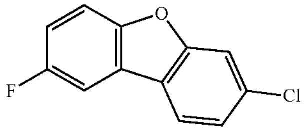 [SMILES: Fc1ccc2oc3cc(Cl)ccc3c2c1] |
| 746 | 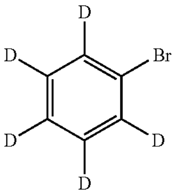 [SMILES: [2H]c1c([2H])c([2H])c(Br)c([2H])c1[2H]] | 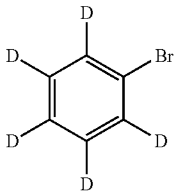 | 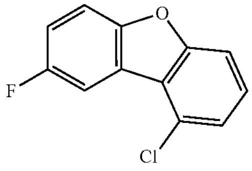 [SMILES: Fc1ccc2oc3cccc(Cl)c3c2c1] |

TABLE 4-continued
| | | | |
|---|---|---|---|
| 747 | 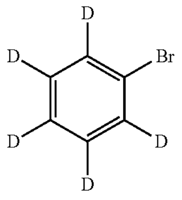 [SMILES: [2H]c1c([2H])c([2H])c(Br)c([2H])c1[2H]] | 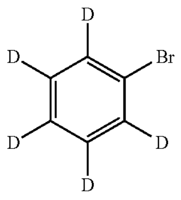 | 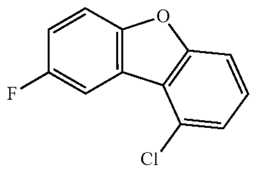 [SMILES: Fc1ccc2oc3cccc(Cl)c3c2c1] |
| 748 | 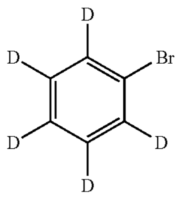 [SMILES: [2H]c1c([2H])c([2H])c(Br)c([2H])c1[2H]] | 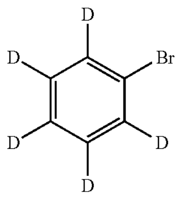 | 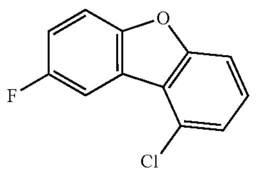 [SMILES: Fc1ccc2oc3cccc(Cl)c3c2c1] |
| 765 | 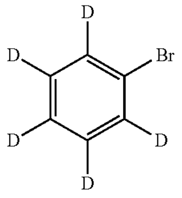 [SMILES: [2H]c1c([2H])c([2H])c(Br)c([2H])c1[2H]] | 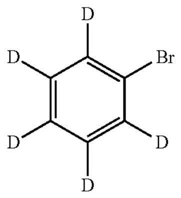 | 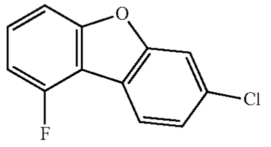 [SMILES: Fc1cccc2oc3cc(Cl)ccc3c12] |
| 766 | 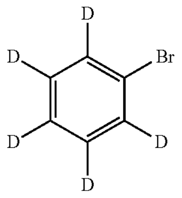 [SMILES: [2H]c1c([2H])c([2H])c(Br)c([2H])c1[2H]] | 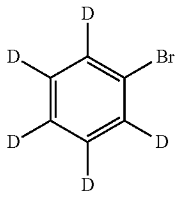 | 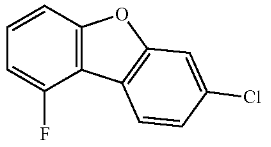 [SMILES: Fc1cccc2oc3cc(Cl)ccc3c12] |
| 767 | 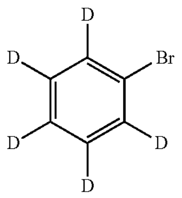 [SMILES: [2H]c1c([2H])c([2H])c(Br)c([2H])c1[2H]] | 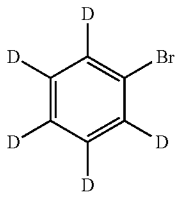 | 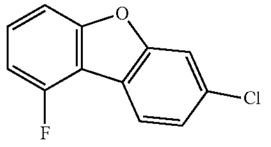 [SMILES: Fc1cccc2oc3cc(Cl)ccc3c12] |
| 772 | 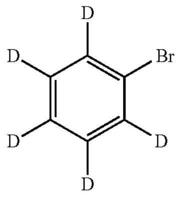 [SMILES: [2H]c1c([2H])c([2H])c(Br)c([2H])c1[2H]] | 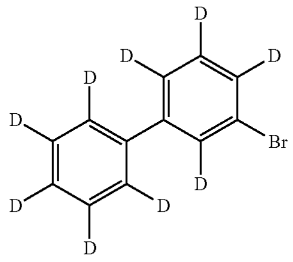 [SMILES: [2H]c1c([2H])c([2H])c(-c2c([2H])c([2H])c([2H])c(Br)c2[2H])c([2H])c1[2H]] | 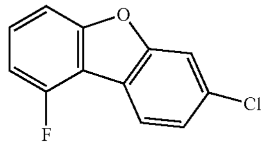 [SMILES: Fc1cccc2oc3cc(Cl)ccc3c12] |
| 773 | 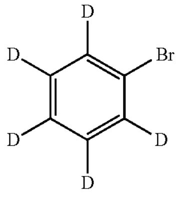 [SMILES: [2H]c1c([2H])c([2H])c(Br)c([2H])c1[2H]] | 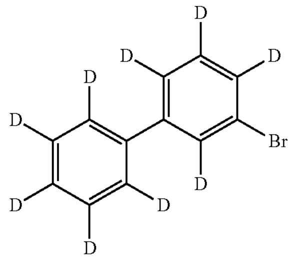 [SMILES: [2H]c1c([2H])c([2H])c(-c2c([2H])c([2H])c([2H])c(Br)c2[2H])c([2H])c1[2H]] | 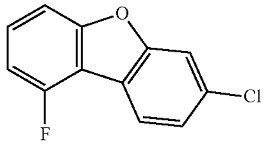 [SMILES: Fc1cccc2oc3cc(Cl)ccc3c12] |

TABLE 4-continued
| | | | |
|---|---|---|---|
| 774 | 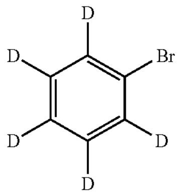 [SMILES: [2H]c1c([2H])c([2H])c(Br)c([2H])c1[2H]] | 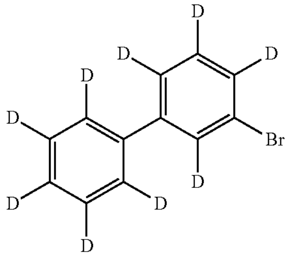 [SMILES: [2H]c1c([2H])c([2H])c(-c2c([2H])c([2H])c([2H])c(Br)c2[2H])c([2H])c1[2H]] | 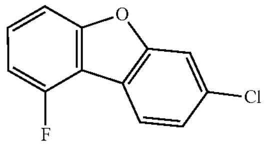 [SMILES: Fc1cccc2oc3cc(Cl)ccc3c12] |
| 775 | 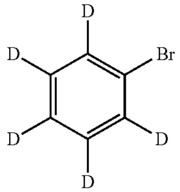 [SMILES: [2H]c1c([2H])c([2H])c(Br)c([2H])c1[2H]] | 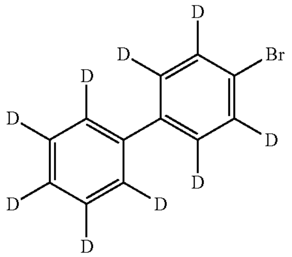 [SMILES: [2H]c1c([2H])c([2H])c(-c2c([2H])c([2H])c(Br)c([2H])c2[2H])c([2H])c1[2H]] | 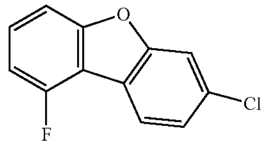 [SMILES: Fc1cccc2oc3cc(Cl)ccc3c12] |
| 779 | 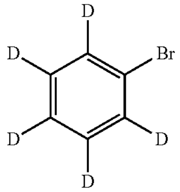 [SMILES: [2H]c1c([2H])c([2H])c(Br)c([2H])c1[2H]] | 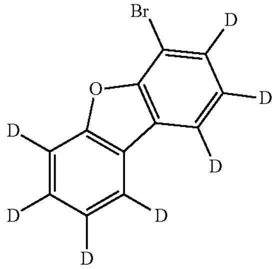 [SMILES: [2H]c1c([2H])c([2H])c2c(oc3c(Br)c([2H])c([2H])c([2H])c32)c1[2H]] | 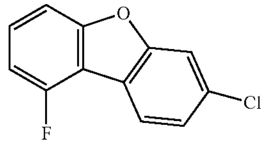 [SMILES: Fc1cccc2oc3cc(Cl)ccc3c12] |
| Compound | C | H | yield |
|---|---|---|---|
| 641 | 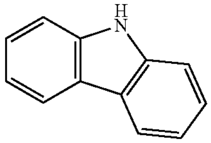 | 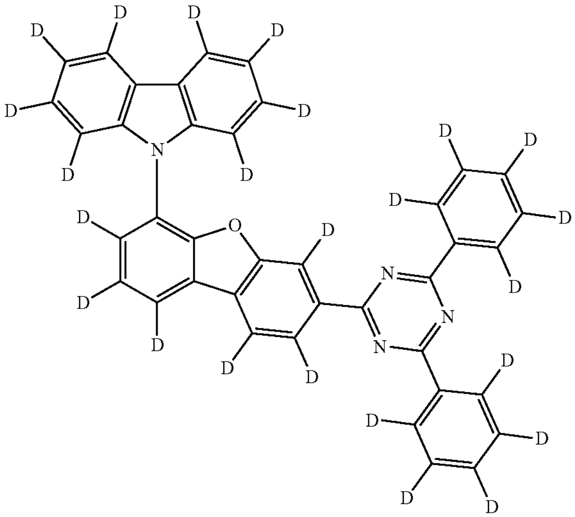 | 83% |

TABLE 4-continued
| | | | |
|---|---|---|---|
| 643 | 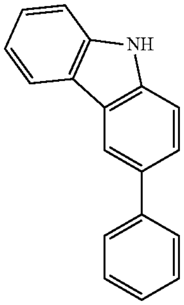 | 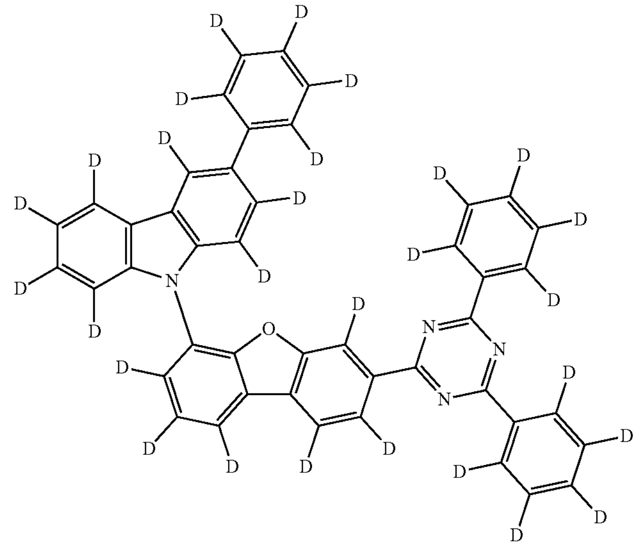 | 78% |
| 645 | 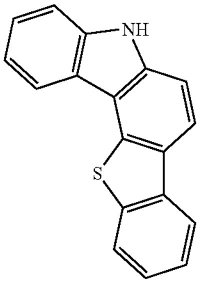 | 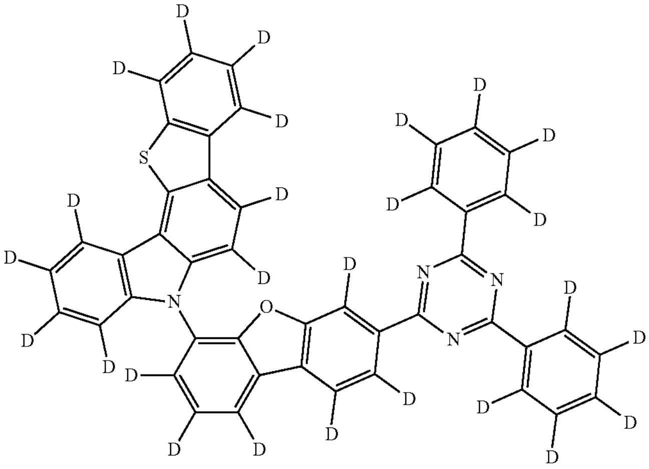 | 72% |
| 648 | 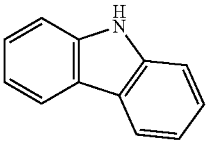 | 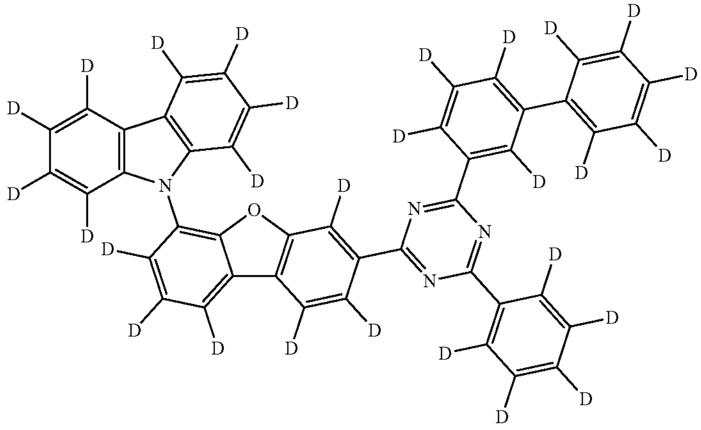 | 63% |

TABLE 4-continued
| | | | |
|---|---|---|---|
| 652 | 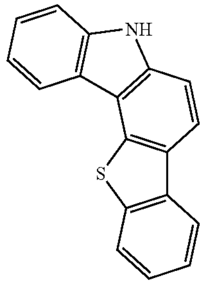 | 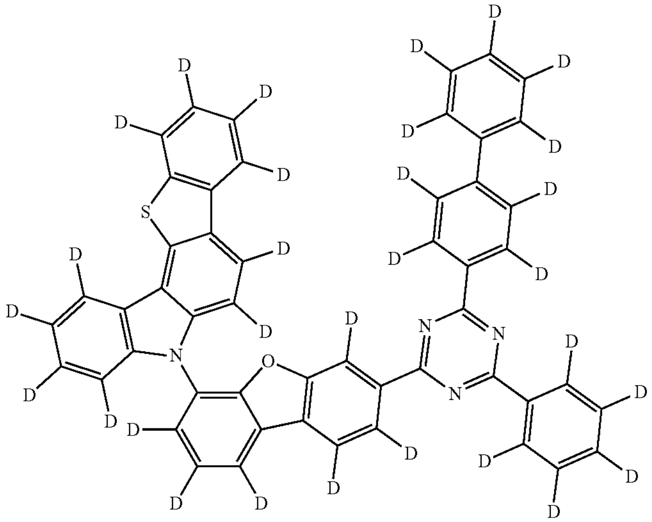 | 68% |
| 662 | 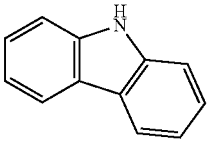 | 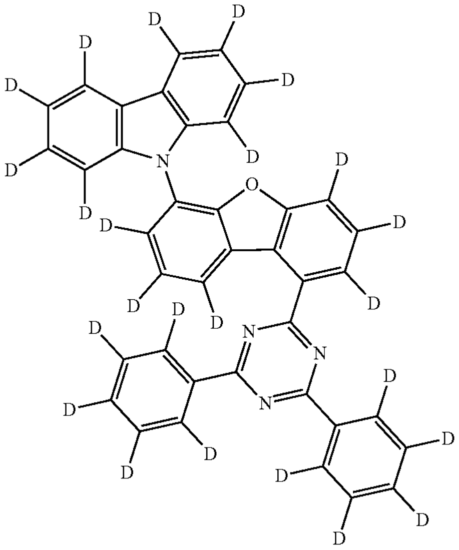 | 79% |
| 664 | 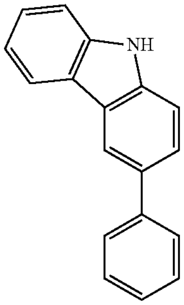 | 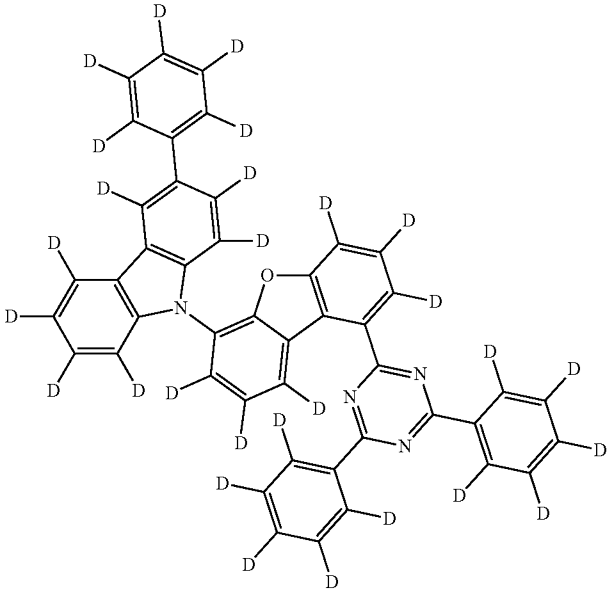 | 83% |

TABLE 4-continued
| | | | |
|---|---|---|---|
| 667 | 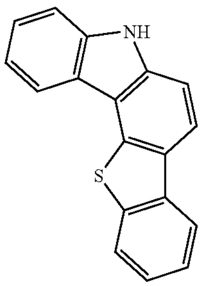 | 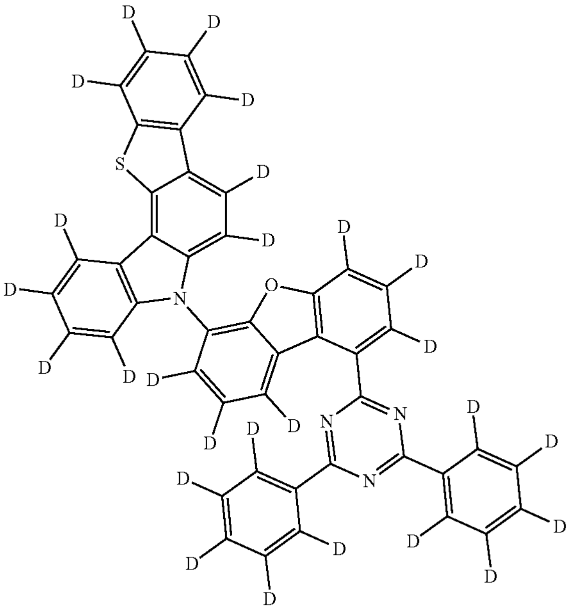 | 79% |
| 669 | 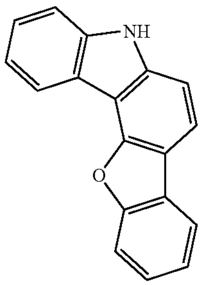 | 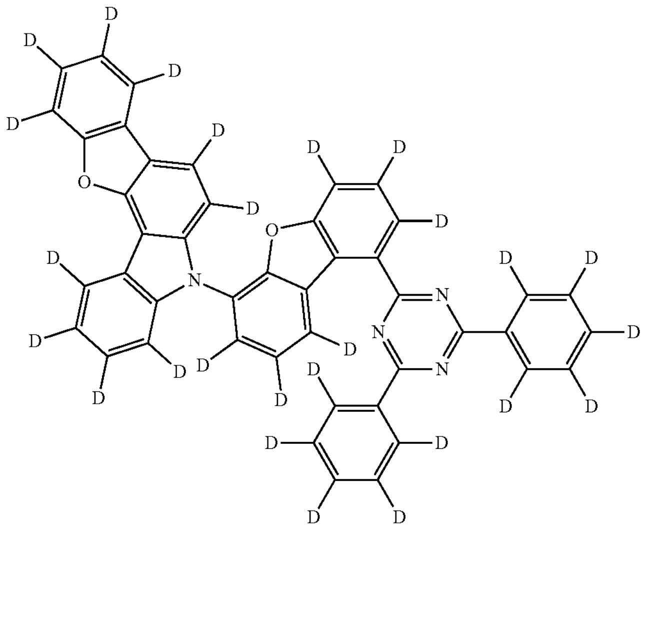 | 74% |

TABLE 4-continued
| | | | |
|---|---|---|---|
| 672 | 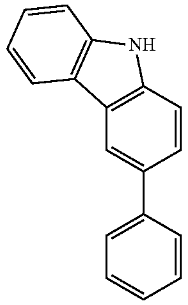 | 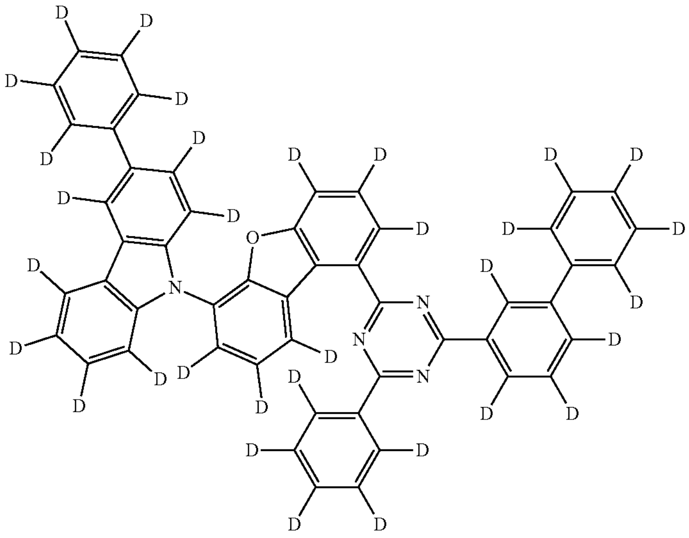 | 82% |
| 676 | 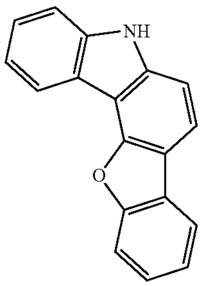 | 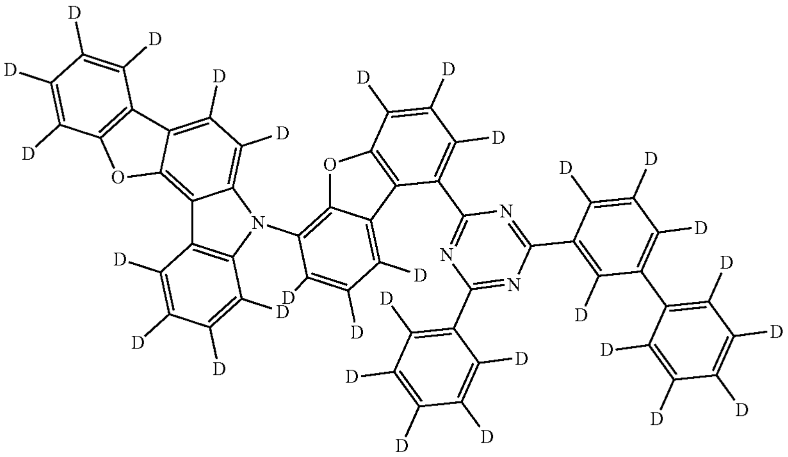 | 72% |
| 677 | 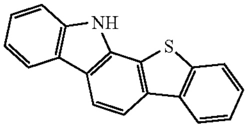 | 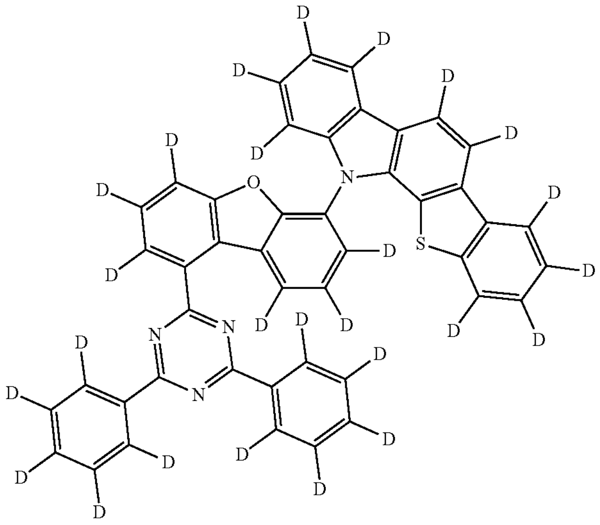 | 74% |

TABLE 4-continued
| | | | |
|---|---|---|---|
| 680 | 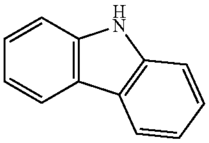 [SMILES: c1ccc2c(c1)[nH]c1ccccc12] | 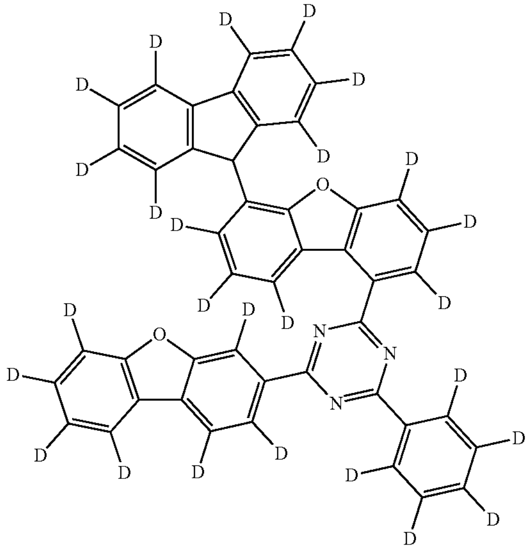 [SMILES: [2H]c1c([2H])c([2H])c(-c2nc(-c3c([2H])c([2H])c4c(oc5c([2H])c([2H])c([2H])c([2H])c54)c3[2H])nc(-c3c([2H])c([2H])c([2H])c4oc5c(C6c7c([2H])c([2H])c([2H])c([2H])c7-c7c([2H])c([2H])c([2H])c([2H])c76)c([2H])c([2H])c([2H])c5c34)n2)c([2H])c1[2H]] | 83% |
| 684 | 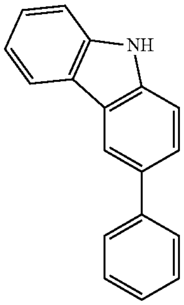 [SMILES: c1ccc(-c2ccc3[nH]c4ccccc4c3c2)cc1] | 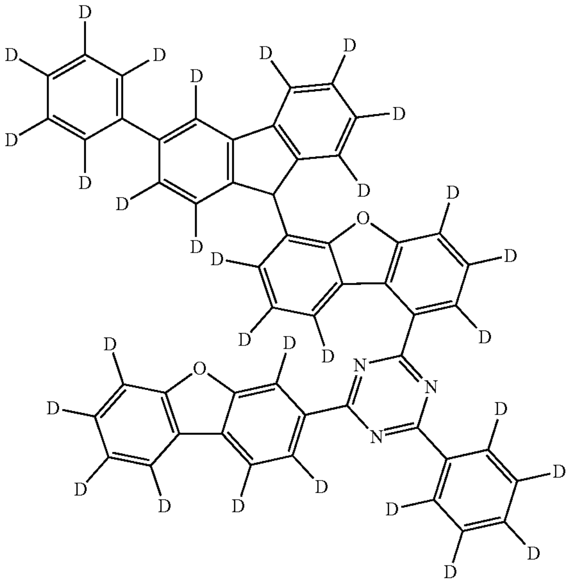 [SMILES: [2H]c1c([2H])c([2H])c(-c2nc(-c3c([2H])c([2H])c4c(oc5c([2H])c([2H])c([2H])c([2H])c54)c3[2H])nc(-c3c([2H])c([2H])c([2H])c4oc5c(C6c7c([2H])c([2H])c([2H])c([2H])c7-c7c([2H])c(-c8c([2H])c([2H])c([2H])c([2H])c8[2H])c([2H])c([2H])c76)c([2H])c([2H])c([2H])c5c34)n2)c([2H])c1[2H]] | 53% |
| 685 | 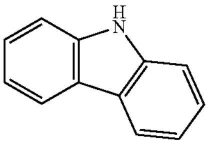 [SMILES: c1ccc2c(c1)[nH]c1ccccc12] | 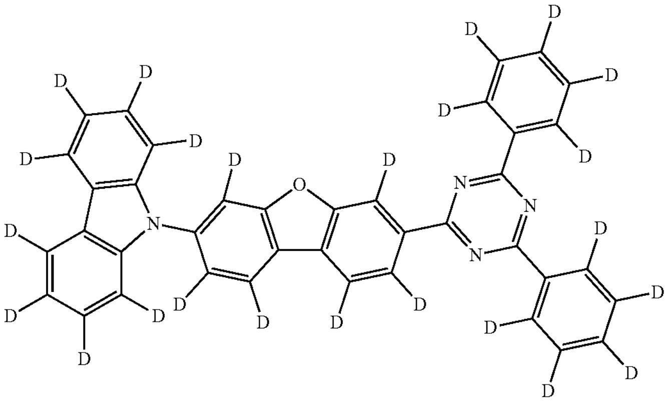 [SMILES: [2H]c1c([2H])c([2H])c(-c2nc(-c3c([2H])c([2H])c([2H])c([2H])c3[2H])nc(-c3c([2H])c([2H])c4c(oc5c([2H])c(-n6c7c([2H])c([2H])c([2H])c([2H])c7c7c([2H])c([2H])c([2H])c([2H])c76)c([2H])c([2H])c54)c3[2H])n2)c([2H])c1[2H]] | 88% |

TABLE 4-continued
| | | | |
|---|---|---|---|
| 686 | 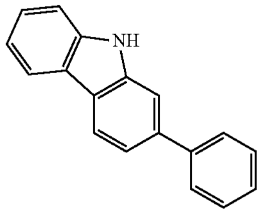 [SMILES: c1ccc(-c2ccc3c(c2)[nH]c2ccccc23)cc1] | 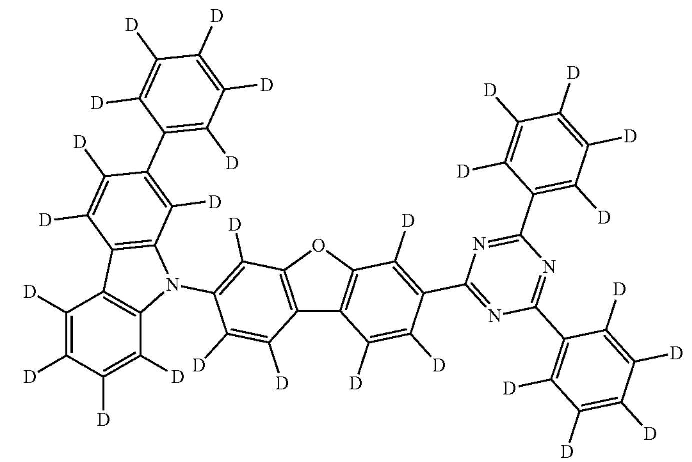 [SMILES: [2H]c1c([2H])c([2H])c(-c2nc(-c3c([2H])c([2H])c([2H])c([2H])c3[2H])nc(-c3c([2H])c([2H])c4c(oc5c([2H])c(-n6c7c([2H])c([2H])c([2H])c([2H])c7c7c([2H])c([2H])c(-c8c([2H])c([2H])c([2H])c([2H])c8[2H])c([2H])c76)c([2H])c([2H])c54)c3[2H])n2)c([2H])c1[2H]] | 92% |
| 689 | 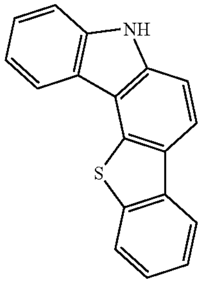 [SMILES: c1ccc2c(c1)[nH]c1ccc3c4ccccc4sc3c12] | 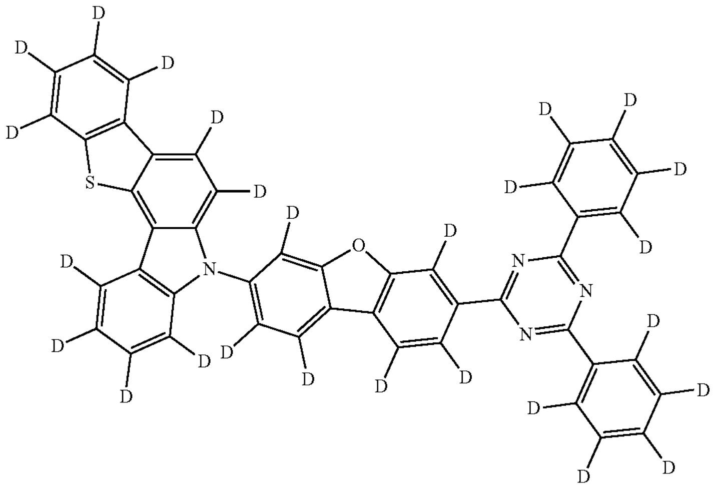 [SMILES: [2H]c1c([2H])c([2H])c(-c2nc(-c3c([2H])c([2H])c([2H])c([2H])c3[2H])nc(-c3c([2H])c([2H])c4c(oc5c([2H])c(-n6c7c([2H])c([2H])c([2H])c([2H])c7c7c8sc9c([2H])c([2H])c([2H])c([2H])c9c8c([2H])c([2H])c76)c([2H])c([2H])c54)c3[2H])n2)c([2H])c1[2H]] | 90% |
| 690 | 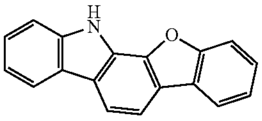 | 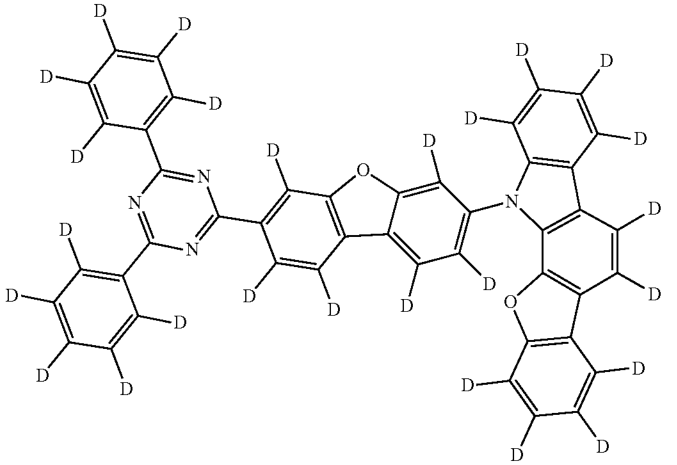 [SMILES: [2H]c1c([2H])c([2H])c(-c2nc(-c3c([2H])c([2H])c([2H])c([2H])c3[2H])nc(-c3c([2H])c([2H])c4c(oc5c([2H])c(-n6c7c([2H])c([2H])c([2H])c([2H])c7c7c([2H])c([2H])c8c(oc9c([2H])c([2H])c([2H])c([2H])c98)c76)c([2H])c([2H])c54)c3[2H])n2)c([2H])c1[2H]] | 74% |

TABLE 4-continued
692 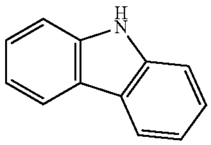 [SMILES: c1ccc2c(c1)[nH]c1ccccc12] 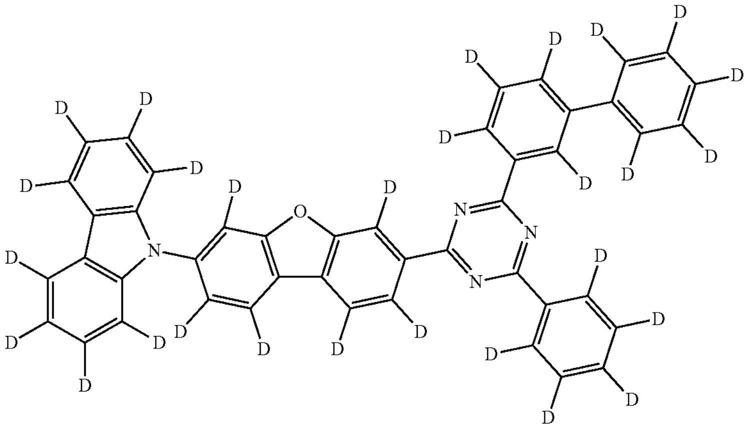 [SMILES: [2H]c1c([2H])c([2H])c(-c2nc(-c3c([2H])c([2H])c([2H])c(-c4c([2H])c([2H])c([2H])c([2H])c4[2H])c3[2H])nc(-c3c([2H])c([2H])c4c(oc5c([2H])c(-n6c7c([2H])c([2H])c([2H])c([2H])c7c7c([2H])c([2H])c([2H])c([2H])c76)c([2H])c([2H])c54)c3[2H])n2)c([2H])c1[2H]] 77%
693 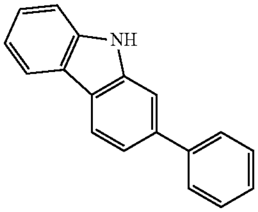 [SMILES: c1ccc(-c2ccc3c(c2)[nH]c2ccccc23)cc1] 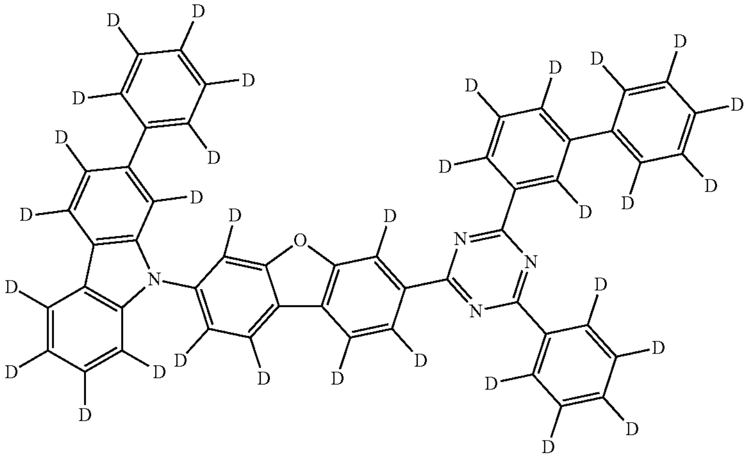 [SMILES: [2H]c1c([2H])c([2H])c(-c2nc(-c3c([2H])c([2H])c([2H])c(-c4c([2H])c([2H])c([2H])c([2H])c4[2H])c3[2H])nc(-c3c([2H])c([2H])c4c(oc5c([2H])c(-n6c7c([2H])c([2H])c([2H])c([2H])c7c7c([2H])c([2H])c(-c8c([2H])c([2H])c([2H])c([2H])c8[2H])c([2H])c76)c([2H])c([2H])c54)c3[2H])n2)c([2H])c1[2H]] 98%
695 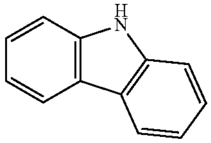 [SMILES: c1ccc2c(c1)[nH]c1ccccc12] 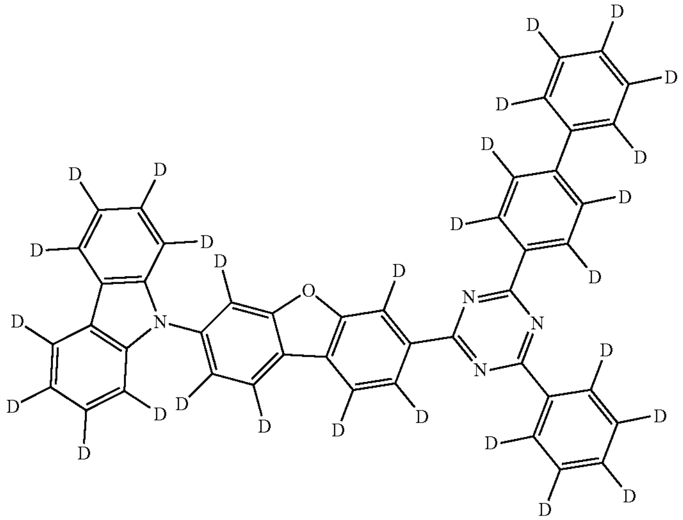 [SMILES: [2H]c1c([2H])c([2H])c(-c2nc(-c3c([2H])c([2H])c(-c4c([2H])c([2H])c([2H])c([2H])c4[2H])c([2H])c3[2H])nc(-c3c([2H])c([2H])c4c(oc5c([2H])c(-n6c7c([2H])c([2H])c([2H])c([2H])c7c7c([2H])c([2H])c([2H])c([2H])c76)c([2H])c([2H])c54)c3[2H])n2)c([2H])c1[2H]] 95%

TABLE 4-continued
| | | | |
|---|---|---|---|
| 696 | 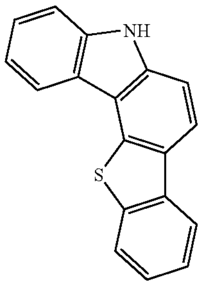 [SMILES: c1ccc2c(c1)[nH]c1ccc3c4ccccc4sc3c12] | 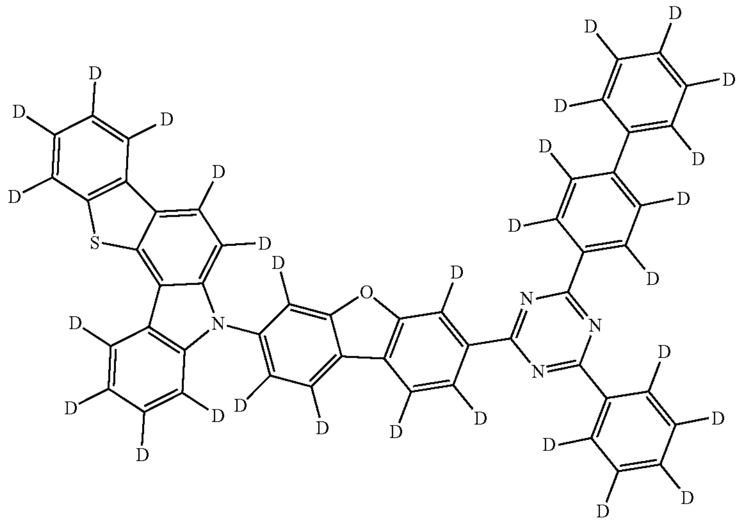 [SMILES: [2H]c1c([2H])c([2H])c(-c2nc(-c3c([2H])c([2H])c(-c4c([2H])c([2H])c([2H])c([2H])c4[2H])c([2H])c3[2H])nc(-c3c([2H])c([2H])c4c(oc5c([2H])c(-n6c7c([2H])c([2H])c([2H])c([2H])c7c7c8sc9c([2H])c([2H])c([2H])c([2H])c9c8c([2H])c([2H])c76)c([2H])c([2H])c54)c3[2H])n2)c([2H])c1[2H]] | 68% |
| 698 | 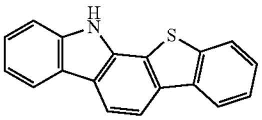 [SMILES: c1ccc2c(c1)[nH]c1c2ccc2c3ccccc3sc21] | 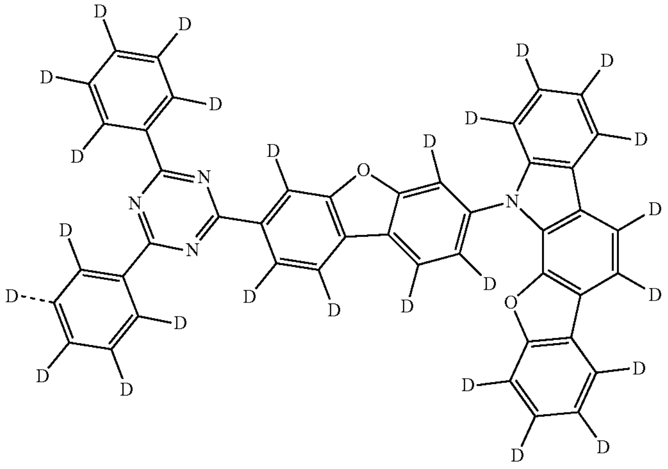 | 51% |
| 708 | 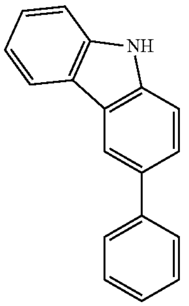 [SMILES: c1ccc(-c2ccc3[nH]c4ccccc4c3c2)cc1] | 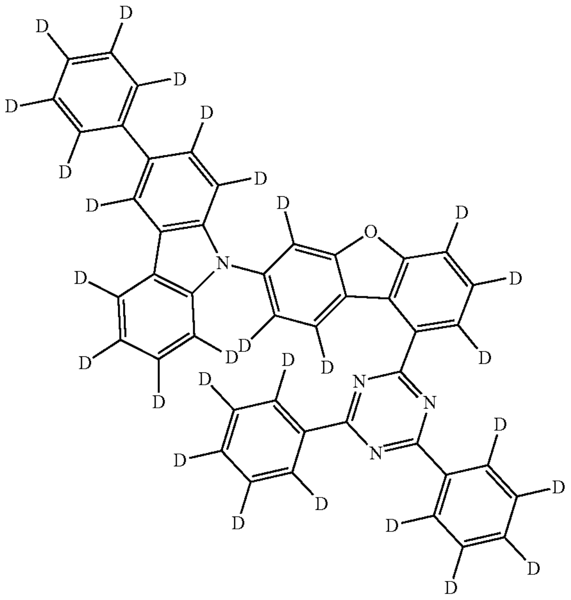 [SMILES: [2H]c1c([2H])c([2H])c(-c2nc(-c3c([2H])c([2H])c([2H])c([2H])c3[2H])nc(-c3c([2H])c([2H])c([2H])c4oc5c([2H])c(-n6c7c([2H])c([2H])c([2H])c([2H])c7c7c([2H])c(-c8c([2H])c([2H])c([2H])c([2H])c8[2H])c([2H])c([2H])c76)c([2H])c([2H])c5c34)n2)c([2H])c1[2H]] | 53% |

TABLE 4-continued
| | | | |
|---|---|---|---|
| 711 | 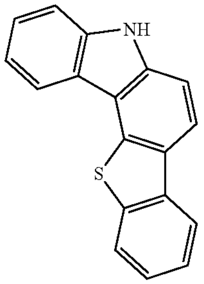 [SMILES: c1ccc2c(c1)[nH]c1ccc3c4ccccc4sc3c12] | 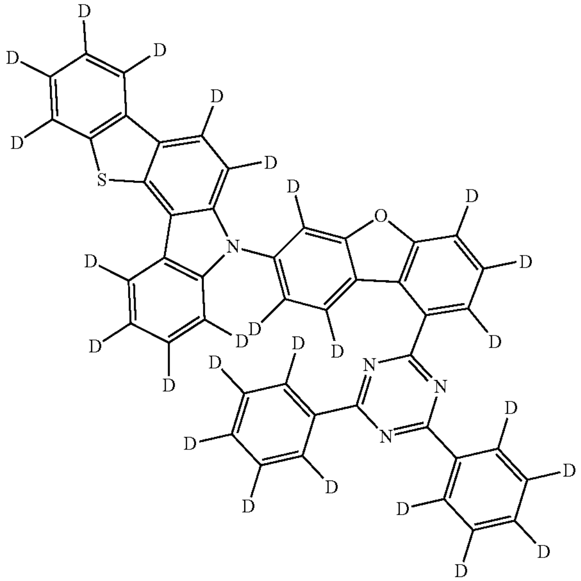 [SMILES: [2H]c1c([2H])c([2H])c(-c2nc(-c3c([2H])c([2H])c([2H])c([2H])c3[2H])nc(-c3c([2H])c([2H])c([2H])c4oc5c([2H])c(-n6c7c([2H])c([2H])c([2H])c([2H])c7c7c8sc9c([2H])c([2H])c([2H])c([2H])c9c8c([2H])c([2H])c76)c([2H])c([2H])c5c34)n2)c([2H])c1[2H]] | 76% |
| 714 | 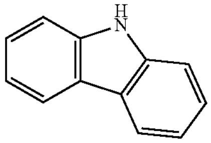 [SMILES: c1ccc2c(c1)[nH]c1ccccc12] | 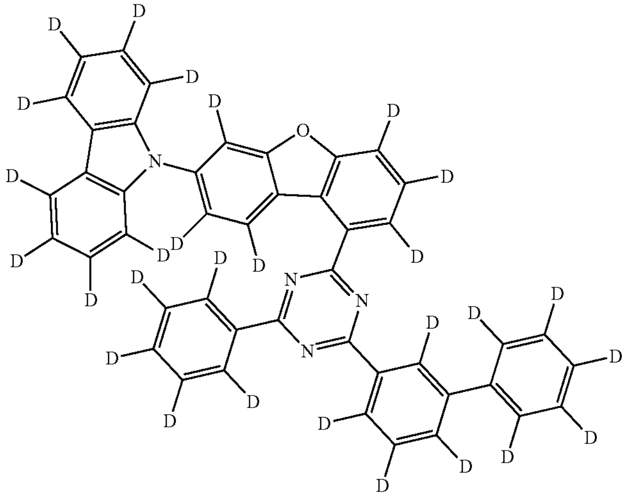 [SMILES: [2H]c1c([2H])c([2H])c(-c2nc(-c3c([2H])c([2H])c([2H])c(-c4c([2H])c([2H])c([2H])c([2H])c4[2H])c3[2H])nc(-c3c([2H])c([2H])c([2H])c4oc5c([2H])c(-n6c7c([2H])c([2H])c([2H])c([2H])c7c7c([2H])c([2H])c([2H])c([2H])c76)c([2H])c([2H])c5c34)n2)c([2H])c1[2H]] | 59% |
| 720 | 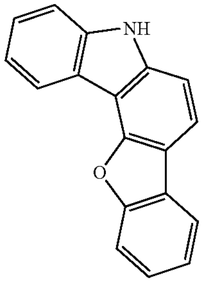 [SMILES: c1ccc2c(c1)[nH]c1ccc3c4ccccc4oc3c12] | 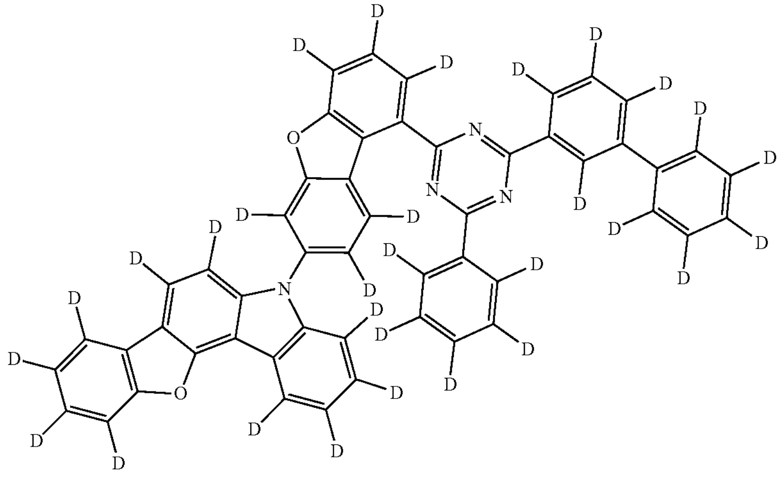 [SMILES: [2H]c1c([2H])c([2H])c(-c2nc(-c3c([2H])c([2H])c([2H])c(-c4c([2H])c([2H])c([2H])c([2H])c4[2H])c3[2H])nc(-c3c([2H])c([2H])c([2H])c4oc5c([2H])c(-n6c7c([2H])c([2H])c([2H])c([2H])c7c7c8oc9c([2H])c([2H])c([2H])c([2H])c9c8c([2H])c([2H])c76)c([2H])c([2H])c5c34)n2)c([2H])c1[2H]] | 66% |

TABLE 4-continued
| | | | |
|---|---|---|---|
| 721 | 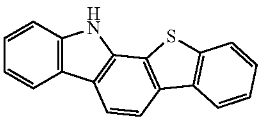 | 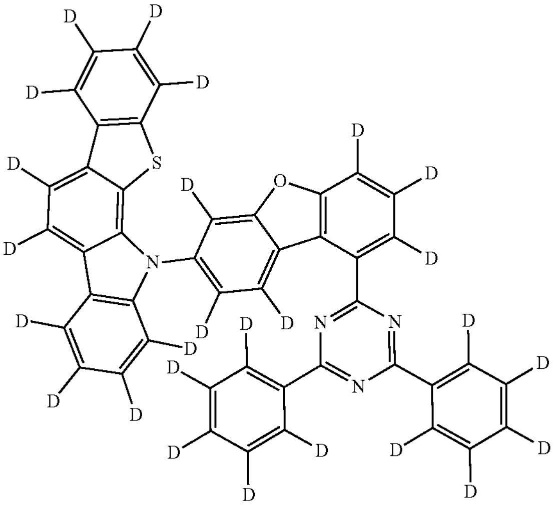 [SMILES: [2H]c1c([2H])c([2H])c(-c2nc(-c3c([2H])c([2H])c([2H])c([2H])c3[2H])nc(-c3c([2H])c([2H])c([2H])c4oc5c([2H])c(-n6c7c([2H])c([2H])c([2H])c([2H])c7c7c([2H])c([2H])c8c(sc9c([2H])c([2H])c([2H])c([2H])c98)c76)c([2H])c([2H])c5c34)n2)c([2H])c1[2H]] | 79% |
| 724 | 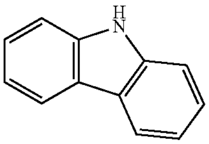 [SMILES: c1ccc2c(c1)[nH]c1ccccc12] | 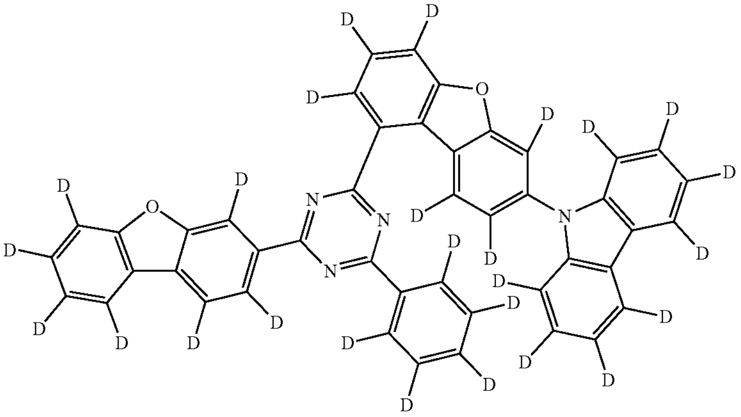 [SMILES: [2H]c1c([2H])c([2H])c(-c2nc(-c3c([2H])c([2H])c4c(oc5c([2H])c([2H])c([2H])c([2H])c54)c3[2H])nc(-c3c([2H])c([2H])c([2H])c4oc5c([2H])c(-n6c7c([2H])c([2H])c([2H])c([2H])c7c7c([2H])c([2H])c([2H])c([2H])c76)c([2H])c([2H])c5c34)n2)c([2H])c1[2H]] | 83% |
| 725 | 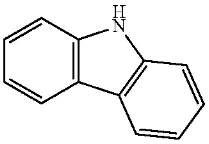 [SMILES: c1ccc2c(c1)[nH]c1ccccc12] | 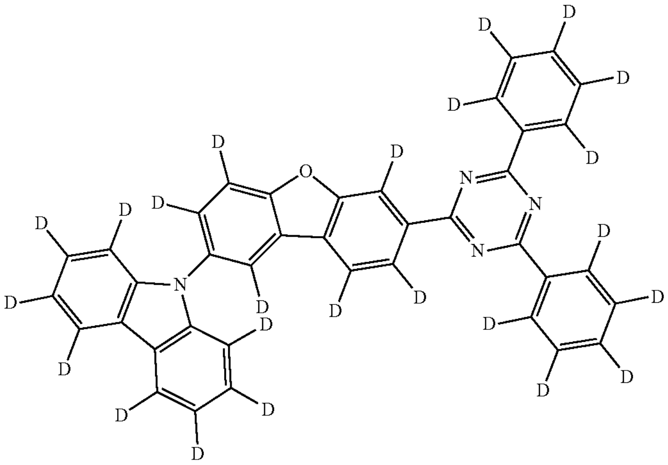 [SMILES: [2H]c1c([2H])c([2H])c(-c2nc(-c3c([2H])c([2H])c([2H])c([2H])c3[2H])nc(-c3c([2H])c([2H])c4c(oc5c([2H])c([2H])c(-n6c7c([2H])c([2H])c([2H])c([2H])c7c7c([2H])c([2H])c([2H])c([2H])c76)c([2H])c54)c3[2H])n2)c([2H])c1[2H]] | 81% |

TABLE 4-continued
726 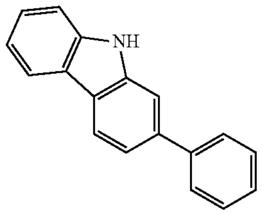 [SMILES: c1ccc(-c2ccc3c(c2)[nH]c2ccccc23)cc1] 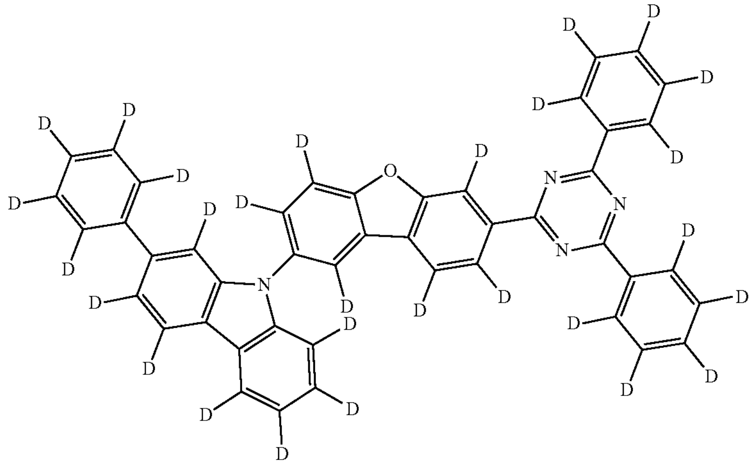 [SMILES: [2H]c1c([2H])c([2H])c(-c2nc(-c3c([2H])c([2H])c([2H])c([2H])c3[2H])nc(-c3c([2H])c([2H])c4c(oc5c([2H])c([2H])c(-n6c7c([2H])c([2H])c([2H])c([2H])c7c7c([2H])c([2H])c(-c8c([2H])c([2H])c([2H])c([2H])c8[2H])c([2H])c76)c([2H])c54)c3[2H])n2)c([2H])c1[2H]] 66%
727 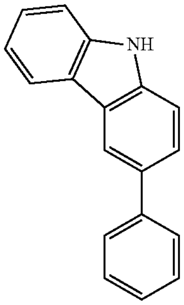 [SMILES: c1ccc(-c2ccc3[nH]c4ccccc4c3c2)cc1] 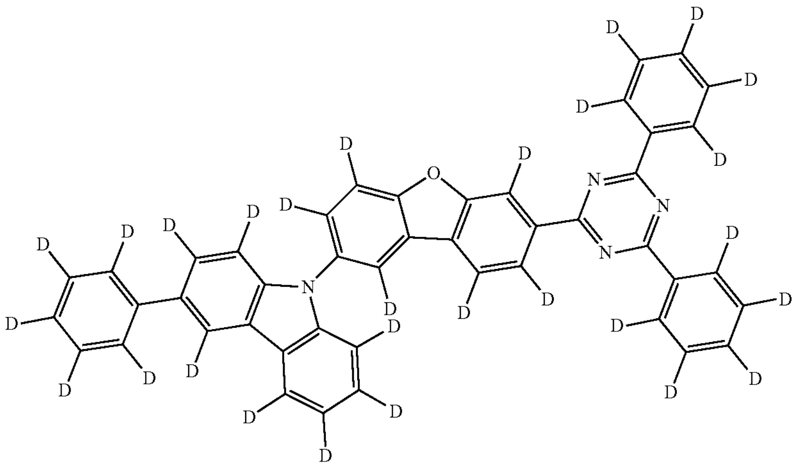 [SMILES: [2H]c1c([2H])c([2H])c(-c2nc(-c3c([2H])c([2H])c([2H])c([2H])c3[2H])nc(-c3c([2H])c([2H])c4c(oc5c([2H])c([2H])c(-n6c7c([2H])c([2H])c([2H])c([2H])c7c7c([2H])c(-c8c([2H])c([2H])c([2H])c([2H])c8[2H])c([2H])c([2H])c76)c([2H])c54)c3[2H])n2)c([2H])c1[2H]] 65%
729 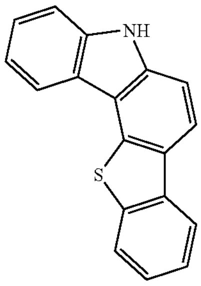 [SMILES: c1ccc2c(c1)[nH]c1ccc3c4ccccc4sc3c12] 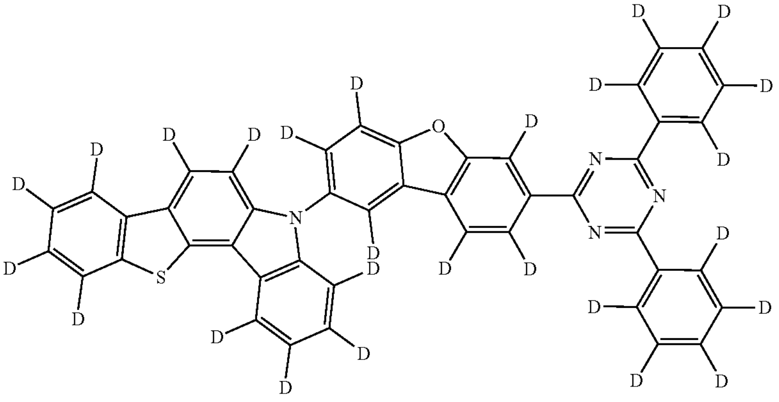 [SMILES: [2H]c1c([2H])c([2H])c(-c2nc(-c3c([2H])c([2H])c([2H])c([2H])c3[2H])nc(-c3c([2H])c([2H])c4c(oc5c([2H])c([2H])c(-n6c7c([2H])c([2H])c([2H])c([2H])c7c7c8sc9c([2H])c([2H])c([2H])c([2H])c9c8c([2H])c([2H])c76)c([2H])c54)c3[2H])n2)c([2H])c1[2H]] 69%

TABLE 4-continued
| | | | |
|---|---|---|---|
| 730 | 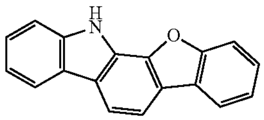 [SMILES: c1ccc2c(c1)[nH]c1c2ccc2c3ccccc3oc21] | 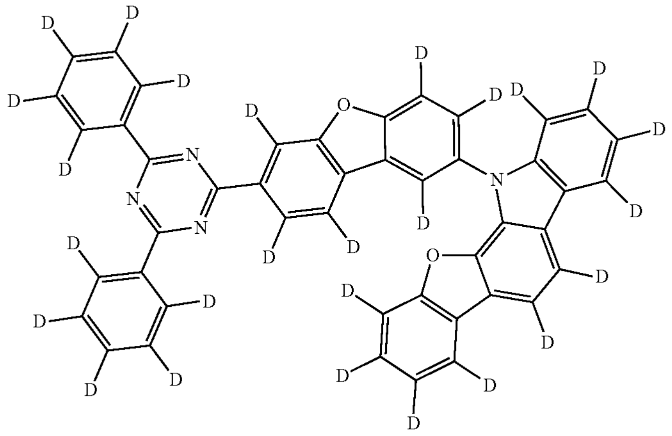 [SMILES: [2H]c1c([2H])c([2H])c(-c2nc(-c3c([2H])c([2H])c([2H])c([2H])c3[2H])nc(-c3c([2H])c([2H])c4c(oc5c([2H])c([2H])c(-n6c7c([2H])c([2H])c([2H])c([2H])c7c7c([2H])c([2H])c8c(oc9c([2H])c([2H])c([2H])c([2H])c98)c76)c([2H])c54)c3[2H])n2)c([2H])c1[2H]] | 72% |
| 732 | 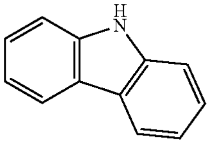 [SMILES: c1ccc2c(c1)[nH]c1ccccc12] | 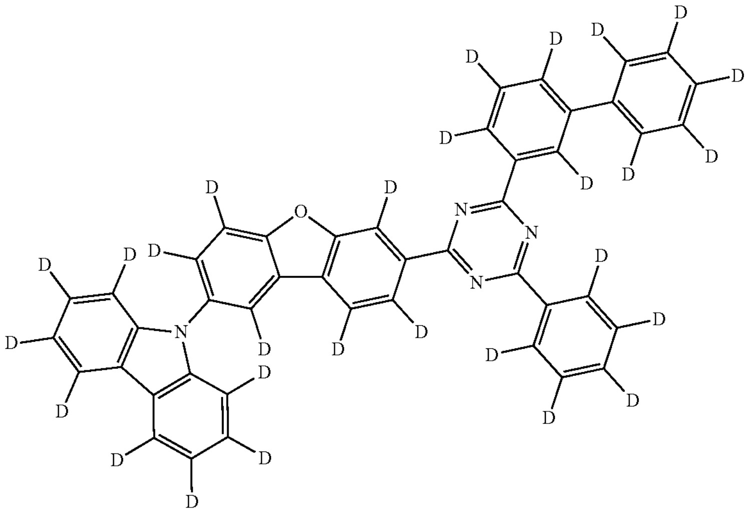 [SMILES: [2H]c1c([2H])c([2H])c(-c2nc(-c3c([2H])c([2H])c([2H])c(-c4c([2H])c([2H])c([2H])c([2H])c4[2H])c3[2H])nc(-c3c([2H])c([2H])c4c(oc5c([2H])c([2H])c(-n6c7c([2H])c([2H])c([2H])c([2H])c7c7c([2H])c([2H])c([2H])c([2H])c76)c([2H])c54)c3[2H])n2)c([2H])c1[2H]] | 74% |
| 734 | 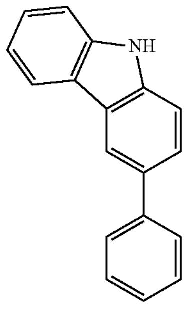 [SMILES: c1ccc(-c2ccc3[nH]c4ccccc4c3c2)cc1] | 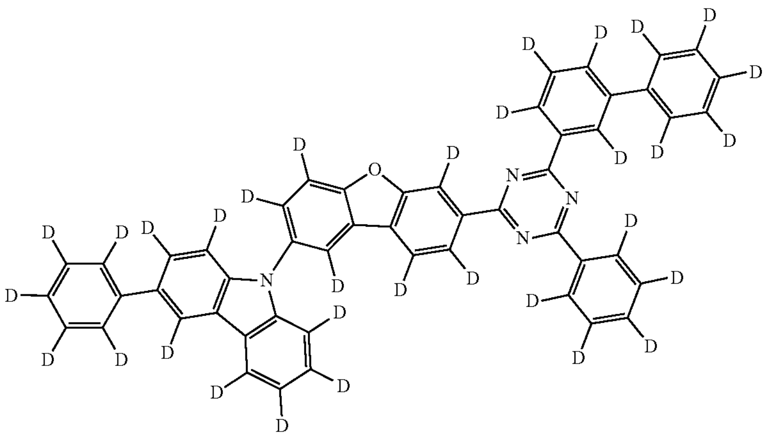 [SMILES: [2H]c1c([2H])c([2H])c(-c2nc(-c3c([2H])c([2H])c([2H])c(-c4c([2H])c([2H])c([2H])c([2H])c4[2H])c3[2H])nc(-c3c([2H])c([2H])c4c(oc5c([2H])c([2H])c(-n6c7c([2H])c([2H])c([2H])c([2H])c7c7c([2H])c(-c8c([2H])c([2H])c([2H])c([2H])c8[2H])c([2H])c([2H])c76)c([2H])c54)c3[2H])n2)c([2H])c1[2H]] | 56% |

TABLE 4-continued
| | | | |
|---|---|---|---|
| 735 | 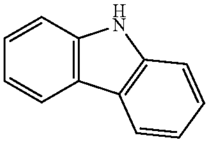 [SMILES: c1ccc2c(c1)[nH]c1ccccc12] | 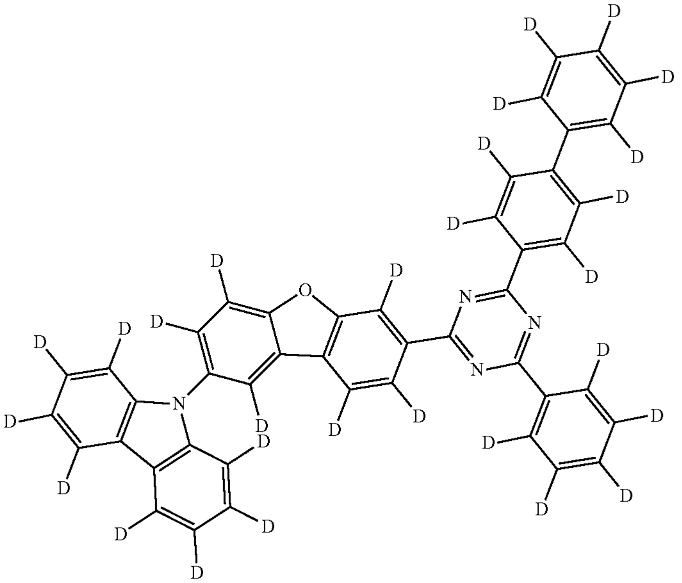 [SMILES: [2H]c1c([2H])c([2H])c(-c2nc(-c3c([2H])c([2H])c(-c4c([2H])c([2H])c([2H])c([2H])c4[2H])c([2H])c3[2H])nc(-c3c([2H])c([2H])c4c(oc5c([2H])c([2H])c(-n6c7c([2H])c([2H])c([2H])c([2H])c7c7c([2H])c([2H])c([2H])c([2H])c76)c([2H])c54)c3[2H])n2)c([2H])c1[2H]] | 72% |
| 738 | 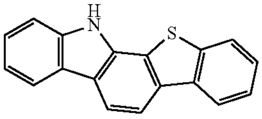 | 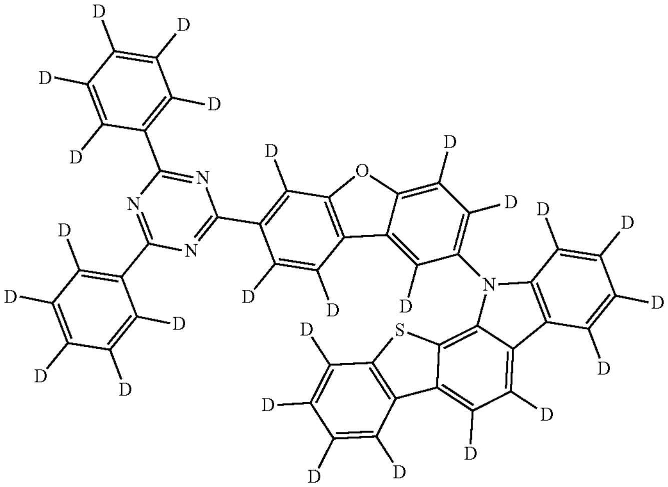 [SMILES: [2H]c1c([2H])c([2H])c(-c2nc(-c3c([2H])c([2H])c([2H])c([2H])c3[2H])nc(-c3c([2H])c([2H])c4c(oc5c([2H])c([2H])c(-n6c7c([2H])c([2H])c([2H])c([2H])c7c7c([2H])c([2H])c8c(sc9c([2H])c([2H])c([2H])c([2H])c98)c76)c([2H])c54)c3[2H])n2)c([2H])c1[2H]] | 77% |
| 741 | 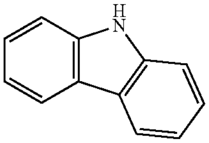 [SMILES: c1ccc2c(c1)[nH]c1ccccc12] | 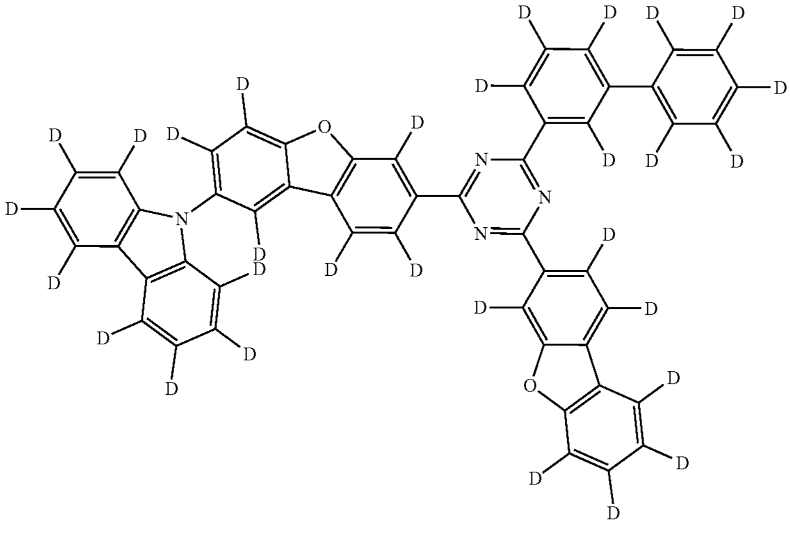 [SMILES: [2H]c1c([2H])c([2H])c(-c2c([2H])c([2H])c([2H])c(-c3nc(-c4c([2H])c([2H])c5c(oc6c([2H])c([2H])c([2H])c([2H])c65)c4[2H])nc(-c4c([2H])c([2H])c5c(oc6c([2H])c([2H])c(-n7c8c([2H])c([2H])c([2H])c([2H])c8c8c([2H])c([2H])c([2H])c([2H])c87)c([2H])c65)c4[2H])n3)c2[2H])c([2H])c1[2H]] | 68% |

TABLE 4-continued
| | | | |
|---|---|---|---|
| 743 | 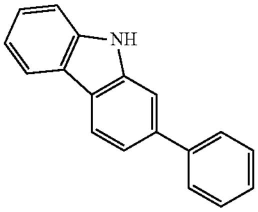 [SMILES: c1ccc(-c2ccc3c(c2)[nH]c2ccccc23)cc1] | 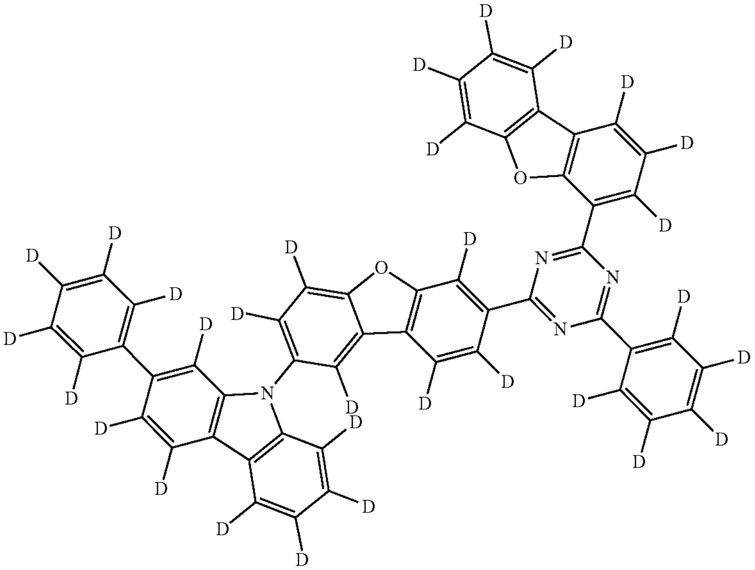 [SMILES: [2H]c1c([2H])c([2H])c(-c2nc(-c3c([2H])c([2H])c4c(oc5c([2H])c([2H])c(-n6c7c([2H])c([2H])c([2H])c([2H])c7c7c([2H])c([2H])c(-c8c([2H])c([2H])c([2H])c([2H])c8[2H])c([2H])c76)c([2H])c54)c3[2H])nc(-c3c([2H])c([2H])c([2H])c4c3oc3c([2H])c([2H])c([2H])c([2H])c34)n2)c([2H])c1[2H]] | 63% |
| 746 | 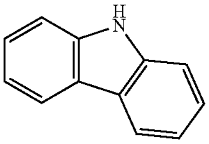 [SMILES: c1ccc2c(c1)[nH]c1ccccc12] | 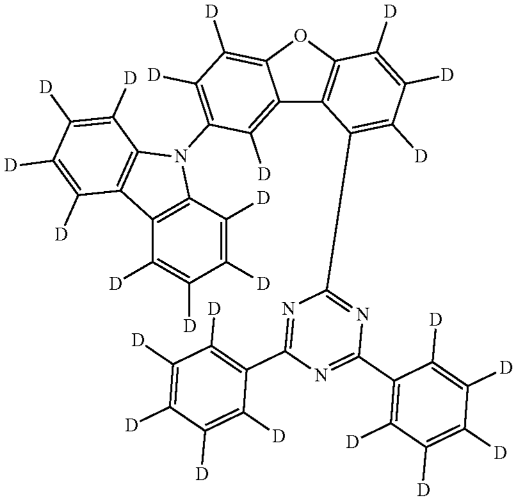 [SMILES: [2H]c1c([2H])c([2H])c(-c2nc(-c3c([2H])c([2H])c([2H])c([2H])c3[2H])nc(-c3c([2H])c([2H])c([2H])c4oc5c([2H])c([2H])c(-n6c7c([2H])c([2H])c([2H])c([2H])c7c7c([2H])c([2H])c([2H])c([2H])c76)c([2H])c5c34)n2)c([2H])c1[2H]] | 79% |
| 747 | 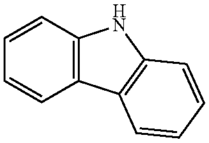 [SMILES: c1ccc2c(c1)[nH]c1ccccc12] | 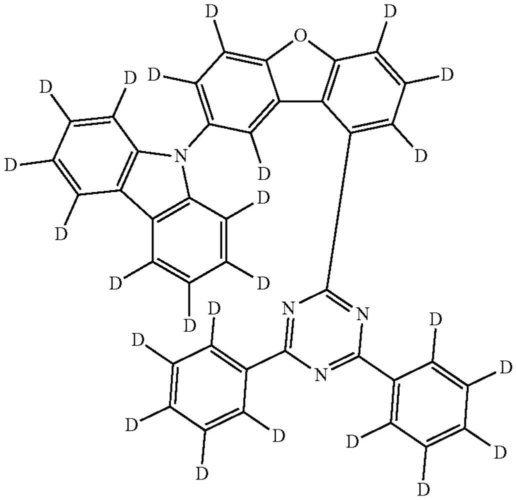 [SMILES: [2H]c1c([2H])c([2H])c(-c2nc(-c3c([2H])c([2H])c([2H])c([2H])c3[2H])nc(-c3c([2H])c([2H])c([2H])c4oc5c([2H])c([2H])c(-n6c7c([2H])c([2H])c([2H])c([2H])c7c7c([2H])c([2H])c([2H])c([2H])c76)c([2H])c5c34)n2)c([2H])c1[2H]] | 81% |

TABLE 4-continued
| | | | |
|---|---|---|---|
| 748 | 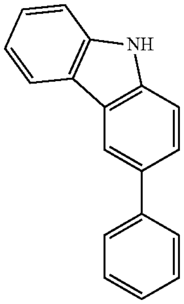 [SMILES: c1ccc(-c2ccc3[nH]c4ccccc4c3c2)cc1] | 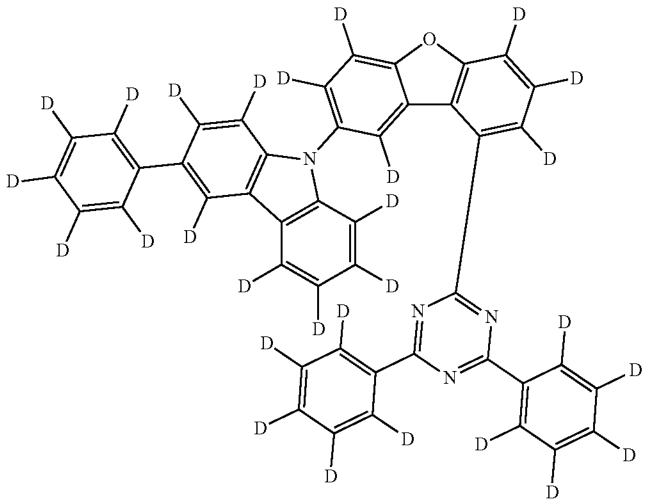 [SMILES: [2H]c1c([2H])c([2H])c(-c2nc(-c3c([2H])c([2H])c([2H])c([2H])c3[2H])nc(-c3c([2H])c([2H])c([2H])c4oc5c([2H])c([2H])c(-n6c7c([2H])c([2H])c([2H])c([2H])c7c7c([2H])c(-c8c([2H])c([2H])c([2H])c([2H])c8[2H])c([2H])c([2H])c76)c([2H])c5c34)n2)c([2H])c1[2H]] | 55% |
| 765 | 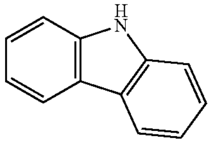 [SMILES: c1ccc2c(c1)[nH]c1ccccc12] | 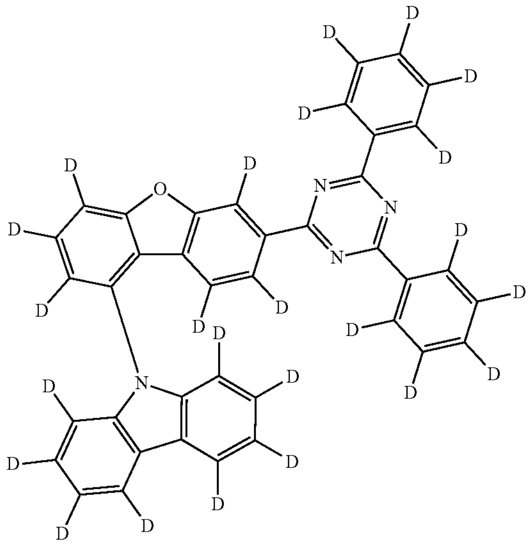 [SMILES: [2H]c1c([2H])c([2H])c(-c2nc(-c3c([2H])c([2H])c([2H])c([2H])c3[2H])nc(-c3c([2H])c([2H])c4c(oc5c([2H])c([2H])c([2H])c(-n6c7c([2H])c([2H])c([2H])c([2H])c7c7c([2H])c([2H])c([2H])c([2H])c76)c54)c3[2H])n2)c([2H])c1[2H]] | 62% |
| 766 | 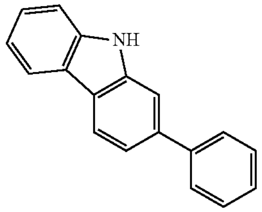 [SMILES: c1ccc(-c2ccc3c(c2)[nH]c2ccccc23)cc1] | 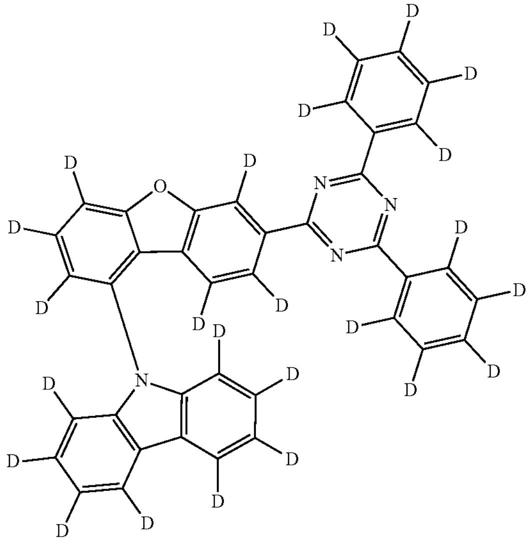 [SMILES: [2H]c1c([2H])c([2H])c(-c2nc(-c3c([2H])c([2H])c([2H])c([2H])c3[2H])nc(-c3c([2H])c([2H])c4c(oc5c([2H])c([2H])c([2H])c(-n6c7c([2H])c([2H])c([2H])c([2H])c7c7c([2H])c([2H])c([2H])c([2H])c76)c54)c3[2H])n2)c([2H])c1[2H]] | 67% |

TABLE 4-continued
| | | | |
|---|---|---|---|
| 767 | 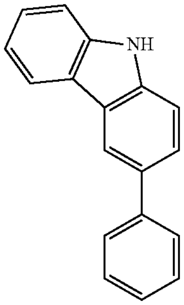 [SMILES: c1ccc(-c2ccc3[nH]c4ccccc4c3c2)cc1] | 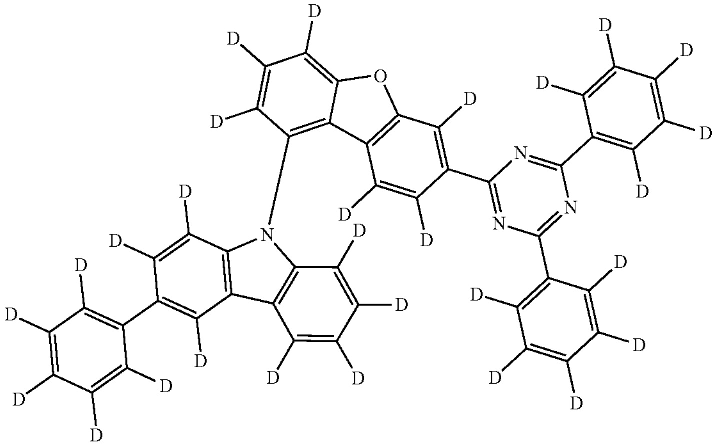 [SMILES: [2H]c1c([2H])c([2H])c(-c2nc(-c3c([2H])c([2H])c([2H])c([2H])c3[2H])nc(-c3c([2H])c([2H])c4c(oc5c([2H])c([2H])c([2H])c(-n6c7c([2H])c([2H])c([2H])c([2H])c7c7c([2H])c(-c8c([2H])c([2H])c([2H])c([2H])c8[2H])c([2H])c([2H])c76)c54)c3[2H])n2)c([2H])c1[2H]] | 69% |
| 772 | 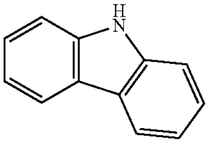 [SMILES: c1ccc2c(c1)[nH]c1ccccc12] | 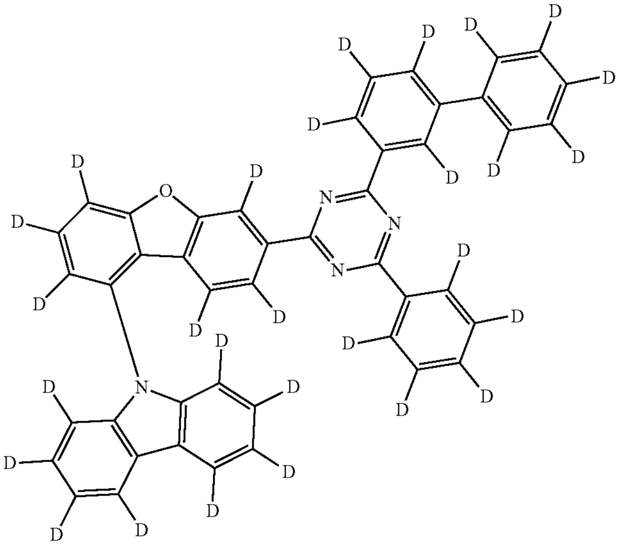 [SMILES: [2H]c1c([2H])c([2H])c(-c2nc(-c3c([2H])c([2H])c([2H])c(-c4c([2H])c([2H])c([2H])c([2H])c4[2H])c3[2H])nc(-c3c([2H])c([2H])c4c(oc5c([2H])c([2H])c([2H])c(-n6c7c([2H])c([2H])c([2H])c([2H])c7c7c([2H])c([2H])c([2H])c([2H])c76)c54)c3[2H])n2)c([2H])c1[2H]] | 68% |
| 773 | 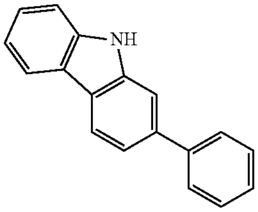 [SMILES: c1ccc(-c2ccc3c(c2)[nH]c2ccccc23)cc1] | 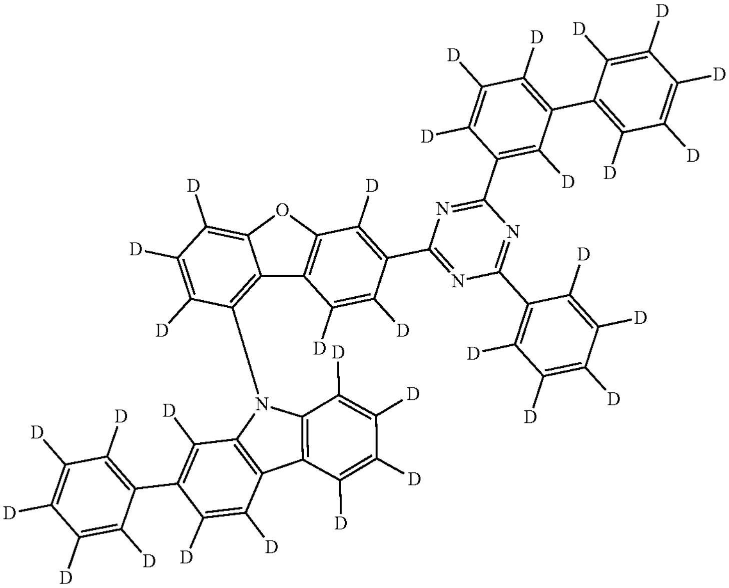 [SMILES: [2H]c1c([2H])c([2H])c(-c2nc(-c3c([2H])c([2H])c([2H])c(-c4c([2H])c([2H])c([2H])c([2H])c4[2H])c3[2H])nc(-c3c([2H])c([2H])c4c(oc5c([2H])c([2H])c([2H])c(-n6c7c([2H])c([2H])c([2H])c([2H])c7c7c([2H])c([2H])c(-c8c([2H])c([2H])c([2H])c([2H])c8[2H])c([2H])c76)c54)c3[2H])n2)c([2H])c1[2H]] | 74% |

TABLE 4-continued
| | | | |
|---|---|---|---|
| 774 | 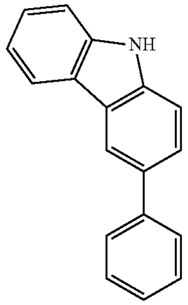 [SMILES: c1ccc(-c2ccc3[nH]c4ccccc4c3c2)cc1] | 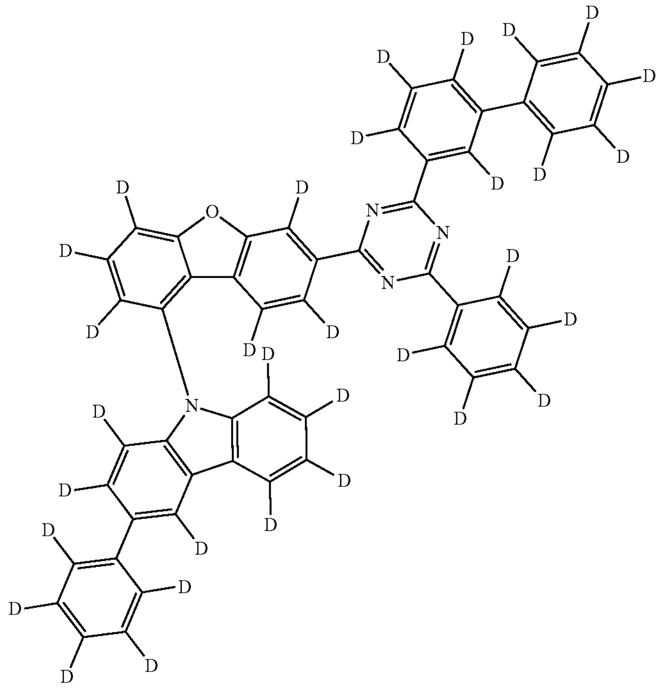 [SMILES: [2H]c1c([2H])c([2H])c(-c2nc(-c3c([2H])c([2H])c([2H])c(-c4c([2H])c([2H])c([2H])c([2H])c4[2H])c3[2H])nc(-c3c([2H])c([2H])c4c(oc5c([2H])c([2H])c([2H])c(-n6c7c([2H])c([2H])c([2H])c([2H])c7c7c([2H])c(-c8c([2H])c([2H])c([2H])c([2H])c8[2H])c([2H])c([2H])c76)c54)c3[2H])n2)c([2H])c1[2H]] | 85% |
| 775 | 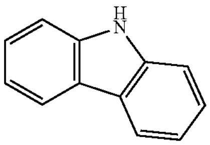 [SMILES: c1ccc2c(c1)[nH]c1ccccc12] | 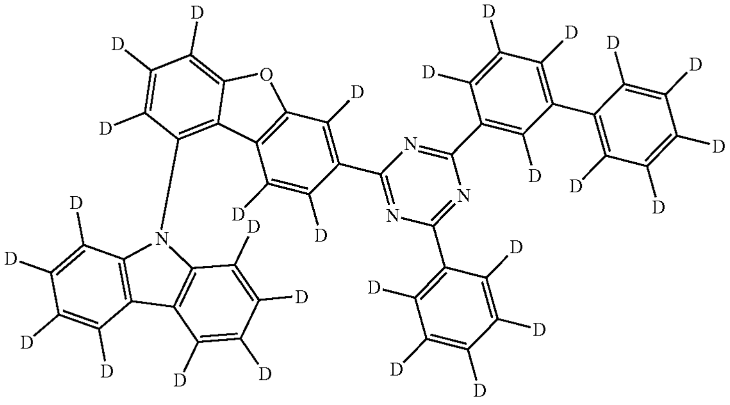 [SMILES: [2H]c1c([2H])c([2H])c(-c2nc(-c3c([2H])c([2H])c([2H])c(-c4c([2H])c([2H])c([2H])c([2H])c4[2H])c3[2H])nc(-c3c([2H])c([2H])c4c(oc5c([2H])c([2H])c([2H])c(-n6c7c([2H])c([2H])c([2H])c([2H])c7c7c([2H])c([2H])c([2H])c([2H])c76)c54)c3[2H])n2)c([2H])c1[2H]] | 93% |
| 779 | 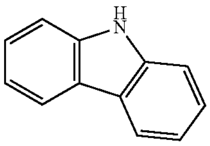 [SMILES: c1ccc2c(c1)[nH]c1ccccc12] | 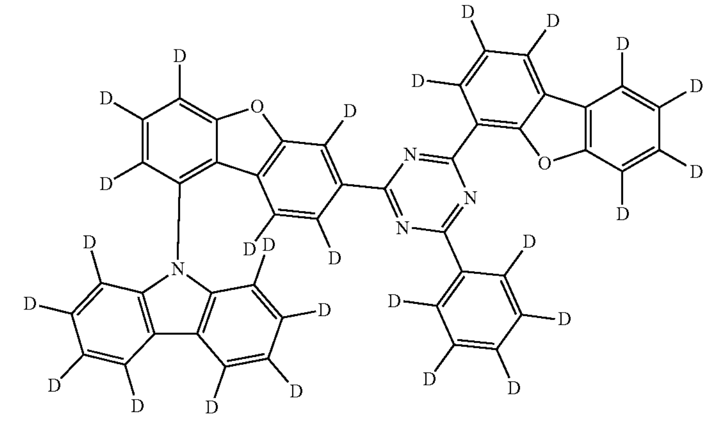 [SMILES: [2H]c1c([2H])c([2H])c(-c2nc(-c3c([2H])c([2H])c4c(oc5c([2H])c([2H])c([2H])c(-n6c7c([2H])c([2H])c([2H])c([2H])c7c7c([2H])c([2H])c([2H])c([2H])c76)c54)c3[2H])nc(-c3c([2H])c([2H])c([2H])c4c3oc3c([2H])c([2H])c([2H])c([2H])c34)n2)c([2H])c1[2H]] | 91% |

[Synthesis 5] The compound 797 (I)

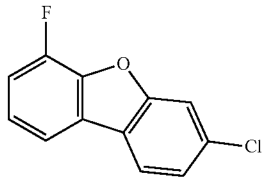

+

[A]

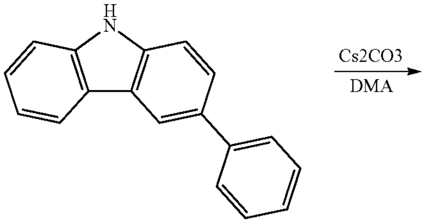

[B]

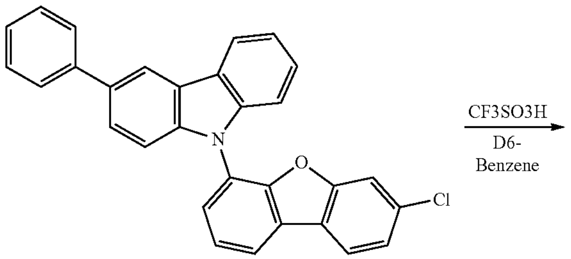

797-1

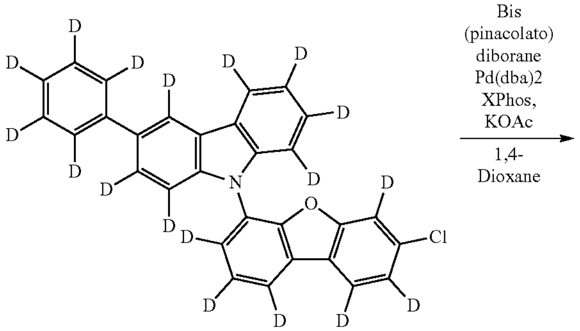

797-2

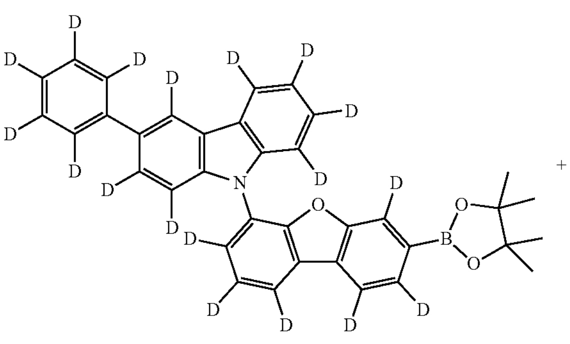

797-3

-continued

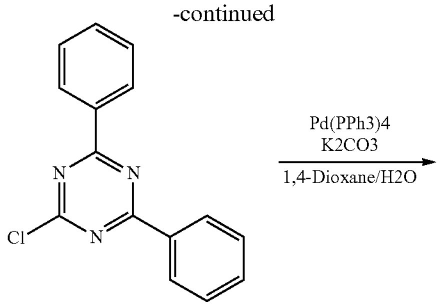

[C]

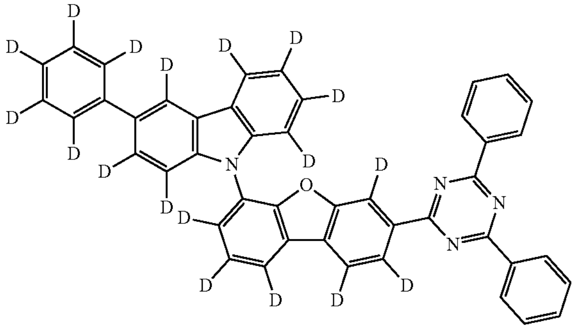

797[I]

(1) The Compound 797-1

In the one-neck round bottom flask, a mixture of 3-chloro-6-fluorodibenzo[b,d]furan (10 g, 0.045 mol), 3-phenyl-9H-carbazole (12.17 g, 0.050 mol)), $Cs_2CO_3$ (29.32 g, 0.09 mol) and dimethylacetamide (100 mL) was refluxed at 170° C. After cooling, the resultant was filtered to remove the solvent and purified by column purification to obtain the compound 797-1. (18.18 g, 91%)

(2) The Compound 797-2

In the one-neck round bottom flask, a mixture of 9-(7-chlorodibenzo[b,d]furan-4-yl)-3-phenyl-9H-carbazole (18.18 g, 0.041 mol), triflic acid (49.23 g, 0.33 mol) and D6-benzene (182 mL) was refluxed at 70° C. After quenching and extraction with dichloromethane and $H_2O$, the resultant was concentrated and filtered through silica gel. After concentration, the resultant was treated with methanol to obtain the compound 797-2. (12.94 g, 68%)

(3) The Compound 797-3

In the one-neck round bottom flask, a mixture of 9-(7-chlorodibenzo[b,d]furan-4-yl-1,2,3,6,8,9-d6)-3-(phenyl-d5)-9H-carbazole-1,2,4,5,6,7,8-d7 (12.94 g, 0.028 mol), bis (pinacolato)diborn (14.22 g, 0.056 mol), $Pd(dba)_2$ (2.56 g, 0.0028) mol), Xphos (2.67 g, 0.0056 mol), potassium acetate (8.24 g, 0.084 mol) and 1,4-dioxane (130 mL) were refluxed at 120° C. After cooling, the resultant was concentrated and filtered through silica gel to obtain the compound 797-3. (13.48 g, 87%)

(4) The Compound 797[I]

In the one-neck round bottom flask, a mixture of 3-(phenyl-d5)-9-(7-(4,4,5,5-tetramethyl-1,3,2-dioxaborolan-2-yl) dibenzo[b,d]furan-4-yl-1,2,3,6,8,9-d6)-9H-carbazole-1,2,4,5,6,7,8-d7 (13.48 g, 0.024 mol), 2-chloro-4,6-diphenyl-1,3,5-triazine (6.96 g, 0.026 mol), Pd(PPh3)4 (1.39 g, 0.0012 mol), K2CO3 (6.63 g, 0.048 mol), 1,4-dioxane (130 mL) and water (40 mL) was refluxed at 120° C. After cooling, the resultant was concentrated and filtered through silica gel to obtain the compound 797[I]. (12.33 g, 78%)

The following compound I was synthesized in the same manner as in the synthesis 5 except that intermediates A, B, and C of Table 5 were used.

TABLE 5
| Compound | A | B | C |
|---|---|---|---|
| 797 | 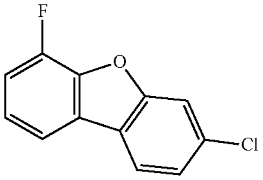 | 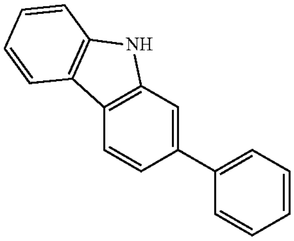 | 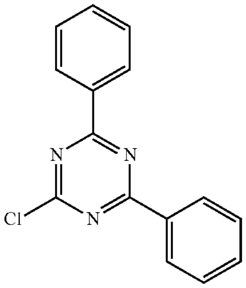 |
| 798 | 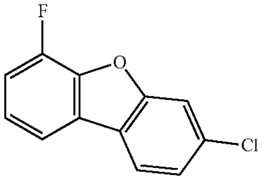 | 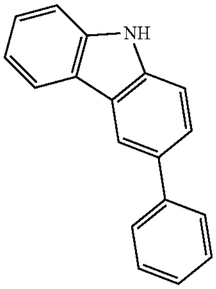 | 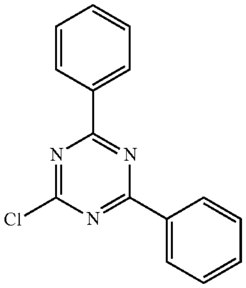 |
| 799 | 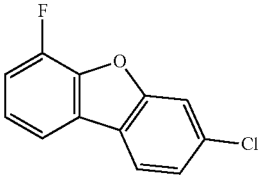 | 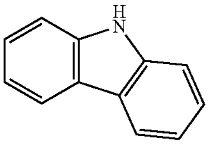 | 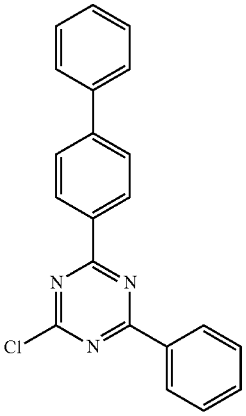 |
| 801 | 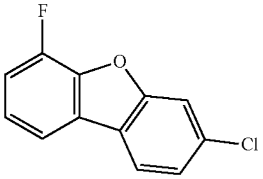 | 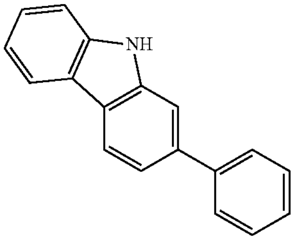 | 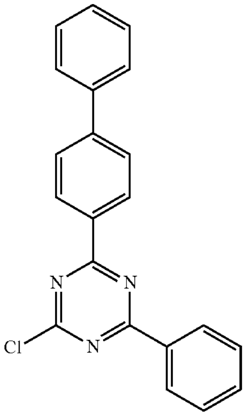 |

TABLE 5-continued
| | | | |
|---|---|---|---|
| 811 | 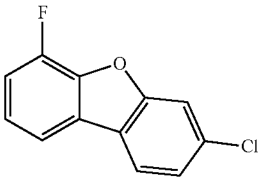 | 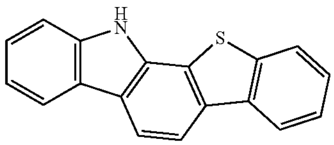 | 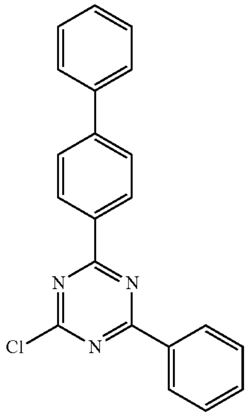 |
| 815 | 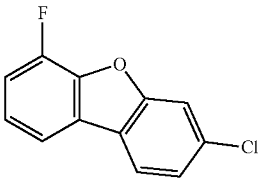 | 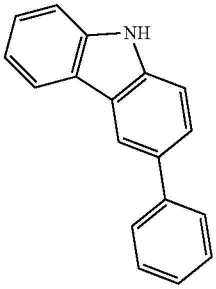 | 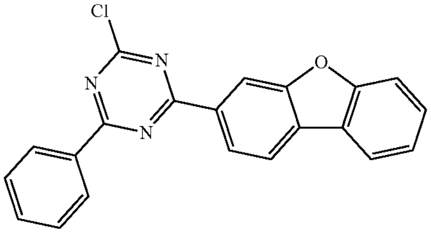 |
| 821 | 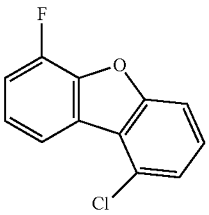 | 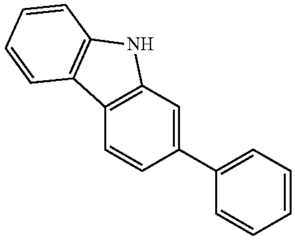 | 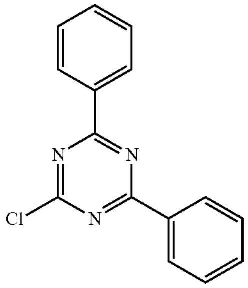 |
| 822 | 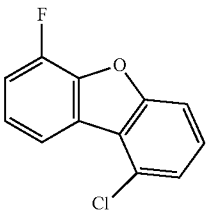 | 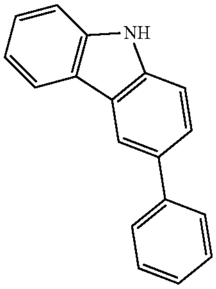 | 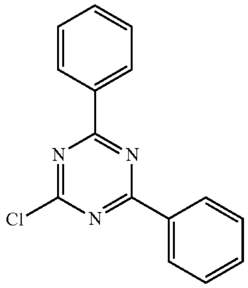 |

TABLE 5-continued
| | | | |
|---|---|---|---|
| 823 | 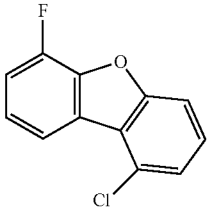 | 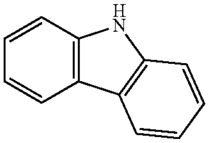 | 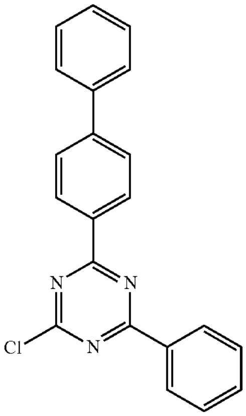 |
| 827 | 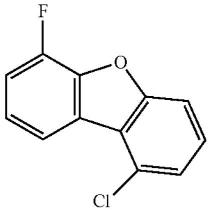 | 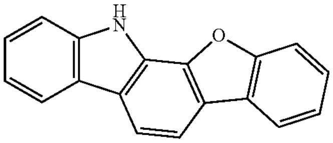 | 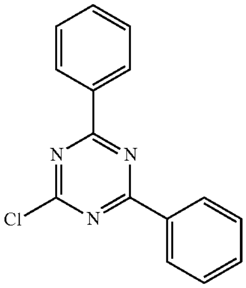 |
| 832 | 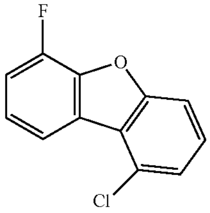 | 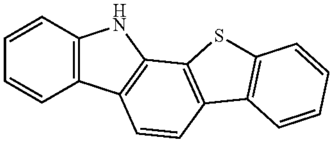 | 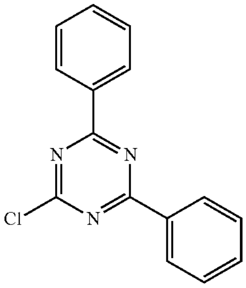 |
| 835 | 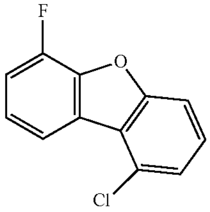 | 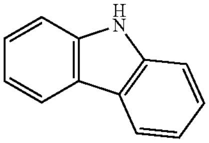 | 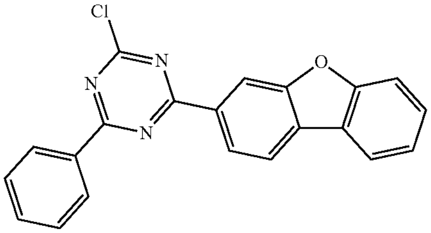 |
| 837 | 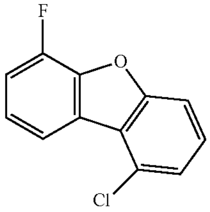 | 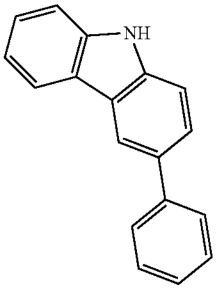 | 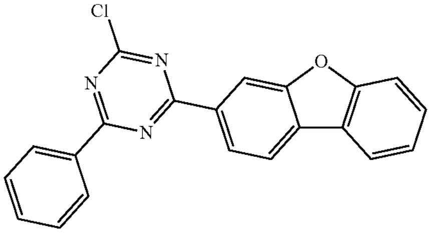 |

TABLE 5-continued
| | | | |
|---|---|---|---|
| 841 | 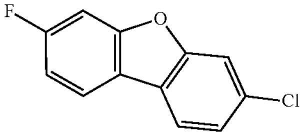 | 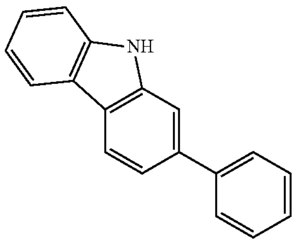 | 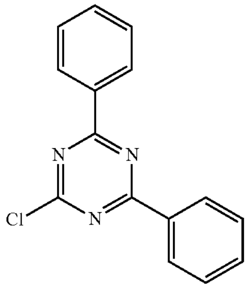 |
| 844 | 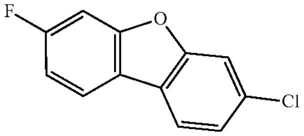 | 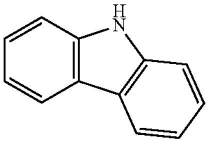 | 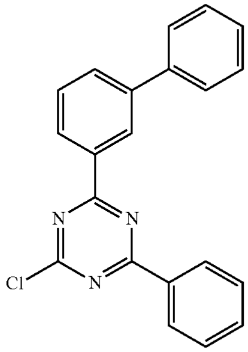 |
| 845 | 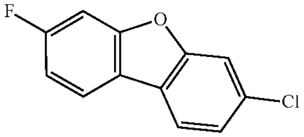 | 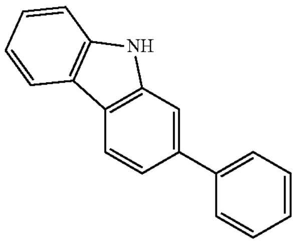 | 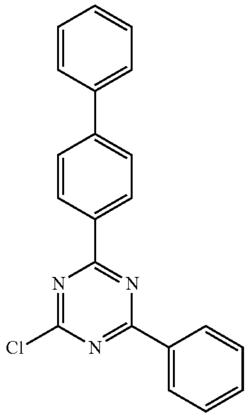 |
| 848 | 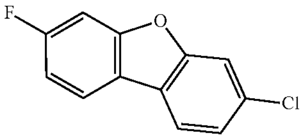 | 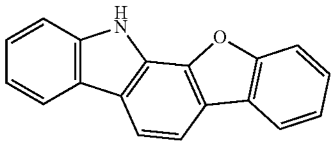 | 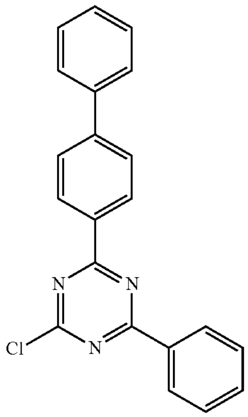 |

TABLE 5-continued
| | | | |
|---|---|---|---|
| 852 | 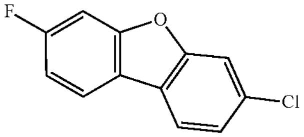 | 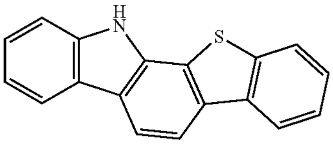 | 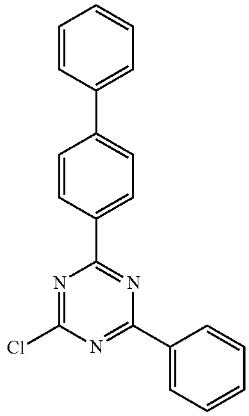 |
| 857 | 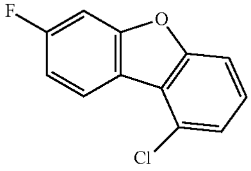 | 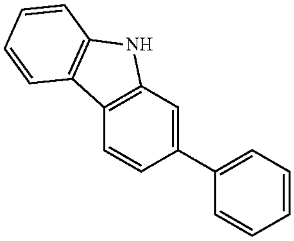 | 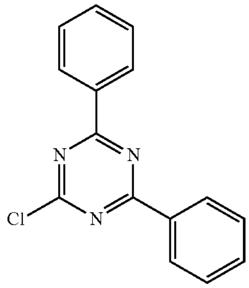 |
| 859 | 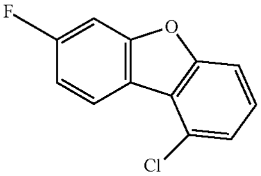 | 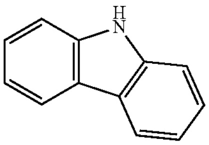 | 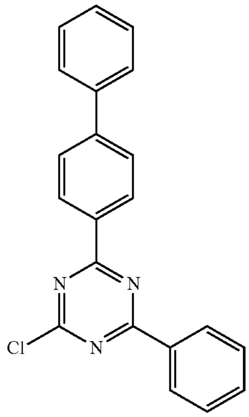 |
| 862 | 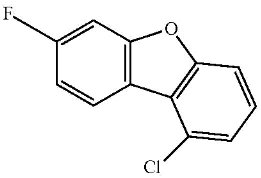 | 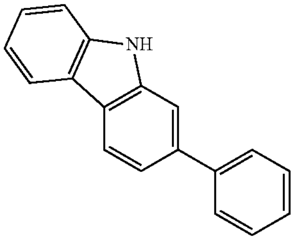 | 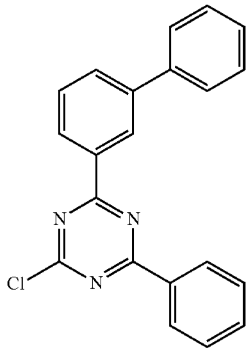 |

TABLE 5-continued
| | | | |
|---|---|---|---|
| 870 | 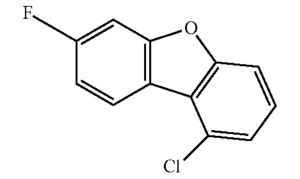 [SMILES: Fc1ccc2c(c1)oc1cccc(Cl)c12] | 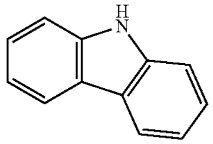 [SMILES: c1ccc2c(c1)[nH]c1ccccc12] | 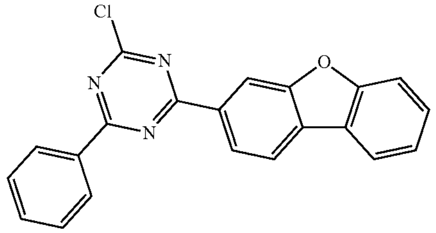 |
| 872 | 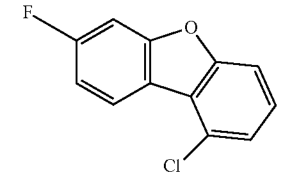 [SMILES: Fc1ccc2c(c1)oc1cccc(Cl)c12] | 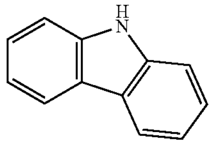 [SMILES: c1ccc2c(c1)[nH]c1ccccc12] | 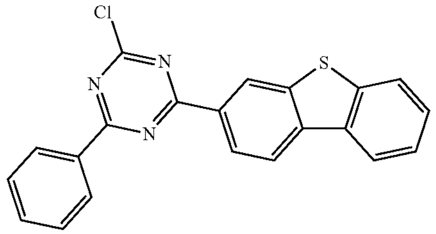 [SMILES: Clc1nc(-c2ccccc2)nc(-c2ccc3c(c2)sc2ccccc23)n1] |
| 874 | 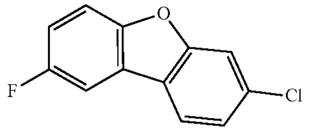 [SMILES: Fc1ccc2oc3cc(Cl)ccc3c2c1] | 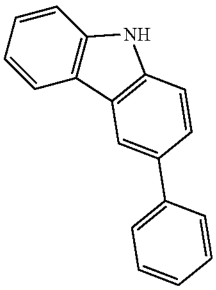 [SMILES: c1ccc(-c2ccc3[nH]c4ccccc4c3c2)cc1] | 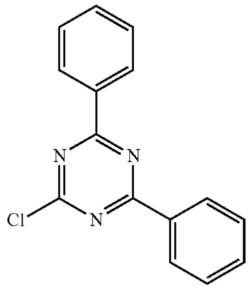 [SMILES: Clc1nc(-c2ccccc2)nc(-c2ccccc2)n1] |
| 875 | 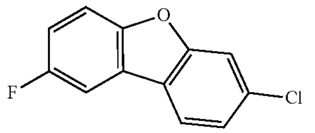 [SMILES: Fc1ccc2oc3cc(Cl)ccc3c2c1] | 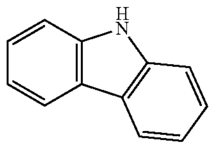 [SMILES: c1ccc2c(c1)[nH]c1ccccc12] | 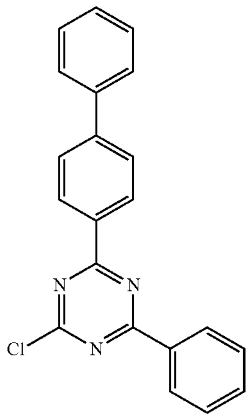 [SMILES: Clc1nc(-c2ccccc2)nc(-c2ccc(-c3ccccc3)cc2)n1] |
| 877 | 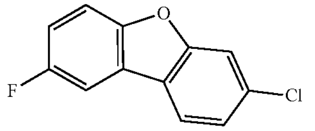 [SMILES: Fc1ccc2oc3cc(Cl)ccc3c2c1] | 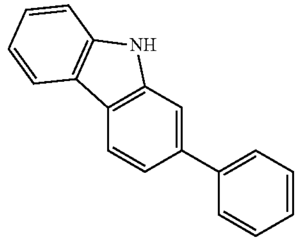 [SMILES: c1ccc(-c2ccc3c(c2)[nH]c2ccccc23)cc1] | 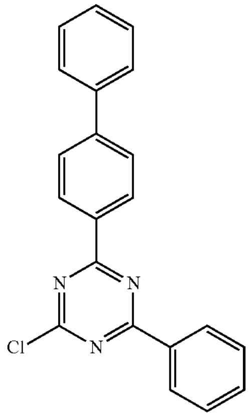 [SMILES: Clc1nc(-c2ccccc2)nc(-c2ccc(-c3ccccc3)cc2)n1] |

TABLE 5-continued
| | | | |
|---|---|---|---|
| 879 | 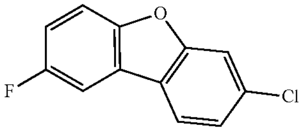 [SMILES: Fc1ccc2oc3cc(Cl)ccc3c2c1] | 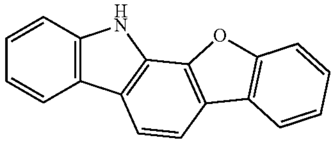 | 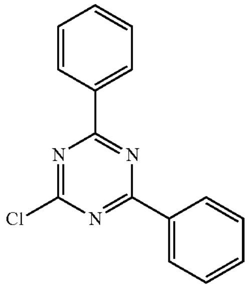 [SMILES: Clc1nc(-c2ccccc2)nc(-c2ccccc2)n1] |
| 884 | 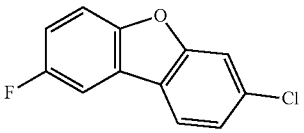 [SMILES: Fc1ccc2oc3cc(Cl)ccc3c2c1] | 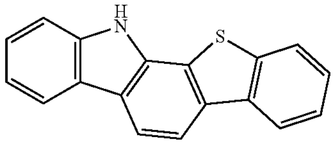 | 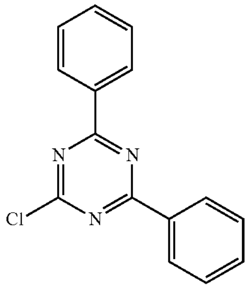 [SMILES: Clc1nc(-c2ccccc2)nc(-c2ccccc2)n1] |
| 888 | 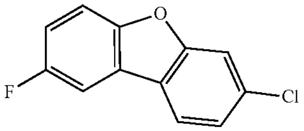 [SMILES: Fc1ccc2oc3cc(Cl)ccc3c2c1] | 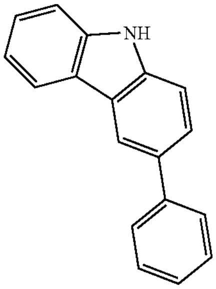 [SMILES: c1ccc(-c2ccc3[nH]c4ccccc4c3c2)cc1] | 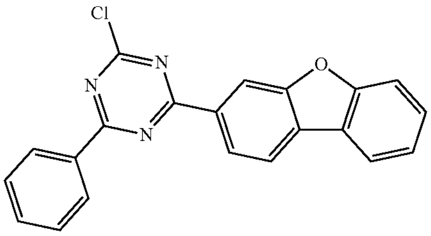 |
| 889 | 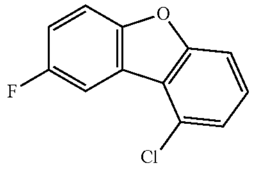 [SMILES: Fc1ccc2oc3cccc(Cl)c3c2c1] | 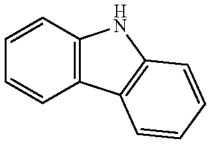 [SMILES: c1ccc2c(c1)[nH]c1ccccc12] | 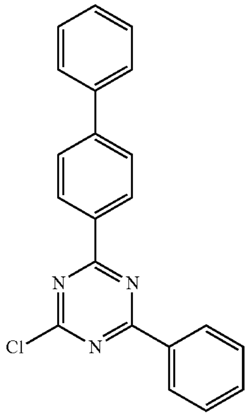 [SMILES: Clc1nc(-c2ccccc2)nc(-c2ccc(-c3ccccc3)cc2)n1] |
| 896 | 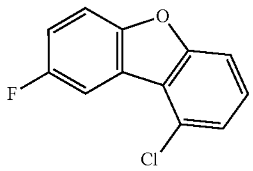 [SMILES: Fc1ccc2oc3cccc(Cl)c3c2c1] | 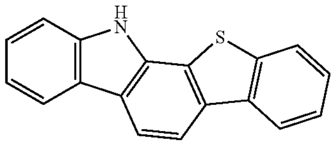 | 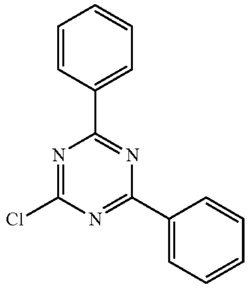 [SMILES: Clc1nc(-c2ccccc2)nc(-c2ccccc2)n1] |

TABLE 5-continued
| | | | |
|---|---|---|---|
| 903 | 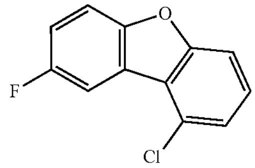 [SMILES: Fc1ccc2oc3cccc(Cl)c3c2c1] | 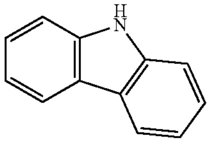 [SMILES: c1ccc2c(c1)[nH]c1ccccc12] | 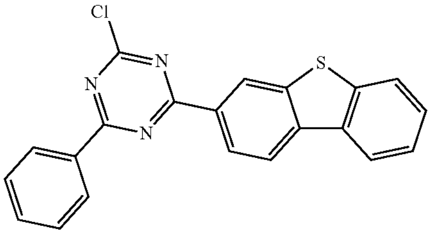 [SMILES: Clc1nc(-c2ccccc2)nc(-c2ccc3c(c2)sc2ccccc23)n1] |
| 907 | 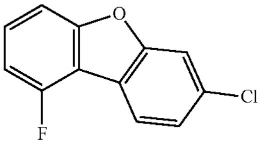 [SMILES: Fc1cccc2oc3cc(Cl)ccc3c12] | 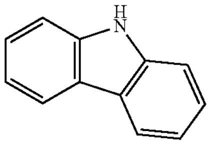 [SMILES: c1ccc2c(c1)[nH]c1ccccc12] | 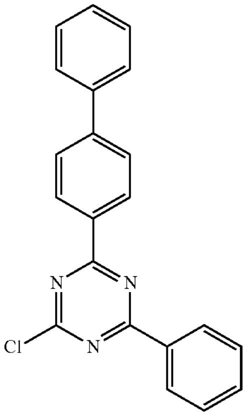 [SMILES: Clc1nc(-c2ccccc2)nc(-c2ccc(-c3ccccc3)cc2)n1] |
| 909 | 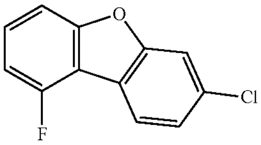 [SMILES: Fc1cccc2oc3cc(Cl)ccc3c12] | 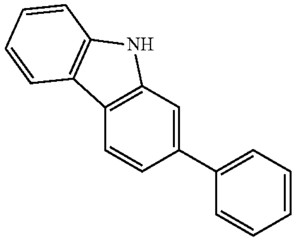 [SMILES: c1ccc(-c2ccc3c(c2)[nH]c2ccccc23)cc1] | 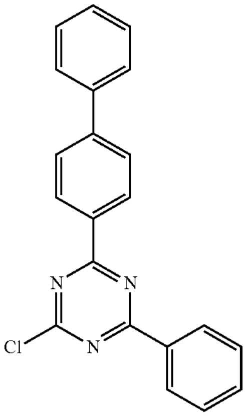 [SMILES: Clc1nc(-c2ccccc2)nc(-c2ccc(-c3ccccc3)cc2)n1] |
| 916 | 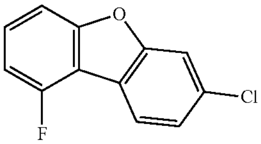 [SMILES: Fc1cccc2oc3cc(Cl)ccc3c12] | 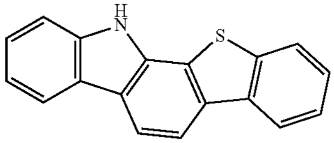 [SMILES: c1ccc2c(c1)[nH]c1c2ccc2c3ccccc3sc21] | 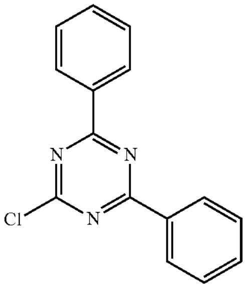 [SMILES: Clc1nc(-c2ccccc2)nc(-c2ccccc2)n1] |
| 918 | 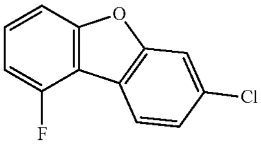 [SMILES: Fc1cccc2oc3cc(Cl)ccc3c12] | 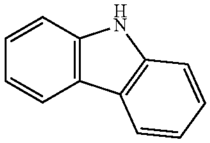 [SMILES: c1ccc2c(c1)[nH]c1ccccc12] | 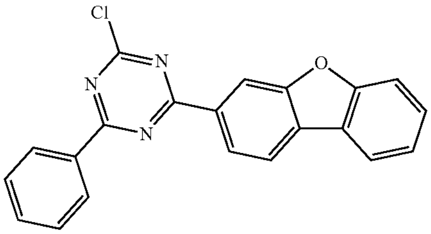 |

TABLE 5-continued
| | | | |
|---|---|---|---|
| 923 | 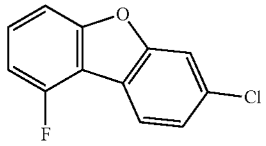 [SMILES: Fc1cccc2oc3cc(Cl)ccc3c12] | 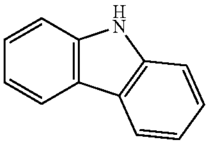 [SMILES: c1ccc2c(c1)[nH]c1ccccc12] | 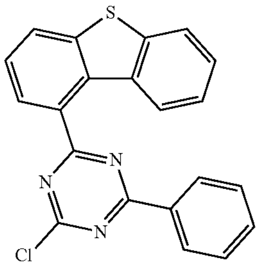 [SMILES: Clc1nc(-c2ccccc2)nc(-c2cccc3sc4ccccc4c23)n1] |
| Compound | I | yield |
|---|---|---|
| 797 | 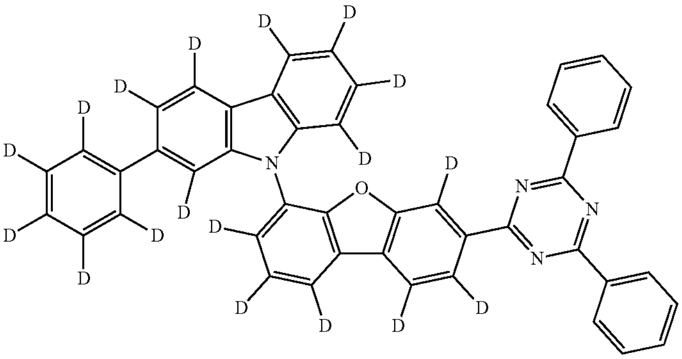 | 78% |
| 798 | 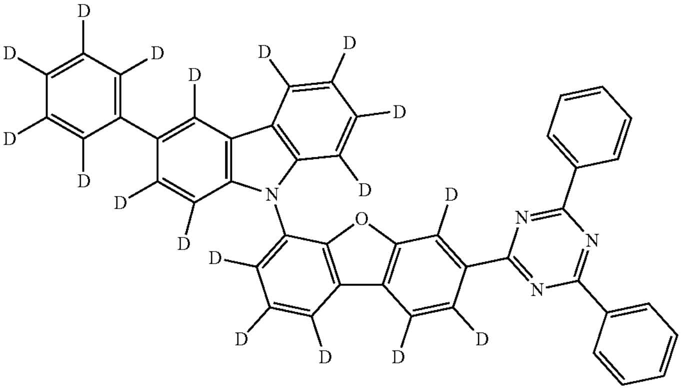 | 71% |
| 799 | 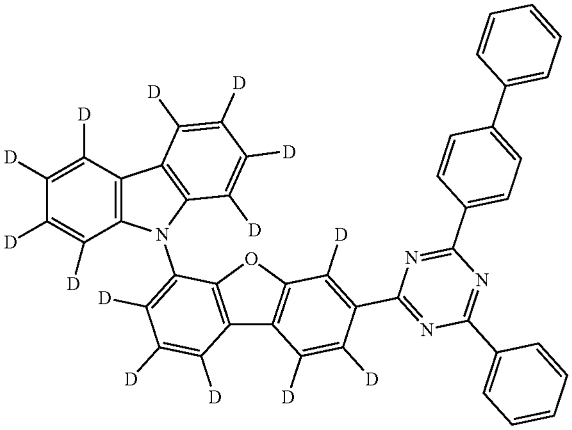 | 88% |

TABLE 5-continued
| | | |
|---|---|---|
| 801 | 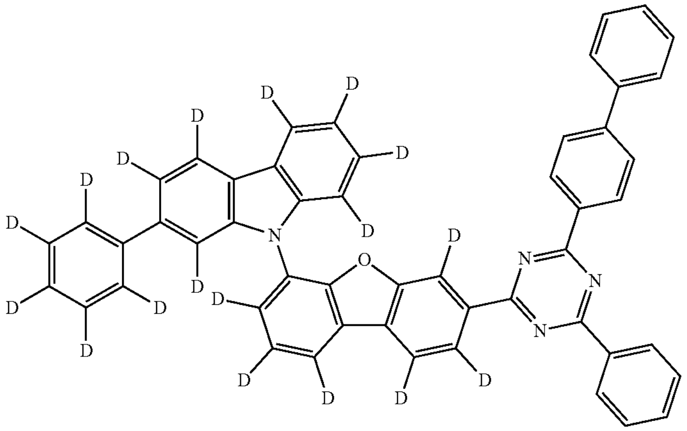 | 73% |
| 811 | 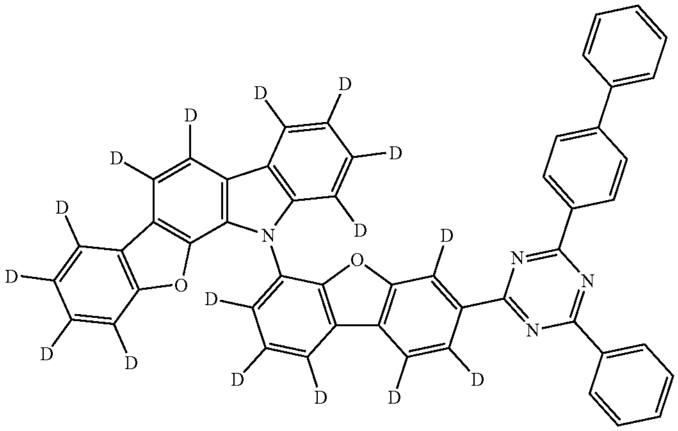 | 83% |
| 815 | 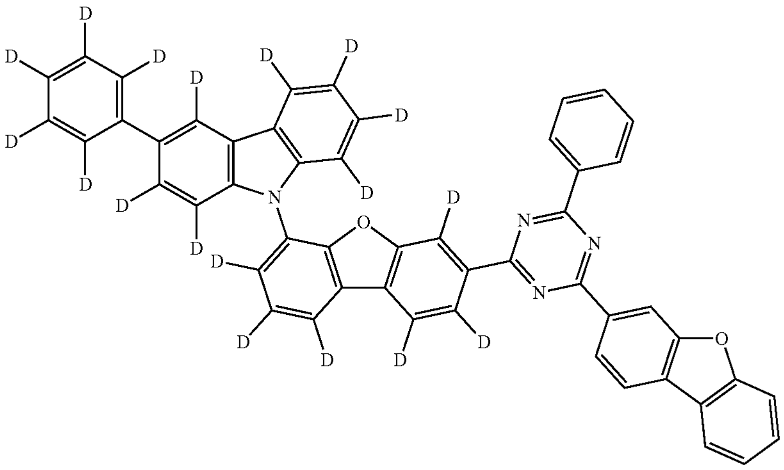 | 63% |

TABLE 5-continued
821 58%
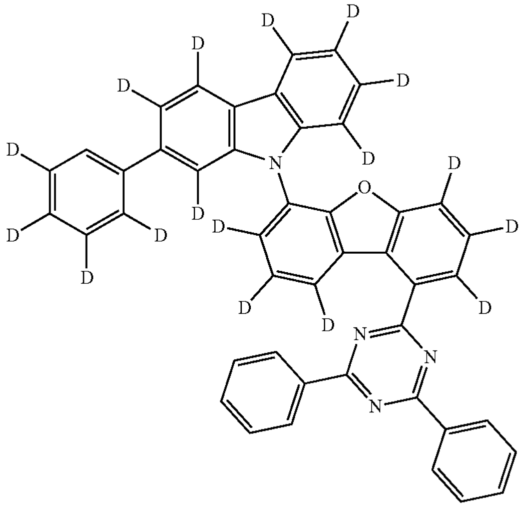 [SMILES: [2H]c1cc(-c2c([2H])c([2H])c3c4c([2H])c([2H])c([2H])c([2H])c4n(-c4c([2H])c([2H])c([2H])c5c4oc4c([2H])c([2H])c([2H])c(-c6nc(-c7ccccc7)nc(-c7ccccc7)n6)c45)c3c2[2H])c([2H])c([2H])c1[2H]]
822 59%
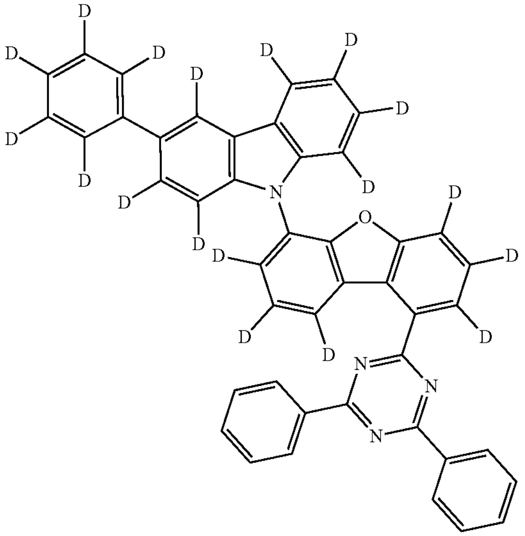 [SMILES: [2H]c1c([2H])c([2H])c(-c2c([2H])c([2H])c3c(c2[2H])c2c([2H])c([2H])c([2H])c([2H])c2n3-c2c([2H])c([2H])c([2H])c3c2oc2c([2H])c([2H])c([2H])c(-c4nc(-c5ccccc5)nc(-c5ccccc5)n4)c23)c([2H])c1[2H]]
823 79%
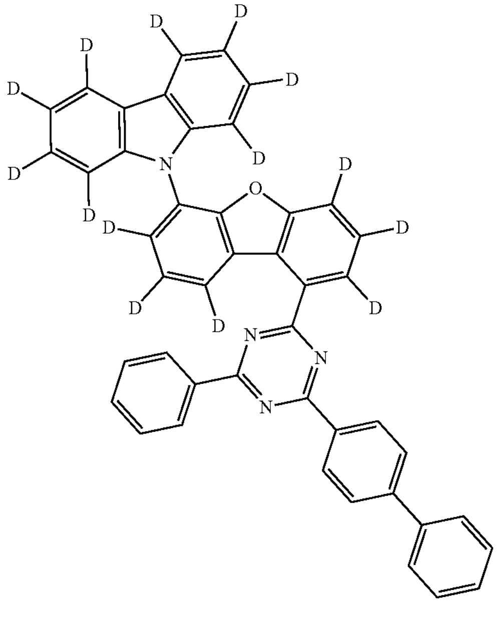 [SMILES: [2H]c1c([2H])c(-c2nc(-c3ccccc3)nc(-c3ccc(-c4ccccc4)cc3)n2)c2c(oc3c(-n4c5c([2H])c([2H])c([2H])c([2H])c5c5c([2H])c([2H])c([2H])c([2H])c54)c([2H])c([2H])c([2H])c32)c1[2H]]

TABLE 5-continued
| | | |
|---|---|---|
| 827 | 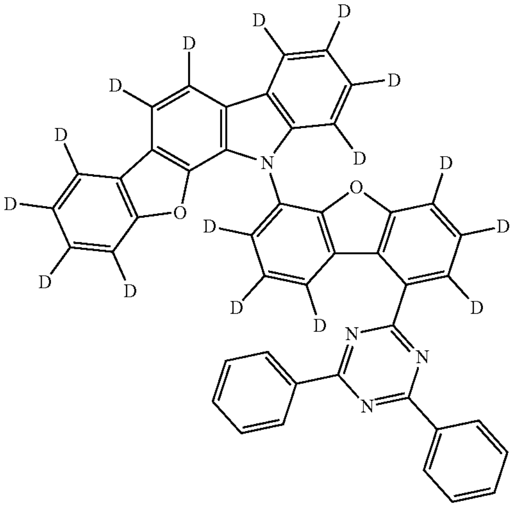 | 74% |
| 832 | 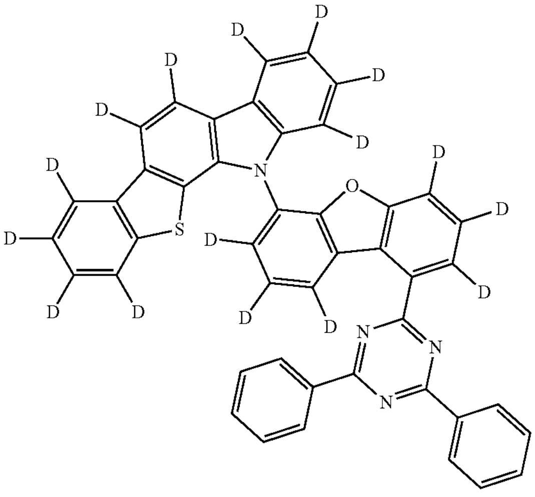 | 68% |
| 835 | 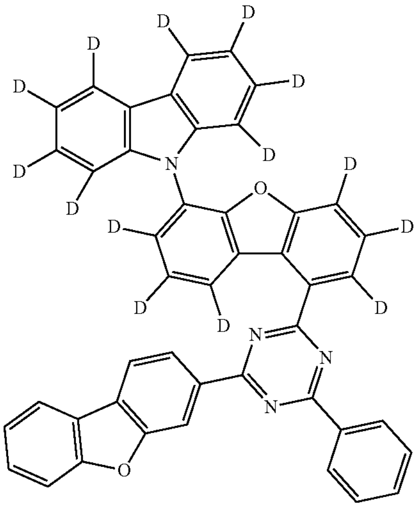 | 59% |

TABLE 5-continued
| | | |
|---|---|---|
| 837 | 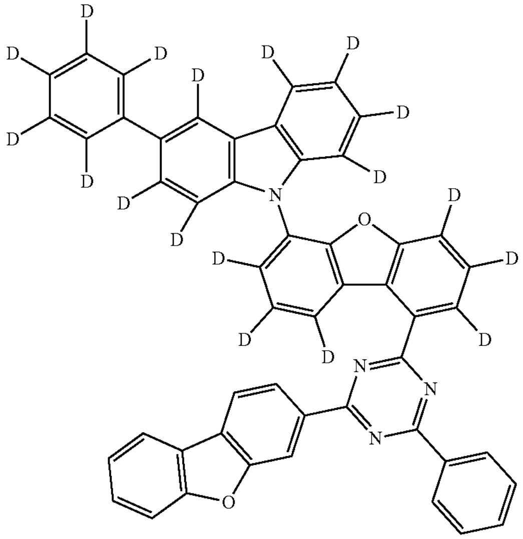 | 61% |
| 841 | 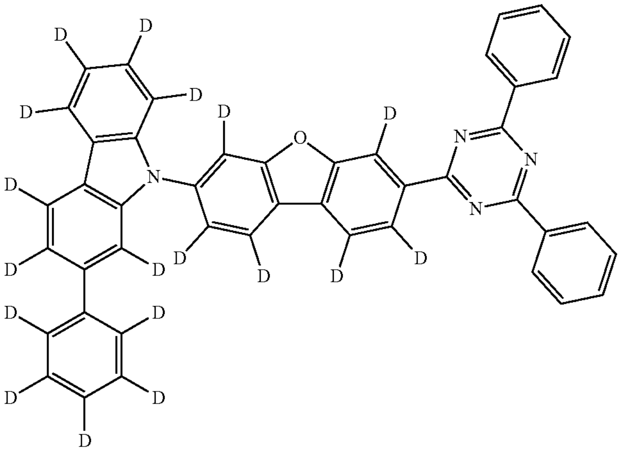 | 83% |
| 844 | 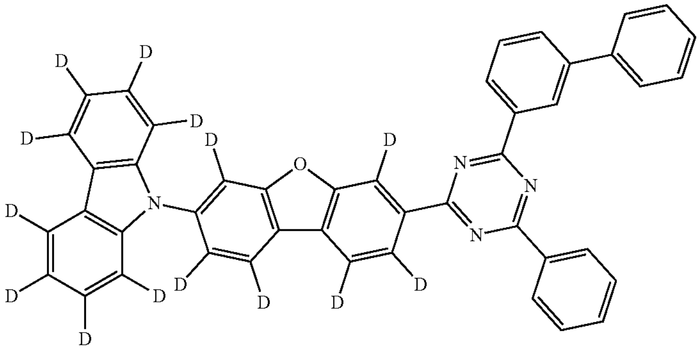 | 79% |

TABLE 5-continued
845 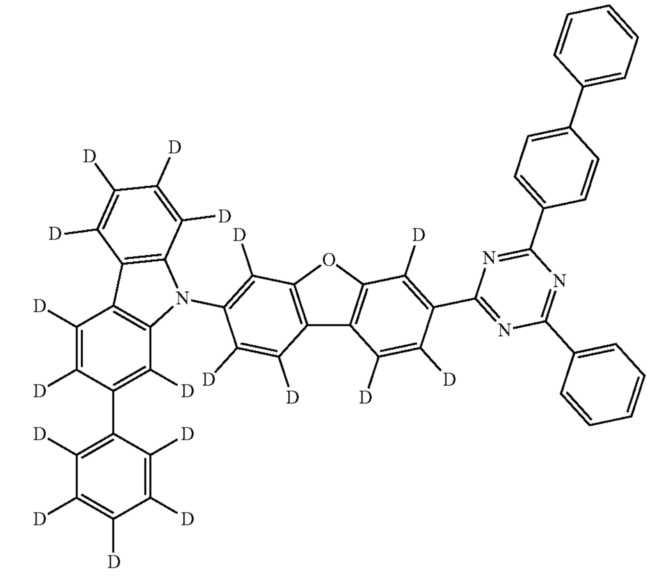 [SMILES: [2H]c1c([2H])c([2H])c(-c2c([2H])c([2H])c3c4c([2H])c([2H])c([2H])c([2H])c4n(-c4c([2H])c([2H])c5c(oc6c([2H])c(-c7nc(-c8ccccc8)nc(-c8ccc(-c9ccccc9)cc8)n7)c([2H])c([2H])c65)c4[2H])c3c2[2H])c([2H])c1[2H]] 68%
848 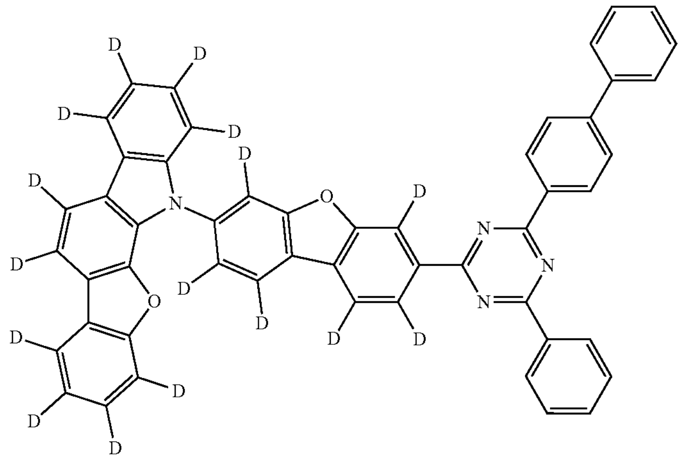 [SMILES: [2H]c1c([2H])c([2H])c2c(oc3c2c([2H])c([2H])c2c4c([2H])c([2H])c([2H])c([2H])c4n(-c4c([2H])c([2H])c5c(oc6c([2H])c(-c7nc(-c8ccccc8)nc(-c8ccc(-c9ccccc9)cc8)n7)c([2H])c([2H])c65)c4[2H])c32)c1[2H]] 78%
852 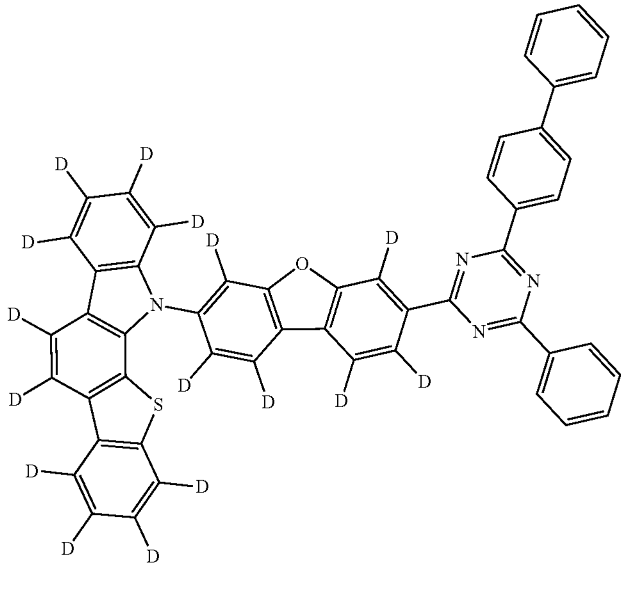 [SMILES: [2H]c1c([2H])c([2H])c2c(sc3c2c([2H])c([2H])c2c4c([2H])c([2H])c([2H])c([2H])c4n(-c4c([2H])c([2H])c5c(oc6c([2H])c(-c7nc(-c8ccccc8)nc(-c8ccc(-c9ccccc9)cc8)n7)c([2H])c([2H])c65)c4[2H])c32)c1[2H]] 91%

TABLE 5-continued
| | | |
|---|---|---|
| 857 | 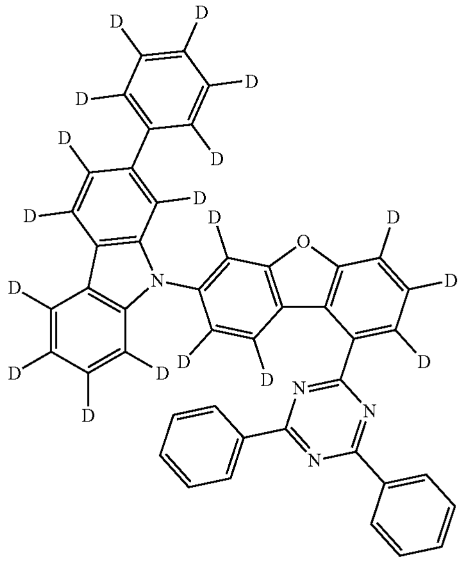 | 88% |
| 859 | 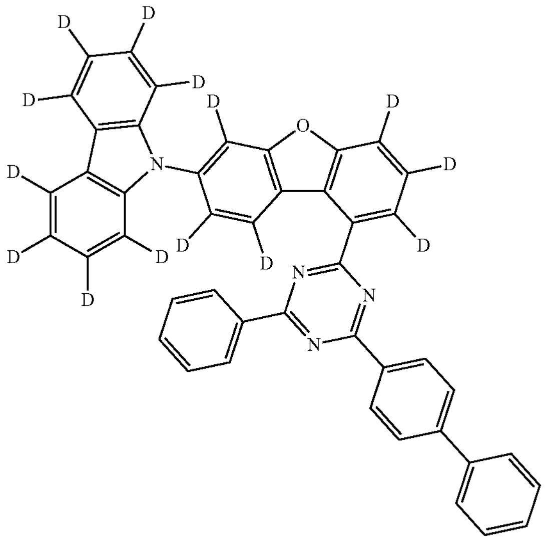 | 81% |

TABLE 5-continued
| | | |
|---|---|---|
| 862 | 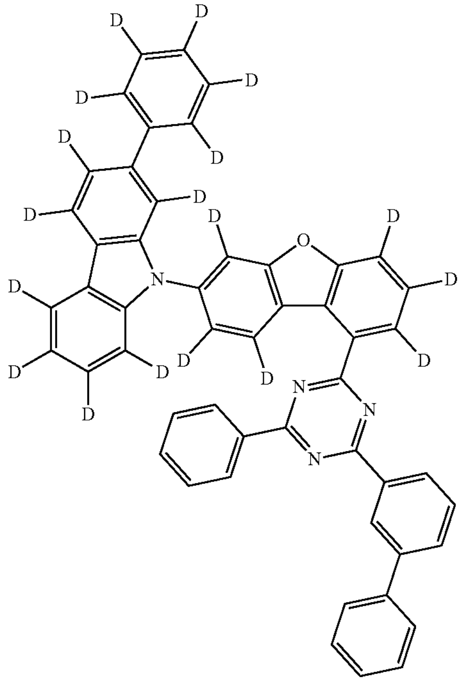 [SMILES: [2H]c1c([2H])c([2H])c(-c2c([2H])c([2H])c3c4c([2H])c([2H])c([2H])c([2H])c4n(-c4c([2H])c([2H])c5c(oc6c([2H])c([2H])c([2H])c(-c7nc(-c8ccccc8)nc(-c8cccc(-c9ccccc9)c8)n7)c65)c4[2H])c3c2[2H])c([2H])c1[2H]] | 77% |
| 870 | 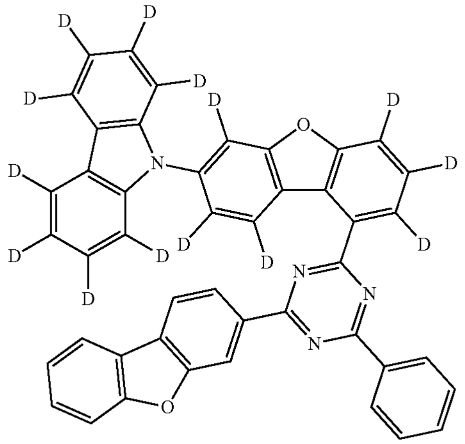 [SMILES: [2H]c1c([2H])c(-c2nc(-c3ccccc3)nc(-c3ccc4c(c3)oc3ccccc34)n2)c2c(oc3c([2H])c(-n4c5c([2H])c([2H])c([2H])c([2H])c5c5c([2H])c([2H])c([2H])c([2H])c54)c([2H])c([2H])c32)c1[2H]] | 93% |
| 872 | 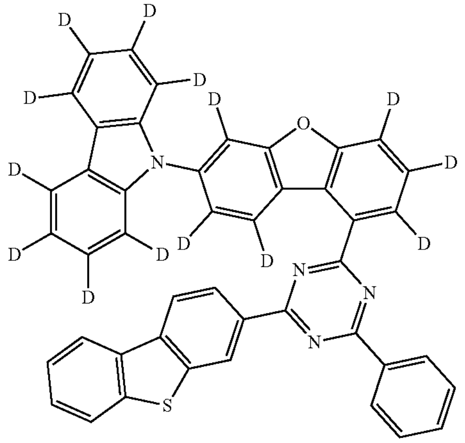 [SMILES: [2H]c1c([2H])c(-c2nc(-c3ccccc3)nc(-c3ccc4c(c3)sc3ccccc34)n2)c2c(oc3c([2H])c(-n4c5c([2H])c([2H])c([2H])c([2H])c5c5c([2H])c([2H])c([2H])c([2H])c54)c([2H])c([2H])c32)c1[2H]] | 85% |

TABLE 5-continued
| | | |
|---|---|---|
| 874 | 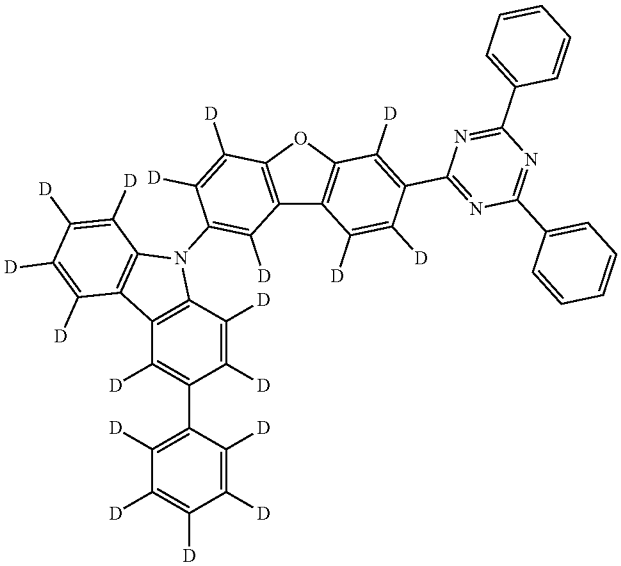 [SMILES: [2H]c1c([2H])c([2H])c(-c2c([2H])c([2H])c3c(c2[2H])c2c([2H])c([2H])c([2H])c([2H])c2n3-c2c([2H])c([2H])c3oc4c([2H])c(-c5nc(-c6ccccc6)nc(-c6ccccc6)n5)c([2H])c([2H])c4c3c2[2H])c([2H])c1[2H]] | 76% |
| 875 | 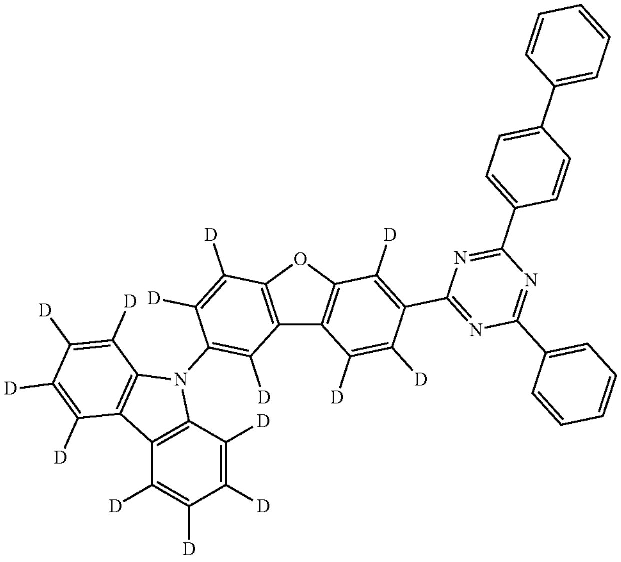 [SMILES: [2H]c1c(-n2c3c([2H])c([2H])c([2H])c([2H])c3c3c([2H])c([2H])c([2H])c([2H])c32)c([2H])c2c(oc3c([2H])c(-c4nc(-c5ccccc5)nc(-c5ccc(-c6ccccc6)cc5)n4)c([2H])c([2H])c32)c1[2H]] | 68% |

TABLE 5-continued
| | | |
|---|---|---|
| 877 | 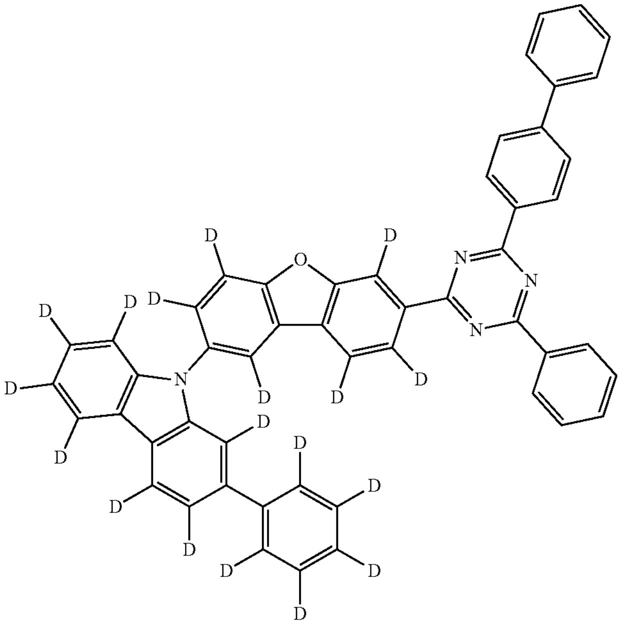 [SMILES: [2H]c1c([2H])c([2H])c(-c2c([2H])c([2H])c3c4c([2H])c([2H])c([2H])c([2H])c4n(-c4c([2H])c([2H])c5oc6c([2H])c(-c7nc(-c8ccccc8)nc(-c8ccc(-c9ccccc9)cc8)n7)c([2H])c([2H])c6c5c4[2H])c3c2[2H])c([2H])c1[2H]] | 77% |
| 879 | 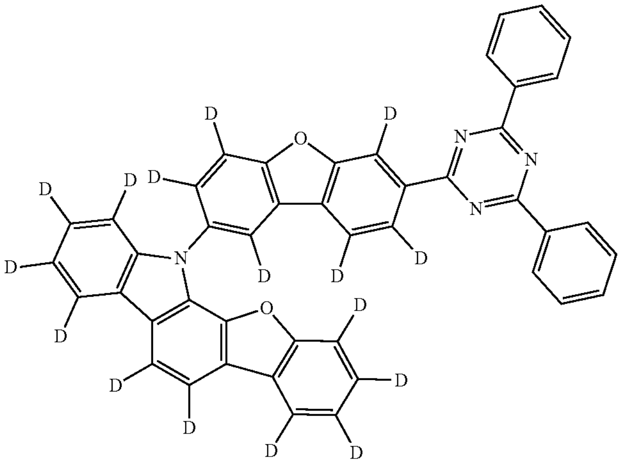 [SMILES: [2H]c1c(-n2c3c([2H])c([2H])c([2H])c([2H])c3c3c([2H])c([2H])c4c(sc5c([2H])c([2H])c([2H])c([2H])c54)c32)c([2H])c2c(oc3c([2H])c(-c4nc(-c5ccccc5)nc(-c5ccccc5)n4)c([2H])c([2H])c32)c1[2H]] | 79% |
| 884 | 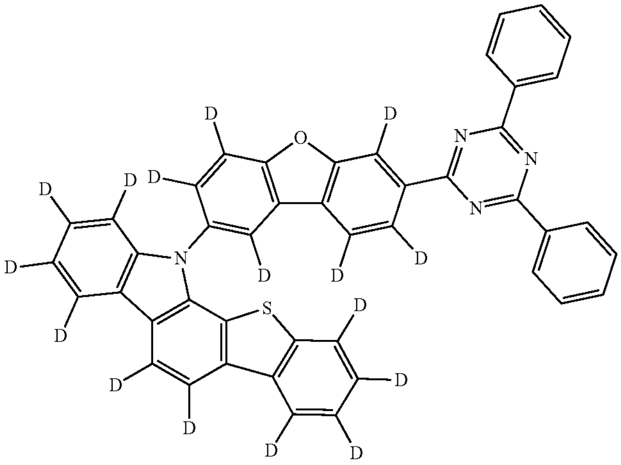 | 69% |

TABLE 5-continued
| | | |
|---|---|---|
| 888 | 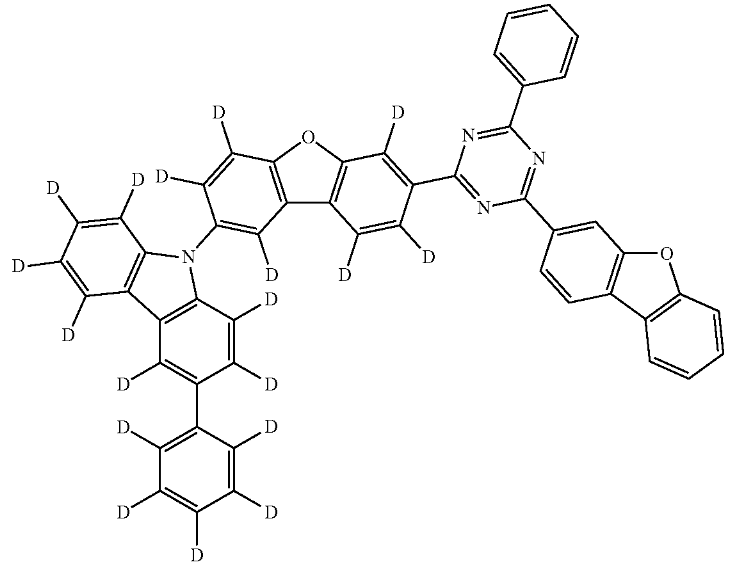 [SMILES: [2H]c1c([2H])c([2H])c(-c2c([2H])c([2H])c3c(c2[2H])c2c([2H])c([2H])c([2H])c([2H])c2n3-c2c([2H])c([2H])c3oc4c([2H])c(-c5nc(-c6ccccc6)nc(-c6ccc7c(c6)oc6ccccc67)n5)c([2H])c([2H])c4c3c2[2H])c([2H])c1[2H]] | 61% |
| 889 | 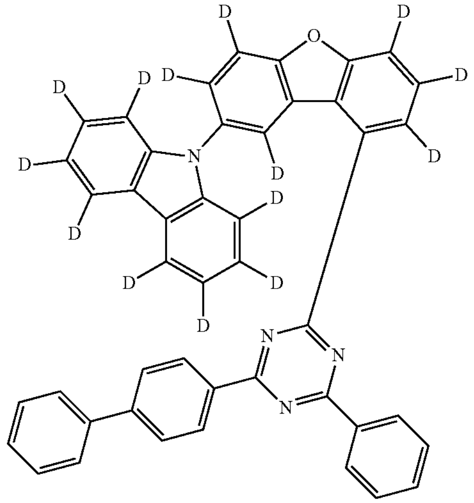 [SMILES: [2H]c1c(-n2c3c([2H])c([2H])c([2H])c([2H])c3c3c([2H])c([2H])c([2H])c([2H])c32)c([2H])c2c(oc3c([2H])c([2H])c([2H])c(-c4nc(-c5ccccc5)nc(-c5ccc(-c6ccccc6)cc5)n4)c32)c1[2H]] | 58% |
| 896 | 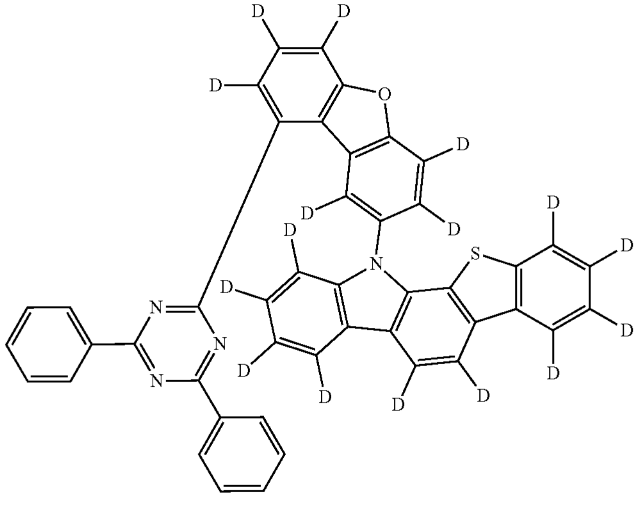 [SMILES: [2H]c1c(-n2c3c([2H])c([2H])c([2H])c([2H])c3c3c([2H])c([2H])c4c(sc5c([2H])c([2H])c([2H])c([2H])c54)c32)c([2H])c2c(oc3c([2H])c([2H])c([2H])c(-c4nc(-c5ccccc5)nc(-c5ccccc5)n4)c32)c1[2H]] | 79% |

TABLE 5-continued
| | | |
|---|---|---|
| 903 | 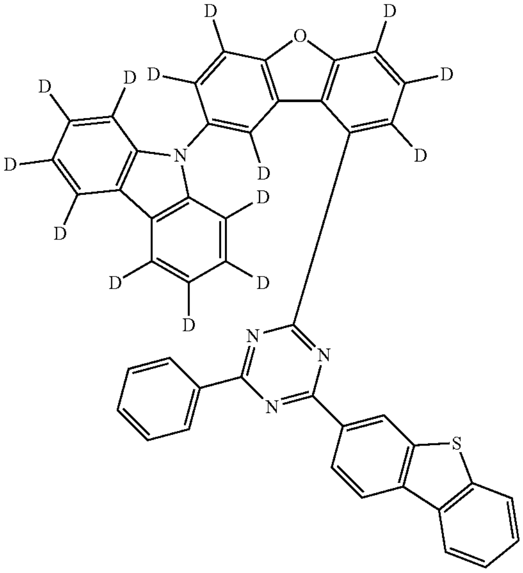 [SMILES: [2H]c1c(-n2c3c([2H])c([2H])c([2H])c([2H])c3c3c([2H])c([2H])c([2H])c([2H])c32)c([2H])c2c(oc3c([2H])c([2H])c([2H])c(-c4nc(-c5ccccc5)nc(-c5ccc6c(c5)sc5ccccc56)n4)c32)c1[2H]] | 83% |
| 907 | 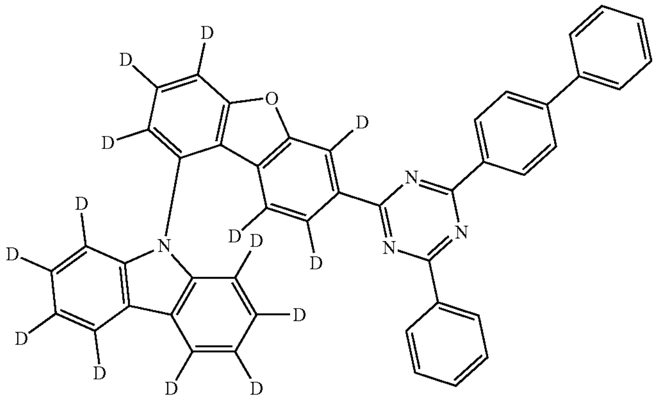 [SMILES: [2H]c1c([2H])c(-n2c3c([2H])c([2H])c([2H])c([2H])c3c3c([2H])c([2H])c([2H])c([2H])c32)c2c(oc3c([2H])c(-c4nc(-c5ccccc5)nc(-c5ccc(-c6ccccc6)cc5)n4)c([2H])c([2H])c32)c1[2H]] | 88% |
| 909 | 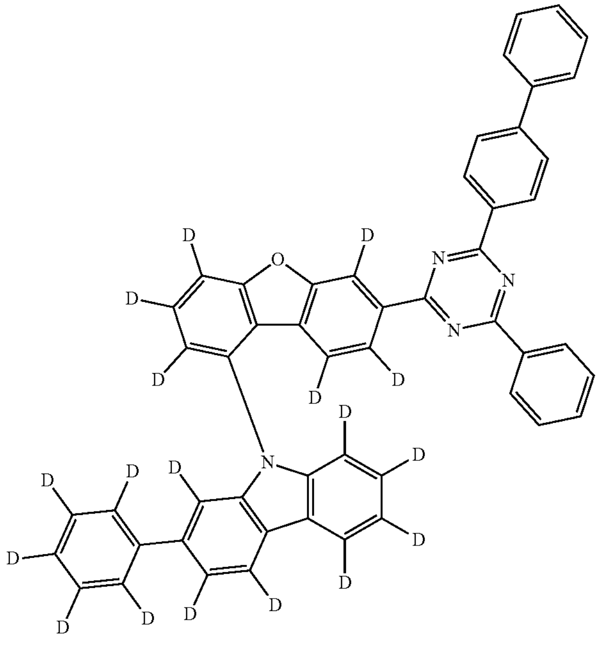 [SMILES: [2H]c1c([2H])c([2H])c(-c2c([2H])c([2H])c3c4c([2H])c([2H])c([2H])c([2H])c4n(-c4c([2H])c([2H])c([2H])c5oc6c([2H])c(-c7nc(-c8ccccc8)nc(-c8ccc(-c9ccccc9)cc8)n7)c([2H])c([2H])c6c45)c3c2[2H])c([2H])c1[2H]] | 59% |

TABLE 5-continued
| | | |
|---|---|---|
| 916 | 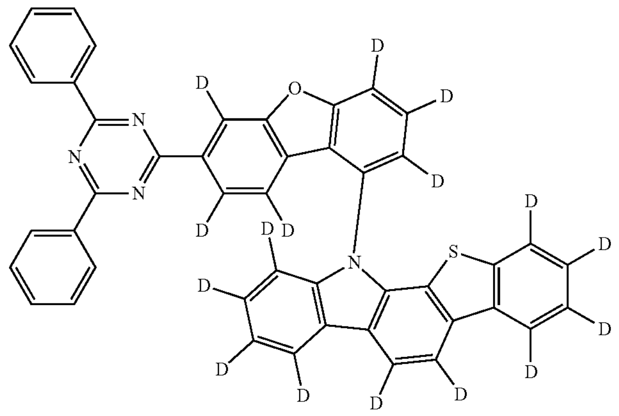 [SMILES: [2H]c1c([2H])c(-n2c3c([2H])c([2H])c([2H])c([2H])c3c3c([2H])c([2H])c4c(sc5c([2H])c([2H])c([2H])c([2H])c54)c32)c2c(oc3c([2H])c(-c4nc(-c5ccccc5)nc(-c5ccccc5)n4)c([2H])c([2H])c32)c1[2H]] | 63% |
| 918 | 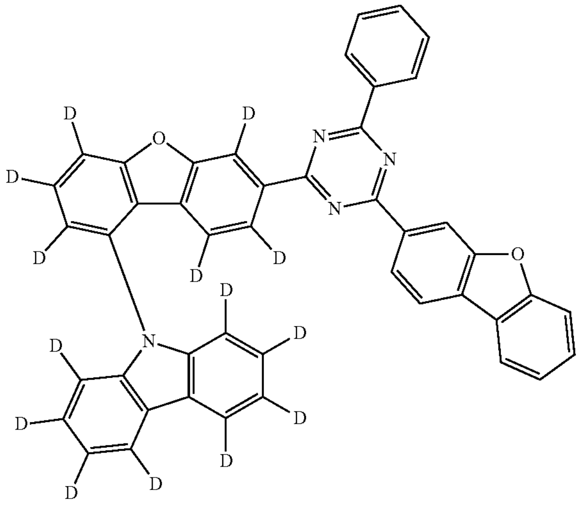 [SMILES: [2H]c1c([2H])c(-n2c3c([2H])c([2H])c([2H])c([2H])c3c3c([2H])c([2H])c([2H])c([2H])c32)c2c(oc3c([2H])c(-c4nc(-c5ccccc5)nc(-c5ccc6c(c5)oc5ccccc56)n4)c([2H])c([2H])c32)c1[2H]] | 77% |
| 923 | 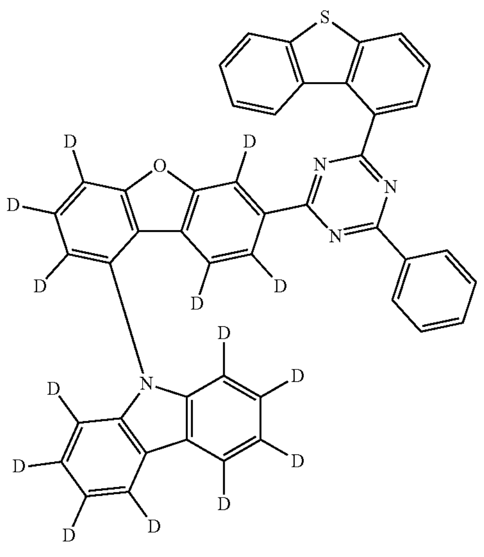 [SMILES: [2H]c1c([2H])c(-n2c3c([2H])c([2H])c([2H])c([2H])c3c3c([2H])c([2H])c([2H])c([2H])c32)c2c(oc3c([2H])c(-c4nc(-c5ccccc5)nc(-c5cccc6sc7ccccc7c56)n4)c([2H])c([2H])c32)c1[2H]] | 78% |

[Synthesis 6] The compound 929 (J)

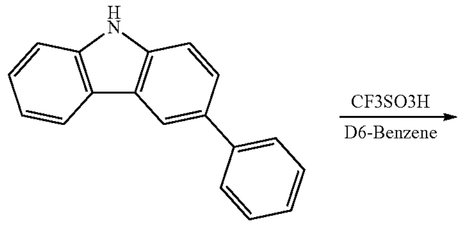

[A]

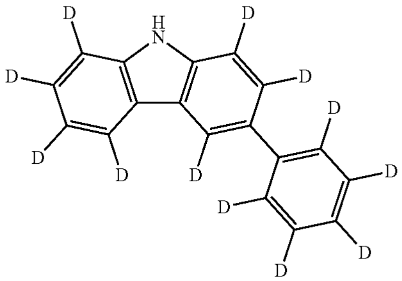

[A]-1

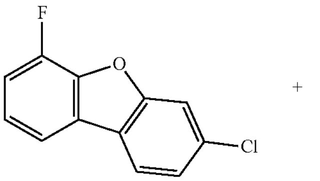

[B]

+

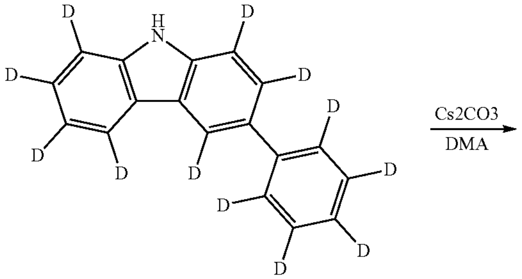

[A]-1

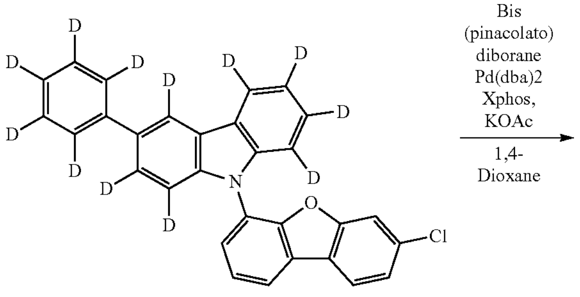

3-1

-continued

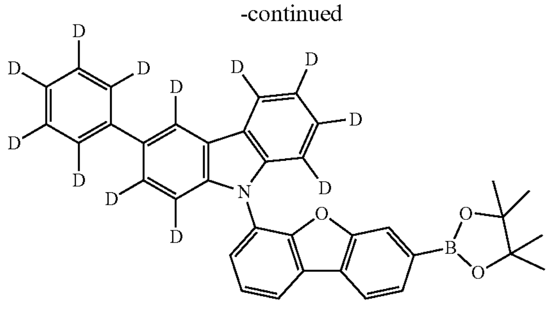

3-2

+

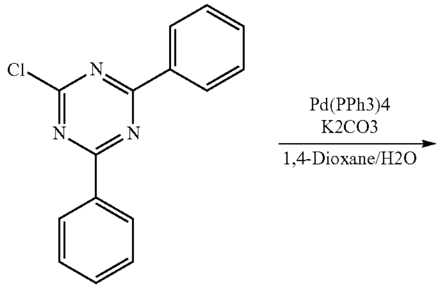

[C]

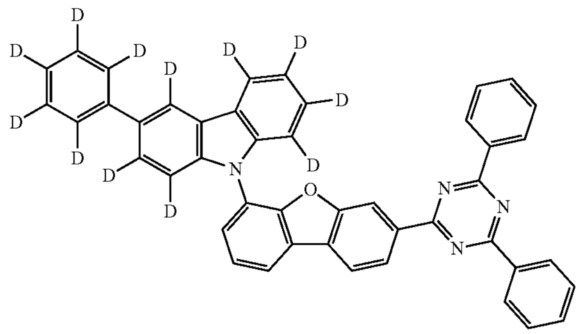

3[E]

(1) The Compound 929-1

In the one-neck round bottom flask, a mixture of 3-chloro-6-fluorodibenzo[b,d]furan (10 g, 0.045 mol), bis(pinacolato) diborn) (22.85 g, 0.090 mol), Pd(dba)$_2$ (4.12) g, 0.0045 mol), Xphos (8.58 g, 0.018 mol), potassium acetate (13.25 g, 00.14 mol) and 1,4-dioxane (100 mL) were refluxed at 120° C. After cooling, the resultant was concentrated and filtered through silica gel to obtain the compound 929-1. (13.77 g, 98%)

(2) The Compound 929-2

In the one-neck round bottom flask, a mixture of 2-(6-fluorodibenzo[b,d]furan-3-yl)-4,4,5,5-tetramethyl-1,3,2-dioxaborolane (13.77 g, 0.044 mol), 2-chloro-4,6-diphenyl-1,3,5-triazine (12.96 g, 0.048 mol), Pd(PPh$_3$)$_4$ (2.54 g, 0.0022 mol), $K_2CO_3$ (12.16 g, 0.088 mol), 1,4-dioxane (130 mL) and water (40 mL) was refluxed at 120° C. After cooling, the resultant was concentrated and filtered through silica gel to obtain the compound 929-2. (12.49 g, 68%)

(3) The Compound 929-3

In the one-neck round bottom flask, a mixture of 2-(6-fluorodibenzo[b,d]furan-3-yl)-4,6-diphenyl-1,3,5-triazine (12.49 g, 0.030 mol), triflic acid (36.02 g, 0.24 mol) and D6-benzene (130 mL) was refluxed at 70° C. After quenching and extraction with dichloromethane and $H_2O$, the resultant was concentrated and filtered through silica gel. After concentration, the resultant was treated with methanol to obtain the compound 929-3. (10.01 g, 77%)

(4) The Compound 929-J

In the one-neck round bottom flask, a mixture of 2-(6-fluorodibenzo[b,d]furan-3-yl-1,2,4,7,8,9-d6)-4,6-bis(phenyl-d5)-1,3,5-triazine (10.01 g, 0.023 mol), 2-phenyl-9H-carbazole (6.16 g, 0.025 mol), $Cs_2CO_3$ (14.99 g, 0.046 mol) and dimethylacetamide (100 mL) were refluxed at 170° C. After cooling, the resultant was filtered to remove the solvent and purified by column to obtain the compound 929 [J]. (14.05 g, 93%)

The following compound J was synthesized in the same manner as in the synthesis 6 except that intermediates A, B, and C of Table 6 were used.

TABLE 6

| Compound | A | B | C |
|---|---|---|---|
| 929 | 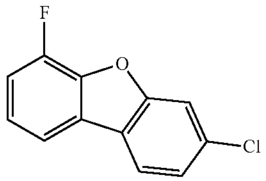 | 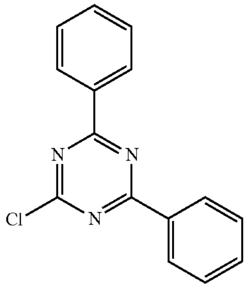 | 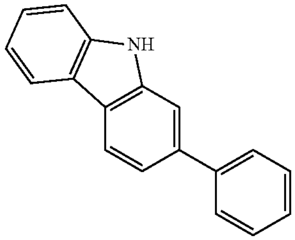 |
| 930 | 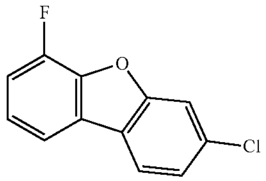 | 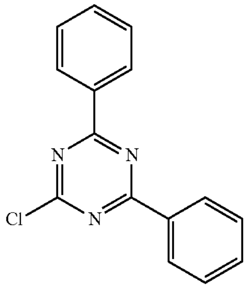 | 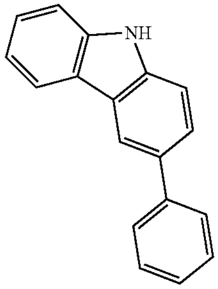 |
| 932 | 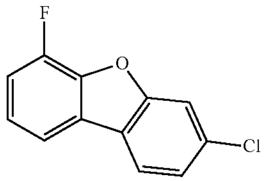 | 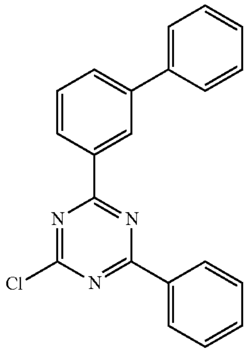 | 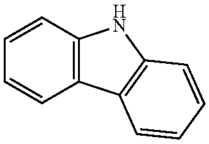 |
| 933 | 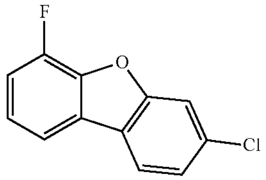 | 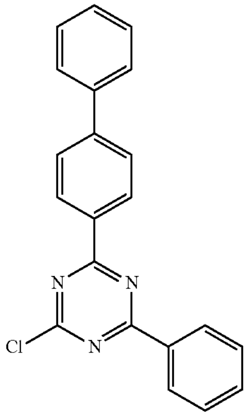 | 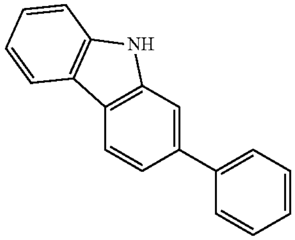 |

TABLE 6-continued
| | | | |
|---|---|---|---|
| 945 | 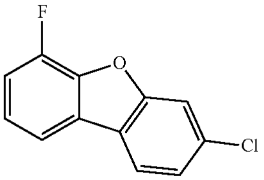 | 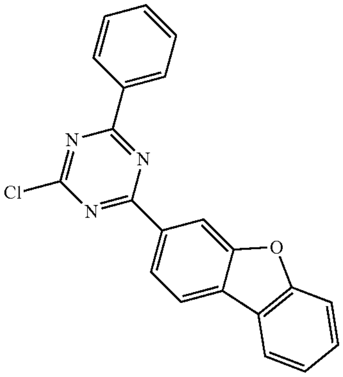 | 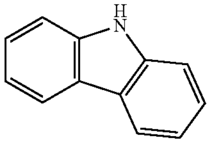 |
| 951 | 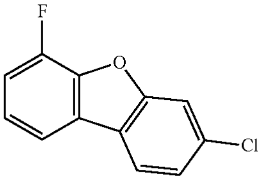 | 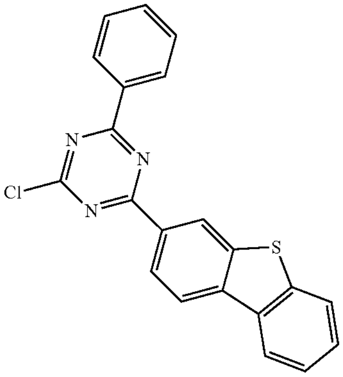 | 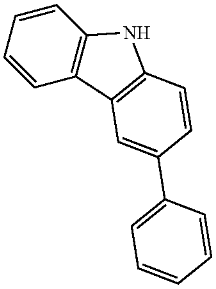 |
| 954 | 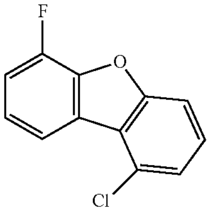 | 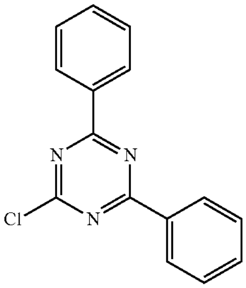 | 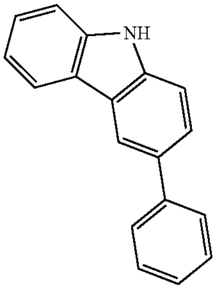 |
| 959 | 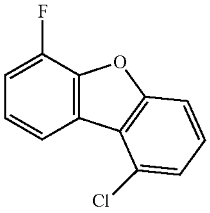 | 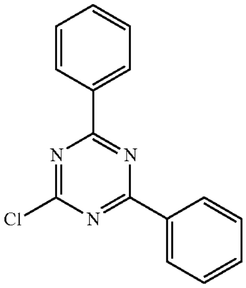 | 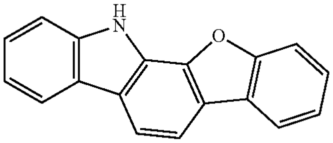 |

TABLE 6-continued
| | | | |
|---|---|---|---|
| 967 | 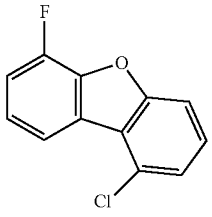 | 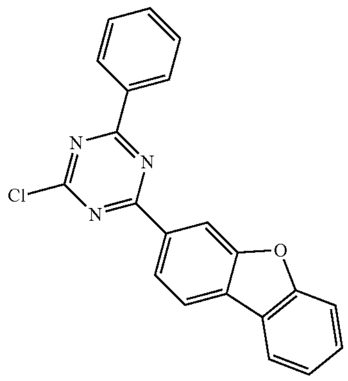 | 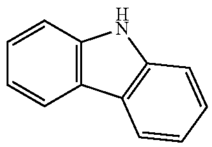 |
| 969 | 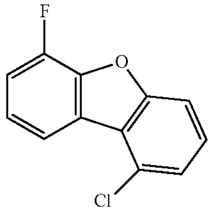 | 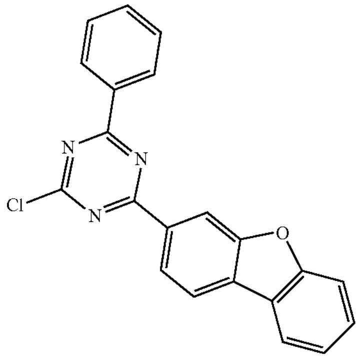 | 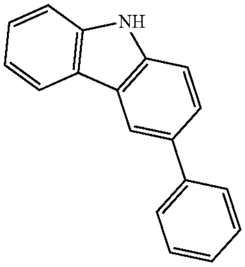 |
| 973 | 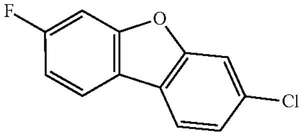 | 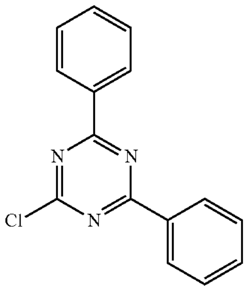 | 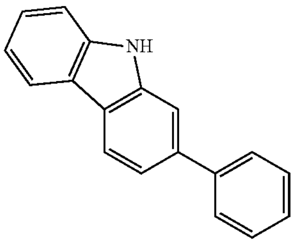 |
| 974 | 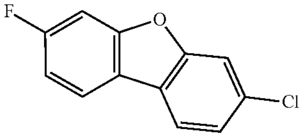 | 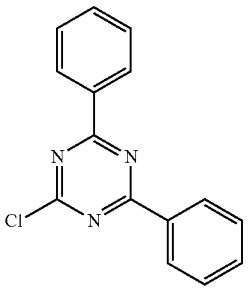 | 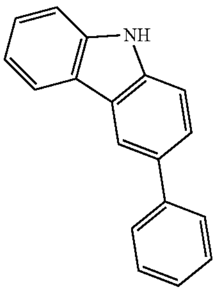 |

TABLE 6-continued
| | | | |
|---|---|---|---|
| 975 | 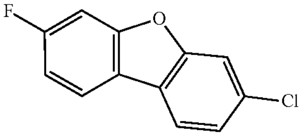 | 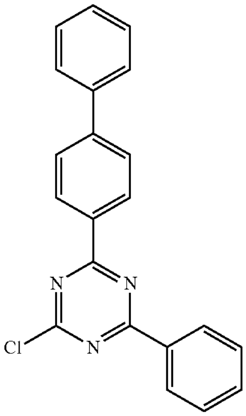 | 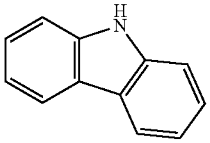 |
| 977 | 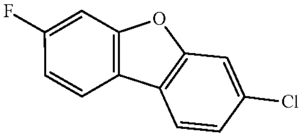 | 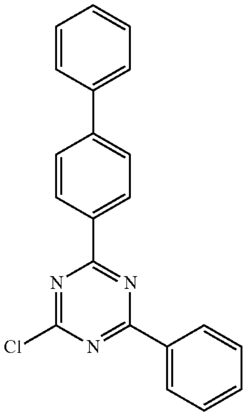 | 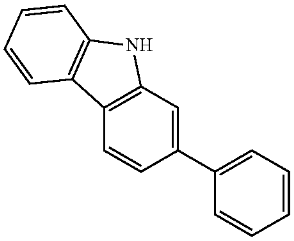 |
| 987 | 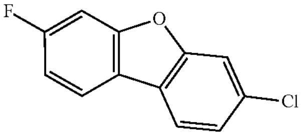 | 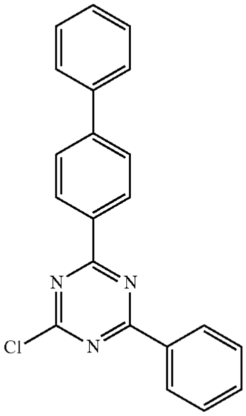 | 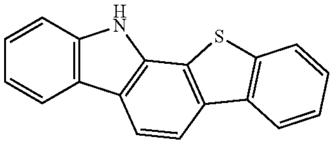 |
| 991 | 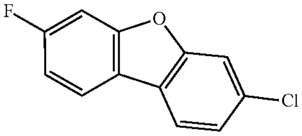 | 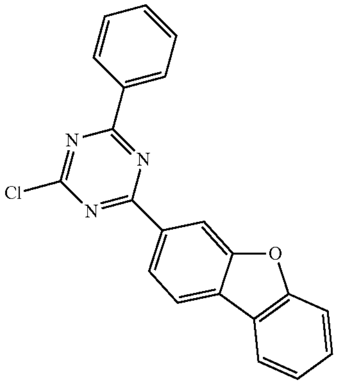 | 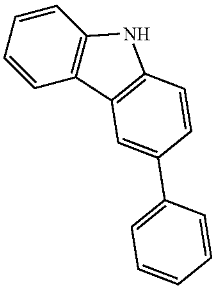 |

TABLE 6-continued
| | | | |
|---|---|---|---|
| 998 | 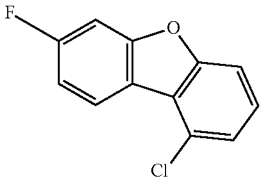 | 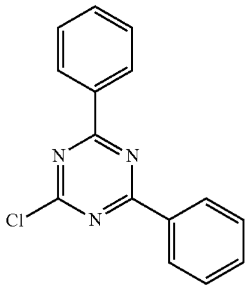 | 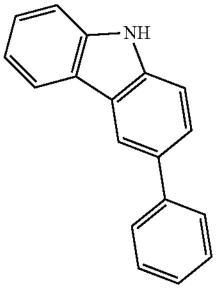 |
| 999 | 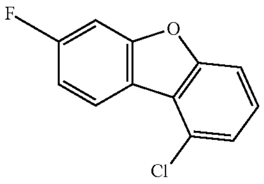 | 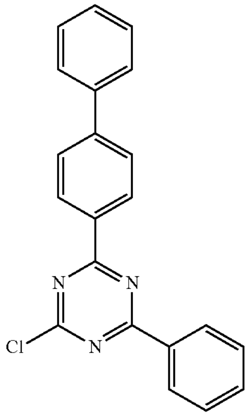 | 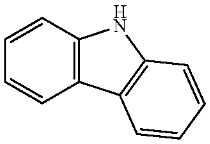 |
| 1003 | 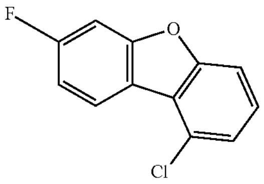 | 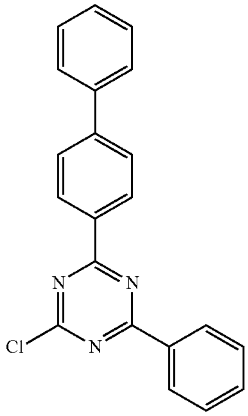 | 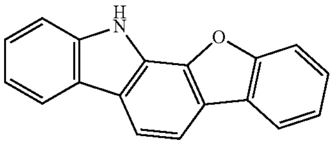 |
| 1009 | 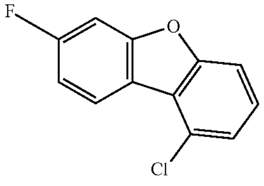 | 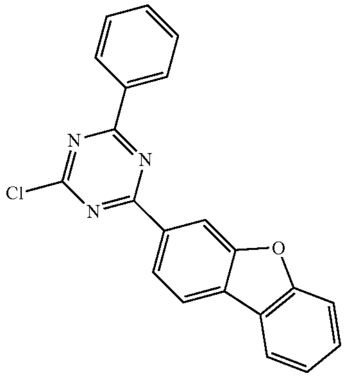 | 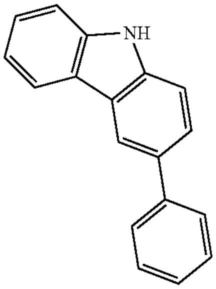 |

TABLE 6-continued
| | | | |
|---|---|---|---|
| 1014 | 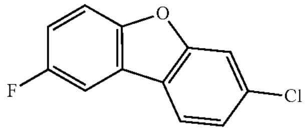 [SMILES: Fc1ccc2oc3cc(Cl)ccc3c2c1] | 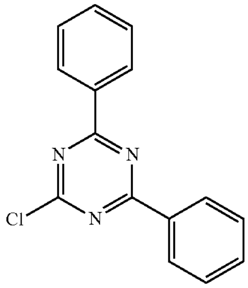 [SMILES: Clc1nc(-c2ccccc2)nc(-c2ccccc2)n1] | 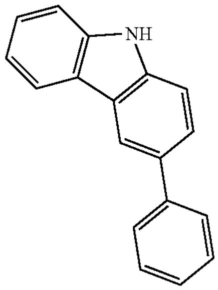 [SMILES: c1ccc(-c2ccc3[nH]c4ccccc4c3c2)cc1] |
| 1016 | 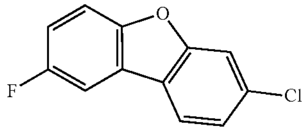 [SMILES: Fc1ccc2oc3cc(Cl)ccc3c2c1] | 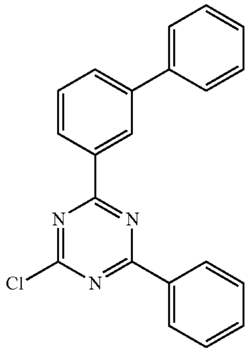 [SMILES: Clc1nc(-c2ccccc2)nc(-c2cccc(-c3ccccc3)c2)n1] | 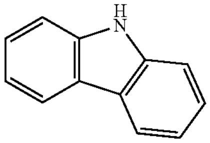 [SMILES: c1ccc2c(c1)[nH]c1ccccc12] |
| 1018 | 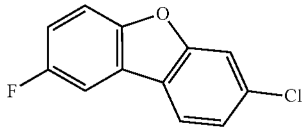 [SMILES: Fc1ccc2oc3cc(Cl)ccc3c2c1] | 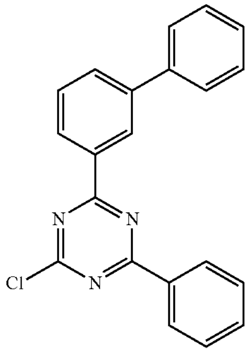 [SMILES: Clc1nc(-c2ccccc2)nc(-c2cccc(-c3ccccc3)c2)n1] | 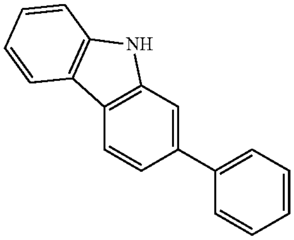 [SMILES: c1ccc(-c2ccc3c(c2)[nH]c2ccccc23)cc1] |
| 1023 | 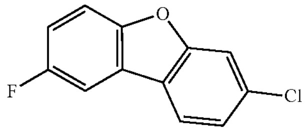 [SMILES: Fc1ccc2oc3cc(Cl)ccc3c2c1] | 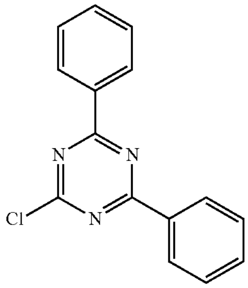 [SMILES: Clc1nc(-c2ccccc2)nc(-c2ccccc2)n1] | 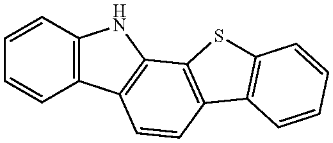 |
| 1033 | 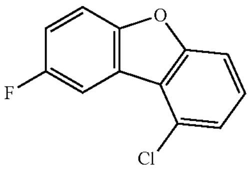 [SMILES: Fc1ccc2oc3cccc(Cl)c3c2c1] | 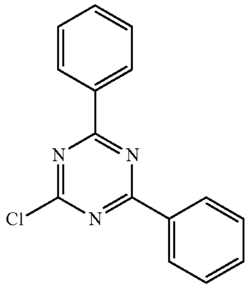 [SMILES: Clc1nc(-c2ccccc2)nc(-c2ccccc2)n1] | 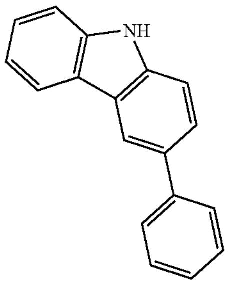 [SMILES: c1ccc(-c2ccc3[nH]c4ccccc4c3c2)cc1] |

TABLE 6-continued
| | | | |
|---|---|---|---|
| 1038 | 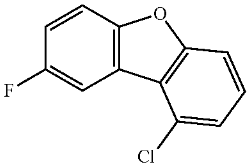 [SMILES: Fc1ccc2oc3cccc(Cl)c3c2c1] | 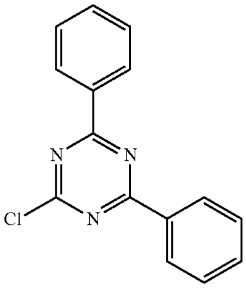 [SMILES: Clc1nc(-c2ccccc2)nc(-c2ccccc2)n1] | 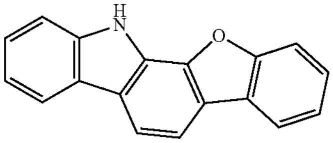 |
| 1046 | 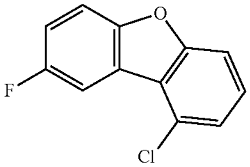 [SMILES: Fc1ccc2oc3cccc(Cl)c3c2c1] | 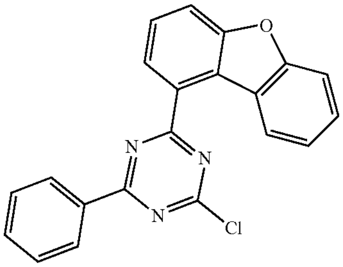 [SMILES: Clc1nc(-c2ccccc2)nc(-c2cccc3oc4ccccc4c23)n1] | 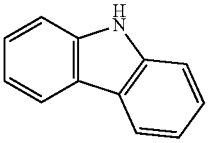 [SMILES: c1ccc2c(c1)[nH]c1ccccc12] |
| 1050 | 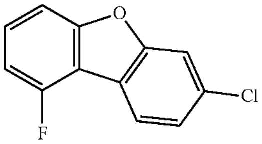 [SMILES: Fc1cccc2oc3cc(Cl)ccc3c12] | 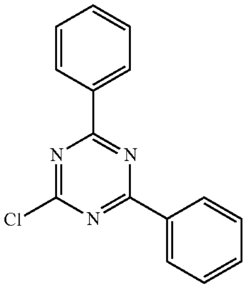 [SMILES: Clc1nc(-c2ccccc2)nc(-c2ccccc2)n1] | 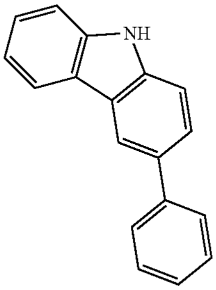 [SMILES: c1ccc(-c2ccc3[nH]c4ccccc4c3c2)cc1] |
| 1051 | 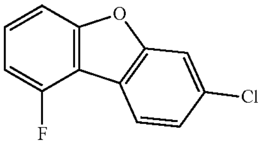 [SMILES: Fc1cccc2oc3cc(Cl)ccc3c12] | 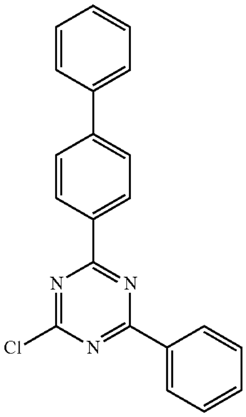 [SMILES: Clc1nc(-c2ccccc2)nc(-c2ccc(-c3ccccc3)cc2)n1] | 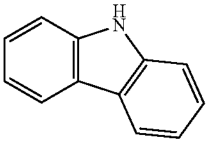 [SMILES: c1ccc2c(c1)[nH]c1ccccc12] |
| 1055 | 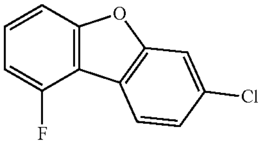 [SMILES: Fc1cccc2oc3cc(Cl)ccc3c12] | 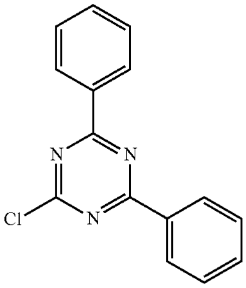 [SMILES: Clc1nc(-c2ccccc2)nc(-c2ccccc2)n1] | 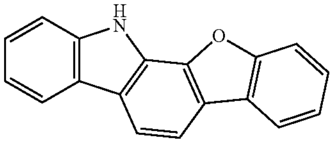 |

TABLE 6-continued
| | | | |
|---|---|---|---|
| 1060 | 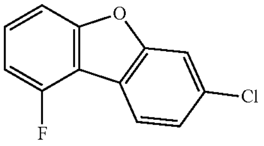 [SMILES: Fc1cccc2oc3cc(Cl)ccc3c12] | 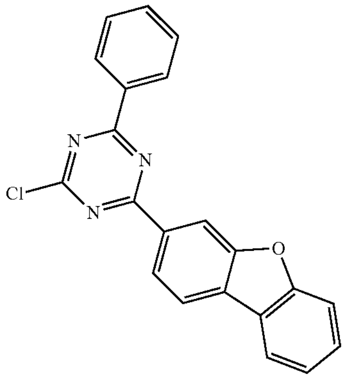 [SMILES: Clc1nc(-c2ccccc2)nc(-c2ccc3c(c2)oc2ccccc23)n1] | 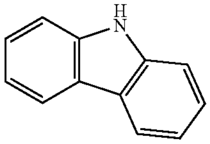 |
| Compound | J | yield |
|---|---|---|
| 929 | 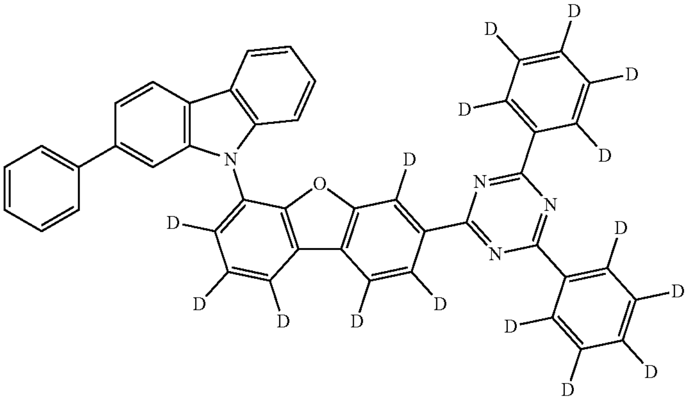 | 93% |
| 930 | 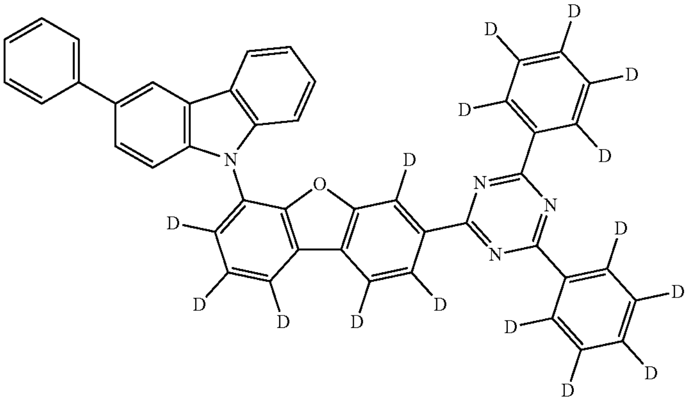 | 77% |

TABLE 6-continued
| | | |
|---|---|---|
| 932 | 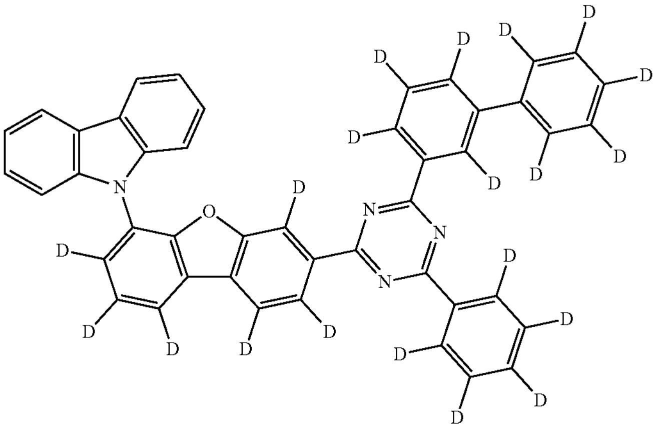 | 86% |
| 933 | 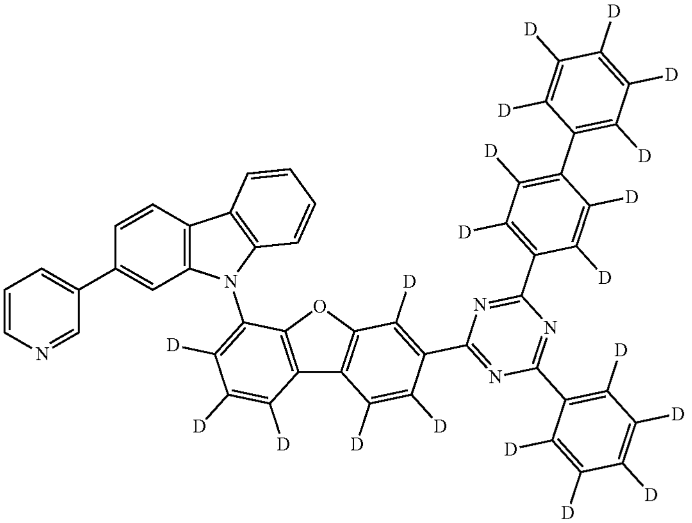 | 71% |
| 945 | 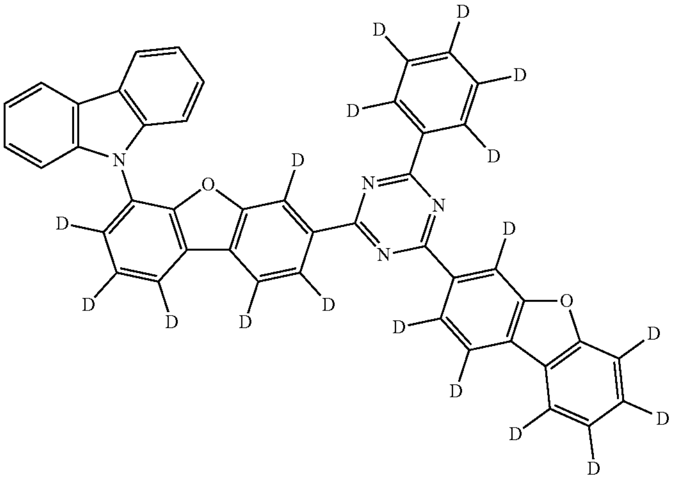 | 59% |

TABLE 6-continued
| | | |
|---|---|---|
| 951 | 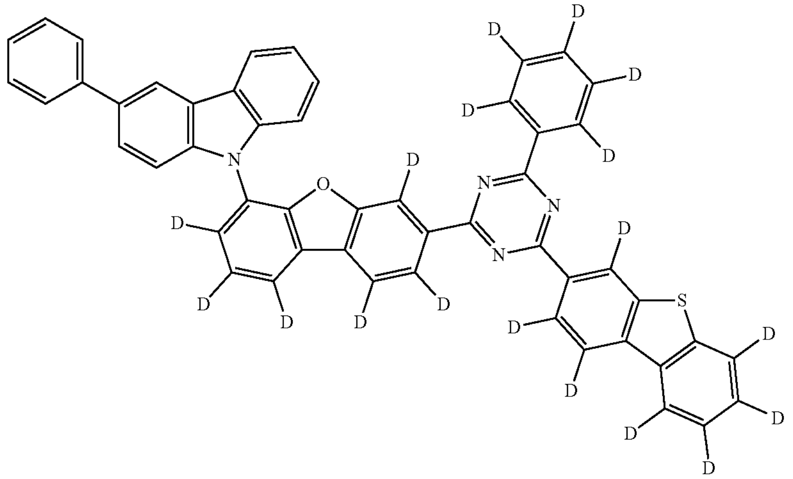 | 68% |
| 954 | 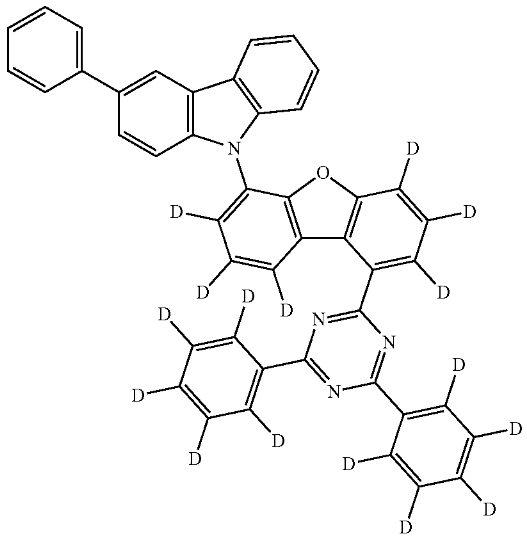 | 55% |
| 959 | 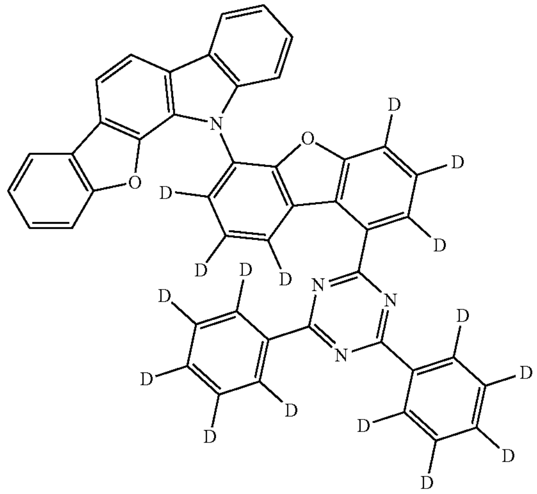 | 79% |

TABLE 6-continued
| | | |
|---|---|---|
| 967 | 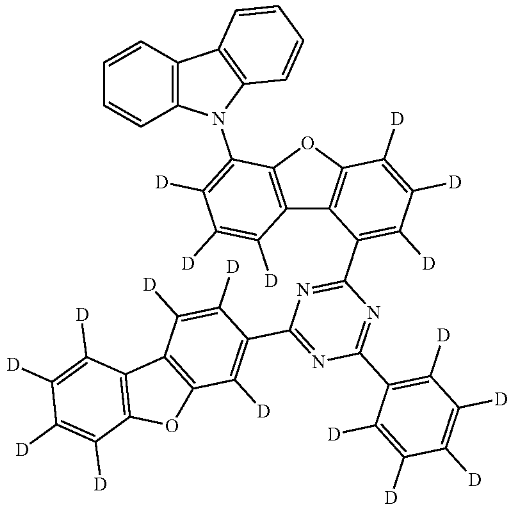 | 81% |
| 969 | 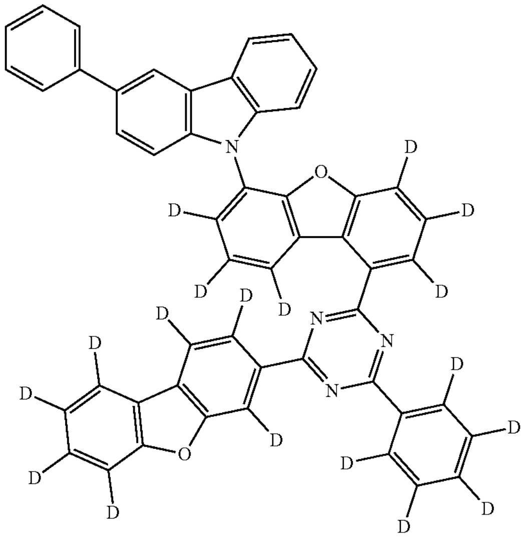 | 77% |
| 973 | 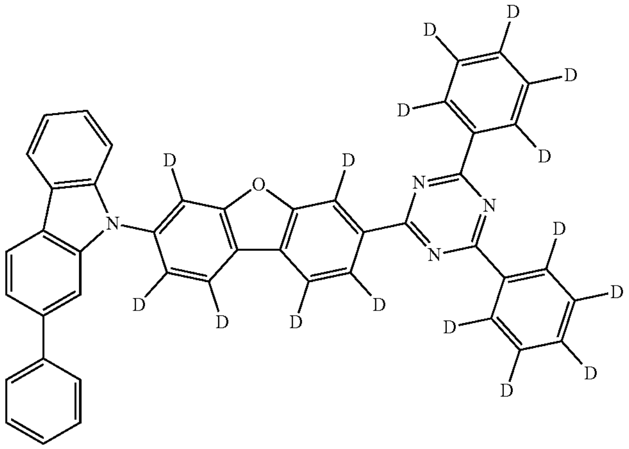 | 86% |

TABLE 6-continued
| | | |
|---|---|---|
| 974 | 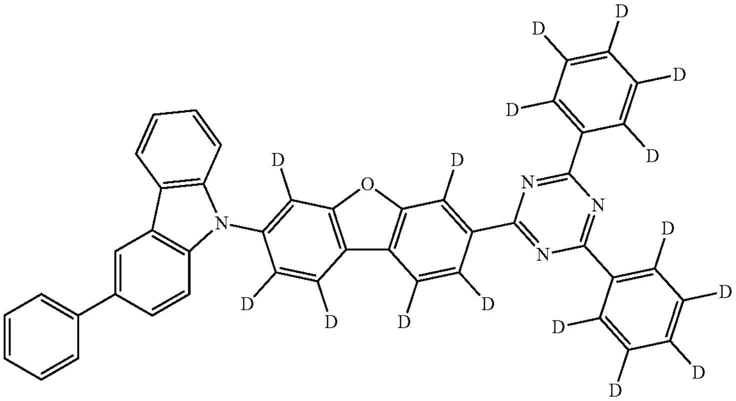 | 69% |
| 975 | 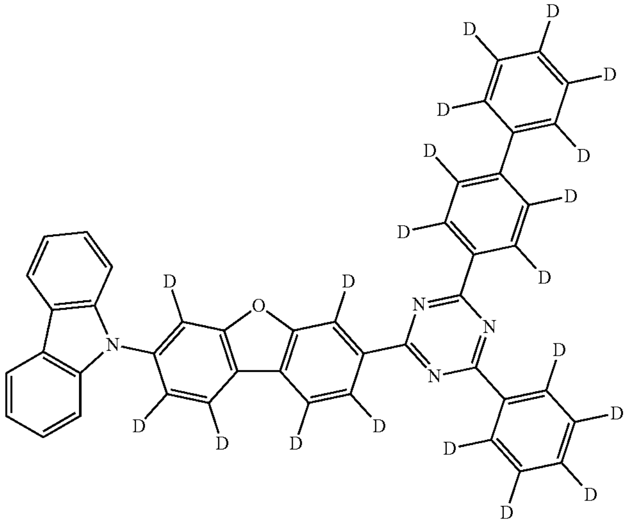 | 91% |
| 977 | 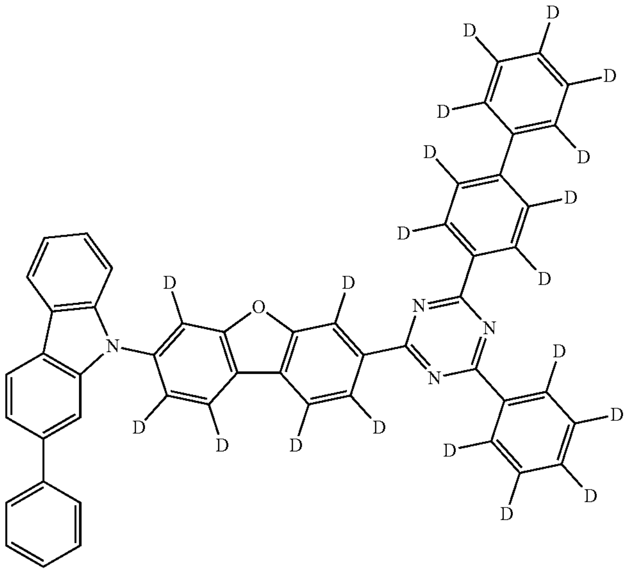 | 67% |

TABLE 6-continued
987 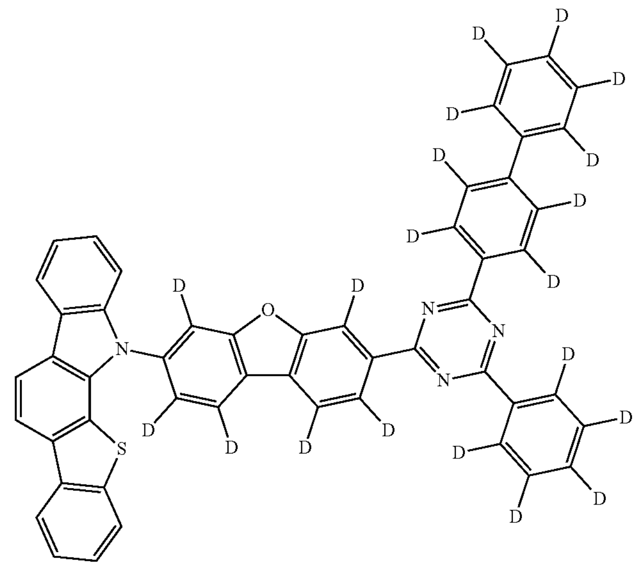 [SMILES: [2H]c1c([2H])c([2H])c(-c2nc(-c3c([2H])c([2H])c(-c4c([2H])c([2H])c([2H])c([2H])c4[2H])c([2H])c3[2H])nc(-c3c([2H])c([2H])c4c(oc5c([2H])c(-n6c7ccccc7c7ccc8c9ccccc9sc8c76)c([2H])c([2H])c54)c3[2H])n2)c([2H])c1[2H]] 92%
991 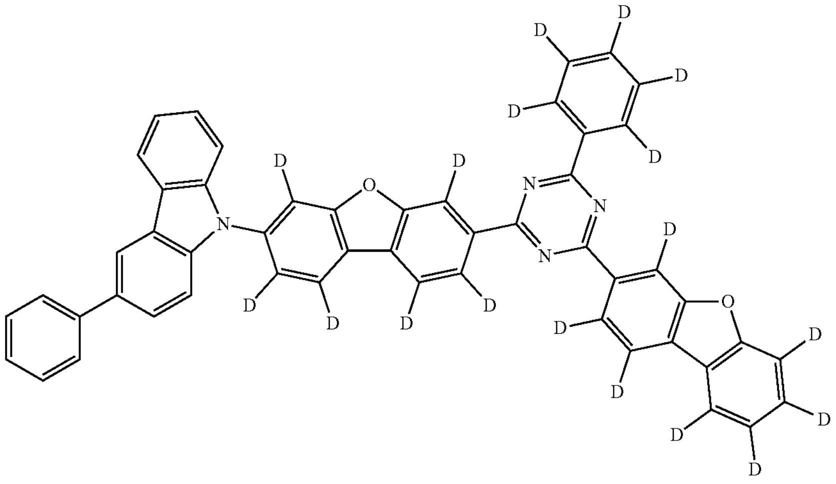 [SMILES: [2H]c1c([2H])c([2H])c(-c2nc(-c3c([2H])c([2H])c4c(oc5c([2H])c([2H])c([2H])c([2H])c54)c3[2H])nc(-c3c([2H])c([2H])c4c(oc5c([2H])c(-n6c7ccccc7c7cc(-c8ccccc8)ccc76)c([2H])c([2H])c54)c3[2H])n2)c([2H])c1[2H]] 95%
998 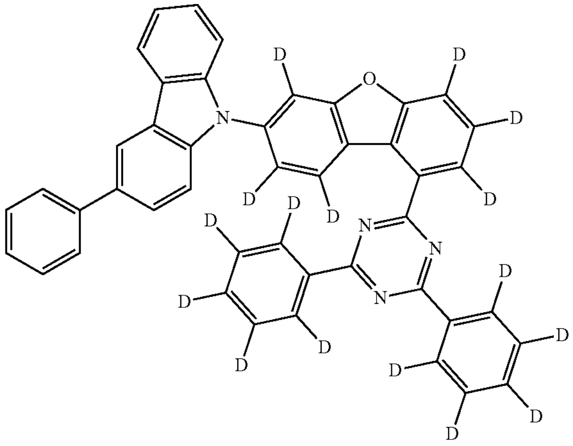 [SMILES: [2H]c1c([2H])c([2H])c(-c2nc(-c3c([2H])c([2H])c([2H])c([2H])c3[2H])nc(-c3c([2H])c([2H])c([2H])c4oc5c([2H])c(-n6c7ccccc7c7cc(-c8ccccc8)ccc76)c([2H])c([2H])c5c34)n2)c([2H])c1[2H]] 74%

TABLE 6-continued
999 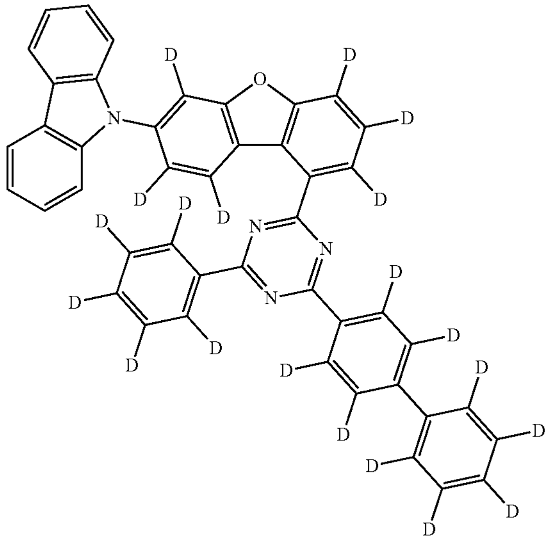 [SMILES: [2H]c1c([2H])c([2H])c(-c2nc(-c3c([2H])c([2H])c(-c4c([2H])c([2H])c([2H])c([2H])c4[2H])c([2H])c3[2H])nc(-c3c([2H])c([2H])c([2H])c4oc5c([2H])c(-n6c7ccccc7c7ccccc76)c([2H])c([2H])c5c34)n2)c([2H])c1[2H]] 59%
1003 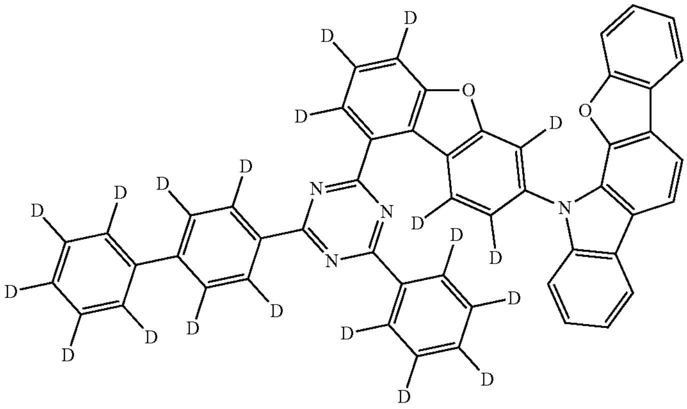 [SMILES: [2H]c1c([2H])c([2H])c(-c2nc(-c3c([2H])c([2H])c(-c4c([2H])c([2H])c([2H])c([2H])c4[2H])c([2H])c3[2H])nc(-c3c([2H])c([2H])c([2H])c4oc5c([2H])c(-n6c7ccccc7c7ccc8c9ccccc9oc8c76)c([2H])c([2H])c5c34)n2)c([2H])c1[2H]] 63%
1009 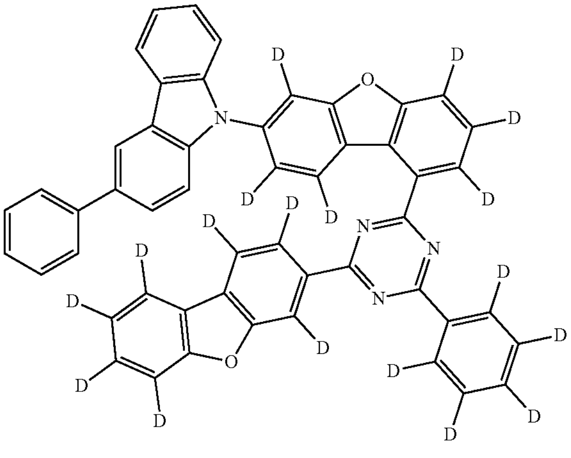 [SMILES: [2H]c1c([2H])c([2H])c(-c2nc(-c3c([2H])c([2H])c4c(oc5c([2H])c([2H])c([2H])c([2H])c54)c3[2H])nc(-c3c([2H])c([2H])c([2H])c4oc5c([2H])c(-n6c7ccccc7c7cc(-c8ccccc8)ccc76)c([2H])c([2H])c5c34)n2)c([2H])c1[2H]] 77%

TABLE 6-continued
1014 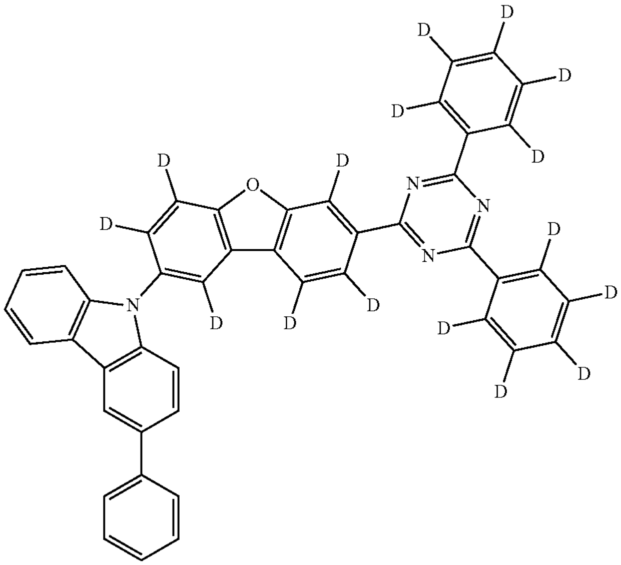 [SMILES: [2H]c1c([2H])c([2H])c(-c2nc(-c3c([2H])c([2H])c([2H])c([2H])c3[2H])nc(-c3c([2H])c([2H])c4c(oc5c([2H])c([2H])c(-n6c7ccccc7c7cc(-c8ccccc8)ccc76)c([2H])c54)c3[2H])n2)c([2H])c1[2H]] 59%
1016 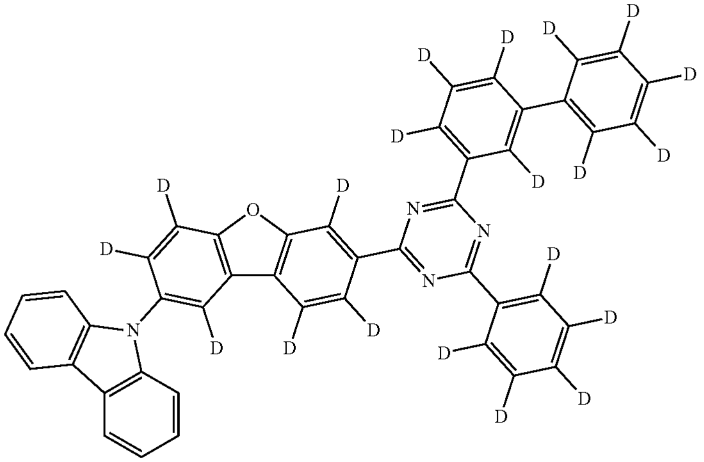 [SMILES: [2H]c1c([2H])c([2H])c(-c2nc(-c3c([2H])c([2H])c([2H])c(-c4c([2H])c([2H])c([2H])c([2H])c4[2H])c3[2H])nc(-c3c([2H])c([2H])c4c(oc5c([2H])c([2H])c(-n6c7ccccc7c7ccccc76)c([2H])c54)c3[2H])n2)c([2H])c1[2H]] 68%
1018 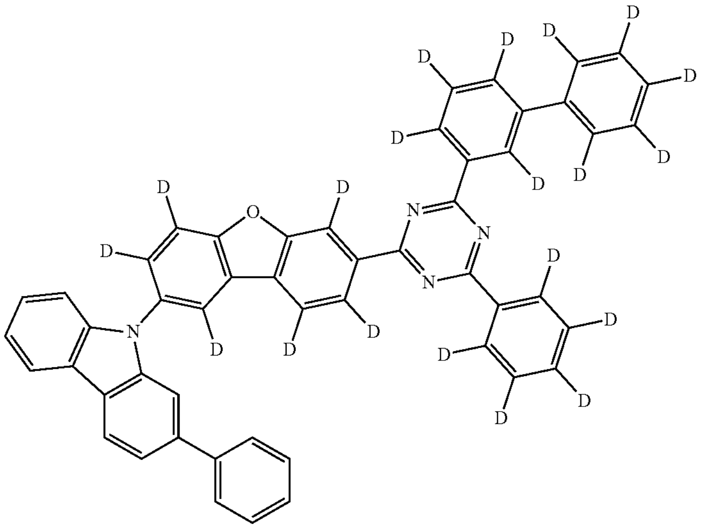 [SMILES: [2H]c1c([2H])c([2H])c(-c2nc(-c3c([2H])c([2H])c([2H])c(-c4c([2H])c([2H])c([2H])c([2H])c4[2H])c3[2H])nc(-c3c([2H])c([2H])c4c(oc5c([2H])c([2H])c(-n6c7ccccc7c7ccc(-c8ccccc8)cc76)c([2H])c54)c3[2H])n2)c([2H])c1[2H]] 74%

TABLE 6-continued
| | | |
|---|---|---|
| 1023 | 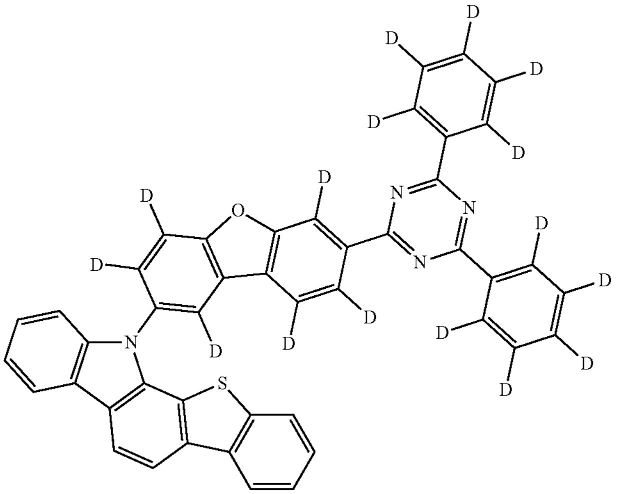 [SMILES: [2H]c1c([2H])c([2H])c(-c2nc(-c3c([2H])c([2H])c([2H])c([2H])c3[2H])nc(-c3c([2H])c([2H])c4c(oc5c([2H])c([2H])c(-n6c7ccccc7c7ccc8c9ccccc9sc8c76)c([2H])c54)c3[2H])n2)c([2H])c1[2H]] | 65% |
| 1033 | 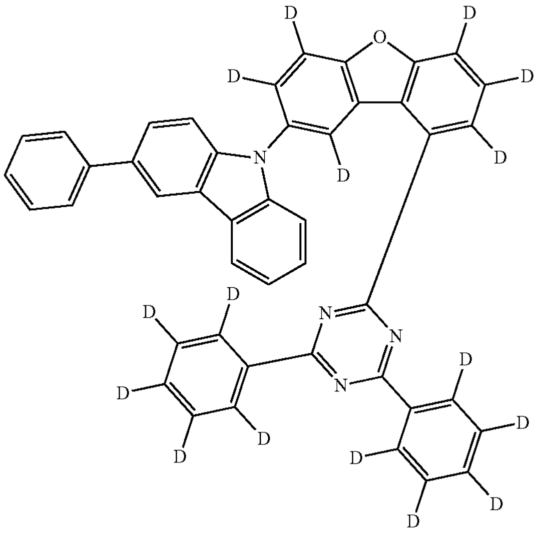 [SMILES: [2H]c1c([2H])c([2H])c(-c2nc(-c3c([2H])c([2H])c([2H])c([2H])c3[2H])nc(-c3c([2H])c([2H])c([2H])c4oc5c([2H])c([2H])c(-n6c7ccccc7c7cc(-c8ccccc8)ccc76)c([2H])c5c34)n2)c([2H])c1[2H]] | 66% |
| 1038 | 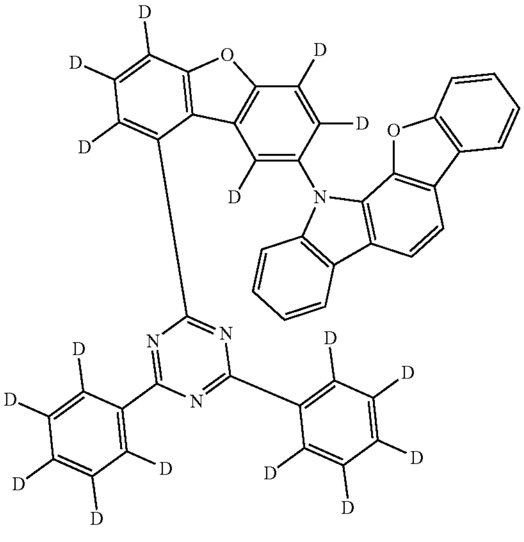 [SMILES: [2H]c1c([2H])c([2H])c(-c2nc(-c3c([2H])c([2H])c([2H])c([2H])c3[2H])nc(-c3c([2H])c([2H])c([2H])c4oc5c([2H])c([2H])c(-n6c7ccccc7c7ccc8c9ccccc9oc8c76)c([2H])c5c34)n2)c([2H])c1[2H]] | 93% |

TABLE 6-continued
| | | |
|---|---|---|
| 1046 | 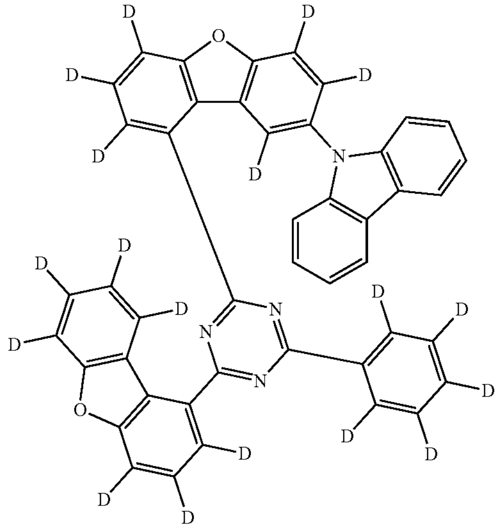 [SMILES: [2H]c1c([2H])c([2H])c(-c2nc(-c3c([2H])c([2H])c([2H])c4oc5c([2H])c([2H])c([2H])c([2H])c5c34)nc(-c3c([2H])c([2H])c([2H])c4oc5c([2H])c([2H])c(-n6c7ccccc7c7ccccc76)c([2H])c5c34)n2)c([2H])c1[2H]] | 87% |
| 1050 | 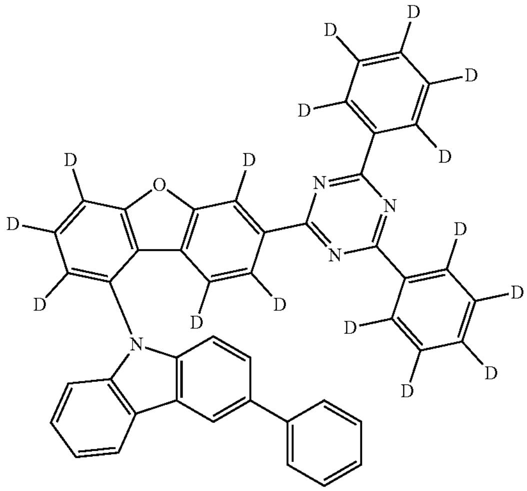 [SMILES: [2H]c1c([2H])c([2H])c(-c2nc(-c3c([2H])c([2H])c([2H])c([2H])c3[2H])nc(-c3c([2H])c([2H])c4c(oc5c([2H])c([2H])c([2H])c(-n6c7ccccc7c7cc(-c8ccccc8)ccc76)c54)c3[2H])n2)c([2H])c1[2H]] | 56% |
| 1051 | 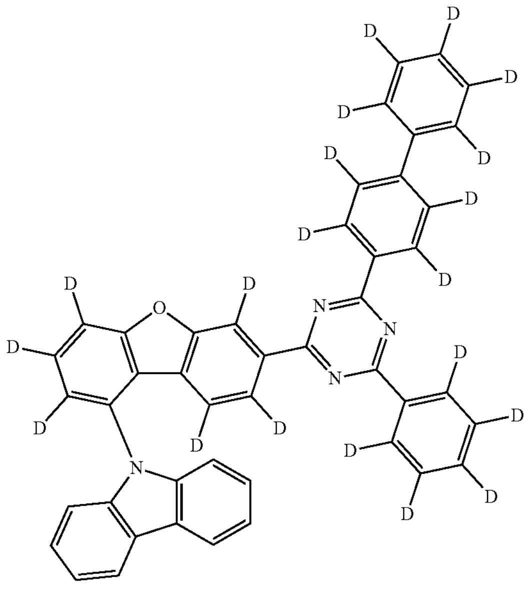 [SMILES: [2H]c1c([2H])c([2H])c(-c2nc(-c3c([2H])c([2H])c(-c4c([2H])c([2H])c([2H])c([2H])c4[2H])c([2H])c3[2H])nc(-c3c([2H])c([2H])c4c(oc5c([2H])c([2H])c([2H])c(-n6c7ccccc7c7ccccc76)c54)c3[2H])n2)c([2H])c1[2H]] | 74% |

TABLE 6-continued
| | | |
|---|---|---|
| 1055 | 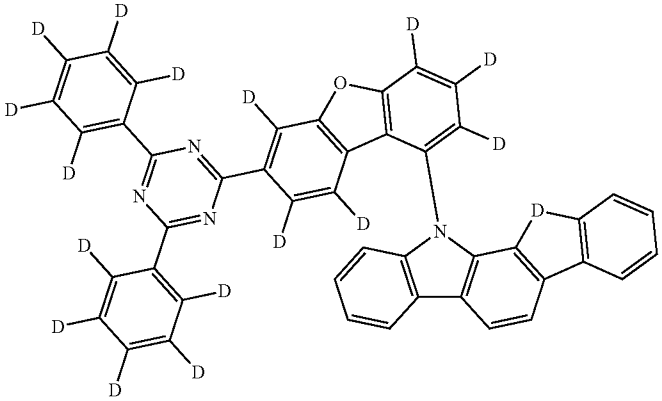 | 69% |
| 1060 | 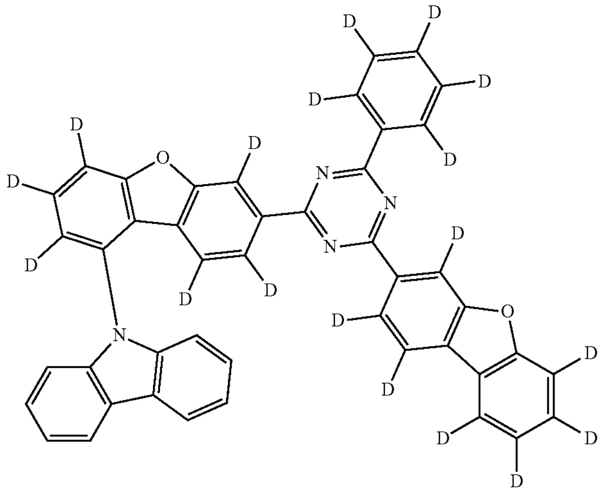 [SMILES: [2H]c1c([2H])c([2H])c(-c2nc(-c3c([2H])c([2H])c4c(oc5c([2H])c([2H])c([2H])c([2H])c54)c3[2H])nc(-c3c([2H])c([2H])c4c(oc5c([2H])c([2H])c([2H])c(-n6c7ccccc7c7ccccc76)c54)c3[2H])n2)c([2H])c1[2H]] | 71% |
[Synthesis 7] The compound 1073 (K)
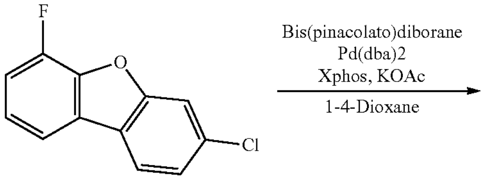
[A]
-continued
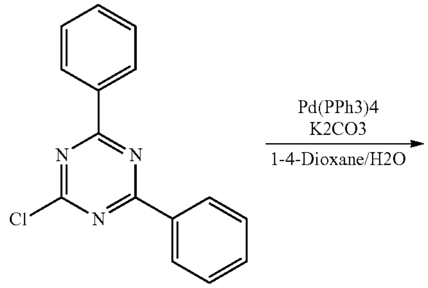
[B]
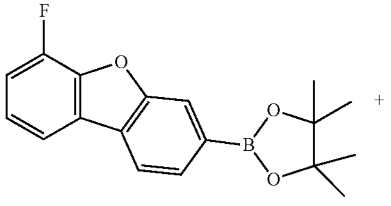
1073-1
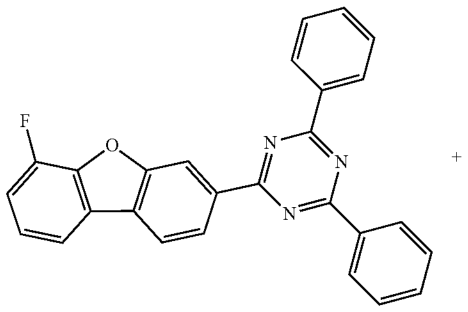
1073-2

-continued

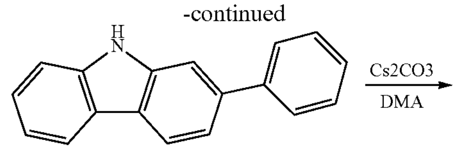

[C]

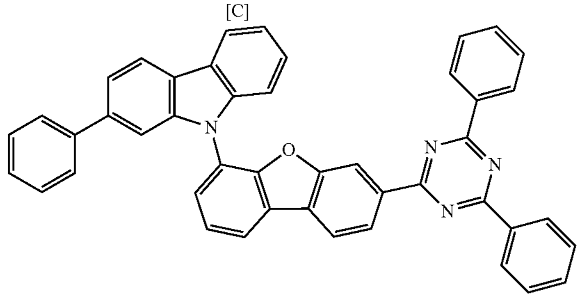

1073[K]

(1) The Compound 1073-1

In the one-neck round bottom flask, a mixture of 3-chloro-6-fluorodibenzo[b,d]furan (10 g, 0.045 mol), bis(pinacolato) diborn (22.85 g, 0.090 mol), Pd(dba)2 (4.12) g, 0.0045 mol), Xphos (8.58 g, 0.018 mol), potassium acetate (13.25 g, 00.14 mol) and 1,4-dioxane (100 mL) were refluxed at 120° C. After cooling, the resultant was concentrated and filtered through silica gel to obtain the compound 1073-1. (13.77 g, 98%)

(2) The Compound 1073-2

In the one-neck round bottom flask, a mixture of 2-(6-fluorodibenzo[b,d]furan-3-yl)-4,4,5,5-tetramethyl-1,3,2-dioxaborolane (13.77 g, 0.044 mol), 2-chloro-4,6-diphenyl-1,3,5-triazine (12.96 g, 0.048 mol), Pd(PPh3)4 (2.54 g, 0.0022 mol), $K_2CO_3$ (12.16 g, 0.088 mol), 1,4-dioxane (130 mL) and water (40 mL) was refluxed at 120° C. After cooling, the resultant was concentrated and filtered through silica gel to obtain the compound 1073-2. (12.49 g, 68%)

(3) The Compound 1073[K]

In the one-neck round bottom flask, a mixture of 2-(6-fluorodibenzo[b,d]furan-3-yl)-4,6-diphenyl-1,3,5-triazine (12.49 g, 0.030 mol), 2-phenyl-9H-carbazole (8.03 g, 0.00.033 mol), $Cs_2CO_3$ (19.55 g, 0.060 mol) and dimethylacetamide (120 mL) were refluxed at 170° C. After cooling, the resultant was filtered to remove the solvent and purified by column to obtain the compound 1073[K]. (16.92 g, 88%)

The following compound K was synthesized in the same manner as in the synthesis 7 except that intermediates A, B, and C of Table 7 were used.

TABLE 7

| Com-pound | A A | B B | C |
|---|---|---|---|
| 1073 | 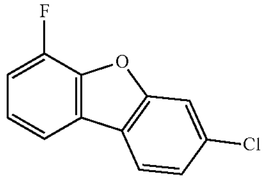 | 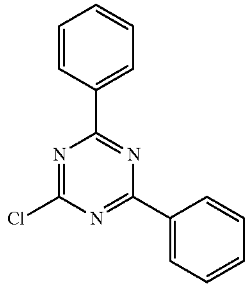 | 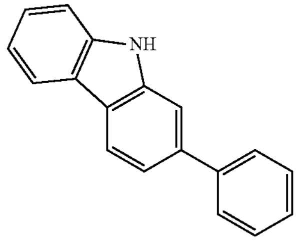 |
| 1079 | 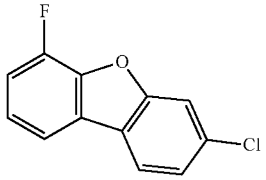 | 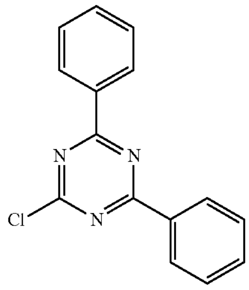 | 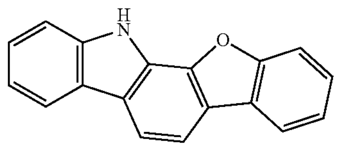 |
| 1084 | 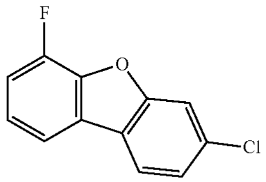 | 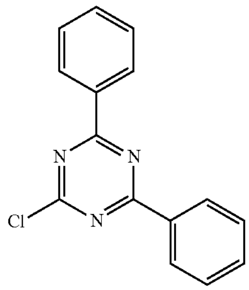 | 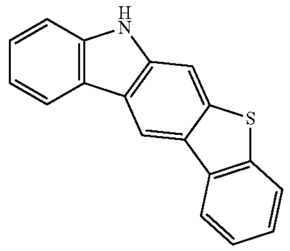 |

TABLE 7-continued
| | | | |
|---|---|---|---|
| 1088 | 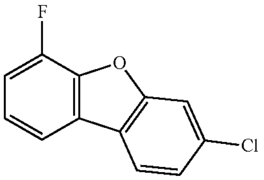 | 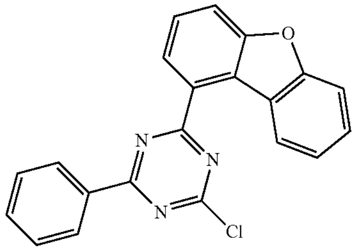 | 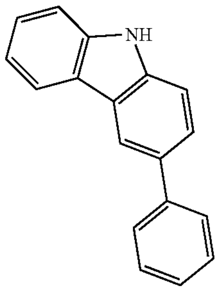 |
| 1090 | 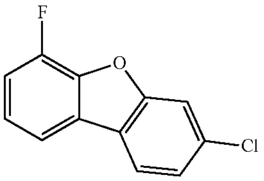 | 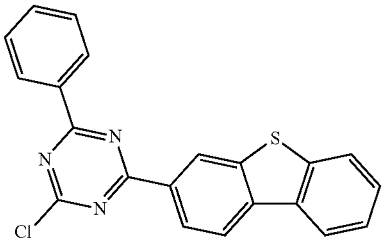 | 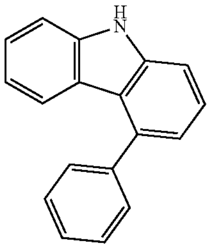 |
| 1094 | 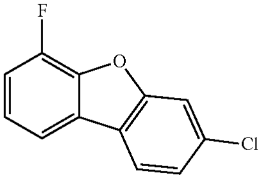 | 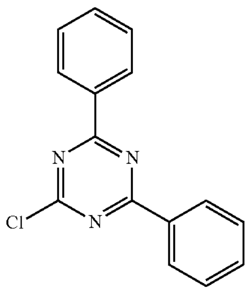 | 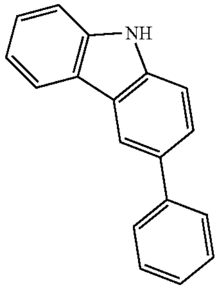 |
| 1098 | 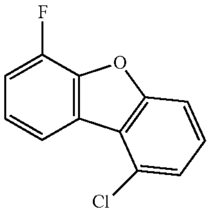 | 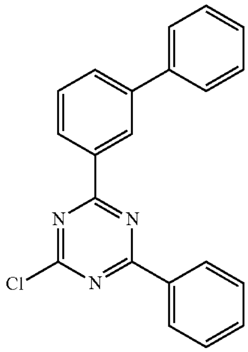 | 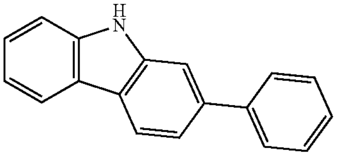 |
| 1100 | 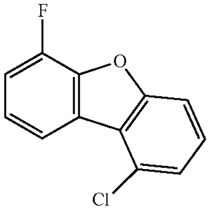 | 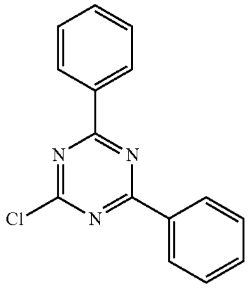 | 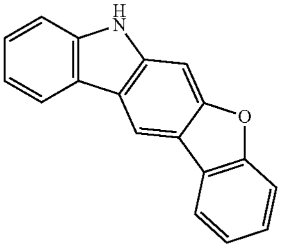 |

TABLE 7-continued
| | | | |
|---|---|---|---|
| 1103 | 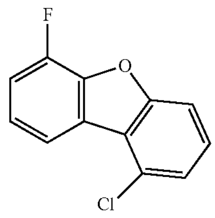 | 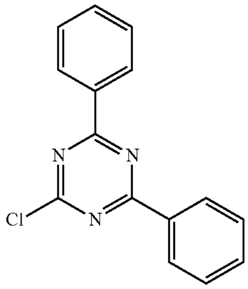 | 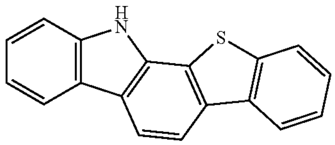 |
| 1108 | 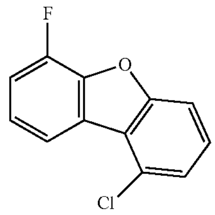 | 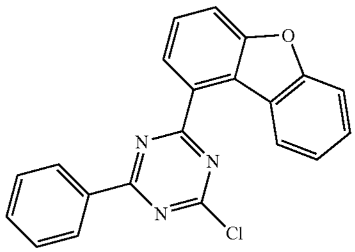 | 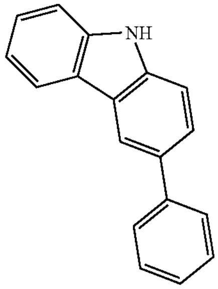 |
| 1113 | 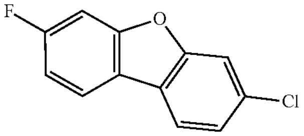 | 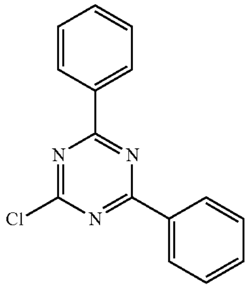 | 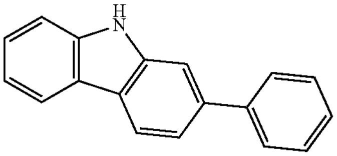 |
| 1114 | 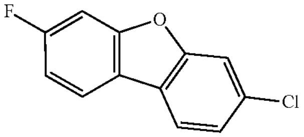 | 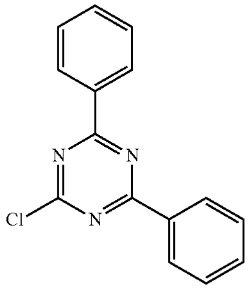 | 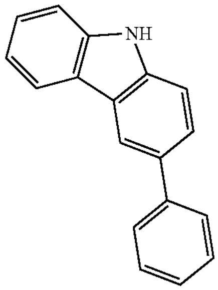 |
| 1116 | 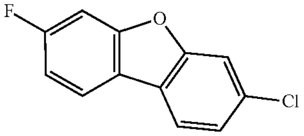 | 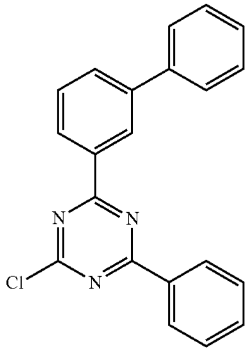 | 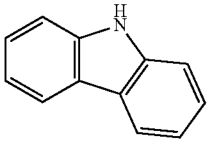 |

TABLE 7-continued
| | | | |
|---|---|---|---|
| 1121 | 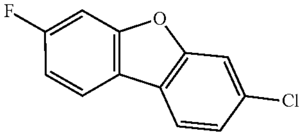 | 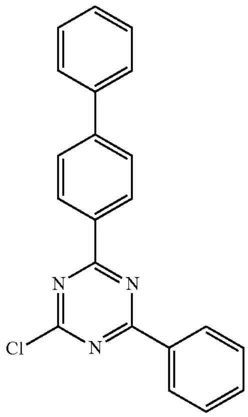 | 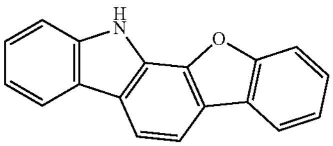 |
| 1123 | 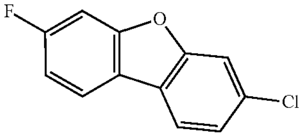 | 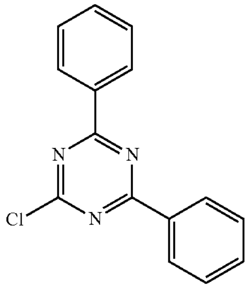 | 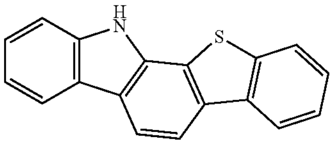 |
| 1127 | 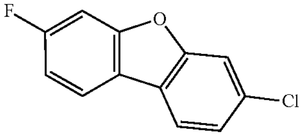 | 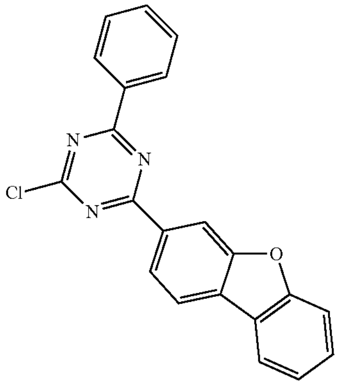 | 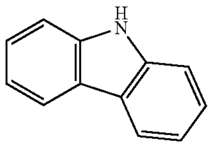 |
| 1133 | 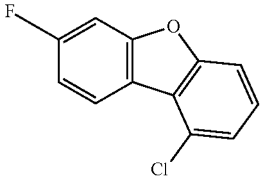 | 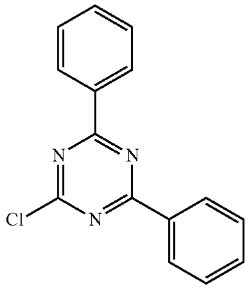 | 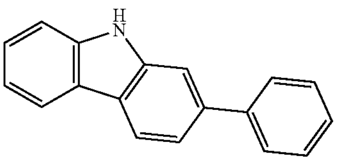 |

TABLE 7-continued
| | | | |
|---|---|---|---|
| 1135 | 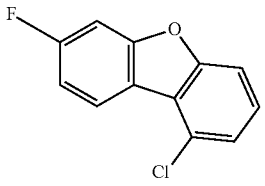 | 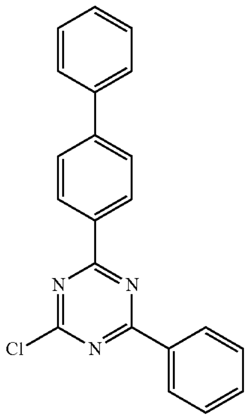 | 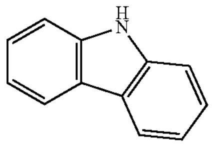 |
| 1138 | 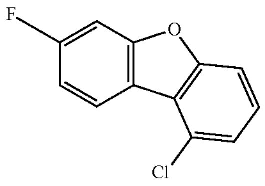 | 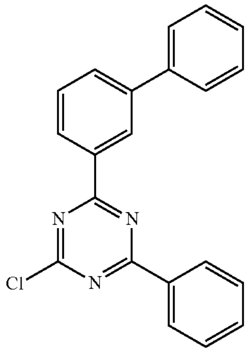 | 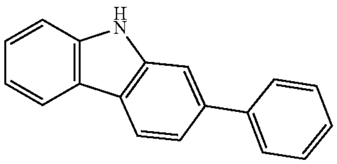 |
| 1143 | 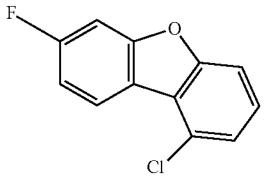 | 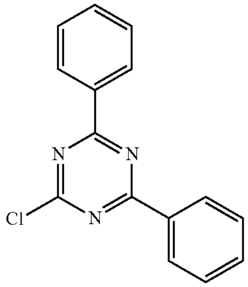 | 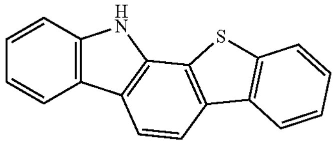 |
| 1145 | 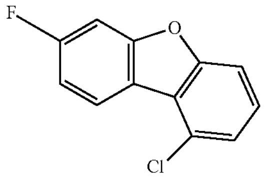 | 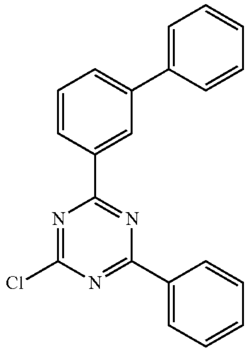 | 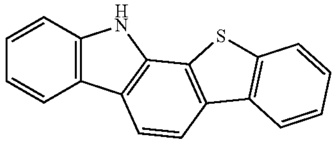 |

TABLE 7-continued
| | | | |
|---|---|---|---|
| 1152 | 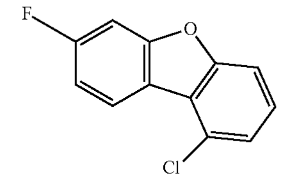 [SMILES: Fc1ccc2c(c1)oc1cccc(Cl)c12] | 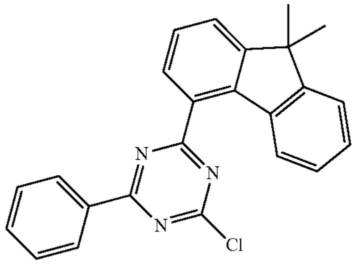 [SMILES: CC1(C)c2ccccc2-c2c(-c3nc(Cl)nc(-c4ccccc4)n3)cccc21] | 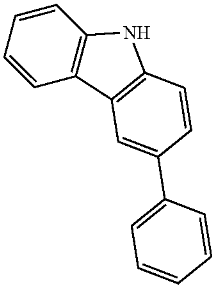 [SMILES: c1ccc(-c2ccc3[nH]c4ccccc4c3c2)cc1] |
| 1159 | 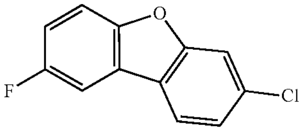 [SMILES: Fc1ccc2oc3cc(Cl)ccc3c2c1] | 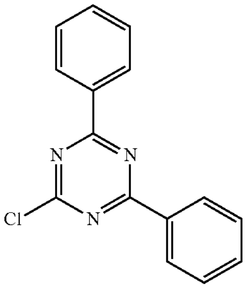 [SMILES: Clc1nc(-c2ccccc2)nc(-c2ccccc2)n1] | 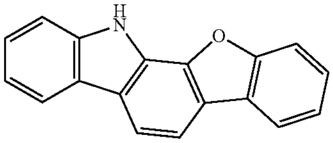 |
| 1163 | 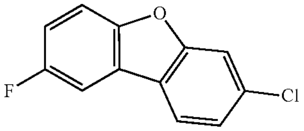 [SMILES: Fc1ccc2oc3cc(Cl)ccc3c2c1] | 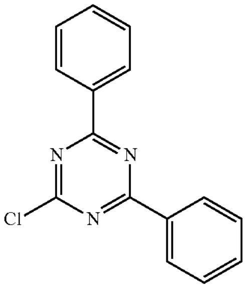 [SMILES: Clc1nc(-c2ccccc2)nc(-c2ccccc2)n1] | 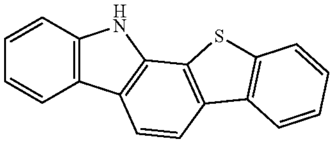 |
| 1169 | 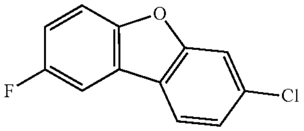 [SMILES: Fc1ccc2oc3cc(Cl)ccc3c2c1] | 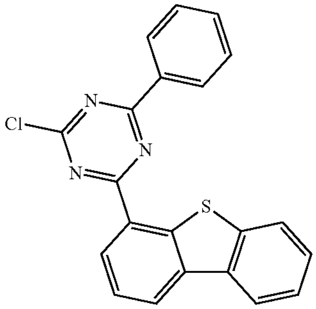 [SMILES: Clc1nc(-c2ccccc2)nc(-c2cccc3c2sc2ccccc23)n1] | 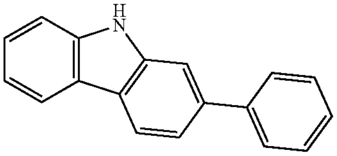 [SMILES: c1ccc(-c2ccc3c(c2)[nH]c2ccccc23)cc1] |
| 1176 | 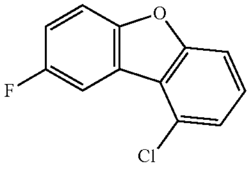 [SMILES: Fc1ccc2oc3cccc(Cl)c3c2c1] | 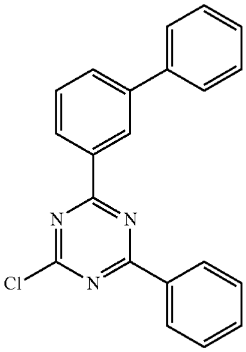 [SMILES: Clc1nc(-c2ccccc2)nc(-c2cccc(-c3ccccc3)c2)n1] | 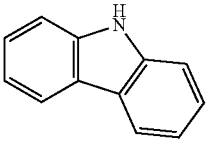 [SMILES: c1ccc2c(c1)[nH]c1ccccc12] |

TABLE 7-continued
| | | | |
|---|---|---|---|
| 1179 | 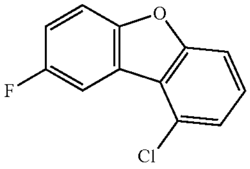 [SMILES: Fc1ccc2oc3cccc(Cl)c3c2c1] | 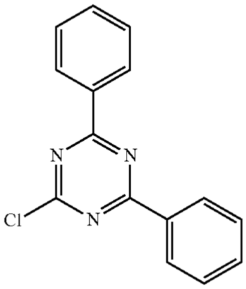 [SMILES: Clc1nc(-c2ccccc2)nc(-c2ccccc2)n1] | 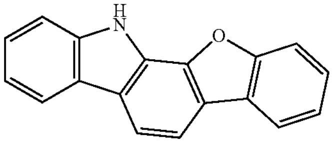 |
| 1193 | 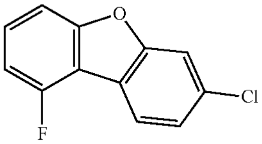 [SMILES: Fc1cccc2oc3cc(Cl)ccc3c12] | 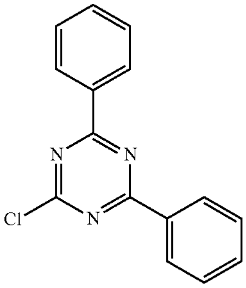 [SMILES: Clc1nc(-c2ccccc2)nc(-c2ccccc2)n1] | 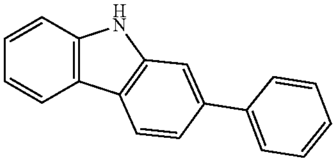 [SMILES: c1ccc(-c2ccc3c(c2)[nH]c2ccccc23)cc1] |
| 1196 | 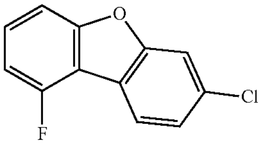 [SMILES: Fc1cccc2oc3cc(Cl)ccc3c12] | 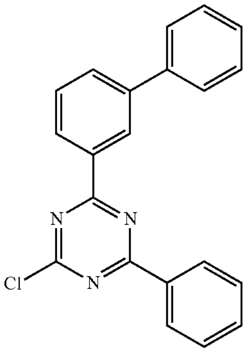 [SMILES: Clc1nc(-c2ccccc2)nc(-c2cccc(-c3ccccc3)c2)n1] | 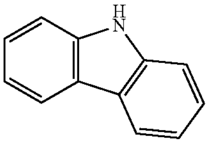 [SMILES: c1ccc2c(c1)[nH]c1ccccc12] |
| 1199 | 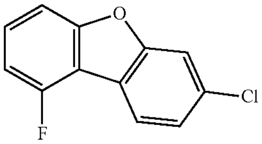 [SMILES: Fc1cccc2oc3cc(Cl)ccc3c12] | 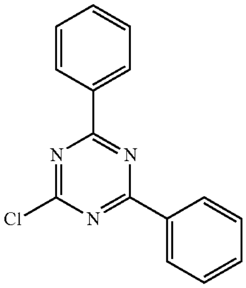 [SMILES: Clc1nc(-c2ccccc2)nc(-c2ccccc2)n1] | 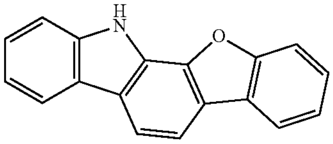 |
| 1207 | 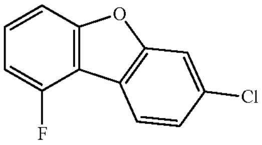 [SMILES: Fc1cccc2oc3cc(Cl)ccc3c12] | 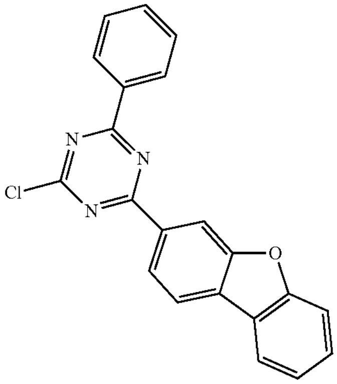 [SMILES: Clc1nc(-c2ccccc2)nc(-c2ccc3c(c2)oc2ccccc23)n1] | 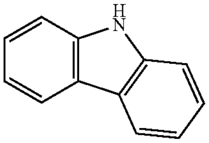 [SMILES: c1ccc2c(c1)[nH]c1ccccc12] |

TABLE 7-continued
| Compound | K | yield |
| --- | --- | --- |
| 1073 | 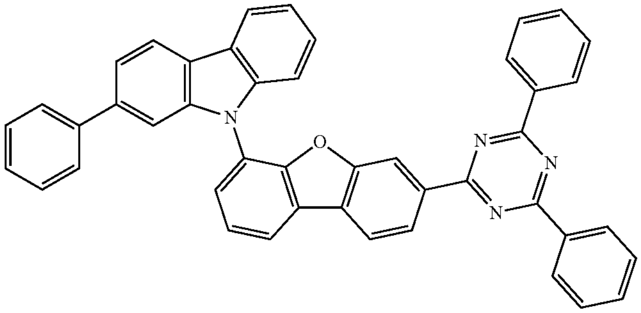 | 88% |
| 1079 | 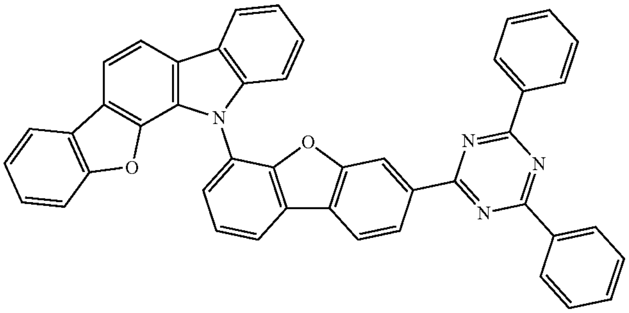 | 73% |
| 1084 | 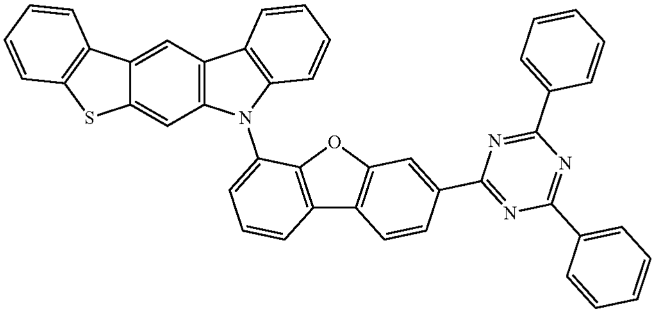 | 75% |
| 1088 | 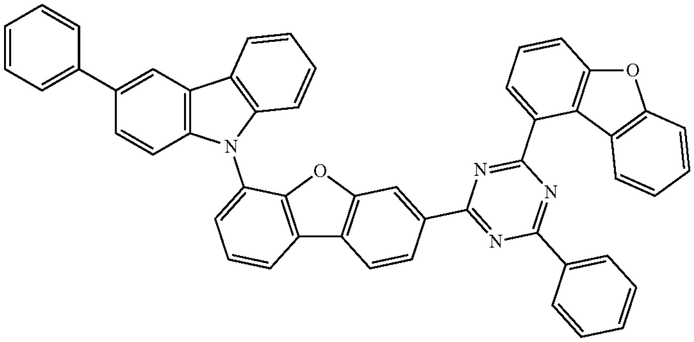 | 79% |

TABLE 7-continued
| | | |
|---|---|---|
| 1090 | 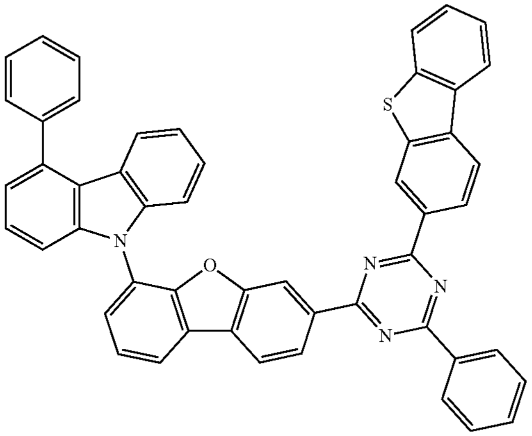 | 83% |
| 1094 | 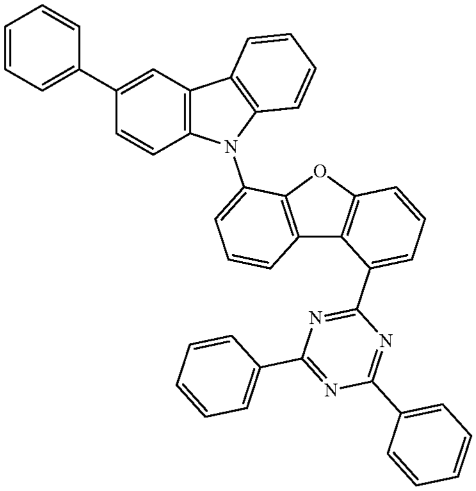 | 68% |
| 1098 | 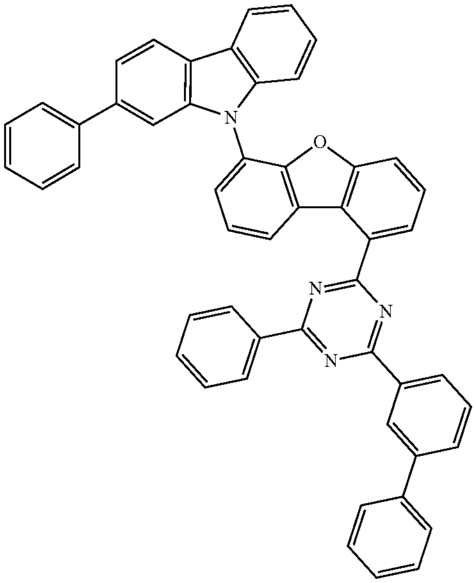 | 67% |

TABLE 7-continued
| | | |
|---|---|---|
| 1100 | 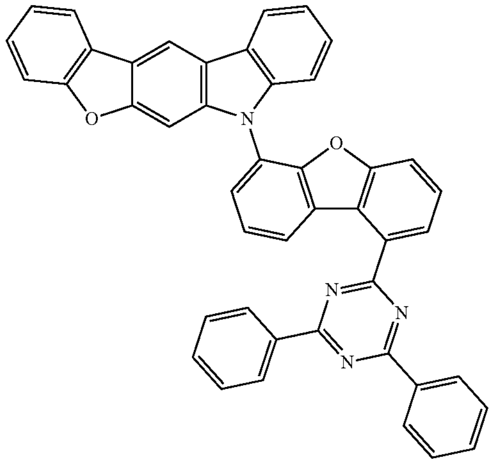 | 59% |
| 1103 | 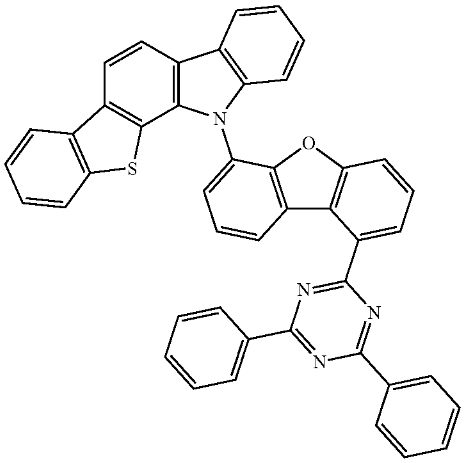 | 68% |
| 1108 | 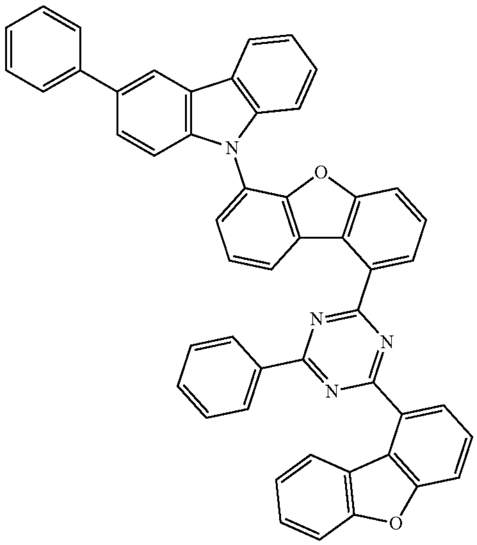 | 71% |

TABLE 7-continued
| | | |
|---|---|---|
| 1113 | 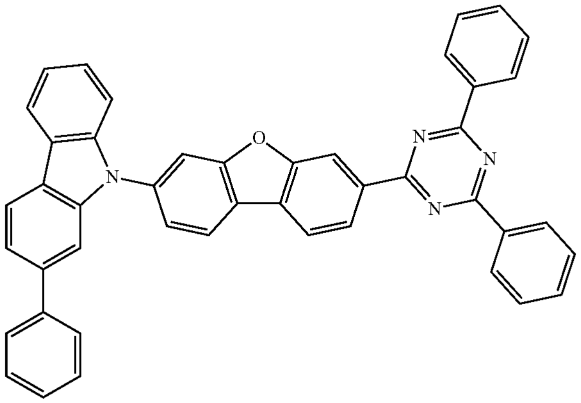 | 83% |
| 1114 | 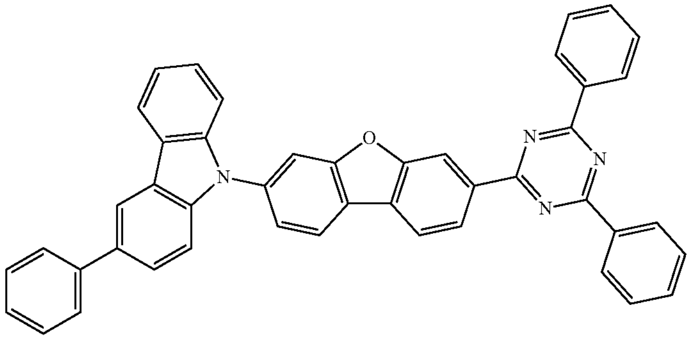 | 69% |
| 1116 | 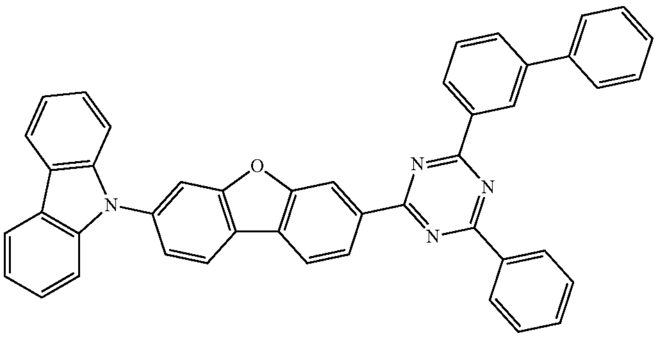 | 73% |
| 1121 | 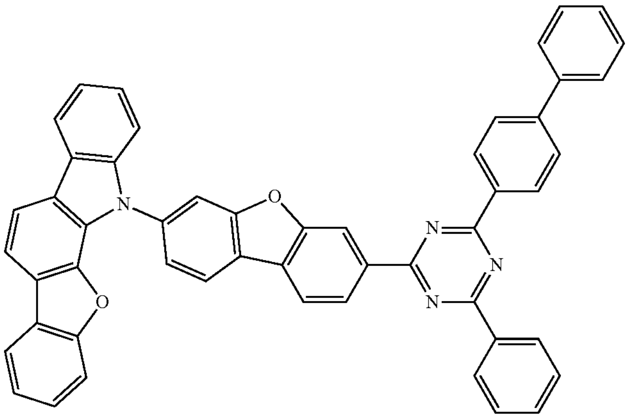 | 88% |

TABLE 7-continued
| | | |
|---|---|---|
| 1123 | 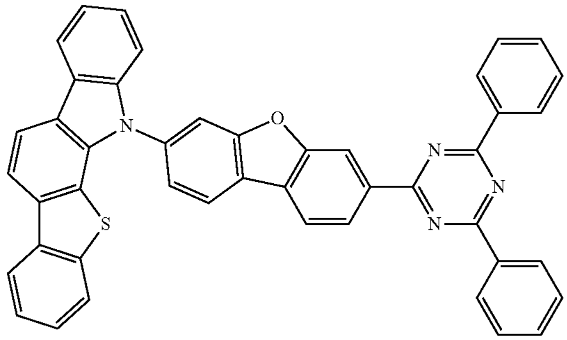 | 91% |
| 1127 | 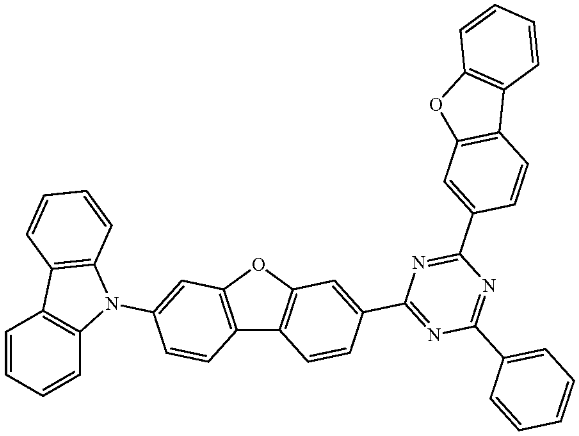 | 79% |
| 1133 | 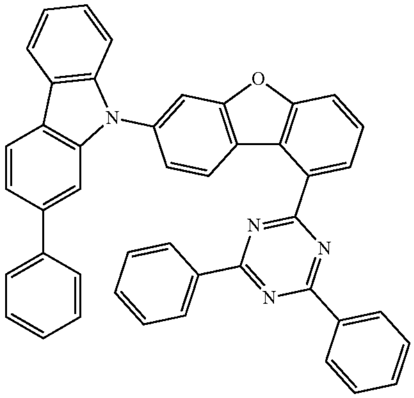 | 89% |

TABLE 7-continued
| | | |
|---|---|---|
| 1135 | 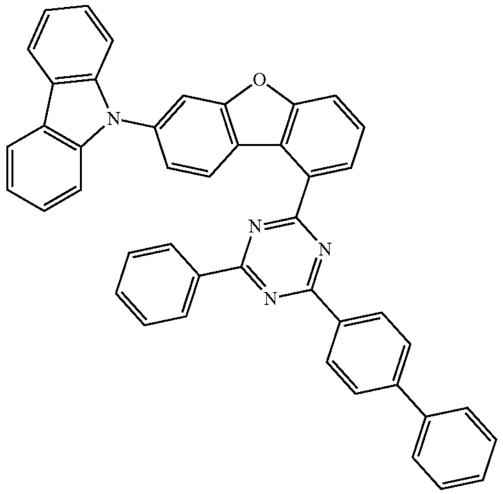 [SMILES: c1ccc(-c2ccc(-c3nc(-c4ccccc4)nc(-c4cccc5oc6cc(-n7c8ccccc8c8ccccc87)ccc6c45)n3)cc2)cc1] | 76% |
| 1138 | 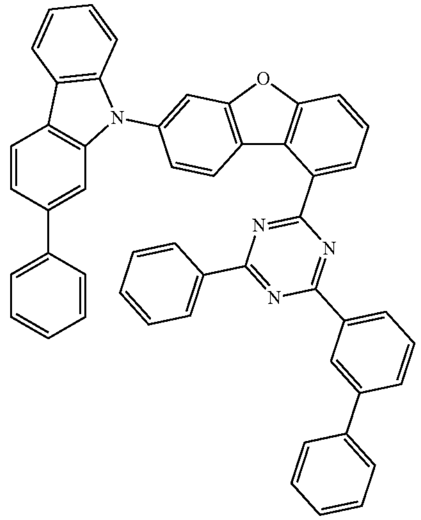 [SMILES: c1ccc(-c2cccc(-c3nc(-c4ccccc4)nc(-c4cccc5oc6cc(-n7c8ccccc8c8ccc(-c9ccccc9)cc87)ccc6c45)n3)c2)cc1] | 59% |
| 1143 | 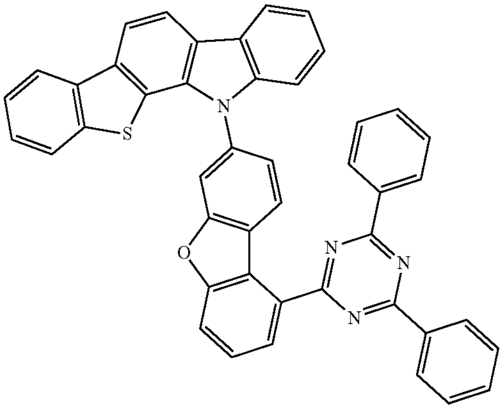 [SMILES: c1ccc(-c2nc(-c3ccccc3)nc(-c3cccc4oc5cc(-n6c7ccccc7c7ccc8c9ccccc9sc8c76)ccc5c34)n2)cc1] | 65% |

TABLE 7-continued
| | | |
|---|---|---|
| 1145 | 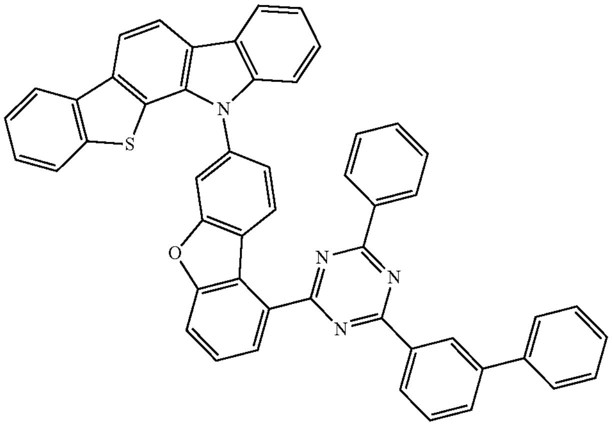 [SMILES: c1ccc(-c2cccc(-c3nc(-c4ccccc4)nc(-c4cccc5oc6cc(-n7c8ccccc8c8ccc9c%10ccccc%10sc9c87)ccc6c45)n3)c2)cc1] | 62% |
| 1152 | 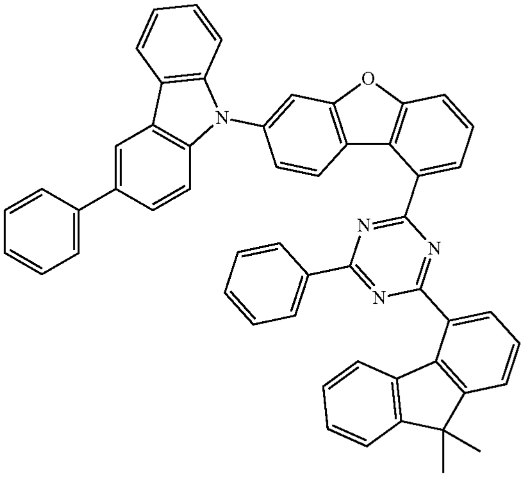 [SMILES: CC1(C)c2ccccc2-c2c(-c3nc(-c4ccccc4)nc(-c4cccc5oc6cc(-n7c8ccccc8c8cc(-c9ccccc9)ccc87)ccc6c45)n3)cccc21] | 73% |
| 1159 | 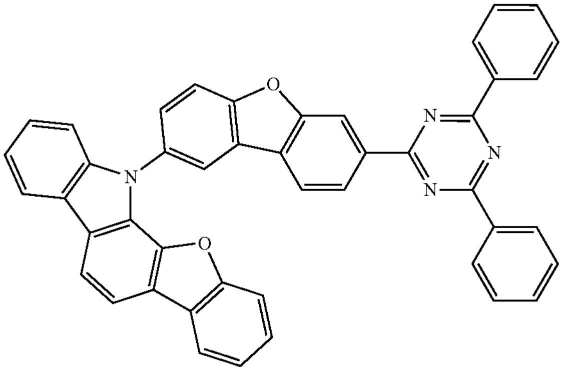 [SMILES: c1ccc(-c2nc(-c3ccccc3)nc(-c3ccc4c(c3)oc3ccc(-n5c6ccccc6c6ccc7c8ccccc8oc7c65)cc34)n2)cc1] | 72% |

TABLE 7-continued
| | | |
|---|---|---|
| 1163 | 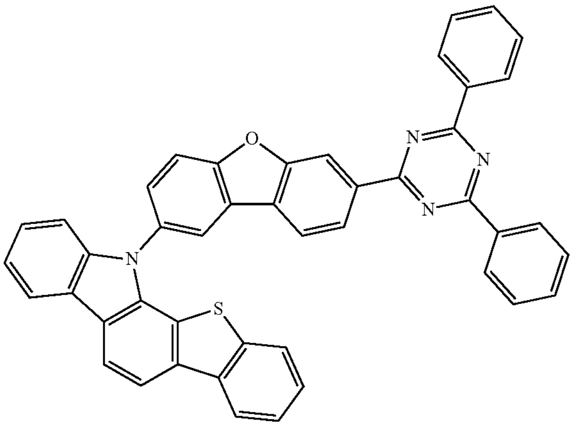 [SMILES: c1ccc(-c2nc(-c3ccccc3)nc(-c3ccc4c(c3)oc3ccc(-n5c6ccccc6c6ccc7c8ccccc8sc7c65)cc34)n2)cc1] | 83% |
| 1169 | 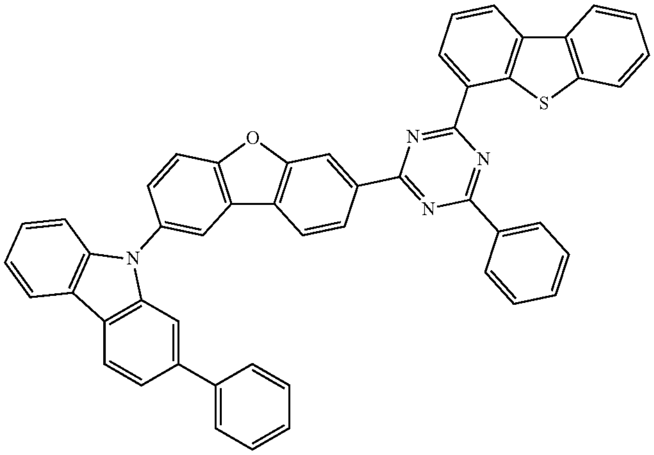 [SMILES: c1ccc(-c2ccc3c4ccccc4n(-c4ccc5oc6cc(-c7nc(-c8ccccc8)nc(-c8cccc9c8sc8ccccc89)n7)ccc6c5c4)c3c2)cc1] | 81% |
| 1176 | 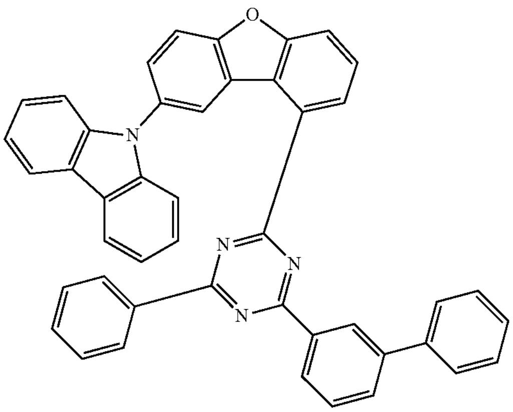 [SMILES: c1ccc(-c2cccc(-c3nc(-c4ccccc4)nc(-c4cccc5oc6ccc(-n7c8ccccc8c8ccccc87)cc6c45)n3)c2)cc1] | 93% |

TABLE 7-continued
| | | |
|---|---|---|
| 1179 | 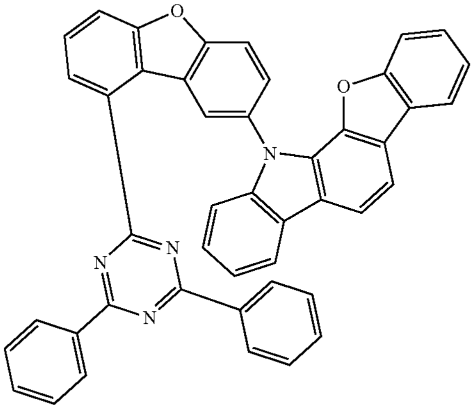 [SMILES: c1ccc(-c2nc(-c3ccccc3)nc(-c3cccc4oc5ccc(-n6c7ccccc7c7ccc8c9ccccc9oc8c76)cc5c34)n2)cc1] | 67% |
| 1193 | 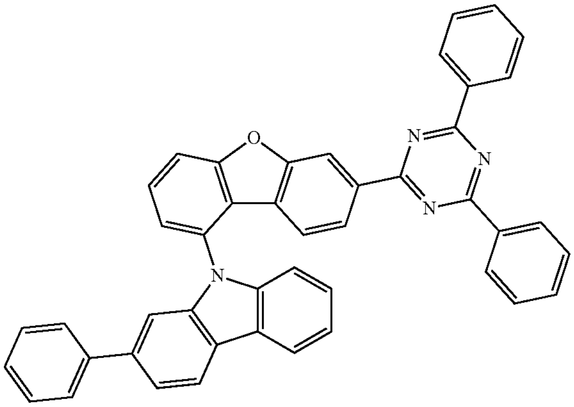 [SMILES: c1ccc(-c2ccc3c4ccccc4n(-c4cccc5oc6cc(-c7nc(-c8ccccc8)nc(-c8ccccc8)n7)ccc6c45)c3c2)cc1] | 66% |
| 1196 | 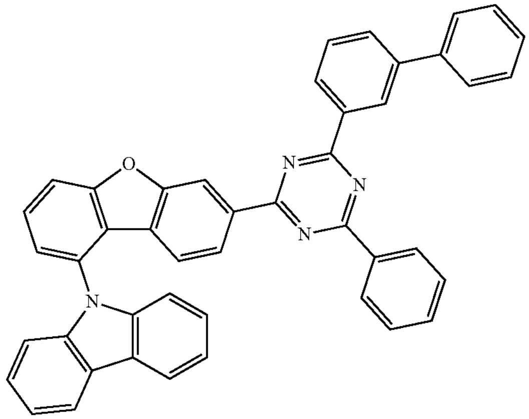 [SMILES: c1ccc(-c2cccc(-c3nc(-c4ccccc4)nc(-c4ccc5c(c4)oc4cccc(-n6c7ccccc7c7ccccc76)c45)n3)c2)cc1] | 76% |
| 1199 | 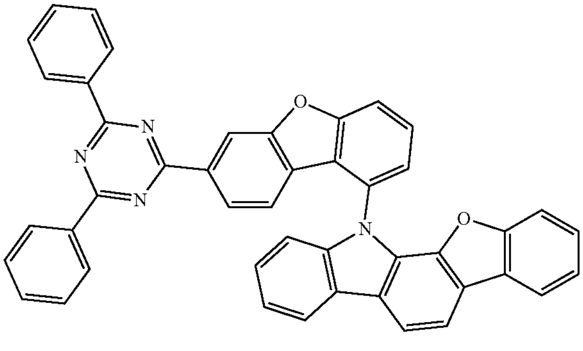 [SMILES: c1ccc(-c2nc(-c3ccccc3)nc(-c3ccc4c(c3)oc3cccc(-n5c6ccccc6c6ccc7c8ccccc8oc7c65)c34)n2)cc1] | 57% |

TABLE 7-continued
| | | |
|---|---|---|
| 1207 | 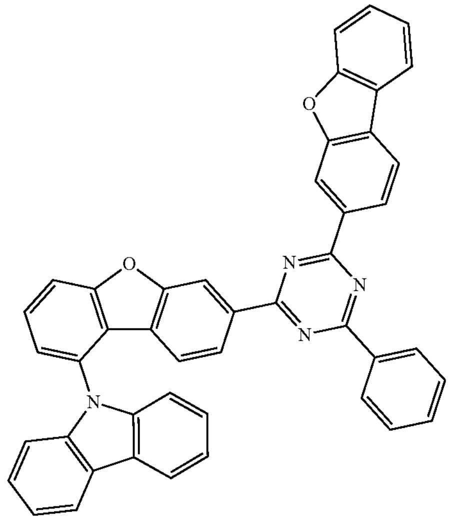 [SMILES: c1ccc(-c2nc(-c3ccc4c(c3)oc3ccccc34)nc(-c3ccc4c(c3)oc3cccc(-n5c6ccccc6c6ccccc65)c34)n2)cc1] | 63% |
[Synthesis 8] The compound 2-2 (E)
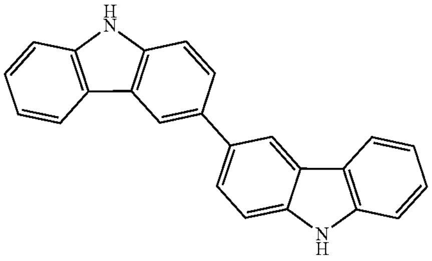
+
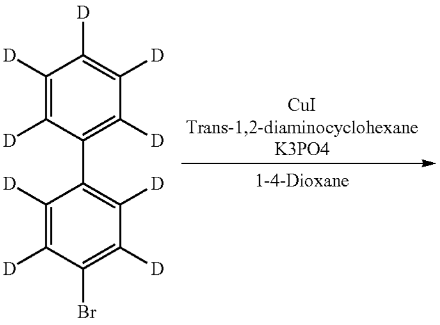
[A]
-continued
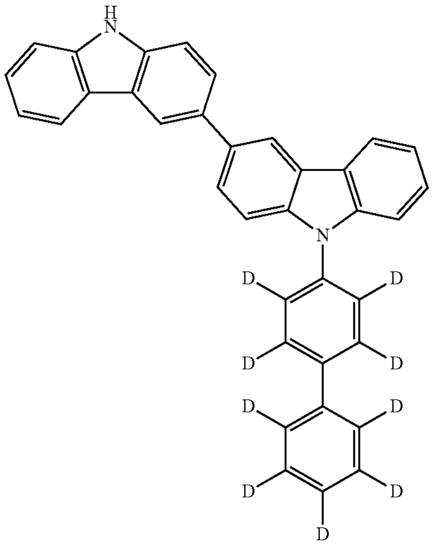
2-2-1
+
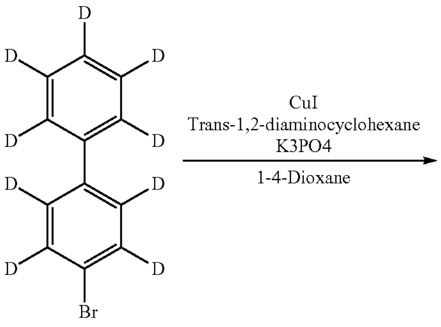
[A']

-continued

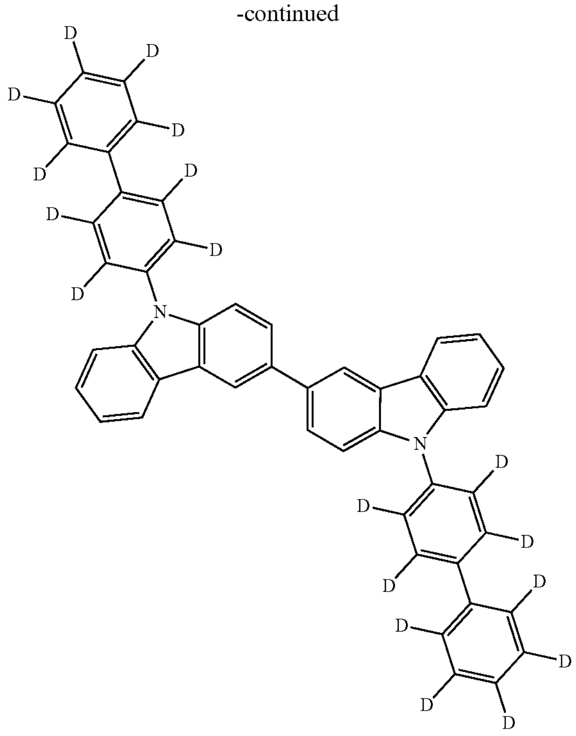

2-26[E]

(1) The Compound 2-2-1

In the one-neck round bottom flask, 9H,9'H-3,3'-bicarbazole (10 g, 0.030 mol), 4-bromo-1,1'-biphenyl-2,2',3,3',4',5,5',6,6'-d9 (7.26 g, 0.030 mol), CuI (0.57 g, 0.003 mol), trans-1,4-diaminocyclohexane (0.34 g, 0.003 mol) and K3PO4 (12.74 g, 0.06 mol) was dissolved in 100 mL of 1,4-oxane at 125° C., and the mixture was reflux for 8 hours. After the reaction was completed, distilled water and DCM were added at room temperature for extraction. The organic layer was dried with MgSO4 and the solvent was removed by a rotary evaporator. The reaction product was purified by column chromatography (DCM:Hex=1:3) and recrystallized with methanol to obtain the compound 2-2-1. (13.92 g, 94%)

(2) The Compound 2-2[E]

In the one-neck round bottom flask, 9-([1,1'-biphenyl]-4-yl-d9)-9H,9'H-3,3'-bicarbazole (13.92 g, 0.028 mol), 4-bromo-1,1'-biphenyl-2,2',3,3',4',5,5',6,6'-d9 (6.83 g, 0.028 mol), CuI (0.53 g, 0.0028 mol), trans-1,4-diaminocyclohexane (0.32 g, 0.0028 mol), $K_3PO_4$ (11.89 g, 0.056 mol) was dissolved in 140 mL of 1,4-oxane at 125° C., and the mixture was reflux for 8 hours. After the reaction was completed, distilled water and DCM were added at room temperature for extraction. The organic layer was dried with MgSO4 and the solvent was removed by a rotary evaporator. The reaction product was purified by column chromatography (DCM:Hex=1:3) and recrystallized with methanol to obtain the compound 2-2[E]. (16.14 g, 88%)

When compounds A and A' are same, the compound 2-2[E] can be directly synthesized by adding 2 equivalents of compound A in the first reaction. That is, when the compounds A and A' are same, the second reaction step may be omitted.

The following compound B was synthesized in the same manner as in the synthesis 8 except that intermediates A and A' of Table 8 were used.

TABLE 8

| Compound | A | A' |
| --- | --- | --- |
| 2-2 | 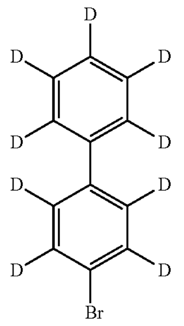 | 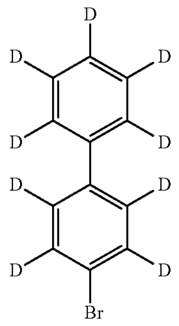 |
| 2-3 | 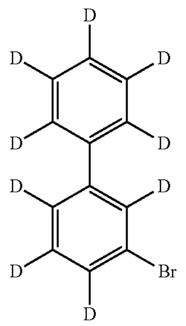 | 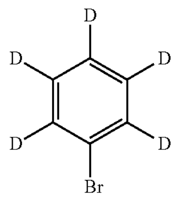 |

TABLE 8-continued
| | | |
|---|---|---|
| 2-5 | 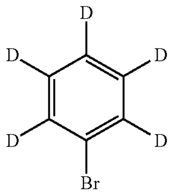 | 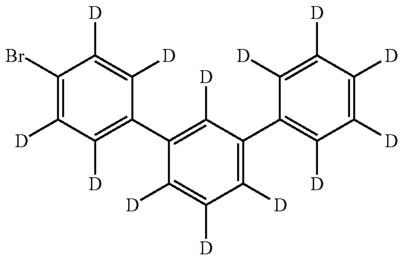 |
| 2-6 | 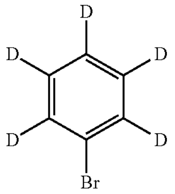 | 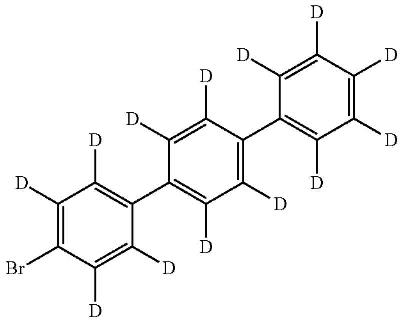 |
| 2-8 | 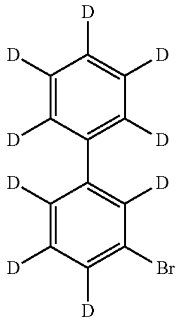 | 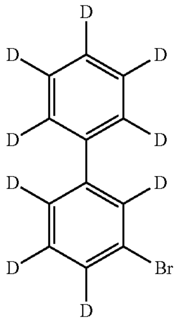 |
| 2-9 | 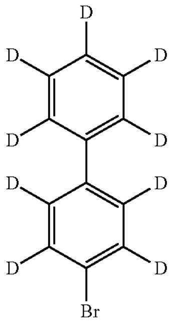 | 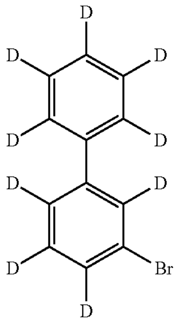 |
| 2-12 | 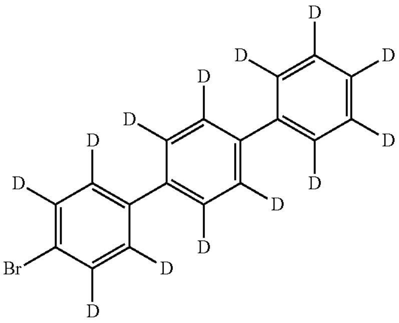 | 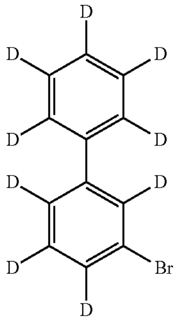 |

TABLE 8-continued
| | | |
|---|---|---|
| 2-14 | 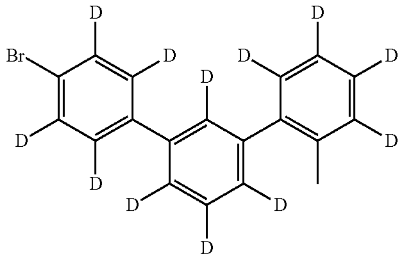 | 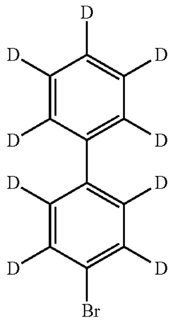 |
| 2-75 | 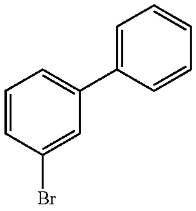 | 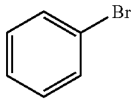 |
| 2-76 | 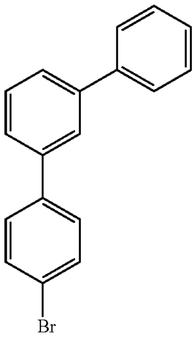 | 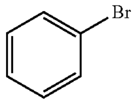 |
| 2-77 | 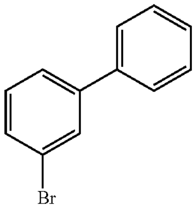 | 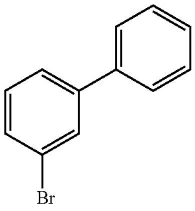 |
| 2-78 | 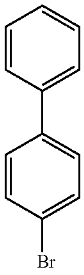 | 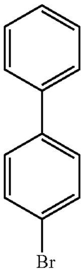 |

TABLE 8-continued
| Compound | B | yield |
| --- | --- | --- |
| 2-2 | 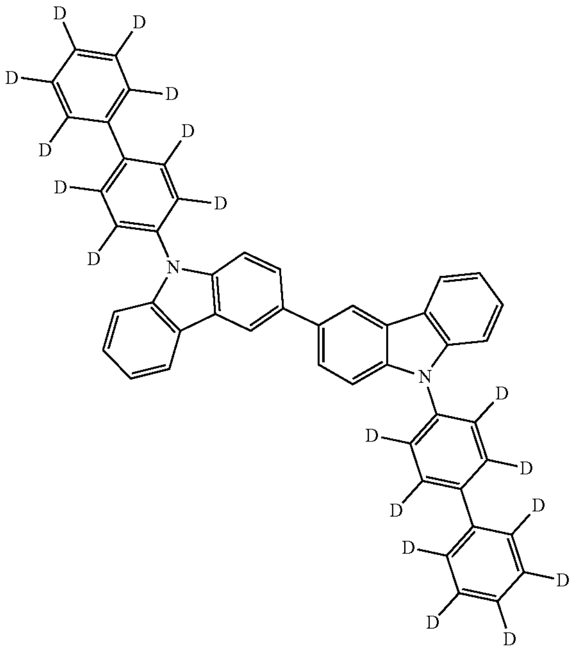 | 88% |
| 2-3 | 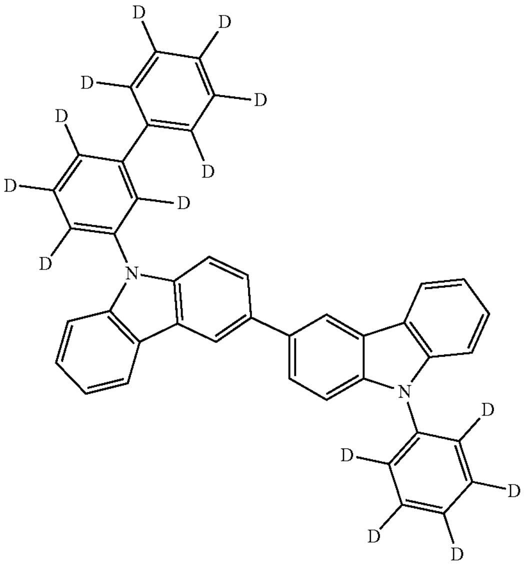 | 95% |

TABLE 8-continued
2-5
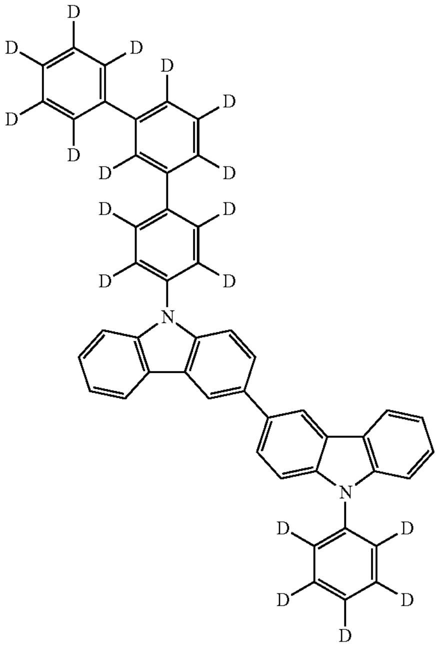 [SMILES: [2H]c1c([2H])c([2H])c(-c2c([2H])c([2H])c([2H])c(-c3c([2H])c([2H])c(-n4c5ccccc5c5cc(-c6ccc7c(c6)c6ccccc6n7-c6c([2H])c([2H])c([2H])c([2H])c6[2H])ccc54)c([2H])c3[2H])c2[2H])c([2H])c1[2H]]
84%
2-6
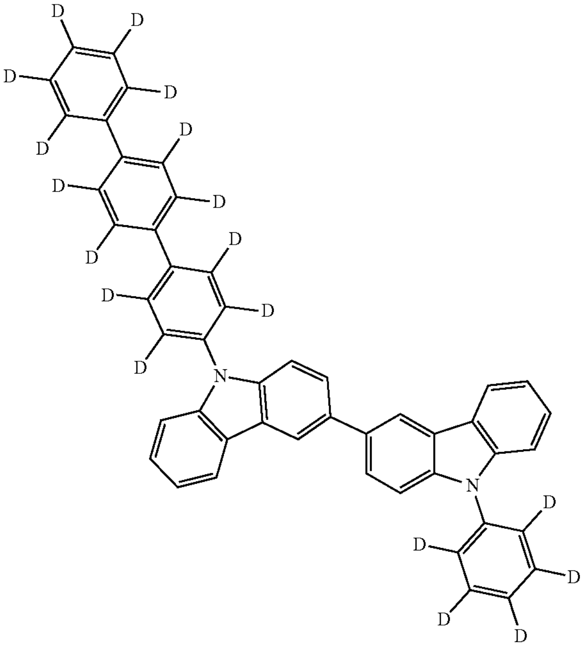 [SMILES: [2H]c1c([2H])c([2H])c(-c2c([2H])c([2H])c(-c3c([2H])c([2H])c(-n4c5ccccc5c5cc(-c6ccc7c(c6)c6ccccc6n7-c6c([2H])c([2H])c([2H])c([2H])c6[2H])ccc54)c([2H])c3[2H])c([2H])c2[2H])c([2H])c1[2H]]
67%

TABLE 8-continued
| | | |
|---|---|---|
| 2-8 | 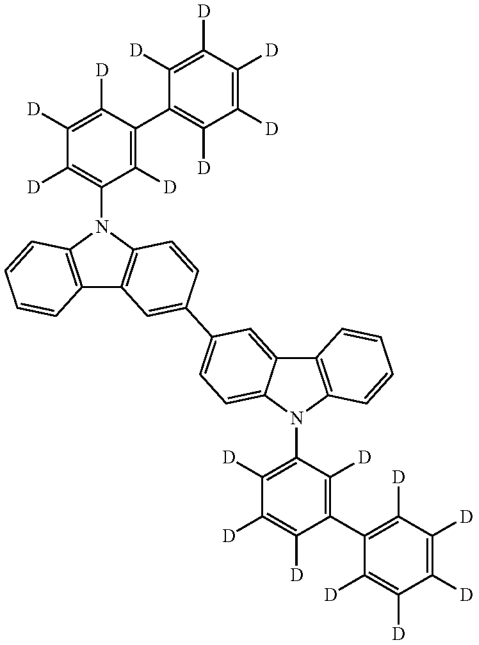 | 83% |
| 2-9 | 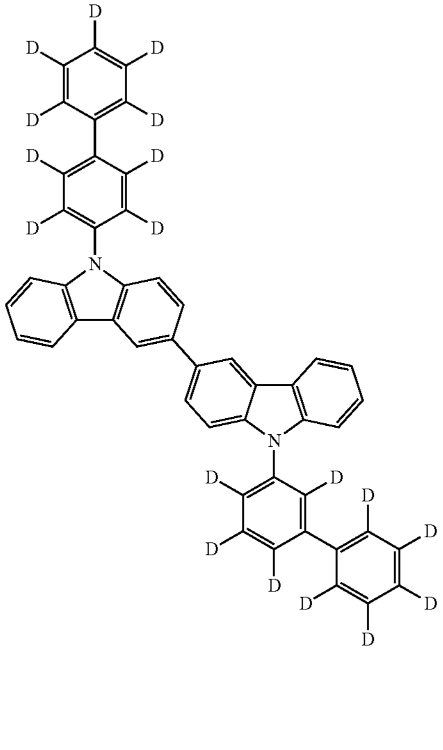 | 74% |

TABLE 8-continued
| | | |
|---|---|---|
| 2-12 | 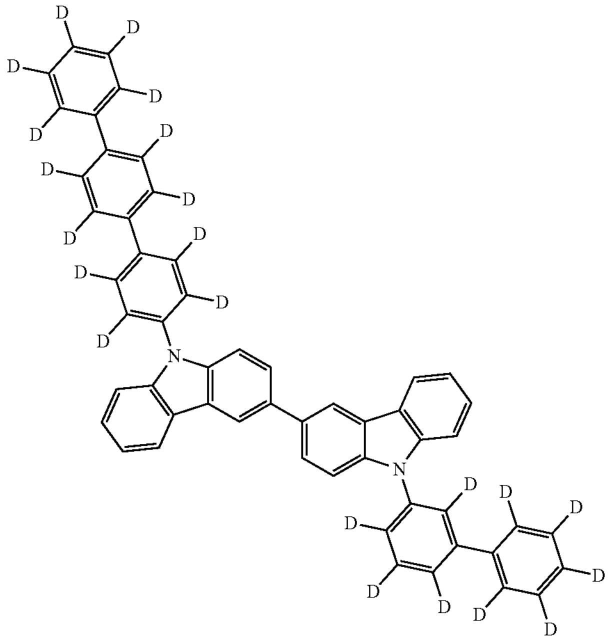 | 69% |
| 2-14 | 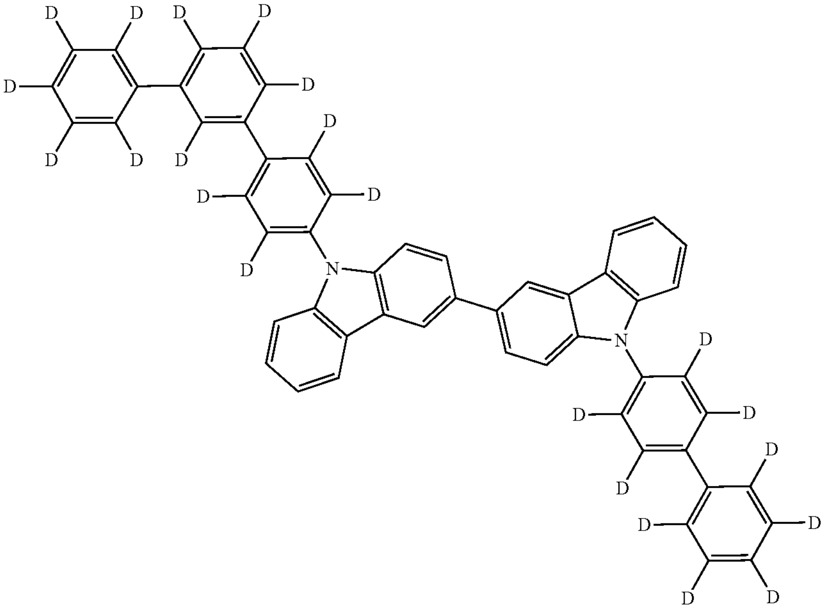 | 57% |

TABLE 8-continued
| | | |
|---|---|---|
| 2-75 | 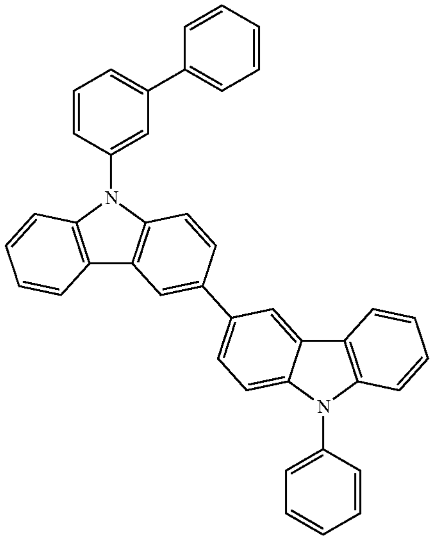 | 68% |
| 2-76 | 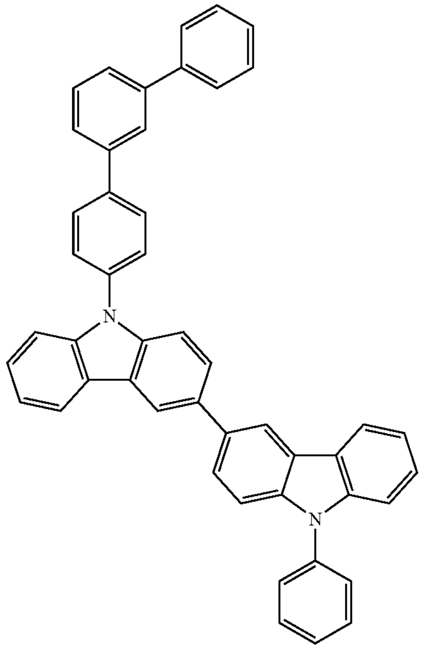 | 72% |

TABLE 8-continued
| | | |
|---|---|---|
| 2-77 | 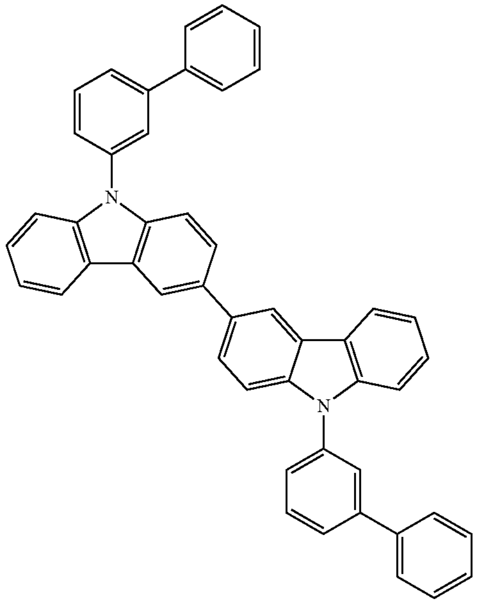 | 83% |
| 2-78 | 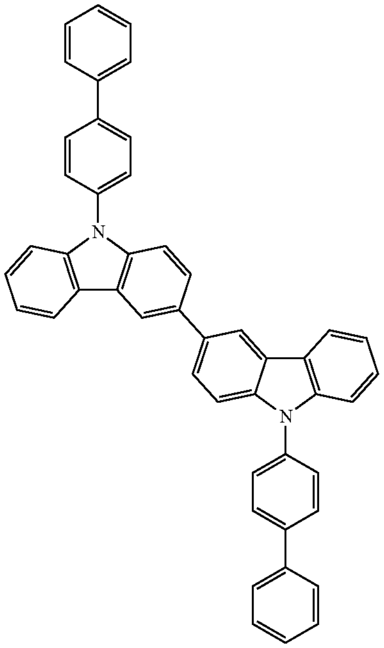 | 88% |
[Synthesis 9] The compound 2-26 (E)
-continued
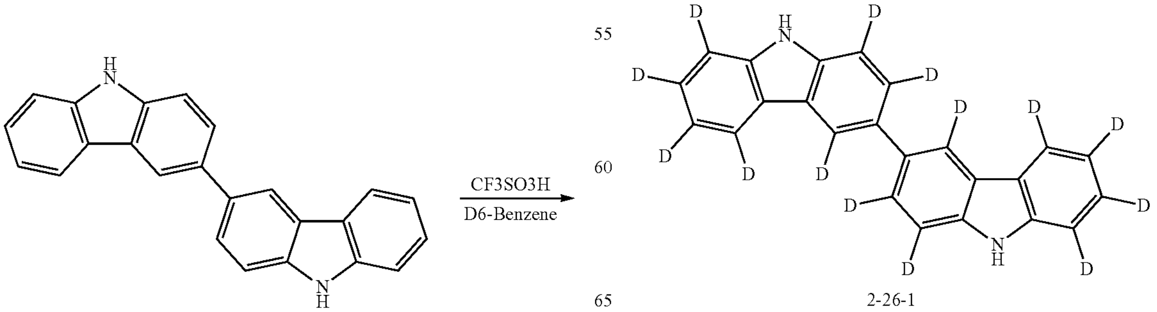
2-26-1
+

-continued

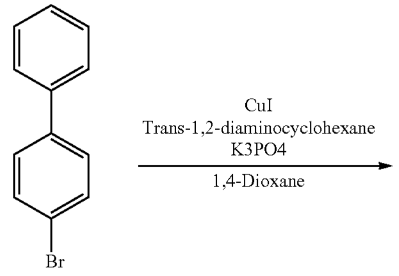

[A]

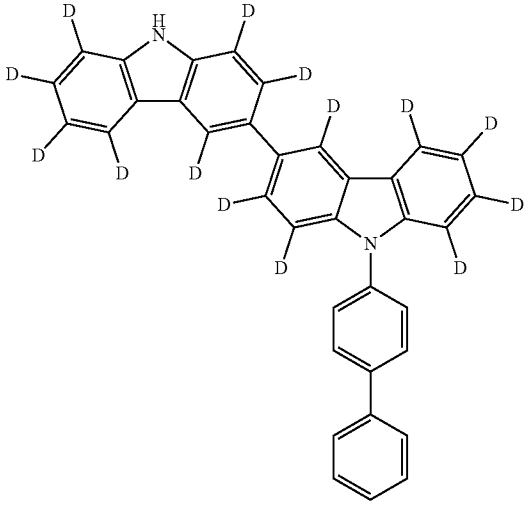

2-26-2

+

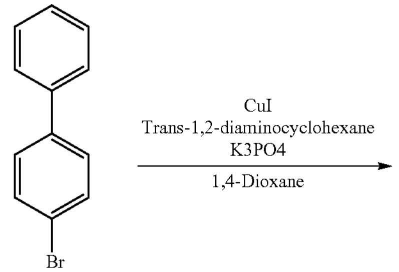

[A']

-continued

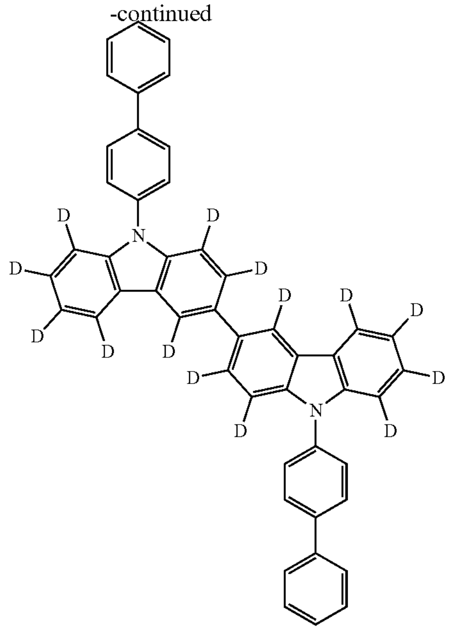

2-26[E]

(1) The Compound 2-26-1

In the one-neck round bottom flask, a mixture of 9H,9'H-3,3'-biscarbazole (10 g, 0.030 mol), triflic acid (34 g, 0.023 mol) and D6-benzene (100 mL) was refluxed at 70° C. After quenching and extraction with dichloromethane and $H_2O$, the resultant was concentrated and filtered through silica gel. After concentration, the resultant was treated with methanol to obtain the compound 2-26-1. (7.07 g, 68%)

(2) The Compound 2-26-2

In the one-neck round bottom flask, 9H,9'H-3,3'-bicarbazole-1,1',2,2',4,4',5,5',6,6',7,7',8,8'-d14 (7.07 g, 0.02 mol), CuI (0.38 g, 0.002 mol), trans-1,4-diaminocyclohexane (0.23 g, 0.002 mol), K3PO4 (8.49 g, 0.04 mol) was dissolved in 70 mL of 1,4-oxane at 125° C., and the mixture was reflux for 8 hours. After the reaction was completed, distilled water and DCM were added at room temperature for extraction. The organic layer was dried with MgSO4 and the solvent was removed by a rotary evaporator. The reaction product was purified by column chromatography (DCM:Hex=1:3) and recrystallized with methanol to obtain the compound 2-26-2. (8.28 g, 83%)

(3) The Compound 2-26[E]

In the one-neck round bottom flask, 9-([1,1'-biphenyl]-4-yl)-9H,9'H-3,3'-bicarbazole-1,1',2,2',4,4',5,5',6,6',7,7',8,8'-d14 (8.28 g, 0.017 mol), CuI (0.32 g, 0.0017 mol), trans-1,4-diaminocyclohexane (0.19 g, 0.0017 mol), and K3PO4 (7.22 g, 0.034 mol) were dissolved in 80 mL of 1,4-oxane and refluxed at 125° C. for 8 hours. After the reaction was completed, distilled water and DCM were added at room temperature for extraction, and the organic layer was dried with MgSO4 and the solvent was removed by a rotary evaporator. The reaction product was purified by column chromatography (DCM:Hex=1:3) and recrystallized from methanol to obtain the compound 2-26[E]. (8.63 g, 78%)

When compounds A and A' are same, the compound 2-26[E] can be directly synthesized by adding 2 equivalents of compound A in the first reaction. That is, when the compounds A and A' are same, the second reaction step may be omitted.

The following compound C was synthesized in the same manner as in the synthesis 9 except that intermediates A and A' of Table 9 were used.

TABLE 9
| Compound | A | A' |
| --- | --- | --- |
| 2-26 | 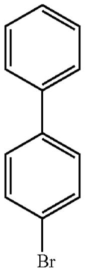 | 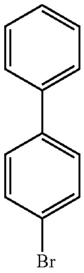 |
| 2-27 | 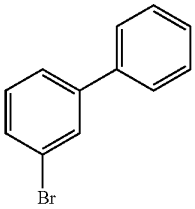 | 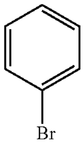 |
| 2-29 | 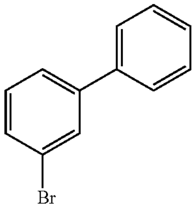 | 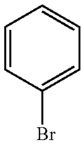 |
| 2-32 | 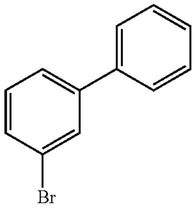 | 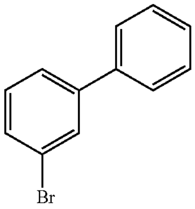 |
| 2-33 | 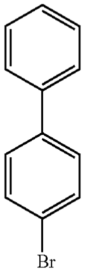 | 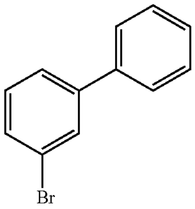 |

TABLE 9-continued
| Compound | C | yield |
| --- | --- | --- |
| 2-26 | 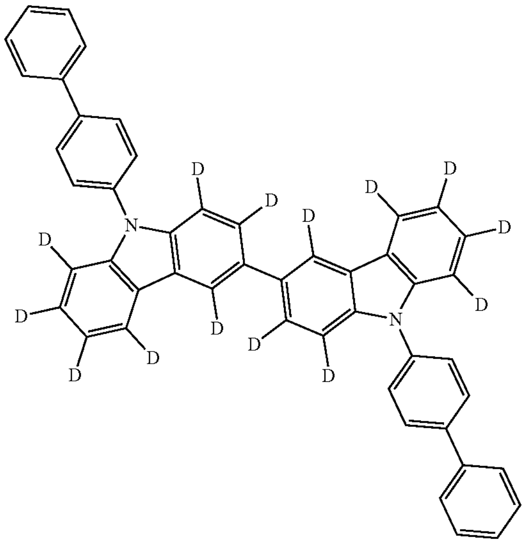 | 78% |
| 2-27 | 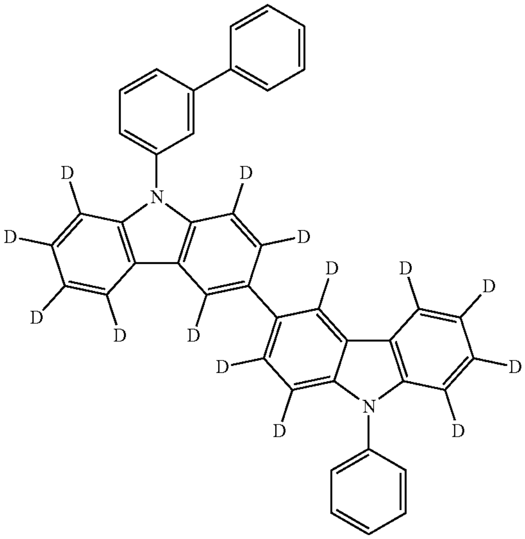 | 90% |

TABLE 9-continued
| | | |
|---|---|---|
| 2-29 | 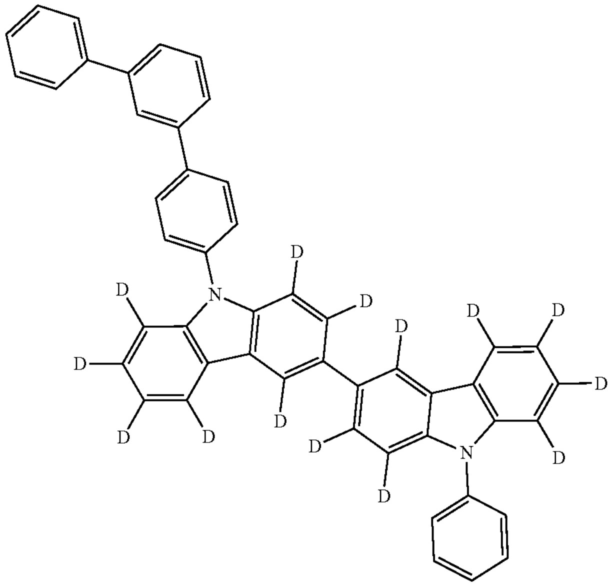 | 74% |
| 2-32 | 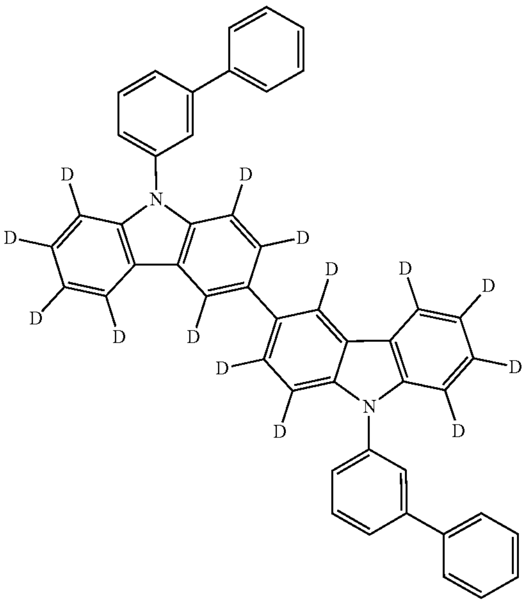 | 69% |

TABLE 9-continued
| | | |
|---|---|---|
| 2-33 | 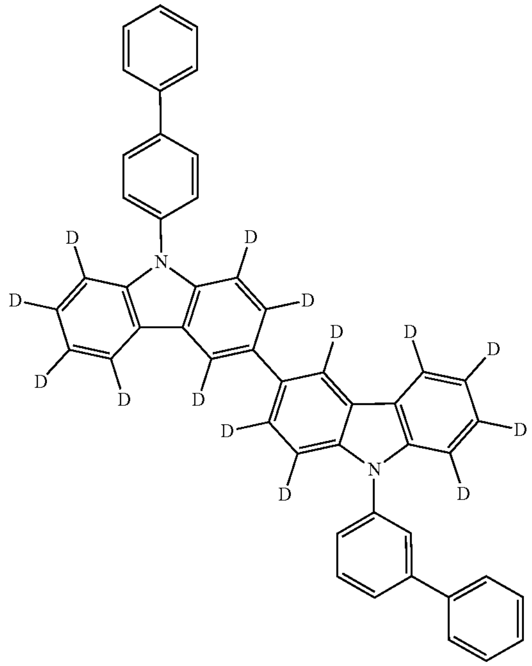 | 93% |
[Synthesis 10] The compound 2-50 (E)
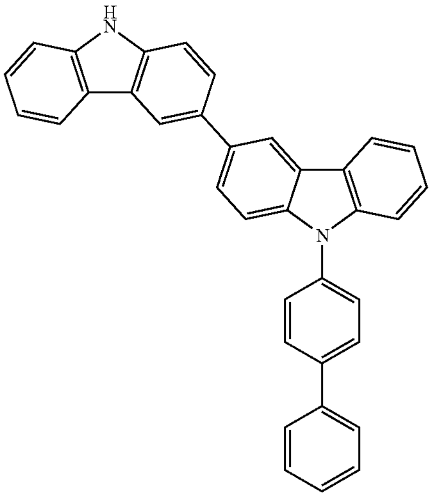
+
[A]
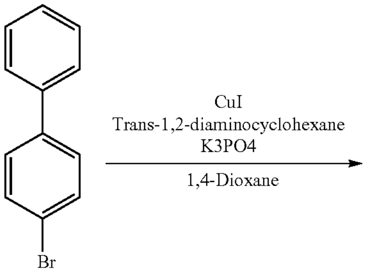
[B]
-continued
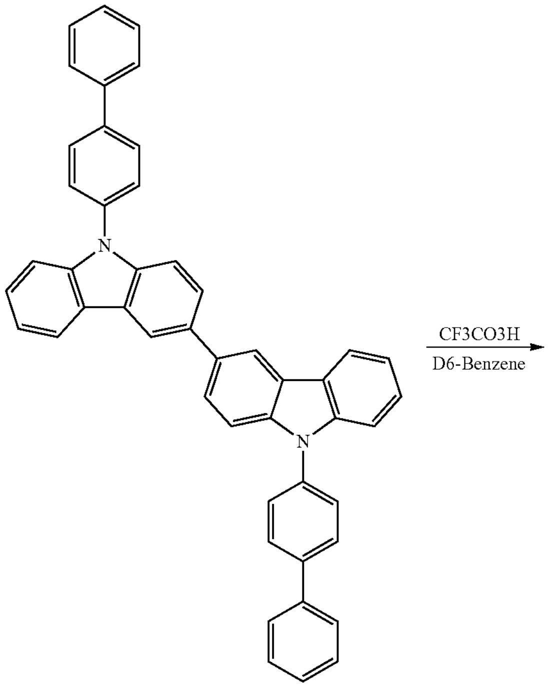
2-50-1

-continued

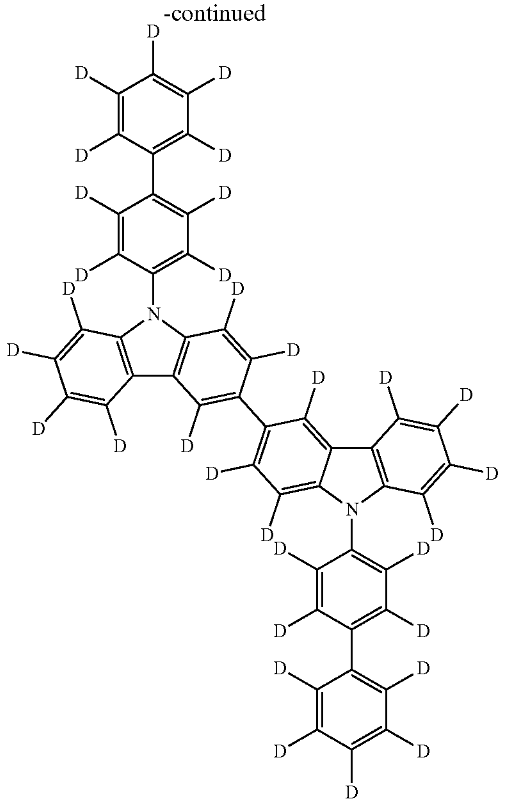

2-50[E]

(1) The Compound 2-50-1

In the one-neck round bottom flask, 9-([1,1'-biphenyl]-4-yl)-9H,9'H-3,3'-bicarbazole (10 g, 0.021 mol), CuI (0.40 g, 0.0021 mol), trans-1,4-diaminocyclohexane (0.024 g, 0.0021 mol), K3PO4 (8.92) g, 0.042 mol) was dissolved in 100 mL of 1,4-oxane and refluxed at 125° C. for 8 hours. After the reaction was completed, distilled water and DCM were added at room temperature for extraction, and the organic layer was dried with MgSO4 and the solvent was removed by a rotary evaporator. The reaction product was purified by column chromatography (DCM:Hex=1:3) and recrystallized from methanol to obtain the compound 2-50-1. (12.17 g, 91%)

(2) The Compound 2-50-E

In the one-neck round bottom flask, a mixture of 9,9'-di([1,1'-biphenyl]-4-yl)-9H,9'H-3,3'-bicarbazole (12.17 g, 0.017 mol), triflic acid (40.8 g, 0.27 mol) and D6-benzene (120 mL) was refluxed at 70° C. After quenching and extraction with dichloromethane and $H_2O$, the resultant was concentrated and filtered through silica gel. After concentration, the resultant was treated with methanol to obtain the compound 2-50[E]. (8.87 g, 78%)

The following compound D was synthesized in the same manner as in the synthesis 10 except that intermediates A and B of Table 10 were used.

TABLE 10

| Compound | A | B |
|---|---|---|
| 2-50 | 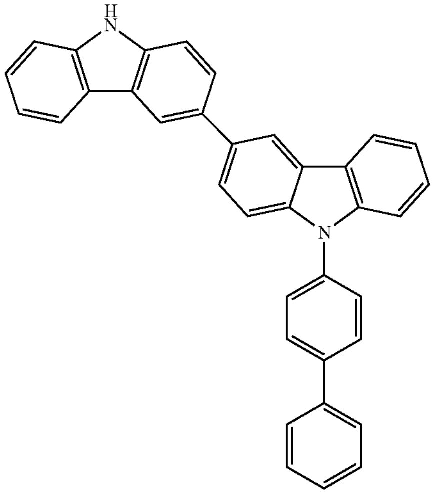 | 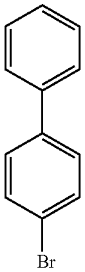 |

TABLE 10-continued
| | | |
|---|---|---|
| 2-51 | 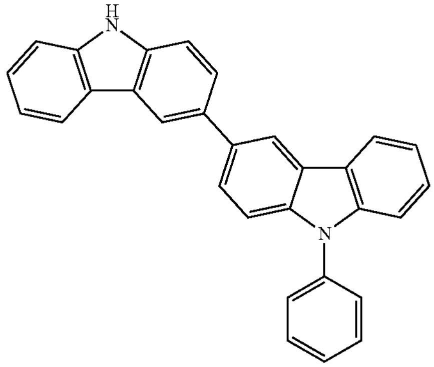 | 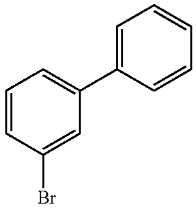 |
| 2-53 | 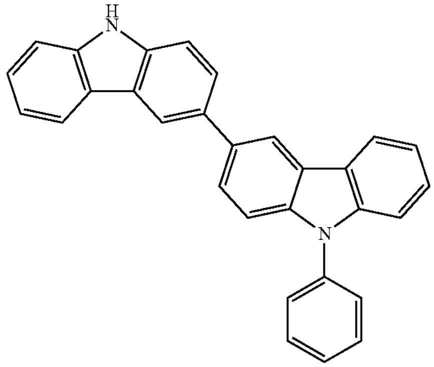 | 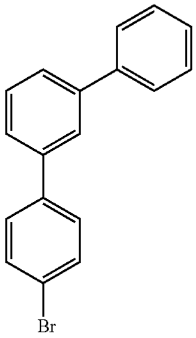 |
| 2-56 | 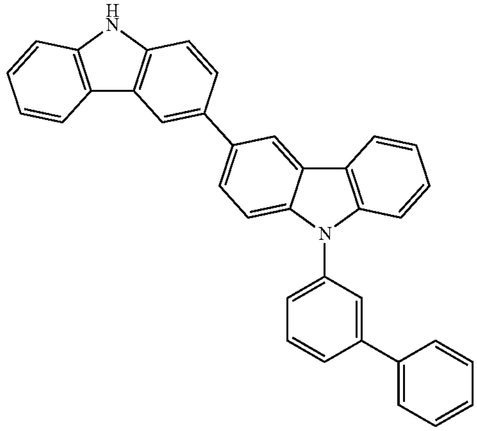 | 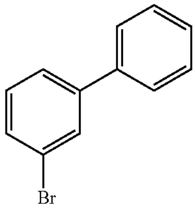 |
| 2-60 | 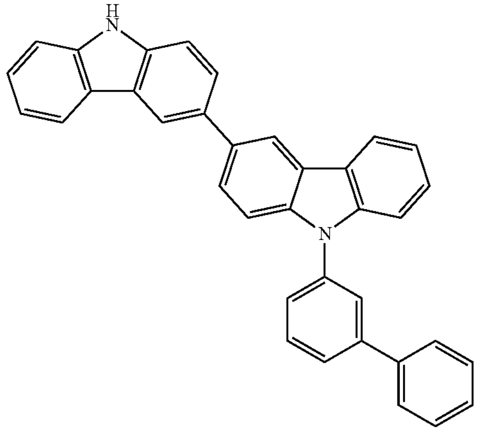 | 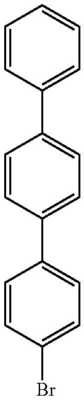 |

TABLE 10-continued
| | | | |
|---|---|---|---|
| 2-62 | 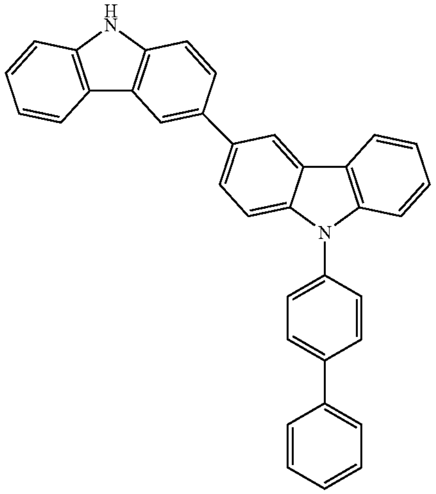 [SMILES: c1ccc(-c2ccc(-n3c4ccccc4c4cc(-c5ccc6[nH]c7ccccc7c6c5)ccc43)cc2)cc1] | | 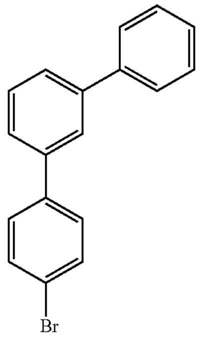 [SMILES: Brc1ccc(-c2cccc(-c3ccccc3)c2)cc1] |
| 2-68 | 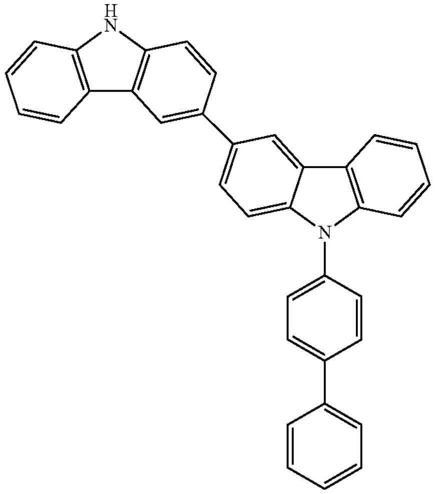 [SMILES: c1ccc(-c2ccc(-n3c4ccccc4c4cc(-c5ccc6[nH]c7ccccc7c6c5)ccc43)cc2)cc1] | | 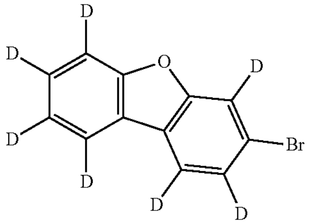 [SMILES: [2H]c1c([2H])c([2H])c2c(oc3c([2H])c(Br)c([2H])c([2H])c32)c1[2H]] |
| Compound | D | yield |
|---|---|---|
| 2-50 | 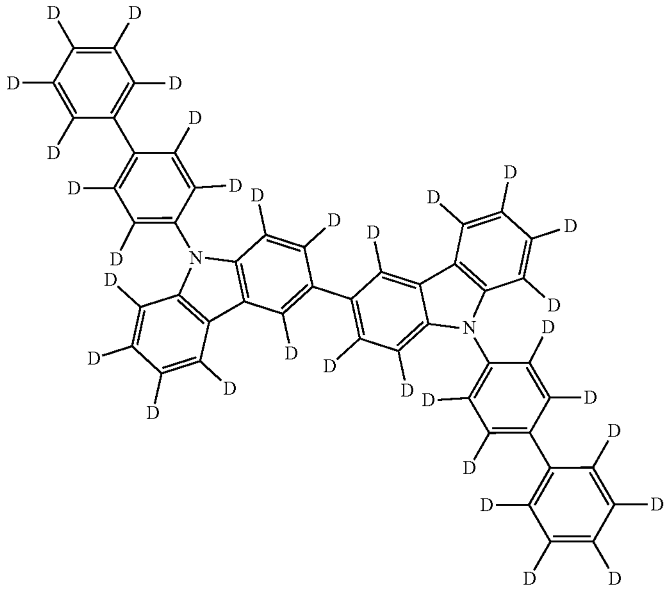 | 78% |

TABLE 10-continued
2-51
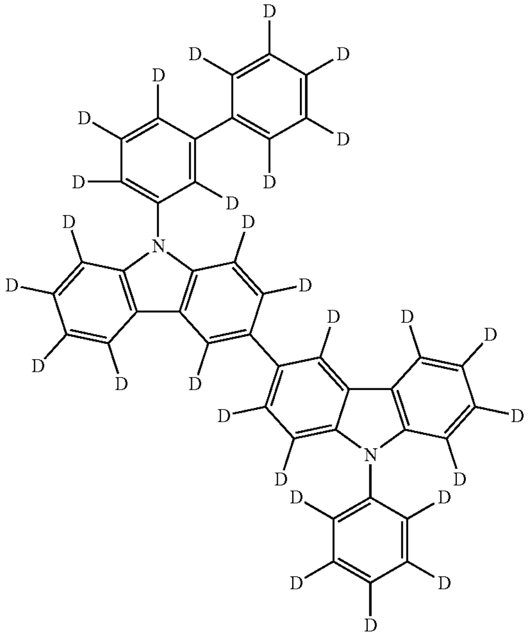 [SMILES: [2H]c1c([2H])c([2H])c(-c2c([2H])c([2H])c([2H])c(-n3c4c([2H])c([2H])c([2H])c([2H])c4c4c([2H])c(-c5c([2H])c([2H])c6c(c5[2H])c5c([2H])c([2H])c([2H])c([2H])c5n6-c5c([2H])c([2H])c([2H])c([2H])c5[2H])c([2H])c([2H])c43)c2[2H])c([2H])c1[2H]]
91%
2-53
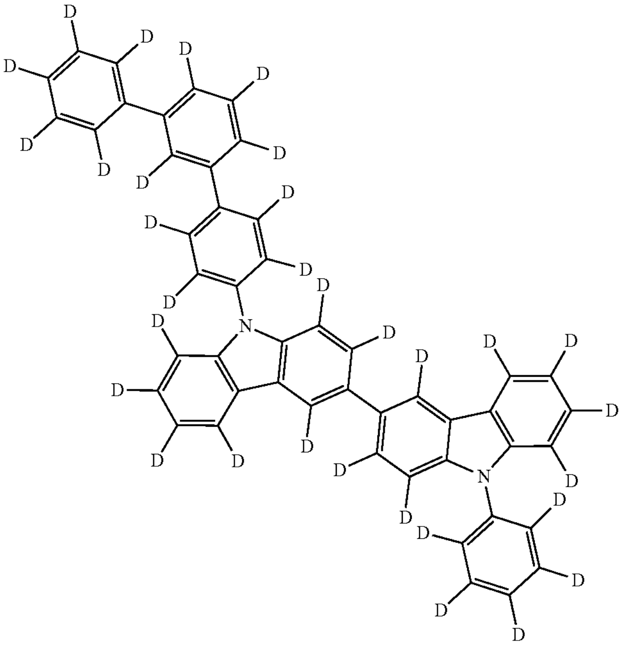 [SMILES: [2H]c1c([2H])c([2H])c(-c2c([2H])c([2H])c([2H])c(-c3c([2H])c([2H])c(-n4c5c([2H])c([2H])c([2H])c([2H])c5c5c([2H])c(-c6c([2H])c([2H])c7c(c6[2H])c6c([2H])c([2H])c([2H])c([2H])c6n7-c6c([2H])c([2H])c([2H])c([2H])c6[2H])c([2H])c([2H])c54)c([2H])c3[2H])c2[2H])c([2H])c1[2H]]
93%

TABLE 10-continued
| | | |
|---|---|---|
| 2-56 | 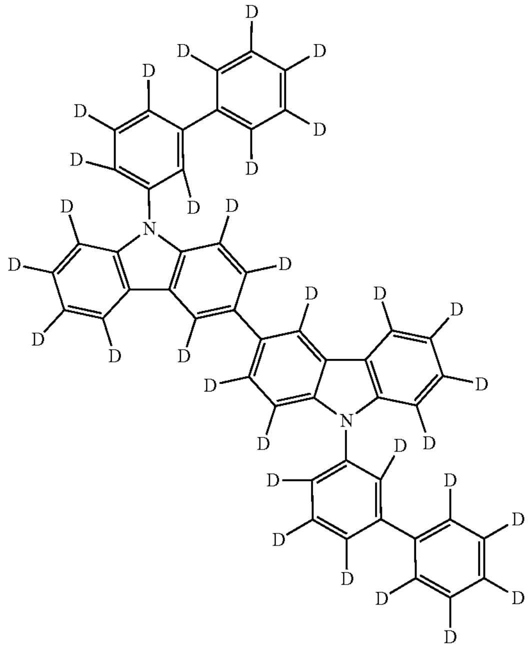 | 76% |
| 2-60 | 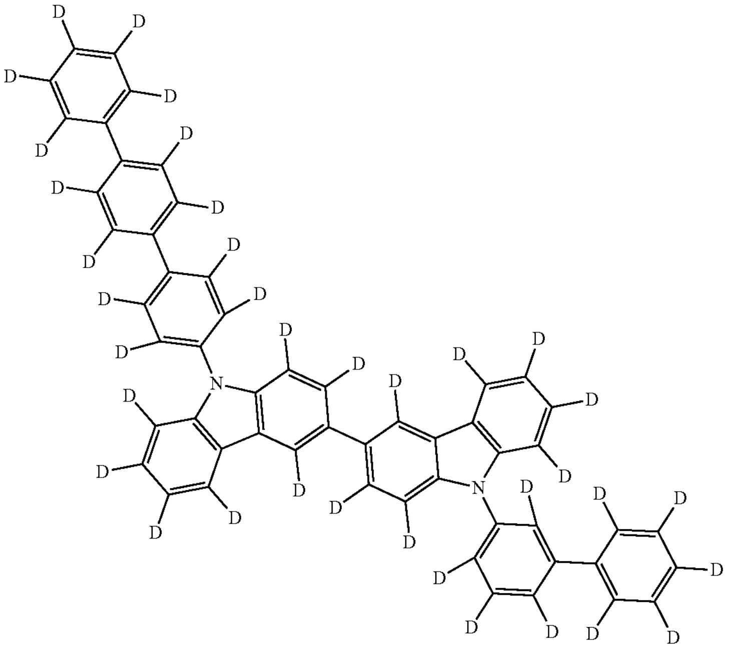 | 72% |

TABLE 10-continued
| | | |
|---|---|---|
| 2-62 | 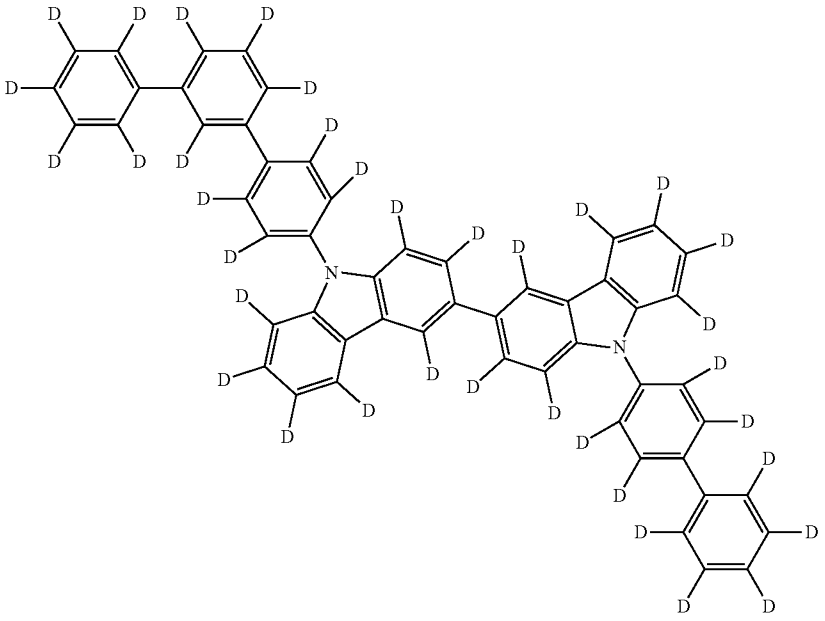 | 88% |
| 2-68 | 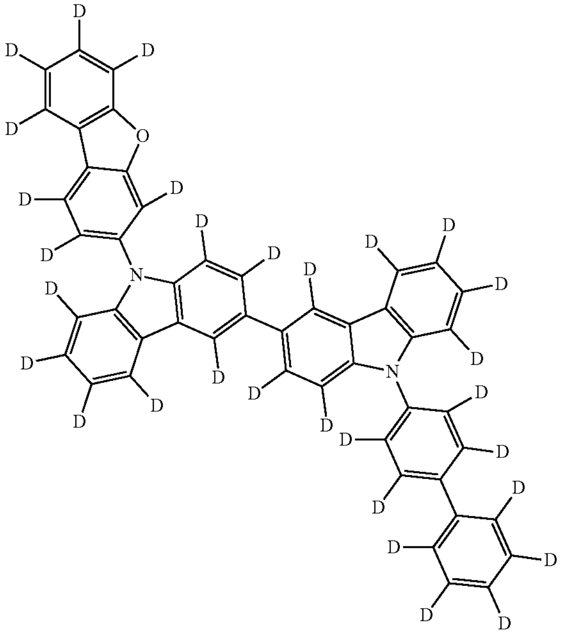 | 76% |

In the reaction of replacing hydrogen with deuterium in an organic compound, as the reaction temperature is higher, the substitution ratio of hydrogen to deuterium becomes higher and the yield becomes lower.

The compounds represented by Formulas 1 and 2 other than the compounds described in synthesis 1 to 10 and Tables 1 to 10 were also synthesized in the same manner as described in synthesis.

Data of the compounds synthesized are as shown in Tables 11 and 12.

TABLE 11

| | FD-Mass | | FD-Mass |
|---|---|---|---|
| 3 | m/z = 652.82 (C45H16D12N4O = 652.30) | 9 | m/z = 680.85 (C45H16D10N4OS = 680.25) |
| 11 | m/z = 664.79 (C45H16D10N4O2 = 664.27) | 12 | m/z = 648.79 (C45H22D8N4O = 648.28) |
| 15 | m/z = m/z = 648.79 (C45H22D8N4O = 648.28) | 26 | m/z = 662.78 (C45H18D8N4O2 = 662.26) |
| 31 | m/z = 742.90 (C51H18D12N4O2 = 742.31) | 33 | m/z = 742.90 (C51H18D12N4O2 = 742.31) |
| 34 | m/z = 572.70 (C39H16D8N4O = 572.25) | 35 | m/z = 652.82 (C45H16D12N4O = 652.30) |
| 42 | m/z = 680.85 (C45H16D10N4OS = 680.25) | 43 | m/z = 664.79 (C45H16D10N4O2 = 664.27) |
| 54 | m/z = 740.89 (C51H20D10N4O2 = 740.30) | 60 | m/z = 758.96 (C51H18D12N4OS = 758.29) |
| 71 | m/z = 646.78 (C45H22D6N4O = 646.26) | 73 | m/z = 735.88 (C51H25D6N5O = 735.29) |
| 82 | m/z = 722.88 (C51H26D6N4O = 722.30) | 98 | m/z = 660.77 (C45H20D6N4O2 = 660.24) |
| 103 | m/z = 646.78 (C45H22D6N4O = 646.26) | 110 | m/z = 676.83 (C45H20D6N4OS = 676.22) |
| 116 | m/z = 646.78 (C45H22D6N4O = 646.26) | 137 | m/z = 574.71 (C39H14D10N4O = 574.26) |
| 147 | m/z = 680.83 (C46H20D10N4O2 = 680.30) | 156 | m/z = 760.97 (C51H16D14N4OS = 760.30) |
| 170 | m/z = 574.71 (C39H14D10N4O = 574.26) | 178 | m/z = 680.85 (C45H16D10N4OS = 680.25) |
| 183 | m/z = 730.90 (C51H18D14N4O = 730.35) | 189 | m/z = 760.97 (C51H16D14N4OS = 760.30) |
| 195 | m/z = 666.80 (C45H14D12N4O2 = 666.28) | 199 | m/z = 666.80 (C45H14N4O2 = 666.28) |
| 205 | m/z = 572.70 (C39H16D8N4O = 572.25) | 206 | m/z = 652.82 (C45H16D12N4O = 652.30) |
| 207 | m/z = 652.82 (C45H16D12N4O = 652.30) | 213 | m/z = 680.85 (C45H16D10N4OS = 680.25) |
| 214 | m/z = 664.79 (C45H16D10N4O2 = 6664.27) | 216 | m/z = 648.79 (C45H20D8N4O = 648.28) |
| 217 | m/z = 728.92 (C51H20D12N4O = 728.33) | 218 | m/z = 728.92 (C51H2D12N4O = 728.33) |
| 219 | m/z = 648.79 (C45H2O2D8N4O = 648.28) | 225 | m/z = 740.89 (C51H20D10N4O2 = 740.330) |
| 228 | m/z = 680.85 (C45H16D10N4OS = 680.25) | 230 | m/z = 6662.78 (C45H18D8N4O2 = 662.26) |
| 234 | m/z = 662.78 (C45H18D8N4O2 = 662.26) | 235 | m/z = 742.90 (C51H18D12N4O2 = 742.31) |
| 236 | m/z = 758.96 (C51H18D12N4OS = 758.29) | 237 | m/z = 742.90 (C51H18D12N4O2 = 742.31) |
| 238 | m/z = 572.70 (C39H16D8N4O = 572.25) | 240 | m/z = 652.82 (C45H16D12N4O = 652.30) |
| 246 | m/z = 680.85 (C45H16D10N4OS = 680.25) | 248 | m/z = 664.79 (C45H16D10N42 = 664.27) |
| 249 | m/z = 648.79 (C45H20D6N4O = 648.28) | 251 | m/z = 728.92 (C51H20D12N4O = 728.33) |
| 252 | m/z = 648.79 (C45H20D6N4O = 648.28) | 257 | m/z = 756.95 (C51H20D10N4OS = 756.28) |
| 261 | m/z = 680.85 (C45H16D10N4OS = 680.25) | 263 | m/z = 662.78 (C45H18D8N4O2 = 662.26) |
| 270 | m/z = 742.90 (C51H18D12N4O2 = 742.31) | 273 | m/z = 570.68 (C39H18D6N4O = 570.23) |
| 274 | m/z = 646.78 (C45H22D6N4O = 55.26) | 278 | m/z = 686.85 (C48H26D6N4O = 686.30) |
| 280 | m/z = 676.83 (C45H20D6N4OS = 676.22) | 286 | m/z = 646.78 (C45H22D6N4O = 646.26) |
| 300 | m/z = 570.68 (C39H18D6N4O = 570.23) | 303 | m/z = 735.88 (C51H25D6N5O = 735.29) |

TABLE 11-continued

| | FD-Mass | | FD-Mass |
|---|---|---|---|
| 307 | m/z = 660.77 (C45H20D6N4O = 660.24) | 308 | m/z = 646.78 (C45H22D6N4O = 646.26) |
| 315 | m/z = 752.92 (C51H24D6N4OS = 752.25) | 318 | m/z = 676.83 (C45H20D6N4OS = 676.22) |
| 320 | m/z = 660.77 (C45H20D6N4O2 = 660.24) | 324 | m/z = 660.77 (C45H20D6N4O2 = 660.24) |
| 328 | m/z = 736.86 (C51H24D6N4O2 = 736.27) | 329 | m/z = 574.71 (C39H14D10N4O = 574.26) |
| 330 | m/z = 650.81 (C45H18D10N4O = 650.29) | 331 | m/z = 650.81 (C45H18D10N4O = 650.29) |
| 334 | m/z = 690.87 (C48H22D10N4O = 690.32) | 336 | m/z = 664.79 (C45H16D10N4O2 = 664.27) |
| 338 | m/z = 654.83 (C45H14D14N4O = 654.31) | 339 | m/z = 730.93 (C51H18D14N4O = 7303.35) |
| 340 | m/z = 730.93 (C51H18D14N4O = 730.35) | 341 | m/z = 654.83 (C45H14D14N4O = 654.31) |
| 344 | m/z = 744.91 (C51H16D14N4O2 = 744.32) | 347 | m/z = 680.85 (C45H16D10N4OS = 680.25) |
| 351 | m/z = 666.80 (C45H14D12N4O2 = 666.28) | 355 | m/z = 574.71 (C39H14D10N4O = 574.26) |
| 356 | m/z = 650.81 (C45H18D10N4O = 650.29) | 357 | m/z = 650.81 (C45H18D10N4O = 650.29) |
| 359 | m/z = 690.87 (C48H22D10N4O = 690.32) | 362 | m/z = 664.79 (C45H16D10N4O2 = 664.27) |
| 366 | m/z = 730.93 (C51H18D14N4O = 730.35) | 371 | m/z = 743.91 (C51H17D13N4O2 = 743.32) |
| 373 | m/z = 680.85 (C45H16D10N4OS = 680.25) | 380 | m/z = 742.90 (C51H18D12N4O2 = 742.31) |
| 386 | m/z = 652.82 (C45H16D12N4O = 652.30) | 387 | m/z = 652.82 (C45H16D12N4O = 652.30) |
| 390 | m/z = 680.85 (C45H16D10N4OS = 6580.25) | 392 | m/z = 664.79 (C45H16D10N4O2 = 664.27) |
| 393 | m/z = 648.79 (C45H20D8N4O = 648.28) | 395 | m/z = 728.92 (C51H20D12N4O = 728.33) |
| 396 | m/z = 648.79 (C45H20D8N4O = 648.28) | 398 | m/z = 756.95 (C51H20D10N4OS = 756.28) |
| 399 | m/z = 740.89 (C51H20D10N4O2 = 740.30) | 400 | m/z = 740.89 (C51H20D10N4O2 = 740.30) |
| 402 | m/z = 680.85 (C45H16D10N4OS = 680.25) | 404 | m/z = 758.96 (C51H18D12N4OS = 758.29) |
| 406 | m/z = 738.88 (C51H22D8N4O2 = 738.29) | 410 | m/z = 572.70 (C39H16D8N4O = 572.25) |
| 411 | m/z = 652.82 (C45H16D12N4O = 652.30) | 435 | m/z = 646.78 (C45H22D6N4O = 646.26) |
| 440 | m/z = 660.77 (C45H20D6N4O2 = 660.24) | 442 | m/z = 646.78 (C45H22D6N4O = 646.26) |
| 444 | m/z = 722.88 (C51H26D6N4O = 722.30) | 445 | m/z = 646.78 (C45H22D6N4O = 646.26) |
| 455 | m/z = 736.86 (C51H24D6N4O2 = 736.27) | 457 | m/z = 570.68 (C39H18D6N4O = 570.23) |
| 473 | m/z = 574.71 (C39H14D10N4O = 574.26) | 474 | m/z = 650.81 (C45H18D10N4O = 650.29) |
| 475 | m/z = 650.81 (C45H18D10N4O = 650.29) | 479 | m/z = 680.85 (C45H16D10N4OS = 680.25) |
| 480 | m/z = 664.79 (C45H16D10N4O2 = 664.27) | 482 | m/z = 654.83 (C45H14D14N4O = 654.31) |
| 483 | m/z = 730.93 (C51H18D14N4O = 730.35) | 484 | m/z = 730.93 (C51H18D14N4O = 730.35) |
| 485 | m/z = 654.83 (C45H14D14N4O = 654.31) | 488 | m/z = 744.91 (C51H16D14N4O2 = 744.32) |
| 495 | m/z = 742.90 (C51H18D12N4O2 = 742.31) | 497 | m/z = 574.71 (C39H14D10N4O = 574.26) |
| 500 | m/z = 650.81 (C45H18D10N4O = 650.29) | 525 | m/z = 572.70 (39H16D8N4O = 572.25) |
| 526 | m/z = 652.82 (C45H16D12N4O = 652.30) | 527 | m/z = 652.82 (C45H16D12N4O = 652.30) |
| 531 | m/z = 728.92 (C51H20D12N4O = 728.33) | 533 | m/z = 680.85 (C45H16D10N4OS = 680.25) |
| 535 | m/z = 664.79 (C45H16D10N4O2 = 664.27) | 536 | m/z = 648.79 (C45H20D8N4O = 648.28) |
| 537 | m/z = 728.92 (C51H20D12N4O = 728.33) | 538 | m/z = 728.92 (C51H20D12N4O = 728.33) |
| 539 | m/z = 648.79 (C45H20D8N4O = 648.28) | 544 | m/z = 756.95 (C51H20D10N4OS = 756.28) |
| 545 | m/z = 740.89 (C51H20D10N4O2 = 740.30) | 546 | m/z = 740.89 (C51H20D10N4O2 = 740.30) |
| 550 | m/z = 662.78 (C45H18D8N4O2 = 662.26) | 569 | m/z = 569.68 (C39H19D5N4O = 569.23) |

TABLE 11-continued

| | FD-Mass | | FD-Mass |
|---|---|---|---|
| 571 | m/z = 646.78 (C45H22D6N4O = 646.26) | 573 | m/z = 735.88 (C51H25D6N5O = 735.29) |
| 579 | m/z = 646.78 (C45H22D6N4O = 646.26) | 580 | m/z = 722.88 (C51H26D6N4O = 722.30) |
| 582 | m/z = 646.78 (C45H22D6N4O = 646.26) | 592 | m/z = 736.86 (C51H24D6N4O2 = 736.27) |
| 605 | m/z = 574.71 (C39H14D10N4O = 574.26) | 606 | m/z = 650.81 (C45H18D0N4O = 650.29) |
| 607 | m/z = 650.81 (C45H18D10N4O650.29) | 608 | m/z = 730.93 (C51H18D14N4O = 730.35) |
| 611 | m/z = 680.85 (C45H16D10N4OS = 680.25) | 612 | m/z = 664.79 (C45H16D10N4O2 = 664.27) |
| 614 | m/z = 730.93 (C51H18D14N4O = 730.35) | 616 | m/z = 654.83 (C45H14D14N4O = 654.31) |
| 620 | m/z = 744.91 (C51H16D14N4O2 = 744.32) | 625 | m/z = 746.92 (C51H14D16N4O2 = 746.34) |
| 627 | m/z = 742.90 (C51H18D12N4O2 = 742.31) | 629 | m/z = 742.90 (C51H18D12N4O2 = 742.31) |
| 630 | m/z = 574.71 (C39H14D10N4O = 574.26) | 641 | m/z = 588.79 (C39D24N4O = 588.35) |
| 643 | m/z = 668.92 (C45D28N4O = 668.40) | 645 | m/z = 696.95 (C45D26N4OS = 696.35) |
| 648 | m/z = 668.92 (C45D28N4O = 668.40) | 652 | m/z = 777.07 (C51D30N4OS = 776.40) |
| 662 | m/z = 588.79 (C39D24N4O = 588.35) | 664 | m/z = 668.92 (C45D28N4O = 668.40) |
| 667 | m/z = 696.95 (C45D26N4OS = 696.35) | 669 | m/z = 680.89 (C45D26N4O2 = 680.37) |
| 672 | m/z = 749.04 (C51D32N4O = 748.46) | 676 | m/z = 680.89 (C45D26N4O2 = 680.37) |
| 677 | m/z = 696.95 (C45D26N4OS = 696.35) | 680 | m/z = 761.01 (C51D30N4O2 = 760.43) |
| 684 | m/z = 761.01 (C51D30N4O2 = 760.43) | 685 | m/z = 588.79 (C29D24N4O = 588.35) |
| 686 | m/z = 668.92 (C45D28N4O = 668.40) | 689 | m/z = 696.95 (C45D26N4OS = 696.35) |
| 690 | m/z = 680.89 (C45D26N4O2 = 680.37) | 692 | m/z = 668.92 (C45D28N4O = 668.40) |
| 693 | m/z = 749.04 (C51D32N4O = 748.46) | 695 | m/z = 668.92 (C45D28N4O = 668.40) |
| 696 | m/z = 777.07 (C51D30N4OS = 776.40) | 698 | m/z = 696.95 (C45D26N4OS = 696.35) |
| 708 | m/z = 668.92 (C45D28N4O = 668.40) | 711 | m/z = 696.95 (C45D26N4OS = 696.35) |
| 714 | m/z = 668.92 (C45D28N4O = 668.40) | 720 | m/z = 761.01 (C51D30N4O2 = 760.43) |
| 721 | m/z = 696.95 (C45D26N4OS = 696.35) | 724 | m/z = 680.89 (C45D26N4O2 = 680.37) |
| 725 | m/z = 588.79 (C39D24N4O = 588.35) | 726 | m/z = 668.92 (C45D28N4O = 668.40) |
| 727 | m/z = 668.92 (C45D28N4O = 668.40) | 729 | m/z = 696.95 (C46D26N4OS = 696.35) |
| 730 | m/z = 680.89 (C45D26N4O2 = 680.37) | 732 | m/z = 668.92 (C45D28N4O = 668.40) |
| 734 | m/z = 749.04 (C51D32N4 = 748.46) | 735 | m/z = 668.92 (C45D28N4O = 668.40) |
| 738 | m/z = 696.95 (C45D26N4OS = 696.35) | 741 | m/z = 761.01 (C51D30N4O2 = 760.43) |
| 743 | m/z = 761.01 (C51D30N4O2 = 760.43) | 746 | m/z = 588.79 (C39D24N4O = 588.35) |
| 748 | m/z = 668.92 (C45D28N4O = 668.40) | 765 | m/z = 588.79 (C39D24N4O = 588.35) |
| 766 | m/z = 668.92 (C45D28N4O = 668.40) | 767 | m/z = 668.92 (C45D28N4O = 668.40) |
| 772 | m/z = 668.92 (C45D28N4O = 668.40) | 773 | m/z = 749.04 (C51D32N4O = 748.46) |
| 774 | m/z = 749.04 (C51D32N4O = 748.46) | 775 | m/z = 668.92 (C45D28N4O = 668.40) |
| 779 | m/z = 680.89 (C45D26N4O2 = 680.37) | 2-2 | m/z = 654.91 (C48H14D18N2 = 654.37) |
| 2-3 | m/z = 574.79 (C42H14D14N2 = 574.31) | 2-5 | m/z = 654.91 (C48N14D18N2 = 654.37) |
| 2-6 | m/z = 654.91 (C48H14D18N2 = 654.37) | 2-8 | m/z = 654.91 (C48H14D18N2 = 654.37) |
| 2-9 | m/z = 654.91 (C48H14D18N2 = 654.37) | 2-12 | m/z = 735.03 (C54H14D22N2 = 734.43) |
| 2-14 | m/z = 735.03 (C54H14D22N2 = 734.43) | 2-26 | m/z = 650.88 (C48H18D14N2 = 650.34) |

TABLE 11-continued

| | FD-Mass | | FD-Mass |
|---|---|---|---|
| 2-27 | m/z = 574.79 ($C_{42}H_{14}D_{14}N_2$ = 574.31) | 2-29 | m/z = 650.88 ($C_{48}H_{18}D_{14}N_2$ = 650.34) |
| 2-32 | m/z = 650.88 ($C_{48}H_{18}D_{14}N_2$ = 650.34) | 2-33 | m/z = 650.88 ($C_{48}H_{18}D_{14}N_2$ = 650.34) |
| 2-50 | m/z = 668.99 ($C_{48}D_{32}N_2$ = 668.46) | 2-51 | m/z = 588.87 ($C_{42}D_{28}N_2$ = 588.40) |
| 2-53 | m/z = 668.99 ($C_{48}D_{32}N_2$ = 668.46) | 2-56 | m/z = 668.99 ($C_{48}D_{32}N_2$ = 668.46) |
| 2-60 | m/z = 749.12 ($C_{54}D_{32}N_2$ = 748.51) | 2-62 | m/z = 749.12 ($C_{54}D_{36}N_2$ = 748.51) |
| 2-68 | m/z = 680.96 ($C_{48}D_{30}N_2O$ = 680.42) | 2-75 | m/z = 560.70 ($C_{42}H_{28}N_2$ = 560.23) |
| 2-76 | m/z = 636.80 ($C_{48}H_{32}N_2$ = 636.26) | 2-77 | m/z = 636.80 ($C_{48}H_{32}N_2$ = 636.26) |
| 2-78 | m/z = 636.80 ($C_{48}H_{32}N_2$ = 636.26) | | |

TABLE 12

| | $^1$H NMR(DMSO, 300 Mz) |
|---|---|
| 3 | δ = 8.36 (4H, m), 8.03 (1H, d), 7.94 (1H, d), 7.76~7.82 (2H, m), 7.46~7.50 (7H, m), 7.31 (1H, d), |
| 9 | δ = 8.36 (4H, m), 8.03 (1H, d), 7.94 (1H, d), 7.76~7.82 (2H, m), 7.46~7.50 (7H, m), 7.31 (1H, d) |
| 11 | δ = 8.36 (4H, m), 8.03 (1H, d), 7.94 (1H, d), 7.76~7.82 (2H, m), 7.46~7.50 (7H, m), 7.31 (1H, d) |
| 12 | δ = 8.36~8.38 (3H, m), 8.03 (1H, d), 7.94 (2H, m), 7.73~7.82 (5H, m), 7.61 (1H, d), 7.41~7.50 (7H, m), 7.31 (1H, d) |
| 15 | δ = 8.36 (2H, m), 7.94~8.03 (4H, m), 7.75~7.82 (4H, m), 7.41~7.50 (7H, m), 7.25~7.31 (3H, m) |
| 26 | δ = 8.36 (2H, m), 7.8.08 (7H, m), 7.31~7.54 (9H, m) |
| 31 | δ = 8.36 (2H, m), 7.76~8.08 (7H, m), 7.31~7.54 (9H, m) |
| 33 | δ = 8.36 (2H, m), 7.76~8.08 (7H, m), 7.31~7.51 (9H, m) |
| 34 | δ = 8.36 (4H, m), 7.94 (1H, d), 7.82 (1H, d), 7.69 (1H, d), 7.46~7.57 (8H, m), 7.31 (1H, d) |
| 35 | δ = 8.36 (4H, m), 7.94 (1H, d), 7.82 (1H, d), 7.69 (1H, d), 7.46~7.57 (8H, m), 7.31 (1H, d) |
| 42 | δ = 8.36 (4H, m), 7.94 (1H, d), 7.82 (1H, d), 7.69 (1H, d), 7.46~7.57 (8H, m), 7.31 (1H, d) |
| 43 | δ = 8.36 (4H, m), 7.94 (1H, d), 7.82 (1H, d), 7.69 (1H, d), 7.46~7.57 (8H, m), 7.31 (1H, d) |
| 54 | δ = 8.36~8.38 (3H, m), 7.94 (2H, m), 7.69~7.75 (5H, m), 7.41~7.61 (9H, m), 7.31 (1H, d) |
| 60 | δ = 8.55 (1H, d), 8.45 (1H, d), 8.36 (2H, m), 7.92~7.94 (3H, m), 7.82 (1H, d), 7.69~7.70 (2H, m), 7.46~7.57 (7H, m), 7.31 (1H, d) |
| 71 | δ = 8.55 (1H, d), 8.36 (4H, m), 7.89~7.99 (3H, m), 7.75~7.77 (3H, m), 7.35~7.50 (10H, m), 7.16 (1H, t) |
| 73 | δ = 8.55 (1H, d), 8.36 (4H, m), 8.19 (1H, d), 7.94 (1H, d), 7.50~7.62 (14H, m), 7.35~7.40 (2H, m), 7.16~7.20 (2H, m) |
| 82 | δ = 8.55 (1H, d), 8.38~8.36 (3H, m), 7.89~7.99 (4H, m), 7.73~7.75 (6H, m), 7.61 (1H, d), 7.35~7.50 (10H, m), 7.16 (1H, t) |
| 98 | δ = 8.55 (1H, d), 8.36 (2H, m), 8.19 (1H, d), 7.94~8.03 (3H, m), 7.76~7.82 (2H, m), 7.50~7.58 (6H, m), 7.31~7.39 (3H, m), 7.16 (1H, t) |
| 103 | δ = 8.55 (1H, d), 8.31~8.36 (5H, m), 7.91~7.94 (2H, t), 7.74~7.75 (3H, m), 7.35~7.50 (10H, m), 7.16 (1H, t) |
| 110 | δ = 8.45 (1H, d), 8.36 (4H, m), 8.19 (1H, d), 8.05 (1H, d), 7.93 (1H, d), 7.49~7.58 (10H, m), 7.33 (1H, d), 7.20 (1H, t) |
| 116 | δ = 8.55 (1H, d), 8.36 (2H, m), 8.19 (1H, d), 7.94~7.96 (3H, m), 7.75 (2H, d), 7.35~7.58 (9H, m), 7.16~7.25 (4H, m) |
| 137 | δ = 8.55 (1H, d), 8.19 (1H, d), 7.94~8.03 (3H, m), 7.76~7.82 (2H, m), 7.46~7.58 (3H, m), 7.31~7.35 (2H, m), 7.16~7.20 (2H, m) |
| 147 | δ = 8.19 (1H, d), 7.94~8.03 (3H, m), 7.76~7.84 (3H, m), 7.31~7.58 (7H, m), 7.13~7.20 (2H, m) |
| 156 | δ = 8.45 (1H, d), 8.19 (1H, d), 7.93~8.05 (4H, m), 7.76~7.82 (2H, m), 7.46~7.58 (5H, m), 7.31~7.33 (2H, t), 7.20 (1H, t) |
| 170 | δ = 8.55 (1H, d), 8.19 (1H, d), 7.94 (2H, d), 7.82 (1H, d), 7.69 (1H, d), 7.46~7.58 (4H, m), 7.31~7.35 (2H, m), 7.16~7.20 (2H, t) |

TABLE 12-continued

| | $^1$H NMR(DMSO, 300 Mz) |
|---|---|
| 178 | δ = 8.45 (1H, d), 8.19 (1H, d), 8.05 (1H, d), 7.93~7.94 (2H, d), 7.82 (1H, d), 7.69 (1H, d), 7.46~7.58 (6H, m), 7.31~7.33 (2H, t), 7.20 (1H, t) |
| 183 | δ = 8.55 (1H, d), 7.69~7.99 (9H, m), 7.31~7.57 (7H, m), 7.16 (1H, t) |
| 189 | δ = 8.45 (1H, d), 8.19 (1H, d), 8.05 (1H, d), 7.94 (2H, d), 7.82 (1H, d), 7.69 (1H, d), 7.46~7.58 (6H, m), 7.31~7.33 (2H, t), 7.20 (1H, t) |
| 195 | δ = 8.55 (1H, d), 8.19 (1H, d), 7.94 (2H, d), 7.82 (1H, d), 7.69 (1H, d), 7.46~7.58 (4H, m), 7.31~7.35 (2H, m), 7.16~7.20 (2H, t) |
| 199 | δ = 8.55 (1H, d), 8.19 (1H, d), 7.94 (2H, d), 7.82 (1H, d), 7.69 (1H, d), 7.46~7.58 (4H, m), 7.31~7.35 (2H, m), 7.16~7.20 (2H, t) |
| 205 | δ = 8.36 (4H, m), 7.98~8.03 (2H, m), 7.76~7.82 (2H, m), 7.50~7.54 (7H, m), 7.25 (1H, d) |
| 206 | δ = 8.36 (4H, m), 7.98~8.03 (2H, m), 7.76~7.82 (2H, m), 7.50~7.54 (7H, m), 7.25 (1H, d) |
| 207 | δ = 8.36 (4H, m), 7.98~8.03 (2H, m), 7.76~7.82 (2H, m), 7.50~7.54 (7H, m), 7.25 (1H, d) |
| 213 | δ = 8.36 (4H, m), 7.98~8.03 (2H, m), 7.76~7.82 (2H, m), 7.50~7.54 (7H, m), 7.25 (1H, d) |
| 214 | δ = 8.36 (4H, m), 7.98~8.03 (2H, m), 7.76~7.82 (2H, m), 7.50~7.54 (7H, m), 7.25 (1H, d) |
| 216 | δ = 8.36~8.38 (3H, m), 7.94~8.03 (3H, m), 7.73~7.82 (5H, m), 7.41~7.61 (8H, m), 7.25 (1H, d) |
| 217 | δ = 8.36~8.38 (3H, m), 7.94~8.03 (3H, m), 7.73~7.82 (5H, m), 7.41~7.61 (8H, m), 7.25 (1H, d) |
| 218 | δ = 8.36~8.38 (3H, m), 7.94~8.03 (3H, m), 7.73~7.82 (5H, m), 7.41~7.61 (8H, m), 7.25 (1H, d)1 |
| 219 | δ = 8.36 (2H, m), 7.96~8.03 (4H, m), 7.75~7.82 (4H, m), 7.41~7.54 (7H, m), 7.25 (2H, d) |
| 225 | δ = 8.36~8.38 (3H, m), 7.94~8.03 (3H, m), 7.73~7.82 (5H, m), 7.41~7.61 (8H, m), 7.25 (1H, d) |
| 228 | δ = 8.36 (4H, m), 7.98~8.03 (2H, m), 7.76~7.82 (2H, m), 7.50~7.54 (7H, m), 7.25 (1H, d) |
| 230 | δ = 8.36 (2H, m), 7.98~8.08 (4H, m), 7.76~7.88 (3H, m), 7.50~7.54 (6H, m), 7.25~7.39 (3H, m) |
| 234 | δ = 8.36 (2H, m), 7.98~8.03 (4H, m), 7.76~7.82 (4H, m), 7.50~7.54 (5H, m), 7.25~7.39 (3H, m) |
| 235 | δ = 8.36 (2H, m), 7.98~8.08 (4H, m), 7.76~7.88 (3H, m), 7.50~7.54 (6H, m), 7.25~7.39 (3H, m) |
| 236 | δ = 8.45 (1H, d), 8.36 (2H, m), 8.12 (1H, s), 7.92~8.03 (5H, m), 7.76~7.82 (2H, m), 7.49~7.56 (6H, m), 7.25 (1H, d) |
| 237 | δ = 8.36 (2H, m), 7.98~8.08 (4H, m), 7.76~7.88 (3H, m), 7.50~7.54 (6H, m), 7.25~7.39 (3H, m) |
| 238 | δ = 8.36 (4H, m), 7.98 (1H, d), 7.82 (1H, d), 7.69 (1H, d), 7.50~7.57 (8H, m), 7.25 (1H, d) |
| 240 | δ = 8.36 (4H, m), 7.98 (1H, d), 7.82 (1H, d), 7.69 (1H, d), 7.50~7.57 (8H, m), 7.25 (1H, d) |
| 246 | δ = 8.36 (4H, m), 7.98 (1H, d), 7.82 (1H, d), 7.69 (1H, d), 7.50~7.57 (8H, m), 7.25 (1H, d) |
| 248 | δ = 8.36 (4H, m), 7.98 (1H, d), 7.82 (1H, d), 7.69 (1H, d), 7.50~7.57 (8H, m), 7.25 (1H, d) |
| 249 | δ = 8.38 (3H, m), 7.94~7.98 (2H, m), 7.69~7.82 (5H, m), 7.41~7.61 (9H, m), 7.25 (1H, d) |

| | $^1$H NMR(DMSO, 300 Mz) |
|---|---|
| 251 | δ = 8.36 (3H, m), 7.94~7.98 (2H, m), 7.69~7.82 (5H, m), 7.41~7.61 (9H, m), 7.25 (1H, d) |
| 252 | δ = 8.36 (2H, m), 7.96~7.98 (3H, m), 7.69~7.82 (4H, m), 7.41~7.57 (8H, m), 7.25 (3H, d) |
| 257 | δ = 8.36 (2H, m), 7.96~7.98 (3H, m), 7.69~7.82 (4H, m), 7.41~7.57 (8H, m), 7.25 (3H, d) |
| 261 | δ = 8.36 (4H, m), 7.98 (1H, d), 7.82 (1H, d), 7.69 (1H, d), 7.50~7.57 (8H, m), 7.25 (1H, d) |
| 263 | δ = 8.36 (2H, m), 8.08 (1H, d), 7.98 (1H, d), 7.82~7.88 (2H, m), 7.69 (1H, d), 7.50~7.57 (7H, m), 7.25~7.39 (3H, m) |
| 270 | δ = 8.36 (2H, m), 7.98~8.03 (3H, m), 7.69~7.82 (4H, m), 7.50~7.57 (6H, m), 7.25~7.39 (3H, m) |
| 273 | δ = 8.55 (1H, d), 8.36 (4H, m), 8.19 (1H, d), 7.94 (1H, d), 7.50~7.58 (8H, m), 7.35 (1H, t), 7.16~7.20 (2H, t) |
| 274 | δ = 8.55 (1H, d), 8.31~8.36 (5H, m), 7.91~7.94 (2H, m), 7.74~7.75 (3H, d), 7.35~7.50 (10H, m), 7.16 (1H, t) |
| 278 | δ = 8.36 (4H, m), 8.19~8.24 (3H, m), 7.88 (1H, s), 7.74 (1H, d), 7.50~7.58 (9H, m), 7.38 (1H, t), 7.20 (1H, t), 1.69 (6H, s) |
| 280 | δ = 8.45 (1H, d), 8.36 (4H, m), 8.19 (1H, d), 8.05 (1H, d), 7.93 (1H, d), 7.49~7.58 (10H, m), 7.33 (1H, d), 7.20 (1H, t) |
| 286 | δ = 8.55 (1H, d), 8.36 (2H, m), 8.19 (1H, d), 7.94~7.96 (3H, m), 7.75 (2H, d), 7.35~7.58 (9H, m), 7.16~7.25 (4H, m) |
| 300 | δ = 8.55 (1H, d), 8.36 (4H, m), 8.19 (1H, d), 7.94 (1H, d), 7.50~7.58 (8H, m), 7.35 (1H, t), 7.16~7.20 (2H, t) |
| 303 | δ = 8.55 (1H, d), 8.36 (4H, m), 8.19 (1H, d), 7.94 (1H, d), 7.50~7.62 (14H, m), 7.35~7.40 (2H, m), 7.16~7.20 (2H, t)/`7.39 (2H, m), 7.13~7.20 (2H, m) |
| 307 | δ = 8.36 (4H, m), 8.19 (1H, d), 7.98 (1H, d), 7.84 (1H, d), 7.50~7.58 (9H, m), 7.13~7.20 (2H, m) |
| 308 | δ = 8.55 (1H, d), 8.36~8.38 (3H, m), 8.19 (1H, d), 7.94 (2H, m), 7.73~7.75 (3H, m), 7.35~7.61 (10H, m), 7.16~7.20 (2H, m) |
| 315 | δ = 8.45 (1H, d), 8.36 (2H, m), 8.19 (1H, d), 8.05 (1H, d), 7.93~7.96 (3H, m), 7.75 (2H, d), 7.33~7.58 (11H, m), 7.20~7.25 (3H, m) |
| 318 | δ = 8.55 (1H, d), 8.45 (1H, d), 8.36 (4H, m), 8.05 (1H, d), 7.93~7.94 (2H, d), 7.49~7.60 (9H, m), 7.35 (2H, t), 7.16 (1H, t) |
| 320 | δ = 8.55 (1H, d), 8.36 (2H, m), 8.19 (1H, d), 8.08 (1H, d), 7.88~7.98 (3H, m), 7.50~7.54 (6H, m), 7.31~7.39 (3H, m), 7.16~7.20 (2H, t) |
| 324 | δ = 8.55 (1H, d), 8.36 (2H, m), 8.19 (1H, d), 7.94~8.03 (3H, m), 7.76~7.82 (2H, m), 7.50~7.58 (6H, m), 7.31~7.39 (3H, m), 7.16~7.20 (2H, m) |
| 328 | δ = 8.55 (1H, d), 8.36 (2H, m), 7.89~8.03 (5H, m), 7.75~7.82 (5H, m), 7.31~7.54 (10H, m), 7.16 (1H, t) |
| 329 | δ = 8.55 (1H, d), 8.19 (1H, d), 7.94~8.03 (3H, m), 7.76~7.82 (2H, m), 7.50~7.58 (3H, m), 7.16~7.35 (4H, m) |
| 330 | δ = 8.55 (1H, d), 8.31 (1H, d), 7.91~8.03 (4H, m), 7.74~7.82 (5H, m), 7.35~7.54 (5H, m), 7.25 (1H, d), 7.16 (1H, t) |
| 331 | δ = 8.55 (1H, d), 7.75~8.03 (9H, m), 7.35~7.54 (5H, m), 7.25 (1H, d), 7.16 (1H, t) |
| 334 | δ = 8.19~8.24 (3H, m), 7.98~8.03 (2H, m), 7.88 (1H, s), 7.74~7.82 (3H, m), 7.50~7.58 (4H, m), 7.38 (1H, t), 7.20~7.25 (2H, m), 1.69 (6H, s) |
| 336 | δ = 8.55 (1H, d), 7.94~8.03 (4H, m), 7.76~7.84 (3H, m), 7.16~7.54 (8H, m) |
| 338 | δ = 8.55 (1H, d), 8.19 (1H, d), 7.94~8.03 (3H, m), 7.76~7.82 (2H, m), 7.50~7.58 (3H, m), 7.16~7.35 (4H, m) |
| 339 | δ = 8.55 (1H, d), 8.31 (1H, d), 7.91~8.03 (4H, m), 7.74~7.82 (5H, m), 7.35~7.54 (5H, m), 7.25 (1H, d), 7.16 (1H, t) |
| 340 | δ = 8.55 (1H, d), 7.75~8.03 (10H, m), 7.35~7.54 (5H, m), 7.25 (1H, d), 7.16 (1H, t) |
| 341 | δ = 8.55 (1H, d), 8.19 (1H, d), 7.94~8.03 (3H, m), 7.76~7.82 (2H, m), 7.50~7.58 (3H, m), 7.16~7.35 (4H, m) |
| 344 | δ = 8.55 (1H, d), 7.94~8.03 (3H, m), 7.76~7.84 (3H, m), 7.16~7.48 (8H, m) |
| 347 | δ = 8.55 (1H, d), 8.45 (1H, d), 7.93~8.05 (5H, m), 7.76~7.82 (2H, m), 7.49~7.60 (4H, m), 7.35 (1H, t), 7.16~7.25 (2H, m) |
| 351 | δ = 8.55 (1H, d), 8.19 (1H, d), 7.94~8.03 (3H, m), 7.76~7.82 (2H, m), 7.50~7.58 (3H, m), 7.16~7.35 (4H, m) |
| 355 | δ = 8.55 (1H, d), 8.19 (1H, d), 7.94~7.98 (2H, m), 7.82 (1H, d), 7.69 (1H, d), 7.50~7.58 (4H, m), 7.35 (1H, t), 7.16~7.25 (3H, m) |
| 356 | δ = 8.55 (1H, d), 8.31 (1H, d), 7.91~7.98 (3H, m), 7.69~7.82 (5H, m), 7.35~7.57 (6H, m), 7.25 (1H, d), 7.16 (1H, t) |
| 357 | δ = 8.55 (1H, d), 7.69~7.99 (9H, m), 7.35~7.57 (6H, m), 7.16~7.25 (2H, m) |
| 359 | δ = 8.19~8.24 (3H, m), 7.98 (1H, d), 7.88 (1H, s), 7.82 (1H, d), 7.69~7.74 (2H, m), 7.50~7.58 (5H, m), 7.38 (1H, t), 7.20~7.25 (2H, m), 1.69 (6H, s) |

| | $^1$H NMR(DMSO, 300 Mz) |
|---|---|
| 362 | δ = 8.55 (1H, d), 7.94~7.98 (3H, m), 7.82~7.84 (2H, t), 7.69 (1H, d), 7.16~7.57 (9H, m) |
| 366 | δ = 8.55 (1H, d), 7.69~7.99 (9H, m), 7.35~7.57 (6H, m), 7.16~7.25 (2H, m) |
| 371 | δ = 8.19 (1H, d), 7.98 (2H, d), 7.82~7.84 (2H, t), 7.69 (1H, d), 7.50~7.58 (5H, m), 7.13~7.39 (5H, m) |
| 373 | δ = 8.55 (1H, d), 8.45 (1H, d), 7.93~8.05 (4H, m), 7.82 (1H, d), 7.69 (1H, d), 7.49~7.60 (5H, m), 7.35 (1H, t), 7.16~7.25 (2H, m) |
| 380 | δ = 8.55 (1H, d), 7.69~7.99 (9H, m), 7.35~7.57 (6H, m), 7.16~7.25 (2H, m) |
| 386 | δ = 8.36 (4H, m), 8.03 (1H, d), 7.74~7.82 (3H, m), 7.61 (1H, s), 7.50 (6H, m), 7.31 (1H, d) |
| 387 | δ = 8.36 (4H, m), 8.03 (1H, d), 7.74~7.82 (3H, m), 7.61 (1H, s), 7.50 (6H, m), 7.31 (1H, d) |
| 390 | δ = 8.36 (4H, m), 8.03 (1H, d), 7.74~7.82 (3H, m), 7.61 (1H, s), 7.50 (6H, m), 7.31 (1H, d) |
| 392 | δ = 8.36~8.38 (3H, m), 8.03 (1H, d), 7.94 (1H, s), 7.73~7.82 (6H, m), 7.61 (2H, m), 7.41~7.50 (6H, m), 7.31 (1H, d) |
| 393 | δ = 8.36~8.38 (3H, m), 8.03 (1H, d), 7.94 (1H, s), 7.73~7.82 (6H, m), 7.61 (2H, m), 7.41~7.50 (6H, m), 7.31 (1H, d) |
| 395 | δ = 8.36 (3H, m), 8.03 (1H, d), 7.94 (1H, s), 7.73~7.82 (6H, m), 7.61 (2H, m), 7.41~7.50 (6H, m), 7.31 (1H, d) |
| 396 | δ = 8.36 (2H, m), 7.96~8.03 (3H, m), 7.74~7.82 (5H, m), 7.61 (1H, s), 7.41~7.50 (6H, m), 7.25~7.31 (3H, m) |
| 398 | δ = 8.36 (2H, m), 7.96~8.03 (3H, m), 7.74~7.82 (5H, m), 7.61 (1H, s), 7.41~7.50 (6H, m), 7.25~7.31 (3H, m) |
| 399 | δ = 8.36~8.38 (3H, m), 8.03 (1H, d), 7.94 (1H, s), 7.74~7.82 (6H, m), 7.61 (2H, m), 7.41~7.50 (6H, m), 7.31 (1H, d) |
| 400 | δ = 8.36~8.38 (3H, m), 8.03 (1H, d), 7.94 (1H, s), 7.73~7.82 (6H, m), 7.61 (2H, m), 7.41~7.50 (6H, m), 7.31 (1H, d) |
| 402 | δ = 8.36 (4H, m), 8.03 (1H, d), 7.74~7.82 (3H, m), 7.61 (1H, s), 7.50 (6H, m), 7.31 (1H, d) |
| 404 | δ = 8.55 (1H, d), 8.45 (1H, d), 8.36 (2H, m0, 8.03 (1H, d), 7.92~7.93 (2H, d), 7.70~7.76 (3H, m), 7.49~7.61 (6H, m), 7.31 (1H, d) |
| 406 | δ = 8.38 (1H, d), 7.94~8.03 (4H, m), 7.73~7.82 (8H, m), 7.31~7.61 (9H, m) |
| 410 | δ = 8.36 (4H, m), 7.82 (1H, d), 7.69~7.74 (2H, m), 7.50~7.61 (8H, m), 7.31 (1H, d) |
| 411 | δ = 8.36 (4H, m), 7.82 (1H, d), 7.69~7.74 (2H, m), 7.50~7.61 (8H, m), 7.31 (1H, d) |
| 435 | δ = 8.55 (1H, d), 8.36 (4H, m), 7.89~7.99 (3H, m), 7.75~7.77 (3H, m), 7.35~7.50 (10H, m), 7.16 (1H, t) |
| 440 | δ = 8.55 (1H, d), 8.36 (4H, m), 7.94~7.98 (2H, m), 7.84 (1H, d), 7.48~7.54 (8H, m), 7.31~7.39 (3H, m), 7.16 (1H, t) |
| 442 | δ = 8.55 (1H, d), 8.36~8.38 (3H, m), 8.19 (1H, d), 7.94 (2H, m), 7.73~7.75 (3H, m), 7.41~7.61 (10H, m), 7.16~7.20 (2H, t) |
| 444 | δ = 8.55 (1H, d), 8.36~8.38 (3H, m), 7.89~7.99 (4H, m), 7.73~7.77 (6H, m), 7.61 (1H, d), 7.35~7.50 (10H, m), 7.16 (1H, t) |
| 445 | δ = 8.55 (1H, d), 8.36 (2H, m), 8.19 (1H, d), 7.94~7.96 (3H, t), 7.75 (2H, d), 7.35~7.58 (9H, m), 7.16~7.25 (4H, m) |
| 455 | δ = 8.55 (1H, d), 8.31~8.36 (3H, m), 8.08 (1H, d), 7.88~7.98 (4H, m), 7.74~7.75 (3H, d), 7.31~7.54 (11H, m), 7.16 (1H, t) |
| 457 | δ = 8.55 (1H, d), 8.36 (4H, m), 8.19 (1H, d), 7.94 (1H, d), 7.50~7.58 (8H, m), 7.35 (1H, t), 7.16~7.20 (2H, t) |
| 473 | δ = 8.55 (1H, d), 8.19 (1H, d), 8.03 (1H, d), 7.94 (1H, d), 7.74~7.82 (3H, m), 7.50~7.61 (3H, m), 7.31~7.35 (2H, m), 7.16~7.20 (2H, t) |
| 474 | δ = 8.55 (1H, d), 8.31 (1H, d), 8.03 (1H, d), 7.91~7.94 (2H, m), 7.74~7.82 (6H, m), 7.61 (1H, s), 7.31~7.49 (5H, m), 7.16 (1H, t) |
| 475 | δ = 8.55 (1H, d), 7.89~8.03 (4H, m), 7.74~7.82 (6H, m), 7.61 (1H, s), 7.31~7.49 (5H, m), 7.16 (1H, t) |
| 479 | δ = 8.45 (1H, d), 8.19 (1H, d), 8.03~8.05 (2H, t), 7.93 (1H, d), 7.74~7.82 (3H, m), 7.49~7.61 (5H, m), 7.31~7.33 (2H, t), 7.20 (1H, t) |
| 480 | δ = 8.55 (1H, d), 7.94~8.03 (2H, m), 7.74~7.84 (4H, m), 7.31~7.61 (7H, m), 7.16 (1H, t) |
| 482 | δ = 8.55 (1H, d), 8.19 (1H, d), 8.03 (1H, d), 7.94 (1H, d), 7.74~7.82 (3H, m), 7.50~7.61 (3H, m), 7.31~7.35 (2H, m), 7.16~7.20 (2H, t) |
| 483 | δ = 8.55 (1H, d), 8.31 (1H, d), 8.03 (1H, d), 7.91~7.94 (2H, m), 7.74~7.82 (6H, m), 7.61 (1H, s), 7.31~7.49 (5H, m), 7.16 (1H, t) |
| 484 | δ = 8.55 (1H, d), 7.89~8.03 (4H, m), 7.74~7.82 (6H, m), 7.61 (1H, s), 7.31~7.49 (5H, m), 7.16 (1H, t) |

TABLE 12-continued

| | $^1$H NMR(DMSO, 300 Mz) |
|---|---|
| 485 | δ = 8.55 (1H, d), 8.19 (1H, d), 8.03 (1H, d), 7.94 (1H, d), 7.74~7.82 (3H, m), 7.50~7.61 (3H, m), 7.31~7.35 (2H, m), 7.16~7.20 (2H, t) |
| 488 | δ = 8.55 (1H, d), 7.94~8.03 (3H, m), 7.74~7.82 (4H, m), 7.31~7.61 (7H, m), 7.16 (1H, t) |
| 495 | δ = 8.55 (1H, d), 8.31 (1H, d), 8.03 (1H, d), 7.91~7.94 (2H, m), 7.74~7.82 (6H, m), 7.61 (1H, s), 7.31~7.49 (5H, m), 7.16 (1H, t) |
| 497 | δ = 8.55 (1H, d), 8.19 (1H, d), 7.94 (1H, d), 7.50~7.82 (7H, m), 7.31~7.35 (2H, m), 7.16~7.20 (2H, t) |
| 500 | δ = 8.55 (1H, d), 7.74~7.99 (9H, m), 7.31~7.61 (7H, m), 7.16 (1H, t) |
| 525 | δ = 8.36 (4H, m), 8.03 (1H, d), 7.76~7.82 (2H, m), 7.50~7.55 (8H, m), 7.25 (1H, d) |
| 526 | δ = 8.36 (4H, m), 8.03 (1H, d), 7.76~7.82 (2H, m), 7.50~7.55 (8H, m), 7.25 (1H, d) |
| 527 | δ = 8.36 (4H, m), 8.03 (1H, d), 7.76~7.82 (2H, m), 7.50~7.55 (8H, m), 7.25 (1H, d) |
| 531 | δ = 8.36~8.38 (3H, m), 8.03 (1H, d), 7.94 (1H, s), 7.73~7.82 (5H, m), 7.41~7.61 (9H, m), 7.25 (1H, d) |
| 533 | δ = 8.36 (4H, m), 8.03 (1H, d), 7.76~7.82 (2H, m), 7.50~7.55 (8H, m), 7.25 (1H, d) |
| 535 | δ = 8.36 (4H, m), 8.03 (1H, d), 7.76~7.82 (2H, m), 7.50~7.55 (8H, m), 7.25 (1H, d) |
| 536 | δ = 8.36 (3H, m), 8.03 (1H, d), 7.94 (1H, s), 7.73~7.82 (5H, m), 7.41~7.61 (9H, m), 7.25 (1H, d) |
| 537 | δ = 8.36~8.38 (3H, m), 8.03 (1H, d), 7.94 (1H, s), 7.73~7.82 (5H, m), 7.41~7.61 (9H, m), 7.25 (1H, d) |
| 538 | δ = 8.36~8.38 (3H, m), 8.03 (1H, d), 7.94 (1H, s), 7.73~7.82 (5H, m), 7.41~7.61 (9H, m), 7.25 (1H, d) |
| 539 | δ = 8.36 (2H, m), 7.96~8.03 (3H, m), 7.75~7.82 (4H, m), 7.41~7.55 (8H, m), 7.25 (3H, d) |
| 544 | δ = 8.36 (2H, m), 7.96~8.03 (3H, m), 7.75~7.82 (4H, m), 7.41~7.55 (8H, m), 7.25 (3H, d) |
| 545 | δ = 8.36~8.38 (3H, m), 8.03 (1H, d), 7.94 (1H, s), 7.73~7.82 (5H, m), 7.41~7.616 (9H, m), 7.25 (1H, d) |
| 546 | δ = 8.36~8.38 (3H, m), 8.03 (1H, d), 7.94 (1H, s), 7.73~7.82 (5H, m), 7.41~7.61 (9H, m), 7.25 (1H, d) |
| 550 | δ = 8.36 (2H, m), 7.98~8.08 (3H, m), 7.76~7.88 (3H, m), 7.50~7.55 (7H, m), 7.25~7.39 (3H, m) |
| 569 | δ = 8.55 (1H, d), 8.36 (4H, m), 8.19 (1H, d), 7.94 (1H, d), 7.50~7.58 (8H, m), 7.35 (1H, t), 7.16~7.20 (2H, t) |
| 571 | δ = 8.55 (1H, d), 8.36 (4H, m), 7.89~7.99 (3H, m), 7.75~7.77 (3H, m), 7.35~7.50 (10H, m), 7.16 (1H, t) |
| 573 | δ = 8.55 (1H, d), 8.36 (4H, m), 8.19 (1H, d), 7.94 (1H, d), 7.50~7.62 (14H, m), 7.35~7.40 (2H, m), 7.16~7.20 (2H, t) |
| 579 | δ = 8.55 (1H, d), 8.36~8.38 (3H, m), 8.19 (1H, d), 7.94 (2H, m), 7.73~7.75 (3H, m), 7.35~7.61 (10H, m), 7.16~7.20 (2H, t) |
| 580 | δ = 8.55 (1H, d), 8.31~8.38 (4H, m), 7.91~7.94 (3H, m), 7.73~7.75 (6H, m), 7.61 (1H, d), 7.35~7.50 (10H, m), 7.16 (1H, t) |
| 582 | δ = 8.55 (1H, d), 8.36 (2H, m), 8.19 (1H, d), 7.94~7.96 (3H, m), 7.75 (2H, d), 7.35~7.58 (9H, m), 7.16~7.25 (4H, m) |
| 592 | δ = 8.55 (1H, d), 8.38 (1H, d), 8.19 (1H, d), 7.94~8.03 (4H, m), 7.73~7.82 (5H, m), 7.31~7.61 (10H, m), 7.16~7.20 (2H, t) |
| 605 | δ = 8.55 (1H, d), 8.19 (1H, d), 8.03 (1H, d), 7.94 (1H, d), 7.76~7.82 (2H, m), 7.50~7.58 (4H, m), 7.16~7.35 (4H, m) |
| 606 | δ = 8.55 (1H, d), 8.31 (1H, d), 8.30 (1H, d), 7.91~7.94 (2H, m), 7.75~7.82 (5H, m), 7.35~7.55 (6H, m), 7.25 (1H, d), 7.16 (1H, t) |
| 607 | δ = 8.55 (1H, d), 7.75~8.03 (9H, m), 7.35~7.55 (6H, m), 7.25 (1H, d), 7.16 (1H, t) |
| 608 | δ = 8.55 (1H, d), 8.31 (1H, d), 8.03 (1H, d), 7.91~7.94 (2H, m), 7.75~7.82 (5H, m), 7.35~7.55 (6H, m), 7.25 (1H, d), 7.16 (1H, t) |
| 611 | δ = 8.45 (1H, d), 8.19 (1H, d), 7.58~8.05 (2H, t), 7.93 (1H, d), 7.76~7.82 (2H, m), 7.49~7.58 (6H, m), 7.20~7.33 (3H, m) |
| 612 | δ = 8.55 (1H, d), 7.94~8.03 (3H, m), 7.76~7.84 (3H, m), 7.16~7.55 (9H, m) |
| 614 | δ = 8.55 (1H, d), 7.75~8.03 (9H, m), 7.35~7.55 (6H, m), 7.25 (1H, d), 7.16 (1H, t) |
| 616 | δ = 8.55 (1H, d), 8.19 (1H, d), 8.03 (1H, d), 7.94 (1H, d), 7.76~7.82 (2H, m), 7.50~7.58 (4H, m), 7.16~7.35 (4H, m) |
| 620 | δ = 8.55 (1H, d), 7.94~8.03 (3H, m), 7.76~7.84 (3H, m), 7.16~7.55 (9H, m) |
| 625 | δ = 8.55 (1H, d), 8.19 (1H, d), 8.03 (1H, d), 7.94 (1H, d), 7.76~7.82 (2H, m), 7.50~7.58 (4H, m), 7.16~7.35 (4H, m) |
| 627 | δ = 8.55 (1H, d), 8.31 (1H, d), 8.03 (1H, d), 7.91~7.94 (2H, m), 7.74~7.82 (5H, m), 7.35~7.55 (6H, m), 7.25 (1H, d), 7.16 (1H, t) |
| 629 | δ = 8.55 (1H, d), 7.75~7.99 (9H, m), 7.35~7.55 (6H, m), 7.25 (1H, d), 7.16 (1H, t) |
| 630 | δ = 8.55 (1H, d), 8.19 (1H, d), 7.94 (2H, d), 7.82 (1H, d), 7.69 (1H, d), 7.50~7.58 (5H, m), 7.35 (1H, t), 7.16~7.25 (3H, m) |
| 641 | δ = no $^1$H NMR peak with 100% deuteration ratio |
| 643 | δ = no $^1$H NMR peak with 100% deuteration ratio |
| 645 | δ = no $^1$H NMR peak with 100% deuteration ratio |
| 648 | δ = no $^1$H NMR peak with 100% deuteration ratio |
| 652 | δ = no $^1$H NMR peak with 100% deuteration ratio |
| 662 | δ = no $^1$H NMR peak with 100% deuteration ratio |
| 664 | δ = no $^1$H NMR peak with 100% deuteration ratio |
| 667 | δ = no $^1$H NMR peak with 100% deuteration ratio |
| 669 | δ = no $^1$H NMR peak with 100% deuteration ratio |
| 672 | δ = no $^1$H NMR peak with 100% deuteration ratio |
| 676 | δ = no $^1$H NMR peak with 100% deuteration ratio |
| 677 | δ = no $^1$H NMR peak with 100% deuteration ratio |
| 680 | δ = no $^1$H NMR peak with 100% deuteration ratio |
| 684 | δ = no $^1$H NMR peak with 100% deuteration ratio |
| 685 | δ = no $^1$H NMR peak with 100% deuteration ratio |
| 686 | δ = no $^1$H NMR peak with 100% deuteration ratio |
| 689 | δ = no $^1$H NMR peak with 100% deuteration ratio |
| 690 | δ = no $^1$H NMR peak with 100% deuteration ratio |
| 692 | δ = no $^1$H NMR peak with 100% deuteration ratio |
| 693 | δ = no $^1$H NMR peak with 100% deuteration ratio |
| 695 | δ = no $^1$H NMR peak with 100% deuteration ratio |
| 696 | δ = no $^1$H NMR peak with 100% deuteration ratio |
| 698 | δ = no $^1$H NMR peak with 100% deuteration ratio |
| 708 | δ = no $^1$H NMR peak with 100% deuteration ratio |
| 711 | δ = no $^1$H NMR peak with 100% deuteration ratio |
| 714 | δ = no $^1$H NMR peak with 100% deuteration ratio |
| 720 | δ = no $^1$H NMR peak with 100% deuteration ratio |
| 721 | δ = no $^1$H NMR peak with 100% deuteration ratio |
| 724 | δ = no $^1$H NMR peak with 100% deuteration ratio |
| 725 | δ = no $^1$H NMR peak with 100% deuteration ratio |
| 726 | δ = no $^1$H NMR peak with 100% deuteration ratio |
| 727 | δ = no $^1$H NMR peak with 100% deuteration ratio |
| 729 | δ = no $^1$H NMR peak with 100% deuteration ratio |
| 730 | δ = no $^1$H NMR peak with 100% deuteration ratio |
| 732 | δ = no $^1$H NMR peak with 100% deuteration ratio |
| 734 | δ = no $^1$H NMR peak with 100% deuteration ratio |
| 735 | δ = no $^1$H NMR peak with 100% deuteration ratio |
| 738 | δ = no $^1$H NMR peak with 100% deuteration ratio |
| 741 | δ = no $^1$H NMR peak with 100% deuteration ratio |
| 743 | δ = no $^1$H NMR peak with 100% deuteration ratio |
| 746 | δ = no $^1$H NMR peak with 100% deuteration ratio |
| 747 | δ = no $^1$H NMR peak with 100% deuteration ratio |
| 748 | δ = no $^1$H NMR peak with 100% deuteration ratio |
| 765 | δ = no $^1$H NMR peak with 100% deuteration ratio |
| 766 | δ = no $^1$H NMR peak with 100% deuteration ratio |
| 767 | δ = no $^1$H NMR peak with 100% deuteration ratio |
| 772 | δ = no $^1$H NMR peak with 100% deuteration ratio |
| 773 | δ = no $^1$H NMR peak with 100% deuteration ratio |
| 774 | δ = no $^1$H NMR peak with 100% deuteration ratio |
| 775 | δ = no $^1$H NMR peak with 100% deuteration ratio |
| 779 | δ = no $^1$H NMR peak with 100% deuteration ratio |
| 2-2 | δ = 8.55 (1H, d), 8.30 (1H, d), 8.13~8.19 (2H, m), 7.89~7.99 (4H, m), 7.77 (1H, d), 7.50~7.58 (2H, m), 7.35 (1H, t), 7.16~7.20 (2H, t) |
| 2-3 | δ = 8.55 (1H, d), 8.30 (1H, d), 8.13~8.19 (2H, m), 7.89~7.99 (4H, m), 7.77 (1H, d), 7.50~7.58 (2H, m), 7.35 (1H, t), 7.16~7.20 (2H, t) |
| 2-5 | δ = 8.55 (1H, d), 8.30 (1H, d), 8.13~8.19 (2H, m), 7.89~7.99 (4H, m), 7.77 (1H, d), 7.50~7.58 (2H, m), 7.35 (1H, t), 7.16~7.20 (2H, t) |
| 2-6 | δ = 8.55 (1H, d), 8.30 (1H, d), 8.13~8.19 (2H, m), 7.89~7.99 (4H, m), 7.77 (1H, d), 7.50~7.58 (2H, m), 7.35 (1H, t), 7.16~7.20 (2H, t) |
| 2-8 | δ = 8.55 (1H, d), 8.30 (1H, d), 8.13~8.19 (2H, m), 7.89~7.99 (4H, m), 7.77 (1H, d), 7.50~7.58 (2H, m), 7.35 (1H, t), 7.16~7.20 (2H, t) |
| 2-9 | δ = 8.55 (1H, d), 8.30 (1H, d), 8.13~8.19 (2H, m), 7.89~7.99 (4H, m), 7.77 (1H, d), 7.50~7.58 (2H, m), 7.35 (1H, t), 7.16~7.20 (2H, t) |

TABLE 12-continued

| | $^1H$ NMR(DMSO, 300 Mz) |
|---|---|
| 2-12 | δ = 8.55 (1H, d), 8.30 (1H, d), 8.13~8.19 (2H, m), 7.89~7.99 (4H, m), 7.77 (1H, d), 7.50~7.58 (2H, m), 7.35 (1H, t), 7.16~7.20 (2H, t) |
| 2-14 | δ = 8.55 (1H, d), 8.30 (1H, d), 8.13~8.19 (2H, m), 7.89~7.99 (4H, m), 7.77 (1H, d), 7.50~7.58 (2H, m), 7.35 (1H, t), 7.16~7.20 (2H, t) |
| 2-26 | δ = 7.91~7.92 (8H, m), 7.75 (4H, d), 7.41~7.49 (6H, m) |
| 2-27 | δ = 8.21 (1H, s), 7.41~7.68 (13H, m) |
| 2-29 | δ = 7.91~7.94 (5H, m), 7.73~7.75 (3H, t), 7.41~7.62 (10H, m) |
| 2-32 | δ = 8.21 (2H, s), 7.60~7.75 (8H, m), 7.41~7.49 (8H, m) |
| 2-33 | δ = 8.21 (1H, s), 7.91~7.92 (4H, m), 7.75~7.68 (6H, m), 7.41~7.49 (7H, m) |
| 2-50 | δ = no $^1H$ NMR peak with 100% deuteration ratio |
| 2-51 | δ = no $^1H$ NMR peak with 100% deuteration ratio |
| 2-53 | δ = no $^1H$ NMR peak with 100% deuteration ratio |
| 2-56 | δ = no $^1H$ NMR peak with 100% deuteration ratio |
| 2-60 | δ = no $^1H$ NMR peak with 100% deuteration ratio |
| 2-62 | δ = no $^1H$ NMR peak with 100% deuteration ratio |
| 2-68 | δ = no $^1H$ NMR peak with 100% deuteration ratio |
| 2-75 | δ = 8.55 (1H, d), 8.30 (1H, d), 8.13~8.21 (3H, m), 7.89~7.99 (4H, m), 7.35~7.77 (17H, m), 7.16~7.20 (2H, t) |
| 2-76 | δ = 8.55 (1H, d), 8.30 (1H, d), 8.13~8.19 (2H, m), 7.89~7.99 (9H, m), 7.73~7.77 (4H, m), 7.35~7.62 (13H, m), 7.16~7.20 (2H, m) |
| 2-77 | δ = 8.55 (1H, d), 8.30 (1H, d), 8.13~8.21 (4H, m), 7.89~7.99 (4H, m), 7.35~7.77 (20H, m), 7.16~7.20 (2H, t) |
| 2-78 | δ = 8.55 (1H, d), 8.30 (1H, d), 8.13~8.19 (2H, m), 7.89~7.99 (12H, m), 7.75~7.77 (5H, m), 7.58 (1H, d), 7.35~7.50 (8H, m), 7.16~7.20 (2H, m) |

EXAMPLES

Example 1_Organic Light Emitting Device

A glass substrate coated with a thin film of ITO with a thickness of 1,500 Å was washed with distilled water and ultrasonic wave. After washing with distilled water, the glass substrate was washed by ultrasonic washing was performed with a solvent, such as acetone, methanol, isopropyl alcohol, and the like, and was dried. The glass substrate was UVO-treated for 5 minutes using UV in a UV washer. After transferring the glass substrate to a plasma cleaner (PT), plasma treatment was performed to remove the ITO work function and residual film in a vacuum state, and then transferred to a thermal deposition equipment for organic deposition.

A hole injection layer of 2-TNATA (4,4',4"-tris[2-naphthyl(phenyl)amino]triphenylamine) as a common layer was formed on the ITO transparent electrode (anode), and a hole transporting layer of NPB (N,N-di(1-naphthyl)-N,N'-diphenyl-(1,1'-biphenyl)-4,4'-diamine) was formed on the hole injection layer.

A light emitting layer was deposited on the hole transporting layer by thermal vacuum deposition as follows. The light emitting layer with a thickness of 400 Å was deposited by using compounds as a host and $Ir(ppy)_3$ as a green dopant with a doping ratio of 7%. A hole blocking layer with 60 Å was formed on the light emitting layer by depositing BCP, and an electron transporting layer with 200 Å was formed on the hole blocking layer by depositing $Alq_3$. An electron injection layer with 10 Å was formed on the electron transporting layer by depositing lithium fluoride (LiF), and a cathode with 1200 Å was formed on the electron injection layer by depositing Al to manufacture the organic light emitting device.

All organic compounds required for organic light emitting device were vacuum sublimated and purified under $10^{-6}$ to $10^{-8}$ torr.

[The Driving Voltage and the Emitting Efficiency of the Organic Light Emitting Device]

The electroluminescence (EL) characteristics of the organic light emitting device were measured with M7000 of McScience, and $T_{90}$ was measured at the reference luminance 6,000 cd/$m_2$ using the lifespan measuring device (M6000) of McScience. The electroluminescence (EL) characteristics of the organic light emitting device are listed in Table 13.

TABLE 13

| | host | V | cd/A | CIE (x, y) | $T_{90}$ |
|---|---|---|---|---|---|
| Ref 1 | A | 6.48 | 41.7 | (0.276, 0.674) | 57 |
| Ref 2 | B | 6.22 | 42.9 | (0.286, 0.673) | 58 |
| Ref 3 | C | 5.51 | 45.0 | (0.286, 0.678) | 77 |
| Ref 4 | D | 5.68 | 44.8 | (0.281, 0.674) | 65 |
| Ref 5 | E | 6.02 | 43.5 | (0.285, 0.676) | 71 |
| Ref 6 | F | 5.90 | 44.1 | (0.284, 0.679) | 69 |
| Ref 7 | G | 5.60 | 44.7 | (0.266, 0.668) | 95 |
| Ref 8 | H | 5.59 | 45.2 | (0.287, 0.672) | 102 |
| Ref 9 | I | 5.55 | 45.0 | (0.278, 0.660) | 83 |
| Ex 1 | 3 | 4.44 | 79.0 | (0.275, 0.680) | 141 |
| Ex 2 | 9 | 4.43 | 77.5 | (0.270, 0.675) | 145 |
| Ex 3 | 11 | 4.42 | 78.8 | (0.269, 0.674) | 140 |
| Ex 4 | 12 | 4.47 | 77.6 | (0.264, 0.677) | 146 |
| Ex 5 | 15 | 4.50 | 78.0 | (0.250, 0.672) | 148 |
| Ex 6 | 26 | 4.45 | 79.2 | (0.285, 0.670) | 144 |
| Ex 7 | 31 | 4.49 | 77.3 | (0.264, 0.685) | 140 |
| Ex 8 | 33 | 4.52 | 78.5 | (0.280, 0.475) | 143 |
| Ex 9 | 34 | 4.31 | 76.0 | (0.271, 0.672) | 153 |
| Ex 10 | 35 | 4.36 | 76.2 | (0.259, 0.673) | 149 |
| Ex 11 | 42 | 4.32 | 77.2 | (0.265, 0.665) | 151 |
| Ex 12 | 43 | 4.38 | 76.3 | (0.287, 0.652) | 145 |
| Ex 13 | 54 | 4.41 | 77.0 | (0.258, 0.663) | 148 |
| Ex 14 | 60 | 4.44 | 76.5 | (0.273, 0.672) | 150 |
| Ex 15 | 71 | 5.50 | 70.0 | (0.249, 0.665) | 122 |
| Ex 16 | 73 | 5.44 | 69.6 | (0.266, 0.658) | 128 |
| Ex 17 | 82 | 5.47 | 68.3 | (0.270, 0.673) | 130 |
| Ex 18 | 98 | 5.51 | 69.5 | (0.281, 0.672) | 124 |
| Ex 19 | 103 | 5.02 | 64.4 | (0.275, 0.670) | 135 |
| Ex 20 | 110 | 5.13 | 62.3 | (0.265, 0.663) | 137 |
| Ex 21 | 116 | 5.28 | 61.5 | (0.258, 0.671) | 133 |
| Ex 22 | 137 | 4.59 | 70.2 | (0.265, 0.669) | 135 |
| Ex 23 | 147 | 7.69 | 68.7 | (0.268, 0.667) | 133 |
| Ex 24 | 156 | 4.72 | 69.5 | (0.277, 0.672) | 130 |
| Ex 25 | 170 | 4.41 | 66.0 | (0.257, 0.660) | 140 |
| Ex 26 | 178 | 4.43 | 67.1 | (0.267, 0.655) | 139 |
| Ex 27 | 183 | 4.59 | 66.3 | (0.268, 0.673) | 141 |
| Ex 28 | 189 | 4.48 | 67.8 | (0.277, 0.675) | 137 |
| Ex 29 | 195 | 4.56 | 67.3 | (0.263, 0.657) | 138 |
| Ex 30 | 199 | 4.42 | 66.9 | (0.256, 0.660) | 142 |
| Ex 31 | 205 | 4.48 | 78.0 | (0.263, 0.672) | 143 |
| Ex 32 | 206 | 4.42 | 76.7 | (0.285, 0.664) | 146 |
| Ex 33 | 207 | 4.50 | 77.9 | (0.267, 0.667) | 149 |
| Ex 34 | 213 | 4.47 | 78.3 | (0.283, 0.673) | 145 |
| Ex 35 | 214 | 4.36 | 77.6 | (0.261, 0.675) | 144 |
| Ex 36 | 216 | 4.39 | 78.2 | (0.267, 0.654) | 148 |
| Ex 37 | 217 | 4.44 | 76.5 | (0.256, 0.660) | 150 |
| Ex 38 | 218 | 4.42 | 77.3 | (0.250, 0.667) | 147 |
| Ex 39 | 219 | 4.38 | 78.5 | (0.267, 0.662) | 143 |
| Ex 40 | 225 | 4.52 | 77.2 | (0.259, 0.664) | 149 |
| Ex 41 | 228 | 4.40 | 76.9 | (0.267, 0.687) | 151 |
| Ex 42 | 230 | 4.47 | 78.1 | (0.279, 0.655) | 148 |
| Ex 43 | 234 | 4.53 | 77.9 | (0.265, 0.674) | 144 |
| Ex 44 | 235 | 4.38 | 77.5 | (0.265, 0.680) | 147 |
| Ex 45 | 236 | 4.39 | 78.3 | (0.247, 0.657) | 145 |
| Ex 46 | 237 | 4.45 | 76.6 | (0.259, 0.669) | 147 |
| Ex 47 | 238 | 4.13 | 75.0 | (0.254, 0.657) | 158 |
| Ex 48 | 240 | 4.11 | 76.6 | (0.262, 0.675) | 153 |
| Ex 49 | 246 | 4.26 | 76.3 | (0.253, 0.671) | 157 |
| Ex 50 | 248 | 4.18 | 75.9 | (0.243, 0.675) | 152 |
| Ex 51 | 249 | 4.33 | 75.5 | (0.262, 0.657) | 149 |
| Ex 52 | 251 | 4.25 | 77.3 | (0.258, 0.667) | 159 |
| Ex 53 | 252 | 4.32 | 75.1 | (0.276, 0.662) | 150 |
| Ex 54 | 257 | 4.19 | 74.9 | (0.265, 0.674) | 158 |
| Ex 55 | 261 | 4.28 | 75.8 | (0.273, 0.687) | 153 |
| Ex 56 | 263 | 4.22 | 77.0 | (0.287, 0.68) | 151 |
| Ex 57 | 270 | 4.16 | 76.2 | (0.274, 0.670) | 155 |

TABLE 13-continued

| | host | V | cd/A | CIE (x, y) | $T_{90}$ |
|---|---|---|---|---|---|
| Ex 58 | 273 | 4.66 | 69.5 | (0.265, 0.671) | 127 |
| Ex 59 | 274 | 7.69 | 71.8 | (0.246, 0.662) | 125 |
| Ex 60 | 278 | 4.73 | 71.3 | (0.264, 0.657) | 126 |
| Ex 61 | 280 | 4.71 | 70.9 | (0.258, 0.686) | 128 |
| Ex 62 | 286 | 4.56 | 71.5 | (0.280, 0.667) | 125 |
| Ex 63 | 300 | 4.20 | 63.3 | (0.276, 0.664) | 135 |
| Ex 64 | 303 | 4.41 | 62.3 | (0.280, 0.671) | 137 |
| Ex 65 | 307 | 4.30 | 61.8 | (0.286, 0.675) | 134 |
| Ex 66 | 308 | 4.29 | 69.7 | (0.271, 0.674) | 131 |
| Ex 67 | 315 | 4.33 | 68.5 | (0.283, 0.675) | 129 |
| Ex 68 | 318 | 4.28 | 63.7 | (0.284, 0.677) | 134 |
| Ex 69 | 320 | 4.32 | 65.2 | (0.277, 0.680) | 135 |
| Ex 70 | 324 | 4.43 | 62.3 | (0.270, 0.673) | 132 |
| Ex 71 | 328 | 4.37 | 61.5 | (0.269, 0.674) | 130 |
| Ex 72 | 329 | 3.93 | 77.7 | (0.265, 0.667) | 136 |
| Ex 73 | 330 | 3.80 | 77.3 | (0.263, 0.655) | 139 |
| Ex 74 | 331 | 3.84 | 76.9 | (0.253, 0.661) | 135 |
| Ex 75 | 334 | 3.99 | 78.1 | (0.253, 0.675) | 140 |
| Ex 76 | 336 | 3.90 | 77.2 | (0.262, 0.651) | 138 |
| Ex 77 | 338 | 3.84 | 77.5 | (0.258, 0.657) | 144 |
| Ex 78 | 339 | 3.92 | 77.9 | (0.266, 0.662) | 146 |
| Ex 79 | 340 | 3.83 | 76.5 | (0.265, 0.675) | 143 |
| Ex 80 | 341 | 4.02 | 78.3 | (0.266, 0.662) | 141 |
| Ex 81 | 344 | 3.68 | 77.2 | (0.274, 0.657) | 138 |
| Ex 82 | 347 | 3.77 | 77.6 | (0.268, 0.683) | 135 |
| Ex 83 | 351 | 3.89 | 78.0 | (0.280, 0.665) | 140 |
| Ex 84 | 355 | 3.52 | 71.2 | (0.276, 0.664) | 150 |
| Ex 85 | 356 | 3.67 | 70.9 | (0.282, 0.671) | 146 |
| Ex 86 | 357 | 3.54 | 74.0 | (0.281, 0.664) | 153 |
| Ex 87 | 359 | 3.50 | 73.5 | (0.267, 0.657) | 145 |
| Ex 88 | 362 | 3.65 | 70.8 | (0.283, 0.663) | 149 |
| Ex 89 | 366 | 3.52 | 71.9 | (0.271, 0.675) | 153 |
| Ex 90 | 371 | 6.62 | 72.6 | (0.267, 0.650) | 145 |
| Ex 91 | 373 | 3.67 | 71.3 | (0.256, 0.662) | 146 |
| Ex 92 | 380 | 3.55 | 70.0 | (0.259, 0.667) | 152 |
| Ex 93 | 386 | 4.27 | 78.7 | (0.283, 0.675) | 147 |
| Ex 94 | 387 | 4.26 | 79.5 | (0.271, 0.664) | 149 |
| Ex 95 | 390 | 4.32 | 79.3 | (0.282, 0.655) | 150 |
| Ex 96 | 392 | 4.29 | 80.0 | (0.281, 0.677) | 148 |
| Ex 97 | 393 | 4.02 | 76.1 | (0.278, 0.683) | 160 |
| Ex 98 | 395 | 4.13 | 78.8 | (0.270, 0.677) | 157 |
| Ex 99 | 396 | 4.10 | 78.2 | (0.268, 0.675) | 159 |
| Ex 100 | 398 | 4.08 | 76.2 | (0.265, 0.667) | 160 |
| Ex 101 | 399 | 4.19 | 77.8 | (0.263, 0.667) | 152 |
| Ex 102 | 400 | 4.20 | 77.2 | (0.263, 0.659) | 157 |
| Ex 103 | 402 | 4.15 | 76.5 | (0.253, 0.665) | 155 |
| Ex 104 | 404 | 4.09 | 77.2 | (0.253, 0.675) | 158 |
| Ex 105 | 406 | 4.12 | 76.0 | (0.272, 0.653) | 161 |
| Ex 106 | 435 | 4.42 | 74.6 | (0.268, 0.650) | 133 |
| Ex 107 | 440 | 4.46 | 73.4 | (0.250, 0.642) | 135 |
| Ex 108 | 442 | 4.57 | 75.1 | (0.259, 0.663) | 138 |
| Ex 109 | 444 | 4.60 | 74.4 | (0.280, 0.675) | 131 |
| Ex 110 | 445 | 4.53 | 74.9 | (0.273, 0.661) | 130 |
| Ex 111 | 455 | 4.58 | 75.2 | (0.282, 0.658) | 135 |
| Ex 112 | 457 | 4.22 | 66.7 | (0.271, 0.670) | 142 |
| Ex 113 | 473 | 4.41 | 74.3 | (0.265, 0.650) | 143 |
| Ex 114 | 474 | 4.37 | 75.2 | (0.266, 0.661) | 140 |
| Ex 115 | 475 | 4.38 | 74.6 | (0.253, 0.665) | 143 |
| Ex 116 | 479 | 4.40 | 75.0 | (0.265, 0.662) | 140 |
| Ex 117 | 480 | 4.31 | 74.9 | (0.258, 0.654) | 142 |
| Ex 118 | 482 | 4.35 | 75.8 | (0.263, 0.680) | 149 |
| Ex 119 | 483 | 4.42 | 74.6 | (0.274, 0.656) | 145 |
| Ex 120 | 484 | 4.33 | 74.4 | (0.267, 0.675) | 142 |
| Ex 121 | 485 | 4.40 | 75.7 | (0.255, 0.678) | 148 |
| Ex 122 | 488 | 4.29 | 74.8 | (0.271, 0.650) | 140 |
| Ex 123 | 495 | 4.38 | 75.9 | (0.265, 0.653) | 151 |
| Ex 124 | 497 | 4.02 | 72.9 | (0.258, 0.644) | 153 |
| Ex 125 | 500 | 4.13 | 71.5 | (0.259, 0.665) | 150 |
| Ex 126 | 525 | 4.58 | 78.3 | (0.283, 0.671) | 158 |
| Ex 127 | 526 | 4.60 | 77.7 | (0.282, 0.670) | 150 |
| Ex 128 | 527 | 4.55 | 77.2 | (0.274, 0.660) | 143 |
| Ex 129 | 531 | 4.69 | 78.3 | (0.288, 0.668) | 149 |
| Ex 130 | 533 | 4.72 | 76.9 | (0.261, 0.675) | 144 |
| Ex 131 | 535 | 4.53 | 78.5 | (0.267, 0.653) | 147 |
| Ex 132 | 536 | 4.58 | 77.6 | (0.272, 0.673) | 157 |
| Ex 133 | 537 | 4.63 | 76.3 | (0.265, 0.655) | 150 |
| Ex 134 | 538 | 4.58 | 78.5 | (0.267, 0.668) | 149 |
| Ex 135 | 539 | 4.66 | 77.4 | (0.253, 0.663) | 142 |

TABLE 13-continued

| | host | V | cd/A | CIE (x, y) | $T_{90}$ |
|---|---|---|---|---|---|
| Ex 136 | 544 | 4.63 | 76.5 | (0.267, 0.661) | 144 |
| Ex 137 | 545 | 4.70 | 76.3 | (0.254, 0.678) | 146 |
| Ex 138 | 546 | 4.68 | 78.4 | (0.271, 0.655) | 153 |
| Ex 139 | 550 | 4.43 | 79.3 | (0.266, 0.657) | 158 |
| Ex 140 | 569 | 4.93 | 66.7 | (0.258, 0.645) | 134 |
| Ex 141 | 571 | 4.88 | 63.7 | (0.281, 0.673) | 138 |
| Ex 142 | 573 | 4.73 | 62.5 | (0.274, 0.662) | 135 |
| Ex 143 | 579 | 4.95 | 68.4 | (0.280, 0.668) | 133 |
| Ex 144 | 580 | 4.90 | 70.6 | (0.265, 0.665) | 132 |
| Ex 145 | 582 | 4.83 | 71.3 | (0.266, 0.650) | 137 |
| Ex 146 | 592 | 4.77 | 68.7 | (0.271, 0.663) | 136 |
| Ex 147 | 605 | 4.68 | 69.3 | (0.263, 0.651) | 132 |
| Ex 148 | 606 | 4.44 | 75.1 | (0.263, 0.662) | 130 |
| Ex 149 | 607 | 4.50 | 74.7 | (0.278, 0.664) | 136 |
| Ex 150 | 611 | 4.53 | 73.6 | (0.273, 0.680) | 135 |
| Ex 151 | 612 | 4.69 | 70.6 | (0.264, 0.666) | 132 |
| Ex 152 | 614 | 4.71 | 69.7 | (0.262, 0.670) | 131 |
| Ex 153 | 616 | 4.60 | 71.8 | (0.265, 0.653) | 133 |
| Ex 154 | 620 | 4.55 | 70.6 | (0.277, 0.673) | 138 |
| Ex 155 | 625 | 4.65 | 65.7 | (0.265, 0.658) | 130 |
| Ex 156 | 627 | 4.59 | 69.3 | (0.265, 0.660) | 132 |
| Ex 157 | 629 | 4.68 | 75.4 | (0.255, 0.663) | 135 |
| Ex 158 | 630 | 4.42 | 66.3 | (0.265, 0.650) | 140 |
| Ex 159 | 641 | 3.70 | 78.3 | (0.264, 0.665) | 158 |
| Ex 160 | 643 | 3.79 | 77.9 | (0.274, 0.654) | 157 |
| Ex 161 | 645 | 3.72 | 76.2 | (0.270, 0.683) | 155 |
| Ex 162 | 648 | 3.76 | 78.7 | (0.264, 0.662) | 153 |
| Ex 163 | 652 | 3.80 | 79.3 | (0.265, 0.676) | 159 |
| Ex 164 | 662 | 3.58 | 78.0 | (0.261, 0.660) | 162 |
| Ex 165 | 664 | 3.68 | 77.9 | (0.263, 0.653) | 168 |
| Ex 166 | 667 | 3.60 | 76.4 | (0.275, 0.675) | 165 |
| Ex 167 | 669 | 3.55 | 76.9 | (0.260, 0.655) | 160 |
| Ex 168 | 672 | 3.68 | 77.3 | (0.265, 0.661) | 163 |
| Ex 169 | 676 | 3.70 | 77.0 | (0.284, 0.665) | 167 |
| Ex 170 | 677 | 3.62 | 76.3 | (0.264, 0.664) | 166 |
| Ex 171 | 680 | 3.58 | 77.5 | (0.275, 0.683) | 168 |
| Ex 172 | 684 | 3.69 | 78.2 | (0.274, 0.663) | 170 |
| Ex 173 | 685 | 3.40 | 75.4 | (0.268, 0.675) | 177 |
| Ex 174 | 686 | 3.41 | 77.6 | (0.268, 0.661) | 172 |
| Ex 175 | 689 | 3.55 | 76.8 | (0.265, 0.652) | 173 |
| Ex 176 | 690 | 3.42 | 75.4 | (0.273, 0.664) | 170 |
| Ex 177 | 692 | 3.52 | 72.9 | (0.264, 0.655) | 172 |
| Ex 178 | 693 | 3.44 | 75.7 | (0.264, 0.665) | 181 |
| Ex 179 | 695 | 3.51 | 77.4 | (0.278, 0.663) | 175 |
| Ex 180 | 696 | 3.50 | 78.3 | (0.270, 0.680) | 179 |
| Ex 181 | 698 | 3.48 | 76.9 | (0.265, 0.673) | 180 |
| Ex 182 | 708 | 3.59 | 75.7 | (0.262, 0.661) | 168 |
| Ex 183 | 711 | 3.52 | 74.3 | (0.264, 0.653) | 165 |
| Ex 184 | 714 | 3.50 | 69.5 | (0.265, 0.672) | 169 |
| Ex 185 | 720 | 3.58 | 73.4 | (0.262, 0.653) | 166 |
| Ex 186 | 721 | 3.63 | 75.9 | (0.260, 0.671) | 172 |
| Ex 187 | 724 | 3.60 | 77.2 | (0.265, 0.650) | 170 |
| Ex 188 | 725 | 3.53 | 81.3 | (0.275, 0.673) | 186 |
| Ex 189 | 726 | 3.55 | 80.4 | (0.261, 0.653) | 183 |
| Ex 190 | 727 | 3.51 | 79.6 | (0.265, 0.666) | 187 |
| Ex 191 | 729 | 3.49 | 78.5 | (0.285, 0.667) | 185 |
| Ex 192 | 730 | 3.43 | 79.6 | (0.264, 0.660) | 183 |
| Ex 193 | 732 | 3.52 | 80.2 | (0.273, 0.683) | 189 |
| Ex 194 | 734 | 3.40 | 77.6 | (0.270, 0.673) | 185 |
| Ex 195 | 735 | 3.48 | 78.4 | (0.265, 0.675) | 188 |
| Ex 196 | 738 | 3.42 | 80.6 | (0.278, 0.667) | 196 |
| Ex 197 | 741 | 3.57 | 81.3 | (0.260, 0.653) | 190 |
| Ex 198 | 743 | 3.55 | 77.6 | (0.283, 0.665) | 195 |
| Ex 199 | 746 | 3.99 | 80.5 | (0.275, 0.662) | 146 |
| Ex 200 | 747 | 4.17 | 77.7 | (0.269, 0.673) | 144 |
| Ex 201 | 748 | 4.20 | 81.2 | (0.268, 0.675) | 148 |
| Ex 202 | 765 | 3.87 | 72.8 | (0.275, 0.655) | 173 |
| Ex 203 | 766 | 3.88 | 75.1 | (0.285, 0.663) | 172 |
| Ex 204 | 767 | 4.08 | 74.8 | (0.267, 0.650) | 163 |
| Ex 205 | 772 | 4.11 | 71.9 | (0.260, 0.668) | 165 |
| Ex 206 | 773 | 3.82 | 73.8 | (0.285, 0.667) | 169 |
| Ex 207 | 774 | 4.02 | 74.4 | (0.262, 0.650) | 173 |
| Ex 208 | 775 | 3.80 | 70.6 | (0.283, 0.648) | 170 |
| Ex 209 | 779 | 4.05 | 75.3 | (0.270, 0.661) | 175 |

-continued
[A]
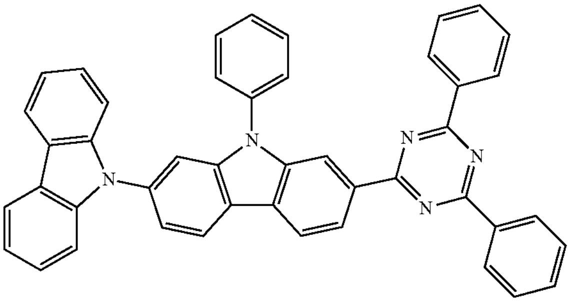
[B]
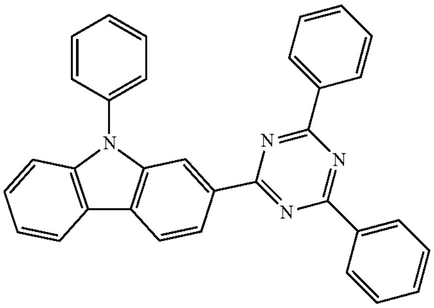
[C]
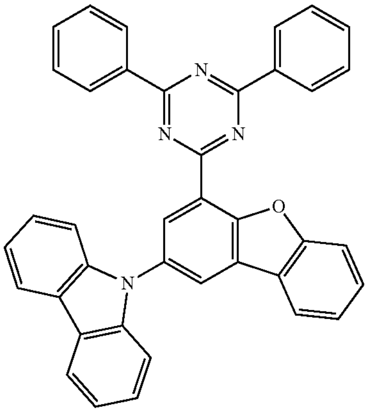
[D]
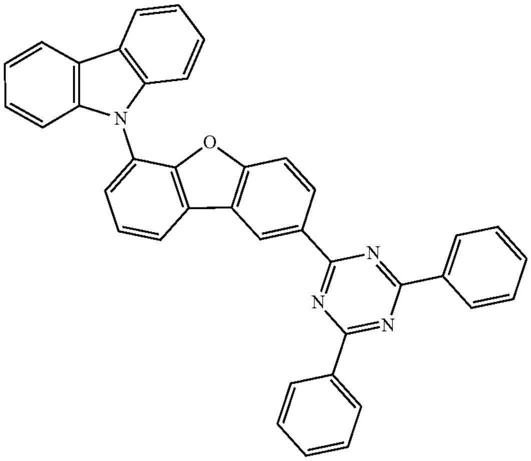
[E]
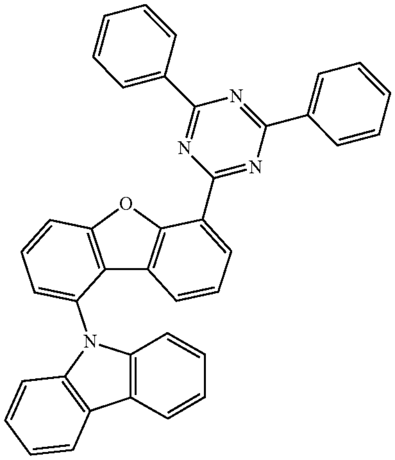
[F]
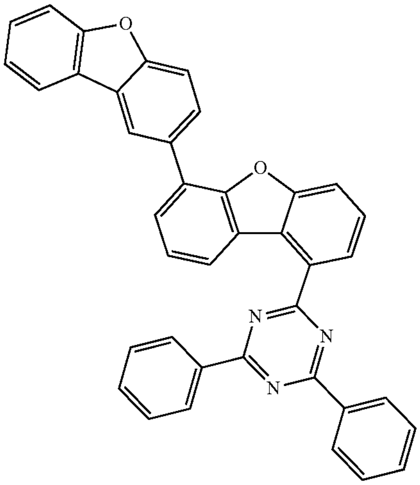
[G]
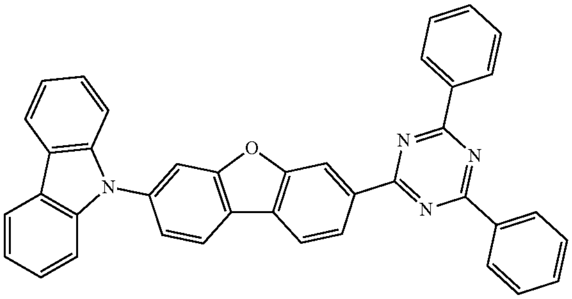

-continued

[H]

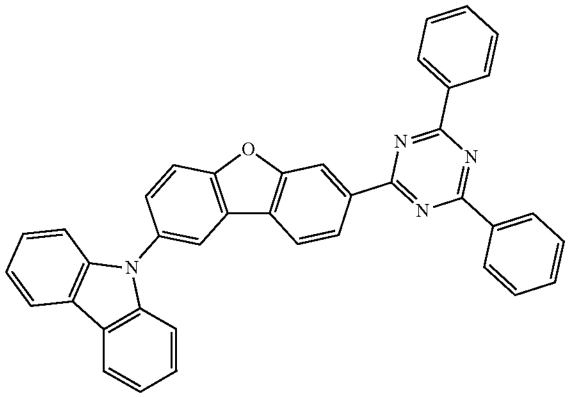

[I]

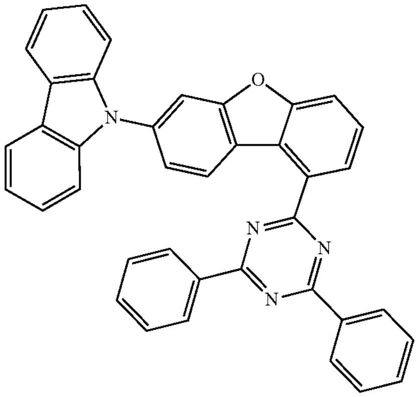

Example 2_Organic Light Emitting Device

A glass substrate coated with a thin film of ITO with a thickness of 1,500 Å was washed with distilled water and ultrasonic wave. After washing with distilled water, the glass substrate was washed by ultrasonic washing was performed with a solvent, such as acetone, methanol, isopropyl alcohol, and the like, and was dried. The glass substrate was UVO-treated for 5 minutes using UV in a UV washer. After transferring the glass substrate to a plasma cleaner (PT), plasma treatment was performed to remove the ITO work function and residual film in a vacuum state, and then transferred to a thermal deposition equipment for organic deposition.

A hole injection layer of 2-TNATA (4,4',4"-tris[2-naphthyl(phenyl)amino]triphenylamine) as a common layer was formed on the ITO transparent electrode (anode), and a hole transporting layer of NPB (N,N'-di(1-naphthyl)-N,N'-diphenyl-(1,1'-biphenyl)-4,4'-diamine) was formed on the hole injection layer.

A light emitting layer was deposited on the hole transporting layer by thermal vacuum deposition as follows. The light emitting layer with a thickness of 400 Å was deposited by using compounds as a host and $Ir(ppy)_3$ as a green dopant with a doping ratio of 7%. A hole blocking layer with 60 Å was formed on the light emitting layer by depositing BCP, and an electron transporting layer with 200 Å was formed on the hole blocking layer by depositing $Alq_3$. An electron injection layer with 10 Å was formed on the electron transporting layer by depositing lithium fluoride (LiF), and a cathode with 1200 Å was formed on the electron injection layer by depositing Al to manufacture the organic light emitting device.

All organic compounds required for organic light emitting device were vacuum sublimated and purified under $10^{-6}$ to $10^{-8}$ torr.

The electroluminescence (EL) characteristics of the organic light emitting device were measured with M7000 of McScience, and T90 was measured at the reference luminance 6,000 cd/$m_2$ using the lifespan measuring device (M6000) of McScience. The driving voltage (V), the emitting efficiency (cd/A), the CIE and the lifespan (T90) of the organic light emitting device are listed in Table 14.

TABLE 14

| | Host | | | | | |
|---|---|---|---|---|---|---|
| | compound | ratio | V | cd/A | CIE(x, y) | $T_{90}$ |
| Ref 10 | E:2-50 | 1:1 | 5.23 | 54.4 | (0.253, 0.704) | 117 |
| Ref 11 | | 1:2 | 5.11 | 53.7 | (0.242, 0.625) | 121 |
| Ref 12 | | 1:3 | 4.99 | 52.3 | (0.265, 0.613) | 123 |
| Ref 13 | F:2-50 | 1:1 | 5.23 | 56.0 | (0.250, 0.714) | 110 |
| Ref 14 | | 1:2 | 5.18 | 55.8 | (0.255, 0.657) | 111 |
| Ref 15 | | 1:3 | 5.03 | 54.6 | (0.259, 0.635) | 117 |
| Ref 16 | G:2-62 | 1:1 | 5.13 | 52.2 | (0.257, 0.704) | 109 |
| Ref 17 | | 1:2 | 5.11 | 51.8 | (0.245, 0.656) | 110 |
| Ref 18 | | 1:3 | 5.07 | 50.1 | (0.253, 0.631) | 115 |
| Ref 19 | H:2-62 | 1:1 | 5.46 | 51.2 | (0.248, 0.612) | 198 |
| Ref 20 | | 1:2 | 5.45 | 50.3 | (0.251, 0.627) | 121 |
| Ref 21 | | 1:3 | 5.40 | 49.7 | (0.256, 0.713) | 124 |
| Ref 22 | I:2-53 | 1:1 | 5.48 | 50.7 | (0.240, 0.615) | 120 |
| Ref 23 | | 1:2 | 5.44 | 49.9 | (0.262, 0.667) | 122 |
| Ref 24 | | 1:3 | 5.43 | 49.5 | (0.253, 0.617) | 125 |
| Ex 210 | 43:2-50 | 1:1 | 3.51 | 101.3 | (0.243, 0.660) | 310 |
| Ex 211 | | 1:2 | 3.49 | 100.8 | (0.240, 0.645) | 318 |
| Ex 212 | | 1:3 | 3.48 | 100.5 | (0.274, 0.659) | 320 |
| Ex 213 | 43:2-78 | 1:1 | 3.62 | 99.5 | (0.261, 0.625) | 300 |
| Ex 214 | | 1:2 | 3.61 | 99.1 | (0.256, 0.680) | 303 |
| Ex 215 | | 1:3 | 3.59 | 98.7 | (0.243, 0.633) | 311 |
| Ex 216 | 195:2-62 | 1:1 | 3.55 | 111.3 | (0.247, 0.610) | 329 |
| Ex 217 | | 1:2 | 3.50 | 110.5 | (0.258, 0.652) | 330 |
| Ex 218 | | 1:3 | 3.49 | 109.2 | (0.253, 0.602) | 334 |
| Ex 219 | 206:2-50 | 1:1 | 3.65 | 115.3 | (0.252, 0.704) | 330 |
| Ex 220 | | 1:2 | 3.62 | 115.0 | (0.240, 0.629) | 336 |
| Ex 221 | | 1:3 | 3.60 | 113.7 | (0.264, 0.610) | 337 |
| Ex 222 | 251:2-53 | 1:1 | 3.62 | 113.9 | (0.250, 0.704) | 339 |
| Ex 223 | | 1:2 | 3.60 | 113.5 | (0.245, 0.657) | 342 |
| Ex 224 | | 1:3 | 3.55 | 110.2 | (0.259, 0.631) | 349 |
| Ex 225 | 251:2-76 | 1:1 | 3.77 | 108.9 | (0.261, 0.643) | 300 |
| Ex 226 | | 1:2 | 3.75 | 105.7 | (0.252, 0.635) | 313 |
| Ex 227 | | 1:3 | 3.70 | 103.5 | (0.258, 0.632) | 322 |
| Ex 228 | 330:2-50 | 1:1 | 3.70 | 119.3 | (0.258, 0.685) | 340 |
| Ex 229 | | 1:2 | 3.66 | 118.4 | (0.231, 0.641) | 342 |
| Ex 230 | | 1:3 | 3.65 | 117.2 | (0.235, 0.714) | 344 |
| Ex 231 | 373:2-62 | 1:1 | 3.65 | 120.3 | (0.241, 0.602) | 348 |
| Ex 232 | | 1:2 | 3.62 | 118.7 | (0.251, 0.625) | 350 |
| Ex 233 | | 1:3 | 3.60 | 117.0 | (0.256, 0.710) | 355 |
| Ex 234 | 387:2-50 | 1:1 | 3.55 | 122.8 | (0.240, 0.613) | 354 |
| Ex 235 | | 1:2 | 3.50 | 120.9 | (0.265, 0.735) | 360 |
| Ex 236 | | 1:3 | 3.47 | 117.9 | (0.250, 0.618) | 363 |
| Ex 237 | 387:2-78 | 1:1 | 3.68 | 112.7 | (0.252, 0.659) | 324 |
| Ex 238 | | 1:2 | 3.65 | 110.8 | (0.276, 0.653) | 328 |
| Ex 239 | | 1:3 | 3.62 | 109.2 | (0.263, 0.615) | 331 |
| Ex 240 | 396:2-50 | 1:1 | 3.55 | 125.5 | (0.263, 0.677) | 359 |
| Ex 241 | | 1:2 | 3.52 | 122.6 | (0.245, 0.659) | 364 |
| Ex 242 | | 1:3 | 3.50 | 120.7 | (0.265, 0.643) | 367 |
| Ex 243 | 3696:2-78 | 1:1 | 3.66 | 124.7 | (0.265, 0.654) | 342 |
| Ex 244 | | 1:2 | 3.63 | 124.0 | (0.253, 0.625) | 344 |
| Ex 245 | | 1:3 | 3.61 | 122.8 | (0.268, 0.624) | 356 |
| Ex 246 | 399:2-53 | 1:1 | 3.54 | 128.7 | (0.252, 0.637) | 362 |
| Ex 247 | | 1:2 | 3.52 | 127.7 | (0.242, 0.632) | 366 |
| Ex 248 | | 1:3 | 3.47 | 126.9 | (0.255, 0.660) | 369 |
| Ex 249 | 399:2-76 | 1:1 | 3.66 | 120.1 | (0.265, 0.628) | 350 |
| Ex 250 | | 1:2 | 3.62 | 120.8 | (0.267, 0.656) | 353 |
| Ex 251 | | 1:3 | 3.60 | 121.7 | (0.259, 0.648) | 362 |
| Ex 252 | 475:2-62 | 1:1 | 3.66 | 125.8 | (0.266, 0.654) | 372 |
| Ex 253 | | 1:2 | 3.65 | 123.7 | (0.243, 0.715) | 377 |
| Ex 254 | | 1:3 | 3.62 | 123.1 | (0.262, 0.628) | 380 |
| Ex 255 | 485:2-50 | 1:1 | 3.63 | 125.5 | (0.263, 0.657) | 382 |
| Ex 256 | | 1:2 | 3.60 | 125.3 | (0.257, 0.647) | 385 |

TABLE 14-continued
| | Host | | | | | |
|---|---|---|---|---|---|---|
| | compound | ratio | V | cd/A | CIE(x, y) | $T_{90}$ |
| Ex 257 | | 1:3 | 3.58 | 124.7 | (0.253, 0.732) | 387 |
| Ex 258 | 531:2-50 | 1:1 | 3.62 | 119.5 | (0.250, 0.610) | 352 |
| Ex 259 | | 1:2 | 3.59 | 116.8 | (0.256, 0.722) | 358 |
| Ex 260 | | 1:3 | 3.55 | 115.7 | (0.252, 0.613) | 360 |
| Ex 261 | 608:2-53 | 1:1 | 3.73 | 117.9 | (0.275, 0.663) | 355 |
| Ex 262 | | 1:2 | 3.75 | 116.6 | (0.265, 0.650) | 358 |
| Ex 263 | | 1:3 | 3.77 | 115.3 | (0.273, 0.664) | 367 |
| Ex 264 | 608:2-76 | 1:1 | 3.88 | 113.7 | (0.273, 0.669) | 348 |
| Ex 265 | | 1:2 | 3.91 | 110.4 | (0.269, 0.656) | 351 |
| Ex 266 | | 1:3 | 3.93 | 109.5 | (0.275, 0.671) | 352 |
| Ex 267 | 667:2-62 | 1:1 | 3.49 | 125.9 | (0.270, 0.662) | 360 |
| Ex 268 | | 1:2 | 3.44 | 122.8 | (0.263, 0.673) | 362 |
| Ex 269 | | 1:3 | 3.42 | 122.6 | (0.268, 0.674) | 366 |
| Ex 270 | 676:2-62 | 1:1 | 3.47 | 124.7 | (0.275, 0.665) | 363 |
| Ex 271 | | 1:2 | 3.42 | 124.4 | (0.275, 0.663) | 369 |
| Ex 272 | | 1:3 | 3.40 | 124.0 | (0.257, 0.652) | 370 |
| Ex 273 | 686:2-50 | 1:1 | 3.20 | 128.7 | (0.260, 0.668) | 406 |
| Ex 274 | | 1:2 | 3.15 | 130.5 | (0.275, 0.667) | 411 |
| Ex 275 | | 1:3 | 3.13 | 130.7 | (0.263, 0.675) | 412 |
| Ex 276 | 692:2-50 | 1:1 | 3.21 | 133.4 | (0.276, 0.651) | 419 |
| Ex 277 | | 1:2 | 3.14 | 132.8 | (0.263, 0.652) | 420 |
| Ex 278 | | 1:3 | 3.10 | 131.6 | (0.273, 0.654) | 422 |
| Ex 279 | 721:2-62 | 1:1 | 3.41 | 129.9 | (0.268, 0.659) | 371 |
| Ex 280 | | 1:2 | 3.38 | 126.6 | (0.265, 0.665) | 377 |
| Ex 281 | | 1:3 | 3.37 | 123.0 | (0.275, 0.664) | 380 |
| Ex 282 | 727:2-53 | 1:1 | 3.09 | 138.8 | (0.264, 0.675) | 413 |
| Ex 283 | | 1:2 | 3.05 | 135.2 | (0.264, 0.663) | 418 |
| Ex 284 | | 1:3 | 3.02 | 133.6 | (0.277, 0.663) | 423 |
| Ex 285 | 735:2-53 | 1:1 | 3.11 | 137.6 | (0.270, 0.681) | 418 |
| Ex 286 | | 1:2 | 3.07 | 136.9 | (0.265, 0.658) | 420 |
| Ex 287 | | 1:3 | 3.00 | 136.5 | (0.273, 0.673) | 429 |
| Ex 288 | 773:2-50 | 1:1 | 3.30 | 138.2 | (0.265, 0.658) | 438 |
| Ex 289 | | 1:2 | 3.29 | 137.7 | (0.265, 0.662) | 442 |
| Ex 290 | | 1:3 | 3.28 | 135.9 | (0.259, 0.663) | 448 |
| Ex 291 | 733:2-78 | 1:1 | 3.44 | 148.5 | (0.275, 0.676) | 429 |
| Ex 292 | | 1:2 | 3.40 | 143.2 | (0.265, 0.657) | 433 |
| Ex 293 | | 1:3 | 3.37 | 141.7 | (0.264, 0.670) | 435 |
| Ex 294 | 775:2-53 | 1:1 | 3.26 | 133.6 | (0.265, 0.653) | 450 |
| Ex 295 | | 1:2 | 3.22 | 136.8 | (0.265, 0.665) | 458 |
| Ex 296 | | 1:3 | 3.10 | 137.2 | (0.268, 0.654) | 463 |
[A]
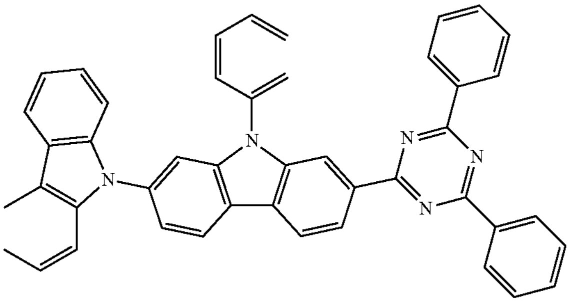
[B]
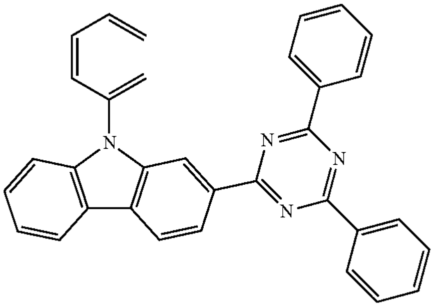
-continued
[C]
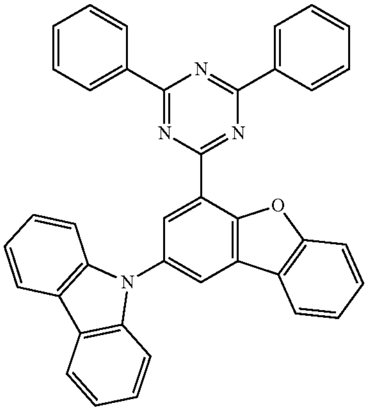
[D]
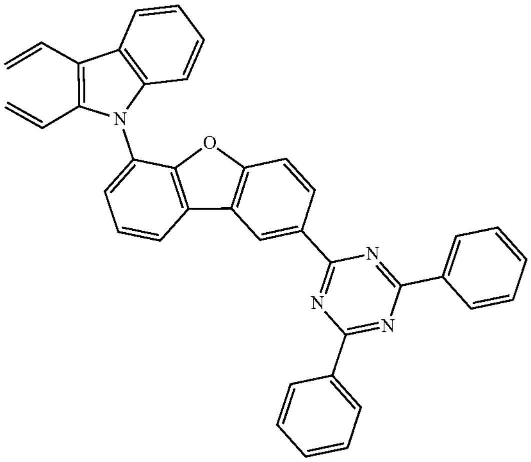
[E]
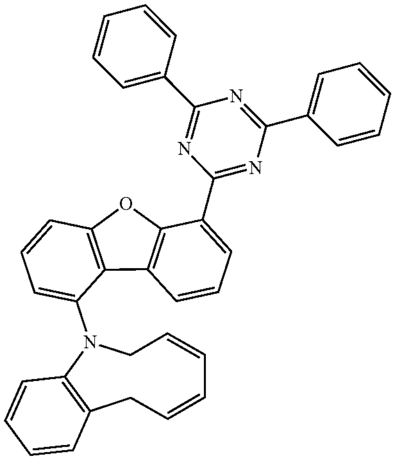

-continued

[F]

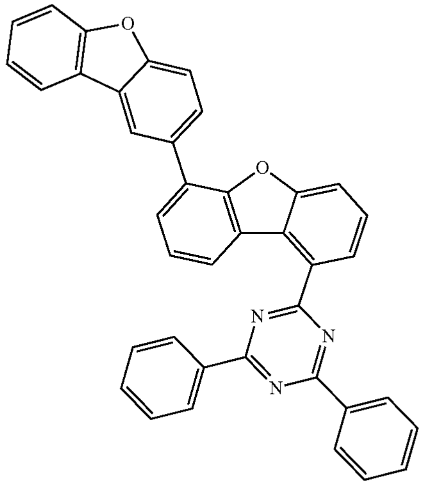

[G]

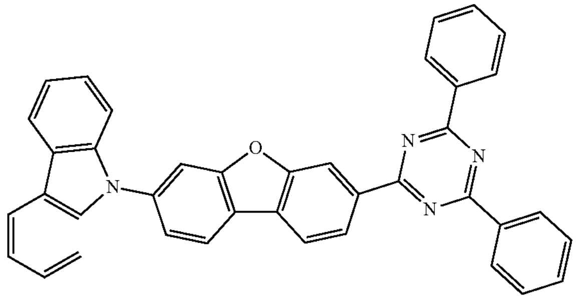

[H]

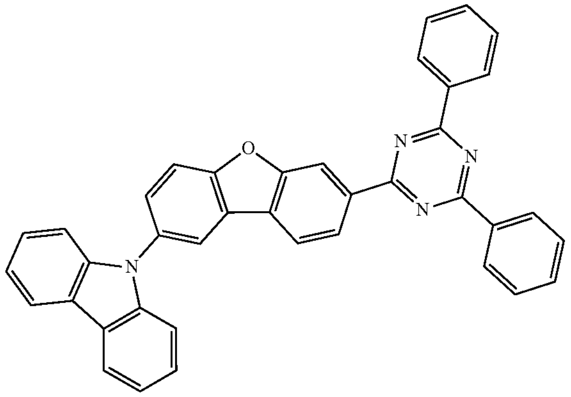

[I]

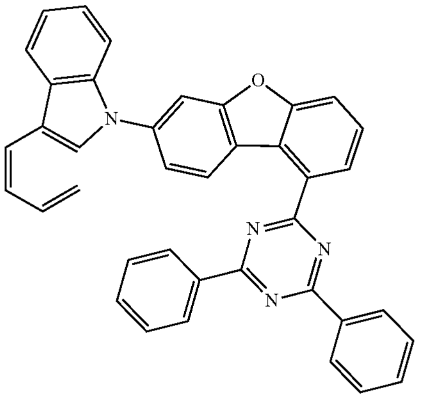

As the results of the above device evaluation, the driving voltage is lowered and the lifespan is increased with higher deuteration ratio of the heterocyclic compounds. When the dibenzofuran moiety (part) serving as a linker connecting the electron transport moiety and the hole transport moiety is substituted with deuterium (D), the driving voltage is improved compared to the non-deuteration compound. However, the effect with the compound with deuterium substitution on the dibenzofuran moiety is smaller than the effect with the compound with deuterium substitution on the electron transport moiety and the hole transport moiety. The vibrational frequency of intermolecular bonds in triazine and carbazole moieties, which directly exchange electrons, is continuously changed because the electrons move so that the stability of intramolecular bonds and molecular structure is affected.

By substituting with deuterium having a higher molecular weight than hydrogen, the change in the vibrational frequency is reduced so that the energy of the molecule is lowered. As a result, the stability of the molecule is increased.

In particular, in the device evaluation, when the deuteration ratio of the compound of Formula 2 of the present disclosure is higher than that of the compound of Formula 1 of the present disclosure, the performance of the device is further improved.

The EBL 307 may include a compound of Formula 10 as an electron blocking material 322.

[Formula 10]

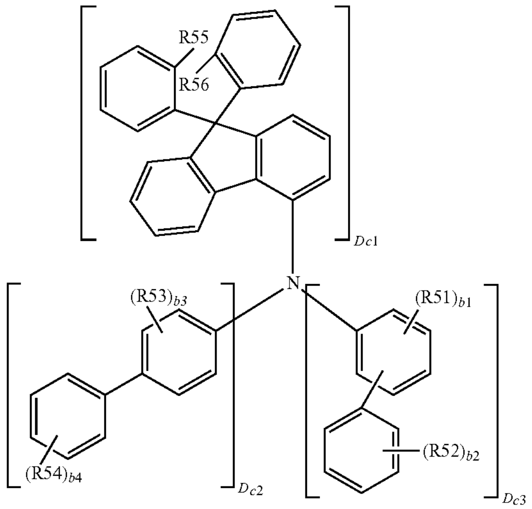

In Formula 10, each of R51 and R52 is independently a substituted or unsubstituted C1 to C10 alkyl, or adjacent two of R51 and R52 is connected to form a ring. In addition, b1 is an integer of 0 to 4, and b2 is an integer of 0 to 5. Each of R53 and R54 is independently a substituted or unsubstituted C1 to C10 alkyl, or adjacent two of R53 and R54 is connected to form a ring. In addition, b3 is an integer of 0 to 4, and b4 is an integer of 0 to 5. Each of R55 and R56 is hydrogen, or adjacent two of R55 and R56 is connected to form a ring. In addition, each of c1, c2 and c3 is independently 0 or a positive integer, and at least one of c1, c2 and c3 is the positive integer. In Formula 10, D denotes a deuterium atom, and each of c1, c2 and c3 denotes a number of the deuterium atom.

Namely, in the compound of Formula 10, at least one hydrogen is substituted by the deuterium atom.

For example, c1 may be the positive integer. It is preferred that c1 is the positive integer and c2 and c3 are 0. In Formula 10, when only the fluorene moiety or the spiro-fluorene moiety is deuterated, the lifespan and the driving performance of the device can be improved with minimizing the increase of the production cost by the deuterium atom. In this case, the deuteration ratio of the fluorene moiety or the spiro-fluorene moiety may be 100%.

The compound of Formula 10 may be one of the compounds in Formula 11.

[Formula 11]

EBL1-1

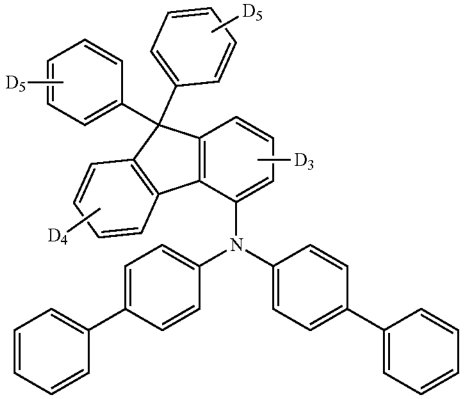

EBL1-2

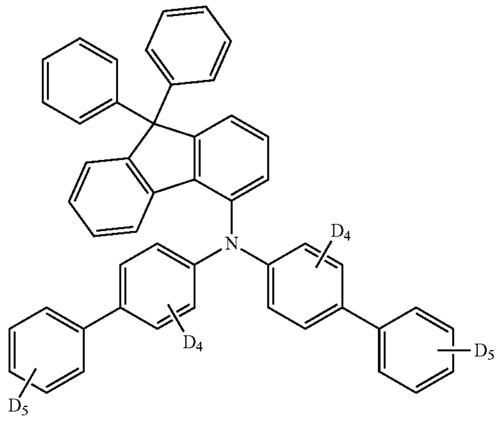

EBL1-3

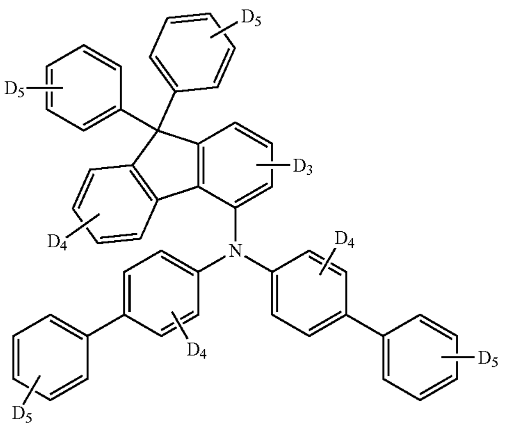

-continued

EBL2-1

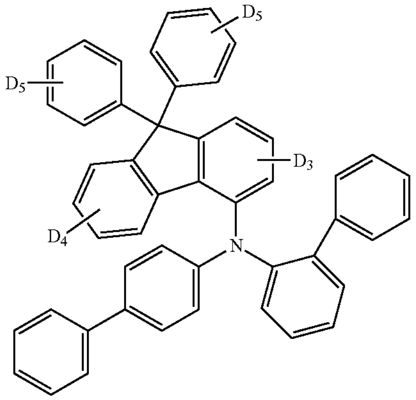

EBL2-2

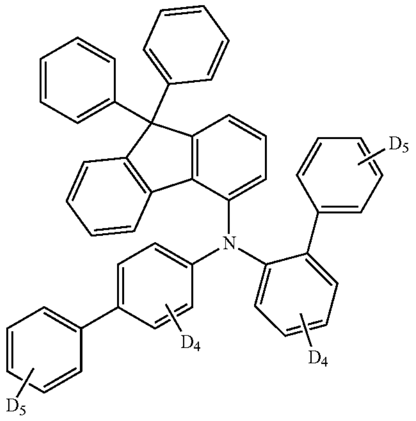

ELB2-3

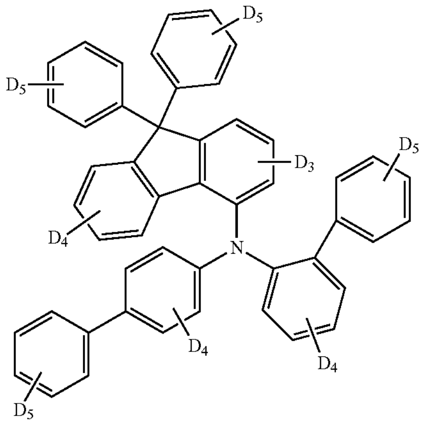

EBL3-1
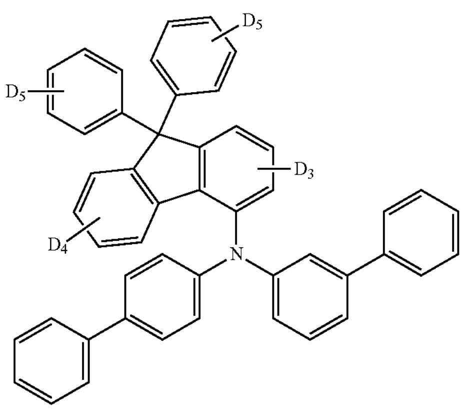
EBL3-2
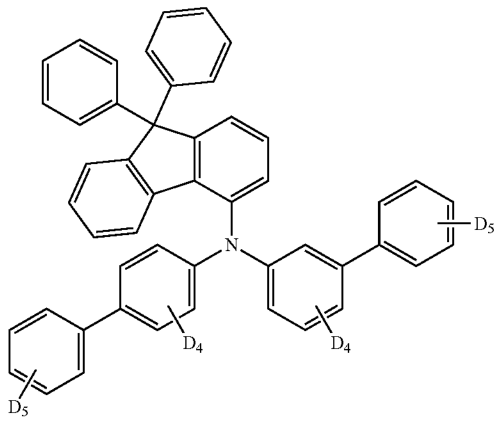
EBL3-3
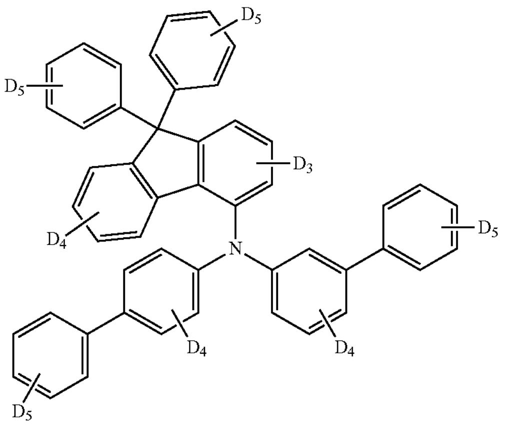
EBL4-1
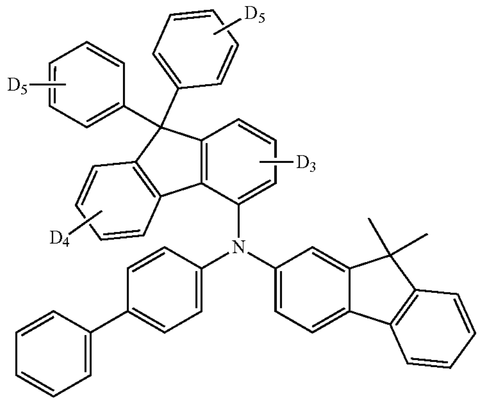
EBL4-2
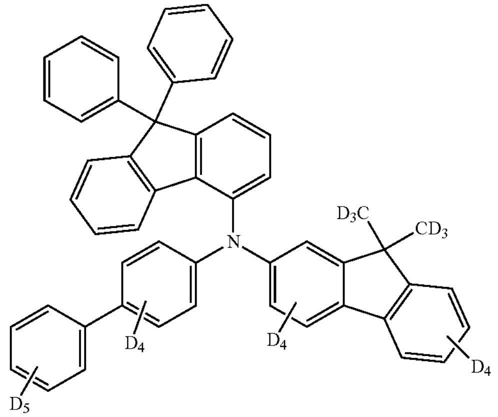
EBL4-3
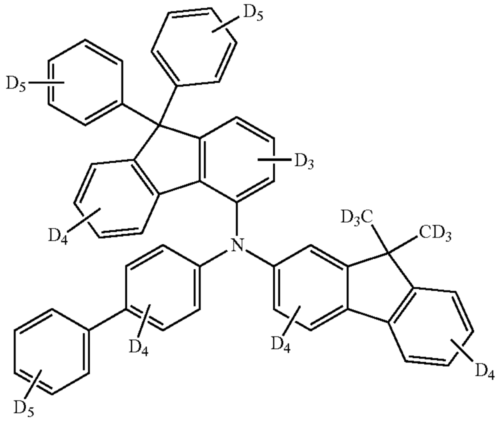

-continued
EBL5-1
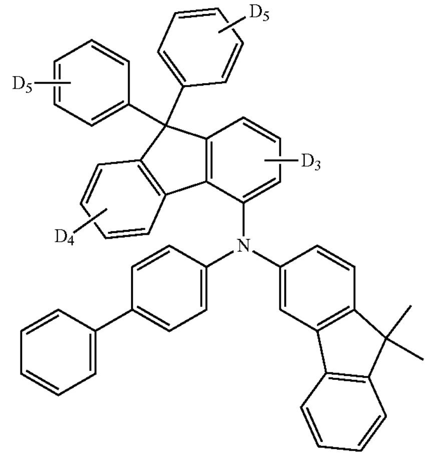
EBL5-2
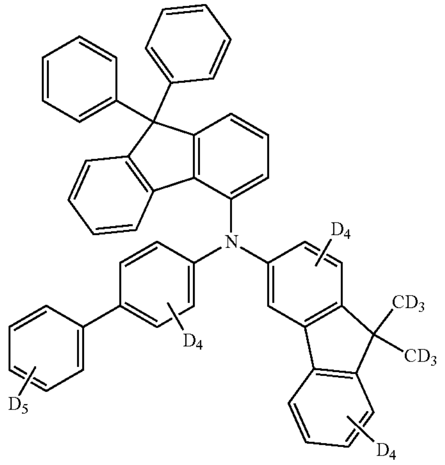
EBL5-3
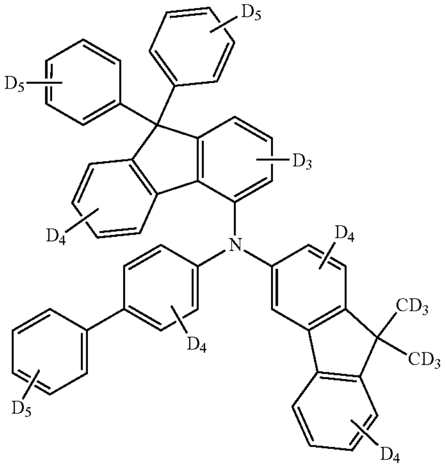
-continued
EBL6-1
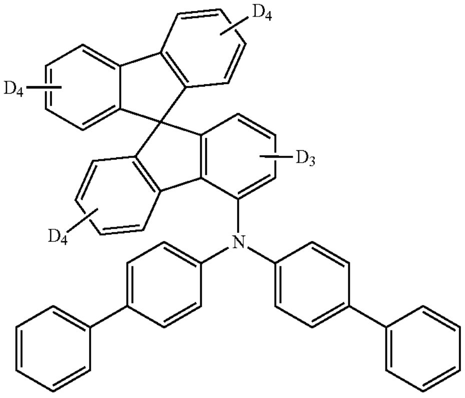
EBL6-2
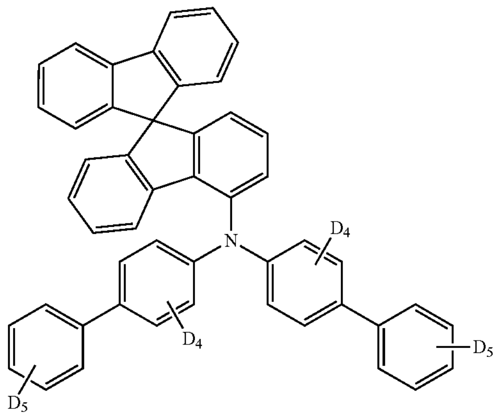
EBL6-3
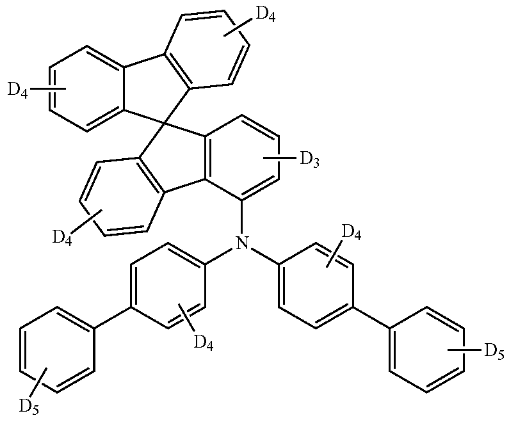

-continued
EBL7-1
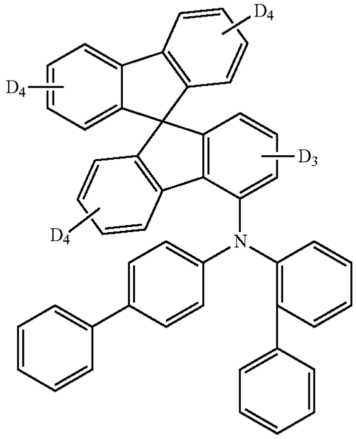
EBL7-2
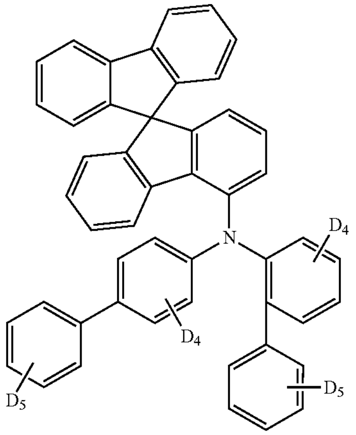
EBL7-3
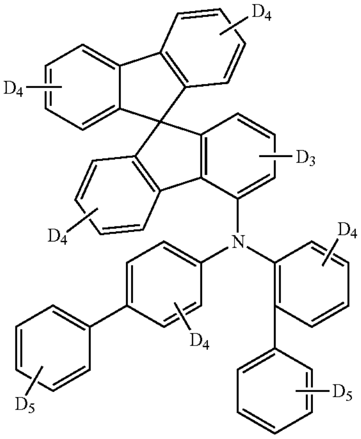
-continued
EBL8-1
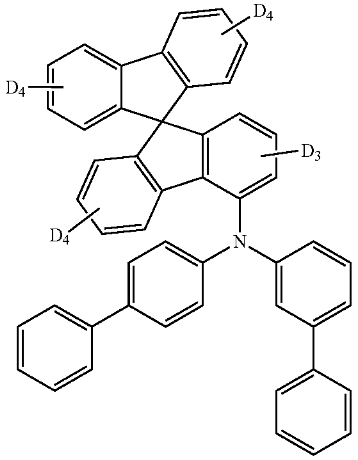
EBL8-2
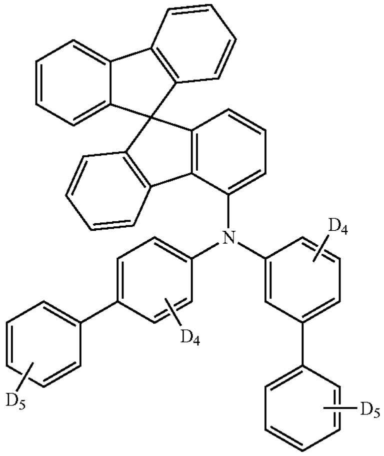
EBL8-3
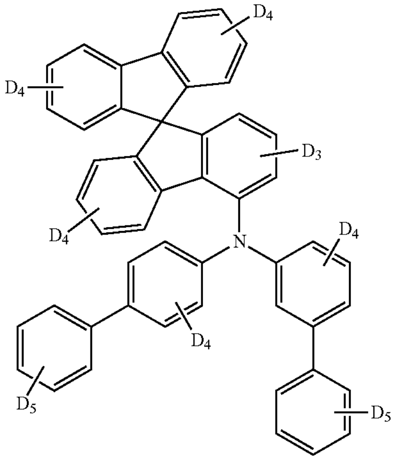

-continued

EBL9-1

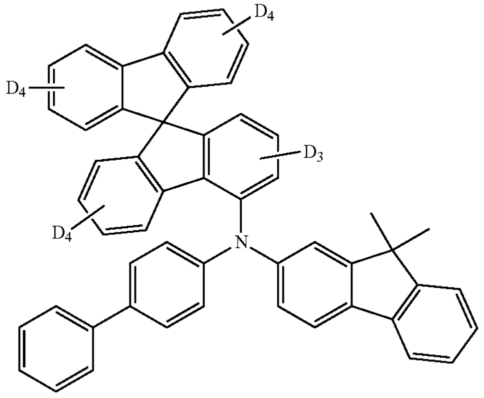

EBL9-2

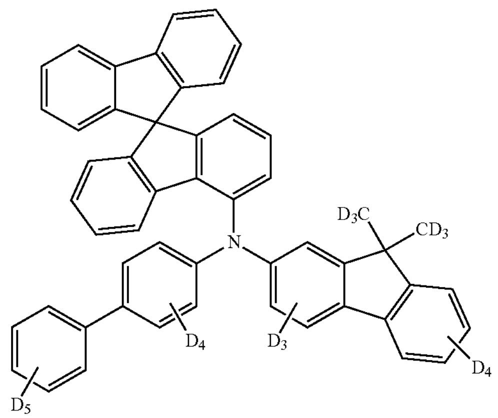

EBL9-3

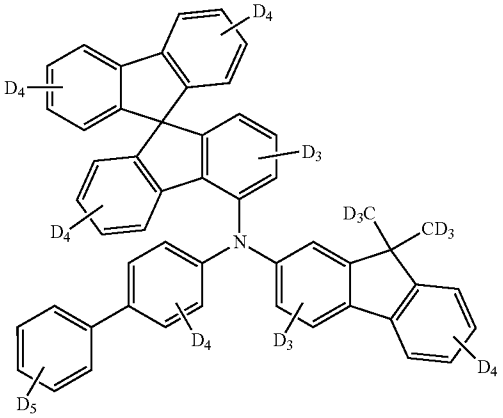

-continued

EBL10-1

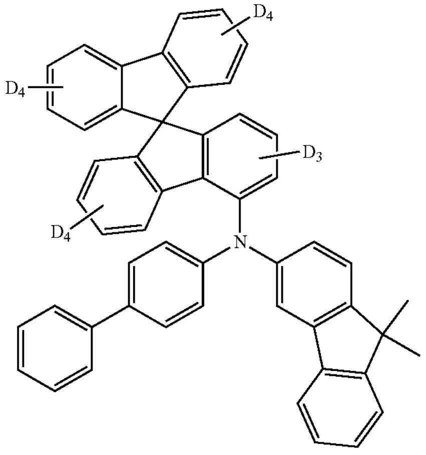

EBL10-2

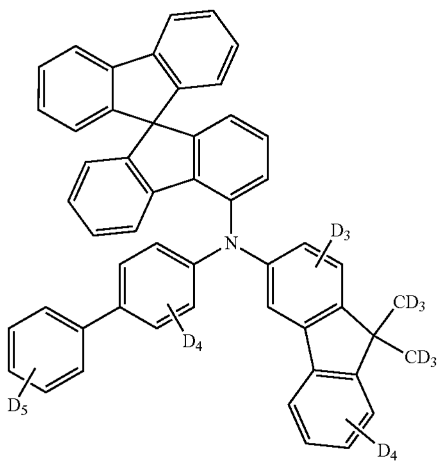

EBL10-3

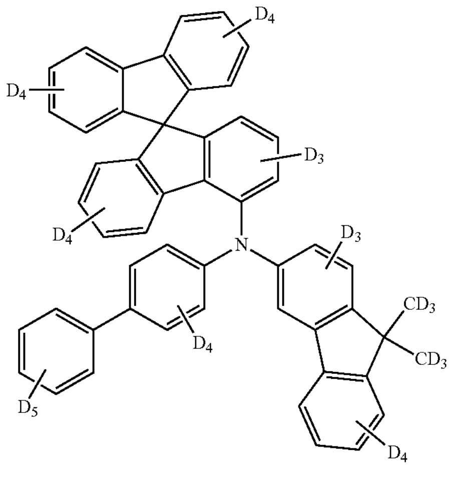

When the EML 303 includes the first compound 312 as the N-type host being the compound in Formula 1, the second compound 314 as the P-type host being the compound in formula 2 and the third compound 316 as the dopant being iridium complex, e.g., $Ir(ppy)_3$, and the EBL 307 being adjacent to the EML 303 includes the electron blocking material 322 being the compound of Formula 10, the emitting property of the organic light emitting device is significantly improved. For example, the third compound 316 as the dopant may be $Ir(ppy)_3$.

In addition, when c1 in Formula 10 is the positive integer and c2 and c3 in Formula 10 are 0, the emitting property of the organic light emitting device is further improved.

When the carbazole moiety in the compound of Formula 1 is deuterated, i.e., c1=positive integer, c2/c3=0 in Formula 1b, the emitting property of the organic light emitting device is further improved.

Synthesis

1. Synthesis of Intermediates (1) Intermediate 1

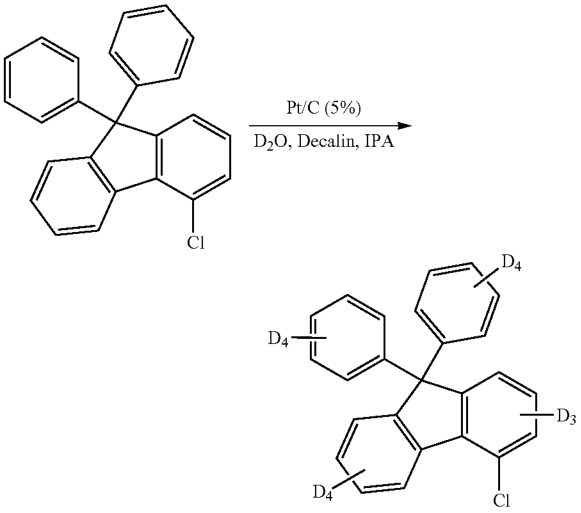

1

After dissolving 8.9 g (25 mmol) of 4-chloro-9,9-diphenyl-9H-fluorene in a mixed solution of 158 mL of $D_2O$, 15.8 mL of IPA, and 316.4 mL of decalin, 5% Pt/C (3.36 g) was added. The solution was stirred in a high pressure reactor at 100° C. for 24 hours, and then cooled to room temperature. Then, dichloromethane was added to separate the organic layer, and the separated organic layer was dried using $MgSO_4$. The residual solution was concentrated. After adding IPA to the concentrated solution, the precipitated material was filtered to obtain the intermediate 1 (8 g). (yield 86%)

(2) Intermediate 2

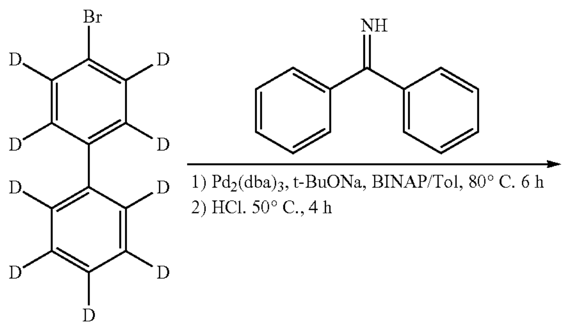

-continued

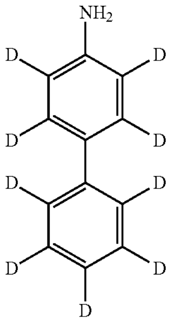

2

After dissolving 24.2 g of 4-bromobiphenyl-d9 in 150 mL of toluene, 29.6 g of 1,1-diphenylmethanimine was added. 42.8 g of t-BuONa, 9.25 g of BINAP (2,2'-bis(diphenylphosphino)-1,1'-binaphthalene) and 6.80 g of $Pd_2(dba)_3$ were sequentially added. The solution was reacted at a temperature of 80° C. under a nitrogen condition for 6 hours. Thereafter, 3N HCl was added to the reaction solution, and then reacted at 50° C. under a nitrogen condition for 4 hours. After the reaction was completed, the solution was filtered and the organic layer was separated. Water in the separated organic layer was removed using $MgSO_4$. The organic layer was separated by column chromatography to separate the product. The separated product was purified through recrystallization to obtain the intermediate 2 (8.3 g). (yield 57%)

(3) Intermediate 3

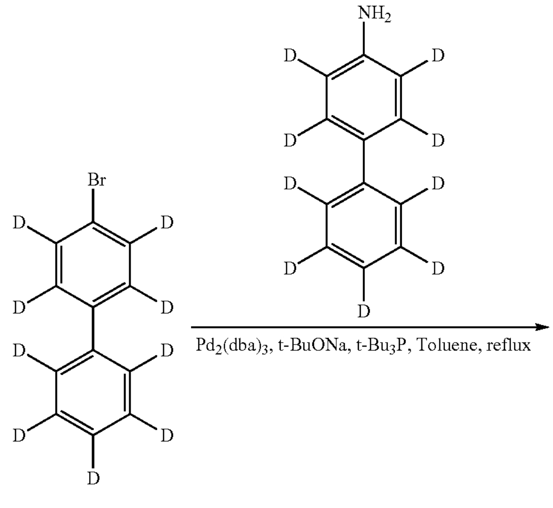

-continued

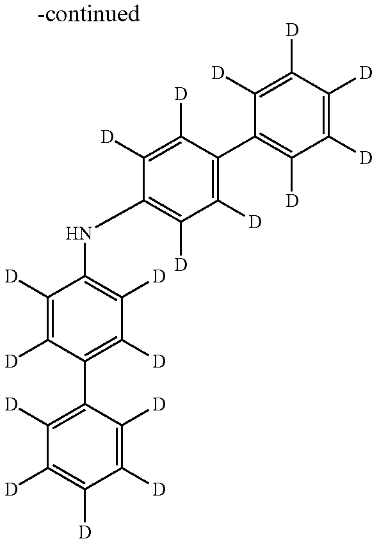

3

After dissolving 4.9 g of 4-bromobiphenyl-d9 in 60 mL of toluene, 2.5 g of the intermediate 6 was added. 1.9 g of t-BuONa, 0.4 g of (t-Bu) 3P, and 0.8 g of Pd2 (dba) 3 were sequentially added. The solution was reacted at 90° C. After the reaction was completed, the solution was filtered and the organic layer was separated. Water in the separated organic layer was removed using $MgSO_4$. The organic layer was separated by column chromatography to separate the product. The separated product was purified through recrystallization to obtain the intermediate 3 (2.7 g). (Yield 40%)

(4) Intermediate 4

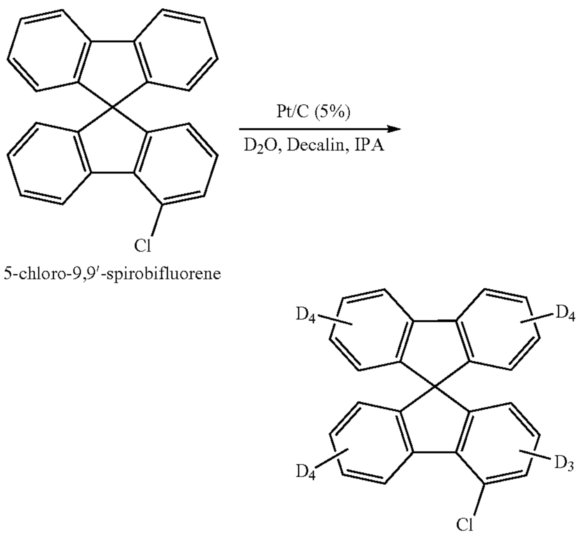

5-chloro-9,9′-spirobifluorene

4

After dissolving 8.8 g (25 mmol) of 5-chloro-9,9'-spirobifluorene in a mixed solution of 160 mL of D20, 16 mL of IPA, and 320 mL of decalin, and 5% Pt/C (3.36 g) were added. The solution was stirred at 100° C. for 24 hours in a high-pressure reactor, and then cooled to room temperature. Then, dichloromethane was added to separate the organic layer, and the separated organic layer was dried using $MgSO_4$. The residual solution was concentrated. After adding IPA to the concentrated solution, the precipitated material was filtered to obtain the intermediate 4 (7.9 g). (yield 86%)

(5) Aniline-D5

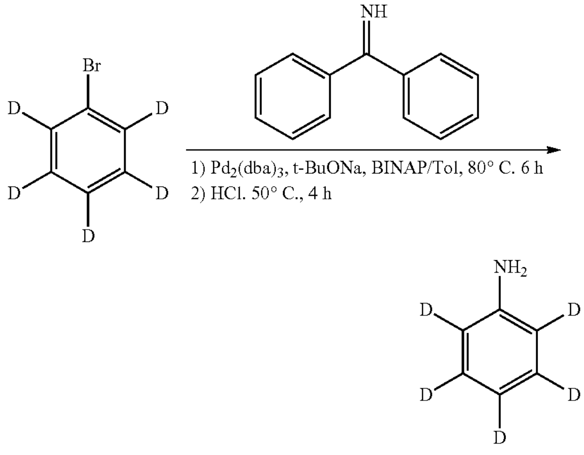

After dissolving 16.2 g of bromobenzene-d5 in 120 mL of toluene, 19.9 g of 1,1-diphenylmethanimine was added. Then, t-BuONa 28.8 g, 6.23 g of BINAP (2,2'-bis(diphenylphosphino)-1,1'-binaphthalene) and 4.58 g of $Pd_2(dba)_3$ are sequentially added. The solution was reacted at a temperature of 80° C. under a nitrogen condition for 6 hours. Thereafter, 3N HCl was added to the reaction solution, and then reacted at 50° C. under a nitrogen condition for 4 hours. After the reaction was completed, the solution is filtered and the organic layer is separated. Water in the separated organic layer was removed using $MgSO_4$. The organic layer was separated by column chromatography to separate the product. The separated product was purified through recrystallization to obtain aniline-d5 (5.6 g). (yield 57%)

(6) Intermediate 5

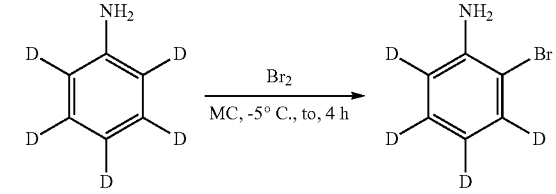

5

After dissolving 5.6 g of aniline-d5 in 50 mL of dichloromethane (MC), 8.21 g of $Br_2$ was added at low temperature (−5° C.), and then reacted for 4 hours while slowly raising the temperature to room temperature. After the reaction was completed, 10 mL of 2M $Na_2S_2O_3$ aqueous solution was added to the reaction mixture and stirred. After separating the organic layer from the mixed layer, the material was washed with 10% $Na_2CO_3$ 10 mL aqueous solution and distilled water. After separating the organic layer, water in the organic layer was removed using $MgSO_4$. After concentrating the organic solution, an excess methanol was added to precipitate the product, and the product was filtered to obtain the intermediate 5 (4.1 g). (yield 41%)

(7) Intermediate 6

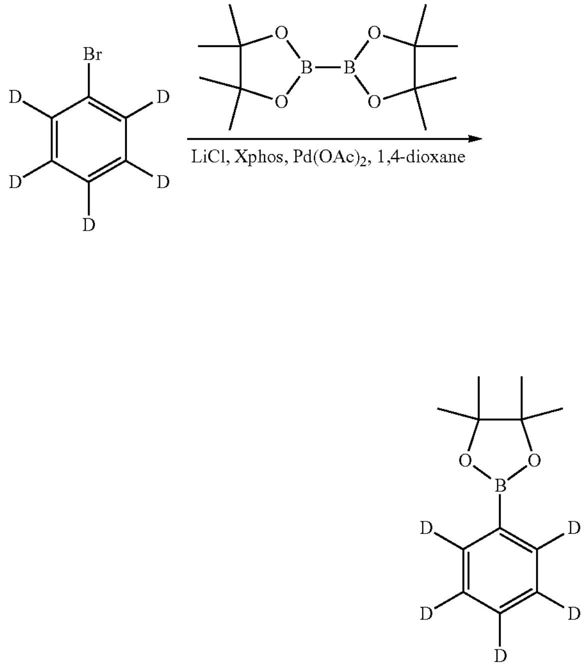

6

After dissolving 5.4 g of bromobenzene-d5 in 80 mL of 1,4-dioxane, 9.3 g of bis(pinacolato)diboron was added. Then, 4.24 g of LiCl, 1.6 g of XPhos, and 0.38 g of $Pd(OAc)_2$ were sequentially added. The solution was reacted at a temperature of 90° C. under a nitrogen condition for 18 hours. After the reaction was completed, the solution is filtered and the organic layer is separated. Water in the separated organic layer was removed using $MgSO_4$. The organic layer was separated by column chromatography to separate the product. The separated product was purified through recrystallization to obtain the intermediate 6 (6.2 g). (Yield 91%)

(8) Intermediate 7

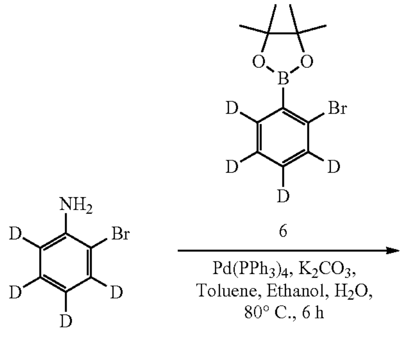

6

5

-continued

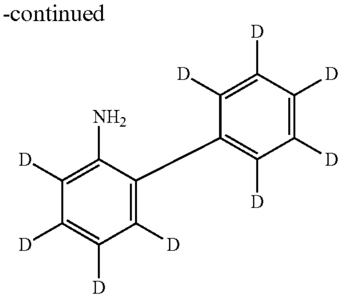

7

After dissolving the intermediate 5 (4.1 g) in 50 mL of toluene, the intermediate 6 (5.1 g) was added. Then, 5 mL of water, 9.7 g of $K_2CO_3$, 5 mL of ethanol, and 1.35 g of $Pd(PPh_3)_4$ were sequentially added. The solution was reacted at a temperature of 80° C. under a nitrogen condition for 12 hours. After the reaction was completed, the solution is filtered and the organic layer is separated. Water in the separated organic layer was removed using $MgSO_4$. The organic layer was separated by column chromatography to separate the product. The separated product was purified through recrystallization to obtain the intermediate 7 (2.5 g). (yield 61%)

(9) Intermediate 8

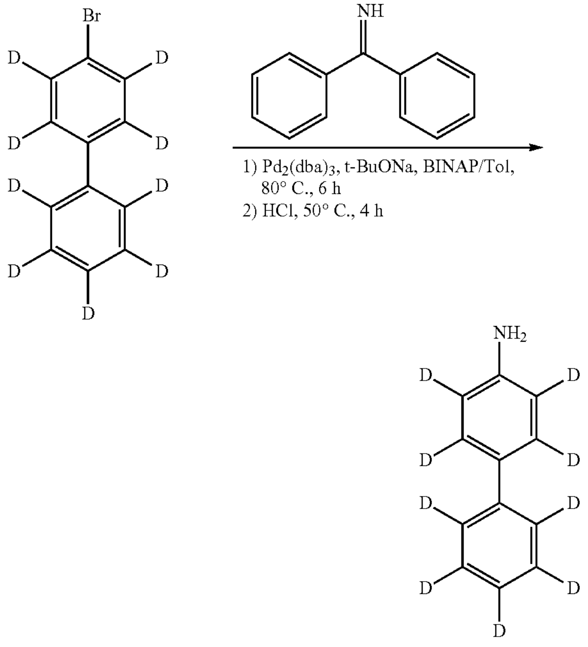

8

After dissolving 24.2 g of 4-bromobiphenyl-d9 in 150 mL of toluene, 29.6 g of 1,1-diphenylmethanimine was added. Then, 42.8 g of t-BuONa, 9.25 g of BINAP (2,2'-bis(diphenylphosphino)-1,1'-binaphthalene) and 6.80 g of $Pd_2(dba)_3$ were sequentially added. The solution was reacted at a temperature of 80° C. under a nitrogen condition for 6 hours. Thereafter, 3N HCl was added to the reaction solution, and then reacted at 50° C. under a nitrogen condition for 4 hours. After the reaction was completed, the solution was filtered and the organic layer was separated. Water in the separated organic layer was removed using $MgSO_4$. The organic layer was separated by column chromatography to separate the product. The separated product was purified through recrystallization to obtain the Intermediate 8 (8.3 g). (yield 57%)

(10) Intermediate 9

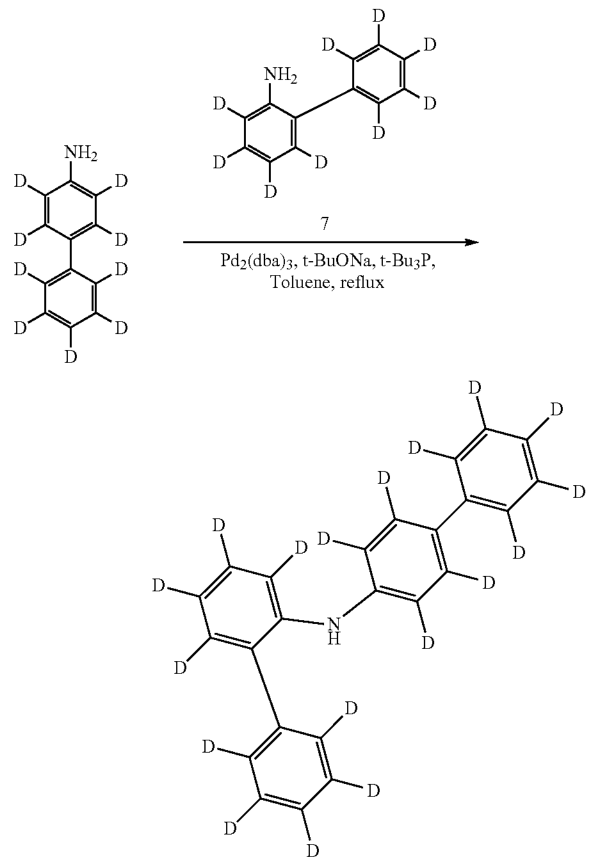

9

After dissolving 4.88 g of 4-bromobiphenyl-d9 in 60 mL of toluene, 2.54 g of the intermediate 7 was added. Then, 1.86 g of t-BuONa, 0.35 g of $(t\text{-}Bu)_3P$, and 0.82 g of $Pd_2(dba)_3$ were sequentially added. The solution was reacted at 90° C. After the reaction was completed, the solution was filtered and the organic layer was separated. Water in the separated organic layer was removed using $MgSO_4$. The organic layer was separated by column chromatography to separate the product. The separated product was purified through recrystallization to obtain the intermediate 9 (2.66 g). (yield 40%)

(11) Intermediate 10

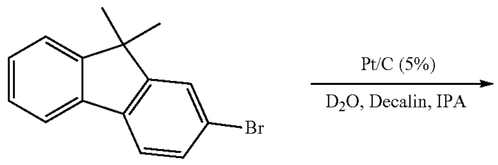

-continued

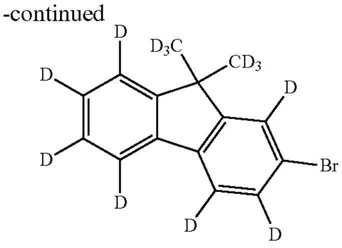

10

After dissolving 6.8 g of 2-bromo-9,9'-dimethylfluorene in a mixed solution of 137 mL of $D_2O$, 14 mL of IPA, and 273 mL of decalin, and 5% Pt/C (2.9 g) was added. The solution was stirred at 100° C. for 24 hours in a high-pressure reactor, and then cooled to room temperature. Then, dichloromethane was added to separate the organic layer, and the separated organic layer was dried using $MgSO_4$. The residual solution was concentrated. After adding IPA to the concentrated solution, the precipitated material was filtered to obtain the intermediate 10 (6.15 g). (yield 86%)

(12) Intermediate 11

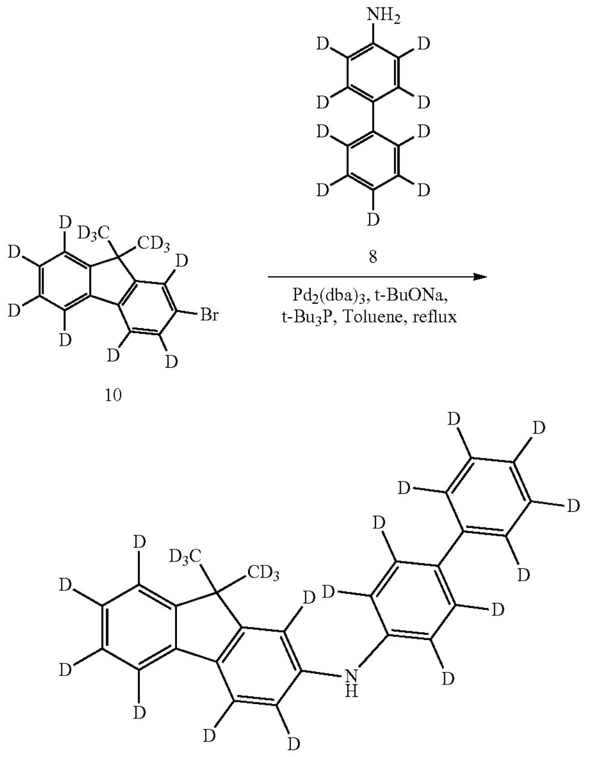

11

After dissolving the intermediate 10 (3 g) in 40 mL of toluene, 1.50 g of the intermediate 8 was added. Then, 1.1 g of t-BuONa, 0.21 g of $(t\text{-}Bu)_3P$, and 0.48 g of $Pd_2(dba)_3$ in sequence. The solution was reacted at 90° C. After the reaction, the solution was filtered and the organic layer was separated. Water in the separated organic layer was removed using $MgSO_4$. The organic layer was separated by column chromatography to separate the product. The separated product was purified through recrystallization to obtain the intermediate 11 (1.66 g). (Yield 40%)

2. Synthesis of the Compound of the EBL (1) The Compound EBL1-1

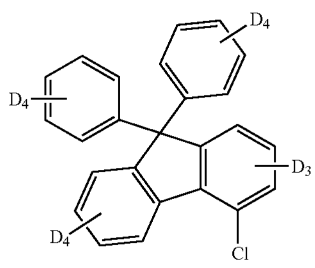

1

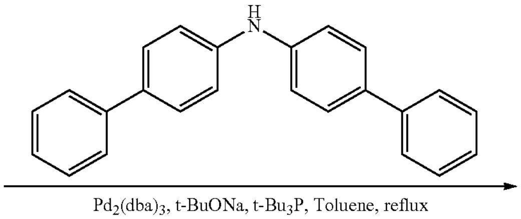

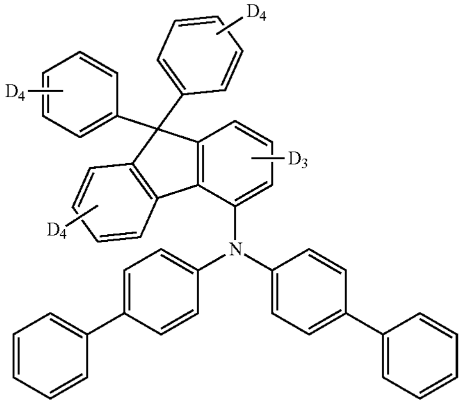

EBL1-1

After dissolving the intermediate 1 (5.61 g) in 60 mL of toluene, 6.51 g of N-(4-biphenylyl)-4-biphenylamine was added. Then, 4.38 g of t-BuONa, 0.31 g of $(t\text{-}Bu)_3P$, and 0.69 g of $Pd_2(dba)_3$ were sequentially added. The solution was reacted with reflux and stirring under a nitrogen condition. After the reaction was completed, the solution is filtered and the organic layer is separated. Water in the separated organic layer was removed using $MgSO_4$. The organic layer was separated by column chromatography to separate the product. The separated product was purified through recrystallization to obtain the compound EBL1-1 (3.82 g). (Yield 39%)

(2) The Compound EBL1-2

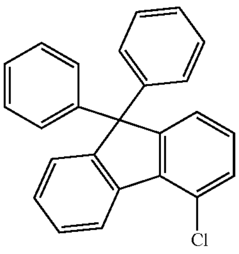

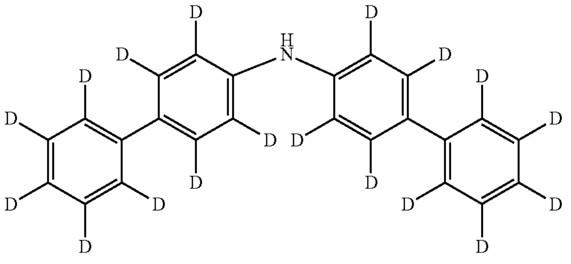

3

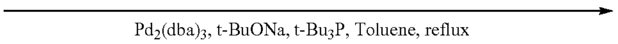

-continued

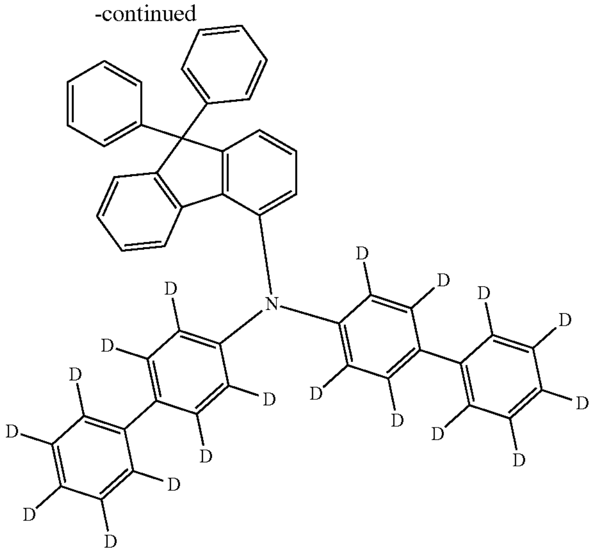

EBL1-2

After dissolving 5.35 g of 4-chloro-9,9-diphenyl-9H-fluorene in 60 mL of toluene, the intermediate 3 (6.87 g) was added. Then, 4.38 g of t-BuONa, 0.31 g of $(t\text{-}Bu)_3P$, and 0.69 g of $Pd_2(dba)_3$ were sequentially added. The solution was reacted with reflux and stirring under a nitrogen condition. After the reaction was completed, the solution is filtered and the organic layer is separated. Water in the separated organic layer was removed using $MgSO_4$. The organic layer was separated by column chromatography to separate the product. The separated product was purified through recrystallization to obtain the compound EBL1-2 (3.83 g). (Yield 39%)

(3) The Compound EBL1-3

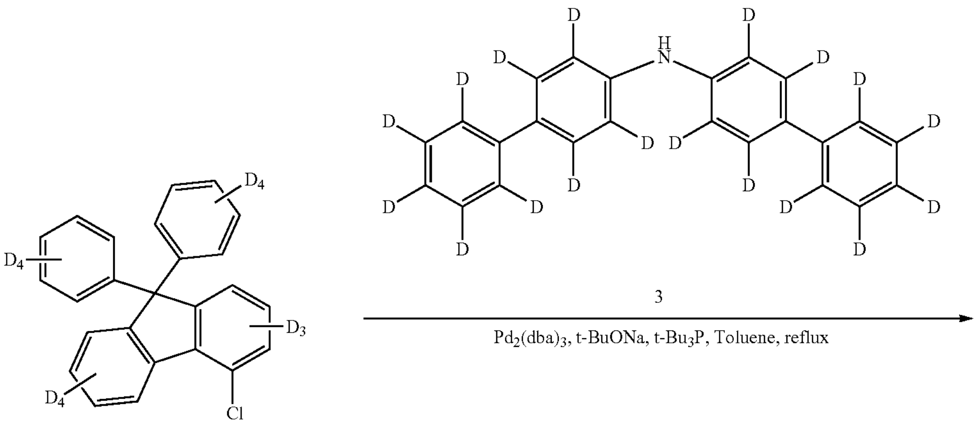

1

-continued

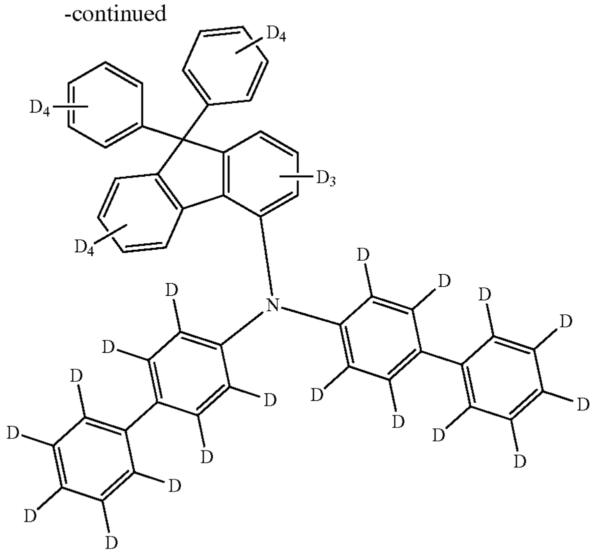

EBL1-3

After dissolving the intermediate 1 (5.61 g) in 60 mL of toluene, the intermediate 3 (6.87 g) was added. Then, 4.38 g of t-BuONa, 0.31 g of $(t\text{-}Bu)_3P$, and 0.69 g of $Pd_2(dba)_3$ were sequentially added. The solution was reacted with reflux and stirring under a nitrogen condition. After the reaction was completed, the solution is filtered and the organic layer is separated. Water in the separated organic layer was removed using $MgSO_4$. The organic layer was separated by column chromatography to separate the product. The separated product was purified through recrystallization to obtain the compound EBL1-3 (3.94 g). (Yield 39%)

(4) The Compound EBL7-1

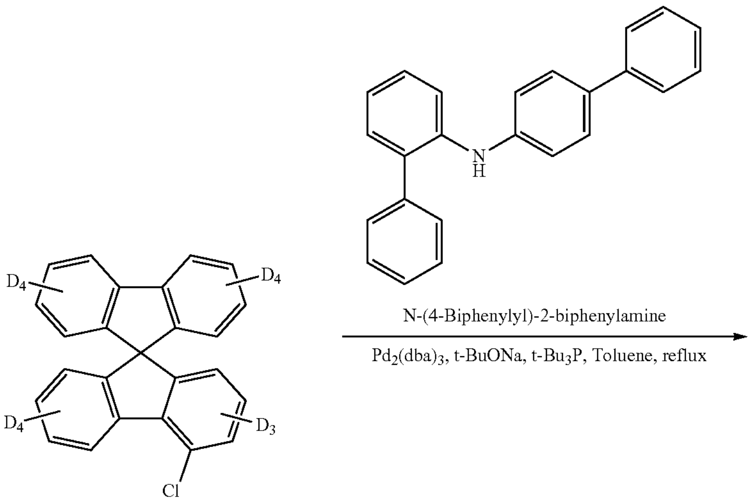

4

-continued

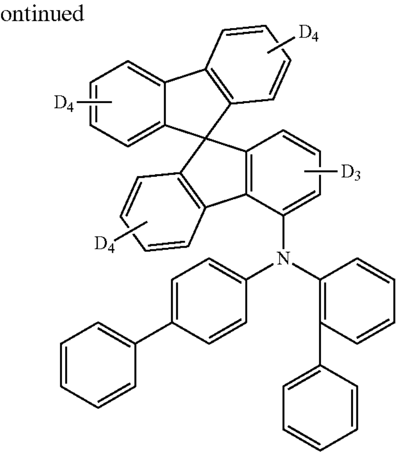

EBL7-1

After dissolving the intermediate 4 (6.26 g) in 60 mL of toluene, 4.63 g of N-(4-biphenylyl)-2-biphenylamine was added. Then, 4.38 g of t-BuONa, 0.31 g of $(t\text{-}Bu)_3P$, and 0.69 g of $Pd_2(dba)_3$ were sequentially added. The solution was reacted with reflux and stirring under a nitrogen condition. After the reaction was completed, the solution is filtered and the organic layer is separated. Water in the separated organic layer was removed using $MgSO_4$. The organic layer was separated by column chromatography to separate the product. The separated product was purified through recrystallization to obtain the compound EBL7-1 (3.78 g). (Yield 34%)

(5) The Compound EBL7-2

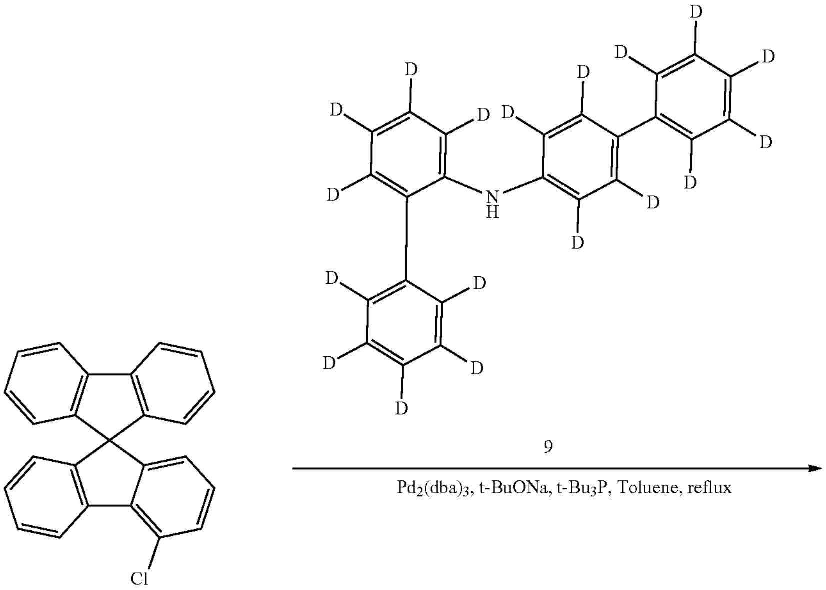

4-chloro-9,9'-spirobifluorene

-continued

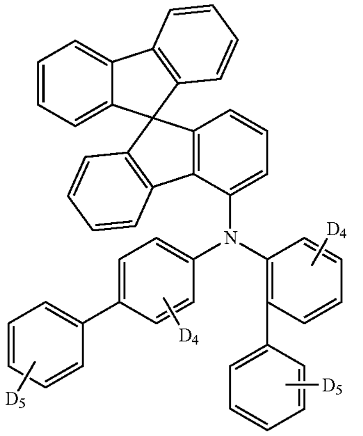

EBL7-2

After dissolving 7 g of 4-chloro-9,9'-spirobifluorene in 60 mL of toluene, the intermediate 9 (5.70 g) was added. Then, 5.11 g of t-BuONa, 0.36 g of $(t\text{-}Bu)_3P$, and 0.88 g of $Pd_2(dba)_3$ were sequentially added. The solution was reacted with reflux and stirring under a nitrogen condition. After the reaction was completed, the solution is filtered and the organic layer is separated. Water in the separated organic layer was removed using $MgSO_4$. The organic layer was separated by column chromatography to separate the product. The separated product was purified through recrystallization to obtain the compound EBL7-2 (4.57 g). (yield 35%)

(6) The Compound EBL7-3

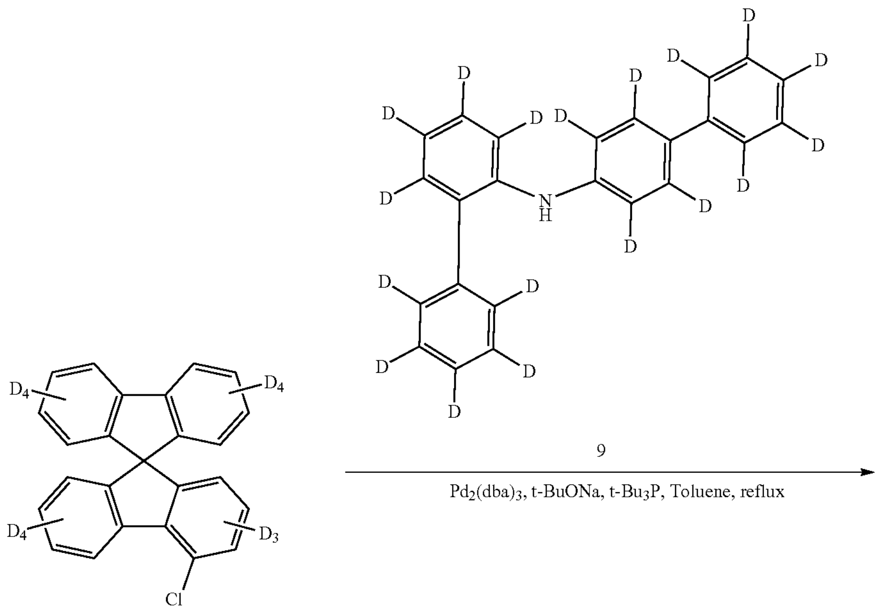

4

-continued

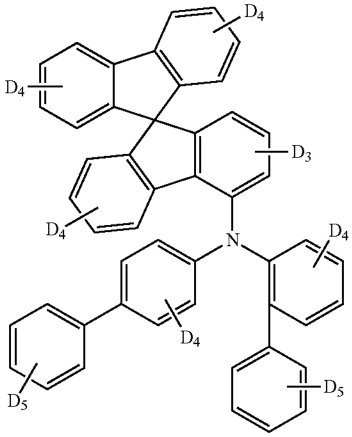

EBL7-3

After dissolving the intermediate 4 (7.3 g) in 60 mL of toluene, the intermediate 9 (5.70 g) was added. Then, 5.11 g of t-BuONa, 0.36 g of $(t\text{-}Bu)_3P$, and 0.88 g of $Pd_2(dba)_3$ were sequentially added. The solution was reacted with reflux and stirring under a nitrogen condition. After the reaction was completed, the solution is filtered and the organic layer is separated. Water in the separated organic layer was removed using $MgSO_4$. The organic layer was separated by column chromatography to separate the product. The separated product was purified through recrystallization to obtain the compound EBL7-3 (4.67 g). (yield 35%)

(7) The Compound EBL9-1

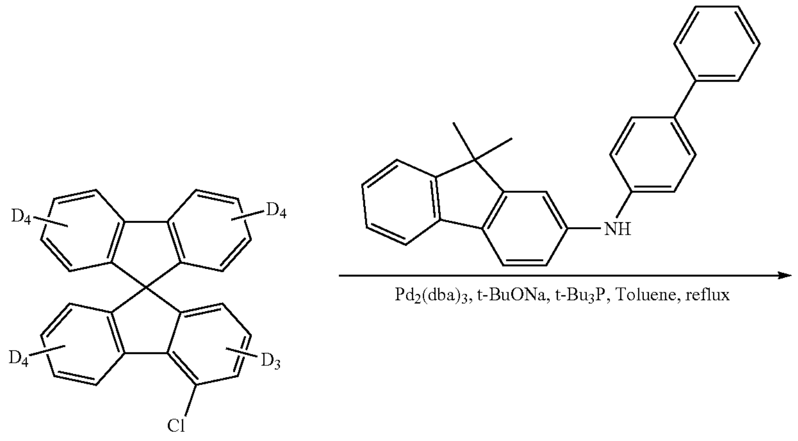

4

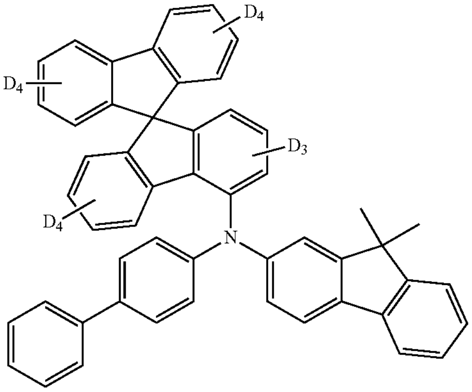

EBL9-1

After dissolving the intermediate 4 (7.3 g) in 60 mL of toluene, 6.07 g of N-(4-biphenylyl)-9,9'-dimethyl-9H-fluorene-2-amine was added. Then, 5.11 g of t-BuONa, 0.36 g of $(t\text{-}Bu)_3P$, and 0.88 g of $Pd_2(dba)_3$ were sequentially added. The solution was reacted with reflux and stirring under a nitrogen condition. After the reaction was completed, the solution is filtered and the organic layer is separated. Water in the separated organic layer was removed using $MgSO_4$. The organic layer was separated by column chromatography to separate the product. The separated product was purified through recrystallization to obtain the compound EBL9-1 (4.82 g). (yield 35%)

(8) The Compound EBL9-2

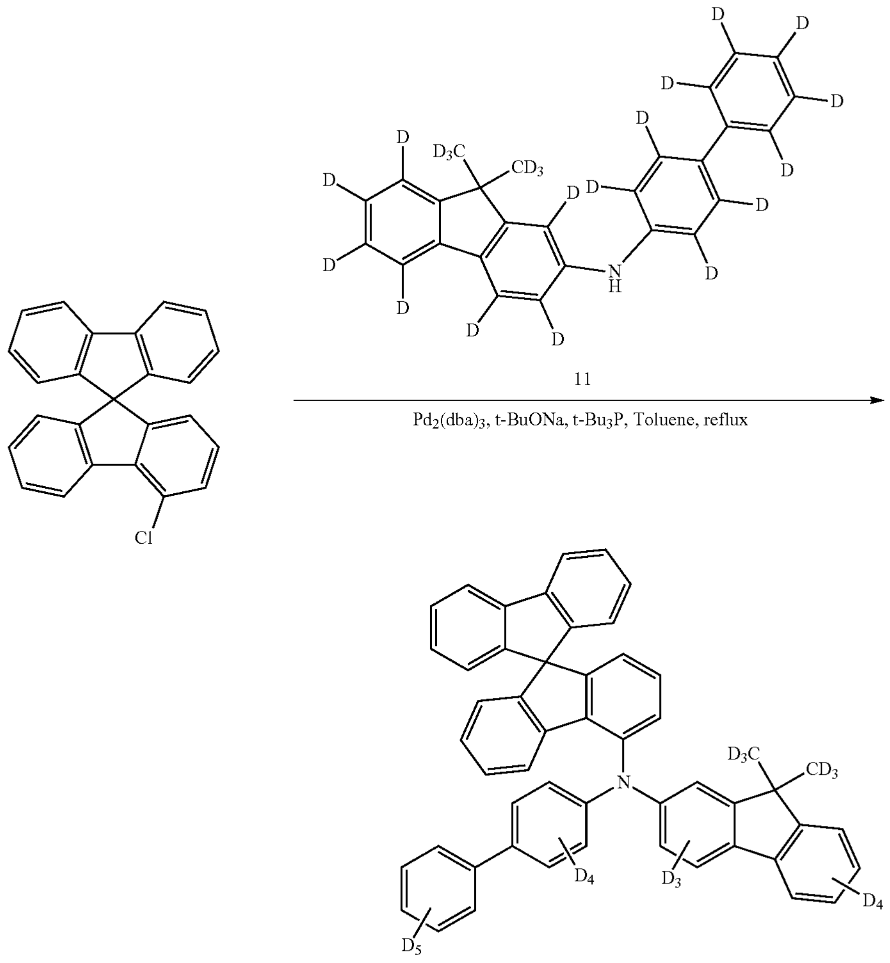

EBL9-2

After dissolving 7 g of 4-chloro-9,9'-spirobifluorene in 60 mL of toluene, the intermediate 11 (6.44 g) was added. Then, 5.11 g of t-BuONa, 0.36 g of $(t\text{-}Bu)_3P$, and 0.88 g of $Pd_2(dba)_3$ were sequentially added. The solution was reacted with reflux and stirring under a nitrogen condition. After the reaction was completed, the solution is filtered and the organic layer is separated. Water in the separated organic layer was removed using $MgSO_4$. The organic layer was separated by column chromatography to separate the product. The separated product was purified through recrystallization to obtain the compound EBL9-2 (4.87 g). (yield 35%)

(9) The Compound EBL9-3

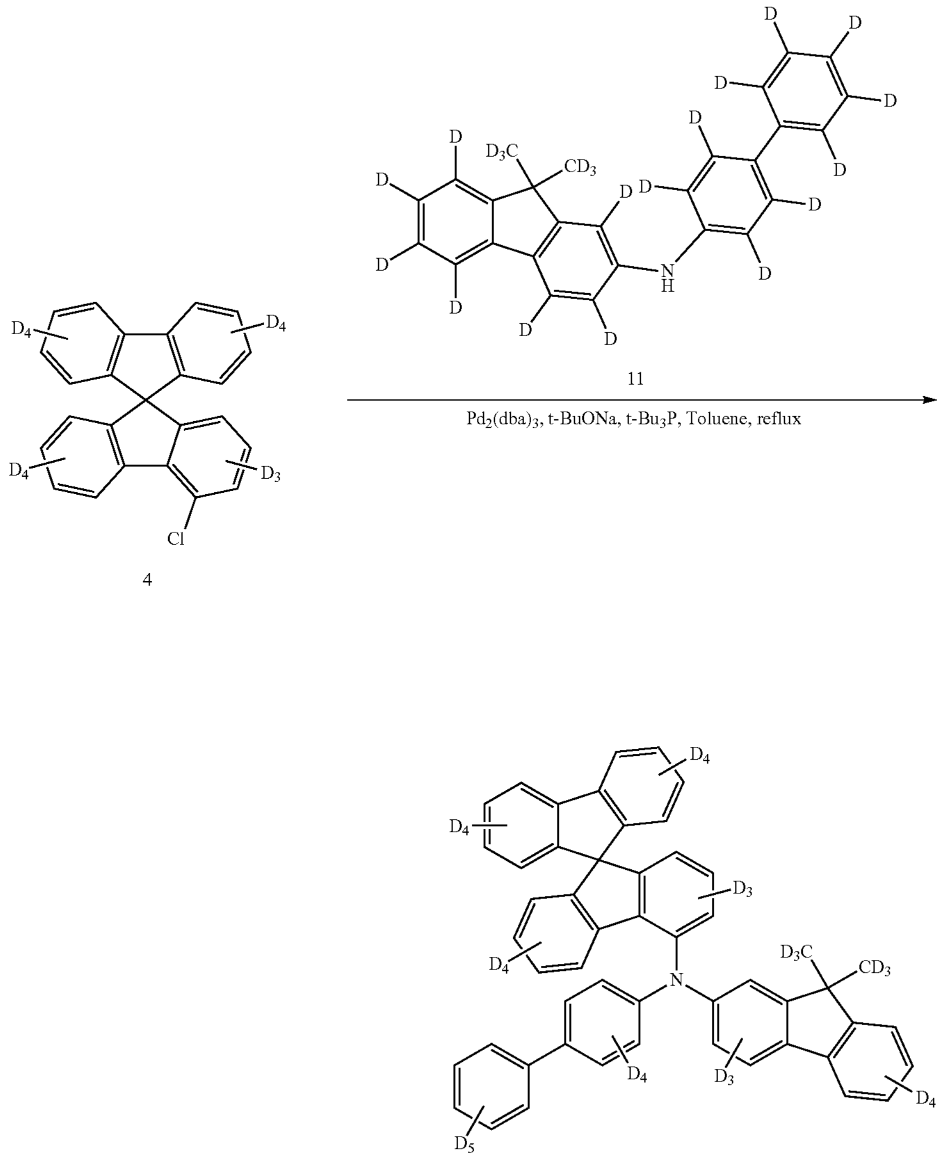

4
11
EBL9-3

After dissolving the intermediate 4 (7.3 g) in 60 mL of toluene, the intermediate 11 (6.44 g) was added. Then, 5.11 g of t-BuONa, 0.36 g of $(t\text{-}Bu)_3P$, and 0.88 g of $Pd_2(dba)_3$ were sequentially added. The solution was reacted with reflux and stirring under a nitrogen condition. After the reaction was completed, the solution is filtered and the organic layer is separated. Water in the separated organic layer was removed using $MgSO_4$. The organic layer was separated by column chromatography to separate the product. The separated product was purified through recrystallization to obtain the compound EBL9-3 (4.98 g). (yield 35%)

The third compound 316 as the dopant in the EML 303 emitting the green light, e.g., a green EML, may be represented by Formula 12.

[Formula 12]

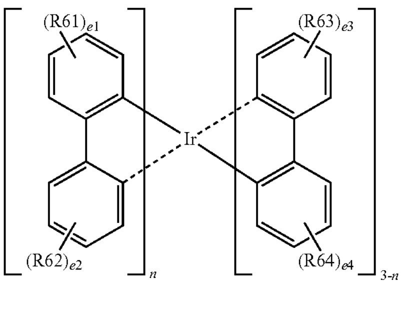

In Formula 12, each of R61, R62, R63 and R64 is independently selected from the group consisting of a substituted or unsubstituted C1 to C10 alkyl group, a substituted or unsubstituted C6 to C30 aryl group and a substituted or unsubstituted C3 to C30 heteroaryl group. In addition, each of e1, e2, e3 and e4 is independently an integer of 0 to 4, and n is an integer of 1 to 3.

For example, the compound of Formula 12 may be one of the compounds in Formula 13.

[Formula 13]

GD1

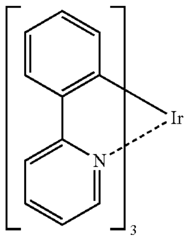

GD2

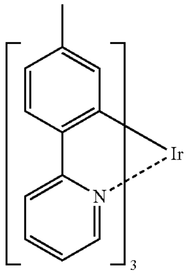

GD3

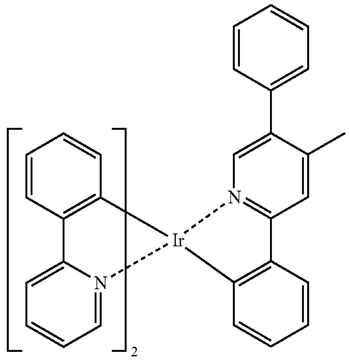

GD4

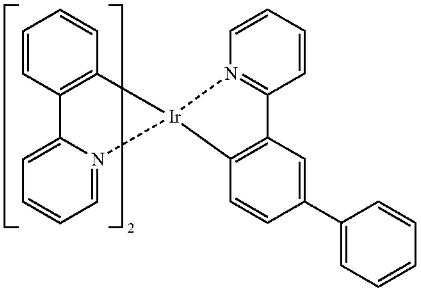

-continued

GD5

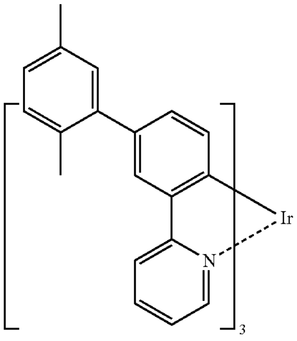

GD6

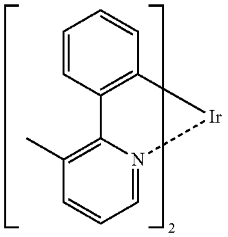

Namely, the green EML 303 may include the first compound 312 of Formula 1 as the N-type host, the second compound 314 of Formula 2 as the P-type host and the third compound 316 of Formula 12 as the dopant or an emitter.

In the green EML 303, a weight % of each of the first and second compounds 312 and 314 may be greater than that of the third compound 316, and the weight % of the first compound 312 and the weight % of second compounds 312 and 314 may be same or different. In the green EML 303, the weight % of the second compound 314 may be greater than that of the first compound 312. In the green EML 303, the third compound 316 may be the weight % of 1 to 25, preferably 5 to 10.

For example, the organic emitting layer (e.g., the organic material layer) may include the EML (the light emitting layer) between the anode and the cathode, the HTL between the anode and the EML, the EBL between the HTL and the EML, and the ETL between the EML and the cathode. In this instance, the EML may contact the EBL and the ETL. Namely, the organic emitting layer may include the EBL without the HBL.

In addition, the organic emitting layer may further include at least one of the HIL between the anode and the HTL and the EIL between the cathode and the ETL.

The EML includes the compound of Formula 1 as the first compound, e.g., the N-type host, and the compound of Formula 2 as the second compound, e.g., the P-type host, and the EBL being adjacent to the EML includes the compound of Formula 10.

In this case, at least one of hydrogens in the compound of Formula 10 is deuterated. Namely, the compound of Formula 10 may be partially deuterated or wholly deuterated. For example, only the fluorene moiety of the spiro-fluorene moiety in Formula 10 may be deuterated. In addition, each of the first compound of Formula 1 and the second compound of Formula 2 may be non-deuterated, partially deuterated or wholly deuterated. For example, the first compound of Formula 1 has a first deuteration ratio, and the second compound of Formula 2 has a second deuteration ration being smaller than the first deuteration ratio. Namely, in combination with the EBL including the compound of Formula 10, which is partially or wholly deuterated, the deuteration ration of the first compound is greater than that of the second compound.

In the organic light emitting diode (OLED, e.g., the organic light emitting device) having the above structure and configuration, the driving voltage is decreased, and the lifespan is significantly increased. In addition, when only the fluorene moiety of the spiro-fluorene moiety in Formula 10 is deuterated, the lifespan and the driving performance of the OLED can be improved with minimizing the increase of the production cost by the deuterium atom. Moreover, when only the carbazole moiety or a fused-carbazole moiety in Formula 1 is deuterated, the lifespan and the driving performance of the OLED can be improved with further minimizing the increase of the production cost by the deuterium atom.

Figure 5:
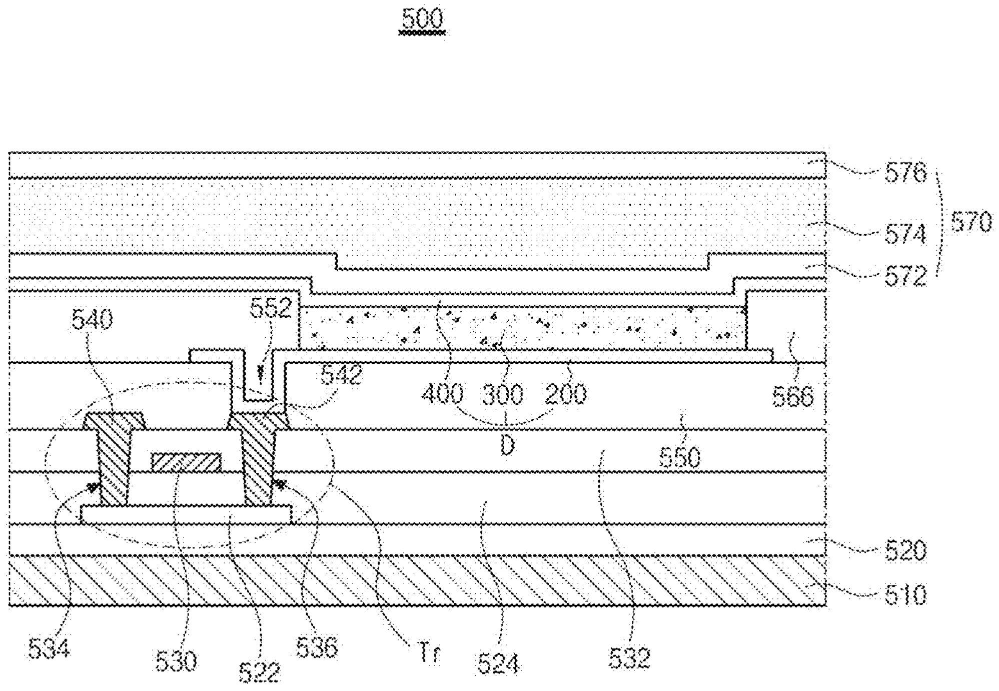
FIG. 5 is a schematic cross-sectional view of an organic light emitting display device according to an embodiment of the present disclosure.

FIG. 5 is a schematic cross-sectional view of an organic light emitting display device according to an embodiment of the present disclosure.

As shown in FIG. 5, the organic light emitting display device 500 includes a substrate 510, a TFT Tr and an OLED D (e.g., the organic light emitting device) connected to the TFT Tr. For example, the organic light emitting display device 500 may include a red pixel, a green pixel and a blue pixel, and the OLED D may be formed in each of the red, green and blue pixels. Namely, the OLEDs D emitting red light, green light and blue light may be provided in the red, green and blue pixels, respectively.

The substrate 510 may be a glass substrate or a flexible substrate. For example, the flexible substrate may be one of a polyimide (PI) substrate, polyethersulfone (PES), polyethylenenaphthalate (PEN), polyethylene terephthalate (PET) and polycarbonate (PC).

A buffer layer 520 is formed on the substrate, and the TFT Tr is formed on the buffer layer 520. The buffer layer 520 may be omitted.

A semiconductor layer 522 is formed on the buffer layer 520. The semiconductor layer 522 may include an oxide semiconductor material or polycrystalline silicon.

When the semiconductor layer 522 includes the oxide semiconductor material, a light-shielding pattern (not shown) may be formed under the semiconductor layer 522. The light to the semiconductor layer 522 is shielded or blocked by the light-shielding pattern such that thermal degradation of the semiconductor layer 522 can be prevented. On the other hand, when the semiconductor layer 522 includes polycrystalline silicon, impurities may be doped into both sides of the semiconductor layer 522.

A gate insulating layer 524 is formed on the semiconductor layer 522. The gate insulating layer 524 may be formed of an inorganic insulating material such as silicon oxide or silicon nitride.

A gate electrode 530, which is formed of a conductive material, e.g., metal, is formed on the gate insulating layer 524 to correspond to a center of the semiconductor layer 522.

In FIG. 5, the gate insulating layer 524 is formed on an entire surface of the substrate 510. Alternatively, the gate insulating layer 524 may be patterned to have the same shape as the gate electrode 530.

An interlayer insulating layer 532, which is formed of an insulating material, is formed on the gate electrode 530. The interlayer insulating layer 532 may be formed of an inorganic insulating material, e.g., silicon oxide or silicon nitride, or an organic insulating material, e.g., benzocyclobutene or photo-acryl.

The interlayer insulating layer 532 includes first and second contact holes 534 and 536 exposing both sides of the semiconductor layer 522. The first and second contact holes 534 and 536 are positioned at both sides of the gate electrode 530 to be spaced apart from the gate electrode 530.

The first and second contact holes 534 and 536 are formed through the gate insulating layer 524. Alternatively, when the gate insulating layer 524 is patterned to have the same shape as the gate electrode 530, the first and second contact holes 534 and 536 is formed only through the interlayer insulating layer 532.

A source electrode 540 and a drain electrode 542, which are formed of a conductive material, e.g., metal, are formed on the interlayer insulating layer 532.

The source electrode 540 and the drain electrode 542 are spaced apart from each other with respect to the gate electrode 530 and respectively contact both sides of the semiconductor layer 522 through the first and second contact holes 534 and 536.

The semiconductor layer 522, the gate electrode 530, the source electrode 540 and the drain electrode 542 constitute the TFT Tr. The TFT Tr serves as a driving element.

In the TFT Tr, the gate electrode 530, the source electrode 540, and the drain electrode 542 are positioned over the semiconductor layer 522. Namely, the TFT Tr has a coplanar structure.

Alternatively, in the TFT Tr, the gate electrode may be positioned under the semiconductor layer, and the source and drain electrodes may be positioned over the semiconductor layer such that the TFT Tr may have an inverted staggered structure. In this instance, the semiconductor layer may include amorphous silicon.

Although not shown, the gate line and the data line cross each other to define the pixel, and the switching TFT is formed to be connected to the gate and data lines. The switching TFT is connected to the TFT Tr as the driving element.

In addition, the power line, which may be formed to be parallel to and spaced apart from one of the gate and data lines, and the storage capacitor for maintaining the voltage of the gate electrode of the TFT Tr in one frame may be further formed.

A planarization layer 550, which includes a drain contact hole 552 exposing the drain electrode 542 of the TFT Tr, is formed to cover the TFT Tr.

A first electrode 200, which is connected to the drain electrode 542 of the TFT Tr through the drain contact hole 552, is separately formed in each pixel region and on the planarization layer 550. The first electrode 200 may be an anode and may be formed of a conductive material having a relatively high work function. For example, the first electrode 200 may be formed of a transparent conductive material, e.g., indium-tin-oxide (ITO) or indium-zinc-oxide (IZO).

When the organic light emitting display device 500 is operated in a bottom-emission type, the first electrode 200 may have a single-layered structure of a layer of the transparent conductive material. Alternatively, when the organic light emitting display device 500 is operated in a top-emission type, the first electrode 200 may further include a reflection layer. For example, the reflection layer may be formed of silver (Ag) or aluminum-palladium-copper (APC) alloy. In the top emission type organic light emitting display device 500, the first electrode 200 may have a triple-layered structure of ITO/Ag/ITO or ITO/APC/ITO.

A bank layer 566 is formed on the planarization layer 550 to cover an edge of the first electrode 200. Namely, the bank layer 566 is positioned at a boundary of the pixel and exposes a center of the first electrode 200 in the pixel region.

An organic emitting layer 300 is formed on the first electrode 200. The organic emitting layer 300 is separately formed in each of the red, green and blue pixel regions.

In the green pixel region, the organic emitting layer 300 may include a single emitting part including the EML.

For example, referring to FIG. 3, the organic emitting layer 300 may include the EML 303, the HIL 301 under the EML 303, the HTL 302 between the EML 303 and the HIL 301, the EBL 307 between the EML 303 and the HTL 302, the EIL 306 over the EML 303, the ETL 305 between the EML 303 and the EIL 306, and the HBL 304 between the EML 303 and the ETL 305.

Alternatively, the HBL 304 may be omitted. In this instance, one side of the EML 303 contacts the EBL 307, and the other side of the EML 303 contacts the ETL 305.

The EML 303 may include the compound of Formula 1 as the first compound 312, e.g., the N-type host, the compound of Formula 2 as the second compound 314, e.g., the P-type host, and the compound of Formula 12 as the third compound 316, e.g., the dopant or emitter.

In addition, the EBL 307 may include the compound of Formula 10 as the electron blocking material 322.

Alternatively, the organic emitting layer 300 may include a plurality of emitting parts each including the EML.

Figure 6:
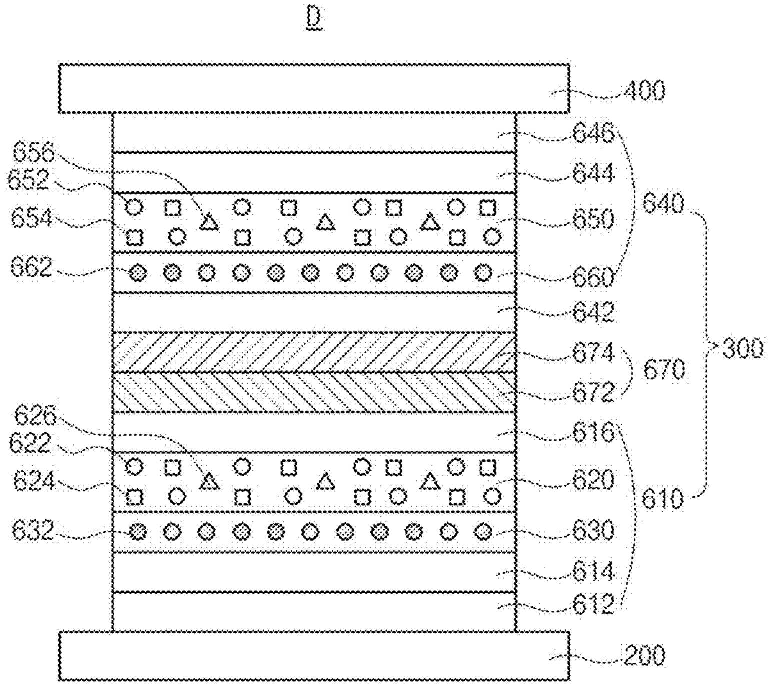
FIG. 6 is a schematic cross-sectional view of an organic light emitting device according to an embodiment of the present disclosure.

Referring to FIG. 6, which is a schematic cross-sectional view of an organic light emitting device according to an embodiment of the present disclosure, the organic emitting layer 300 includes a first emitting part 610 including a first green EML 620 and a second emitting part 640 including a second green EML 650. The organic emitting layer 300 may further include a charge generation layer (CGL) 670 between the first and second emitting parts 610 and 640.

The first emitting part 610 may further include a first EBL 630 between the first green EML 620 and the first electrode 200.

In addition, the first emitting part 610 may further include a first HTL 614 between the first EML 630 and the first electrode 200 and a first ETL 616 between the first green EML 620 and the second emitting part 640. For example, the first ETL 616 may be positioned between the first green EML 620 and the CGL 670.

Moreover, the first emitting part 610 may further include an HIL 612 between the first HTL 614 and the first electrode 200.

The second emitting part 640 may further include a second EBL 660 between the second green EML 650 and the first emitting part 610.

In addition, the second emitting part 640 may further include a second HTL 642 between the second EBL 660 and the first emitting part 610 and a second ETL 644 between the second green EML 650 and the second electrode 400.

Moreover, the second emitting part 640 may further include an EIL 646 between the second ETL 644 and the second electrode 400.

The CGL 670 is positioned between the first emitting part 610 and the second emitting part 640. Namely, the first and second emitting parts 610 and 640 are connected through the CGL 670. The CGL 670 may be a P-N junction CGL of an N-type CGL 672 and a P-type CGL 674.

The N-type CGL 672 is positioned between the first ETL 616 and the second HTL 642, and the P-type CGL 674 is positioned between the N-type CGL 672 and the second HTL 642.

The first green EML 620 includes a first compound 622, a second compound 624 and a third compound 626, and the second green EML 650 includes a fourth compound 652, a fifth compound 654 and a sixth compound 656.

In the first green EML 620, the first compound 622 may be an N-type host, e.g., a first host, the second compound 624 may be a P-type host, e.g., a second host, and the third compound 626 may be an emitter, e.g., a dopant. In the second green EML 650, the fourth compound 652 may be an N-type host, e.g., a first host, the fifth compound 654 may be a P-type host, e.g., a second host, and the sixth compound 656 may be an emitter, e.g., a dopant.

At least one of the first compound 622 and the fourth compound 652 is a compound of formula 1, and at least one of the second compound 624 and the fifth compound 654 is a compound of Formula 2. In addition, at least one of the third compound 626 and the sixth compound 656 is a compound of Formula 12.

For example, the first compound 622 and the fourth compound 652 are the compound of Formula 1 and are same or different. The second compound 624 and the fifth compound 654 are the compound of Formula 2 and are same or different. The third compound 626 and the sixth compound 656 are the compound of Formula 12 and are same or different.

Each of the first and fourth compounds 622 and 652 may be non-deuterated, partially deuterated or wholly deuterated. For example, a1 in Formula 1b may be a positive integer.

Each of the second and fifth compounds 624 and 654 may be non-deuterated, partially deuterated or wholly deuterated.

For example, in the green EML 620, the deuteration ratio of the first compound 622 may be greater than that of the second compound 624. In addition, in the green EML 650, the deuteration ratio of the fourth compound 652 may be greater than that of the fifth compound 654.

In the green EML 620, a weight % of the second compound 624 may be smaller than that of the first compound 622 and may be greater than that of the third compound 626. In addition, in the green EML 650, a weight % of the fifth compound 654 may be smaller than that of the fourth compound 652 and may be greater than that of the sixth compound 656.

The first EBL 630 includes a first electron blocking material 632, and the second EML 660 includes a second electron blocking material 662. Each of the first and second electron blocking materials 632 and 662 is a compound of Formula 10. For example, the first and second electron blocking materials 632 and 662 may be the compound of Formula 10 and may be same or different.

Each of the first and second electron blocking materials 632 and 662 may be partially deuterated or wholly deuterated. Namely, at least one of c1, c2 and c3 in Formula 10 may be a positive integer. For example, when only the fluorene moiety or the spiro-fluorene moiety may be deuterated, i.e., c1=positive integer and c2=c3=0, the lifespan and the driving performance of the device can be improved with minimizing the increase of the production cost by the deuterium atom.

Referring to FIG. 5, the second electrode 400 is formed over the substrate 510 including the organic emitting layer 300. The second electrode 400 may be positioned over an entire surface of a display area and may be formed of a conductive material having a relatively low work function to serve as a cathode. For example, the second electrode 400 may be formed of one of aluminum (Al), magnesium (Mg), silver (Ag) and their alloys, e.g., Al—Mg alloy (AlMg) or Ag—Mg alloy (MgAg). In the top emission type OLED, the second electrode 400 has a thin profile to be transparent (or semi-transparent).

The first electrode 200, the organic emitting layer 300 and the second electrode 400 constitute the OLED D.

An encapsulation film (or an encapsulation layer) 570 is formed on the second electrode 400 to prevent penetration of moisture into the OLED D. The encapsulation film 570 includes a first inorganic insulating layer 572, an organic insulating layer 574 and a second inorganic insulating layer 576 sequentially stacked, but it is not limited thereto. The encapsulation film 570 may be omitted.

The organic light emitting display device 500 may further include a polarization plate (not shown) for reducing an ambient light reflection. For example, the polarization plate may be a circular polarization plate. In the bottom-emission type organic light emitting display device 500, the polarization plate may be disposed under the substrate 510. In the top-emission type organic light emitting display device 500, the polarization plate may be disposed on or over the encapsulation film 570.

In addition, in the top-emission type organic light emitting display device 500, a cover window (not shown) may be attached to the encapsulation film 570 or the polarization plate. In this instance, the substrate 510 and the cover window have a flexible property such that a flexible organic light emitting display device may be provided.

Figure 7:
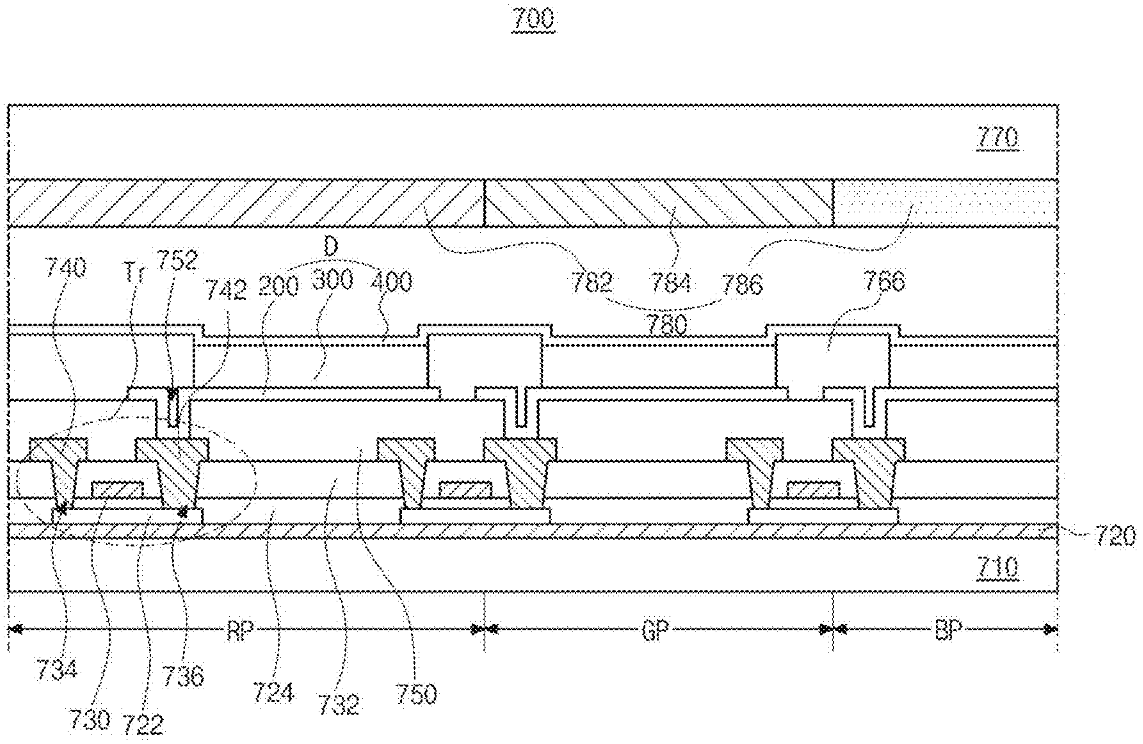
FIG. 7 is a schematic cross-sectional view of an organic light emitting display device according to an embodiment of the present disclosure.
Figure 8:
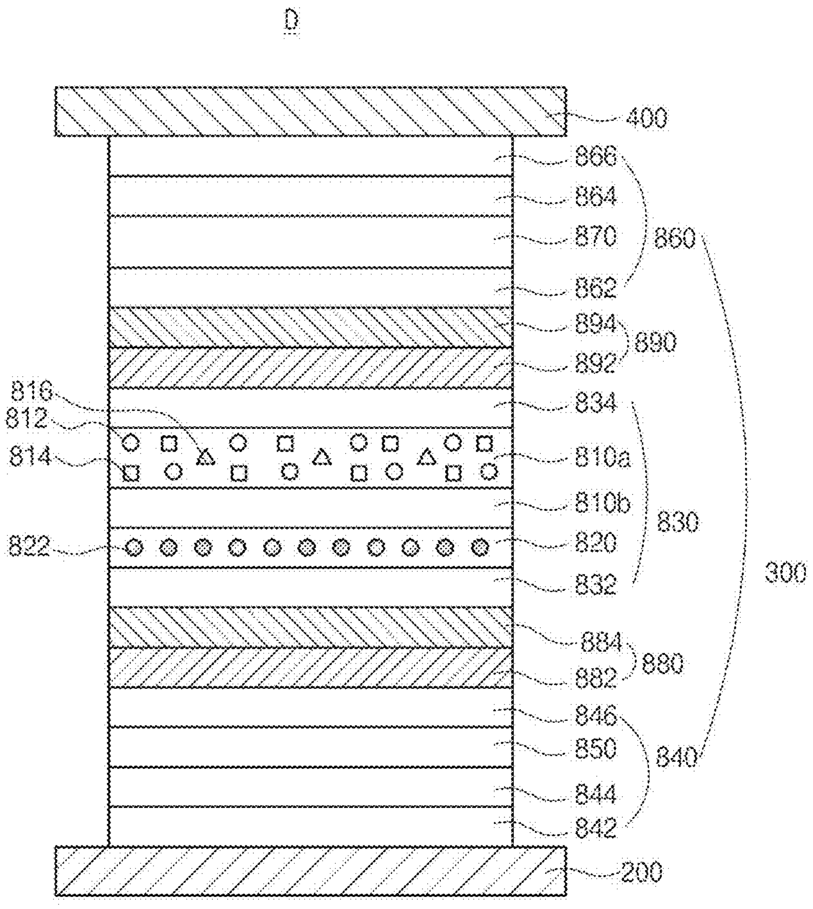
FIG. 8 is a schematic cross-sectional view of an organic light emitting display device according to an embodiment of the present disclosure.
Figure 9:
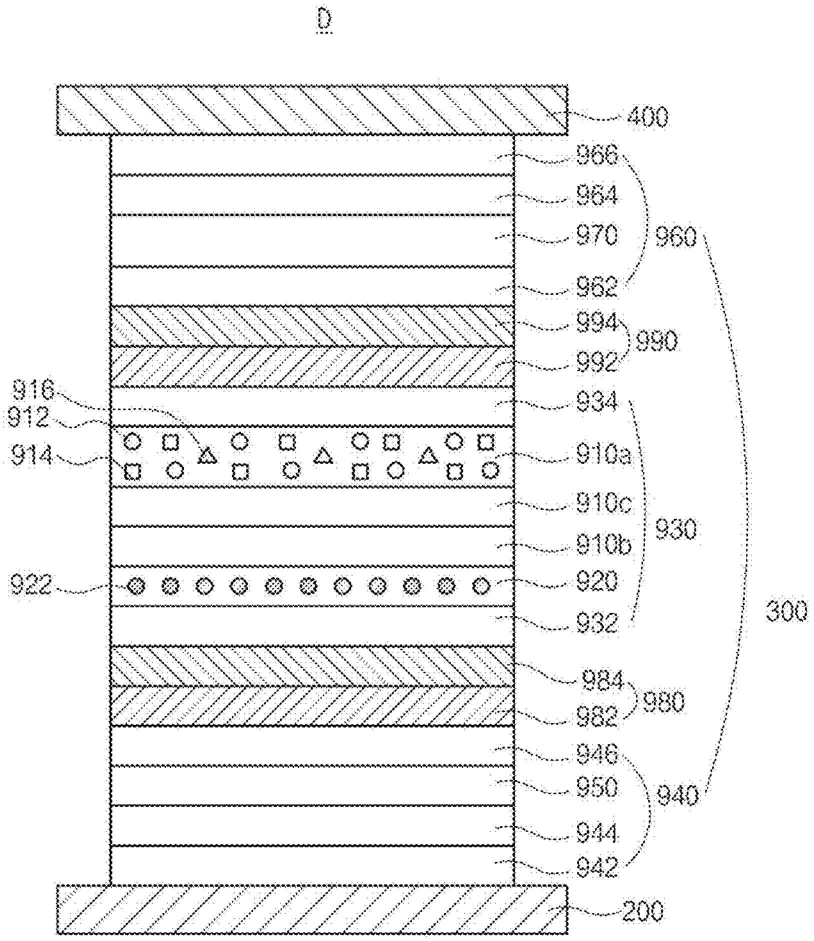
FIG. 9 is a schematic cross-sectional view of an organic light emitting device according to an embodiment of the present disclosure.

FIG. 7 is a schematic cross-sectional view of an organic light emitting display device according to an embodiment of the present disclosure. FIG. 8 is a schematic cross-sectional view of an organic light emitting display device according to an embodiment of the present disclosure, and FIG. 9 is a schematic cross-sectional view of an organic light emitting device according to an embodiment of the present disclosure.

As shown in FIG. 7, the organic light emitting display device 700 includes a first substrate 710, where a red pixel RP, a green pixel GP and a blue pixel BP are defined, a second substrate 770 facing the first substrate 710, an OLED D, which is positioned between the first and second substrates 710 and 770 and providing white emission, and a color filter layer 780 between the OLED D and the second substrate 770.

Each of the first and second substrates 710 and 770 may be a glass substrate or a flexible substrate. For example, the flexible substrate may be one of a polyimide (PI) substrate, polyethersulfone (PES), polyethylenenaphthalate (PEN), polyethylene terephthalate (PET) and polycarbonate (PC).

A buffer layer 720 is formed on the first substrate, and the TFT Tr corresponding to each of the red, green and blue pixels RP, GP and BP is formed on the buffer layer 720. The buffer layer 720 may be omitted.

A semiconductor layer 722 is formed on the buffer layer 720. The semiconductor layer 722 may include an oxide semiconductor material or polycrystalline silicon.

A gate insulating layer 724 is formed on the semiconductor layer 722. The gate insulating layer 724 may be formed of an inorganic insulating material such as silicon oxide or silicon nitride.

A gate electrode 730, which is formed of a conductive material, e.g., metal, is formed on the gate insulating layer 724 to correspond to a center of the semiconductor layer 722.

An interlayer insulating layer 732, which is formed of an insulating material, is formed on the gate electrode 730. The interlayer insulating layer 732 may be formed of an inorganic insulating material, e.g., silicon oxide or silicon nitride, or an organic insulating material, e.g., benzocyclobutene or photo-acryl.

The interlayer insulating layer 732 includes first and second contact holes 734 and 736 exposing both sides of the semiconductor layer 722. The first and second contact holes 734 and 736 are positioned at both sides of the gate electrode 730 to be spaced apart from the gate electrode 730.

A source electrode 740 and a drain electrode 742, which are formed of a conductive material, e.g., metal, are formed on the interlayer insulating layer 732.

The source electrode 740 and the drain electrode 742 are spaced apart from each other with respect to the gate electrode 730 and respectively contact both sides of the semiconductor layer 722 through the first and second contact holes 734 and 736.

The semiconductor layer 722, the gate electrode 730, the source electrode 740 and the drain electrode 742 constitute the TFT Tr. The TFT Tr serves as a driving element.

Although not shown, the gate line and the data line cross each other to define the pixel, and the switching TFT is formed to be connected to the gate and data lines. The switching TFT is connected to the TFT Tr as the driving element.

In addition, the power line, which may be formed to be parallel to and spaced apart from one of the gate and data lines, and the storage capacitor for maintaining the voltage of the gate electrode of the TFT Tr in one frame may be further formed.

A planarization layer 750, which includes a drain contact hole 752 exposing the drain electrode 742 of the TFT Tr, is formed to cover the TFT Tr.

A first electrode 200, which is connected to the drain electrode 742 of the TFT Tr through the drain contact hole 752, is separately formed in each pixel and on the planarization layer 750. The first electrode 200 may be an anode and may be formed of a conductive material, e.g., a transparent conductive oxide (TCO), having a relatively high work function. The first electrode 200 may further include a reflection electrode or a reflection layer. For example, the reflection electrode or the reflection layer may be formed of silver (Ag) or aluminum-palladium-copper (APC) alloy. In the top emission type organic light emitting display device 700, the first electrode 200 may have a triple-layered structure of ITO/Ag/ITO or ITO/APC/ITO.

A bank layer 766 is formed on the planarization layer 750 to cover an edge of the first electrode 760. Namely, the bank layer 766 is positioned at a boundary of the pixel and exposes a center of the first electrode 760 in the pixel. Since the OLED D emits the white light in the red, green and blue pixels RP, GP and BP, the organic emitting layer 300 may be formed as a common layer in the red, green and blue pixels RP, GP and BP without separation. The bank layer 766 may be formed to prevent a current leakage at an edge of the first electrode 760 and may be omitted.

An organic emitting layer 762 is formed on the first electrode 200.

Referring to FIG. 8, the organic emitting layer 300 includes a first emitting part 830 including a green EML 810*a*, a second emitting part 840 including a first blue EML 850 and a third emitting part 860 including a second blue EML 870. In addition, the organic emitting layer 300 may further include a first CGL 880 between the first and second emitting parts 830 and 840 and a second CGL 890 between the first and third emitting parts 830 and 860. In addition, the first emitting part 830 may further include a red EML 810*b*.

The second emitting part 840 is positioned between the first electrode 200 and the first emitting part 830, and the third emitting part 860 is positioned between the first emitting part 830 and the second electrode 400. In addition, the second emitting part 840 is positioned between the first electrode 200 and the first CGL 880, and the third emitting part 860 is positioned between the second CGL 890 and the second electrode 400. Namely, the second emitting part 840, the first CGL 880, the first emitting part 830, the second CGL 890 and the third emitting part 860 are sequentially stacked on the first electrode 200.

In the first emitting part 830, the red EML 810*a* may be positioned under the green EML 810*a*.

The first emitting part 830 may further include an EBL 820 under the red EML 810*b*.

In addition, the first emitting part 830 may further include a first ETL 834 over the green EML 810*a* and a first HTL 832 under the EBL 820.

For example, in the first emitting part 830, the EBL 820 may be positioned between the red EML 810*b* and the first HTL 832, and the green EML 810*a* may be positioned between the red EML 810*b* and the first ETL 834.

The second emitting part 840 may further include at least one of a second HTL 844 under the first blue EML 850 and a second ETL 846 over the first blue EML 850. In addition, the second emitting part 840 may further include an HIL 842 between the first electrode 200 and the second HTL 844.

Moreover, the second emitting part 840 may further include at least one of an EBL (not shown) between the second HTL 844 and the first blue EML 850 and an HBL (not shown) between the second ETL 846 and the first blue EML 850.

The third emitting part 860 may further include at least one of a third HTL 862 under the second blue EML 870 and a third ETL 864 over the second blue EML 870. In addition, the third emitting part 860 may further include an EIL 866 between the second electrode 400 and the third ETL 864.

Moreover, the third emitting part 860 may further include at least one of an EBL (not shown) between the third HTL 862 and the second blue EML 870 and an HBL (not shown) between the third ETL 864 and the second blue EML 870.

The green EML 810*a* includes a first compound 812, a second compound 814 and a third compound 816. The first compound 812 may be an N-type host, e.g., a first host, the second compound 814 may be a P-type host, e.g., a second host, and the third compound 816 may be an emitter, e.g., a dopant.

The first compound 812 is a compound of formula 1, and the second compound 814 is a compound of Formula 2. In addition, the third compound 816 is a compound of Formula 12.

The first compound 812 may be non-deuterated, partially deuterated or wholly deuterated. For example, a1 in Formula 1b may be a positive integer.

The second compound 814 may be non-deuterated, partially deuterated or wholly deuterated.

For example, in the green EML 810*a*, the deuteration ratio of the first compound 812 may be greater than that of the second compound 814.

In the green EML 810, a weight % of the second compound 814 may be smaller than that of the first compound 812 and may be greater than that of the third compound 816.

In the first emitting part 830, the EBL 820 includes an electron blocking material 822. The electron blocking material 822 is a compound of Formula 10.

The electron blocking material 822 may be partially deuterated or wholly deuterated. Namely, at least one of c1, c2 and c3 in Formula 10 may be a positive integer. For example, when only the fluorene moiety or the spiro-fluorene moiety may be deuterated, i.e., c1=positive integer and c2=c3=0, the lifespan and the driving performance of the device can be improved with minimizing the increase of the production cost by the deuterium atom.

The red EML 810*b* may include a red host and a red dopant. The red dopant may include at least one of a red phosphorescent compound, a red fluorescent compound and a red delayed fluorescent compound. In the red EML 810*b*, the red host may have a weight % being greater than the red dopant. In the red EML 810*b*, the red dopant may be doped with a weight % of 1 to 10, preferably 1 to 5.

For example, the red host may be selected from the group consisting of 9,9'-diphenyl-9H,9'H-3,3'-bicarbazole (BCzPh), CBP, 1,3,5-tris(carbazole-9-yl)benzene (TCP), TCTA, 4,4'-bis(carbazole-9-yl)-2,2'-dimethylbipheyl (CDBP), 2,7-bis(carbazole-9-yl)-9,9-dimethylfluorene (DMFL-CBP), 2,2',7,7'-tetrakis(carbazole-9-yl)-9,9-spioro-fluorene (Spiro-CBP), DPEPO, 4'-(9H-carbazol-9-yl)biphenyl-3,5-dicarbonitrile (PCzB-2CN), 3'-(9H-carbazol-9-yl)biphenyl-3,5-dicarbonitrile (mCzB-2CN), 3,6-bis(carbazole-9-yl)-9-(2-ethyl-hexyl)-9H-carbazole (TCz1), bis(2-hydroxylphenyl)-pyridine)beryllium (Bepp2), bis(10-hydroxylbenzo[h]quinolinato)beryllium (Bebq2), and 1,3,5-tris(1-pyrenyl)benzene (TPB3), but it is not limited thereto.

In addition, the red dopant may be selected from the group consisting of bis(2-(4,6-dimethyl)phenylquinoline)](2,2,6,6-tetramethylheptane-3,5-dionate)iridium(III), bis[2-(4-n-hexylphenyl)quinoline](acetylacetonate)iridium(III) (Hex-Ir(phq)$_2$(acac)), tris[2-(4-n-hexylphenyl)quinoline]iridium(III) (Hex-Ir(phq)$_3$), tris[2-phenyl-4-methylquinoline]iridium(III) (Ir(Mphq)$_3$), bis(2-phenylquinoline)(2,2,6,6-tetramethylheptene-3,5-dionate)iridium(III) (Ir(dpm)PQ$_2$), bis(phenylisoquinoline)(2,2,6,6-tetramethylheptene-3,5-dionate)iridium(III) (Ir(dpm)(piq)$_2$), bis[(4-n-hexylphenyl)isoquinoline](acetylacetonate)iridium(III) (Hex-Ir(piq)$_2$(acac)), tris[2-(4-n-hexylphenyl)quinoline]iridium(III) (Hex-Ir(piq)$_3$), tris(2-(3-methylphenyl)-7-methyl-quinolato)iridium (Ir(dmpq)$_3$), bis[2-(2-methylphenyl)-7-methyl-quinoline](acetylacetonate)iridium(III) (Ir(dmpq)$_2$(acac)), and bis[2-(3,5-dimethylphenyl)-4-methyl-quinoline](acetylacetonate)iridium(III) (Ir(mphmq)$_2$(acac)), but it is not limited thereto.

The first blue EML 850 in the second emitting part 840 includes a first blue host and a first blue dopant, and the second blue EML 870 in the third emitting part 860 includes a second blue host and a second blue dopant.

Each of the first and second blue dopant may include at least one of a blue phosphorescent compound, a blue fluorescent compound and a blue delayed fluorescent compound. In the first blue EML 850, the first blue host may have a weight % being greater than the first blue dopant. In the second blue EML 870, the second blue host may have a weight % being greater than the second blue dopant. In each of the first and second blue EMLs 850 and 870, each of the first and second blue dopants may be doped with a weight % of 1 to 10, preferably 1 to 5.

For example, each of the first and second blue hosts may be independently selected from the group consisting of mCP, 9-(3-(9H-carbazol-9-yl)phenyl)-9H-carbazole-3-carbonitrile (mCP-CN), mCBP, CBP—CN, 9-(3-(9H-carbazol-9-yl)phenyl)-3-(diphenylphosphoryl)-9H-carbazole (mCPPO1) 3,5-di(9H-carbazol-9-yl)biphenyl (Ph-mCP), TSPO1, 9-(3'-(9H-carbazol-9-yl)-[1,1'-biphenyl]-3-yl)-9H-pyrido[2,3-b]indole (CzBPCb), bis(2-methylphenyl)diphenylsilane (UGH-1), 1,4-bis(triphenylsilyl)benzene (UGH-2), 1,3-bis(triphenylsilyl)benzene (UGH-3), 9,9-spiorobifluoren-2-yl-diphenyl-phosphine oxide (SPPO1), and 9,9'-(5-(triphenylsilyl)-1,3-phenylene)bis(9H-carbazole) (SimCP), but it is not limited thereto.

Each of the first and second blue dopants may be independently selected from the group consisting of perylene, 4,4'-bis[4-(di-p-tolylamino)styryl]biphenyl (DPAVBi), 4-(di-p-tolylamino)-4-4'-[(di-p-tolylamino)styryl]stilbene (DPAVB), 4,4'-bis[4-(diphenylamino)styryl]biphenyl (BDAVBi), 2,7-bis(4-diphenylamino)styryl)-9,9-spiorfluorene (spiro-DPVBi), [1,4-bis[2-[4-[N,N-di(p-tolyl)amino] phenyl]vinyl] benzene (DSB), 1-4-di-[4-(N,N-diphenyl) amino]styryl-benzene (DSA), 2,5,8,11-tetra-tetr-butylperylene (TBPe), bis(2-hydroxylphenyl)-pyridine) beryllium (Bepp2), 9-(9-Phenylcarbazole-3-yl)-10-(naphthalene-1-yl)anthracene (PCAN), mer-tris(1-phenyl-3-methylimidazolin-2-ylidene-C,C(2)'iridium(III) (mer-Ir (pmi)3), fac-Tris(1,3-diphenyl-benzimidazolin-2-ylidene-C, C(2)'iridium(III) (fac-Ir(dpbic)3), bis(3,4,5-trifluoro-2-(2-pyridyl)phenyl-(2-carboxypyridyl)iridium(III) (Ir(tfpd) 2pic), tris(2-(4,6-difluorophenyl)pyridine))iridium(III) (Ir $(Fppy)_3$), and bis[2-(4,6-difluorophenyl)pyridinato-C2,N] (picolinato)iridium(III) (FIrpic), but it is not limited thereto.

For example, each of the first and second blue EMLs 850 and 870 may include an anthracene derivative as a host and a boron derivative as a dopant.

The first CGL 880 is positioned between the first and second emitting parts 830 and 840, and the second CGL 890 is positioned between the first and third emitting parts 830 and 860. Namely, the first and second emitting parts 830 and 840 is connected to each other by the first CGL 880, and the first and third emitting parts 830 and 860 is connected to each other by the second CGL 890. The first CGL 880 may be a P-N junction CGL of an N-type CGL 882 and a P-type CGL 884, and the second CGL 890 may be a P-N junction CGL of an N-type CGL 892 and a P-type CGL 894.

The N-type CGL 882 of the first CGL 880 is positioned between the first HTL 832 and the second ETL 846, and the P-type CGL 884 of the first CGL 880 is positioned between the N-type CGL 882 and the first HTL 832.

The N-type CGL 892 of the second CGL 890 is positioned between the first ETL 834 and the third HTL 862, and the P-type CGL 894 of the second CGL 890 is positioned between the N-type CGL 892 and the third HTL 862.

As mentioned above, the OLED D of the present disclosure includes the first emitting part 830 including the green EML 810*a* and the red EML 810*b*, the second emitting part 840 including the first blue EML 850 and the third emitting part 860 including the second blue EML 870 and provides the white emission.

The green EML 810*a* includes the compound of Formula 1 as a first compound 812 and the compound of Formula 2 as a second compound 814. As a result, in the OLED D, the driving voltage is reduced, and the emitting efficiency and the lifespan are improved.

In addition, the first emitting part 830, which includes the green EML 810*a*, includes the EBL 820, and the EBL 820 includes the compound of Formula 10 as an electron blocking material 822. As a result, in the OLED D, the driving voltage is further reduced, and the emitting efficiency and the lifespan are further improved.

Referring to FIG. 9, the organic emitting layer 300 includes a first emitting part 930 including a green EML 910*a*, a red EML 910*b* and a yellow-green EML 910*c*, a second emitting part 940 including a first blue EML 950 and a third emitting part 960 including a second blue EML 970. In addition, the organic emitting layer 300 may further include a first CGL 980 between the first and second emitting parts 930 and 940 and a second CGL 990 between the first and third emitting parts 930 and 960.

The second emitting part 940 is positioned between the first electrode 200 and the first emitting part 930, and the third emitting part 960 is positioned between the first emitting part 930 and the second electrode 400. In addition, the second emitting part 940 is positioned between the first electrode 200 and the first CGL 980, and the third emitting part 960 is positioned between the second CGL 990 and the second electrode 400. Namely, the second emitting part 840, the first CGL 980, the first emitting part 930, the second CGL 990 and the third emitting part 960 are sequentially stacked on the first electrode 200.

In the first emitting part 930, the red EML 910*a* may be positioned under the yellow-green EML 910*c*, and the green EML 910*a* may be positioned on the yellow-green EML 910*c*. Namely, an EML having a double-layered structure of the green and red EMLs 810*a* and 810*b* is included in the first emitting part 830 of the OLED D in FIG. 8, while an EML having a triple-layered structure of the green, red and yellow-green EMLs 910*a*, 910*b* and 910*c* is included in the first emitting part 930 of the OLED D in FIG. 9.

The first emitting part 930 may further include an EBL 920 under the red EML 910*b*.

In addition, the first emitting part 930 may further include a first ETL 934 over the green EML 910*a* and a first HTL 932 under the EBL 920.

For example, in the first emitting part 930, the red EML 910*b* may be positioned between the EBL 920 and the yellow-green EML 910*c*, and the green EML 910*a* may be positioned between the yellow-green EML 910*c* and the first ETL 934.

The second emitting part 940 may further include at least one of a second HTL 944 under the first blue EML 950 and a second ETL 946 over the first blue EML 950. In addition, the second emitting part 940 may further include an HIL 942 between the first electrode 200 and the second HTL 944.

Moreover, the second emitting part 940 may further include at least one of an EBL (not shown) between the second HTL 944 and the first blue EML 950 and an HBL (not shown) between the second ETL 946 and the first blue EML 950.

The third emitting part 960 may further include at least one of a third HTL 962 under the second blue EML 970 and a third ETL 964 over the second blue EML 970. In addition, the third emitting part 960 may further include an EIL 966 between the second electrode 400 and the third ETL 964.

Moreover, the third emitting part 960 may further include at least one of an EBL (not shown) between the third HTL 962 and the second blue EML 970 and an HBL (not shown) between the third ETL 964 and the second blue EML 970.

The green EML 910*a* includes a first compound 912, a second compound 914 and a third compound 916. The first compound 912 may be an N-type host, e.g., a first host, the second compound 914 may be a P-type host, e.g., a second host, and the third compound 916 may be an emitter, e.g., a dopant.

The first compound 912 is a compound of formula 1, and the second compound 914 is a compound of Formula 2. In addition, the third compound 916 is a compound of Formula 12.

The first compound 912 may be non-deuterated, partially deuterated or wholly deuterated. For example, a1 in Formula 1b may be a positive integer.

The second compound 914 may be non-deuterated, partially deuterated or wholly deuterated.

For example, in the green EML 910*a*, the deuteration ratio of the first compound 912 may be greater than that of the second compound 914.

In the green EML 910, a weight % of the second compound 914 may be smaller than that of the first compound 912 and may be greater than that of the third compound 916.

In the first emitting part 930, the EBL 920 includes an electron blocking material 922. The electron blocking material 922 is a compound of Formula 10.

The electron blocking material 922 may be partially deuterated or wholly deuterated. Namely, at least one of c1, c2 and c3 in Formula 10 may be a positive integer. For example, when only the fluorene moiety or the spiro-fluorene moiety may be deuterated, i.e., c1=positive integer and c2=c3=0, the lifespan and the driving performance of the device can be improved with minimizing the increase of the production cost by the deuterium atom.

The red EML 910*b* may include a red host and a red dopant. The red dopant may include at least one of a red phosphorescent compound, a red fluorescent compound and a red delayed fluorescent compound. In the red EML 910*b*, the red host may have a weight % being greater than the red dopant. In the red EML 910*b*, the red dopant may be doped with a weight % of 1 to 10, preferably 1 to 5.

The yellow-green EML 910*c* may include a yellow-green host and a yellow-green dopant. The yellow-green dopant may include at least one of a yellow-green phosphorescent compound, a yellow-green fluorescent compound and a yellow-green delayed fluorescent compound. In the yellow-green EML 910*c*, the yellow-green host may have a weight % being greater than the yellow-green dopant. In the yellow-green EML 910*c*, the yellow-green dopant may be doped with a weight % of 1 to 10, preferably 1 to 5.

The first blue EML 950 in the second emitting part 940 includes a first blue host and a first blue dopant, and the second blue EML 970 in the third emitting part 960 includes a second blue host and a second blue dopant.

Each of the first and second blue dopant may include at least one of a blue phosphorescent compound, a blue fluorescent compound and a blue delayed fluorescent compound. In the first blue EML 950, the first blue host may have a weight % being greater than the first blue dopant. In the second blue EML 970, the second blue host may have a weight % being greater than the second blue dopant. In each of the first and second blue EMLs 950 and 970, each of the first and second blue dopants may be doped with a weight % of 1 to 10, preferably 1 to 5.

For example, each of the first and second blue EMLs 950 and 970 may include an anthracene derivative as a host and a boron derivative as a dopant.

The first CGL 980 is positioned between the first and second emitting parts 930 and 940, and the second CGL 990 is positioned between the first and third emitting parts 930 and 960. Namely, the first and second emitting parts 930 and 940 is connected to each other by the first CGL 980, and the first and third emitting parts 930 and 960 is connected to each other by the second CGL 990. The first CGL 980 may be a P-N junction CGL of an N-type CGL 982 and a P-type CGL 984, and the second CGL 990 may be a P-N junction CGL of an N-type CGL 992 and a P-type CGL 994.

The N-type CGL 982 of the first CGL 980 is positioned between the first HTL 932 and the second ETL 946, and the P-type CGL 984 of the first CGL 980 is positioned between the N-type CGL 982 and the first HTL 932.

The N-type CGL 992 of the second CGL 990 is positioned between the first ETL 934 and the third HTL 962, and the P-type CGL 994 of the second CGL 990 is positioned between the N-type CGL 992 and the third HTL 962.

As mentioned above, the OLED D of the present disclosure includes the first emitting part 930 including the green EML 910*a*, the red EML 910*b* and the yellow-green EML 910*c*, the second emitting part 940 including the first blue EML 950 and the third emitting part 960 including the second blue EML 970 and provides the white emission.

The green EML 910*a* includes the compound of Formula 1 as a first compound 912 and the compound of Formula 2 as a second compound 914. As a result, in the OLED D, the driving voltage is reduced, and the emitting efficiency and the lifespan are improved.

In addition, the first emitting part 930, which includes the green EML 910*a*, includes the EBL 920, and the EBL 920 includes the compound of Formula 10 as an electron blocking material 922. As a result, in the OLED D, the driving voltage is further reduced, and the emitting efficiency and the lifespan are further improved.

Referring to FIG. 7 again, a second electrode 400 is formed over the substrate 410 where the organic emitting layer 300 is formed.

In the organic light emitting display device 700, since the light emitted from the organic emitting layer 300 is incident to the color filter layer 780 through the second electrode 400, the second electrode 400 has a thin profile for transmitting the light.

The first electrode 200, the organic emitting layer 300 and the second electrode 400 constitute the OLED D.

The color filter layer 780 is positioned over the OLED D and includes a red color filter 782, a green color filter 784 and a blue color filter 786 respectively corresponding to the red, green and blue pixels RP, GP and BP. The red color filter 782 may include at least one of red dye and red pigment, the green color filter 784 may include at least one of green dye and green pigment, and the blue color filter 786 may include at least one of blue dye and blue pigment.

Although not shown, the color filter layer 480 may be attached to the OLED D by using an adhesive layer. Alternatively, the color filter layer 780 may be formed directly on the OLED D.

An encapsulation film (not shown) may be formed to prevent penetration of moisture into the OLED D. For example, the encapsulation film may include a first inorganic insulating layer, an organic insulating layer and a second inorganic insulating layer sequentially stacked, but it is not limited thereto. The encapsulation film may be omitted.

A polarization plate (not shown) for reducing an ambient light reflection may be disposed over the top-emission type OLED D. For example, the polarization plate may be a circular polarization plate.

In the OLED of FIG. 7, the first and second electrodes 200 and 400 are a reflection electrode and a transparent (or semi-transparent) electrode, respectively, and the color filter layer 780 is disposed over the OLED D. Alternatively, when the first and second electrodes 200 and 400 are a transparent (or semi-transparent) electrode and a reflection electrode, respectively, the color filter layer 780 may be disposed between the OLED D and the first substrate 710.

A color conversion layer (not shown) may be formed between the OLED D and the color filter layer 780. The color conversion layer may include a red color conversion layer, a green color conversion layer and a blue color conversion layer respectively corresponding to the red, green and blue pixels RP, GP and BP. The white light from the OLED D is converted into the red light, the green light and the blue light by the red, green and blue color conversion layer, respectively. For example, the color conversion layer may include a quantum dot. Accordingly, the color purity of the organic light emitting display device 700 may be further improved.

The color conversion layer may be included instead of the color filter layer 780.

As described above, in the organic light emitting display device 700, the OLED D in the red, green and blue pixels RP, GP and BP emits the white light, and the white light from the organic light emitting diode D passes through the red color filter 782, the green color filter 784 and the blue color filter 786. As a result, the red light, the green light and the blue light are provided from the red pixel RP, the green pixel GP and the blue pixel BP, respectively.

In FIG. 7, the OLED D emitting the white light is used for a display device. Alternatively, the OLED D may be formed on an entire surface of a substrate without at least one of the driving element and the color filter layer to be used for a lightening device. The display device and the lightening device each including the OLED D of the present disclosure may be referred to as an organic light emitting device.

[OLED]

On an anode (ITO), an HIL (the compound of Formula 14, 50 Å), an HTL (the compound of Formula 15, 1000 Å), an EBL (EML, 150 Å), a green EML (a first host (NH), a second host (PH) and a dopant (the compound GD1 of Formula 13, 7 wt %), 300 Å), an ETL (the compound of Formula 16, 300 Å), an EIL (LiF, 13.5 Å) and a cathode (Al, 1000 Å) are sequentially stacked to manufacture the OLED.

[Formula 14]

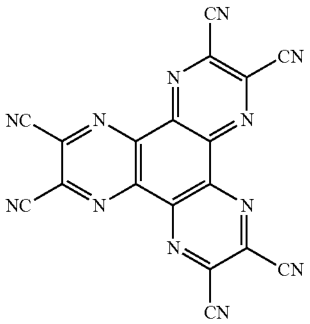

[Formula 15]

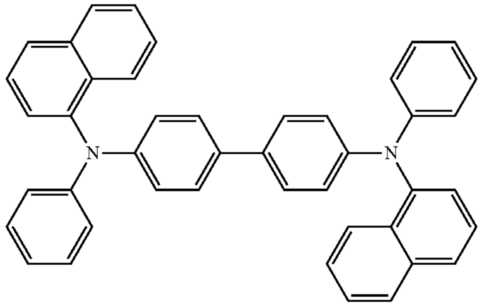

-continued

[Formula 16]

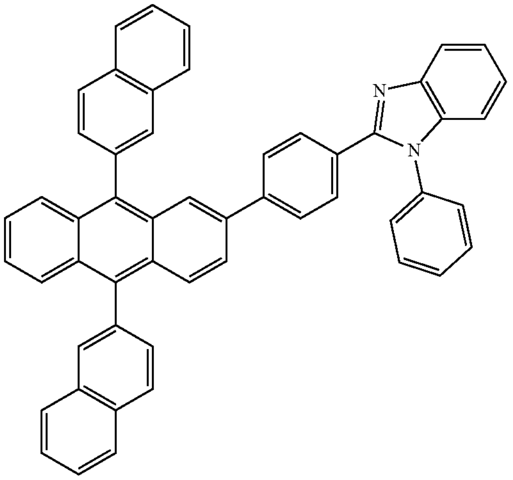

The green EML is formed by using a material combination of the first compound in Formula 1c as the first host "NH", the second compound in Formula 2a as the second host "PH", and the EBL is formed by using the compound in Formula 11 and the compound in Formula 17 as the electron blocking material.

EBL_Ref1

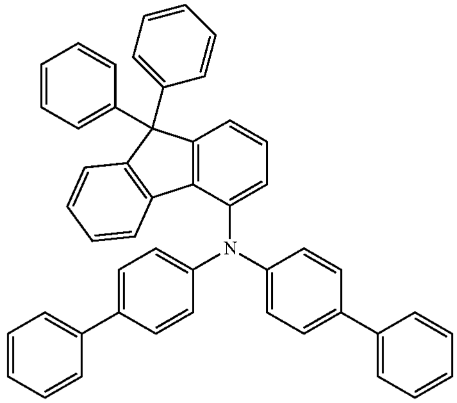

EBL_Ref7

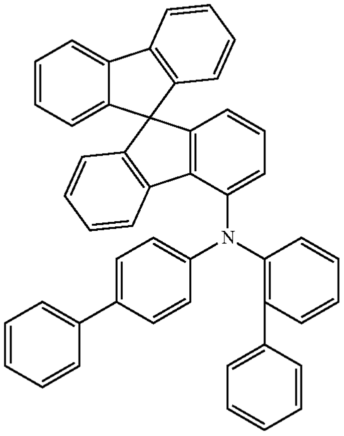

-continued

EBL_Ref9

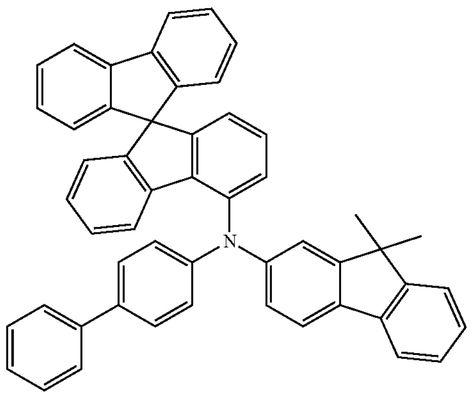

The deuteration ratio of the electron blocking material, the first compound "NH" and the second compound "PH" are listed in Table 15.

TABLE 15

| Compound | Deuteration ratio | Compound | Deuteration ratio |
|---|---|---|---|
| EBL_Ref1 | 0% | 2-78 | 0% |
| EBL1-1 | 49% | 2-2 | 56% |
| EBL1-2 | 51% | 2-26 | 44% |
| EBL1-3 | 100% | 2-50 | 100% |
| EBL_Ref7 | 0% | 1113 | 0% |
| EBL7-1 | 49% | 206 | 43% |
| EBL7-2 | 51% | 274 | 21% |
| EBL7-3 | 100% | 330 | 36% |
| EBL_Ref9 | 0% | 841 | 64% |
| EBL9-1 | 49% | 973 | 57% |
| EBL9-2 | 51% | 686 | 100% |
| EBL9-3 | 100% | | |

The emission properties, i.e., the driving voltage (V), the emitting efficiency (Efficiency) and the lifespan (L), of the OLED are measured and listed in Table 16.

TABLE 16

| | Host | | Weight ratio | | DATA | | |
|---|---|---|---|---|---|---|---|
| EBL | PH | NH | PH | NH | V | Efficiency | L |
| Ref1 | 2-78 | 1113 | 1 | 1 | 3.90 | 121 | 276 |
| Ref1 | 2-78 | 1113 | 2 | 1 | 3.80 | 121 | 270 |
| Ref1 | 2-78 | 1113 | 3 | 1 | 3.70 | 120 | 265 |
| Ref1 | 2-78 | 206 | 1 | 1 | 3.89 | 120 | 360 |
| Ref1 | 2-78 | 206 | 2 | 1 | 3.79 | 120 | 355 |
| Ref1 | 2-78 | 206 | 3 | 1 | 3.69 | 120 | 351 |
| Ref1 | 2-78 | 274 | 1 | 1 | 3.90 | 121 | 290 |
| Ref1 | 2-78 | 274 | 2 | 1 | 3.80 | 120 | 288 |
| Ref1 | 2-78 | 274 | 3 | 1 | 3.70 | 120 | 287 |
| Ref1 | 2-78 | 330 | 1 | 1 | 3.90 | 121 | 305 |
| Ref1 | 2-78 | 330 | 2 | 1 | 3.80 | 120 | 304 |
| Ref1 | 2-78 | 330 | 3 | 1 | 3.70 | 120 | 302 |
| Ref1 | 2-78 | 841 | 1 | 1 | 3.88 | 121 | 390 |
| Ref1 | 2-78 | 841 | 2 | 1 | 3.78 | 120 | 383 |
| Ref1 | 2-78 | 841 | 3 | 1 | 3.68 | 120 | 380 |
| Ref1 | 2-78 | 973 | 1 | 1 | 3.90 | 121 | 311 |
| Ref1 | 2-78 | 973 | 2 | 1 | 3.80 | 120 | 309 |
| Ref1 | 2-78 | 973 | 3 | 1 | 3.70 | 120 | 305 |
| Ref1 | 2-78 | 686 | 1 | 1 | 3.88 | 121 | 415 |
| Ref1 | 2-78 | 686 | 2 | 1 | 3.78 | 120 | 412 |
| Ref1 | 2-78 | 686 | 3 | 1 | 3.68 | 120 | 410 |
| Ref1 | 2-2 | 1113 | 1 | 1 | 3.90 | 121 | 282 |
| Ref1 | 2-2 | 1113 | 2 | 1 | 3.80 | 120 | 280 |
| Ref1 | 2-2 | 1113 | 3 | 1 | 3.70 | 120 | 276 |

TABLE 16-continued

| | Host | | Weight ratio | | DATA | | |
|---|---|---|---|---|---|---|---|
| EBL | PH | NH | PH | NH | V | Efficiency | L |
| Ref1 | 2-2 | 206 | 1 | 1 | 3.89 | 121 | 370 |
| Ref1 | 2-2 | 206 | 2 | 1 | 3.79 | 121 | 365 |
| Ref1 | 2-2 | 206 | 3 | 1 | 3.69 | 120 | 359 |
| Ref1 | 2-2 | 274 | 1 | 1 | 3.90 | 120 | 290 |
| Ref1 | 2-2 | 274 | 2 | 1 | 3.80 | 120 | 288 |
| Ref1 | 2-2 | 274 | 3 | 1 | 3.70 | 120 | 285 |
| Ref1 | 2-2 | 330 | 1 | 1 | 3.90 | 120 | 305 |
| Ref1 | 2-2 | 330 | 2 | 1 | 3.80 | 120 | 300 |
| Ref1 | 2-2 | 330 | 3 | 1 | 3.70 | 119 | 297 |
| Ref1 | 2-2 | 841 | 1 | 1 | 3.88 | 120 | 400 |
| Ref1 | 2-2 | 841 | 2 | 1 | 3.78 | 120 | 390 |
| Ref1 | 2-2 | 841 | 3 | 1 | 3.68 | 120 | 380 |
| Ref1 | 2-2 | 973 | 1 | 1 | 3.90 | 120 | 310 |
| Ref1 | 2-2 | 973 | 2 | 1 | 3.80 | 120 | 305 |
| Ref1 | 2-2 | 973 | 3 | 1 | 3.70 | 119 | 300 |
| Ref1 | 2-2 | 686 | 1 | 1 | 3.88 | 120 | 425 |
| Ref1 | 2-2 | 686 | 2 | 1 | 3.78 | 120 | 420 |
| Ref1 | 2-2 | 686 | 3 | 1 | 3.68 | 120 | 415 |
| Ref1 | 2-26 | 1113 | 1 | 1 | 3.88 | 120 | 305 |
| Ref1 | 2-26 | 1113 | 2 | 1 | 3.78 | 120 | 301 |
| Ref1 | 2-26 | 1113 | 3 | 1 | 3.68 | 120 | 298 |
| Ref1 | 2-26 | 206 | 1 | 1 | 3.87 | 120 | 405 |
| Ref1 | 2-26 | 206 | 2 | 1 | 3.77 | 120 | 400 |
| Ref1 | 2-26 | 206 | 3 | 1 | 3.67 | 120 | 395 |
| Ref1 | 2-26 | 274 | 1 | 1 | 3.88 | 120 | 320 |
| Ref1 | 2-26 | 274 | 2 | 1 | 3.78 | 120 | 315 |
| Ref1 | 2-26 | 274 | 3 | 1 | 3.68 | 120 | 312 |
| Ref1 | 2-26 | 330 | 1 | 1 | 3.88 | 120 | 328 |
| Ref1 | 2-26 | 330 | 2 | 1 | 3.78 | 120 | 324 |
| Ref1 | 2-26 | 330 | 3 | 1 | 3.68 | 120 | 320 |
| Ref1 | 2-26 | 841 | 1 | 1 | 3.86 | 120 | 425 |
| Ref1 | 2-26 | 841 | 2 | 1 | 3.76 | 120 | 420 |
| Ref1 | 2-26 | 841 | 3 | 1 | 3.66 | 120 | 415 |
| Ref1 | 2-26 | 973 | 1 | 1 | 3.88 | 120 | 340 |
| Ref1 | 2-26 | 973 | 2 | 1 | 3.78 | 120 | 335 |
| Ref1 | 2-26 | 973 | 3 | 1 | 3.68 | 120 | 330 |
| Ref1 | 2-26 | 686 | 1 | 1 | 3.86 | 120 | 450 |
| Ref1 | 2-26 | 686 | 2 | 1 | 3.76 | 120 | 445 |
| Ref1 | 2-26 | 686 | 3 | 1 | 3.66 | 120 | 440 |
| Ref1 | 2-50 | 1113 | 1 | 1 | 3.87 | 120 | 318 |
| Ref1 | 2-50 | 1113 | 2 | 1 | 3.77 | 120 | 310 |
| Ref1 | 2-50 | 1113 | 3 | 1 | 3.67 | 120 | 305 |
| Ref1 | 2-50 | 206 | 1 | 1 | 3.86 | 120 | 415 |
| Ref1 | 2-50 | 206 | 2 | 1 | 3.76 | 120 | 410 |
| Ref1 | 2-50 | 206 | 3 | 1 | 3.66 | 120 | 405 |
| Ref1 | 2-50 | 274 | 1 | 1 | 3.87 | 120 | 335 |
| Ref1 | 2-50 | 274 | 2 | 1 | 3.77 | 120 | 330 |
| Ref1 | 2-50 | 274 | 3 | 1 | 3.67 | 120 | 325 |
| Ref1 | 2-50 | 330 | 1 | 1 | 3.87 | 120 | 350 |
| Ref1 | 2-50 | 330 | 2 | 1 | 3.77 | 120 | 345 |
| Ref1 | 2-50 | 330 | 3 | 1 | 3.67 | 120 | 340 |
| Ref1 | 2-50 | 841 | 1 | 1 | 3.85 | 120 | 445 |
| Ref1 | 2-50 | 841 | 2 | 1 | 3.75 | 120 | 440 |
| Ref1 | 2-50 | 841 | 3 | 1 | 3.65 | 120 | 435 |
| Ref1 | 2-50 | 973 | 1 | 1 | 3.87 | 120 | 355 |
| Ref1 | 2-50 | 973 | 2 | 1 | 3.77 | 120 | 350 |
| Ref1 | 2-50 | 973 | 3 | 1 | 3.67 | 120 | 345 |
| Ref1 | 2-50 | 686 | 1 | 1 | 3.85 | 120 | 480 |
| Ref1 | 2-50 | 686 | 2 | 1 | 3.75 | 120 | 474 |
| Ref1 | 2-50 | 686 | 3 | 1 | 3.65 | 120 | 470 |
| 1-1 | 2-78 | 1113 | 1 | 1 | 3.90 | 120 | 302 |
| 1-1 | 2-78 | 1113 | 2 | 1 | 3.80 | 120 | 296 |
| 1-1 | 2-78 | 1113 | 3 | 1 | 3.70 | 120 | 291 |
| 1-1 | 2-78 | 206 | 1 | 1 | 3.89 | 120 | 400 |
| 1-1 | 2-78 | 206 | 2 | 1 | 3.79 | 120 | 396 |
| 1-1 | 2-78 | 206 | 3 | 1 | 3.69 | 120 | 391 |
| 1-1 | 2-78 | 274 | 1 | 1 | 3.90 | 120 | 320 |
| 1-1 | 2-78 | 274 | 2 | 1 | 3.80 | 120 | 316 |
| 1-1 | 2-78 | 274 | 3 | 1 | 3.70 | 120 | 311 |
| 1-1 | 2-78 | 330 | 1 | 1 | 3.90 | 120 | 333 |
| 1-1 | 2-78 | 330 | 2 | 1 | 3.80 | 120 | 327 |
| 1-1 | 2-78 | 330 | 3 | 1 | 3.70 | 120 | 322 |
| 1-1 | 2-78 | 841 | 1 | 1 | 3.88 | 120 | 425 |
| 1-1 | 2-78 | 841 | 2 | 1 | 3.78 | 120 | 420 |
| 1-1 | 2-78 | 841 | 3 | 1 | 3.68 | 120 | 414 |
| 1-1 | 2-78 | 973 | 1 | 1 | 3.90 | 120 | 343 |

TABLE 16-continued

| | Host | | Weight ratio | | DATA | | |
|---|---|---|---|---|---|---|---|
| EBL | PH | NH | PH | NH | V | Efficiency | L |
| 1-1 | 2-78 | 973 | 2 | 1 | 3.80 | 120 | 336 |
| 1-1 | 2-78 | 973 | 3 | 1 | 3.70 | 120 | 330 |
| 1-1 | 2-78 | 686 | 1 | 1 | 3.88 | 120 | 465 |
| 1-1 | 2-78 | 686 | 2 | 1 | 3.78 | 120 | 458 |
| 1-1 | 2-78 | 686 | 3 | 1 | 3.68 | 120 | 450 |
| 1-1 | 2-2 | 1113 | 1 | 1 | 3.90 | 120 | 315 |
| 1-1 | 2-2 | 1113 | 2 | 1 | 3.80 | 120 | 308 |
| 1-1 | 2-2 | 1113 | 3 | 1 | 3.70 | 120 | 300 |
| 1-1 | 2-2 | 206 | 1 | 1 | 3.89 | 120 | 400 |
| 1-1 | 2-2 | 206 | 2 | 1 | 3.79 | 120 | 392 |
| 1-1 | 2-2 | 206 | 3 | 1 | 3.69 | 120 | 388 |
| 1-1 | 2-2 | 274 | 1 | 1 | 3.90 | 120 | 325 |
| 1-1 | 2-2 | 274 | 2 | 1 | 3.80 | 120 | 318 |
| 1-1 | 2-2 | 274 | 3 | 1 | 3.70 | 120 | 314 |
| 1-1 | 2-2 | 330 | 1 | 1 | 3.90 | 120 | 340 |
| 1-1 | 2-2 | 330 | 2 | 1 | 3.80 | 120 | 333 |
| 1-1 | 2-2 | 330 | 3 | 1 | 3.70 | 120 | 328 |
| 1-1 | 2-2 | 841 | 1 | 1 | 3.88 | 120 | 435 |
| 1-1 | 2-2 | 841 | 2 | 1 | 3.78 | 120 | 430 |
| 1-1 | 2-2 | 841 | 3 | 1 | 3.68 | 120 | 424 |
| 1-1 | 2-2 | 973 | 1 | 1 | 3.90 | 120 | 350 |
| 1-1 | 2-2 | 973 | 2 | 1 | 3.80 | 120 | 345 |
| 1-1 | 2-2 | 973 | 3 | 1 | 3.70 | 120 | 339 |
| 1-1 | 2-2 | 686 | 1 | 1 | 3.88 | 120 | 460 |
| 1-1 | 2-2 | 686 | 2 | 1 | 3.78 | 120 | 452 |
| 1-1 | 2-2 | 686 | 3 | 1 | 3.68 | 120 | 445 |
| 1-1 | 2-26 | 1113 | 1 | 1 | 3.88 | 120 | 330 |
| 1-1 | 2-26 | 1113 | 2 | 1 | 3.78 | 120 | 326 |
| 1-1 | 2-26 | 1113 | 3 | 1 | 3.68 | 120 | 319 |
| 1-1 | 2-26 | 274 | 1 | 1 | 3.88 | 120 | 350 |
| 1-1 | 2-26 | 274 | 2 | 1 | 3.78 | 120 | 344 |
| 1-1 | 2-26 | 274 | 3 | 1 | 3.68 | 120 | 336 |
| 1-1 | 2-26 | 330 | 1 | 1 | 3.88 | 120 | 370 |
| 1-1 | 2-26 | 330 | 2 | 1 | 3.78 | 120 | 364 |
| 1-1 | 2-26 | 330 | 3 | 1 | 3.68 | 120 | 358 |
| 1-1 | 2-26 | 973 | 1 | 1 | 3.88 | 120 | 376 |
| 1-1 | 2-26 | 973 | 2 | 1 | 3.78 | 120 | 370 |
| 1-1 | 2-26 | 973 | 3 | 1 | 3.68 | 120 | 362 |
| 1-1 | 2-50 | 1113 | 1 | 1 | 3.87 | 120 | 350 |
| 1-1 | 2-50 | 1113 | 2 | 1 | 3.77 | 120 | 345 |
| 1-1 | 2-50 | 1113 | 3 | 1 | 3.67 | 120 | 340 |
| 1-1 | 2-50 | 274 | 1 | 1 | 3.87 | 120 | 370 |
| 1-1 | 2-50 | 274 | 2 | 1 | 3.77 | 120 | 362 |
| 1-1 | 2-50 | 274 | 3 | 1 | 3.67 | 120 | 354 |
| 1-1 | 2-50 | 330 | 1 | 1 | 3.87 | 120 | 385 |
| 1-1 | 2-50 | 330 | 2 | 1 | 3.77 | 120 | 378 |
| 1-1 | 2-50 | 330 | 3 | 1 | 3.67 | 120 | 370 |
| 1-1 | 2-50 | 973 | 1 | 1 | 3.87 | 120 | 395 |
| 1-1 | 2-50 | 973 | 2 | 1 | 3.77 | 120 | 388 |
| 1-1 | 2-50 | 973 | 3 | 1 | 3.67 | 120 | 380 |
| 1-2 | 2-78 | 1113 | 1 | 1 | 3.90 | 120 | 287 |
| 1-2 | 2-78 | 1113 | 2 | 1 | 3.80 | 120 | 280 |
| 1-2 | 2-78 | 1113 | 3 | 1 | 3.70 | 120 | 272 |
| 1-2 | 2-78 | 206 | 1 | 1 | 3.89 | 120 | 370 |
| 1-2 | 2-78 | 206 | 2 | 1 | 3.79 | 120 | 365 |
| 1-2 | 2-78 | 206 | 3 | 1 | 3.69 | 120 | 360 |
| 1-2 | 2-78 | 274 | 1 | 1 | 3.90 | 120 | 298 |
| 1-2 | 2-78 | 274 | 2 | 1 | 3.80 | 120 | 292 |
| 1-2 | 2-78 | 274 | 3 | 1 | 3.70 | 120 | 284 |
| 1-2 | 2-78 | 330 | 1 | 1 | 3.90 | 120 | 320 |
| 1-2 | 2-78 | 330 | 2 | 1 | 3.80 | 120 | 312 |
| 1-2 | 2-78 | 330 | 3 | 1 | 3.70 | 120 | 305 |
| 1-2 | 2-78 | 841 | 1 | 1 | 3.88 | 120 | 398 |
| 1-2 | 2-78 | 841 | 2 | 1 | 3.78 | 120 | 394 |
| 1-2 | 2-78 | 841 | 3 | 1 | 3.68 | 120 | 390 |
| 1-2 | 2-78 | 973 | 1 | 1 | 3.90 | 120 | 318 |
| 1-2 | 2-78 | 973 | 2 | 1 | 3.80 | 120 | 310 |
| 1-2 | 2-78 | 973 | 3 | 1 | 3.70 | 120 | 302 |
| 1-2 | 2-78 | 686 | 1 | 1 | 3.88 | 120 | 428 |
| 1-2 | 2-78 | 686 | 2 | 1 | 3.78 | 120 | 425 |
| 1-2 | 2-78 | 686 | 3 | 1 | 3.68 | 120 | 420 |
| 1-2 | 2-2 | 1113 | 1 | 1 | 3.90 | 120 | 290 |
| 1-2 | 2-2 | 1113 | 2 | 1 | 3.80 | 120 | 282 |
| 1-2 | 2-2 | 1113 | 3 | 1 | 3.70 | 120 | 274 |
| 1-2 | 2-2 | 206 | 1 | 1 | 3.89 | 120 | 378 |
| 1-2 | 2-2 | 206 | 2 | 1 | 3.79 | 120 | 373 |

TABLE 16-continued

| | Host | | Weight ratio | | DATA | | |
|---|---|---|---|---|---|---|---|
| EBL | PH | NH | PH | NH | V | Efficiency | L |
| 1-2 | 2-2 | 206 | 3 | 1 | 3.69 | 120 | 368 |
| 1-2 | 2-2 | 274 | 1 | 1 | 3.90 | 120 | 304 |
| 1-2 | 2-2 | 274 | 2 | 1 | 3.80 | 120 | 298 |
| 1-2 | 2-2 | 274 | 3 | 1 | 3.70 | 120 | 291 |
| 1-2 | 2-2 | 330 | 1 | 1 | 3.90 | 120 | 320 |
| 1-2 | 2-2 | 330 | 2 | 1 | 3.80 | 120 | 312 |
| 1-2 | 2-2 | 330 | 3 | 1 | 3.70 | 120 | 303 |
| 1-2 | 2-2 | 841 | 1 | 1 | 3.88 | 120 | 408 |
| 1-2 | 2-2 | 841 | 2 | 1 | 3.78 | 120 | 404 |
| 1-2 | 2-2 | 841 | 3 | 1 | 3.68 | 120 | 400 |
| 1-2 | 2-2 | 973 | 1 | 1 | 3.90 | 120 | 325 |
| 1-2 | 2-2 | 973 | 2 | 1 | 3.80 | 120 | 320 |
| 1-2 | 2-2 | 973 | 3 | 1 | 3.70 | 120 | 315 |
| 1-2 | 2-2 | 686 | 1 | 1 | 3.88 | 120 | 440 |
| 1-2 | 2-2 | 686 | 2 | 1 | 3.78 | 120 | 436 |
| 1-2 | 2-2 | 686 | 3 | 1 | 3.68 | 120 | 432 |
| 1-2 | 2-26 | 1113 | 1 | 1 | 3.88 | 120 | 315 |
| 1-2 | 2-26 | 1113 | 2 | 1 | 3.78 | 120 | 308 |
| 1-2 | 2-26 | 1113 | 3 | 1 | 3.68 | 120 | 300 |
| 1-2 | 2-26 | 274 | 1 | 1 | 3.88 | 120 | 330 |
| 1-2 | 2-26 | 274 | 2 | 1 | 3.78 | 120 | 324 |
| 1-2 | 2-26 | 274 | 3 | 1 | 3.68 | 120 | 318 |
| 1-2 | 2-26 | 330 | 1 | 1 | 3.88 | 120 | 345 |
| 1-2 | 2-26 | 330 | 2 | 1 | 3.78 | 120 | 338 |
| 1-2 | 2-26 | 330 | 3 | 1 | 3.68 | 120 | 331 |
| 1-2 | 2-26 | 973 | 1 | 1 | 3.88 | 120 | 350 |
| 1-2 | 2-26 | 973 | 2 | 1 | 3.78 | 120 | 342 |
| 1-2 | 2-26 | 973 | 3 | 1 | 3.68 | 120 | 333 |
| 1-2 | 2-50 | 1113 | 1 | 1 | 3.87 | 120 | 326 |
| 1-2 | 2-50 | 1113 | 2 | 1 | 3.77 | 120 | 316 |
| 1-2 | 2-50 | 1113 | 3 | 1 | 3.67 | 120 | 306 |
| 1-2 | 2-50 | 274 | 1 | 1 | 3.87 | 120 | 345 |
| 1-2 | 2-50 | 274 | 2 | 1 | 3.77 | 120 | 338 |
| 1-2 | 2-50 | 274 | 3 | 1 | 3.67 | 120 | 330 |
| 1-2 | 2-50 | 330 | 1 | 1 | 3.87 | 120 | 360 |
| 1-2 | 2-50 | 330 | 2 | 1 | 3.77 | 120 | 350 |
| 1-2 | 2-50 | 330 | 3 | 1 | 3.67 | 120 | 340 |
| 1-2 | 2-50 | 973 | 1 | 1 | 3.87 | 120 | 368 |
| 1-2 | 2-50 | 973 | 2 | 1 | 3.77 | 120 | 360 |
| 1-2 | 2-50 | 973 | 3 | 1 | 3.67 | 120 | 352 |
| 1-3 | 2-78 | 1113 | 1 | 1 | 3.90 | 120 | 320 |
| 1-3 | 2-78 | 1113 | 2 | 1 | 3.80 | 120 | 310 |
| 1-3 | 2-78 | 1113 | 3 | 1 | 3.70 | 120 | 300 |
| 1-3 | 2-78 | 206 | 1 | 1 | 3.89 | 120 | 415 |
| 1-3 | 2-78 | 206 | 2 | 1 | 3.79 | 120 | 411 |
| 1-3 | 2-78 | 206 | 3 | 1 | 3.69 | 120 | 408 |
| 1-3 | 2-78 | 274 | 1 | 1 | 3.90 | 120 | 335 |
| 1-3 | 2-78 | 274 | 2 | 1 | 3.80 | 120 | 327 |
| 1-3 | 2-78 | 274 | 3 | 1 | 3.70 | 120 | 318 |
| 1-3 | 2-78 | 330 | 1 | 1 | 3.90 | 120 | 350 |
| 1-3 | 2-78 | 330 | 2 | 1 | 3.80 | 120 | 342 |
| 1-3 | 2-78 | 330 | 3 | 1 | 3.70 | 120 | 333 |
| 1-3 | 2-78 | 841 | 1 | 1 | 3.88 | 120 | 445 |
| 1-3 | 2-78 | 841 | 2 | 1 | 3.78 | 120 | 442 |
| 1-3 | 2-78 | 841 | 3 | 1 | 3.68 | 120 | 438 |
| 1-3 | 2-78 | 973 | 1 | 1 | 3.90 | 120 | 355 |
| 1-3 | 2-78 | 973 | 2 | 1 | 3.80 | 120 | 348 |
| 1-3 | 2-78 | 973 | 3 | 1 | 3.70 | 120 | 340 |
| 1-3 | 2-78 | 686 | 1 | 1 | 3.88 | 120 | 480 |
| 1-3 | 2-78 | 686 | 2 | 1 | 3.78 | 120 | 478 |
| 1-3 | 2-78 | 686 | 3 | 1 | 3.68 | 120 | 475 |
| 1-3 | 2-2 | 1113 | 1 | 1 | 3.90 | 120 | 324 |
| 1-3 | 2-2 | 1113 | 2 | 1 | 3.80 | 120 | 315 |
| 1-3 | 2-2 | 1113 | 3 | 1 | 3.70 | 120 | 305 |
| 1-3 | 2-2 | 206 | 1 | 1 | 3.89 | 120 | 420 |
| 1-3 | 2-2 | 206 | 2 | 1 | 3.79 | 120 | 416 |
| 1-3 | 2-2 | 206 | 3 | 1 | 3.69 | 120 | 411 |
| 1-3 | 2-2 | 274 | 1 | 1 | 3.90 | 120 | 340 |
| 1-3 | 2-2 | 274 | 2 | 1 | 3.80 | 120 | 333 |
| 1-3 | 2-2 | 274 | 3 | 1 | 3.70 | 120 | 325 |
| 1-3 | 2-2 | 330 | 1 | 1 | 3.90 | 120 | 355 |
| 1-3 | 2-2 | 330 | 2 | 1 | 3.80 | 120 | 348 |
| 1-3 | 2-2 | 330 | 3 | 1 | 3.70 | 120 | 340 |
| 1-3 | 2-2 | 841 | 1 | 1 | 3.88 | 120 | 456 |
| 1-3 | 2-2 | 841 | 2 | 1 | 3.78 | 120 | 448 |
| 1-3 | 2-2 | 841 | 3 | 1 | 3.68 | 120 | 440 |

TABLE 16-continued

| EBL | Host PH | Host NH | Weight ratio PH | Weight ratio NH | DATA V | DATA Efficiency | DATA L |
|---|---|---|---|---|---|---|---|
| 1-3 | 2-2 | 973 | 1 | 1 | 3.90 | 120 | 362 |
| 1-3 | 2-2 | 973 | 2 | 1 | 3.80 | 120 | 354 |
| 1-3 | 2-2 | 973 | 3 | 1 | 3.70 | 120 | 345 |
| 1-3 | 2-2 | 686 | 1 | 1 | 3.88 | 120 | 485 |
| 1-3 | 2-2 | 686 | 2 | 1 | 3.78 | 120 | 482 |
| 1-3 | 2-2 | 686 | 3 | 1 | 3.68 | 120 | 478 |
| 1-3 | 2-26 | 1113 | 1 | 1 | 3.88 | 120 | 350 |
| 1-3 | 2-26 | 1113 | 2 | 1 | 3.78 | 120 | 340 |
| 1-3 | 2-26 | 1113 | 3 | 1 | 3.68 | 120 | 328 |
| 1-3 | 2-26 | 274 | 1 | 1 | 3.88 | 120 | 366 |
| 1-3 | 2-26 | 274 | 2 | 1 | 3.78 | 120 | 358 |
| 1-3 | 2-26 | 274 | 3 | 1 | 3.68 | 120 | 348 |
| 1-3 | 2-26 | 330 | 1 | 1 | 3.88 | 120 | 384 |
| 1-3 | 2-26 | 330 | 2 | 1 | 3.78 | 120 | 376 |
| 1-3 | 2-26 | 330 | 3 | 1 | 3.68 | 120 | 365 |
| 1-3 | 2-26 | 973 | 1 | 1 | 3.88 | 120 | 396 |
| 1-3 | 2-26 | 973 | 2 | 1 | 3.78 | 120 | 388 |
| 1-3 | 2-26 | 973 | 3 | 1 | 3.68 | 120 | 378 |
| 1-3 | 2-50 | 1113 | 1 | 1 | 3.87 | 120 | 366 |
| 1-3 | 2-50 | 1113 | 2 | 1 | 3.77 | 120 | 356 |
| 1-3 | 2-50 | 1113 | 3 | 1 | 3.67 | 120 | 345 |
| 1-3 | 2-50 | 274 | 1 | 1 | 3.87 | 120 | 384 |
| 1-3 | 2-50 | 274 | 2 | 1 | 3.77 | 120 | 376 |
| 1-3 | 2-50 | 274 | 3 | 1 | 3.67 | 120 | 367 |
| 1-3 | 2-50 | 330 | 1 | 1 | 3.87 | 120 | 400 |
| 1-3 | 2-50 | 330 | 2 | 1 | 3.77 | 120 | 392 |
| 1-3 | 2-50 | 330 | 3 | 1 | 3.67 | 120 | 384 |
| 1-3 | 2-50 | 973 | 1 | 1 | 3.87 | 120 | 408 |
| 1-3 | 2-50 | 973 | 2 | 1 | 3.77 | 120 | 400 |
| 1-3 | 2-50 | 973 | 3 | 1 | 3.67 | 120 | 392 |
| 1-1 | 2-26 | 206 | 1 | 1 | 3.87 | 120 | 435 |
| 1-1 | 2-26 | 206 | 2 | 1 | 3.77 | 120 | 428 |
| 1-1 | 2-26 | 206 | 3 | 1 | 3.67 | 120 | 420 |
| 1-1 | 2-26 | 841 | 1 | 1 | 3.86 | 120 | 470 |
| 1-1 | 2-26 | 841 | 2 | 1 | 3.76 | 120 | 462 |
| 1-1 | 2-26 | 841 | 3 | 1 | 3.66 | 120 | 452 |
| 1-1 | 2-26 | 686 | 1 | 1 | 3.86 | 120 | 505 |
| 1-1 | 2-26 | 686 | 2 | 1 | 3.76 | 120 | 495 |
| 1-1 | 2-26 | 686 | 3 | 1 | 3.66 | 120 | 480 |
| 1-1 | 2-50 | 206 | 1 | 1 | 3.86 | 120 | 460 |
| 1-1 | 2-50 | 206 | 2 | 1 | 3.76 | 120 | 452 |
| 1-1 | 2-50 | 206 | 3 | 1 | 3.66 | 120 | 446 |
| 1-1 | 2-50 | 841 | 1 | 1 | 3.85 | 120 | 490 |
| 1-1 | 2-50 | 841 | 2 | 1 | 3.75 | 120 | 483 |
| 1-1 | 2-50 | 841 | 3 | 1 | 3.65 | 120 | 475 |
| 1-1 | 2-50 | 686 | 1 | 1 | 3.85 | 120 | 525 |
| 1-1 | 2-50 | 686 | 2 | 1 | 3.75 | 120 | 522 |
| 1-1 | 2-50 | 686 | 3 | 1 | 3.65 | 120 | 520 |
| 1-2 | 2-26 | 206 | 1 | 1 | 3.87 | 120 | 405 |
| 1-2 | 2-26 | 206 | 2 | 1 | 3.77 | 120 | 400 |
| 1-2 | 2-26 | 206 | 3 | 1 | 3.67 | 120 | 395 |
| 1-2 | 2-26 | 841 | 1 | 1 | 3.86 | 120 | 438 |
| 1-2 | 2-26 | 841 | 2 | 1 | 3.76 | 120 | 434 |
| 1-2 | 2-26 | 841 | 3 | 1 | 3.66 | 120 | 430 |
| 1-2 | 2-26 | 686 | 1 | 1 | 3.86 | 120 | 470 |
| 1-2 | 2-26 | 686 | 2 | 1 | 3.76 | 120 | 466 |
| 1-2 | 2-26 | 686 | 3 | 1 | 3.66 | 120 | 462 |
| 1-2 | 2-50 | 206 | 1 | 1 | 3.86 | 120 | 425 |
| 1-2 | 2-50 | 206 | 2 | 1 | 3.76 | 120 | 420 |
| 1-2 | 2-50 | 206 | 3 | 1 | 3.66 | 120 | 415 |
| 1-2 | 2-50 | 841 | 1 | 1 | 3.85 | 120 | 456 |
| 1-2 | 2-50 | 841 | 2 | 1 | 3.75 | 120 | 452 |
| 1-2 | 2-50 | 841 | 3 | 1 | 3.65 | 120 | 448 |
| 1-2 | 2-50 | 686 | 1 | 1 | 3.85 | 120 | 494 |
| 1-2 | 2-50 | 686 | 2 | 1 | 3.75 | 120 | 490 |
| 1-2 | 2-50 | 686 | 3 | 1 | 3.65 | 120 | 485 |
| 1-3 | 2-26 | 206 | 1 | 1 | 3.87 | 120 | 454 |
| 1-3 | 2-26 | 206 | 2 | 1 | 3.77 | 120 | 450 |
| 1-3 | 2-26 | 206 | 3 | 1 | 3.67 | 120 | 445 |
| 1-3 | 2-26 | 841 | 1 | 1 | 3.86 | 120 | 492 |
| 1-3 | 2-26 | 841 | 2 | 1 | 3.76 | 120 | 489 |
| 1-3 | 2-26 | 841 | 3 | 1 | 3.66 | 120 | 485 |
| 1-3 | 2-26 | 686 | 1 | 1 | 3.86 | 120 | 526 |
| 1-3 | 2-26 | 686 | 2 | 1 | 3.76 | 120 | 523 |
| 1-3 | 2-26 | 686 | 3 | 1 | 3.66 | 120 | 520 |
| 1-3 | 2-50 | 206 | 1 | 1 | 3.86 | 120 | 476 |

TABLE 16-continued

| EBL | Host PH | Host NH | Weight ratio PH | Weight ratio NH | DATA V | DATA Efficiency | DATA L |
|---|---|---|---|---|---|---|---|
| 1-3 | 2-50 | 206 | 2 | 1 | 3.76 | 120 | 472 |
| 1-3 | 2-50 | 206 | 3 | 1 | 3.66 | 120 | 468 |
| 1-3 | 2-50 | 841 | 1 | 1 | 3.85 | 120 | 508 |
| 1-3 | 2-50 | 841 | 2 | 1 | 3.75 | 120 | 505 |
| 1-3 | 2-50 | 841 | 3 | 1 | 3.65 | 120 | 502 |
| 1-3 | 2-50 | 686 | 1 | 1 | 3.85 | 120 | 550 |
| 1-3 | 2-50 | 686 | 2 | 1 | 3.75 | 120 | 546 |
| 1-3 | 2-50 | 686 | 3 | 1 | 3.65 | 120 | 543 |
| Ref7 | 2-78 | 1113 | 1 | 1 | 4.15 | 120 | 298 |
| Ref7 | 2-78 | 1113 | 2 | 1 | 4.1 | 120 | 292 |
| Ref7 | 2-78 | 1113 | 3 | 1 | 4.05 | 121 | 286 |
| Ref7 | 2-78 | 206 | 1 | 1 | 4.13 | 120 | 390 |
| Ref7 | 2-78 | 206 | 2 | 1 | 4.09 | 120 | 380 |
| Ref7 | 2-78 | 206 | 3 | 1 | 4.05 | 121 | 374 |
| Ref7 | 2-78 | 274 | 1 | 1 | 4.15 | 120 | 310 |
| Ref7 | 2-78 | 274 | 2 | 1 | 4.1 | 120 | 303 |
| Ref7 | 2-78 | 274 | 3 | 1 | 4.05 | 121 | 297 |
| Ref7 | 2-78 | 330 | 1 | 1 | 4.15 | 120 | 325 |
| Ref7 | 2-78 | 330 | 2 | 1 | 4.1 | 120 | 320 |
| Ref7 | 2-78 | 330 | 3 | 1 | 4.05 | 121 | 310 |
| Ref7 | 2-78 | 841 | 1 | 1 | 4.13 | 120 | 420 |
| Ref7 | 2-78 | 841 | 2 | 1 | 4.09 | 120 | 410 |
| Ref7 | 2-78 | 841 | 3 | 1 | 4.05 | 121 | 400 |
| Ref7 | 2-78 | 973 | 1 | 1 | 4.15 | 120 | 335 |
| Ref7 | 2-78 | 973 | 2 | 1 | 4.1 | 120 | 325 |
| Ref7 | 2-78 | 973 | 3 | 1 | 4.05 | 121 | 315 |
| Ref7 | 2-78 | 686 | 1 | 1 | 4.16 | 120 | 445 |
| Ref7 | 2-78 | 686 | 2 | 1 | 4.1 | 120 | 435 |
| Ref7 | 2-78 | 686 | 3 | 1 | 4.05 | 121 | 425 |
| Ref7 | 2-2 | 1113 | 1 | 1 | 4.15 | 120 | 300 |
| Ref7 | 2-2 | 1113 | 2 | 1 | 4.1 | 120 | 295 |
| Ref7 | 2-2 | 1113 | 3 | 1 | 4.05 | 121 | 285 |
| Ref7 | 2-2 | 206 | 1 | 1 | 4.13 | 120 | 390 |
| Ref7 | 2-2 | 206 | 2 | 1 | 4.09 | 120 | 380 |
| Ref7 | 2-2 | 206 | 3 | 1 | 4.05 | 121 | 375 |
| Ref7 | 2-2 | 274 | 1 | 1 | 4.15 | 120 | 320 |
| Ref7 | 2-2 | 274 | 2 | 1 | 4.1 | 120 | 310 |
| Ref7 | 2-2 | 274 | 3 | 1 | 4.05 | 121 | 305 |
| Ref7 | 2-2 | 330 | 1 | 1 | 4.15 | 120 | 335 |
| Ref7 | 2-2 | 330 | 2 | 1 | 4.1 | 120 | 325 |
| Ref7 | 2-2 | 330 | 3 | 1 | 4.05 | 121 | 320 |
| Ref7 | 2-2 | 841 | 1 | 1 | 4.13 | 120 | 435 |
| Ref7 | 2-2 | 841 | 2 | 1 | 4.09 | 120 | 430 |
| Ref7 | 2-2 | 841 | 3 | 1 | 4.05 | 121 | 420 |
| Ref7 | 2-2 | 973 | 1 | 1 | 4.15 | 120 | 340 |
| Ref7 | 2-2 | 973 | 2 | 1 | 4.1 | 120 | 330 |
| Ref7 | 2-2 | 973 | 3 | 1 | 4.05 | 121 | 325 |
| Ref7 | 2-2 | 686 | 1 | 1 | 4.16 | 120 | 455 |
| Ref7 | 2-2 | 686 | 2 | 1 | 4.1 | 120 | 450 |
| Ref7 | 2-2 | 686 | 3 | 1 | 4.05 | 121 | 445 |
| Ref7 | 2-26 | 1113 | 1 | 1 | 4.15 | 120 | 330 |
| Ref7 | 2-26 | 1113 | 2 | 1 | 4.1 | 120 | 325 |
| Ref7 | 2-26 | 1113 | 3 | 1 | 4.05 | 121 | 320 |
| Ref7 | 2-26 | 206 | 1 | 1 | 4.13 | 120 | 425 |
| Ref7 | 2-26 | 206 | 2 | 1 | 4.09 | 120 | 420 |
| Ref7 | 2-26 | 206 | 3 | 1 | 4.05 | 121 | 415 |
| Ref7 | 2-26 | 274 | 1 | 1 | 4.15 | 120 | 350 |
| Ref7 | 2-26 | 274 | 2 | 1 | 4.1 | 120 | 340 |
| Ref7 | 2-26 | 274 | 3 | 1 | 4.05 | 121 | 335 |
| Ref7 | 2-26 | 330 | 1 | 1 | 4.15 | 120 | 365 |
| Ref7 | 2-26 | 330 | 2 | 1 | 4.1 | 120 | 355 |
| Ref7 | 2-26 | 330 | 3 | 1 | 4.05 | 121 | 350 |
| Ref7 | 2-26 | 841 | 1 | 1 | 4.13 | 120 | 460 |
| Ref7 | 2-26 | 841 | 2 | 1 | 4.09 | 120 | 450 |
| Ref7 | 2-26 | 841 | 3 | 1 | 4.05 | 121 | 440 |
| Ref7 | 2-26 | 973 | 1 | 1 | 4.15 | 120 | 370 |
| Ref7 | 2-26 | 973 | 2 | 1 | 4.1 | 120 | 360 |
| Ref7 | 2-26 | 973 | 3 | 1 | 4.05 | 121 | 355 |
| Ref7 | 2-26 | 686 | 1 | 1 | 4.16 | 120 | 495 |
| Ref7 | 2-26 | 686 | 2 | 1 | 4.1 | 120 | 485 |
| Ref7 | 2-26 | 686 | 3 | 1 | 4.05 | 121 | 480 |
| Ref7 | 2-50 | 1113 | 1 | 1 | 4.15 | 120 | 345 |
| Ref7 | 2-50 | 1113 | 2 | 1 | 4.1 | 120 | 340 |
| Ref7 | 2-50 | 1113 | 3 | 1 | 4.05 | 121 | 335 |
| Ref7 | 2-50 | 206 | 1 | 1 | 4.13 | 120 | 450 |
| Ref7 | 2-50 | 206 | 2 | 1 | 4.09 | 120 | 440 |

TABLE 16-continued

| | Host | | Weight ratio | | DATA | | |
|---|---|---|---|---|---|---|---|
| EBL | PH | NH | PH | NH | V | Efficiency | L |
| Ref7 | 2-50 | 206 | 3 | 1 | 4.05 | 121 | 435 |
| Ref7 | 2-50 | 274 | 1 | 1 | 4.15 | 120 | 360 |
| Ref7 | 2-50 | 274 | 2 | 1 | 4.1 | 120 | 355 |
| Ref7 | 2-50 | 274 | 3 | 1 | 4.05 | 121 | 350 |
| Ref7 | 2-50 | 330 | 1 | 1 | 4.15 | 120 | 380 |
| Ref7 | 2-50 | 330 | 2 | 1 | 4.1 | 120 | 375 |
| Ref7 | 2-50 | 330 | 3 | 1 | 4.05 | 121 | 370 |
| Ref7 | 2-50 | 841 | 1 | 1 | 4.13 | 120 | 480 |
| Ref7 | 2-50 | 841 | 2 | 1 | 4.09 | 120 | 475 |
| Ref7 | 2-50 | 841 | 3 | 1 | 4.05 | 121 | 465 |
| Ref7 | 2-50 | 973 | 1 | 1 | 4.15 | 120 | 385 |
| Ref7 | 2-50 | 973 | 2 | 1 | 4.1 | 120 | 375 |
| Ref7 | 2-50 | 973 | 3 | 1 | 4.05 | 121 | 370 |
| Ref7 | 2-50 | 686 | 1 | 1 | 4.16 | 120 | 520 |
| Ref7 | 2-50 | 686 | 2 | 1 | 4.1 | 120 | 510 |
| Ref7 | 2-50 | 686 | 3 | 1 | 4.05 | 121 | 500 |
| 7-1 | 2-78 | 1113 | 1 | 1 | 4.15 | 120 | 330 |
| 7-1 | 2-78 | 1113 | 2 | 1 | 4.1 | 120 | 325 |
| 7-1 | 2-78 | 1113 | 3 | 1 | 4.05 | 121 | 320 |
| 7-1 | 2-78 | 206 | 1 | 1 | 4.13 | 120 | 425 |
| 7-1 | 2-78 | 206 | 2 | 1 | 4.09 | 120 | 420 |
| 7-1 | 2-78 | 206 | 3 | 1 | 4.05 | 121 | 415 |
| 7-1 | 2-78 | 274 | 1 | 1 | 4.15 | 120 | 345 |
| 7-1 | 2-78 | 274 | 2 | 1 | 4.1 | 120 | 340 |
| 7-1 | 2-78 | 274 | 3 | 1 | 4.05 | 121 | 335 |
| 7-1 | 2-78 | 330 | 1 | 1 | 4.15 | 120 | 360 |
| 7-1 | 2-78 | 330 | 2 | 1 | 4.1 | 120 | 355 |
| 7-1 | 2-78 | 330 | 3 | 1 | 4.05 | 121 | 350 |
| 7-1 | 2-78 | 841 | 1 | 1 | 4.13 | 120 | 455 |
| 7-1 | 2-78 | 841 | 2 | 1 | 4.09 | 120 | 450 |
| 7-1 | 2-78 | 841 | 3 | 1 | 4.05 | 121 | 445 |
| 7-1 | 2-78 | 973 | 1 | 1 | 4.15 | 120 | 365 |
| 7-1 | 2-78 | 973 | 2 | 1 | 4.1 | 120 | 355 |
| 7-1 | 2-78 | 973 | 3 | 1 | 4.05 | 121 | 350 |
| 7-1 | 2-78 | 686 | 1 | 1 | 4.16 | 120 | 500 |
| 7-1 | 2-78 | 686 | 2 | 1 | 4.1 | 120 | 495 |
| 7-1 | 2-78 | 686 | 3 | 1 | 4.05 | 121 | 490 |
| 7-1 | 2-2 | 1113 | 1 | 1 | 4.15 | 120 | 335 |
| 7-1 | 2-2 | 1113 | 2 | 1 | 4.1 | 120 | 325 |
| 7-1 | 2-2 | 1113 | 3 | 1 | 4.05 | 121 | 320 |
| 7-1 | 2-2 | 206 | 1 | 1 | 4.13 | 120 | 435 |
| 7-1 | 2-2 | 206 | 2 | 1 | 4.09 | 120 | 430 |
| 7-1 | 2-2 | 206 | 3 | 1 | 4.05 | 121 | 420 |
| 7-1 | 2-2 | 274 | 1 | 1 | 4.15 | 120 | 355 |
| 7-1 | 2-2 | 274 | 2 | 1 | 4.1 | 120 | 350 |
| 7-1 | 2-2 | 274 | 3 | 1 | 4.05 | 121 | 340 |
| 7-1 | 2-2 | 330 | 1 | 1 | 4.15 | 120 | 370 |
| 7-1 | 2-2 | 330 | 2 | 1 | 4.1 | 120 | 365 |
| 7-1 | 2-2 | 330 | 3 | 1 | 4.05 | 121 | 355 |
| 7-1 | 2-2 | 841 | 1 | 1 | 4.13 | 120 | 465 |
| 7-1 | 2-2 | 841 | 2 | 1 | 4.09 | 120 | 460 |
| 7-1 | 2-2 | 841 | 3 | 1 | 4.05 | 121 | 450 |
| 7-1 | 2-2 | 973 | 1 | 1 | 4.15 | 120 | 375 |
| 7-1 | 2-2 | 973 | 2 | 1 | 4.1 | 120 | 370 |
| 7-1 | 2-2 | 973 | 3 | 1 | 4.05 | 121 | 365 |
| 7-1 | 2-2 | 686 | 1 | 1 | 4.16 | 120 | 505 |
| 7-1 | 2-2 | 686 | 2 | 1 | 4.1 | 120 | 495 |
| 7-1 | 2-2 | 686 | 3 | 1 | 4.05 | 121 | 490 |
| 7-1 | 2-26 | 1113 | 1 | 1 | 4.15 | 120 | 365 |
| 7-1 | 2-26 | 1113 | 2 | 1 | 4.1 | 120 | 355 |
| 7-1 | 2-26 | 1113 | 3 | 1 | 4.05 | 121 | 345 |
| 7-1 | 2-26 | 274 | 1 | 1 | 4.15 | 120 | 380 |
| 7-1 | 2-26 | 274 | 2 | 1 | 4.1 | 120 | 375 |
| 7-1 | 2-26 | 274 | 3 | 1 | 4.05 | 121 | 370 |
| 7-1 | 2-26 | 330 | 1 | 1 | 4.15 | 120 | 395 |
| 7-1 | 2-26 | 330 | 2 | 1 | 4.1 | 120 | 390 |
| 7-1 | 2-26 | 330 | 3 | 1 | 4.05 | 121 | 385 |
| 7-1 | 2-26 | 973 | 1 | 1 | 4.15 | 120 | 405 |
| 7-1 | 2-26 | 973 | 2 | 1 | 4.1 | 120 | 400 |
| 7-1 | 2-26 | 973 | 3 | 1 | 4.05 | 121 | 390 |
| 7-1 | 2-50 | 1113 | 1 | 1 | 4.15 | 120 | 380 |
| 7-1 | 2-50 | 1113 | 2 | 1 | 4.1 | 120 | 375 |
| 7-1 | 2-50 | 1113 | 3 | 1 | 4.05 | 121 | 370 |
| 7-1 | 2-50 | 274 | 1 | 1 | 4.15 | 120 | 400 |
| 7-1 | 2-50 | 274 | 2 | 1 | 4.1 | 120 | 390 |
| 7-1 | 2-50 | 274 | 3 | 1 | 4.05 | 121 | 385 |

TABLE 16-continued

| | Host | | Weight ratio | | DATA | | |
|---|---|---|---|---|---|---|---|
| EBL | PH | NH | PH | NH | V | Efficiency | L |
| 7-1 | 2-50 | 330 | 1 | 1 | 4.15 | 120 | 415 |
| 7-1 | 2-50 | 330 | 2 | 1 | 4.1 | 120 | 405 |
| 7-1 | 2-50 | 330 | 3 | 1 | 4.05 | 121 | 400 |
| 7-1 | 2-50 | 973 | 1 | 1 | 4.15 | 120 | 425 |
| 7-1 | 2-50 | 973 | 2 | 1 | 4.1 | 120 | 420 |
| 7-1 | 2-50 | 973 | 3 | 1 | 4.05 | 121 | 415 |
| 7-2 | 2-78 | 1113 | 1 | 1 | 4.15 | 120 | 305 |
| 7-2 | 2-78 | 1113 | 2 | 1 | 4.1 | 120 | 300 |
| 7-2 | 2-78 | 1113 | 3 | 1 | 4.05 | 121 | 295 |
| 7-2 | 2-78 | 206 | 1 | 1 | 4.13 | 120 | 400 |
| 7-2 | 2-78 | 206 | 2 | 1 | 4.09 | 120 | 390 |
| 7-2 | 2-78 | 206 | 3 | 1 | 4.05 | 121 | 385 |
| 7-2 | 2-78 | 274 | 1 | 1 | 4.15 | 120 | 325 |
| 7-2 | 2-78 | 274 | 2 | 1 | 4.1 | 120 | 320 |
| 7-2 | 2-78 | 274 | 3 | 1 | 4.05 | 121 | 310 |
| 7-2 | 2-78 | 330 | 1 | 1 | 4.15 | 120 | 340 |
| 7-2 | 2-78 | 330 | 2 | 1 | 4.1 | 120 | 335 |
| 7-2 | 2-78 | 330 | 3 | 1 | 4.05 | 121 | 325 |
| 7-2 | 2-78 | 841 | 1 | 1 | 4.13 | 120 | 430 |
| 7-2 | 2-78 | 841 | 2 | 1 | 4.09 | 120 | 420 |
| 7-2 | 2-78 | 841 | 3 | 1 | 4.05 | 121 | 415 |
| 7-2 | 2-78 | 973 | 1 | 1 | 4.15 | 120 | 340 |
| 7-2 | 2-78 | 973 | 2 | 1 | 4.1 | 120 | 335 |
| 7-2 | 2-78 | 973 | 3 | 1 | 4.05 | 121 | 325 |
| 7-2 | 2-78 | 686 | 1 | 1 | 4.16 | 120 | 460 |
| 7-2 | 2-78 | 686 | 2 | 1 | 4.1 | 120 | 450 |
| 7-2 | 2-78 | 686 | 3 | 1 | 4.05 | 121 | 445 |
| 7-2 | 2-2 | 1113 | 1 | 1 | 4.15 | 120 | 310 |
| 7-2 | 2-2 | 1113 | 2 | 1 | 4.1 | 120 | 305 |
| 7-2 | 2-2 | 1113 | 3 | 1 | 4.05 | 121 | 295 |
| 7-2 | 2-2 | 206 | 1 | 1 | 4.13 | 120 | 410 |
| 7-2 | 2-2 | 206 | 2 | 1 | 4.09 | 120 | 405 |
| 7-2 | 2-2 | 206 | 3 | 1 | 4.05 | 121 | 400 |
| 7-2 | 2-2 | 274 | 1 | 1 | 4.15 | 120 | 325 |
| 7-2 | 2-2 | 274 | 2 | 1 | 4.1 | 120 | 320 |
| 7-2 | 2-2 | 274 | 3 | 1 | 4.05 | 121 | 315 |
| 7-2 | 2-2 | 330 | 1 | 1 | 4.15 | 120 | 350 |
| 7-2 | 2-2 | 330 | 2 | 1 | 4.1 | 120 | 340 |
| 7-2 | 2-2 | 330 | 3 | 1 | 4.05 | 121 | 335 |
| 7-2 | 2-2 | 841 | 1 | 1 | 4.13 | 120 | 440 |
| 7-2 | 2-2 | 841 | 2 | 1 | 4.09 | 120 | 435 |
| 7-2 | 2-2 | 841 | 3 | 1 | 4.05 | 121 | 430 |
| 7-2 | 2-2 | 973 | 1 | 1 | 4.15 | 120 | 350 |
| 7-2 | 2-2 | 973 | 2 | 1 | 4.1 | 120 | 345 |
| 7-2 | 2-2 | 973 | 3 | 1 | 4.05 | 121 | 340 |
| 7-2 | 2-2 | 686 | 1 | 1 | 4.16 | 120 | 475 |
| 7-2 | 2-2 | 686 | 2 | 1 | 4.1 | 120 | 470 |
| 7-2 | 2-2 | 686 | 3 | 1 | 4.05 | 121 | 465 |
| 7-2 | 2-26 | 1113 | 1 | 1 | 4.15 | 120 | 340 |
| 7-2 | 2-26 | 1113 | 2 | 1 | 4.1 | 120 | 330 |
| 7-2 | 2-26 | 1113 | 3 | 1 | 4.05 | 121 | 325 |
| 7-2 | 2-26 | 274 | 1 | 1 | 4.15 | 120 | 355 |
| 7-2 | 2-26 | 274 | 2 | 1 | 4.1 | 120 | 350 |
| 7-2 | 2-26 | 274 | 3 | 1 | 4.05 | 121 | 340 |
| 7-2 | 2-26 | 330 | 1 | 1 | 4.15 | 120 | 375 |
| 7-2 | 2-26 | 330 | 2 | 1 | 4.1 | 120 | 370 |
| 7-2 | 2-26 | 330 | 3 | 1 | 4.05 | 121 | 365 |
| 7-2 | 2-26 | 973 | 1 | 1 | 4.15 | 120 | 380 |
| 7-2 | 2-26 | 973 | 2 | 1 | 4.1 | 120 | 375 |
| 7-2 | 2-26 | 973 | 3 | 1 | 4.05 | 121 | 370 |
| 7-2 | 2-50 | 1113 | 1 | 1 | 4.15 | 120 | 355 |
| 7-2 | 2-50 | 1113 | 2 | 1 | 4.1 | 120 | 350 |
| 7-2 | 2-50 | 1113 | 3 | 1 | 4.05 | 121 | 340 |
| 7-2 | 2-50 | 274 | 1 | 1 | 4.15 | 120 | 370 |
| 7-2 | 2-50 | 274 | 2 | 1 | 4.1 | 120 | 365 |
| 7-2 | 2-50 | 274 | 3 | 1 | 4.05 | 121 | 355 |
| 7-2 | 2-50 | 330 | 1 | 1 | 4.15 | 120 | 390 |
| 7-2 | 2-50 | 330 | 2 | 1 | 4.1 | 120 | 385 |
| 7-2 | 2-50 | 330 | 3 | 1 | 4.05 | 121 | 375 |
| 7-2 | 2-50 | 973 | 1 | 1 | 4.15 | 120 | 400 |
| 7-2 | 2-50 | 973 | 2 | 1 | 4.1 | 120 | 390 |
| 7-2 | 2-50 | 973 | 3 | 1 | 4.05 | 121 | 385 |
| 7-3 | 2-78 | 1113 | 1 | 1 | 4.15 | 120 | 345 |
| 7-3 | 2-78 | 1113 | 2 | 1 | 4.1 | 120 | 340 |
| 7-3 | 2-78 | 1113 | 3 | 1 | 4.05 | 121 | 335 |
| 7-3 | 2-78 | 206 | 1 | 1 | 4.13 | 120 | 450 |

TABLE 16-continued

| | Host | | Weight ratio | | DATA | | |
|---|---|---|---|---|---|---|---|
| EBL | PH | NH | PH | NH | V | Efficiency | L |
| 7-3 | 2-78 | 206 | 2 | 1 | 4.09 | 120 | 440 |
| 7-3 | 2-78 | 206 | 3 | 1 | 4.05 | 121 | 435 |
| 7-3 | 2-78 | 274 | 1 | 1 | 4.15 | 120 | 360 |
| 7-3 | 2-78 | 274 | 2 | 1 | 4.1 | 120 | 355 |
| 7-3 | 2-78 | 274 | 3 | 1 | 4.05 | 121 | 345 |
| 7-3 | 2-78 | 330 | 1 | 1 | 4.15 | 120 | 380 |
| 7-3 | 2-78 | 330 | 2 | 1 | 4.1 | 120 | 375 |
| 7-3 | 2-78 | 330 | 3 | 1 | 4.05 | 121 | 370 |
| 7-3 | 2-78 | 841 | 1 | 1 | 4.13 | 120 | 480 |
| 7-3 | 2-78 | 841 | 2 | 1 | 4.09 | 120 | 475 |
| 7-3 | 2-78 | 841 | 3 | 1 | 4.05 | 121 | 465 |
| 7-3 | 2-78 | 973 | 1 | 1 | 4.15 | 120 | 385 |
| 7-3 | 2-78 | 973 | 2 | 1 | 4.1 | 120 | 375 |
| 7-3 | 2-78 | 973 | 3 | 1 | 4.05 | 121 | 370 |
| 7-3 | 2-78 | 686 | 1 | 1 | 4.16 | 120 | 520 |
| 7-3 | 2-78 | 686 | 2 | 1 | 4.1 | 120 | 510 |
| 7-3 | 2-78 | 686 | 3 | 1 | 4.05 | 121 | 505 |
| 7-3 | 2-2 | 1113 | 1 | 1 | 4.15 | 120 | 350 |
| 7-3 | 2-2 | 1113 | 2 | 1 | 4.1 | 120 | 340 |
| 7-3 | 2-2 | 1113 | 3 | 1 | 4.05 | 121 | 335 |
| 7-3 | 2-2 | 206 | 1 | 1 | 4.13 | 120 | 455 |
| 7-3 | 2-2 | 206 | 2 | 1 | 4.09 | 120 | 450 |
| 7-3 | 2-2 | 206 | 3 | 1 | 4.05 | 121 | 445 |
| 7-3 | 2-2 | 274 | 1 | 1 | 4.15 | 120 | 370 |
| 7-3 | 2-2 | 274 | 2 | 1 | 4.1 | 120 | 365 |
| 7-3 | 2-2 | 274 | 3 | 1 | 4.05 | 121 | 355 |
| 7-3 | 2-2 | 330 | 1 | 1 | 4.15 | 120 | 385 |
| 7-3 | 2-2 | 330 | 2 | 1 | 4.1 | 120 | 375 |
| 7-3 | 2-2 | 330 | 3 | 1 | 4.05 | 121 | 370 |
| 7-3 | 2-2 | 841 | 1 | 1 | 4.13 | 120 | 490 |
| 7-3 | 2-2 | 841 | 2 | 1 | 4.09 | 120 | 480 |
| 7-3 | 2-2 | 841 | 3 | 1 | 4.05 | 121 | 475 |
| 7-3 | 2-2 | 973 | 1 | 1 | 4.15 | 120 | 390 |
| 7-3 | 2-2 | 973 | 2 | 1 | 4.1 | 120 | 385 |
| 7-3 | 2-2 | 973 | 3 | 1 | 4.05 | 121 | 375 |
| 7-3 | 2-2 | 686 | 1 | 1 | 4.16 | 120 | 525 |
| 7-3 | 2-2 | 686 | 2 | 1 | 4.1 | 120 | 520 |
| 7-3 | 2-2 | 686 | 3 | 1 | 4.05 | 121 | 510 |
| 7-3 | 2-26 | 1113 | 1 | 1 | 4.15 | 120 | 380 |
| 7-3 | 2-26 | 1113 | 2 | 1 | 4.1 | 120 | 375 |
| 7-3 | 2-26 | 1113 | 3 | 1 | 4.05 | 121 | 370 |
| 7-3 | 2-26 | 274 | 1 | 1 | 4.15 | 120 | 400 |
| 7-3 | 2-26 | 274 | 2 | 1 | 4.1 | 120 | 390 |
| 7-3 | 2-26 | 274 | 3 | 1 | 4.05 | 121 | 385 |
| 7-3 | 2-26 | 330 | 1 | 1 | 4.15 | 120 | 415 |
| 7-3 | 2-26 | 330 | 2 | 1 | 4.1 | 120 | 405 |
| 7-3 | 2-26 | 330 | 3 | 1 | 4.05 | 121 | 400 |
| 7-3 | 2-26 | 973 | 1 | 1 | 4.15 | 120 | 425 |
| 7-3 | 2-26 | 973 | 2 | 1 | 4.1 | 120 | 420 |
| 7-3 | 2-26 | 973 | 3 | 1 | 4.05 | 121 | 415 |
| 7-3 | 2-50 | 1113 | 1 | 1 | 4.15 | 120 | 395 |
| 7-3 | 2-50 | 1113 | 2 | 1 | 4.1 | 120 | 390 |
| 7-3 | 2-50 | 1113 | 3 | 1 | 4.05 | 121 | 385 |
| 7-3 | 2-50 | 274 | 1 | 1 | 4.15 | 120 | 410 |
| 7-3 | 2-50 | 274 | 2 | 1 | 4.1 | 120 | 405 |
| 7-3 | 2-50 | 274 | 3 | 1 | 4.05 | 121 | 400 |
| 7-3 | 2-50 | 330 | 1 | 1 | 4.15 | 120 | 435 |
| 7-3 | 2-50 | 330 | 2 | 1 | 4.1 | 120 | 430 |
| 7-3 | 2-50 | 330 | 3 | 1 | 4.05 | 121 | 420 |
| 7-3 | 2-50 | 973 | 1 | 1 | 4.15 | 120 | 445 |
| 7-3 | 2-50 | 973 | 2 | 1 | 4.1 | 120 | 440 |
| 7-3 | 2-50 | 973 | 3 | 1 | 4.05 | 121 | 435 |
| 7-1 | 2-26 | 206 | 1 | 1 | 4.13 | 120 | 470 |
| 7-1 | 2-26 | 206 | 2 | 1 | 4.09 | 120 | 465 |
| 7-1 | 2-26 | 206 | 3 | 1 | 4.05 | 121 | 460 |
| 7-1 | 2-26 | 841 | 1 | 1 | 4.13 | 120 | 505 |
| 7-1 | 2-26 | 841 | 2 | 1 | 4.09 | 120 | 495 |
| 7-1 | 2-26 | 841 | 3 | 1 | 4.05 | 121 | 490 |
| 7-1 | 2-26 | 686 | 1 | 1 | 4.16 | 120 | 540 |
| 7-1 | 2-26 | 686 | 2 | 1 | 4.1 | 120 | 530 |
| 7-1 | 2-26 | 686 | 3 | 1 | 4.05 | 121 | 525 |
| 7-1 | 2-50 | 206 | 1 | 1 | 4.13 | 120 | 490 |
| 7-1 | 2-50 | 206 | 2 | 1 | 4.09 | 120 | 480 |
| 7-1 | 2-50 | 206 | 3 | 1 | 4.05 | 121 | 475 |
| 7-1 | 2-50 | 841 | 1 | 1 | 4.13 | 120 | 530 |
| 7-1 | 2-50 | 841 | 2 | 1 | 4.09 | 120 | 525 |

TABLE 16-continued

| | Host | | Weight ratio | | DATA | | |
|---|---|---|---|---|---|---|---|
| EBL | PH | NH | PH | NH | V | Efficiency | L |
| 7-1 | 2-50 | 841 | 3 | 1 | 4.05 | 121 | 520 |
| 7-1 | 2-50 | 686 | 1 | 1 | 4.16 | 120 | 570 |
| 7-1 | 2-50 | 686 | 2 | 1 | 4.1 | 120 | 560 |
| 7-1 | 2-50 | 686 | 3 | 1 | 4.05 | 121 | 555 |
| 7-2 | 2-26 | 206 | 1 | 1 | 4.13 | 120 | 440 |
| 7-2 | 2-26 | 206 | 2 | 1 | 4.09 | 120 | 435 |
| 7-2 | 2-26 | 206 | 3 | 1 | 4.05 | 121 | 430 |
| 7-2 | 2-26 | 841 | 1 | 1 | 4.13 | 120 | 475 |
| 7-2 | 2-26 | 841 | 2 | 1 | 4.09 | 120 | 465 |
| 7-2 | 2-26 | 841 | 3 | 1 | 4.05 | 121 | 460 |
| 7-2 | 2-26 | 686 | 1 | 1 | 4.16 | 120 | 510 |
| 7-2 | 2-26 | 686 | 2 | 1 | 4.1 | 120 | 505 |
| 7-2 | 2-26 | 686 | 3 | 1 | 4.05 | 121 | 495 |
| 7-2 | 2-50 | 206 | 1 | 1 | 4.13 | 120 | 460 |
| 7-2 | 2-50 | 206 | 2 | 1 | 4.09 | 120 | 450 |
| 7-2 | 2-50 | 206 | 3 | 1 | 4.05 | 121 | 445 |
| 7-2 | 2-50 | 841 | 1 | 1 | 4.13 | 120 | 495 |
| 7-2 | 2-50 | 841 | 2 | 1 | 4.09 | 120 | 490 |
| 7-2 | 2-50 | 841 | 3 | 1 | 4.05 | 121 | 480 |
| 7-2 | 2-50 | 686 | 1 | 1 | 4.16 | 120 | 530 |
| 7-2 | 2-50 | 686 | 2 | 1 | 4.1 | 120 | 525 |
| 7-2 | 2-50 | 686 | 3 | 1 | 4.05 | 121 | 520 |
| 7-3 | 2-26 | 206 | 1 | 1 | 4.13 | 120 | 490 |
| 7-3 | 2-26 | 206 | 2 | 1 | 4.09 | 120 | 480 |
| 7-3 | 2-26 | 206 | 3 | 1 | 4.05 | 121 | 475 |
| 7-3 | 2-26 | 841 | 1 | 1 | 4.13 | 120 | 530 |
| 7-3 | 2-26 | 841 | 2 | 1 | 4.09 | 120 | 525 |
| 7-3 | 2-26 | 841 | 3 | 1 | 4.05 | 121 | 520 |
| 7-3 | 2-26 | 686 | 1 | 1 | 4.16 | 120 | 570 |
| 7-3 | 2-26 | 686 | 2 | 1 | 4.1 | 120 | 560 |
| 7-3 | 2-26 | 686 | 3 | 1 | 4.05 | 121 | 555 |
| 7-3 | 2-50 | 206 | 1 | 1 | 4.13 | 120 | 515 |
| 7-3 | 2-50 | 206 | 2 | 1 | 4.09 | 120 | 510 |
| 7-3 | 2-50 | 206 | 3 | 1 | 4.05 | 121 | 505 |
| 7-3 | 2-50 | 841 | 1 | 1 | 4.13 | 120 | 555 |
| 7-3 | 2-50 | 841 | 2 | 1 | 4.09 | 120 | 545 |
| 7-3 | 2-50 | 841 | 3 | 1 | 4.05 | 121 | 540 |
| 7-3 | 2-50 | 686 | 1 | 1 | 4.16 | 120 | 590 |
| 7-3 | 2-50 | 686 | 2 | 1 | 4.1 | 120 | 585 |
| 7-3 | 2-50 | 686 | 3 | 1 | 4.05 | 121 | 575 |
| Ref9 | 2-78 | 1113 | 1 | 1 | 3.8 | 122 | 265 |
| Ref9 | 2-78 | 1113 | 2 | 1 | 3.75 | 122 | 260 |
| Ref9 | 2-78 | 1113 | 3 | 1 | 3.7 | 123 | 255 |
| Ref9 | 2-78 | 206 | 1 | 1 | 3.78 | 122 | 345 |
| Ref9 | 2-78 | 206 | 2 | 1 | 3.74 | 122 | 340 |
| Ref9 | 2-78 | 206 | 3 | 1 | 3.7 | 123 | 335 |
| Ref9 | 2-78 | 274 | 1 | 1 | 3.81 | 122 | 278 |
| Ref9 | 2-78 | 274 | 2 | 1 | 3.75 | 122 | 272 |
| Ref9 | 2-78 | 274 | 3 | 1 | 3.7 | 123 | 267 |
| Ref9 | 2-78 | 330 | 1 | 1 | 3.82 | 122 | 295 |
| Ref9 | 2-78 | 330 | 2 | 1 | 3.76 | 122 | 290 |
| Ref9 | 2-78 | 330 | 3 | 1 | 3.7 | 123 | 284 |
| Ref9 | 2-78 | 841 | 1 | 1 | 3.77 | 122 | 370 |
| Ref9 | 2-78 | 841 | 2 | 1 | 3.73 | 122 | 365 |
| Ref9 | 2-78 | 841 | 3 | 1 | 3.69 | 123 | 360 |
| Ref9 | 2-78 | 973 | 1 | 1 | 3.82 | 122 | 300 |
| Ref9 | 2-78 | 973 | 2 | 1 | 3.76 | 122 | 295 |
| Ref9 | 2-78 | 973 | 3 | 1 | 3.7 | 123 | 290 |
| Ref9 | 2-78 | 686 | 1 | 1 | 3.8 | 122 | 400 |
| Ref9 | 2-78 | 686 | 2 | 1 | 3.75 | 122 | 395 |
| Ref9 | 2-78 | 686 | 3 | 1 | 3.7 | 123 | 390 |
| Ref9 | 2-2 | 1113 | 1 | 1 | 3.8 | 122 | 270 |
| Ref9 | 2-2 | 1113 | 2 | 1 | 3.75 | 122 | 265 |
| Ref9 | 2-2 | 1113 | 3 | 1 | 3.7 | 123 | 260 |
| Ref9 | 2-2 | 206 | 1 | 1 | 3.78 | 122 | 355 |
| Ref9 | 2-2 | 206 | 2 | 1 | 3.74 | 122 | 350 |
| Ref9 | 2-2 | 206 | 3 | 1 | 3.7 | 123 | 345 |
| Ref9 | 2-2 | 274 | 1 | 1 | 3.81 | 122 | 284 |
| Ref9 | 2-2 | 274 | 2 | 1 | 3.75 | 122 | 278 |
| Ref9 | 2-2 | 274 | 3 | 1 | 3.7 | 123 | 272 |
| Ref9 | 2-2 | 330 | 1 | 1 | 3.82 | 122 | 300 |
| Ref9 | 2-2 | 330 | 2 | 1 | 3.76 | 122 | 295 |
| Ref9 | 2-2 | 330 | 3 | 1 | 3.7 | 123 | 290 |
| Ref9 | 2-2 | 841 | 1 | 1 | 3.77 | 122 | 380 |
| Ref9 | 2-2 | 841 | 2 | 1 | 3.73 | 122 | 375 |
| Ref9 | 2-2 | 841 | 3 | 1 | 3.69 | 123 | 370 |

TABLE 16-continued

| | Host | | Weight ratio | | DATA | | |
|---|---|---|---|---|---|---|---|
| EBL | PH | NH | PH | NH | V | Efficiency | L |
| Ref9 | 2-2 | 973 | 1 | 1 | 3.82 | 122 | 300 |
| Ref9 | 2-2 | 973 | 2 | 1 | 3.76 | 122 | 295 |
| Ref9 | 2-2 | 973 | 3 | 1 | 3.7 | 123 | 290 |
| Ref9 | 2-2 | 686 | 1 | 1 | 3.8 | 122 | 405 |
| Ref9 | 2-2 | 686 | 2 | 1 | 3.75 | 122 | 400 |
| Ref9 | 2-2 | 686 | 3 | 1 | 3.7 | 123 | 395 |
| Ref9 | 2-26 | 1113 | 1 | 1 | 3.8 | 122 | 295 |
| Ref9 | 2-26 | 1113 | 2 | 1 | 3.75 | 122 | 290 |
| Ref9 | 2-26 | 1113 | 3 | 1 | 3.7 | 123 | 285 |
| Ref9 | 2-26 | 206 | 1 | 1 | 3.78 | 122 | 380 |
| Ref9 | 2-26 | 206 | 2 | 1 | 3.74 | 122 | 375 |
| Ref9 | 2-26 | 206 | 3 | 1 | 3.7 | 123 | 370 |
| Ref9 | 2-26 | 274 | 1 | 1 | 3.81 | 122 | 305 |
| Ref9 | 2-26 | 274 | 2 | 1 | 3.75 | 122 | 300 |
| Ref9 | 2-26 | 274 | 3 | 1 | 3.7 | 123 | 295 |
| Ref9 | 2-26 | 330 | 1 | 1 | 3.82 | 122 | 320 |
| Ref9 | 2-26 | 330 | 2 | 1 | 3.76 | 122 | 315 |
| Ref9 | 2-26 | 330 | 3 | 1 | 3.7 | 123 | 310 |
| Ref9 | 2-26 | 841 | 1 | 1 | 3.77 | 122 | 410 |
| Ref9 | 2-26 | 841 | 2 | 1 | 3.73 | 122 | 405 |
| Ref9 | 2-26 | 841 | 3 | 1 | 3.69 | 123 | 400 |
| Ref9 | 2-26 | 973 | 1 | 1 | 3.82 | 122 | 325 |
| Ref9 | 2-26 | 973 | 2 | 1 | 3.76 | 122 | 320 |
| Ref9 | 2-26 | 973 | 3 | 1 | 3.7 | 123 | 315 |
| Ref9 | 2-26 | 686 | 1 | 1 | 3.8 | 122 | 435 |
| Ref9 | 2-26 | 686 | 2 | 1 | 3.75 | 122 | 430 |
| Ref9 | 2-26 | 686 | 3 | 1 | 3.7 | 123 | 425 |
| Ref9 | 2-50 | 1113 | 1 | 1 | 3.8 | 122 | 300 |
| Ref9 | 2-50 | 1113 | 2 | 1 | 3.75 | 122 | 295 |
| Ref9 | 2-50 | 1113 | 3 | 1 | 3.7 | 123 | 290 |
| Ref9 | 2-50 | 206 | 1 | 1 | 3.78 | 122 | 400 |
| Ref9 | 2-50 | 206 | 2 | 1 | 3.74 | 122 | 395 |
| Ref9 | 2-50 | 206 | 3 | 1 | 3.7 | 123 | 390 |
| Ref9 | 2-50 | 274 | 1 | 1 | 3.81 | 122 | 320 |
| Ref9 | 2-50 | 274 | 2 | 1 | 3.75 | 122 | 315 |
| Ref9 | 2-50 | 274 | 3 | 1 | 3.7 | 123 | 310 |
| Ref9 | 2-50 | 330 | 1 | 1 | 3.82 | 122 | 335 |
| Ref9 | 2-50 | 330 | 2 | 1 | 3.76 | 122 | 328 |
| Ref9 | 2-50 | 330 | 3 | 1 | 3.7 | 123 | 322 |
| Ref9 | 2-50 | 841 | 1 | 1 | 3.77 | 122 | 430 |
| Ref9 | 2-50 | 841 | 2 | 1 | 3.73 | 122 | 425 |
| Ref9 | 2-50 | 841 | 3 | 1 | 3.69 | 123 | 420 |
| Ref9 | 2-50 | 973 | 1 | 1 | 3.82 | 122 | 340 |
| Ref9 | 2-50 | 973 | 2 | 1 | 3.76 | 122 | 335 |
| Ref9 | 2-50 | 973 | 3 | 1 | 3.7 | 123 | 328 |
| Ref9 | 2-50 | 686 | 1 | 1 | 3.8 | 122 | 455 |
| Ref9 | 2-50 | 686 | 2 | 1 | 3.75 | 122 | 450 |
| Ref9 | 2-50 | 686 | 3 | 1 | 3.7 | 123 | 445 |
| 9-1 | 2-78 | 1113 | 1 | 1 | 3.8 | 122 | 290 |
| 9-1 | 2-78 | 1113 | 2 | 1 | 3.75 | 122 | 284 |
| 9-1 | 2-78 | 1113 | 3 | 1 | 3.7 | 123 | 278 |
| 9-1 | 2-78 | 206 | 1 | 1 | 3.78 | 122 | 385 |
| 9-1 | 2-78 | 206 | 2 | 1 | 3.74 | 122 | 380 |
| 9-1 | 2-78 | 206 | 3 | 1 | 3.7 | 123 | 374 |
| 9-1 | 2-78 | 274 | 1 | 1 | 3.81 | 122 | 305 |
| 9-1 | 2-78 | 274 | 2 | 1 | 3.75 | 122 | 300 |
| 9-1 | 2-78 | 274 | 3 | 1 | 3.7 | 123 | 295 |
| 9-1 | 2-78 | 330 | 1 | 1 | 3.82 | 122 | 320 |
| 9-1 | 2-78 | 330 | 2 | 1 | 3.76 | 122 | 315 |
| 9-1 | 2-78 | 330 | 3 | 1 | 3.7 | 123 | 310 |
| 9-1 | 2-78 | 841 | 1 | 1 | 3.77 | 122 | 410 |
| 9-1 | 2-78 | 841 | 2 | 1 | 3.73 | 122 | 405 |
| 9-1 | 2-78 | 841 | 3 | 1 | 3.69 | 123 | 400 |
| 9-1 | 2-78 | 973 | 1 | 1 | 3.82 | 122 | 325 |
| 9-1 | 2-78 | 973 | 2 | 1 | 3.76 | 122 | 320 |
| 9-1 | 2-78 | 973 | 3 | 1 | 3.7 | 123 | 315 |
| 9-1 | 2-78 | 686 | 1 | 1 | 3.8 | 122 | 435 |
| 9-1 | 2-78 | 686 | 2 | 1 | 3.75 | 122 | 430 |
| 9-1 | 2-78 | 686 | 3 | 1 | 3.7 | 123 | 425 |
| 9-1 | 2-2 | 1113 | 1 | 1 | 3.8 | 122 | 295 |
| 9-1 | 2-2 | 1113 | 2 | 1 | 3.75 | 122 | 290 |
| 9-1 | 2-2 | 1113 | 3 | 1 | 3.7 | 123 | 285 |
| 9-1 | 2-2 | 206 | 1 | 1 | 3.78 | 122 | 390 |
| 9-1 | 2-2 | 206 | 2 | 1 | 3.74 | 122 | 385 |
| 9-1 | 2-2 | 206 | 3 | 1 | 3.7 | 123 | 380 |
| 9-1 | 2-2 | 274 | 1 | 1 | 3.81 | 122 | 310 |

TABLE 16-continued

| | Host | | Weight ratio | | DATA | | |
|---|---|---|---|---|---|---|---|
| EBL | PH | NH | PH | NH | V | Efficiency | L |
| 9-1 | 2-2 | 274 | 2 | 1 | 3.75 | 122 | 305 |
| 9-1 | 2-2 | 274 | 3 | 1 | 3.7 | 123 | 300 |
| 9-1 | 2-2 | 330 | 1 | 1 | 3.82 | 122 | 325 |
| 9-1 | 2-2 | 330 | 2 | 1 | 3.76 | 122 | 320 |
| 9-1 | 2-2 | 330 | 3 | 1 | 3.7 | 123 | 315 |
| 9-1 | 2-2 | 841 | 1 | 1 | 3.77 | 122 | 415 |
| 9-1 | 2-2 | 841 | 2 | 1 | 3.73 | 122 | 410 |
| 9-1 | 2-2 | 841 | 3 | 1 | 3.69 | 123 | 405 |
| 9-1 | 2-2 | 973 | 1 | 1 | 3.82 | 122 | 330 |
| 9-1 | 2-2 | 973 | 2 | 1 | 3.76 | 122 | 325 |
| 9-1 | 2-2 | 973 | 3 | 1 | 3.7 | 123 | 320 |
| 9-1 | 2-2 | 686 | 1 | 1 | 3.8 | 122 | 445 |
| 9-1 | 2-2 | 686 | 2 | 1 | 3.75 | 122 | 440 |
| 9-1 | 2-2 | 686 | 3 | 1 | 3.7 | 123 | 435 |
| 9-1 | 2-26 | 1113 | 1 | 1 | 3.8 | 122 | 320 |
| 9-1 | 2-26 | 1113 | 2 | 1 | 3.75 | 122 | 315 |
| 9-1 | 2-26 | 1113 | 3 | 1 | 3.7 | 123 | 310 |
| 9-1 | 2-26 | 274 | 1 | 1 | 3.81 | 122 | 335 |
| 9-1 | 2-26 | 274 | 2 | 1 | 3.75 | 122 | 328 |
| 9-1 | 2-26 | 274 | 3 | 1 | 3.7 | 123 | 322 |
| 9-1 | 2-26 | 330 | 1 | 1 | 3.82 | 122 | 350 |
| 9-1 | 2-26 | 330 | 2 | 1 | 3.76 | 122 | 345 |
| 9-1 | 2-26 | 330 | 3 | 1 | 3.7 | 123 | 340 |
| 9-1 | 2-26 | 973 | 1 | 1 | 3.82 | 122 | 355 |
| 9-1 | 2-26 | 973 | 2 | 1 | 3.76 | 122 | 350 |
| 9-1 | 2-26 | 973 | 3 | 1 | 3.7 | 123 | 345 |
| 9-1 | 2-50 | 1113 | 1 | 1 | 3.8 | 122 | 335 |
| 9-1 | 2-50 | 1113 | 2 | 1 | 3.75 | 122 | 328 |
| 9-1 | 2-50 | 1113 | 3 | 1 | 3.7 | 123 | 322 |
| 9-1 | 2-50 | 274 | 1 | 1 | 3.81 | 122 | 350 |
| 9-1 | 2-50 | 274 | 2 | 1 | 3.75 | 122 | 345 |
| 9-1 | 2-50 | 274 | 3 | 1 | 3.7 | 123 | 340 |
| 9-1 | 2-50 | 330 | 1 | 1 | 3.82 | 122 | 365 |
| 9-1 | 2-50 | 330 | 2 | 1 | 3.76 | 122 | 360 |
| 9-1 | 2-50 | 330 | 3 | 1 | 3.7 | 123 | 355 |
| 9-1 | 2-50 | 973 | 1 | 1 | 3.82 | 122 | 375 |
| 9-1 | 2-50 | 973 | 2 | 1 | 3.76 | 122 | 370 |
| 9-1 | 2-50 | 973 | 3 | 1 | 3.7 | 123 | 365 |
| 9-2 | 2-78 | 1113 | 1 | 1 | 3.8 | 122 | 270 |
| 9-2 | 2-78 | 1113 | 2 | 1 | 3.75 | 122 | 265 |
| 9-2 | 2-78 | 1113 | 3 | 1 | 3.7 | 123 | 260 |
| 9-2 | 2-78 | 206 | 1 | 1 | 3.78 | 122 | 355 |
| 9-2 | 2-78 | 206 | 2 | 1 | 3.74 | 122 | 350 |
| 9-2 | 2-78 | 206 | 3 | 1 | 3.7 | 123 | 345 |
| 9-2 | 2-78 | 274 | 1 | 1 | 3.81 | 122 | 285 |
| 9-2 | 2-78 | 274 | 2 | 1 | 3.75 | 122 | 280 |
| 9-2 | 2-78 | 274 | 3 | 1 | 3.7 | 123 | 275 |
| 9-2 | 2-78 | 330 | 1 | 1 | 3.82 | 122 | 300 |
| 9-2 | 2-78 | 330 | 2 | 1 | 3.76 | 122 | 295 |
| 9-2 | 2-78 | 330 | 3 | 1 | 3.7 | 123 | 290 |
| 9-2 | 2-78 | 841 | 1 | 1 | 3.77 | 122 | 385 |
| 9-2 | 2-78 | 841 | 2 | 1 | 3.73 | 122 | 378 |
| 9-2 | 2-78 | 841 | 3 | 1 | 3.69 | 123 | 373 |
| 9-2 | 2-78 | 973 | 1 | 1 | 3.82 | 122 | 305 |
| 9-2 | 2-78 | 973 | 2 | 1 | 3.76 | 122 | 300 |
| 9-2 | 2-78 | 973 | 3 | 1 | 3.7 | 123 | 295 |
| 9-2 | 2-78 | 686 | 1 | 1 | 3.8 | 122 | 405 |
| 9-2 | 2-78 | 686 | 2 | 1 | 3.75 | 122 | 400 |
| 9-2 | 2-78 | 686 | 3 | 1 | 3.7 | 123 | 395 |
| 9-2 | 2-2 | 1113 | 1 | 1 | 3.8 | 122 | 275 |
| 9-2 | 2-2 | 1113 | 2 | 1 | 3.75 | 122 | 270 |
| 9-2 | 2-2 | 1113 | 3 | 1 | 3.7 | 123 | 265 |
| 9-2 | 2-2 | 206 | 1 | 1 | 3.78 | 122 | 365 |
| 9-2 | 2-2 | 206 | 2 | 1 | 3.74 | 122 | 360 |
| 9-2 | 2-2 | 206 | 3 | 1 | 3.7 | 123 | 355 |
| 9-2 | 2-2 | 274 | 1 | 1 | 3.81 | 122 | 290 |
| 9-2 | 2-2 | 274 | 2 | 1 | 3.75 | 122 | 284 |
| 9-2 | 2-2 | 274 | 3 | 1 | 3.7 | 123 | 278 |
| 9-2 | 2-2 | 330 | 1 | 1 | 3.82 | 122 | 305 |
| 9-2 | 2-2 | 330 | 2 | 1 | 3.76 | 122 | 300 |
| 9-2 | 2-2 | 330 | 3 | 1 | 3.7 | 123 | 295 |
| 9-2 | 2-2 | 841 | 1 | 1 | 3.77 | 122 | 390 |
| 9-2 | 2-2 | 841 | 2 | 1 | 3.73 | 122 | 385 |
| 9-2 | 2-2 | 841 | 3 | 1 | 3.69 | 123 | 380 |
| 9-2 | 2-2 | 973 | 1 | 1 | 3.82 | 122 | 310 |
| 9-2 | 2-2 | 973 | 2 | 1 | 3.76 | 122 | 305 |

TABLE 16-continued

| | Host | | Weight ratio | | DATA | | |
|---|---|---|---|---|---|---|---|
| EBL | PH | NH | PH | NH | V | Efficiency | L |
| 9-2 | 2-2 | 973 | 3 | 1 | 3.7 | 123 | 300 |
| 9-2 | 2-2 | 686 | 1 | 1 | 3.8 | 122 | 415 |
| 9-2 | 2-2 | 686 | 2 | 1 | 3.75 | 122 | 410 |
| 9-2 | 2-2 | 686 | 3 | 1 | 3.7 | 123 | 405 |
| 9-2 | 2-26 | 1113 | 1 | 1 | 3.8 | 122 | 300 |
| 9-2 | 2-26 | 1113 | 2 | 1 | 3.75 | 122 | 295 |
| 9-2 | 2-26 | 1113 | 3 | 1 | 3.7 | 123 | 290 |
| 9-2 | 2-26 | 274 | 1 | 1 | 3.81 | 122 | 315 |
| 9-2 | 2-26 | 274 | 2 | 1 | 3.75 | 122 | 310 |
| 9-2 | 2-26 | 274 | 3 | 1 | 3.7 | 123 | 305 |
| 9-2 | 2-26 | 330 | 1 | 1 | 3.82 | 122 | 330 |
| 9-2 | 2-26 | 330 | 2 | 1 | 3.76 | 122 | 325 |
| 9-2 | 2-26 | 330 | 3 | 1 | 3.7 | 123 | 320 |
| 9-2 | 2-26 | 973 | 1 | 1 | 3.82 | 122 | 336 |
| 9-2 | 2-26 | 973 | 2 | 1 | 3.76 | 122 | 331 |
| 9-2 | 2-26 | 973 | 3 | 1 | 3.7 | 123 | 326 |
| 9-2 | 2-50 | 1113 | 1 | 1 | 3.8 | 122 | 314 |
| 9-2 | 2-50 | 1113 | 2 | 1 | 3.75 | 122 | 308 |
| 9-2 | 2-50 | 1113 | 3 | 1 | 3.7 | 123 | 302 |
| 9-2 | 2-50 | 274 | 1 | 1 | 3.81 | 122 | 330 |
| 9-2 | 2-50 | 274 | 2 | 1 | 3.75 | 122 | 323 |
| 9-2 | 2-50 | 274 | 3 | 1 | 3.7 | 123 | 318 |
| 9-2 | 2-50 | 330 | 1 | 1 | 3.82 | 122 | 345 |
| 9-2 | 2-50 | 330 | 2 | 1 | 3.76 | 122 | 340 |
| 9-2 | 2-50 | 330 | 3 | 1 | 3.7 | 123 | 333 |
| 9-2 | 2-50 | 973 | 1 | 1 | 3.82 | 122 | 352 |
| 9-2 | 2-50 | 973 | 2 | 1 | 3.76 | 122 | 347 |
| 9-2 | 2-50 | 973 | 3 | 1 | 3.7 | 123 | 342 |
| 9-3 | 2-78 | 1113 | 1 | 1 | 3.8 | 122 | 305 |
| 9-3 | 2-78 | 1113 | 2 | 1 | 3.75 | 122 | 300 |
| 9-3 | 2-78 | 1113 | 3 | 1 | 3.7 | 123 | 295 |
| 9-3 | 2-78 | 206 | 1 | 1 | 3.78 | 122 | 396 |
| 9-3 | 2-78 | 206 | 2 | 1 | 3.74 | 122 | 391 |
| 9-3 | 2-78 | 206 | 3 | 1 | 3.7 | 123 | 386 |
| 9-3 | 2-78 | 274 | 1 | 1 | 3.81 | 122 | 320 |
| 9-3 | 2-78 | 274 | 2 | 1 | 3.75 | 122 | 315 |
| 9-3 | 2-78 | 274 | 3 | 1 | 3.7 | 123 | 310 |
| 9-3 | 2-78 | 330 | 1 | 1 | 3.82 | 122 | 335 |
| 9-3 | 2-78 | 330 | 2 | 1 | 3.76 | 122 | 330 |
| 9-3 | 2-78 | 330 | 3 | 1 | 3.7 | 123 | 325 |
| 9-3 | 2-78 | 841 | 1 | 1 | 3.77 | 122 | 427 |
| 9-3 | 2-78 | 841 | 2 | 1 | 3.73 | 122 | 422 |
| 9-3 | 2-78 | 841 | 3 | 1 | 3.69 | 123 | 417 |
| 9-3 | 2-78 | 973 | 1 | 1 | 3.82 | 122 | 341 |
| 9-3 | 2-78 | 973 | 2 | 1 | 3.76 | 122 | 336 |
| 9-3 | 2-78 | 973 | 3 | 1 | 3.7 | 123 | 331 |
| 9-3 | 2-78 | 686 | 1 | 1 | 3.8 | 122 | 457 |
| 9-3 | 2-78 | 686 | 2 | 1 | 3.75 | 122 | 452 |
| 9-3 | 2-78 | 686 | 3 | 1 | 3.7 | 123 | 447 |
| 9-3 | 2-2 | 1113 | 1 | 1 | 3.8 | 122 | 311 |
| 9-3 | 2-2 | 1113 | 2 | 1 | 3.75 | 122 | 306 |
| 9-3 | 2-2 | 1113 | 3 | 1 | 3.7 | 123 | 299 |
| 9-3 | 2-2 | 206 | 1 | 1 | 3.78 | 122 | 404 |
| 9-3 | 2-2 | 206 | 2 | 1 | 3.74 | 122 | 397 |
| 9-3 | 2-2 | 206 | 3 | 1 | 3.7 | 123 | 393 |
| 9-3 | 2-2 | 274 | 1 | 1 | 3.81 | 122 | 326 |
| 9-3 | 2-2 | 274 | 2 | 1 | 3.75 | 122 | 321 |
| 9-3 | 2-2 | 274 | 3 | 1 | 3.7 | 123 | 316 |
| 9-3 | 2-2 | 330 | 1 | 1 | 3.82 | 122 | 342 |
| 9-3 | 2-2 | 330 | 2 | 1 | 3.76 | 122 | 337 |
| 9-3 | 2-2 | 330 | 3 | 1 | 3.7 | 123 | 332 |
| 9-3 | 2-2 | 841 | 1 | 1 | 3.77 | 122 | 435 |
| 9-3 | 2-2 | 841 | 2 | 1 | 3.73 | 122 | 430 |
| 9-3 | 2-2 | 841 | 3 | 1 | 3.69 | 123 | 425 |
| 9-3 | 2-2 | 973 | 1 | 1 | 3.82 | 122 | 348 |
| 9-3 | 2-2 | 973 | 2 | 1 | 3.76 | 122 | 343 |
| 9-3 | 2-2 | 973 | 3 | 1 | 3.7 | 123 | 336 |
| 9-3 | 2-2 | 686 | 1 | 1 | 3.8 | 122 | 466 |
| 9-3 | 2-2 | 686 | 2 | 1 | 3.75 | 122 | 461 |
| 9-3 | 2-2 | 686 | 3 | 1 | 3.7 | 123 | 456 |
| 9-3 | 2-26 | 1113 | 1 | 1 | 3.8 | 122 | 335 |
| 9-3 | 2-26 | 1113 | 2 | 1 | 3.75 | 122 | 330 |
| 9-3 | 2-26 | 1113 | 3 | 1 | 3.7 | 123 | 325 |
| 9-3 | 2-26 | 274 | 1 | 1 | 3.81 | 122 | 352 |
| 9-3 | 2-26 | 274 | 2 | 1 | 3.75 | 122 | 347 |
| 9-3 | 2-26 | 274 | 3 | 1 | 3.7 | 123 | 342 |

TABLE 16-continued

| | Host | | Weight ratio | | DATA | | |
|---|---|---|---|---|---|---|---|
| EBL | PH | NH | PH | NH | V | Efficiency | L |
| 9-3 | 2-26 | 330 | 1 | 1 | 3.82 | 122 | 369 |
| 9-3 | 2-26 | 330 | 2 | 1 | 3.76 | 122 | 364 |
| 9-3 | 2-26 | 330 | 3 | 1 | 3.7 | 123 | 359 |
| 9-3 | 2-26 | 973 | 1 | 1 | 3.82 | 122 | 375 |
| 9-3 | 2-26 | 973 | 2 | 1 | 3.76 | 122 | 370 |
| 9-3 | 2-26 | 973 | 3 | 1 | 3.7 | 123 | 365 |
| 9-3 | 2-50 | 1113 | 1 | 1 | 3.8 | 122 | 350 |
| 9-3 | 2-50 | 1113 | 2 | 1 | 3.75 | 122 | 345 |
| 9-3 | 2-50 | 1113 | 3 | 1 | 3.7 | 123 | 340 |
| 9-3 | 2-50 | 274 | 1 | 1 | 3.81 | 122 | 368 |
| 9-3 | 2-50 | 274 | 2 | 1 | 3.75 | 122 | 363 |
| 9-3 | 2-50 | 274 | 3 | 1 | 3.7 | 123 | 358 |
| 9-3 | 2-50 | 330 | 1 | 1 | 3.82 | 122 | 386 |
| 9-3 | 2-50 | 330 | 2 | 1 | 3.76 | 122 | 380 |
| 9-3 | 2-50 | 330 | 3 | 1 | 3.7 | 123 | 373 |
| 9-3 | 2-50 | 973 | 1 | 1 | 3.82 | 122 | 393 |
| 9-3 | 2-50 | 973 | 2 | 1 | 3.76 | 122 | 388 |
| 9-3 | 2-50 | 973 | 3 | 1 | 3.7 | 123 | 383 |
| 9-1 | 2-26 | 206 | 1 | 1 | 3.78 | 122 | 420 |
| 9-1 | 2-26 | 206 | 2 | 1 | 3.74 | 122 | 415 |
| 9-1 | 2-26 | 206 | 3 | 1 | 3.7 | 123 | 410 |
| 9-1 | 2-26 | 841 | 1 | 1 | 3.77 | 122 | 450 |
| 9-1 | 2-26 | 841 | 2 | 1 | 3.73 | 122 | 445 |
| 9-1 | 2-26 | 841 | 3 | 1 | 3.69 | 123 | 440 |
| 9-1 | 2-26 | 686 | 1 | 1 | 3.8 | 122 | 480 |
| 9-1 | 2-26 | 686 | 2 | 1 | 3.75 | 122 | 475 |
| 9-1 | 2-26 | 686 | 3 | 1 | 3.7 | 123 | 470 |
| 9-1 | 2-50 | 206 | 1 | 1 | 3.78 | 122 | 440 |
| 9-1 | 2-50 | 206 | 2 | 1 | 3.74 | 122 | 435 |
| 9-1 | 2-50 | 206 | 3 | 1 | 3.7 | 123 | 430 |
| 9-1 | 2-50 | 841 | 1 | 1 | 3.77 | 122 | 470 |
| 9-1 | 2-50 | 841 | 2 | 1 | 3.73 | 122 | 465 |
| 9-1 | 2-50 | 841 | 3 | 1 | 3.69 | 123 | 459 |
| 9-1 | 2-50 | 686 | 1 | 1 | 3.8 | 122 | 500 |
| 9-1 | 2-50 | 686 | 2 | 1 | 3.75 | 122 | 495 |
| 9-1 | 2-50 | 686 | 3 | 1 | 3.7 | 123 | 490 |
| 9-2 | 2-26 | 206 | 1 | 1 | 3.78 | 122 | 390 |
| 9-2 | 2-26 | 206 | 2 | 1 | 3.74 | 122 | 385 |
| 9-2 | 2-26 | 206 | 3 | 1 | 3.7 | 123 | 380 |
| 9-2 | 2-26 | 841 | 1 | 1 | 3.77 | 122 | 420 |
| 9-2 | 2-26 | 841 | 2 | 1 | 3.73 | 122 | 415 |
| 9-2 | 2-26 | 841 | 3 | 1 | 3.69 | 123 | 410 |
| 9-2 | 2-26 | 686 | 1 | 1 | 3.8 | 122 | 450 |
| 9-2 | 2-26 | 686 | 2 | 1 | 3.75 | 122 | 445 |
| 9-2 | 2-26 | 686 | 3 | 1 | 3.7 | 123 | 440 |
| 9-2 | 2-50 | 206 | 1 | 1 | 3.78 | 122 | 408 |
| 9-2 | 2-50 | 206 | 2 | 1 | 3.74 | 122 | 403 |
| 9-2 | 2-50 | 206 | 3 | 1 | 3.7 | 123 | 398 |
| 9-2 | 2-50 | 841 | 1 | 1 | 3.77 | 122 | 439 |
| 9-2 | 2-50 | 841 | 2 | 1 | 3.73 | 122 | 434 |
| 9-2 | 2-50 | 841 | 3 | 1 | 3.69 | 123 | 429 |
| 9-2 | 2-50 | 686 | 1 | 1 | 3.8 | 122 | 471 |
| 9-2 | 2-50 | 686 | 2 | 1 | 3.75 | 122 | 466 |
| 9-2 | 2-50 | 686 | 3 | 1 | 3.7 | 123 | 461 |
| 9-3 | 2-26 | 206 | 1 | 1 | 3.78 | 122 | 436 |
| 9-3 | 2-26 | 206 | 2 | 1 | 3.74 | 122 | 430 |
| 9-3 | 2-26 | 206 | 3 | 1 | 3.7 | 123 | 424 |
| 9-3 | 2-26 | 841 | 1 | 1 | 3.77 | 122 | 469 |
| 9-3 | 2-26 | 841 | 2 | 1 | 3.73 | 122 | 464 |
| 9-3 | 2-26 | 841 | 3 | 1 | 3.69 | 123 | 459 |
| 9-3 | 2-26 | 686 | 1 | 1 | 3.8 | 122 | 503 |
| 9-3 | 2-26 | 686 | 2 | 1 | 3.75 | 122 | 498 |
| 9-3 | 2-26 | 686 | 3 | 1 | 3.7 | 123 | 493 |
| 9-3 | 2-50 | 206 | 1 | 1 | 3.78 | 122 | 456 |
| 9-3 | 2-50 | 206 | 2 | 1 | 3.74 | 122 | 451 |
| 9-3 | 2-50 | 206 | 3 | 1 | 3.7 | 123 | 446 |
| 9-3 | 2-50 | 841 | 1 | 1 | 3.77 | 122 | 491 |
| 9-3 | 2-50 | 841 | 2 | 1 | 3.73 | 122 | 486 |

TABLE 16-continued

| | Host | | Weight ratio | | DATA | | |
|---|---|---|---|---|---|---|---|
| EBL | PH | NH | PH | NH | V | Efficiency | L |
| 9-3 | 2-50 | 841 | 3 | 1 | 3.69 | 123 | 481 |
| 9-3 | 2-50 | 686 | 1 | 1 | 3.8 | 122 | 526 |
| 9-3 | 2-50 | 686 | 2 | 1 | 3.75 | 122 | 521 |
| 9-3 | 2-50 | 686 | 3 | 1 | 3.7 | 123 | 515 |

Referring to Table 15, the compounds EBL_Ref1, EBL_Ref7 and EBL_Ref9 are anon-deuterated compound, the compounds EBL1-1, EBL1-2, EBL1-3, EBL7-1, EBL7-2, EBL7-3, EBL9-1, EBL9-2 and EBL9-3 are a partially-deuterated compound or a wholly-deuterated compound.

As shown in Table 16, in comparison to the OLEDs using the compounds EBL_Ref1, EBL_Ref7 and EBL_Ref9 in the EBL, the lifespan of the OLEDs using the compounds EBL1-1, EBL1-2, EBL1-3, EBL7-1, EBL7-2, EBL7-3, EBL9-1, EBL9-2 and EBL9-3 is significantly increased.

Namely, when the EBL includes the compound of Formula 10, which is partially or wholly deuterated, the lifespan of the OLED is significantly increased.

In addition, in comparison to the OLEDs using the compounds EBL1-2, 7-2 and 9-2, the lifespan of the OLEDs using the compounds EBL1-1, EBL7-1 and EBL9-1 is increased. Namely, although the compounds EBL1-1, EBL7-1 and EBL9-1 have the deuteration ratio being smaller than the compounds EBL1-2, 7-2 and 9-2, respectively, the lifespan of the OLED using the compounds EBL1-1, EBL7-1 and EBL9-1 is increased because the fluorene moiety or the spiro-fluorene moiety in the compounds EBL1-1, EBL7-1 and EBL9-1 is deuterated.

In other words, when the compound of Formula 10, where the fluorene moiety or the spiro-fluorene moiety is deuterated, is used for the electron blocking layer, the OLED has a sufficient lifespan with minimizing the increase of the production cost by the deuterium atom.

Moreover, in comparison to the OLEDs using the compound 1113, the lifespan of the OLEDs using the compounds 206, 274, 330, 841, 973, 686 is increased.

Namely, when the first compound "NH" being partially or wholly deuterated is used, the lifespan of the OLED is increased.

Further, in comparison to the OLEDs using the compound 973 as the first host "NH", the lifespan of the OLEDs using the compound 206 as the first host "NH" is increased. Namely, although the compound 206 has the deuteration ratio being smaller than the compound 973, the lifespan of the OLED using the compound 206 is increased because the carbazole moiety in the compound 206 is deuterated.

In other words, when the compound of Formula 1, where the carbazole moiety or the fused-carbazole moiety is deuterated, is used for the first host of the green EML, the OLED has a sufficient lifespan with minimizing the increase of the production cost by the deuterium atom.

In addition, when the deuteration ratio of the first compound "NH" is greater than that of the second compound "PH", the lifespan of the OLED is increased. For example, in comparison to the OLED using the compound 1113 having the deuteration ratio of 0% and the compound 2-26 having the deuteration ratio of 44%, the lifespan of the OLED using the compound 206 having the deuteration ration of 43% and the compound 2-78 having the deuteration ratio of 0% is increased.

It will be apparent to those skilled in the art that various modifications and variations can be made in the embodiments of the present disclosure without departing from the spirit or scope of the present disclosure. Thus, it is intended that the modifications and variations cover this disclosure provided they come within the scope of the appended claims and their equivalents.

What is claimed is:

1. An organic light emitting device, comprising:

a first electrode;

a second electrode facing the first electrode;

a first emitting material layer between the first and second electrodes; and a first electron blocking layer between the first emitting material layer and the first electrode, wherein one or more of the at least one organic material layer includes a first compound and a second compound, wherein the first compound is represented by Formula 1:

[Formula 1]

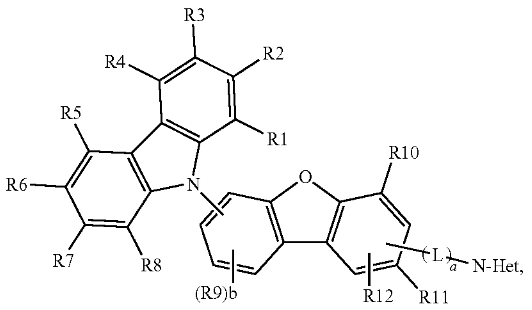

wherein N-Het is substituted or unsubstituted and a monocyclic or polycyclic C2 to C60 heterocyclic group having at least one nitrogen atom, wherein L is a direct bond, a substituted or unsubstituted C6 to C60 arylene group or a substituted or unsubstituted C2 to C60 heteroarylene group, and a is an integer of 1 to 3, wherein when a is 2 or more, two or more L are same or different, wherein R1 to R12 are same or different, wherein each of R1 to R12 is independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —P(═O)RR'; —SiRR'R"; and —NRR', or adjacent two or more of R1 to R12 are bonded to each other to form a substituted or unsubstituted C6 to C60 aromatic hydrocarbon ring or a substituted or unsubstituted C2 to C60 heterocyclic ring, wherein b is an integer of 1 to 3, wherein when b is 2 or more, two or more R9 are the same as or different, wherein R, R' and R" are the same or different, wherein each of R, R' and R" is independently selected from the group consisting of a substituted or unsubstituted C1 to C60 alkyl group; a substituted or unsubstituted C6 to C60 aryl group; or a substituted or unsubstituted C2 to C60 a heteroaryl group, wherein a deuteration ratio of the heterocyclic compound is 20% to 100%, wherein the second compound is represented by Formula 2:

[Formula 2]

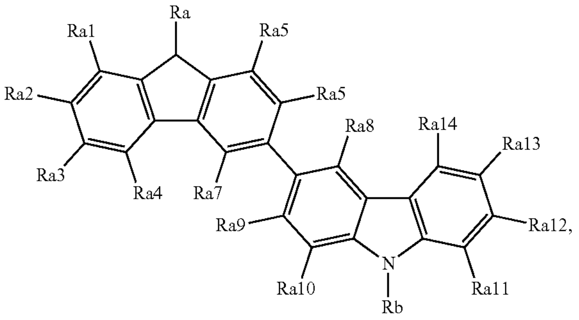

wherein Ra and Rb are same or different, and each of Ra and Rb is independently a substituted or unsubstituted C6 to C60 aryl group or a substituted or unsubstituted C2 to C60 heteroaryl group, wherein Ra1 to Ra14 are same or different, and wherein each of Ra1 to Ra14 is independently selected from the group consisting of hydrogen; deuterium; halogen; a cyano group; a substituted or unsubstituted C1 to C60 alkyl group; a substituted or unsubstituted C6 to C60 aryl group and a substituted or unsubstituted C2 to C60 heteroaryl group, or adjacent two or more of Ra1 to Ra14 are bonded to each other to form a substituted or unsubstituted C6 to C60 aromatic hydrocarbon ring or a substituted or unsubstituted C2 to C60 heterocyclic ring, wherein the electron blocking layer includes a first electron blocking material represented by Formula 10:

[Formula 10]

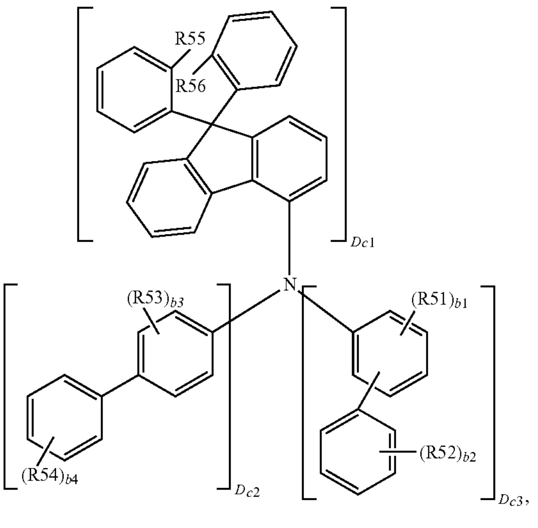

wherein each of R51 and R52 is independently a substituted or unsubstituted C1 to C10 alkyl, or adjacent two of R51 and R52 is connected to form a ring, wherein b1 is an integer of 0 to 4, and b2 is an integer of 0 to 5, wherein each of R53 and R54 is independently a substituted or unsubstituted C1 to C10 alkyl, or adjacent two of R53 and R54 is connected to form a ring, wherein b3 is an integer of 0 to 4, and b4 is an integer of 0 to 5, wherein each of R55 and R56 is hydrogen, or adjacent two of R55 and R56 is connected to form a ring, wherein each of c1, c2 and c3 is independently 0 or a positive integer, and at least one of c1, c2 and c3 is the positive integer, and wherein Dc1, Dc2 and Dc3 refer the number of hydrogens replaced with deuterium.

2. The organic light emitting device according to claim 1, wherein the at least one organic material layer includes an emitting material layer, and the emitting material layer includes the first compound.

3. The organic light emitting device according to claim 1, wherein the at least one organic material layer includes an electron auxiliary layer, and the electron auxiliary layer includes the first compound.

4. The organic light emitting device according to claim 1, wherein the at least one organic material layer includes a hole blocking layer, and the hole blocking layer includes the first compound.

5. The organic light emitting device according to claim 1, wherein a deuteration ratio of the second compound is 20% to 100%.

6. The organic light emitting device according to claim 1, wherein c1 is the positive integer, and c2 and c3 are 0.

7. The organic light emitting device according to claim 1, wherein the first emitting material layer further includes a third compound represented by Formula 12:

[Formula 12]

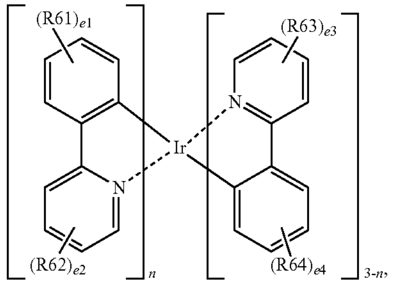

wherein each of R61, R62, R63 and R64 is independently selected from the group consisting of a substituted or unsubstituted C1 to C10 alkyl group, a substituted or unsubstituted C6 to C30 aryl group and a substituted or unsubstituted C3 to C30 heteroaryl group, and wherein each of e1, e2, e3 and e4 is independently an integer of 0 to 4, and n is an integer of 1 to 3.

8. The organic light emitting device according to claim 7, wherein the third compound is one of compounds in Formula 13:

[Formula 13]

GD1

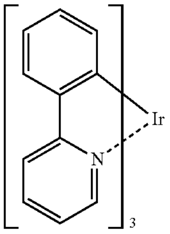

-continued

GD2

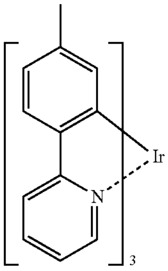

GD3

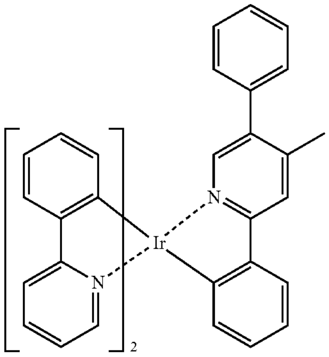

GD4

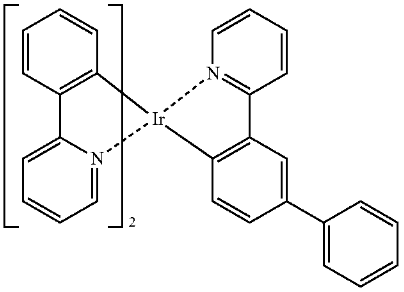

GD5

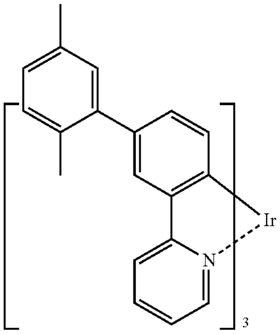

GD6

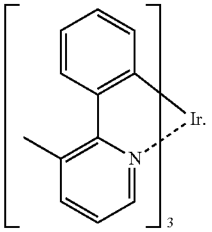

9. The organic light emitting device according to claim 1, wherein the at least one organic material layer further includes a second emitting material layer between the first emitting material layer and the second electrode and a second electron blocking layer between the first and second emitting material layers.

10. The organic light emitting device according to claim 1, wherein a deuteration ratio of the first compound is greater than that of the second compound.

11. The organic light emitting device according to claim 1, wherein Formula 1 is represented by one of Formulas 3 to 6:

[Formula 3]

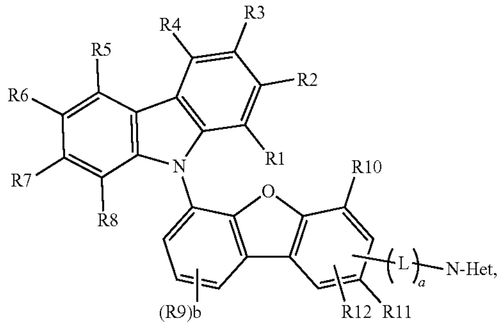

[Formula 4]

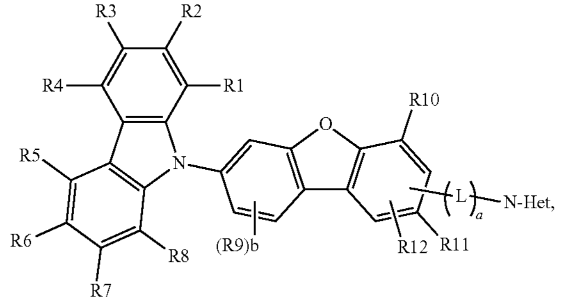

[Formula 5]

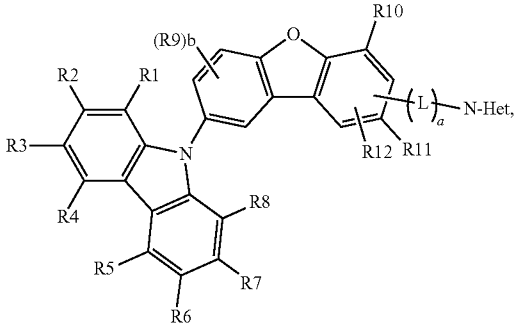

and

[Formula 6]

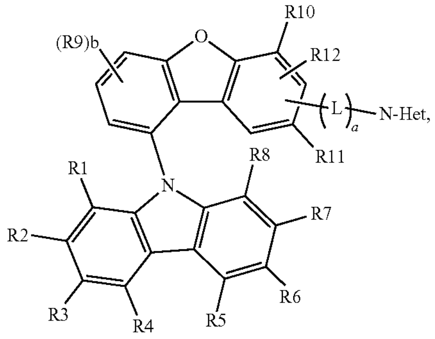

wherein the definitions of N-Het, R1 to R12, L, a, and b are same as those in Formula 1.

12. The organic light emitting device according to claim 1, wherein Formula 1 is represented by one of Formula 7 or Formula 8:

[Formula 7]

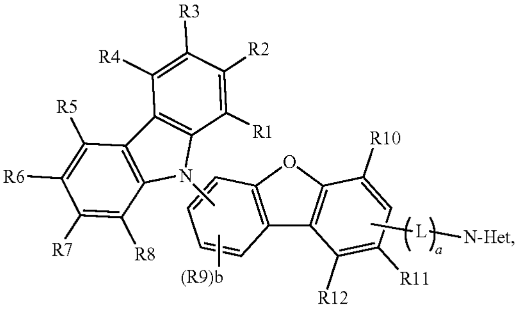

and

[Formula 8]

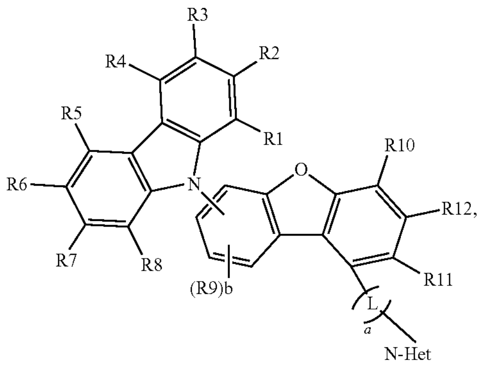

wherein the definitions of N-Het, R1 to R12, L, a, and b are the same as those in Formula 1.

13. The organic light emitting device according to claim 1, wherein Formula 1 is divided into structures in Formulas 1-1 to 1-3:

[Formula 1-1]

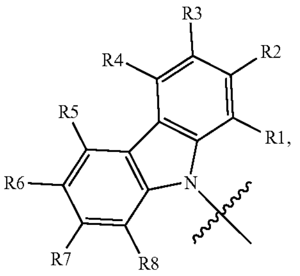

[Formula 1-2]

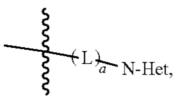

and

-continued

[Formula 1-3]

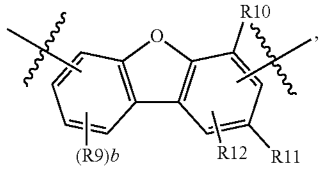

wherein the definitions of N-Het, R1 to R12, L, a, and b are same as those in Formula 1, and the mark

is a bonding position between the structures of Formulas 1-1 to 1-3, wherein a deuteration ratio of the structure of Formula 1-1, the structure of Formula 1-2 or the structure of Formula 1-3 is 100%, or a deuteration ratio of the structure of Formula 1-1, the structure of Formula 1-2 and the structure of Formula 1-3 is 100%.

14. The organic light emitting device according to claim 1, wherein N-Het in Formula 1 is represented by one of structures of Formula 1a:

[Formula 1a]

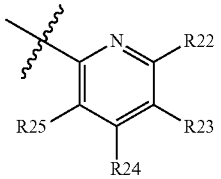

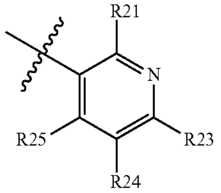

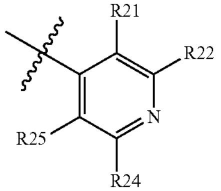

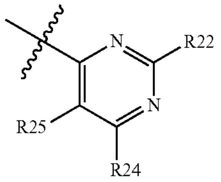

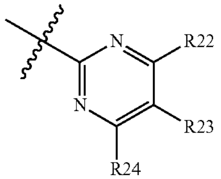

-continued

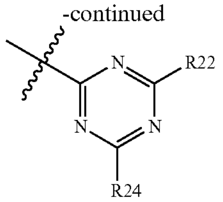

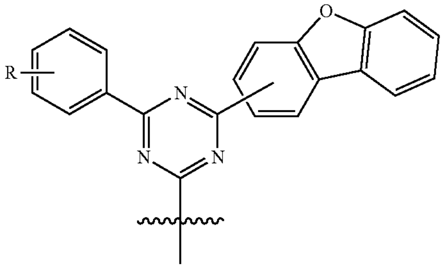

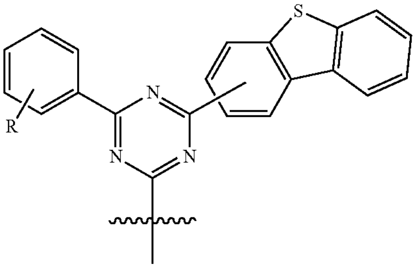

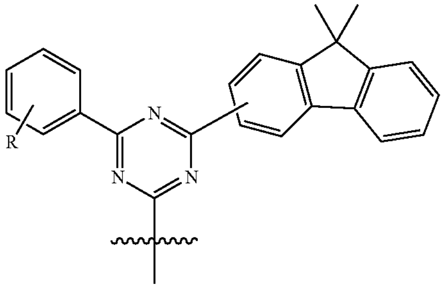

, wherein R21 to R25 are same or different, wherein each of R21 to R25 is independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; and a substituted or unsubstituted C2 to C60 heteroaryl group, or adjacent two or more of R21 to R25 are bonded to each other to form a substituted or unsubstituted C6 to C60 aromatic hydrocarbon ring or a substituted or unsubstituted C2 to C60 heterocyclic ring, wherein R is selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; and a substituted or unsubstituted C2 to C60 heteroaryl group.

15. The organic light emitting device according to claim 1, wherein the first compound d is one of compounds in Formula 1c:

[Formula 1c]

331

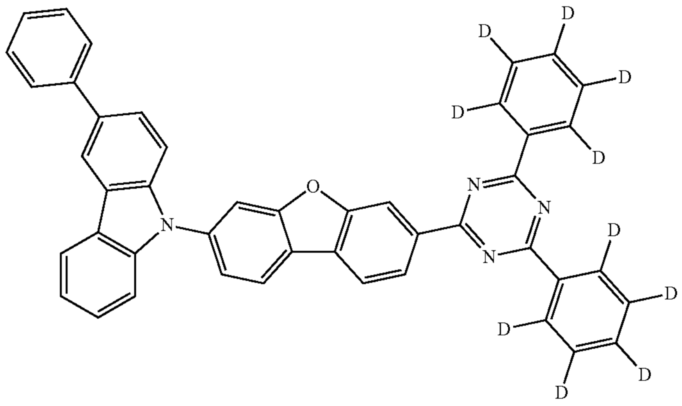

-continued
729
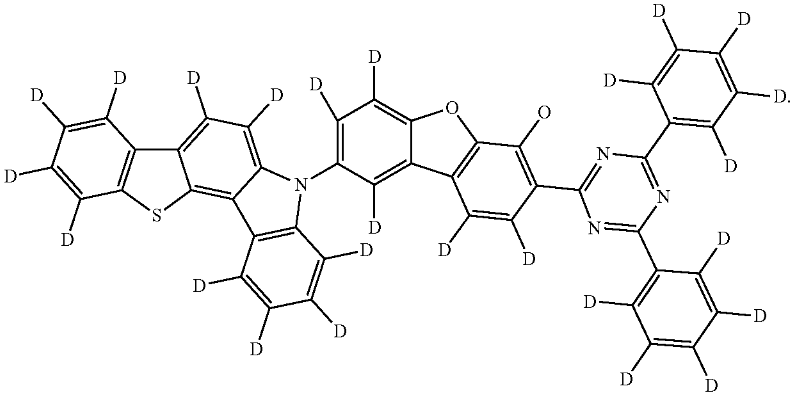
16. The organic light emitting device according to claim 1, wherein the second compound is one of compounds of Formula 2b:
[Formula 2b]
2-2
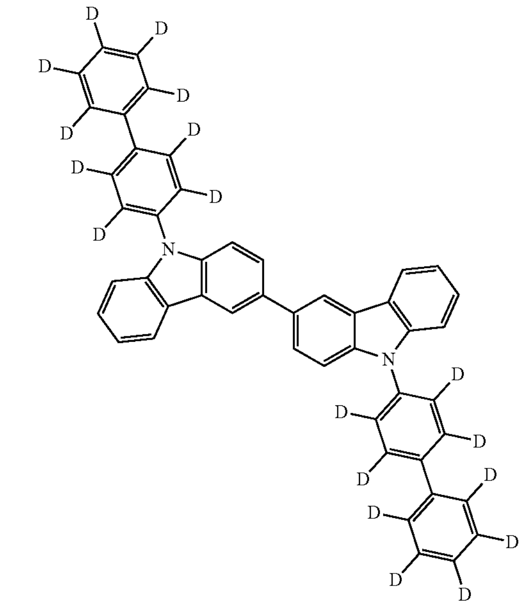
-continued
2-50
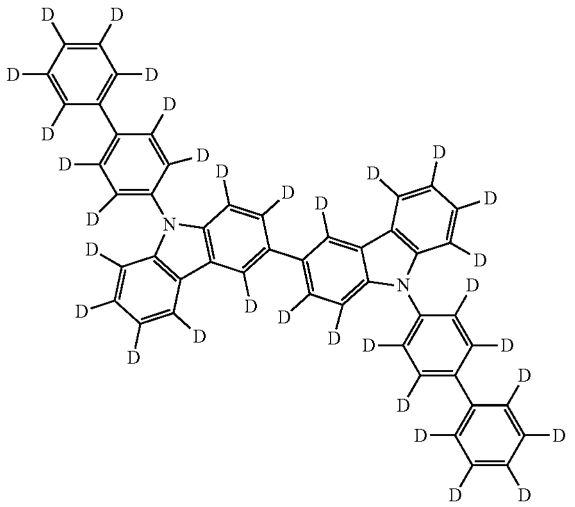
2-53
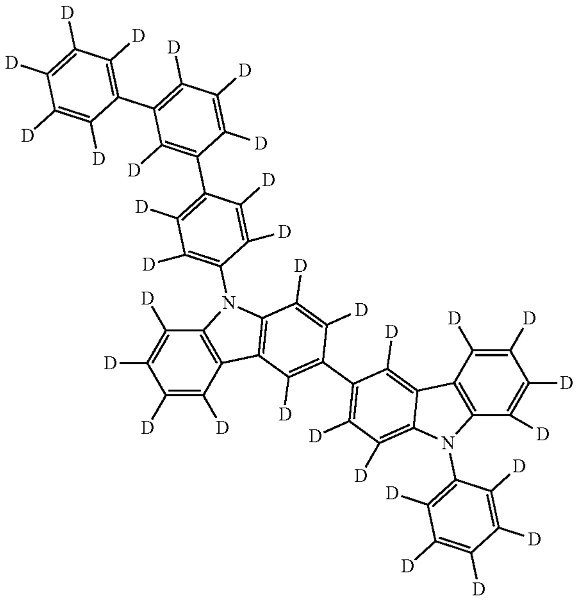

-continued
2-76
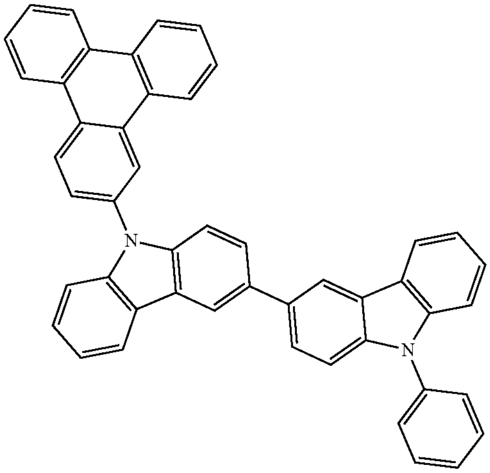
2-78
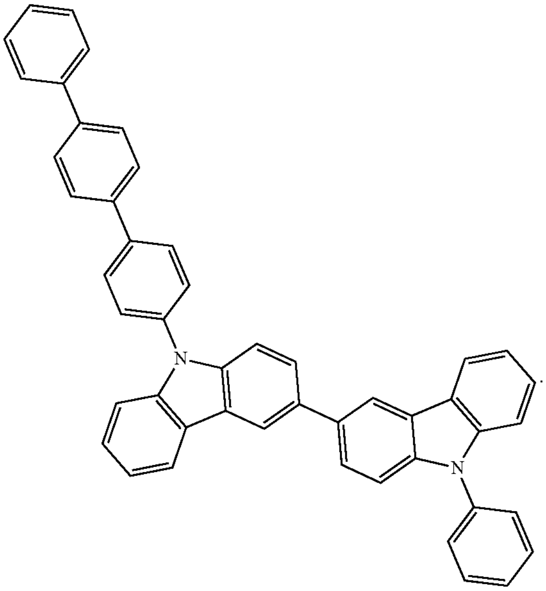
.
17. The organic light emitting device according to claim 1, wherein the first electron blocking material is one of compounds in Formula 11:
[Formula 11]
EBL1-3
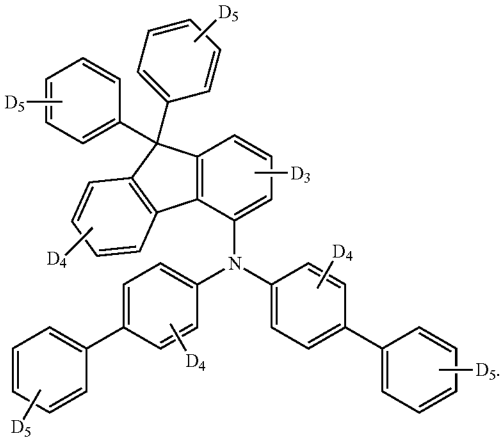
.
* * * * *